United States Patent
Bacon et al.

(10) Patent No.: US 10,336,762 B2
(45) Date of Patent: Jul. 2, 2019

(54) PYRROLO[1,2-B]PYRIDAZINE DERIVATIVES

(71) Applicant: Gilead Sciences, Inc., Foster City, CA (US)

(72) Inventors: Elizabeth M. Bacon, Burlingame, CA (US); Gediminas Brizgys, Menlo Park, CA (US); Elbert Chin, San Mateo, CA (US); Chienhung Chou, Dublin, CA (US); Jeromy J. Cottell, Redwood City, CA (US); John O. Link, San Francisco, CA (US); James G. Taylor, Burlingame, CA (US); Winston C. Tse, Redwood City, CA (US); Nathan E. Wright, Foster City, CA (US); Zheng-Yu Yang, Palo Alto, CA (US); Jennifer R. Zhang, Union City, CA (US); Sheila M. Zipfel, San Mateo, CA (US)

(73) Assignee: Gilead Sciences, Inc., Foster City, CA (US)

(*) Notice: Subject to any disclaimer, the term of this patent is extended or adjusted under 35 U.S.C. 154(b) by 0 days.

(21) Appl. No.: 15/898,095

(22) Filed: Feb. 15, 2018

(65) Prior Publication Data
US 2018/0230157 A1 Aug. 16, 2018

Related U.S. Application Data

(60) Provisional application No. 62/460,013, filed on Feb. 16, 2017.

(51) Int. Cl.
C07D 401/04 (2006.01)
C07D 413/04 (2006.01)
C07D 487/04 (2006.01)
C07D 453/00 (2006.01)
C07D 519/00 (2006.01)
A61P 29/00 (2006.01)

(52) U.S. Cl.
CPC ............ *C07D 487/04* (2013.01); *A61P 29/00* (2018.01); *C07D 453/00* (2013.01); *C07D 519/00* (2013.01)

(58) Field of Classification Search
CPC ... C07D 401/04; C07D 413/04; C07D 487/04
See application file for complete search history.

(56) References Cited

U.S. PATENT DOCUMENTS

| | | | |
|---|---|---|---|
| 7,635,774 B2 | 12/2009 | Frenkel et al. |
| 8,293,923 B2 | 10/2012 | Guckian et al. |
| 8,987,311 B2 | 3/2015 | Dodd et al. |
| 9,067,948 B2 | 6/2015 | Harriman et al. |
| 9,073,892 B2 | 7/2015 | Jorand-Lebrun et al. |
| 9,169,252 B2 | 10/2015 | Santella et al. |
| 9,169,260 B2 | 10/2015 | McElroy et al. |
| 9,212,190 B2 | 12/2015 | Harriman et al. |
| 9,216,991 B2 | 12/2015 | Crosignani et al. |
| 9,221,809 B2 | 12/2015 | Seganish et al. |
| 9,242,975 B2 | 1/2016 | Paidi et al. |
| 9,255,110 B2 | 2/2016 | Arora et al. |
| 9,340,554 B2 | 5/2016 | Romero et al. |
| 9,518,065 B2 | 12/2016 | Romero et al. |
| 9,540,333 B2 | 1/2017 | Santella et al. |
| 9,546,153 B2 | 1/2017 | Bhide et al. |
| 9,567,320 B2 | 2/2017 | Jorand-Lebrun et al. |
| 9,586,948 B2 | 3/2017 | Seganish et al. |
| 9,598,440 B2 | 3/2017 | Seganish et al. |
| 9,617,282 B2 | 4/2017 | Jenkins et al. |
| 9,624,246 B2 | 4/2017 | Chen et al. |
| 9,657,009 B2 | 5/2017 | Bhide et al. |
| 9,732,095 B2 | 8/2017 | Gummadi et al. |
| 9,751,892 B2 | 9/2017 | Greenwood et al. |
| 9,765,059 B2 | 9/2017 | Collins et al. |
| 9,790,221 B2 | 10/2017 | Jorand-Lebrun et al. |
| 9,790,234 B2 | 10/2017 | Romero et al. |
| 9,815,836 B2 | 11/2017 | Chen et al. |

(Continued)

FOREIGN PATENT DOCUMENTS

WO WO-2008016643 A2 2/2008
WO WO-2011043371 A1 4/2011
(Continued)

OTHER PUBLICATIONS

Bhide, R.S. et al. (2017) "Discovery and structure-based design of 4,6-diaminonicotinamides as potent and selective IRAK4 inhibitors," Bioorg. Med. Chem. Lett., 27:4908-4913.

Balasubramanian, W.R. et al. (2016) "Efficacy and safety of highly selective novel IRAK4 inhibitors for treatment of ABC-DLBCL," Abstract # 4798, Aurigene Accelerating Discovery, Aurigene Discovery Technologies, Bangalore, India, 1 page.

Picard, C. et al. (2011) "Infectious Diseases in Patients with IRAK-4, MyD88, NEMO, or IκBα Deficiency," Clinical Microbiology Reviews, 24(3):490-497.

(Continued)

*Primary Examiner* — Bruck Kifle
(74) *Attorney, Agent, or Firm* — Philip B. Polster

(57) ABSTRACT

Provided is a compound of Formula (I)

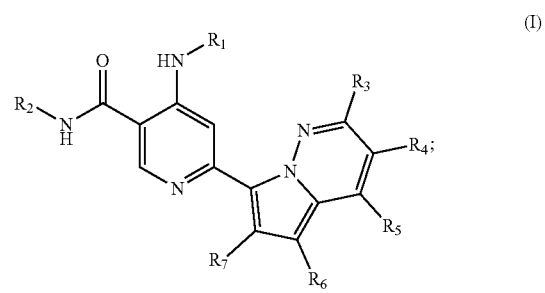

wherein the variable groups are defined herein.

125 Claims, No Drawings

(56) References Cited

U.S. PATENT DOCUMENTS

| | | |
|---|---|---|
| 9,862,715 B2 | 1/2018 | Paidi et al. |
| 9,879,022 B2 | 1/2018 | Trzupek et al. |
| 9,890,145 B2 | 2/2018 | Yoshida et al. |
| 9,890,152 B2 | 2/2018 | Bryan et al. |
| 9,926,330 B2 | 3/2018 | Altman et al. |
| 9,932,350 B2 | 4/2018 | Altman et al. |
| 9,943,516 B2 | 4/2018 | Altman et al. |
| 9,951,064 B2 | 4/2018 | Bryan et al. |
| 9,951,086 B2 | 4/2018 | Bothe et al. |
| 9,969,710 B2 | 5/2018 | Jorand-Lebrun et al. |
| 9,969,749 B2 | 5/2018 | Altman et al. |
| 9,982,000 B2 | 5/2018 | Kelley et al. |
| 10,000,480 B2 | 6/2018 | Moslin et al. |
| 10,030,034 B2 | 7/2018 | Ho et al. |
| 10,064,861 B2 | 9/2018 | Jorand-Lebrun et al. |
| 2007/0037803 A1 | 2/2007 | Frenkel et al. |
| 2012/0115861 A1 | 5/2012 | Calderini et al. |
| 2014/0018361 A1 | 1/2014 | Harriman et al. |
| 2014/0194417 A1 | 7/2014 | Greenwood et al. |
| 2015/0191464 A1 | 7/2015 | Santella et al. |
| 2015/0284405 A1 | 10/2015 | Trzupek et al. |
| 2015/0329498 A1 | 11/2015 | Romero et al. |
| 2016/0166576 A1 | 6/2016 | Lim et al. |
| 2016/0207936 A1 | 7/2016 | Arora et al. |
| 2016/0311833 A1 | 10/2016 | Bothe et al. |
| 2016/0326151 A1 | 11/2016 | Gummadi et al. |
| 2017/0152263 A1 | 6/2017 | Gummadi et al. |
| 2017/0204093 A1 | 7/2017 | Chan et al. |
| 2017/0349570 A1 | 12/2017 | Bothe et al. |
| 2017/0369476 A1 | 12/2017 | Chen et al. |
| 2018/0051027 A1 | 2/2018 | Lim et al. |
| 2018/0051028 A1 | 2/2018 | Lim et al. |
| 2018/0051029 A1 | 2/2018 | Lim et al. |
| 2018/0051030 A1 | 2/2018 | Lim et al. |
| 2018/0051035 A1 | 2/2018 | Lim et al. |
| 2018/0111917 A1 | 4/2018 | Tso et al. |
| 2018/0169094 A1 | 6/2018 | Jorand-Lebrun et al. |
| 2018/0179213 A1 | 6/2018 | Duncia et al. |
| 2018/0186799 A1 | 7/2018 | Gardner et al. |
| 2018/0201609 A1 | 7/2018 | Gummadi et al. |
| 2018/0208605 A1 | 7/2018 | Gummadi et al. |
| 2018/0214447 A1 | 8/2018 | Ben Neriah et al. |
| 2018/0230127 A1 | 8/2018 | Anderson et al. |
| 2018/0237426 A1 | 8/2018 | Jorand-Lebrun et al. |
| 2018/0244646 A1 | 8/2018 | Lee et al. |
| 2018/0244677 A1 | 8/2018 | Xu et al. |
| 2018/0289685 A1 | 10/2018 | Bothe et al. |
| 2018/0298015 A1 | 10/2018 | Bryan et al. |
| 2018/0305351 A1 | 10/2018 | Brys et al. |
| 2018/0346458 A1 | 12/2018 | Yen et al. |

FOREIGN PATENT DOCUMENTS

| | | |
|---|---|---|
| WO | WO-2013042137 A1 | 3/2013 |
| WO | WO 2016210036 | * 12/2016 |
| WO | WO-2016210036 A1 | 12/2016 |
| WO | WO-2017004133 A1 | 1/2017 |
| WO | WO-2017004134 A1 | 1/2017 |
| WO | WO-2017024589 A1 | 2/2017 |
| WO | WO-2017108744 A1 | 6/2017 |
| WO | WO-2017127430 A1 | 7/2017 |
| WO | WO-2017186689 A1 | 11/2017 |
| WO | WO-2017205762 A1 | 11/2017 |
| WO | WO-2017205766 A1 | 11/2017 |
| WO | WO-2017205769 A1 | 11/2017 |
| WO | WO-2017207385 A1 | 12/2017 |
| WO | WO-2018083085 A1 | 5/2018 |

OTHER PUBLICATIONS

Dudhgaonkar, S. et al. (2016) "Selective IRAK4 Inhibition Attenuates Disease in Murine Lupus Models and Demonstrates Steroid Sparing Activity," Journal of Immunology, 198:1308-1319.

\* cited by examiner

PYRROLO[1,2-B]PYRIDAZINE DERIVATIVES

CROSS REFERENCE TO RELATED APPLICATIONS

This application claims priority benefit to U.S. Provisional Application Ser. No. 62/460,013, filed on Feb. 16, 2017, the disclosure of which is incorporated by reference in its entirety.

FIELD

The present disclosure relates to novel compounds that are inhibitors of the kinase IRAK4. The disclosure also relates to methods for preparing the compounds and to pharmaceutical compositions comprising such compounds.

BACKGROUND

Interleukin-1 receptor-associated kinase-4 (IRAK4) is a serine-threonine kinase which acts as a mediator in interleukin-1/Toll-like receptor (IL-1/TLR) signaling cascades. More particularly, IRAK4 is involved in activation of adaptor protein myeloid differentiation primary response gene 88 (MyD88) signaling cascades and is hypothesized to play a role in inflammation related disorders as well as in oncology and non-alcoholic steatohepatitis (NASH). Signaling through IL-1R/TLR results in the activation of MyD88 which recruits IRAK4 and IRAK1 to form a signaling complex. This complex then interacts with a series of kinases, adaptor proteins, and ligases, ultimately resulting in the activation of nuclear factor kappa-light-chain-enhancer of activated B cells (NF-κB) and activator protein-1, inducing the generation of inflammatory cytokines.

Therefore, inhibitors of IRAK4 may be useful in the treatment of inflammatory disorders, including autoimmune disorders, such as rheumatoid arthritis (RA), inflammatory bowel disease (IBD), gout, Lyme arthritis, systemic lupus erythematosus (SLE), Sjogren's syndrome and viral myocarditis. (Joosten, L. A. B et al., TOLL-LIKE RECEPTORS AND CHRONIC INFLAMMATION IN RHEUMATIC DISEASES: NEW DEVELOPMENTS, Nat. Rev. Rheumatol., 346| Jun. 2016 12; 344-357 Published online 12 May 2016) (Valaperti, A. et al., INNATE IMMUNE INTERLEUKIN-1RECEPTOR-ASSOCIATED KINASE 4 EXACERBATES VIRAL MYOCARDITIS BY REDUCING CCR5⁺ CD11b⁺ MONOCYTE MIGRATION AND IMPAIRING INTERFERON PRODUCTION, Circulation, 128| Sep. 2013 14; 1542-1554), as well as Type I interferonopathies, such as Aicardi-Goutières syndrome, Familial chilblain lupus, and Retinal vasculopathy with cerebral leukodystrophy, (Lee-Kirsch et al., TYPE I INTERFERONOPATHIES—AN EXPANDING DISEASE SPECTRUM OF IMMUNODYSREGULATION, Semin. Immunopathol. (2015) 37:349-357).

In addition, certain cancers, including lymphomas, may contain one or more mutations in the MYD88 adaptor protein, leading to a constitutively active signaling cascade that may promote survival of tumor cells. (Kelly et al., IRAK4 inhibitors for autoimmunity and lymphoma, J. Exp. Med. 2015 Vol. 212 No. 13 2189-2201)

Therefore, an inhibitor of IRAK4 may be useful in the treatment of cancers, including lymphomas.

There are currently no approved IRAK4 inhibiting pharmaceuticals. Therefore, it would be useful to provide an IRAK4 inhibiting compound with properties suitable for administration as a pharmaceutical agent to a mammal, particularly a human.

WO2016210034, WO2016210036, WO2015150995, WO2016127024, and WO2016210037 recite compounds said to be useful as IRAK4 inhibitors.

SUMMARY OF THE INVENTION

Provided herein are compounds and pharmaceutical compositions useful as inhibitors of IRAK4. Some compounds of the disclosure may find use in pharmaceutical compositions, together with at least one pharmaceutically acceptable excipient, for treating a subject in need thereof. Compounds of the present disclosure also have been found to inhibit production of TNFα, IL-6, IL-1β and IL-23, all of which are mediators of inflammation. The disclosure also provides compositions, including pharmaceutical compositions, kits that include the compounds, and methods of using and making the compounds.

In one embodiment of the disclosure, there is provided a compound of Formula (I)

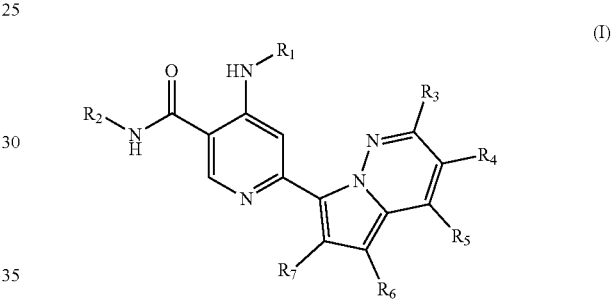

(I)

wherein:
$R^1$ and $R^2$ are each independently selected from:
$C_{1-10}$ alkyl optionally substituted with $Z^1$;
$C_{3-10}$ cycloalkyl optionally substituted with $Z^1$;
5-10 membered heteroaryl optionally substituted with $Z^1$;
$C_{6-10}$ aryl optionally substituted with $Z^1$;
4-7 membered monocyclic heterocyclyl optionally substituted with $Z^1$;
6-12 membered bicyclic heterocyclyl optionally substituted with $Z^1$; or
—N($R^{12}$)($R^{12}$), —S(O)$_2$$R^{12}$, —S(O)$_2$N($R^{12}$)($R^{12}$), or —H;
$R^3$ and $R^4$ are each independently selected from:
H, halo, —NO$_2$, —CN, —O—$R^{12}$, —C(O)—$R^{12}$, —C(O)—N($R^{12}$)($R^{12}$), —N($R^{12}$)($R^{12}$), —N($R^{12}$)C(O)—$R^{12}$, —N($R^{12}$)C(O)O—$R^{12}$, —N($R^{12}$)S(O)$_2$($R^{12}$), —N($R^{12}$)C(O)—N($R^{12}$)($R^{12}$), —S(O)$_2$$R^{12}$ or —S(O)$_2$N($R^{12}$)($R^{12}$);
$C_{1-9}$ alkyl optionally substituted with $Z^1$;
$C_{2-9}$ alkynyl optionally substituted with $Z^1$;
$C_{2-9}$ alkenyl optionally substituted with $Z^1$;
5-10 membered heteroaryl optionally substituted with $Z^1$;
$C_{6-10}$ aryl optionally substituted with $Z^1$;
4-12 membered heterocyclyl optionally substituted with $Z^1$; or
$C_{3-10}$ cycloalkyl optionally substituted with $Z^1$;
$R^5$, $R^6$ and $R^7$ are each independently selected from:
H, halo, —NO$_2$, —CN, —O—$R^{12}$, —C(O)—$R^{12}$, —C(O)—N($R^{12}$)($R^{12}$), —N($R^{12}$)($R^{12}$), —N($R^{12}$)C(O)—$R^{12}$, —N($R^{12}$)C(O)O—$R^{12}$, or —N($R^{12}$)S(O)$_2$($R^{12}$);

$C_{1-5}$ alkyl optionally substituted with $Z^1$; or

Cyclopropyl, oxetanyl or azetidinyl optionally substituted with $Z^1$;

$Z^1$ is independently oxo, halo, —$NO_2$, —$N_3$, —CN, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^{12}$, —C(O)—$R^{12}$, —C(O)O—$R^{12}$, —C(O)—N($R^{12}$)($R^{12}$), —N($R^{12}$)($R^{12}$), —N($R^{12}$)$_2$($R^{12}$)$^+$, —N($R^{12}$)C(O)—$R^{12}$, —N($R^{12}$)C(O)O—$R^{12}$, —N($R^{12}$)C(O)N($R^{12}$)($R^{12}$), —N($R^{12}$)S(O)$_2$($R^{12}$), —N$R^{12}$S(O)$_2$N($R^{12}$)($R^{12}$), —N$R^{12}$S(O)$_2$O($R^{12}$), —OC(O)$R^{12}$, —OC(O)O$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2R^{12}$ or —S(O)$_2$N($R^{12}$)($R^{12}$);

wherein any alkyl, alkenyl, alkynyl, cycloalkyl, haloalkyl, aryl, heteroaryl or heterocyclyl is optionally substituted with $Z^{1a}$;

each $Z^{1a}$ is independently oxo, halo, —$NO_2$, —CN, —$N_3$, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^{12}$, —C(O)$R^{12}$, —C(O)O—$R^{12}$, —C(O)N($R^{12}$)($R^{12}$), —N($R^{12}$)($R^{12}$), —N($R^{12}$)$_2$($R^{12}$)$^+$, —N($R^{12}$)—C(O)$R^{12}$, —N($R^{12}$)C(O)O($R^{12}$), —N($R^{12}$)C(O)N($R^{12}$)($R^{12}$), —N($R^{12}$)S(O)$_2$($R^{12}$), —N($R^{12}$)S(O)$_2$—N($R^{12}$)($R^{12}$), —N($R^{12}$)S(O)$_2$O($R^{12}$), —OC(O)$R^{12}$, —OC(O)O$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2R^{12}$ or —S(O)$_2$N($R^{12}$)($R^{12}$);

wherein any alkyl, alkenyl, alkynyl, cycloalkyl, haloalkyl, aryl, heteroaryl or heterocyclyl is optionally substituted with $Z^{1b}$;

each $R^{12}$ is independently H, $C_{1-9}$ alkyl, $C_{2-6}$ alkenyl, $C_{2-6}$ alkynyl, $C_{3-15}$ cycloalkyl, aryl, heteroaryl or heterocyclyl;

wherein any alkyl, alkenyl, alkynyl, cycloalkyl, aryl, heteroaryl or heterocyclyl is optionally substituted with $Z^{1a}$;

each $Z^{1b}$ is independently oxo, hydroxy, halo, —$NO_2$, —$N_3$, —CN, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O($C_{1-9}$ alkyl), —O($C_{2-6}$ alkenyl), —O($C_{2-6}$ alkynyl), —O($C_{3-15}$ cycloalkyl), —O($C_{1-8}$ haloalkyl), —O(aryl), —O(heteroaryl), —O(heterocyclyl), —$NH_2$, —NH($C_{1-9}$ alkyl), —NH($C_{2-6}$ alkenyl), —NH($C_{2-6}$ alkynyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —N($C_{2-6}$ alkenyl)$_2$, —N($C_{2-6}$ alkynyl)$_2$, —N($C_{3-15}$ cycloalkyl)$_2$, —N($C_{1-8}$ haloalkyl)$_2$, —N(aryl)$_2$, —N(heteroaryl)$_2$, —N(heterocyclyl)$_2$, —N($C_{1-9}$ alkyl)($C_{3-15}$ cycloalkyl), —N($C_{1-9}$ alkyl)($C_{2-6}$ alkenyl), —N($C_{1-9}$ alkyl)($C_{2-6}$ alkynyl), —N($C_{1-9}$ alkyl)($C_{3-15}$ cycloalkyl), —N($C_{1-9}$ alkyl)($C_{1-8}$ haloalkyl), —N($C_{1-9}$ alkyl)(aryl), —N($C_{1-9}$ alkyl)(heteroaryl), —N($C_{1-9}$ alkyl)(heterocyclyl), —C(O)($C_{1-9}$ alkyl), —C(O)($C_{2-6}$ alkenyl), —C(O)($C_{2-6}$ alkynyl), —C(O)($C_{3-15}$ cycloalkyl), —C(O)($C_{1-8}$ haloalkyl), —C(O)(aryl), —C(O)(heteroaryl), —C(O)(heterocyclyl), —C(O)O($C_{1-9}$ alkyl), —C(O)O($C_{2-6}$ alkenyl), —C(O)O($C_{2-6}$ alkynyl), —C(O)O($C_{3-15}$ cycloalkyl), —C(O)O($C_{1-8}$ haloalkyl), —C(O)O(aryl), —C(O)O(heteroaryl), —C(O)O(heterocyclyl), —C(O)$NH_2$, —C(O)NH($C_{1-9}$ alkyl), —C(O)NH($C_{2-6}$ alkenyl), —C(O)NH($C_{2-6}$ alkynyl), —C(O)NH($C_{3-15}$ cycloalkyl), —C(O)NH($C_{1-8}$ haloalkyl), —C(O)NH(aryl), —C(O)NH(heteroaryl), —C(O)NH(heterocyclyl), —C(O)N($C_{1-9}$ alkyl)$_2$, —C(O)N($C_{3-15}$ cycloalkyl)$_2$, —C(O)N($C_{2-6}$ alkenyl)$_2$, —C(O)N($C_{2-6}$ alkynyl)$_2$, —C(O)N($C_{3-15}$ cycloalkyl)$_2$, —C(O)N($C_{1-8}$ haloalkyl)$_2$, —C(O)N(aryl)$_2$, —C(O)N(heteroaryl)$_2$, —C(O)N(heterocyclyl)$_2$, —NHC(O)($C_{1-9}$ alkyl), —NHC(O)($C_{2-6}$ alkenyl), —NHC(O)($C_{2-6}$ alkynyl), —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkenyl), —NHC(O)O($C_{2-6}$ alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —NHC(O)NH($C_{2-6}$ alkenyl), —NHC(O)NH($C_{2-6}$ alkynyl), —NHC(O)NH($C_{3-15}$ cycloalkyl), —NHC(O)NH($C_{1-8}$ haloalkyl), —NHC(O)NH(aryl), —NHC(O)NH(heteroaryl), —NHC(O)NH(heterocyclyl), —SH, —S($C_{1-9}$ alkyl), —S($C_{2-6}$ alkenyl), —S($C_{2-6}$ alkynyl), —S($C_{3-15}$ cycloalkyl), —S($C_{1-8}$ haloalkyl), —S(aryl), —S(heteroaryl), —S(heterocyclyl), —NHS(O)($C_{1-9}$ alkyl), —N($C_{1-9}$ alkyl)(S(O)($C_{1-9}$ alkyl), —S(O)N($C_{1-9}$ alkyl)$_2$, —S(O)($C_{1-9}$ alkyl), —S(O)(NH)($C_{1-9}$ alkyl), —S(O)($C_{2-6}$ alkenyl), —S(O)($C_{2-6}$ alkynyl), —S(O)($C_{3-15}$ cycloalkyl), —S(O)($C_{1-8}$ haloalkyl), —S(O)(aryl), —S(O)(heteroaryl), —S(O)(heterocyclyl), —S(O)$_2$($C_{1-9}$ alkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), or —S(O)$_2$N($C_{1-9}$ alkyl)$_2$;

wherein any alkyl, cycloalkyl, aryl, heteroaryl, or heterocyclyl is optionally substituted with one or more halo, $C_{1-9}$ alkyl, $C_{1-8}$ haloalkyl, —OH, —$NH_2$, —NH($C_{1-9}$ alkyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —S(O)(NH)($C_{1-9}$ alkyl), S(O)$_2$($C_{1-9}$ alkyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), —S(O)$_2$N($C_{1-9}$ alkyl)$_2$, —O($C_{3-15}$ cycloalkyl), —O($C_{1-8}$ haloalkyl), —O(aryl), —O(heteroaryl), —O(heterocyclyl), or —O($C_{1-9}$ alkyl); and with the proviso that when $R^1$ is $C_3$ alkyl, $R^2$ is $C_5$ alkyl substituted with F and hydroxyl, $R^3$, $R^5$, $R^6$, $R^7$ are H, and $R^4$ is CN, then $R^1$ is substituted with $Z^1$;

or a pharmaceutically acceptable salt, stereoisomer, mixture of stereoisomers, or deuterated analog thereof.

In another embodiment, or a pharmaceutically acceptable salt, stereoisomer, mixture of stereoisomers, or deuterated analog thereof, $R^1$ is $C_{1-10}$ alkyl optionally substituted with $Z^1$, with the proviso that when $R^1$ is $C_3$ alkyl, $R^2$ is $C_5$ alkyl substituted with F and hydroxyl, $R^3$, $R^5$, $R^6$, $R^7$ are H, and $R^4$ is CN, then $R^1$ is substituted with $Z^1$.

In another embodiment, when $R^1$ or $R^2$ is $C_{1-10}$ alkyl, $C_{3-10}$ cycloalkyl, 5-10 membered heteroaryl, $C_{6-10}$ aryl, 4-7 membered monocyclic heterocyclyl, or 6-12 membered bicyclic heterocyclyl, two $Z^1$ groups either attached to the same atom on the $R^1$ or the $R^2$ group, or two $Z^1$ groups attached to adjacent atoms on the $R^1$ or the $R^2$ group, append together to form a 3-6 membered cycloalkyl or 3-6 membered heterocyclyl.

In another embodiment, or a pharmaceutically acceptable salt, stereoisomer, mixture of stereoisomers, or deuterated analog thereof, $R^1$ is

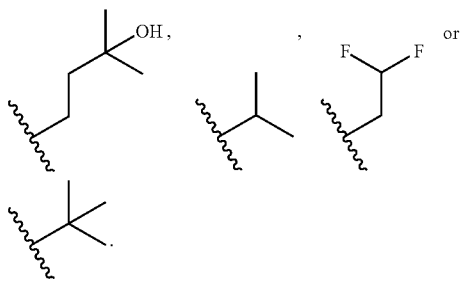

In another embodiment, or a pharmaceutically acceptable salt, stereoisomer, mixture of stereoisomers, or deuterated analog thereof, $R^1$ is methyl.

In another embodiment, or a pharmaceutically acceptable salt, stereoisomer, mixture of stereoisomers, or deuterated analog thereof, $R^1$ is $C_{6-10}$ alkyl optionally substituted with $Z^1$.

In another embodiment, or a pharmaceutically acceptable salt, stereoisomer, mixture of stereoisomers, or deuterated analog thereof, $R^1$ is $C_{1-5}$ alkyl substituted with one or more substituents selected from —Cl, oxo, —CN, $C_{2-6}$ alkenyl, $C_{2-6}$ alkynyl, cyclopropyl, naphthyl, heteroaryl, nitrogen or sulfur containing monocyclic heterocyclyl, bicyclic heterocyclyl, $C_{7-15}$ cycloalkyl, —O—$R^9$, —C(O)—$R^{12}$, —C(O)O—$R^{12}$, —C(O)—N($R^{12}$)($R^{12}$), —N($R^{12}$)($R^{12}$), —N($R^{12}$)$_2$($R^{12}$)$^+$, —N($R^{12}$)C(O)—$R^{12}$, —N($R^{12}$)C(O)O—$R^{12}$, —N($R^{12}$)C(O)N($R^{12}$)($R^{12}$), —N($R^{12}$)S(O)$_2$($R^{12}$), —N$R^{12}$S(O)$_2$N($R^{12}$)($R^{12}$), —N$R^{12}$S(O)$_2$O($R^{12}$), —OC(O)$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2R^{12}$ or —S(O)$_2$N($R^{12}$)($R^{12}$);

$R^9$ at each occurrence is independently $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl;

wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl is optionally substituted with $Z^{1a}$;

wherein said $C_{1-5}$ alkyl is also optionally substituted with $Z^1$; and wherein each said $C_{2-6}$ alkenyl, $C_{2-6}$ alkynyl, cyclopropyl, naphthyl, heteroaryl, nitrogen or sulfur containing monocyclic heterocyclyl, bicyclic heterocyclyl, or $C_{7-15}$ cycloalkyl is optionally substituted with $Z^{1a}$.

In another embodiment, or a pharmaceutically acceptable salt, stereoisomer, mixture of stereoisomers, or deuterated analog thereof, $R^1$ is

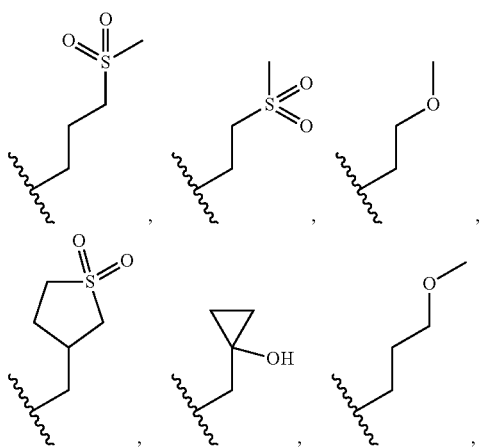

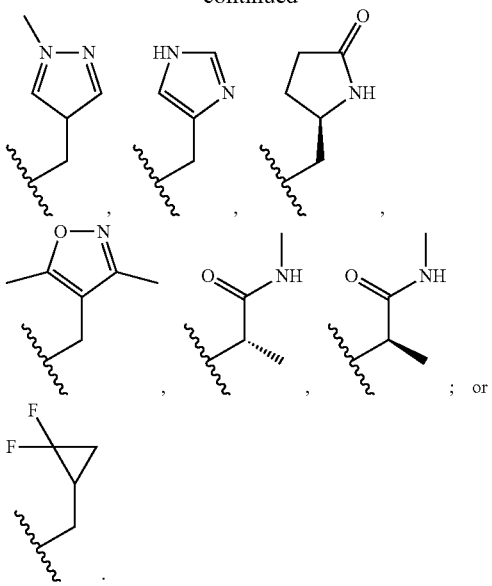

In another embodiment, or a pharmaceutically acceptable salt, stereoisomer, mixture of stereoisomers, or deuterated analog thereof, $R^1$ is $C_{1-5}$ alkyl optionally substituted with $Z^1$;

wherein said $C_{1-5}$ alkyl is substituted with one or more $C_{4-6}$ cycloalkyl, oxetanyl, tetrahydrofuranyl, tetrahydropyranyl, or phenyl;

wherein said $C_{4-6}$ cycloalkyl, oxetanyl, tetrahydrofuranyl, tetrahydropyranyl, or phenyl is optionally substituted with $Z^{1a}$;

wherein said $C_{4-6}$ cycloalkyl, oxetanyl, tetrahydrofuranyl, tetrahydropyranyl, or phenyl is substituted by one or more halo, oxo, —CN, $C_{2-6}$ alkyl, $C_{2-6}$ alkenyl, $C_{2-6}$ alkynyl, $C_{3-7}$ cycloalkyl, aryl, heteroaryl, heterocyclyl, —O—$R^9$, —C(O)—$R^{12}$, —C(O)O—$R^{12}$, —C(O)—N($R^{12}$)($R^{12}$), —N($R^{12}$)($R^{12}$), —N($R^{12}$)$_2$($R^{12}$)$^+$, —N($R^{12}$)C(O)—$R^{12}$, —N($R^{12}$)C(O)O—$R^{12}$, —N($R^{12}$)C(O)N($R^{12}$)($R^{12}$), —N($R^{12}$)S(O)$_2$($R^{12}$), —N$R^{12}$S(O)$_2$N($R^{12}$)($R^{12}$), —N$R^{12}$S(O)$_2$O($R^{12}$), —OC(O)$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2R^{12}$ or —S(O)$_2$N($R^{12}$)($R^{12}$); and wherein each said $C_{2-6}$ alkyl, $C_{2-6}$ alkenyl, $C_{2-6}$ alkynyl, $C_{3-7}$ cycloalkyl, aryl, heteroaryl, or heterocyclyl is optionally substituted with $Z^{1b}$.

In another embodiment, or a pharmaceutically acceptable salt, stereoisomer, mixture of stereoisomers, or deuterated analog thereof, $R^1$ is $C_{1-5}$ alkyl optionally substituted with F or —OH and substituted with one or more substituents selected from $C_{4-6}$ cycloalkyl, oxetanyl, tetrahydrofuranyl, tetrahydropyranyl, or phenyl; wherein said $C_{4-6}$ cycloalkyl, oxetanyl, tetrahydrofuranyl, tetrahydropyranyl, or phenyl is substituted with two or more substituents selected from —OH and —CH$_3$ and optionally substituted with $Z^{1a}$.

In another embodiment, or a pharmaceutically acceptable salt, stereoisomer, mixture of stereoisomers, or deuterated analog thereof, $R^1$ is $C_{3-10}$ cycloalkyl optionally substituted with $Z^1$.

In another embodiment, or a pharmaceutically acceptable salt, stereoisomer, mixture of stereoisomers, or deuterated analog thereof, $R^1$ is

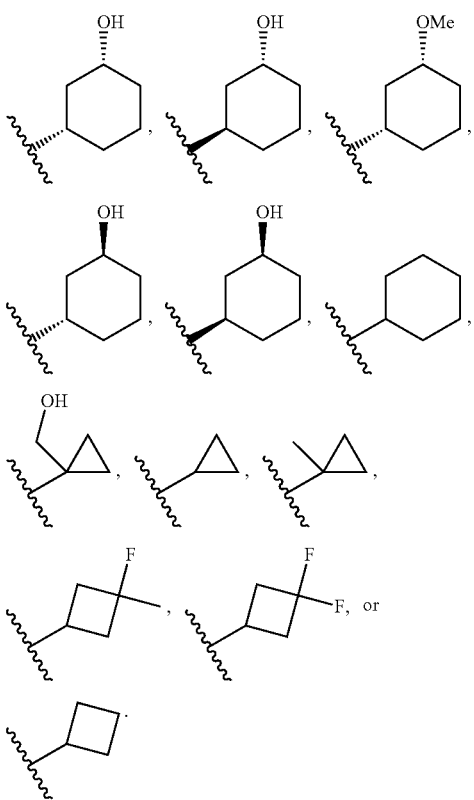

In another embodiment, or a pharmaceutically acceptable salt, stereoisomer, mixture of stereoisomers, or deuterated analog thereof, $R^1$ is

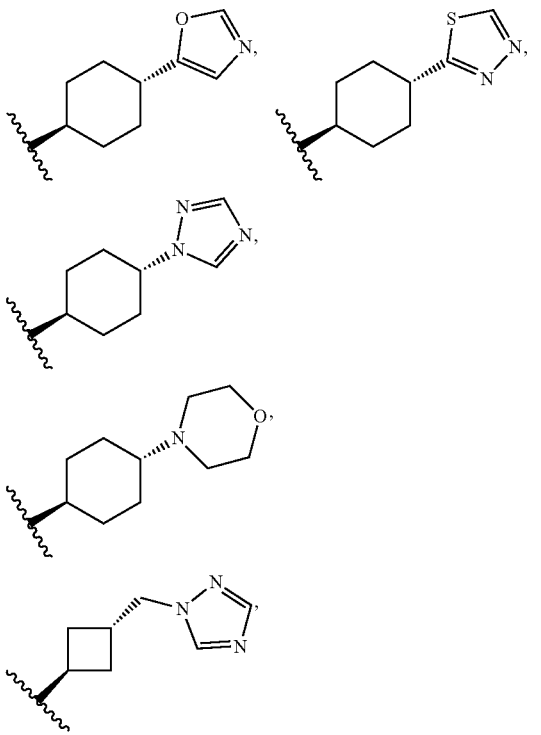

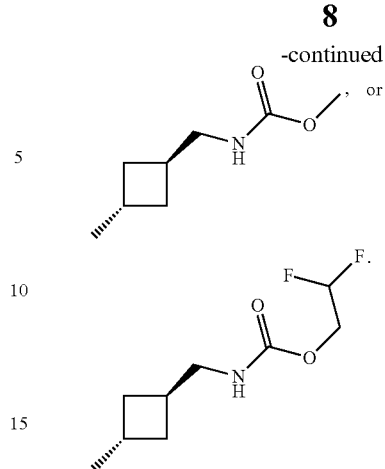

In another embodiment, or a pharmaceutically acceptable salt, stereoisomer, mixture of stereoisomers, or deuterated analog thereof, $R^1$ is $C_{3-10}$ cycloalkyl optionally substituted with $Z^1$.

In another embodiment, or a pharmaceutically acceptable salt, stereoisomer, mixture of stereoisomers, or deuterated analog thereof, $R^1$ is $C_{7-10}$ cycloalkyl optionally substituted with $Z^1$, wherein when said $C_7$-$C_{10}$ cycloalkyl is bicyclo [2.2.1]heptanyl, then said $C_{7-10}$ cycloalkyl is substituted with at least one of oxo, —Cl, —NO$_2$, —CN, —N$_3$, $C_{5-9}$ alkyl, $C_{2-6}$ alkenyl, $C_{2-6}$ alkynyl, $C_{7-15}$ cycloalkyl, $C_{5-8}$ haloalkyl, aryl, pyrazolyl, —O—$R^9$, —C(O)O—$R^{12}$, —C(O)N($R^{12}$)($R^{12}$), —N($R^{12}$)($R^{12}$), —N($R^{12}$)$_2$($R^{12}$)$^+$, —N($R^{12}$)—C(O)$R^{12}$, —N($R^{12}$)C(O)O($R^{12}$), —N($R^{12}$)C(O)N($R^{12}$)($R^{12}$), —N($R^{12}$)S(O)$_2$($R^{12}$), —N($R^{12}$)S(O)$_2$—N($R^{12}$)($R^{12}$), —N($R^{12}$)S(O)$_2$O($R^{12}$), —OC(O)$R^{12}$, —OC(O)O$R^{12}$, —OC(O)—N($R^{12}$)($R^{12}$), —Si($R^{12}$)$_3$, —S—$R^{12}$, —S(O)$R^{12}$, —S(O)(NH)$R^{12}$, or —S(O)$_2$N($R^{12}$)($R^{12}$).

In another embodiment, or a pharmaceutically acceptable salt, stereoisomer, mixture of stereoisomers, or deuterated analog thereof, $R^1$ is

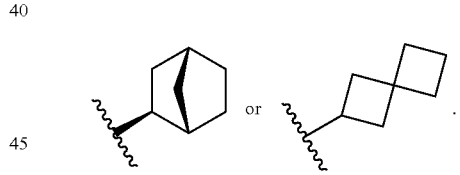

In another embodiment, or a pharmaceutically acceptable salt, stereoisomer, mixture of stereoisomer, or deuterated analog thereof, $R^1$ is a 3-10 membered bridged bicyclic group optionally substituted with one or more $Z^1$ group. An example of such a 3-10 membered bridged bicyclic group is

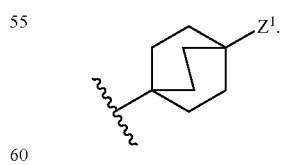

In another embodiment, or a pharmaceutically acceptable salt, stereoisomer, mixture of stereoisomers, or deuterated analog thereof, $R^1$ is a 3-10 membered bridged hetero bicyclic group optionally substituted with one or more $Z^1$ group. An example of such a 3-10 membered bridged bicyclic group is

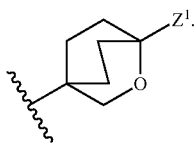

In another embodiment, or a pharmaceutically acceptable salt, stereoisomer, mixture of stereoisomers, or deuterated analog thereof, $R^1$ is $C_{3-6}$ cycloalkyl substituted with one or more —O—$R^{16}$; wherein said $C_{3-6}$ cycloalkyl is optionally substituted with $Z^1$;

$R^{16}$ at each occurrence is independently $C_{5-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl; wherein each $C_{5-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl is optionally substituted with $Z^{1a}$ In another embodiment, or a pharmaceutically acceptable salt, stereoisomer, mixture of stereoisomers, or deuterated analog thereof, $R^1$ is $C_{3-6}$ cycloalkyl substituted with one or more —C(O)—$R^{11}$; wherein said $C_{3-6}$ cycloalkyl is optionally substituted with $Z^1$; wherein $R^{11}$ at each occurrence is independently $C_{1-9}$ alkyl, $C_{2-6}$ alkenyl, $C_{2-6}$ alkynyl, $C_{3-15}$ cycloalkyl, aryl, heterocyclyl, or heteroaryl, wherein each $C_{1-9}$ alkyl is optionally substituted with —$NO_2$, —$N_3$, —CN, $C_{2-6}$ alkenyl, $C_{2-6}$ alkynyl, $C_{3-15}$ cycloalkyl, $C_{4-8}$ haloalkyl, aryl, heteroaryl, heterocyclyl, —O—$R^{12}$, —C(O)—$R^{12}$, —C(O)O—$R^{12}$, —C(O)—N($R^{12}$)($R^{12}$), —N($R^{12}$)($R^{12}$), —N($R^{12}$)$_2$($R^{12}$)$^+$, —N($R^{12}$)C(O)—$R^{12}$, —N($R^{12}$)C(O)O—$R^{12}$, —N($R^{12}$)C(O)N($R^{12}$)($R^{12}$), —N($R^{12}$)S(O)$_2$($R^{12}$), —N$R^{12}$S(O)$_2$N($R^{12}$)($R^{12}$), —N$R^{12}$S(O)$_2$O($R^{12}$), —OC(O)$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2R^{12}$ or —S(O)$_2$N($R^{12}$)($R^{12}$); and wherein each said $C_{2-6}$ alkenyl, $C_{2-6}$ alkynyl, $C_{3-15}$ cycloalkyl, aryl, heterocyclyl, or heteroaryl is optionally substituted with $Z^{1a}$;

In another embodiment, or a pharmaceutically acceptable salt, stereoisomer, mixture of stereoisomers, or deuterated analog thereof, $R^1$ is $C_{3-6}$ cycloalkyl substituted with one or more oxo, $C_{5-6}$ alkyl, $C_{2-6}$ alkenyl, $C_{2-6}$ alkynyl, $C_{3-15}$ cycloalkyl, aryl, heteroaryl, heterocyclyl, —C(O)O—$R^{12}$, —C(O)—N($R^9$)($R^9$), —C(O)N(H)($C_{4-9}$ alkyl), —C(O)N(H)($C_{3-10}$ cycloalkyl), —C(O)N(H)(heterocyclyl), —C(O)N(H)(aryl), —C(O)N(H)(heteroaryl)-N($R^{12}$)($R^{12}$), —N($R^{12}$)$_2$($R^{12}$)$^+$, —N($R^{12}$)C(O)—$R^{12}$, —N($R^{12}$)C(O)O—$R^{12}$, —N($R^{12}$)C(O)N($R^{12}$)($R^{12}$), —N($R^{12}$)S(O)$_2$($R^{12}$), —N$R^{12}$S(O)$_2$N($R^{12}$)($R^{12}$), —N$R^{12}$S(O)$_2$O($R^{12}$), —OC(O)$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2R^{12}$ or —S(O)$_2$N($R^{12}$)($R^{12}$); wherein said $C_{5-6}$ alkyl, $C_{2-6}$ alkenyl, $C_{2-6}$ alkynyl, $C_{3-15}$ cycloalkyl, aryl, heteroaryl, heterocyclyl, —C(O)N(H)($C_{4-9}$ alkyl), —C(O)N(H)($C_{3-10}$ cycloalkyl), —C(O)N(H)(heterocyclyl), —C(O)N(H)(aryl), or —C(O)N(H)(heteroaryl) is optionally substituted with $Z^{1a}$; and wherein said $C_{3-6}$ cycloalkyl is optionally substituted with $Z^1$; wherein when $C_{3-6}$ cycloalkyl is bicyclo[1.1.1]pentanyl; then said bicyclo[1.1.1]pentanyl is substituted with one or more oxo, —$NO_2$, —$N_3$, $C_{5-9}$ alkyl, $C_{2-6}$ alkenyl, $C_{7-15}$ cycloalkyl, $C_{5-8}$ haloalkyl, aryl, pyrazolyl, —O—$R^{16}$, —C(O)$R^{11}$, —C(O)O—$R^{12}$, —C(O)N($R^9$)($R^9$), —C(O)N(H)($C_4$ alkyl), —C(O)N(H)($R^{16}$), —N($R^{12}$)($R^{12}$), —N($R^{12}$)$_2$($R^{12}$)$^+$, —N($R^{12}$)—C(O)$R^{12}$, —N($R^{12}$)C(O)O($R^{12}$), —N($R^{12}$)C(O)N($R^{12}$)($R^{12}$), —N($R^{12}$)S(O)$_2$($R^{12}$), —N($R^{12}$)S(O)$_2$—N($R^{12}$)($R^{12}$), —N($R^{12}$)S(O)$_2$O($R^{12}$), —OC(O)$R^{12}$, —OC(O)OR$^{12}$, —OC(O)—N($R^{12}$)($R^{12}$), —Si($R^{12}$)$_3$, —S—$R^{12}$, —S(O)$R^{12}$, —S(O)(NH)$R^{12}$, or —S(O)$_2$N($R^{12}$)($R^{12}$).

In another embodiment, or a pharmaceutically acceptable salt, stereoisomer, mixture of stereoisomers, or deuterated analog thereof, $R^1$ is

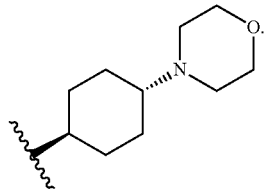 [SMILES: *[C@H]1CC[C@H](N2CCOCC2)CC1]

In another embodiment, or a pharmaceutically acceptable salt, stereoisomer, mixture of stereoisomers, or deuterated analog thereof, $R^1$ is $C_{3-6}$ cycloalkyl substituted with $C_4$ alkyl, wherein said $C_4$ alkyl is optionally substituted with halo, —$NO_2$, —CN, —$N_3$, $C_{2-6}$ alkenyl, $C_{2-6}$ alkynyl, $C_{3-15}$ cycloalkyl, aryl, heteroaryl, heterocyclyl, —O—$R^9$, —C(O)—$R^{12}$, —C(O)O—$R^{12}$, —C(O)—N($R^{12}$)($R^{12}$), —N($R^{12}$)($R^{12}$), —N($R^{12}$)$_2$($R^{12}$)$^+$, —N($R^{12}$)C(O)—$R^{12}$, —N($R^{12}$)C(O)O—$R^{12}$, —N($R^{12}$)C(O)N($R^{12}$)($R^{12}$), —N($R^{12}$)S(O)$_2$($R^{12}$), —N$R^{12}$S(O)$_2$N($R^{12}$)($R^{12}$), —N$R^{12}$S(O)$_2$O($R^{12}$), —OC(O)$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2R^{12}$ or —S(O)$_2$N($R^{12}$)($R^{12}$);

wherein said $C_{2-6}$ alkenyl, $C_{2-6}$ alkynyl, $C_{3-15}$ cycloalkyl, aryl, heteroaryl, or heterocyclyl is optionally substituted with $Z^{1a}$; and wherein said $C_{3-6}$ cycloalkyl is optionally substituted with $Z^1$;

wherein when said $C_{3-6}$ cycloalkyl is bicyclo[0.1.1.1]pentanyl substituted with $C_4$ alkyl then said $C_4$ alkyl is further substituted with oxo, —$NO_2$, —$N_3$, $C_{5-9}$ alkyl, $C_{2-6}$ alkenyl, $C_{2-6}$ alkynyl, $C_{7-15}$ cycloalkyl, $C_{5-8}$ haloalkyl, aryl, heteroaryl, —O—$R^9$, —C(O)$R^{12}$, —C(O)O—$R^{12}$, —C(O)N($R^{12}$)($R^{12}$), —N($R^{12}$)($R^{12}$), —N($R^{12}$)$_2$($R^{12}$)$^+$, —N($R^{12}$)—C(O)$R^{12}$, —N($R^{12}$)C(O)O($R^{12}$), —N($R^{12}$)C(O)N($R^{12}$)($R^{12}$), —N($R^{12}$)S(O)$_2$($R^{12}$), —N($R^{12}$)S(O)$_2$—N($R^{12}$)($R^{12}$), —N($R^{12}$)S(O)$_2$O($R^{12}$), —OC(O)$R^{12}$, —OC(O)OR$^{12}$, —OC(O)—N($R^{12}$)($R^{12}$), —Si($R^{12}$)$_3$, —S—$R^{12}$, —S(O)$R^{12}$, —S(O)(NH)$R^{12}$, or —S(O)$_2$N($R^{12}$)($R^{12}$).

In another embodiment, or a pharmaceutically acceptable salt, stereoisomer, mixture of stereoisomers, or deuterated analog thereof, $R^1$ is $C_{3-6}$ cycloalkyl optionally substituted with $Z^1$; and wherein said $C_{3-6}$ cycloalkyl is substituted with four or more substituents selected from the group consisting of F, —OH, —Cl, —CN, $C_{1-3}$ alkyl, $C_{1-3}$ fluoroalkyl, $C_{1-4}$ hydroxyalkyl, $C_{1-4}$ alkoxy, —C(O)$NH_2$, —C(O)NH($C_{1-3}$ alkyl); and —C(O)($C_{1-3}$ fluoroalkyl).

In another embodiment, or a pharmaceutically acceptable salt, stereoisomer, mixture of stereoisomers, or deuterated analog thereof, $R^1$ is $C_{3-6}$ cycloalkyl substituted with $C_{1-3}$ fluoroalkyl, or —C(O)($C_{1-3}$ fluoroalkyl) wherein said $C_{3-6}$ cycloalkyl is also optionally substituted with $Z^1$; wherein said $C_{1-3}$ fluoroalkyl or —C(O)($C_{1-3}$ fluoroalkyl) is further substituted with at least one oxo, —Cl, —$NO_2$, —CN, —$N_3$, $C_{3-9}$ alkyl, $C_{2-6}$ alkenyl, $C_{2-6}$ alkynyl, $C_{3-15}$ cycloalkyl, $C_{3-8}$ haloalkyl, aryl, heteroaryl, heterocyclyl, —O—$R^{12}$, —C(O)$R^{12}$, —C(O)O—$R^{12}$, —C(O)N($R^{12}$)($R^{12}$), —N($R^{12}$)($R^{12}$), —N($R^{12}$)$_2$($R^{12}$)$^+$, —N($R^{12}$)—C(O)$R^{12}$, —N($R^{12}$)C(O)O($R^{12}$), —N($R^{12}$)C(O)N($R^{12}$)($R^{12}$), —N($R^{12}$)S(O)$_2$($R^{12}$), —N(R$^{12}$)S(O)$_2$—N(R$^{12}$)(R$^{12}$), —N(R$^{12}$)S(O)$_2$O(R$^{12}$), —OC(O)R$^{12}$, —OC(O)OR$^{12}$, —OC(O)—N(R$^{12}$)(R$^{12}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{12}$)(R$^{12}$); and wherein said C$_{3-9}$ alkyl, C$_{2-6}$ alkenyl, C$_{2-6}$ alkynyl, C$_{3-15}$ cycloalkyl, C$_{3-8}$ haloalkyl, aryl, heteroaryl, heterocyclyl is optionally substituted with Z$^{1b}$.

In another embodiment, or a pharmaceutically acceptable salt, stereoisomer, mixture of stereoisomers, or deuterated analog thereof, R$^1$ is C$_{3-6}$ cycloalkyl substituted with at least one C$_{1-3}$ alkyl or C$_{1-4}$ hydroxyalkyl wherein said C$_{3-6}$ cycloalkyl is optionally substituted with Z$^1$;

wherein said C$_{1-3}$ alkyl or C$_{1-4}$ hydroxyalkyl is further substituted with oxo, chloro, —NO$_2$, —CN, —N$_3$, C$_{4-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O—R$^9$, —C(O)R$^{12}$, —C(O)O—R$^{12}$, —C(O)N(R$^{12}$)(R$^{12}$), —N(R$^{12}$)(R$^{12}$), —N(R$^{12}$)$_2$(R$^{12}$)$^+$, —N(R$^{12}$)—C(O)R$^{12}$, —N(R$^{12}$)C(O)O(R$^{12}$), —N(R$^{12}$)C(O)N(R$^{12}$)(R$^{12}$),—N(R$^{12}$)S(O)$_2$(R$^{12}$), —N(R$^{12}$)S(O)$_2$—N(R$^{12}$)(R$^{12}$), —N(R$^{12}$)S(O)$_2$O(R$^{12}$), —OC(O)R$^{12}$, —OC(O)OR$^{12}$, —OC(O)—N(R$^{12}$)(R$^{12}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{12}$)(R$^{12}$); and wherein said C$_{4-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl is optionally substituted with Z$^b$.

In another embodiment, or a pharmaceutically acceptable salt, stereoisomer, mixture of stereoisomers, or deuterated analog thereof, R$^1$ is C$_{3-6}$ cycloalkyl substituted with at least one C$_{1-4}$ alkoxy or C(O)NH(C$_{1-3}$ alkyl); wherein said C$_{3-6}$ cycloalkyl is optionally substituted with Z$^1$ and wherein said C$_{1-4}$ alkoxy or C(O)NH(C$_{1-3}$ alkyl) is further substituted with oxo, halo, —NO$_2$, —CN, —N$_3$, C$_{4-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O—R$^{12}$, —C(O)R$^{12}$, —C(O)O—R$^{12}$, —C(O)N(R$^{12}$)(R$^{12}$), —N(R$^{12}$)(R$^{12}$), —N(R$^{12}$)$_2$(R$^{12}$)$^+$, —N(R$^{12}$)—C(O)R$^{12}$, —N(R$^{12}$)C(O)O(R$^{12}$), —N(R$^{12}$)C(O)N(R$^{12}$)(R$^{12}$), —N(R$^{12}$)S(O)$_2$(R$^{12}$), —N(R$^{12}$)S(O)$_2$—N(R$^{12}$)(R$^{12}$), —N(R$^{12}$)S(O)$_2$O(R$^{12}$), —OC(O)R$^{12}$, —OC(O)OR$^{12}$, —OC(O)—N(R$^{12}$)(R$^{12}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{12}$)(R$^{12}$); wherein said C$_{4-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl is optionally substituted with Z$^{1b}$.

In another embodiment, or a pharmaceutically acceptable salt, stereoisomer, mixture of stereoisomers, or deuterated analog thereof, R$^1$ is 5-10 membered heteroaryl optionally substituted with Z$^1$.

In another embodiment, or a pharmaceutically acceptable salt, stereoisomer, mixture of stereoisomers, or deuterated analog thereof, R$^1$ is 5-10 membered heteroaryl optionally substituted with Z$^1$, wherein when said 5-10 membered heteroaryl is furanyl, pyranyl, pyrraolyl, imidazolyl, pyrazolyl, triazoyl, pyridinyl, pyrimidinyl, pyridazinyl, pyrazinyl, thiaphenyl, oxazoyl, thiazoyl, said 5-10 membered heteroaryl is optionally substituted with a 5-12 membered bicyclic ring or a 5-12 membered hetero bicyclic ring, wherein the bicyclic ring and the hetero bicyclic ring may be fused, spiro or bridged.

In another embodiment, or a pharmaceutically acceptable salt, stereoisomer, mixture of stereoisomers, or deuterated analog thereof, R$^1$ is

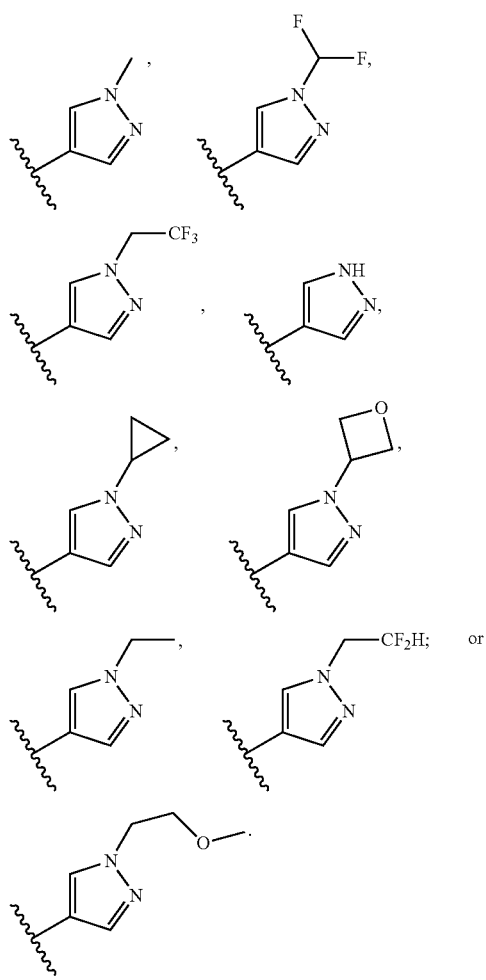

In another embodiment, or a pharmaceutically acceptable salt, stereoisomer, mixture of stereoisomers, or deuterated analog thereof, R$^1$ is imidazolyl, triazolyl, oxazolyl, isoxazolyl, pyridinyl, thiadiazole, oxadiazole, pyrimidinyl, pyridizinyl, pyrazinyl, isothiazolyl, tetrazolyl, thiophenyl, furanyl, triazinyl, or 8-10 membered heteroaryl optionally substituted with Z$^1$.

In another embodiment, or a pharmaceutically acceptable salt, stereoisomer, mixture of stereoisomers, or deuterated analog thereof, R$^1$ is

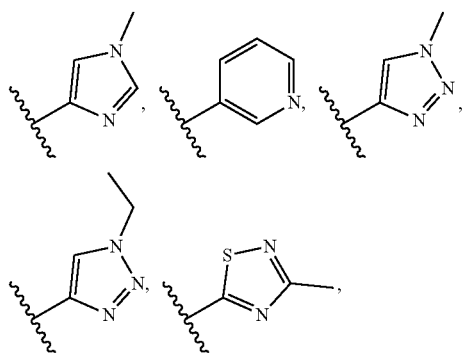

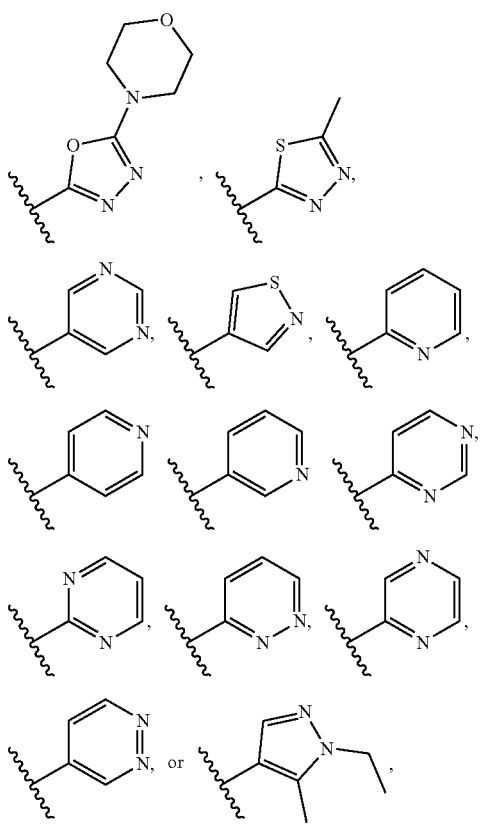

In another embodiment, or a pharmaceutically acceptable salt, stereoisomer, mixture of stereoisomers, or deuterated analog thereof, R¹ is

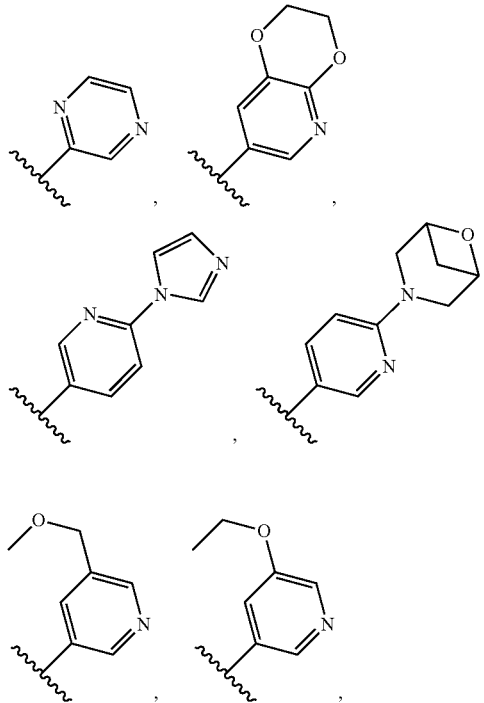

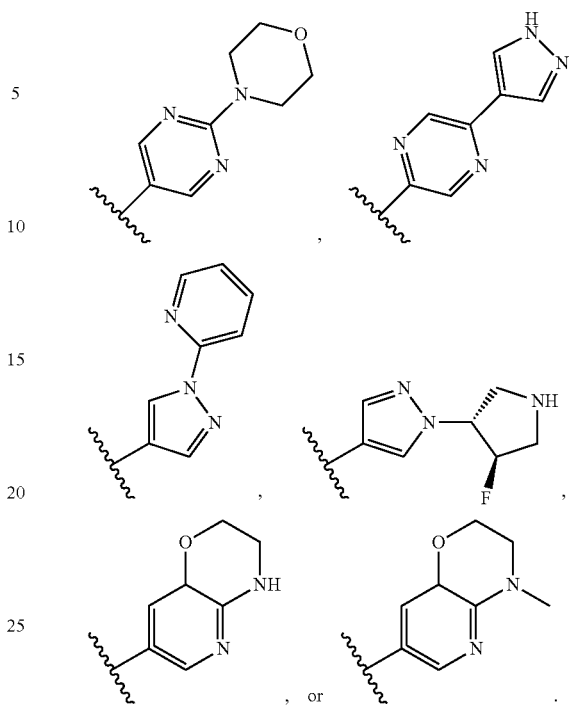

In another embodiment, or a pharmaceutically acceptable salt, stereoisomer, mixture of stereoisomers, or deuterated analog thereof, R¹ is a 6 membered heteroaryl optionally substituted with Z¹.

In another embodiment, or a pharmaceutically acceptable salt, stereoisomer, mixture of stereoisomers, or deuterated analog thereof, R¹ is pyridine.

In another embodiment, or a pharmaceutically acceptable salt, stereoisomer, mixture of stereoisomers, or deuterated analog thereof, R¹ is a 4-7 membered monocyclic heterocyclyl optionally substituted with Z¹.

In another embodiment, or a pharmaceutically acceptable salt, stereoisomer, mixture of stereoisomers, or deuterated analog thereof, R¹ is

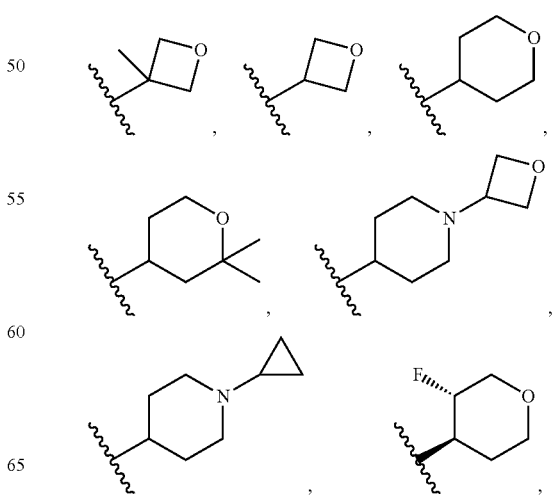

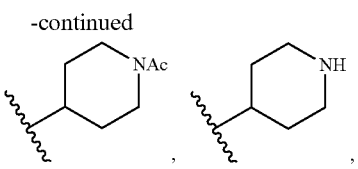

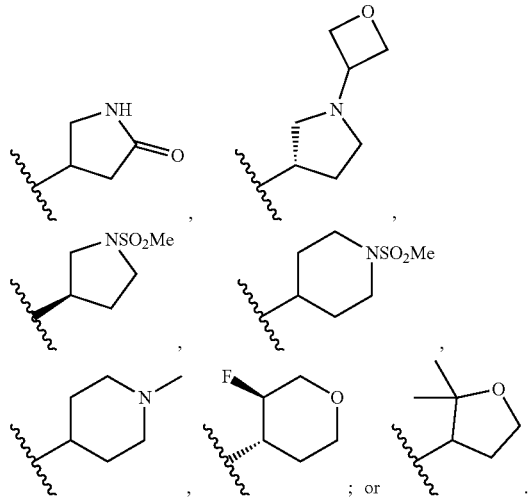

In another embodiment, or a pharmaceutically acceptable salt, stereoisomer, mixture of stereoisomers, or deuterated analog thereof, $R^1$ is azetidinyl, morpholinyl, thiomorpholinyl, 4-7 membered sultam, 4-7 membered cyclic carbamate, 4-7 membered cyclic carbonate, or 4-7 membered cyclic sulfide optionally substituted with $Z^1$.

In another embodiment, or a pharmaceutically acceptable salt, stereoisomer, mixture of stereoisomers, or deuterated analog thereof, $R^1$ is

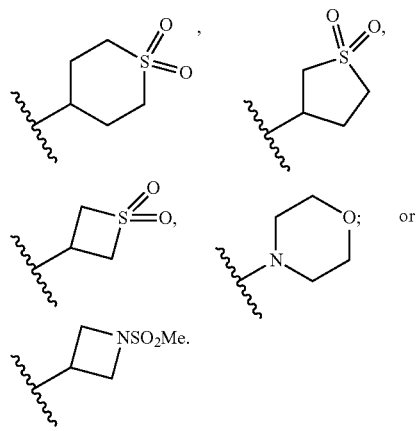

In another embodiment, or a pharmaceutically acceptable salt, stereoisomer, mixture of stereoisomers, or deuterated analog thereof, $R^1$ is 6-12 membered bicyclic heterocyclyl optionally substituted with $Z^1$; wherein when said 6-12 membered bicyclic heterocyclyl is 4,5,6,7-tetrahydropyrazolo[1,5-a]pyrazinyl then said 6-12 membered bicyclic heterocyclyl is substituted with at least one oxo, $C_{3-6}$ cycloalkyl, or $C(O)(C_{1-5}$ alkyl).

In another embodiment, or a pharmaceutically acceptable salt, stereoisomer, mixture of stereoisomers, or deuterated analog thereof, $R^1$ is 6-12 membered bicyclic optionally substituted with $Z^1$; wherein when said 6-12 membered bicyclic is bicyclo[2.2.2] octane, then said 6-12 membered bicyclic is substituted with $C_{1-3}$ alkyl, $C_{2-6}$ alkenyl, $C_{2-6}$ alkynl, 3-6 membered cyclo alkyl, 3-6 membered heterocyclyl, 5-6 membered aryl, 5-6 membered heteroaryl, where the $C_{1-3}$ alkyl, $C_{2-6}$ alkenyl, $C_{2-6}$ alkynl, 3-6 membered cyclo alkyl, 3-6 membered heterocyclyl, 5-6 membered aryl, 5-6 membered heteroaryl groups can further be substituted with one or more $Z^{1a}$ group(s).

In another embodiment, or a pharmaceutically acceptable salt, stereoisomer, mixture of stereoisomers, or deuterated analog thereof, $R^1$ is 6-12 membered bicyclic heterocyclyl optionally substituted with $Z^1$; wherein when said 6-12 membered bicyclic heterocyclyl is 2-oxabicyclo[2.2.2]octane, then said 6-12 membered bicyclic heterocyclyl is substituted with $C_{1-3}$ alkyl, $C_{2-6}$ alkenyl, $C_{2-6}$ alkynl, 3-6 membered cyclo alkyl, 3-6 membered heterocyclyl, 5-6 membered aryl, 5-6 membered heteroaryl, where the $C_{1-3}$ alkyl, $C_{2-6}$ alkenyl, $C_{2-6}$ alkynl, 3-6 membered cyclo alkyl, 3-6 membered heterocyclyl, 5-6 membered aryl, 5-6 membered heteroaryl groups can further be substituted with one or more $Z^{1a}$ group(s).

In another embodiment, or a pharmaceutically acceptable salt, stereoisomer, mixture of stereoisomers, or deuterated analog thereof, $R^1$ is

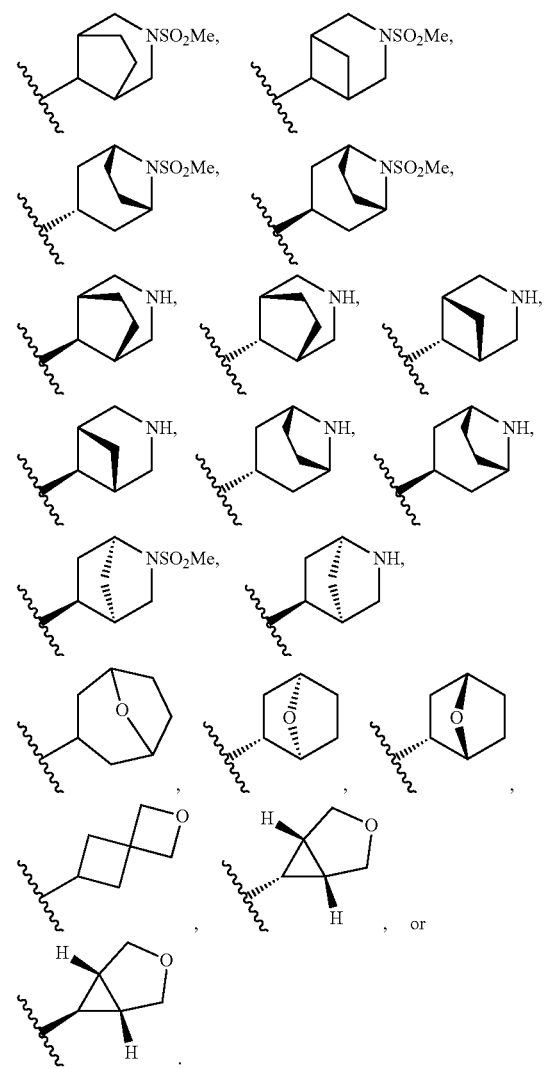

In another embodiment, or a pharmaceutically acceptable salt, stereoisomer, mixture of stereoisomers, or deuterated analog thereof, $R^1$ is

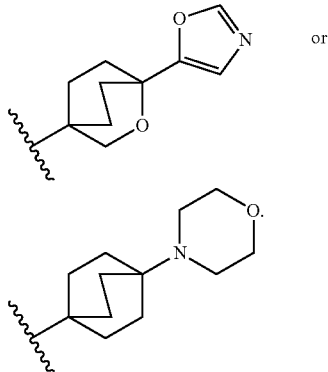

or

In another embodiment, or a pharmaceutically acceptable salt, stereoisomer, mixture of stereoisomers, or deuterated analog thereof, $R^1$ is oxetanyl, tetrahydrofuranyl, tetrahydropyranyl, pyrrolidinyl, piperidinyl, pyrazolyl, or thiazolyl; wherein said oxetanyl, tetrahydrofuranyl, tetrahydropyranyl, pyrrolidinyl, piperidinyl, pyrazolyl or thiazolyl, is substituted with one or more substituents selected from —Cl, oxo, —CN, $C_{5-9}$ alkyl, $C_{2-6}$ alkenyl, $C_{2-6}$ alkynyl, $C_{7-10}$ cycloalkyl, aryl, pyridinyl, pyridizinyl, 5-10 membered bicyclic heteroaryl, 5-membered heteroaryl, nitrogen or sulfur containing monocyclic heterocyclyl, bicyclic heterocyclyl, —O—$R^9$, —C(O)—$R^{11}$, —C(O)O—$R^{12}$, —C(O)—N($R^{12}$)($R^{12}$), —N($R^{12}$)($R^{12}$), —N($R^{12}$)$_2$($R^{12}$)$^+$, —N($R^{12}$)C(O)—$R^{12}$, —N($R^{12}$)C(O)O—$R^{12}$, —N($R^{12}$)C(O)N($R^{12}$)($R^{12}$), —N($R^{12}$)S(O)$_2$($R^{12}$), —N$R^{12}$S(O)$_2$N($R^{12}$)($R^{12}$), —N$R^{12}$S(O)$_2$O($R^{12}$), —OC(O)$R^{12}$, —OC(O)—N($R^{12}$)($R^{12}$), —Si($R^{12}$)$_3$, —S—$R^{12}$, —S(O)$R^{12}$, —S(O)(NH)$R^{12}$, or —S(O)$_2$N($R^{12}$)($R^{12}$); wherein said $C_{5-9}$ alkyl, $C_{2-6}$ alkenyl, $C_{2-6}$ alkynyl, $C_{7-10}$ cycloalkyl, aryl, pyridinyl, pyridizinyl, 5-10 membered bicyclic heteroaryl, 5-membered heteroaryl, nitrogen or sulfur containing monocyclic heterocyclyl or bicyclic heterocyclyl is optionally substituted with $Z^{1a}$; wherein said oxetanyl, tetrahydrofuranyl, tetrahydropyranyl, pyrrolidinyl, piperidinyl, pyrazolyl, thiazolyl, is optionally substituted with $Z^1$.

In another embodiment, or a pharmaceutically acceptable salt, stereoisomer, mixture of stereoisomers, or deuterated analog thereof, $R^1$ is oxetanyl, tetrahydrofuranyl, tetrahydropyranyl, pyrrolidinyl, piperidinyl, pyrazolyl, or thiazolyl; wherein said oxetanyl, tetrahydrofuranyl, tetrahydropyranyl, pyrrolidinyl, piperidinyl, pyrazolyl, or thiazolyl, is optionally substituted with $Z^1$;
wherein said oxetanyl, tetrahydrofuranyl, tetrahydropyranyl, pyrrolidinyl, piperidinyl, pyrazolyl, thiazolyl, is substituted with 3 or more substituents selected from F, —OH, $C_{1-4}$ alkyl, $C_{1-3}$ hydroxyalkyl, $C_{1-4}$ fluoroalkyl, —(CH$_2$)$_{1-3}$O($C_{1-3}$ alkyl), —C(O)($C_{1-3}$ fluoroalkyl), —S(O)$_2$($C_{1-3}$ alkyl), $C_{3-6}$ cycloalkyl, $C_{3-6}$ fluorocycloalkyl, oxetanyl, tetrahydrofuranyl, tetrahydropyranyl, pyrimidinyl, fluoropyrimidinyl, or methoxyprimidinyl.

In another embodiment, or a pharmaceutically acceptable salt, stereoisomer, mixture of stereoisomers, or deuterated analog thereof, $R^1$ is pyrrolidinyl, piperidinyl, pyrazolyl or thiazolyl; wherein said pyrrolidinyl, piperidinyl, pyrazolyl or thiazolyl is optionally substituted with $Z^1$; wherein said pyrrolidinyl, piperidinyl, pyrazolyl or thiazolyl is substituted with one or more substituents independently selected from —(CH$_2$)$_{1-3}$O($C_{1-3}$ alkyl), —S(O)$_2$($C_{1-3}$ alkyl), oxetanyl, tetrahydrofuranyl, tetrahydropyranyl, or CH$_2$($C_{3-6}$ cycloalkyl); and wherein said —(CH$_2$)$_{1-3}$O($C_{1-3}$ alkyl), —S(O)$_2$($C_{1-3}$ alkyl), oxetanyl, tetrahydrofuranyl, tetrahydropyranyl or CH$_2$($C_{3-6}$ cycloalkyl) are independently substituted with one or more oxo, halo, —NO$_2$, —CN, —N$_3$, $C_{3-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^{12}$, —C(O)$R^{12}$, —C(O)O—$R^{12}$, —C(O)N($R^{12}$)($R^{12}$), —N($R^{12}$)($R^{12}$), —N($R^{12}$)$_2$($R^{12}$)$^+$, —N($R^{12}$)—C(O)$R^{12}$, —N($R^{12}$)C(O)O($R^{12}$), —N($R^{12}$)C(O)N($R^{12}$)($R^{12}$), —N($R^{12}$)S(O)$_2$($R^{12}$), —N($R^{12}$)S(O)$_2$—N($R^{12}$)($R^{12}$), —N($R^{12}$)S(O)$_2$O($R^{12}$), —OC(O)$R^{12}$, —OC(O)O$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2$$R^{12}$ or —S(O)$_2$N($R^{12}$)($R^{12}$);
wherein said $C_{3-9}$ alkyl, $C_{2-6}$ alkenyl, $C_{2-6}$ alkynyl, $C_{3-15}$ cycloalkyl, $C_{1-8}$ haloalkyl, aryl, heteroaryl, or heterocyclyl is optionally substituted with $Z^{1b}$.

In another embodiment, or a pharmaceutically acceptable salt, stereoisomer, mixture of stereoisomers, or deuterated analog thereof, $R^1$ is oxetanyl, tetrahydrofuranyl, tetrahydropyranyl, pyrrolidinyl, piperidinyl, pyrazolyl, or thiazolyl; wherein said oxetanyl, tetrahydrofuranyl, tetrahydropyranyl, pyrrolidinyl, piperidinyl, pyrazolyl, or thiazolyl is optionally substituted with a —F or —OH and is substituted with one or more substituents independently selected from $C_{1-4}$ alkyl or $C_{1-3}$ hydroxyalkyl;
wherein said $C_{1-4}$ alkyl or $C_{1-3}$ hydroxyalkyl is substituted with one or more oxo, —Cl, —NO$_2$, —CN, —N$_3$, $C_{4-9}$ alkyl, $C_{2-6}$ alkenyl, $C_{2-6}$ alkynyl, $C_{7-15}$ cycloalkyl, $C_{1-8}$ haloalkyl, aryl, heteroaryl, heterocyclyl, —O—$R^{16}$, —C(O)$R^{12}$, —C(O)O—$R^{12}$, —C(O)N($R^{12}$)($R^{12}$), —N($R^{12}$)($R^{12}$), —N($R^{12}$)$_2$($R^{12}$)$^+$, —N($R^{12}$)—C(O)$R^{12}$, —N($R^{12}$)C(O)O($R^{12}$), —N($R^{12}$)C(O)N($R^{12}$)($R^{12}$), —N($R^{12}$)S(O)$_2$($R^{12}$), —N($R^{12}$)S(O)$_2$—N($R^{12}$)($R^{12}$), —N($R^{12}$)S(O)$_2$O($R^{12}$), —OC(O)$R^{12}$, —OC(O)O$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2$$R^{12}$ or —S(O)$_2$N($R^{12}$)($R^{12}$); and
wherein any alkyl, hydroxyalkyl, alkenyl, alkynyl, cycloalkyl, aryl, heteroaryl or heterocyclyl is optionally substituted with $Z^{1b}$.

In another embodiment, or a pharmaceutically acceptable salt, stereoisomer, mixture of stereoisomers, or deuterated analog thereof, wherein:
$R^1$ is oxetanyl, tetrahydrofuranyl, tetrahydropyranyl, pyrrolidinyl, piperidinyl, pyrazolyl, or thiazolyl; wherein said oxetanyl, tetrahydrofuranyl, tetrahydropyranyl, pyrrolidinyl, piperidinyl, pyrazolyl, or thiazolyl is optionally substituted with a —F or —OH and is substituted with one or more substituents independently selected from $C_{1-4}$ fluoroalkyl, —C(O)($C_{1-3}$ fluoroalkyl), $C_{3-6}$ cycloalkyl, $C_{3-6}$ fluorocycloalkyl, and fluoropyrimidinyl;
wherein said $C_{1-4}$ fluoroalkyl, —C(O)($C_{1-3}$ fluoroalkyl), $C_{3-6}$ cycloalkyl, $C_{3-6}$ fluorocycloalkyl or fluoropyrimidyl is substituted with one or more oxo, —Cl, —NO$_2$, —CN, —N$_3$, $C_{4-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^{12}$, —C(O)$R^{12}$, —C(O)O—$R^{12}$, —C(O)N($R^{12}$)($R^{12}$), —N($R^{12}$)($R^{12}$), —N($R^{12}$)$_2$($R^{12}$)$^+$, —N($R^{12}$)—C(O)$R^{12}$, —N($R^{12}$)C(O)O($R^{12}$), —N($R^{12}$)C(O)N($R^{12}$)($R^{12}$), —N($R^{12}$)S(O)$_2$($R^{12}$), —N($R^{12}$)S(O)$_2$—N($R^{12}$)($R^{12}$), —N($R^{12}$)S(O)$_2$O($R^{12}$), —OC(O)$R^{12}$, —OC(O)

OR$^{12}$, —OC(O)—N(R$^{12}$)(R$^{12}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{12}$)(R$^{12}$);

wherein any alkyl, alkenyl, alkynyl, cycloalkyl, aryl, heteroaryl or heterocyclyl is optionally substituted with Z$^{1b}$.

In another embodiment, or a pharmaceutically acceptable salt, stereoisomer, mixture of stereoisomers, or deuterated analog thereof, R$^1$ is C$_{6-10}$ aryl optionally substituted with Z$^1$.

In another embodiment, or a pharmaceutically acceptable salt, stereoisomer, mixture of stereoisomers, or deuterated analog thereof, R$^1$ is

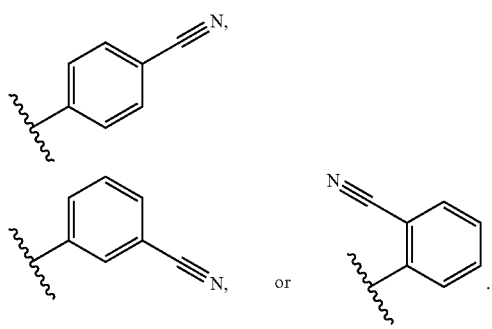

In another embodiment, or a pharmaceutically acceptable salt, stereoisomer, mixture of stereoisomers, or deuterated analog thereof, R$^1$ is

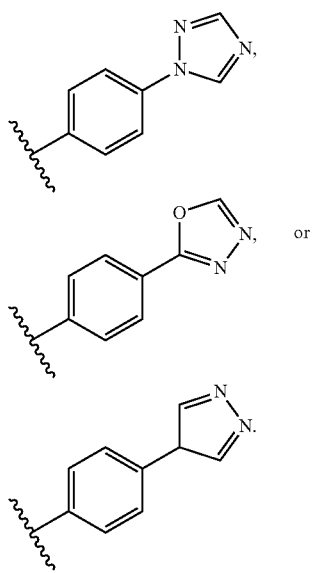

In another embodiment, or a pharmaceutically acceptable salt, stereoisomer, mixture of stereoisomers, or deuterated analog thereof, R$^1$ is C$_{6-10}$ aryl is substituted with one or more C$_{1-6}$ alkyl, C$_{2-6}$ alkenyl, C$_{2-6}$ alkynyl, C$_{3-15}$ cycloalkyl, aryl, heteroaryl, heterocyclyl, —O—R$^9$, —C(O)R$^{11}$, —C(O)O—R$^{12}$, —C(O)NH(C$_{3-6}$ cycloalkyl), —C(O)NH(C$_{4-6}$ alkyl), —C(O)heterocyclyl, N(R$^{12}$)(R$^{12}$), —N(R$^{12}$)$_2$(R$^{12}$)$^+$, —N(R$^{12}$)C(O)—R$^{12}$, —N(R$^{12}$)C(O)O—R$^{12}$, —N(R$^{12}$)C(O)N(R$^{12}$)(R$^{12}$), —N(R$^{12}$)S(O)$_2$(R$^{12}$), —NR$^{12}$S(O)$_2$N(R$^{12}$)(R$^{12}$), —NR$^{12}$S(O)$_2$O(R$^{12}$), —OC(O)R$^{12}$, —OC(O)—N(R$^{12}$)(R$^{12}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{12}$)(R$^{12}$);

wherein said C$_{1-6}$ alkyl, C$_{2-6}$ alkenyl, C$_{2-6}$ alkynyl, C$_{3-15}$ cycloalkyl, aryl, heteroaryl, heterocyclyl, —C(O)NH(C$_{3-6}$ cycloalkyl), —C(O)NH(C$_{4-6}$ alkyl), or —C(O)heterocyclyl is optionally substituted with Z$^{1a}$;

wherein said C$_{6-10}$ aryl is optionally substituted with Z$^1$.

In another embodiment, or a pharmaceutically acceptable salt, stereoisomer, mixture of stereoisomers, or deuterated analog thereof, R$^1$ is C$_{6-10}$ aryl substituted with one or more —C(O)NH(C$_{1-3}$ alkyl) and optionally substituted with Z$^{1a}$;

wherein said —C(O)NH(C$_{1-3}$ alkyl) is substituted with one or more oxo, halo, —NO$_2$, —CN, —N$_3$, C$_{3-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O—R$^{12}$, —C(O)R$^{12}$, —C(O)O—R$^{12}$, —C(O)N(R$^{12}$)(R$^{12}$), —N(R$^{12}$)(R$^{12}$), —N(R$^{12}$)$_2$(R$^{12}$)$^+$, —N(R$^{12}$)—C(O)R$^{12}$, —N(R$^{12}$)C(O)O(R$^{12}$), —N(R$^{12}$)C(O)N(R$^{12}$)(R$^{12}$), —N(R$^{12}$)S(O)$_2$(R$^{12}$), —N(R$^{12}$)S(O)$_2$—N(R$^{12}$)(R$^{12}$), —N(R$^{12}$)S(O)$_2$O(R$^{12}$), —OC(O)R$^{12}$, —OC(O)OR$^{12}$, —OC(O)—N(R$^{12}$)(R$^{12}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{12}$)(R$^{12}$);

wherein said C$_{3-9}$ alkyl, C$_{2-6}$ alkenyl, C$_{2-6}$ alkynyl, C$_{3-15}$ cycloalkyl, C$_{1-8}$ haloalkyl, aryl, heteroaryl, or heterocyclyl is optionally substituted with Z$^{1b}$.

In another embodiment, or a pharmaceutically acceptable salt, stereoisomer, mixture of stereoisomers, or deuterated analog thereof, R$^1$ is C$_{6-10}$ aryl substituted with one or more —C(O)(C$_{1-3}$ fluoroalkyl); wherein said —C(O)(C$_{1-3}$ fluoroalkyl) is substituted with one or more oxo, —Cl, —NO$_2$, —CN, —N$_3$, C$_{3-9}$ alkyl, C$_{2-6}$ alkenyl, C$_{2-6}$ alkynyl, C$_{3-15}$ cycloalkyl, C$_{3-8}$ haloalkyl, aryl, heteroaryl, heterocyclyl, —O—R$^{12}$, —C(O)R$^{12}$, —C(O)O—R$^{12}$, —C(O)N(R$^{12}$)(R$^{12}$), —N(R$^{12}$)(R$^{12}$), —N(R$^{12}$)$_2$(R$^{12}$)$^+$, —N(R$^{12}$)—C(O)R$^{12}$, —N(R$^{12}$)C(O)O(R$^{12}$), —N(R$^{12}$)C(O)N(R$^{12}$)(R$^{12}$), —N(R$^{12}$)S(O)$_2$(R$^{12}$), —N(R$^{12}$)S(O)$_2$—N(R$^{12}$)(R$^{12}$), —N(R$^{12}$)S(O)$_2$O(R$^{12}$), —OC(O)R$^{12}$, —OC(O)OR$^{12}$, —OC(O)—N(R$^{12}$)(R$^{12}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{12}$)(R$^{12}$);

wherein said C$_{3-9}$ alkyl, C$_{2-6}$ alkenyl, C$_{2-6}$ alkynyl, C$_{3-15}$ cycloalkyl, C$_{3-8}$ haloalkyl, aryl, heteroaryl, or heterocyclyl is optionally substituted with Z$^{1b}$; and wherein said C$_{6-10}$ aryl is optionally substituted with Z$^1$.

In another embodiment, or a pharmaceutically acceptable salt, stereoisomer, mixture of stereoisomers, or deuterated analog thereof, R$^1$ is —N(R$^{12}$)(R$^{12}$), —S(O)$_2$R$^{12}$, —S(O)$_2$N(R$^{12}$)(R$^{12}$), or —H.

In another embodiment, or a pharmaceutically acceptable salt, stereoisomer, mixture of stereoisomers, or deuterated analog thereof, R$^1$ is

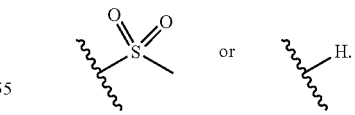

In another embodiment, or a pharmaceutically acceptable salt, stereoisomer, mixture of stereoisomers, or deuterated analog thereof, R$^2$ is C$_{1-10}$ alkyl optionally substituted with Z$^1$.

In another embodiment, or a pharmaceutically acceptable salt, stereoisomer, mixture of stereoisomers, or deuterated analog thereof, R$^2$ is C$_{1-10}$ alkyl.

In another embodiment, or a pharmaceutically acceptable salt, stereoisomer, mixture of stereoisomers, or deuterated analog thereof, R$^2$ is methyl.

In another embodiment, or a pharmaceutically acceptable salt, stereoisomer, mixture of stereoisomers, or deuterated analog thereof, $R^2$ is $C_{7-10}$ alkyl, optionally substituted with $Z^1$.

In another embodiment, or a pharmaceutically acceptable salt, stereoisomer, mixture of stereoisomers, or deuterated analog thereof, $R^2$ is $C_{1-6}$ alkyl substituted with one or more —O($C_{1-2}$ alkyl), —NHC(O)($C_{1-3}$ alkyl), or —S(O)$_2$($C_{1-3}$ alkyl); wherein said —O($C_{1-2}$ alkyl) is substituted with one or more oxo, —Cl, —NO$_2$, —CN, —N$_3$, $C_{2-9}$ alkyl, $C_{2-6}$ alkenyl, $C_{2-6}$ alkynyl, $C_{3-15}$ cycloalkyl, $C_{2-8}$ haloalkyl, aryl, heteroaryl, heterocyclyl, —O—R$^{12}$, —C(O)R$^{12}$, —C(O)O—R$^{12}$, —C(O)N(R$^{12}$)(R$^{12}$), —N(R$^{12}$)(R$^{12}$), —N(R$^{12}$)$_2$(R$^{12}$)$^+$, —N(R$^{12}$)—C(O)R$^{12}$, —N(R$^{12}$)C(O)O(R$^{12}$), —N(R$^{12}$)C(O)N(R$^{12}$)(R$^{12}$), —N(R$^{12}$)S(O)$_2$(R$^{12}$), —N(R$^{12}$)S(O)$_2$—N(R$^{12}$)(R$^{12}$), —N(R$^{12}$)S(O)$_2$O(R$^{12}$), —OC(O)R$^{12}$, —OC(O)OR$^{12}$, —OC(O)—N(R$^{12}$)(R$^{12}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{12}$)(R$^{12}$);

and said —O($C_{1-2}$ alkyl) is optionally substituted with —F; wherein said —NHC(O)($C_{1-3}$ alkyl), or —S(O)$_2$($C_{1-3}$ alkyl) is substituted with one or more oxo, halo, —NO$_2$, —CN, —N$_3$, $C_{3-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—R$^{12}$, —C(O)R$^{12}$, —C(O)O—R$^{12}$, —C(O)N(R$^{12}$)(R$^{12}$), —N(R$^{12}$)(R$^{12}$), —N(R$^{12}$)$_2$(R$^{12}$)$^+$, —N(R$^{12}$)—C(O)R$^{12}$, —N(R$^{12}$)C(O)O(R$^{12}$), —N(R$^{12}$)C(O)N(R$^{12}$)(R$^{12}$), —N(R$^{12}$)S(O)$_2$(R$^{12}$), —N(R$^{12}$)S(O)$_2$—N(R$^{12}$)(R$^{12}$), —N(R$^{12}$)S(O)$_2$O(R$^{12}$), —OC(O)R$^{12}$, —OC(O)OR$^{12}$, —OC(O)—N(R$^{12}$)(R$^{12}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{12}$)(R$^{12}$);

wherein said $C_{1-6}$ alkyl is optionally substituted with $Z^{1a}$; and wherein each said $C_{2-9}$ alkyl, $C_{3-9}$ alkyl, $C_{2-6}$ alkenyl, $C_{2-6}$ alkynyl, $C_{3-15}$ cycloalkyl, $C_{1-8}$ haloalkyl, $C_{2-8}$ haloalkyl, aryl, heteroaryl, or heterocyclyl is optionally substituted with $Z^{1b}$.

In another embodiment, or a pharmaceutically acceptable salt, stereoisomer, mixture of stereoisomers, or deuterated analog thereof, $R^2$ is,

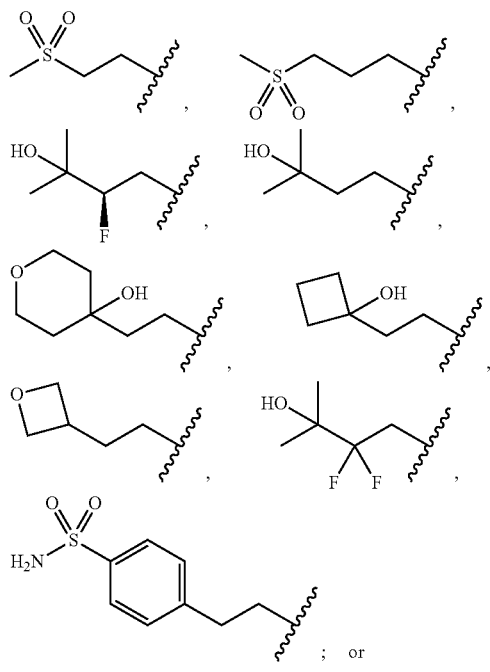

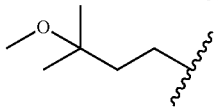

; or

In another embodiment, or a pharmaceutically acceptable salt, stereoisomer, mixture of stereoisomers, or deuterated analog thereof, $R^2$ is $C_{4-6}$ alkyl substituted with one or more substituents selected from —Cl, $C_{2-6}$ alkenyl, $C_{2-6}$ alkynyl, $C_{3-15}$ cycloalkyl, aryl, heteroaryl, monocyclic heterocyclyl, bicyclic heterocyclyl, —O($C_{3-9}$ alkyl), —O($C_{3-10}$ cycloalkyl), —O(heterocyclyl), —O(aryl), —O(heteroaryl), —C(O)—R$^{12}$, —C(O)O—R$^{12}$, —C(O)—N(R$^{12}$)(R$^{12}$), —N(R$^{12}$)(R$^{12}$), —N(R$^{12}$)$_2$(R$^{12}$)$^+$, —N(R$^{12}$)C(O)($C_{4-9}$ alkyl), —N(R$^{12}$)C(O)($C_{3-10}$ cycloalkyl), —N(R$^{12}$)C(O)(heterocyclyl), —N(R$^{12}$)C(O)(aryl), —N(R$^{12}$)C(O)(heteroaryl), —N(R$^{12}$)C(O)O—R$^{12}$, —N(R$^{12}$)C(O)N(R$^{12}$)(R$^{12}$), —N(R$^{12}$)S(O)$_2$(R$^{12}$), —NR$^{12}$S(O)$_2$N(R$^{12}$)(R$^{12}$), —NR$^{12}$S(O)$_2$O(R$^{12}$), —OC(O)R$^{12}$, —OC(O)—N(R$^{12}$)(R$^{12}$), —Si(R$^{12}$)$_3$, —S—R$^{12}$, —S(O)R$^{12}$, —S(O)(NH)R$^{12}$, —S(O)$_2$($C_{4-9}$ alkyl), —S(O)$_2$(aryl), —S(O)$_2$($C_{3-10}$ cycloalkyl), —S(O)$_2$(heterocyclyl), —S(O)$_2$(heteroaryl), or —S(O)$_2$N(R$^{12}$)(R$^{12}$); wherein said $C_{4-6}$ alkyl is also optionally substituted with $Z^1$; and wherein said $C_{2-6}$ alkenyl, $C_{2-6}$ alkynyl, $C_{3-15}$ cycloalkyl, aryl, heteroaryl, monocyclic heterocyclyl, bicyclic heterocyclyl, —O($C_{3-9}$ alkyl), —O($C_{3-10}$ cycloalkyl), —O(heterocyclyl), —O(aryl), —O(heteroaryl), —N(R$^{12}$)C(O)($C_{4-9}$ alkyl), —N(R$^{12}$)C(O)($C_{3-10}$ cycloalkyl), —N(R$^{12}$)C(O)(heterocyclyl), —N(R$^{12}$)C(O)(aryl), —N(R$^{12}$)C(O)(heteroaryl), —S(O)$_2$($C_{4-9}$ alkyl), —S(O)$_2$(aryl), —S(O)$_2$($C_{3-10}$ cycloalkyl), —S(O)$_2$(heterocyclyl), —S(O)$_2$(heteroaryl), —NHC(O)($C_{1-3}$ alkyl), or —S(O)$_2$($C_{1-3}$ alkyl) is optionally substituted with $Z^{1a}$.

In another embodiment, or a pharmaceutically acceptable salt, stereoisomer, mixture of stereoisomers, or deuterated analog thereof, $R^2$ is $C_{4-6}$ alkyl substituted with one or more —O(CH$_2$)$_2$R$^{17}$ or —O(CH$_2$)R$^{17}$; R$^{17}$ at each occurrence is independently $C_{3-15}$ cycloalkyl, aryl, heterocyclyl, heteroaryl, —O—R$^{12}$, —C(O)—R$^{12}$, —C(O)O—R$^{12}$, —C(O)—N(R$^{12}$)(R$^{12}$), —N(R$^{12}$)(R$^{12}$), —N(R$^{12}$)$_2$(R$^{12}$)$^+$, —N(R$^{12}$)C(O)—R$^{12}$, —N(R$^{12}$)C(O)O—R$^{12}$, —N(R$^{12}$)C(O)N(R$^{12}$)(R$^{12}$), —N(R$^{12}$)S(O)$_2$(R$^{12}$), —NR$^{12}$S(O)$_2$N(R$^{12}$)(R$^{12}$), —NR$^{12}$S(O)$_2$O(R$^{12}$), —OC(O)R$^{12}$, —OC(O)—N(R$^{12}$)(R$^{12}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{12}$)(R$^{12}$);

wherein said $C_{3-15}$ cycloalkyl, aryl, heterocyclyl, and heteroaryl optionally is substituted with $Z^{1b}$; and wherein said $C_{4-6}$ alkyl is also optionally substituted with $Z^1$ In another embodiment, or a pharmaceutically acceptable salt, stereoisomer, mixture of stereoisomers, or deuterated analog thereof, $R^2$ is $C_{4-6}$ alkyl substituted with five or more substituents selected from F, hydroxyl, —CN, —OCH$_3$, —OCD$_3$, —NHC(O)($C_{1-3}$ alkyl), —S(O)$_2$($C_{1-3}$ alkyl), or $C_{1-2}$ fluoroalkoxy; and wherein said $C_{4-6}$ alkyl is optionally substituted with $Z^1$.

In another embodiment, or a pharmaceutically acceptable salt, stereoisomer, mixture of stereoisomers, or deuterated analog thereof, $R^2$ is $C_{1-3}$ alkyl substituted with one or more substituents selected from —Cl, $C_{2-6}$ alkenyl, $C_{2-6}$ alkynyl, cyclopropyl, napthyl, bicyclic heterocyclyl, $C_{7-15}$ cycloalkyl, —O(CH$_2$)$_2$R$^{17}$, —O(CH$_2$)R$^{17}$, —O($C_{3-9}$ alkyl), —O($C_{3-10}$ cycloalkyl), —O(heterocyclyl), —O(aryl), —O(heteroaryl), —C(O)($C_{1-9}$ alkyl), —C(O)(cyclopropyl), —C(O)O—R$^{12}$, —C(O)—N(R$^{12}$)(R$^{12}$), —N(R$^{12}$)(R$^{12}$), —N(R$^{12}$)$_2$(R$^{12}$)$^+$, —N(R$^{12}$)C(O)(C$_{4-9}$ alkyl), —N(R$^{12}$)C(O) (C$_{3-10}$ cycloalkyl), —N(R$^{12}$)C(O)(heterocyclyl), —N(R$^{12}$) C(O)(aryl), —N(R$^{12}$)C(O)(heteroaryl), —N(R$^{12}$)C(O)O— R$^{12}$, —N(R$^{12}$)C(O)N(R$^{12}$)(R$^{12}$), —N(R$^{12}$)S(O)$_2$(R$^{12}$), —NR$^{12}$S(O)$_2$N(R$^{12}$)(R$^{12}$), —NR$^{12}$S(O)$_2$O(R$^{12}$), —OC(O) R$^{12}$, —OC(O)—N(R$^{12}$)(R$^{12}$), —Si(R$^{12}$)$_3$, —S—R$^{12}$, —S(O)R$^{12}$, —S(O)(NH)R$^{12}$, —S(O)$_2$(C$_{4-9}$ alkyl), —S(O)$_2$ (aryl), —S(O)$_2$(C$_{3-10}$ cycloalkyl), —S(O)$_2$(heterocyclyl), —S(O)$_2$(heteroaryl), or —S(O)$_2$N(R$^9$)(R$^{12}$);

wherein said C$_{1-3}$ alkyl is also optionally substituted with Z$^1$; and wherein said C$_{2-6}$ alkenyl, C$_{2-6}$ alkynyl, cyclopropyl, napthyl, bicyclic heterocyclyl, C$_{7-15}$ cycloalkyl, —O(C$_{3-9}$ alkyl), —O(C$_{3-10}$ cycloalkyl), —O(heterocyclyl), —O(aryl), —O(heteroaryl), —N(R$^{12}$)C(O)(C$_{4-9}$ alkyl), —N(R$^{12}$)C(O)(C$_{3-10}$ cycloalkyl), —N(R$^{12}$)C(O)(heterocyclyl), —N(R$^{12}$)C(O)(aryl), —N(R$^{12}$)C(O)(heteroaryl), —S(O)$_2$(C$_{4-9}$ alkyl), —S(O)$_2$(aryl), —S(O)$_2$(C$_{3-10}$ cycloalkyl), —S(O)$_2$(heterocyclyl), or —S(O)$_2$(heteroaryl) is optionally substituted with Z$^{1a}$.

In another embodiment, or a pharmaceutically acceptable salt, stereoisomer, mixture of stereoisomers, or deuterated analog thereof, R$^2$ is

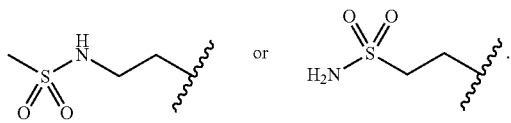

In another embodiment, or a pharmaceutically acceptable salt, stereoisomer, mixture of stereoisomers, or deuterated analog thereof, R$^2$ is C$_{1-3}$ alkyl substituted with one or more substituents selected from azetidinyl, tetrahydrofuranyl, triazolyl, oxazolyl, isoxazolyl, thiadiazole, oxadiazole, pyrimidinyl, pyridizinyl, pyrazinyl, isothiazolyl, tetrazolyl, furanyl, thiomorpholinyl, 4-7 membered sultam, 4-7 membered cyclic carbamate, 4-7 membered cyclic carbonate, 4-7 membered cyclic sulfide, or 8-10 membered heteroaryl; any of which is optionally substituted with Z$^{1a}$; and wherein said C$_{1-3}$ alkyl is also optionally substituted with Z$^1$.

In another embodiment, or a pharmaceutically acceptable salt, stereoisomer, mixture of stereoisomers, or deuterated analog thereof, R$^2$ is

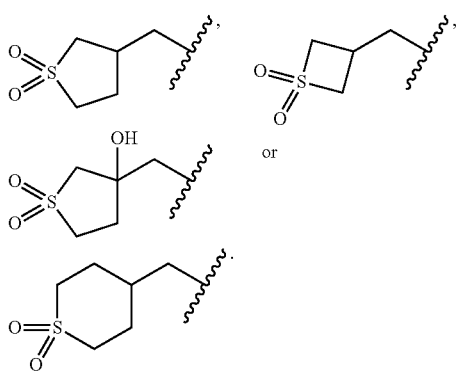

In another embodiment, or a pharmaceutically acceptable salt, stereoisomer, mixture of stereoisomers, or deuterated analog thereof, R$^2$ is C$_{1-3}$ alkyl substituted with one substituent selected from phenyl, oxetanyl, tetrahydropyranyl, morpholinyl, piperidinyl, imidazolyl, pyridinyl, thiophenyl, or C$_{4-6}$ cycloalkyl;

wherein said phenyl, oxetanyl, tetrahydropyranyl, morpholinyl, piperidinyl, imidazolyl, pyridinyl, thiophenyl, or C$_{4-6}$ cycloalkyl is substituted with one or more oxo, —NO$_2$, —N$_3$, —CN, C$_{4-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O(C$_{3-6}$ alkyl), —O(C$_{3-6}$ cycloalkyl), —O(heterocyclyl), —C(O)—R$^{12}$, —C(O)O—R$^{12}$, —C(O)—N(R$^{12}$) (R$^{12}$), —N(R$^{12}$)(R$^{12}$), —N(R$^{12}$)$_2$(R$^{12}$)$^+$, —N(R$^{12}$)C (O)—R$^{12}$, —N(R$^{12}$)C(O)O—R$^{12}$, —N(R$^{12}$)C(O)N(R$^{12}$) (R$^{12}$), —N(R$^{12}$)S(O)$_2$(R$^{12}$), —NR$^{12}$S(O)$_2$N(R$^{12}$)(R$^{12}$), —NR$^{12}$S(O)$_2$O(R$^{12}$), —OC(O)R$^{12}$, —OC(O)—N(R$^{12}$) (R$^{12}$), —Si(R$^{12}$)$_3$, —S—R$^{12}$, —S(O)R$^{12}$, —S(O)(NH) R$^{12}$, —S(O)$_2$R$^{12}$ or —S(O)$_2$N(R$^9$)(R$^{12}$); and wherein any alkyl, alkenyl, alkynyl, cycloalkyl, haloalkyl, aryl, heteroaryl or heterocyclyl is optionally substituted with Z$^{1a}$.

In another embodiment, or a pharmaceutically acceptable salt, stereoisomer, mixture of stereoisomers, or deuterated analog thereof, R$^2$ is C$_{1-3}$ alkyl optionally substituted with Z$^1$ and is substituted with one substituent selected from phenyl, oxetanyl, tetrahydropyranyl, morpholinyl, piperidinyl, imidazolyl, pyridinyl, thiophenyl, or C$_{4-6}$ cycloalkyl; wherein said phenyl, oxetanyl, tetrahydropyranyl, morpholinyl, piperidinyl, imidazolyl, pyridinyl, thiophenyl, or C$_{4-6}$ cycloalkyl is substituted with four or more substituents selected from —F, —Cl, —OH, C$_{1-3}$ alkyl, —O(C$_{1-2}$ alkyl) or —S(O)$_2$NH$_2$.

In another embodiment, or a pharmaceutically acceptable salt, stereoisomer, mixture of stereoisomers, or deuterated analog thereof, R$^2$ is C$_{1-3}$ alkyl substituted with oxo and optionally substituted with one or more substituents selected from halo, azetidinyl, pyrrolidinyl, piperazinyl, tetrahydrofuranyl, thiomorpholinyl, —CN, C$_{1-9}$ alkyl, C$_{2-6}$ alkenyl, C$_{2-6}$ alkynyl, cyclopropyl, C$_{7-15}$ cycloalkyl, C$_{1-8}$ haloalkyl, —O—R$^{12}$, —C(O)—R$^{12}$, —C(O)O—R$^{12}$, —C(O)—N (R$^{12}$)(R$^{12}$), —N(R$^{12}$)(R$^{12}$), —N(R$^{12}$)$_2$(R$^{12}$)$^+$, —N(R$^{12}$)C (O)—R$^{12}$, —N(R$^{12}$)C(O)O—R$^{12}$, —N(R$^{12}$)C(O)N(R$^{12}$) (R$^{12}$), —N(R$^{12}$)S(O)$_2$(R$^{12}$), —NR$^{12}$S(O)$_2$N(R$^{12}$)(R$^{12}$), —NR$^{12}$S(O)$_2$O(R$^{12}$), —OC(O)R$^{12}$, —OC(O)—N(R$^{12}$) (R$^{12}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^9$)(R$^{12}$); and wherein said C$_{1-3}$ alkyl is optionally substituted with Z$^1$;

wherein said, C$_{1-9}$ alkyl, C$_{2-6}$ alkenyl, C$_{2-6}$ alkynyl, cyclopropyl, C$_{7-15}$ cycloalkyl, C$_{1-8}$ haloalkyl, azetidinyl, pyrrolidinyl, piperazinyl, tetrahydrofuranyl, or thiomorpholinyl is optionally substituted with Z$^{1a}$.

In another embodiment, or a pharmaceutically acceptable salt, stereoisomer, mixture of stereoisomers, or deuterated analog thereof, R$^2$ is C$_3$ alkyl substituted with five or more substituents selected from —F, —OH, —OCH$_3$, —CN, —NHC(O)(C$_{1-3}$ alkyl), C$_{1-2}$ fluoroalkoxy, or —S(O)$_2$(C$_{1-3}$ alkyl).

In another embodiment, or a pharmaceutically acceptable salt, stereoisomer, mixture of stereoisomers, or deuterated analog thereof, R$^2$ is C$_{3-10}$ cycloalkyl optionally substituted with Z$^1$.

In another embodiment, or a pharmaceutically acceptable salt, stereoisomer, mixture of stereoisomers, or deuterated analog thereof, R$^2$ is

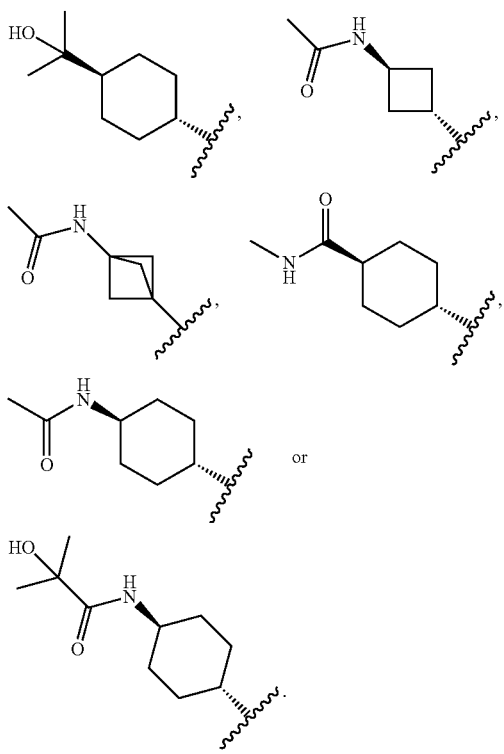

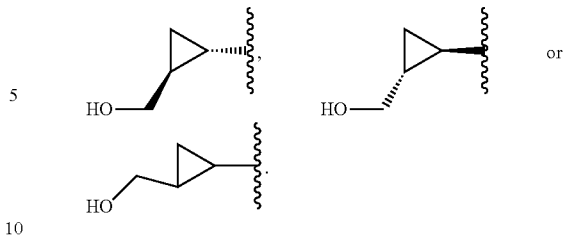

In another embodiment, or a pharmaceutically acceptable salt, stereoisomer, mixture of stereoisomers, or deuterated analog thereof, $R^2$ is

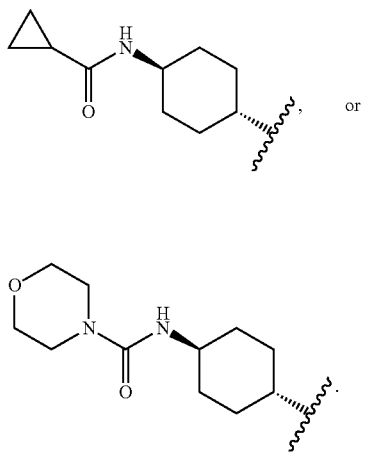

In another embodiment, or a pharmaceutically acceptable salt, stereoisomer, mixture of stereoisomers, or deuterated analog thereof, $R^2$ is cyclopropyl optionally substituted with $Z^1$.

In another embodiment, or a pharmaceutically acceptable salt, stereoisomer, mixture of stereoisomers, or deuterated analog thereof, $R^2$ is $C_{7-10}$ cycloalkyl optionally substituted with $Z^1$.

In another embodiment, or a pharmaceutically acceptable salt, stereoisomer, mixture of stereoisomers, or deuterated analog thereof, $R^2$ is In another embodiment, or a pharmaceutically acceptable salt, stereoisomer, mixture of stereoisomers, or deuterated analog thereof, $R^2$ is $C_{4-6}$ cycloalkyl substituted with one or more substituents selected from -halo, oxo, —CN, $C_{1-4}$ alkyl, $C_{5-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O($C_{4-9}$ alkyl), —O($C_{3-10}$ cycloalkyl), —O(heterocyclyl), —O(aryl), —O(heteroaryl), —N($R^{12}$)C(O)($C_{5-9}$ alkyl), —N($R^{12}$)C(O)($C_{3-10}$ cycloalkyl), —N($R^{12}$)C(O)(heterocyclyl), —N($R^{12}$)C(O)(aryl), —N($R^{12}$)C(O)(heteroaryl), —NH($R^{12}$), —N($R^{12}$)($C_{4-9}$ alkyl), —N($R^{12}$)($C_{3-10}$ cycloalkyl), —N($R^{12}$)(heterocyclyl), —N($R^{12}$)(aryl), —N($R^{12}$)(heteroaryl), —N($R^{12}$)C(O)O($C_{4-9}$ alkyl), —N($R^{12}$)C(O)O($C_{3-10}$ cycloalkyl), —N($R^{12}$)C(O)O(heterocyclyl), —N($R^{12}$)C(O)O(aryl), —N($R^{12}$)C(O)O(heteroaryl), —C(O)N($R^{12}$)($C_{5-9}$ alkyl), —C(O)N($R^{12}$)($C_{7-10}$ cycloalkyl), —C(O)N($R^{12}$)(heterocyclyl), —C(O)N($R^{12}$)(aryl), —C(O)N($R^{12}$)(heteroaryl), —C(O)N($R^9$)($R^9$), —C(O)O—$R^{12}$, —N($R^{12}$)$_2$($R^{12}$)$^+$, —N($R^{12}$)C(O)N($R^{12}$)($R^{12}$), —N($R^{12}$)S(O)$_2$($R^{12}$), —N$R^{12}$S(O)$_2$N($R^{12}$)($R^{12}$), —N($R^{12}$)S(O)$_2$O($R^{12}$), —OC(O)$R^{12}$, —OC(O)—N($R^{12}$)($R^{12}$), —Si($R^{12}$)$_3$, —S—$R^{12}$, —S(O)$R^{12}$, —S(O)$_2$$R^{12}$, —S(O)(NH)$R^{12}$, or —S(O)$_2$N($R^{12}$)($R^{12}$); wherein said $C_{4-6}$ cycloalkyl is also optionally substituted with $Z^1$; wherein said $C_{1-4}$ alkyl is optionally substituted with oxo, halo, —NO$_2$, —CN, —N$_3$, $C_{4-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^{16}$, —O($C_{4-9}$ alkyl), —C(O)$R^{12}$, —C(O)O—$R^{12}$, —C(O)N($R^{12}$)($R^{12}$), —N($R^{12}$)($R^{12}$), —N($R^{12}$)$_2$($R^{12}$)$^+$, —N($R^{12}$)—C(O)$R^{12}$, —N($R^{12}$)C(O)O($R^{12}$), —N($R^{12}$)C(O)N($R^{12}$)($R^{12}$), —N($R^{12}$)S(O)$_2$($R^{12}$), —N($R^{12}$)S(O)$_2$—N($R^{12}$)($R^{12}$), —N($R^{12}$)S(O)$_2$O($R^{12}$), —OC(O)$R^{12}$, —OC(O)O$R^{12}$, —OC(O)—N($R^{12}$)($R^{12}R^{12}$), —Si($R^{12}$)$_3$, —S—$R^{12}$, —S(O)$R^{12}$, —S(O)(NH)$R^{12}$, —S(O)$_2$$R^{12}$ or —S(O)$_2$N($R^{12}$)($R^{12}$); and wherein each said $C_{5-9}$ alkyl, $C_{2-6}$ alkenyl, $C_{2-6}$ alkynyl, $C_{3-15}$ cycloalkyl, $C_{1-8}$ haloalkyl, —O($C_{4-9}$ alkyl), —O($C_{3-10}$ cycloalkyl), —O(heterocyclyl), —O(aryl), —O(heteroaryl), —N($R^{12}$)C(O)($C_{5-9}$ alkyl), —N($R^{12}$)C(O)($C_{3-10}$ cycloalkyl), —N($R^{12}$)C(O)(heterocyclyl), —N($R^{12}$)C(O)(aryl), —N($R^{12}$)C(O)(heteroaryl), —N($R^{12}$)($C_{4-9}$ alkyl), —N($R^{12}$)($C_{3-10}$ cycloalkyl), —N($R^{12}$)(heterocyclyl), —N($R^{12}$)(aryl), —N($R^{12}$)(heteroaryl), —N($R^{12}$)C(O)O($C_{4-9}$ alkyl), —N($R^{12}$)C(O)O($C_{3-10}$ cycloalkyl), —N($R^{12}$)C(O)O(heterocyclyl), —N($R^{12}$)C(O)O(aryl), —N($R^{12}$)C(O)O(heteroaryl), —C(O)N($R^{12}$)($C_{5-9}$ alkyl), —C(O)N($R^{12}$)($C_{7-10}$ cycloalkyl), —C(O)N($R^{12}$)(heterocyclyl), —C(O)N($R^{12}$)(aryl), —C(O)N($R^{12}$)(heteroaryl), aryl, heteroaryl, or heterocyclyl is optionally substituted with $Z^{1a}$.

In another embodiment, or a pharmaceutically acceptable salt, stereoisomer, mixture of stereoisomers, or deuterated analog thereof, $R^2$ is

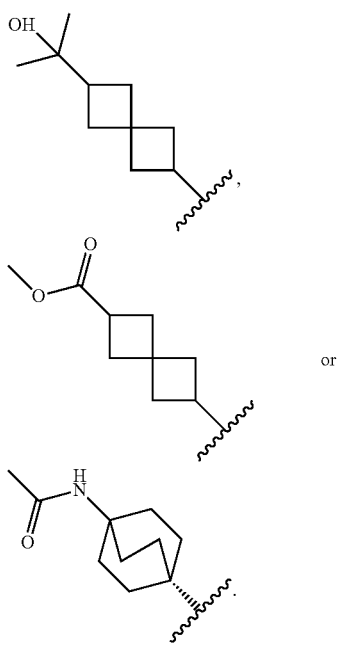

or

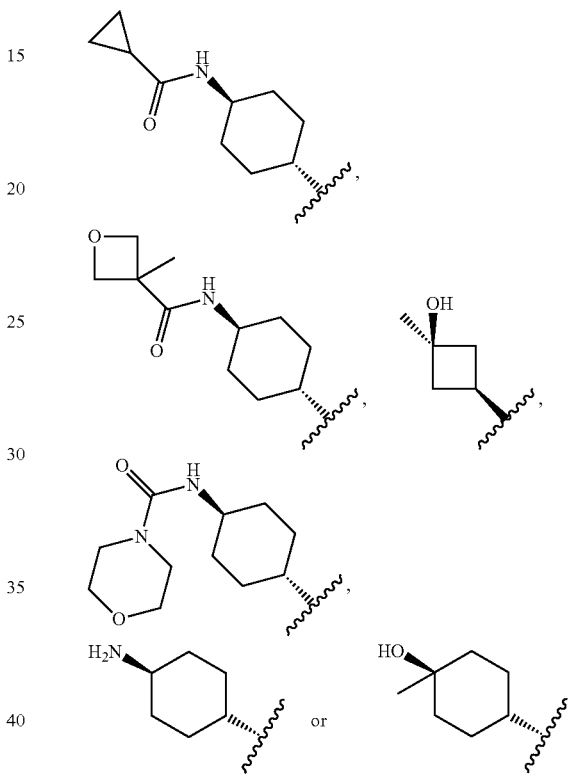

In another embodiment, or a pharmaceutically acceptable salt, stereoisomer, mixture of stereoisomers, or deuterated analog thereof, $R^2$ is $C_{4-6}$ cycloalkyl substituted with one or more substituents selected from $C_{1-4}$ hydroxyalkyl, $C_{1-3}$ alkoxy, —$(CH_2)_{1-3}O(C_{1-3}$ alkyl), —C(O)NH($C_{1-4}$ alkyl), —C(O)NH($C_{3-6}$ cycloalkyl), —N($C_{1-3}$ alkyl)$_2$, —NHC(O)O($C_{1-3}$ alkyl), —NHC(O)($C_{1-4}$ hydroxyalkyl); wherein said $C_{4-6}$ cycloalkyl is optionally substituted with $Z^1$;
wherein said —C(O)NH($C_{3-6}$ cycloalkyl) is substituted with $Z^{1a}$; wherein said $C_{1-4}$ hydroxyalkyl or —NHC(O)($C_{1-4}$ hydroxyalkyl) is substituted with oxo, halo, —NO$_2$, —CN, —N$_3$, $C_{4-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^9$, —C(O)$R^{12}$, —C(O)O—$R^{12}$, —C(O)N($R^{12}$)($R^{12}$), —N($R^{12}$)($R^{12}$), —N($R^{12}$)$_2$($R^{12}$)$^+$, —N($R^{12}$)—C(O)$R^{12}$, —N($R^{12}$)C(O)O($R^{12}$), —N($R^{12}$)C(O)N($R^{12}$)($R^{12}$), —N($R^{12}$)S(O)$_2$($R^{12}$), —N($R^{12}$)S(O)$_2$—N($R^{12}$)($R^{12}$), —N($R^{12}$)S(O)$_2$O($R^{12}$), —OC(O)$R^{12}$, —OC(O)O$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2R^{12}$ or —S(O)$_2$N($R^{12}$)($R^{12}$);
wherein said $C_{1-3}$ alkoxy, —$(CH_2)_{1-3}O(C_{1-3}$ alkyl), —N($C_{1-3}$ alkyl)$_2$, —NHC(O)O($C_{1-3}$ alkyl) is substituted with oxo, halo, —NO$_2$, —CN, —N$_3$, $C_{3-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^{12}$, —C(O)$R^{12}$, —C(O)O—$R^{12}$, —C(O)N($R^{12}$)($R^{12}$), —N($R^{12}$)($R^{12}$), —N($R^{12}$)$_2$($R^{12}$)$^+$, —N($R^{12}$)—C(O)$R^{12}$, —N($R^{12}$)C(O)O($R^{12}$), —N($R^{12}$)C(O)N($R^{12}$)($R^{12}$), —N($R^{12}$)S(O)$_2$($R^{12}$), —N($R^{12}$)S(O)$_2$—N($R^{12}$)($R^{12}$), —N($R^{12}$)S(O)$_2$O($R^{12}$), —OC(O)$R^{12}$, —OC(O)O$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2R^{12}$ or —S(O)$_2$N($R^{12}$)($R^{12}$); wherein said —C(O)NH($C_{1-4}$ alkyl) is substituted with oxo, halo, —NO$_2$, —CN, —N$_3$, $C_{4-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^{12}$, —C(O)$R^{12}$, —C(O)O—$R^{12}$, —C(O)N($R^{12}$)($R^{12}$), —N($R^{12}$)($R^{12}$), —N($R^{12}$)$_2$($R^{12}$)$^+$, —N($R^{12}$)—C(O)$R^{12}$, —N($R^{12}$)C(O)O($R^{12}$), —N($R^{12}$)C(O)N($R^{12}$)($R^{12}$), —N($R^{12}$)S(O)$_2$($R^{12}$), —N($R^{12}$)S(O)$_2$—N($R^{12}$)($R^{12}$), —N($R^{12}$)S(O)$_2$O($R^{12}$), —OC(O)$R^{12}$, —OC(O)O$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2R^{12}$ or —S(O)$_2$N($R^{12}$)($R^{12}$); and wherein each said $C_{3-9}$ alkyl, $C_{4-9}$ alkyl, $C_{2-6}$ alkenyl, $C_{2-6}$ alkynyl, $C_{3-15}$ cycloalkyl, $C_{1-8}$ haloalkyl, aryl, heteroaryl, or heterocyclyl is optionally substituted with $Z^{1b}$.

In another embodiment, or a pharmaceutically acceptable salt, stereoisomer, mixture of stereoisomers, or deuterated analog thereof, $R^2$ is In another embodiment, or a pharmaceutically acceptable salt, stereoisomer, mixture of stereoisomers, or deuterated analog thereof, $R^2$ is $C_{4-6}$ cycloalkyl substituted with one or more —NHC(O)($C_{1-3}$ alkyl); wherein at least one —NHC(O)($C_{1-3}$ alkyl) is substituted with one or more oxo, halo, —NO$_2$, —CN, —N$_3$, $C_{3-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^9$, —C(O)$R^{12}$, —C(O)O—$R^{12}$, —C(O)N($R^{12}$)($R^{12}$), —N($R^{12}$)($R^{12}$), —N($R^{12}$)$_2$($R^{12}$)$^+$, —N($R^{12}$)—C(O)$R^{12}$, —N($R^{12}$)C(O)O($R^{12}$), —N($R^{12}$)C(O)N($R^{12}$)($R^{12}$), —N($R^{12}$)S(O)$_2$($R^{12}$), —N($R^{12}$)S(O)$_2$—N($R^{12}$)($R^{12}$), —N($R^{12}$)S(O)$_2$O($R^{12}$), —OC(O)$R^{12}$, —OC(O)O$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2R^{12}$ or —S(O)$_2$N($R^{12}$)($R^{12}$);
wherein said $C_{4-6}$ cycloalkyl is optionally substituted with $Z^1$; and
wherein said $C_{3-9}$ alkyl, $C_{2-6}$ alkenyl, $C_{2-6}$ alkynyl, $C_{3-15}$ cycloalkyl, $C_{1-8}$ haloalkyl, aryl, heteroaryl, or heterocyclyl is optionally substituted with $Z^{1a}$.

In another embodiment, or a pharmaceutically acceptable salt, stereoisomer, mixture of stereoisomers, or deuterated analog thereof, $R^2$ is

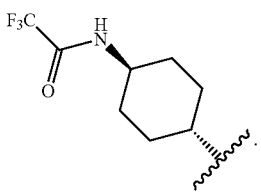

In another embodiment, or a pharmaceutically acceptable salt, stereoisomer, mixture of stereoisomers, or deuterated analog thereof, $R^2$ is $C_{4-6}$ cycloalkyl substituted with three or more substituents selected from —OH, $C_{1-4}$ hydroxyalkyl, $C_{1-3}$ alkoxy, —(CH$_2$)$_{1-3}$O(C$_{1-3}$ alkyl), —C(O)NH(C$_{1-4}$ alkyl), —C(O)NH(C$_{3-6}$ cycloalkyl), —N(C$_{1-3}$ alkyl)$_2$, —NHC(O)(C$_{1-3}$ alkyl), —NHC(O)O(C$_{1-3}$ alkyl), or —NHC(O)(C$_{1-4}$ hydroxyalkyl); and wherein said $C_{4-6}$ cycloalkyl is optionally substituted with $Z^1$.

In another embodiment, or a pharmaceutically acceptable salt, stereoisomer, mixture of stereoisomers, or deuterated analog thereof, $R^2$ is s 5-10 membered heteroaryl optionally substituted with $Z^1$.

In another embodiment, or a pharmaceutically acceptable salt, stereoisomer, mixture of stereoisomers, or deuterated analog thereof, $R^2$ is oxazolyl, isoxazolyl, thiadiazole, thiazole, oxadiazole, isothiazolyl, tetrazolyl, thiophenyl, furanyl, or a 6-10 membered heteroaryl; any of which is optionally substituted with $Z^1$;

In another embodiment, or a pharmaceutically acceptable salt, stereoisomer, mixture of stereoisomers, or deuterated analog thereof, $R^2$ is 4-7 membered monocyclic heterocyclyl optionally substituted with $Z^1$.

In another embodiment, or a pharmaceutically acceptable salt, stereoisomer, mixture of stereoisomers, or deuterated analog thereof, $R^2$ is

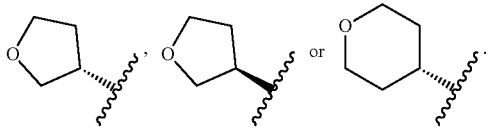

In another embodiment, or a pharmaceutically acceptable salt, stereoisomer, mixture of stereoisomers, or deuterated analog thereof, $R^2$ is azetidinyl, oxetanyl, pyrrolidinyl, morpholinyl, thiomorpholinyl, 4-7 membered sultam, 4-7 membered cyclic carbamate, 4-7 membered cyclic carbonate, or 4-7 membered cyclic sulfide; any of which is optionally substituted with $Z^1$.

In another embodiment, or a pharmaceutically acceptable salt, stereoisomer, mixture of stereoisomers, or deuterated analog thereof, $R^2$ is

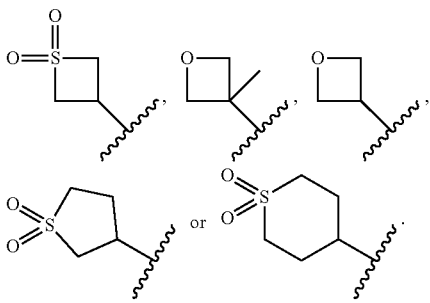

In another embodiment, or a pharmaceutically acceptable salt, stereoisomer, mixture of stereoisomers, or deuterated analog thereof, $R^2$ is tetrahydrofuranyl, tetrahydropyranyl, piperidinyl, piperazinyl pyrrolyl, pyrazolyl, imidazolyl, or triazolyl; wherein said tetrahydrofuranyl, tetrahydropyranyl, piperidinyl, piperazinyl pyrrolyl, pyrazolyl, imidazolyl, or triazolyl is substituted with one or more substituents selected from oxo, halo, —CN, $C_{2-4}$ alkyl, $C_{5-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—R$^{12}$, —C(O)—R$^{12}$, —C(O)O—R$^{12}$, —C(O)—N(R$^{12}$)(R$^{12}$), —N(R$^{12}$)(R$^{12}$), —N(R$^{12}$)$_2$(R$^{12}$)$^+$, —N(R$^{12}$)C(O)—R$^{12}$, —N(R$^{12}$)C(O)O—R$^{12}$, —N(R$^{12}$)C(O)N(R$^{12}$)(R$^{12}$), —N(R$^{12}$)S(O)$_2$(R$^{12}$), —NR$^{12}$S(O)$_2$N(R$^{12}$)(R$^{12}$), —NR$^{12}$S(O)$_2$O(R$^{12}$), —OC(O)R$^{12}$, —OC(O)—N(R$^{12}$)(R$^{12}$), —Si(R$^{12}$)$_3$, —S—R$^{12}$, —S(O)R$^{12}$, —S(O)$_2$(C$_{4-9}$ alkyl), —S(O)$_2$(C$_{3-10}$ cycloalkyl), —S(O)$_2$(heterocyclyl), —S(O)$_2$(aryl), —S(O)$_2$(heteroaryl), —S(O)(NH)R$^{12}$, or —S(O)$_2$N(R$^{12}$)(R$^{12}$);

wherein said tetrahydrofuranyl, tetrahydropyranyl, piperidinyl, piperazinyl, pyrrolyl, pyrazolyl, imidazolyl, or triazolyl is optionally substituted with $Z^{1a}$;

wherein said $C_{2-4}$ alkyl is optionally substituted with halo, —NO$_2$, —CN, —N$_3$, $C_{3-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—R$^9$, —C(O)R$^{12}$, —C(O)O—R$^{12}$, —C(O)N(R$^{12}$)(R$^{12}$), —N(R$^{12}$)(R$^{12}$), —N(R$^{12}$)$_2$(R$^{12}$)$^+$, —N(R$^{12}$)—C(O)R$^{12}$, —N(R$^{12}$)C(O)O(R$^{12}$), —N(R$^{12}$)C(O)N(R$^{12}$)(R$^{12}$), —N(R$^{12}$)S(O)$_2$(R$^{12}$), —N(R$^{12}$)S(O)$_2$—N(R$^{12}$)(R$^{12}$), —N(R$^{12}$)S(O)$_2$O(R$^{12}$), —OC(O)R$^{12}$, —OC(O)OR$^{12}$, —OC(O)—N(R$^{12}$)(R$^{12}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{12}$)(R$^{12}$); and wherein each said $C_{3-9}$ alkyl, $C_{5-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —S(O)$_2$(C$_{4-9}$ alkyl), —S(O)$_2$(C$_{3-10}$ cycloalkyl), —S(O)$_2$(heterocyclyl), —S(O)$_2$(aryl), or —S(O)$_2$(heteroaryl) is optionally substituted with $Z^{1a}$.

In another embodiment, or a pharmaceutically acceptable salt, stereoisomer, mixture of stereoisomers, or deuterated analog thereof, $R^2$ is

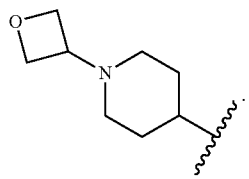 [SMILES: *C1CCN(C2COC2)CC1 ; "."]

In another embodiment, or a pharmaceutically acceptable salt, stereoisomer, mixture of stereoisomers, or deuterated analog thereof, $R^2$ is tetrahydrofuranyl, tetrahydropyranyl, piperidinyl, piperazinyl pyrrolyl, pyrazolyl, imidazolyl, or triazolyl; wherein said tetrahydrofuranyl, tetrahydropyranyl, piperidinyl, piperazinyl, pyrrolyl, pyrazolyl, imidazolyl, or triazolyl is substituted with one or more $C_1$ alkyl; wherein said tetrahydrofuranyl, tetrahydropyranyl, piperidinyl, piperazinyl, pyrrolyl, pyrazolyl, imidazolyl, or triazolyl is optionally substituted with $Z^1$;

wherein said $C_1$ alkyl is optionally substituted with oxo, halo, —NO$_2$, —CN, —N$_3$, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—R$^9$, —C(O)R$^{12}$, —C(O)O—R$^{12}$, —C(O)N(R$^9$)(R$^9$), —C(O)N(R$^{12}$)(C$_{4-9}$ alkyl), —C(O)N(R$^{12}$)(C$_{3-10}$ cycloalkyl), —C(O)N(R$^{12}$)(heterocyclyl), —C(O)N(R$^{12}$)(aryl), —C(O)N(R$^{12}$)(heteroaryl), —N(R$^{12}$)(R$^{12}$), —N(R$^{12}$)$_2$(R$^{12}$)$^+$, —N(R$^{12}$)—C(O)R$^{12}$, —N(R$^{12}$)C(O)O (R$^{12}$), —N(R$^{12}$)C(O)N(R$^{12}$)(R$^{12}$), —N(R$^{12}$)S(O)$_2$(R$^{12}$), —N(R$^{12}$)S(O)$_2$—N(R$^{12}$)(R$^{12}$), —N(R$^{12}$)S(O)$_2$O(R$^{12}$), —OC(O)R$^{12}$, —OC(O)OR$^{12}$, —OC(O)—N(R$^{12}$)(R$^{12}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{12}$)(R$^{12}$); and wherein said C$_{2-6}$ alkenyl, C$_{2-6}$ alkynyl, C$_{3-15}$ cycloalkyl, C$_{1-8}$ haloalkyl, aryl, heteroaryl, heterocyclyl, —C(O)N(R$^{12}$)(C$_{3-10}$ cycloalkyl), —C(O)N(R$^{12}$)(heterocyclyl), —C(O)N(R$^{12}$)(aryl), —C(O)N(R$^{12}$)(heteroaryl) is optionally substituted with Z$^{1a}$.

In another embodiment, or a pharmaceutically acceptable salt, stereoisomer, mixture of stereoisomers, or deuterated analog thereof, R$^2$ is tetrahydrofuranyl, tetrahydropyranyl, piperidinyl, piperazinyl pyrrolyl, pyrazolyl, imidazolyl, or triazolyl; any of which is optionally substituted with Z$^1$; wherein said tetrahydrofuranyl, tetrahydropyranyl, piperidinyl, piperazinyl pyrrolyl, pyrazolyl, imidazolyl, or triazolyl is substituted with one or more S(O)$_2$(C$_{1-3}$ alkyl); wherein said S(O)$_2$(C$_{1-3}$ alkyl) is substituted with oxo, halo, —NO$_2$, —CN, —N$_3$, C$_{3-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O—R$^{12}$, —C(O)R$^{12}$, —C(O)O—R$^{12}$, —C(O)N(R$^{12}$)(R$^{12}$), —N(R$^{12}$)(R$^{12}$), —N(R$^{12}$)$_2$(R$^{12}$)$^+$, —N(R$^{12}$)—C(O)R$^{12}$, —N(R$^{12}$)C(O)O(R$^{12}$), —N(R$^{12}$)C(O)N(R$^{12}$)(R$^{12}$), —N(R$^{12}$)S(O)$_2$(R$^{12}$), —N(R$^{12}$)S(O)$_2$—N(R$^{12}$)(R$^{12}$), —N(R$^{12}$)S(O)$_2$O(R$^{12}$), —OC(O)R$^{12}$, —OC(O)OR$^{12}$, —OC(O)—N(R$^{12}$)(R$^{12}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{12}$)(R$^{12}$); and wherein said C$_{3-9}$ alkyl, C$_{2-6}$ alkenyl, C$_{2-6}$ alkynyl, C$_{3-15}$ cycloalkyl, C$_{1-8}$ haloalkyl, aryl, heteroaryl, or heterocyclyl is optionally substituted with Z$^{1b}$.

In another embodiment, or a pharmaceutically acceptable salt, stereoisomer, mixture of stereoisomers, or deuterated analog thereof, R$^2$ is tetrahydrofuranyl, tetrahydropyranyl, piperidinyl, piperazinyl pyrrolyl, pyrazolyl, imidazolyl, or triazolyl; any of which is optionally substituted with Z$^1$; wherein said tetrahydrofuranyl, tetrahydropyranyl, piperidinyl, piperazinyl pyrrolyl, pyrazolyl, imidazolyl, or triazolyl is substituted with one or more C$_{1-4}$ hydroxyalkyl; wherein said C$_{1-4}$ hydroxyalkyl is substituted with oxo, halo, —NO$_2$, —CN, —N$_3$, C$_{4-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O—R$^9$, —C(O)R$^{12}$, —C(O)O—R$^{12}$, —C(O)N(R$^{12}$)(R$^{12}$), —N(R$^{12}$)(R$^{12}$), —N(R$^{12}$)$_2$(R$^{12}$)$^+$, —N(R$^{12}$)—C(O)R$^{12}$, —N(R$^{12}$)C(O)O(R$^{12}$), —N(R$^{12}$)C(O)N(R$^{12}$)(R$^{12}$), —N(R$^{12}$)S(O)$_2$(R$^{12}$), —N(R$^{12}$)S(O)$_2$—N(R$^{12}$)(R$^{12}$), —N(R$^{12}$)S(O)$_2$O(R$^{12}$), —OC(O)R$^{12}$, —OC(O)OR$^{12}$, —OC(O)—N(R$^{12}$)(R$^{12}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{12}$)(R$^{12}$); and wherein said C$_{4-9}$ alkyl, C$_{2-6}$ alkenyl, C$_{2-6}$ alkynyl, C$_{3-15}$ cycloalkyl, C$_{1-8}$ haloalkyl, aryl, heteroaryl, or heterocyclyl is optionally substituted with Z$^{1b}$.

In another embodiment, or a pharmaceutically acceptable salt, stereoisomer, mixture of stereoisomers, or deuterated analog thereof, R$^2$ is tetrahydrofuranyl, tetrahydropyranyl, piperidinyl, piperazinyl pyrrolyl, pyrazolyl, imidazolyl, or triazolyl; any of which is optionally substituted with Z$^1$; wherein said tetrahydrofuranyl, tetrahydropyranyl, piperidinyl, piperazinyl pyrrolyl, pyrazolyl, imidazolyl, or triazolyl is substituted with one or more —CH$_2$C(O)NH(C$_{1-6}$ alkyl); wherein said —CH$_2$C(O)NH(C$_{1-6}$ alkyl) is substituted with oxo, —Cl, —NO$_2$, —CN, —N$_3$, C$_{6-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O—R$^9$, —C(O)R$^{12}$, —C(O)O—R$^{12}$, —C(O)N(R$^{12}$)(R$^{12}$), —N(R$^{12}$)(R$^{12}$), —N(R$^{12}$)$_2$(R$^{12}$)$^+$, —N(R$^{12}$)—C(O)R$^{12}$, —N(R$^{12}$)C(O)O(R$^{12}$), —N(R$^{12}$)C(O)N(R$^{12}$)(R$^{12}$), —N(R$^{12}$)S(O)$_2$(R$^{12}$), —N(R$^{12}$)S(O)$_2$—N(R$^{12}$)(R$^{12}$), —N(R$^{12}$)S(O)$_2$O(R$^{12}$), —OC(O)R$^{12}$, —OC(O)OR$^{12}$, —OC(O)—N(R$^{12}$)(R$^{12}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{12}$)(R$^{12}$); wherein said —CH$_2$C(O)NH(C$_{1-6}$ alkyl) is optionally substituted with Z$^{1a}$; and wherein said C$_{6-9}$ alkyl, C$_{2-6}$ alkenyl, C$_{2-6}$ alkynyl, C$_{3-15}$ cycloalkyl, C$_{1-8}$ haloalkyl, aryl, heteroaryl, or heterocyclyl is optionally substituted with Z$^{1b}$.

In another embodiment, or a pharmaceutically acceptable salt, stereoisomer, mixture of stereoisomers, or deuterated analog thereof, R$^2$ is tetrahydrofuranyl, tetrahydropyranyl, piperidinyl, piperazinyl, pyrrolyl, pyrazolyl, imidazolyl, or triazolyl; wherein said tetrahydrofuranyl, tetrahydropyranyl, piperidinyl, piperazinyl, pyrrolyl, pyrazolyl, imidazolyl, or triazolyl is substituted with one or more —CH$_2$C(O)NH (C$_{4-6}$ alkyl); and wherein said tetrahydrofuranyl, tetrahydropyranyl, piperidinyl, piperazinyl pyrrolyl, pyrazolyl, imidazolyl, or triazolyl is optionally substituted with Z$^1$.

In another embodiment, or a pharmaceutically acceptable salt, stereoisomer, mixture of stereoisomers, or deuterated analog thereof, R$^2$ is C$_{6-10}$ aryl optionally substituted with Z$^1$.

In another embodiment, or a pharmaceutically acceptable salt, stereoisomer, mixture of stereoisomers, or deuterated analog thereof, R$^2$ is 6-12 membered bicyclic heterocyclyl optionally substituted with Z$^1$; wherein when said 6-12 membered bicyclic heterocyclyl is 1-oxa-7-azaspiro[3.5]nonanyl, then said 1-oxa-7-azaspiro[3.5]nonanyl is substituted with one or more Z$^1$.

In another embodiment, or a pharmaceutically acceptable salt, stereoisomer, mixture of stereoisomers, or deuterated analog thereof, R$^2$ is

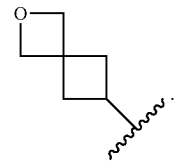 [SMILES: *C1CC2(COC2)C1 ; "."]

In another embodiment, or a pharmaceutically acceptable salt, stereoisomer, mixture of stereoisomers, or deuterated analog thereof, R$^2$ is —N(R$^{12}$)(R$^{12}$), —S(O)$_2$R$^{12}$, —S(O)$_2$N(R$^{12}$)(R$^{12}$); or —H.

In another embodiment, or a pharmaceutically acceptable salt, stereoisomer, mixture of stereoisomers, or deuterated analog thereof, R$^2$ is

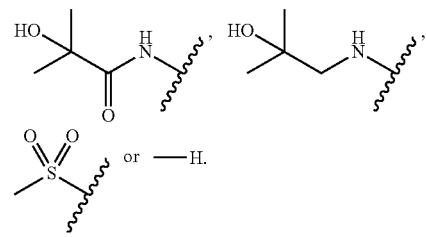

In another embodiment, or a pharmaceutically acceptable salt, stereoisomer, mixture of stereoisomers, or deuterated analog thereof, R$^3$ is selected from H, halo, —NO$_2$, —CN, —O—R$^{12}$, —C(O)—R$^{12}$, —C(O)—N(R$^{12}$)(R$^{12}$), —N(R$^{12}$)(R$^{12}$), —N(R$^{12}$)C(O)—R$^{12}$, —N(R$^{12}$)C(O)O—R$^{12}$, —N(R$^{12}$)S(O)$_2$(R$^{12}$), —N(R$^{12}$)C(O)—N(R$^{12}$)(R$^{12}$), —S(O)$_2$R$^{12}$), —SR$^{12}$ and —S(O)$_2$N(R$^{12}$)(R$^{12}$).

In another embodiment, a pharmaceutically acceptable salt, stereoisomer, mixture of stereoisomers, or deuterated analog thereof, R$^3$ is selected from —O—R$^{12}$, —C(O)—R$^{12}$, —C(O)—N(R$^{12}$)(R$^{12}$), —N(R$^9$)(R$^9$), —NH(R$^9$), —N(R$^{12}$)C(O)—R$^{12}$, —N(R$^{12}$)C(O)O—R$^{12}$, —N(R$^{12}$)S(O)$_2$(R$^{12}$), —N(R$^{12}$)C(O)—N(R$^{12}$)(R$^{12}$), —S(O)$_2$(R$^{12}$), —S—R$^{12}$ or —S(O)$_2$N(R$^{12}$)(R$^{12}$);

wherein when said —N(H)(R$^9$) is NH(C$_{1-3}$ alkyl), —N(H)(R$^9$) is NH(C$_{1-4}$ hydroxyalkyl), or —O—R$^{12}$ is —O(C$_{1-3}$ alkyl), then said NH(C$_{1-3}$ alkyl), NH(C$_{1-4}$ hydroxyalkyl), or —O(C$_{1-3}$ alkyl) is further substituted with one or more oxo, halo, —NO$_2$, —CN, —N$_3$, C$_{4-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O—R$^9$, —C(O)R$^{12}$, —C(O)O—R$^{12}$, —C(O)N(R$^{12}$)(R$^{12}$), —N(R$^{12}$)(R$^{12}$), —N(R$^{12}$)$_2$(R$^{12}$), —N(R$^{12}$)—C(O)R$^{12}$, —N(R$^{12}$)C(O)O(R$^{12}$), —N(R$^{12}$)C(O)N(R$^{12}$)(R$^{12}$), —N(R$^{12}$)S(O)$_2$(R$^{12}$), —N(R$^{12}$)S(O)$_2$—N(R$^{12}$)(R$^{12}$), —N(R$^{12}$)S(O)$_2$O(R$^{12}$), —OC(O)R$^{12}$, —OC(O)OR$^{12}$, —OC(O)—N(R$^{12}$)(R$^{12}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{12}$)(R$^{12}$); and wherein said C$_{4-9}$ alkyl, C$_{2-6}$ alkenyl, C$_{2-6}$ alkynyl, C$_{3-15}$ cycloalkyl, C$_{1-8}$ haloalkyl, aryl, heteroaryl, or heterocyclyl is optionally substituted with Z$^{1a}$.

In another embodiment, or a pharmaceutically acceptable salt, stereoisomer, mixture of stereoisomers, or deuterated analog thereof, R$^3$ is

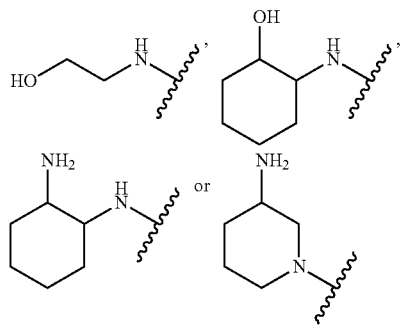

In another embodiment, a pharmaceutically acceptable salt, stereoisomer, mixture of stereoisomers, or deuterated analog thereof, R$^3$ is selected from —O(C$_4$ alkyl) or —N(H)(C$_4$ alkyl); wherein said —O(C$_4$ alkyl) is optionally substituted with Z$^{1a}$; wherein said —N(H)(C$_4$ alkyl) is optionally substituted with oxo, halo, —NO$_2$, —CN, —N$_3$, C$_{1-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O—R$^9$, —C(O)R$^{12}$, —C(O)O—R$^{12}$, —C(O)N(R$^{12}$)(R$^{12}$), —N(R$^{12}$)(R$^{12}$), —N(R$^{12}$)$_2$(R$^{12}$)$^+$, —N(R$^{12}$)—C(O)R$^{12}$, —N(R$^{12}$)C(O)O(R$^{12}$), —N(R$^{12}$)C(O)N(R$^{12}$)(R$^{12}$), —N(R$^{12}$)S(O)$_2$(R$^{12}$), —N(R$^{12}$)S(O)$_2$—N(R$^{12}$)(R$^{12}$), —N(R$^{12}$)S(O)$_2$O(R$^{12}$), —OC(O)R$^{12}$, —OC(O)OR$^{12}$, —OC(O)—N(R$^{12}$)(R$^{12}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{12}$)(R$^{12}$); wherein said C$_{1-9}$ alkyl, C$_{2-6}$ alkenyl, C$_{2-6}$ alkynyl, C$_{3-15}$ cycloalkyl, C$_{1-8}$ haloalkyl, aryl, heteroaryl, or heterocyclyl is optionally substituted with Z$^{1a}$.

In another embodiment, or a pharmaceutically acceptable salt, stereoisomer, mixture of stereoisomers, or deuterated analog thereof, R$^3$ is C$_{1-9}$ alkyl optionally substituted with Z$^1$.

In another embodiment, or a pharmaceutically acceptable salt, stereoisomer, mixture of stereoisomers, or deuterated analog thereof, R$^3$ is C$_{1-2}$ alkyl optionally substituted with F and further substituted with one or more oxo, —Cl, —NO$_2$, —N$_3$, —CN, C$_{3-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O—R$^{12}$, —C(O)—R$^{12}$, —C(O)O—R$^{12}$, —C(O)—N(R$^{12}$)(R$^{12}$), —N(R$^{12}$)(R$^{12}$), —N(R$^{12}$)$_2$(R$^{12}$)$^+$, —N(R$^{12}$)C(O)—R$^{12}$, —N(R$^{12}$)C(O)O—R$^{12}$, —N(R$^{12}$)C(O)N(R$^{12}$)(R$^{12}$), —N(R$^{12}$)S(O)$_2$(R$^{12}$), —NR$^{12}$S(O)$_2$N(R$^{12}$)(R$^{12}$), —NR$^{12}$S(O)$_2$O(R$^{12}$), —OC(O)R$^{12}$, —OC(O)—N(R$^{12}$)(R$^{12}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{12}$)(R$^{12}$); and wherein said C$_{3-9}$ alkyl, C$_{2-6}$ alkenyl, C$_{2-6}$ alkynyl, C$_{3-15}$ cycloalkyl, C$_{1-8}$ haloalkyl, aryl, heteroaryl, or heterocyclyl is optionally substituted with Z$^{1a}$.

In another embodiment, or a pharmaceutically acceptable salt, stereoisomer, mixture of stereoisomers, or deuterated analog thereof, R$^3$ is

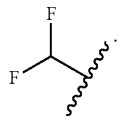

In another embodiment, or a pharmaceutically acceptable salt, stereoisomer, mixture of stereoisomers, or deuterated analog thereof, R$^3$ is C$_3$ alkyl substituted with one or more Z$^1$.

In another embodiment, or a pharmaceutically acceptable salt, stereoisomer, mixture of stereoisomers, or deuterated analog thereof, R$^3$ is C$_{4-9}$ alkyl optionally substituted with Z$^1$.

In another embodiment, or a pharmaceutically acceptable salt, stereoisomer, mixture of stereoisomers, or deuterated analog thereof, R$^3$ is C$_{2-9}$ alkynyl optionally substituted with Z$^1$.

In another embodiment, or a pharmaceutically acceptable salt, stereoisomer, mixture of stereoisomers, or deuterated analog thereof, R$^3$ is

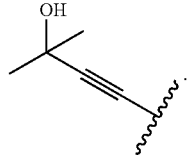 [SMILES: *C#CC(C)(C)O ; "."]

In another embodiment, or a pharmaceutically acceptable salt, stereoisomer, mixture of stereoisomers, or deuterated analog thereof, R$^3$ is C$_{2-9}$ alkenyl optionally substituted with Z$^1$.

In another embodiment, or a pharmaceutically acceptable salt, stereoisomer, mixture of stereoisomers, or deuterated analog thereof, R$^3$ is a 5-10 membered heteroaryl optionally substituted with Z$^1$.

In another embodiment, or a pharmaceutically acceptable salt, stereoisomer, mixture of stereoisomers, or deuterated analog thereof, R$^3$ is a 5-10 membered heteroaryl optionally substituted with Z$^1$; wherein if said 5-10 membered heteroaryl is pyridinyl, then said pyridinyl is further substituted with one or more Z$^1$.

In another embodiment, or a pharmaceutically acceptable salt, stereoisomer, mixture of stereoisomers, or deuterated analog thereof, $R^3$ is $C_{6-10}$ aryl optionally substituted with $Z^1$.

In another embodiment, or a pharmaceutically acceptable salt, stereoisomer, mixture of stereoisomers, or deuterated analog thereof, $R^3$ is $C_{6-10}$ aryl optionally substituted with $Z^1$;
wherein when said $C_{6-10}$ aryl is cyanophenyl then said cyanophenyl is further substituted with one or more oxo, halo, $-NO_2$, $-N_3$, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, $-O-R^{12}$, $-C(O)R^{12}$, $-C(O)O-R^{12}$, $-C(O)N(R^{12})(R^{12})$, $-N(R^{12})(R^{12})$, $-N(R^{12})_2(R^{12})^+$, $-N(R^{12})-C(O)R^{12}$, $-N(R^{12})C(O)O(R^{12})$, $-N(R^{12})C(O)N(R^{12})(R^{12})$, $-N(R^{12})S(O)_2(R^{12})$, $-N(R^{12})S(O)_2-N(R^{12})(R^{12})$, $-N(R^{12})S(O)_2O(R^{12})$, $-OC(O)R^{12}$, $-OC(O)OR^{12}$, $-OC(O)-N(R^{12})(R^{12})$, $-Si(R^{12})_3$, $-S-R^{12}$, $-S(O)R^{12}$, $-S(O)(NH)R^{12}$, $-S(O)_2R^{12}$ or $-S(O)_2N(R^{12})(R^{12})$; and wherein said $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl is optionally substituted with $Z^{1a}$.

In another embodiment, or a pharmaceutically acceptable salt, stereoisomer, mixture of stereoisomers, or deuterated analog thereof, $R^3$ is a 4-12 membered heterocyclyl optionally substituted with $Z^1$.

In another embodiment, or a pharmaceutically acceptable salt, stereoisomer, mixture of stereoisomers, or deuterated analog thereof, $R^3$ is a 4-12 membered heterocyclyl optionally substituted with $Z^1$; wherein when said 4-12 membered heterocyclyl is hydroxypyrrolidinyl then said hydroxypyrrolidinyl is further substituted with one or more oxo, halo, $-CN$, $-NO_2$, $-N_3$, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, $-O-R^9$, $-C(O)R^{12}$, $-C(O)O-R^{12}$, $-C(O)N(R^{12})(R^{12})$, $-N(R^{12})(R^{12})$, $-N(R^{12})_2(R^{12})^+$, $-N(R^{12})-C(O)R^{12}$, $-N(R^{12})C(O)O(R^{12})$, $-N(R^{12})C(O)N(R^{12})(R^{12})$, $-N(R^{12})S(O)_2(R^{12})$, $-N(R^{12})S(O)_2-N(R^{12})(R^{12})$, $-N(R^{12})S(O)_2O(R^{12})$, $-OC(O)R^{12}$, $-OC(O)OR^{12}$, $-OC(O)-N(R^{12})(R^{12})$, $-Si(R^{12})_3$, $-S-R^{12}$, $-S(O)R^{12}$, $-S(O)(NH)R^{12}$, $-S(O)_2R^{12}$ or $-S(O)_2N(R^{12})(R^{12})$;
wherein said $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, or heterocyclyl is optionally substituted with $Z^{1a}$.

In another embodiment, or a pharmaceutically acceptable salt, stereoisomer, mixture of stereoisomers, or deuterated analog thereof, $R^3$ is $C_{3-10}$ cycloalkyl optionally substituted with $Z^1$.

In another embodiment, or a pharmaceutically acceptable salt, stereoisomer, mixture of stereoisomers, or deuterated analog thereof, $R^3$ is $C_{3-6}$ cycloalkyl substituted with one or more $Z^1$.

In another embodiment, or a pharmaceutically acceptable salt, stereoisomer, mixture of stereoisomers, or deuterated analog thereof, $R^3$ is $C_{7-10}$ cycloalkyl optionally substituted with $Z^1$.

In another embodiment, or a pharmaceutically acceptable salt, stereoisomer, mixture of stereoisomers, or deuterated analog thereof, $R^4$ is H, halo, $-NO_2$, $-CN$, $-O-R^{12}$, $-C(O)-R^{12}$, $-C(O)-N(R^{12})(R^{12})$, $-N(R^{12})(R^{12})$, $-N(R^{12})C(O)-R^{12}$, $-N(R^{12})C(O)O-R^{12}$, $-N(R^{12})S(O)_2(R^{12})$, $-N(R^{12})C(O)-N(R^{12})(R^{12})$, $-S(O)_2R^{12}$, $-SR^{12}$ or $-S(O)_2N(R^{12})(R^{12})$.

In another embodiment, or a pharmaceutically acceptable salt, stereoisomer, mixture of stereoisomers, or deuterated analog thereof, $R^4$ is

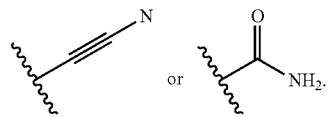

In another embodiment, or a pharmaceutically acceptable salt, stereoisomer, mixture of stereoisomers, or deuterated analog thereof, $R^4$ is $-O-R^{12}$, $-C(O)-R^{12}$, $-C(O)-N(R^{12})(R^{12})$, $-N(R^9)(R^9)$, $-NH(R^9)$, $-N(R^{12})C(O)-R^{12}$, $-N(R^{12})C(O)O-R^{12}$, $-N(R^{12})S(O)_2(R^{12})$, $-N(R^{12})C(O)-N(R^{12})(R^{12})$, $-S(O)_2(R^{12})$, $-S-R^{12}$ or $-S(O)_2N(R^{12})(R^{12})$; wherein when said $-N(H)(R^9)$ is $NH(C_{1-3}$ alkyl), $-N(H)(R^9)$ is $NH(C_{1-4}$ hydroxyalkyl), or $-O-R^{12}$ is $-O(C_{1-3}$ alkyl), then said $NH(C_{1-3}$ alkyl), $NH(C_{1-4}$ hydroxyalkyl), or $-O(C_{1-3}$ alkyl) is further substituted with one or more oxo, halo, $-NO_2$, $-CN$, $-N_3$, $C_{4-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, $-O-R^9$, $-C(O)R^{12}$, $-C(O)O-R^{12}$, $-C(O)N(R^{12})(R^{12})$, $-N(R^{12})(R^{12})$, $-N(R^{12})_2(R^{12})^+$, $-N(R^{12})-C(O)R^{12}$, $-N(R^{12})C(O)O(R^{12})$, $-N(R^{12})C(O)N(R^{12})(R^{12})$, $-N(R^{12})S(O)_2(R^{12})$, $-N(R^{12})S(O)_2-N(R^{12})(R^{12})$, $-N(R^{12})S(O)_2O(R^{12})$, $-OC(O)R^{12}$, $-OC(O)OR^{12}$, $-OC(O)-N(R^{12})(R^{12})$, $-Si(R^{12})_3$, $-S-R^{12}$, $-S(O)R^{12}$, $-S(O)(NH)R^{12}$, $-S(O)_2R^{12}$ or $-S(O)_2N(R^{12})(R^{12})$; and wherein said $C_{4-9}$ alkyl, $C_{2-6}$ alkenyl, $C_{2-6}$ alkynyl, $C_{3-15}$ cycloalkyl, $C_{1-8}$ haloalkyl, aryl, heteroaryl, or heterocyclyl is optionally substituted with $Z^{1a}$.

In another embodiment, or a pharmaceutically acceptable salt, stereoisomer, mixture of stereoisomers, or deuterated analog thereof, $R^4$ is selected from $-O(C_4$ alkyl) or $-N(H)(C_4$ alkyl); wherein said $-O(C_4$ alkyl) is optionally substituted with $Z^{1a}$;
wherein said $-N(H)(C_4$ alkyl) is optionally substituted with oxo, halo, $-NO_2$, $-CN$, $-N_3$, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, $-O-R^9$, $-C(O)R^{12}$, $-C(O)O-R^{12}$, $-C(O)N(R^{12})(R^{12})$, $-N(R^{12})(V)$, $-N(R^{12})_2(R^{12})^+$, $-N(R^{12})-C(O)R^{12}$, $-N(R^{12})C(O)O(R^{12})$, $-N(R^{12})C(O)N(R^{12})(R^{12})$, $-N(R^{12})S(O)_2(R^{12})$, $-N(R^{12})S(O)_2-N(R^{12})(R^{12})$, $-N(R^{12})S(O)_2O(R^{12})$, $-OC(O)R^{12}$, $-OC(O)OR^{12}$, $-OC(O)-N(R^{12})(R^{12})$, $-Si(R^{12})_3$, $-S-R^{12}$, $-S(O)R^{12}$, $-S(O)(NH)R^{12}$, $-S(O)_2R^{12}$ or $-S(O)_2N(R^{12})(R^{12})$;
wherein said $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl is optionally substituted with $Z^{1a}$.

In another embodiment, or a pharmaceutically acceptable salt, stereoisomer, mixture of stereoisomers, or deuterated analog thereof, $R^4$ is $C_{1-9}$ alkyl optionally substituted with $Z^1$.

In another embodiment, or a pharmaceutically acceptable salt, stereoisomer, mixture of stereoisomers, or deuterated analog thereof, $R^4$ is $C_{1-2}$ alkyl optionally substituted with F and further substituted with one or more oxo, $-Cl$, $-NO_2$, $-N_3$, $-CN$, $C_{3-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, $-O-R^{12}$, $-C(O)-R^{12}$, $-C(O)O-R^{12}$, $-C(O)-N(R^{12})(R^{12})$, $-N(R^{12})(R^{12})$, $-N(R^{12})_2(R^{12})^+$, $-N(R^{12})C(O)-R^{12}$, $-N(R^{12})C(O)O-R^{12}$, $-N(R^{12})C(O)N(R^{12})(R^{12})$, $-N(R^{12})S(O)_2(R^{12})$, $-NR^{12}S(O)_2N(R^{12})(R^{12})$, $-NR^{12}S(O)_2O(R^{12})$, $-OC(O)R^{12}$, $-OC(O)-N(R^{12})(R^{12})$, $-Si(R^{12})_3$, $-S-R^{12}$, $-S(O)R^{12}$, $-S(O)(NH)R^{12}$, $-S(O)_2R^{12}$ or $-S(O)_2N(R^{12})(R^{12})$; and wherein said $C_{3-9}$ alkyl, $C_{2-6}$ alkenyl, $C_{2-6}$ alkynyl, $C_{3-15}$ cycloalkyl, $C_{1-8}$ haloalkyl, aryl, heteroaryl, or heterocyclyl is optionally substituted with $Z^{1a}$.

In another embodiment, or a pharmaceutically acceptable salt, stereoisomer, mixture of stereoisomers, or deuterated analog thereof, $R^4$ is $C_3$ alkyl substituted with one or more $Z^1$.

In another embodiment, or a pharmaceutically acceptable salt, stereoisomer, mixture of stereoisomers, or deuterated analog thereof, $R^4$ is $C_{4-9}$ alkyl optionally substituted with $Z^1$.

In another embodiment, or a pharmaceutically acceptable salt, stereoisomer, mixture of stereoisomers, or deuterated analog thereof, $R^4$ is $C_{2-9}$ alkynyl optionally substituted with $Z^1$.

In another embodiment, or a pharmaceutically acceptable salt, stereoisomer, mixture of stereoisomers, or deuterated analog thereof, $R^4$ is $C_{2-9}$ alkenyl optionally substituted with $Z^1$.

In another embodiment, or a pharmaceutically acceptable salt, stereoisomer, mixture of stereoisomers, or deuterated analog thereof, $R^4$ is a 5-10 membered heteroaryl optionally substituted with $Z^1$.

In another embodiment, or a pharmaceutically acceptable salt, stereoisomer, mixture of stereoisomers, or deuterated analog thereof, $R^4$ is

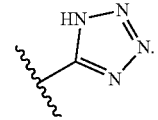

In another embodiment, or a pharmaceutically acceptable salt, stereoisomer, mixture of stereoisomers, or deuterated analog thereof, $R^4$ is a 5-10 membered heteroaryl optionally substituted with $Z^1$; wherein when said 5-10 membered heteroaryl is pyridinyl then said pyridinyl is further substituted with one or more $Z^1$.

In another embodiment, or a pharmaceutically acceptable salt, stereoisomer, mixture of stereoisomers, or deuterated analog thereof, $R^4$ is $C_{6-10}$ aryl optionally substituted with $Z^1$.

In another embodiment, or a pharmaceutically acceptable salt, stereoisomer, mixture of stereoisomers, or deuterated analog thereof, $R^4$ is $C_{6-10}$ aryl optionally substituted with $Z^1$;
wherein when said $C_{6-10}$ aryl is cyanophenyl then said cyanophenyl is further substituted with one or more oxo, halo, —$NO_2$, —$N_3$, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^{12}$, —C(O)$R^{12}$, —C(O)O—$R^{12}$, —C(O)N($R^{12}$)($R^{12}$), —N($R^{12}$)($R^{12}$), —N($R^{12}$)$_2$($R^{12}$)$^+$, —N($R^{12}$)—C(O)$R^{12}$, —N($R^{12}$)C(O)O($R^{12}$), —N($R^{12}$)C(O)N($R^{12}$)($R^{12}$), —N($R^{12}$)S(O)$_2$($R^{12}$), —N($R^{12}$)S(O)$_2$—N($R^{12}$)($R^{12}$), —N($R^{12}$)S(O)$_2$O($R^{12}$), —OC(O)$R^{12}$, —OC(O)O$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2$$R^{12}$ or —S(O)$_2$N($R^{12}$)($R^{12}$); and wherein said $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl is optionally substituted with $Z^{1a}$.

In another embodiment, or a pharmaceutically acceptable salt, stereoisomer, mixture of stereoisomers, or deuterated analog thereof, $R^4$ is a 4-12 membered heterocyclyl optionally substituted with $Z^1$.

In another embodiment, or a pharmaceutically acceptable salt, stereoisomer, mixture of stereoisomers, or deuterated analog thereof, $R^4$ is a 4-12 membered heterocyclyl optionally substituted with $Z^1$; wherein when said 4-12 membered heterocyclyl is hydroxypyrrolidinyl then said hydroxypyrrolidinyl is further substituted with one or more oxo, halo, —CN, —$NO_2$, —$N_3$, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^9$, —C(O)$R^{12}$, —C(O)O—$R^{12}$, —C(O)N($R^{12}$)($R^{12}$), —N($R^{12}$)($R^{12}$), —N($R^{12}$)$_2$($R^{12}$)$^+$, —N($R^{12}$)—C(O)$R^{12}$, —N($R^{12}$)C(O)O($R^{12}$), —N($R^{12}$)C(O)N($R^{12}$)($R^{12}$), —N($R^{12}$)S(O)$_2$($R^{12}$), —N($R^{12}$)S(O)$_2$—N($R^{12}$)($R^{12}$), —N($R^{12}$)S(O)$_2$O($R^{12}$), —OC(O)$R^{12}$, —OC(O)O$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2$$R^{12}$ or —S(O)$_2$N($R^{12}$)($R^{12}$);
wherein said $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocylyl is optionally substituted with $Z^{1a}$.

In another embodiment, or a pharmaceutically acceptable salt, stereoisomer, mixture of stereoisomers, or deuterated analog thereof, $R^4$ is $C_{3-10}$ cycloalkyl optionally substituted with $Z^1$.

In another embodiment, or a pharmaceutically acceptable salt, stereoisomer, mixture of stereoisomers, or deuterated analog thereof, $R^4$ is $C_{3-6}$ cycloalkyl substituted with one or more $Z^1$.

In another embodiment, or a pharmaceutically acceptable salt, stereoisomer, mixture of stereoisomers, or deuterated analog thereof, $R^4$ is $C_{7-10}$ cycloalkyl optionally substituted with $Z^1$.

In another embodiment, or a pharmaceutically acceptable salt, stereoisomer, mixture of stereoisomers, or deuterated analog thereof, at least one of $R^5$, $R^6$ or $R^7$ is independently selected from H, halo, —$NO_2$, —CN, —O—$R^{12}$, —C(O)—$R^{12}$, —C(O)—N($R^{12}$)($R^{12}$), —N($R^9$)($R^9$), NH($R^9$), —N($R^{12}$)C(O)—$R^{12}$, —N($R^{12}$)C(O)O—$R^{12}$, or —N($R^{12}$)S(O)$_2$($R^{12}$).

In another embodiment, or a pharmaceutically acceptable salt, stereoisomer, mixture of stereoisomers, or deuterated analog thereof, at least one of $R^5$, $R^6$ or $R^7$ is independently selected from —$NO_2$, —O—$R^{12}$, —C(O)—$R^{12}$, —C(O)—N($R^{12}$)($R^{12}$), —N($R^9$)($R^9$), —N($R^{12}$)C(O)—$R^{12}$, —N($R^{12}$)C(O)O—$R^{12}$, or —N($R^{12}$)S(O)$_2$($R^{12}$).

In another embodiment, or a pharmaceutically acceptable salt, stereoisomer, mixture of stereoisomers, or deuterated analog thereof, at least one of $R^5$, $R^6$ or $R^7$ is independently $C_{1-5}$ alkyl optionally substituted with $Z^1$.

In another embodiment, or a pharmaceutically acceptable salt, stereoisomer, mixture of stereoisomers, or deuterated analog thereof, at least one of $R^5$, $R^6$ or $R^7$ is independently $C_{1-2}$ alkyl optionally substituted with F and substituted with one or more oxo, —Cl, —$NO_2$, —$N_3$, —CN, $C_{3-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^{12}$, —C(O)—$R^{12}$, —C(O)O—$R^{12}$, —C(O)—N($R^{12}$)($R^{12}$), —N($R^{12}$)($R^{12}$), —N($R^{12}$)$_2$($R^{12}$), —N($R^{12}$)C(O)—$R^{12}$, —N($R^{12}$)C(O)O—$R^{12}$, —N($R^{12}$)C(O)N($R^{12}$)($R^{12}$), —N($R^{12}$)S(O)$_2$($R^{12}$), —N$R^{12}$S(O)$_2$N($R^{12}$)($R^{12}$), —N$R^{12}$S(O)$_2$O($R^{12}$), —OC(O)$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2$$R^{12}$ or —S(O)$_2$N($R^{12}$)($R^{12}$); wherein any alkyl, alkenyl, alkynyl, cycloalkyl, haloalkyl, aryl, heteroaryl or heterocyclyl is optionally substituted with $Z^{1a}$.

In another embodiment, or a pharmaceutically acceptable salt, stereoisomer, mixture of stereoisomers, or deuterated analog thereof, at least one of $R^5$, $R^6$ or $R^7$ is independently $C_3$ alkyl substituted with one or more $Z^1$.

In another embodiment, or a pharmaceutically acceptable salt, stereoisomer, mixture of stereoisomers, or deuterated analog thereof, at least one of $R^5$, $R^6$ or $R^7$ is independently $C_{4-5}$ alkyl optionally substituted with $Z^1$.

In another embodiment, or a pharmaceutically acceptable salt, stereoisomer, mixture of stereoisomers, or deuterated analog thereof, at least one of $R^5$, $R^6$ or $R^7$ is independently cyclopropyl, oxetanyl, or azetidinyl optionally substituted with $Z^1$.

In another embodiment, or a pharmaceutically acceptable salt, stereoisomer, mixture of stereoisomers, or deuterated analog thereof, at least one of $R^5$, $R^6$ or $R^7$ is independently cyclopropyl, oxetanyl, or azetidinyl; wherein said cyclopropyl is substituted with one or more $Z^1$; wherein said oxetanyl or azetidinyl is optionally substituted with $Z^1$.

In another embodiment, or a pharmaceutically acceptable salt, stereoisomer, mixture of stereoisomers, or deuterated analog thereof, no more than two of $R^3$, $R^4$, $R^5$, $R^6$ or $R^7$ are H.

In another embodiment, or a pharmaceutically acceptable salt, stereoisomer, mixture of stereoisomers, or deuterated analog thereof, $R^3$ is H or F.

In another embodiment, or a pharmaceutically acceptable salt, stereoisomer, mixture of stereoisomers, or deuterated analog thereof, $R^4$ is H, F, —CN or Cl.

In another embodiment, or a pharmaceutically acceptable salt, stereoisomer, mixture of stereoisomers, or deuterated analog thereof, $R^5$ is H or F.

In another embodiment, or a pharmaceutically acceptable salt, stereoisomer, mixture of stereoisomers, or deuterated analog thereof, $R^6$ is H or F.

In another embodiment, or a pharmaceutically acceptable salt, stereoisomer, mixture of stereoisomers, or deuterated analog thereof, $R^7$ is H or F.

In another embodiment, or a pharmaceutically acceptable salt, stereoisomer, mixture of stereoisomers, or deuterated analog thereof, $Z^1$ is selected H, halo, —CN, $C_{1-9}$ alkyl, $C_{3-15}$ cycloalkyl, aryl, heteroaryl, heterocyclyl, —O—$R^{12}$, —C(O)—$R^{12}$, —C(O)—N($R^{12}$)($R^{12}$), —N($R^{12}$)($R^{12}$), —N($R^{12}$)C(O)—$R^{12}$, —N($R^{12}$)C(O)O—$R^{12}$, —N($R^{12}$)S(O)$_2$($R^{12}$), —OC(O)—N($R^{12}$)($R^{12}$), —S(O)$_2$$R^{12}$ or —S(O)$_2$N($R^{12}$)($R^{12}$); and wherein any alkyl, cycloalkyl, aryl, heteroaryl or heterocyclyl is optionally substituted with $Z^{1a}$.

Another embodiment of the present disclosure provides a pharmaceutical composition comprising a compound of the disclosure, together with a pharmaceutically acceptable carrier, and optionally a diluent.

Another embodiment of the present disclosure provides a method of treating an inflammation related disease or disorder in a patient in need thereof, comprising administering to said patient a compound of the disclosure, or a pharmaceutical composition thereof.

DETAILED DESCRIPTION OF THE INVENTION

Definitions

The following description sets forth exemplary methods, parameters and the like. It should be recognized, however, that such description is not intended as a limitation on the scope of the present disclosure but is instead provided as a description of exemplary embodiments.

A dash ("-") that is not between two letters or symbols is used to indicate a point of attachment for a substituent. For example, —C(O)NH$_2$ is attached through the carbon atom. A dash at the front or end of a chemical group is a matter of convenience; chemical groups may be depicted with or without one or more dashes without losing their ordinary meaning. A wavy line drawn through a line in a structure indicates a point of attachment of a group. Unless chemically or structurally required, no directionality is indicated or implied by the order in which a chemical group is written or named.

The prefix "$C_{u-v}$" indicates that the following group has from u to v carbon atoms. For example, "$C_{1-6}$ alkyl" indicates that the alkyl group has from 1 to 6 carbon atoms.

Reference to "about" a value or parameter herein includes (and describes) embodiments that are directed to that value or parameter per se. In certain embodiments, the term "about" includes the indicated amount ±10%. In other embodiments, the term "about" includes the indicated amount ±5%. In certain other embodiments, the term "about" includes the indicated amount ±1%. Also, to the term "about X" includes description of "X". Also, the singular forms "a" and "the" include plural references unless the context clearly dictates otherwise. Thus, e.g., reference to "the compound" includes a plurality of such compounds and reference to "the assay" includes reference to one or more assays and equivalents thereof known to those skilled in the art.

"Alkyl" refers to an unbranched or branched saturated hydrocarbon chain. As used herein, alkyl has 1 to 20 carbon atoms (i.e., $C_{1-20}$ alkyl), 1 to 8 carbon atoms (i.e., $C_{1-8}$ alkyl), 1 to 6 carbon atoms (i.e., $C_{1-6}$ alkyl), or 1 to 4 carbon atoms (i.e., $C_{1-4}$ alkyl). Examples of alkyl groups include methyl, ethyl, propyl, isopropyl, n-butyl, sec-butyl, iso-butyl, tert-butyl, pentyl, 2-pentyl, isopentyl, neopentyl, hexyl, 2-hexyl, 3-hexyl, and 3-methylpentyl. When an alkyl residue having a specific number of carbons is named by chemical name or identified by molecular formula, all positional isomers having that number of carbons may be encompassed; thus, for example, "butyl" includes n-butyl (i.e. —(CH$_2$)$_3$CH$_3$), sec-butyl (i.e. —CH(CH$_3$)CH$_2$CH$_3$), isobutyl (i.e. —CH$_2$CH (CH$_3$)$_2$) and tert-butyl (i.e. —C(CH$_3$)$_3$); and "propyl" includes n-propyl (i.e. —(CH$_2$)$_2$CH$_3$) and isopropyl (i.e. —CH(CH$_3$)$_2$).

"Alkenyl" refers to an alkyl group containing at least one carbon-carbon double bond and having from 2 to 20 carbon atoms (i.e., $C_{2-20}$ alkenyl), 2 to 8 carbon atoms (i.e., $C_{2-8}$ alkenyl), 2 to 6 carbon atoms (i.e., $C_{2-6}$ alkenyl), or 2 to 4 carbon atoms (i.e., $C_{2-4}$ alkenyl). Examples of alkenyl groups include ethenyl, propenyl, butadienyl (including 1,2-butadienyl and 1,3-butadienyl).

"Alkynyl" refers to an alkyl group containing at least one carbon-carbon triple bond and having from 2 to 20 carbon atoms (i.e., $C_{2-20}$ alkynyl), 2 to 8 carbon atoms (i.e., $C_{2-8}$ alkynyl), 2 to 6 carbon atoms (i.e., $C_{2-6}$ alkynyl), or 2 to 4 carbon atoms (i.e., $C_{2-4}$ alkynyl). The term "alkynyl" also includes those groups having one triple bond and one double bond.

"Alkoxy" refers to the group "alkyl-O—". Examples of alkoxy groups include methoxy, ethoxy, n-propoxy, isopropoxy, n-butoxy, tert-butoxy, sec-butoxy, n-pentoxy, n-hexoxy, and 1,2-dimethylbutoxy.

"Haloalkoxy" refers to an alkoxy group as defined above, wherein one or more hydrogen atoms are replaced by a halogen.

"Alkylthio" refers to the group "alkyl-S—".

"Amino" refers to the group —NR$^y$R$^y$ wherein each R$^y$ is independently selected from the group consisting of hydrogen, alkyl, alkenyl, alkynyl, aryl, heterocyclyl, cycloalkyl or heteroaryl, each of which is optionally substituted, as defined herein.

"Aryl" refers to an aromatic carbocyclic group having a single ring (e.g. monocyclic) or multiple rings (e.g. bicyclic or tricyclic) including fused systems. As used herein, aryl has 6 to 20 ring carbon atoms (i.e., $C_{6-20}$ aryl), 6 to 12 carbon ring atoms (i.e., $C_{6-12}$ aryl), or 6 to 10 carbon ring atoms (i.e., $C_{6-10}$ aryl). Examples of aryl groups include phenyl, naphthyl, fluorenyl, and anthryl. Aryl, however, does not encompass or overlap in any way with heteroaryl defined below. If one or more aryl groups are fused with a heteroaryl, the resulting ring system is heteroaryl. If one or more aryl groups are fused with a heterocyclyl, the resulting ring system is heterocyclyl.

"Cyano" refers to the group —CN.

"Keto" or "oxo" refers to a group =O.

"Carbamoyl" refers to both an "O-carbamoyl" group which refers to the group —O—C(O)NR$^y$R$^z$ and an "N-carbamoyl" group which refers to the group —NR$^y$C(O)OR$^z$, wherein R$^y$ and R$^z$ are independently selected from the group consisting of hydrogen, alkyl, aryl, haloalkyl, or heteroaryl; each of which may be optionally substituted.

"Carboxyl" refers to —C(O)OH.

"Ester" refers to both —OC(O)R and —C(O)OR, wherein R is a substituent; each of which may be optionally substituted, as defined herein.

"Cycloalkyl" refers to a saturated or partially unsaturated cyclic alkyl group having a single ring or multiple rings including fused, bridged, and spiro ring systems. The term "cycloalkyl" includes cycloalkenyl groups (i.e. the cyclic group having at least one double bond). As used herein, cycloalkyl has from 3 to 20 ring carbon atoms (i.e., $C_{3-20}$ cycloalkyl), 3 to 12 ring carbon atoms (i.e., $C_{3-12}$ cycloalkyl), 3 to 10 ring carbon atoms (i.e., $C_{3-10}$ cycloalkyl), 3 to 8 ring carbon atoms (i.e., $C_{3-8}$ cycloalkyl), or 3 to 6 ring carbon atoms (i.e., $C_{3-6}$ cycloalkyl). Examples of cycloalkyl groups include cyclopropyl, cyclobutyl, cyclopentyl, and cyclohexyl.

"Halogen" or "halo" includes fluoro, chloro, bromo, and iodo. "Haloalkyl" refers to an unbranched or branched alkyl group as defined above, wherein one or more hydrogen atoms are replaced by a halogen. For example, where a residue is substituted with more than one halogen, it may be referred to by using a prefix corresponding to the number of halogen moieties attached. Dihaloalkyl and trihaloalkyl refer to alkyl substituted with two ("di") or three ("tri") halo groups, which may be, but are not necessarily, the same halogen. Examples of haloalkyl include difluoromethyl (—CHF$_2$) and trifluoromethyl (—CF$_3$).

"Heteroalkyl" refers to an alkyl group in which one or more of the carbon atoms (and any associated hydrogen atoms) are each independently replaced with the same or different heteroatomic group. The term "heteroalkyl" includes unbranched or branched saturated chain having carbon and heteroatoms. By way of example, 1, 2 or 3 carbon atoms may be independently replaced with the same or different heteroatomic group. Heteroatomic groups include, but are not limited to, —NR—, —O—, —S—, —S(O)—, —S(O)$_2$—, and the like, where R is H, alkyl, aryl, cycloalkyl, heteroalkyl, heteroaryl or heterocyclyl, each of which may be optionally substituted. Examples of heteroalkyl groups include —OCH$_3$, —CH$_2$OCH$_3$, —SCH$_3$, —CH$_2$SCH$_3$, —NRCH$_3$, and —CH$_2$NRCH$_3$, where R is hydrogen, alkyl, aryl, arylalkyl, heteroalkyl, or heteroaryl, each of which may be optionally substituted. As used herein, heteroalkyl include 1 to 10 carbon atoms, 1 to 8 carbon atoms, or 1 to 4 carbon atoms; and 1 to 3 heteroatoms, 1 to 2 heteroatoms, or 1 heteroatom.

"Heteroaryl" refers to an aromatic group having a single ring, multiple rings, or multiple fused rings, with one or more ring heteroatoms independently selected from nitrogen, oxygen, and sulfur. As used herein, heteroaryl includes 1 to 20 ring carbon atoms (i.e., $C_{1-20}$ heteroaryl), 3 to 12 ring carbon atoms (i.e., $C_{3-12}$ heteroaryl), or 3 to 8 carbon ring atoms (i.e., $C_{3-8}$ heteroaryl); and 1 to 5 heteroatoms, 1 to 4 heteroatoms, 1 to 3 ring heteroatoms, 1 to 2 ring heteroatoms, or 1 ring heteroatom independently selected from nitrogen, oxygen, and sulfur. Examples of heteroaryl groups include pyrimidinyl, purinyl, pyridyl, pyridazinyl, benzothiazolyl, and pyrazolyl. Examples of the fused-heteroaryl rings include, but are not limited to, benzo[d]thiazolyl, quinolinyl, isoquinolinyl, benzo[b]thiophenyl, indazolyl, benzo[d]imidazolyl, pyrazolo[1,5-a]pyridinyl, and imidazo[1,5-a]pyridinyl, where the heteroaryl can be bound via either ring of the fused system. Any aromatic ring, having a single or multiple fused rings, containing at least one heteroatom, is considered a heteroaryl regardless of the attachment to the remainder of the molecule (i.e., through any one of the fused rings). Heteroaryl does not encompass or overlap with aryl as defined above.

"Heterocyclyl" refers to a saturated or unsaturated cyclic alkyl group, with one or more ring heteroatoms independently selected from nitrogen, oxygen and sulfur. The term "heterocyclyl" includes heterocycloalkenyl groups (i.e. the heterocyclyl group having at least one double bond), bicyclic heterocyclyl groups, bridged-heterocyclyl groups, fused-heterocyclyl groups, and spiro-heterocyclyl groups. A heterocyclyl may be a single ring or multiple rings wherein the multiple rings may be fused, bridged, or spiro. Any non-aromatic ring containing at least one heteroatom is considered a heterocyclyl, regardless of the attachment (i.e., can be bound through a carbon atom or a heteroatom). Further, the term heterocyclyl is intended to encompass any non-aromatic ring containing at least one heteroatom, which ring may be fused to an aryl or heteroaryl ring, regardless of the attachment to the remainder of the molecule. As used herein, heterocyclyl has 2 to 20 ring atoms (i.e., 4-20 membered heterocyclyl), 2 to ring atoms (i.e., 4-12 membered heterocyclyl), 4 to 10 ring atoms (i.e., 4-10 membered heterocyclyl), 4 to 8 ring atoms (i.e., 4-8 membered heterocyclyl), or 4 to 6 ring carbon atoms (i.e., 4-6 membered heterocyclyl); having 1 to 5 ring heteroatoms, 1 to 4 ring heteroatoms, 1 to 3 ring heteroatoms, 1 to 2 ring heteroatoms, or 1 ring heteroatom independently selected from nitrogen, sulfur or oxygen. A heterocyclyl may contain one or more oxo and/or thioxo groups. Examples of heterocyclyl groups include pyrrolidinyl, piperidinyl, piperazinyl, oxetanyl, dioxolanyl, azetidinyl, azetidinyl, morpholinyl, thiomorpholinyl, 4-7 membered sultam, 4-7 membered cyclic carbamate, 4-7 membered cyclic carbonate, 4-7 membered cyclic sulfide and morpholinyl. As used herein, the term "bridged-heterocyclyl" refers to a four- to ten-membered cyclic moiety connected at two non-adjacent atoms of the heterocyclyl with one or more (e.g. 1 or 2) four- to ten-membered cyclic moiety having at least one heteroatom where each heteroatom is independently selected from nitrogen, oxygen, and sulfur. As used herein, bridged-heterocyclyl includes bicyclic and tricyclic ring systems. Also used herein, the term "spiro-heterocyclyl" refers to a ring system in which a three- to ten-membered heterocyclyl has one or more additional ring, wherein the one or more additional ring is three- to ten-membered cycloalkyl or three- to ten-membered heterocyclyl, where a single atom of the one or more additional ring is also an atom of the three- to ten-membered heterocyclyl. Examples of the spiro-heterocyclyl rings include bicyclic and tricyclic ring systems, such as 2-oxa-7-azaspiro[3.5]nonanyl, 2-oxa-6-azaspiro[3.4]octanyl, and 6-oxa-1-azaspiro[3.3]heptanyl. Examples of the fused-heterocyclyl rings include, but are not limited to, 1,2,3,4-tetrahydroisoquinolinyl, 1-oxo-1,2,3,4-tetrahydroisoquinolinyl, 1-oxo-1,2-dihydroisoquinolinyl, 4,5,6,7-tetrahydrothieno[2,3-c]pyridinyl, indolinyl, and isoindolinyl, where the heterocyclyl can be bound via either ring of the fused system. As used herein, a bicyclic heterocyclyl group is a heterocyclyl group attached at two points to another cyclic group, wherein the other cyclic group may itself be a heterocyclic group, or a carbocyclic group.

As used herein, the term "nitrogen or sulfur containing heterocyclyl" means a heterocyclyl moiety that contains at least one nitrogen atom or at least one sulfur atom, or both a nitrogen atom and a sulfur atom within the ring structure. It is to be understood that other heteroatoms, including oxygen, may be present in addition to the nitrogen, sulfur, or combinations thereof. Examples of nitrogen or sulfur containing heterocyclyls include morpholinyl, thiomorpholinyl, thiazolyl, isothiazolyl, oxazolidinone 1,2 dithiolyl, piperidinyl, piperazinyl, and the like.

"Hydroxy" or "hydroxyl" refers to the group —OH. "Hydroxyalkyl" refers to an unbranched or branched alkyl group as defined above, wherein one or more hydrogen atoms are replaced by a hydroxyl.

"Nitro" refers to the group —$NO_2$.

"Sulfonyl" refers to the group —$S(O)_2R$, where R is a substituent, or a defined group.

"Alkylsulfonyl" refers to the group —$S(O)_2R$, where R is a substituent, or a defined group.

"Alkylsulfinyl" refers to the group —S(O)R, where R is a substituent, or a defined group.

"Thiocyanate"—SCN.

"Thiol" refers to the group —SR, where R is a substituent, or a defined group.

"Thioxo" or "thione" refer to the group (=S) or (S).

Certain commonly used alternative chemical names may be used. For example, a divalent group such as a divalent "alkyl" group, a divalent "aryl" group, etc., may also be referred to as an "alkylene" group or an "alkylenyl" group, an "arylene" group or an "arylenyl" group, respectively. Also, unless indicated explicitly otherwise, where combinations of groups are referred to herein as one moiety, e.g. arylalkyl, the last mentioned group contains the atom by which the moiety is attached to the rest of the molecule.

The terms "optional" or "optionally" means that the subsequently described event or circumstance may or may not occur, and that the description includes instances where said event or circumstance occurs and instances in which it does not. Also, the term "optionally substituted" refers to any one or more hydrogen atoms on the designated atom or group may or may not be replaced by a moiety other than hydrogen. "Optionally substituted" may be zero to the maximum number of possible substitutions, and each occurrence is independent. When the term "substituted" is used, then that substitution is required to be made at a substitutable hydrogen atom of the indicated substituent. An optional substitution may be the same or different from a (required) substitution.

When a moiety is "optionally substituted," and reference is made to a general term, such as any "alkyl," "alkenyl," "alkynyl," "haloalkyl," "cycloalkyl," "aryl" or "heteroaryl," then the general term can refer to any antecedent specifically recited term, such as ($C_{1-3}$ alkyl), ($C_{4-6}$ alkyl), —O($C_{1-4}$ alkyl), ($C_{3-10}$ cycloalkyl), O—($C_{3-10}$ cycloalkyl) and the like. For example, "any aryl" includes both "aryl" and "—O(aryl)" as well as examples of aryl, such as phenyl or naphthyl and the like. Also, the term "any heterocyclyl" includes both the terms "heterocyclyl" and O-(heterocyclyl)," as well as examples of heterocyclyls, such as oxetanyl, tetrahydropyranyl, morpholino, piperidinyl and the like. In the same manner, the term "any heteroaryl" includes the terms "heteroaryl" and "O-(heteroryl)," as well as specific heteroaryls, such as pyridine and the like.

Some of the compounds exist as tautomers. Tautomers are in equilibrium with one another. For example, amide containing compounds may exist in equilibrium with imidic acid tautomers. Regardless of which tautomer is shown, and regardless of the nature of the equilibrium among tautomers, the compounds are understood by one of ordinary skill in the art to comprise both amide and imidic acid tautomers. Thus, the amide containing compounds are understood to include their imidic acid tautomers. Likewise, the imidic acid containing compounds are understood to include their amide tautomers.

Any formula or structure given herein, is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2H$ (deuterium, D), $^3H$ (tritium), $^{11}C$, $^{13}C$, $^{14}C$, $^{15}N$, $^{18}F$, $^{31}P$, $^{32}P$, $^{35}S$, $^{36}Cl$ and $^{125}I$. Various isotopically labeled compounds of the present disclosure, for example those into which radioactive isotopes such as $^3H$, $^{13}C$ and $^{14}C$ are incorporated. Such isotopically labelled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of patients.

The disclosure also includes "deuterated analogues" of compounds of Formula I in which from 1 to n hydrogens attached to a carbon atom is/are replaced by deuterium, in which n is the number of hydrogens in the molecule. Such compounds exhibit increased resistance to metabolism and are thus useful for increasing the half-life of any compound of Formula I when administered to a mammal, particularly a human. See, for example, Foster, "Deuterium Isotope Effects in Studies of Drug Metabolism," Trends Pharmacol. Sci. 5(12):524-527 (1984). Such compounds are synthesized by means well known in the art, for example by employing starting materials in which one or more hydrogens have been replaced by deuterium.

Deuterium labelled or substituted therapeutic compounds of the disclosure may have improved DMPK (drug metabolism and pharmacokinetics) properties, relating to distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}F$ labeled compound may be useful for PET or SPECT studies. Isotopically labeled compounds of this disclosure and prodrugs thereof can generally be prepared by carrying out the procedures disclosed in the schemes or in the examples and preparations described below by substituting a readily available isotopically labeled reagent for a nonisotopically labeled reagent. It is understood that deuterium in this context is regarded as a substituent in the compound of Formula I.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition. Accordingly, in the compounds of this disclosure any atom specifically designated as a deuterium (D) is meant to represent deuterium.

In many cases, the compounds of this disclosure are capable of forming acid and/or base salts by virtue of the presence of amino and/or carboxyl groups or groups similar thereto.

Provided are also pharmaceutically acceptable salts, hydrates, solvates, tautomeric forms, polymorphs, and prodrugs of the compounds described herein. "Pharmaceutically acceptable" or "physiologically acceptable" refer to compounds, salts, compositions, dosage forms and other materials which are useful in preparing a pharmaceutical composition that is suitable for veterinary or human pharmaceutical use.

The term "pharmaceutically acceptable salt" of a given compound refers to salts that retain the biological effectiveness and properties of the given compound, and which are not biologically or otherwise undesirable. "Pharmaceutically acceptable salts" or "physiologically acceptable salts" include, for example, salts with inorganic acids and salts with an organic acid. In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare nontoxic pharmaceutically acceptable addition salts. Pharmaceutically acceptable acid addition salts may be prepared from inorganic and organic acids. Salts derived from inorganic acids include hydrochloric acid, hydrobromic acid, sulfuric acid, nitric acid, phosphoric acid, and the like. Salts derived from organic acids include acetic acid, propionic acid, glycolic acid, pyruvic acid, oxalic acid, malic acid, malonic acid, succinic acid, maleic acid, fumaric acid, tartaric acid, citric acid, benzoic acid, cinnamic acid, mandelic acid, methanesulfonic acid, ethanesulfonic acid, p-toluene-sulfonic acid, salicylic acid, and the like. Likewise, pharmaceutically acceptable base addition salts can be prepared from inorganic and organic bases. Salts derived from inorganic bases include, by way of example only, sodium, potassium, lithium, ammonium, calcium and magnesium salts. Salts derived from organic bases include, but are not limited to, salts of primary, secondary and tertiary amines, such as alkyl amines (i.e., $NH_2(alkyl)$), dialkyl amines (i.e., $HN(alkyl)_2$), trialkyl amines (i.e., $N(alkyl)_3$), substituted alkyl amines (i.e., $NH_2$(substituted alkyl)), di(substituted alkyl) amines (i.e., $HN$(substituted alkyl)$_2$), tri (substituted alkyl) amines (i.e., $N$(substituted alkyl)$_3$), alkenyl amines (i.e., $NH_2$(alkenyl)), dialkenyl amines (i.e., $HN(alkenyl)_2$), trialkenyl amines (i.e., $N(alkenyl)_3$), substituted alkenyl amines (i.e., $NH_2$(substituted alkenyl)), di(substituted alkenyl) amines (i.e., $HN$(substituted alkenyl)$_2$), tri(substituted alkenyl) amines (i.e., $N$(substituted alkenyl)$_3$, mono-, di- or tri-cycloalkyl amines (i.e., $NH_2$(cycloalkyl), $HN(cycloalkyl)_2$, $N(cycloalkyl)_3$), mono-, di- or tri-arylamines (i.e., $NH_2(aryl)$, $HN(aryl)_2$, $N(aryl)_3$), or mixed amines, etc. Specific examples of suitable amines include, by way of example only, isopropylamine, trimethyl amine, diethyl amine, tri(iso-propyl) amine, tri(n-propyl) amine, ethanolamine, 2-dimethylaminoethanol, piperazine, piperidine, morpholine, N-ethylpiperidine, and the like.

The term "substituted" means that any one or more hydrogen atoms on the designated atom or group is replaced with one or more substituents other than hydrogen, provided that the designated atom's normal valence is not exceeded. The one or more substituents include, but are not limited to, alkyl, alkenyl, alkynyl, alkoxy, acyl, amino, amido, amidino, aryl, azido, carbamoyl, carboxyl, carboxyl ester, cyano, guanidino, halo, haloalkyl, haloalkoxy, heteroalkyl, heteroaryl, heterocyclyl, hydroxy, hydrazino, imino, oxo, nitro, alkylsulfinyl, sulfonic acid, alkylsulfonyl, thiocyanate, thiol, thione, or combinations thereof. Polymers or similar indefinite structures arrived at by defining substituents with further substituents appended ad infinitum (e.g., a substituted aryl having a substituted alkyl which is itself substituted with a substituted aryl group, which is further substituted by a substituted heteroalkyl group, etc.) are not intended for inclusion herein. Unless otherwise noted, the maximum number of serial substitutions in compounds described herein is three. For example, serial substitutions of substituted aryl groups with two other substituted aryl groups are limited to ((substituted aryl)substituted aryl) substituted aryl. Similarly, the above definitions are not intended to include impermissible substitution patterns (e.g., methyl substituted with 5 fluorines or heteroaryl groups having two adjacent oxygen ring atoms). Such impermissible substitution patterns are well known to the skilled artisan. When used to modify a chemical group, the term "substituted" may describe other chemical groups defined herein. Unless specified otherwise, where a group is described as optionally substituted, any substituents of the group are themselves unsubstituted. For example, in some embodiments, the term "substituted alkyl" refers to an alkyl group having one or more substituents including hydroxyl, halo, alkoxy, cycloalkyl, heterocyclyl, aryl, and heteroaryl. In other embodiments, the one or more substituents may be further substituted with halo, alkyl, haloalkyl, hydroxyl, alkoxy, cycloalkyl, heterocyclyl, aryl, or heteroaryl, each of which is substituted. In other embodiments, the substituents may be further substituted with halo, alkyl, haloalkyl, alkoxy, hydroxyl, cycloalkyl, heterocyclyl, aryl, or heteroaryl, each of which is unsubstituted One skilled in the art will recognize that substituents and other moieties of the compounds of the generic formula herein should be selected in order to provide a compound which is sufficiently stable to provide a pharmaceutically useful compound which can be formulated into an acceptably stable pharmaceutical composition. Compounds which have such stability are contemplated as falling within the scope of the present invention. It should be understood by one skilled in the art that any combination of the definitions and substituents described above should not result in an inoperable species or compound.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

As used herein, "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions is contemplated. Supplementary active ingredients can also be incorporated into the compositions.

A "solvate" is formed by the interaction of a solvent and a compound. Solvates of salts of the compounds described herein are also provided. Hydrates of the compounds described herein are also provided.

Combinations

Patients being treated by administration of the IRAK4 inhibitors of the disclosure often exhibit diseases or conditions that benefit from treatment with other therapeutic agents. These diseases or conditions can be of an inflammatory nature or can be related to cancer, metabolic disorders, gastrointestinal disorders and the like. Thus, one aspect of the disclosure is a method of treating an inflammation related disease or condition, or a metabolic disorder, gastrointestinal disorder, or cancer and the like comprising administering a compound of the in combination with one or more compounds useful for the treatment of such diseases to a subject, particularly a human subject, in need thereof.

In some embodiments, a compound of the present disclosure is co-formulated with the additional one or more active ingredients. In some embodiments, the other active ingredient is administered at approximately the same time, in a separate dosage form. In some embodiments, the other active ingredient is administered sequentially, and may be administered at different times in relation to a compound of the present disclosure.

Combinations for Inflammatory Diseases and Conditions

For example, a compound of the present disclosure may be combined with one or more 5-Lipoxygenase inhibitors, Acetylcholinesterase inhibitors, ACTH receptor agonists, Activin receptor antagonists, Acyltransferase inhibitors, Adrenocorticotrophic hormone ligands, AKT1 gene inhibitors, Alkaline phosphatase modulators, Alkaline phosphatase stimulators, Androgen receptor agonists, Apolipoprotein $C_3$ antagonists, Bactericidal permeability protein stimulators, Beta adrenoceptor antagonists, Beta-glucuronidase inhibitors, B-lymphocyte antigen CD20 inhibitors, Bradykinin receptor modulators, BTK kinase inhibitors, Calcineurin inhibitors, Calcium channel inhibitors, Cannabinoid CB1 receptor modulators, Cannabinoid CB2 receptor modulators, Cannabinoid receptor antagonists, Cannabinoid receptor modulators, Cathepsin S inhibitors, CCN protein stimulators, CCR3 chemokine antagonists, CCR5 chemokine antagonists, CCR9 chemokine antagonists, CD3 modulators, CD40 ligand inhibitors, CD40 ligand receptor antagonists, CD49b antagonists, CD49d antagonists, CD89 agonists, Cell adhesion molecule inhibitors, Chemokine CXC ligand inhibitors, CHST15 gene inhibitors, Collagen modulators, CSF-1 agonists, CSF-1 antagonists, CXC10 chemokine ligand inhibitors, CXCR2 chemokine antagonists, Cyclic GMP phosphodiesterase inhibitors, Cyclooxygenase 2 inhibitors, Cyclooxygenase inhibitors, Cyclooxygenase stimulators, Cytochrome P450 3A4 inhibitors, Cytotoxic T-lymphocyte protein-4 stimulators, Dihydroceramide delta 4 desaturase inhibitors, Dihydroorotate dehydrogenase inhibitors, DNA polymerase inhibitors, EGFR family tyrosine kinase receptor modulators, Eosinophil peroxidase inhibitors, Eotaxin ligand inhibitors, EP4 prostanoid receptor agonists, Epidermal growth factor agonists, Epidermal growth factor ligands, Estrogen receptor beta agonists, Factor XIII agonists, FGF-10 ligands, FGF2 receptor agonists, Fractalkine ligand inhibitors, Free fatty acid receptor 2 antagonists, GATA 3 transcription factor inhibitors, Glucagon-like peptide 2 agonists, Glucocorticoid agonists, GM-CSF receptor agonists, G-protein coupled receptor 84 antagonists, Guanylate cyclase receptor agonists, Histamine H2 receptor antagonists, Histone acetyltransferase inhibitors, Histone deacetylase inhibitors, HLA class II antigen modulators, Hydrolase inhibitors, ICAM1 gene inhibitors, ICAM-1 inhibitors, IL1 gene inhibitors, IL-10 agonists, IL10 gene stimulators, IL-11 agonists, IL-12 antagonists, IL12 gene inhibitors, IL-13 antagonists, IL-17 antagonists, IL-2 antagonists, IL-2 receptor alpha subunit inhibitors, IL-21 antagonists, IL-23 antagonists, IL-6 antagonists, IL6 gene inhibitors, IL-6 receptor modulators, IL-7 antagonists, IL-8 antagonists, Immunoglobulin G1 agonists, Immunoglobulin G2 modulators, Inosine monophosphate dehydrogenase inhibitors, Insulin sensitizers, Integrin alpha-4/beta-1 antagonists, Integrin alpha-4/beta-7 antagonists, Integrin alpha-E antagonists, Integrin antagonists, Integrin beta-7 antagonists, Interferon beta ligands, Interleukin 17E ligand inhibitors, Interleukin ligand inhibitors, Interleukin receptor 17A antagonists, Interleukin receptor 17B antagonists, Interleukin-1 beta ligands, Interleukin-1 beta ligand modulators, Interleukin-6 ligand inhibitors, JAK tyrosine kinase inhibitors, Jak1 tyrosine kinase inhibitors, JAK2 gene inhibitors, Jak3 tyrosine kinase inhibitors, Jun N terminal kinase inhibitors, LanC like protein 2 modulators, Leukotriene BLT receptor antagonists, Lipoxygenase modulators, L-Selectin antagonists, MAdCAM inhibitors, Matrix metalloprotease inhibitors, Matrix metalloprotease modulators, Melanocortin agonists, Membrane copper amine oxidase inhibitors, Metalloprotease-2 inhibitors, Metalloprotease-9 inhibitors, MIP 3 alpha ligand inhibitors, Mitochondrial 10 kDa heat shock protein stimulators, Monocyte differentiation antigen CD14 inhibitors, mTOR inhibitors, Mucin stimulators, NAD-dependent deacetylase sirtuin-1 stimulators, Natriuretic peptide receptor C agonists, Neuregulin-4 ligands, Nicotinic acetylcholine receptor agonists, Nicotinic ACh receptor alpha 4 subunit modulators, Nicotinic ACh receptor alpha 7 subunit stimulators, Nicotinic ACh receptor beta 2 subunit modulators, NK1 receptor antagonists, NKG2 D activating NK receptor antagonists, Nuclear factor kappa B inhibitors, Opioid growth factor receptor agonists, Opioid receptor antagonists, Opioid receptor delta antagonists, Oxidoreductase inhibitors, P2X7 purinoceptor agonists, p38 MAP kinase inhibitors, PARP inhibitors, PDE 4 inhibitors, PDGF receptor agonists, Phagocytosis stimulating peptide modulators, Phospho MurNAc pentapeptide transferase inhibitors, Phospholipase A2 inhibitors, Platelet activating factor receptor antagonists, Potassium channel inhibitors, PPAR alpha agonists, PPAR delta agonists, PPAR gamma agonists, Protein CYR61 stimulators, Protein fimH inhibitors, Protein kinase C alpha inhibitors, Protein kinase C beta inhibitors, Protein kinase C delta inhibitors, Protein kinase C epsilon inhibitors, Protein kinase C eta inhibitors, Protein kinase C theta inhibitors, Protein kinase G inhibitors, Protein kinase inhibitors, P-selectin glycoprotein ligand-1 inhibitors, PurH purine biosynthesis protein inhibitors, Retinoic acid receptor alpha agonists, Retinoic acid receptor beta agonists, Retinoid receptor agonists, RNA polymerase inhibitors, SMAD-7 inhibitors, Sodium channel inhibitors, Somatostatin receptor agonists, Sphingosine 1 phosphate phosphatase 1 stimulators, Sphingosine 1 phosphate phosphatase modulators, Sphingosine kinase 1 inhibitors, Sphingosine kinase 2 inhibitors, Sphingosine-1-phosphate receptor-1 agonists, Sphingosine-1-phosphate receptor-1 antagonists, Sphingosine-I-phosphate receptor-1 modulators, Sphingosine-1-phosphate receptor-5 modulators, STAT3 gene inhibitors, STAT-3 inhibitors, STAT-4 inhibitors, Stem cell antigen-1 inhibitors, Superoxide dismutase modulators, Superoxide dismutase stimulators, SYK kinase inhibitors, T cell surface glycoprotein CD28 inhibitors, TGF beta 1 ligand inhibitors, Thymulin agonists, TLR-2 antagonists, TLR-4 antagonists, TLR-9 agonists, TNF alpha ligand inhibitors, TNF alpha ligand modulators, TNF antagonists, TPL2 kinase inhibitors, Trefoil factor modulators, Tryptase inhibitors, Tryptophan 5-hydroxylase inhibitors, Tumor necrosis factor 14 ligand modulators, TYK2 kinase inhibitors, Type I TNF receptor antagonists, Type II TNF receptor modulators, Unspecified growth factor receptor modulators, Vanilloid VR1 agonists, Vitamin D3 receptor agonists, Zonulin inhibitors, abatacept; acemannan; adalimumab; DCCT-10; apremilast; AST-120; balsalazide; balsalazide sodium; basiliximab; beclomethasone dipropionate; budesonide; D-9421; budesonide MMX; catridecacog; certolizumab pegol; *Clostridium butyricum*; etanercept; fingolimod; glatiramer acetate; golimumab; infliximab; infliximab biosimilar; infliximab follow-on biologic; interferon beta-la, Biogen; lenalidomide; mesalazine; GED-0001; AJG-501; metenkefalin acetate with tridecactide acetat, mycophenolate mofetil; naltrexone; natalizumab; nitazoxanide; olsalazine; oprelvekin; propionyl-L-carnitine; recombinant interferon beta-la, Serono; remestemcel-L; rifaximin; rituximab; ropivacaine; rosiglitazone; sargramostim; secukinumab; SPD-480; tacrolimus; tamibarotene; teduglutide; thalidomide; tocilizumab; RO-4877533; tofacitinib; CP-690550; *Trichuris suis* ova; ASP-1002; ustekinumab; valganciclovir; vedolizumab; zileuton; anti-CD3 imaging agent (antibody fragment, cancer/autoimmune disease), ImaginAb; AVX-470; ciclosporin; CXCR1/2 ligands mAb (immunology), Eli Lilly; FFP-102; GSK-3050002; INN-108; IR-777; SGM-1019; peg-ilodecakin; PF-06480605; PF-06651600; SER-287; Syn-1002; Thetanix; tolerogenic dendritic cell therapy (injectable, Crohns disease), Hospital Clinic of Barcelona/Fundacio Clinic; TOP-1288; VBY-036; VBY-129; 946414-98-8; BMS-936557; 99mTc-annexin V-128; ABC-294640; abrilumab; Alequel; AMG-139; amiselimod; APD-334; ASP-3291; beclomethasone dipropionate; bertilimumab; ciclosporin; clazakizumab; DLX-105; dolcanatide; E-6011; ETX-201; FFP-104; filgotinib; foralumab; GED-0507-34-Levo; givinostat; GLPG-0974; GLPG-1205; iberogast N (ulcerative colitis), Bayer; BAY98-7410; INV-103; JNJ-40346527; K(D)PT; KAG-308; KHK-4083; KRP-203; larazotide acetate; CB-01-05-MMX; LY-3074828; mesalamine with N-acetylcysteine; midismase; molgramostim follow on biologic with fosfomycin with carbapenem (intraintestinal, Crohn's disease), Reponex; multipotent adult progenitor cell therapy (ischemia/cerebral palsy), Athersys/Healios; NN-8828; olokizumab; OvaSave; P-28-GST; PDA-002; PF-4236921; PF-547659; prednisolone; PUR-0110; QBECO; RBX-2660; repurposed naltrexone (low dose, liver disease, Crohn's disease), TaiwanJ; JKB-122; SB-012; sotrastaurin; STNM-01; TAK-114; tetomilast; Debio-0512; TRK-170; TRX-318; vatelizumab; VB-201; ZP-1848; zucapsaicin; ABT-494; alicaforsen; Ampion; BI-655066; briakinumab; cannabidiol; carotegast methyl; cobitolimod; dexamethasone sodium phosphate; elafibranor; etrolizumab; GS-5745; HMPL-004; LP-02; mesalazine; metronidazole mongersen; ocrelizumab; ozanimod; peficitinib; RHB-104; rifaximin; tildrakizumab; tralokinumab; brodalumab; laquinimod; plecanatide; telotristat etiprate; infliximab biosimilar, Samsung Bioepis; AZD-058; and rifabutin with clarithromycin and further with clofazimine.

Also, the following non-exhaustive list of classes of compounds and compounds may be combined with a compound of the present disclosure: 5-Lipoxygenase inhibitors, such as zileuton, etalocibm FPL-64170, E-3040, and BU-4601A; Acetylcholinesterase inhibitors, such as BL-7040; ACTH receptor agonists, such as metenkefalin acetate with tridecactide acetate, and FAR-404; Activin receptor antagonists such as follistatin; Acyltransferase inhibitors such as AZD-0585; Adrenocorticotrophic hormone ligands, such as metenkefalin acetate with tridecactide acetate, and FAR-404; AKT1 gene inhibitors, such as vidofludimus; Alkaline phosphatase modulators such as recombinant human alkaline phosphatase (oral, ulcerative colitis), AM-Pharma; Alkaline phosphatase stimulators such as bovine alkaline phosphatase; Androgen receptor agonists, such as PB-005; Apolipoprotein $C_3$ antagonists, such as AZD-0585; Bactericidal permeability protein stimulators, such as opebacan; Beta adrenoceptor antagonists, such as NM-001; Beta-glucuronidase inhibitors, such as KD-018; B-lymphocyte antigen CD20 inhibitors, such as ocrelizumab, rituximab; Bradykinin receptor modulators, such as givinostat; Calcineurin inhibitors, such as tacrolimus, ciclosporin; Calcium channel inhibitors, such as clotrimazole; Cannabinoid CB1 receptor modulators, such as GWP42003-P, cannabidiol; Cannabinoid CB2 receptor modulators, such as GWP42003-P, cannabidiol; Cannabinoid receptor antagonists, such as fingolimod; Cannabinoid receptor modulators, such as GWP42003-P, cannabidiol; Cathepsin S inhibitors, such as VBY-129, VBY-036; CCN protein stimulators, such as CSA-13; CCR3 chemokine antagonists, such as bertilimumab; CCR5 chemokine antagonists, such as HGS-1025; CCR9 chemokine antagonists, such as MLN-3126, vercirnon, CCX-025; CD3 modulators, such as visilizumab; CD40 ligand inhibitors, such as FFP-104; CD40 ligand receptor antagonists, such as FFP-104, FFP-102, toralizumab; CD49b antagonists, such as vatelizumab; CD49d antagonists, such as ELND-004; CD89 agonists, such as HF-1020; Cell adhesion molecule inhibitors, such as natalizumab, alicaforsen (intravenous), ASP-2002, ISIS-2302; Chemokine CXC ligand inhibitors, such as CXCR1/2 ligands mAb (immunology), Eli Lilly; CHST15 gene inhibitors, such as STNM-01; Collagen modulators, such as adipose-derived stem cell therapy (Celution System), Cytori, DCCT-10; CSF-1 agonists, such as sargramostim, molgramostim follow on biologic with fosfomycin with carbapenem (intraintestinal, Crohn's disease), Reponex; CSF-1 antagonists, such as JNJ-40346527; CXC10 chemokine ligand inhibitors, such as 946414-98-8, BMS-936557; CXCR2 chemokine antagonists, such as elubrixin; Cyclic GMP phosphodiesterase inhibitors, such as CEL-031; Cyclooxygenase 2 inhibitors, such as P-54; Cyclooxygenase inhibitors, such as mesalazine, 4-aminosalicylate sodium, AJG-501, AGI-022; Cyclooxygenase stimulators, such as nicotine polacrilex; Cytochrome P450 3A4 inhibitors, such as KD-018; Cytotoxic T-lymphocyte protein-4 stimulators, such as abatacept; Dihydroceramide delta 4 desaturase inhibitors, such as ABC-294640; Dihydroorotate dehydrogenase inhibitors, such as vidofludimus; DNA polymerase inhibitors, such as valganciclovir; EGFR family tyrosine kinase receptor modulators, such as neuregulin 4 (Crohn's disease/ulcerative colitis/necrotizing enterocolitis), Avexegen Therapeutics/Children's Hospital of Los Angeles; Eosinophil peroxidase inhibitors, such as AWEPOPD-01, AWEPO-003; Eotaxin ligand inhibitors, such as bertilimumab; EP4 prostanoid receptor agonists, such as KAG-308; Epidermal growth factor agonists, such as heparin-EGF-like factor, Scios Nova; Epidermal growth factor ligands, such as Hebervis; Estrogen receptor beta agonists, such as prinaberel; Factor XIII agonists, such as catridecacog; FGF-10 ligands, such as repifermin; FGF2 receptor agonists, such as F2A; Fractalkine ligand inhibitors, such as E-6011; Free fatty acid receptor 2 antagonists, such as GLPG-0974; GATA 3 transcription factor inhibitors, such as SB-012; Glucagon-like peptide 2 agonists, such as teduglutide, ZP-1848, NB-1002; Glucocorticoid agonists, such as budesonide, beclomethasone dipropionate, dexamethasone sodium phosphate, AJG-511, DOR-201, D-9421-C; GM-CSF receptor agonists, such as sargramostim, molgramostim follow on biologic with fosfomycin with carbapenem (intraintestinal, Crohn's disease), Reponex; G-protein coupled receptor 84 antagonists, such as GLPG-1205; Guanylate cyclase receptor agonists, such as dolcanatide, SP-333; Histamine H2 receptor antagonists, such as bismuth, Medeva; Histone acetyltransferase inhibitors, such as TIP60 inhibitors (ulcerative colitis/inflammatory bowel disease/autoimmune diseases), University of Pennsylvania; Histone deacetylase inhibitors, such as givinostat; HLA class II antigen modulators, such as HLA class II protein modulators (Crohns disease), Nextera AS; Hydrolase inhibitors, such as SC-56938; ICAM1 gene inhibitors, such as alicaforsen; ICAM-1 inhibitors, such as alicaforsen (intravenous), ISIS-2302; IL1 gene inhibitors, such as PLR-14; IL-10 agonists, such as peg-ilodecakin, AM-0010; IL10 gene stimulators, such as gene therapy (IL-10), Imperial College; IL-11 agonists, such as oprelvekin, YM-294; IL-12 antagonists, such as ustekinumab, briakinumab, apilimod; IL12 gene inhibitors, such as RDP-58; IL-13 antagonists, such as tralokinumab, anrukinzumab; IL-17 antagonists, such as secukinumab, vidofludimus; IL-2 antagonists, such as daclizumab; IL-2 receptor alpha subunit inhibitors, such as basiliximab, daclizumab, BSX-003, Ro-34-7375; IL-21 antagonists, such as NN-8828, ATR-107; IL-23 antagonists, such as tildrakizumab, ustekinumab, BI-655066, AMG-139, briakinumab, LY-3074828, apilimod; IL-6 antagonists, such as tocilizumab, clazakizumab, olokizumab, HMPL-004, AMG-220, FM-101; IL6 gene inhibitors, such as YSIL6-T-PS; IL-6 receptor modulators, such as tocilizumab; IL-7 antagonists, such as interleukin-7 receptor modulators (ulcerative colitis/T-cell acute lymphoblastic leukaemia), Effimune; IL-8 antagonists, such as elubrixin, clotrimazole; Immunoglobulin G1 agonists, such as HF-1020; Immunoglobulin G2 modulators, such as PF-547659; Inosine monophosphate dehydrogenase inhibitors, such as mycophenolate mofetil; Insulin sensitizers, such as elafibranor, rosiglitazone, HE-3286, EGS-21; Integrin alpha-4/beta-1 antagonists, such as natalizumab, TRK-170, firategrast; Integrin alpha-4/beta-7 antagonists, such as etrolizumab, vedolizumab, abrilumab, carotegast methyl, TRK-170, firategrast; Integrin alpha-E antagonists, such as etrolizumab; Integrin antagonists, such as vatelizumab, ASP-2002; Integrin beta-7 antagonists, such as etrolizumab; Interferon beta ligands, such as interferon beta-1a, recombinant interferon beta-1a, Serono; Interleukin 17E ligand inhibitors, such as anti-IL-17BR humanized antibody (lung fibrosis/asthma/ulcerative colitis), Medical Research Council Technology; Interleukin ligand inhibitors, such as HE-3286; Interleukin receptor 17A antagonists, such as brodalumab; Interleukin receptor 17B antagonists, such as anti-IL-17BR humanized antibody (lung fibrosis/asthma/ulcerative colitis), Medical Research Council Technology; Interleukin-1 beta ligands, such as K(D)PT, PUR-0110, HMPL-004; Interleukin-1 beta ligand modulators, such as PUR-0110, HMPL-004; Interleukin-6 ligand inhibitors, such as PF-4236921; JAK tyrosine kinase inhibitors, such as tofacitinib, peficitinib; Jak1 tyrosine kinase inhibitors, such as ABT-494, tofacitinib, filgotinib, peficitinib, GLPG-0555, solcitinib; JAK2 gene inhibitors, such as vidofludimus; Jak3 tyrosine kinase inhibitors, such as tofacitinib, peficitinib; Jun N terminal kinase inhibitors, such as semapimod; LanC like protein 2 modulators, such as BT-11; Leukotriene BLT receptor antagonists, such as ONO-4057, etalocib, SC-53228, SC-52798; Lipoxygenase modulators, such as mesalazine; L-Selectin antagonists, such as BNP-001; MAdCAM inhibitors, such as vedolizumab, PF-547659; Matrix metalloprotease inhibitors, such as D-5410; Matrix metalloprotease modulators, such as D-5410; Melanocortin agonists, such as ASP-3291; Membrane copper amine oxidase inhibitors, such as vepalimomab; Metalloprotease-2 inhibitors, such as KD-018, RWJ-68354; Metalloprotease-9 inhibitors, such as GS-5745; MIP 3 alpha ligand inhibitors, such as GSK-3050002; Mitochondrial 10 kDa heat shock protein stimulators, such as INV-103; Monocyte differentiation antigen CD14 inhibitors, such as CD14 anti-inflammatory, Cornell; mTOR inhibitors, such as P-2281; Mucin stimulators, such as rebamipide; NAD-dependent deacetylase sirtuin-1 stimulators, such as SRT-2104; Natriuretic peptide receptor C agonists, such as plecanatide; Neuregulin-4 ligands, such as neuregulin 4 (Crohn's disease/ulcerative colitis/necrotizing enterocolitis), Avexegen Therapeutics/Children's Hospital of Los Angeles; Nicotinic acetylcholine receptor agonists, such as TC-2403, nicotine polacrilex, nicotine; Nicotinic ACh receptor alpha 4 subunit modulators, such as TC-2403; Nicotinic ACh receptor alpha 7 subunit stimulators, such as GTS-21; Nicotinic ACh receptor beta 2 subunit modulators, such as TC-2403; NK1 receptor antagonists, such as KD-018, nolpitantium besilate; NKG2 D activating NK receptor antagonists, such as NNC-0142-002; Nuclear factor kappa B inhibitors, such as KD-018, cobitolimod, CSA-13, HE-3286, HMPL-004, Avrina, mesalamine with N-acetylcysteine, P-54; Opioid growth factor receptor agonists, such as metenkefalin acetate with tridecactide acetate, FAR-404; Opioid receptor antagonists, such as naltrexone, IRT-103; Opioid receptor delta antagonists, such as KD-018; Oxidoreductase inhibitors, such as olsalazine; P2X7 purinoceptor agonists, such as givinostat; p38 MAP kinase inhibitors, such as RDP-58, doramapimod, semapimod, RWJ-68354; PARP inhibitors, such as EB-47, INO-1003; PDE 4 inhibitors, such as apremilast, tetomilast, CC-1088; PDGF receptor agonists, such as oprelvekin, YM-294; Phagocytosis stimulating peptide modulators, such as 99mTc-RP-128; Phospho MurNAc pentapeptide transferase inhibitors, such as SQ-641; Phospholipase A2 inhibitors, such as varespladib methyl; Platelet activating factor receptor antagonists, such as dersalazine sodium; Potassium channel inhibitors, such as clotrimazole; PPAR alpha agonists, such as elafibranor (GFT-1007); PPAR delta agonists, such as elafibranor (GFT-1007); PPAR gamma agonists, such as rosiglitazone, GED-0507-34-Levo, etalocib; Protein CYR61 stimulators, such as CSA-13; Protein fimH inhibitors, such as EB-8018; Protein kinase C alpha inhibitors, such as sotrastaurin (AEB-071); Protein kinase C beta inhibitors, such as sotrastaurin (AEB-071); Protein kinase C delta inhibitors, such as sotrastaurin (AEB-071); Protein kinase C epsilon inhibitors, such as sotrastaurin (AEB-071); Protein kinase C eta inhibitors, such as sotrastaurin (AEB-071); Protein kinase C theta inhibitors, such as sotrastaurin (AEB-071); Protein kinase G inhibitors, such as CEL-031; Protein kinase inhibitors, such as TOP-1288; P-selectin glycoprotein ligand-1 inhibitors, such as SEL-K2; PurH purine biosynthesis protein inhibitors, such as mycophenolate mofetil; Retinoic acid receptor alpha agonists, such as tamibarotene; Retinoic acid receptor beta agonists, such as tamibarotene; Retinoid receptor agonists, such as tamibarotene; RNA polymerase inhibitors, such as rifaximin; SMAD-7 inhibitors, such as mongersen (GED-0301); Sodium channel inhibitors, such as ropivacaine; Somatostatin receptor agonists, such as vapreotide; Sphingosine 1 phosphate phosphatase 1 stimulators, such as APD-334; Sphingosine 1 phosphate phosphatase modulators, such as SiP modulators (oral, multiple sclerosis/ulcerative colitis/rheumatoid arthritis), Akaal Pharma; Sphingosine kinase 1 inhibitors, such as ABC-294640; Sphingosine kinase 2 inhibitors, such as ABC-294640; Sphingosine-1-phosphate receptor-1 agonists, such as ozanimod (RPC-1063), KRP-203; Sphingosine-1-phosphate receptor-1 antagonists, such as amiselimod (MT-1303); Sphingosine-1-phosphate receptor-1 modulators, such as fingolimod (FTY-720), ozanimod (RPC-1063), amiselimod (MT-1303); Sphingosine-1-phosphate receptor-5 modulators, such as ozanimod; STAT3 gene inhibitors, such as vidofludimus; STAT-3 inhibitors, such as TAK-114; STAT-4 inhibitors, such as STAT-4 antisense oligonucleotide (Crohns disease/colitis), NIAID; Stem cell antigen-1 inhibitors, such as Ampion, DMI-9523; Superoxide dismutase modulators, such as midismase, LT-0011; Superoxide dismutase stimulators, such as superoxide dismutase; T cell surface glycoprotein CD28 inhibitors, such as abatacept; TGF beta 1 ligand inhibitors, such as mongersen, GED-0301; Thymulin agonists, such as Syn-1002; TLR-2 antagonists, such as VB-201; TLR-4 antagonists, such as JKB-122, VB-201; TLR-9 agonists, such as BL-7040, cobitolimod; TNF alpha ligand inhibitors, such as adalimumab, certolizumab pegol, infliximab biosimilar, infliximab, golimumab, ISIS-104838, CSA-13, DLX-105, adalimumab biosimilar, dersalazine sodium, Debio-0512, HMPL-004, DLX-105, infliximab follow-on biologic, AZD-9773, CYT-020-TNFQb, DOM-0200; TNF alpha ligand modulators, such as PUR-0110, CDP-571; TNF antagonists, such as etanercept, certolizumab pegol, AVX-470, onercept; Trefoil factor modulators, such as AG-012; Tryptase inhibitors, such as APC-2059; Tryptophan 5-hydroxylase inhibitors, such as telotristat etiprate; Tumor necrosis factor 14 ligand modulators, such as SAR-252067; Type I TNF receptor antagonists, such as DOM-0100; Type II TNF receptor modulators, such as etanercept; Unspecified growth factor receptor modulators, such as AP-005; Vanilloid VR1 agonists, such as zucapsaicin; Vitamin D3 receptor agonists, such as calcitriol; and Zonulin inhibitors, such as larazotide acetate, AT-1001.

Also, the following non-exhaustive list of classes of compounds and compounds may be combined with a compound of the present disclosure: 14-3-3 protein eta inhibitors, 5-Lipoxygenase inhibitors, Abl tyrosine kinase inhibitors, ACTH receptor agonists, Adenosine A3 receptor agonists, Adenosine deaminase inhibitors, ADP ribosyl cyclase-1 modulators, ADP ribosylation factor 6 inhibitors, Adrenocorticotrophic hormone ligands, Aggrecanase-2 inhibitors, Albumin modulators, AP1 transcription factor inhibitors, Basigin inhibitors, Bcr protein inhibitors, B-lymphocyte antigen CD19 inhibitors, B-lymphocyte antigen CD20 inhibitors, B-lymphocyte antigen CD20 modulators, B-lymphocyte stimulator ligand inhibitors, Bradykinin receptor modulators, BRAF gene inhibitors, Branched amino acid aminotransferase 1 inhibitors, Bromodomain containing protein inhibitors, Btk tyrosine kinase inhibitors, Cadherin-11 antagonists, Calcineurin inhibitors, Calcium channel inhibitors, Carbonic anhydrase inhibitors, Cathepsin K inhibitors, Cathepsin S inhibitors, CCR1 chemokine antagonists, CCR2 chemokine antagonists, CCR3 gene modulators, CCR5 chemokine antagonists, CD126 antagonists, CD29 modulators, CD3 modulators, CD39 agonists, CD4 agonists, CD4 antagonists, CD40 ligand inhibitors, CD40 ligand receptor antagonists, CD40 ligand receptor modulators, CD52 antagonists, CD73 agonists, CD79b modulators, CD80 antagonists, CD86 antagonists, CD95 antagonists, Cell adhesion molecule inhibitors, Choline kinase inhibitors, Clusterin stimulators, Complement C5 factor inhibitors, Complement Factor stimulators, C-reactive protein inhibitors, CSF-1 antagonists, CXC10 chemokine ligand inhibitors, CXCR4 chemokine antagonists, Cyclin-dependent kinase inhibitor 1 inhibitors, Cyclin-dependent kinase-2 inhibitors, Cyclin-dependent kinase-4 inhibitors, Cyclin-dependent kinase-5 inhibitors, Cyclin-dependent kinase-6 inhibitors, Cyclin-dependent kinase-7 inhibitors, Cyclin-dependent kinase-9 inhibitors, Cyclooxygenase 2 inhibitors, Cyclooxygenase 2 modulators, Cyclooxygenase inhibitors, Cytosolic phospholipase A2 inhibitors, Cytotoxic T-lymphocyte protein-4 modulators, Cytotoxic T-lymphocyte protein-4 stimulators, DHFR inhibitors, Diamine acetyltransferase inhibitors, Dihydroorotate dehydrogenase inhibitors, Elongation factor 2 inhibitors, Eotaxin 2 ligand inhibitors, EP4 prostanoid receptor antagonists, Erythropoietin receptor agonists, Fas ligands, FGF-2 ligand inhibitors, FK506 binding protein-12 modulators, Folate antagonists, Folate receptor agonists, Folate receptor beta antagonists, Folate receptor modulators, Fractalkine ligand inhibitors, Fyn tyrosine kinase inhibitors, G protein coupled receptor 15 antagonists, GABA A receptor modulators, Glucocorticoid agonists, Glucocorticoid antagonists, Glucocorticoid induced leucine zipper stimulators, GM-CSF ligand inhibitors, GM-CSF receptor antagonists, GM-CSF receptor modulators, Growth regulated protein alpha ligand inhibitors, Hwith Kwith ATPase inhibitors, Histamine H4 receptor antagonists, Histone deacetylase inhibitors, Histone deacetylase-6 inhibitors, HIV-1 gp120 protein inhibitors, HLA class II antigen DQ-2 alpha modulators, HLA class II antigen inhibitors, HLA class II antigen modulators, Hsp 70 family inhibitors, Hypoxia inducible factor-1 inhibitors, IFNB gene stimulators, I-kappa B kinase beta inhibitors, I-kappa B kinase inhibitors, IL-1 antagonists, IL-10 agonists, IL-11 agonists, IL-12 antagonists, IL-15 antagonists, IL-17 antagonists, IL-17 receptor modulators, IL-2 agonists, IL-2 antagonists, IL-21 antagonists, IL-23 antagonists, IL-3 antagonists, IL-4 agonists, IL-6 antagonists, IL-6 receptor modulators, Immunoglobulin antagonists, Immunoglobulin G1 agonists, Immunoglobulin G1 antagonists, Immunoglobulin G1 modulators, Immunoglobulin G2 antagonists, Immunoglobulin G2 modulators, Immunoglobulin gamma Fc receptor II modulators, Immunoglobulin gamma Fc receptor IIB antagonists, Immunoglobulin kappa modulators, Immunoglobulin M antagonists, Inducible nitric oxide synthase inhibitors, Inosine monophosphate dehydrogenase inhibitors, Insulin sensitizers, Integrin alpha-1/beta-1 antagonists, Integrin alpha-4/beta-1 antagonists, Integrin antagonists, Interferon beta ligands, Interferon gamma ligands, Interleukin 17A ligand inhibitors, Interleukin 17F ligand inhibitors, Interleukin 23A inhibitors, Interleukin ligands, Interleukin receptor 17A antagonists, Interleukin-1 beta ligand inhibitors, Interleukin-10 ligands, Interleukin-2 ligands, Interleukin-4 ligands, Interleukin-6 ligand inhibitors, Itk tyrosine kinase inhibitors, JAK tyrosine kinase inhibitors, Jak1 tyrosine kinase inhibitors, Jak2 tyrosine kinase inhibitors, JAK3 gene inhibitors, Jak3 tyrosine kinase inhibitors, Jun N terminal kinase inhibitors, KCNA voltage-gated potassium channel-3 modulators, Kelch like ECH associated protein 1 modulators, Kit tyrosine kinase inhibitors, LanC like protein 2 modulators, LITAF gene inhibitors, Lymphocyte function antigen-3 receptor antagonists, Lyn tyrosine kinase inhibitors, Macrophage mannose receptor 1 modulators, MAdCAM inhibitors, MAP kinase modulators, MAP3K2 gene inhibitors, MAPKAPK5 inhibitors, Matrix metalloprotease inhibitors, MCL1 gene inhibitors, MEK protein kinase inhibitors, MEK-1 protein kinase inhibitors, MEK-2 protein kinase inhibitors, Membrane copper amine oxidase inhibitors, Metalloprotease-2 inhibitors, Metalloprotease-9 inhibitors, Midkine ligand inhibitors, Mitochondrial 10 kDa heat shock protein stimulators, mTOR complex 1 inhibitors, mTOR inhibitors, NAD ADP ribosyltransferase stimulators, NAMPT gene inhibitors, NF kappa B inhibitor stimulators, NFAT gene inhibitors, NFE2L2 gene stimulators, Nicotinic acetylcholine receptor antagonists, NK cell receptor modulators, NKG2 A B activating NK receptor antagonists, NKG2 D activating NK receptor antagonists, Nuclear erythroid 2-related factor 2 stimulators, Nuclear factor kappa B inhibitors, Nuclear factor kappa B modulators, Nuclear factor kappa B p105 inhibitors, Opioid growth factor receptor agonists, Opioid receptor delta antagonists, Osteoclast differentiation factor antagonists, Osteoclast differentiation factor ligand inhibitors, Oxidoreductase inhibitors, P2X7 purinoceptor agonists, p38 MAP kinase alpha inhibitors, p38 MAP kinase inhibitors, PDE 4 inhibitors, PDE 5 inhibitors, PDGF receptor agonists, PDGF receptor antagonists, PDGF-B ligand inhibitors, PERK gene inhibitors, Phosphoinositide-3 kinase delta inhibitors, Phosphoinositide-3 kinase gamma inhibitors, Phospholipase A2 inhibitors, Platelet activating factor receptor antagonists, PPAR gamma agonists, Programmed cell death protein 1 modulators, Prostaglandin D synthase stimulators, Protein arginine deiminase inhibitors, Protein tyrosine kinase inhibitors, PurH purine biosynthesis protein inhibitors, Rho associated protein kinase 2 inhibitors, Seprase inhibitors, Signal transducer CD24 modulators, Signal transduction inhibitors, Sodium glucose transporter-2 inhibitors, Sphingosine 1 phosphate phosphatase modulators, STAT3 gene inhibitors, Superoxide dismutase stimulators, SYK family tyrosine kinase inhibitors, Syk tyrosine kinase inhibitors, Syndecan-1 inhibitors, T cell receptor antagonists, T cell receptor modulators, T cell surface glycoprotein CD28 inhibitors, T cell surface glycoprotein CD28 stimulators, TAK1 binding protein modulators, Talin modulators, T-cell differentiation antigen CD6 inhibitors, T-cell surface glycoprotein CD8 inhibitors, Tenascin modulators, TGF beta agonists, Thymulin agonists, TLR-2 antagonists, TLR-4 antagonists, TLR-9 antagonists, TNF alpha ligand inhibitors, TNF alpha ligand modulators, TNF antagonists, TNF gene inhibitors, TNF receptor modulators, TNFSF11 gene inhibitors, Transcription factor p65 inhibitors, Transcription factor RelB inhibitors, Transferrin modulators, Tumor necrosis factor 13C receptor antagonists, Tumor necrosis factor 15 ligand inhibitors, Tumor necrosis factor ligand 13 inhibitors, Tumor necrosis factor ligand inhibitors, Type I IL-1 receptor antagonists, Type I TNF receptor antagonists, Type II TNF receptor modulators, Unspecified GPCR agonists, VEGF receptor antagonists, VEGF-2 receptor antagonists, VEGF-2 receptor modulators, VEGF-B ligand inhibitors, X-linked inhibitor of apoptosis protein inhibitors, Zap70 tyrosine kinase inhibitors, 99mTc labelled annexin V-128, abatacept, abatacept biosimilar, ABBV-257, ABT-122, ABT-494, acalabrutinib, aceclofenac, actarit, MS-392, adalimumab, adalimumab biosimilar, adalimumab follow-on biologic, AK-106, ALX-0061, aminopterin, anakinra, anakinra biosimilar, anakinra follow-on biologic, ARG-301, ASLAN-003, ASP-5094, AT-132, AZD-9567, baricitinib, BI-655064, bimekizumab, BiP (rheumatoid arthritis), Kings College London, BLHP-006, blisibimod, BMS-986104, BMS-986142, ABBV-105, BTT-1023, canakinumab, Cartistem, CCX-354, CD24-IgFc, celecoxib, cerdulatinib, certolizumab pegol, CF-101, CFZ-533, CHR-5154, cibinetide, ciclosporin, clazakizumab, CNTO-6785, corticotropin, Mallinckrodt, CR-6086, CreaVax-RA, CWG-92, CWG-940, Cx-611, DE-098, deflazacort, Rheumavax, denosumab, diacerein, diclofenac, E-6011, eicosapentaenoic acid monoglycerides, etanercept, etanercept biosimilar, etanercept follow-on biologic, etodolac, etoricoxib, filgotinib, fosdagrocorat, gerilimzumab, ginsenoside C-K, givinostat, goat polyclonal antibodies, golimumab, GS-5745, GS-9876, GSK-3196165, HM-71224, HMPL-523, hyaluronate sodium, IB-RA (injectable, rheumatoid arthritis), Innobioscience, IB-RA (oral, rheumatoid arthritis), Innobioscience, iguratimod, IMD-2560, imidazole salicylate, infliximab, infliximab biobetter, infliximab biosimilar, INSIX RA, interferon gamma follow-on biologic, interleukin-2 (injectable), interleukin-2 follow-on biologic, INV-103, IR-501, itolizumab, JNJ-40346527, Ka Shu Ning, KD-025, ketoprofen with omeprazole, leflunomide, lenzilumab, LLDT-8, lumiracoxib, LY-3090106, masitinib, mavrilimumab, MBS-2320, MEDI-5117, meloxicam, methotrexate, MGD-010, misoprostol with diclofenac, MM-A01-01, monalizumab, MORAb-022, MPC-300-IV, MRC-375, nabumetone, namilumab, naproxen with esomeprazole, naproxen with esomeprazole strontium, ocaratuzumab, ofatumumab, OHR-118, olokizumab, OM-89, once-daily naproxen (oral controlled release, pain), Alvogen, ONO-4059, Oralgam, ozoralizumab, peficitinib, pelubiprofen, PF-06687234, piperidone hydrochloridum, piroxicam, prednisolone, prednisone, Prosorba, PRT-2607, PRTX-100, PRX-167700, QBSAU, rabeximod, RCT-18, recombinant human CD22 monoclonal antibody (iv infusion), Lonn Ryonn Pharma/SinoMab Bioscience (Shenzhen), recombinant human interleukin-1 receptor antagonist (rheumatoid arthritis), Shanghai Fudan-Zhangjiang Bio-Pharmaceutical, recombinant human interleukin-2 recombinant TNF receptor 2-Fc fusion protein mutant, RG-6125, RhuDex, rifabutin with clarithromycin with clofazimine, rituximab, rituximab biosimilar, rituximab follow-on biologic, RPI-78, SAN-300, sarilumab, SBI-087, seliciclib, SHR-0302, sirukumab, spebrutinib, SSS-07, KDDF-201110-06, Syn-1002, T-5224, TAB-08, tacrolimus, TAK-020, TAK-079, tarenflurbil (transdermal spraygel, skin disease/rheumatoid arthritis), MIKA Pharma/GALENpharma, technetium Tc 99m tilmanocept, technetium[99Tc] methylenediphosphonate, tenoxicam, Debio-0512, tocilizumab, tofacitinib, *Trichuris suis* ova, umbilical cord-derived mesenchymal stem cells (iv, RA/liver disease), Alliancells/Zhongyuan Union, ustekinumab, VAY-736, VB-201, WF-10, XmAb-5871, YHB-1411-2; 14-3-3 protein eta inhibitors, such as anti-AGX-020 mAbs (rheumatoid arthritis), Augurex; 5-Lipoxygenase inhibitors, such as tenoxicam, darbufelone, tebufelone, licofelone, ZD-2138, etalocib, tenidap, tepoxalin, flobufen, SKF-86002, PGV-20229, L-708780, WY-28342, T-0757, T-0799, ZM-216800, L-699333, BU-4601A, SKF-104351, CI-986; Abl tyrosine kinase inhibitors, such as imatinib; ACTH receptor agonists, such as FAR-404, metenkefalin acetate with tridecactide acetate; Adenosine A3 receptor agonists, such as CF-101; Adenosine deaminase inhibitors, such as cladribine, pentostatin, FR-221647; ADP ribosyl cyclase-1 modulators, such as indatuximab ravtansine; ADP ribosylation factor 6 inhibitors, such as NAV-2729; Adrenocorticotrophic hormone ligands, such as corticotropin, Mallinckrodt, FAR-404, metenkefalin acetate with tridecactide acetate; Aggrecanase-2 inhibitors, such as GIBH-R-001-2; Albumin modulators, such as ALX-0061, ONS-1210; API transcription factor inhibitors, such as T-5224, tarenflurbil, SP-10030; Basigin inhibitors, such as ERG-240; Bcr protein inhibitors, such as imatinib; B-lymphocyte antigen CD19 inhibitors, such as XmAb-5871, MDX-1342; B-lymphocyte antigen CD20 inhibitors, such as ocrelizumab, ofatumumab, rituximab, rituximab biosimilar, veltuzumab, rituximab follow-on biologic, ocaratuzumab, BLX-301, IDEC-102, ABP-798, GP-2013, MK-8808, HLX-01, CT-P10, TL-011, PF-05280586, IBPM-001RX, IBI-301, AME-133v, BCD-020, BT-D004, SAIT-101; B-lymphocyte antigen CD20 modulators, such as rituximab biosimilar, SBI-087, TRU-015, DXL-625; B-lymphocyte stimulator ligand inhibitors, such as belimumab, RCT-18, blisibimod, tabalumab, atacicept, briobacept; Bradykinin receptor modulators, such as givinostat; BRAF gene inhibitors, such as binimetinib; Branched amino acid aminotransferase 1 inhibitors, such as ERG-240; Bromodomain containing protein inhibitors, such as RVX-297, ZEN-003694; Btk tyrosine kinase inhibitors, such as acalabrutinib, HM-71224, spebrutinib, BTK inhibitor (rheumatoid arthritis), Humanwell Healthcare/Wuxi AppTech, BMS-986142, TAK-020, ONO-4059, TAS-5315, ABBV-105, AC-0025, RN-486, CG-026806, GDC-0834; Cadherin-11 antagonists, such as RG-6125; Calcineurin inhibitors, such as HS-378, ciclosporin; Calcium channel inhibitors, such as RP-3128; Carbonic anhydrase inhibitors, such as polmacoxib; Cathepsin K inhibitors, such as CRA-013783, T-5224, AM-3876, VEL-0230, NPI-2019; Cathepsin S inhibitors, such as MIV-247, AM-3876, RWJ-445380, NPI-2019; CCR1 chemokine antagonists, such as BX-471, BMS-817399, BI-638683, CCX-354, MLN-3701, MLN-3897, CP-481715, PS-375179; CCR2 chemokine antagonists, such as MK-0812, AZD-6942; CCR3 gene modulators, such as CM-102; CCR5 chemokine antagonists, such as maraviroc, OHR-118, NIBR-6465, AZD-5672, AZD-8566; CD126 antagonists, such as sarilumab; CD29 modulators, such as PF-06687234; CD3 modulators, such as otelixizumab; CD39 agonists, such as AAV5-CD39/CD73 (rheumatoid arthritis), Arthrogen; CD4 agonists, such as maraviroc; CD4 antagonists, such as tregalizumab, zanolimumab, MTRX-1011A, BW-4162W94, EP-1645, clenoliximab; CD40 ligand inhibitors, such as dapirolizumab pegol; CD40 ligand receptor antagonists, such as BI-655064, anti-CD40-XTEN, teneliximab; CD40 ligand receptor modulators, such as CFZ-533; CD52 antagonists, such as alemtuzumab; CD73 agonists, such as AAV5-CD39/CD73 (rheumatoid arthritis), Arthrogen; CD79b modulators, such as MGD-010; CD80 antagonists, such as RhuDex, XENP-9523, ASP-2408, abatacept biobetter; CD86 antagonists, such as ES-210, abatacept biosuperior, ASP-2408, XENP-9523; CD95 antagonists, such as DE-098, CS-9507; Cell adhesion molecule inhibitors, such as natalizumab, alicaforsen, NPC-17923, TK-280, PD-144795; Choline kinase inhibitors, such as choline kinase inhibitors (rheumatoid arthritis), UC San Diego; Clusterin stimulators, such as alemtuzumab; Complement C5 factor inhibitors, such as eculizumab, antisense oligonucleotides (rheumatoid arthritis), Leiden University Medical Center; Complement Factor stimulators, such as CM-101; C-reactive protein inhibitors, such as IB-RA (oral, rheumatoid arthritis), Innobioscience, ISIS-353512; CSF-1 antagonists, such as masitinib, FPA-008, JNJ-27301937, JNJ-40346527, PLX-5622, CT-1578, PD-360324, JNJ-28312141; CXC10 chemokine ligand inhibitors, such as 946414-98-8, BMS-936557; CXCR4 chemokine antagonists, such as plerixafor; Cyclin-dependent kinase inhibitor 1 inhibitors, such as CDK-1/2/5/7/9 inhibitors (cancer/tumorogenesis/rheumatoid arthritis), Bio-Patterns; Cyclin-dependent kinase-2 inhibitors, such as seliciclib, BP-14; Cyclin-dependent kinase-4 inhibitors, such as CDK-4/6 inhibitor (rheumatoid arthritis), Teijin; Cyclin-dependent kinase-5 inhibitors, such as BP-14; Cyclin-dependent kinase-6 inhibitors, such as CDK-4/6 inhibitor (rheumatoid arthritis), Teijin; Cyclin-dependent kinase-7 inhibitors, such as BP-14, seliciclib; Cyclin-dependent kinase-9 inhibitors, such as BP-14, seliciclib; Cyclooxygenase 2 inhibitors, such as celecoxib, etoricoxib, polmacoxib, laflunimus, etodolac, meloxicam, IB-RA (injectable, rheumatoid arthritis), Innobioscience, IB-RA (oral, rheumatoid arthritis), Innobioscience, SKLB-023, meloxicam, lumiracoxib; Cyclooxygenase 2 modulators, such as DRGT-46; Cyclooxygenase inhibitors, such as aceclofenac, diclofenac, imidazole salicylate, naproxcinod, naproxen etemesil, misoprostol with diclofenac, nabumetone, naproxen with esomeprazole, naproxen with esomeprazole strontium, once-daily naproxen (oral controlled release, pain), Alvogen, pelubiprofen, LY-210073, tenoxicam, licofelone, NS-398, bromfenac, L-746483, LY-255283, tenidap, tepoxalin, flobufen, ibuprofen, flurbiprofen, SKF-86002, SC-57666, WY-28342, CI-986, bermoprofen; Cytosolic phospholipase A2 inhibitors, such as AVX-002; Cytotoxic T-lymphocyte protein-4 modulators, such as belatacept, ES-210; Cytotoxic T-lymphocyte protein-4 stimulators, such as abatacept, abatacept biosimilar, BMS-188667; DHFR inhibitors, such as methotrexate, MPI-2505, MBP-Y003; Diamine acetyltransferase inhibitors, such as diminazene aceturate; Dihydroorotate dehydrogenase inhibitors, such as DHODH inhibitors (rheumatoid arthritis/autoimmune diseases), East China University of Science and Technology, ASLAN-003, laflunimus, leflunomide, HWA-486, ABR-224050; Elongation factor 2 inhibitors, such as denileukin diftitox; Eotaxin 2 ligand inhibitors, such as CM-102; EP4 prostanoid receptor antagonists, such as CR-6086; Erythropoietin receptor agonists, such as cibinetide; Fas ligands, such as AP-300; FGF-2 ligand inhibitors, such as RBM-007; FK506 binding protein-12 modulators, such as temsirolimus; Folate antagonists, such as methotrexate, MBP-Y003; Folate receptor agonists, such as folate receptor modulators (chimeric protein, cancer/rheumatoid arthritis), Proda Biotech; Folate receptor modulators, such as technetium (99mTc) etarfolatide; Fractalkine ligand inhibitors, such as E-6011; Fyn tyrosine kinase inhibitors, such as masitinib, laflunimus; G protein coupled receptor 15 antagonists, such as GPR15 antagonists (rheumatoid arthritis/HIV-mediated enteropathy), Omeros; GABA A receptor modulators, such as laflunimus; Glucocorticoid agonists, such as prednisolone, fosdagrocorat; Glucocorticoid antagonists, such as REC-200; Glucocorticoid induced leucine zipper stimulators, such as ART-G01; GM-CSF ligand inhibitors, such as namilumab, MORAb-022, lenzilumab; GM-CSF receptor antagonists, such as mavrilimumab; GM-CSF receptor modulators, such as GSK-3196165; Growth regulated protein alpha ligand inhibitors, such as T-5224; Hwith Kwith ATPase inhibitors, such as naproxen with esomeprazole, naproxen with esomeprazole strontium, ketoprofen with omeprazole, KEO-25001, HC-1004, PN-40020; Histamine H4 receptor antagonists, such as toreforant, GD-48; Histone deacetylase inhibitors, such as givinostat, CHR-5154; Histone deacetylase-6 inhibitors, such as CKD-506; HIV-1 gp120 protein inhibitors, such as maraviroc; HLA class II antigen DQ-2 alpha modulators, such as NexVax2; HLA class II antigen inhibitors, such as HLA-DR1/DR4 inhibitors (rheumatoid arthritis), Provid; HLA class II antigen modulators, such as ARG-301, recombinant T-cell receptor ligand (rheumatoid arthritis), Artielle; Hsp 70 family inhibitors, such as gusperimus trihydrochloride; Hypoxia inducible factor-1 inhibitors, such as 2-methoxyestradiol; IFNB gene stimulators, such as ART-102; I-kappa B kinase beta inhibitors, such as IMD-2560, IMD-0560; I-kappa B kinase inhibitors, such as bardoxolone methyl; IL-1 antagonists, such as rilonacept, IBPB-007-IL, antisense oligonucleotides (rheumatoid arthritis), Leiden University Medical Center, recombinant human interleukin-1 receptor antagonist (rheumatoid arthritis), Shanghai Fudan-Zhangjiang Bio-Pharmaceutical; IL-10 agonists, such as peg-ilodecakin; IL-11 agonists, such as oprelvekin; IL-12 antagonists, such as ustekinumab, briakinumab, ddRNAi therapy (rheumatoid arthritis), Medistem/Benitec; IL-15 antagonists, such as AMG-714, BNZ-132-2; IL-17 antagonists, such as ixekizumab, secukinumab, KD-025; IL-17 receptor modulators, such as CNTO-6785; IL-2 agonists, such as interleukin-2 follow-on biologic; IL-2 antagonists, such as IB-RA (injectable, rheumatoid arthritis), Innobioscience, IB-RA (oral, rheumatoid arthritis), Innobioscience, BNZ-132-2; IL-21 antagonists, such as NN-8828, BNZ-132-2; IL-23 antagonists, such as ustekinumab, briakinumab; IL-3 antagonists, such as anti-IL-3 mAbs (rheumatoid arthritis), University of Regensburg; IL-4 agonists, such as SER-130-AMI; IL-6 antagonists, such as olokizumab, clazakizumab, sirukumab, SA-237, tocilizumab, ALX-0061, FB-704A, OP-R003, peptide IL-6 antagonist, MEDI-5117, T-5224, humanized anti-IL-6 mAb, tocilizumab biosimilar, IL-6 neutralizing human antibodies, anti-IL6 antibody, RN-486, BLX-1002, AMG-220, FM-101, K-832, BLX-1025, esonarimod, TA-383; IL-6 receptor modulators, such as tocilizumab, tocilizumab biosimilar, RO-4877533; Immunoglobulin antagonists, such as iguratimod; Immunoglobulin G1 agonists, such as canakinumab, infliximab biobetter, infliximab biosimilar, BX-2922, STI-002, HF-1020; Immunoglobulin G1 antagonists, such as YHB-1411-2; Immunoglobulin G1 modulators, such as CFZ-533, lenzilumab; Immunoglobulin G2 antagonists, such as denosumab; Immunoglobulin G2 modulators, such as PF-547659; Immunoglobulin gamma Fc receptor II modulators, such as MGD-010; Immunoglobulin gamma Fc receptor IIB antagonists, such as XmAb-5871; Immunoglobulin kappa modulators, such as lenzilumab; Immunoglobulin M antagonists, such as IB-RA (injectable, rheumatoid arthritis), Innobioscience, IB-RA (oral, rheumatoid arthritis), Innobioscience; Inducible nitric oxide synthase inhibitors, such as SKLB-023; Inosine monophosphate dehydrogenase inhibitors, such as mycophenolate mofetil; Insulin sensitizers, such as rosiglitazone, THR-0921, HE-3286, BLX-1002; Integrin alpha-1/beta-1 antagonists, such as SAN-300; Integrin alpha-4/beta-1 antagonists, such as natalizumab; Integrin antagonists, such as PEG-HM-3, CY-9652; Interferon beta ligands, such as recombinant interferon beta-la, TA-383; Interferon gamma ligands, such as interferon gamma follow-on biologic; Interleukin 17A ligand inhibitors, such as ABT-122, bimekizumab, ABBV-257; Interleukin 17F ligand inhibitors, such as bimekizumab; Interleukin 23A inhibitors, such as guselkumab; Interleukin ligands, such as IBPB-007-IL; Interleukin receptor 17A antagonists, such as brodalumab; Interleukin-1 beta ligand inhibitors, such as canakinumab, rilonacept, T-5224, gevokizumab, BLX-1002, LY-2189102, PMI-001, K-832, CDP-484; Interleukin-10 ligands, such as PF-06687234; Interleukin-2 ligands, such as denileukin diftitox, recombinant interleukin-2, interleukin-2 follow-on biologic, recombinant human interleukin-2, interleukin-2 (injectable); Interleukin-4 ligands, such as Tetravil; Interleukin 6 ligand inhibitors, such as gerilimzumab, PF-4236921; Itk tyrosine kinase inhibitors, such as ARN-4079; JAK tyrosine kinase inhibitors, such as tofacitinib, SHR-0302, cerdulatinib, peficitinib, deuterated tofacitinib analog, SD-900, CVXL-0074; Jak1 tyrosine kinase inhibitors, such as ABT-494, baricitinib, ruxolitinib, filgotinib, tofacitinib, itacitinib, peficitinib, NIP-585, CS-944X, YJC-50018, GLPG-0555, MRK-12; Jak2 tyrosine kinase inhibitors, such as baricitinib, ruxolitinib, CT-1578; JAK3 gene inhibitors, such as GBL-5b; Jak3 tyrosine kinase inhibitors, such as decernotinib, tofacitinib, peficitinib, AC-0025, CS-944X, DNX-04042, MTF-003, ARN-4079, PS-020613; Jun N terminal kinase inhibitors, such as IQ-1S; KCNA voltage-gated potassium channel-3 modulators, such as MRAD-P1; Kelch like ECH associated protein 1 modulators, such as dimethyl fumarate; Kit tyrosine kinase inhibitors, such as imatinib, masitinib; LanC like protein 2 modulators, such as BT-11; LITAF gene inhibitors, such as GBL-5b; Lymphocyte function antigen-3 receptor antagonists, such as alefacept; Lyn tyrosine kinase inhibitors, such as masitinib; Macrophage mannose receptor 1 modulators, such as technetium Tc 99m tilmanocept; MAdCAM inhibitors, such as PF-547659; MAP kinase modulators, such as SKLB-023; MAP3K2 gene inhibitors, such as GBL-5b; MAPKAPK5 inhibitors, such as GLPG-0259; Matrix metalloprotease inhibitors, such as GLPG-0259; MCL1 gene inhibitors, such as seliciclib; MEK protein kinase inhibitors, such as binimetinib, AD-GL0001; MEK-1 protein kinase inhibitors, such as binimetinib; MEK-2 protein kinase inhibitors, such as binimetinib; Membrane copper amine oxidase inhibitors, such as BTT-1023, PRX-167700, vepalimomab; Metalloprotease-2 inhibitors, such as ERG-240; Metalloprotease-9 inhibitors, such as GS-5745, ERG-240; Midkine ligand inhibitors, such as CAB-102; Mitochondrial 10 kDa heat shock protein stimulators, such as INV-103; mTOR complex 1 inhibitors, such as everolimus; mTOR inhibitors, such as everolimus, temsirolimus; NAD ADP ribosyltransferase stimulators, such as denileukin diftitox; NAMPT gene inhibitors, such as ART-D01; NF kappa B inhibitor stimulators, such as denosumab; NFAT gene inhibitors, such as T-5224; NFE2L2 gene stimulators, such as bardoxolone methyl; Nicotinic acetylcholine receptor antagonists, such as RPI-78, RPI-MN; NK cell receptor modulators, such as masitinib; NKG2 A B activating NK receptor antagonists, such as monalizumab; NKG2 D activating NK receptor antagonists, such as NNC-0142-002; Nuclear erythroid 2-related factor 2 stimulators, such as dimethyl fumarate; Nuclear factor kappa B inhibitors, such as bardoxolone methyl, IB-RA (injectable, rheumatoid arthritis), Innobioscience, dehydroxymethylepoxyquinomicin, HE-3286, IMD-0560, MP-42, tarenflurbil, VGX-1027, SKLB-023, SP-650003, MG-132, SIM-916, VGX-350, VGX-300, GIT-027, SP-100030, MLN-1145, NVP-IKK-005; Nuclear factor kappa B modulators, such as REM-1086; Nuclear factor kappa B p105 inhibitors, such as REM-1086; Opioid growth factor receptor agonists, such as metenkefalin acetate with tridecactide acetate, FAR-404; Opioid receptor delta antagonists, such as HS-378; Osteoclast differentiation factor antagonists, such as denosumab, cyclic peptidomimetics (rheumatoid arthritis/osteoporosis), University of Michigan; Osteoclast differentiation factor ligand inhibitors, such as denosumab; Oxidoreductase inhibitors, such as etodolac, imidazole salicylate; P2X7 purinoceptor agonists, such as givinostat; p38 MAP kinase alpha inhibitors, such as VX-745, BMS-582949 prodrugs, BMS-751324; p38 MAP kinase inhibitors, such as BCT-197, losmapimod, ARRY-797; PDE 4 inhibitors, such as apremilast; PDE 5 inhibitors, such as PDE5 inhibitors (rheumatoid arthritis), University of Rochester; PDGF receptor agonists, such as oprelvekin; PDGF receptor antagonists, such as imatinib, masitinib; PDGF-B ligand inhibitors, such as SL-1026; PERK gene inhibitors, such as binimetinib; Phosphoinositide-3 kinase delta inhibitors, such as duvelisib, RP-6503, CT-732, INK-007, GNE-293; Phosphoinositide-3 kinase gamma inhibitors, such as duvelisib, RP-6503; Phospholipase A2 inhibitors, such as AVX-002, human secreted phospholipase A2 type IIA-integrin binding inhibiting peptides (rheumatoid arthritis/asthma/Alzheimer's disease/cancer), University of California, Davis, AK-106, varespladib methyl, Ro-31-4493, BM-162353, Ro-23-9358, YM-26734; Platelet activating factor receptor antagonists, such as piperidone hydrochloridum; PPAR gamma agonists, such as rosiglitazone, THR-0921, rosiglitazone XR, etalocib; Programmed cell death protein 1 modulators, such as INSIX RA; Prostaglandin D synthase stimulators, such as HF-0220; Protein arginine deiminase inhibitors, such as PAD inhibitors (rheumatoid arthritis), Leiden University Medical Center/LURIS; Protein tyrosine kinase inhibitors, such as leflunomide; PurH purine biosynthesis protein inhibitors, such as mycophenolate mofetil; Rho associated protein kinase 2 inhibitors, such as KD-025; Seprase inhibitors, such as anti-fibroblast-activation protein (FAP) antibody radiotracers (rheumatoid arthritis), Hoffmann-La Roche/Radboud University; Signal transducer CD24 modulators, such as CD24-IgFc; Signal transduction inhibitors, such as imatinib; Sodium glucose transporter-2 inhibitors, such as THR-0921; Sphingosine 1 phosphate phosphatase modulators, such as SiP modulators (oral, multiple sclerosis/ulcerative colitis/rheumatoid arthritis), Akaal Pharma; STAT3 gene inhibitors, such as bardoxolone methyl, vidofludimus; Superoxide dismutase stimulators, such as imisopasem manganese; SYK family tyrosine kinase inhibitors, such as MK-8457; Syk tyrosine kinase inhibitors, such as fostamatinib, entospletinib, KDDF-201110-06, HMPL-523, cerdulatinib, AB-8779, GS-9876, PRT-2607, CVXL-0074, CG-103065 and CG-026806; Syndecan-1 inhibitors, such as indatuximab ravtansine; T cell receptor antagonists, such as TCR inhibiting SCHOOL peptides (systemic/topical, rheumatoid arthritis/dermatitis/scleroderma), SignaBlok, CII modified peptide (rheumatoid arthritis), Peking University; T cell receptor modulators, such as ARG-301; T cell surface glycoprotein CD28 inhibitors, such as abatacept, belatacept, abatacept biosimilar, RhuDex, BMS-188667; T cell surface glycoprotein CD28 stimulators, such as TAB-08; TAK1 binding protein modulators, such as epigallocatechin 3-gallate; Talin modulators, such as short-form talin regulators (rheumatoid arthritis), KayteeBio; T-cell differentiation antigen CD6 inhibitors, such as itolizumab; T-cell surface glycoprotein CD8 inhibitors, such as tregalizumab; Tenascin modulators, such as Tetravil; TGF beta agonists, such as tregalizumab; Thymulin agonists, such as Syn-1002; TLR-2 antagonists, such as VB-201, P-13; TLR-4 antagonists, such as VB-201, P-13; TLR-9 antagonists, such as P-13; TNF alpha ligand inhibitors, such as adalimumab biosimilarYHB-1411-2, adalimumab, infliximab, infliximab biosimilar, recombinant humanized anti-TNF-alpha monoclonal antibody, certolizumab pegol, golimumab, ozoralizumab, AT-132, etanercept biosimilar, ISIS-104838, ISU-202, CT-P17, MB-612, Debio-0512, anti-TNF alpha human monoclonal antibody, infliximab biobetter, UB-721, KN-002, DA-3113, BX-2922, R-TPR-015, BOW-050, PF-06410293, CKD-760, CHS-1420, GS-071, ABP-710, STI-002, BOW-015, FKB-327, BAX-2200, HLX-03, BI-695501, CNTO-148, MYL-1401AABP-501, HOT-3010, BAX-2923, SCH-215596, ABT-D2E7, BAT-1406, XPro-1595, Atsttrin, SSS-07, golimumab biosimilar, TA-101, adalimumab follow-on biologic, BLX-1002, ABX-0401, TAQ-588, golimumab biosimilar, TeHL-1, placulumab, PMI-001, tgAAV-TNFR:Fc, K-832, CYT-007-TNFQb, SSR-150106, PassTNF, Verigen, DOM-0200, DOM-0215, AME-527, anti-TNF-alpha mAb, GENZ-38167, BLX-1028, CYT-020-TNFQb, CC-1080, CC-1069; TNF alpha ligand modulators, such as MM-A01-01, CDP-571, camobucol; TNF antagonists, such as etanercept, certolizumab pegol, etanercept follow-on biologic, etanercept biosimilar, DNX-114, TNF antagonist with IL-12 antagonist (rheumatoid arthritis), University of Oxford, BN-006, SCB-131, pegsunercept, GBL-5b, ACE-772, onercept, DE-096, PN-0615, lenercept, ITF-1779, MDL-201112, BAX-2200, SCB-808, DA-3853, HD-203; TNF gene inhibitors, such as GIBH-R-001-2; TNF receptor modulators, such as recombinant TNF receptor 2-Fc fusion protein mutant, T-0001, tgAAV-TNFR:Fc; TNFSF11 gene inhibitors, such as denosumab; Transcription factor p65 inhibitors, such as REM-1086; Transcription factor RelB inhibitors, such as REM-1086; Transferrin modulators, such as methotrexate, MBP-Y003; Tumor necrosis factor 13C receptor antagonists, such as VAY-736; Tumor necrosis factor 15 ligand inhibitors, such as anti-TL1A antibodies (rheumatoid arthritis/inflammatory bowel disease), NIAMS; Tumor necrosis factor ligand 13 inhibitors, such as atacicept; Tumor necrosis factor ligand inhibitors, such as ABBV-257, etanercept biosimilar, ABT-122; Type I IL-1 receptor antagonists, such as anakinra, anakinra biosimilar, anakinra follow-on biologic, AXXO; Type I TNF receptor antagonists, such as NM-9405; Type II TNF receptor modulators, such as etanercept, SCB-131, etanercept biosimilar, etanercept follow-on biologic, BAX-2200, SCB-808, LBEC-0101, DMB-3853, DWP-422, BT-D001, DA-3853; Unspecified GPCR agonists, such as NCP-70X; VEGF receptor antagonists, such as 2-methoxyestradiol and NSC-650853, SL-1026; VEGF-2 receptor antagonists, such as CG-026806; VEGF-2 receptor modulators, such as VEGFR2 neutralizing antibody (rheumatoid arthritis), University of Rochester; VEGF-B ligand inhibitors, such as CSL-346; X-linked inhibitor of apoptosis protein inhibitors, such as IAP inhibitors (oral), Pharmascience; and Zap70 tyrosine kinase inhibitors, such as MK-8457, CT-5332.

Combinations for Metabolic Diseases or Conditions

Examples of metabolic disorders include, without limitation, diabetes, including type I and type II diabetes, metabolic syndrome, dyslipidemia, obesity, glucose intolerance, hypertension, elevated serum cholesterol, and elevated triglycerides.

Examples of therapeutic agents used to treat metabolic disorders include antihypertensive agents and lipid lowering agents. Additional therapeutic agents used to treat metabolic disorders include insulin, sulfonylureas, biguanides, alpha-glucosidase inhibitors, and incretin mimetics. Thus, one aspect of the disclosure is a method of treating a metabolic disease comprising administering a compound of the disclosure in combination with one or more compounds useful for the treatment of metabolic diseases to a subject, particularly a human subject, in need thereof.

Pharmaceutical Compositions

While it is possible for the active ingredients to be administered alone it may be preferable to present them as pharmaceutical formulations (compositions). The formulations, both for veterinary and for human use, of the invention comprise at least one active ingredient, as above defined, together with one or more acceptable carriers therefor and optionally other therapeutic ingredients. The carrier(s) must be "acceptable" in the sense of being compatible with the other ingredients of the formulation and physiologically innocuous to the recipient thereof.

The formulations include those suitable for the foregoing administration routes. The formulations may conveniently be presented in unit dosage form and may be prepared by any of the methods well known in the art of pharmacy. Techniques and formulations generally are found in *Remington's Pharmaceutical Sciences* (Mack Publishing Co., Easton, Pa.). Such methods include the step of bringing into association the active ingredient with inactive ingredients (e.g., a carrier, pharmaceutical excipient, etc.) which constitutes one or more accessory ingredients. In general the formulations are prepared by uniformly and intimately bringing into association the active ingredient with liquid carriers or finely divided solid carriers or both, and then, if necessary, shaping the product.

In certain embodiments, formulations suitable for oral administration are presented as discrete units such as capsules, cachets or tablets each containing a predetermined amount of the active ingredient.

In certain embodiments, the pharmaceutical formulations include one or more compounds of the invention together with one or more pharmaceutically acceptable carriers or excipients and optionally other therapeutic agents. Pharmaceutical formulations containing the active ingredient may be in any form suitable for the intended method of administration. When used for oral use for example, tablets, troches, lozenges, aqueous or oil suspensions, dispersible powders or granules, emulsions, hard or soft capsules, syrups or elixirs may be prepared. Compositions intended for oral use may be prepared according to any method known to the art for the manufacture of pharmaceutical compositions and such compositions may contain one or more agents including sweetening agents, flavoring agents, coloring agents and preserving agents, in order to provide a palatable preparation. Tablets containing the active ingredient in admixture with non-toxic pharmaceutically acceptable excipient which are suitable for manufacture of tablets are acceptable. These excipients may be, for example, inert diluents, such as calcium or sodium carbonate, lactose, lactose monohydrate, croscarmellose sodium, povidone, calcium or sodium phosphate; granulating and disintegrating agents, such as maize starch, or alginic acid; binding agents, such as cellulose, microcrystalline cellulose, starch, gelatin or acacia; and lubricating agents, such as magnesium stearate, stearic acid or talc. Tablets may be uncoated or may be coated by known techniques including microencapsulation to delay disintegration and adsorption in the gastrointestinal tract and thereby provide a sustained action over a longer period. For example, a time delay material such as glyceryl monostearate or glyceryl distearate alone or with a wax may be employed.

The amount of active ingredient that is combined with the inactive ingredients to produce a dosage form will vary depending upon the host treated and the particular mode of administration. For example, in some embodiments, a dosage form for oral administration to humans contains approximately 1 to 1000 mg of active material formulated with an appropriate and convenient amount of carrier material (e.g., inactive ingredient or excipient material). In certain embodiments, the carrier material varies from about 5 to about 95% of the total compositions (weight: weight). In some embodiments, the pharmaceutical compositions described herein contain about 1 to 800 mg, 1 to 600 mg, 1 to 400 mg, 1 to 200 mg, 1 to 100 mg or 1 to 50 mg of the compound of Formula I, or a pharmaceutically acceptable salt thereof. In some embodiments, the pharmaceutical compositions described herein contain not more than about 400 mg of the compound of Formula I. In some embodiments, the pharmaceutical compositions described herein contain about 100 mg of the compound of Formula I, or a pharmaceutically acceptable salt thereof.

It should be understood that in addition to the ingredients particularly mentioned above the formulations disclosed herein may include other agents conventional in the art having regard to the type of formulation in question, for example those suitable for oral administration may include flavoring agents.

Veterinary compositions comprising at least one active ingredient as above defined together with a veterinary carrier are further provided.

Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

Effective dose of active ingredient depends at least on the nature of the condition being treated, toxicity, whether the compound is being used prophylactically (lower doses), the method of delivery, and the pharmaceutical formulation, and will be determined by the clinician using conventional dose escalation studies.

ROUTES OF ADMINISTRATION

One or more compounds of Formula I (herein referred to as the active ingredients), or a pharmaceutically acceptable salt thereof, are administered by any route appropriate to the condition to be treated. Suitable routes include oral, rectal, nasal, topical (including buccal and sublingual), vaginal and parenteral (including subcutaneous, intramuscular, intravenous, intradermal, intrathecal and epidural), and the like. It will be appreciated that the preferred route may vary with for example the condition of the recipient. An advantage of the compounds of this invention is that they are orally bioavailable and can be dosed orally. Accordingly, in one embodiment, the pharmaceutical compositions described herein are oral dosage forms. In certain embodiments, the pharmaceutical compositions described herein are oral solid dosage forms.

Formulation Example 1

Hard gelatin capsules containing the following ingredients are prepared:

| Ingredient | Quantity (mg/capsule) |
| --- | --- |
| Active Ingredient | 30.0 |
| Starch | 305.0 |
| Magnesium stearate | 5.0 |

The above ingredients are mixed and filled into hard gelatin capsules.

Formulation Example 2

A tablet Formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets.

Formulation Example 3

A dry powder inhaler formulation is prepared containing the following components:

| Ingredient | Weight % |
|---|---|
| Active Ingredient | 5 |
| Lactose | 95 |

The active ingredient is mixed with the lactose and the mixture is added to a dry powder inhaling appliance.

Formulation Example 4

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in sterile water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinylpyrrolidone is mixed with the resultant powders, which are then passed through a 16 mesh U.S. sieve. The granules so produced are dried at 50° C. to 60° C. and passed through a 16 mesh U.S. sieve. The sodium carboxymethyl starch, magnesium stearate and talc, previously passed through a No. 30 mesh U.S. sieve, are then added to the granules which, after mixing, are compressed on a tablet machine to yield tablets each weighing 120 mg.

Formulation Example 5

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

Formulation Example 6

Suspensions, each containing 50 mg of active ingredient per 5.0 mL dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The active ingredient, sucrose and xanthan gum are blended, passed through a No. 10 mesh U.S. sieve and then mixed with a previously made solution of the microcrystalline cellulose and sodium carboxymethyl cellulose in water. The sodium benzoate, flavor and color are diluted with some of the water and added with stirring. Sufficient water is then added to produce the required volume.

Formulation Example 7

A subcutaneous formulation may be prepared as follows:

| Ingredient | Quantity |
|---|---|
| Active Ingredient | 5.0 mg |
| Corn Oil | 1.0 mL |

Formulation Example 8

An injectable preparation is prepared having the following composition:

| Ingredients | Amount |
|---|---|
| Active ingredient | 2.0 mg/mL |
| Mannitol, USP | 50 mg/mL |
| Gluconic acid, USP | q.s. (pH 5-6) |
| water (distilled, sterile) | q.s. to 1.0 mL |
| Nitrogen Gas, NF | q.s. |

Formulation Example 9

A topical preparation is prepared having the following composition:

| Ingredients | grams |
| --- | --- |
| Active ingredient | 0.2-10 |
| Span 60 | 2.0 |
| Tween 60 | 2.0 |
| Mineral oil | 5.0 |
| Petrolatum | 0.10 |
| Methyl paraben | 0.15 |
| Propyl paraben | 0.05 |
| BHA (butylated hydroxy anisole) | 0.01 |
| Water | q.s. to100 |

All of the above ingredients, except water, are combined and heated to 60° C. with stirring. A sufficient quantity of water at 60° C. is then added with vigorous stirring to emulsify the ingredients and water then added q.s. 100 g.

Formulation Example 10

Sustained Release Composition

| Ingredient | Weight Range % |
| --- | --- |
| Active ingredient | 50-95 |
| Microcrystalline cellulose (filler) | 1-35 |
| Methacrylic acid copolymer | 1-35 |
| Sodium hydroxide | 0.1-1.0 |
| Hydroxypropyl methylcellulose | 0.5-5.0 |
| Magnesium stearate | 0.5-5.0 |

Sustained release formulations of this disclosure may be prepared as follows: compound and pH-dependent binder and any optional excipients are intimately mixed (dry-blended). The dry-blended mixture is then granulated in the presence of an aqueous solution of a strong base which is sprayed into the blended powder. The granulate is dried, screened, mixed with optional lubricants (such as talc or magnesium stearate) and compressed into tablets. Preferred aqueous solutions of strong bases are solutions of alkali metal hydroxides, such as sodium or potassium hydroxide, preferably sodium hydroxide, in water (optionally containing up to 25% of water-miscible solvents such as lower alcohols).

The resulting tablets may be coated with an optional film-forming agent, for identification, taste-masking purposes and to improve ease of swallowing. The film forming agent will typically be present in an amount ranging from between 2% and 4% of the tablet weight. Suitable film-forming agents are well known to the art and include hydroxypropyl methylcellulose, cationic methacrylate copolymers (dimethylaminoethyl methacrylate/methyl-butyl methacrylate copolymers—Eudragit® E—Röhm. Pharma) and the like. These film-forming agents may optionally contain colorants, plasticizers and other supplemental ingredients.

The compressed tablets preferably have a hardness sufficient to withstand 8 Kp compression. The tablet size will depend primarily upon the amount of compound in the tablet. The tablets will include from 300 to 1100 mg of compound free base. Preferably, the tablets will include amounts of compound free base ranging from 400-600 mg, 650-850 mg and 900-1100 mg.

In order to influence the dissolution rate, the time during which the compound containing powder is wet mixed is controlled. Preferably the total powder mix time, i.e. the time during which the powder is exposed to sodium hydroxide solution, will range from 1 to 10 minutes and preferably from 2 to 5 minutes. Following granulation, the particles are removed from the granulator and placed in a fluid bed dryer for drying at about 60° C.

Formulation Example 11

A tablet Formula Is prepared using the ingredients below:

| Ingredient | Quantity (mg/tablet) |
| --- | --- |
| Active Ingredient | 300.0 |
| Cellulose, microcrystalline | 100.0 |
| Colloidal silicon dioxide | 10.0 |
| Stearic acid | 5.0 |

The components are blended and compressed to form tablets.

EXAMPLES

The following examples are included to demonstrate specific embodiments of the disclosure. It should be appreciated by those of skill in the art that the techniques disclosed in the examples which follow represent techniques to function well in the practice of the disclosure, and thus can be considered to constitute specific modes for its practice. However, those of skill in the art should, in light of the present disclosure, appreciate that many changes can be made in the specific embodiments which are disclosed and still obtain a like or similar result without departing from the spirit and scope of the disclosure.

List of Abbreviations and Acronyms

| Abbreviation | Meaning |
| --- | --- |
| ° C. | Degree Celsius |
| Ac | Acetyl |
| aq. | Aqueous |
| ATP | Adenosine triphosphate |
| $B_2Pin_2$ | Bis(pinacolato)diboron |
| BOC | tert-Butoxycarbonyl |
| Br | Broad |
| BSA | Bovine serum albumin |
| D | Doublet |
| DCM | Dichloromethane |
| dd | Doublet of doublets |
| ddd | Doublet of doublet of doublets |
| DIPEA | N,N-Diisopropylethylamine (Hünig's Base) |
| DMA | Dimethylacetamide |
| DME | 1,2-Dimethoxyethane |
| DMF | Dimethylformamide |
| DMSO | Dimethylsulfoxide |
| Dt | Doublet-triplet |
| DTT | Dithiothreitol (Cleland's reagent) |
| $EC_{50}$ | The half maximal effective concentration |
| EDC | 1-(3-dimethylaminopropyl)-3-ethylcarbodiimide |
| EDTA | Ethylenediaminetetraacetic acid |
| EGFR | Epidermal growth factor receptor |
| Eq | Equivalents |
| ES/MS | Electrospray mass spectrometry |
| Et | Ethyl |
| EtOAc | Ethyl acetate |
| EtOH | Ethanol (Ethyl alcohol) |
| FBS | Fetal bovine serum |
| G | Grams |
| HATU | 1-[Bis(dimethylamino)methylene]-1H-1,2,3-triazolo[4,5-b]pyridinium 3-oxid hexafluorophosphate |
| HEPES | 2-[4-(2-hydroxyethyl)piperazin-1-yl]ethanesulfonic acid |
| HCl | Hydrochloric acid |
| HPLC | High pressure liquid chromatography |

| Abbreviation | Meaning |
|---|---|
| Hrs | Hours |
| HTRF® | Homogeneous time resolved fluorescence, a registered trademark of Cisbio Bioassays, parc marcel boiteux 30200 codolet, France |
| Hz | Hertz |
| IBD | Inflammatory bowel disease |
| $IC_{50}$ | Half-maximal inhibitory concentration |
| i-pr | Isopropyl |
| J | Coupling constant (MHz) |
| $K_3PO_4$ | Tripotasium phosphate |
| KOtBu | Potassium tert-butoxide |
| KOAc | Potassium Acetate |
| LCMS | Liquid chromatography-mass spectrometry |
| Li HMDS | Lithium bis(trimethylsilyl)amide |
| LiOH | Lithium hydroxide |
| LiI | Lithium iodide |
| LPS | Lipopolysaccharide |
| M | Molar |
| M | multiplet |
| M+ | Mass peak |
| M + H+ | Mass peak plus hydrogen |
| Me | Methyl |
| MeCN | Acetonitrile |
| MeOH | Methanol (Methyl alcohol) |
| MeLi | Methyllithium |
| MeMgX | Methylmagnesium halide (Grignard reagent), where X is Fluoro, Chloro, Bromo or Iodo |
| $Me_6Sn_2$ | Hexamethyldistannane (hexamethylditin) |
| Mg | Milligram |
| $MgSO_4$ | Magnesium sulfate |
| MHz | Megahertz |
| Min | Minute |
| ml/mL | Milliliter |
| mM | Millimolar |
| Mmol | Millimole |
| MS | Mass spectroscopy |
| MsCl | Mesyl chloride |
| NBS | N-Bromosuccinimide |
| n- | Normal |
| nBu/Bu | n-Butyl (normal Butyl) |
| n-BuLi | n-Butyl Lithium |
| NaH | Sodium hydride |
| $NaHCO_3$ | Sodium bicarbonate |
| $NaN_3$ | Sodium azide |
| $Na_3PO_4$ | Trisodium phosphate |
| $Na_2SO_4$ | Sodium sulfate |
| nL | Nanoliter |
| Nm | Nanometer |
| NMP | 1-methylpyrrolidin-2-one |
| NMR | Nuclear magnetic resonance |
| NP-40 | Nonyl phenoxypolyethoxylethanol |
| Pd-PEPPSI™-IPent | [1,3-bis(2,6-di-3-pentylphenyl)imidazol-2-ylidene](3-chloropyridyl)palladium(II) dichloride |
| Pen-Strep | Penicillin-Streptomycin (5,000 units of penicillin G sodium salt, and 5,000 μg streptomycin sulfate in 0.85% saline) |
| Ph | Phenyl |
| Q | Quartet |
| q.s. | Quantity sufficient to achieve a stated function |
| RP | Reverse phase |
| RPMI | Roswell Park Memorial Institute medium |
| Rt | Room temperature |
| S | Singlet |
| sat. | Saturated |
| Selectfluor® | 1-Chloromethyl-4-fluoro-1,4-diazoniabicyclo[2.2.2]octane bis (a trademark of Air Products and Chemicals) |
| SFC | Supercritical fluid chromatography |
| SiliaMetS® Thiol | Silica-based Palladium scavenger, registered trademark of Silicycle |
| T | Triplet |
| THF | Tetrahydrofuran |
| TFA | Trifluoroacetic acid |
| XPhos Pd G3 | (2-Dicyclohexylphosphino-2',4',6'-triisopropyl-1,1'-biphenyl)[2-(2'-amino-1,1'-biphenyl)]palladium(II) methanesulfonate |

1. General Schemes

Scheme 1:

The compounds of formula 1.5 may be accessed according to the method outlined in Scheme 1. 1-aminopyrrole 1.1 maybe be condensed with a suitable coupling partner to produce substituted pyrrolo[1,2-b]pyridazine 1.2 using a suitable catalyst (e.g, HCl, etc.) and suitable solvent (e.g., EtOH, etc.). Halogenation at the position shown using a known halogenating reagent (e.g., NBS, etc.) can form the intermediate 1.3, wherein X is chloro, bromo, or iodo and where intermediate 1.3 can be further substituted either via C—H activation or electrophilic aromatic substitution with a suitable reagent (e.g., selectfluor, etc.) to produce intermediate 1.4. Halogen metal exchange of -X to -M can then be achieved using a suitable reagent (e.g, n-BuLi, etc.) or transition metal coupling using a palladium catalyst and metal source (e.g., $B_2Pin_2$, $Me_6Sn_2$, etc.) to give intermediate 1.5, wherein M is a metal, such as tin or boron. Alternatively, a substituted 1-amino pyrrole 1.6 can be converted to the pyrrolo[1,2-b]pyridazine heterocycle 1.7 by the condensation described above. Heterocycle 1.7 can be converted via halogenation to an intermediate of the type 1.4.

Scheme 2:

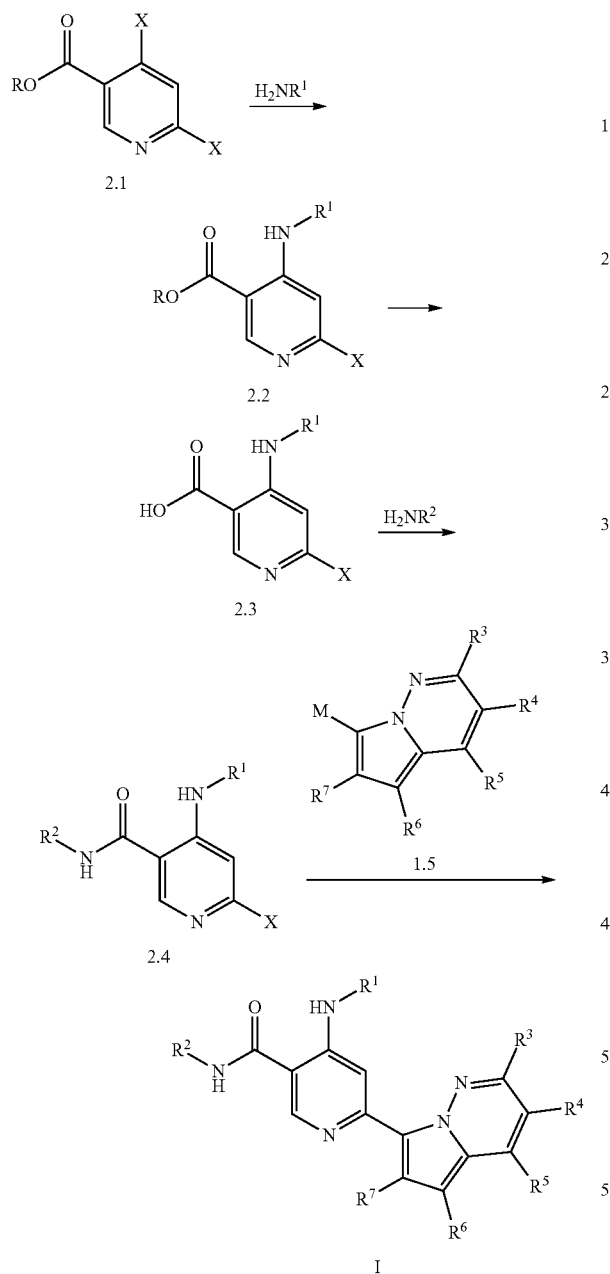

Scheme 3:

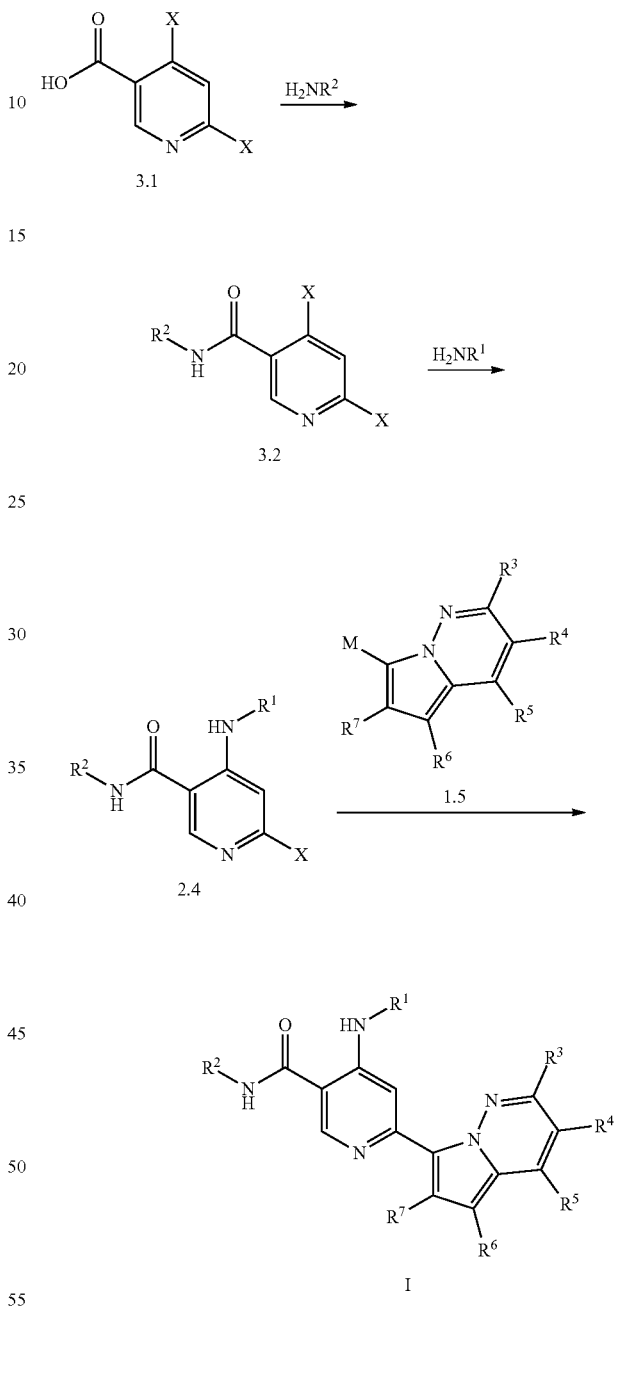

Compounds of Formula (I) may be assembled by first reacting an amine with intermediate 2.1 at C-4 to give intermediate 2.2. Following conversion to the acid 2.3 using a suitable reagent (e.g, LiOH, LiI and pyridine, etc.) a second amine can be introduced to give amide 2.4 using standard amide bond forming conditions (e.g., DIPEA with HATU, etc.). Coupling of the metal-containing species (1.5) with intermediate 2.4 using a suitable catalyst, such as a palladium catalyst, can afford a compound of Formula (I).

Alternatively, compounds of formula (I) may be assembled by first addition of an amine to carboxylic acid 3.1 using standard amide bond formation (e.g., DIPEA with HATU, etc.) to give amide 3.2. Addition of an amine to the C-4 position of 3.2 may produce intermediate 2.4 which can in turn be coupled with intermediate 1.5 using a suitable catalyst, such as a palladium catalyst, to yield a compound of Formula (I).

Scheme 4:

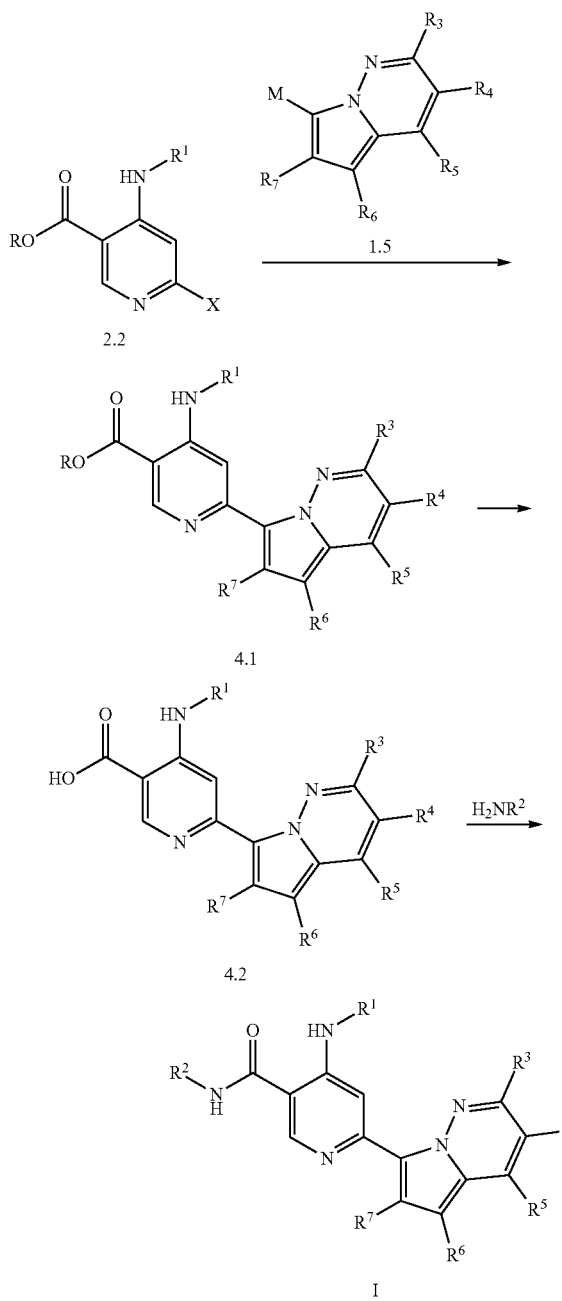

A compound of Formula (I) can also be prepared as shown in Scheme 4 beginning with the coupling of intermediate 2.2 and heterocycle 1.5 using a suitable catalyst, such as a palladium catalyst, to give compound 4.1. Conversion of the ester 4.1 to carboxylic acid 4.2 may be accomplished using known conditions (e.g. LiOH, LiI with pyridine, etc.). A compound of Formula (I) can be accessed by addition of an amine to intermediate 4.2 using standard amide bond forming conditions (e.g. HATU with DIPEA, etc.).

Scheme 5:

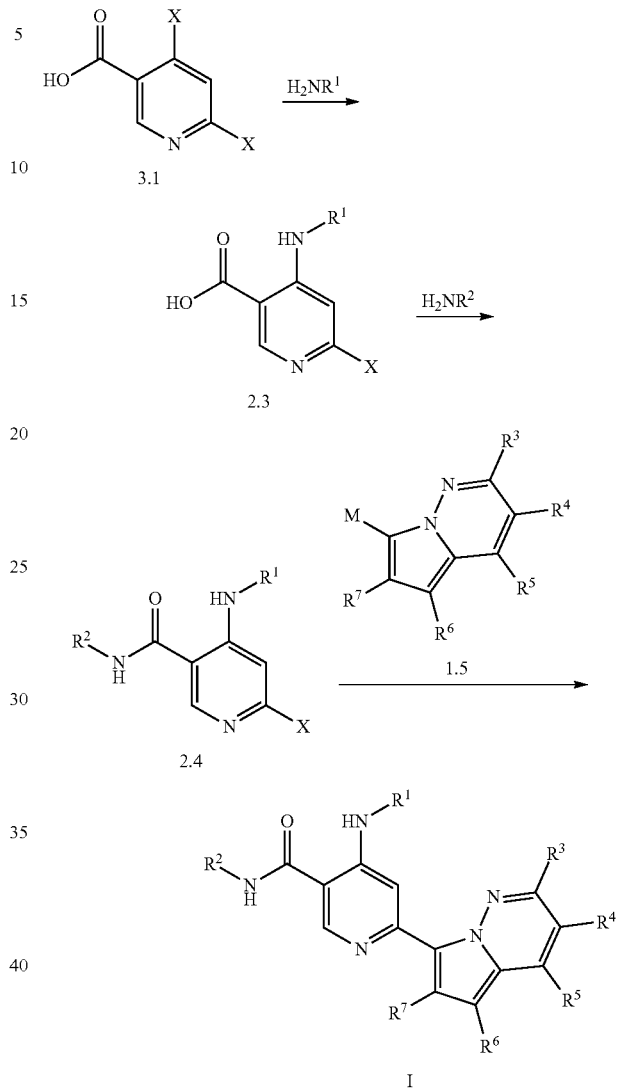

As shown in Scheme 5, an amine may be added to C-4 of compound 3.1 using base (e.g. NaH, LiHMDS, etc.) to directly yield intermediate 2.3. This can be converted to compound (I) in the same manner as illustrated in Scheme 2.

Scheme 6:

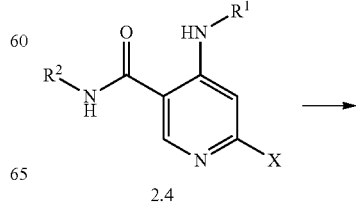

75
-continued

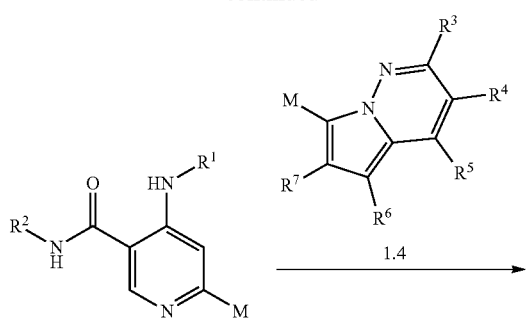

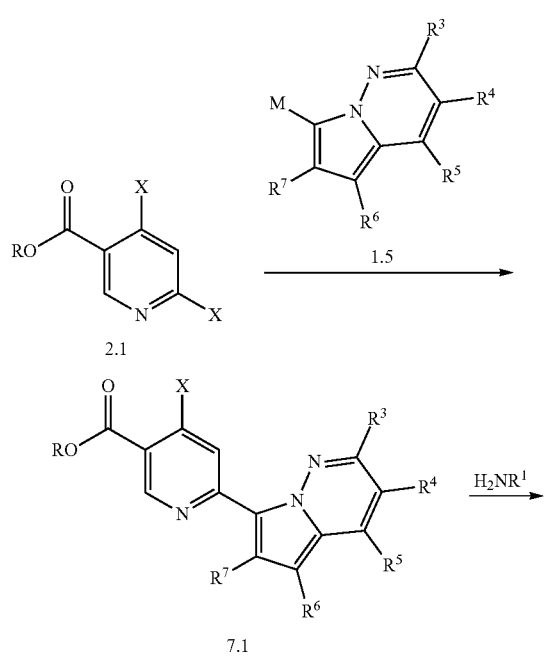

Beginning from intermediate 2.4, the compound may be reacted with an appropriate reagent (e.g. hexamethylditin, etc.) to afford compound 6.1. This can be coupled with halogenated heterocycle 1.4 using an appropriate catalyst (e.g. palladium catalyst, etc.) to yield compound (I).

Scheme 7:

76
-continued

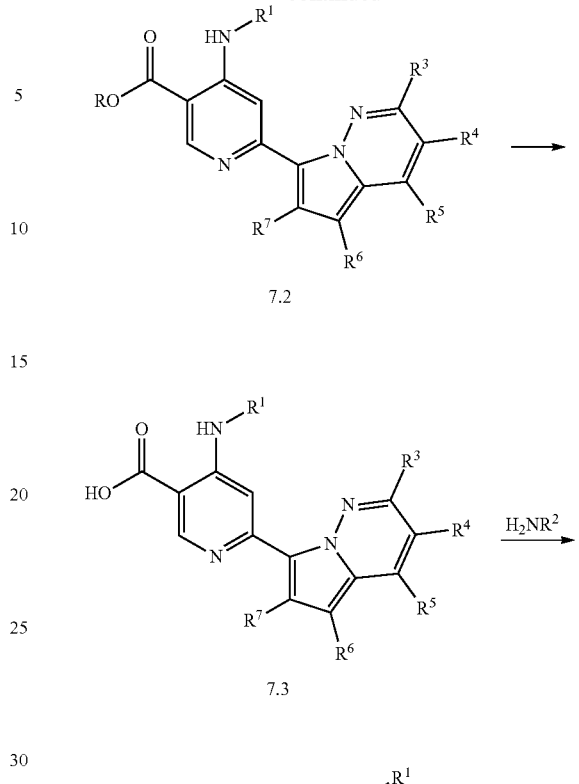

In an alternate ordering of the synthesis, compound 2.1 may be initially coupled with intermediate 1.5 using a suitable catalyst, such as a palladium catalyst, to give monohalogenated product 7.1. Addition of an amine can produce intermediate ester 7.2 after which conversion to the carboxylic acid can yield intermediate 7.3. Addition of an amide using amide bond forming conditions (e.g., DIPEA with HATU, etc.) may produce compound (I).

Scheme 8:

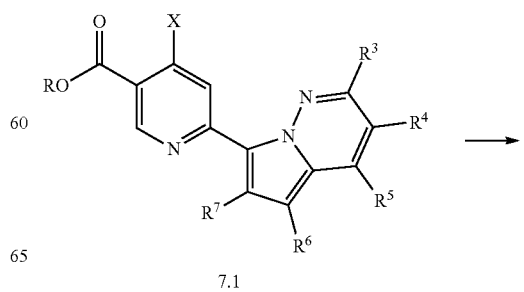

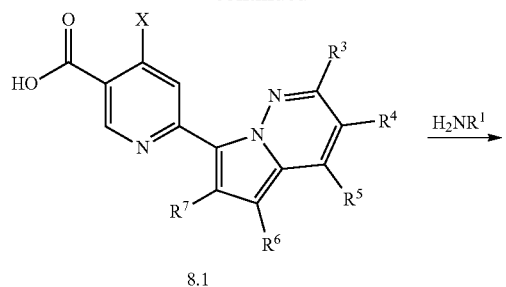

8.1

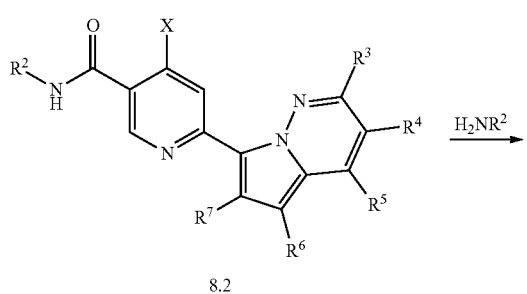

8.2

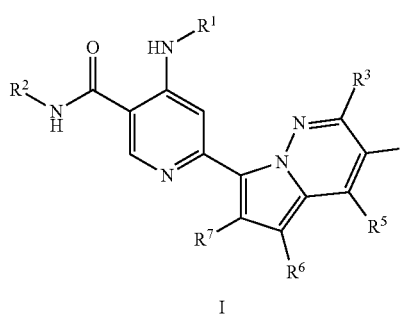

I

Additionally, as shown in Scheme 8, ester 7.1 may be converted to the corresponding carboxylic acid 8.1 via known hydrolysis conditions (e.g. LiOH, LiI with pyridine, etc.). Amide bond formation using standard conditions (e.g., DIPEA with HATU, etc.) to produce intermediate 8.2 can then be followed by introduction of an amine into the C-4 position to give compound (I).

Scheme 9:

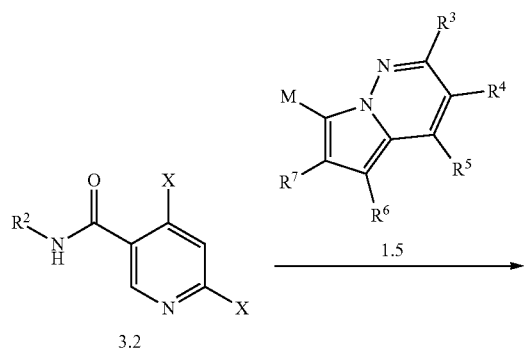

3.2

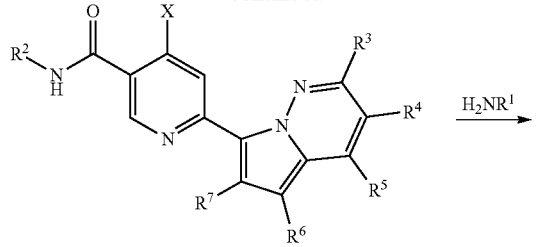

8.2

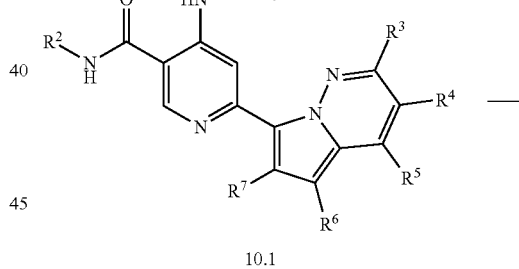

I

Beginning with amide intermediate 3.2, coupling with heterocycle 1.5 using a suitable catalyst (e.g. palladium catalyst, etc.) may yield monohalogenated intermediate 9.2 which can be converted to compound (I) as described in Scheme 8.

Scheme 10:

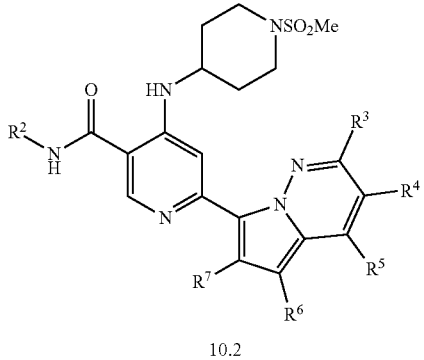

10.1

10.2

It is also noted that synthetic manipulations of the incorporated groups are possible following their incorporation. A specific illustrative example of an alteration to the $R^1$ group is shown in Scheme 10 wherein the secondary amine 10.1 is reacted to form a methyl sulfonamide 10.2. Other functional groups may also be present in the R¹ and can be manipulated. These groups and manipulations can include, but are not limited to, oxidation, elimination or displacement using suitable reagents known to those skilled in the art. The order of synthetic manipulations may be carried out in a fashion that is consistent with the methods outlined in Schemes 1-9 and should not be limited to the final step of compound preparation.

Scheme 11:

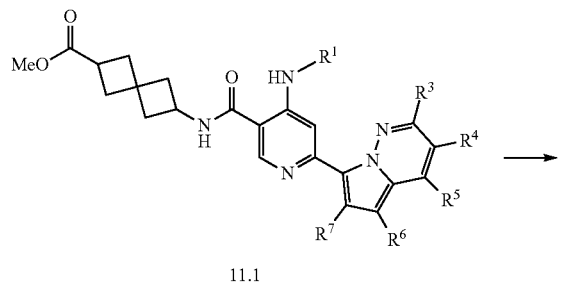

11.1

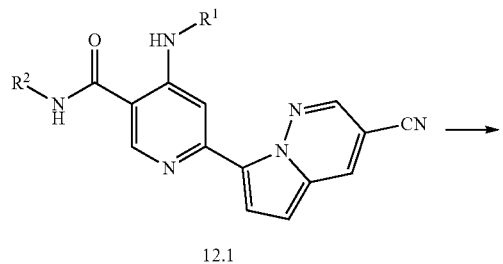

11.2

Variations of the R² group may also be performed following formation of the amide. An illustrative example is shown in Scheme 11, though the groups present or synthetic manipulations performed are not limited to those shown in Scheme 11, wherein a methyl ester 11.1 is reacted with MeMgX or MeLi to yield the shown tertiary alcohol 11.2. The order of synthetic manipulations may be carried out in a fashion that is consistent with the methods outlined in Schemes 1-9 and should not be limited to the final step of compound preparation.

Scheme 12:

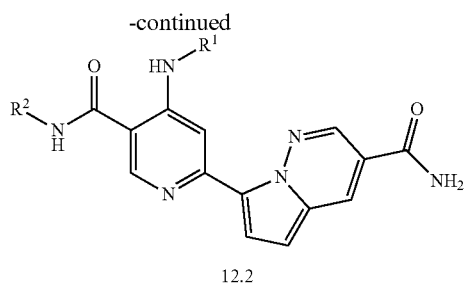

12.1

-continued 12.2

Manipulations of the R³, R⁴, R⁵, R⁶, and R⁷ groups present on the pyrrolo[1,2-b]pyridazine heterocycle may also be performed following its attachment to the pyridine core. An illustrative example is shown in Scheme 12 though the groups present and manipulations performed are not limited to those shown in the Scheme. A compound such as 12.1 with a cyano group may be converted to the corresponding carboxamide 12.2. The order of synthetic manipulations may be carried out in a fashion that is consistent with the methods outlined in Schemes 1-9 and should not be limited to the final step of compound preparation.

2. Synthesis of Intermediates

Preparation of Intermediate I-1

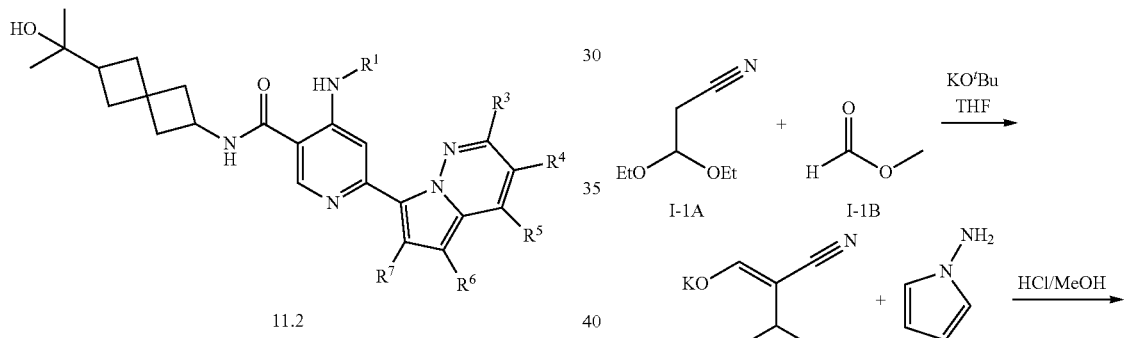

1,3-Diethoxy-2-formylpropionitrile Potassium Salt (I-1C)

To a stirred solution of 3,3-diethoxypropane-nitrile (I-1A, 283.80 g, 1.98 moles) and methyl formate (I-1B, 148.80 g, 2.48 moles) in anhydrous THF (1.1 L) at 10° C. was added 1.0 M potassium tert-butoxide in THF (2.2 L, 2.2 moles). The temperature was maintained in the range of 10° C. to 15° C. throughout the 45 minute addition. Following the addition, the resulting slurry was stirred for 2 hours at ambient temperature. Hexane (400 mL) was then added and stirring was continued for another 20 min. The slurry was filtered and the cake washed with 1/1 hexanes/THF and dried overnight at 60° C. in a vacuum oven to provide I-1C. $^1$H-NMR (CD$_3$OD) was consistent with the desired structure.

Pyrrolo[1,2-b]pyridazine-3-carbonitrile (I-1E)

A stirred suspension of 3,3-diethoxy-2-formylpropionitrile potassium salt (I-1C, 5.10 g, 24.36 mmol) was cooled to 0° C., and concentrated HCl (7.11 mL, 85.26 mmol) was added dropwise at such a rate that the internal temperature of the reaction did not go above 20° C. After addition was complete, the reaction was stirred at room temperature for 20 minutes. To this reaction mixture was added a solution of 1-aminopyrrole (I-1D, 1.00 g, 12.18 mmol) in methanol (4.0 mL). After addition, the reaction mixture was refluxed at 90° C. for 2 hours. When heating was complete, the reaction was cooled to room temperature and concentrated to about half of the original volume. Saturated aqueous sodium bicarbonate was added carefully to the resulting residue until bubbling stopped. The solution was extracted with two portions of ethyl acetate. The combined organic layers were dried over sodium sulfate, filtered, concentrated in vacuo, and the resulting residue was purified by silica gel chromatography (eluent: EtOAc/hexanes) to provide I-1E.

1H NMR (400 MHz, Chloroform-d) δ 8.16-8.03 (m, 2H), 7.93 (ddd, J=2.6, 1.4, 0.6 Hz, 1H), 7.04 (dd, J=4.5, 2.7 Hz, 1H), 6.84 (dd, J=4.6, 1.4 Hz, 1H).

7-bromopyrrolo[1,2-b]pyridazine-3-carbonitrile (I-1F)

To a solution of pyrrolo[1,2-b]pyridazine-3-carbonitrile (I-1E, 840.0 mg, 5.9 mmol) in MeCN (30 mL) at room temperature was added N-bromosuccinimide in one portion. The reaction was stirred at room temperature for 30 minutes then poured into saturated aqueous sodium bicarbonate. The solution was concentrated in vacuo to remove the acetonitrile. The resulting aqueous layer was extracted with three portions of EtOAc. The combined organic layers were dried over sodium sulfate, filtered, concentrated in vacuo, and purified by silica gel chromatography (eluent: EtOAc/hexanes) to provide I-1F.

1H NMR (400 MHz, Chloroform-d) δ 8.28 (d, J=2.1 Hz, 1H), 8.10 (d, J=2.1 Hz, 1H), 7.12 (d, J=4.8 Hz, 1H), 6.93 (d, J=4.8 Hz, 1H).

7-(4,4,5,5-tetramethyl-1,3,2-dioxaborolan-2-yl)pyrrolo[1,2-b]pyridazine-3-carbonitrile (I-1)

A microwave vial was charged with 7-bromopyrrolo[1,2-b]pyridazine-3-carbonitrile (I-1F, 416.5 mg, 1.9 mmol), bis(pinacolato)diboron (762.1 mg, 3.0 mmol), potassium acetate (552.3 mg, 5.6 mmol), and bis(triphenylphosphine)palladium(II) dichloride (65.8 mg, 0.094 mmol). Dioxane (8.0 mL) and DMF (4.0 mL) were added, and the reaction mixture was degassed with bubbling argon for 2 minutes. The vial was sealed and the reaction was heated at 120° C. in a microwave reactor for 60 minutes. After cooling, the reaction mixture was filtered and concentrated in vacuo. The resulting residue was partitioned between EtOAc and water. The aqueous layer was extracted with a second portion of EtOAc, and the combined organic layers were dried over sodium sulfate, filtered through a plug of Celite, and concentrated in vacuo. The resulting residue was purified by silica gel chromatography (eluent: EtOAc/hexanes) to provide I-1.

1H NMR (400 MHz, Chloroform-d) δ 8.31 (d, J=2.3 Hz, 1H), 8.14 (d, J=2.2 Hz, 1H), 7.52 (d, J=4.6 Hz, 1H), 6.84 (d, J=4.6 Hz, 1H), 1.41 (s, 12H).

Preparation of Intermediate I-2

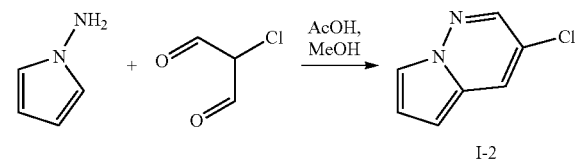

3-chloropyrrolo[1,2-b]pyridazine (I-2)

1-aminopyrrole (0.50 g, 6.1 mmol) was dissolved in 3:1 MeOH:AcOH (16 mL) at room temperature after which 2-chloromalonaldehyde (0.78 g, 7.3 mmol) was added. The resulting mixture was stirred at room temperature for 30 min. then heated to 80° C. for 16 hrs. The solvents were removed by rotary evaporation and the crude residue partitioned between water and EtOAc. The layers were separated and the aqueous layer was extracted once with EtOAc. The organic layers were combined, dried with MgSO$_4$, filtered and concentrated. The crude residue was then purified via silica gel chromatography (eluent: EtOAc/hexanes) to give the product 3-chloropyrrolo[1,2-b]pyridazine (I-2).

1H NMR (400 MHZ, CHLOROFORM-D) Δ 7.93 (D, J=2.5 HZ, 1H), 7.75-7.70 (M, 1H), 7.69 (D, J=2.5 HZ, 1H), 6.86 (DD, J=4.3, 2.8 HZ, 1H), 6.45 (DD, J=4.3, 1.4 HZ, 1H).

Preparation of Intermediate I-3

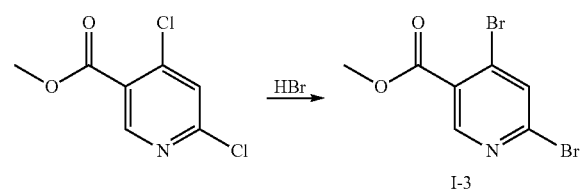

Methyl 4,6-dibromonicotinate (I-3)

Methyl 4,6-dichloronicotinate (5.0 g, 24.3 mmol) was suspended in hydrogen bromide (33% in Acetic Acid, 24 mL). The reaction vessel was sealed and heated to 60° C. for 4 hours. The reaction was cooled to room temperature and diluted with H$_2$O. The resulting solids were filtered, washed with H$_2$O. The solids were then suspended in H$_2$O and basified with aqueous sodium hydroxide. The resulting aqueous solution was extracted with EtOAc (3 times). The resulting organic layers were combined, dried over Na$_2$SO$_4$, and concentrated to provide methyl 4,6-dibromonicotinate.

ES/MS: 296.182 (M+H+).

Preparation of Intermediate I-4

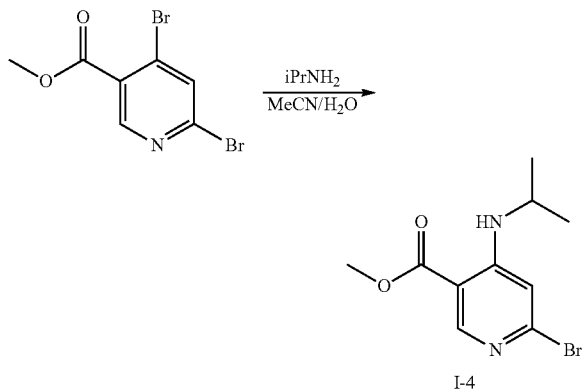

Methyl 6-bromo-4-(isopropylamino)nicotinate (I-4)

To a solution of methyl 4,6-dibromonicotinate (7.16 g, 24.3 mmol) in acetonitrile (125 mL) and H₂O (3 mL) was added isopropylamine (15.3 mL, 177 mmol). The reaction vessel was sealed and heated to 80° C. for 2 hours. The resulting solution was cooled to room temperature and concentrated to dryness. The resulting oil was purified by silica gel chromatography (eluent: EtOAc/hexanes) to provide methyl 6-bromo-4-(isopropylamino)nicotinate.

ES/MS: 273.569 (M+H⁺).

1H NMR (400 MHz, Chloroform-d) δ 8.60 (s, 1H), 8.08 (s, 1H), 6.72 (s, 1H), 3.87 (s, 3H), 3.68 (dq, J=13.1, 6.5 Hz, 1H), 1.28 (d, J=6.4 Hz, 6H).

Preparation of Intermediate I-5

6-bromo-4-chloronicotinic acid

To a solution of methyl 6-bromo-4-chloronicotinate (15 g, 59.89 mmol) in methanol (240 mL) was added lithium hydroxide (2.93 g, 119.77 mmol) in water (68 mL). The solution was heated to 43° C. overnight and subsequently cooled to room temperature. Aqueous hydrochloric acid (1M, 120 mL) was added and volatiles were removed in vacuo. The resulting slurry was filtered and washed with H₂O to provide 6-bromo-4-chloronicotinic acid.

ES/MS: 237.967 (M+H⁺).

1H NMR (400 MHz, DMSO-d6) δ 8.75 (s, 1H), 8.03 (s, 1H).

(R)-6-bromo-4-chloro-N-(2-fluoro-3-hydroxy-3-methylbutyl)nicotinamide

To a solution of 6-bromo-4-chloronicotinic acid (3 g, 12.69 mmol) in DMF (42 mL) was added HATU (6.27 g, 16.49 mmol), (R)-4-amino-3-fluoro-2-methylbutan-2-ol hydrochloride (2.4 g, 15.23 mmol), and N,N-Diisopropylethylamine (5.62 ml, 32.26 mmol). The resulting solution was stirred at room temperature overnight and subsequently diluted with ethyl acetate. The organic solution was washed with saturated aqueous lithium chloride (3 times), then dried over Na₂SO₄, and the concentrated. The residue was purified by silica gel chromatography (eluent: EtOAc/hexanes) to provide (R)-6-bromo-4-chloro-N-(2-fluoro-3-hydroxy-3-methylbutyl)nicotinamide.

ES/MS: 341.089 (M+H⁺).

1H NMR (400 MHz, DMSO-d₆) δ 8.88 (t, J=5.5 Hz, 1H), 8.41 (s, 1H), 8.01 (s, 1H), 4.82 (s, 1H), 4.28 (ddd, J=49.3, 9.4, 2.0 Hz, 1H), 3.84-3.63 (m, 1H), 3.40-3.22 (m, 1H), 1.13 (d, J=7.0 Hz, 6H).

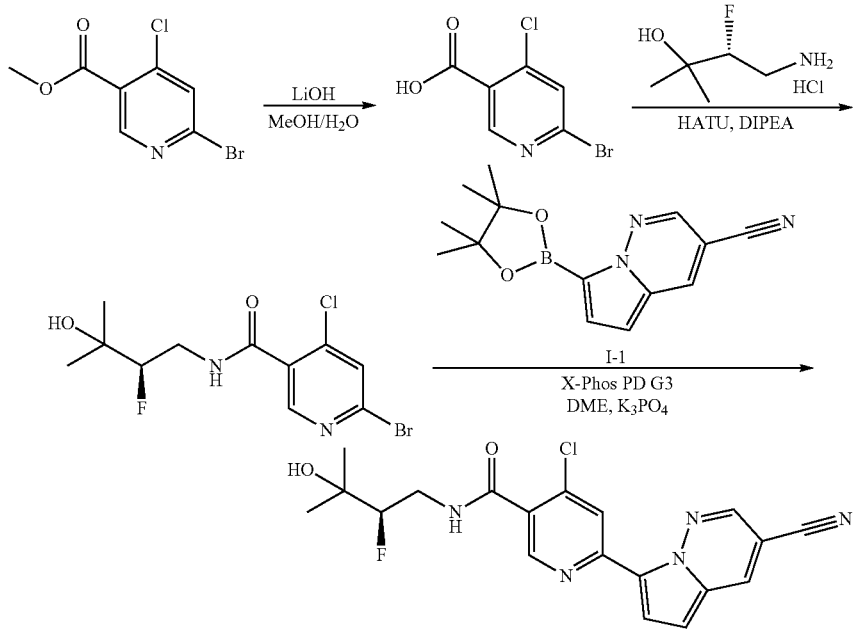

(R)-4-chloro-6-(3-cyanopyrrolo[1,2-b]pyridazin-7-yl)-N-(2-fluoro-3-hydroxy-3-methylbutyl)nicotinamide (I-5)

To a solution of (R)-6-bromo-4-chloro-N-(2-fluoro-3-hydroxy-3-methylbutyl)nicotinamide (0.2 g, 0.59 mmol) in DME (3.9 mL) was added 7-(4,4,5,5-tetramethyl-1,3,2-dioxaborolan-2-yl)pyrrolo[1,2-b]pyridazine-3-carbonitrile (0.24 g, 0.9 mmol), XPhos Pd G3 (0.05 g, 0.06 mmol), and aqueous potassium phosphate tribasic (2M, 0.59 mL, 1.18 mmol). The resulting solution was degassed with argon and heated to 120° C. for 12 minutes in a microwave reactor. The crude reaction mixture was purified by silica gel chromatography (eluent: EtOAc/hexanes) to provide (R)-4-chloro-6-(3-cyanopyrrolo[1,2-b]pyridazin-7-yl)-N-(2-fluoro-3-hydroxy-3-methylbutyl)nicotinamide.

ES/MS: 402.220 (M+H$^+$).

Preparation of Intermediate I-6

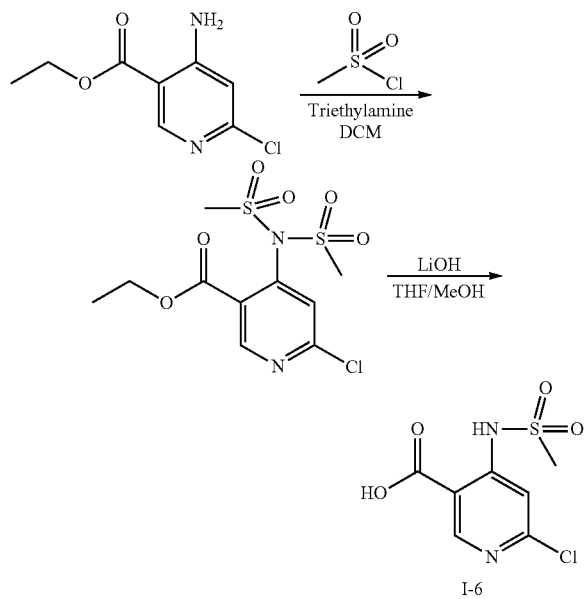

Ethyl 6-chloro-4-(N-(methylsulfonyl)methylsulfonamido)nicotinate

To a solution of ethyl 4-amino-6-chloronicotinate (334 mg, 1.67 mmol) and triethylamine (0.7 mL, 5 mmol) in dichloromethane (5 mL), was added methanesulfonyl chloride (0.39 mL, 5 mmol) slowly. The mixture was stirred overnight. Diluted with EtOAc (20 mL) and washed with aqueous NaHCO$_3$, and brine. The organic layer was dried and concentrated. The mixture was purified by silica gel chromatography (eluent: EtOAc/hexanes) to afford desired product.

ES/MS: 357 [M+H]$^+$

6-chloro-4-(methylsulfonamido)nicotinic acid (I-6)

To a solution of ethyl 6-chloro-4-(N-(methylsulfonyl)methylsulfonamido)nicotinate (60 mg, 0.17 mmol) in THF/MeOH (1 mL/0.5 mL), Lithium hydroxide (20 mg, 0.8 mmol) was added. It was heated to 50° C. for 3 hours. Acidified by HCl (1N) and extracted with EtOAc. The organic layer was dried and concentrated to give I-6 which was used without further purification.

ES/MS: 251 [M+H]$^+$

Preparation of Intermediate I-7

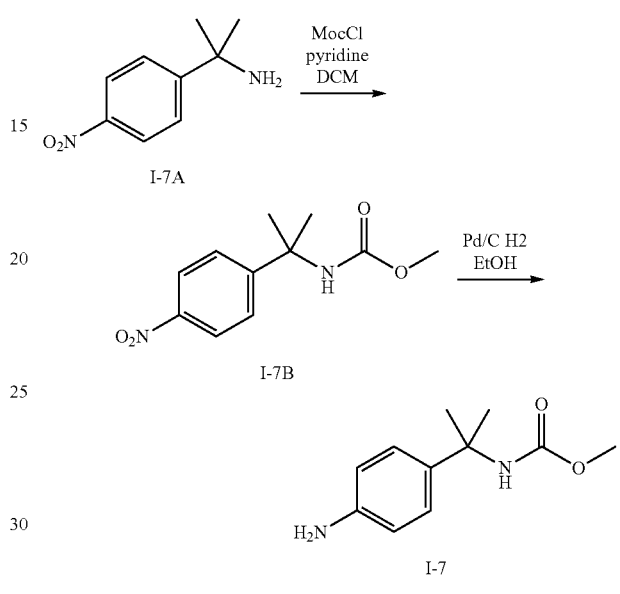

Methyl (2-(4-nitrophenyl)propan-2-yl)carbamate (I-7B)

To a solution of 2-(4-nitrophenyl)propan-2-amine (I-7A, 250 mg, 1.15 mmol) and pyridine (0.25 ml, 3.15 mmol) in DCM (10 mL) at 0 deg, was added methyl chloroformate (0.11 ml, 1.43 mmol). The reaction was gradually warmed to room temperature and stirred for 2 days. The reaction was concentrated, diluted with EtOAc and washed with 1N HCl three times. The organic extract was dried over sodium sulfate to give I-7B.

ES/MS: 239.0 (M+H$^+$).

1H NMR (400 MHz, Chloroform-d) δ 8.18 (d, J=8.9 Hz, 2H), 7.56 (d, J=8.9 Hz, 2H), 5.20 (s, 1H), 3.58 (s, 3H), 1.66 (s, 6H).

Methyl (2-(4-aminophenyl)propan-2-yl)carbamate (I-7)

A solution of methyl (2-(4-nitrophenyl)propan-2-yl)carbamate (I-7B, 101 mg, 0.424 mmol) in EtOH (10 mL) was degassed with argon and vacuum. Pd/C (10%, 26 m g, 0.0248 mmol) was added and the mixture was stirred with a balloon of H$_2$ overnight. The reaction was filtered over a Celite plug, rinsed with EtOAc and the filtrate was concentrated to give I-7.

1H NMR (400 MHz, Chloroform-d) δ 7.21-7.16 (m, 2H), 6.70-6.57 (m, 2H), 5.03 (s, 1H), 3.58 (s, 3H), 3.46 (s, 2H), 1.63 (s, 6H).

Preparation of Intermediate I-8

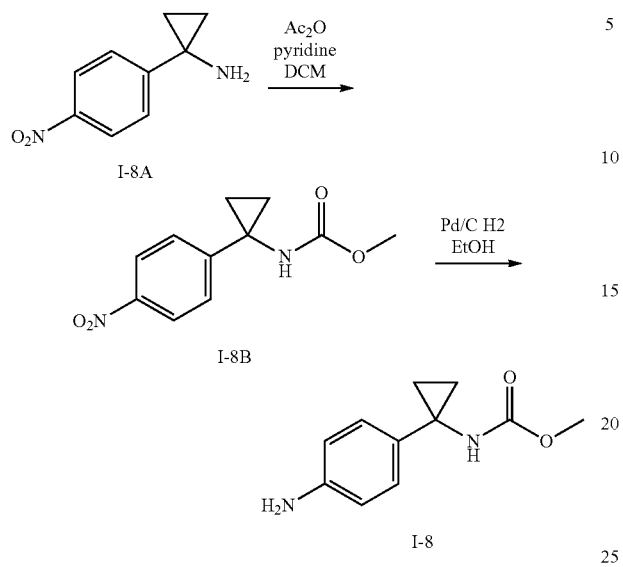

Methyl (1-(4-nitrophenyl)cyclopropyl)carbamate (I-8B)

To a solution of 1-(4-nitrophenyl)cyclopropan-1-amine (I-8A, 250 mg, 1.16 mmol) and pyridine (0.3 ml, 3.72 mmol) in DCM (10 mL) at 0 deg, was added methyl chloroformate (0.1 ml, 1.30 mmol). The reaction was gradually warmed to room temperature and stirred for 2 days. The reaction was concentrated, diluted with EtOAc and washed with 1N HCl three times. The organic extract was dried over sodium sulfate to give I-8B.
1H NMR (400 MHz, Chloroform-d) δ 8.14 (d, J=8.9 Hz, 2H), 7.33 (d, J=8.9 Hz, 2H), 5.44 (s, 1H), 3.69 (s, 3H), 1.40 (m, 4H).

Methyl (1-(4-aminophenyl)cyclopropyl)carbamate (I-8)

A solution of methyl (1-(4-nitrophenyl)cyclopropyl)carbamate (I-8B, 227 mg, 0.961 mmol) in EtOH (15 mL) was degassed with argon and vacuum. To this was added Pd/C (10%, 60 mg, 0.0564 mmol) and the mixture was stirred with a balloon of $H_2$ overnight. The reaction was filtered over a Celite plug, rinsed with EtOAc and the filtrate was concentrated to give I-8.
1H NMR (400 MHz, Chloroform-d) δ 7.08 (dd, J=33.4, 8.0 Hz, 2H), 6.72-6.56 (m, 2H), 5.44 (s, 1H), 3.62 (d, J=4.8 Hz, 3H), 3.09 (d, J=47.9 Hz, 2H), 1.22 (t, J=7.0 Hz, 4H).

Preparation of Intermediate I-9

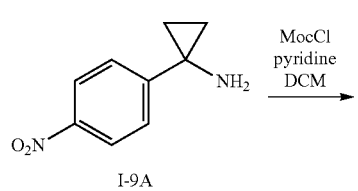

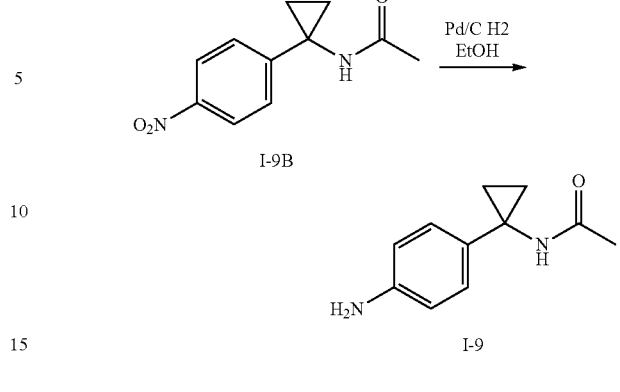

Methyl (1-(4-nitrophenyl)cyclopropyl)acetamide (I-9B)

To a solution of 1-(4-nitrophenyl)cyclopropan-1-amine (I-9A, 250 mg, 1.16 mmol) and pyridine (0.3 ml, 3.72 mmol) in DCM (10 mL) at 0° C., was added acetic anhydride (0.12 ml, 1.27 mmol) The reaction was gradually warmed to room temperature and stirred for 2 days. The reaction was concentrated, diluted with EtOAc and washed with 1N HCl three times. The organic extract was dried over sodium sulfate, filtered and concentrated to give I-9B.
ES/MS: 221.0 (M+H$^+$).
1H NMR (400 MHz, Chloroform-d) δ 8.13 (d, J=8.9 Hz, 2H), 7.30 (d, J=8.9 Hz, 2H), 6.15 (s, 1H), 2.04 (s, 3H), 1.40 (s, 4H).

Methyl (1-(4-aminophenyl)cyclopropyl)acetamide (I-9)

A solution of methyl (1-(4-nitrophenyl)cyclopropyl)acetamide (I-9B, 217 mg, 0.985 mmol) in EtOH (15 mL) was degassed with argon and vacuum, then added Pd/C (10%, 60 mg, 0.0564 mmol) and stirred with a balloon of $H_2$ overnight. The reaction was filtered over a Celite plug, rinsed with EtOAc and the filtrate was concentrated to give I-9.
1H NMR (400 MHz, Chloroform-d) δ 7.06 (d, J=8.4 Hz, 2H), 6.64 (d, J=8.4 Hz, 2H), 5.59 (d, J=8.1 Hz, 1H), 3.72-3.38 (m, 2H), 1.95 (s, 3H), 0.85 (t, J=7.4 Hz, 4H).

Preparation of Intermediate I-10

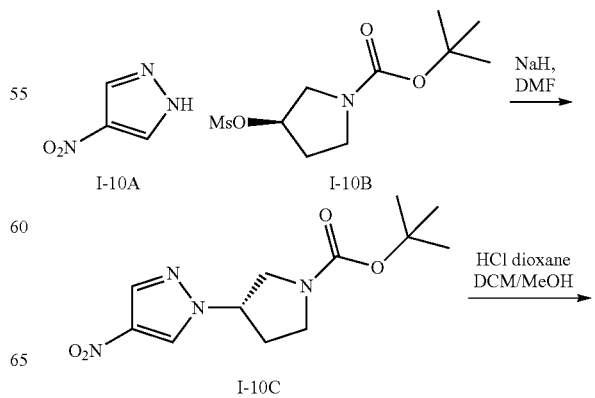

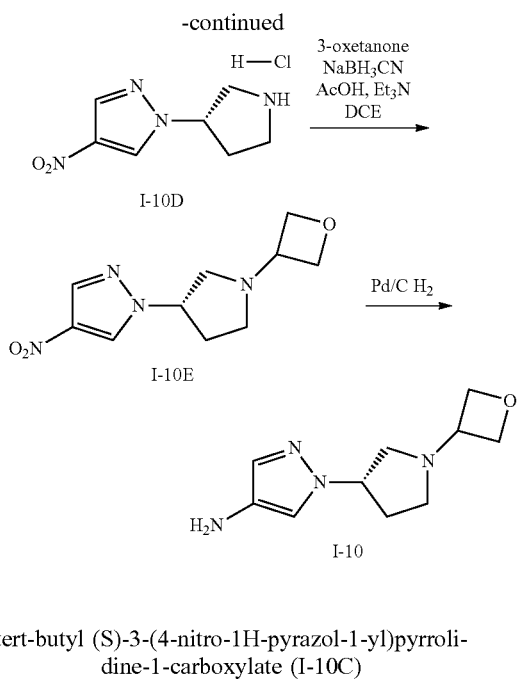

tert-butyl (S)-3-(4-nitro-1H-pyrazol-1-yl)pyrrolidine-1-carboxylate (I-10C)

To a solution of 4-nitro-1H-pyrazole (I-10A, 250 mg, 2.211 mmol) in DMF (5 mL) at 0° C., was added sodium hydride, 60% disp. in oil (60%, 133 mg, 3.316 mmol). After stirring for 1.5 hr, a solution of tert-butyl (R)-3-((methylsulfonyl)oxy)pyrrolidine-1-carboxylate (I-10B, 704 mg, 2.653 mmol) in 5 mL DMF was added and the mixture was heated at 95° C. overnight. The reaction mixture was diluted with EtOAc and washed with brine twice. The organic extract was dried over sodium sulfate and purified by silica gel chromatography (eluent: EtOAc/hexanes) to provide I-10C.

1H NMR (400 MHz, Chloroform-d) δ 8.16 (s, 1H), 8.13-8.01 (m, 1H), 4.89 (p, J=5.7 Hz, 1H), 3.87 (dd, J=12.0, 6.5 Hz, 1H), 3.77 (s, 1H), 3.57 (s, 2H), 2.60-2.34 (m, 2H), 1.48 (s, 9H).

(S)-4-nitro-1-(pyrrolidin-3-yl)-1H-pyrazole hydrochloride (I-10D)

To a solution of tert-butyl (S)-3-(4-nitro-1H-pyrazol-1-yl)pyrrolidine-1-carboxylate (I-10C, 248.3 mg, 0.880 mmol) in DCM (3 mL) was added 750 uL HCl (4.0M in dioxane). After 4 hr, HCl (1 mL) and MeOH (1 mL) was added. The reaction was heated at 40° C. overnight. The reaction mixture was concentrated to dryness to give I-10D.

ES/MS: 183.2 (M+H$^+$).

(S)-4-nitro-1-(1-(oxetan-3-yl)pyrrolidin-3-yl)-1H-pyrazole (I-10E)

To a solution of (S)-4-nitro-1-(pyrrolidin-3-yl)-1H-pyrazole hydrochloride (I-10D, 186 mg, 0.851 mmol), triethylamine (0.12 mL, 0.861 mmol), and 3-oxetanone (0.250 mL, 4.267 mmol) in DCE (5 mL), was added AcOH (250 uL). The reaction was stirred at room temperature for 3 hr. Sodium cyanoborohydride (270 mg, 4.296 mmol) was added and the reaction was heated at 55° C. overnight. The reaction was partitioned with DCM and brine. The organic extract was dried over sodium sulfate and the resulting residue was purified by silica gel chromatography (eluent: EtOAc/hexanes) to provide I-10E.

ES/MS: 239.2 (M+H$^+$).

1H NMR (400 MHz, Chloroform-d) δ 8.39 (d, J=0.6 Hz, 1H), 8.05 (d, J=0.7 Hz, 1H), 5.01-4.86 (m, 1H), 4.72 (td, J=6.6, 2.8 Hz, 2H), 4.67 (t, J=6.1 Hz, 1H), 4.63 (t, J=6.1 Hz, 1H), 3.77 (tt, J=6.8, 5.8 Hz, 1H), 2.98 (ddd, J=17.9, 9.1, 3.8 Hz, 2H), 2.86 (dd, J=10.2, 6.7 Hz, 1H), 2.63-2.45 (m, 2H), 2.30-2.05 (m, 1H).

(S)-1-(1-(oxetan-3-yl)pyrrolidin-3-yl)-1H-pyrazol-4-amine (I-10)

A solution of (S)-4-nitro-1-(1-(oxetan-3-yl)pyrrolidin-3-yl)-1H-pyrazole (I-10E, 82.8 mg, 0.348 mmol) in EtOH (5 mL) was degassed with argon and vacuum, and then Pd/C (10%, 22 mg, 0.021 mmol) was added and the mixture was stirred with a balloon of H$_2$ overnight. The reaction was filtered over a Celite plug, rinsed with EtOAc and the filtrate was concentrated to give I-10.

ES/MS: 209.1 (M+H$^+$).

1H NMR (400 MHz, Chloroform-d) δ 7.21 (d, J=0.9 Hz, 1H), 7.12 (d, J=1.0 Hz, 1H), 4.77 (ddt, J=9.4, 7.2, 4.7 Hz, 1H), 4.69 (td, J=6.6, 2.7 Hz, 2H), 4.63 (dt, J=10.4, 6.0 Hz, 2H), 3.82-3.62 (m, 1H), 2.82 (pd, J=8.8, 7.9, 3.9 Hz, 3H), 2.53 (td, J=8.5, 6.3 Hz, 1H), 2.41 (dtd, J=13.8, 8.6, 5.4 Hz, 1H), 2.25-2.04 (m, 1H).

Preparation of Intermediate I-11

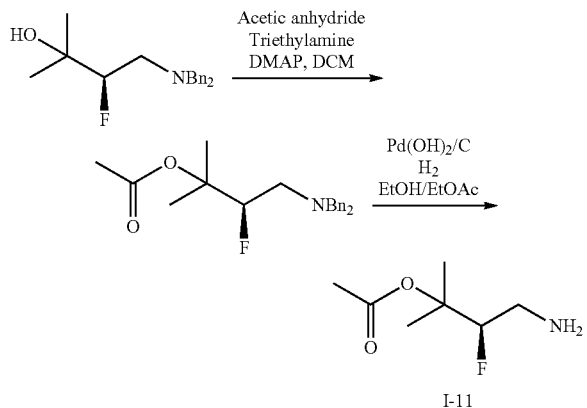

(R)-4-(dibenzylamino)-3-fluoro-2-methylbutan-2-yl acetate

To a solution of (R)-4-(dibenzylamino)-3-fluoro-2-methylbutan-2-ol (800.0 mg, 2.6 mmol) and acetic anhydride (0.276 mL, 2.9 mmol) was added DMAP (16.2 mg, 0.13 mmol) and triethylamine (0.56 mL, 4.0 mmol). The reaction mixture was heated to 100° C. until complete consumption of starting material was observed by mass spectrometry. Upon completion, the reaction mixture was concentrated in vacuo and purified by silica gel column chromatography (eluent: EtOAc/hexanes) to provide the desired product.

ES/MS: 344.2 (M+H$^+$).

(R)-4-amino-3-fluoro-2-methylbutan-2-yl acetate (I-11)

To a solution of R)-4-(dibenzylamino)-3-fluoro-2-methylbutan-2-yl acetate (748.0 mg, 2.2 mmol) in EtOH (8.0 mL)

and EtOAc (8.0 mL) was added Pd(OH)$_2$ on carbon. The atmosphere was evacuated and back-flushed with hydrogen three times and then maintained under a hydrogen environment for the course of the reaction. After three hours, the reaction mixture was filtered and concentrated in vacuo to provide I-11 which was used without additional purification.

ES/MS: 164.0 (M+H$^+$).

Preparation of Intermediate I-12

Tert-butyl (3-acetamidobicyclo[1.1.1]pentan-1-yl)carbamate

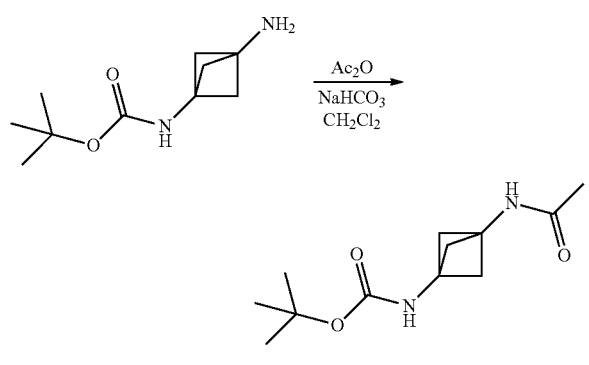

I-12

Tert-butyl (3-acetamidobicyclo[1.1.1]pentan-1-yl)carbamate

To a solution of tert-butyl (3-aminobicyclo[1.1.1]pentan-1-yl)carbamate (303 mg, 1.5 mmol) in CH$_2$Cl$_2$ (7.5 mL) at 0° C. was added saturated aqueous sodium bicarbonate (15 mL) and acetic anhydride (0.73 mL, 7.7 mmol). The biphasic solution was warmed to room temperature and stirred for 24 hours. The mixture was extracted with CH$_2$Cl$_2$ (3 times). The combine organic layers were dried over MgSO$_4$ and concentrated to dryness. The resulting material was used without further purification.

1H NMR (400 MHz, Chloroform-d) δ 5.80 (s, 1H), 4.93 (s, 1H), 2.31 (s, 6H), 1.94 (s, 3H), 1.44 (s, 9H).

Preparation of Intermediate I-13

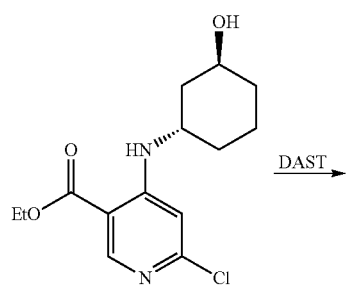

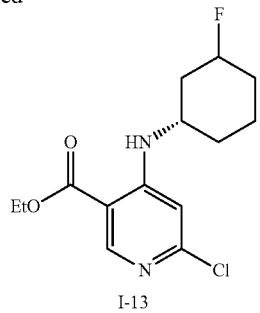

I-13

Ethyl 6-chloro-4-(((1S)-3-fluorocyclohexyl)amino)nicotinate

Ethyl 6-chloro-4-(((1S,3S)-3-hydroxycyclohexyl)amino)nicotinate (0.13 g, 0.44 mmol) was dissolved in DCM (6 mL) and brought to 0° C. DAST (0.069 mL, 0.52 mmol) was then added dropwise over 1 minute. After 5 minutes the reaction mixture was quenched by the addition of saturated aqueous NaHCO$_3$ solution (1 mL, poured into water (5 mL) and extracted with EtOAc (3×5 mL). The organic layers were combined, dried over MgSO4, filtered and concentrated to give a crude residue which was further purified by silica gel chromatography (eluent: EtOAc/hexanes) to provide the desired product.

ES/MS: 301.4 [M+H$^+$].

Preparation of Intermediate I-14

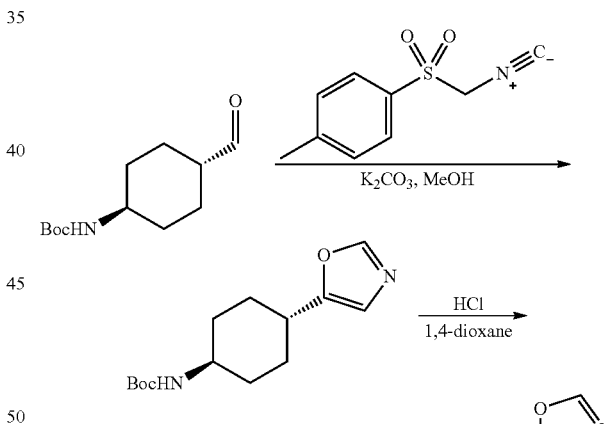

(1r,4r)-4-(oxazol-5-yl)cyclohexan-1-amine hydrochloride (I-14)

To a solution of tert-butyl ((1r,4r)-4-formylcyclohexyl)carbamate (500 mg, 2.2 mmol) in MeOH (10 mL) was added p-toluenesulfonylmethylisocyanide (430 mg, 2.2 mmol) and the resulting mixture heated at 65° C. for 12 hours. The mixture was poured into water (10 mL) and extracted with 2×20 mL EtOAc. The combined organic layers were dried over MgSO$_4$, filtered and concentrated. The resulting crude residue was purified by silica gel chromatography (eluent: EtOAc/hexanes) to give pure tert-butyl ((1r,4r)-4-(oxazol-5-yl)cyclohexyl)carbamate. This was then dissolved in HCl (4.0M in dioxane, 4 mL, 16 mmol) and stirred at room temperature for 3 hours after which the reaction mixture was concentrated to dryness directly to give I-14 as an HCl salt which was used without further purification.

ES/MS: 167.1 [M+H]$^+$

Preparation of Intermediate I-15

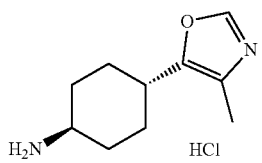

(1r,4r)-4-(4-methyloxazol-5-yl)cyclohexan-1-amine hydrochloride (I-15)

(1r,4r)-4-(4-methyloxazol-5-yl)cyclohexan-1-amine hydrochloride was prepared identically as described for I-14 substituting p-toluenesulfonylmethylisocyanide with 1-methyl-1-tosylmethyl isocyanide.

ES/MS: 181.1 [M+H]$^+$

Preparation of Intermediate I-16

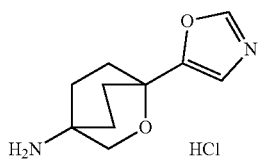 [SMILES: NC12CCC(c3cnco3)(CC1)OC2 ; Cl]

1-(oxazol-5-yl)-2-oxabicyclo[2.2.2]octan-4-amine hydrochloride (I-16)

1-(oxazol-5-yl)-2-oxabicyclo[2.2.2]octan-4-amine hydrochloride was prepared identically as described for I-14 substituting tert-butyl ((1r,4r)-4-formylcyclohexyl)carbamate with tert-butyl (1-formyl-2-oxabicyclo[2.2.2]octan-4-yl)carbamate.

ES/MS: 195.1 [M+H]$^+$

Preparation of Intermediate I-17

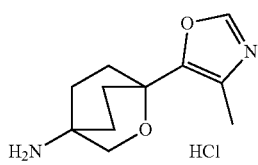

1-(4-methyloxazol-5-yl)-2-oxabicyclo[2.2.2]octan-4-amine hydrochloride (I-17

1-(4-methyloxazol-5-yl)-2-oxabicyclo[2.2.2]octan-4-amine hydrochloride was prepared identically as described for I-16 substituting p-toluenesulfonylmethylisocyanide with 1-methyl-1-tosylmethyl isocyanide.

ES/MS: 209.1 [M+H]$^+$

Preparation of Intermediate I-18

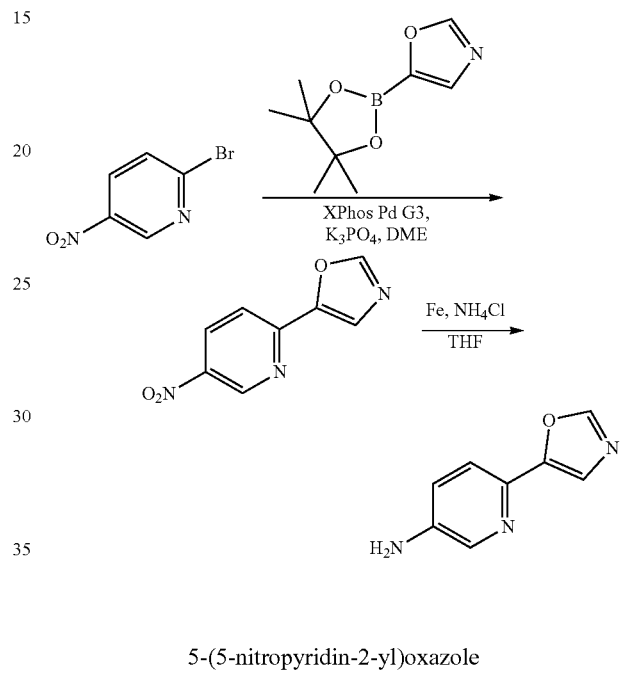

5-(5-nitropyridin-2-yl)oxazole

To a solution of 2-bromo-5-nitropyridine (125 mg, 0.62 mmol) in DME (2.5 mL) was added XPhos Pd G3 (43 mg, 0.051 mmol), 5-(4,4,5,5-tetramethyl-1,3,2-dioxaborolan-2-yl)oxazole (132 mg, 0.68 mmol) and K$_3$PO$_4$ (0.5M in water, 1.5 mL, 0.77 mmol). The resulting mixture was heated in a microwave reactor at 120° C. for 20 minutes after which it was poured into water (5 mL) and extracted with EtOAc (2×15 mL)). The combined organic layers were dried over MgSO$_4$, filtered and concentrated. The resulting crude residue was purified by silica gel chromatography (eluent: EtOAc/hexanes) to give 5-(5-nitropyridin-2-yl)oxazole.

ES/MS: 192.0 [M+H]$^+$ 6-(oxazol-5-yl)pyridin-3-amine (I-18)

5-(5-nitropyridin-2-yl)oxazole (178 mg, 0.093 mmol) was dissolved in THF (3 mL) after which saturated aqueous NH$_4$Cl solution (1 mL) and iron (312 mg, 5.6 mmol) were added and the resulting mixture heated to reflux for 2 hours. The mixture was then filtered through a pad of celite which was rinsed with MeOH (5 mL), added to water (5 mL), and extracted with EtOAc (2×15 mL). The combined organic layers were dried over MgSO$_4$, filtered and concentrated to give I-18 which was used without further purification.

ES/MS: 162.1 [M+H]$^+$

Preparation of Intermediate I-19

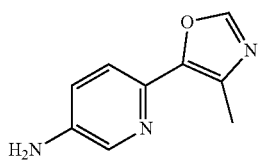

4-methyl-5-(5-nitropyridin-2-yl)oxazole

To a solution of 5-nitropicolinaldehyde (500 mg, 3.3 mmol) in MeOH (10 mL) was added 1-methyl-1-tosylmethyl isocyanide (825 mg, 3.9 mmol) and the resulting mixture heated at 65° C. for 12 hours. The mixture was poured into water (10 mL) and extracted with 2×20 mL EtOAc. The combined organic layers were dried over MgSO$_4$, filtered and concentrated. The resulting crude residue was purified by silica gel chromatography (eluent: EtOAc/hexanes) to give the desired product.
ES/MS: 206.1 [M+H]$^+$ 6-(4-methyloxazol-5-yl)pyridin-3-amine (I-19)

4-methyl-5-(5-nitropyridin-2-yl)oxazole (200 mg, 0.098 mmol) was dissolved in THF (3 mL) after which saturated aqueous NH$_4$Cl solution (1 mL) and iron (327 mg, 5.8 mmol) were added and the resulting mixture heated to reflux for 2 hours. The mixture was then filtered through a pad of celite which was rinsed with MeOH (5 mL), added to water (5 mL), and extracted with EtOAc (2×15 mL). The combined organic layers were dried over MgSO$_4$, filtered and concentrated to give I-19 which was used without further purification.
ES/MS: 176.1 [M+H]$^+$

Preparation of Intermediate I-20

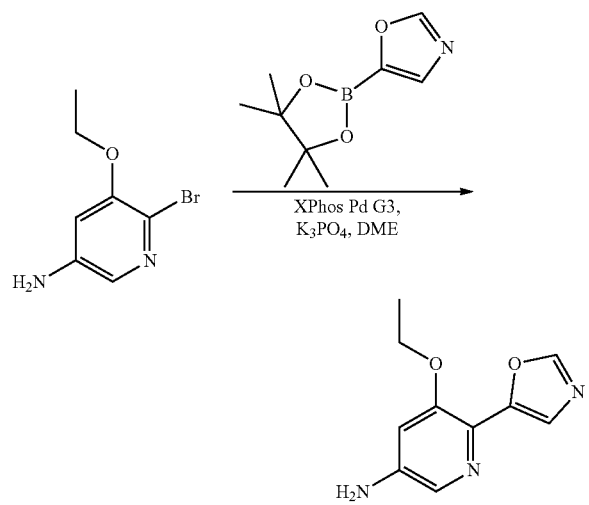

5-ethoxy-6-(oxazol-5-yl)pyridin-3-amine (I-20)

To a solution of 6-bromo-5-ethoxypyridin-3-amine (100 mg, 0.51 mmol) in DME (2 mL) was added XPhos Pd G3 (33 mg, 0.038 mmol), 5-(4,4,5,5-tetramethyl-1,3,2-dioxaborolan-2-yl)oxazole (99 mg, 0.51 mmol) and K$_3$PO$_4$ (0.5M in water, 1.2 mL, 0.58 mmol). The resulting mixture was heated in a microwave reactor at 120° C. for 20 minutes after which it was poured into water (5 mL) and extracted with EtOAc (2×15 mL)). The combined organic layers were dried over MgSO$_4$, filtered and concentrated to give the desired product which was used without further purification.
ES/MS: 206.1 [M+H]$^+$

Preparation of Intermediate I-21

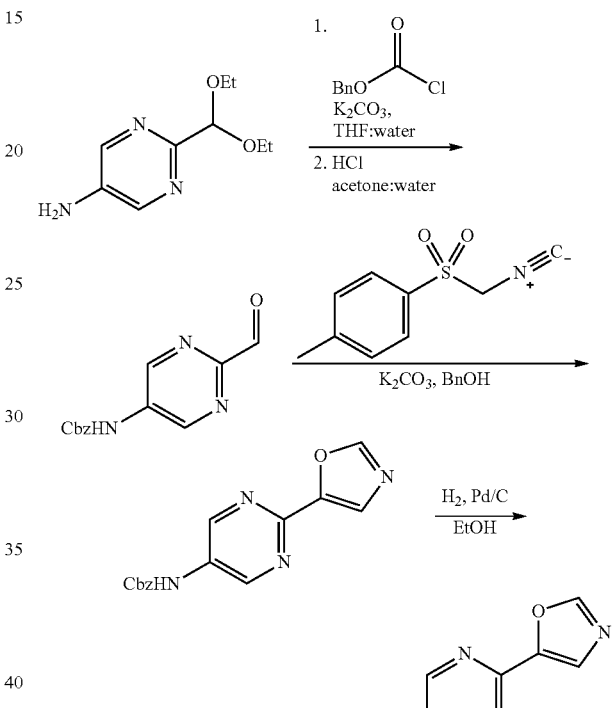

Benzyl (2-formylpyrimidin-5-yl)carbamate

To a solution of 2-(diethoxymethyl)pyrimidin-5-amine (1.00 g, 5.07 mmol) in 1:1 THF:water (12 mL) was added K$_2$CO$_3$ (1.40 g, 10.1 mmol) and benzyl chloroformate (0.79 mL, 5.58 mmol) and the resulting mixture stirred at room temperature for 16 hours. The reaction mixture was poured into water (10 mL) and extracted with EtOAc (2×30 mL). The combined organic layers were dried over MgSO$_4$, filtered and concentrated. The resulting crude residue was purified by silica gel chromatography (eluent: EtOAc/hexanes) to give the desired product which was then dissolved in acetone (10 mL) and 1N HCl (6 mL) and stirred at room temperature for 16 h. The acetone was removed by rotary evaporation and the resulting mixture partitioned between saturated aqueous NaHCO$_3$ solution (10 mL) and EtOAc (25 mL), the aqueous extracted once more with EtOAc (25 mL), and the combined organics dried over MgSO$_4$, filtered and concentrated to give benzyl (2-formylpyrimidin-5-yl)carbamate which was used without further purification.
ES/MS: 258.1 [M+H]$^+$

Benzyl (2-(oxazol-5-yl)pyrimidin-5-yl)carbamate

To a solution of benzyl (2-formylpyrimidin-5-yl)carbamate (225 mg, 0.88 mmol) in BnOH (4 mL) was added p-toluenesulfonylmethylisocyanide (171 mg, 0.88 mmol) and the resulting mixture heated at 65° C. for 16 hours. The mixture was poured into water (10 mL) and extracted with 2×30 mL EtOAc. The combined organic layers were dried over MgSO$_4$, filtered and concentrated. The resulting crude residue, still containing a significant amount of BnOH, was purified by silica gel chromatography (eluent: EtOAc/hexanes) to give the desired product.

ES/MS: 297.2 [M+H]$^+$

2-(oxazol-5-yl)pyrimidin-5-amine (I-21)

To a solution of benzyl (2-(oxazol-5-yl)pyrimidin-5-yl)carbamate (225 mg, 0.076 mmol) in EtOH (10 mL) in a 50 mL round bottom flask was added 10% Pd/C (323 mg, 0.015 mmol). The head space was flushed with H$_2$ gas and an H$_2$ balloon then applied to the reaction flask. After 13 hours the reaction mixture was filtered through celite, rinsed with EtOH (2×15 mL) and the resulting EtOH solution concentrated to dryness to give crude I-21 which was used without further purification.

ES/MS: 163.1 [M+H]$^+$

Preparation of Intermediate I-22

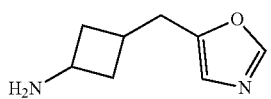

3-(oxazol-5-ylmethyl)cyclobutan-1-amine hydrochloride (I-22)

3-(oxazol-5-ylmethyl)cyclobutan-1-amine hydrochloride was prepared identically as described for I-14 substituting tert-butyl ((1r,4r)-4-formylcyclohexyl)carbamate with the known compound tert-butyl (3-(2-oxoethyl)cyclobutyl)carbamate.

ES/MS: 153.1 [M+H]$^+$

Preparation of Intermediate I-23

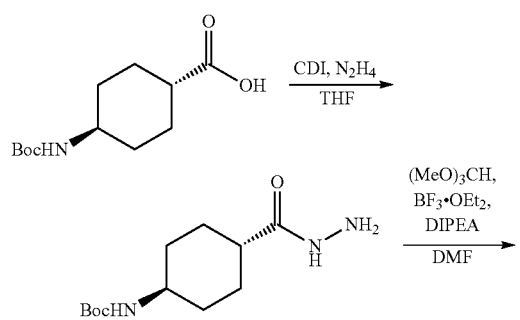

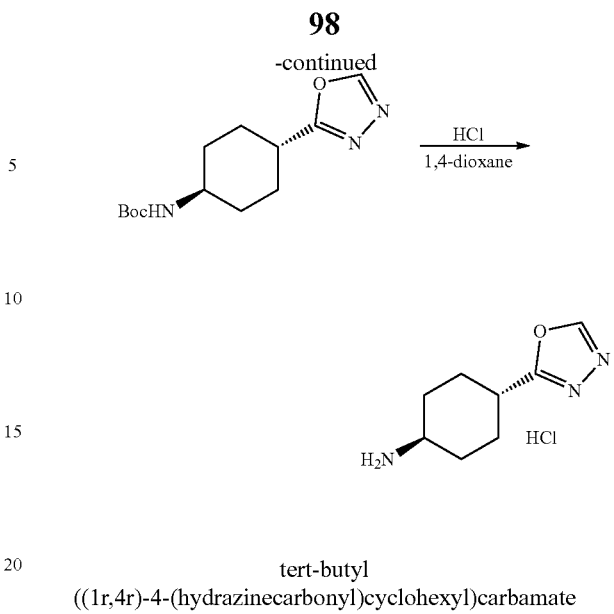

tert-butyl ((1r,4r)-4-(hydrazinecarbonyl)cyclohexyl)carbamate

To a solution of (1r,4r)-4-((tert-butoxycarbonyl)amino)cyclohexane-1-carboxylic acid (1.5 g, 6.2 mmol) in THF (60 mL) was added CDI (1.25 g, 7.7 mmol) as a single solid portion and the resulting mixture allowed to stir at room temperature for 16 hours. Hydrazine hydrate (1.05 g, 21 mmol) was then added as a single portion and left to stir for 30 minutes after which the reaction mixture was filtered, the filter cake washed with THF (1×50 mL) and dried under vacuum to give the desired product which was carried forward without further purification.

ES/MS: 258.0 [M+H]$^+$ tert-butyl ((1r,4r)-4-(1,3,4-oxadiazol-2-yl)cyclohexyl)carbamate

To a solution of tert-butyl ((1r,4r)-4-(hydrazinecarbonyl)cyclohexyl)carbamate (556 mg, 2.2 mmol) in DMF (10 mL) was added trimethyl orthoformate (1.3 mL, 12 mmol) and BF$_3$.OEt$_2$ (0.01 mL, 0.011 mmol) under argon. The reaction mixture was heated to 50° C. for 4 hours after which it was allowed to cool to room temperature, DIPEA (0.23 mL, 1.3 mmol) was added and the mixture allowed to stir for 12 hours. Upon completion the reaction mixture was poured into water (15 mL) and extracted with EtOAc (2×30 mL). The combined organic layers were dried over MgSO$_4$, filtered and concentrated. The resulting crude residue was purified by silica gel chromatography (eluent: EtOAc/hexanes) to give the desired product.

ES/MS: 268.0 [M+H]$^+$

(1r,4r)-4-(1,3,4-oxadiazol-2-yl)cyclohexan-1-amine hydrochloride (I-23)

tert-butyl ((1r,4r)-4-(1,3,4-oxadiazol-2-yl)cyclohexyl)carbamate (100 mg, 0.37 mmol) was then dissolved in HCl (4.0M in dioxane, 4 mL, 16 mmol) and stirred at room temperature for 3 hours after which the reaction mixture was concentrated to dryness directly to give I-23 as an HCl salt which was used without further purification.

ES/MS: 168.1 [M+H]$^+$

Preparation of Intermediate I-24

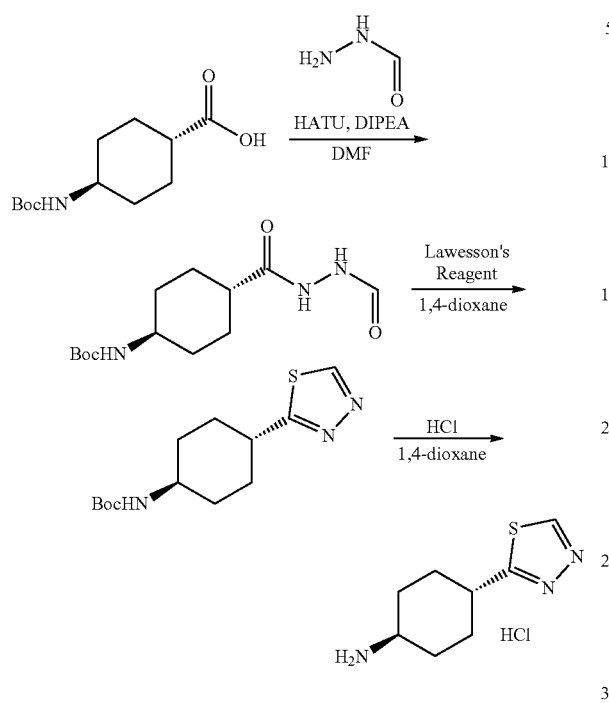

tert-butyl ((1r,4r)-4-(2-formylhydrazine-1-carbonyl)cyclohexyl)carbamate

To a solution of (1r,4r)-4-((tert-butoxycarbonyl)amino)cyclohexane-1-carboxylic acid (250 mg, 1.0 mmol) in DMF (2 mL) was added formic acid hydrazide (80 mg, 1.3 mmol), HATU (469 mg, 1.2 mmol), and finally DIPEA (0.45 mL, 2.6 mmol) and the resulting mixture stirred at room temperature for 15 minutes. Upon completion, the reaction mixture was poured into water (5 mL) and extracted with EtOAc (2×15 mL). The combined organic layers were dried over MgSO$_4$, filtered and concentrated. The resulting crude residue was purified by silica gel chromatography (eluent: EtOAc/hexanes) to give the desired product.
ES/MS: 285.9 [M+H]$^+$ tert-butyl ((1r,4r)-4-(1,3,4-thiadiazol-2-yl)cyclohexyl)carbamate

To a solution of tert-butyl ((1r,4r)-4-(2-formylhydrazine-1-carbonyl)cyclohexyl)carbamate (193 mg, 0.68 mmol) in dioxane (5 mL) was added Lawesson's Reagent (301 mg, 0.74 mmol) and the resulting reaction mixture heated to 100° C. for 3 hours. Upon completion, the reaction mixture was poured into water (5 mL) and extracted with EtOAc (2×15 mL). The combined organic layers were dried over MgSO$_4$, filtered and concentrated. The resulting crude residue was purified by silica gel chromatography (eluent: EtOAc/hexanes) to give the desired product.
ES/MS: 284.0 [M+H]$^+$

(1r,4r)-4-(1,3,4-thiadiazol-2-yl)cyclohexan-1-amine hydrochloride (I-24)

tert-butyl ((1r,4r)-4-(1,3,4-thiadiazol-2-yl)cyclohexyl)carbamate (59 mg, 0.21 mmol) was then dissolved in HCl (4.0M in dioxane, 4 mL, 16 mmol) and stirred at room temperature for 7 hours after which the reaction mixture was concentrated to dryness directly to give I-24 as an HCl salt which was used without further purification.
ES/MS: 184.1 [M+H]$^+$

Preparation of Intermediate I-25

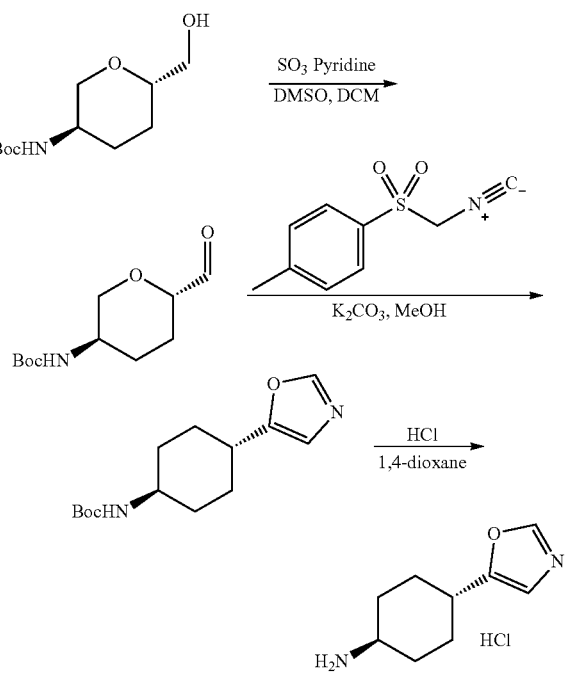

tert-butyl ((3R,6S)-6-formyltetrahydro-2H-pyran-3-yl)carbamate

To a solution of tert-butyl ((3R,6S)-6-(hydroxymethyl)tetrahydro-2H-pyran-3-yl)carbamate (200 mg, 0.87 mmol) in DCM (5 mL) at −10° C. was added DIPEA (2.3 mL, 13 mmol) as a single portion followed by a solution of pyridine-SO$_3$ (1:1) complex (2.1 g, 13 mmol) in DMSO (7 mL) dropwise over 2 minutes. Reaction vessel was transferred to a 0° C. bath and stirred for 1.5 hours then allowed to warm to room temperature over 2.5 hours. Reaction mixture was then brought to −10° C., pyridine-SO$_3$ (1:1) complex (400 mg, 2.4 mmol) was added as a single portion, and the reaction mixture allowed to warm to room temperature over 2 hours. Upon completion, reaction mixture was poured into water (20 mL) and extracted with EtOAc (2×50 mL). The combined organic layers were washed with water (2×30 mL), dried over MgSO$_4$, filtered, concentrated and the resulting crude aldehyde was carried forward without further purification.
ES/MS: 230.0 [M+H]$^+$ tert-butyl ((3R,6S)-6-(oxazol-5-yl)tetrahydro-2H-pyran-3-yl)carbamate tert-butyl ((3R,6S)-6-formyltetrahydro-2H-pyran-3-yl) carbamate (200 mg, 0.87 mmol) in MeOH (5 mL) was added p-toluenesulfonylmethylisocyanide (170 mg, 0.87 mmol) and the resulting mixture heated at 65° C. for 14 hours. The mixture was poured into water (10 mL) and extracted with 2×20 mL EtOAc. The combined organic layers were dried over MgSO$_4$, filtered and concentrated. The resulting crude residue was purified by silica gel chromatography (eluent: EtOAc/hexanes) to give the desired product.

ES/MS: 269.1 [M+H]$^+$

(3R,6S)-6-(oxazol-5-yl)tetrahydro-2H-pyran-3-amine hydrochloride (I-25)

tert-butyl ((3R,6S)-6-(oxazol-5-yl)tetrahydro-2H-pyran-3-yl)carbamate (73 mg, 0.27 mmol) was then dissolved in HCl (4.0M in dioxane, 4 mL, 16 mmol) and stirred at room temperature for 6 hours after which the reaction mixture was concentrated to dryness directly to give I-25 as an HCl salt which was used without further purification.

ES/MS: 169.1 [M+H]$^+$

Preparation of Intermediate I-26

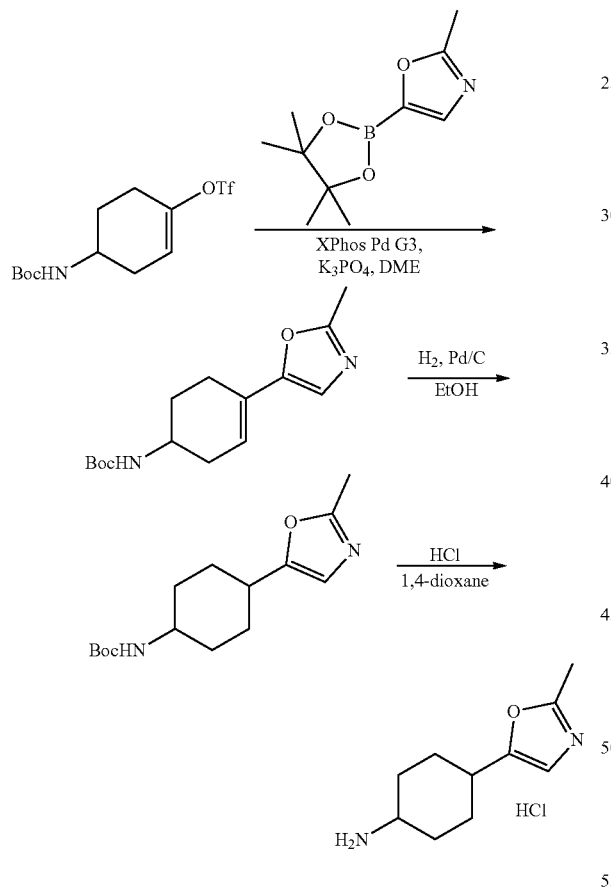

tert-butyl (4-(2-methyloxazol-5-yl)cyclohex-3-en-1-yl)carbamate

To a solution of 4-((tert-butoxycarbonyl)amino)cyclohex-1-en-1-yl trifluoromethanesulfonate (150 mg, 0.43 mmol) in DME (3 mL) was added XPhos Pd G3 (18 mg, 0.022 mmol), 2-methyl-5-(4,4,5,5-tetramethyl-1,3,2-dioxaborolan-2-yl) oxazole (109 mg, 0.52 mmol) and K$_3$PO$_4$ (0.5M in water, 1.3 mL, 0.65 mmol). The resulting mixture was heated in a microwave reactor at 120° C. for 20 minutes after which it was poured into water (5 mL) and extracted with EtOAc (2×15 mL)). The combined organic layers were dried over MgSO$_4$, filtered and concentrated. The resulting crude residue was purified by silica gel chromatography (eluent: EtOAc/hexanes) to give the desired product.

ES/MS: 279.2 [M+H]$^+$ tert-butyl (4-(2-methyloxazol-5-yl)cyclohexyl)carbamate

To a solution of tert-butyl (4-(2-methyloxazol-5-yl)cyclohex-3-en-1-yl)carbamate (140 mg, 0.50 mmol) in EtOH (6 mL) in a 50 mL round bottom flask was added 10% Pd/C (107 mg, 0.10 mmol). The head space was flushed with H$_2$ gas and an H$_2$ balloon then applied to the reaction flask. After 2 hours the reaction mixture was filtered through celite, rinsed with EtOH (2×15 mL) and the resulting EtOH solution concentrated to dryness to give the desired product which was used without further purification.

ES/MS: 281.2 [M+H]$^+$

4-(2-methyloxazol-5-yl)cyclohexan-1-amine hydrochloride (I-26)

tert-butyl (4-(2-methyloxazol-5-yl)cyclohexyl)carbamate (141 mg, 0.50 mmol) was then dissolved in HCl (4.0M in dioxane, 4 mL, 16 mmol) and stirred at room temperature for 2 hours after which the reaction mixture was concentrated to dryness directly to give I-26 as an HCl salt which was used without further purification.

ES/MS: 181.1 [M+H]$^+$

Preparation of Intermediate I-27

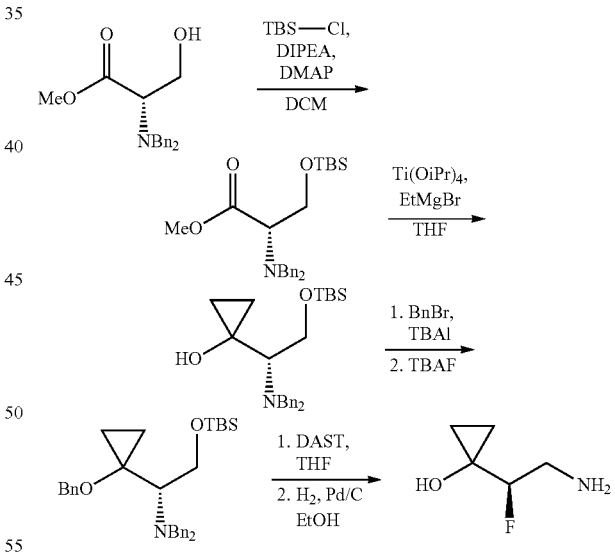

Methyl N,N-dibenzyl-O-(tert-butyldimethylsilyl)-L-serinate

To a solution of methyl dibenzyl-L-serinate (2.0 g, 10 mmol) in DCM (10 mL) was added TBS-Cl (1.7 g, 11 mmol), DMAP (61 mg, 0.50 mmol) and DIPEA (3.5 mL, 20 mmol) and the resulting solution stirred at room temperature for 3 hours. Upon completion, the reaction mixture was poured into water (20 mL) and extracted with DCM (2×20 mL). The combined organic layers were dried over MgSO$_4$, filtered and concentrated. The resulting crude residue was purified by silica gel chromatography (eluent: EtOAc/hexanes) to give the desired product.
ES/MS: 414.4 [M+H]+

(S)-1-(2-((tert-butyldimethylsilyl)oxy)-1-(dibenzylamino)ethyl)cyclopropan-1-ol To a solution of methyl N,N-dibenzyl-O-(tert-butyldimethylsilyl)-L-serinate (500 mg, 1.1 mmol) in THF (8 mL) at 0° C. was added Ti(OEt)₄ (0.11 mL, 0.36 mmol) followed by the dropwise addition of a solution of EtMgBr (3.0M in Et₂O, 1.2 mL, 3.6 mmol) diluted with THF to a total volume of 4 mL. After 16 hours of stirring Ti(OEt)₄ (0.29 mL, 0.97 mmol) was added followed by the dropwise addition of a solution of EtMgBr (3.0M in Et₂O, 1.2 mL, 3.6 mmol) diluted with THF to a total volume of 4 mL. After 20 minutes the starting ester was fully consumed and the reaction quenched with the careful addition of saturated aqueous NH₄Cl solution (5 mL), EtOAc was added (20 mL) and the reaction mixture stirred vigorously for 20 minutes. The reaction mixture was poured into water (20 mL) and extracted with EtOAc (2×40 mL). The combined organic layers were dried over MgSO₄, filtered and concentrated. The resulting crude residue was purified by silica gel chromatography (eluent: EtOAc/hexanes) to give the desired product.
ES/MS: 412.5 [M+H]+

(S)-2-(1-(benzyloxy)cyclopropyl)-2-(dibenzylamino)ethan-1-ol

To a solution of (S)-1-(2-((tert-butyldimethylsilyl)oxy)-1-(dibenzylamino)ethyl)cyclopropan-1-ol (349 mg, 0.85 mmol) in THF (8 mL) at 0° C. was added NaH (60% dispersion in mineral oil, 102 mg, 2.5 mmol) then benzyl bromide (0.12 mL, 1.0 mmol) after which the reaction mixture was allowed to warm to room temperature over 2 hours. Benzyl bromide (1.0 mL, 8.5 mmol) and TBAI (63 mg, 0.17 mmol) were added as single portions and the resulting reaction mixture stirred for 16 hours. Upon completion the reaction mixture was poured into water (20 mL) and extracted with EtOAc (2×40 mL). The combined organic layers were dried over MgSO₄, filtered and concentrated. The resulting crude residue was purified by silica gel chromatography (eluent: EtOAc/hexanes) to give (S)—N,N-dibenzyl-1-(1-(benzyloxy)cyclopropyl)-2-((tert-butyldimethylsilyl)oxy)ethan-1-amine (425 mg, 0.85 mmol) which was then dissolved in THF (5 mL) at room temperature and treated with TBAF (1.0M in THF, 1.0 mL, 1.0 mmol). After 24 hours the reaction mixture was poured into water (5 mL) and extracted with EtOAc (2×15 mL). The combined organic layers were dried over MgSO₄, filtered and concentrated. The resulting crude residue was purified by silica gel chromatography (eluent: EtOAc/hexanes) to give the desired product.
ES/MS: 388.4 [M+H]+

(R)-1-(2-amino-1-fluoroethyl)cyclopropan-1-ol (I-27)

To a solution of (S)-2-(1-(benzyloxy)cyclopropyl)-2-(dibenzylamino)ethan-1-ol (328 mg, 0.85 mmol) in THF (6 mL) in a Teflon vial was added (diethylamino)sulfur trifluoride (0.14 mL, 1.0 mmol) dropwise at 0° C. The reaction mixture was allowed to warm to room temperature over 4 hours after which it was poured into saturated aqueous NaHCO₃ solution (10 mL) and extracted with EtOAc (2×25 mL). The combined organic layers were dried over MgSO₄, filtered and concentrated. The resulting crude residue was purified by silica gel chromatography (eluent: EtOAc/hexanes) to give (R)-N,N-dibenzyl-2-(1-(benzyloxy)cyclopropyl)-2-fluoroethan-1-amine. To a solution of (R)-N,N-dibenzyl-2-(1-(benzyloxy)cyclopropyl)-2-fluoroethan-1-amine (330 mg, 0.85 mmol) in EtOH (8 mL) and EtOAc (2 mL) in a 50 mL round bottom flask was added 10% Pd/C (270 mg, 0.25 mmol). The head space was flushed with H₂ gas and an H₂ balloon then applied to the reaction flask. After 16 hours the reaction mixture was filtered through celite, rinsed with EtOH (2×15 mL) and the resulting EtOH solution concentrated to dryness to give I-27 which was used without further purification.
ES/MS: 120.1 [M+H]+

Preparation of Intermediate I-28

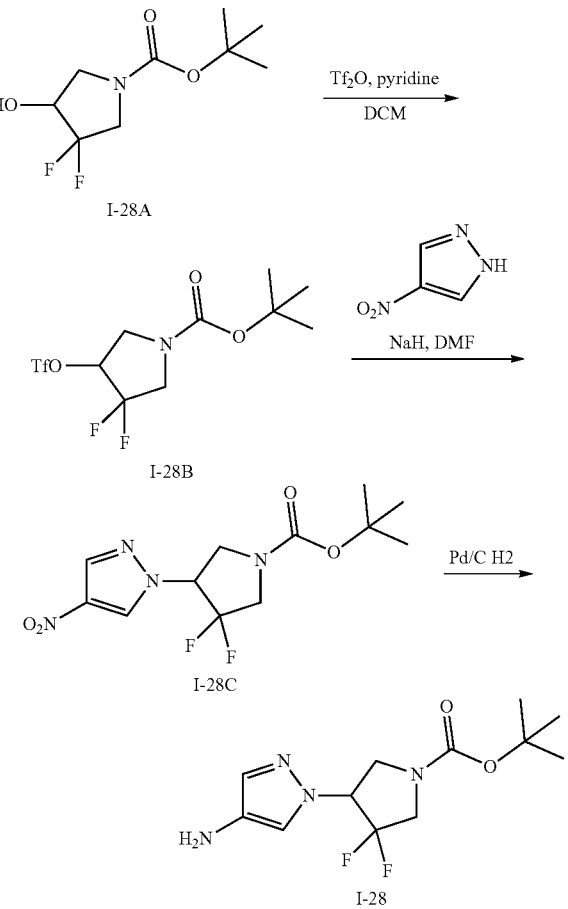

tert-butyl 3,3-difluoro-4-(((trifluoromethyl)sulfonyl)oxy)pyrrolidine-1-carboxylate (I-28B)

To a solution of tert-butyl 3,3-difluoro-4-hydroxypyrrolidine-1-carboxylate (I-28A, 939 mg, 4.188 mmol) in DCM (40 mL) at −10° C., was added pyridine (2.2 ml, 21.35 mmol). Trifluoromethanesulfonic anhydride (1M solution in methylene chloride, 10.5 ml) was added via addition funnel over ~10 min. Stirred an additional 2 hr at −10° C. The reaction was quenched with 1 M citric acid to pH 4.5 (~5 mL). The organic layer was separated, and the aqueous was extracted with DCM. The combined organic extracts were dried over sodium sulfate to give I-28B.

1H NMR (400 MHz, Chloroform-d) δ 5.16 (s, 1H), 4.05-3.65 (m, 4H), 1.48 (s, 9H) 19F NMR (376 MHz, Chloroform-d) δ −75.01 (d, J=33.7 Hz), −78.87, −108.16 (dd, J=246.8, 81.5 Hz), −120.31 (dd, J=308.9, 247.6 Hz).

tert-butyl 3,3-difluoro-4-(4-nitro-1H-pyrazol-1-yl) pyrrolidine-1-carboxylate (I-28C)

To a solution of 4-nitro-1H-pyrazole (I-28C, 250 mg, 2.211 mmol) in DMF (5 mL) at 0° C., was added sodium hydride, 60% disp. in oil (138 mg, 3.45 mmol). After stirring for 1 hr, added a solution of tert-butyl 3,3-difluoro-4-(((trifluoromethyl)sulfonyl)oxy)pyrrolidine-1-carboxylate (I-28B, 943 mg, 2.653 mmol) in 5 mL DMF and heated at 95° C. overnight. The reaction mixture was diluted with EtOAc and washed with brine twice. The organic extract was dried over sodium sulfate and purified by silica gel chromatography (eluent: EtOAc/hexanes) to provide I-28C.

1H NMR (400 MHz, Chloroform-d) δ 8.16 (s, 1H), 8.13-8.01 (m, 1H), 4.89 (p, J=5.7 Hz, 1H), 3.87 (dd, J=12.0, 6.5 Hz, 1H), 3.77 (s, 1H), 3.57 (s, 2H), 2.60-2.34 (m, 2H), 1.48 (s, 9H).

tert-butyl 4-(4-amino-1H-pyrazol-1-yl)-3,3-difluoro-pyrrolidine-1-carboxylate (I-28)

A solution of tert-butyl 3,3-difluoro-4-(4-nitro-1H-pyrazol-1-yl)pyrrolidine-1-carboxylate (I-28C, 165 mg, 0.518 mmol) in EtOH (15 mL) was degassed with argon and vacuum. Added Pd/C (10%, 28 mg, 0.026 mmol) and stirred with a balloon of hydrogen for 2 d. The reaction was filtered over a Celite plug, rinsed with EtOAc and the filtrate was concentrated to give I-28.

ES/MS: 288.9 (M+).

1H NMR (400 MHz, Chloroform-d) δ 7.30 (s, 1H), 7.20 (d, J=5.8 Hz, 1H), 4.92-4.69 (m, 1H), 4.01 (dd, J=13.6, 6.5 Hz, 2H), 3.95-3.76 (m, 2H), 1.47 (d, J=3.8 Hz, 9H).

Preparation of Intermediate I-29

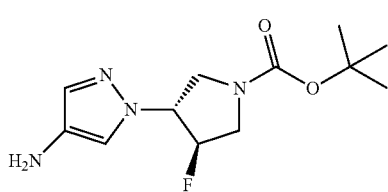

I-29 tert-butyl (3R,4R)-3-(4-amino-1H-pyrazol-1-yl)-4-fluoropyrrolidine-1-carboxylate was prepared similarly to I-28, but substituting tert-butyl 3,3-difluoro-4-hydroxypyrrolidine-1-carboxylate with tert-butyl (3R,4S)-3-fluoro-4-hydroxypyrrolidine-1-carboxylate in the first step.

ES/MS: 270.9 (M+).

1H NMR (400 MHz, Chloroform-d) δ 7.29 (s, 1H), 7.13 (d, J=15.0 Hz, 1H), 5.26 (dd, J=50.9, 21.6 Hz, 1H), 4.82 (d, J=14.0 Hz, 1H), 4.06-3.38 (m, 6H), 1.49 (s, 9H).

19F NMR (376 MHz, Chloroform-d) δ −177.64, −182.29 (m)

Preparation of Intermediate I-30

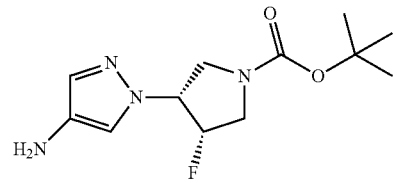

I-30 tert-butyl (3R,4S)-3-(4-amino-1H-pyrazol-1-yl)-4-fluoro-pyrrolidine-1-carboxylate was prepared similarly to I-28, but substituting tert-butyl 3,3-difluoro-4-hydroxypyrrolidine-1-carboxylate with tert-butyl (3S,4S)-3-fluoro-4-hydroxypyrrolidine-1-carboxylate in the first step.

ES/MS: 271.9 (M+H+).

1H NMR (400 MHz, Chloroform-d) δ 7.21 (d, J=14.5 Hz, 2H), 5.23 (ddd, J=53.9, 7.0, 3.6 Hz, 1H), 4.84 (d, J=27.9 Hz, 1H), 4.04 (dt, J=15.3, 9.5 Hz, 1H), 3.99-3.59 (m, 3H), 2.73 (s, 2H), 1.50 (s, 9H).

19F NMR (376 MHz, Chloroform-d) δ −179.08. −204.08 (m)

Preparation of Intermediate I-31

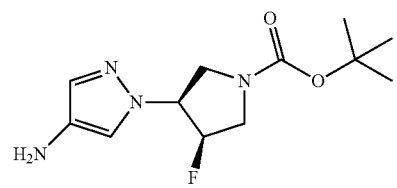

I-31 tert-butyl (3S,4R)-3-(4-amino-1H-pyrazol-1-yl)-4-fluoro-pyrrolidine-1-carboxylate was prepared similarly to I-28, but substituting tert-butyl 3,3-difluoro-4-hydroxypyrrolidine-1-carboxylate with tert-butyl (3R,4R)-3-fluoro-4-hydroxypyrrolidine-1-carboxylate in the first step.

ES/MS: 270.9 (M+).

1H NMR (400 MHz, Chloroform-d) δ 7.21 (d, J=14.1 Hz, 2H), 5.47-5.04 (m, 1H), 5.00-4.71 (m, 1H), 4.18-3.99 (m, 1H), 3.99-3.52 (m, 2H), 2.73 (s, 2H), 1.50 (s, 9H).

19F NMR (376 MHz, Chloroform-d) δ −193.69 (ddd, J=60.6, 32.8, 24.6 Hz).

Preparation of Intermediate I-32

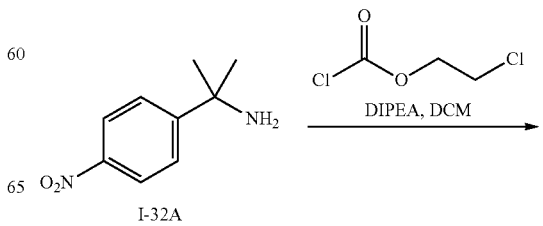

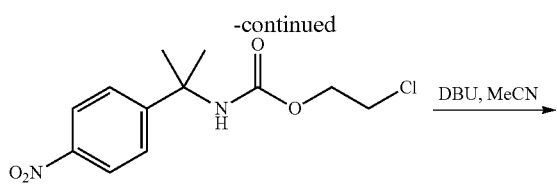

2-chloroethyl (2-(4-nitrophenyl)propan-2-yl)carbamate (EC-I-5B)

To a solution of 2-(4-nitrophenyl)propan-2-amine (250 mg, 1.154 mmol) and N,N-diisopropylethylamine (0.5 ml, 2.87 mmol) in DCM (5 mL) at 0° C., was added 2-chloroethyl carbonochloridate (0.15 ml, 1.45 mmol). The reaction was gradually warmed to rt and stirred for 2 hr. The reaction was diluted with DCM and washed with 1N HCl and brine. The organic extract was dried over sodium sulfate to give I-32B.

3-(2-(4-nitrophenyl)propan-2-yl)oxazolidin-2-one (I-32C)

To a solution of 2-chloroethyl (2-(4-nitrophenyl)propan-2-yl)carbamate (I-32B, 330.8 mg, 1.154 mmol) in CH3CN (5 mL), was added 1,8-diazabicyclo[5.4.0]undec-7-ene (0.85 ml, 5.69 mmol). The reaction was heated at 80° C. for 3 hr. The reaction was diluted with EtOAc and washed with 1N HCl and brine. The organic extract was dried over sodium sulfate to give I-32C.

ES/MS: 251.0 (M+H+).

1H NMR (400 MHz, Chloroform-d) δ 8.24-8.15 (m, 2H), 7.60-7.51 (m, 2H), 4.34 (dd, J=8.5, 7.2 Hz, 2H), 3.72-3.63 (m, 2H), 1.74 (s, 6H).

3-(2-(4-aminophenyl)propan-2-yl)oxazolidin-2-one (I-32)

To a suspension of 3-(2-(4-nitrophenyl)propan-2-yl)oxazolidin-2-one (I-32C, 278 mg, 1.111 mmol) in EtOH (20 mL), was added calcium chloride (185 mg, 1.667 mmol) and iron powder (326 mg, 5.838 mmol). Added 2 mL water and heated the reaction mixture to 60° C. overnight. The reaction was filtered through a Celite plug and washed with EtOAc. The filtrate was washed with saturated NaHCO3 solution and brine and dried over sodium sulfate to give product I-32

1H NMR (400 MHz, Chloroform-d) δ 7.19 (d, J=8.6 Hz, 2H), 6.65 (d, J=8.6 Hz, 2H), 4.26-4.07 (m, 2H), 3.47-3.23 (m, 2H), 1.74 (s, 6H).

Preparation of Intermediate I-33

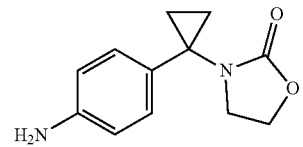

3-(1-(4-aminophenyl)cyclopropyl)oxazolidin-2-one (I-33)

3-(1-(4-aminophenyl)cyclopropyl)oxazolidin-2-one was prepared similarly to I-32, but substituting 2-(4-nitrophenyl)propan-2-amine with 1-(4-nitrophenyl)cyclopropan-1-amine in the first step.

ES/MS: 219.1 (M+H+).

1H NMR (400 MHz, Chloroform-d) δ 7.23-7.17 (m, 2H), 6.68-6.58 (m, 2H), 4.21 (dd, J=8.8, 7.3 Hz, 2H), 3.56-3.43 (m, 2H), 1.36-1.23 (m, 2H), 1.20-1.06 (m, 2H).

Preparation of Intermediate I-34

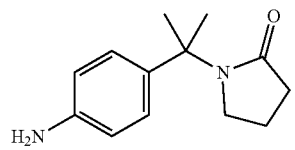

1-(2-(4-aminophenyl)propan-2-yl)pyrrolidin-2-one (I-34)

1-(2-(4-aminophenyl)propan-2-yl)pyrrolidin-2-one was prepared similarly to I-32, but substituting 2-chloroethyl carbonochloridate with 4-chlorobutanoyl chloride in the first step.

ES/MS: 218.9 (M+).

1H NMR (400 MHz, Chloroform-d) δ 7.12 (d, J=8.5 Hz, 2H), 6.63 (d, J=8.6 Hz, 2H), 3.69 (d, J=20.0 Hz, 2H), 3.30 (t, J=7.0 Hz, 2H), 2.36 (t, J=8.1 Hz, 2H), 1.89 (tt, J=7.7, 6.8 Hz, 2H), 1.72 (s, 6H).

Preparation of Intermediate I-35

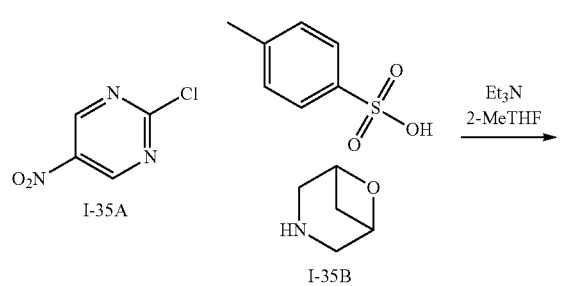

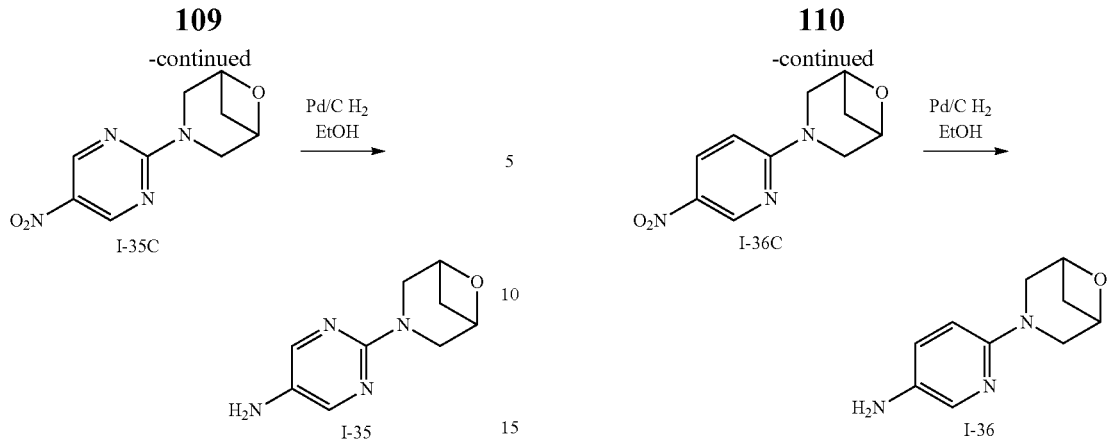

3-(5-nitropyrimidin-2-yl)-6-oxa-3-azabicyclo[3.1.1]heptane (I-35C)

To a solution of 2-chloro-5-nitropyrimidine (0.200 g, 1.254 mmol) and 6-oxa-3-azabicyclo[3.1.1]heptane 4-methylbenzenesulfonate (0.394 g, 1.452 mmol) in 2Me-THF (6 mL), was added triethylamine (0.4 ml, 2.870 mmol). The reaction was stirred at rt overnight. The reaction was partitioned with DCM and water. The organic extract washed with brine and dried over sodium sulfate to give I-35C.

ES/MS: 223.0.9 (M+H$^+$).

1H NMR (400 MHz, Chloroform-d) δ 9.18 (s, 1H), 4.80 (d, J=6.6 Hz, 2H), 4.08 (d, J=13.8 Hz, 2H), 3.97 (d, J=13.9 Hz, 2H), 3.37 (q, J=7.4 Hz, 1H), 1.95 (d, J=9.2 Hz, 1H).

2-(6-oxa-3-azabicyclo[3.1.1]heptan-3-yl)pyrimidin-5-amine (I-35)

A solution of 3-(5-nitropyrimidin-2-yl)-6-oxa-3-azabicyclo[3.1.1]heptane (I-35C, 264 mg, 1.263 mmol) in EtOH (15 mL) was degassed with argon and vacuum. Added Pd/C (10%, 66 mg, 0.062 mmol) and stirred with a balloon of hydrogen overnight. The reaction was filtered over a Celite plug, rinsed with EtOAc and the filtrate was concentrated to give I-35.

ES/MS: 193.1 (M+H$^+$).

1H NMR (400 MHz, Chloroform-d) δ 8.05 (s, 2H), 4.74 (d, J=6.5 Hz, 2H), 3.98-3.69 (m, 5H), 3.26 (q, J=7.2 Hz, 1H), 3.18 (s, 2H), 1.99 (d, J=8.7 Hz, 1H).

Preparation of Intermediate I-36

3-(5-nitropyridin-2-yl)-6-oxa-3-azabicyclo[3.1.1]heptane (I-36C)

To a solution of 2-chloro-5-nitropyridine (I-36A, 0.200 g, 1.261 mmol) and 6-oxa-3-azabicyclo[3.1.1]heptane 4-methylbenzenesulfonate (I-36B, 0.396 g, 1.461 mmol) in 2Me-THF (6 mL), was added triethylamine (0.4 ml, 2.870 mmol). The reaction was stirred at rt. Added 321 mg of I-36B and trimethylamine (0.4 mL) and heated at 50° C. for 2 d.

The reaction was partitioned with DCM and water. The organic extract washed with brine and dried over sodium sulfate to give I-36C.

ES/MS: 222.1 (M+H$^+$).

1H NMR (400 MHz, Chloroform-d) δ 9.14 (d, J=2.7 Hz, 1H), 8.31 (dd, J=9.5, 2.7 Hz, 1H), 6.55 (d, J=9.5 Hz, 1H), 4.83 (d, J=6.6 Hz, 2H), 4.34-3.52 (m, 4H), 3.37 (dt, J=9.4, 6.8 Hz, 1H), 1.98 (d, J=9.1 Hz, 1H).

6-(6-oxa-3-azabicyclo[3.1.1]heptan-3-yl)pyridin-3-amine (I-36)

A solution of 3-(5-nitropyridin-2-yl)-6-oxa-3-azabicyclo[3.1.1]heptane (I-36C, 245 mg, 1.108 mmol) in EtOH (15 mL) was degassed with argon and vacuum. Added Pd/C (10%, 60 mg, 0.056 mmol) and stirred with a balloon of hydrogen overnight. The reaction was filtered over a Celite plug, rinsed with EtOAc and the filtrate was concentrated to give I-36.

ES/MS: 192.2 (M+H$^+$).

1H NMR (400 MHz, Chloroform-d) δ 7.84 (d, J=2.9 Hz, 1H), 7.07 (dd, J=8.7, 2.9 Hz, 1H), 6.46 (d, J=8.9 Hz, 1H), 4.76 (d, J=6.6 Hz, 2H), 3.80-3.61 (m, 5H), 3.26 (q, J=7.1 Hz, 1H), 2.05 (d, J=8.6 Hz, 1H).

Preparation of Intermediate I-37

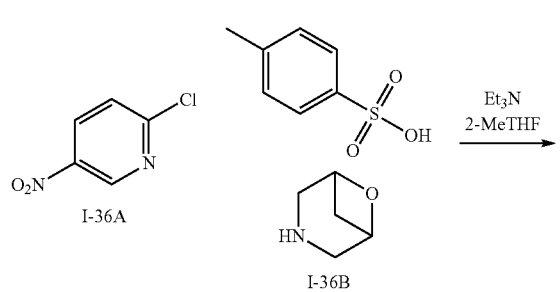

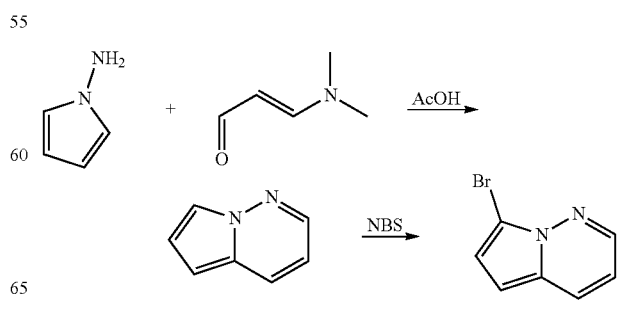

Pyrrolo[1,2-b]pyridazine

To a solution of 1H-pyrrol-1-amine (500 mg, 6.09 mmol) in acetic acid (4 mL) was added (E)-3-(dimethylamino)acrylaldehyde (0.7 mL, 7 mmol). The resulting mixture was stirred at room temperature for 18 hours and diluted with CH$_2$Cl$_2$. The organic layer was washed with water and aqueous, saturated NaHCO$_3$. The aqueous layers were back-extracted with CH$_2$Cl$_2$ and the resulting organic layers were dried over MgSO$_4$ and carefully concentrated. The resulting yellow oil was purified by bulb-to-bulb distillation to provide the product.

ES/MS: 119.0 (M+H$^+$).

1H NMR (400 MHz, Chloroform-d) δ 8.05-7.99 (m, 1H), 7.81-7.69 (m, 2H), 6.88 (dd, J=4.3, 2.7 Hz, 1H), 6.52 (dd, J=9.2, 4.3 Hz, 2H).

7-Bromopyrrolo[1,2-b]pyridazine (I-37)

To a solution of pyrrolo[1,2-b]pyridazine (100 mg, 0.85 mmol) in CH$_2$Cl$_2$ (1.5 mL) and acetonitrile (0.5 mL) at 0° C. was added N-bromosuccinimide (150 mg, 0.84 mmol). The mixture was stirred at 0° C. for 10 min and loaded directly onto a SiO$_2$ column for purification (eluent: EtOAc/hexanes) to provide the desired product.

ES/MS: 199.0 (M+H$^+$).

Preparation of Intermediate I-38

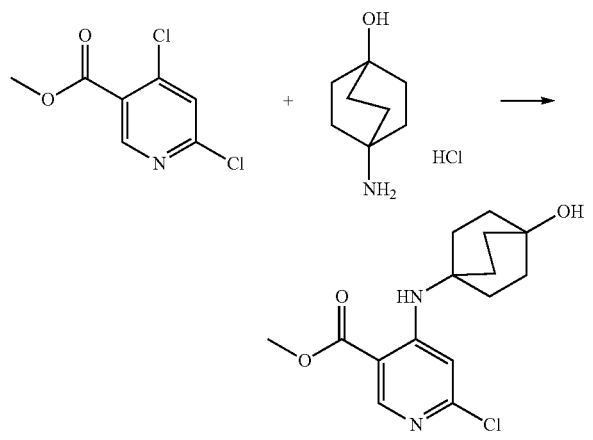

Methyl 6-chloro-4-((4-hydroxybicyclo[2.2.2]octan-1-yl)amino)nicotinate (I-38)

To a solution of methyl 4,6-dichloronicotinate (870 mg, 4.22 mmol) and 1-aminobicyclo[2.2.2]octan-4-ol hydrochloride (500 mg, 2.81 mmol) in butyronitrile (12 mL) was added cesium carbonate (1.98 g, 6.08 mmol). The resulting slurry was heated to 120° C. for 24 hours. The mixture was cooled, diluted with EtOAc, and filtered. The solids were washed with EtOAc and the combined filtrates were concentrated and purified by SiO$_2$ chromotography (eluent: 2-5% MeOH/CH$_2$Cl$_2$) to provide the desired product.

ES/MS: 311.3 (M+H$^+$).

Preparation of Intermediate I-39

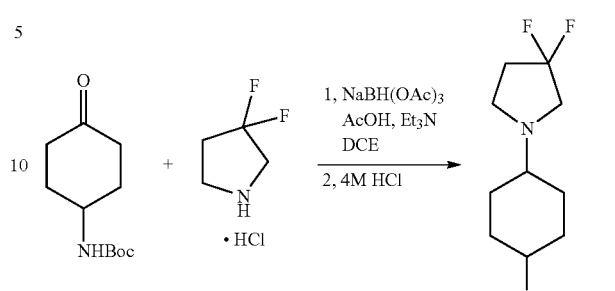

4-(3,3-difluoropyrrolidin-1-yl)cyclohexan-1-amine hydrochloride (I-39)

To a suspension of tert-butyl (4-oxocyclohexyl)carbamate (0.5 g, 2.34 mmol), 3,3-Difluoropyrrolidine hydrochloride (0.37 g, 2.56 mmol), acetic acid (0.21 g, 3.5 mmol), and Sodium triacetoxyborohydride (0.75 g, 3.5 mmol) in MeOH (3 mL) and DCE (6 mL), was stirred for overnight. Diluted with EtOAc and washed with sodium bicarbonate saturated solution. The organic layer was dried and concentrated. Used without further purification.

ES/MS: 205 (M+H$^+$).

Preparation of Intermediate I-40

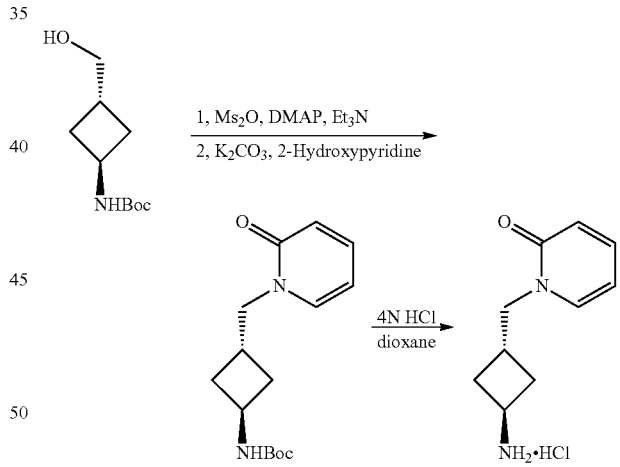

tert-butyl ((1r,3r)-3-((2-oxopyridin-1(2H)-yl)methyl)cyclobutyl)carbamate

To a solution of tert-butyl ((1r,3r)-3-(hydroxymethyl)cyclobutyl)carbamate (0.62 g, 3 mmol), trimethylamine (0.86 mL, 6 mmol) and 4-(Dimethylamino)pyridine (38 mg, 0.3 mmol) in DCM (5 mL), Methanesulfonic anhydride (0.64 g, 4 mmol) was added to the solution. It was stirred for 16 hours then diluted with EtOAc and washed with NaHCO$_3$ (sat.). The organic layer was dried and concentrated. The crude mixture and 2-Hydroxypyridine and Potassium carbonate (0.74 g, 5 mmol) were dissolved in DMSO. It was heated at 70° C. for 16 hours. Cooled it down and filtered.

The filtrate was purified on RP-HPLC (eluent: water/MeCN*0.1% TFA) to yield the product.
ES/MS: 279 (M+H+).

1-(((1r,3r)-3-aminocyclobutyl)methyl)pyridin-2(1H)-one hydrochloride (I-40)

tert-butyl ((1r,3r)-3-((2-oxopyridin-1(2H)-yl)methyl)cyclobutyl)carbamate (250 mg, 0.9 mmol) was dissolved in 3 mL of 4M HCl in dioxane. After 2 hours, the solvent was removed. Used without further purification.

Preparation of Intermediate I-41

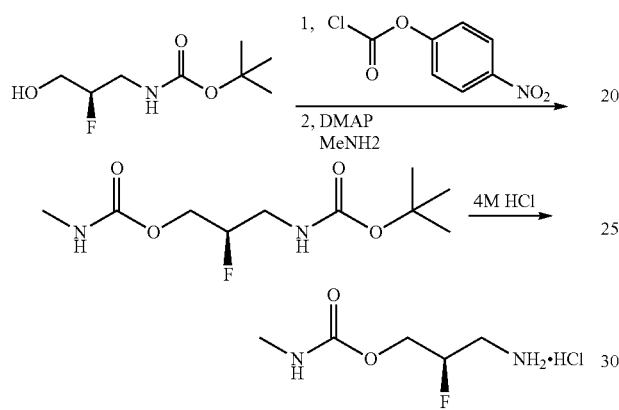

tert-butyl (R)-(2-fluoro-3-((methylcarbamoyl)oxypropyl)carbamate

To a solution of tert-butyl (R)-(2-fluoro-3-hydroxypropyl)carbamate (170 mg, 0.88 mmol) 4-nitrophenyl carbonochloridate (710 mg, 3.5 mmol) and 4-(Dimethylamino)pyridine (430 mg, 3.5 mmol) in DCM (5 mL) and pyridine (5 mL), was stirred at r.t. for overnight. Methylamine was added to the mixture and the resulting mixture stirred. Upon completion the solvent was removed and the crude material was purified RP-HPLC (eluent: water/MeCN*0.1% TFA) to yield the product.
ES/MS: 251 (M+H+).

(R)-3-amino-2-fluoropropyl methylcarbamate hydrochloride (I-41)

tert-butyl (R)-(2-fluoro-3-((methylcarbamoyl)oxy)propyl)carbamate was dissolved in 4M HCl in dioxane, was stirred for 2 hours. The solvent was removed and resulting material used without further purification.

Preparation of Intermediate I-42

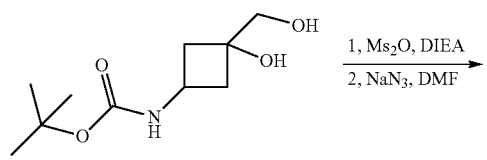

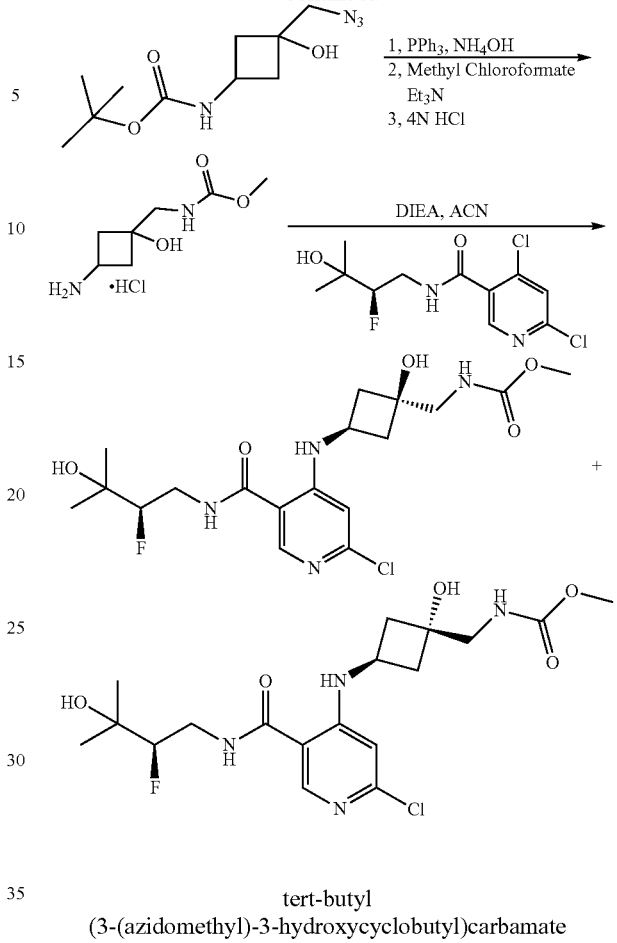

tert-butyl (3-(azidomethyl)-3-hydroxycyclobutyl)carbamate

To a flask of tert-butyl (3-hydroxy-3-(hydroxymethyl)cyclobutyl)carbamate (1.8 g, 8 mmol) and N-ethyldiisopropylamine (3.6 mL, 21 mmol) in DCM (20 mL), methanesulfonic anhydride (1.59 g, 9 mmol) was added and stirred overnight. The mixture was diluted with EtOAc and washed with saturated NaHCO3 and brine. The organic layer was dried and concentrated. The mixture was dissolved in DMF and sodium azide (1.58 g, 24 mmol) was added to the suspension. It was stirred at 65° C. for 8 hours then diluted with EtOAc and washed with saturated NaHCO3 and brine. The organic layer was dried and concentrated. Used without further purification.
ES/MS: 243 (M+H+).

methyl ((3-amino-1-hydroxycyclobutyl)methyl)carbamate hydrochloride

To a solution of tert-butyl (3-(azidomethyl)-3-hydroxycyclobutyl)carbamate (2 g, 8.3 mmol), triphenylphosphine (3.2 g, 12 mmol) and ammonium hydroxide (4.6 mL, 33 mol) in THF (15 mL)/MeOH (15 mL)/H2O (3 mL), was stirred for overnight at room temperature. The solids were filtered and the filtrate was concentrated. The residue was dissolved in 20 mL of DCM, trimethylamine (4.8 mL, 34 mmol) and methyl chloroformate (1.1 mL, 14 mmol) was added to the mixture. It was stirred for 1 hour. MeOH (3 mL) was added and the solvent removed. The mixture was purified by SiO2 flash column (eluent: EtOAc/Hexane). The product was dissolved in 2 mL of 4 N HCl in dioxane. After 1 hour, the solvent was removed. Used without further purification.

methyl (((1S,3s)-3-((2-chloro-5-(((R)-2-fluoro-3-hydroxy-3-methylbutyl)carbamoyl)pyridin-4-yl)amino)-1-hydroxycyclobutyl)methyl)carbamate methyl (((1R,3r)-3-((2-chloro-5-(((R)-2-fluoro-3-hydroxy-3-methylbutyl)carbamoyl)pyridin-4-yl)amino)-1-hydroxycyclobutyl)methyl)carbamate (R)-4,6-dichloro-N-(2-fluoro-3-hydroxy-3-methylbutyl)nicotinamide (25 mg, 0.09 mmol) and methyl ((3-amino-1-hydroxycyclobutyl)methyl)carbamate hydrochloride (36 mg, 0.17 mmol) and N-ethyldiisopropylamine (0.06 mL, 0.34 mmol) in 1 mL of MeCN. The mixture was heated at 80° C. for 24 hours. The solvent was removed, then purified by RP-HPLC (eluent: water/MeCN*0.1% TFA).
ES/MS: 433.4 (M+H$^+$).
ES/MS: 433.4 (M+H$^+$).

Preparation of Intermediate I-43

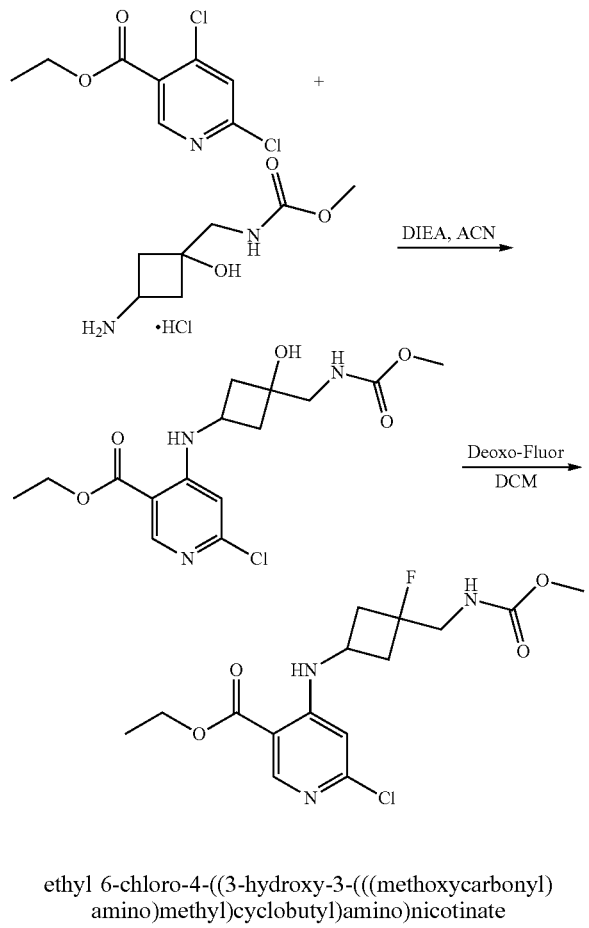

ethyl 6-chloro-4-((3-hydroxy-3-(((methoxycarbonyl)amino)methyl)cyclobutyl)amino)nicotinate To a flask of ethyl 4,6-dichloronicotinate (0.8 g, 3.6 mmol and methyl ((3-amino-1-hydroxycyclobutyl)methyl)carbamate hydrochloride (1.25 g, 5.4 mmol) and N-ethyldiisopropylamine (1.9 mL, 10.9 mmol) in 10 mL of MeCN. The mixture was heated at 60° C. for 24 hours. The solvent was removed, then purified by RP-HPLC (eluent: water/MeCN*0.1% TFA). The product fractions were combined and neutralized with saturated NaHCO$_3$ solution to give product.
ES/MS: 358.7 (M+H$^+$).

ethyl 6-chloro-4-((3-fluoro-3-(((methoxycarbonyl)amino)methyl)cyclobutyl)amino)nicotinate (I-43)

To a flask of ethyl 6-chloro-4-((3-hydroxy-3-(((methoxycarbonyl)amino)methyl)cyclobutyl)amino)nicotinate (500 mg, 1.4 mmol) in 5 mL of DCM, bis(2-methoxyethyl)aminosulfur trifluoride (0.3 mL, 1.7 mmol) was added to the solution. It was stirred for 20 minutes. Diluted with EtOAc and washed with saturated NaHCO$_3$ and brine. The organic layer was dried and concentrated, then purified by RP-HPLC (eluent: water/MeCN*0.1% TFA).
ES/MS: 360.3 (M+H$^+$).

Preparation of Intermediate I-44

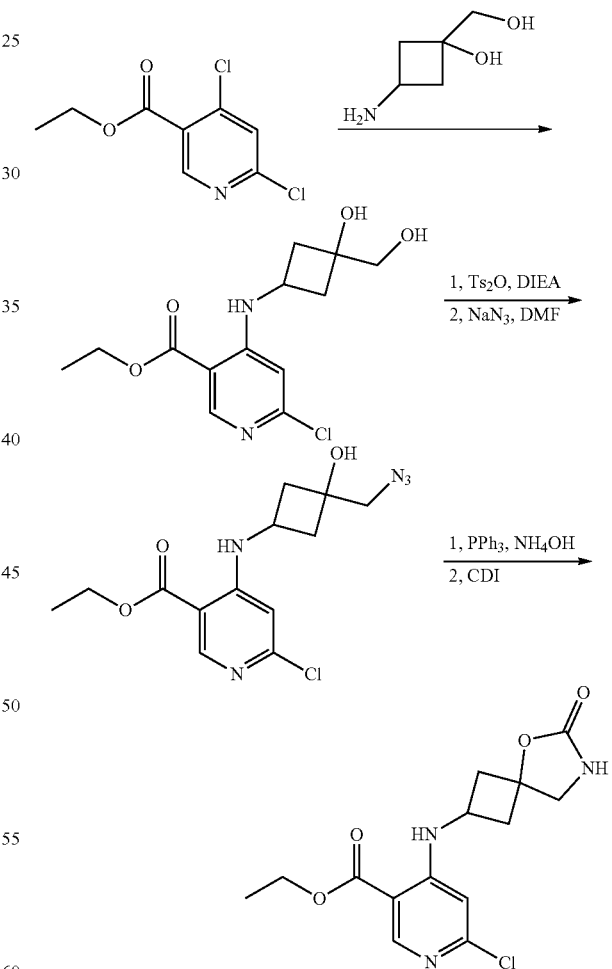

ethyl 6-chloro-4-((3-hydroxy-3-(hydroxymethyl)cyclobutyl)amino)nicotinate

To a flask of ethyl 4,6-dichloronicotinate (0.58 g, 2.6 mmol) and 3-amino-1-(hydroxymethyl)cyclobutan-1-ol (0.81 g, 5.3 mmol) and N-ethyldiisopropylamine (1.8 mL, 10.5 mmol) in 5 mL of MeCN. The mixture was heated at 80° C. for 48 hours. The solvent was removed, then purified by RP-HPLC (eluent: water/MeCN*0.1% TFA). The product fractions were combined and neutralized with saturated NaHCO3 solution to give product.
ES/MS: 301.2 (M+H⁺).

ethyl 4-((3-(azidomethyl)-3-hydroxycyclobutyl)amino)-6-chloronicotinate

To a flask of ethyl 6-chloro-4-((3-hydroxy-3-(hydroxymethyl)cyclobutyl)amino)nicotinate (0.75 g, 2 mmol) and N-ethyldiisopropylamine (1.1 mL, 6 mmol) in DCM (5 mL), p-Toluenesulfonic anhydride (1.63 g, 5 mmol) was added to the solution. It was stirred for overnight. Diluted with EtOAc and washed with saturated NaHCO₃ and brine. The organic layer was dried and concentrated. The residue was dissolved in DMF and sodium azide (0.53 g, 8 mmol) was added to the suspension. It was stirred at 65° C. for 8 hours. Diluted with EtOAc and washed with saturated NaHCO₃ and brine. The organic layer was dried and concentrated. Used without further purification.
ES/MS: 326.3 (M+H⁺).

ethyl 6-chloro-4-((6-oxo-5-oxa-7-azaspiro[3.4]octan-2-yl)amino)nicotinate (I-44)

To a solution of ethyl 4-((3-(azidomethyl)-3-hydroxycyclobutyl)amino)-6-chloronicotinate (0.6 g, 1.84 mmol), triphenylphosphine (0.73 g, 2.8 mmol) and ammonium hydroxide (1 mL, 7 mol) in THF (5 mL)/MeOH (5 mL)/H2O (1 mL), was stirred for overnight. The solids were filtered and the filtrate was concentrated. The residue was dissolved in 10 mL of DCM and 1,1'-Carbonyldiimidazole (272 mg, 2 mmol) was added to the mixture. It was stirred for 16 hours, diluted with EtOAc and washed with 20 mL of 0.5 N HCl twice. The organic layer was dried and concentrated. The mixture was purified on flash column (50% EtOAc/Hexane).
ES/MS: 326.2 (M+H⁺).

Preparation of Intermediate I-45 tert-butyl ((1r,4r)-4-(5-(trimethylsilyl)isoxazol-3-yl)cyclohexyl)carbamate

To a solution of tert-butyl ((1r,4r)-4-formylcyclohexyl)carbamate (0.5 g, 2.2 mmol) in methanol (10 mL) and water (9 mL) was added NH₂OH-HCl (0.2 g, 2.9 mmol). Then, 2.9 mL of 1N sodium hydroxide was added. The reaction mixture was stirred at r.t. for overnight. Water (30 mL) was added, the precipitate filtered off and washed with water to give the white solid. The solid and trimethylsilylacetylene (0.62 mL, 4.4 mmol) in THF, 2.1 mL of 13% sodium hypochlorite solution was added to the solution. It was stirred for 16 hours. Diluted with EtOAc and washed with saturated Na₂S₂O₃. The organic layer was dried and concentrated, and purified by flash column (eluent: EtOAc/Hexane).
ES/MS: 338.9 (M+H⁺).

(1r,4r)-4-(isoxazol-3-yl)cyclohexan-1-amine hydrochloride (I-45)

To a solution of tert-butyl ((1r,4r)-4-(5-(trimethylsilyl)isoxazol-3-yl)cyclohexyl)carbamate (0.45 g, 1 mmol) in 4 mL of EtOH and 1.5 mL of 28% NH4OH, was stirred for 16 hours. Removed the solvent and purified by flash column (eluent: EtOAc/Hexane). The product was collected and dissolved in 5 mL of 4M HCl in dioxane. The mixture was stirred for 3 hours. Removed the solvent and dried in the vacuum. Used without further purification.

Preparation of Intermediate I-46

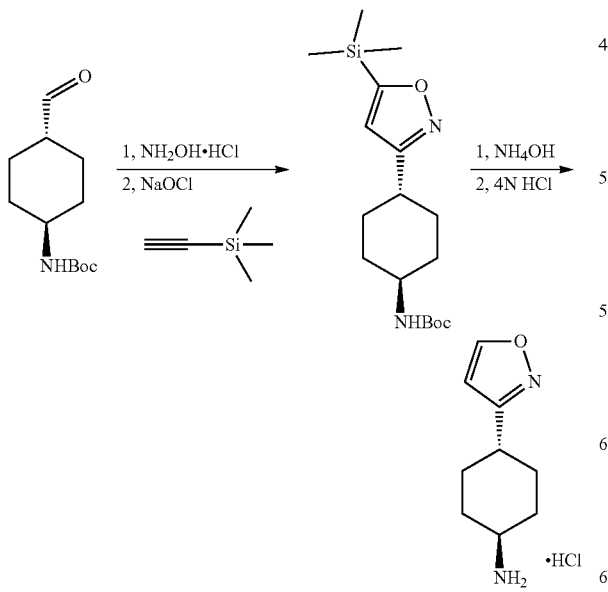

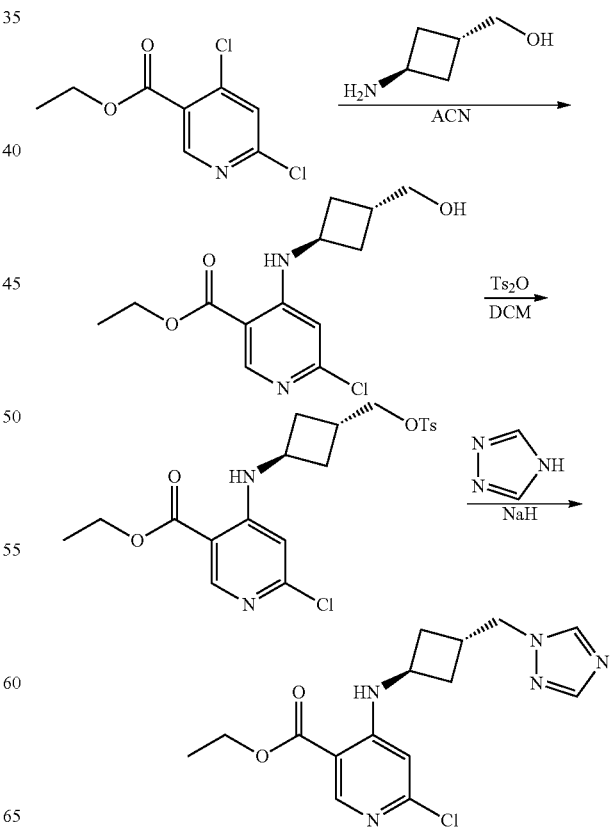

ethyl 6-chloro-4-(((1r,3r)-3-(hydroxymethyl)cyclobutyl)amino)nicotinate

A solution of ethyl 4,6-dichloronicotinate (0.45 g, 2 mmol) and ((1r,3r)-3-aminocyclobutyl)methanol (0.56 g, 4 mmol) and N-ethyldiisopropylamine (1.4 mL, 8 mmol) in 5 mL of MeCN was heated at 80° C. for 16 hours. The solvent was removed, then purified by RP-HPLC (eluent: water/MeCN*0.1% TFA).

ES/MS: 285.3 (M+H$^+$).

ethyl 6-chloro-4-(((1r,3r)-3-((tosyloxy)methyl)cyclobutyl)amino)nicotinate

To a flask of ethyl 6-chloro-4-(((1r,3r)-3-(hydroxymethyl)cyclobutyl)amino)nicotinate (0.58 g, 2 mmol) and N-ethyldiisopropylamine (0.89 mL, 5 mmol) in DCM (5 mL), p-Toluenesulfonic anhydride (1.33 g, 4 mmol) was added to the solution. It was stirred for overnight then diluted with EtOAc and washed with saturated NaHCO$_3$ and brine. The organic layer was dried and concentrated. The solvent was removed, then purified by RP-HPLC (eluent: water/MeCN*0.1% TFA). The product fractions were combined and neutralized with saturated NaHCO$_3$ solution to give product.

ES/MS: 439.5 (M+H$^+$).

ethyl 4-(((1r,3r)-3-((1H-1,2,4-triazol-1-yl)methyl)cyclobutyl)amino)-6-chloronicotinate (I-46)

To a suspension of 1,2,4-triazole (28 mg, 0.4 mmol) and 60% of sodium hydride (14.6 mg, 0.36 mmol) in 1 mL of NMP, ethyl 6-chloro-4-(((1r,3r)-3-((tosyloxy)methyl)cyclobutyl)amino)nicotinate (100 mg, 0.23 mmol) was added to the suspension after 10 minutes. The mixture was stirred for 16 hours then diluted with EtOAc and washed with brine. The organic layer was dried and concentrated. The mixture was purified purified by RP-HPLC (eluent: water/MeCN*0.1% TFA).

ES/MS: 336.2 (M+H$^+$).

Preparation of Intermediate I-47

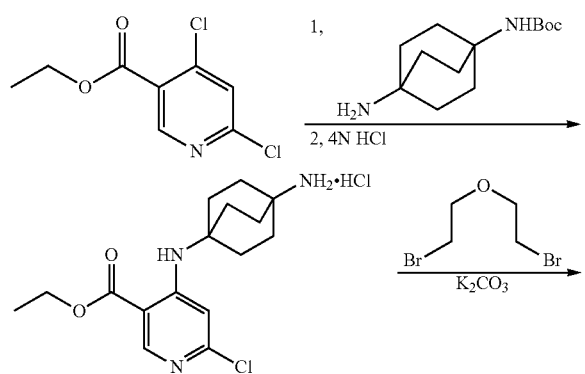

-continued

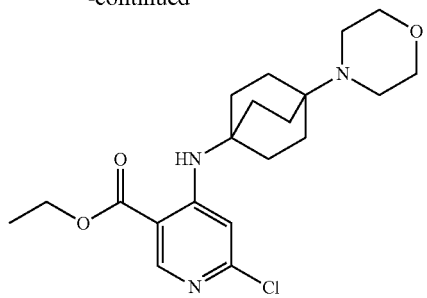

ethyl 4-((4-aminobicyclo[2.2.2]octan-1-yl)amino)-6-chloronicotinate hydrochloride To a flask of ethyl 4,6-dichloronicotinate (1 g, 5 mmol) and tert-butyl (4-aminobicyclo[2.2.2]octan-1-yl)carbamate (2.18 g, 9 mmol) and N-ethyldiisopropylamine (1.58 mL, 9 mmol) in 3 mL of NMP. The mixture was heated at 90° C. for 16 hours. The solvent was removed and purified by flash column (eluent: EtOAc/Hexane). The product was collected and dissolved in 20 mL of 4 M HCl in dioxane. The mixture was stirred for 2 hours. The solvent was removed and used without further purification.

ES/MS: 324.3 (M+H$^+$).

ethyl 6-chloro-4-((4-morpholinobicyclo[2.2.2]octan-1-yl)amino)nicotinate (I-47)

To a solution of ethyl 4-((4-aminobicyclo[2.2.2]octan-1-yl)amino)-6-chloronicotinate hydrochloride (150 mg, 0.45 mmol) and N-ethyldiisopropylamine (0.32 mL, 1.85 mmol) in ACN, 2-Bromoethyl ether (215 mg, 0.93 mmol) was added to the solution. It was heated to 110° C. sealed tube for 16 hours. The solvent was removed, then purified by RP-HPLC (eluent: water/MeCN*0.1% TFA).

ES/MS: 394.7 (M+H$^+$).

3. Example Procedures and Compound Examples

Procedure 1: Example 1

(R)-6-(3-cyanopyrrolo[1,2-b]pyridazin-7-yl)-N-(2-fluoro-3-hydroxy-3-methylbutyl)-4-((3-methyloxetan-3-yl)amino)nicotinamide

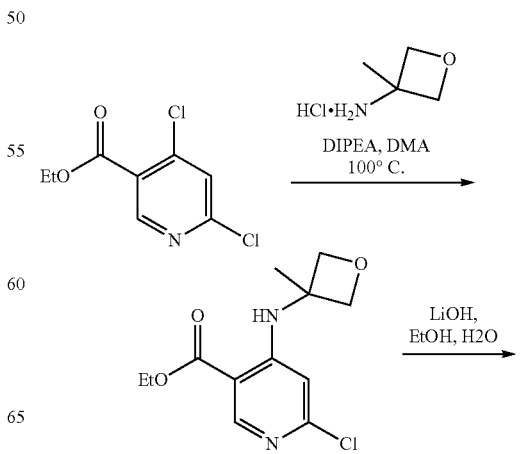

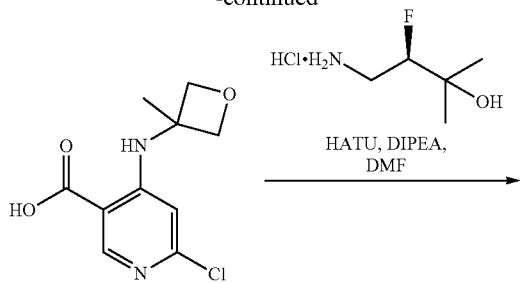

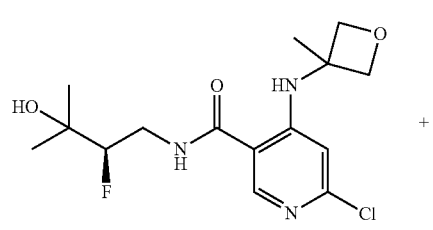

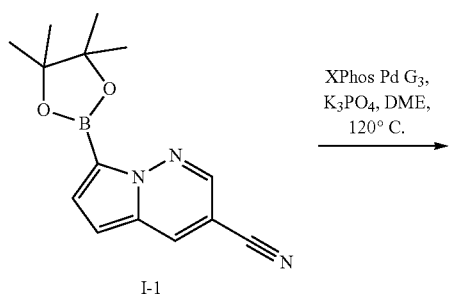

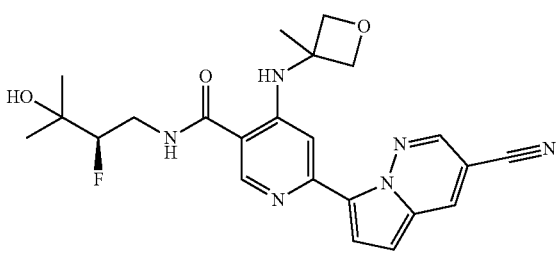

Example 1

Ethyl 6-chloro-4-((3-methyloxetan-3-yl)amino)nicotinate

A mixture of ethyl 4,6-dichloronicotinate (150 mg, 0.68 mmol), 3-methyloxetan-3-amine hydrochloride (101 mg, 0.818 mmol), and N,N-Diisopropylethylamine (0.3 ml, 1.7 mmol) in dimethylacetamide (4 mL) was heated at 100° C. for 16 hours. The reaction was cooled to room temperature. Water and EtOAc were added. The aqueous layer was extracted with EtOAc and the combined organic layers were dried over sodium sulfate. Filtration and evaporation of solvents yielded the crude product, which was purified by silica gel chromatography (eluent: EtOAc/hexanes).

ES/MS: 271.4 (M+H$^+$).

6-chloro-4-((3-methyloxetan-3-yl)amino)nicotinic acid ethyl 6-chloro-4-((3-methyloxetan-3-yl)amino)nicotinate (113 mg, 0.42 mmol) was dissolved in 2 mL ethanol. Water (1 mL) was added, followed by lithium hydroxide (30 mg, 1.25 mmol) and the mixture was stirred at room temperature. Upon completion, ethanol was removed under reduced pressure and 2N HCl was added. The product was extracted into ethyl acetate. Upon removed of the solvent under reduced pressure, the crude product was obtained and used without further purification.

ES/MS: 243.1 (M+H$^+$).

(R)-6-chloro-N-(2-fluoro-3-hydroxy-3-methylbutyl)-4-((3-methyloxetan-3-yl)amino)nicotinamide A mixture of 6-chloro-4-((3-methyloxetan-3-yl)amino) nicotinic acid (40 mg, 0.17 mmol), (R)-4-amino-3-fluoro-2-methylbutan-2-ol hydrochloride (31 mg, 0.20 mmol), 1-[Bis(dimethylamino)methylene]-1H-1,2,3-triazolo[4,5-b]pyridinium 3-oxid hexafluorophosphate (75.21 mg, 0.20 mmol) and N,N-diisopropylethylamine (0.09 ml, 0.49 mmol) in 0.6 mL DMF was stirred at room temperature for 1 hour. Water was added, and the product was extracted into ethyl acetate. The ethyl acetate solution was concentrated under reduced pressure. The crude product was purified by silica gel chromatography (eluent: EtOAc/hexanes).

ES/MS: 346.2 (M+H$^+$).

(R)-6-(3-cyanopyrrolo[1,2-b]pyridazin-7-yl)-N-(2-fluoro-3-hydroxy-3-methylbutyl)-4-((3-methyloxetan-3-yl)amino)nicotinamide (Example 1)

A mixture of (R)-6-chloro-N-(2-fluoro-3-hydroxy-3-methylbutyl)-4-((3-methyloxetan-3-yl)amino)nicotinamide (15 mg, 0.043 mmol), 7-(4,4,5,5-tetramethyl-1,3,2-dioxaborolan-2-yl)pyrrolo[1,2-b]pyridazine-3-carbonitrile (I-1) (18 mg, 0.067 mmol), XPhos Pd G3 (4 mg), and 2M Potassium phosphate tribasic (0.07 ml) in 1 mL DME was degassed with argon for 3 minutes, then capped and heated under microwave conditions at 120° C. for 20 minutes. The crude material was purified RP-HPLC (eluent: water/MeCN*0.1% TFA) to yield the product as a trifluoroacetate salt.

ES/MS: 453.2 (M+H$^+$).

1H NMR (400 MHz, Acetonitrile-d3) δ 9.76 (s, 1H), 8.64 (s, 1H), 8.62 (d, J=2.2 Hz, 1H), 8.58 (d, J=2.2 Hz, 1H), 8.00 (d, J=5.1 Hz, 1H), 7.77 (s, 1H), 7.42 (s, 1H), 7.16 (d, J=5.1 Hz, 1H), 4.86 (d, J=6.5 Hz, 2H), 4.72 (d, J=6.5 Hz, 2H), 1.83 (s, 3H), 1.27 (d, J=2.0 Hz, 6H).

Alternatively, borylation and suzuki cross coupling can be carried out in tandem:

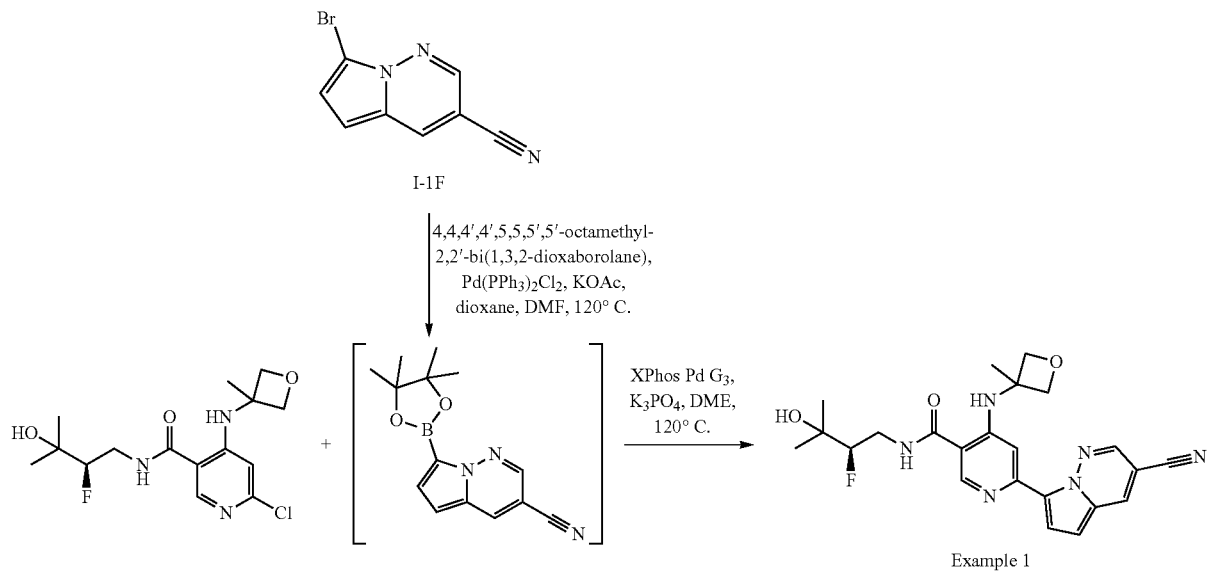

(R)-6-(3-cyanopyrrolo[1,2-b]pyridazin-7-yl)-N-(2-fluoro-3-hydroxy-3-methylbutyl)-4-((3-methyloxetan-3-yl)amino)nicotinamide (Example 1)

A mixture of 7-bromopyrrolo[1,2-b]pyridazine-3-carbonitrile (I-1F) (32 mg, 0.144 mmol), 4,4,4',4',5,5,5',5'-octamethyl-2,2'-bi(1,3,2-dioxaborolane) (59 mg, 0.23 mmol), potassium acetate (43 mg, 0.44 mmol), trans-dichlorobis(triphenylphosphine)palladium (II) (5 mg, 0.01 mmol), dioxane (0.32 ml) and DMF (0.16 ml) was degassed with Argon for 3 minutes. The vial was capped and the mixture was heated under microwave conditions at 120° C. for 20 minutes. The vial was uncapped, and (R)-6-chloro-N-(2-fluoro-3-hydroxy-3-methylbutyl)-4-((3-methyloxetan-3-yl)amino)nicotinamide (28 mg, 0.14 mmol), XPhos Pd G3 (11 mg, 0.013 mmol), 2M Potassium phosphate tribasic (0.13 ml) and 0.8 mL DME were added. The mixture was degassed with argon for 3 minutes, then capped and heated under microwave conditions at 120° C. for 20 minutes. The crude material was purified RP-HPLC (eluent: water/MeCN*0.1% TFA) to yield the product as a trifluoroacetate salt.

Procedure 2: Example 2

6-(3-cyanopyrrolo[1,2-b]pyridazin-7-yl)-N-((R)-2-fluoro-3-hydroxy-3-methylbutyl)-4-(((1S,3R)-3-hydroxycyclohexyl)amino)nicotinamide

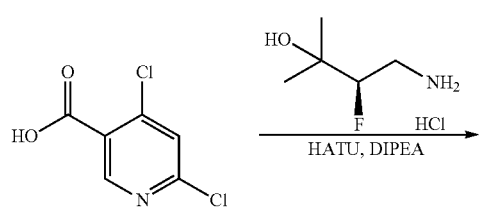

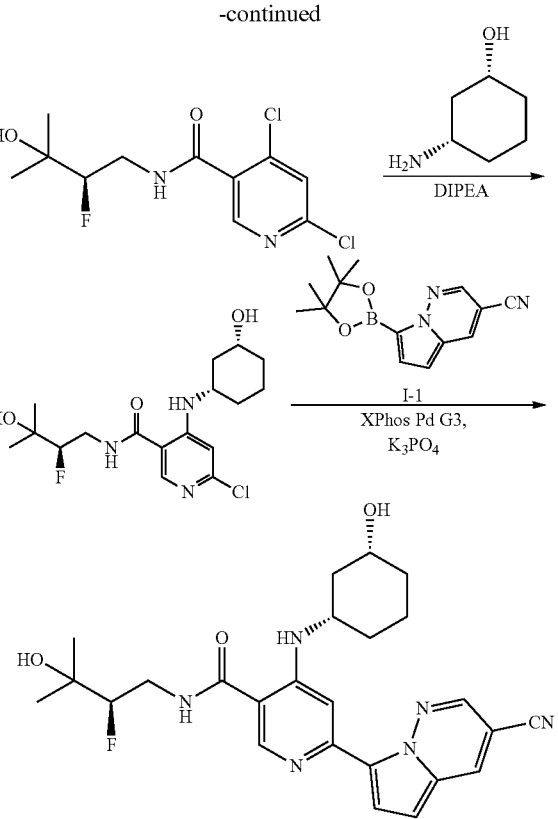

(R)-4,6-dichloro-N-(2-fluoro-3-hydroxy-3-methylbutyl)nicotinamide 4,6-dichloronicotinic acid (3.0 g, 16 mmol) and the HCl salt of (R)-4-amino-3-fluor-2-methylbutan-2-ol (2.7 g, 17 mmol) were suspended in DMF (60 mL) at room temperature. To the resulting suspension was added HATU (7.13 g, 18.8 mmol) as a single portion followed by DIPEA (2.7 mL, 16 mmol) as a single portion and the reaction mixture stirred at room temperature for 1 hr. The solvent was removed and the resulting residue partitioned between EtOAc and water. The layers were separated, the water layer extracted twice more with EtOAc. The organic layers were then combined, dried over MgSO₄, filtered and concentrated with the resulting crude residue then purified via silica gel chromatography (eluent: EtOAc/hexanes) to give the desired product.

ES/MS: 295.2 (M+H⁺).

6-chloro-N-((R)-2-fluoro-3-hydroxy-3-methylbutyl)-4-(((1S,3R)-3-hydroxycyclohexyl)amino)nicotinamide (R)-4,6-dichloro-N-(2-fluoro-3-hydroxy-3-methylbutyl) nicotinamide (0.53 g, 1.8 mmol) and (1R,3S)-3-aminocyclohexan-1-ol were added to a microwave vial followed by DMA (5 mL) and DIPEA (0.80 mL, 4.5 mmol). The resulting solution was heated to 160° C. in a microwave reactor for 40 min. The reaction mixture was then poured into water and extracted 3 times with EtOAc. The organic layers were then combined, dried, filtered and concentrated with the resulting crude residue then purified via silica gel chromatography (eluent: EtOAc/hexanes/MeOH) to give the desired product. Note: In some instances, heating to 160° C. in a microwave reactor for 3 hours is necessary.

ES/MS: 374.3 (M+H⁺).

6-(3-cyanopyrrolo[1,2-b]pyridazin-7-yl)-N-((R)-2-fluoro-3-hydroxy-3-methylbutyl)-4-(((1S,3R)-3-hydroxycyclohexyl)amino)nicotinamide (Example 2)

6-chloro-N-((R)-2-fluoro-3-hydroxy-3-methylbutyl)-4-(((1S,3R)-3-hydroxycyclohexyl)amino)nicotinamide (0.018 g, 0.048 mmol) and 7-(4,4,5,5-tetramethyl-1,3,2-dioxaborolan-2-yl)pyrrolo[1,2-b]pyridazine-3-carbonitrile (0.023 g, 0.087 mmol) were added to a microwave vial followed by DME (0.8 mL), XPhos Pd G3 (4.1 mg, 0.005 mmol) and K₃PO₄ (0.5M in water, 0.19 mL, 0.096 mmol). The resulting mixture was purged with argon for 2 minutes, sealed and heated to 120° C. in a microwave reactor for 10 min. The reaction mixture was filtered and purified by RP-HPLC (eluent: water/MeCN*0.1% TFA). The product fractions were combined and lyophilized to give the final product as a TFA salt.

ES/MS: 481.4 (M+H⁺).

1H NMR (400 MHz, Methanol-d4) δ 8.76 (d, J=2.2 Hz, 1H), 8.67 (d, J=2.2 Hz, 1H), 8.54 (s, 1H), 8.01 (d, J=5.0 Hz, 1H), 7.86 (s, 1H), 7.21 (d, J=5.1 Hz, 1H), 4.61-4.28 (m, 1H), 4.14-3.75 (m, 3H), 3.48 (td, J=15.6, 15.2, 9.4 Hz, 1H), 2.32 (d, J=12.5 Hz, 1H), 2.00 (d, J=37.3 Hz, 3H), 1.70-1.34 (m, 4H), 1.29 (d, J=1.6 Hz, 6H).

Alternatively, the final step can be carried as a tandem borylation of 7-bromopyrrolo[1,2-b]pyridazine-3-carbonitrile (I-1F) following by a terminating Suzuki coupling as described above in Procedure 1.

Procedure 3: Example 3

6-(3-cyanopyrrolo[1,2-b]pyridazin-7-yl)-N-((1r,4r)-4-(2-hydroxypropan-2-yl)cyclohexyl)-4-(isopropylamino)nicotinamide

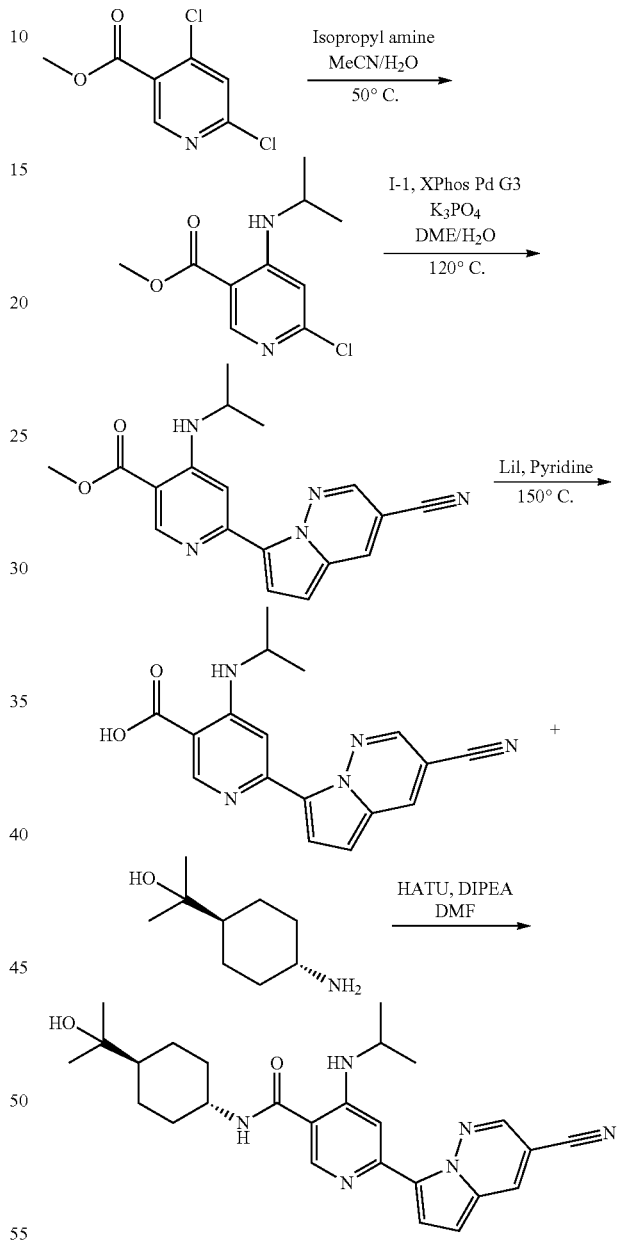

Example 3

Methyl 6-chloro-4-(isopropylamino)nicotinate

To methyl 4,6-dichloronicotinate (2.0 g, 9.7 mmol) in MeCN (40.0 mL) and water (1.12 mL) was added isopropyl amine (4.17 mL, 48.5 mmol). The reaction mixture was heated to 50° C. for 18 hours, then cooled and concentrated in vacuo. The residue was taken in EtOAc and washed with brine. The organic layer was isolated, dried over sodium sulfate, filtered, concentrated in vacuo, and purified by silica gel chromatography (eluent: EtOAc/hexanes) to provide the desired product.

ES/MS: 229.3 [M+H⁺].

Methyl 6-(3-cyanopyrrolo[1,2-b]pyridazin-7-yl)-4-(isopropylamino)nicotinate

A microwave vial was charged with methyl 6-chloro-4-(isopropylamino)nicotinate (300.0 mg, 1.3 mmol), I-1 (459.0 mmol, 1.7 mmol), XPhos Pd G3 (111.0 mg, 0.13 mmol), and K₃PO₄ (557.0 mg, 2.6 mmol) and taken under argon. To the vial was added DME (6.0 mL) and water (5.2 mL), and the suspension was degassed with bubbling argon for 60 seconds. The vial was sealed and heated in a microwave reactor at 120° C. for 10 minutes. After cooling, the reaction mixture was concentrated in vacuo, and the resulting residue taken in EtOAc and filtered through a pad of celite. The solution was washed with brine, dried over sodium sulfate, filtered, concentrated in vacuo, and purified by silica gel chromatography (eluent: EtOAc/hexanes) to provide the desired product.

ES/MS: 336.2 [M+H⁺].

6-(3-cyanopyrrolo[1,2-b]pyridazin-7-yl)-4-(isopropylamino)nicotinic acid

A microwave vial was charged with methyl 6-(3-cyanopyrrolo[1,2-b]pyridazin-7-yl)-4-(isopropylamino)nicotinate (100.0 mg, 0.30 mmol) and lithium iodide (399.1 mg, 3.0 mmol), then pyridine (3.0 mL) was added. The vial was sealed and heated to 150° C. in a microwave reactor for 60 minutes. After cooling, the reaction mixture was concentrated in vacuo. The residue was taken in water and acidified to pH ~4 by slow addition of 2N HCl. The resulting solid was isolated by filtration and washed with water and a minimal amount of EtOAc. The solid was dried under vacuum to provide desired compound, which was used without additional purification.

ES/MS: 322.2 [M+H⁺].

6-(3-cyanopyrrolo[1,2-b]pyridazin-7-yl)-N-((1r,4r)-4-(2-hydroxypropan-2-yl)cyclohexyl)-4-(isopropylamino)nicotinamide (Example 3)

A round bottom flask was charged with 6-(3-cyanopyrrolo[1,2-b]pyridazin-7-yl)-4-(isopropylamino)nicotinic acid (15.0 mg, 0.047 mmol), trans-2-(4-amino-cyclohexyl)-propan-2-ol (7.7 mg, 0.049 mmol), and HATU (18.6 mg, 0.049 mmol). The solids were dissolved in DMF (1.0 mL), then DIPEA (17.5 µL, 0.098 mmol) was added. The reaction mixture was stirred at room temperature for 60 minutes. The reaction was filtered and directly purified by reverse phase high pressure liquid chromatography (eluent: water/MeCN*0.1% TFA) to provide the final compound.

ES/MS: 461.4 [M+H⁺].

1H NMR (400 MHz, Chloroform-d) δ 9.99 (d, J=7.5 Hz, 1H), 9.03 (s, 1H), 8.45 (d, J=2.2 Hz, 1H), 8.32 (d, J=2.1 Hz, 1H), 8.10 (d, J=5.1 Hz, 1H), 7.93 (s, 1H), 7.69 (d, J=7.6 Hz, 1H), 7.09 (d, J=5.0 Hz, 1H), 3.93 (h, J=6.4 Hz, 1H), 3.89-3.77 (m, 1H), 2.08 (d, J=12.2 Hz, 2H), 1.93 (d, J=12.5 Hz, 2H), 1.43 (d, J=6.4 Hz, 6H), 1.40-1.21 (m, 3H), 1.19 (s, 6H).

Procedure 4: Example 4

(R)-6-(3-cyanopyrrolo[1,2-b]pyridazin-7-yl)-N-(2-fluoro-3-hydroxy-3-methylbutyl)-4-(pyridin-3-ylamino)nicotinamide

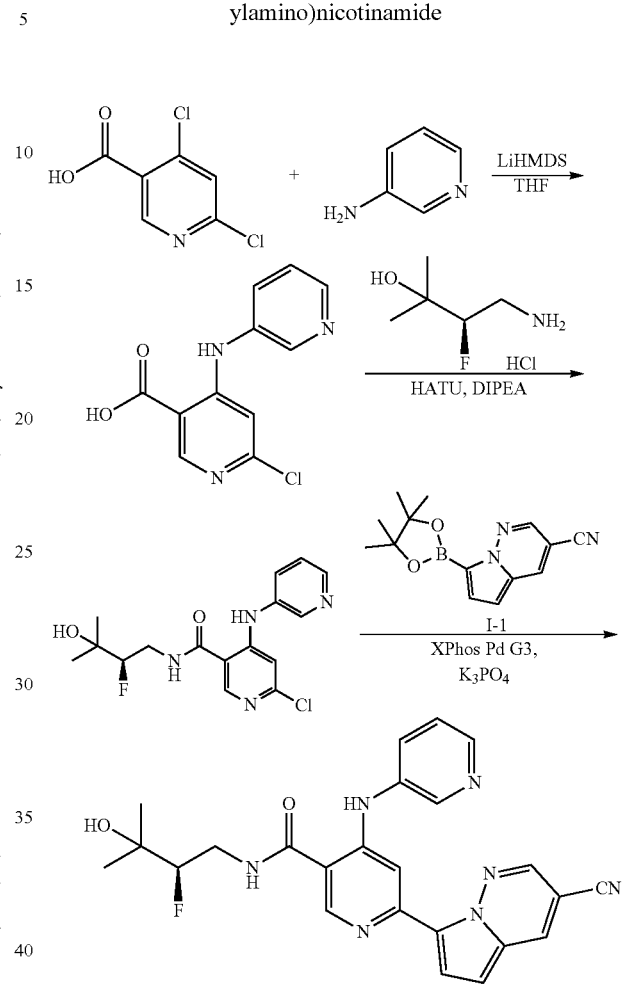

Example 4

6-chloro-4-(pyridin-3-ylamino)nicotinic acid 3-aminopyridine (0.41 g, 4.4 mmol) was dissolved in THF (7 mL) and brought to −78° C. LiHMDS (1.0M in THF, 6.3 mL, 6.3 mmol) was added dropwise and the resulting solution stirred for 30 min. at −78° C. 4,6-dichloronicotinic acid (0.40 g, 2.1 mmol) suspended in THF (3 mL) was then added dropwise and the resulting mixture stirred at −78° C. for 5 min. after which the cold bath was removed and the reaction mixture allowed to warm to room temperature and stir for 16 hrs. The reaction was then quenched with 1.0M aqueous HCl and the organic solvents removed by rotary evaporation. The resulting aqueous residue was diluted with water and the pH adjusted to pH 4-5 using 1.0M aqueous HCl and 1.0M aqueous NaOH at which point the solid was filtered, washed with MeOH and dried to give the desired product.

ES/MS: 250.0 [M+H⁺].

(R)-6-chloro-N-(2-fluoro-3-hydroxy-3-methylbutyl)-4-(pyridin-3-ylamino)nicotinamide 6-chloro-4-(pyridin-3-ylamino)nicotinic acid (0.050 g, 0.20 mmol) and the HCl salt of (R)-4-amino-3-fluor-2- methylbutan-2-ol (0.063 g, 0.40 mmol) were suspended in DMF (2 mL) at room temperature. To the resulting suspension was added HATU (0.16 g, 0.42 mmol) as a single portion followed by DIPEA (0.09 mL, 0.50 mmol) as a single portion and the reaction mixture stirred at room temperature for 20 min. The reaction mixture was partitioned between EtOAc and water. The layers were separated, the water layer extracted twice more with EtOAc. The organic layers were then combined, dried, filtered and concentrated with the resulting crude residue then purified via silica gel chromatography (eluent: EtOAc/hexanes/MeOH) to give the desired product.

ES/MS: 353.1 [M+H$^+$].

(R)-6-(3-cyanopyrrolo[1,2-b]pyridazin-7-yl)-N-(2-fluoro-3-hydroxy-3-methylbutyl)-4-(pyridin-3-ylamino)nicotinamide (Example 4)

(R)-6-chloro-N-(2-fluoro-3-hydroxy-3-methylbutyl)-4-(pyridin-3-ylamino)nicotinamide (25 mg, 0.071 mmol) and 7-(4,4,5,5-tetramethyl-1,3,2-dioxaborolan-2-yl)pyrrolo[1,2-b]pyridazine-3-carbonitrile (34 mg, 0.13 mmol) were added to a microwave vial followed by DME (0.8 mL), XPhos Pd G3 (6.0 mg, 0.007 mmol) and K$_3$PO$_4$ (0.5M in water, 0.28 mL, 0.14 mmol). The resulting mixture was purged with argon for 2 minutes, sealed and heated to 120° C. in a microwave reactor for 10 min. The reaction mixture was filtered and purified by RP-HPLC (eluent: water/MeCN*0.1% TFA). The product fractions were combined and lyophilized to give the final product.

ES/MS: 460.2 [M+H$^+$].

1H NMR (400 MHz, Methanol-d4) δ 8.77 (d, J=2.3 Hz, 1H), 8.77 (s, 1H), 8.71 (d, J=2.2 Hz, 1H), 8.62 (dd, J=4.9, 1.4 Hz, 1H), 8.57 (d, J=2.2 Hz, 1H), 8.22 (s, 1H), 8.08 (ddd, J=8.2, 2.6, 1.4 Hz, 1H), 7.84 (d, J=5.1 Hz, 1H), 7.73 (ddd, J=8.2, 4.9, 0.8 Hz, 1H), 7.16 (d, J=5.0 Hz, 1H), 4.47 (ddd, J=49.0, 9.3, 2.1 Hz, 1H), 3.99 (ddd, J=36.4, 14.5, 2.1 Hz, 1H), 3.62-3.45 (m, 1H), 1.30 (d, J=1.6 Hz, 6H).

Procedure 5: Example 5

6-(3-cyanopyrrolo[1,2-b]pyridazin-7-yl)-N-(6-(2-hydroxypropan-2-yl)spiro[3.3]heptan-2-yl)-4-(isopropylamino)nicotinamide

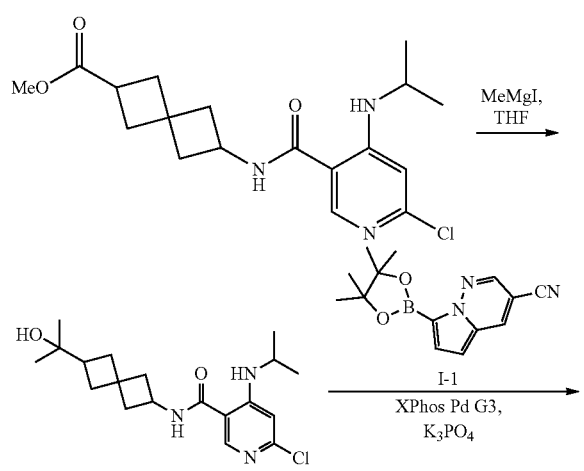

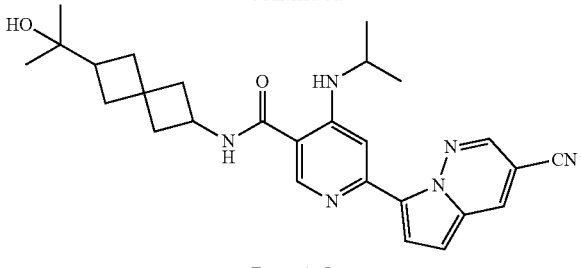

Example 5

6-chloro-N-(6-(2-hydroxypropan-2-yl)spiro[3.3]heptan-2-yl)-4-(isopropylamino)nicotinamide Methyl 6-(6-chloro-4-(isopropylamino)nicotinamido)spiro[3.3]heptane-2-carboxylate (obtained as outlined in steps 1 and 2 of Procedure 2) (50 mg, 0.14 mmol) was dissolved in THF (2 mL) and brought to 0° C. using an ice/water bath. MeMgI (3.0M in ether, 0.14 mL, 0.41 mmol) was then added dropwise and the resulting mixture stirred for 15 min. at 0° C. More MeMgI (3.0M in ether, 0.27 mL, 0.42 mmol) was then added dropwise at 0° C., and the resulting mixture stirred for 30 min. at which time it was quenched dropwise using water. The mixture was extracted with EtOAc and the combined organic layers washed with brine, dried over MgSO$_4$, filtered, concentrated and purified via silica gel chromatography (eluent: EtOAc/hexanes) to yield the desired product.

ES/MS: 366.3 [M+H$^+$].

6-(3-cyanopyrrolo[1,2-b]pyridazin-7-yl)-N-(6-(2-hydroxypropan-2-yl)spiro[3.3]heptan-2-yl)-4-(isopropylamino)nicotinamide (Example 5)

6-chloro-N-(6-(2-hydroxypropan-2-yl)spiro[3.3]heptan-2-yl)-4-(isopropylamino)nicotinamide (0.024 g, 0.066 mmol) and 7-(4,4,5,5-tetramethyl-1,3,2-dioxaborolan-2-yl)pyrrolo[1,2-b]pyridazine-3-carbonitrile (0.032 mg, 0.12 mmol) were added to a microwave vial followed by DME (0.8 mL), XPhos Pd G3 (5.6 mg, 0.007 mmol) and Na$_3$PO$_4$ (0.5M in water, 0.26 mL, 0.13 mmol). The resulting mixture was purged with argon for 2 minutes, sealed and heated to 120° C. in a microwave reactor for 10 min. The reaction mixture was filtered and purified by RP-HPLC (eluent: water/MeCN*0.1% TFA). The product fraction were combined and lyophilized to give the final product.

ES/MS: 473.3 [M+H$^+$].

1H NMR (400 MHz, Methanol-d4) δ 8.74 (d, J=2.2 Hz, 1H), 8.65 (d, J=2.2 Hz, 1H), 8.53 (s, 1H), 7.97 (d, J=5.0 Hz, 1H), 7.81 (s, 1H), 7.20 (d, J=5.1 Hz, 1H), 4.44-4.28 (m, 1H), 4.13 (hept, J=6.5 Hz, 1H), 2.62-2.48 (m, 1H), 2.37-2.20 (m, 2H), 2.18-1.93 (m, 5H), 1.90-1.78 (m, 1H), 1.39 (d, J=6.4 Hz, 6H), 1.08 (s, 3H), 1.07 (s, 3H).

Procedure 6: Example 6

6-(3-cyanopyrrolo[1,2-b]pyridazin-7-yl)-4-(isopropylamino)-N-(tetrahydro-2H-pyran-4-yl)nicotinamide

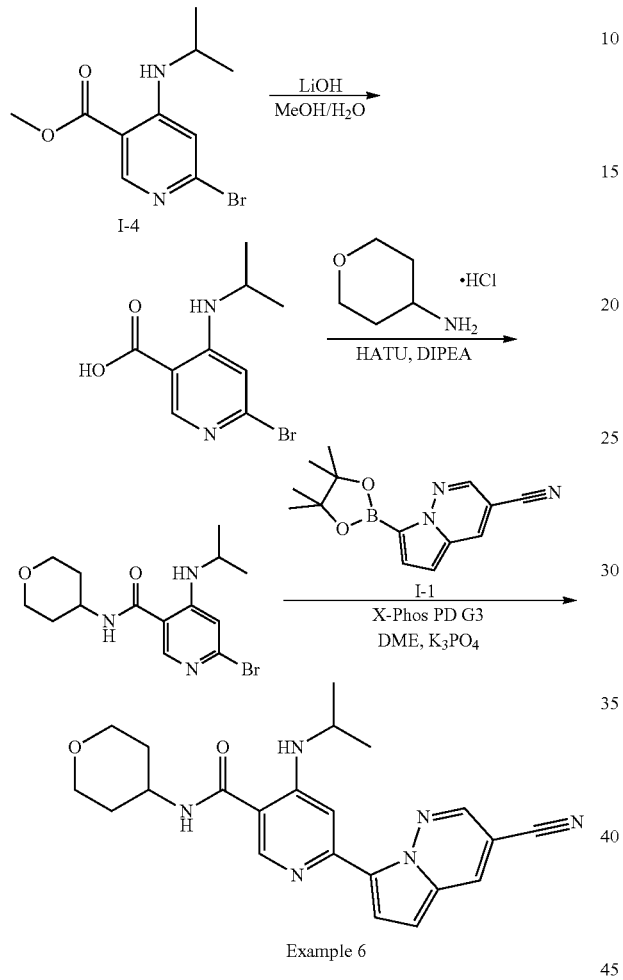

Example 6

6-bromo-4-(isopropylamino)nicotinic acid

To a solution of methyl 6-bromo-4-(isopropylamino)nicotinate (1.25 g, 4.58 mmol) in a methanol (16 mL) was added aqueous lithium hydroxide (2.5 M, 3.7 mL, 9.25 mmol). The solution was heated to 45° C. for 2.5 hours and cooled to room temperature. Aqueous hydrochloric acid (1M, 9.1 mL) was added and volitiles were removed in vacuo. The resulting slurry was filtered and washed with H₂O to provide 6-bromo-4-(isopropylamino)nicotinic acid.
ES/MS: 259.419 (M+H⁺).

6-bromo-4-(isopropylamino)-N-(tetrahydro-2H-pyran-4-yl)nicotinamide

To a solution of 6-bromo-4-(isopropylamino)nicotinic acid (50 mg, 0.19 mmol) in CH₂Cl₂ (2 mL) was added HATU (95 mg, 0.25 mmol), tetrahydropyran-4-amine hydrochloride (32 mg, 0.23 mmol), and DIPEA (0.10 mL, 0.57 mmol). The resulting solution was stirred at room temperature for 1 hour and diluted with CH₂Cl₂. The organic solution was washed with saturated aqueous ammonium chloride (2 times), then dried over Na₂SO₄, and the concentrated to provide 6-bromo-4-(isopropylamino)-N-(tetrahydro-2H-pyran-4-yl)nicotinamide.
ES/MS: 344.139 (M+H⁺).

6-(3-cyanopyrrolo[1,2-b]pyridazin-7-yl)-4-(isopropylamino)-N-(tetrahydro-2H-pyran-4-yl)nicotinamide To a solution of 6-bromo-4-(isopropylamino)-N-(tetrahydro-2H-pyran-4-yl)nicotinamide (66 mg, 0.19 mmol) in DME (2.5 mL) was added 7-(4,4,5,5-tetramethyl-1,3,2-dioxaborolan-2-yl)pyrrolo[1,2-b]pyridazine-3-carbonitrile (73 mg, 0.27 mmol), XPhos Pd G3 (15 mg, 0.018 mmol), and potassium phosphate tribasic (2M, 0.25 mL, 0.50 mmol). The resulting solution was degassed with argon and heated to 150° C. for 30 minutes. To the reaction mixture was added SiliaMetS® Thiol (50 mg) and the resulting slurry was filtered and wash with DMF. The crude solution was purified by preparative RP-HPLC (eluent: water/MeCN*0.1% TFA) to provide 6-(3-cyanopyrrolo[1,2-b]pyridazin-7-yl)-4-(isopropylamino)-N-(tetrahydro-2H-pyran-4-yl)nicotinamide as the TFA salt.
ES/MS: 405.379 (M+H⁺).
1H NMR (400 MHz, Methanol-d4) δ 8.74 (d, J=2.2 Hz, 1H), 8.65 (d, J=2.2 Hz, 1H), 8.55 (s, 1H), 7.98 (d, J=5.0 Hz, 1H), 7.84 (s, 1H), 7.20 (d, J=5.1 Hz, 1H), 4.12 (ddt, J=15.2, 11.0, 5.3 Hz, 2H), 4.05-3.94 (m, 2H), 3.53 (td, J=11.8, 2.1 Hz, 2H), 1.99-1.88 (m, 2H), 1.67 (qd, J=11.9, 4.4 Hz, 2H), 1.39 (d, J=6.4 Hz, 6H).

Procedure 7: Example 7

6-(3-cyanopyrrolo[1,2-b]pyridazin-7-yl)-4-(isopropylamino)-N-(oxetan-3-yl)nicotinamide Example 7

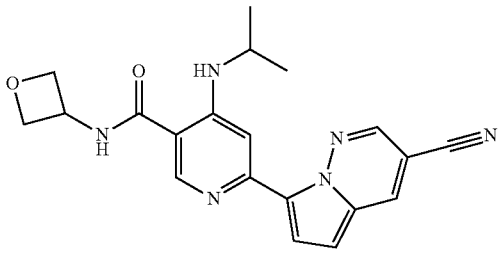

6-(3-cyanopyrrolo[1,2-b]pyridazin-7-yl)-4-(isopropylamino)-N-(oxetan-3-yl)nicotinamide Starting from bromo-4-(isopropylamino)nicotinic acid (I-4) (30 mg, 0.12 mmol), 6-(3-cyanopyrrolo[1,2-b]pyridazin-7-yl)-4-(isopropylamino)-N-(oxetan-3-yl)nicotinamide was prepared following the procedures for Example 6, substituting oxetan-3-amine (14 mg, 0.19 mmol) for tetrahydropyran-4-amine hydrochloride. The resulting TFA salt was neutralized with aqueous saturated sodium bicarbonate and extracted with ethyl acetate. The organic layers were dried over Na2SO4 and concentrated. The resulting material was purified by silica gel chromatography (eluent: EtOAc/hexanes/MeOH) to provide the product as a free base.

ES/MS: 377.235 (M+H$^+$).

1H NMR (400 MHz, Methanol-d4) δ 8.63 (s, 1H), 8.55 (d, J=2.2 Hz, 1H), 8.48 (d, J=2.2 Hz, 1H), 8.13 (s, 1H), 7.80 (d, J=4.8 Hz, 1H), 7.08 (d, J=4.9 Hz, 1H), 5.09 (dt, J=7.7, 6.7 Hz, 1H), 4.93 (t, J=7.0 Hz, 2H), 4.72 (t, J=6.6 Hz, 2H), 3.87 (p, J=6.3 Hz, 1H), 1.33 (d, J=6.3 Hz, 6H).

Procedure 8: Example 8

6-(3-cyanopyrrolo[1,2-b]pyridazin-7-yl)-N-((R)-2-fluoro-3-hydroxy-3-methylbutyl)-4-((5-oxopyrrolidin-3-yl)amino)nicotinamide

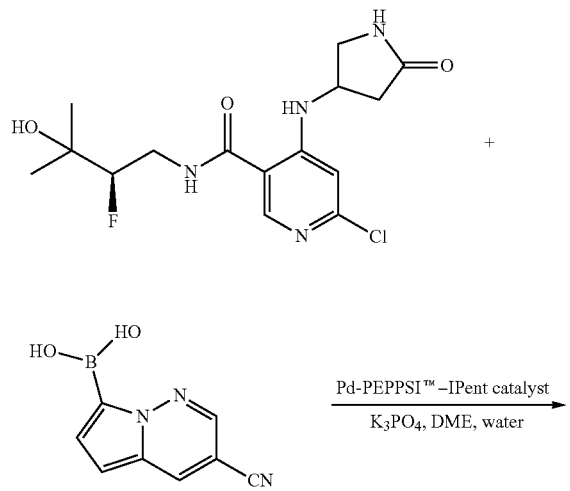

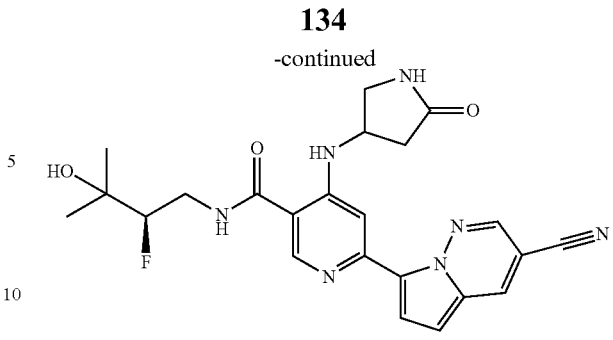

Example 8

6-(3-cyanopyrrolo[1,2-b]pyridazin-7-yl)-N-((R)-2-fluoro-3-hydroxy-3-methylbutyl)-4-((5-oxopyrrolidin-3-yl)amino)nicotinamide (Example 8)

6-chloro-N-((R)-2-fluoro-3-hydroxy-3-methylbutyl)-4-((5-oxopyrrolidin-3-yl)amino)nicotinamide (obtained as described in Procedure 2 replacing (1R,3S)-3-aminocyclohexan-1-ol with 4-aminopyrrolidin-2-one) (30 mg, 0.084 mmol), (3-cyanopyrrolo[1,2-b]pyridazin-7-yl)boronic acid (19 mg, 0.1 mmol) and Pd-PEPPSI™-IPent catalyst (6.6 mg, 0.008 mmol) were charged in a microwave tube. Dimethoxyethane (1 mL) and Potassium phosphate tribasic aqueous solution (1 M, 0.25 mL) were added. The reaction mixture was heated to 120° C. in a microwave reactor for 20 minutes and then cooled to room temperature. It was purified by RP-HPLC (eluent: water/MeCN*0.1% TFA) to yield the title compound as a TFA salt.

ES/MS: 466.28 [M+H]$^+$.

$^1$H NMR (400 MHz, Methanol-d4) δ 8.75 (d, J=2.2 Hz, 1H), 8.69 (d, J=2.1 Hz, 1H), 8.64 (s, 1H), 8.04 (d, J=5.1 Hz, 1H), 7.87 (s, 1H), 7.22 (d, J=5.1 Hz, 1H), 4.84-4.68 (m, 1H), 4.42 (ddd, J=49.0, 9.4, 2.1 Hz, 1H), 4.07-3.72 (m, 2H), 3.61-3.40 (m, 2H), 2.99 (dd, J=17.1, 8.0 Hz, 1H), 2.48 (dd, J=17.1, 4.7 Hz, 1H), 1.28 (d, J=1.7 Hz, 6H).

Procedure 9: Example 9

7-(5-(((1,1-dioxidotetrahydrothiophen-3-yl)methyl)carbamoyl)-4-(isopropylamino)pyridin-2-yl)pyrrolo[1,2-b]pyridazine-3-carboxamide

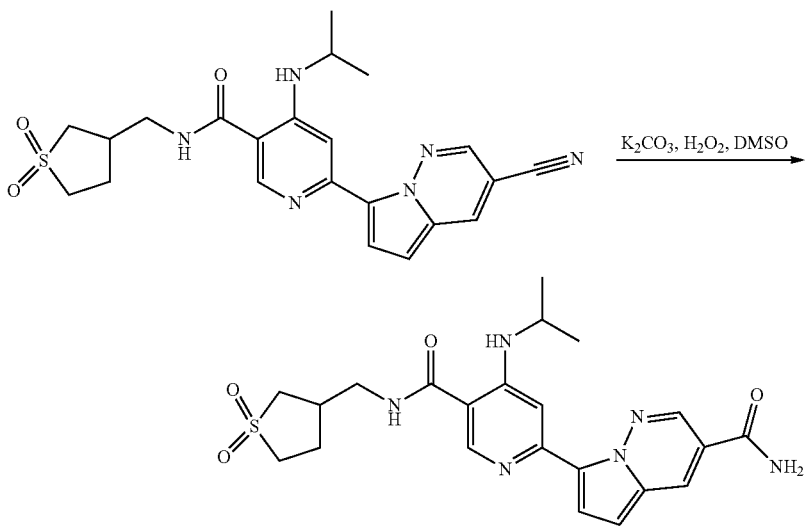

Example 9

7-(5-(((1,1-dioxidotetrahydrothiophen-3-yl)methyl)carbamoyl)-4-(isopropylamino)pyridin-2-yl)pyrrolo[1,2-b]pyridazine-3-carboxamide (Example 9)

To a mixture of 6-(3-cyanopyrrolo[1,2-b]pyridazin-7-yl)-N-((1,1-dioxidotetrahydrothiophen-3-yl)methyl)-4-(isopropylamino)nicotinamide (Obtained according to the method described in Procedure 1) (5 mg, 0.011 mmol) and potassium carbonate (15 mg, 0.11 mmol) in DMSO (0.5 mL) was added 8 drops of 30% hydrogen peroxide solution. After stirring at ambient temperature for 10 min, it was purified by RP-HPLC (eluent: water/MeCN*0.1% TFA) to yield the title compound as a TFA salt.

ES/MS: 471.21 [M+H]$^+$.

$^1$H NMR (400 MHz, Methanol-d4) δ 8.91 (d, J=2.2 Hz, 1H), 8.68 (d, J=2.3 Hz, 1H), 8.55 (s, 1H), 7.97 (d, J=5.0 Hz, 1H), 7.80 (s, 1H), 7.11 (d, J=5.0 Hz, 1H), 4.15 (p, J=6.4 Hz, 1H), 3.54 (qd, J=13.7, 6.4 Hz, 2H), 3.26-3.02 (m, 2H), 2.97-2.73 (m, 2H), 2.50-2.29 (m, 1H), 2.08-1.81 (m, 1H), 1.40 (d, J=6.4 Hz, 6H).

Procedure 10: Example 10

(R)-6-(3-cyanopyrrolo[1,2-b]pyridazin-7-yl)-N-(2-fluoro-3-hydroxy-3-methylbutyl)-4-(methylsulfonamido)nicotinamide

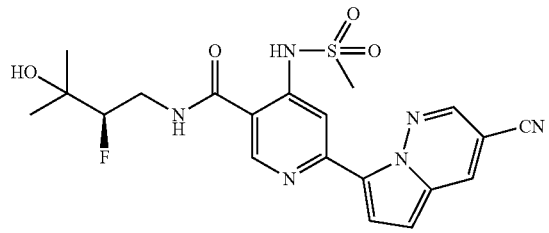

Example 10

(R)-6-(3-cyanopyrrolo[1,2-b]pyridazin-7-yl)-N-(2-fluoro-3-hydroxy-3-methylbutyl)-4-(methylsulfonamido)nicotinamide (Example 10)

(R)-6-(3-cyanopyrrolo[1,2-b]pyridazin-7-yl)-N-(2-fluoro-3-hydroxy-3-methylbutyl)-4-(methylsulfonamido)nicotinamide (Example 10) was prepared as shown in Procedure 1 substituting 6-chloro-4-((3-methyloxetan-3-yl)amino)nicotinic acid with 6-chloro-4-(methylsulfonamido)nicotinic acid (I-6).

Example 10

ES/MS: 461.1 [M+H]$^+$.

1H NMR (400 MHz, Methanol-d4) δ 8.84 (s, 1H), 8.55 (d, J=11.5 Hz, 2H), 8.34 (s, 1H), 7.78 (s, 1H), 7.11 (d, J=5.0 Hz, 1H), 4.52-4.25 (m, 1H), 4.01 (dd, J=35.5, 14.9 Hz, 1H), 3.50 (td, J=14.8, 9.4 Hz, 1H), 2.01 (s, 1H), 1.27 (s, 7H).

Procedure 11: Example 11

(R)-4-amino-6-(3-cyanopyrrolo[1,2-b]pyridazin-7-yl)-N-(2-fluoro-3-hydroxy-3-methylbutyl)nicotinamide

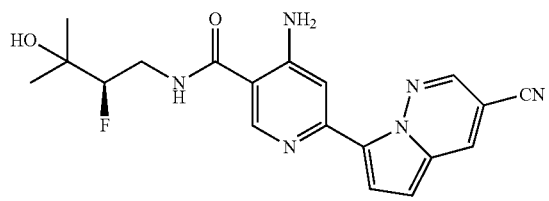

Example 11

(R)-4-amino-6-(3-cyanopyrrolo[1,2-b]pyridazin-7-yl)-N-(2-fluoro-3-hydroxy-3-methylbutyl)nicotinamide (Example 11)

(R)-4-amino-6-(3-cyanopyrrolo[1,2-b]pyridazin-7-yl)-N-(2-fluoro-3-hydroxy-3-methylbutyl)nicotinamide (Example 11) was prepared as shown in Procedure 1 substituting ethyl 6-chloro-4-((3-methyloxetan-3-yl)amino)nicotinate with 4-amino-6-chloronicotinate.

Example 11

ES/MS: 383.2 [M+H]+.

1H NMR (400 MHz, Methanol-d4) δ 8.73 (d, J=2.2 Hz, 1H), 8.62 (d, J=2.2 Hz, 1H), 8.56 (s, 1H), 7.87 (s, 1H), 7.83 (d, J=5.0 Hz, 1H), 7.19 (d, J=5.0 Hz, 1H), 4.42 (ddd, J=49.1, 9.3, 2.2 Hz, 1H), 4.10-3.80 (m, 1H), 3.60-3.38 (m, 1H), 1.28 (d, J=1.6 Hz, 6H).

Procedure 12: Example 12

N-((1r,4r)-4-aminocyclohexyl)-6-(3-cyanopyrrolo[1,2-b]pyridazin-7-yl)-4-(isopropylamino)nicotinamide

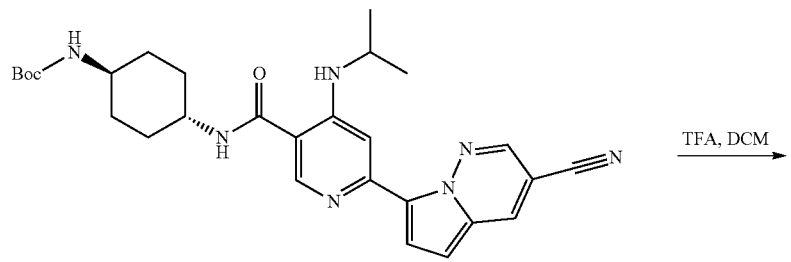

TFA, DCM

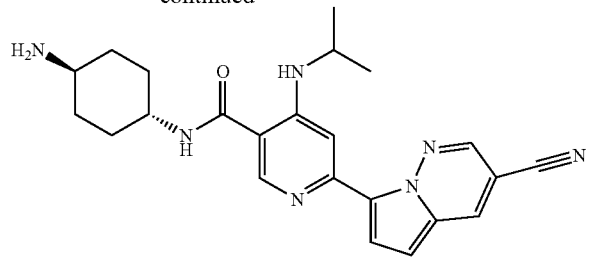

Example 12

N-((1r,4r)-4-aminocyclohexyl)-6-(3-cyanopyrrolo[1,2-b]pyridazin-7-yl)-4-(isopropylamino)nicotinamide (Example 12)

Tert-butyl ((1r,4r)-4-(6-(3-cyanopyrrolo[1,2-b]pyridazin-7-yl)-4-(isopropylamino)nicotinamido)cyclohexyl)carbamate (obtained as described in Procedure 3 substituting trans-2-(4-amino-cyclohexyl)-propan-2-ol with trans-N-Boc-1,4-cyclohexanediamine) (57.5 mg, 0.11 mmol) was taken in DCM (1.0 mL), and then trifluoroacetic acid (1.0 mL) was added. The reaction mixture was stirred at room temperature for 30 minutes, then concentrated in vacuo. The residue was taken up in DMF and purified by reverse phase high pressure liquid chromatography (eluent: water/MeCN*0.1% TFA) to provide the final compound.

ES/MS: 418.3 [M+H$^+$].

1H NMR (400 MHz, Methanol-d4) δ 8.75 (d, J=2.2 Hz, 1H), 8.66 (d, J=2.2 Hz, 1H), 8.57 (s, 1H), 8.00 (d, J=5.0 Hz, 1H), 7.86 (s, 1H), 7.21 (d, J=5.0 Hz, 1H), 4.15 (hept, J=6.2 Hz, 1H), 3.89 (d, J=9.7 Hz, 1H), 3.14 (s, 1H), 2.15 (d, J=10.2 Hz, 4H), 1.69-1.45 (m, 4H), 1.40 (d, J=6.3 Hz, 6H).

Procedure 13: Example 13

N-((1r,4r)-4-acetamidocyclohexyl)-6-(3-cyanopyrrolo[1,2-b]pyridazin-7-yl)-4-(isopropylamino)nicotinamide

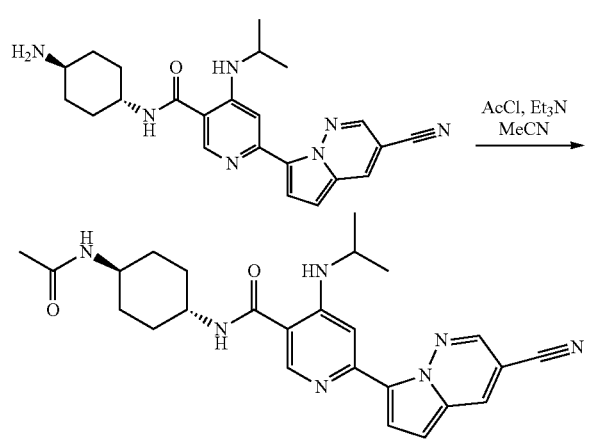

Example 13

N-((1r,4r)-4-acetamidocyclohexyl)-6-(3-cyanopyrrolo[1,2-b]pyridazin-7-yl)-4-(isopropylamino)nicotinamide N-((1r,4r)-4-aminocyclohexyl)-6-(3-cyanopyrrolo[1,2-b]pyridazin-7-yl)-4-(isopropylamino)nicotinamide (obtained as described in Procedure 12) (15.0 mg, 0.04 mmol) was taken in MeCN (1.0 mL). Triethylamine (0.015 mL, 0.11 mmol) was added followed by the rapid dropwise addition of acetyl chloride (3 μL, 0.04 mmol). The reaction mixture was stirred at room temperature for 15 minutes, then concentrated in vacuo. The residue was taken up in DMF and purified by reverse phase high pressure liquid chromatography (eluent: water/MeCN*0.1% TFA) to provide the final compound.

ES/MS: 460.3 [M+H$^+$].

1H NMR (400 MHz, Methanol-d4) δ 8.75 (d, J=2.2 Hz, 1H), 8.66 (d, J=2.2 Hz, 1H), 8.54 (s, 1H), 7.99 (d, J=5.0 Hz, 1H), 7.84 (s, 1H), 7.21 (d, J=5.0 Hz, 1H), 4.15 (hept, J=6.9, 6.4 Hz, 1H), 3.94-3.81 (m, 1H), 3.73-3.58 (m, 1H), 2.11-1.96 (m, 4H), 1.93 (s, 3H), 1.59-1.45 (m, 2H), 1.45-1.36 (m, 8H).

Procedure 14: Example 14

4-(((1R,3r,5S)-8-azabicyclo[3.2.1]octan-3-yl)amino)-6-(3-cyanopyrrolo[1,2-b]pyridazin-7-yl)-N-((R)-2-fluoro-3-hydroxy-3-methylbutyl)nicotinamide

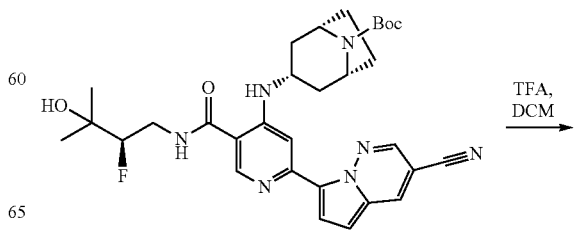

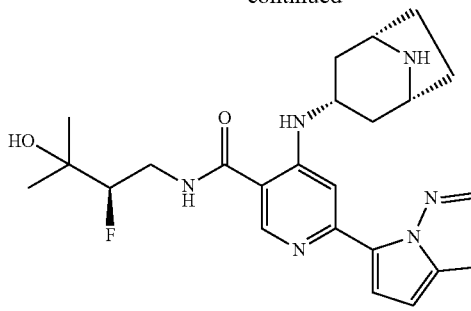

Example 14

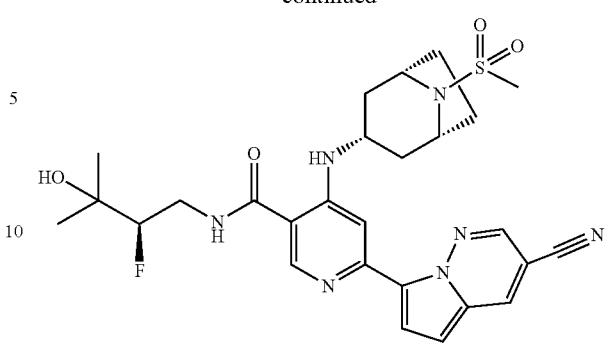

Example 15

4-(((1R,3r,5S)-8-azabicyclo[3.2.1]octan-3-yl)amino)-6-(3-cyanopyrrolo[1,2-b]pyridazin-7-yl)-N-((R)-2-fluoro-3-hydroxy-3-methylbutyl)nicotinamide (1R,3r,5S)-3-((2-(3-cyanopyrrolo[1,2-b]pyridazin-7-yl)-5-(((R)-2-fluoro-3-hydroxy-3-methylbutyl)carbamoyl)pyridin-4-yl)amino)-8-azabicyclo[3.2.1]octane-8-carboxylate (obtained as described in Procedure 2 substituting (1R,3S)-3-aminocyclohexan-1-ol with N-Boc-endo-3-aminotropane) (70.0 mg, 0.12 mmol) was taken in DCM (1.0 mL), and then trifluoroacetic acid (1.0 mL) was added. The reaction mixture was stirred at room temperature for 30 minutes, then concentrated in vacuo. The residue was taken up in DMF and purified by reverse phase high pressure liquid chromatography (eluent: water/MeCN*0.1% TFA) to provide the final compound.

ES/MS: 492.3 [M+H$^+$].

1H NMR (400 MHz, Methanol-d4) δ 8.76 (d, J=2.2 Hz, 1H), 8.70 (d, J=0.8 Hz, 1H), 8.66 (d, J=2.2 Hz, 1H), 8.02 (d, J=5.1 Hz, 1H), 7.78 (s, 1H), 7.22 (d, J=5.1 Hz, 1H), 4.43 (ddd, J=49.1, 9.3, 2.2 Hz, 1H), 4.36-4.26 (m, 1H), 4.16 (s, 2H), 3.93 (ddd, J=36.2, 14.6, 2.2 Hz, 1H), 3.64-3.49 (m, 1H), 2.62-2.50 (m, 2H), 2.47-2.37 (m, 2H), 2.33-2.19 (m, 4H), 1.30 (d, J=1.7 Hz, 6H).

Procedure 15: Example 15

6-(3-cyanopyrrolo[1,2-b]pyridazin-7-yl)-N-((R)-2-fluoro-3-hydroxy-3-methylbutyl)-4-(((1R,3r,5S)-8-(methylsulfonyl)-8-azabicyclo[3.2.1]octan-3-yl)amino)nicotinamide 4-(((1R,3r,5S)-8-azabicyclo[3.2.1]octan-3-yl)amino)-6-(3-cyanopyrrolo[1,2-b]pyridazin-7-yl)-N-((R)-2-fluoro-3-hydroxy-3-methylbutyl)nicotinamide (obtained as describe in Procedure 14) (7.0 mg, 0.014 mmol) was taken in DCM (0.5 mL). Triethylamine (9.9 µL, 0.071 mmol) was added followed by the rapid dropwise addition of mesyl chloride (1.1 µL, 0.014 mmol). The reaction mixture was stirred at room temperature for 30 minutes, then concentrated in vacuo. The residue was taken up in DMF and purified by reverse phase high pressure liquid chromatography (eluent: water/MeCN*0.1% TFA) to provide the final compound.

ES/MS: 570.2 [M+H$^+$].

1H NMR (400 MHz, Methanol-d4) δ 8.75 (d, J=2.1 Hz, 1H), 8.68 (d, J=2.2 Hz, 1H), 8.63 (s, 1H), 8.00 (d, J=5.1 Hz, 1H), 7.78 (s, 1H), 7.21 (d, J=5.1 Hz, 1H), 4.51-4.31 (m, 3H), 4.24 (t, J=6.4 Hz, 1H), 3.94 (ddd, J=36.2, 14.6, 2.2 Hz, 1H), 3.59-3.45 (m, 1H), 3.00 (s, 3H), 2.48 (dd, J=13.0, 7.7 Hz, 2H), 2.31-2.11 (m, 4H), 2.05 (d, J=14.6 Hz, 2H), 1.30 (d, J=1.7 Hz, 6H).

Procedure 16: Example 16

(R)-4-((1-acetylpiperidin-4-yl)amino)-6-(3-cyanopyrrolo[1,2-b]pyridazin-7-yl)-N-(2-fluoro-3-hydroxy-3-methylbutyl)nicotinamide

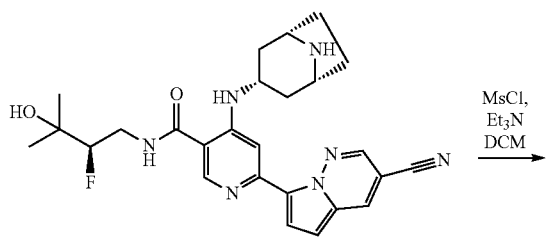

MsCl, Et$_3$N
DCM

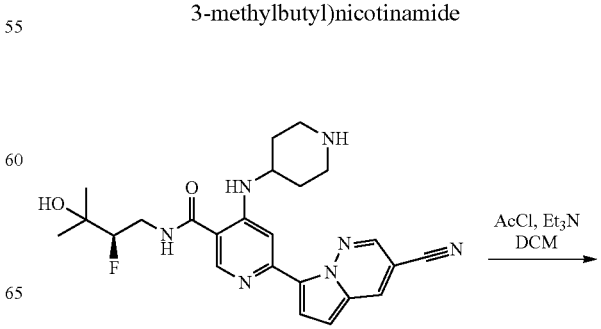

AcCl, Et$_3$N
DCM

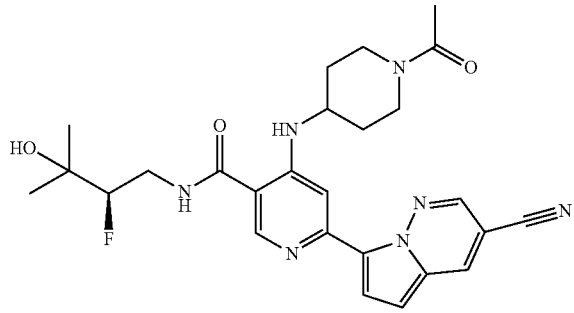

Example 16

(R)-4-((1-acetylpiperidin-4-yl)amino)-6-(3-cyanopyrrolo[1,2-b]pyridazin-7-yl)-N-(2-fluoro-3-hydroxy-3-methylbutyl)nicotinamide (R)-6-(3-cyanopyrrolo[1,2-b]pyridazin-7-yl)-N-(2-fluoro-3-hydroxy-3-methylbutyl)-4-(piperidin-4-ylamino)nicotinamide (obtained as described in Procedure 14 substituting (1R,3r,5S)-3-((2-(3-cyanopyrrolo[1,2-b]pyridazin-7-yl)-5-(((R)-2-fluoro-3-hydroxy-3-methylbutyl)carbamoyl)pyridin-4-yl)amino)-8-azabicyclo[3.2.1]octane-8-carboxylate with tert-butyl (R)-4-((2-(3-cyanopyrrolo[1,2-b]pyridazin-7-yl)-5-((2-fluoro-3-hydroxy-3-methylbutyl)carbamoyl)pyridin-4-yl)amino)piperidine-1-carboxylate) (10.0 mg, 0.02 mmol) was taken in DCM (1.0 mL). Triethylamine (0.015 mL, 0.11 mmol) was added followed by the rapid dropwise addition of acetyl chloride (1.5 µL, 0.02 mmol). The reaction mixture was stirred at room temperature for 15 minutes, then concentrated in vacuo. The residue was taken up in DMF and purified by reverse phase high pressure liquid chromatography (eluent: water/MeCN*0.1% TFA) to provide the final compound.

ES/MS: 508.3 [M+H$^+$].

1H NMR (400 MHz, Methanol-d4) δ 8.76 (d, J=2.2 Hz, 1H), 8.68 (d, J=2.2 Hz, 1H), 8.60 (s, 1H), 8.05 (d, J=5.1 Hz, 1H), 7.91 (s, 1H), 7.22 (d, J=5.1 Hz, 1H), 4.52-4.31 (m, 2H), 4.22-4.11 (m, 1H), 3.93 (dd, J=34.6, 14.4 Hz, 2H), 3.58-3.38 (m, 2H), 3.17-3.04 (m, 1H), 2.16 (s, 4H), 1.80-1.53 (m, 2H), 1.29 (d, J=1.6 Hz, 6H).

Procedure 17: Example 17

(R)-6-(3-(1H-tetrazol-5-yl)pyrrolo[1,2-b]pyridazin-7-yl)-N-(2-fluoro-3-hydroxy-3-methylbutyl)-4-(isopropylamino)nicotinamide

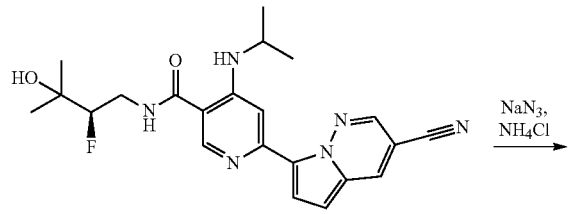

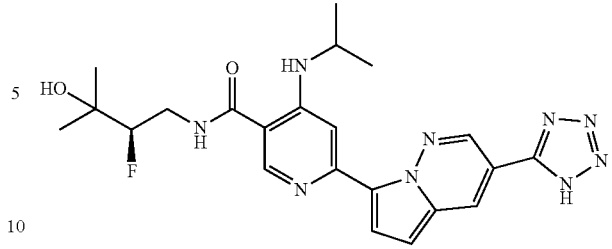

Example 17

(R)-6-(3-(1H-tetrazol-5-yl)pyrrolo[1,2-b]pyridazin-7-yl)-N-(2-fluoro-3-hydroxy-3-methylbutyl)-4-(isopropylamino)nicotinamide (Example 17)

To a solution of (R)-6-(3-cyanopyrrolo[1,2-b]pyridazin-7-yl)-N-(2-fluoro-3-hydroxy-3-methylbutyl)-4-(isopropylamino)nicotinamide (28 mg, 0.065 mmol) in 0.13 mL DMF was added ammonium chloride (4 mg, 0.08 mmol) and then sodium azide (5 mg, 0.08 mmol). The mixture was heated at 120° C. for 1 hour. The reaction was cooled to room temperature. The reaction mixture was diluted with water and methanol and purified by RP-HPLC (eluent: water/MeCN*0.1% TFA) to yield the product as a trifluoroacetate salt.

ES/MS 468.30 (M+H$^+$).

$^1$H NMR (400 MHz, Methanol-d$_4$) δ 9.13 (s, 1H), 8.81-8.75 (m, 1H), 8.53 (s, 1H), 7.97 (d, J=5.0 Hz, 1H), 7.76 (s, 1H), 7.10 (d, J=5.0 Hz, 1H), 4.43 (ddd, J=49.1, 9.4, 2.1 Hz, 1H), 4.16 (p, J=6.3 Hz, 1H), 3.93 (ddd, J=36.3, 14.6, 2.1 Hz, 1H), 3.49 (td, J=15.3, 9.3 Hz, 1H), 1.41 (d, J=6.4 Hz, 6H), 1.29 (d, J=1.6 Hz, 6H).

Procedure 18: Examples 18 (Isomer 1) and 19 (Isomer 2)

6-(3-cyanopyrrolo[1,2-b]pyridazin-7-yl)-N-(2-(hydroxymethyl)cyclopropyl)-4-(isopropylamino)nicotinamide trans, racemic mixture trans, isomer 1

-continued

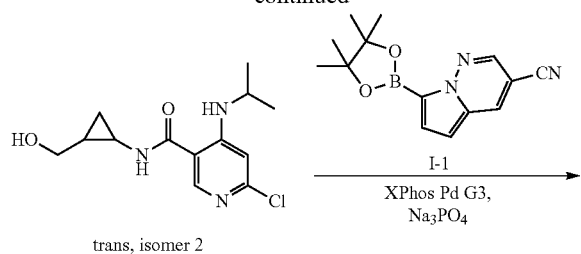

trans, isomer 2

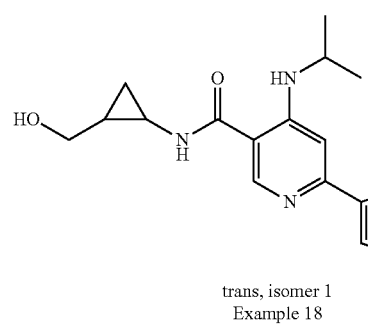

trans, isomer 1
Example 18

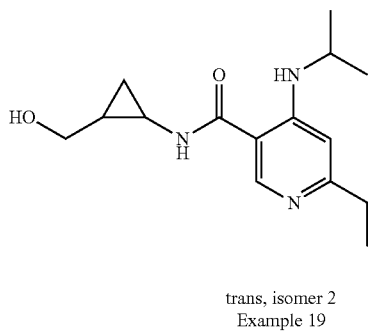

trans, isomer 2
Example 19

6-(3-cyanopyrrolo[1,2-b]pyridazin-7-yl)-N-(2-(hydroxymethyl)cyclopropyl)-4-(isopropylamino)nicotinamide Isomer 1 (Example 18) and Isomer 2 (Example 19)

trans, racemic 6-chloro-N-(2-(hydroxymethyl)cyclopropyl)-4-(isopropylamino)nicotinamide (obtained as described in Procedure 1 substituting trans, racemic (2-aminocyclopropyl)methanol for (R)-4-amino-3-fluoro-2-methylbutan-2-ol) was separated into two distinct enantiomers (trans, isomer 1 and trans, isomer 2). Each isomer was separately elaborated to final compounds (Example 18 and Example 19) as described for the final step of Procedure 1 substituting 6-chloro-N-(2-(hydroxymethyl)cyclopropyl)-4-(isopropylamino)nicotinamide for (R)-6-chloro-N-(2-fluoro-3-hydroxy-3-methylbutyl)-4-((3-methyloxetan-3-yl)amino)nicotinamide.

Example 18

ES/MS: 391.1 [M+H$^+$].

1H NMR (400 MHz, Methanol-d4) δ 8.74 (d, J=2.2 Hz, 1H), 8.65 (d, J=2.2 Hz, 1H), 8.49 (s, 1H), 7.98 (d, J=5.1 Hz, 1H), 7.84 (s, 1H), 7.20 (d, J=5.0 Hz, 1H), 4.15 (p, J=6.4 Hz, 1H), 3.54 (d, J=6.6 Hz, 2H), 2.83-2.71 (m, 1H), 1.40 (d, J=6.4 Hz, 6H), 1.38-1.26 (m, 1H), 0.94-0.79 (m, 2H).

Example 19

ES/MS: 391.2 [M+H$^+$].

1H NMR (400 MHz, Methanol-d4) δ 8.74 (d, J=2.2 Hz, 1H), 8.65 (d, J=2.1 Hz, 1H), 8.49 (s, 1H), 7.98 (d, J=5.0 Hz, 1H), 7.84 (s, 1H), 7.20 (d, J=5.1 Hz, 1H), 4.15 (p, J=6.4 Hz, 1H), 3.54 (d, J=6.6 Hz, 2H), 2.77 (dt, J=7.6, 4.0 Hz, 1H), 1.40 (d, J=6.4 Hz, 6H), 1.36-1.29 (m, 1H), 0.95-0.82 (m, 2H).

Procedure 19: Example 152

6-(3-cyanopyrrolo[1,2-b]pyridazin-7-yl)-4-(isopropylamino)-N-(6-oxospiro[3.3]heptan-2-yl)nicotinamide

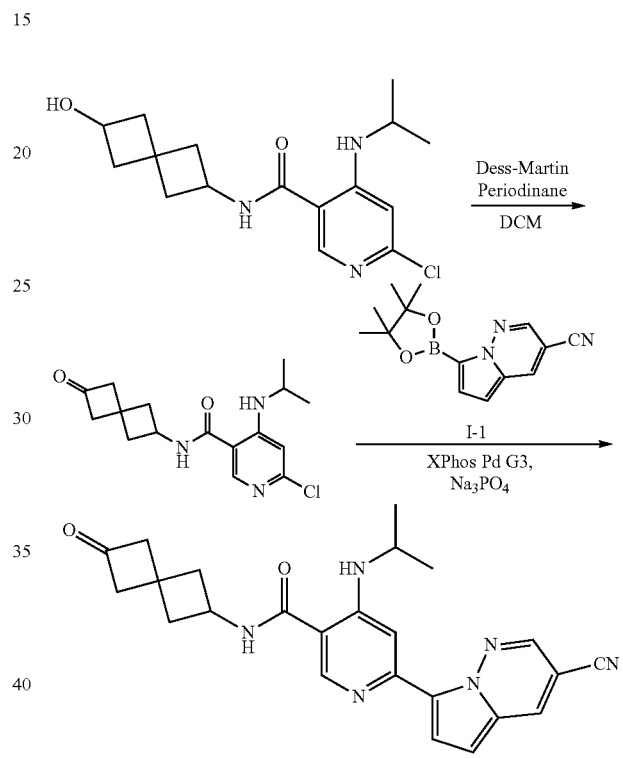

Example 152

6-chloro-4-(isopropylamino)-N-(6-oxospiro[3.3]heptan-2-yl)nicotinamide 6-chloro-N-(6-hydroxyspiro[3.3]heptan-2-yl)-4-(isopropylamino)nicotinamide (0.25 g, 0.77 mmol) was dissolved in DCM (5 mL) after which Dess-Martin periodinane (0.39 g, 0.93 mmol) was added as a single portion and the resulting mixture stirred at room temperature. After 30 minutes, the reaction mixture was poured into saturated aqueous NaHCO$_3$ solution (20 mL) and extracted twice with EtOAc (2×25 mL). The organic layers were dried over MgSO$_4$, filtered and concentrated. The resulting material was purified by silica gel chromatography (eluent: EtOAc/hexanes) to provide the desired product.

ES/MS: 322.4 [M+H$^+$].

6-(3-cyanopyrrolo[1,2-b]pyridazin-7-yl)-4-(isopropylamino)-N-(6-oxospiro[3.3]heptan-2-yl)nicotinamide (Example 152)

6-chloro-4-(isopropylamino)-N-(6-oxospiro[3.3]heptan-2-yl)nicotinamide (0.020 g, 0.062 mmol) and 7-(4,4,5,5- tetramethyl-1,3,2-dioxaborolan-2-yl)pyrrolo[1,2-b]pyridazine-3-carbonitrile (0.021 g, 0.081 mmol) were added to a microwave vial followed by DME (0.8 mL), XPhos Pd G3 (5.3 mg, 0.006 mmol) and Na$_3$PO$_4$ (0.5M in water, 0.25 mL, 0.12 mmol). The resulting mixture was purged with argon for 2 minutes, sealed and heated to 120° C. in a microwave reactor for 10 min. The reaction mixture was filtered and purified by RP-HPLC (eluent: water/MeCN*0.1% TFA). The product fraction were combined and lyophilized to give the final product.

ES/MS: 429.3 [M+H$^+$]

1H NMR (400 MHz, Methanol-d4) δ 8.75 (d, J=2.2 Hz, 1H), 8.66 (dd, J=2.2, 0.4 Hz, 1H), 8.57 (s, 1H), 7.99 (dd, J=5.0, 0.5 Hz, 1H), 7.84 (s, 1H), 7.21 (d, J=5.2 Hz, 1H), 4.59-4.43 (m, 1H), 4.22-4.08 (m, 1H), 3.25-3.18 (m, 2H), 3.15-3.07 (m, 2H), 2.66 (ddd, J=9.3, 7.7, 2.8 Hz, 2H), 2.47-2.36 (m, 2H), 1.40 (d, J=6.4 Hz, 6H).

Procedure 20: Example 153

6-(3-cyanopyrrolo[1,2-b]pyridazin-7-yl)-N-(6-hydroxy-6-methylspiro[3.3]heptan-2-yl)-4-(isopropylamino)nicotinamide

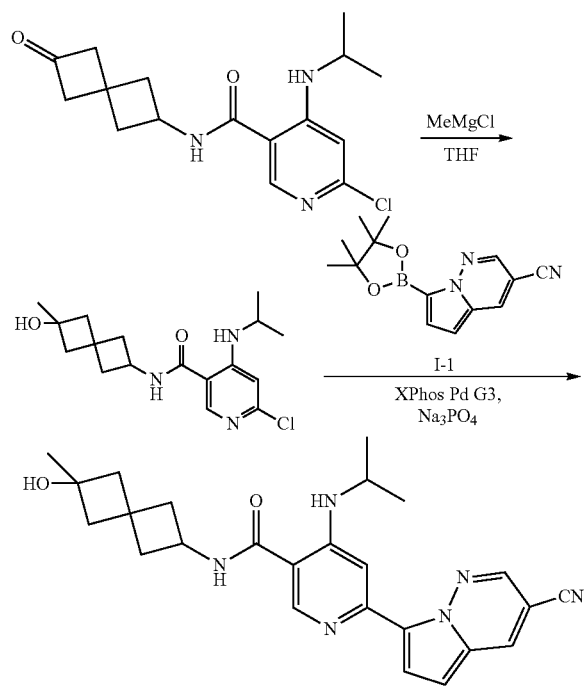

Example 153

6-chloro-N-(6-hydroxy-6-methylspiro[3.3]heptan-2-yl)-4-(isopropylamino)nicotinamide 6-chloro-4-(isopropylamino)-N-(6-oxospiro[3.3]heptan-2-yl)nicotinamide (0.10 g, 0.31 mmol) was dissolved in THF (5 mL) and brought to 0° C. using an ice/water bath. MeMgCl (3.0M in THF, 0.36 mL, 1.1 mmol) was then added dropwise at 0° C. After 30 minutes, the reaction mixture was carefully quenched with water (1 mL) allowed to warm to room temperature and poured into water (10 mL). The resulting mixture was extracted with EtOAc (2×25 mL) and the combined organics dried over MgSO$_4$, filtered and concentrated. The resulting material was purified by silica gel chromatography (eluent: EtOAc/hexanes) to provide the desired product.

ES/MS: 338.5 [M+H$^+$]

6-(3-cyanopyrrolo[1,2-b]pyridazin-7-yl)-N-(6-hydroxy-6-methylspiro[3.3]heptan-2-yl)-4-(isopropylamino)nicotinamide (Example 153)

6-chloro-N-(6-hydroxy-6-methylspiro[3.3]heptan-2-yl)-4-(isopropylamino)nicotinamide (0.020 g, 0.059 mmol) and 7-(4,4,5,5-tetramethyl-1,3,2-dioxaborolan-2-yl)pyrrolo[1,2-b]pyridazine-3-carbonitrile (0.021 g, 0.77 mmol) were added to a microwave vial followed by DME (0.8 mL), XPhos Pd G3 (5.0 mg, 0.006 mmol) and Na$_3$PO$_4$ (0.5M in water, 0.24 mL, 0.12 mmol). The resulting mixture was purged with argon for 2 minutes, sealed and heated to 120° C. in a microwave reactor for 10 min. The reaction mixture was filtered and purified by RP-HPLC (eluent: water/MeCN*0.1% TFA). The product fraction were combined and lyophilized to give the final product.

ES/MS: 445.3 [M+H$^+$]

1H NMR (400 MHz, Methanol-d4) δ 8.74 (d, J=2.1 Hz, 1H), 8.69-8.59 (m, 1H), 8.54 (s, 1H), 8.04-7.91 (m, 1H), 7.82 (s, 1H), 7.20 (d, J=5.1 Hz, 1H), 4.36 (p, J=8.2 Hz, 1H), 4.13 (p, J=6.4 Hz, 1H), 2.52 (ddd, J=11.8, 7.4, 5.0 Hz, 1H), 2.47-2.37 (m, 1H), 2.31-1.97 (m, 6H), 1.39 (d, J=6.4 Hz, 6H), 1.31 (s, 3H).

Procedure 21: Example 146

(R)-6-(3-cyanopyrrolo[1,2-b]pyridazin-7-yl)-N-(2-fluoro-3-hydroxy-3-methylbutyl)-4-((5-methyl-1,3,4-thiadiazol-2-yl)amino)nicotinamide

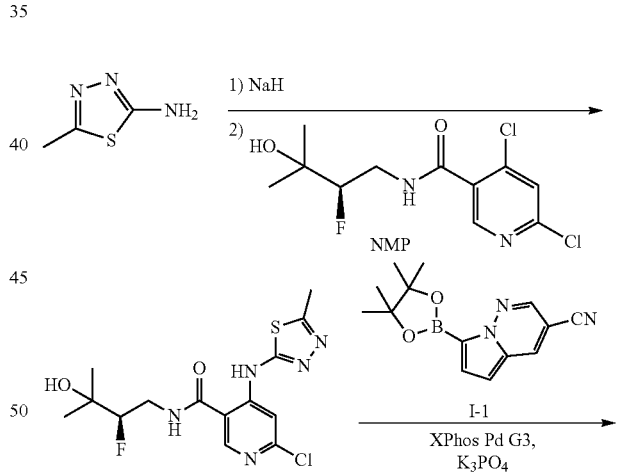

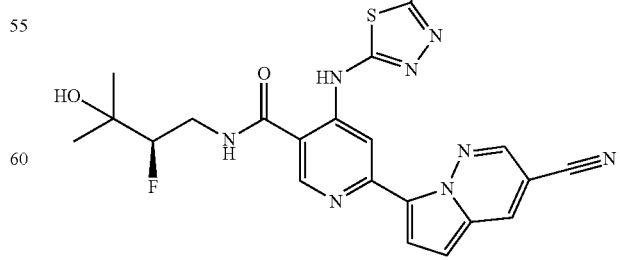

Example 146

(R)-6-chloro-N-(2-fluoro-3-hydroxy-3-methylbutyl)-4-((5-methyl-1,3,4-thiadiazol-2-yl)amino)nicotinamide To a stirring solution of 2-Amino-5-methyl-1,3,4-thiadiazole (0.03 g, 0.27 mmol) in 1-methylpyrrolidin-2-one (0.4 mL) was added Sodium hydride (60% dispersion in mineral oil, 0.01 g, 0.27 mmol) at room temperature. (R)-4,6-dichloro-N-(2-fluoro-3-hydroxy-3-methylbutyl)nicotinamide (0.05 g, 0.17 mmol) was diluted in 1-methylpyrrolidin-2-one (0.4 mL) and was added to the deprotonated amine solution. The mixture was stirred at room temperature for several hours. The crude reaction mixture was filtered through a plug of silica gel (eluent: ethyl acetate), concentrated, and further purified by RP-HPLC (eluent: water/MeCN*0.1% TFA). The combined product fractions were basified with sodium bicarbonate solution (aq), and extracted with ethyl acetate (3x). The combined organic layers were dried over sodium sulfate, filtered and concentrated to give the desired product.

ES/MS: 374.1 (M+H⁺).

(R)-6-(3-cyanopyrrolo[1,2-b]pyridazin-7-yl)-N-(2-fluoro-3-hydroxy-3-methylbutyl)-4-((5-methyl-1,3,4-thiadiazol-2-yl)amino)nicotinamide (Example 146)

(R)-6-chloro-N-(2-fluoro-3-hydroxy-3-methylbutyl)-4-((5-methyl-1,3,4-thiadiazol-2-yl)amino)nicotinamide (0.02 g, 0.06 mmol) and 7-(4,4,5,5-tetramethyl-1,3,2-dioxaborolan-2-yl)pyrrolo[1,2-b]pyridazine-3-carbonitrile (0.02 g, 0.08 mmol) were added to a microwave vial followed by DME (0.3 mL), XPhos Pd G3 (0.005 g, 0.006 mmol) and K₃PO₄ (2M in water, 0.058 mL, 0.116 mmol). The resulting mixture was purged with argon for 2 minutes, sealed and heated to 120° C. in a microwave reactor for 15 min. The reaction mixture was filtered and purified by RP-HPLC (eluent: water/MeCN*0.1% TFA). The product fractions were combined and lyophilized to give the final product as a TFA salt.

ES/MS: 481.1 (M+H⁺).

1H NMR (400 MHz, DMSO-d6) δ 12.06 (s, 1H), 9.42 (d, J=22.2 Hz, 1H), 9.19 (s, 1H), 8.97 (s, 1H), 8.87 (d, J=2.3 Hz, 1H), 8.80 (s, 1H), 7.89 (d, J=4.8 Hz, 1H), 7.13 (d, J=4.7 Hz, 1H), 2.69 (s, 3H), 1.17 (d, J=6.3 Hz, 6H), 1.12 (d, J=1.8 Hz, 3H).

Alternatively, the final step can be carried as a tandem borylation of 7-bromopyrrolo[1,2-b]pyridazine-3-carbonitrile (I-1F) following by a terminating Suzuki coupling as described above in Procedure 1.

Procedure 22: Example 134

6-(3-cyanopyrrolo[1,2-b]pyridazin-7-yl)-4-(isopropylamino)-N-((1r,4r)-4-(3-methyloxetane-3-carboxamido)cyclohexyl)nicotinamide

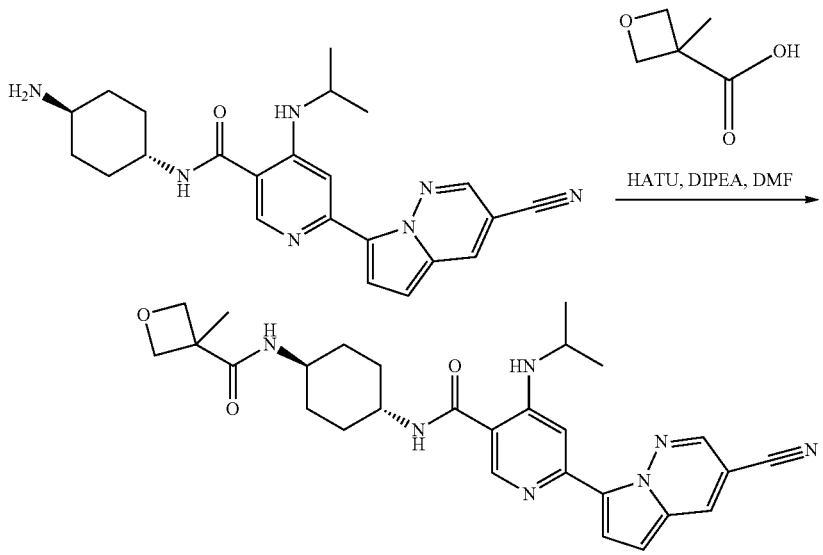

Example 134

6-(3-cyanopyrrolo[1,2-b]pyridazin-7-yl)-4-(isopropylamino)-N-((1r,4r)-4-(3-methyloxetane-3-carboxamido)cyclohexyl)nicotinamide (Example 134)

3-methyloxetane-3-carboxylic acid (7.2 mg, 0.062 mmol) and HATU (24.9 mg, 0.065 mmol) were taken in DMF (0.5 mL). DIPEA (16.7 μL, 0.093 mmol) was added, and the mixture was stirred at room temperature for 5 minutes. After 5 minutes, a solution of N-((1r,4r)-4-aminocyclohexyl)-6-(3-cyanopyrrolo[1,2-b]pyridazin-7-yl)-4-(isopropylamino)nicotinamide (obtained as described in Procedure 12) (13.0 mg, 0.031 mmol) in DMF (0.5 mL) and DIPEA (22.2 μL, 0.13 mmol) was added rapidly dropwise. The reaction mixture was stirred at room temperature for 15 minutes then filtered and purified by reverse phase high pressure liquid chromatography (eluent: water/MeCN*0.1% TFA) to provide the final compound.

ES/MS: 516.3 [M+H⁺].

1H NMR (400 MHz, Methanol-d4) δ 8.75 (d, J=2.2 Hz, 1H), 8.66 (d, J=2.2 Hz, 1H), 8.55 (s, 1H), 7.99 (d, J=5.1 Hz, 1H), 7.84 (s, 1H), 7.21 (d, J=5.1 Hz, 1H), 4.91-4.85 (m, 2H), 4.39 (d, J=6.1 Hz, 2H), 4.22-4.10 (m, 1H), 3.94-3.81 (m, 1H), 3.79-3.67 (m, 2H), 2.13-1.93 (m, 4H), 1.59 (s, 3H), 1.55-1.38 (m, 9H).

Procedure 23: Example 122

6-(3-cyanopyrrolo[1,2-b]pyridazin-7-yl)-N-((3-hydroxy-1,1-dioxidotetrahydrothiophen-3-yl)methyl)-4-(isopropylamino)nicotinamide

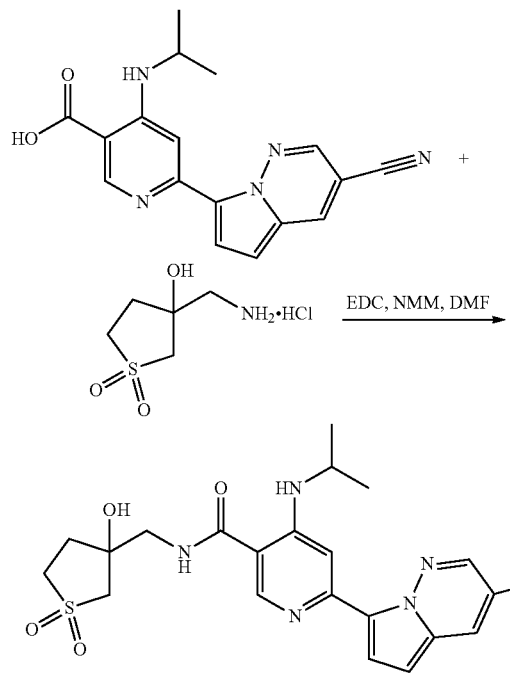

Example 122

6-(3-cyanopyrrolo[1,2-b]pyridazin-7-yl)-N-((3-hydroxy-1,1-dioxidotetrahydrothiophen-3-yl)methyl)-4-(isopropylamino)nicotinamide (Example 122)

To a mixture of 6-(3-cyanopyrrolo[1,2-b]pyridazin-7-yl)-4-(isopropylamino)nicotinic acid (10.0 mg, 0.031 mmol) (obtained as described in Procedure 3), 3-(aminomethyl)-3-hydroxytetrahydrothiophene 1,1-dioxide hydrochloride (6.0 mg, 0.04 mmol),1-(3-dimethylaminopropyl)-3-ethylcarbodiimide hydrochloride (7.5 mg, 0.039 mmol) and 1-hydroxybenzotriazole (0.4 mg, 0.003 mmol) was added DMF (0.5 mL), then N-Methylmorpholine (8 μL, 0.072 mmol). The reaction mixture was stirred at room temperature for overnight. The reaction was filtered and directly purified by reverse phase high pressure liquid chromatography (eluent: water/MeCN*0.1% TFA) to provide the final compound.

ES/MS: 469.13 [M+H$^+$].

$^1$H NMR (400 MHz, Methanol-d4) δ 8.74 (d, J=2.2 Hz, 1H), 8.66 (d, J=2.2 Hz, 1H), 8.60 (s, 1H), 7.99 (d, J=5.1 Hz, 1H), 7.86 (s, 1H), 7.21 (d, J=5.1 Hz, 1H), 4.15 (p, J=6.4 Hz, 1H), 3.63 (s, 2H), 3.50-3.09 (m, 4H), 2.46-2.19 (m, 2H), 1.40 (d, J=6.4 Hz, 6H)

Procedure 24: Example 140

(R)-4-((4-cyanophenyl)amino)-6-(3-cyanopyrrolo[1,2-b]pyridazin-7-yl)-N-(2-fluoro-3-hydroxy-3-methylbutyl)nicotinamide

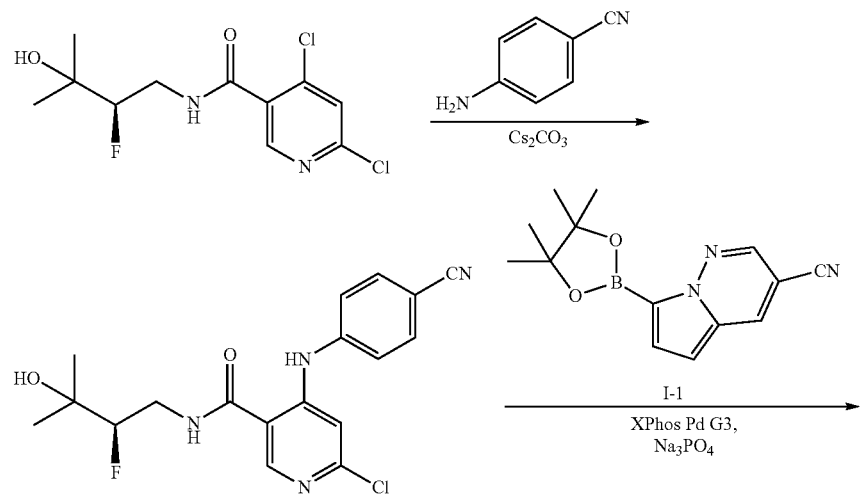

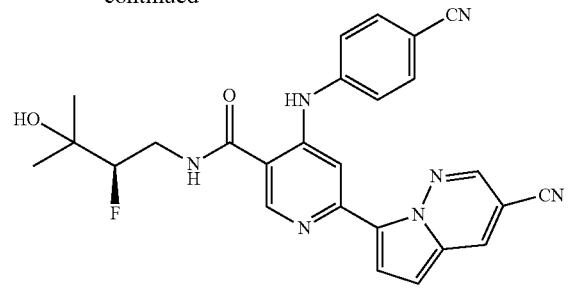

Example 140

(R)-6-chloro-4-((4-cyanophenyl)amino)-N-(2-fluoro-3-hydroxy-3-methylbutyl)nicotinamide To a mixture of (R)-4,6-dichloro-N-(2-fluoro-3-hydroxy-3-methylbutyl)nicotinamide (150 mg, 0.5 mmol), p-Aminobenzonitrile (90 mg, 0.76 mmol) and Cesium carbonate (331 mg, 1.0 mmol) was added 1.5 mL of DMF. The reaction mixture was stirred at 90° C. for 5 h and cooled to room temperature. The reaction mixture was partitioned between EtOAc and water. The organic layer was separated, washed with brine, dried over $Na_2SO_4$. Filtered and concentrated. The crude was purified by reverse phase high pressure liquid chromatography (eluent: water/MeCN*0.1% TFA) to provide the title compound.

ES/MS: 377.16 [M+H$^+$].

(R)-4-((4-cyanophenyl)amino)-6-(3-cyanopyrrolo[1,2-b]pyridazin-7-yl)-N-(2-fluoro-3-hydroxy-3-methylbutyl)nicotinamide (Example 140)

(R)-4-((4-cyanophenyl)amino)-6-(3-cyanopyrrolo[1,2-b]pyridazin-7-yl)-N-(2-fluoro-3-hydroxy-3-methylbutyl)nicotinamide was synthesized in an identical manner as described in the final step for Procedure 1 substituting (R)-6-chloro-4-((4-cyanophenyl)amino)-N-(2-fluoro-3-hydroxy-3-methylbutyl)nicotinamide for (R)-6-chloro-N-(2-fluoro-3-hydroxy-3-methylbutyl)-4-((3-methyloxetan-3-yl)amino)nicotinamide.

ES/MS: 484.17 [M+H$^+$].

1H NMR (400 MHz, Methanol-d4) δ 8.76 (d, J=9.6 Hz, 2H), 8.51 (dd, J=21.6, 2.2 Hz, 2H), 7.96-7.68 (m, 3H), 7.61-7.37 (m, 2H), 7.06 (d, J=4.8 Hz, 1H), 4.45 (ddd, J=49.0, 9.1, 2.2 Hz, 1H), 3.93 (ddd, J=35.8, 14.5, 2.3 Hz, 1H), 3.65-3.41 (m, 1H), 1.29 (d, J=1.7 Hz, 6H).

Procedure 25: Example 245

6-(3-cyanopyrrolo[1,2-b]pyridazin-7-yl)-N-((R)-2-fluoro-3-hydroxy-3-methylbutyl)-4-(((3aR,5s,6aS)-2-methyloctahydrocyclopenta[c]pyrrol-5-yl)amino)nicotinamide

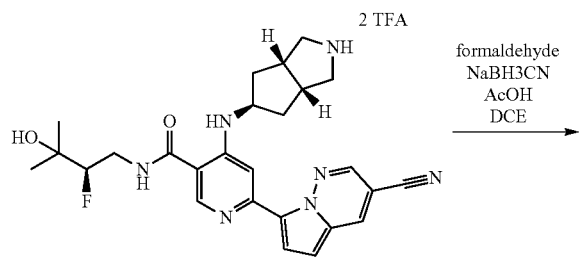

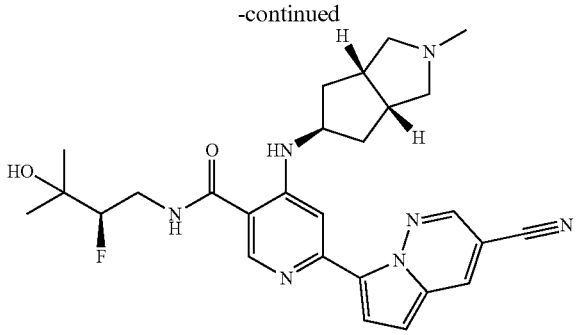

Example 245

6-(3-cyanopyrrolo[1,2-b]pyridazin-7-yl)-N-((R)-2-fluoro-3-hydroxy-3-methylbutyl)-4-(((3aR,5s,6aS)-2-methyloctahydrocyclopenta[c]pyrrol-5-yl)amino)nicotinamide 6-(3-cyanopyrrolo[1,2-b]pyridazin-7-yl)-N-((R)-2-fluoro-3-hydroxy-3-methylbutyl)-4-(((3aR,5s,6aS)-octahydrocyclopenta[c]pyrrol-5-yl)amino)nicotinamide bis(2,2,2-trifluoroacetate) (30.5 mg, 0.042 mmol) was taken in DCE (3.0 mL), and then formaldehyde solution (0.040 ml, 0.402 mmol) and acetic acid (5 drops) were added. The reaction mixture was stirred for 1 hour. Sodium cyanoborohydride (9.18 mg, 0.145 mmol) was added and the reaction was stirred for 2 hours. The reaction mixture was diluted with EtOAc and washed with brine. The aqueous was extracted with EtOAc. The combined organic extracts were dried over sodium sulfate and purified by reverse phase high pressure liquid chromatography (eluent: water/MeCN*0.1% TFA) to provide the final compound.

ES/MS: 506.3 (M+H$^+$).

1H NMR (400 MHz, Methanol-d4) δ 8.76 (s, 1H), 8.67 (s, 1H), 8.62 (s, 1H), 8.01 (d, J=5.1 Hz, 1H), 7.88 (s, 1H), 7.22 (d, J=5.0 Hz, 1H), 4.41 (ddd, J=49.3, 9.4, 2.0 Hz, 1H), 4.01-3.83 (m, 2H), 3.64-3.44 (m, 3H), 3.16-3.07 (m, OH), 2.97 (d, J=10.7 Hz, 6H), 2.25 (s, 2H), 2.02 (t, J=18.2 Hz, 2H), 1.28 (d, J=1.6 Hz, 6H).

Procedure 26: Example 206

6-(3-cyanopyrrolo[1,2-b]pyridazin-7-yl)-N-((R)-2-fluoro-3-hydroxy-3-methylbutyl)-4-((1-((R)-1-(oxetan-3-yl)pyrrolidin-3-yl)-1H-pyrazol-4-yl)amino)nicotinamide

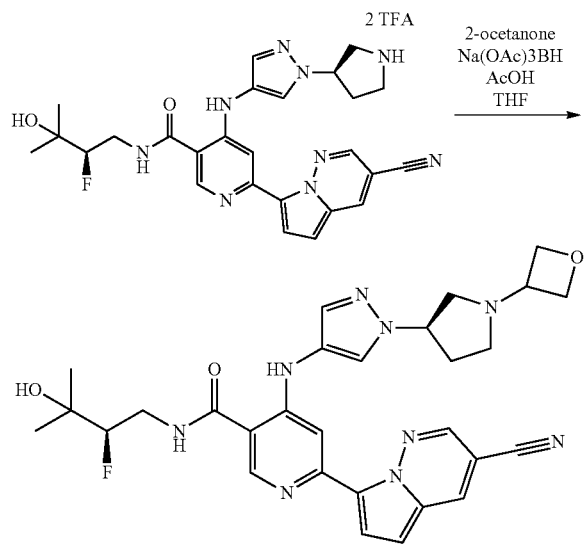

Example 206

6-(3-cyanopyrrolo[1,2-b]pyridazin-7-yl)-N-((R)-2-fluoro-3-hydroxy-3-methylbutyl)-4-((1-((R)-1-(oxetan-3-yl)pyrrolidin-3-yl)-1H-pyrazol-4-yl)amino)nicotinamide To a solution of 6-(3-cyanopyrrolo[1,2-b]pyridazin-7-yl)-N-((R)-2-fluoro-3-hydroxy-3-methylbutyl)-4-((1-((R)-pyrrolidin-3-yl)-1H-pyrazol-4-yl)amino)nicotinamide (41.1 mg, 0.06 mmol) and oxetanone (0.02 ml, 0.341 mmol) in DCM (2 mL) and THF (2 mL), was added AcOH (5 drops). After 5 hr, added sodium triacetoxyborohydride (22 mg, 0.104 mmol). The reaction was stirred overnight. The reaction mixture was diluted with DCM and washed with 1N NaOH. The organic extract was dried over sodium sulfate and purified by reverse phase high pressure liquid chromatography (eluent: water/MeCN*0.1% TFA) to provide the final compound.

ES/MS: 574.3 (M+H$^+$).

1H NMR (400 MHz, Methanol-d4) δ 8.72 (d, J=2.2 Hz, 1H), 8.70 (s, 1H), 8.59 (d, J=2.2 Hz, 1H), 8.14-8.05 (m, 2H), 7.85 (d, J=5.1 Hz, 1H), 7.83 (s, 1H), 7.18 (d, J=5.1 Hz, 1H), 5.39 (s, 1H), 4.96 (td, J=7.7, 3.2 Hz, 2H), 4.83-4.72 (m, 2H), 4.70 (d, J=6.0 Hz, 1H), 4.45 (ddd, J=49.1, 9.3, 2.1 Hz, 1H), 4.10-3.70 (m, 3H), 3.66-3.42 (m, 1H), 2.73 (dd, J=14.7, 7.7 Hz, 1H), 2.61-2.45 (m, 1H), 1.29 (d, J=1.6 Hz, 6H).

Procedure 27: Example 226

(R)-6-(3-cyanopyrrolo[1,2-b]pyridazin-7-yl)-4-((5-(difluoromethyl)pyridin-3-yl)amino)-N-(2-fluoro-3-hydroxy-3-methylbutyl)nicotinamide

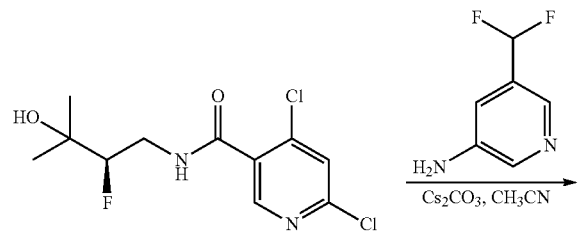

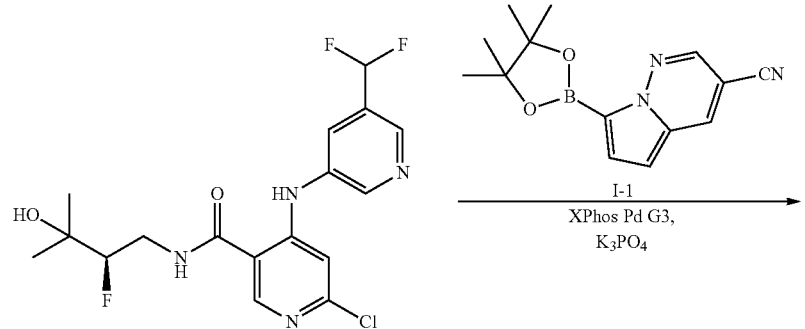

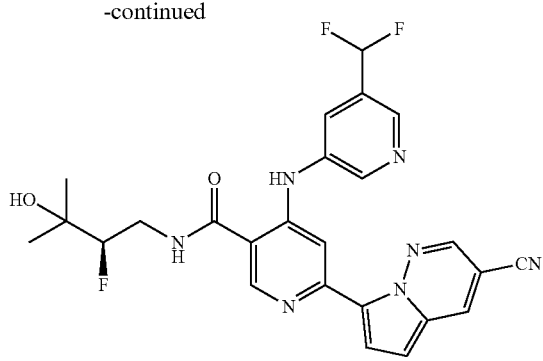

Example 226

(R)-6-chloro-4-((5-(difluoromethyl)pyridin-3-yl)amino)-N-(2-fluoro-3-hydroxy-3-methylbutyl)nicotinamide R)-4,6-dichloro-N-(2-fluoro-3-hydroxy-3-methylbutyl) nicotinamide (0.050 g, 0.169 mmol) and 5-(difluoromethyl) pyridin-3-amine (0.046 mg, 0.315 mmol) were added to a vial followed by MeCN (1 mL) and Cs$_2$CO$_3$ (0.11 g, 0.339 mmol). The resulting solution was heated to 90° C. overnight The reaction mixture was then poured into water and extracted with EtOAc. The organic layer was dried, filtered and concentrated with the resulting crude residue then purified via silica gel chromatography (eluent: EtOAc/hexanes/MeOH) to give the desired product.

ES/MS: 403.1 (M$^+$).

(R)-6-(3-cyanopyrrolo[1,2-b]pyridazin-7-yl)-4-((5-(difluoromethyl)pyridin-3-yl)amino)-N-(2-fluoro-3-hydroxy-3-methylbutyl)nicotinamide (R)-6-chloro-4-((5-(difluoromethyl)pyridin-3-yl)amino)-N-(2-fluoro-3-hydroxy-3-methylbutyl)nicotinamide (0.020 g, 0.05 mmol) and 7-(4,4,5,5-tetramethyl-1,3,2-dioxaborolan-2-yl)pyrrolo[1,2-b]pyridazine-3-carbonitrile (0.027 g, 0.099 mmol) were added to a microwave vial followed by DME (1.5 mL), XPhos Pd G3 (5.8 mg, 0.007 mmol) and K$_3$PO$_4$ (0.5M in water, 0.25 mL, 0.125 mmol). The resulting mixture was purged with argon for 2 minutes, sealed and heated to 120° C. in a microwave reactor for 10 min. The reaction mixture was filtered and purified by RP-HPLC (eluent: water/MeCN*0.1% TFA). The product fractions were combined and lyophilized to give the final product as a TFA salt.

ES/MS: 510.2 (M+H$^+$).

1H NMR (400 MHz, Methanol-d4) δ 8.91-8.84 (m, 1H), 8.78 (s, 2H), 8.71 (d, J=2.2 Hz, 1H), 8.52 (d, J=2.2 Hz, 1H), 8.26 (s, 1H), 8.22 (s, 1H), 7.86 (d, J=5.0 Hz, 1H), 7.17 (d, J=5.1 Hz, 1H), 7.06 (t, J=55.2 Hz, 1H), 4.47 (ddd, J=49.0, 9.3, 2.1 Hz, 1H), 4.00 (ddd, J=36.5, 14.6, 2.1 Hz, 1H), 3.54 (ddd, J=16.2, 14.6, 9.3 Hz, 1H), 1.30 (d, J=1.6 Hz, 6H).

Procedure 28: Example 316

4-(((1r,4R)-4-aminocyclohexyl)amino)-6-(3-cyanopyrrolo[1,2-b]pyridazin-7-yl)-N-((R)-2-fluoro-3-hydroxy-3-methylbutyl)nicotinamide hydrochloride

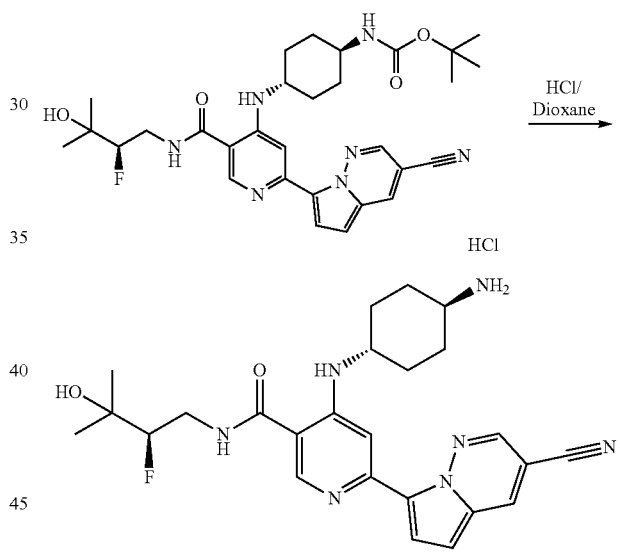

Example 316

4-(((1r,4R)-4-aminocyclohexyl)amino)-6-(3-cyanopyrrolo[1,2-b]pyridazin-7-yl)-N-((R)-2-fluoro-3-hydroxy-3-methylbutyl)nicotinamide hydrochloride To tert-butyl ((1R,4r)-4-((2-(3-cyanopyrrolo[1,2-b]pyridazin-7-yl)-5-(((R)-2-fluoro-3-hydroxy-3-methylbutyl)carbamoyl)pyridin-4-yl)amino)cyclohexyl)carbamate (obtained as described in Procedure 2 substituting (1R,3S)-3-aminocyclohexan-1-ol with trans-N-Boc-1,4-cyclohexanediamine) (493.8 mg, 0.85 mmol) was added HCl (4M in 1,4-Dioxane, 3.0 mL). The reaction mixture was stirred at 40° C. for 15 minutes. Upon completion, the reaction was concentrated in vacuo. The residue was triturated with diethylether for 1 hour, and the resulting solid was isolated by vacuum filtration to provide the desired product. Material for subsequent reactions was used without additional purification. Material for biological testing was purified by reverse phase high pressure liquid chromatography (eluent: water/MeCN*0.1% TFA) to provide the final compound.

ES/MS: 480.3 [M+H⁺].

1H NMR (400 MHz, Methanol-d4) δ 8.76 (d, J=2.2 Hz, 1H), 8.64 (d, J=2.2 Hz, 1H), 8.60 (s, 1H), 8.03 (d, J=5.0 Hz, 1H), 7.87 (s, 1H), 7.22 (d, J=5.1 Hz, 1H), 4.42 (ddd, J=49.0, 9.3, 2.1 Hz, 1H), 4.02-3.81 (m, 2H), 3.50 (ddd, J=16.1, 14.5, 9.4 Hz, 1H), 3.23 (tt, J=11.4, 3.6 Hz, 1H), 2.34-2.25 (m, 2H), 2.24-2.14 (m, 2H), 1.79-1.54 (m, 4H), 1.29 (d, J=1.7 Hz, 6H).

Procedure 29: Example 326

4-(((1r,4R)-4-acetamidocyclohexyl)amino)-6-(3-cyanopyrrolo[1,2-b]pyridazin-7-yl)-N-((R)-2-fluoro-3-hydroxy-3-methylbutyl)nicotinamide

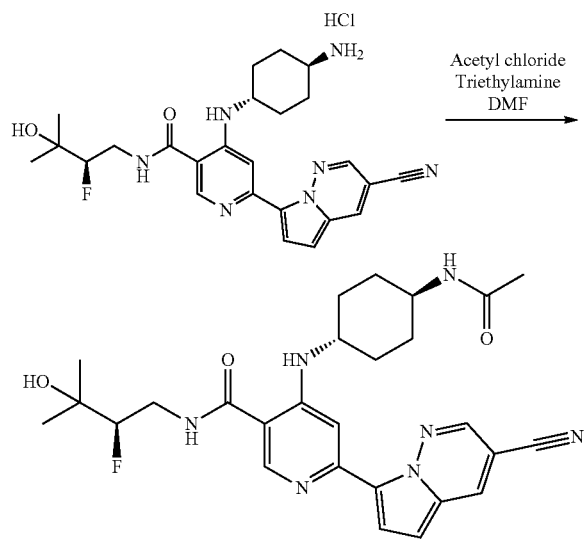

Example 326

4-(((1r,4R)-4-acetamidocyclohexyl)amino)-6-(3-cyanopyrrolo[1,2-b]pyridazin-7-yl)-N-((R)-2-fluoro-3-hydroxy-3-methylbutyl)nicotinamide To a solution of crude 4-(((r,4R)-4-aminocyclohexyl)amino)-6-(3-cyanopyrrolo[,2-b]pyridazin-7-yl)-N-((R)-2-fluoro-3-hydroxy-3-methylbutyl)nicotinamide hydrochloride (obtained as described in Procedure 28) (30.0 mg, 0.063 mmol) in DMF (1.0 mL) was added triethylamine (52.3 μL, 0.38 mmol) followed by acetyl chloride (35.7 μL. 0.50 mmol). The reaction mixture was stirred at room temperature for 15 minutes, then filtered and directly purified by reverse phase high pressure liquid chromatography (eluent: water/MeCN*0.1% TFA) to provide the final compound.

ES/MS: 522.3 [M+H⁺].

1H NMR (400 MHz, Methanol-d4) δ 8.99 (t, J=5.4 Hz, 1H), 8.75 (d, J=2.2 Hz, 1H), 8.64 (d, J=2.1 Hz, 1H), 8.57 (s, 1H), 8.02 (d, J=5.1 Hz, 1H), 7.86 (s, 1H), 7.22 (d, J=5.1 Hz, 1H), 4.42 (ddd, J=49.0, 9.3, 2.0 Hz, 1H), 4.04-3.80 (m, 2H), 3.79-3.67 (m, 1H), 3.57-3.41 (m, 1H), 2.22 (d, J=11.2 Hz, 2H), 2.05 (d, J=11.7 Hz, 2H), 1.95 (s, 3H), 1.65-1.45 (m, 4H), 1.29 (d, J=1.6 Hz, 6H).

Procedure 30: Example 315

6-(3-cyanopyrrolo[1,2-b]pyridazin-7-yl)-N-((R)-2-fluoro-3-hydroxy-3-methylbutyl)-4-(((1r,4R)-4-(methylsulfonamido)cyclohexyl)amino)nicotinamide

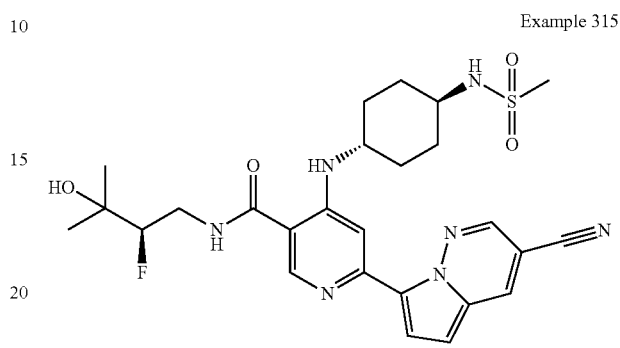

Example 315

6-(3-cyanopyrrolo[1,2-b]pyridazin-7-yl)-N-((R)-2-fluoro-3-hydroxy-3-methylbutyl)-4-(((1r,4R)-4-(methylsulfonamido)cyclohexyl)amino)nicotinamide 6-(3-cyanopyrrolo[1,2-b]pyridazin-7-yl)-N-((R)-2-fluoro-3-hydroxy-3-methylbutyl)-4-(((1r,4R)-4-(methylsulfonamido)cyclohexyl)amino)nicotinamide was prepared as described in Procedure 29 substituting acetyl chloride with methansulfonyl chloride.

ES/MS: 558.2 [M+H⁺].

1H NMR (400 MHz, Methanol-d4) δ 8.76 (d, J=2.2 Hz, 1H), 8.66 (d, J=2.2 Hz, 1H), 8.57 (s, 1H), 8.02 (d, J=5.1 Hz, 1H), 7.87 (s, 1H), 7.22 (d, J=5.1 Hz, 1H), 4.42 (dd, J=49.0, 7.6 Hz, 1H), 4.02-3.79 (m, 2H), 3.58-3.41 (m, 2H), 2.99 (s, 3H), 2.30-2.09 (m, 4H), 1.68-1.48 (m, 4H), 1.29 (d, J=1.6 Hz, 6H).

Procedure 31: Example 286

6-(3-cyanopyrrolo[1,2-b]pyridazin-7-yl)-4-(((1r,4R)-4-(3,3-dimethylureido)cyclohexyl)amino)-N-((R)-2-fluoro-3-hydroxy-3-methylbutyl)nicotinamide

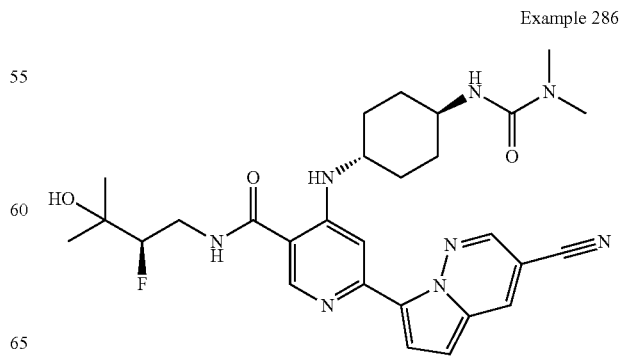

Example 286

6-(3-cyanopyrrolo[1,2-b]pyridazin-7-yl)-4-(((1r,4R)-4-(3,3-dimethylureido)cyclohexyl)amino)-N-((R)-2-fluoro-3-hydroxy-3-methylbutyl)nicotinamide 6-(3-cyanopyrrolo[1,2-b]pyridazin-7-yl)-4-(((1r,4R)-4-(3,3-dimethylureido)cyclohexyl)amino)-N-((R)-2-fluoro-3-hydroxy-3-methylbutyl)nicotinamide was prepared as described in Procedure 29 substituting acetyl chloride with dimethylcarbamoyl chloride.

ES/MS: 551.3 [M+H$^+$].

1H NMR (400 MHz, Methanol-d4) δ 8.76 (d, J=2.2 Hz, 1H), 8.65 (d, J=2.2 Hz, 1H), 8.56 (s, 1H), 7.99 (d, J=5.1 Hz, 1H), 7.90 (s, 1H), 7.22 (d, J=5.1 Hz, 1H), 4.43 (ddd, J=49.1, 9.2, 2.1 Hz, 1H), 4.04-3.86 (m, 1H), 3.86-3.75 (m, 1H), 3.69-3.57 (m, 1H), 3.55-3.41 (m, 1H), 2.91 (s, 6H), 2.33-2.16 (m, 2H), 2.12-2.00 (m, 2H), 1.64-1.47 (m, 4H), 1.29 (d, J=1.6 Hz, 6H).

Procedure 32: Example 285

6-(3-cyanopyrrolo[1,2-b]pyridazin-7-yl)-4-(((1r,4R)-4-((N,N-dimethylsulfamoyl)amino)cyclohexyl)amino)-N-((R)-2-fluoro-3-hydroxy-3-methylbutyl)nicotinamide

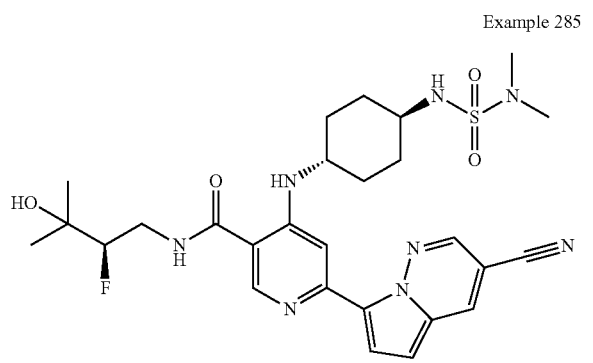 [SMILES: CN(C)S(=O)(=O)N[C@H]1CC[C@H](Nc2cc(-c3ccc4cc(C#N)cnn34)ncc2C(=O)NC[C@@H](F)C(C)(C)O)CC1]

Example 285

6-(3-cyanopyrrolo[1,2-b]pyridazin-7-yl)-4-(((1r,4R)-4-((N,N-dimethylsulfamoyl)amino)cyclohexyl)amino)-N-((R)-2-fluoro-3-hydroxy-3-methylbutyl)nicotinamide 6-(3-cyanopyrrolo[1,2-b]pyridazin-7-yl)-4-(((1r,4R)-4-((N,N-dimethylsulfamoyl)amino)cyclohexyl)amino)-N-((R)-2-fluoro-3-hydroxy-3-methylbutyl)nicotinamide was prepared as described in Procedure 29 substituting acetyl chloride with dimethylsulfamoyl chloride.

ES/MS: 587.3 [M+H$^+$].

1H NMR (400 MHz, Methanol-d4) δ 8.76 (d, J=2.1 Hz, 1H), 8.65 (d, J=2.2 Hz, 1H), 8.56 (s, 1H), 8.01 (d, J=5.1 Hz, 1H), 7.86 (s, 1H), 7.22 (d, J=5.1 Hz, 1H), 4.53-4.27 (m, 1H), 4.03-3.71 (m, 2H), 3.56-3.41 (m, 2H), 2.77 (s, 6H), 2.28-2.07 (m, 4H), 1.67-1.49 (m, 4H), 1.29 (d, J=1.6 Hz, 6H).

Procedure 33: Example 282

6-(3-cyanopyrrolo[1,2-b]pyridazin-7-yl)-N-((R)-2-fluoro-3-hydroxy-3-methylbutyl)-4-(((1r,4R)-4-(3-methyloxetane-3-carboxamido)cyclohexyl)amino) nicotinamide

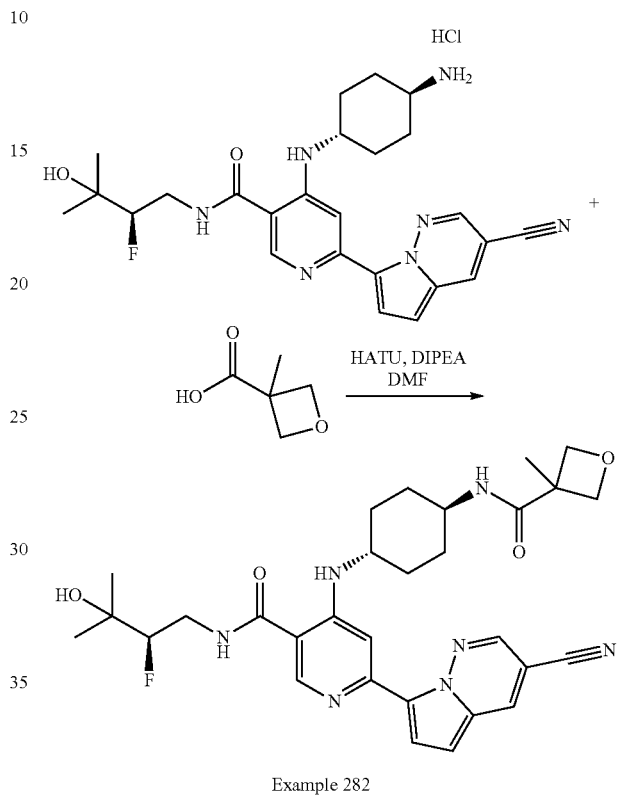

Example 282

6-(3-cyanopyrrolo[1,2-b]pyridazin-7-yl)-N-((R)-2-fluoro-3-hydroxy-3-methylbutyl)-4-(((1r,4R)-4-(3-methyloxetane-3-carboxamido)cyclohexyl)amino) nicotinamide A flask was charged with 4-(((r,4R)-4-aminocyclohexyl)amino)-6-(3-cyanopyrrolo[1,2-b]pyridazin-7-yl)-N-((R)-2-fluoro-3-hydroxy-3-methylbutyl)nicotinamide hydrochloride (prepared as described in Procedure 28) (8.0 mg, 0.017 mmol), 3-methyloxetane-3-carboxylic acid (3.9 mg, 0.033 mmol), and HATU (13.3 mg, 0.035 mmol). The solids were dissolved in DMF (1.0 mL), and then DIPEA (8.9 μL, 0.050 mmol) was added. The reaction mixture was stirred at room temperature for 10 minutes then filtered and directly purified by reverse phase high pressure liquid chromatography (eluent: water/MeCN*0.1% TFA) to provide the final compound.

ES/MS: 578.3 [M+H$^+$].

1H NMR (400 MHz, Methanol-d4) δ 8.76 (d, J=2.2 Hz, 1H), 8.65 (d, J=2.1 Hz, 1H), 8.57 (s, 1H), 8.01 (d, J=5.1 Hz, 1H), 7.88 (s, 1H), 7.22 (d, J=5.0 Hz, 1H), 4.87-4.86 (m, 2H), 4.52-4.33 (m, 3H), 4.03-3.73 (m, 3H), 3.55-3.40 (m, 1H), 2.30-2.17 (m, 2H), 2.12-1.99 (m, 2H), 1.69-1.48 (m, 7H), 1.30 (d, J=1.6 Hz, 6H).

Procedure 34: Example 289

6-(3-cyanopyrrolo[1,2-b]pyridazin-7-yl)-N-((R)-2-fluoro-3-hydroxy-3-methylbutyl)-4-(((1r,4R)-4-((2,2,2-trifluoroethyl)amino)cyclohexyl)amino)nicotinamide

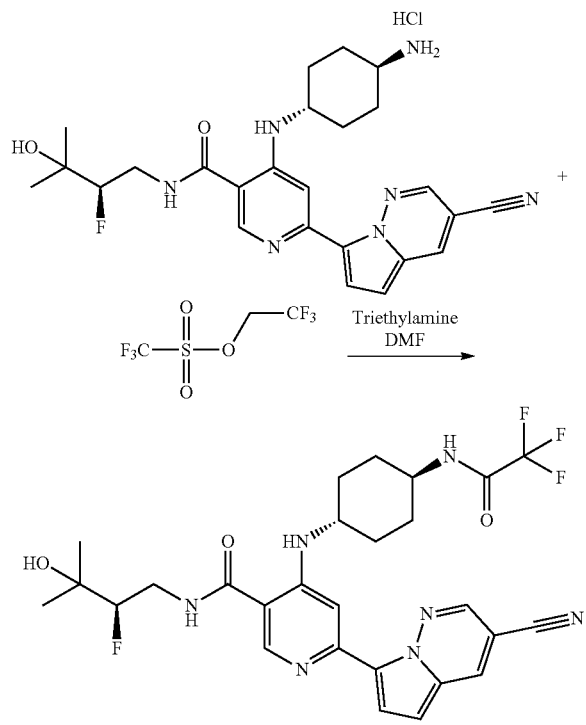

Example 289

6-(3-cyanopyrrolo[1,2-b]pyridazin-7-yl)-N-((R)-2-fluoro-3-hydroxy-3-methylbutyl)-4-(((1r,4R)-4-((2,2,2-trifluoroethyl)amino)cyclohexyl)amino)nicotinamide To a solution of 4-(((1r,4R)-4-aminocyclohexyl)amino)-6-(3-cyanopyrrolo[1,2-b]pyridazin-7-yl)-N-((R)-2-fluoro-3-hydroxy-3-methylbutyl)nicotinamide hydrochloride (prepared as described in Procedure 28) (8.0 mg, 0.017 mmol) in DMF was added triethylamine (9.3 µL, 0.067 mmol) followed by 2,2,2-trifluoroethyl trifluoromethanesulfonate. The reaction mixture was stirred at room temperature for 15 minutes then filtered and directly purified by reverse phase high pressure liquid chromatography (eluent: water/MeCN*0.1% TFA) to provide the final compound.

ES/MS: 562.2 [M+H$^+$].

1H NMR (400 MHz, Methanol-d4) δ 8.76 (d, J=2.2 Hz, 1H), 8.65 (d, J=2.2 Hz, 1H), 8.59 (s, 1H), 8.01 (d, J=5.0 Hz, 1H), 7.88 (s, 1H), 7.22 (d, J=5.1 Hz, 1H), 4.56-4.28 (m, 1H), 4.03-3.81 (m, 2H), 3.82-3.65 (m, 2H), 3.58-3.42 (m, 1H), 3.08-2.99 (m, 1H), 2.43-2.26 (m, 2H), 2.26-2.14 (m, 2H), 1.66-1.47 (m, 4H), 1.29 (d, J=1.6 Hz, 6H).

Procedure 35: Example 293

(R)-4-(6-(3-cyanopyrrolo[1,2-b]pyridazin-7-yl)-4-(((1r,4R)-4-((methoxycarbonyl)amino)cyclohexyl)amino)nicotinamido)-3-fluoro-2-methylbutan-2-yl acetate

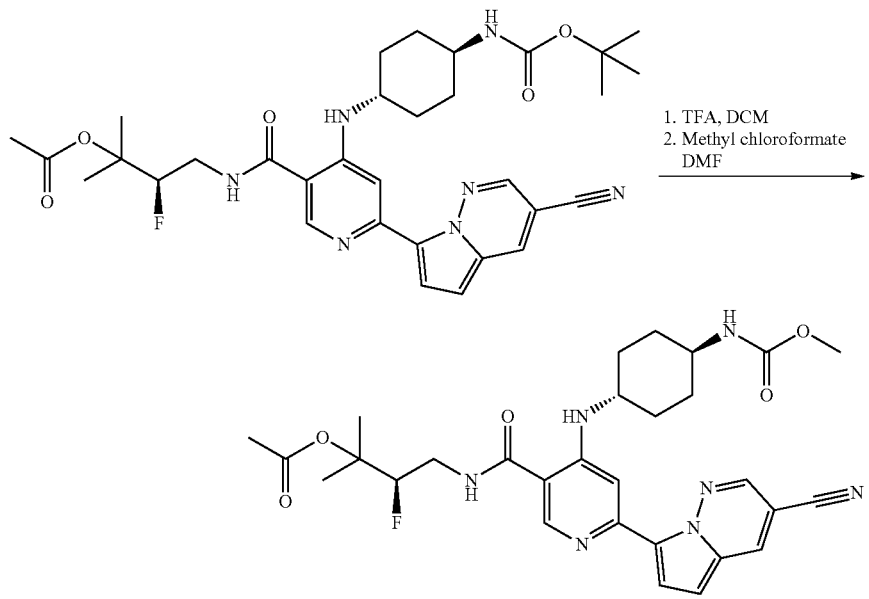

Example 293

(R)-4-(6-(3-cyanopyrrolo[1,2-b]pyridazin-7-yl)-4-(((1r,4R)-4-((methoxycarbonyl)amino)cyclohexyl)amino)nicotinamido)-3-fluoro-2-methylbutan-2-yl acetate To a solution of (R)-4-(4-(((1r,4R)-4-((tert-butoxycarbonyl)amino)cyclohexyl)amino)-6-(3-cyanopyrrolo[1,2-b]pyridazin-7-yl)nicotinamido)-3-fluoro-2-methylbutan-2-yl acetate (obtained as described in Procedure 2 substituting (R)-4-amino-3-fluoro-2-methylbutan-2-ol with (R)-4-amino-3-fluoro-2-methylbutan-2-yl acetate) (103.0 mg, 0.17 mmol) in DCM (2.0 mL) was added trifluoroacetic acid (2.0 mL). The reaction mixture was stirred at room temperature for 15 minutes the concentrated in vacuo to dryness. To a solution of the crude residue in DMF (1.5 mL) was added triethylamine (138.6 μL, 0.99 mmol) followed by methyl chloroformate (38.4 μL, 0.50 mmol). The reaction mixture was stirred at room temperature for 15 minutes then filtered and directly purified by reverse phase high pressure liquid chromatography (eluent: water/MeCN*0.1% TFA) to provide the final compound.

ES/MS: 580.3 [M+H$^+$].

1H NMR (400 MHz, Methanol-d4) δ 8.76 (d, J=2.2 Hz, 1H), 8.66 (d, J=2.1 Hz, 1H), 8.58 (s, 1H), 8.01 (d, J=5.1 Hz, 1H), 7.88 (s, 1H), 7.22 (d, J=5.0 Hz, 1H), 4.83 (ddd, J=49.0, 9.3, 1.9 Hz, 1H), 4.02-3.79 (m, 2H), 3.64 (s, 3H), 3.59-3.42 (m, 2H), 2.27-2.16 (m, 2H), 2.13-2.03 (m, 2H), 2.03 (s, 3H), 1.66-1.44 (m, 10H).

Procedure 36: Example 301

N-((1s,4S)-4-acetamidocyclohexyl)-4-(((1r,4R)-4-acetamidocyclohexyl)amino)-6-(3-cyanopyrrolo[1,2-b]pyridazin-7-yl)nicotinamide To a solution of tert-butyl ((1R,4r)-4-((5-(((1s,4S)-4-((tert-butoxycarbonyl)amino)cyclohexyl)carbamoyl)-2-(3-cyanopyrrolo[1,2-b]pyridazin-7-yl)pyridin-4-yl)amino)cyclohexyl)carbamate (obtained as described in Procedure 2 substituting (R)-4-amino-3-fluoro-2-methylbutan-2-ol with trans-N-Boc-1,4-cyclohexanediamine) (75.5 mg, 0.11 mmol) in DCM (1.0 mL) was added trifluoroacetic acid (1.0 mL). The reaction mixture was stirred at room temperature for 15 minutes the concentrated in vacuo to dryness. To a solution of the crude residue in DMF (1.0 mL) was added triethylamine (61.4 μL, 0.44 mmol) followed by acetyl chloride (15.7 μL, 0.22 mmol). The reaction mixture was stirred at room temperature for 15 minutes then filtered and directly purified by reverse phase high pressure liquid chromatography (eluent: water/MeCN*0.1% TFA) to provide the final compound.

ES/MS: 557.2 [M+H$^+$].

1H NMR (400 MHz, Methanol-d4) δ 8.79-8.72 (m, 1H), 8.64 (dd, J=2.2, 0.4 Hz, 1H), 8.54 (s, 1H), 8.00 (d, J=5.0 Hz, 1H), 7.85 (s, 1H), 7.21 (d, J=5.1, 0.4 Hz, 1H), 3.94-3.78 (m, 2H), 3.79-3.60 (m, 2H), 2.25-2.19 (m, 2H), 2.09-2.03 (m, 3H), 1.99 (d, J=14.0 Hz, 3H), 1.95 (s, 3H), 1.93 (s, 3H), 1.65-1.29 (m, 8H).

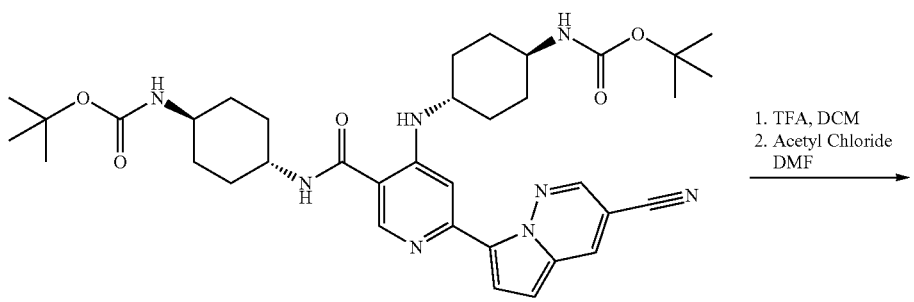

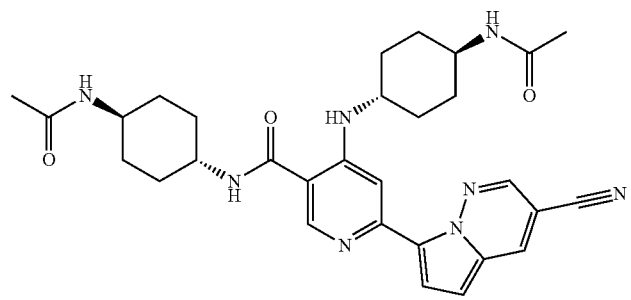

Example 301

Procedure 37: Example 302 (Isomer 1) and
Example 303 (Isomer 2)

6-(3-cyanopyrrolo[1,2-b]pyridazin-7-yl)-N-((R)-2-fluoro-3-hydroxy-3-methylbutyl)-4-((2-(hydroxymethyl)cyclopropyl)amino)nicotinamide

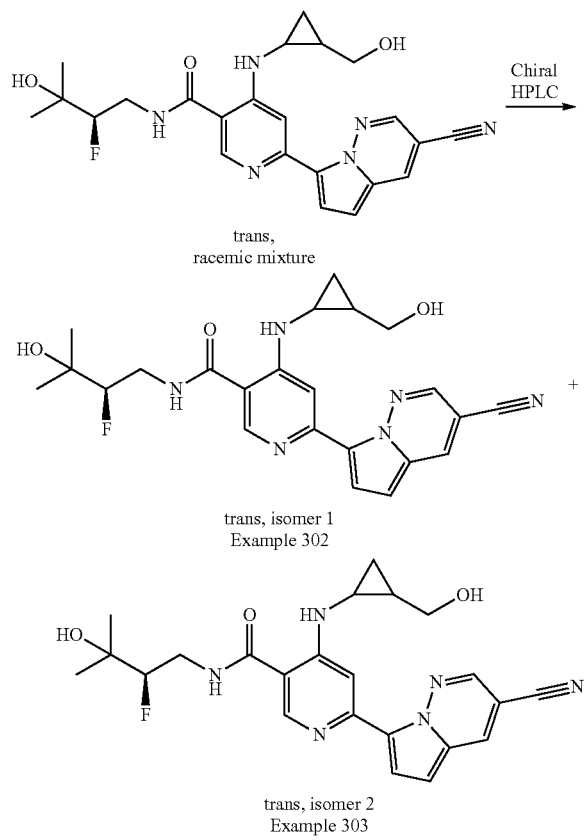 [SMILES: CC(C)(O)[C@H](F)CNC(=O)c1cnc(-c2ccc3cc(C#N)cnn23)cc1NC1CC1CO ; CC(C)(O)[C@H](F)CNC(=O)c1cnc(-c2ccc3cc(C#N)cnn23)cc1NC1CC1CO ; CC(C)(O)[C@H](F)CNC(=O)c1cnc(-c2ccc3cc(C#N)cnn23)cc1NC1CC1CO]

6-(3-cyanopyrrolo[1,2-b]pyridazin-7-yl)-N-((R)-2-fluoro-3-hydroxy-3-methylbutyl)-4-((2-(hydroxymethyl)cyclopropyl)amino)nicotinamide isomer 1 (Example 302) and isomer 2 (Example 303)

trans, racemic 6-(3-cyanopyrrolo[1,2-b]pyridazin-7-yl)-N-((R)-2-fluoro-3-hydroxy-3-methylbutyl)-4-((2-(hydroxymethyl)cyclopropyl)amino)nicotinamide (obtained as described in Procedure 2 substituting (R)-4-amino-3-fluoro-2-methylbutan-2-ol with trans, racemic (2-aminocyclopropyl)methanol) was separated into two distinct enantiomers (trans, isomer 1 and trans, isomer 2) by reverse phase high pressure liquid chromatography (eluent: IPA/MeCN) to provide the final compounds.

Example 302

ES/MS: 453.3 [M+H⁺].
1H NMR (400 MHz, Methanol-d4) δ 8.76 (d, J=2.2 Hz, 1H), 8.68 (d, J=2.1 Hz, 1H), 8.56 (s, 1H), 8.46 (s, 1H), 8.09 (d, J=5.0 Hz, 1H), 7.21 (d, J=5.1 Hz, 1H), 4.43 (ddd, J=49.1, 9.3, 2.2 Hz, 1H), 4.03 (dd, J=11.4, 4.9 Hz, 1H), 3.93 (ddd, J=36.4, 14.6, 2.1 Hz, 1H), 3.54-3.41 (m, 1H), 3.24 (dd, J=11.4, 9.2 Hz, 1H), 2.73 (dt, J=7.3, 3.7 Hz, 1H), 1.45-1.34 (m, 1H), 1.29 (d, J=1.7 Hz, 6H), 1.14-0.99 (m, 2H).

Example 303

ES/MS: 453.3 [M+H⁺].
1H NMR (400 MHz, Methanol-d4) δ 8.76 (d, J=2.2 Hz, 1H), 8.68 (d, J=2.1 Hz, 1H), 8.56 (s, 1H), 8.46 (s, 1H), 8.09 (d, J=5.1 Hz, 1H), 7.21 (d, J=5.0 Hz, 1H), 4.42 (ddd, J=49.0, 9.3, 2.2 Hz, 1H), 4.03 (dd, J=11.4, 4.9 Hz, 1H), 3.93 (ddd, J=36.4, 14.6, 2.2 Hz, 1H), 3.55-3.38 (m, 1H), 3.24 (dd, J=11.4, 9.2 Hz, 1H), 2.76-2.68 (m, 1H), 1.47-1.34 (m, 1H), 1.29 (d, J=1.7 Hz, 6H), 1.14-0.99 (m, 2H).

Procedure 38: Example 325

(R)-6-(3-cyanopyrrolo[1,2-b]pyridazin-7-yl)-N-(2-fluoro-3-hydroxy-3-methylbutyl)-4-((1-(3-methyloxetane-3-carbonyl)piperidin-4-yl)amino)nicotinamide

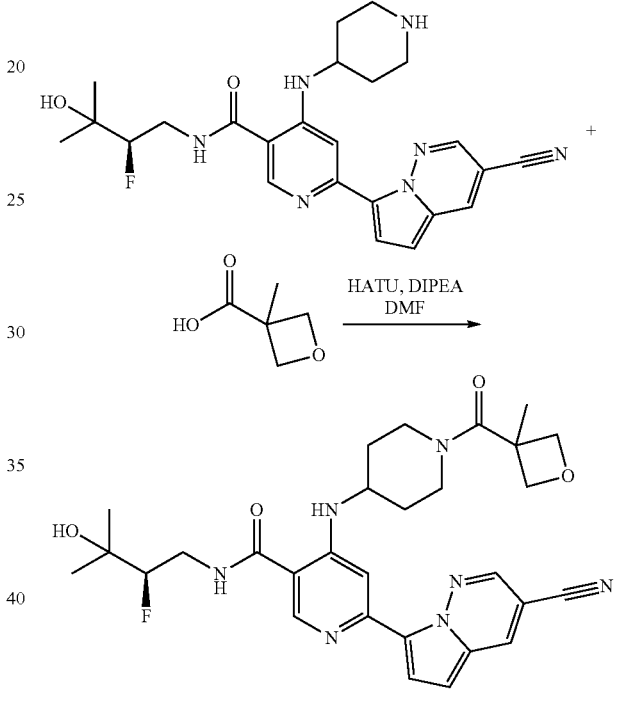

(R)-6-(3-cyanopyrrolo[1,2-b]pyridazin-7-yl)-N-(2-fluoro-3-hydroxy-3-methylbutyl)-4-((1-(3-methyloxetane-3-carbonyl)piperidin-4-yl)amino)nicotinamide To a solution of crude (R)-6-(3-cyanopyrrolo[1,2-b]pyridazin-7-yl)-N-(2-fluoro-3-hydroxy-3-methylbutyl)-4-(piperidin-4-ylamino)nicotinamide (obtained as described in Procedure 14) (16.0 mg, 0.034 mmol), 3-methyloxetane-3-carboxylic acid (8.0 mg, 0.069 mmol), and HATU (27.4 mg, 0.072 mmol) in DMF (2.0 mL) was added DIPEA (43.0 µL, 0.24 mmol). The reaction mixture was stirred at room temperature for 5 minutes then filtered and directly purified by reverse phase high pressure liquid chromatography (eluent: water/MeCN*0.1% TFA) to provide the final compound.

ES/MS: 564.3 [M+H⁺].
1H NMR (400 MHz, Methanol-d4) δ 8.76 (d, J=2.2 Hz, 1H), 8.69 (d, J=2.2 Hz, 1H), 8.61 (s, 1H), 8.05 (d, J=5.1 Hz, 1H), 7.91 (s, 1H), 7.23 (d, J=5.1 Hz, 1H), 4.98 (d, J=5.9 Hz, 2H), 4.52-4.33 (m, 4H), 4.23-4.11 (m, 1H), 3.93 (dd, J=36.2, 14.4 Hz, 1H), 3.58-3.42 (m, 1H), 3.30-3.18 (m, 2H), 3.19-3.07 (m, 1H), 2.23-2.12 (m, 2H), 1.78-1.61 (m, 5H), 1.29 (d, J=1.7 Hz, 6H).

Procedure 39: Example 269

6-(3-cyanopyrrolo[1,2-b]pyridazin-7-yl)-N-((R)-2-fluoro-3-hydroxy-3-methylbutyl)-4-(((1R,4R)-4-((5-methyl-1,3,4-oxadiazol-2-yl)amino)cyclohexyl)amino)nicotinamide

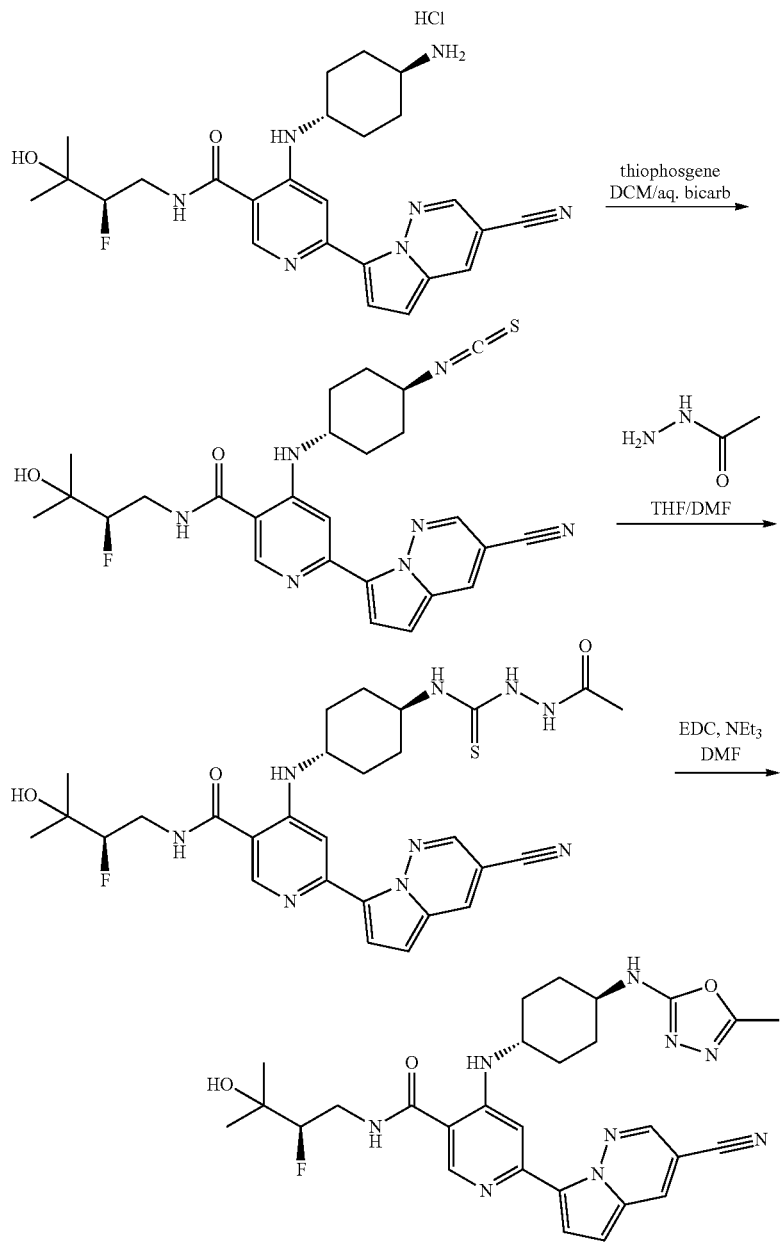

Example 269

6-(3-cyanopyrrolo[1,2-b]pyridazin-7-yl)-N-((R)-2-fluoro-3-hydroxy-3-methylbutyl)-4-(((1R,4R)-4-isothiocyanatocyclohexyl)amino)nicotinamide To a solution of 4-(((1R,4R)-4-aminocyclohexyl)amino)-6-(3-cyanopyrrolo[1,2-b]pyridazin-7-yl)-N-((R)-2-fluoro-3-hydroxy-3-methylbutyl)nicotinamide hydrochloride (obtained as described in Procedure 28) (20.0 mg, 0.039 mmol) in a biphasic solution of DCM (1.0 mL) and saturated aqueous sodium bicarbonate (1.0 mL) was added thiophosgene (3.3 μL, 0.043 mmol). The reaction mixture was stirred at room temperature for 15 minutes then concentrated in vacuo to provide the crude desired product which was used without additional purification.

ES/MS: 522.3 [M+H$^+$].

4-(((1R,4R)-4-(2-acetylhydrazine-1-carbothioamido) cyclohexyl)amino)-6-(3-cyanopyrrolo[1,2-b] pyridazin-7-yl)-N-((R)-2-fluoro-3-hydroxy-3-methylbutyl)nicotinamide To a solution of crude 6-(3-cyanopyrrolo[1,2-b]pyridazin-7-yl)-N-((R)-2-fluoro-3-hydroxy-3-methylbutyl)-4-(((1R,4R)-4-isothiocyanatocyclohexyl)amino)nicotinamide (20.2 mg, 0.039 mmol) in THF (2.0 mL) and DMF (0.1 mL) was added acylhydrazine (4.8 mg, 0.058 mmol). The reaction mixture was stirred at room temperature for 16 hours then concentrated in vacuo to provide the crude desired product which was used without additional purification.
ES/MS: 596.1 [M+H$^+$].

6-(3-cyanopyrrolo[1,2-b]pyridazin-7-yl)-N-((R)-2-fluoro-3-hydroxy-3-methylbutyl)-4-(((1R,4R)-4-((5-methyl-1,3,4-oxadiazol-2-yl)amino)cyclohexyl)amino)nicotinamide To a solution of crude 4-(((1R,4R)-4-(2-acetylhydrazine-1-carbothioamido)cyclohexyl)amino)-6-(3-cyanopyrrolo[1,2-b]pyridazin-7-yl)-N-((R)-2-fluoro-3-hydroxy-3-methylbutyl)nicotinamide (23.1 mg, 0.039 mmol) in DMF (1.5 mL) was added EDC (24.1 mg, 0.16 mmol) and triethylamine (43.3 µL, 0.31 mmol). The reaction mixture was stirred at room temperature for 60 hours then filtered and directly purified by reverse phase high pressure liquid chromatography (eluent: water/MeCN*0.1% TFA) to provide the final compound.
ES/MS: 562.3 [M+H$^+$].

1H NMR (400 MHz, Methanol-d4) δ 8.76 (d, J=2.2 Hz, 1H), 8.65 (d, J=2.2 Hz, 1H), 8.57 (s, 1H), 8.02 (d, J=5.1 Hz, 1H), 7.87 (s, 1H), 7.22 (d, J=5.1 Hz, 1H), 4.43 (ddd, J=49.2, 9.5, 2.0 Hz, 1H), 4.04-3.81 (m, 2H), 3.59-3.41 (m, 2H), 2.37 (s, 3H), 2.31-2.15 (m, 4H), 1.72-1.53 (m, 4H), 1.30 (d, J=1.6 Hz, 6H).

Procedure 40: Example 268

Methyl ((1R,4R)-4-((5-((cyanomethyl)carbamoyl)-2-(3-cyanopyrrolo[1,2-b]pyridazin-7-yl)pyridin-4-yl)amino)cyclohexyl)carbamate

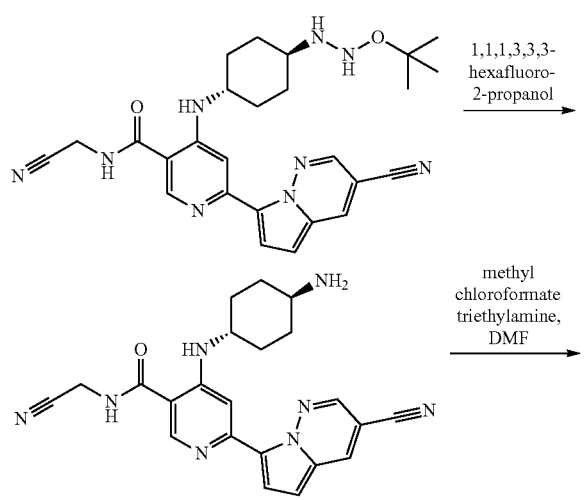

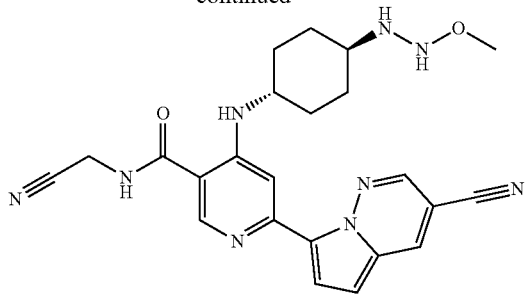

Example 268

4-(((1R,4R)-4-aminocyclohexyl)amino)-N-(cyanomethyl)-6-(3-cyanopyrrolo[1,2-b]pyridazin-7-yl)nicotinamide tert-butyl ((1R,4R)-4-((5-((cyanomethyl)carbamoyl)-2-(3-cyanopyrrolo[1,2-b]pyridazin-7-yl)pyridin-4-yl)amino)cyclohexyl)carbamate (14 mg, 0.02 mmol) was taken in 1,1,1,3,3,3-hexafluoro-2-propanol (0.1 mL). The reaction mixture was heated thermally at 150° C. for 4 hours. The reaction was cooled and concentrated in vacuo to provide the crude desired product which was used without additional purification.
ES/MS: 415.2 [M+H$^+$].

methyl ((1R,4R)-4-((5-((cyanomethyl)carbamoyl)-2-(3-cyanopyrrolo[1,2-b]pyridazin-7-yl)pyridin-4-yl)amino)cyclohexyl)carbamate methyl ((1R,4R)-4-((5-((cyanomethyl)carbamoyl)-2-(3-cyanopyrrolo[1,2-b]pyridazin-7-yl)pyridin-4-yl)amino)cyclohexyl)carbamate was prepared as described in Procedure 29 substituting 4-(((1R,4R)-4-aminocyclohexyl)amino)-6-(3-cyanopyrrolo[1,2-b]pyridazin-7-yl)-N-((R)-2-fluoro-3-hydroxy-3-methylbutyl)nicotinamide hydrochloride with 4-(((1R,4R)-4-aminocyclohexyl)amino)-N-(cyanomethyl)-6-(3-cyanopyrrolo[1,2-b]pyridazin-7-yl)nicotinamide and acetyl chloride with methyl chloroformate.
ES/MS: 473.3 [M+H$^+$].

1H NMR (499 MHz, Methanol-d4) δ 8.76 (d, J=2.1 Hz, 1H), 8.66 (d, J=2.1 Hz, 1H), 8.58 (s, 1H), 8.02 (d, J=5.0 Hz, 1H), 7.92 (s, 1H), 7.22 (d, J=5.0 Hz, 1H), 4.37 (s, 2H), 3.90-3.79 (m, 1H), 3.64 (s, 3H), 3.54-3.47 (m, 1H), 2.22 (d, J=12.5 Hz, 2H), 2.08 (d, J=12.5 Hz, 2H), 1.56 (tt, J=24.3, 12.1 Hz, 4H).

Procedure 41: Example 377

(R)-4-(benzo[b]thiophen-2-ylamino)-6-(3-cyanopyrrolo[1,2-b]pyridazin-7-yl)-N-(2-fluoro-3-hydroxy-3-methylbutyl)nicotinamide

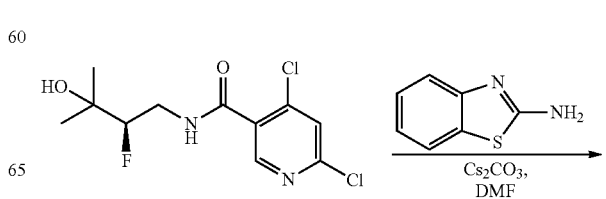

-continued

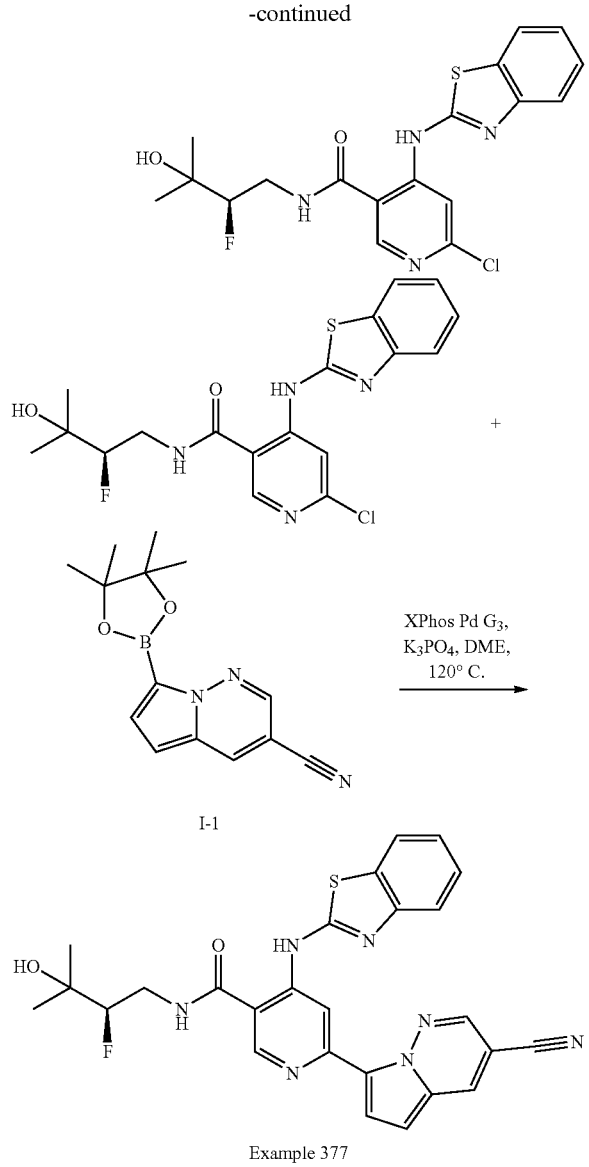

I-1

Example 377

(R)-4-(benzo[d]thiazol-2-ylamino)-6-chloro-N-(2-fluoro-3-hydroxy-3-methylbutyl)nicotinamide A mixture of (R)-4,6-dichloro-N-(2-fluoro-3-hydroxy-3-methylbutyl)nicotinamide (50 mg, 0.17 mmol), 2-aminobenzothiazole (77 mg, 0.51 mmol), and cesium carbonate (195 mg, 0.60 mmol) in dimethylformamide (1.2 mL) was stirred at room temperature for 48 hours. EtOAc was added and the solids were removed via filtration through celite. The filtrate was concentrated and the resulting oil was purified via preparative HPLC (eluent: water/MeCN*0.1% TFA). The desired fractions were concentrated and dissolved in EtOAc. After washing with saturated sodium bicarbonate, the organic layer was dried over MgSO₄ and concentrated to provide the product.

ES/MS: 409.3 (M+H⁺).

(R)-4-(benzo[b]thiophen-2-ylamino)-6-(3-cyanopyrrolo[1,2-b]pyridazin-7-yl)-N-(2-fluoro-3-hydroxy-3-methylbutyl)nicotinamide A mixture of (R)-4-(benzo[d]thiazol-2-ylamino)-6-chloro-N-(2-fluoro-3-hydroxy-3-methylbutyl)nicotinamide (29 mg, 0.07 mmol), 7-(4,4,5,5-tetramethyl-1,3,2-dioxaborolan-2-yl)pyrrolo[1,2-b]pyridazine-3-carbonitrile (I-1) (25 mg, 0.09 mmol), XPhos Pd G3 (6 mg), and 2M Potassium phosphate tribasic (0.15 ml) in 1 mL DME was degassed with argon for 3 minutes, then capped and heated under microwave conditions at 120° C. for 20 minutes. The crude material was purified via RP-HPLC (eluent: water/MeCN*0.1% TFA) to yield the product as a trifluoroacetate salt.

ES/MS: 516.1 (M+H⁺).

1H NMR (400 MHz, Methanol-d4) δ 8.85 (s, 1H), 8.66 (d, J=10.4 Hz, 2H), 7.93 (d, J=5.0 Hz, 1H), 7.85 (d, J=7.9 Hz, 1H), 7.50 (t, J=7.7 Hz, 1H), 7.35 (t, J=7.7 Hz, 1H), 7.17 (d, J=5.0 Hz, 1H), 4.49 (ddd, J=49.0, 9.3, 2.2 Hz, 1H), 3.99 (dd, J=36.0, 14.6 Hz, 1H), 3.58 (dd, J=15.3, 9.4 Hz, 1H), 1.32 (d, J=1.6 Hz, 6H).

Procedure 42: Example 373

(R)-4-((3-carbamoylbicyclo[1.1.1]pentan-1-yl)amino)-6-(3-cyanopyrrolo[1,2-b]pyridazin-7-yl)-N-(2-fluoro-3-hydroxy-3-methylbutyl)nicotinamide

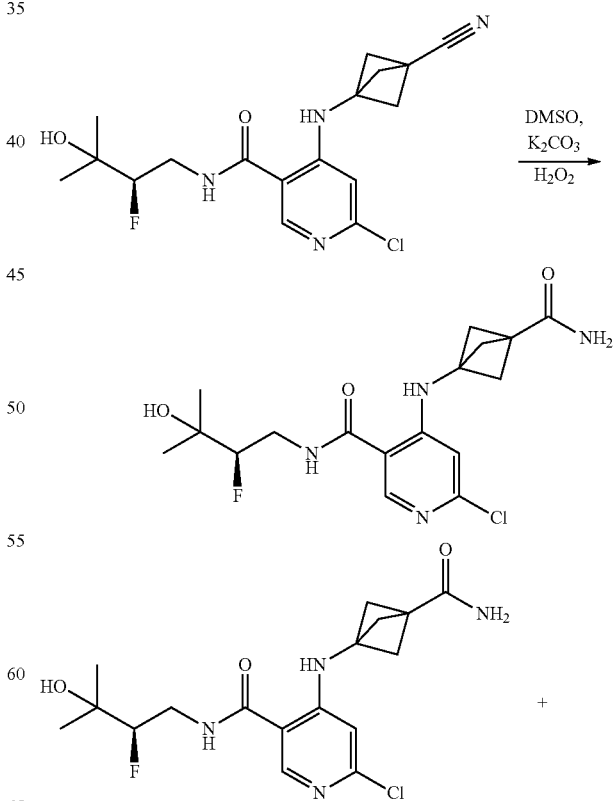

-continued

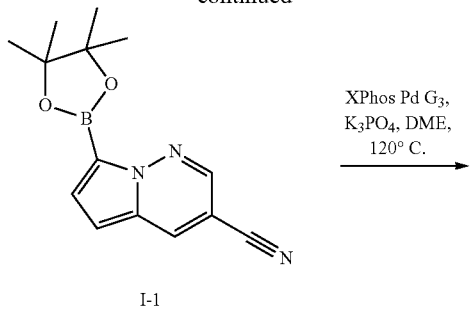

I-1

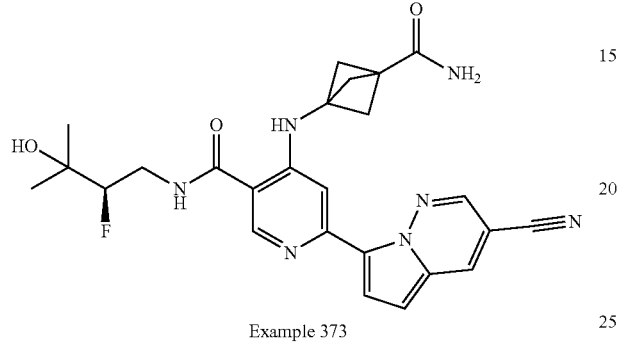

Example 373

(R)-6-chloro-4-((3-cyanobicyclo[1.1.1]pentan-1-yl)amino)-N-(2-fluoro-3-hydroxy-3-methylbutyl)nicotinamide (R)-6-chloro-4-((3-cyanobicyclo[1.1.1]pentan-1-yl)amino)-N-(2-fluoro-3-hydroxy-3-methylbutyl)nicotinamide was prepared according to the Example 2 using the appropriate starting material(s).

(R)-4-((3-carbamoylbicyclo[1.1.1]pentan-1-yl)amino)-6-chloro-N-(2-fluoro-3-hydroxy-3-methylbutyl)nicotinamide A mixture of (R)-6-chloro-4-((3-cyanobicyclo[1.1.1]pentan-1-yl)amino)-N-(2-fluoro-3-hydroxy-3-methylbutyl)nicotinamide (36 mg, 0.10 mmol), potassium carbonate (135 mg, 0.98 mmol), and hydrogen peroxide 30% aqueous solution (0.1 mL, 0.98 mmol) in DMSO (1 mL) was stirred at room temperature for 3 hours. The resulting solution was filtered and purified via preparative HPLC (eluent: water/MeCN*0.1% TFA). The desired fractions were lyophilized to provide the product.
ES/MS: 385.1 (M+H$^+$).

(R)-4-((3-carbamoylbicyclo[1.1.1]pentan-1-yl)amino)-6-(3-cyanopyrrolo[1,2-b]pyridazin-7-yl)-N-(2-fluoro-3-hydroxy-3-methylbutyl)nicotinamide A mixture of (R)-4-((3-carbamoylbicyclo[1.1.1]pentan-1-yl)amino)-6-chloro-N-(2-fluoro-3-hydroxy-3-methylbutyl)nicotinamide (35 mg, 0.07 mmol), 7-(4,4,5,5-tetramethyl-1,3,2-dioxaborolan-2-yl)pyrrolo[1,2-b]pyridazine-3-carbonitrile (I-1) (25 mg, 0.09 mmol), XPhos Pd G3 (5 mg), and 2M Potassium phosphate tribasic (0.064 ml) in 1 mL DME was degassed with argon for 3 minutes, then capped and heated under microwave conditions at 120° C. for 20 minutes. The crude material was purified via RP-HPLC (eluent: water/MeCN*0.1% TFA) to yield the product as a trifluoroacetate salt.

ES/MS: 492.1 (M+H$^+$).

1H NMR (400 MHz, Methanol-d4) δ 8.84 (d, J=2.1 Hz, 1H), 8.76 (d, J=2.2 Hz, 1H), 8.61 (s, 1H), 8.50 (s, 1H), 7.93 (d, J=5.1 Hz, 1H), 7.23 (d, J=5.1 Hz, 1H), 4.42 (ddd, J=49.0, 9.4, 2.0 Hz, 1H), 3.93 (ddd, J=36.5, 14.6, 2.1 Hz, 1H), 3.47 (td, J=15.8, 9.4 Hz, 1H), 2.61 (s, 6H), 1.28 (d, J=1.6 Hz, 6H).

Procedure 43: Example 369

6-(3-cyanopyrrolo[1,2-b]pyridazin-7-yl)-N-isopropyl-4-(isopropylamino)nicotinamide

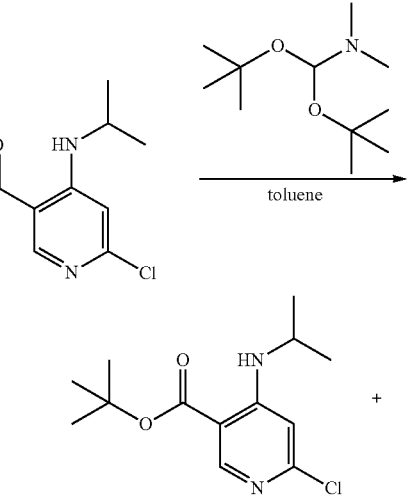

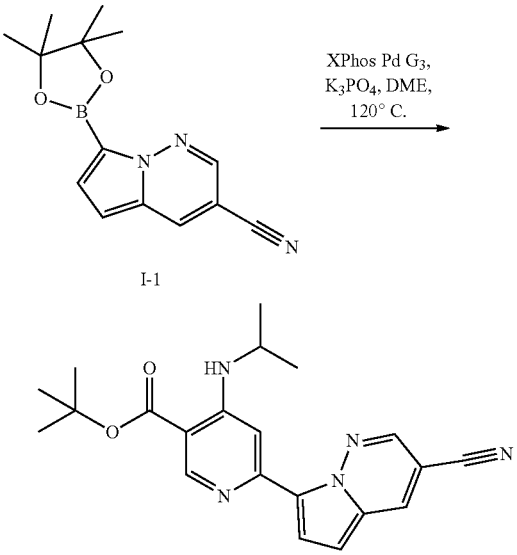

I-1

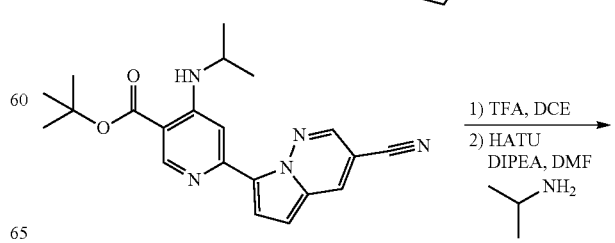

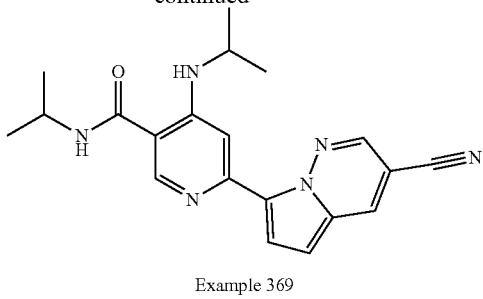

Example 369

6-Chloro-4-(isopropylamino)nicotinic acid

6-Chloro-4-(isopropylamino)nicotinic acid was prepared according to Procedure 1 using the appropriate starting material(s).

Tert-butyl 6-chloro-4-(isopropylamino)nicotinate

A solution of 6-Chloro-4-(isopropylamino)nicotinic acid (1.35 g, 6.23 mmol) in toluene (11 mL) was heated to 90° C. N,N-diemthylformamide di-tert-butyl acetal (7.63 g, 37.5 mmol) in toluene (11 mL) was added dropwise over 2 hour. The resulting solution was stirred at 90° C. for 12 hours and cooled to room temperature. The reaction mixture was diluted with EtOAc and washed with 5% aqueous lithium chloride (3 times). The aqueous layers were back extracted with EtOAc and the combine organic layers were dried over $Na_2SO_4$ and concentrated. The crude product was purified by $SiO_2$ chromatography (eluent: EtOAc/hexanes) to provide the desired ester.

ES/MS: 271.4 (M+H$^+$).

Tert-butyl 6-(3-cyanopyrrolo[1,2-b]pyridazin-7-yl)-4-(isopropylamino)nicotinate

A mixture of tert-butyl 6-chloro-4-(isopropylamino)nicotinate (300 mg, 1.1 mmol), 7-(4,4,5,5-tetramethyl-1,3,2-dioxaborolan-2-yl)pyrrolo[1,2-b]pyridazine-3-carbonitrile (I-1) (374 mg, 1.4 mmol), XPhos Pd G3 (76 mg), and 2M Potassium phosphate tribasic (1.0 ml) in 10 mL DME was degassed with argon for 3 minutes, then capped and heated under microwave conditions at 120° C. for 20 minutes. The reaction mixture was diluted with EtOAc and washed with water and brine. The aqueous layers were back extracted with EtOAc and the combine organic layers were dried over $Na_2SO_4$ and concentrated. The crude product was purified by $SiO_2$ chromatography (eluent: EtOAc/hexanes) to provide the desired ester.

ES/MS: 378.0 (M+H$^+$).

Tert-butyl 6-(3-cyanopyrrolo[1,2-b]pyridazin-7-yl)-4-(isopropylamino)nicotinate

To a solution of tert-butyl 6-(3-cyanopyrrolo[1,2-b]pyridazin-7-yl)-4-(isopropylamino)nicotinate (399 mg, 1.06 mmol) in DCE (6 mL) was added trifluroacetic acid (0.8 mL, 10.5 mmol) and the resulting solution was heated to 80° C. for 6 hours. The resulting mixture was cooled to room temperature, diluted with water, and concentrated. The resulting solids were filtered, washed with water, and dissolved in a mixture of dichloromethane and methanol. The solution was then dried over $MgSO_4$ and concentrated. The resulting crude product was then used without further purification.

ES/MS: 322.2 (M+H$^+$).

6-(3-cyanopyrrolo[1,2-b]pyridazin-7-yl)-N-isopropyl-4-(isopropylamino)nicotinamide To a solution of tert-butyl 6-(3-cyanopyrrolo[1,2-b]pyridazin-7-yl)-4-(isopropylamino)nicotinate (10 mg, 0.03 mmol) in DMF (1 mL) was added HATU (14.6 mg, 0.04 mmol) and isopropylamine (0.02 mL, 0.23 mmol). The resulting solution was stirred at room temperature for 1 hour and then purified via RP-HPLC (eluent: water/MeCN*0.1% TFA) to yield the product as a trifluoroacetate salt.

ES/MS: 363.3 (M+H$^+$).

1H NMR (400 MHz, Methanol-d4) δ 8.74 (d, J=2.1 Hz, 1H), 8.65 (dd, J=2.2, 0.4 Hz, 1H), 8.53 (s, 1H), 7.98 (dd, J=5.1, 0.5 Hz, 1H), 7.83 (d, J=0.5 Hz, 1H), 7.20 (d, J=5.1 Hz, 1H), 4.21 (td, J=7.4, 6.6, 5.6 Hz, 1H), 4.17-4.09 (m, 1H), 1.40 (d, J=6.4 Hz, 6H), 1.28 (d, J=6.6 Hz, 6H).

Procedure 44: Example 351

(1S,3S)-3-((2-(3-cyanopyrrolo[1,2-b]pyridazin-7-yl)-5-(((R)-2-fluoro-3-hydroxy-3-methylbutyl)carbamoyl)pyridin-4-yl)amino)cyclobutyl methylcarbamate

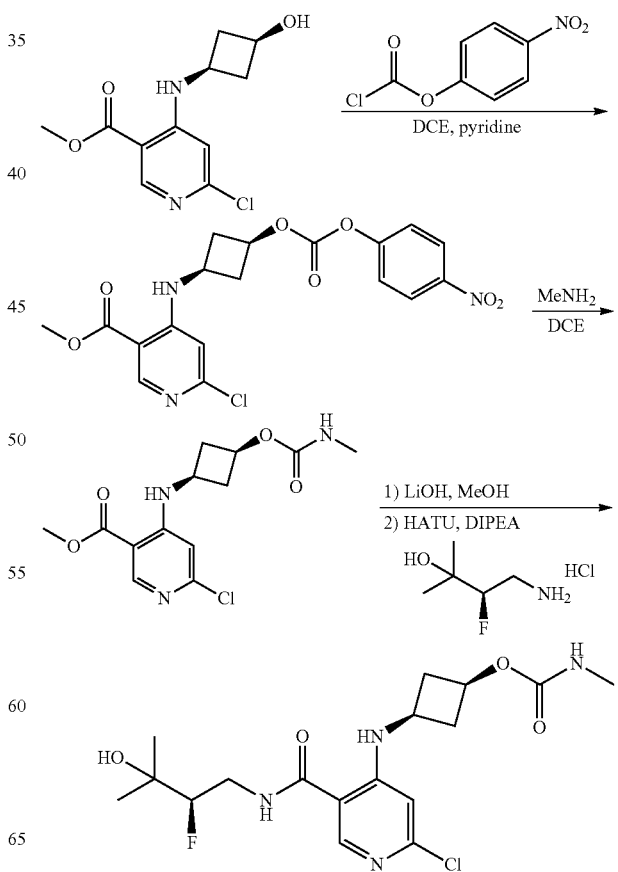

-continued

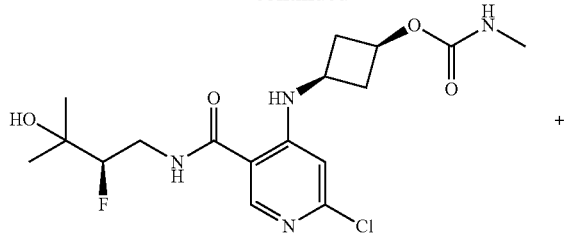

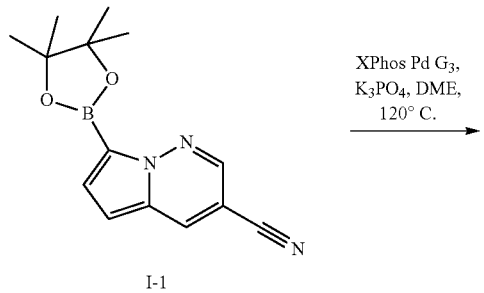

I-1

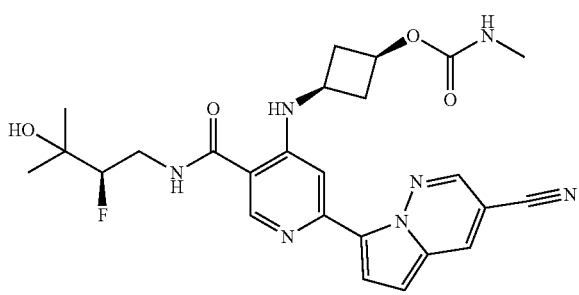

Example 351

Methyl 6-chloro-4-(((1S,3S)-3-hydroxycyclobutyl)amino)nicotinate

Methyl 6-chloro-4-(((1s,3s)-3-hydroxycyclobutyl)amino)nicotinate was prepared according to the Procedure 1 using the appropriate starting material(s).

Methyl 6-chloro-4-(((1S,3S)-3-(((4-nitrophenoxy)carbonyl)oxy)cyclobutyl)amino)nicotinate To a solution of methyl 6-chloro-4-(((1S,3S)-3-hydroxycyclobutyl)amino)nicotinate (151 mg, 0.58 mmol) in DCE (3 mL) and pyridine (0.5 mL) was added 4-nitrophenyl chloroformate (142 mg, 0.70 mmol). The reaction was stirred for 18 hours and then filtered through celite. The filtrate was then concentrated and the resulting material was purified by SiO$_2$ chromatography (eluent: EtOAc/hexanes) to provide the desired carbonate.
ES/MS: 422.2 (M+H$^+$).

Methyl 6-chloro-4-(((1S,3S)-3-((methylcarbamoyl)oxy)cyclobutyl)amino)nicotinate

To a solution of methyl 6-chloro-4-(((1S,3S)-3-(((4-nitrophenoxy)carbonyl)oxy)cyclobutyl)amino)nicotinate (60 mg, 0.14 mmol) in DCE (1 mL) was added methylamine (2M in THF, 0.15 mL, 0.3 mmol). The reaction was stirred at room temperature for 48 hours and diluted with dichloromethane. After washing with aqueous sodium bicarbonate, the organic layer was dried over Ns$_2$SO$_4$ and concentrated. The crude material was purified by SiO$_2$ chromatography (eluent: EtOAc/hexanes) to provide the desired carbamate.
ES/MS: 314.2 (M+H$^+$).

(1S,3S)-3-((2-(3-cyanopyrrolo[1,2-b]pyridazin-7-yl)-5-(((R)-2-fluoro-3-hydroxy-3-methylbutyl)carbamoyl)pyridin-4-yl)amino)cyclobutyl methylcarbamate Starting from methyl 6-chloro-4-(((1s,3s)-3-((methylcarbamoyl)oxy)cyclobutyl)amino)nicotinate, (1S,3s)-3-((2-(3-cyanopyrrolo[1,2-b]pyridazin-7-yl)-5-(((R)-2-fluoro-3-hydroxy-3-methylbutyl)carbamoyl)pyridin-4-yl)amino)cyclobutyl methylcarbamate was prepared according to the Procedure 1 using the appropriate starting material(s).
ES/MS: 510.3 (M+H$^+$).
1H NMR (400 MHz, Methanol-d4) δ 8.75 (d, J=2.2 Hz, 1H), 8.70 (d, J=2.2 Hz, 1H), 8.57 (s, 1H), 7.99 (d, J=5.1 Hz, 1H), 7.77 (s, 1H), 7.21 (d, J=5.1 Hz, 1H), 4.43 (ddd, J=49.1, 9.4, 2.1 Hz, 1H), 4.07 (p, J=7.8 Hz, 1H), 4.02-3.83 (m, 1H), 3.58-3.40 (m, 1H), 3.19-3.05 (m, 2H), 2.69 (s, 3H), 2.19 (q, J=9.3 Hz, 2H), 1.29 (d, J=1.6 Hz, 6H). (1H obscured by solvent)

Procedure 45: Example 345

N-(3-amino-3-methylbutyl)-6-(3-cyanopyrrolo[1,2-b]pyridazin-7-yl)-4-((4-hydroxybicyclo[2.2.2]octan-1-yl)amino)nicotinamide

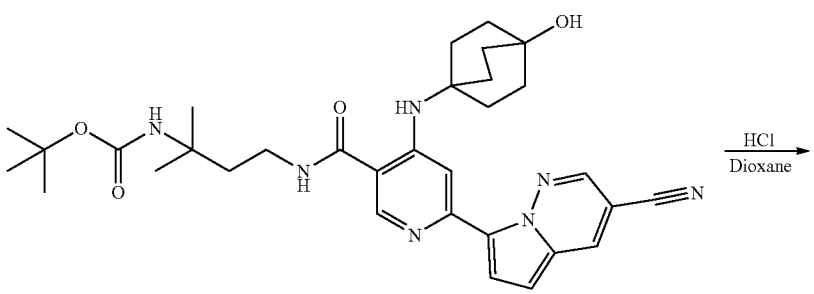

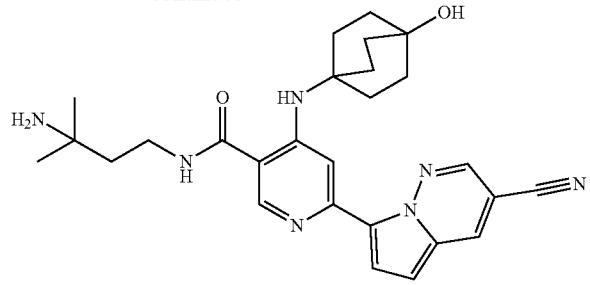

Example 345

Tert-butyl (4-(6-(3-cyanopyrrolo[1,2-b]pyridazin-7-yl)-4-((4-hydroxybicyclo[2.2.2]octan-1-yl)amino)nicotinamido)-2-methylbutan-2-yl)carbamate Tert-butyl (4-(6-(3-cyanopyrrolo[1,2-b]pyridazin-7-yl)-4-((4-hydroxybicyclo[2.2.2]octan-1-yl)amino)nicotinamido)-2-methylbutan-2-yl)carbamate was prepared according to the Procedure 1 using the appropriate starting material(s).

N-(3-amino-3-methylbutyl)-6-(3-cyanopyrrolo[1,2-b]pyridazin-7-yl)-4-((4-hydroxybicyclo[2.2.2]octan-1-yl)amino)nicotinamide To a solution of tert-butyl (4-(6-(3-cyanopyrrolo[1,2-b]pyridazin-7-yl)-4-((4-hydroxybicyclo[2.2.2]octan-1-yl)amino)nicotinamido)-2-methylbutan-2-yl)carbamate (205 mg, 0.35 mmol) in DCE (1.4 mL) was added HCl (4M in dioxane, 0.9 mL, 3.6 mmol). The reaction was stirred at room temperature for 3 hour and then concentrated to dryness. The crude material was purified via RP-HPLC (eluent: water/MeCN*0.1% TFA) to yield the product as a trifluoroacetate salt.

ES/MS: 488.6 (M+H⁺).

1H NMR (400 MHz, Methanol-d4) δ 8.75 (d, J=2.2 Hz, 1H), 8.69 (d, J=2.1 Hz, 1H), 8.53 (s, 1H), 8.30 (s, 1H), 7.93 (d, J=5.0 Hz, 1H), 7.21 (d, J=5.1 Hz, 1H), 3.52-3.43 (m, 2H), 2.32-2.18 (m, 6H), 2.02-1.83 (m, 8H), 1.41 (s, 6H).

Procedure 46: Example 343

Methyl (4-(6-(3-cyanopyrrolo[1,2-b]pyridazin-7-yl)-4-((4-hydroxybicyclo[2.2.2]octan-1-yl)amino)nicotinamido)-2-methylbutan-2-yl)carbamate

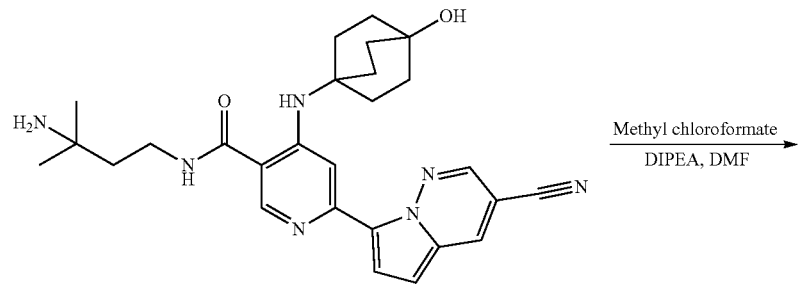

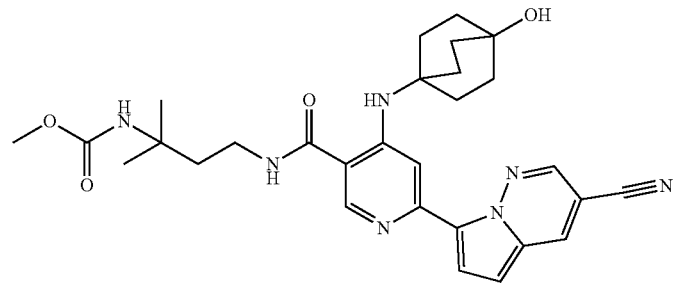

Example 343

Methyl (4-(6-(3-cyanopyrrolo[1,2-b]pyridazin-7-yl)-4-((4-hydroxybicyclo[2.2.2]octan-1-yl)amino)nicotinamido)-2-methylbutan-2-yl)carbamate To a solution of N-(3-amino-3-methylbutyl)-6-(3-cyanopyrrolo[1,2-b]pyridazin-7-yl)-4-((4-hydroxybicyclo[2.2.2]octan-1-yl)amino)nicotinamide (25 mg, 0.045 mmol), in DMF (0.5 mL) was added n-ethyldiisopropylamine (0.075 mL, 0.43 mmol) and methyl chloroformate (0.006 mL, 0.078 mmol). The resulting solution was stirred at room temperature for 30 min and purified via RP-HPLC (eluent: water/MeCN*0.1% TFA) to yield the product as a trifluoroacetate salt.

ES/MS: 546.4 (M+H$^+$).

1H NMR (400 MHz, Methanol-d4) δ 8.75 (d, J=2.2 Hz, 1H), 8.69 (d, J=2.1 Hz, 1H), 8.47 (s, 1H), 8.25 (s, 1H), 7.91 (d, J=5.1 Hz, 1H), 7.21 (d, J=5.0 Hz, 1H), 3.56 (s, 3H), 3.42-3.35 (m, 2H), 2.25 (t, J=7.8 Hz, 6H), 2.05-1.96 (m, 2H), 1.90 (dd, J=10.3, 5.7 Hz, 6H), 1.31 (s, 6H).

Procedure 47: Example 337

(R)-4-((4-benzylthiazol-2-yl)amino)-6-(3-cyanopyrrolo[1,2-b]pyridazin-7-yl)-N-(2-fluoro-3-hydroxy-3-methylbutyl)nicotinamide

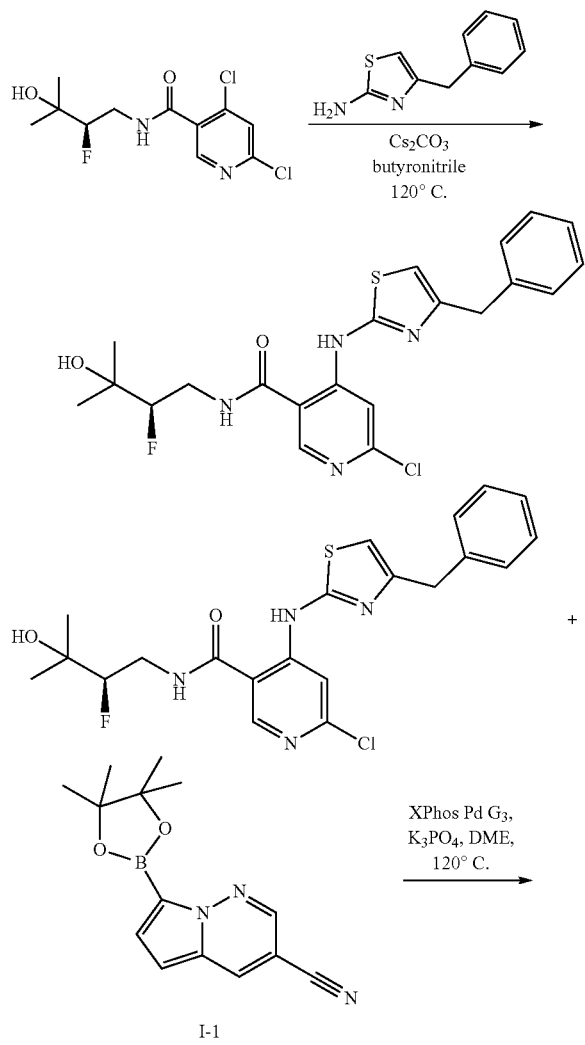

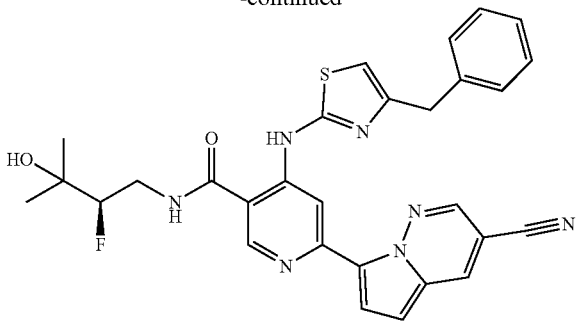

Example 337

(R)-4-((4-benzylthiazol-2-yl)amino)-6-chloro-N-(2-fluoro-3-hydroxy-3-methylbutyl)nicotinamide To a solution of (R)-4,6-dichloro-N-(2-fluoro-3-hydroxy-3-methylbutyl)nicotinamide (50 mg, 0.17 mmol) in butyronitrile (2 mL) was added 4-benzylthiazol-2-amine (50 mg, 0.26 mmol) and cesium carbonate (110 mg, 0.34 mmol), The resulting slurry was heated to 120° C. for 18 hours. Upon cooling, the reaction was diluted with EtOAc and washed with water and brine. The aqueous layers were back-extracted with EtOAc. The combined organic layers were dried over MgSO$_4$ and concentrated to dryness. The crude material was then purified via RP-HPLC (eluent: water/MeCN*0.1% TFA). The resulting product fractions were concentrated, dissolved in MeOH and neutralized through a PL-HCO3-MP SPE column. Concentration of the filtrate provided the desired product.

ES/MS: 450.0 (M+H$^+$).

Methyl (4-(6-(3-cyanopyrrolo[1,2-b]pyridazin-7-yl)-4-((4-hydroxybicyclo[2.2.2]octan-1-yl)amino)nicotinamido)-2-methylbutan-2-yl)carbamate A mixture of (R)-4-((4-benzylthiazol-2-yl)amino)-6-chloro-N-(2-fluoro-3-hydroxy-3-methylbutyl)nicotinamide (29 mg, 0.06 mmol), 7-(4,4,5,5-tetramethyl-1,3,2-dioxaborolan-2-yl)pyrrolo[1,2-b]pyridazine-3-carbonitrile (I-1) (23 mg, 0.08 mmol), XPhos Pd G3 (4 mg), and 2M Potassium phosphate tribasic (0.1 ml) in 1 mL DME was degassed with argon for 3 minutes, then capped and heated under microwave conditions at 120° C. for 20 minutes, diluted with MeOH and concentrated to dryness. The crude product was purified by SiO$_2$ chromatography (eluent: MeOH/CH$_2$Cl$_2$). The resulting material was then purified via RP-HPLC (eluent: water/MeCN*0.1% TFA) to yield the product as a trifluoroacetate salt.

ES/MS: 566.2 (M+H$^+$).

1H NMR (400 MHz, Methanol-d4) δ 9.68 (s, 1H), 8.81 (s, 1H), 8.63 (s, 1H), 8.11 (s, 1H), 7.62 (s, 1H), 7.32 (d, J=3.4 Hz, 4H), 7.26 (d, J=7.6 Hz, 1H), 7.13 (d, J=5.0 Hz, 1H), 6.89 (s, 1H), 4.47 (ddd, J=48.9, 9.2, 2.1 Hz, 1H), 4.11 (s, 2H), 3.98 (ddd, J=36.1, 14.5, 2.3 Hz, 1H), 3.61-3.49 (m, 1H), 1.31 (d, J=1.7 Hz, 6H).

Procedure 48: Example 338

(R)-2-((2-(3-cyanopyrrolo[1,2-b]pyridazin-7-yl)-5-((2-fluoro-3-hydroxy-3-methylbutyl)carbamoyl)pyridin-4-yl)amino)-N-methylthiazole-4-carboxamide

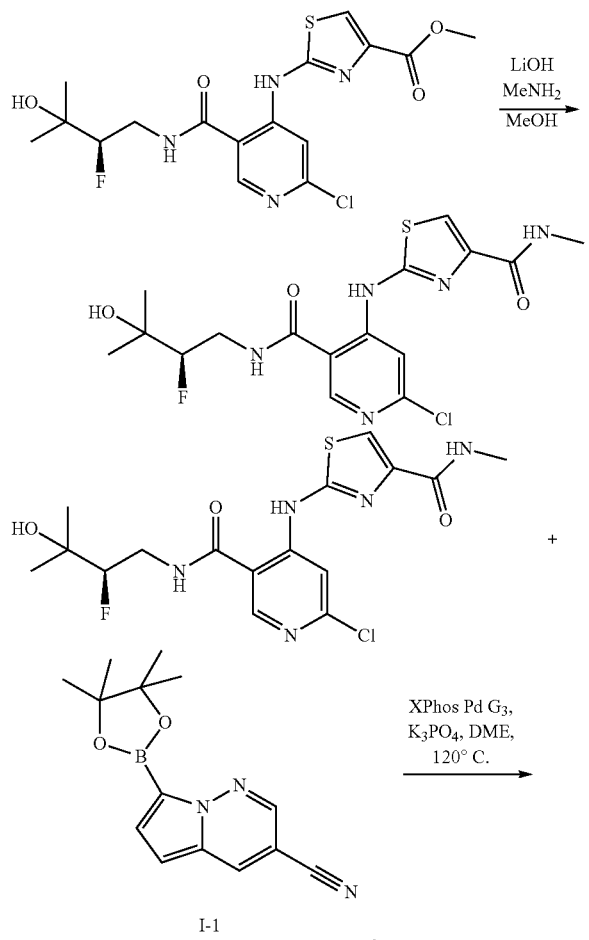

Methyl (R)-2-((2-chloro-5-((2-fluoro-3-hydroxy-3-methylbutyl)carbamoyl)pyridin-4-yl)amino)thiazole-4-carboxylate Methyl (R)-2-((2-chloro-5-((2-fluoro-3-hydroxy-3-methylbutyl)carbamoyl)pyridin-4-yl)amino)thiazole-4-carboxylate was prepared according to the Procedure 48 using the appropriate starting material(s).

(R)-2-((2-chloro-5-((2-fluoro-3-hydroxy-3-methylbutyl)carbamoyl)pyridin-4-yl)amino)-N-methylthiazole-4-carboxamide To a solution of methyl (R)-2-((2-chloro-5-((2-fluoro-3-hydroxy-3-methylbutyl)carbamoyl)pyridin-4-yl)amino)thiazole-4-carboxylate (44 mg, 0.1 mmol) in MeOH (0.5 mL) was added methylamine (2M in THF, 0.3 mL, 0.6 mmol) and aqueous lithium hydroxide (2.5 M, 0.1 mL, 0.25 mmol). The resulting mixture was stirred at room temperature for 18 h and concentrated in vacuo. The crude material was purified via RP-HPLC (eluent: water/MeCN*0.1% TFA) and the desired fractions were concentrated to dryness. The resulting trifluoroacetate salt was neutralized with aqueous sodium bicarbonate and extracted with EtOAc (3×). The combine organic layers were dried over magnesium sulfate and concentrated to yield the desired amide.

(R)-2-((2-(3-cyanopyrrolo[1,2-b]pyridazin-7-yl)-5-((2-fluoro-3-hydroxy-3-methylbutyl)carbamoyl)pyridin-4-yl)amino)-N-methylthiazole-4-carboxamide A mixture of (R)-2-((2-chloro-5-((2-fluoro-3-hydroxy-3-methylbutyl)carbamoyl)pyridin-4-yl)amino)-N-methylthiazole-4-carboxamide (10 mg, 0.02 mmol), 7-(4,4,5,5-tetramethyl-1,3,2-dioxaborolan-2-yl)pyrrolo[1,2-b]pyridazine-3-carbonitrile (I-1) (12 mg, 0.05 mmol), XPhos Pd G3 (3 mg), and 2M Potassium phosphate tribasic (0.05 ml) in 0.5 mL DME was degassed with argon for 3 minutes, then capped and heated under microwave conditions at 120° C. for 20 minutes, diluted with MeOH, filtered and concentrated to dryness. The resulting material was then purified via RP-HPLC (eluent: water/MeCN*0.1% TFA) to yield the product as a trifluoroacetate salt.

ES/MS: 523.1 (M+H$^+$).

1H NMR (400 MHz, Methanol-d4) δ 9.78 (s, 1H), 8.84 (s, 1H), 8.67 (d, J=2.2 Hz, 1H), 8.56 (d, J=2.2 Hz, 1H), 7.94 (d, J=5.0 Hz, 1H), 7.85 (s, 1H), 7.17 (d, J=5.0 Hz, 1H), 4.57-4.32 (m, 1H), 3.97 (dd, J=35.4, 13.6 Hz, 1H), 3.61-3.39 (m, 1H), 2.94 (s, 3H), 1.31 (d, J=1.6 Hz, 6H).

Procedure 49: Example 334

6-(3-cyanopyrrolo[1,2-b]pyridazin-7-yl)-4-((4-hydroxybicyclo[2.2.2]octan-1-yl)amino)-N-(2-(methylamino)-2-oxoethyl)nicotinamide

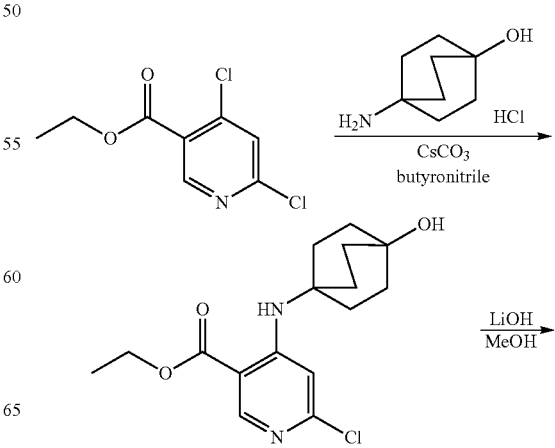

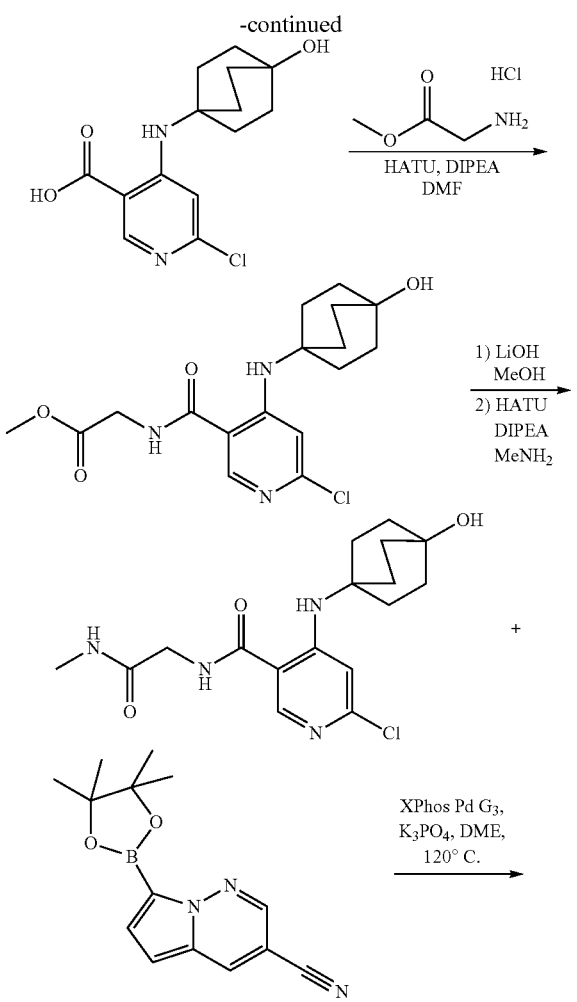

I-1

Example 334

Ethyl 6-chloro-4-((4-hydroxybicyclo[2.2.2]octan-1-yl)amino)nicotinate

To a solution of ethyl 4,6-dichloronicotinate (1.86 g, 8.45 mmol) in butyronitrile (24 mL) was added 1-aminobicyclo[2.2.2]octan-4-ol hydrochloride (1 g, 5.63 mmol) and cesium carbonate (3.67 g, 11.3 mmol). The resulting slurry was sealed and heated to 120° C. for 24 hours. The resulting mixture was diluted with EtOAc and washed with water and brine. The aqueous layers were back-extracted with EtOAc and the combined organic layers were dried over MgSO₄ and concentrated to dryness. The crude material was purified by SiO₂ chromatography (eluent: MeOH/CH₂Cl₂) to provide the desired product.
ES/MS: 325.6 (M+H⁺).

6-Chloro-4-((4-hydroxybicyclo[2.2.2]octan-1-yl)amino)nicotinic acid

To a solution of ethyl 6-chloro-4-((4-hydroxybicyclo[2.2.2]octan-1-yl)amino)nicotinate (1.37 g, 4.22 mmol) in EtOH (40 mL) was added lithium hydroxide (2.5 M in H₂O, 4.25 mL, 10.6 mmol). The resulting solution was heated to 50° C. for 3 hours, cooled to room temperature and neutralized with 2M hydrochloric acid (5.3 mL). The resulting solution was concentrated to dryness and diluted with water at 0° C. The resulting solids were filtered and washed with water. The resulting product was dried in vacuo and used without further purification.
ES/MS: 297.5 (M+H⁺).

Methyl (6-chloro-4-((4-hydroxybicyclo[2.2.2]octan-1-yl)amino)nicotinoyl)glycinate To a solution of 6-chloro-4-((4-hydroxybicyclo[2.2.2]octan-1-yl)amino)nicotinic acid (300 mg, 1.0 mmol) in DMF (5 mL) was added glycine methyl ester hydrochloride (190 mg, 1.5 mmol), HATU (577 mg, 1.5 mmol), and DIPEA (0.5 mL, 2.9 mmol). The resulting mixture was stirred at room temperature for 18 hours and diluted with EtOAc. The resulting solution was washed with 50% aqueous NH₄Cl (2 times). The resulting aqueous layers were back-extracted with EtOAc and the combined organic layers were dried over MgSO₄ and concentrated to dryness. The crude material was purified by SiO₂ chromatography (eluent: MeOH/CH₂Cl₂) to provide the desired product.
ES/MS: 368.6 (M+H⁺).

6-Chloro-4-((4-hydroxybicyclo[2.2.2]octan-1-yl)amino)-N-(2-(methylamino)-2-oxoethyl)nicotinamide To a solution of methyl (6-chloro-4-((4-hydroxybicyclo[2.2.2]octan-1-yl)amino)nicotinoyl)glycinate (343 mg, 0.93 mmol) in MeOH (9 mL) was added 2.5 M aqueous lithium hydroxide (0.95 mL, 2.38 mmol). The resulting solution was stirred at room temperature for 1 hour and neutralized with 2M hydrochloride acid. The resulting solution was concentrated to dryness and used without further purification.
To a solution of the crude acid (38 mg, 0.1 mmol) in DMF (1.5 mL) was added methylamine (2M in THF, 0.2 mL, 0.4 mmol), HATU (62 mg, 0.16 mmol), and DIPEA (0.05 mL, 0.32 mmol). The resulting solution was stirred at room temperature for 18 hours, diluted with EtOAc, and washed with 50% aqueous NH₄Cl (2 times) The resulting aqueous layers were back-extracted with EtOAc and the combined organic layers were dried over MgSO₄ and concentrated to dryness. The crude material was purified by SiO₂ chromatography (eluent: MeOH/CH₂Cl₂) to provide the desired product.
ES/MS: 367.1 (M+H⁺).

6-(3-cyanopyrrolo[1,2-b]pyridazin-7-yl)-4-((4-hydroxybicyclo[2.2.2]octan-1-yl)amino)-N-(2-(methylamino)-2-oxoethyl)nicotinamide A mixture of 6-chloro-4-((4-hydroxybicyclo[2.2.2]octan-1-yl)amino)-N-(2-(methylamino)-2-oxoethyl)nicotinamide (15 mg, 0.04 mmol), 7-(4,4,5,5-tetramethyl-1,3,2-dioxaborolan-2-yl)pyrrolo[1,2-b]pyridazine-3-carbonitrile (I-1) (10 mg, 0.04 mmol), XPhos Pd G3 (3 mg), and 2M Potassium phosphate tribasic (0.04 ml) in 0.75 mL DME was degassed with argon for 3 minutes, then capped and heated under microwave conditions at 120° C. for 20 minutes, diluted with MeOH, filtered and concentrated to dryness. The resulting material was then purified via RP-HPLC (eluent: water/MeCN*0.1% TFA) to yield the product as a trifluoroacetate salt.

ES/MS: 474.2 (M+H$^+$).

1H NMR (400 MHz, Methanol-d4) δ 8.77 (d, J=2.2 Hz, 1H), 8.71 (d, J=2.2 Hz, 1H), 8.60 (s, 1H), 8.31 (s, 1H), 7.93 (d, J=5.0 Hz, 1H), 7.22 (d, J=5.1 Hz, 1H), 4.00 (s, 2H), 2.78 (s, 3H), 2.30-2.17 (m, 6H), 1.90 (dd, J=10.1, 5.9 Hz, 6H).

Procedure 50: Example 399

6-(3-cyanopyrrolo[1,2-b]pyridazin-7-yl)-N-((R)-2-fluoro-3-hydroxy-3-methylbutyl)-4-((4-(2-oxooxazo-lidin-3-yl)bicyclo[2.2.2]octan-1-yl)amino)nicotina-mide

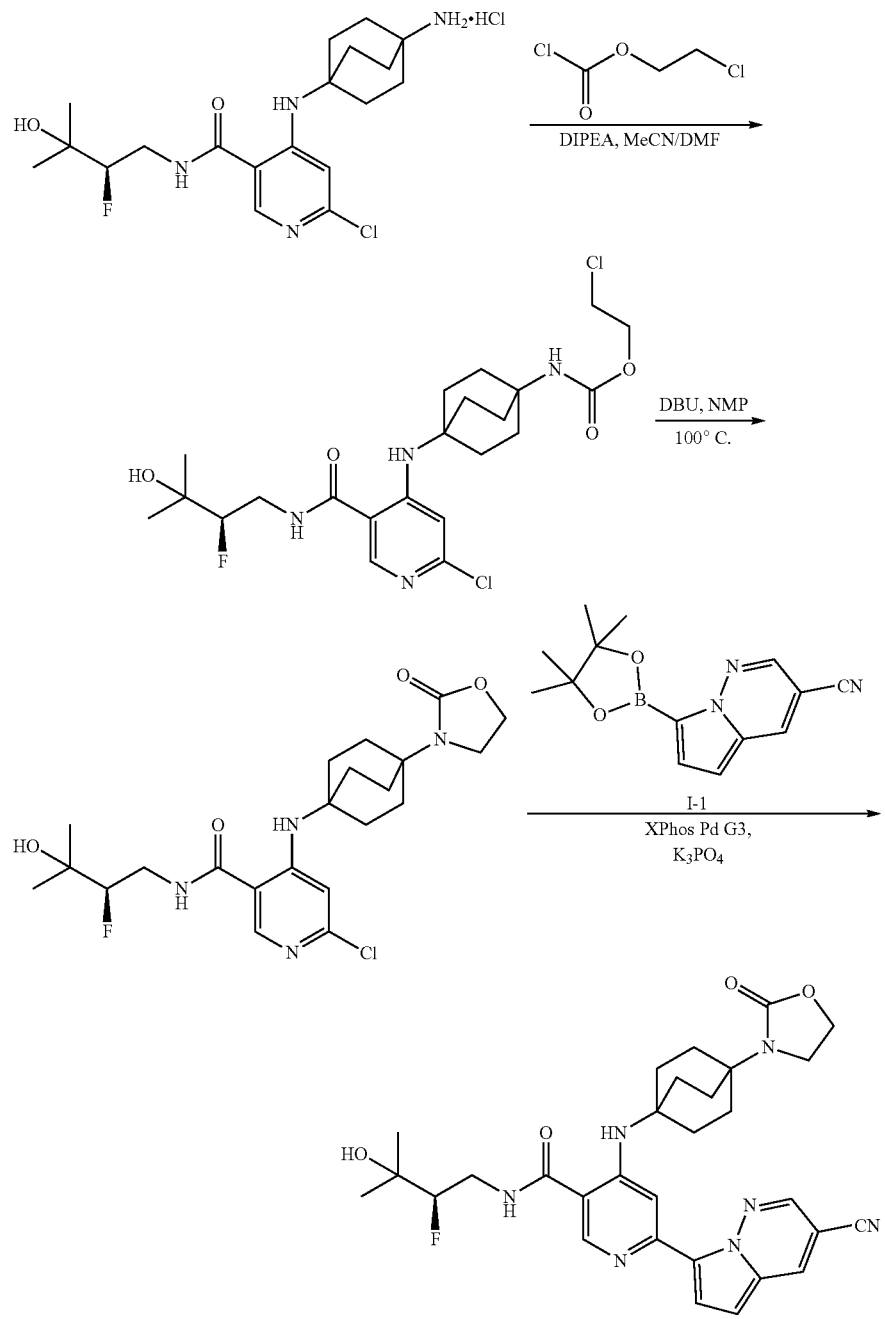

Example 339

2-Chloroethyl (R)-(4-((2-chloro-5-((2-fluoro-3-hydroxy-3-methylbutyl)carbamoyl)pyridin-4-yl)amino)bicyclo[2.2.2]octan-1-yl)carbamate To a suspension of (R)-4-((4-aminobicyclo[2.2.2]octan-1-yl)amino)-6-chloro-N-(2-fluoro-3-hydroxy-3-methylbutyl)nicotinamide hydrochloride (150 mg, 0.34 mmol) and DIPEA (1.57 mL, 9 mmol) in MeCN (3 mL) and DMF (1 mL) was added 2-chloroethyl chloroformate (98.5 mg, 0.69 mmol). Then reaction was stirred for 1 hour, diluted with EtOAc (30 mL) and washed with sodium bicarbonate solution and brine. The organic layer was concentrated to provide desired product which was used without further purification.

ES/MS: 505.2 (M+H+).

(R)-6-chloro-N-(2-fluoro-3-hydroxy-3-methylbutyl)-4-((4-(2-oxooxazolidin-3-yl)bicyclo[2.2.2]octan-1-yl)amino)nicotinamide 2-Chloroethyl (R)-(4-((2-chloro-5-((2-fluoro-3-hydroxy-3-methylbutyl)carbamoyl)pyridin-4-yl)amino)bicyclo[2.2.2]octan-1-yl)carbamate (40 mg, 0.08 mmol) was dissolved in DMF (4 mL), and DBU (60.3 mg, 0.4 mmol) was added to the solution. Then it was heated to 100° C. for 3 hours, cooled to room temperature and filtered. The crude material was purified RP-HPLC (eluent: water/MeCN*0.1% TFA) to yield the product as a trifluoroacetate salt.

ES/MS: 469.2 (M+H+).

6-(3-cyanopyrrolo[1,2-b]pyridazin-7-yl)-N-((R)-2-fluoro-3-hydroxy-3-methylbutyl)-4-((4-(2-oxooxazolidin-3-yl)bicyclo[2.2.2]octan-1-yl)amino)nicotinamide A mixture of (R)-6-chloro-N-(2-fluoro-3-hydroxy-3-methylbutyl)-4-((4-(2-oxooxazolidin-3-yl)bicyclo[2.2.2]octan-1-yl)amino)nicotinamide (37 mg, 0.08 mmol), 7-(4,4,5,5-tetramethyl-1,3,2-dioxaborolan-2-yl)pyrrolo[1,2-b]pyridazine-3-carbonitrile (I-1) (43 mg, 0.16 mmol), XPhos Pd G3 (7 mg), and 2M Potassium phosphate tribasic (0.08 ml) in 1 mL DME was degassed with argon for 3 minutes, then capped and heated under microwave conditions at 120° C. for 20 minutes. The crude material was purified RP-HPLC (eluent: water/MeCN*0.1% TFA) to yield the product as a trifluoroacetate salt.

ES/MS: 453.2 (M+H+).

1H NMR (400 MHz, Chloroform-d) δ 8.38 (d, J=0.9 Hz, 1H), 8.32-8.25 (m, 2H), 8.19 (dd, J=2.3, 0.9 Hz, 1H), 7.73 (dd, J=4.8, 1.0 Hz, 1H), 6.93 (dd, J=4.8, 0.9 Hz, 1H), 4.46-4.24 (m, 1H), 4.19 (dd, J=8.9, 6.8 Hz, 2H), 3.85 (ddd, J=30.8, 14.6, 3.0 Hz, 1H), 3.61-3.56 (m, 2H), 3.48-3.40 (m, 1H), 2.11 (s, 12H), 1.28-1.19 (m, 6H).

Procedure 51: Example 416

6-(3-cyanopyrrolo[1,2-b]pyridazin-7-yl)-N-((R)-2-fluoro-3-hydroxy-3-methylbutyl)-4-((4-(methylcarbamoyl)bicyclo[2.2.2]octan-1-yl)amino)nicotinamide

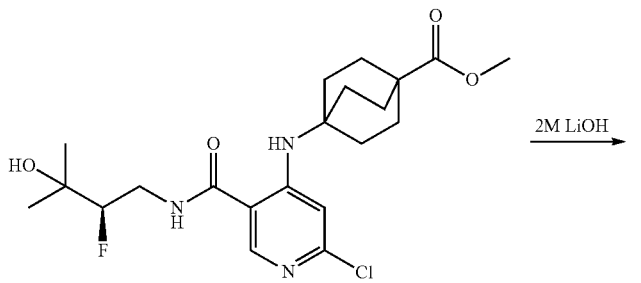

2M LiOH

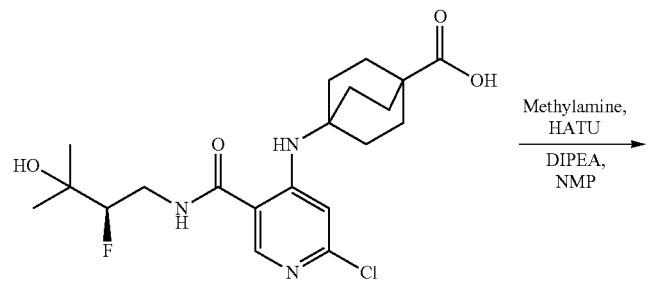

Methylamine, HATU
DIPEA, NMP

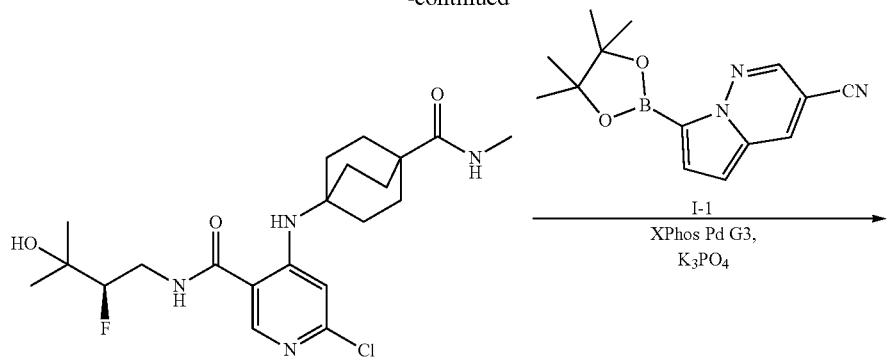

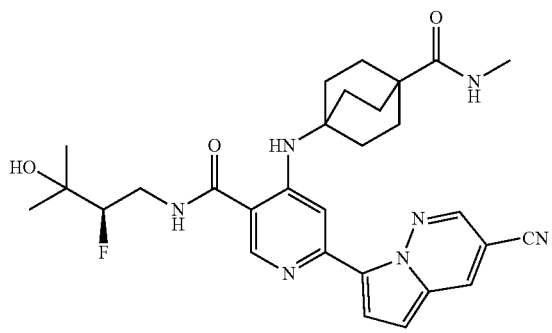

Example 416

(R)-4-((2-chloro-5-((2-fluoro-3-hydroxy-3-methyl-butyl)carbamoyl)pyridin-4-yl)amino)bicyclo[2.2.2]octane-1-carboxylic acid Methyl (R)-4-((2-chloro-5-((2-fluoro-3-hydroxy-3-methylbutyl)carbamoyl)pyridin-4-yl)amino)bicyclo[2.2.2]octane-1-carboxylate (800 mg, 2 mmol) was dissolved in 2 mL of THF and 1 mL of MeOH. Lithium hydroxide (43.5 mg, 2 mmol) was added and the mixture was stirred at room temperature. Upon completion, solvent was removed under reduced pressure and 1N HCl was added. The product was extracted into ethyl acetate. Upon removal of the solvent under reduced pressure, the crude product was obtained and used without further purification.

ES/MS: 428.4 (M+H+).

(R)-6-Chloro-N-(2-fluoro-3-hydroxy-3-methylbutyl)-4-((4-(methylcarbamoyl)bicyclo[2.2.2]octan-1-yl)amino)nicotinamide A mixture of (R)-4-((2-chloro-5-((2-fluoro-3-hydroxy-3-methylbutyl)carbamoyl)pyridin-4-yl)amino)bicyclo[2.2.2]octane-1-carboxylic acid (30 mg, 0.07 mmol), methylamine (2M in THF, 11 mg, 0.35 mmol), 1-[Bis(dimethylamino)methylene]-1H-1,2,3-triazolo[4,5-b]pyridinium 3-oxid hexafluorophosphate (53.3 mg, 0.14 mmol) and N,N-diisopropylethylamine (0.09 ml, 0.49 mmol) in 1 mL of DMF was stirred at room temperature for 1 hour. The reaction was diluted with EtOAc and washed with aqueous sodium bicarbonate (2×). The organic layer was dried over sodium sulfate and concentrated to dryness. The crude material was used directly in the next step.

ES/MS: 441.3 (M+H+).

6-(3-cyanopyrrolo[1,2-b]pyridazin-7-yl)-N-((R)-2-fluoro-3-hydroxy-3-methylbutyl)-4-((4-(methylcarbamoyl)bicyclo[2.2.2]octan-1-yl)amino)nicotinamide A mixture of (R)-6-chloro-N-(2-fluoro-3-hydroxy-3-methylbutyl)-4-((4-(methylcarbamoyl)bicyclo[2.2.2]octan-1-yl)amino)nicotinamide (31 mg, 0.07 mmol), 7-(4,4,5,5-tetramethyl-1,3,2-dioxaborolan-2-yl)pyrrolo[1,2-b]pyridazine-3-carbonitrile (I-1) (38 mg, 0.14 mmol), XPhos Pd G3 (7 mg), and 2M Potassium phosphate tribasic (0.07 ml) in 1 mL DME was degassed with argon for 3 minutes, then capped and heated under microwave conditions at 120° C. for 20 minutes. The crude material was purified RP-HPLC (eluent: water/MeCN*0.1% TFA) to yield the product as a trifluoroacetate salt.

ES/MS: 548.4 (M+H+).

1H NMR (400 MHz, Methanol-d4) δ 8.76 (s, 2H), 8.54 (s, 1H), 8.45 (s, 1H), 7.93 (d, J=5.1 Hz, 1H), 7.22 (d, J=5.1 Hz, 1H), 4.40 (dd, J=48.7, 9.0 Hz, 1H), 3.91 (dd, J=36.5, 14.5 Hz, 1H), 3.72 (p, J=6.6 Hz, 1H), 3.56-3.40 (m, 1H), 2.73 (d, J=3.8 Hz, 3H), 2.18 (t, J=7.8 Hz, 6H), 2.02 (t, J=7.4 Hz, 6H), 1.28 (d, J=1.7 Hz, 6H).

Procedure 52: Example 405

6-(3-cyanopyrrolo[1,2-b]pyridazin-7-yl)-N-((R)-2-fluoro-3-hydroxy-3-methylbutyl)-4-((4-(2-oxoazetidin-1-yl)bicyclo[2.2.2]octan-1-yl)amino)nicotinamide

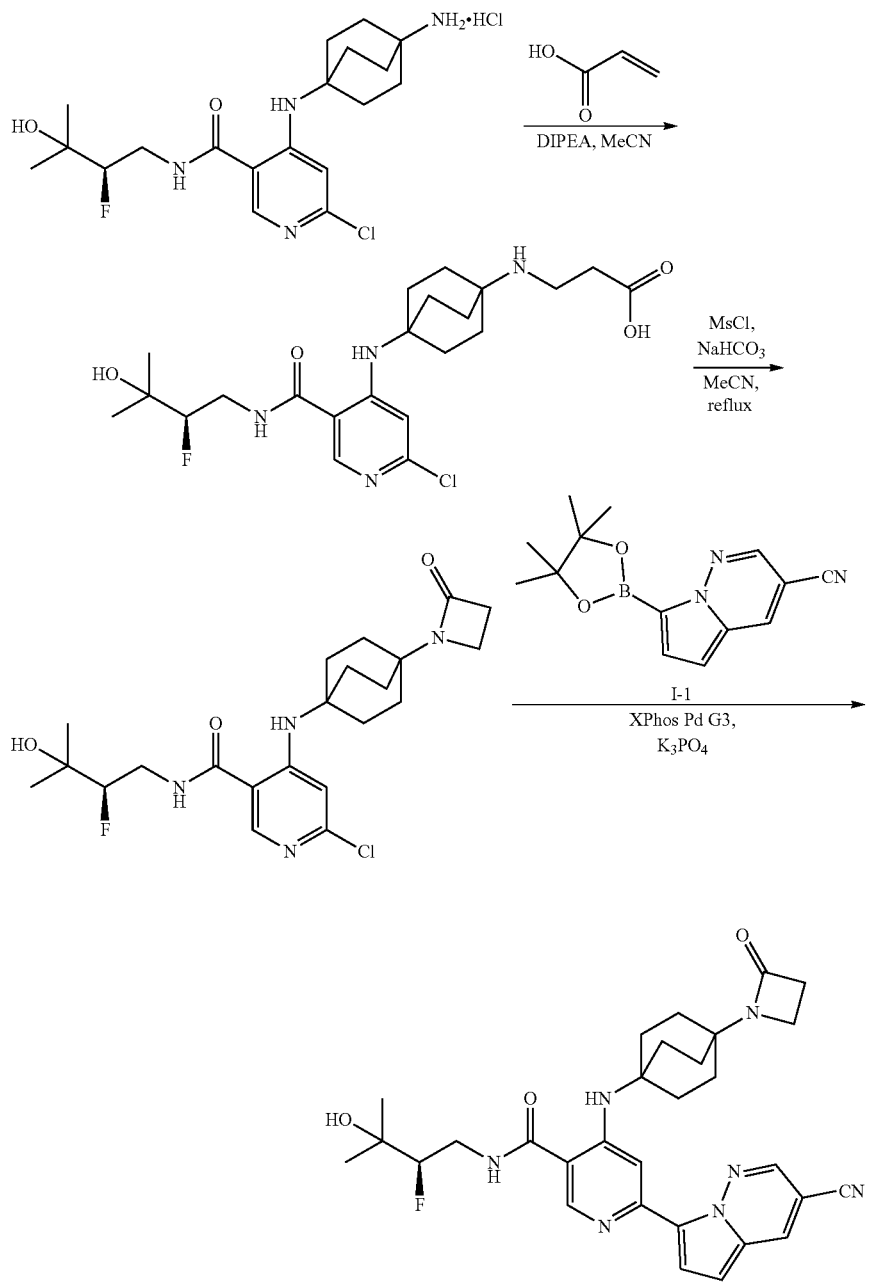

Example 405

(R)-3-((4-((2-chloro-5-((2-fluoro-3-hydroxy-3-methylbutyl)carbamoyl)pyridin-4-yl)amino)bicyclo[2.2.2]octan-1-yl)amino)propanoic acid To a solution of (R)-4-((4-aminobicyclo[2.2.2]octan-1-yl)amino)-6-chloro-N-(2-fluoro-3-hydroxy-3-methylbutyl)nicotinamide hydrochloride (300 mg, 0.69 mmol) in MeCN (4 mL) was added acrylic acid (497 mg, 6.9 mmol) and diisopropylethylamine (891 mg, 6.9 mmol). The reaction was heated to 80° C. for 4 hours. The solvent was removed in vacuo and crude material was dried by high vacuum overnight to provide the desired product which was used without further purification.

ES/MS: 471.2 (M+H+).

(R)-6-chloro-N-(2-fluoro-3-hydroxy-3-methylbutyl)-4-((4-(2-oxoazetidin-1-yl)bicyclo[2.2.2]octan-1-yl)amino)nicotinamide To a suspension of (R)-3-((4-((2-chloro-5-((2-fluoro-3-hydroxy-3-methylbutyl)carbamoyl)pyridin-4-yl)amino)bicyclo[2.2.2]octan-1-yl)amino)propanoic acid (250 mg, 0.53 mmol) and Sodium bicarbonate (1646 mg, 26.5 mmol) in MeCN (30 mL) was added methanesulfonyl chloride (608 mg, 5.3 mmol). The mixture was heated to reflux for overnight, cooled to room temperature and concentrated in vacuo. The crude material was purified RP-HPLC (eluent: water/MeCN*0.1% TFA) to yield the product as a trifluoroacetate salt.

ES/MS: 453.3 (M+H+).

6-(3-cyanopyrrolo[1,2-b]pyridazin-7-yl)-N-((R)-2-fluoro-3-hydroxy-3-methylbutyl)-4-((4-(2-oxoazetidin-1-yl)bicyclo[2.2.2]octan-1-yl)amino)nicotinamide A mixture of (R)-6-chloro-N-(2-fluoro-3-hydroxy-3-methylbutyl)-4-((4-(2-oxoazetidin-1-yl)bicyclo[2.2.2]octan-1-yl)amino)nicotinamide (12 mg, 0.026 mmol), 7-(4,4,5,5-tetramethyl-1,3,2-dioxaborolan-2-yl)pyrrolo[1,2-b]pyridazine-3-carbonitrile (I-1) (14.3 mg, 0.053 mmol), XPhos Pd G3 (3 mg), and 2M Potassium phosphate tribasic (0.03 ml) in 1 mL DME was degassed with argon for 3 minutes, then capped and heated under microwave conditions at 120° C. for 20 minutes. The crude material was purified RP-HPLC (eluent: water/MeCN*0.1% TFA) to yield the product as a trifluoroacetate salt.

ES/MS: 560.4 (M+H+).

1H NMR (400 MHz, Methanol-d4) δ 8.85-8.69 (m, 2H), 8.54 (s, 1H), 8.35 (s, 1H), 7.93 (d, J=5.0 Hz, 1H), 7.22 (d, J=5.1 Hz, 1H), 4.40 (ddd, J=49.1, 9.4, 2.1 Hz, 1H), 3.91 (ddd, J=36.5, 14.5, 2.1 Hz, 1H), 3.46 (ddd, J=15.7, 14.6, 9.4 Hz, 1H), 2.79 (t, J=4.0 Hz, 2H), 2.19 (dt, J=24.1, 6.2 Hz, 12H), 1.28 (d, J=1.7 Hz, 6H).

Procedure 53: Example 417 and Example 418

4-((3-cyanopyrrolo[1,2-b]pyridazin-7-yl)-5-(((R)-2-fluoro-3-hydroxy-3-methylbutyl)carbamoyl)pyridin-4-yl)amino)bicyclo[2.2.2]octan-1-yl acetate and 4-((5-(((R)-3-acetoxy-2-fluoro-3-methylbutyl)carbamoyl)-2-(3-cyanopyrrolo[1,2-b]pyridazin-7-yl)pyridin-4-yl)amino)bicyclo[2.2.2]octan-1-yl acetate

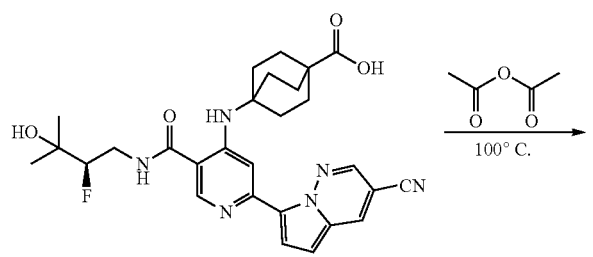

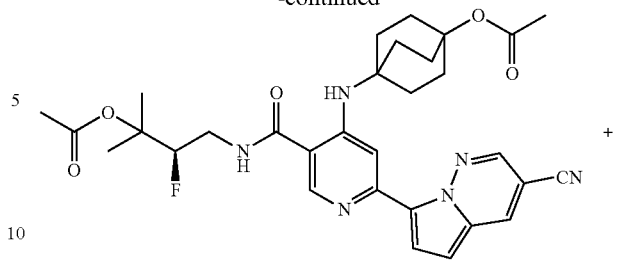

Example 417

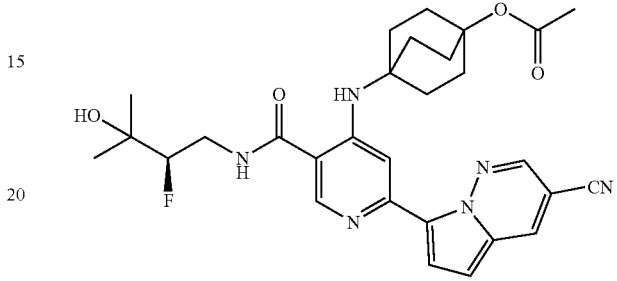

Example 418

4-((2-(3-cyanopyrrolo[1,2-b]pyridazin-7-yl)-5-(((R)-2-fluoro-3-hydroxy-3-methylbutyl)carbamoyl)pyridin-4-yl)amino)bicyclo[2.2.2]octan-1-yl acetate and 4-((5-(((R)-3-acetoxy-2-fluoro-3-methylbutyl)carbamoyl)-2-(3-cyanopyrrolo[1,2-b]pyridazin-7-yl)pyridin-4-yl)amino)bicyclo[2.2.2]octan-1-yl acetate 6-(3-cyanopyrrolo[1,2-b]pyridazin-7-yl)-N-((R)-2-fluoro-3-hydroxy-3-methylbutyl)-4-((4-hydroxybicyclo[2.2.2]octan-1-yl)amino)nicotinamide (130 mg, 0.26 mmol) in acetic anhydride (3 mL), was heated to 100° C. for 8 hours. The solvent was removed in vacuo and the crude material was purified RP-HPLC (eluent: water/MeCN*0.1% TFA) to yield the products as trifluoroacetate salts.

4-((5-(((R)-3-acetoxy-2-fluoro-3-methylbutyl)carbamoyl)-2-(3-cyanopyrrolo[1,2-b]pyridazin-7-yl)pyridin-4-yl)amino)bicyclo[2.2.2]octan-1-yl acetate

Example 417

ES/MS: 591.4 (M+H+).

1H NMR (400 MHz, Methanol-d4) δ 8.76 (d, J=2.2 Hz, 1H), 8.72 (d, J=2.2 Hz, 1H), 8.56 (s, 1H), 8.31 (s, 1H), 7.94 (d, J=5.1 Hz, 1H), 7.22 (d, J=5.1 Hz, 1H), 4.74 (dd, J=9.4, 2.0 Hz, 1H), 3.88 (ddd, J=36.8, 14.6, 2.0 Hz, 1H), 3.50 (ddd, J=16.3, 14.6, 9.4 Hz, 1H), 2.28 (s, 12H), 2.01 (s, 3H), 1.56 (d, J=1.7 Hz, 6H).

4-((2-(3-cyanopyrrolo[1,2-b]pyridazin-7-yl)-5-(((R)-2-fluoro-3-hydroxy-3-methylbutyl)carbamoyl)pyridin-4-yl)amino)bicyclo[2.2.2]octan-1-yl acetate

Example 418

ES/MS: 548.4 (M+H+).

1H NMR (400 MHz, Methanol-d4) δ 8.75 (d, J=2.2 Hz, 1H), 8.72 (d, J=2.2 Hz, 1H), 8.55 (s, 1H), 8.30 (s, 1H), 7.94 (d, J=5.0 Hz, 1H), 7.22 (d, J=5.1 Hz, 1H), 4.40 (ddd, J=49.1, 9.4, 2.1 Hz, 1H), 3.90 (ddd, J=36.5, 14.5, 2.1 Hz, 1H), 3.55-3.38 (m, 1H), 2.28 (s, 12H), 1.97 (s, 3H), 1.28 (d, J=1.7 Hz, 6H).

Procedure 54: Example 414

6-(3-cyanopyrrolo[1,2-b]pyridazin-7-yl)-N-((R)-2-fluoro-3-hydroxy-3-methylbutyl)-4-((4-methoxybicyclo[2.2.2]octan-1-yl)amino)nicotinamide

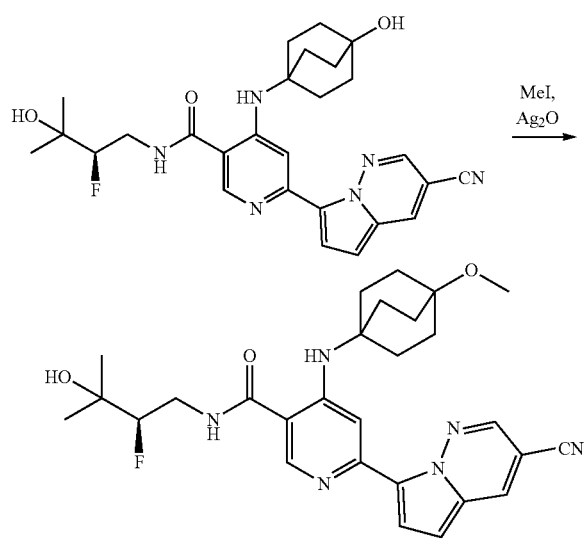

Example 414

6-(3-cyanopyrrolo[1,2-b]pyridazin-7-yl)-N-((R)-2-fluoro-3-hydroxy-3-methylbutyl)-4-((4-methoxybicyclo[2.2.2]octan-1-yl)amino)nicotinamide To a suspension of 6-(3-cyanopyrrolo[1,2-b]pyridazin-7-yl)-N-((R)-2-fluoro-3-hydroxy-3-methylbutyl)-4-((4-hydroxybicyclo[2.2.2]octan-1-yl)amino)nicotinamide (25 mg, 0.049 mmol) in acetonitrile (1 mL) were added Iodomethane (70 mg, 0.5 mmol) and Silver(I) oxide (22.9, 0.1 mmol). The mixture was stirred for overnight, filtered and concentrated. The crude material was purified RP-HPLC (eluent: water/MeCN*0.1% TFA) to yield the product as a trifluoroacetate salt.

ES/MS: 521.2 (M+H+).

1H NMR (400 MHz, Chloroform-d) δ 8.43 (d, J=1.5 Hz, 1H), 8.38-8.23 (m, 2H), 8.20 (d, J=2.2 Hz, 1H), 7.90 (dd, J=4.9, 2.2 Hz, 1H), 6.98 (d, J=4.9 Hz, 1H), 4.74-4.41 (m, 1H), 4.13-3.91 (m, 1H), 3.73-3.39 (m, 1H), 2.30-2.11 (m, 6H), 1.88 (dq, J=7.5, 4.5, 4.0 Hz, 6H), 1.33-1.22 (m, 6H).

Procedure 55: Example 386

6-(3-cyanopyrrolo[1,2-b]pyridazin-7-yl)-N-(5-cyanopyridin-2-yl)-4-(((1S,3R)-3-hydroxycyclohexyl)amino)nicotinamide

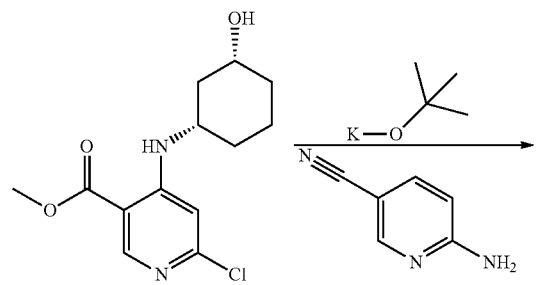

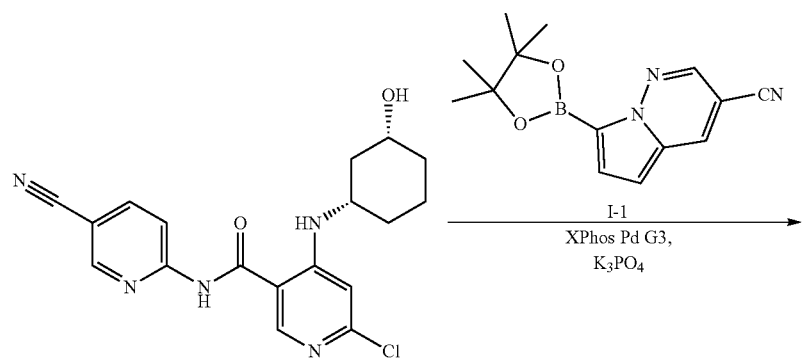

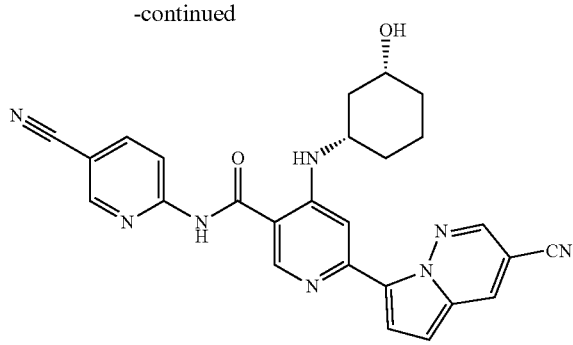

Example 386

6-Chloro-N-(5-cyanopyridin-2-yl)-4-(((1S,3R)-3-hydroxycyclohexyl)amino)nicotinamide To a solution of methyl 6-chloro-4-(((1S,3R)-3-hydroxycyclohexyl)amino)nicotinate (78 mg, 0.27 mmol) and 6-aminonicotinonitrile (33 mg, 0.27 mmol) in THF (1 mL) was added potassium tert-butoxide (33.8 mg, 0.3 mmol). The mixture was stirred for 2 hours, acidified with 1 N HCl and concentrated in vacuo. The crude material was purified RP-HPLC (eluent: water/MeCN*0.1% TFA) to yield the product as a trifluoroacetate salt.
ES/MS: 372.2 (M+H+).

6-(3-cyanopyrrolo[1,2-b]pyridazin-7-yl)-N-(5-cyanopyridin-2-yl)-4-(((1S,3R)-3-hydroxycyclohexyl)amino)nicotinamide A mixture of (R)-6-chloro-N-(2-fluoro-3-hydroxy-3-methylbutyl)-4-((4-(2-oxoazetidin-1-yl)bicyclo[2.2.2]octan-1-yl)amino)nicotinamide (13 mg, 0.035 mmol), 7-(4,4,5,5-tetramethyl-1,3,2-dioxaborolan-2-yl)pyrrolo[1,2-b]pyridazine-3-carbonitrile (I-1) (18.8 mg, 0.7 mmol), XPhos Pd G3 (5 mg), and 2M Potassium phosphate tribasic (0.035 ml) in 1 mL DME was degassed with argon for 3 minutes, then capped and heated under microwave conditions at 120° C. for 20 minutes. The crude material was purified RP-HPLC (eluent: water/MeCN*0.1% TFA) to yield the product as a trifluoroacetate salt.
ES/MS: 479.3 (M+H+).
1H NMR (400 MHz, Methanol-d4) δ 8.80 (s, 1H), 8.77 (d, J=2.2 Hz, 1H), 8.75 (dd, J=2.3, 0.9 Hz, 1H), 8.68 (d, J=2.2 Hz, 1H), 8.38 (dd, J=8.8, 0.9 Hz, 1H), 8.20 (dd, J=8.8, 2.3 Hz, 1H), 8.06 (d, J=5.1 Hz, 1H), 8.01 (s, 1H), 7.23 (d, J=5.1 Hz, 1H), 4.27 (dt, J=9.6, 5.3 Hz, 1H), 4.14 (s, 1H), 2.18-1.84 (m, 2H), 1.83-1.68 (m, 4H), 1.46-1.23 (m, 2H).

Procedure 56: Example 412

(R)-4-((2-(3-cyanopyrrolo[1,2-b]pyridazin-7-yl)-5-((2-fluoro-3-hydroxy-3-methylbutyl)carbamoyl)pyridin-4-yl)amino)bicyclo[2.2.2]octan-1-yl methylcarbamate

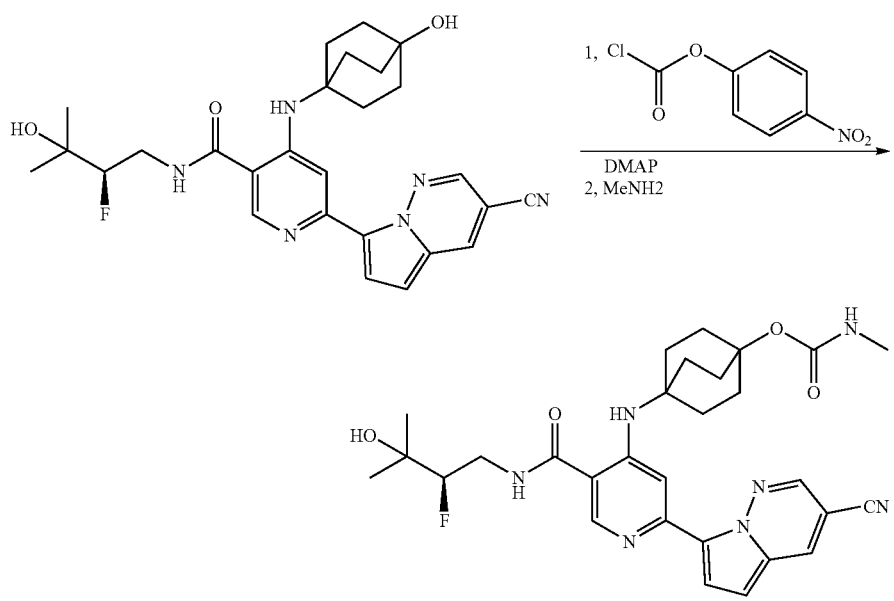

Example 412

201

(R)-4-((2-(3-cyanopyrrolo[1,2-b]pyridazin-7-yl)-5-((2-fluoro-3-hydroxy-3-methylbutyl)carbamoyl)pyridin-4-yl)amino)bicyclo[2.2.2]octan-1-yl methylcarbamate To a solution of (R)-6-(3-cyanopyrrolo[1,2-b]pyridazin-7-yl)-N-(2-fluoro-3-hydroxy-3-methylbutyl)-4-((4-hydroxybicyclo[2.2.2]octan-1-yl)amino)nicotinamide (100 mg, 0.2 mmol), 4-nitrophenyl carbonochloridate (120 mg, 0.6 mmol) and 4-(Dimethylamino)pyridine (73 mg, 0.6 mmol) in DCM (1 mL) and pyridine (2 mL), was stirred at r.t. for overnight. Methylamine was added to the mixture. Removed the solvent and the crude material was purified RP-HPLC (eluent: water/MeCN*0.1% TFA) to yield the product as a trifluoroacetate salt.

202

ES/MS: 564.5 (M+H+).
1H NMR (400 MHz, Methanol-d4) δ 8.75 (s, 2H), 8.55 (s, 1H), 8.36 (s, 1H), 7.94 (d, J=5.1 Hz, 1H), 7.22 (d, J=5.1 Hz, 1H), 4.40 (ddd, J=49.1, 9.4, 2.1 Hz, 1H), 3.90 (ddd, J=36.4, 14.6, 2.2 Hz, 1H), 3.47 (ddd, J=16.0, 14.5, 9.4 Hz, 1H), 2.64 (s, 3H), 2.26 (s, 12H), 1.28 (d, J=1.7 Hz, 6H).

Procedure 57: Examples 528 and 529

6-(3-cyanopyrrolo[1,2-b]pyridazin-7-yl)-N-((R)-2-fluoro-3-hydroxy-3-methylbutyl)-4-(((1S)-3-hydroxy-3-methylcyclohexyl)amino)nicotinamide

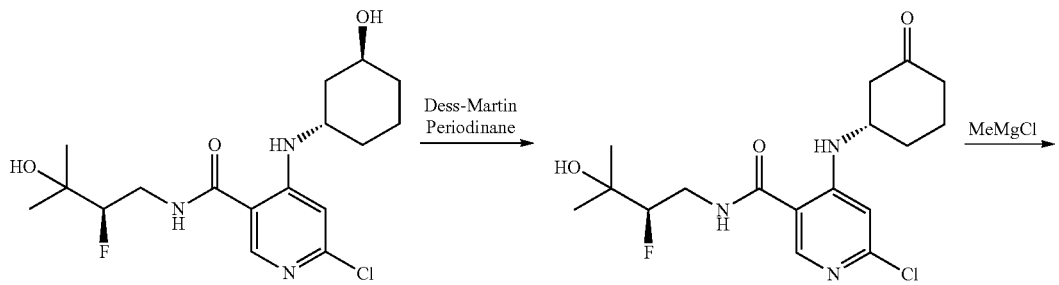

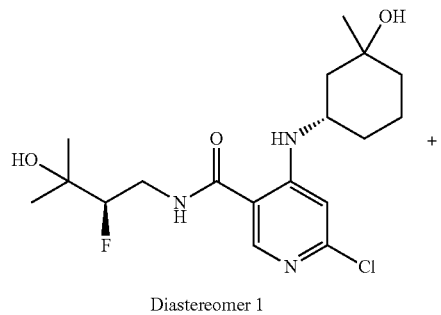

Diastereomer 1

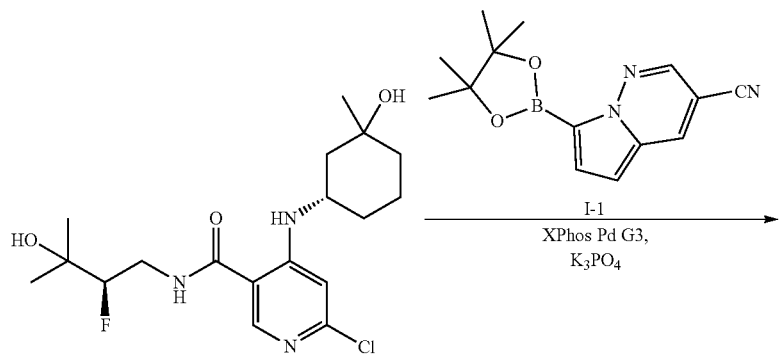

Diastereomer 2

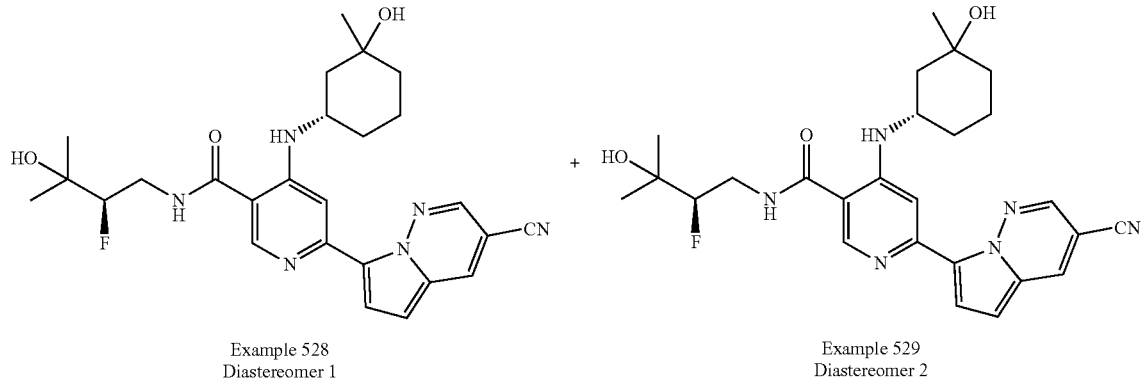

Example 528
Diastereomer 1

Example 529
Diastereomer 2

6-chloro-N-((R)-2-fluoro-3-hydroxy-3-methylbutyl)-4-(((S)-3-oxocyclohexyl)amino)nicotinamide 6-chloro-N-((R)-2-fluoro-3-hydroxy-3-methylbutyl)-4-(((1S,3S)-3-hydroxycyclohexyl)amino)nicotinamide (0.30 g, 0.80 mmol) was dissolved in DCM (6 mL) after which Dess-Martin periodinane (0.41 g, 0.96 mmol) was added as a single portion and the resulting mixture stirred at room temperature. After 30 minutes, the reaction mixture was poured into saturated aqueous NaHCO$_3$ solution (20 mL) and extracted twice with EtOAc (2×25 mL). The organic layers were dried over MgSO$_4$, filtered and concentrated. The resulting material was purified by silica gel chromatography (eluent: EtOAc/hexanes) to provide the desired product.
ES/MS: 372.2 [M+H$^+$].

6-chloro-N-((R)-2-fluoro-3-hydroxy-3-methylbutyl)-4-(((1S)-3-hydroxy-3-methylcyclohexyl)amino)nicotinamide 6-chloro-N-((R)-2-fluoro-3-hydroxy-3-methylbutyl)-4-(((S)-3-oxocyclohexyl)amino)nicotinamide (0.20 g, 0.54 mmol) was dissolved in THF (5 mL) and brought to 0° C. using an ice/water bath. MeMgCl (3.0M in THF, 0.72 mL, 2.2 mmol) was then added dropwise at 0° C. After 30 minutes, the reaction mixture was carefully quenched with water (1 mL) allowed to warm to room temperature and poured into water (10 mL). The resulting mixture was extracted with EtOAc (2×25 mL) and the combined organics dried over MgSO$_4$, filtered and concentrated. The resulting material was purified by silica gel chromatography (eluent: EtOAc/hexanes) to provide the desired products with one diastereomer eluting as a mixture with unreacted starting ketone and the second diastereomer isolated pure.
ES/MS: 388.3 [M+H$^+$]

6-(3-cyanopyrrolo[1,2-b]pyridazin-7-yl)-N-((R)-2-fluoro-3-hydroxy-3-methylbutyl)-4-(((1S)-3-hydroxy-3-methylcyclohexyl)amino)nicotinamide (Examples 528 and 529)

Each isomer of 6-chloro-N-((R)-2-fluoro-3-hydroxy-3-methylbutyl)-4-(((1S)-3-hydroxy-3-methylcyclohexyl)amino)nicotinamide was separately elaborated to final compounds (Example 528 and Example 529) as described for the final step of Procedure 1 substituting 6-chloro-N-((R)-2-fluoro-3-hydroxy-3-methylbutyl)-4-(((1S)-3-hydroxy-3-methylcyclohexyl)amino)nicotinamide for (R)-6-chloro-N-(2-fluoro-3-hydroxy-3-methylbutyl)-4-((3-methyloxetan-3-yl)amino)nicotinamide.

Example 528

ES/MS: 495.4 [M+H$^+$].
1H NMR (400 MHz, Methanol-d4) δ 8.74 (d, J=2.2 Hz, 1H), 8.64 (d, J=2.2 Hz, 1H), 8.46 (s, 1H), 7.97 (d, J=5.1 Hz, 1H), 7.80 (s, 1H), 7.20 (d, J=5.0 Hz, 1H), 4.42 (ddd, J=49.0, 9.3, 2.1 Hz, 1H), 4.28-4.13 (m, 1H), 4.04-3.81 (m, 1H), 3.52-3.36 (m, 1H), 2.04-1.85 (m, 2H), 1.85-1.65 (m, 3H), 1.62-1.48 (m, 1H), 1.29 (s, 3H), 1.28 (d, J=1.7 Hz, 6H).

Example 529

ES/MS: 495.4 [M+H$^+$].
1H NMR (400 MHz, Methanol-d4) δ 8.74 (d, J=2.2 Hz, 1H), 8.65 (d, J=2.2 Hz, 1H), 8.55 (s, 1H), 8.04 (d, J=5.0 Hz, 1H), 7.89 (s, 1H), 7.21 (d, J=5.1 Hz, 1H), 4.41 (ddd, J=49.1, 9.4, 2.1 Hz, 1H), 4.18-4.04 (m, 1H), 4.01-3.79 (m, 1H), 3.58-3.40 (m, 1H), 2.22-2.02 (m, 2H), 2.00-1.82 (m, 1H), 1.78-1.65 (m, 2H), 1.53-1.32 (m, 3H), 1.30-1.25 (m, 9H).

Procedure 58: Example 524

6-(3-cyanopyrrolo[1,2-b]pyridazin-7-yl)-N-((R)-2-fluoro-3-hydroxy-3-methylbutyl)-4-(((1S,3R)-3-morpholinocyclohexyl)amino)nicotinamide

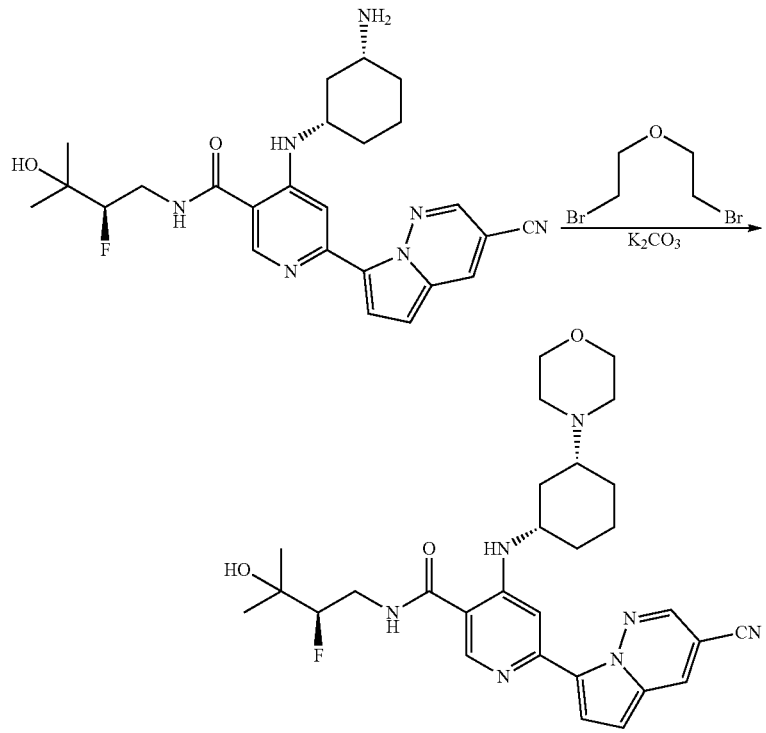

Example 524

6-(3-cyanopyrrolo[1,2-b]pyridazin-7-yl)-N-((R)-2-fluoro-3-hydroxy-3-methylbutyl)-4-(((1S,3R)-3-morpholinocyclohexyl)amino)nicotinamide 4-(((1S,3R)-3-aminocyclohexyl)amino)-6-(3-cyanopyrrolo[1,2-b]pyridazin-7-yl)-N—((R)-2-fluoro-3-hydroxy-3-methylbutyl)nicotinamide (27 mg, TFA salt, 0.045 mmol) (obtained as described in Procedure 14 substituting tert-butyl ((1R,3S)-3-((2-(3-cyanopyrrolo[1,2-b]pyridazin-7-yl)-5-(((R)-2-fluoro-3-hydroxy-3-methylbutyl)carbamoyl)pyridin-4-yl)amino)cyclohexyl)carbamate for (1R,3r,5S)-3-((2-(3-cyanopyrrolo[1,2-b]pyridazin-7-yl)-5-(((R)-2-fluoro-3-hydroxy-3-methylbutyl)carbamoyl)pyridin-4-yl)amino)-8-azabicyclo[3.2.1]octane-8-carboxylate) was dissolved in acetonitrile (1 mL) after which potassium carbonate (31 mg, 0.23 mmol) and 1-Bromo-2-(2-bromoethoxy)ethane (13 mg, 0.057 mmol) were then added. The reaction vial was sealed and heated to 80° C. for 18 hours. The reaction mixture was partitioned between EtOAc and water. The layers were separated and the water layer extracted twice more with EtOAc. The organic layers were then combined, dried, filtered and concentrated with the resulting crude residue the purified by RP-HPLC (eluent: water/MeCN*0.1% TFA). The product fractions were combined and lyophilized to give the final product.

ES/MS: 550.3 [M+H$^+$].

1H NMR (400 MHz, Methanol-d4) δ 8.77 (d, J=2.2 Hz, 1H), 8.67 (d, J=2.2 Hz, 1H), 8.62 (s, 1H), 8.03 (d, J=5.0 Hz, 1H), 7.88 (s, 1H), 7.22 (d, J=5.1 Hz, 1H), 4.41 (ddd, J=49.1, 9.4, 2.0 Hz, 1H), 4.23-3.98 (m, 4H), 3.99-3.83 (m, 1H), 3.82-3.70 (m, 4H), 3.58-3.42 (m, 3H), 2.64-2.54 (m, 1H), 2.29-2.17 (m, 2H), 2.17-2.05 (m, 1H), 1.79-1.38 (m, 4H), 1.28 (d, J=1.6 Hz, 6H).

Procedure 59: Examples 515, 516, and 517

6-(3-cyanopyrrolo[1,2-b]pyridazin-7-yl)-N—((R)-2-fluoro-3-hydroxy-3-methylbutyl)-4-((3-(methylsulfonyl)cyclohexyl)amino)nicotinamide

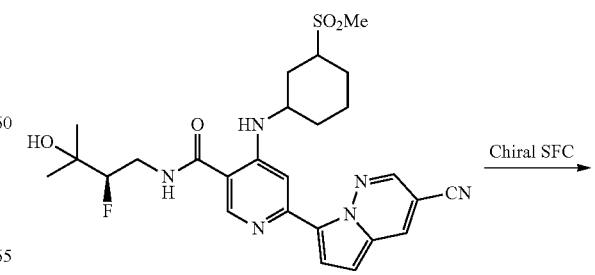

Chiral SFC

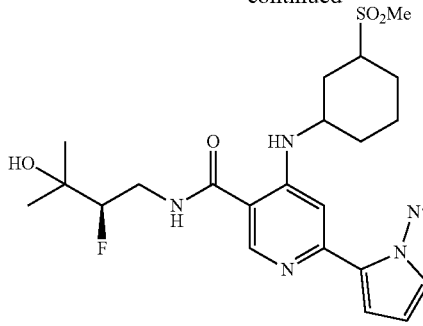

Example 515
Diastereomer 1

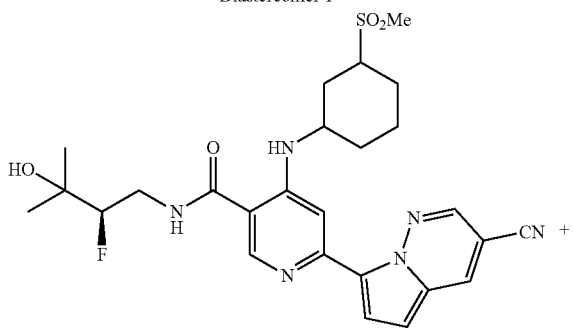

Example 516
Diastereomer 2, 3

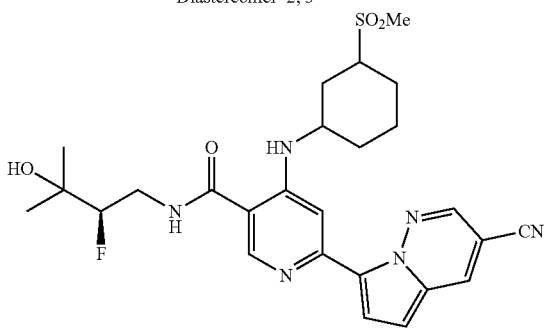

Example 517
Diastereomer 4

6-(3-cyanopyrrolo[1,2-b]pyridazin-7-yl)-N—((R)-2-fluoro-3-hydroxy-3-methylbutyl)-4-((3-(methylsulfonyl)cyclohexyl)amino)nicotinamide 6-(3-cyanopyrrolo[1,2-b]pyridazin-7-yl)-N—((R)-2-fluoro-3-hydroxy-3-methylbutyl)-4-((3-(methylsulfonyl)cyclohexyl)amino)nicotinamide (140 mg, 0.26 mmol) as a mixture of 4 diastereomers (obtained as described in Procedure 2 substituting 6-chloro-N—((R)-2-fluoro-3-hydroxy-3-methylbutyl)-4-((3-(methylsulfonyl)cyclohexyl)amino)nicotinamide for 2-fluoro-3-hydroxy-3-methylbutyl)-4-(((1S,3R)-3-hydroxycyclohexyl)amino)nicotinamide) was purified using chiral SFC to give two diastereomers pure and two diastereomers as a mixture.

Example 515

ES/MS: 543.5 [M+H$^+$].
1H NMR (400 MHz, Methanol-d4) δ 8.74 (d, J=2.2 Hz, 1H), 8.67 (d, J=2.2 Hz, 1H), 8.63 (s, 1H), 8.02 (d, J=5.1 Hz, 1H), 7.93 (s, 1H), 7.21 (d, J=5.1 Hz, 1H), 4.55-4.33 (m, 2H), 3.94 (ddd, J=36.6, 14.5, 2.1 Hz, 1H), 3.62-3.43 (m, 1H), 3.41-3.31 (m, 1H), 2.98 (s, 3H), 2.36-2.21 (m, 2H), 2.21-2.10 (m, 1H), 2.09-1.98 (m, 1H), 1.98-1.84 (m, 3H), 1.83-1.69 (m, 1H), 1.29 (d, J=1.6 Hz, 6H).

Example 516

ES/MS: 543.4 [M+H$^+$].

Example 517

ES/MS: 543.3 [M+H$^+$].
1H NMR (400 MHz, Methanol-d4) δ 8.75 (d, J=2.2 Hz, 1H), 8.69 (d, J=2.2 Hz, 1H), 8.59 (s, 1H), 7.99 (d, J=5.1 Hz, 1H), 7.94 (s, 1H), 7.21 (d, J=5.0 Hz, 1H), 4.57-4.30 (m, 1H), 4.06-3.83 (m, 2H), 3.62-3.41 (m, 1H), 3.37-3.31 (m, 1H), 2.96 (s, 3H), 2.70 (d, J=12.4 Hz, 1H), 2.35-2.01 (m, 3H), 1.80-1.41 (m, 4H), 1.28 (d, J=1.7 Hz, 6H).

Procedure 60: Example 510

(R)-6-(3-cyanopyrrolo[1,2-b]pyridazin-7-yl)-N-(2-fluoro-3-hydroxy-3-methylbutyl)-4-((6-hydroxy-6-methylspiro[3.3]heptan-2-yl)amino)nicotinamide

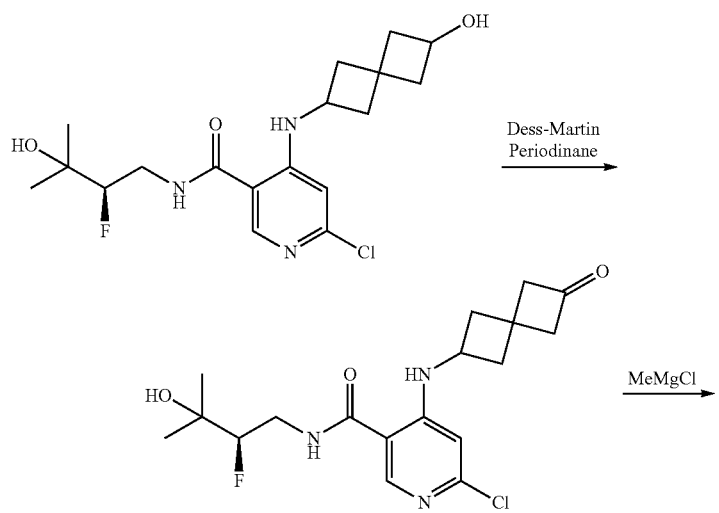

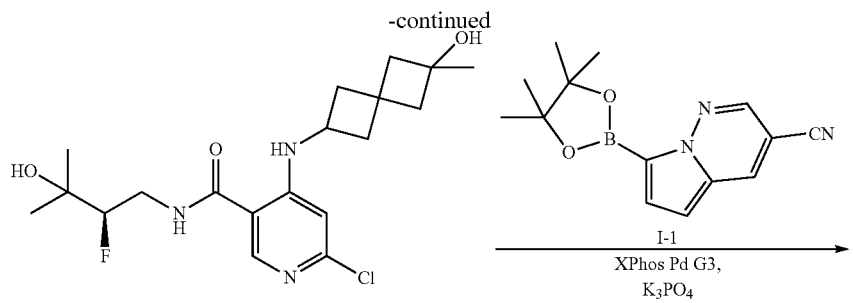

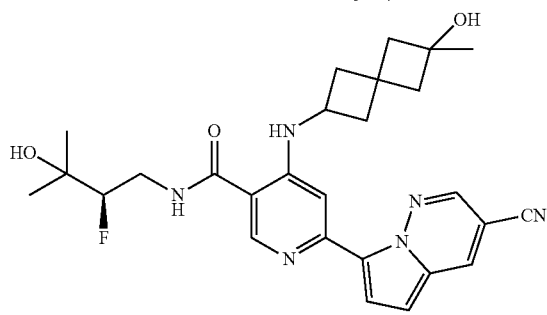

Example 510

(R)-6-chloro-N-(2-fluoro-3-hydroxy-3-methylbutyl)-4-((6-oxospiro[3.3]heptan-2-yl)amino)nicotinamide (R)-6-chloro-N-(2-fluoro-3-hydroxy-3-methylbutyl)-4-((6-hydroxyspiro[3.3]heptan-2-yl)amino)nicotinamide (0.20 g, 0.52 mmol) was dissolved in DCM (10 mL) after which Dess-Martin periodinane (0.26 g, 0.62 mmol) was added as a single portion and the resulting mixture stirred at room temperature. After 30 minutes, the reaction mixture was poured into saturated aqueous NaHCO$_3$ solution (20 mL) and extracted twice with EtOAc (2×25 mL). The organic layers were dried over MgSO$_4$, filtered and concentrated. The resulting material was purified by silica gel chromatography (eluent: EtOAc/hexanes) to provide the desired product.

ES/MS: 384.3 [M+H$^+$].

(R)-6-chloro-N-(2-fluoro-3-hydroxy-3-methylbutyl)-4-((6-hydroxy-6-methylspiro[3.3]heptan-2-yl)amino) nicotinamide (R)-6-chloro-N-(2-fluoro-3-hydroxy-3-methylbutyl)-4-((6-oxospiro[3.3]heptan-2-yl)amino)nicotinamide (0.14 g, 0.37 mmol) was dissolved in THF (5 mL) and brought to 0° C. using an ice/water bath. MeMgCl (3.0M in THF, 0.43 mL, 1.3 mmol) was then added dropwise at 0° C. After 30 minutes, the reaction mixture was carefully quenched with water (1 mL) allowed to warm to room temperature and poured into water (10 mL). The resulting mixture was extracted with EtOAc (2×25 mL) and the combined organics dried over MgSO$_4$, filtered and concentrated. The resulting material was purified by silica gel chromatography (eluent: EtOAc/hexanes) to provide the desired product.

ES/MS: 400.4 [M+H$^+$]

(R)-6-(3-cyanopyrrolo[1,2-b]pyridazin-7-yl)-N-(2-fluoro-3-hydroxy-3-methylbutyl)-4-((6-hydroxy-6-methylspiro[3.3]heptan-2-yl)amino)nicotinamide (Example 510)

(R)-6-chloro-N-(2-fluoro-3-hydroxy-3-methylbutyl)-4-((6-hydroxy-6-methylspiro[3.3]heptan-2-yl)amino)nicotinamide was elaborated to final compound (Example 510) as described for the final step of Procedure 1 substituting (R)-6-chloro-N-(2-fluoro-3-hydroxy-3-methylbutyl)-4-((6-hydroxy-6-methylspiro[3.3]heptan-2-yl)amino)nicotinamide for (R)-6-chloro-N-(2-fluoro-3-hydroxy-3-methylbutyl)-4-((3-methyloxetan-3-yl) amino)nicotinamide.

ES/MS: 507.3 [M+H$^+$].

1H NMR (400 MHz, Methanol-d4) δ 8.75 (d, J=2.1 Hz, 1H), 8.68 (d, J=2.1 Hz, 1H), 8.56 (s, 1H), 7.99 (d, J=5.1 Hz, 1H), 7.67 (s, 1H), 7.21 (d, J=5.1 Hz, 1H), 4.53-4.33 (m, 1H), 4.32-4.22 (m, 1H), 4.03-3.82 (m, 1H), 3.59-3.37 (m, 1H), 2.82-2.62 (m, 2H), 2.39-2.23 (m, 2H), 2.24-2.05 (m, 4H), 1.32 (s, 3H), 1.29 (d, J=1.6 Hz, 6H).

Procedure 61: Example 505

N-((1r,4S)-4-acrylamidocyclohexyl)-6-(3-cyanopyrrolo[1,2-b]pyridazin-7-yl)-4-(((1S,3R)-3-hydroxycyclohexyl)amino)nicotinamide

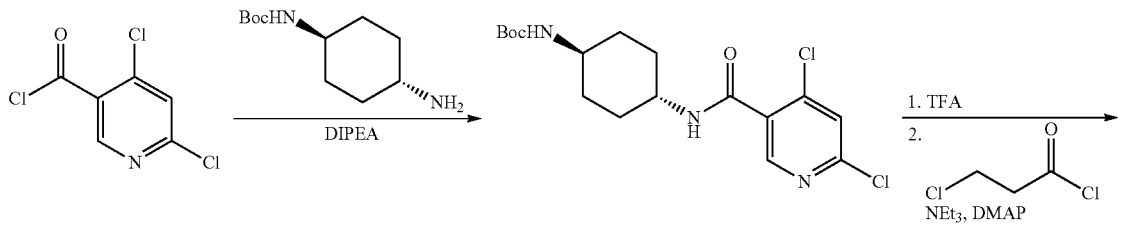

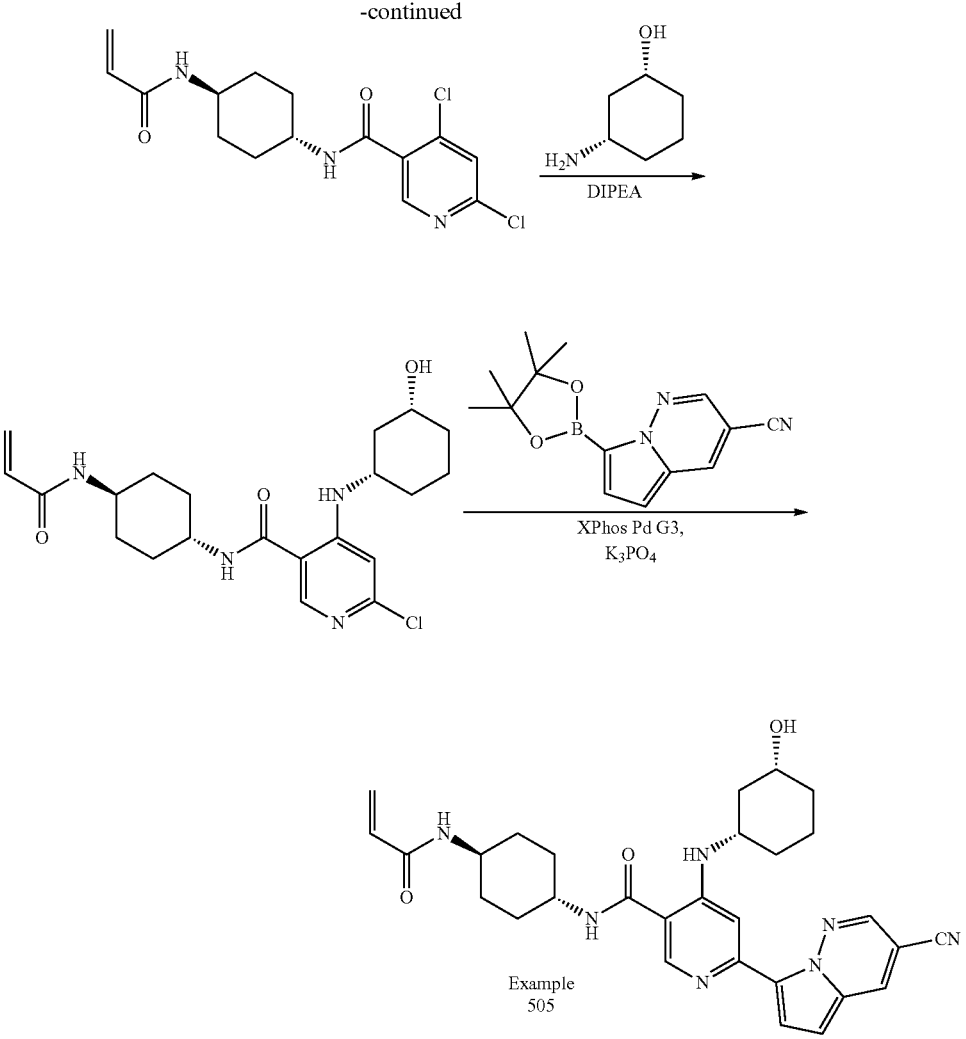

Tert-butyl ((1r,4r)-4-(4,6-dichloronicotinamido)cyclohexyl)carbamate 4,6-dichloronicotinoyl chloride (11.0 g, 52.1 mmol) was dissolved in DCM (150 mL) and added dropwise over 1 hr to a solution of tert-butyl ((1r,4r)-4-aminocyclohexyl)carbamate (11.7 g, 54.7 mmol) in DCM (100 mL) at 0° C. After 10 minutes the reaction mixture was added to a separator funnel and washed with 0.1N HCl (30 mL) then brine (30 mL). The organic layer was dried over MgSO$_4$, filtered and concentrated to give crude product. The crude product was triturated with hexanes/DCM (1:1) to give the desired compound which was used without further purification.

N-((1r,4r)-4-acrylamidocyclohexyl)-4,6-dichloronicotinamide

Tert-butyl ((1r,4r)-4-(4,6-dichloronicotinamido)cyclohexyl)carbamate (0.30 g, 0.77 mmol) was dissolved in DCM (2 mL) and TFA (1 mL) and stirred at 25° C. After 10 minutes the reaction mixture was concentrated directly to dryness. The amine intermediate was then taken up in DCM (6 mL) after which trimethylamine (0.32 mL, 2.3 mmol) and DMAP (4.7 mg, 0.038 mmol) were added and the resulting solution brought to 0° C. 3-chloropropanoyl chloride (0.081 mL, 0.85 mmol) was then added after which the cold bath was removed and the reaction mixture allowed to warm up to 25° C. over 1 hour. The reaction mixture was poured into water (5 mL) and extracted with EtOAc (3×5 mL). The combined organic layers were dried over MgSO$_4$, filtered, concentrated and purified by silica gel chromatography (eluent: EtOAc/hexanes) to provide the desired product.
ES/MS: 342.1 [M+H$^+$].

N-((1r,4S)-4-acrylamidocyclohexyl)-6-(3-cyanopyrrolo[1,2-b]pyridazin-7-yl)-4-(((1S,3R)-3-hydroxycyclohexyl)amino)nicotinamide (Example 505)

N-((1r,4r)-4-acrylamidocyclohexyl)-4,6-dichloronicotinamide was elaborated to final compound (Example 505) as described for the final 2 steps of Procedure 2 substituting N-((1r,4r)-4-acrylamidocyclohexyl)-4,6-dichloronicotinamide for (R)-4,6-dichloro-N-(2-fluoro-3-hydroxy-3-methylbutyl)nicotinamide.
ES/MS: 528.3 [M+H$^+$].
1H NMR (400 MHz, Methanol-d4) δ 8.74 (d, J=2.2 Hz, 1H), 8.65 (d, J=2.2 Hz, 1H), 8.55 (s, 1H), 8.01 (d, J=5.0 Hz, 1H), 7.90 (s, 1H), 7.21 (d, J=5.0 Hz, 1H), 6.28-6.14 (m, 2H), 5.65 (t, J=6.0 Hz, 1H), 4.31-4.15 (m, 1H), 4.15-4.03 (m, 1H), 3.95-3.82 (m, 1H), 3.82-3.66 (m, 1H), 2.12-1.96 (m, 6H), 1.97-1.84 (m, 1H), 1.82-1.73 (m, 1H), 1.73-1.63 (m, 4H), 1.62-1.30 (m, 4H).

Procedure 62: Example 501

(1R,3S)-3-((2-(3-cyanopyrrolo[1,2-b]pyridazin-7-yl)-5-(((R)-2-fluoro-3-hydroxy-3-methylbutyl)carbamoyl)pyridin-4-yl)amino)cyclohexyl acetate

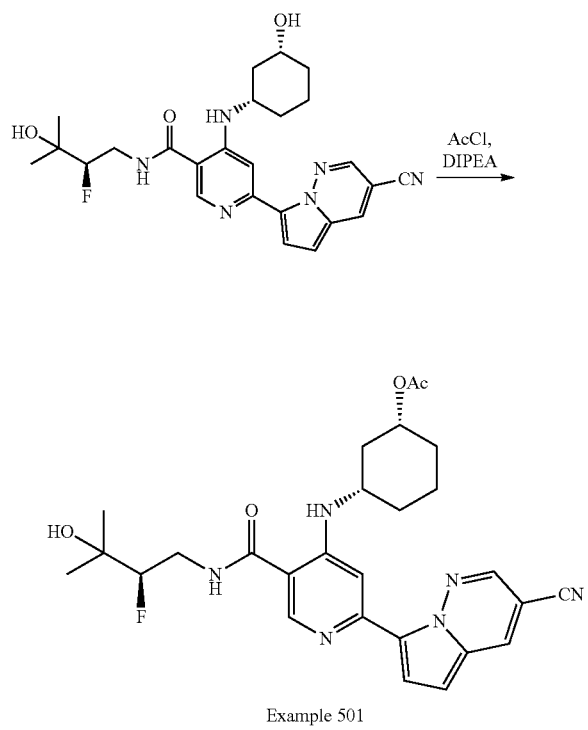

Example 501

N-((1r,4S)-4-acrylamidocyclohexyl)-6-(3-cyanopyrrolo[1,2-b]pyridazin-7-yl)-4-(((1S,3R)-3-hydroxycyclohexyl)amino)nicotinamide (Example 501)

6-(3-cyanopyrrolo[1,2-b]pyridazin-7-yl)-N—((R)-2-fluoro-3-hydroxy-3-methylbutyl)-4-(((1S,3R)-3-hydroxycyclohexyl)amino)nicotinamide (Example 2, 48 mg, 0.10 mmol) was dissolved in THF (1 mL) at 25° C. To this solution was added DIPEA (0.087 mL, 0.50 mmol) followed by acetic anhydride (0.094 mL, 1.0 mmol). After 15 minutes the reaction mixture was poured into water (3 mL, and extracted with EtOAc (3×5 mL). The combined organic layers were dried over MgSO4, filtered, concentrated and purified by silica gel chromatography (eluent: EtOAc/hexanes) to provide the desired product.

ES/MS: 523.3 [M+H$^+$].

1H NMR (400 MHz, Methanol-d4) δ 8.75 (d, J=2.2 Hz, 1H), 8.65 (d, J=2.2 Hz, 1H), 8.59 (s, 1H), 7.94 (d, J=5.1 Hz, 1H), 7.79 (s, 1H), 7.21 (d, J=5.1 Hz, 1H), 5.20-5.05 (m, 1H), 4.42 (ddd, J=49.1, 9.3, 2.1 Hz, 1H), 4.30-4.11 (m, 1H), 3.93 (ddd, J=36.4, 14.6, 2.1 Hz, 1H), 3.58-3.41 (m, 1H), 2.27-2.15 (m, 1H), 2.12-2.06 (m, 1H), 2.08 (s, 3H), 1.95-1.70 (m, 5H), 1.70-1.55 (m, 1H), 1.28 (d, J=1.6 Hz, 6H).

Procedure 63: Example 493

N-(2-acetamidothiazol-4-yl)-6-(3-cyanopyrrolo[1,2-b]pyridazin-7-yl)-4-(isopropylamino)nicotinamide

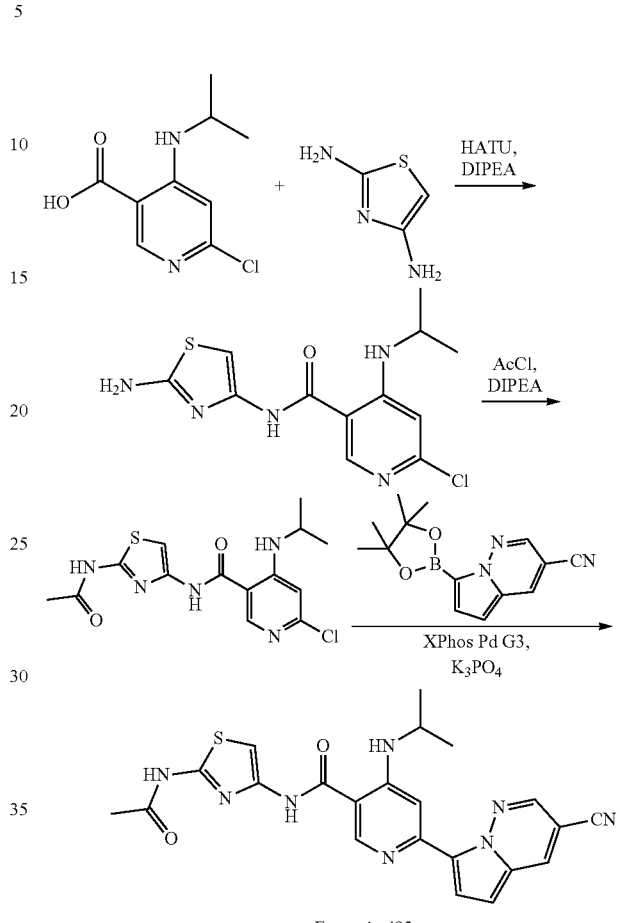

Example 493

N-(2-aminothiazol-4-yl)-6-chloro-4-(isopropylamino)nicotinamide

A mixture of 6-chloro-4-(isopropylamino)nicotinic acid (0.15 g, 0.70 mmol), 2,4-diamino thiazole hydrochloride (0.21 g, 1.4 mmol), 1-[Bis(dimethylamino)methylene]-1H-1,2,3-triazolo[4,5-b]pyridinium 3-oxid hexafluorophosphate (0.32 g, 0.84 mmol) and N,N-diisopropylethylamine (0.40 ml, 2.3 mmol) in 20 mL DMF was stirred at room temperature for 1 hour. Water was added, and the product was extracted into ethyl acetate. The ethyl acetate solution was concentrated under reduced pressure. The crude product was purified by silica gel chromatography (eluent: EtOAc/hexanes).

ES/MS: 312.1 (M+H$^+$).

N-(2-acetamidothiazol-4-yl)-6-chloro-4-(isopropylamino)nicotinamide

N-(2-aminothiazol-4-yl)-6-chloro-4-(isopropylamino)nicotinamide (50 mg, 0.16 mmol) was dissolved in DMF (1 mL) at 25° C. To this solution was added DIPEA (0.084 mL, 0.48 mmol) followed by acetyl chloride (0.013 mL, 0.18 mmol). After 30 minutes the reaction mixture was poured into water (3 mL, and extracted with EtOAc (3×5 mL). The combined organic layers were dried over MgSO4, filtered, concentrated and purified by silica gel chromatography (eluent: EtOAc/hexanes) to provide the desired product.

ES/MS: 354.3 (M+H$^+$).

215

N-(2-acetamidothiazol-4-yl)-6-(3-cyanopyrrolo[1,2-b]pyridazin-7-yl)-4-(isopropylamino)nicotinamide (Example 493)

N-(2-acetamidothiazol-4-yl)-6-chloro-4-(isopropylamino)nicotinamide was elaborated to final compound (Example 493) as described for the final step of Procedure 1 substituting N-(2-acetamidothiazol-4-yl)-6-chloro-4-(isopropylamino)nicotinamide for (R)-6-chloro-N-(2-fluoro-3-hydroxy-3-methylbutyl)-4-((3-methyloxetan-3-yl)amino) nicotinamide.

ES/MS: 461.3 [M+H$^+$].

1H NMR (400 MHz, Methanol-d4) δ 8.81 (s, 1H), 8.74 (d, J=2.1 Hz, 1H), 8.67 (d, J=2.2 Hz, 1H), 8.01 (d, J=5.1 Hz, 1H), 7.97 (s, 1H), 7.21 (d, J=5.1 Hz, 1H), 7.20 (s, 1H), 4.28-4.08 (m, 1H), 2.14 (s, 3H), 1.44 (d, J=6.4 Hz, 6H).

Procedure 64: Example 479

4-((3-acetamidobicyclo[1.1.1]pentan-1-yl)amino)-6-(3-cyanopyrrolo[1,2-b]pyridazin-7-yl)-N-((1r,4r)-4-(methylcarbamoyl)cyclohexyl)nicotinamide

216

(1r,4r)-4-(4-((3-acetamidobicyclo[1.1.1]pentan-1-yl)amino)-6-chloronicotinamido)cyclohexane-1-carboxylic acid methyl (1r,4r)-4-(4-((3-acetamidobicyclo[1.1.1]pentan-1-yl)amino)-6-chloronicotinamido)cyclohexane-1-carboxylate (0.097 g, 0.22 mmol) (Obtained as described in steps 1-3 of Procedure 1 substituting N-(3-aminobicyclo[1.1.1]pentan-1-yl)acetamide for 3-methyloxetane-3-amine and methyl (1r,4r)-4-aminocyclohexane-1-carboxylate for (R)-4-amino-3-fluoro-2-methylbutan-2-ol hydrochloride) was dissolved in Ethanol (2 mL) after which lithium hydroxide (16 mg, 0.69 mmol) was added as a solution in water (0.8 mL). The resulting solution was stirred for 2 hours at which time the ethanol was removed, the remaining aqueous solution adjusted to pH 3-4 using 1.0M HCl and the desired product collected by filtration.

ES/MS: 421.3 (M+H$^+$).

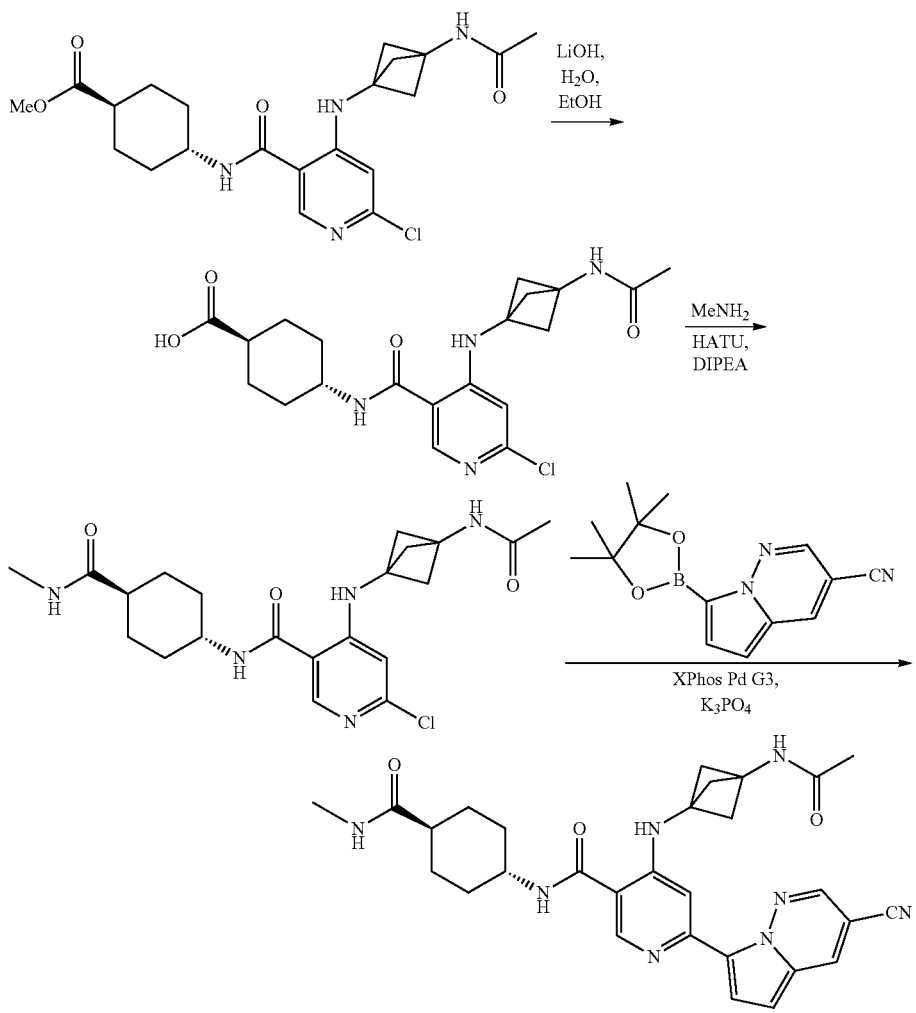

Example 479

4-((3-acetamidobicyclo[1.1.1]pentan-1-yl)amino)-6-chloro-N-((1r,4r)-4-(methylcarbamoyl)cyclohexyl)nicotinamide A mixture of (1r,4r)-4-(4-((3-acetamidobicyclo[1.1.1]pentan-1-yl)amino)-6-chloronicotinamido)cyclohexane-1-carboxylic acid (23 mg, 0.055 mmol), methylamine hydrochloride (4.4 mg, 0.066 mmol), 1-[Bis(dimethylamino)methylene]-1H-1,2,3-triazolo[4,5-b]pyridinium 3-oxid hexafluorophosphate (25 mg, 0.066 mmol) and N,N-diisopropylethylamine (0.03 ml, 0.16 mmol) in 1 mL DMF was stirred at room temperature for 10 minutes. Water was added, and the product was extracted into ethyl acetate. The ethyl acetate solution was concentrated under reduced pressure. The crude product was purified by silica gel chromatography (eluent: EtOAc/hexanes).

ES/MS: 434.2 (M+H$^+$).

4-((3-acetamidobicyclo[1.1.1]pentan-1-yl)amino)-6-(3-cyanopyrrolo[1,2-b]pyridazin-7-yl)-N-((1r,4r)-4-(methylcarbamoyl)cyclohexyl)nicotinamide (Example 479)

4-((3-acetamidobicyclo[1.1.1]pentan-1-yl)amino)-6-chloro-N-((1r,4r)-4-(methylcarbamoyl)cyclohexyl)nicotinamide was elaborated to final compound (Example 479) as described for the final step of Procedure 1 substituting 4-((3-acetamidobicyclo[1.1.1]pentan-1-yl)amino)-6-chloro-N-((1r,4r)-4-(methylcarbamoyl)cyclohexyl)nicotinamide for (R)-6-chloro-N-(2-fluoro-3-hydroxy-3-methylbutyl)-4-((3-methyloxetan-3-yl)amino)nicotinamide.

ES/MS: 541.3 [M+H$^+$].

1H NMR (400 MHz, Methanol-d4) δ 8.79 (d, J=2.2 Hz, 1H), 8.77 (d, J=2.2 Hz, 1H), 8.60 (s, 1H), 8.56 (s, 1H), 7.95 (d, J=5.2 Hz, 1H), 7.23 (d, J=5.1 Hz, 1H), 3.97-3.79 (m, 1H), 2.71 (s, 3H), 2.65 (s, 6H), 2.26-2.13 (m, 1H), 2.09 (d, J=12.2 Hz, 2H), 1.97 (s, 3H), 1.92 (d, J=13.0 Hz, 2H), 1.73-1.54 (m, 2H), 1.50-1.31 (m, 2H).

Procedure 65: Example 381

(R)-4-((4-((aminooxy)carbonyl)phenyl)amino)-6-(3-cyanopyrrolo[1,2-b]pyridazin-7-yl)-N-(2-fluoro-3-hydroxy-3-methylbutyl)nicotinamide

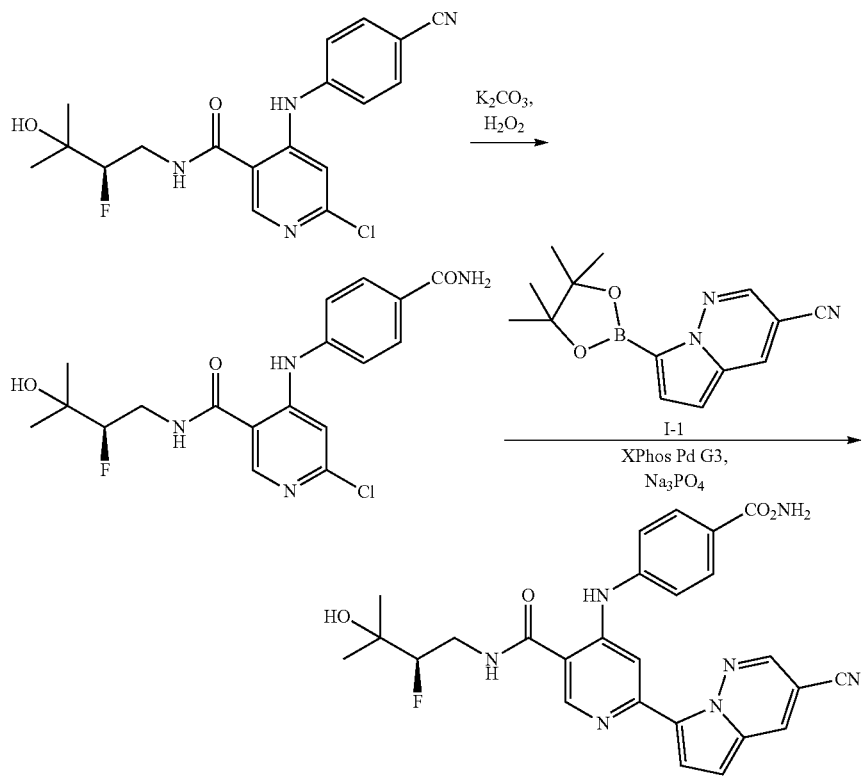

Example 381

(R)-4-((4-carbamoylphenyl)amino)-6-chloro-N-(2-fluoro-3-hydroxy-3-methylbutyl)nicotinamide (R)-6-chloro-4-((4-cyanophenyl)amino)-N-(2-fluoro-3-hydroxy-3-methylbutyl)nicotinamide (80 mg, 0.21 mmol) (synthesized as described in Procedure 24) was dissolved in DMSO (2 mL). Potassium carbonate (0.29 g, 2.1 mmol) and 30% H$_2$O$_2$ (0.22 mL, 2.1 mmol) were then added and the reaction mixture allowed to stir overnight at 25° C. The reaction mixture was then partitioned between EtOAc and water, the organic layer was dried over MgSO4, filtered concentrated and purified by reverse phase high pressure liquid chromatography (eluent: water/MeCN*0.1% TFA) to provide the title compound.

ES/MS: 395.17 [M+H$^+$].

(R)-4-((4-((aminooxy)carbonyl)phenyl)amino)-6-(3-cyanopyrrolo[1,2-b]pyridazin-7-yl)-N-(2-fluoro-3-hydroxy-3-methylbutyl)nicotinamide (Example 381)

(R)-4-((4-((aminooxy)carbonyl)phenyl)amino)-6-(3-cyanopyrrolo[1,2-b]pyridazin-7-yl)-N-(2-fluoro-3-hydroxy-3-methylbutyl)nicotinamide was synthesized in an identical manner as described in the final step for Procedure 1 substituting (R)-4-((4-carbamoylphenyl)amino)-6-chloro-N-(2-fluoro-3-hydroxy-3-methylbutyl)nicotinamide for (R)-6-chloro-N-(2-fluoro-3-hydroxy-3-methylbutyl)-4-((3-methyloxetan-3-yl)amino)nicotinamide.

ES/MS: 502.3 [M+H$^+$].

1H NMR (400 MHz, Methanol-d4) δ 8.75 (s, 1H), 8.69 (d, J=2.2 Hz, 1H), 8.60 (d, J=2.2 Hz, 1H), 8.53 (s, 1H), 8.06 (d, J=8.5 Hz, 2H), 7.84 (d, J=4.9 Hz, 1H), 7.58 (d, J=8.5 Hz, 2H), 7.15 (d, J=5.0 Hz, 1H), 4.47 (dd, J=49.1, 7.4 Hz, 1H), 3.98 (dd, J=36.2, 15.1 Hz, 1H), 3.76-3.35 (m, 1H), 1.30 (d, J=1.6 Hz, 6H).

Procedure 66: Example 535

(R)-4-((4-amino-4-methylcyclohexyl)amino)-6-(3-cyanopyrrolo[1,2-b]pyridazin-7-yl)-N-(2-fluoro-3-hydroxy-3-methylbutyl)nicotinamide

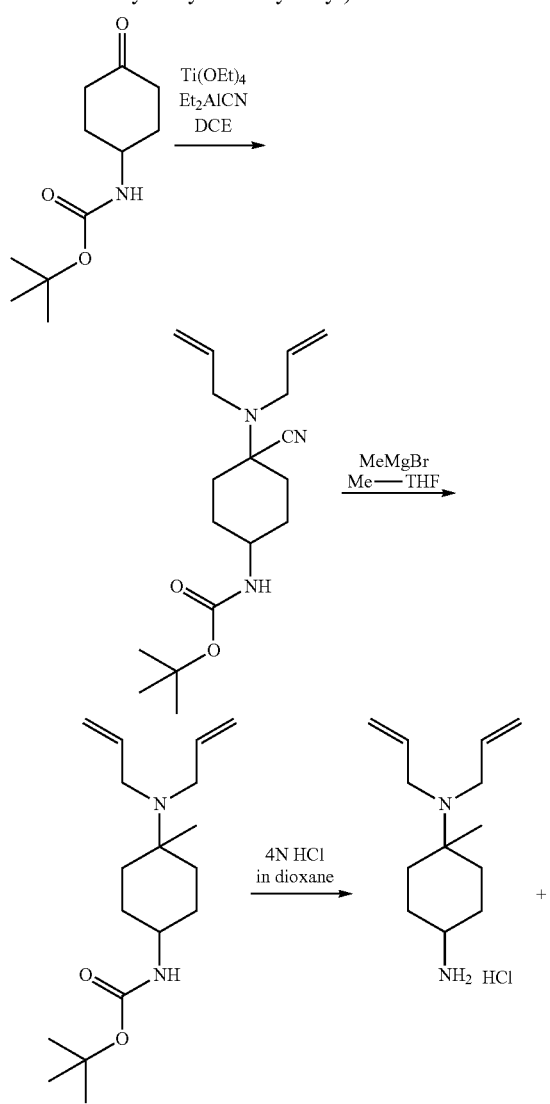

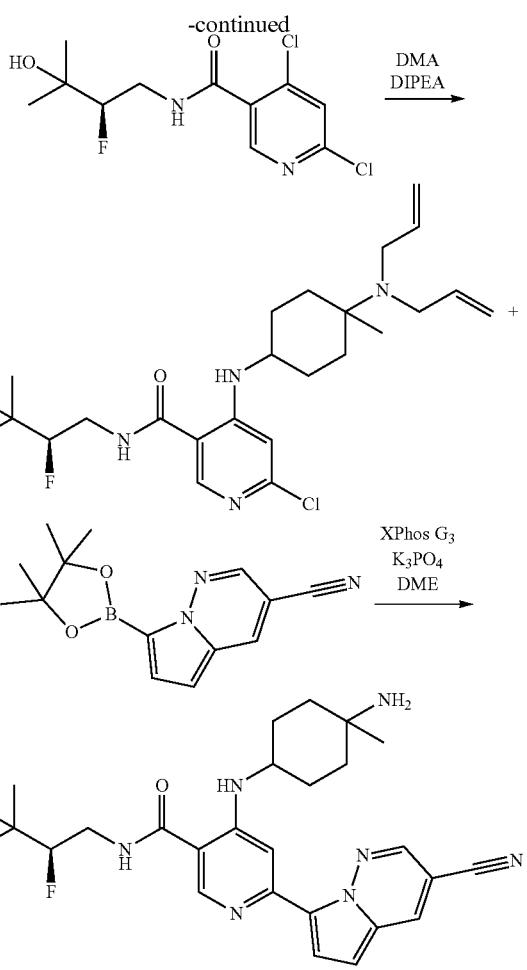

Example 535 tert-butyl (4-cyano-4-(diallylamino)cyclohexyl)carbamate

To a suspension of N-4-boc-aminocyclohexanone (3.54 g, 16.6 mmol) and diallylamine (2.04 ml, 16.6 mmol) in 0.5M DCE (33 ml) at 0° C. was added titanium (iv) ethoxide (3.79 g, 16.6 mmol). The mixture was allowed to stir and warm to room temperature slowly for 21 hours. The reddish brown clear solution was re-cooled to 0° C. and 1M diethylaluminum cyanide solution, 1.0 M in toluene (19.92 ml) was added with vigorous stirring. This mixture was allowed to warm to room temperature and was stirred at this temperature for 5 hours. The reaction mixture was diluted with 40 mL dichloromethane and 40 mL ethyl acetate. Celite (4 g) was added, and the mixture was re-cooled to 0° C. Water (10 mL) was added slowly with vigorous stirring. After stirring 5 minutes at room temperature, anhydrous sodium sulfate was added and the mixture was filtered over a pad of celite, then concentrated. The crude product was purified by silica gel chromatography (eluent: EtOAc/hexanes).

$^1$H NMR (400 MHz, Chloroform-d) δ 5.87 (dtt, J=16.7, 10.3, 6.2 Hz, 2H), 5.30-5.06 (m, 4H), 4.46 (s, 1H), 3.43 (m, 1H), 3.32 (tt, J=6.3, 1.4 Hz, 4H), 2.34-2.18 (m, 2H), 2.13-1.97 (m, 2H), 1.84 (dddd, J=31.7, 11.2, 8.7, 3.6 Hz, 1H), 1.72-1.46 (m, 3H), 1.42 (s, 9H).

tert-butyl (4-(diallylamino)-4-methylcyclohexyl)carbamate tert-butyl (4-cyano-4-(diallylamino)cyclohexyl)carbamate (0.2 g, 0.63 mmol) was dissolved in 0.2 M 2-methyltetrahydrofuran (3.2 ml) and cooled in an ice water bath before methylmagnesium bromide (3.4M in MeTHF, 0.58 ml, 1.97 mmol) was added. The mixture was allowed to warm to room temperature, at which point LC/MS indicates near completion. After continued stirring at room temperature for 14 hours, the mixture was cooled in an ice water bath and quenched with saturated ammonium chloride solution, then extracted with ethyl acetate. The organic phase was dried over anhydrous sodium sulfate, filtered, and concentrated to give the crude product.

ES/MS: 309.1 [M+H$^+$].

(R)-6-chloro-4-((4-(diallylamino)-4-methylcyclohexyl)amino)-N-(2-fluoro-3-hydroxy-3-methylbutyl)nicotinamide tert-butyl (4-(diallylamino)-4-methylcyclohexyl)carbamate (0.14 g, 0.47 mmol) was treated with hydrogen chloride solution, (4.0 M in 1,4-dioxane, 1.17 ml, 4.68 mmol) in 0.2 M 1,4-dioxane (2.33 ml) at room temperature for 16 hours. The reaction mixture was diluted with diethyl ether and the precipitated product was isolated by vacuum filtration, washed with diethyl ether and dried under vacuum for 1 hour to give N1,N1-diallyl-1-methylcyclohexane-1,4-diamine hydrochloride (119.44 mg, 0.49 mmol). To this was added (R)-4,6-dichloro-N-(2-fluoro-3-hydroxy-3-methylbutyl)nicotinamide (120 mg, 0.41 mmol) and N,N-Diisopropylethylamine (0.29 ml, 1.63 mmol) in DMA (0.4 ml). The mixture was heated under microwave irradiation at 160° C. for 30 minutes. The crude reaction mixture was diluted with ethyl acetate, washed with saturated sodium bicarbonate, water, and brine. The organic layer was dried over anhydrous sodium sulfate, filtered and concentrated. The crude product was purified by RP-HPLC (eluent: water/MeCN*0.1% TFA). The eluted product solution was basified with saturated sodium bicarbonate and extracted with ethyl acetate. The organic layer was dried over anhydrous sodium sulfate, filtered and concentrated to give the product as the free base.

ES/MS: 467.5 [M+H$^+$].

(R)-4-((4-amino-4-methylcyclohexyl)amino)-6-(3-cyanopyrrolo[1,2-b]pyridazin-7-yl)-N-(2-fluoro-3-hydroxy-3-methylbutyl)nicotinamide A mixture of (R)-6-chloro-4-((4-(diallylamino)-4-methylcyclohexyl)amino)-N-(2-fluoro-3-hydroxy-3-methylbutyl)nicotinamide (90 mg), the boronate ester (78 mg), XPhos Pd G3 (17 mg), 2 M Potassium phosphate tribasic (0.2 ml) and 0.15 M DME (1.22 ml) was degassed for 1 minute, then heated under microwave irradiation at 125° C. for 25 minutes. The crude material was purified by RP-HPLC (eluent: water/MeCN*0.1% TFA) to yield the product as a trifluoroacetate salt.

ES/MS: 494.3 [M+H$^+$].

1H NMR (400 MHz, Methanol-d4) δ 8.76 (d, J=2.2 Hz, 1H), 8.67 (d, J=2.1 Hz, 1H), 8.64 (s, 1H), 8.05-7.99 (m, 1H), 7.89 (s, 1H), 7.22 (d, J=5.0 Hz, 1H), 4.42 (ddd, J=49.1, 9.5, 2.2 Hz, 1H), 4.07 (s, 1H), 3.91 (ddd, J=36.5, 14.6, 2.2 Hz, 1H), 3.61-3.43 (m, 1H), 2.23-1.71 (m, 8H), 1.45 (s, 3H), 1.29 (d, J=1.7 Hz, 6H).

Procedure 67: Example 542

6-(3-cyanopyrrolo[1,2-b]pyridazin-7-yl)-N—((R)-2-fluoro-3-hydroxy-3-methylbutyl)-4-(((1r,3R)-3-((2,2,2-trifluoroacetamido)methyl)cyclobutyl)amino)nicotinamide

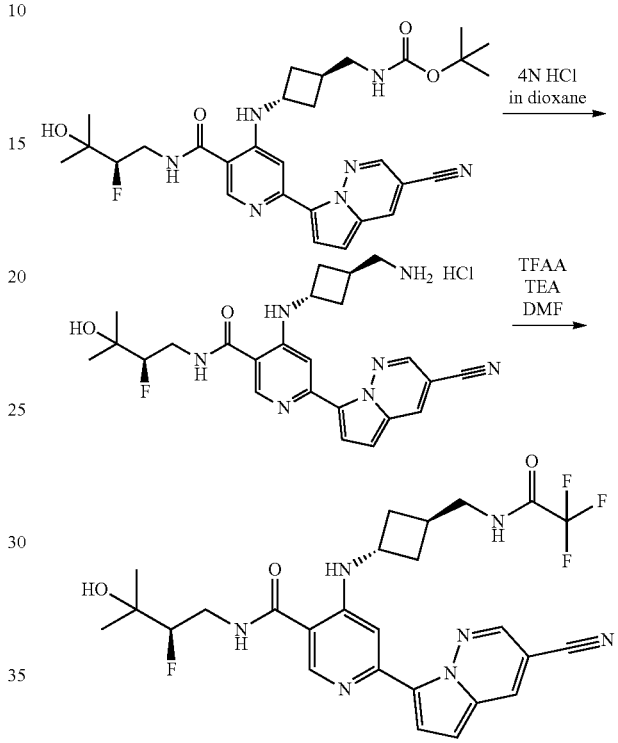

Example 542

4-(((1r,3R)-3-(aminomethyl)cyclobutyl)amino)-6-(3-cyanopyrrolo[1,2-b]pyridazin-7-yl)-N—((R)-2-fluoro-3-hydroxy-3-methylbutyl)nicotinamide A solution of tert-butyl (((1R,3r)-3-((2-(3-cyanopyrrolo[1,2-b]pyridazin-7-yl)-5-(((R)-2-fluoro-3-hydroxy-3-methylbutyl)carbamoyl)pyridin-4-yl)amino)cyclobutyl)methyl)carbamate (475 mg, Example 549) in 6 mL 1,4-dioxane was treated with 3.5 mL of 4 M hydrogen chloride solution in 1,4-dioxane. The mixture was stirred for 7 hours. Diethyl ether was added to fully precipitate the salt, which was collected by vacuum filtration and dried under vacuum. This product was used without further purification for most examples, but further purification is possible by RP-HPLC (eluent: water/MeCN*0.1% TFA) to provide the product as a trifluoroacetate salt.

ES/MS: 466.3 [M+H$^+$].

1H NMR (400 MHz, Methanol-d4) δ 8.75 (d, J=2.2 Hz, 1H), 8.68 (d, J=2.1 Hz, 1H), 8.62 (s, 1H), 8.03 (d, J=5.1 Hz, 1H), 7.67 (s, 1H), 7.20 (d, J=5.1 Hz, 1H), 4.59-4.29 (m, 2H), 3.92 (ddd, J=36.4, 14.7, 2.1 Hz, 1H), 3.51 (ddd, J=16.0, 14.5, 9.4 Hz, 1H), 3.22 (d, J=7.9 Hz, 2H), 2.74 (tt, J=8.8, 4.5 Hz, 1H), 2.55 (ddd, J=12.7, 7.4, 4.3 Hz, 2H), 2.41 (ddd, J=13.2, 9.2, 6.4 Hz, 2H), 1.29 (d, J=1.6 Hz, 6H).

6-(3-cyanopyrrolo[1,2-b]pyridazin-7-yl)-N—((R)-2-fluoro-3-hydroxy-3-methylbutyl)-4-(((1r,3R)-3-((2,2,2-trifluoroacetamido)methyl)cyclobutyl)amino)nicotinamide a mixture of 4-(((1r,3R)-3-(aminomethyl)cyclobutyl)amino)-6-(3-cyanopyrrolo[1,2-b]pyridazin-7-yl)-N—((R)-2-fluoro-3-hydroxy-3-methylbutyl)nicotinamide (13.5 mg), trifluoroacetic anhydride (0.012 mL) and triethylamine (0.015 mL) in DMF (0.15 mL) was stirred at room temperature. Additional trifluoroacetic anhydride was required to complete the reaction. The crude material was purified by RP-HPLC (eluent: water/MeCN*0.1% TFA) to yield the product as a trifluoroacetate salt.

ES/MS: 562.3 [M+H⁺].

1H NMR (400 MHz, Methanol-d4) δ 8.75 (m, 2H), 8.58 (s, 1H), 7.98 (d, J=5.0 Hz, 1H), 7.81 (s, 1H), 7.22 (d, J=5.1 Hz, 1H), 4.56-4.31 (m, 2H), 3.94 (ddd, J=36.6, 14.5, 2.1 Hz, 1H), 3.61-3.40 (m, 3H), 2.65 (dd, J=8.2, 3.5 Hz, 1H), 2.48 (ddd, J=11.8, 7.7, 3.8 Hz, 2H), 2.39-2.24 (m, 2H), 1.29 (d, J=1.7 Hz, 6H).

Procedure 68: Example 545

Methyl (((1R,3r)-3-((2-(3-cyanopyrrolo[1,2-b]pyridazin-7-yl)-5-(((R)-2-fluoro-3-hydroxy-3-methylbutyl)carbamoyl)pyridin-4-yl)amino)cyclobutyl)methyl)carbamate

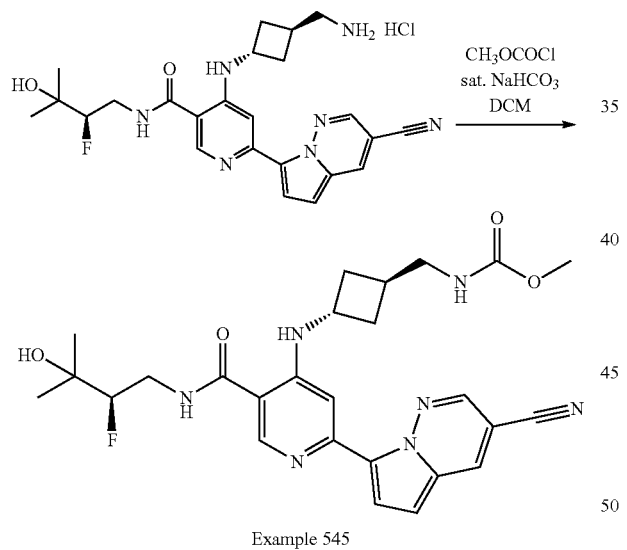

Example 545

Methyl (((1R,3r)-3-((2-(3-cyanopyrrolo[1,2-b]pyridazin-7-yl)-5-(((R)-2-fluoro-3-hydroxy-3-methylbutyl)carbamoyl)pyridin-4-yl)amino)cyclobutyl)methyl)carbamate A suspension of 4-(((1r,3R)-3-(aminomethyl)cyclobutyl)amino)-6-(3-cyanopyrrolo[1,2-b]pyridazin-7-yl)-N—((R)-2-fluoro-3-hydroxy-3-methylbutyl)nicotinamide (430 mg) in 17 mL dichloromethane was treated with 8.5 mL saturated sodium bicarbonate solution and then with methyl chloroformate (2.65 ml, 5% solution in DCM) at room temperature with vigorous stirring. The reaction is complete within 10 minutes. The mixture was diluted with DCM. The aqueous phase was removed and extracted with DCM. The combined organic layer was dried over anhydrous sodium sulfate, filtered and concentrated. The crude material was purified by RP-HPLC (eluent: water/MeCN*0.1% TFA) to yield the product as a trifluoroacetate salt.

ES/MS: 524.3 [M+H⁺].

1H NMR (400 MHz, Methanol-d4) δ 8.76 (d, J=2.2 Hz, 1H), 8.73 (d, J=2.2 Hz, 1H), 8.57 (s, 1H), 7.99 (d, J=5.1 Hz, 1H), 7.82 (s, 1H), 7.20 (d, J=5.1 Hz, 1H), 4.54-4.31 (m, 2H), 3.92 (ddd, J=36.6, 14.5, 2.2 Hz, 1H), 3.68 (s, 3H), 3.49 (ddd, J=16.1, 14.5, 9.4 Hz, 1H), 3.35 (d, J=7.5 Hz, 2H), 2.54 (s, 1H), 2.50-2.38 (m, 2H), 2.34-2.15 (m, 2H), 1.29 (d, J=1.7 Hz, 6H).

Procedure 69: Example 551

N-(3-acetamido-2,2-difluoropropyl)-6-(3-cyanopyrrolo[1,2-b]pyridazin-7-yl)-4-(isopropylamino)nicotinamide

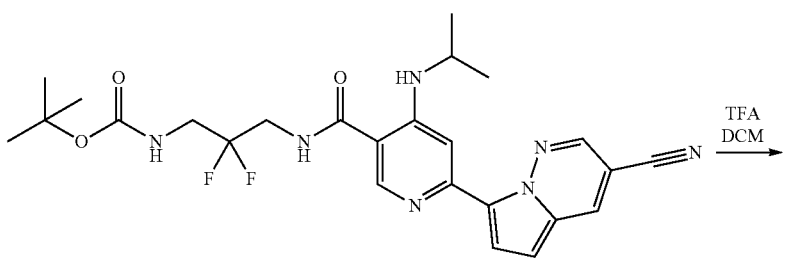

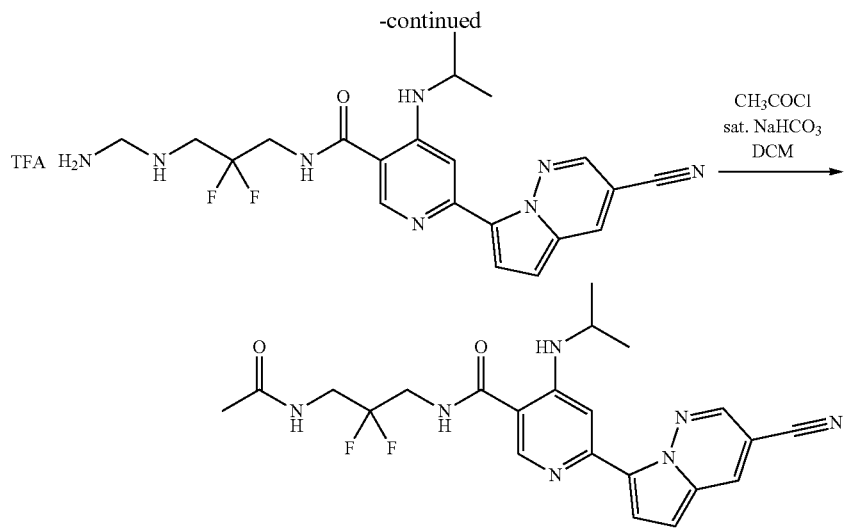

Example 551

N-(3-amino-2,2-difluoropropyl)-6-(3-cyanopyrrolo[1,2-b]pyridazin-7-yl)-4-(isopropylamino)nicotinamide trifluoroacetate A solution of tert-butyl (3-(6-(3-cyanopyrrolo[1,2-b]pyridazin-7-yl)-4-(isopropylamino)nicotinamido)-2,2-difluoropropyl)carbamate (172 mg) in 3 mL DCM and 1 mL trifluoroacetic acid was stirred at room temperature for 1 hour. The mixture was poured into saturated sodium bicarbonate and extracted with ethyl acetate. The organic phase was dried with anhydrous sodium sulfate, filtered and concentrated. Additional product was obtained by freeze drying the aqueous phase and later extracting the solids with methanol. The crude product obtained thusly was used without further purification with an assumed yield of 100%, as the mass is high due to inorganic salt contamination. A fraction of the product was purified by RP-HPLC (eluent: water/MeCN*0.1% TFA) to yield the product as a trifluoroacetate salt.

ES/MS: 414.3 [M+H$^+$].

1H NMR (400 MHz, Methanol-d4) δ 8.60-8.51 (m, 2H), 8.47 (d, J=2.2 Hz, 1H), 8.15 (s, 1H), 7.79 (d, J=4.9 Hz, 1H), 7.07 (d, J=4.8 Hz, 1H), 3.94-3.78 (m, 3H), 2.97 (t, J=14.0 Hz, 2H), 1.34 (d, J=6.4 Hz, 6H).

N-(3-acetamido-2,2-difluoropropyl)-6-(3-cyanopyrrolo[1,2-b]pyridazin-7-yl)-4-(isopropylamino)nicotinamide A mixture of N-(3-amino-2,2-difluoropropyl)-6-(3-cyanopyrrolo[1,2-b]pyridazin-7-yl)-4-(isopropylamino)nicotinamide (50% purity, 33 mg,), 1.1M Sodium bicarbonate (181.41 µl), and 0.1M DCM (399.1 µl) was stirred vigorously as acetyl chloride (4.27 µl) was added. Additional portions of acetyl chloride drove the reaction to completion. The product was purified by RP-HPLC (eluent: water/MeCN*0.1% TFA) to yield the product as a trifluoroacetate salt.

ES/MS: 456.3 [M+H$^+$].

1H NMR (400 MHz, Methanol-d4) δ 8.75 (d, J=2.2 Hz, 1H), 8.66 (d, J=2.2 Hz, 1H), 8.58 (s, 1H), 8.00 (d, J=5.1 Hz, 1H), 7.84 (s, 1H), 7.21 (d, J=5.1 Hz, 1H), 4.23-4.06 (m, 1H), 3.85 (t, J=13.9 Hz, 2H), 3.78-3.62 (m, 2H), 2.02 (s, 3H), 1.40 (d, J=6.4 Hz, 6H).

Procedure 70: Example 620

Methyl (((1R,3r)-3-((2-(3-cyanopyrrolo[1,2-b]pyridazin-7-yl)-5-(((R)-2-fluoro-3-hydroxy-3-methylbutyl)carbamoyl)pyridin-4-yl)amino)cyclobutyl)methyl)(methyl)carbamate

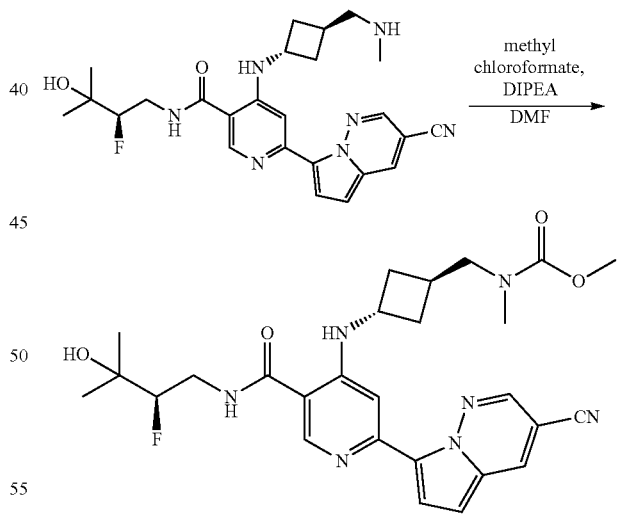

Methyl (((1R,3r)-3-((2-(3-cyanopyrrolo[1,2-b]pyridazin-7-yl)-5-(((R)-2-fluoro-3-hydroxy-3-methylbutyl)carbamoyl)pyridin-4-yl)amino)cyclobutyl)methyl)(methyl)carbamate (Example 620)

To a solution of 6-(3-cyanopyrrolo[1,2-b]pyridazin-7-yl)-N—((R)-2-fluoro-3-hydroxy-3-methylbutyl)-4-(((1r,3R)-3-((methylamino)methyl)cyclobutyl)amino)nicotinamide (120 mg, 0.25 mmol, prepared as described in Procedure 75 substituting 2.0 M CH₃NH₂ in THF for CF₃CH₂NH₂) in DMF (3 mL) at room temperature was added DIPEA (0.22 mL, 1.25 mmol) and methyl chloroformate (47 mg, 0.50 mmol). After 10 minutes the reaction mixture was poured into water (5 mL) and extracted with EtOAc (2×15 mL). The combined organic layers were dried over MgSO₄, filtered and concentrated. The resulting crude residue was purified by RP-HPLC (eluent: water/MeCN*0.1% TFA) to yield the final product as a TFA salt.

ES/MS: 538.3 [M+H]⁺

1H NMR (400 MHz, Methanol-d4) δ 8.74 (d, J=2.2 Hz, 1H), 8.68 (d, J=2.1 Hz, 1H), 8.56 (s, 1H), 7.98 (d, J=5.1 Hz, 1H), 7.75 (s, 1H), 7.20 (d, J=5.1 Hz, 1H), 4.43 (ddd, J=49.0, 9.3, 2.1 Hz, 1H), 4.25 (p, J=8.0 Hz, 1H), 3.94 (ddd, J=36.3, 14.5, 2.1 Hz, 1H), 3.67 (s, 3H), 3.60-3.43 (m, 1H), 3.39 (d, J=7.0 Hz, 2H), 2.93 (s, 3H), 2.80-2.68 (m, 2H), 2.58-2.41 (m, 1H), 2.05-1.79 (m, 2H), 1.29 (d, J=1.6 Hz, 7H).

Procedure 71: Example 622

6-(3-cyanopyrrolo[1,2-b]pyridazin-7-yl)-4-((4-hydroxybicyclo[2.2.2]octan-1-yl)amino)-N-((4-(2-hydroxypropan-2-yl)oxazol-2-yl)methyl)nicotinamide (5 mL) was added methylmagnesium chloride (3.0 M in Et₂O, 0.34 mL, 1.0 mmol) dropwise at room temperature. After 15 minutes the reaction mixture was quenched by the slow addition of water (5 mL) and extracted with EtOAc (2×15 mL). The combined organic layers were dried over MgSO₄, filtered and concentrated. The resulting crude residue was purified by silica gel chromatography (eluent: EtOAc/hexanes) to give the desired product.

ES/MS: 435.6 [M+H]⁺

6-(3-cyanopyrrolo[1,2-b]pyridazin-7-yl)-4-((4-hydroxybicyclo[2.2.2]octan-1-yl)amino)-N-((4-(2-hydroxypropan-2-yl)oxazol-2-yl)methyl)nicotinamide (Example 622)

6-(3-cyanopyrrolo[1,2-b]pyridazin-7-yl)-4-((4-hydroxybicyclo[2.2.2]octan-1-yl)amino)-N-((4-(2-hydroxypropan-2-yl)oxazol-2-yl)methyl)nicotinamide was prepared as described in the final step of Procedure 2 substituting 6-chloro-N((R)-2-fluoro-3-hydroxy-3-methylbutyl)-4-(((1S,3R)-3-hydroxycyclohexyl)amino)nicotinamide with 6-chloro-4-((4-hydroxybicyclo[2.2.2]octan-1-yl)amino)-N-

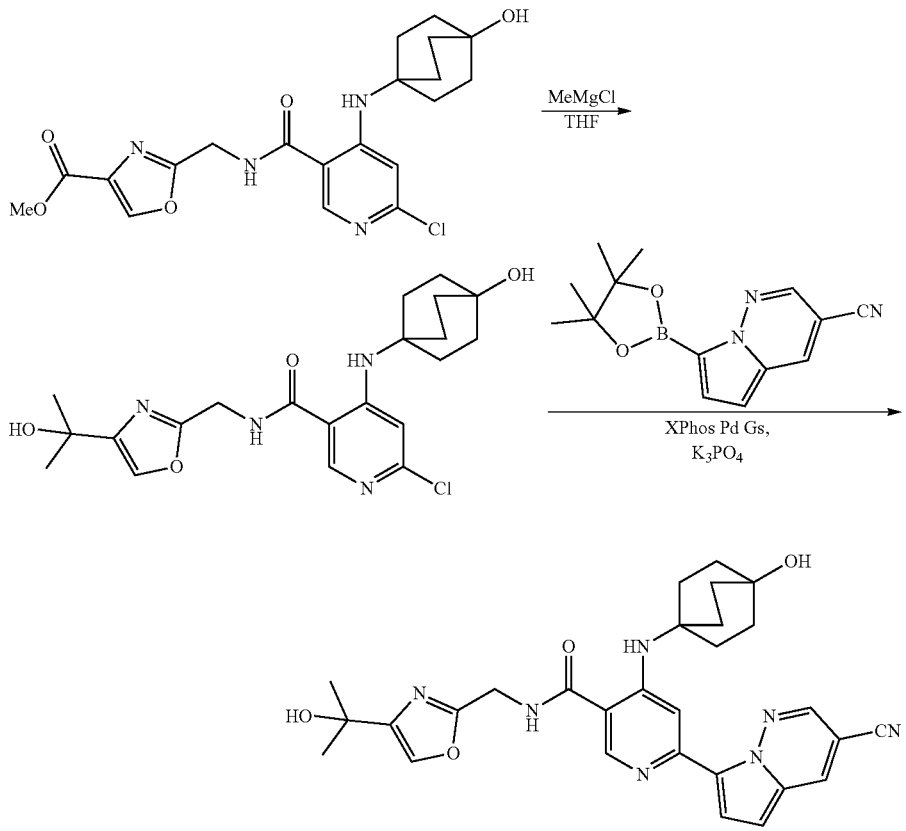

6-chloro-4-((4-hydroxybicyclo[2.2.2]octan-1-yl)amino)-N-((4-(2-hydroxypropan-2-yl)oxazol-2-yl)methyl)nicotinamide To a solution of methyl 2-(((6-chloro-4-((4-hydroxybicyclo[2.2.2]octan-1-yl)amino)nicotinamido)methyl)oxazole-4-carboxylate (88 mg, 0.20 mmol, prepared as described in Procedure 1 with the appropriate starting materials) in THF ((4-(2-hydroxypropan-2-yl)oxazol-2-yl)methyl)nicotinamide.

ES/MS: 542.4 [M+H]⁺

1H NMR (400 MHz, Methanol-d4) δ 8.76 (d, J=2.2 Hz, 1H), 8.70 (d, J=2.2 Hz, 1H), 8.62 (s, 1H), 8.31 (s, 1H), 7.93 (d, J=5.1 Hz, 1H), 7.69 (s, 1H), 7.22 (d, J=5.1 Hz, 1H), 4.65 (s, 2H), 2.34-2.16 (m, 6H), 2.09-1.82 (m, 6H), 1.50 (s, 6H).

Procedure 72: Example 638 and Example 640

(R)-6-(3-cyanopyrrolo[1,2-b]pyridazin-7-yl)-N-(2-fluoro-3-hydroxy-3-methylbutyl)-4-((3-(oxazol-5-ylmethyl)cyclobutyl)amino)nicotinamide

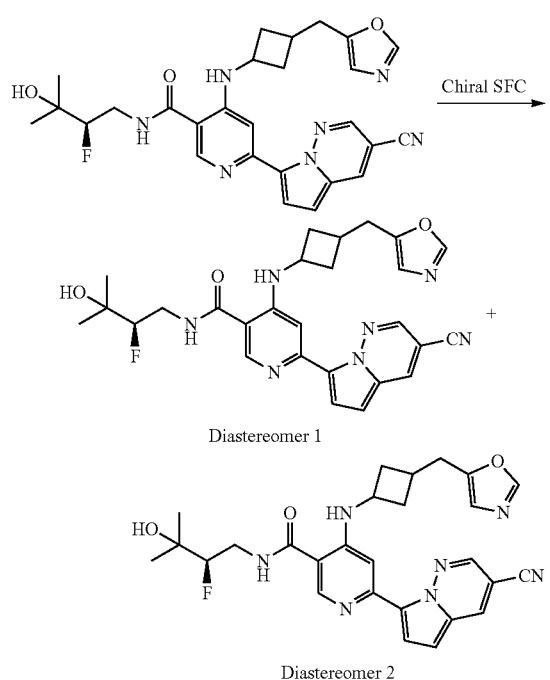

(R)-6-(3-cyanopyrrolo[1,2-b]pyridazin-7-yl)-N-(2-fluoro-3-hydroxy-3-methylbutyl)-4-((3-(oxazol-5-ylmethyl)cyclobutyl)amino)nicotinamide (R)-6-(3-cyanopyrrolo[1,2-b]pyridazin-7-yl)-N-(2-fluoro-3-hydroxy-3-methylbutyl)-4-((3-(oxazol-5-ylmethyl)cyclobutyl)amino)nicotinamide (20 mg, 0.039 mmol) as a mixture of two isomers was separated using an SFC OJ-H column, co-solvent: 30% MeOH/DEA.

Diastereomer 1 Example 638

ES/MS: 518.4 [M+H]$^+$
1H NMR (400 MHz, Methanol-d4) δ 8.75 (d, J=2.2 Hz, 1H), 8.66 (d, J=2.2 Hz, 1H), 8.57 (s, 1H), 8.11 (s, 1H), 7.98 (d, J=5.1 Hz, 1H), 7.64 (s, 1H), 7.21 (d, J=5.1 Hz, 1H), 6.92 (s, 1H), 4.57-4.30 (m, 2H), 4.08-3.83 (m, 1H), 3.58-3.42 (m, 1H), 3.08-2.95 (m, 2H), 2.88-2.73 (m, 1H), 2.59-2.43 (m, 2H), 2.42-2.30 (m, 2H), 1.29 (d, J=1.7 Hz, 6H).

Diastereomer 2 Example 640

ES/MS: 518.4 [M+H]$^+$
1H NMR (400 MHz, Methanol-d4) δ 8.74 (d, J=2.2 Hz, 1H), 8.67 (d, J=2.2 Hz, 1H), 8.55 (s, 1H), 8.09 (s, 1H), 7.97 (d, J=5.1 Hz, 1H), 7.73 (s, 1H), 7.20 (d, J=5.0 Hz, 1H), 6.88 (d, J=1.1 Hz, 1H), 4.56-4.33 (m, 1H), 4.33-4.19 (m, 1H), 4.08-3.79 (m, 1H), 3.65-3.41 (m, 1H), 2.91 (d, J=7.3 Hz, 2H), 2.89-2.77 (m, 1H), 2.68-2.48 (m, 1H), 1.95-1.76 (m, 2H), 1.29 (d, J=1.6 Hz, 6H).

Procedure 73: Example 645 and Example 646

(R)-6-(3-cyanopyrrolo[1,2-b]pyridazin-7-yl)-N-(2-fluoro-3-hydroxy-3-methylbutyl)-4-((4-(2-methyloxazol-5-yl)cyclohexyl)amino)nicotinamide

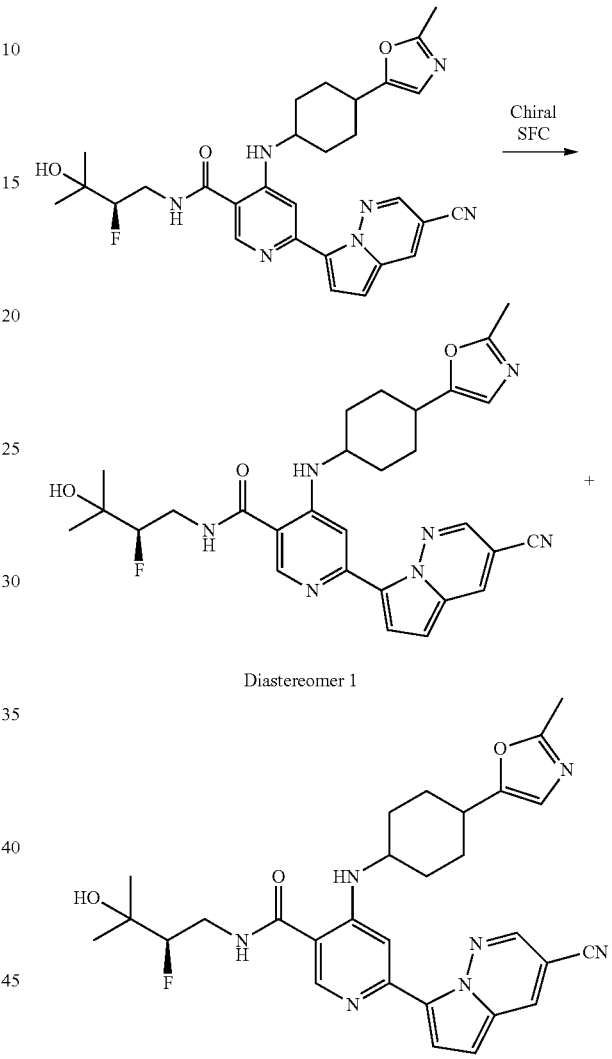

(R)-6-(3-cyanopyrrolo[1,2-b]pyridazin-7-yl)-N-(2-fluoro-3-hydroxy-3-methylbutyl)-4-((4-(2-methyloxazol-5-yl)cyclohexyl)amino)nicotinamide (R)-6-(3-cyanopyrrolo[1,2-b]pyridazin-7-yl)-N-(2-fluoro-3-hydroxy-3-methylbutyl)-4-((4-(2-methyloxazol-5-yl)cyclohexyl)amino)nicotinamide (49 mg, 0.090 mmol) as a mixture of two isomers was separated using an SFC OD-H column, co-solvent: 30% EtOH.

Diastereomer 1 Example 645

ES/MS: 546.5 [M+H]$^+$
1H NMR (400 MHz, Methanol-d4) δ 8.75 (d, J=2.2 Hz, 1H), 8.66 (d, J=2.2 Hz, 1H), 8.60 (s, 1H), 8.00 (d, J=5.1 Hz, 1H), 7.86 (s, 1H), 7.21 (d, J=5.0 Hz, 1H), 6.76 (d, J=1.2 Hz, 1H), 4.41 (ddd, J=49.1, 9.4, 2.1 Hz, 1H), 4.24-4.15 (m, 1H), 4.05-3.82 (m, 1H), 3.59-3.42 (m, 1H), 3.02-2.90 (m, 1H), 2.42 (s, 3H), 2.17-1.90 (m, 6H), 1.90-1.74 (m, 2H), 1.28 (d, J=1.7 Hz, 6H).

Diastereomer 2 Example 646

ES/MS: 546.4 [M+H]+

1H NMR (400 MHz, Methanol-d4) δ 8.74 (d, J=2.2 Hz, 1H), 8.66 (d, J=2.2 Hz, 1H), 8.57 (s, 1H), 8.02 (d, J=5.1 Hz, 1H), 7.88 (s, 1H), 7.21 (d, J=5.1 Hz, 1H), 6.73 (d, J=1.0 Hz, 1H), 4.56-4.29 (m, 1H), 4.04-3.82 (m, 2H), 3.60-3.42 (m, 1H), 2.90-2.73 (m, 1H), 2.41 (s, 3H), 2.32-2.13 (m, 4H), 1.83-1.52 (m, 4H), 1.29 (d, J=1.7 Hz, 6H).

Procedure 74: Example 694

6-(3-cyanopyrrolo[1,2-b]pyridazin-7-yl)-N—((R)-2-fluoro-3-hydroxy-3-methylbutyl)-4-(((1r,3R)-3-(((5-methyl-1,3,4-oxadiazol-2-yl)amino)methyl)cyclobutyl)amino)nicotinamide

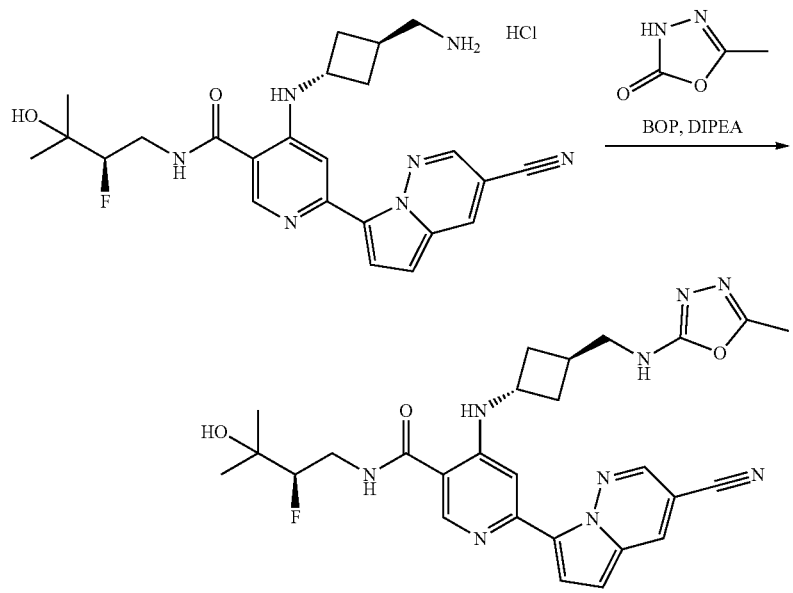

A solution of 4-(((1r,3R)-3-(aminomethyl)cyclobutyl) amino)-6-(3-cyanopyrrolo[1,2-b]pyridazin-7-yl)-N—((R)-2-fluoro-3-hydroxy-3-methylbutyl)nicotinamide hydrochloride (33 mg, 0.07 mmol), 5-methyl-1,3,4-oxadiazol-2(3H)-one (6.58 mg, 0.07 mmol) and N,N-Diisopropylethylamine (68.7 µl, 0.39 mmol) in DMF (200 µl) was treated with (Benzotriazol-1-yloxy)tris(dimethylamino)phosphonium hexafluorophosphate (30.53 mg, 0.07 mmol). After stirring at room temperature overnight, the reaction mixture was added to cold water and extracted into ethyl acetate. The organic phase was dried over anhydrous sodium sulfate, filtered, concentrated and purified by RP-HPLC (eluent: water/MeCN*0.1% TFA).

ES/MS: 548.3 [M+H+].

1H NMR (400 MHz, Methanol-d4) δ 8.75 (d, J=2.2 Hz, 1H), 8.66 (d, J=2.2 Hz, 1H), 8.57 (s, 1H), 7.99 (d, J=5.0 Hz, 1H), 7.74 (s, 1H), 7.21 (d, J=5.1 Hz, 1H), 4.58-4.31 (m, 2H), 3.93 (ddd, J=36.5, 14.6, 2.1 Hz, 1H), 3.57-3.36 (m, 3H), 2.76-2.61 (m, 1H), 2.50 (ddd, J=12.4, 7.4, 3.6 Hz, 2H), 2.38 (s, 3H), 2.37-2.23 (m, 2H), 1.29 (d, J=1.6 Hz, 6H).

Procedure 75: Example 700

6-(3-cyanopyrrolo[1,2-b]pyridazin-7-yl)-N—((R)-2-fluoro-3-hydroxy-3-methylbutyl)-4-(((1r,3R)-3-(((2,2,2-trifluoroethyl)amino)methyl)cyclobutyl)amino)nicotinamide

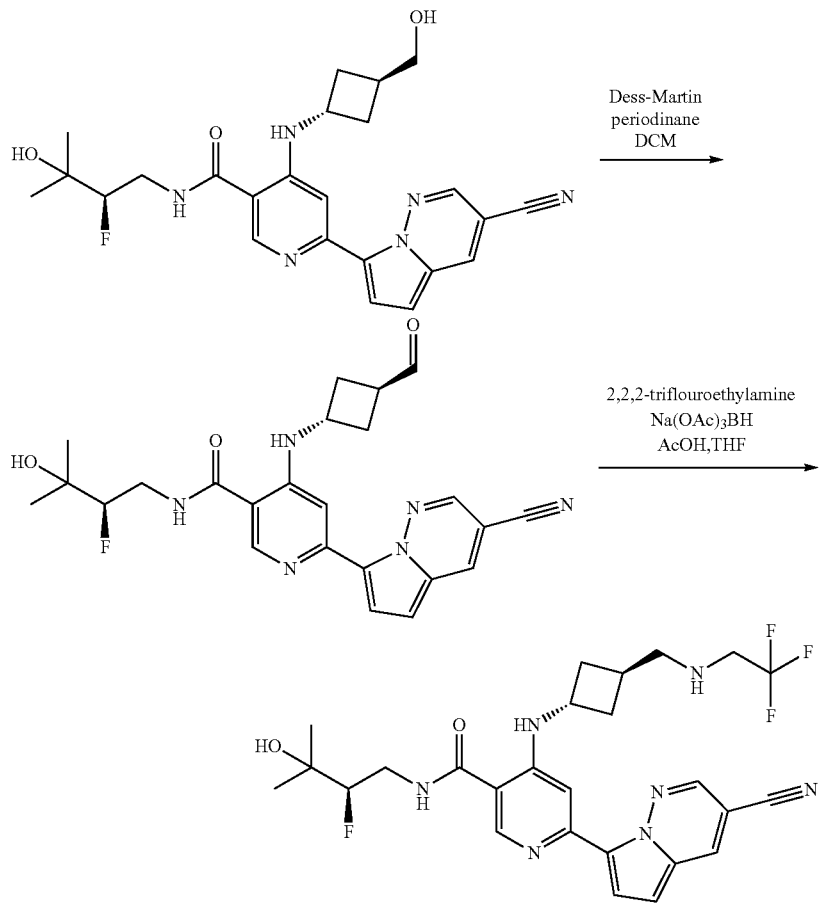

6-(3-cyanopyrrolo[1,2-b]pyridazin-7-yl)-N—((R)-2-fluoro-3-hydroxy-3-methylbutyl)-4-(((1r,3R)-3-formylcyclobutyl)amino)nicotinamide To a suspension of 6-(3-cyanopyrrolo[1,2-b]pyridazin-7-yl)-N—((R)-2-fluoro-3-hydroxy-3-methylbutyl)-4-(((1r,3R)-3-(hydroxymethyl)cyclobutyl)amino)nicotinamide, prepared by procedure 2, (120 mg, 0.257 mol) in DCM (1 mL) was added Dess Martin periodinane (130.92 mg, 0.31 mol). Sonication for several minutes resulted in a solution. After 30 minutes stirring at room temperature, the reaction was complete by LCMS. The reaction was diluted with DCM, washed with saturated sodium bicarbonate, and then back extracted with ethyl acetate. The dried and concentrated crude product was chromatographed using 100% ethyl acetate to give the product.

ES/MS: 465.4 (M+H⁺).

6-(3-cyanopyrrolo[1,2-b]pyridazin-7-yl)-N—((R)-2-fluoro-3-hydroxy-3-methylbutyl)-4-(((1r,3R)-3-(((2,2,2-trifluoroethyl)amino)methyl)cyclobutyl)amino)nicotinamide (Example 700)

To a solution of 6-(3-cyanopyrrolo[1,2-b]pyridazin-7-yl)-N—((R)-2-fluoro-3-hydroxy-3-methylbutyl)-4-(((1r,3R)-3-formylcyclobutyl)amino)nicotinamide (30 mg, 0.06 mmol) and 2,2,2-trifluoroethylamine hydrochloride (7.14 mg, 0.07 mmol) in DCM (0.33 mL) was added AcOH (2 drops). After 1 hr, sodium triacetoxyborohydride (27 mg, 0.13 mmol) was added. The reaction was stirred overnight then purified by silica gel chromatography using a gradient of increasing ethyl acetate in dichloromethane to provide the title compound.

ES/MS: 548.3 (M+H⁺).

1H NMR (400 MHz, Methanol-d4) δ 8.76 (d, J=2.2 Hz, 1H), 8.67 (d, J=2.2 Hz, 1H), 8.61 (d, J=4.8 Hz, 1H), 8.02-7.95 (m, 1H), 7.77 (s, 1H), 7.64 (s, 1H), 7.22 (d, J=5.1 Hz, 1H), 4.52-4.32 (m, 2H), 3.94 (qd, J=9.1, 4.0 Hz, 3H), 3.59-3.41 (m, 1H), 3.40-3.33 (m, 1H), 3.25 (d, J=7.0 Hz, 1H), 2.88 (d, J=15.4 Hz, 1H), 2.67-2.51 (m, 2H), 2.51-2.35 (m, 1H), 1.99 (q, J=10.0, 8.3 Hz, 1H), 1.29 (t, J=1.5 Hz, 6H).

Procedure 76: Example 702

6-(3-cyanopyrrolo[1,2-b]pyridazin-7-yl)-N—((R)-2-fluoro-3-hydroxy-3-methylbutyl)-4-(((1r,3R)-3-((oxetan-3-ylamino)methyl)cyclobutyl)amino)nicotinamide

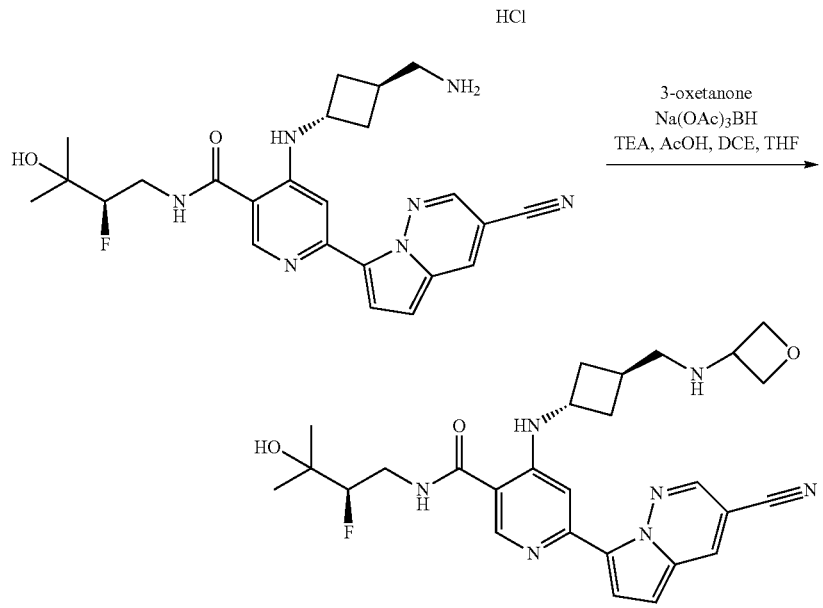

6-(3-cyanopyrrolo[1,2-b]pyridazin-7-yl)-N—((R)-2-fluoro-3-hydroxy-3-methylbutyl)-4-(((1r,3R)-3-((oxetan-3-ylamino)methyl)cyclobutyl)amino)nicotinamide To a mixture of 4-(((1r,3R)-3-(aminomethyl)cyclobutyl)amino)-6-(3-cyanopyrrolo[1,2-b]pyridazin-7-yl)-N—((R)-2-fluoro-3-hydroxy-3-methylbutyl)nicotinamide hydrochloride (31.9 mg, 0.06 mmol), 3-oxetanone (0.02 ml, 0.32 mmol) and Triethylamine (0.01 ml, 0.06 mmol) in 0.2M DCE (0.32 ml) and 0.2M THF (0.32 ml) was added Acetic acid glacial (0.02 ml, 0.33 mmol) and the reaction was stirred for 3 hours at room temperature. Then, sodium cyanoborohydride (20.17 mg, 0.32 mmol) was added and the reaction was stirred at 55° C. overnight. Saturated sodium bicarbonate was added and the product was extracted into DCM, dried over anhydrous sodium sulfate, filtered, concentrated and purified by RP-HPLC HPLC (eluent: water/MeCN*0.1% TFA).

ES/MS: 522.3 [M+H$^+$].

1H NMR (400 MHz, Methanol-d4) δ 8.78 (d, J=2.1 Hz, 1H), 8.69 (s, 1H), 8.64 (s, 1H), 7.99 (d, J=5.1 Hz, 1H), 7.70 (s, 1H), 7.24 (d, J=5.0 Hz, 1H), 4.97 (t, J=7.5 Hz, 1H), 4.72 (dd, J=8.1, 5.2 Hz, 1H), 4.57-4.36 (m, 3H), 4.07-3.84 (m, 2H), 3.72-3.39 (m, 2H), 3.29 (d, J=8.0 Hz, 2H), 2.83 (d, J=5.3 Hz, 1H), 2.67-2.39 (m, 4H), 1.32 (d, J=1.6 Hz, 6H).

Procedure 77: Example 704

6-(3-cyanopyrrolo[1,2-b]pyridazin-7-yl)-4-(((1r,3R)-3-((4-cyclopropyl-1H-1,2,3-triazol-1-yl)methyl)cyclobutyl)amino)-N—((R)-2-fluoro-3-hydroxy-3-methylbutyl)nicotinamide

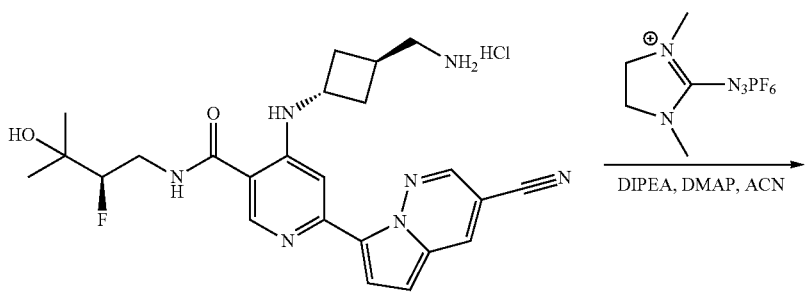

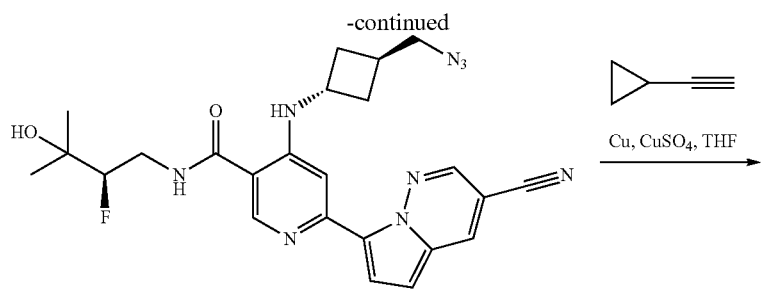

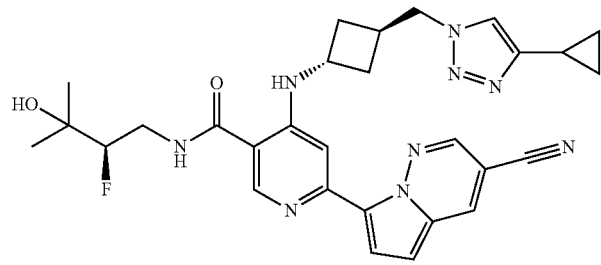

4-(((1r,3R)-3-(azidomethyl)cyclobutyl)amino)-6-(3-cyanopyrrolo[1,2-b]pyridazin-7-yl)-N—((R)-2-fluoro-3-hydroxy-3-methylbutyl)nicotinamide To an ice water bath chilled mixture of 4-(((1r,3R)-3-(aminomethyl)cyclobutyl)amino)-6-(3-cyanopyrrolo[1,2-b]pyridazin-7-yl)-N—((R)-2-fluoro-3-hydroxy-3-methylbutyl)nicotinamide hydrochloride (50 mg, 0.1 mmol), DMAP (14.6 mg, 0.12 mmol) and N-Ethyldiisopropylamine (34.7 μl, 0.2 mmol) in 0.9 mL of acetonitrile was added hexafluoro-16-phosphane, 2-azido-1,3-dimethyl-4,5-dihydro-1H-imidazol-3-ium salt (ADMP, 34.08 mg, 0.12 mmol). The mixture was warmed to 30° C. and stirred overnight, then for 1 hour at 40° C. This solution was cooled to room temperature and used without further processing.

6-(3-cyanopyrrolo[1,2-b]pyridazin-7-yl)-4-(((1r,3R)-3-((4-cyclopropyl-1H-1,2,3-triazol-1-yl)methyl)cyclobutyl)amino)-N—((R)-2-fluoro-3-hydroxy-3-methylbutyl)nicotinamide (Example 704)

Half of the solution containing 4-(((1r,3R)-3-(azidomethyl)cyclobutyl)amino)-6-(3-cyanopyrrolo[1,2-b]pyridazin-7-yl)-N—((R)-2-fluoro-3-hydroxy-3-methylbutyl)nicotinamide from the step above was diluted with 1 mL THF. To this solution was added 0.5M 10% CuSO4 (0.1 ml), copper (9 mg), and finally ethynylcyclopropane, 0.4M in THF (0.12 ml). After stirring overnight, the mixture was concentrated, then diluted with 1.8 mL methanol for purification by RP-HPLC HPLC (eluent: water/MeCN*0.1% TFA).

ES/MS: 558.2 [M+H+].

1H NMR (400 MHz, Acetonitrile-d3) δ 8.68 (s, 1H), 8.60 (d, J=1.9 Hz, 2H), 8.07 (d, J=5.3 Hz, 1H), 7.54 (d, J=6.4 Hz, 2H), 7.18 (d, J=5.1 Hz, 1H), 4.52 (d, J=7.6 Hz, 2H), 4.42-4.21 (m, 1H), 3.61-3.39 (m, 1H), 1.27 (m, 7H), 1.02-0.87 (m, 2H), 0.87-0.70 (m, 2H).

Procedure 78: Example 706

6-(3-cyanopyrrolo[1,2-b]pyridazin-7-yl)-N—((R)-2-fluoro-3-hydroxy-3-methylbutyl)-4-(((1r,3R)-3-(methoxymethyl)cyclobutyl)amino)nicotinamide

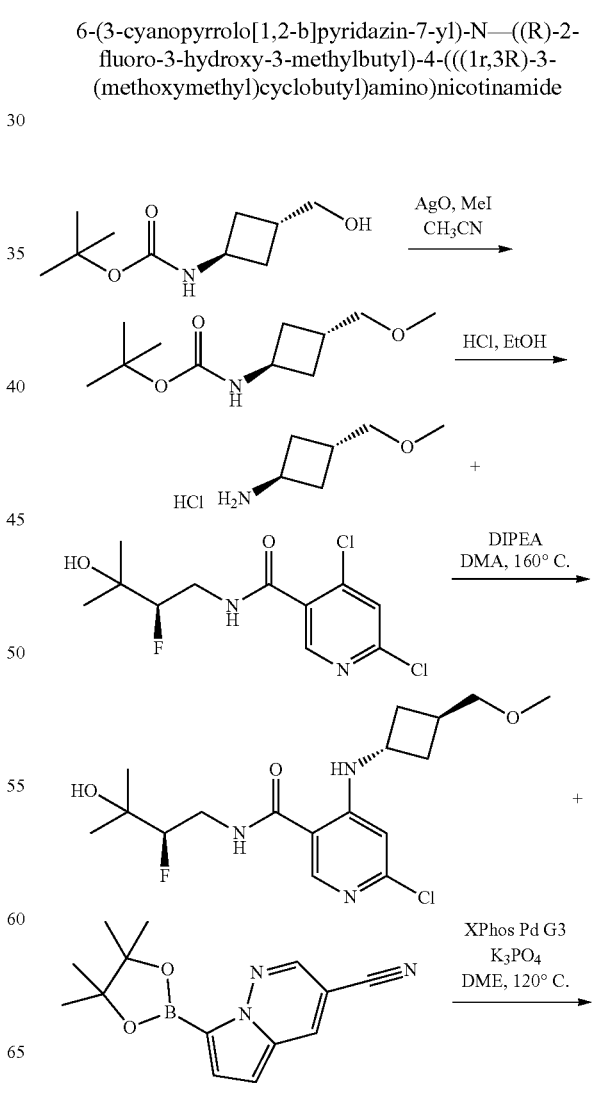

-continued

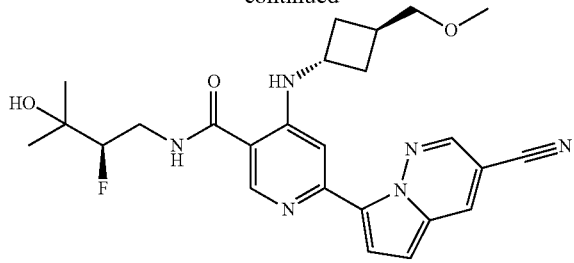

tert-butyl ((1r,3r)-3-(methoxymethyl)cyclobutyl)carbamate

A mixture of tert-butyl ((1r,3r)-3-(hydroxymethyl)cyclobutyl)carbamate (230 mg, 1.14 mmol), 11 mL acetonitrile, Silver oxide (141.55 mg, 1.14 mmol), and iodomethane (11.49 ml, 97.14 mmol) was heated at 40° C. for 26 hours. The mixture was allowed to cool to room temperature and was filtered. The filtrate was concentrated and then further dried under reduced pressure to provide the crude product, which was used without further purification.

(1r,3r)-3-(methoxymethyl)cyclobutan-1-amine hydrochloride tert-butyl ((1r,3r)-3-(methoxymethyl)cyclobutyl)carbamate (246 mg, 1 mmol) and 1.25M HCl in EtOH (4.57 ml) was stirred overnight. The mixture was concentrated and diethyl ether was added. The mixture was sonicated briefly and the resulting solid was filtered and washed with a small amount of diethyl ether to provide the product.

6-chloro-N—((R)-2-fluoro-3-hydroxy-3-methylbutyl)-4-(((1r,3R)-3-(methoxymethyl)cyclobutyl) amino)nicotinamide (R)-4,6-dichloro-N-(2-fluoro-3-hydroxy-3-methylbutyl) nicotinamide 1 (50 mg, 0.17 mmol), (1r,3r)-3-(methoxymethyl)cyclobutan-1-amine hydrochloride (70% purity, 44.04 mg, 0.2 mmol), N,N-Diisopropylethylamine (0.12 ml, 0.68 mmol) and DMA (0.17 ml) were heated in the microwave at 160° C. for 10 minutes. The reaction mixture was chromatographed using a 25-100% ethyl acetate in hexanes gradient to obtain the product.

ES/MS: 374.3 [M+H$^+$].

6-(3-cyanopyrrolo[1,2-b]pyridazin-7-yl)-N—((R)-2-fluoro-3-hydroxy-3-methylbutyl)-4-(((1r,3R)-3-(methoxymethyl)cyclobutyl)amino)nicotinamide (Example 706)

6-chloro-N—((R)-2-fluoro-3-hydroxy-3-methylbutyl)-4-(((1r,3R)-3-(methoxymethyl)cyclobutyl)amino)nicotinamide (19 mg, 0.058 mmol), 7-(4,4,5,5-tetramethyl-1,3,2-dioxaborolan-2-yl)pyrrolo[1,2-b]pyridazine-3-carbonitrile (20.52 mg, 0.076 mmol), XPhos Pd G3 (4.44 mg, 0.01 mmol), 2M Potassium phosphate tribasic (0.05 ml), and 0.15M DME (0.32 ml) were degassed together for 1 minute, then heated at 120° C. in the microwave for 15 minutes. The crude mixture was purified by RP-HPLC HPLC (eluent: water/MeCN*0.1% TFA).

ES/MS: 481.3 [M+H$^+$].

1H NMR (400 MHz, Methanol-d4) δ 8.78 (d, J=2.1 Hz, 1H), 8.69 (s, 1H), 8.59 (s, 1H), 8.00 (d, J=5.1 Hz, 1H), 7.67 (s, 1H), 7.24 (d, J=5.2 Hz, 1H), 6.96 (d, J=4.6 Hz, 1H), 4.57-4.35 (m, 2H), 4.07-3.87 (m, 1H), 3.59 (d, J=6.5 Hz, 2H), 3.45 (s, 3H), 3.16 (s, 1H), 2.77-2.65 (m, 1H), 2.54 (d, J=11.7 Hz, 2H), 2.33 (d, J=13.6 Hz, 2H), 1.33-1.31 (m, 6H).

Procedure 79: Example 830

Methyl (((1R,3r)-3-((2-(3-cyanopyrrolo[1,2-b] pyridazin-7-yl)-5-(((1r,4R)-4-(cyclopropanecarboxamido)cyclohexyl)carbamoyl)pyridin-4-yl)amino) cyclobutyl)methyl)carbamate

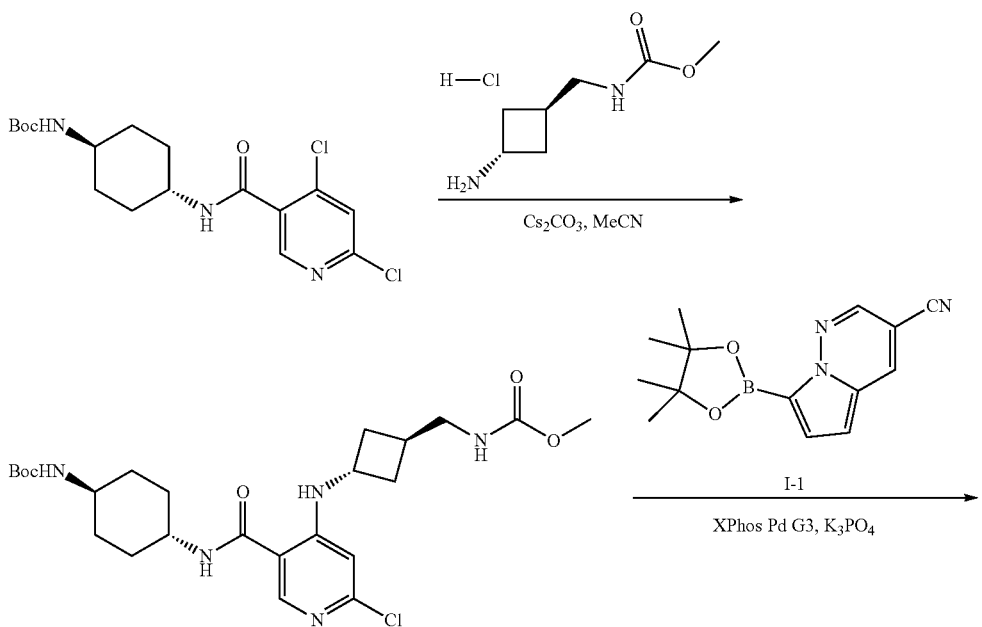

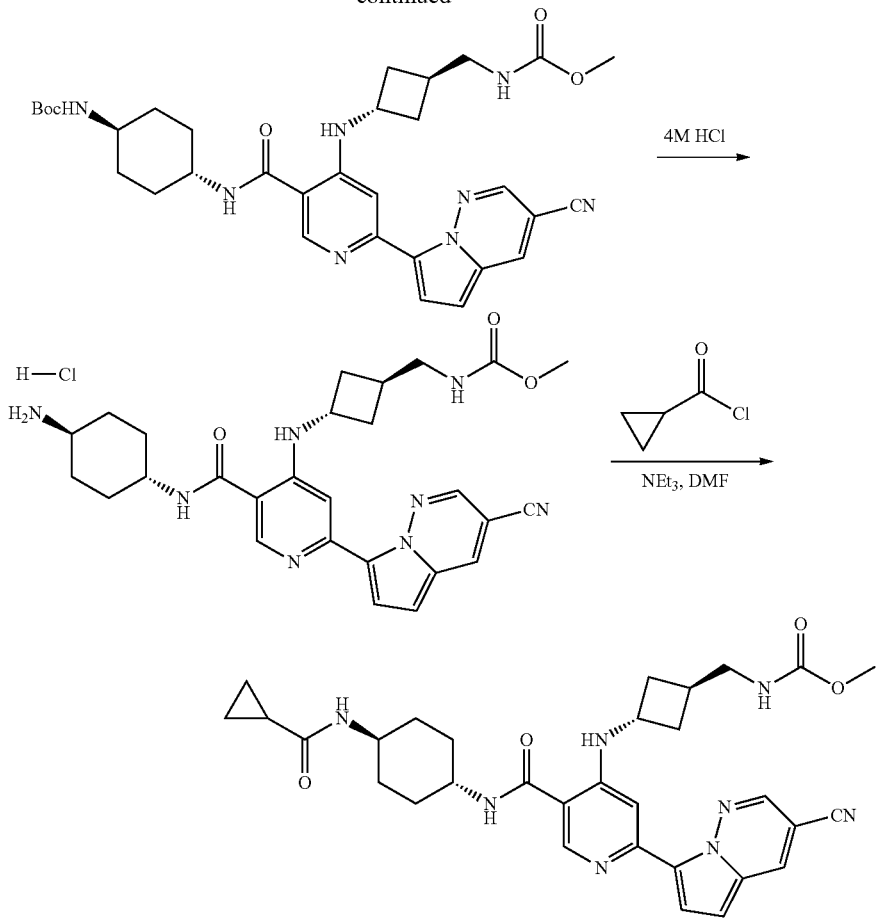

Example 830 tert-butyl ((1R,4r)-4-(6-chloro-4-(((1r,3R)-3-(((methoxycarbonyl)amino)methyl)cyclobutyl)amino)nicotinamido)cyclohexyl)carbamate A microwave vial was charged with tert-butyl ((1r,4r)-4-(4,6-dichloronicotinamido)cyclohexyl)carbamate (obtained as described in Procedure 61) (60.0 mg, 0.16 mmol), methyl (((1r,3r)-3-aminocyclobutyl)methyl)carbamate hydrochloride (45.1 mg, 0.23 mmol), and cesium carbonate (201.4 mg, 0.62 mmol). Butyronitrile (1.0 mL) was added to the vial, and the vial was sealed and heated thermally at 100° C. for 15 hours. The reaction mixture was cooled, diluted with MeOH, filtered through a plug of Celite, and concentrated in vacuo. The resulting residue was purified by silica gel chromatography (eluent: MeOH/DCM) to provide the product.

ES/MS: 510.2 [M+H$^+$].

tert-butyl ((1R,4r)-4-(6-(3-cyanopyrrolo[1,2-b]pyridazin-7-yl)-4-(((1r,3R)-3-(((methoxycarbonyl)amino)methyl)cyclobutyl)amino)nicotinamido)cyclohexyl)carbamate A microwave vial was charged with tert-butyl ((1R,4r)-4-(6-chloro-4-(((1r,3R)-3-(((methoxycarbonyl)amino)methyl)cyclobutyl)amino)nicotinamido)cyclohexyl)carbamate (44.5 mg, 0.087 mmol), 7-(4,4,5,5-tetramethyl-1,3,2-dioxaborolan-2-yl)pyrrolo[1,2-b]pyridazine-3-carbonitrile (30.5 mg, 0.11 mmol), XPhos Pd G3 (7.4 mg, 0.0087 mmol), and potassium phosphate (37.0 mg, 0.17 mmol). DME (1.5 mL) and water (0.35 mL) were added, and solution was degassed with bubbling argon for 60 seconds. The vial was sealed and heated in a microwave reactor at 125° C. for 25 minutes. Upon completion, the reaction mixture was cooled, diluted with MeOH, filtered through a plug of Celite, and concentrated in vacuo to provide the crude product which was used without additional purification.

ES/MS: 617.4 [M+H$^+$].

methyl (((1R,3r)-3-((5-(((1r,4R)-4-aminocyclohexyl)carbamoyl)-2-(3-cyanopyrrolo[1,2-b]pyridazin-7-yl)pyridin-4-yl)amino)cyclobutyl)methyl)carbamate hydrochloride Crude tert-butyl ((1R,4r)-4-(6-(3-cyanopyrrolo[1,2-b]pyridazin-7-yl)-4-(((1r,3R)-3-(((methoxycarbonyl)amino)methyl)cyclobutyl)amino)nicotinamido)cyclohexyl)carbamate (53.5 mg, 0.087 mmol) was taken in 4M HCl in Dioxane. The reaction mixture was stirred at room temperature for 2 hours. Et$_2$O (3.0 mL) was added, and the reaction mixture was stirred at room temperature for 15 minutes. The reaction mixture was concentrated in vacuo to provide the crude product which was used without purification.

ES/MS: 517.4 [M+H$^+$].

methyl (((1R,3r)-3-((2-(3-cyanopyrrolo[1,2-b]pyridazin-7-yl)-5-(((1r,4R)-4-(cyclopropanecarboxamido)cyclohexyl)carbamoyl)pyridin-4-yl)amino)cyclobutyl)methyl)carbamate (Example 830)

Crude methyl ((((1R,3r)-3-((5-(((r,4R)-4-aminocyclohexyl)carbamoyl)-2-(3-cyanopyrrolo[1,2-b]pyridazin-7-yl)pyridin-4-yl)amino)cyclobutyl)methyl)carbamate hydrochloride (44.8 mg, 0.087 mmol) was taken in DMF (1.0 mL). Triethylamine (48.4 µL, 0.35 mmol) was added followed by cyclopropanecarbonyl chloride (12.6 µL, 0.14 mmol). The reaction mixture was filtered and directly purified by RP-HPLC (eluent: water/MeCN*0.1% TFA) to provide the product as the trifluoroacetate salt.

ES/MS: 585.8 [M+H$^+$].

1H NMR (400 MHz, Methanol-d4) δ 8.85-8.71 (m, 2H), 8.56 (s, 1H), 7.98 (d, J=5.0 Hz, 1H), 7.82 (s, 1H), 7.22 (d, J=5.1 Hz, 1H), 4.52-4.31 (m, 1H), 4.05-3.81 (m, 1H), 3.82-3.58 (m, 4H), 3.36 (d, J=7.4 Hz, 2H), 2.71-2.52 (m, 1H), 2.53-2.41 (m, 2H), 2.33-2.21 (m, 2H), 2.17-1.89 (m, 4H), 1.67-1.29 (m, 5H), 0.90-0.79 (m, 2H), 0.78-0.67 (m, 2H).

Procedure 80: Example 888 methyl (R)-(5-((2-(3-cyanopyrrolo[1,2-b]pyridazin-7-yl)-5-((2-fluoro-3-hydroxy-3-methylbutyl)carbamoyl)pyridin-4-yl)amino)pyridin-2-yl)carbamate

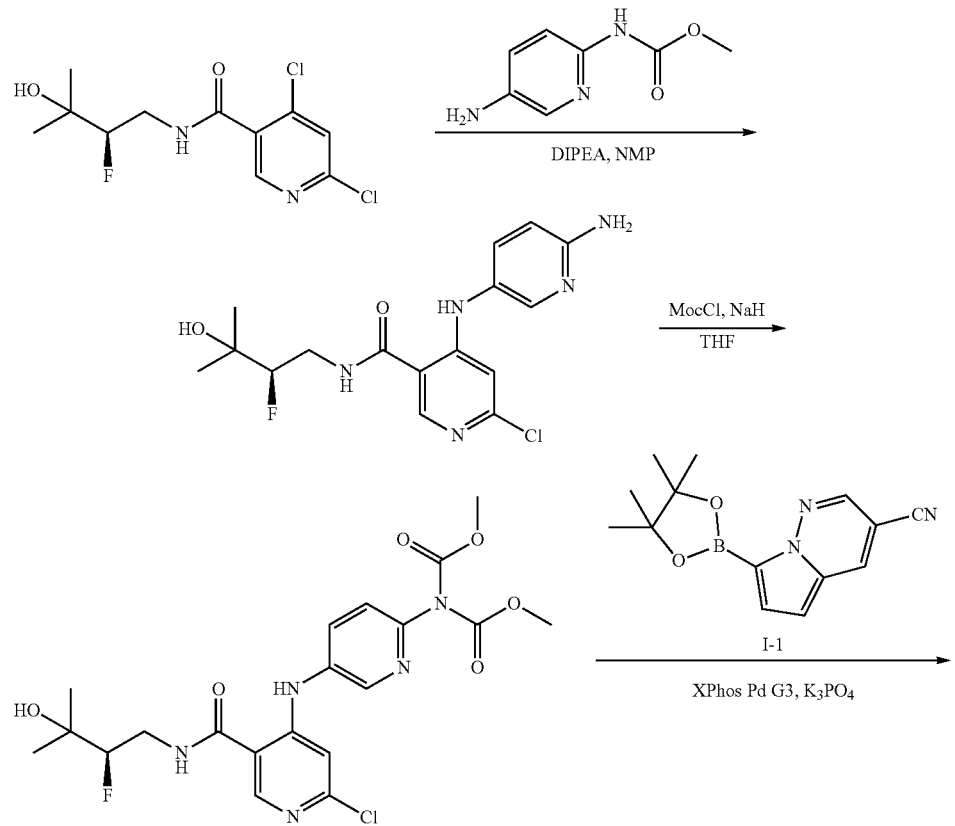

Intermediate 80A

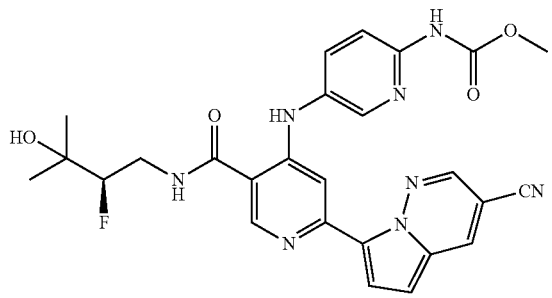

Example 888

(R)-4-((6-aminopyridin-3-yl)amino)-6-chloro-N-(2-fluoro-3-hydroxy-3-methylbutyl)nicotinamide (R)-4,6-dichloro-N-(2-fluoro-3-hydroxy-3-methylbutyl) nicotinamide (50 mg, 0.169 mmol) and methyl (5-aminopyridin-2-yl)carbamate (38 mg, 0.227 mmol) were added to a vial followed by NMP (1.5 mL) and DIPEA (0.075 mL, 0.431 mmol). The resulting solution was heated to 160° C. for 4 hr. The reaction mixture was then poured into water and extracted with EtOAc. The organic layer was dried, filtered and concentrated, then purified by RP-HPLC (eluent: water/MeCN*0.1% TFA). The product fractions were combined and neutralized with saturated NaHCO3 solution to give product.

ES/MS: 368.1 (M+).

1H NMR (400 MHz, Methanol-d4) δ 8.39 (s, 1H), 7.85 (d, J=2.6 Hz, 1H), 7.43 (dd, J=8.8, 2.6 Hz, 1H), 6.70 (d, J=8.8 Hz, 1H), 6.56 (s, 1H), 4.45 (ddd, J=49.1, 9.2, 2.2 Hz, 1H), 3.92 (ddd, J=35.9, 14.5, 2.3 Hz, 1H), 3.58-3.41 (m, 1H), 1.30 (d, J=1.7 Hz, 6H).

Intermediate 80A

To a solution of (R)-4-((6-aminopyridin-3-yl)amino)-6-chloro-N-(2-fluoro-3-hydroxy-3-methylbutyl)nicotinamide (50 mg, 0.033 mmol) in THF (2 ml), was added NaH (1.58 mg, 60% 0.045 mmol). After 10 min, added methyl chloroformate (0.01 ml, 0.13 mmol). After 1 hr, the reaction was diluted with EtOAc and washed brine. The organic layer was dried, filtered and concentrated to give the desired product.

ES/MS: 484.1 (M+).

methyl (R)-(5-((2-(3-cyanopyrrolo[1,2-b]pyridazin-7-yl)-5-((2-fluoro-3-hydroxy-3-methylbutyl)carbamoyl)pyridin-4-yl)amino)pyridin-2-yl)carbamate (Example 888)

Intermediate 80A (0.014 g, 0.05 mmol) and 7-(4,4,5,5-tetramethyl-1,3,2-dioxaborolan-2-yl)pyrrolo[1,2-b]pyridazine-3-carbonitrile (0.013 g, 0.027 mmol) were added to a microwave vial followed by DME (1.5 mL), XPhos Pd G3 (2.6 mg, 0.003 mmol) and K3PO4 (0.5M in water, 0.15 mL, 0.075 mmol). The resulting mixture was purged with argon for 2 minutes, sealed and heated to 100° C. for 2 hr. The reaction mixture was filtered and purified by RP-HPLC (eluent: water/MeCN*0.1% TFA). The product fractions were combined and lyophilized to give the final product as a TFA salt.

ES/MS: 533.2 (M+H+).

1H NMR (400 MHz, Methanol-d4) δ 8.74 (s, 1H), 8.58 (d, J=2.1 Hz, 1H), 8.40 (s, 1H), 8.13 (d, J=8.8 Hz, 1H), 8.07 (s, 1H), 7.91 (d, J=9.0 Hz, 1H), 7.84 (d, J=5.1 Hz, 1H), 7.19 (d, J=5.1 Hz, 1H), 4.50 (dd, J=48.9, 9.3 Hz, 1H), 4.12-3.89 (m, 1H), 3.83 (d, J=10.7 Hz, 2H), 3.61-3.43 (m, 1H), 1.32 (d, J=9.6 Hz, 6H).

Procedure 81: Example 793

N-(((1R,3r)-3-((2-(3-cyanopyrrolo[1,2-b]pyridazin-7-yl)-5-(((R)-2-fluoro-3-hydroxy-3-methylbutyl)carbamoyl)pyridin-4-yl)amino)cyclobutyl)methyl)-4-methylpiperazine-1-carboxamide

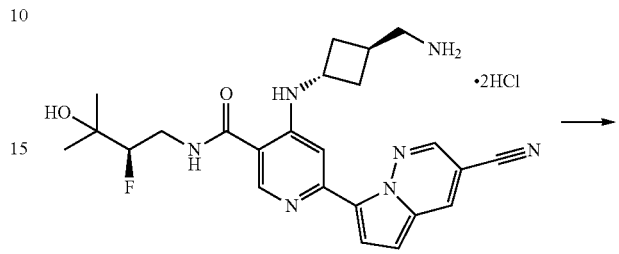

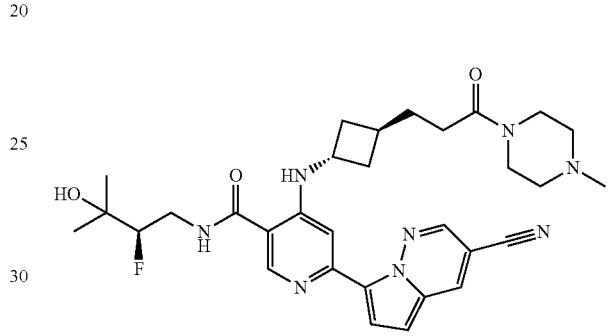

N-(((1R,3r)-3-((2-(3-cyanopyrrolo[1,2-b]pyridazin-7-yl)-5-(((R)-2-fluoro-3-hydroxy-3-methylbutyl)carbamoyl)pyridin-4-yl)amino)cyclobutyl)methyl)-4-methylpiperazine-1-carboxamide (Example 793)

To a slurry of 4-(((1r,3R)-3-(aminomethyl)cyclobutyl)amino)-6-(3-cyanopyrrolo[1,2-b]pyridazin-7-yl)-N—((R)-2-fluoro-3-hydroxy-3-methylbutyl)nicotinamide bis-hydrochloride (14 mg, 0.03 mmol) in THF (0.3 mL) at 0° C. was added 4-nitrophenyl chloroformate (8 mg, 0.04 mmol) and N-ethyldiisopropylamine (0.04 mL, 0.23 mmol). The resulting solution was then stirred for 1 hour at 0° C. before 1-methylpiperazine (15 uL, 0.14 mmol) was added. The solution was stirred at room temperature for 4 hours and diluted with DMF. Volatiles were removed in vacuo and the resulting solution was purified by RP-HPLC (eluent: water/MeCN*0.1% TFA) to yield the product as a trifluoroacetate salt.

ES/MS: 592.4 (M+H+).

1H NMR (400 MHz, Methanol-d4) δ 8.78-8.70 (m, 2H), 8.59 (s, 1H), 7.99 (d, J=5.1 Hz, 1H), 7.84 (s, 1H), 7.21 (d, J=5.1 Hz, 1H), 4.53-4.33 (m, 2H), 4.23 (s, 2H), 3.92 (ddd, J=36.4, 14.5, 2.1 Hz, 1H), 3.57-3.46 (m, 1H), 3.44 (d, J=7.8 Hz, 2H), 3.27-3.02 (m, 6H), 2.92 (s, 3H), 2.57 (td, J=8.3, 3.9 Hz, 1H), 2.47 (ddt, J=11.3, 7.6, 3.5 Hz, 2H), 2.25 (dtd, J=12.7, 7.1, 2.3 Hz, 2H), 1.29 (d, J=1.6 Hz, 6H).

19F NMR (376 MHz, Methanol-d4) δ -195.76 (ddd, J=51.1, 36.6, 16.3 Hz).

Procedure 82: Example 803

6-(3-cyanopyrrolo[1,2-b]pyridazin-7-yl)-4-((4-hydroxybicyclo[2.2.2]octan-1-yl)amino)-N-(3-(methylamino)-3-oxopropyl)nicotinamide

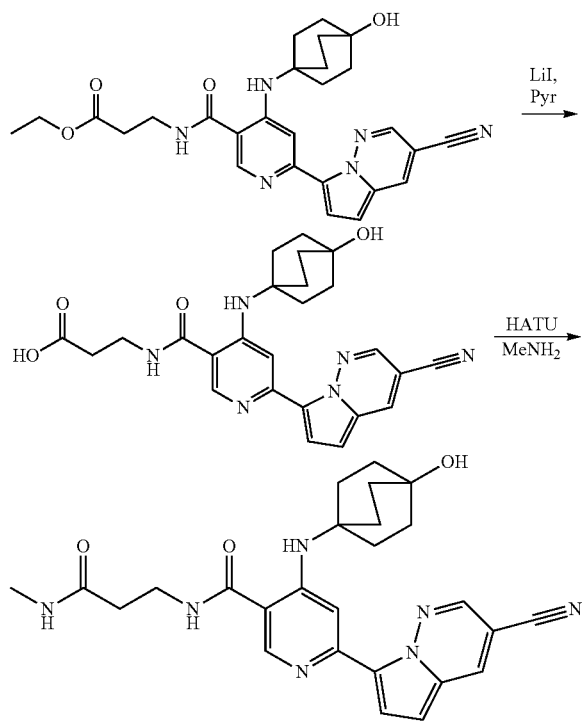

Ethyl 3-(6-(3-cyanopyrrolo[1,2-b]pyridazin-7-yl)-4-((4-hydroxybicyclo[2.2.2]octan-1-yl)amino)nicotinamido)propanoate Ethyl 3-(6-(3-cyanopyrrolo[1,2-b]pyridazin-7-yl)-4-((4-hydroxybicyclo[2.2.2]octan-1-yl)amino)nicotinamido)propanoate was prepared according to Procedure 3 using the appropriate starting materials.

3-(6-(3-Cyanopyrrolo[1,2-b]pyridazin-7-yl)-4-((4-hydroxybicyclo[2.2.2]octan-1-yl)amino)nicotinamido)propanoic acid Ethyl 3-(6-(3-cyanopyrrolo[1,2-b]pyridazin-7-yl)-4-((4-hydroxybicyclo[2.2.2]octan-1-yl)amino)nicotinamido)propanoate (180 mg, 0.36 mmol) and lithium iodide (482 mg, 3.6 mmol) were combined in pyridine (3.5 mL) and heated to 180° C. (MW) for 45 min and then 30 min. The resulting solution was diluted with 1N aqueous hydrochloric acid and extracted 3 times with $CH_2Cl_2$/MeOH (10:1). The resulting aqueous layer was then filtered and the resulting ppt was combined with the collected organic layers and concentrated to dryness. The resulting crude hydrochloride salt was used without further purification.

ES/MS: 475.4 (M+H$^+$).

6-(3-cyanopyrrolo[1,2-b]pyridazin-7-yl)-4-((4-hydroxybicyclo[2.2.2]octan-1-yl)amino)-N-(3-(methylamino)-3-oxopropyl)nicotinamide (Example 803)

To a solution of 3-(6-(3-Cyanopyrrolo[1,2-b]pyridazin-7-yl)-4-((4-hydroxybicyclo[2.2.2]octan-1-yl)amino)nicotinamido)propanoic acid hydrochloride (47 mg, 0.09 mmol) in DMF (1 mL) was added methylamine (2M in THF, 0.23 mL, 0.46 mmol) and HATU (45 mg, 0.118 mmol). The resulting solution was stirred at room temperature for 1 hour and the mixture was purified by RP-HPLC (eluent: water/MeCN*0.1% TFA) to yield the product as a trifluoroacetate salt.

ES/MS: 488.5 (M+H$^+$).

1H NMR (400 MHz, Methanol-d4) δ 8.79 (d, J=2.1 Hz, 1H), 8.72 (d, J=2.1 Hz, 1H), 8.50 (s, 1H), 8.29 (s, 1H), 7.95 (d, J=5.1 Hz, 1H), 7.25 (d, J=5.1 Hz, 1H), 3.64 (t, J=6.6 Hz, 2H), 2.76 (s, 3H), 2.53 (t, J=6.7 Hz, 2H), 2.27 (dd, J=10.4, 5.7 Hz, 6H), 1.93 (dd, J=10.3, 5.7 Hz, 6H).

Procedure 83: Example 965

(R)-4-(((6-chloropyridin-3-yl)amino)-6-(3-cyanopyrrolo[1,2-b]pyridazin-7-yl)-N-(2-fluoro-3-hydroxy-3-methylbutyl)nicotinamide

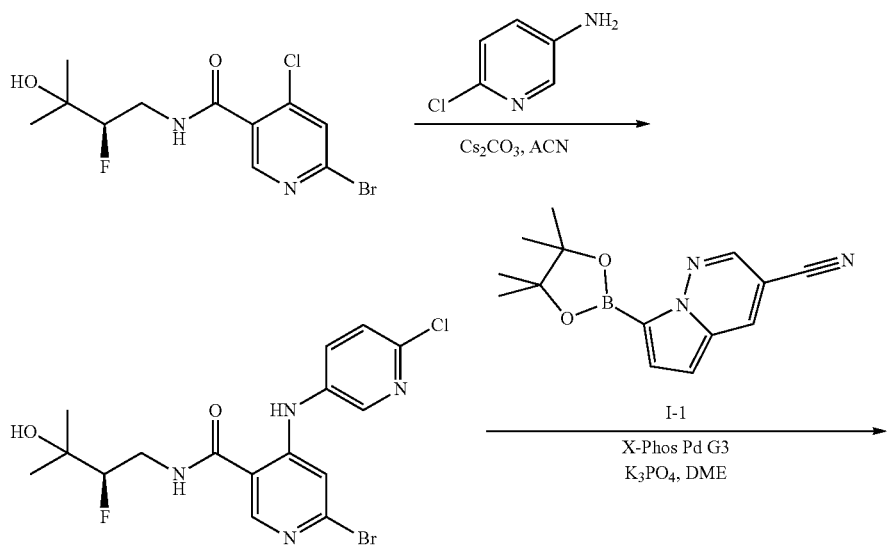

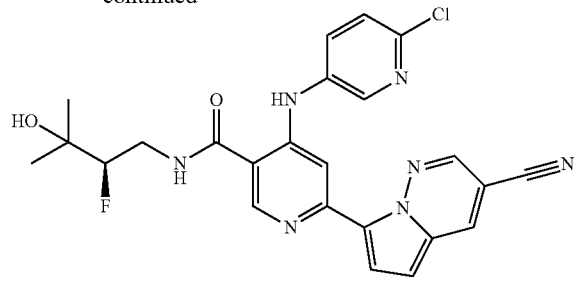

(R)-6-bromo-4-((6-chloropyridin-3-yl)amino)-N-(2-fluoro-3-hydroxy-3-methylbutyl)nicotinamide To a mixture of (R)-6-bromo-4-chloro-N-(2-fluoro-3-hydroxy-3-methylbutyl)nicotinamide (100 mg, 0.29 mmol), 6-chloropyridin-3-amine (49 mg, 0.38 mmol) and Cesium carbonate (192 mg, 0.60 mmol) was added 2.0 mL of ACN. The reaction mixture was stirred at 90° C. overnight after which it was cooled to room temperature. The reaction mixture was partitioned between EtOAc and water. The organic layer was separated, washed with brine, dried over Na$_2$SO$_4$. Filtered and concentrated. The crude was purified by reverse phase high pressure liquid chromatography (eluent: water/MeCN*0.1% TFA). Product fractions were combined, concentrated and then basified by sodium bicarbonate solution and extracted with ethyl acetate (3×) to provide the title compound as a free base.

ES/MS: 433.1 and 431.5 [M+H$^+$].

(R)-4-((6-chloropyridin-3-yl)amino)-6-(3-cyanopyrrolo[1,2-b]pyridazin-7-yl)-N-(2-fluoro-3-hydroxy-3-methylbutyl)nicotinamide (Example 965)

A mixture of (R)-6-bromo-4-((6-chloropyridin-3-yl)amino)-N-(2-fluoro-3-hydroxy-3-methylbutyl)nicotinamide (57 mg, 0.13 mmol), 7-(4,4,5,5-tetramethyl-1,3,2-dioxaborolan-2-yl)pyrrolo[1,2-b]pyridazine-3-carbonitrile (I-1) (51 mg, 0.19 mmol), XPhos Pd G3 (11 mg), and 2M Potassium phosphate tribasic (0.14 ml) in 1.3 mL DME was degassed with argon for 3 minutes, then capped and heated under microwave conditions at 50° C. for 20 minutes. The crude material was purified RP-HPLC (eluent: water/MeCN*0.1% TFA) to yield the product as a trifluoroacetate salt.

ES/MS: 494.3 (M+H$^+$).

1H NMR (400 MHz, Methanol-d4) δ 8.75 (s, 1H), 8.71 (d, J=2.2 Hz, 1H), 8.60 (d, J=2.2 Hz, 1H), 8.54 (dd, J=2.8, 0.7 Hz, 1H), 8.12 (s, 1H), 7.97 (dd, J=8.5, 2.8 Hz, 1H), 7.85 (d, J=5.1 Hz, 1H), 7.68 (dd, J=8.5, 0.7 Hz, 1H), 7.16 (d, J=5.1 Hz, 1H), 4.46 (ddd, J=49.0, 9.3, 2.1 Hz, 1H), 3.99 (ddd, J=36.4, 14.6, 2.1 Hz, 1H), 3.53 (ddd, J=16.2, 14.6, 9.3 Hz, 1H), 1.30 (d, J=1.7 Hz, 6H).

Procedure 84: Example 972

(R)-4-((5-(1H-pyrazol-4-yl)pyrazin-2-yl)amino)-6-(3-cyanopyrrolo[1,2-b]pyridazin-7-yl)-N-(2-fluoro-3-hydroxy-3-methylbutyl)nicotinamide

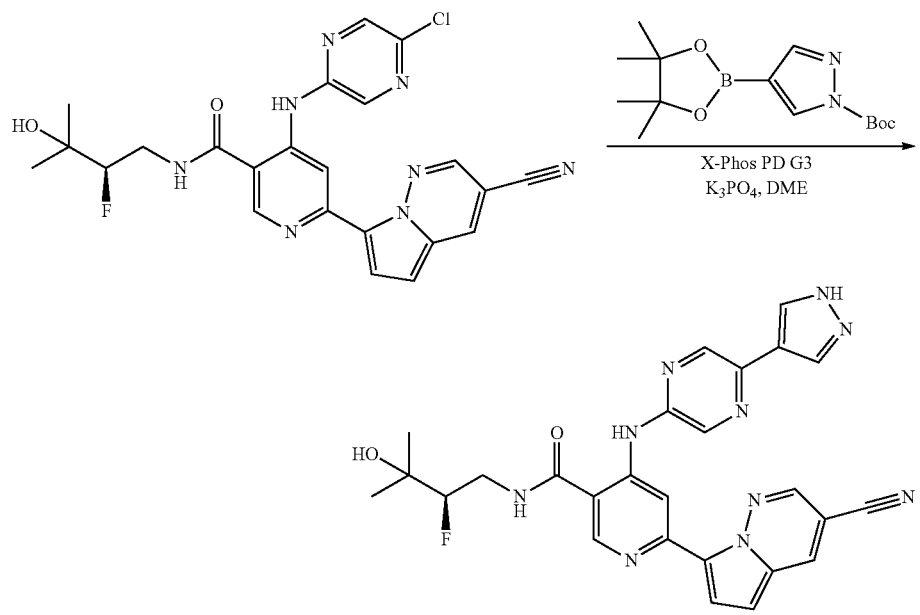

251

(R)-4-((5-(1H-pyrazol-4-yl)pyrazin-2-yl)amino)-6-(3-cyanopyrrolo[1,2-b]pyridazin-7-yl)-N-(2-fluoro-3-hydroxy-3-methylbutyl)nicotinamide (Example 972)

A mixture of (R)-4-((5-chloropyrazin-2-yl)amino)-6-(3-cyanopyrrolo[1,2-b]pyridazin-7-yl)-N-(2-fluoro-3-hydroxy-3-methylbutyl)nicotinamide (15 mg, 0.03 mmol), tert-butyl 4-(4,4,5,5-tetramethyl-1,3,2-dioxaborolan-2-yl)-1H-pyrazole-1-carboxylate (18 mg, 0.06 mmol), XPhos Pd G3 (3 mg), and 2M Potassium phosphate tribasic (0.03 ml) in 0.3 mL DME was degassed with argon for 3 minutes, then capped and heated under microwave conditions at 120° C. for 30 minutes. The crude material was purified RP-HPLC (eluent: water/MeCN*0.1% TFA) to yield the product as a trifluoroacetate salt.
ES/MS: 527.2 (M+H$^+$).
1H NMR (400 MHz, Methanol-d4) δ 10.04 (s, 1H), 8.84 (d, J=1.5 Hz, 1H), 8.80 (s, 1H), 8.75 (d, J=2.2 Hz, 1H), 8.70 (d, J=2.1 Hz, 1H), 8.47 (d, J=1.4 Hz, 1H), 8.24 (s, 2H), 7.93 (d, J=4.9 Hz, 1H), 7.19 (d, J=5.0 Hz, 1H), 4.49 (ddd, J=49.3, 9.1, 1.9 Hz, 1H), 4.00 (ddd, J=36.1, 14.7, 1.8 Hz, 1H), 3.65-3.48 (m, 1H), 1.32 (s, 6H).

Procedure 85: Example 962

252

3-(6-chloro-4-((4-hydroxybicyclo[2.2.2]octan-1-yl)amino)nicotinamido)-2,2-difluoropropanoic acid Made in the same manner as (6-chloro-4-((4-hydroxybicyclo[2.2.2]octan-1-yl)amino)nicotinoyl)glycine in Procedure 49 substituting methyl 3-amino-2,2-difluoropropanoate.

3-(6-(3-cyanopyrrolo[1,2-b]pyridazin-7-yl)-4-((4-hydroxybicyclo[2.2.2]octan-1-yl)amino)nicotinamido)-2,2-difluoropropanoic acid A mixture of 3-(6-chloro-4-((4-hydroxybicyclo[2.2.2]octan-1-yl)amino)nicotinamido)-2,2-difluoropropanoic acid (140 mg, 0.34 mmol), 7-(4,4,5,5-tetramethyl-1,3,2-dioxaborolan-2-yl)pyrrolo[1,2-b]pyridazine-3-carbonitrile (I-1) (126 mg, 0.47 mmol), XPhos Pd G3 (29 mg), and 2M Potassium phosphate tribasic (0.34 ml) in 1.7 mL DME was degassed with argon for 3 minutes, then capped and heated under microwave conditions at 120° C. for 20 minutes. The crude material was purified RP-HPLC (eluent: water/MeCN*0.1% TFA) to yield the product as a trifluoroacetate salt.
ES/MS: 511.3 (M+H$^+$).

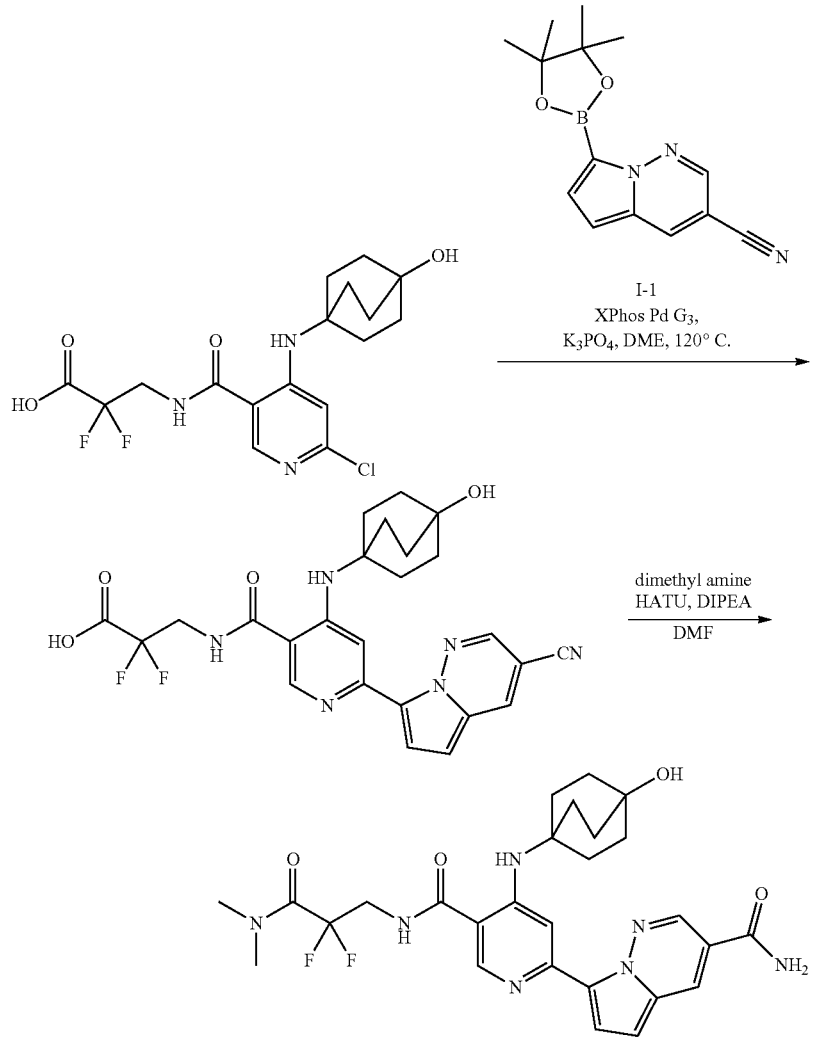

7-(5-((3-(dimethylamino)-2,2-difluoro-3-oxopropyl)carbamoyl)-4-((4-hydroxybicyclo[2.2.2]octan-1-yl)amino)pyridin-2-yl)pyrrolo[1,2-b]pyridazine-3-carboxamide (Example 962)

To a solution of 3-(6-(3-carbamoylpyrrolo[1,2-b]pyridazin-7-yl)-4-((4-hydroxybicyclo[2.2.2]octan-1-yl)amino)nicotinamido)-2,2-difluoropropanoic acid (83 mg, 0.15 mmol) in DMF (0.75 mL) was added 2M Dimethylamine (0.15 ml), HATU (85 mg, 0.22 mmol), and DIPEA (0.13 mL, 0.76 mmol). The resulting mixture was stirred at room temperature for 18 hours and subsequently diluted with EtOAc. In addition to the expected HATU coupling, hydrolysis of the nitrile group was also observed and therefore that product was isolated. The resulting solution was washed with 50% aqueous NH₄Cl (2 times) The resulting aqueous layers were back-extracted with EtOAc and the combined organic layers were dried over MgSO₄ and concentrated to dryness. The crude material was then purified via RP-HPLC (eluent: water/MeCN*0.1% TFA) to yield the product as a trifluoroacetate salt.

ES/MS: 556.2 (M+H⁺).

1H NMR (400 MHz, Methanol-d4) δ 8.69 (d, J=2.3 Hz, 1H), 8.59 (d, J=2.3 Hz, 1H), 8.52 (s, 1H), 8.40 (s, 1H), 7.96 (d, J=5.2 Hz, 1H), 7.23 (d, J=5.0 Hz, 1H), 3.96 (t, J=13.7 Hz, 2H), 3.48 (q, J=7.1 Hz, 4H), 3.16-3.10 (m, 1H), 2.99 (s, 1H), 2.85 (s, 1H), 2.26 (t, J=7.9 Hz, 6H), 2.02 (s, 1H), 1.90 (t, J=7.9 Hz, 6H), 1.36 (dd, J=6.7, 3.2 Hz, 2H), 1.28 (s, 1H), 1.17 (t, J=7.0 Hz, 5H), 0.92-0.84 (m, 1H).

Procedure 86: Example 756 and Example 757

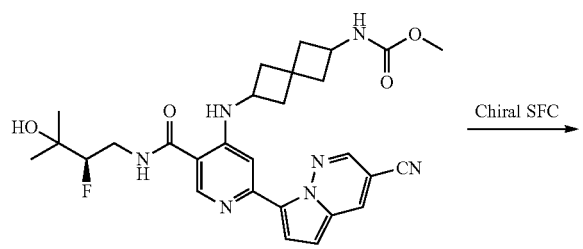

Diastereomer 1

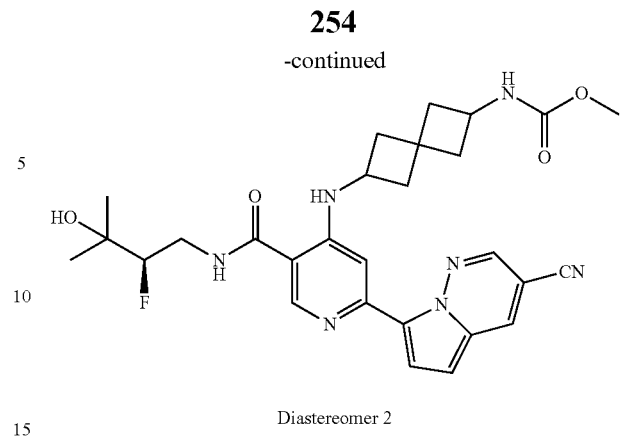

Diastereomer 2

Methyl (R)-(6-((2-(3-cyanopyrrolo[1,2-b]pyridazin-7-yl)-5-((2-fluoro-3-hydroxy-3-methylbutyl)carbamoyl)pyridin-4-yl)amino)spiro[3.3]heptan-2-yl)carbamate Methyl (R)-(6-((2-(3-cyanopyrrolo[1,2-b]pyridazin-7-yl)-5-((2-fluoro-3-hydroxy-3-methylbutyl)carbamoyl)pyridin-4-yl)amino)spiro[3.3]heptan-2-yl)carbamate (14 mg) as a mixture of two isomers was separated using an SFC AD-H column, co-solvent: 30% IPA/DEA.

Diastereomer 1 Example 756

ES/MS: 550.3 (M+H⁺).

1H NMR (400 MHz, Methanol-d4) δ 8.75 (d, J=2.2 Hz, 1H), 8.68 (d, J=2.2 Hz, 1H), 8.55 (s, 1H), 7.98 (d, J=5.0 Hz, 1H), 7.69 (s, 1H), 7.21 (d, J=5.1 Hz, 1H), 4.35 (dd, J=9.3, 2.1 Hz, 1H), 4.26 (q, J=7.7 Hz, 1H), 4.06-3.83 (m, 2H), 3.61 (s, 3H), 3.58-3.37 (m, 1H), 2.81-2.72 (m, J=11.4 Hz, 1H), 2.60 (ddt, J=17.5, 11.8, 6.7 Hz, 2H), 2.35 (dt, J=12.2, 6.1 Hz, 1H), 2.24-1.96 (m, 4H), 1.28 (d, J=1.6 Hz, 6H).

Diastereomer 2 Example 757

ES/MS: 550.3 (M+H⁺).

1H NMR (400 MHz, Methanol-d4) δ 8.75 (d, J=2.2 Hz, 1H), 8.68 (d, J=2.2 Hz, 1H), 8.55 (s, 1H), 7.98 (d, J=5.1 Hz, 1H), 7.69 (s, 1H), 7.21 (d, J=5.1 Hz, 1H), 4.42 (ddd, J=49.0, 9.3, 2.1 Hz, 1H), 4.27 (p, J=7.6 Hz, 1H), 4.12-3.83 (m, 2H), 3.61 (s, 3H), 3.57-3.36 (m, 2H), 2.79 (t, J=5.9 Hz, 1H), 2.60 (ddt, J=17.2, 11.7, 6.5 Hz, 2H), 2.42-2.26 (m, 1H), 2.24-2.06 (m, 3H), 2.02 (s, 1H), 1.28 (d, J=1.7 Hz, 6H).

Procedure 87: Example 764 and Example 765

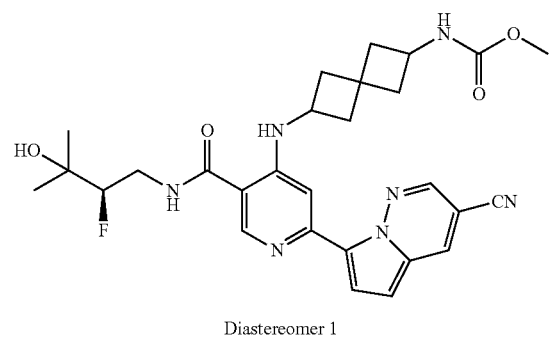

Diastereomer 1

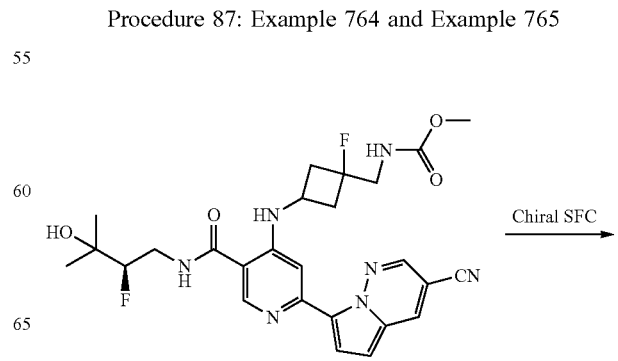

-continued

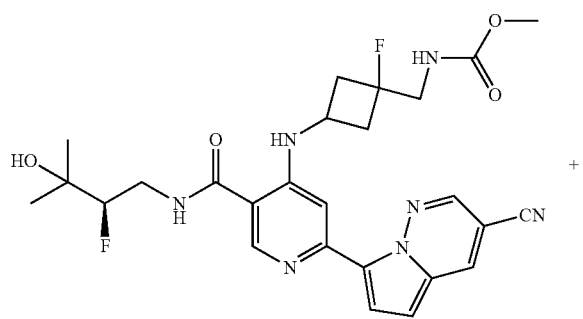

Diastereomer 1

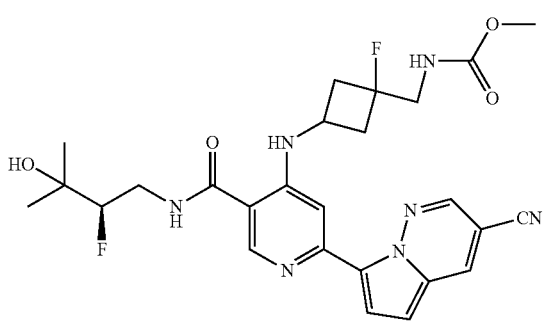

Diastereomer 2

Methyl (R)-((3-((2-(3-cyanopyrrolo[1,2-b]pyridazin-7-yl)-5-((2-fluoro-3-hydroxy-3-methylbutyl)carbamoyl)pyridin-4-yl)amino)-1-fluorocyclobutyl)methyl) carbamate Methyl (R)-((3-((2-(3-cyanopyrrolo[1,2-b]pyridazin-7-yl)-5-((2-fluoro-3-hydroxy-3-methylbutyl)carbamoyl)pyridin-4-yl)amino)-1-fluorocyclobutyl)methyl)carbamate (160 mg) as a mixture of two isomers was separated using an IC SFC column, co-solvent: 50% EtOH/DEA.

Diastereomer 1 Example 764

ES/MS: 542.4 (M+H⁺).
1H NMR (400 MHz, Methanol-d4) δ 8.79 (s, 1H), 8.62 (s, 1H), 8.54 (s, 1H), 8.03 (s, 1H), 7.90 (d, J=5.0 Hz, 1H), 7.12 (d, J=4.9 Hz, 1H), 4.55-4.31 (m, 1H), 4.09-3.81 (m, 2H), 3.75 (s, 3H), 3.53 (dt, J=24.8, 7.7 Hz, 3H), 2.97 (d, J=8.0 Hz, 2H), 2.51-2.16 (m, 2H), 1.29 (s, 6H).

Diastereomer 2 Example 765

ES/MS: 542.4 (M+H⁺).
1H NMR (400 MHz, Methanol-d4) δ 8.69 (d, J=2.2 Hz, 1H), 8.63 (d, J=2.2 Hz, 1H), 8.58 (s, 1H), 7.95 (d, J=5.0 Hz, 1H), 7.73 (s, 1H), 7.17 (d, J=5.0 Hz, 1H), 4.56-4.33 (m, 2H), 3.94 (ddd, J=36.2, 14.6, 2.2 Hz, 1H), 3.62 (s, 3H), 3.53-3.40 (m, 3H), 2.89 (ddd, J=19.0, 14.3, 8.4 Hz, 2H), 2.42 (ddd, J=19.8, 14.1, 5.7 Hz, 2H), 1.29 (d, J=1.6 Hz, 6H).

Procedure 88: Example 676 and Example 677

6-(3-cyanopyrrolo[1,2-b]pyridazin-7-yl)-4-((6,7-dihydro-5H-cyclopenta[c]pyridin-6-yl)amino)-N—((R)-2-fluoro-3-hydroxy-3-methylbutyl)nicotinamide

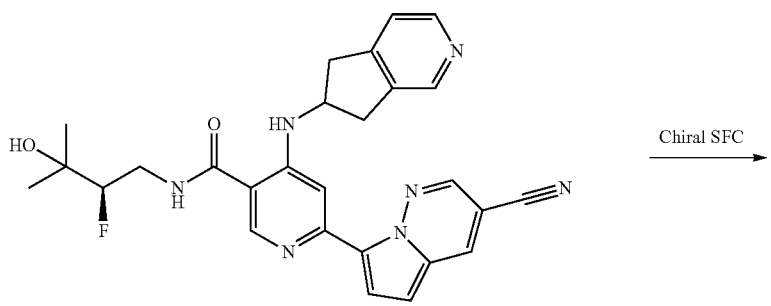

Chiral SFC →

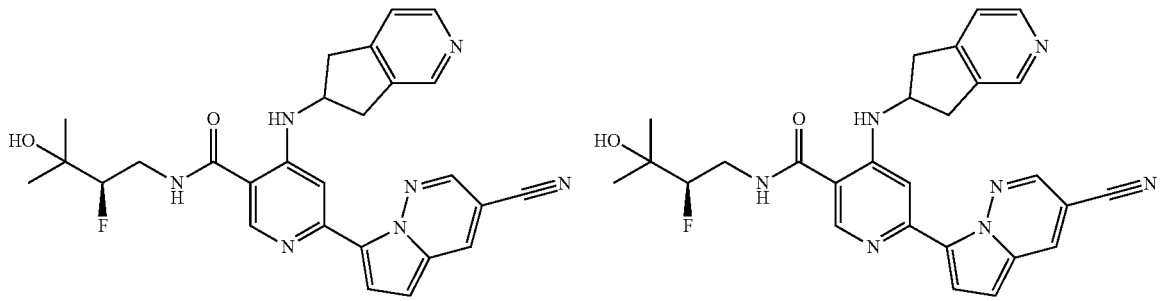

Diastereomer 1　　　　　　　　　　Diastereomer 2

6-(3-cyanopyrrolo[1,2-b]pyridazin-7-yl)-4-((6,7-dihydro-5H-cyclopenta[c]pyridin-6-yl)amino)-N—((R)-2-fluoro-3-hydroxy-3-methylbutyl)nicotinamide 6-(3-cyanopyrrolo[1,2-b]pyridazin-7-yl)-4-((6,7-dihydro-5H-cyclopenta[c]pyridin-6-yl)amino)-N—((R)-2-fluoro-3-hydroxy-3-methylbutyl)nicotinamide (75 mg, 0.15 mmol) as a mixture of two isomers was separated using an SFC OD-H column, co-solvent: 30% MeOH/DEA.

Diastereomer 1 Example 676

ES/MS: 500.4 (M+H+).
1H NMR (400 MHz, Methanol-d4) δ 8.83-8.73 (m, 2H), 8.72-8.59 (m, 3H), 8.06 (d, J=5.1 Hz, 1H), 8.04-7.92 (m, 2H), 7.23 (d, J=5.1 Hz, 1H), 5.04 (tt, J=7.4, 5.0 Hz, 1H), 4.38 (ddd, J=49.0, 9.3, 2.1 Hz, 1H), 4.01-3.73 (m, 3H), 3.58-3.35 (m, 3H), 1.25 (d, J=1.7 Hz, 6H).;

Diastereomer 2 Example 677

ES/MS: 500.3 (M+H+).
1H NMR (400 MHz, Methanol-d4) δ 8.84-8.71 (m, 2H), 8.71-8.58 (m, 3H), 8.15-7.88 (m, 3H), 7.23 (d, J=5.0 Hz, 1H), 5.03 (ddd, J=12.3, 7.4, 5.0 Hz, 1H), 4.38 (ddd, J=49.0, 9.4, 2.1 Hz, 1H), 4.03-3.73 (m, 3H), 3.60-3.33 (m, 3H), 1.25 (d, J=1.6 Hz, 6H).

Compound Table

The following compounds were prepared according to the Examples and Procedures described herein (and indicated in Table 1 under Example/Procedure) using the appropriate starting material(s) and appropriate protecting group chemistry as needed.

TABLE 1

| Structure | compound | ES/MS m/z | procedure | Name |
|---|---|---|---|---|
| 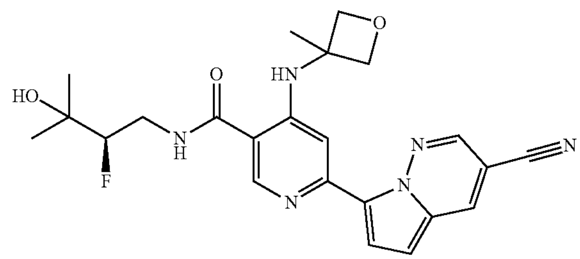 [SMILES: CC1(Nc2cc(-c3ccc4cc(C#N)cnn34)ncc2C(=O)NC[C@@H](F)C(C)(C)O)COC1] | 1 | 453.2 | 1 | (R)-6-(3-cyanopyrrolo[1,2-b]pyridazin-7-yl)-N-(2-fluoro-3-hydroxy-3-methylbutyl)-4-((3-methyloxetan-3-yl)amino)nicotinamide |
| 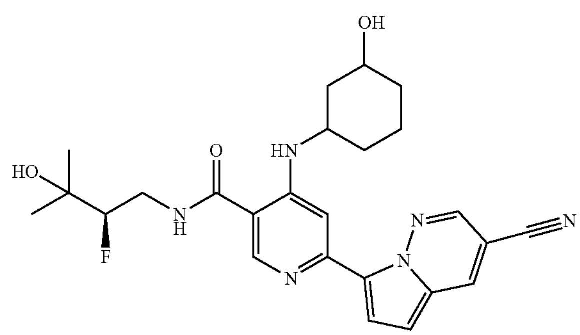 [SMILES: CC(C)(O)[C@H](F)CNC(=O)c1cnc(-c2ccc3cc(C#N)cnn23)cc1NC1CCCC(O)C1] | 2 | 481.4 | 2 | 6-(3-cyanopyrrolo[1,2-b]pyridazin-7-yl)-N-((R)-2-fluoro-3-hydroxy-3-methylbutyl)-4-(((1S,3R)-3-hydroxycyclohexyl)amino)nicotinamide |
| 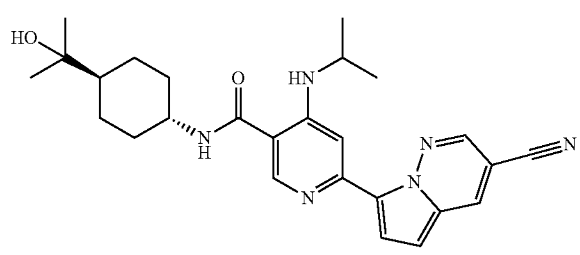 [SMILES: CC(C)Nc1cc(-c2ccc3cc(C#N)cnn23)ncc1C(=O)N[C@H]1CC[C@H](C(C)(C)O)CC1] | 3 | 461.4 | 3 | 6-(3-cyanopyrrolo[1,2-b]pyridazin-7-yl)-N-((1r,4r)-4-(2-hydroxypropan-2-yl)cyclohexyl)-4-(isopropylamino)nicotinamide |
| 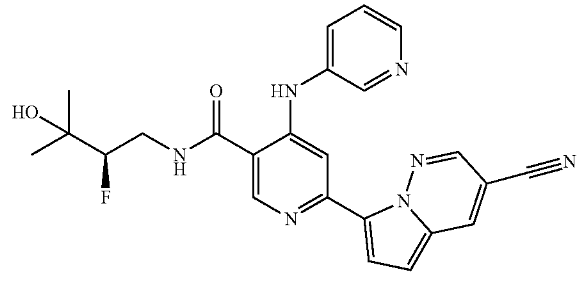 [SMILES: CC(C)(O)[C@H](F)CNC(=O)c1cnc(-c2ccc3cc(C#N)cnn23)cc1Nc1cccnc1] | 4 | 460.2 | 4 | (R)-6-(3-cyanopyrrolo[1,2-b]pyridazin-7-yl)-N-(2-fluoro-3-hydroxy-3-methylbutyl)-4-(pyridin-3-ylamino)nicotinamide |

TABLE 1-continued

| Structure | compound | ES/MS m/z | procedure | Name |
|---|---|---|---|---|
| 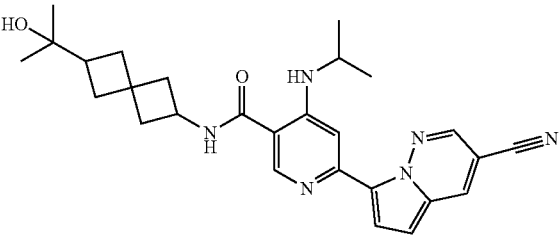 [SMILES: CC(C)Nc1cc(-c2ccc3cc(C#N)cnn23)ncc1C(=O)NC1CC2(C1)CC(C(C)(C)O)C2] | 5 | 473.3 | 5 | 6-(3-cyanopyrrolo[1,2-b]pyridazin-7-yl)-N-(6-(2-hydroxypropan-2-yl)spiro[3.3]heptan-2-yl)-4-(isopropylamino)nicotinamide |
| 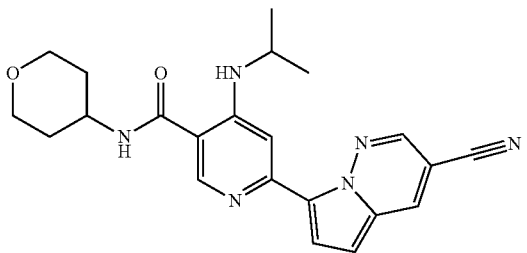 [SMILES: CC(C)Nc1cc(-c2ccc3cc(C#N)cnn23)ncc1C(=O)NC1CCOCC1] | 6 | 405.4 | 6 | 6-(3-cyanopyrrolo[1,2-b]pyridazin-7-yl)-4-(isopropylamino)-N-(tetrahydro-2H-pyran-4-yl)nicotinamide |
| 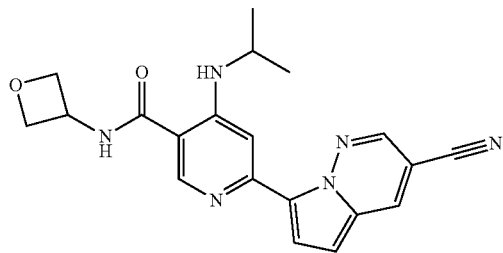 [SMILES: CC(C)Nc1cc(-c2ccc3cc(C#N)cnn23)ncc1C(=O)NC1COC1] | 7 | 377.2 | 7 | 6-(3-cyanopyrrolo[1,2-b]pyridazin-7-yl)-4-(isopropylamino)-N-(oxetan-3-yl)nicotinamide |
| 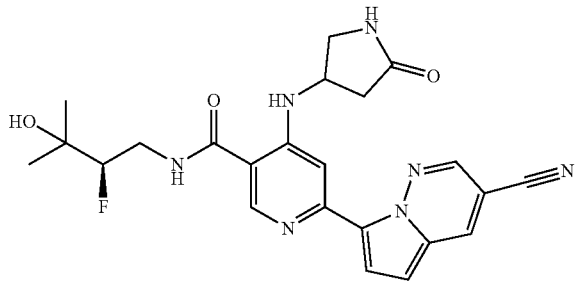 [SMILES: CC(C)(O)[C@H](F)CNC(=O)c1cnc(-c2ccc3cc(C#N)cnn23)cc1NC1CNC(=O)C1] | 8 | 466.3 | 8 | 6-(3-cyanopyrrolo[1,2-b]pyridazin-7-yl)-N-((R)-2-fluoro-3-hydroxy-3-methylbutyl)-4-((5-oxopyrrolidin-3-yl)amino)nicotinamide |
| 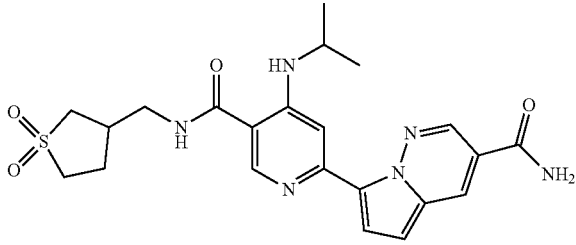 [SMILES: CC(C)Nc1cc(-c2ccc3cc(C(N)=O)cnn23)ncc1C(=O)NCC1CCS(=O)(=O)C1] | 9 | 471.2 | 9 | 7-(5-(((1,1-dioxidotetrahydrothiophen-3-yl)methyl)carbamoyl)-4-(isopropylamino)pyridin-2-yl)pyrrolo[1,2-b]pyridazine-3-carboxamide |

TABLE 1-continued

| Structure | compound | ES/MS m/z | procedure | Name |
|---|---|---|---|---|
| 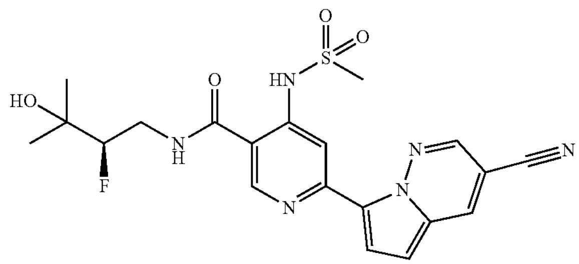 [SMILES: CC(C)(O)[C@H](F)CNC(=O)c1cnc(-c2ccc3cc(C#N)cnn23)cc1NS(C)(=O)=O] | 10 | 461.1 | 10 | (R)-6-(3-cyanopyrrolo[1,2-b]pyridazin-7-yl)-N-(2-fluoro-3-hydroxy-3-methylbutyl)-4-(methylsulfonamido)nicotinamide |
| 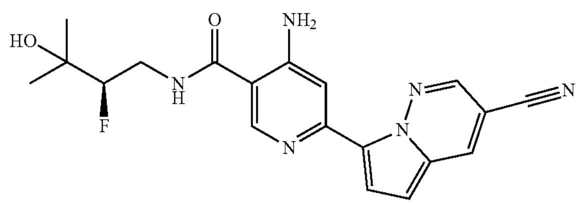 [SMILES: CC(C)(O)[C@H](F)CNC(=O)c1cnc(-c2ccc3cc(C#N)cnn23)cc1N] | 11 | 383.2 | 11 | (R)-4-amino-6-(3-cyano-pyrrolo[1,2-b]pyridazin-7-yl)-N-(2-fluoro-3-hydroxy-3-methylbutyl)nicotinamide |
| 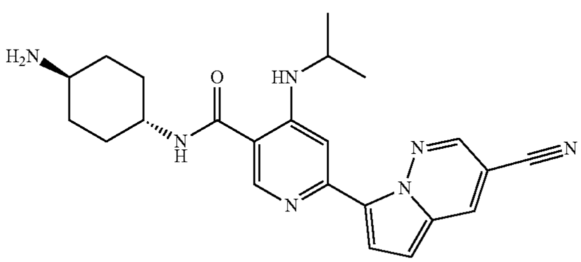 [SMILES: CC(C)Nc1cc(-c2ccc3cc(C#N)cnn23)ncc1C(=O)N[C@H]1CC[C@H](N)CC1] | 12 | 418.3 | 12 | N-((1r,4r)-4-aminocyclohexyl)-6-(3-cyano-pyrrolo[1,2-b]pyridazin-7-yl)-4-(isopropylamino)nicotinamide |
| 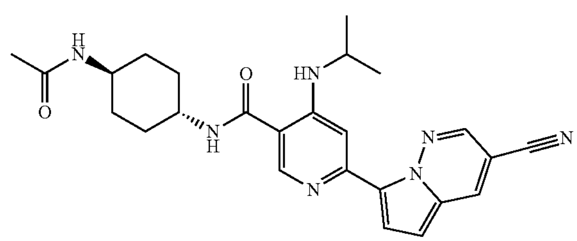 [SMILES: CC(=O)N[C@H]1CC[C@H](NC(=O)c2cnc(-c3ccc4cc(C#N)cnn34)cc2NC(C)C)CC1] | 13 | 460.3 | 13 | N-((1r,4r)-4-acetamido-cyclohexyl)-6-(3-cyano-pyrrolo[1,2-b]pyridazin-7-yl)-4-(isopropylamino)nicotinamide |
| 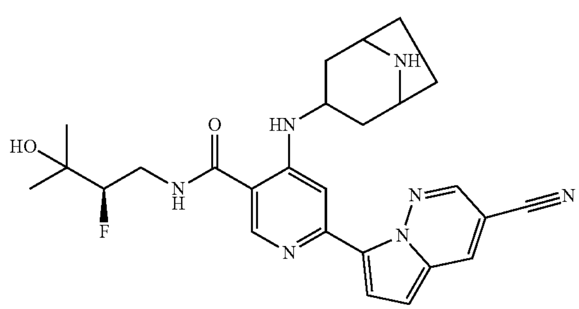 [SMILES: CC(C)(O)[C@H](F)CNC(=O)c1cnc(-c2ccc3cc(C#N)cnn23)cc1NC1CC2CCC(C1)N2] | 14 | 492.3 | 14 | 4-(((1R,3r,5S)-8-azabicyclo[3.2.1]octan-3-yl)amino)-6-(3-cyano-pyrrolo[1,2-b]pyridazin-7-yl)-N-((R)-2-fluoro-3-hydroxy-3-methylbutyl)nicotinamide |

TABLE 1-continued

| Structure | compound | ES/MS m/z | procedure | Name |
|---|---|---|---|---|
| 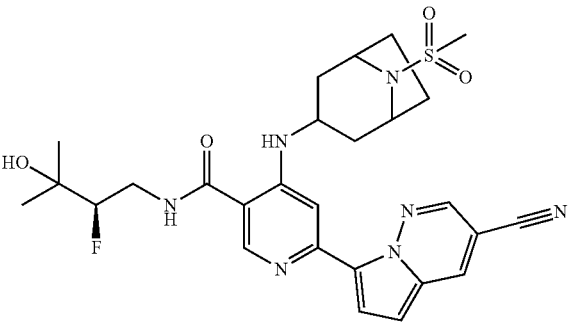 [SMILES: CC(C)(O)[C@H](F)CNC(=O)c1cnc(-c2ccc3cc(C#N)cnn23)cc1NC1CC2CCC(C1)N2S(C)(=O)=O] | 15 | 570.2 | 15 | 6-(3-cyanopyrrolo[1,2-b]pyridazin-7-yl)-N-((R)-2-fluoro-3-hydroxy-3-methylbutyl)-4-(((1R,3r,5S)-8-(methylsulfonyl)-8-azabicyclo[3.2.1]octan-3-yl)amino)nicotinamide |
| 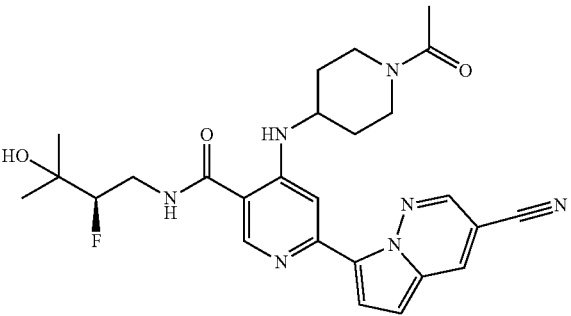 [SMILES: CC(=O)N1CCC(Nc2cc(-c3ccc4cc(C#N)cnn34)ncc2C(=O)NC[C@@H](F)C(C)(C)O)CC1] | 16 | 508.3 | 16 | (R)-4-((1-acetylpiperidin-4-yl)amino)-6-(3-cyano-pyrrolo[1,2-b]pyridazin-7-yl)-N-(2-fluoro-3-hydroxy-3-methylbutyl)nicotinamide |
| 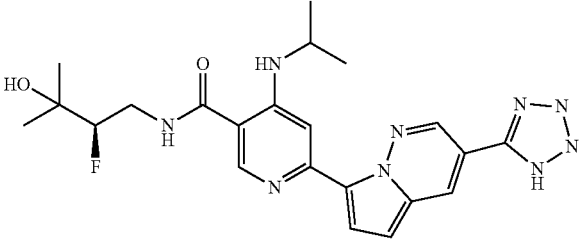 [SMILES: CC(C)Nc1cc(-c2ccc3cc(C4=NNNN4)cnn23)ncc1C(=O)NC[C@@H](F)C(C)(C)O] | 17 | 468.3 | 17 | (R)-6-(3-(1H-tetrazol-5-yl)pyrrolo[1,2-b]pyridazin-7-yl)-N-(2-fluoro-3-hydroxy-3-methylbutyl)-4-(isopropylamino)nicotinamide |
| 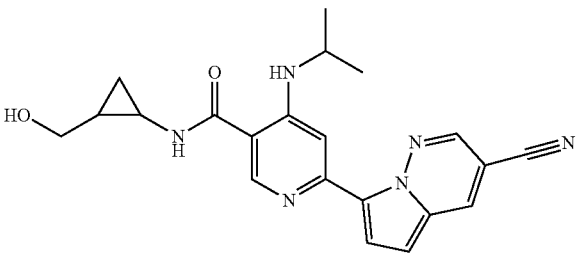 [SMILES: CC(C)Nc1cc(-c2ccc3cc(C#N)cnn23)ncc1C(=O)NC1CC1CO]
diastereomer 1 | 18 | 391.1 | 18 | 6-(3-cyanopyrrolo[1,2-b]pyridazin-7-yl)-N-(2-(hydroxymethyl)cyclopropyl)-4-(isopropylamino)nicotinamide |
| 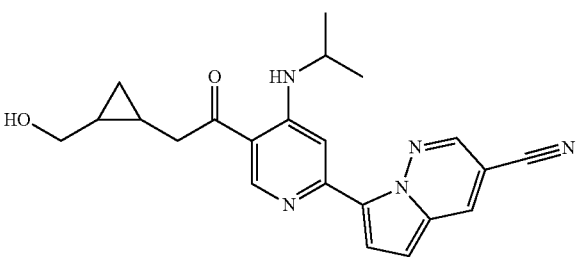 [SMILES: CC(C)Nc1cc(-c2ccc3cc(C#N)cnn23)ncc1C(=O)CC1CC1CO]
diastereomer 2 | 19 | 391.2 | 18 | 7-(5-(2-(2-(hydroxy-methyl)cyclopropyl)acetyl)-4-(isopropylamino)pyridin-2-yl)pyrrolo[1,2-b]pyridazine-3-carbonitrile |

TABLE 1-continued

| Structure | compound | ES/MS m/z | procedure | Name |
|---|---|---|---|---|
| 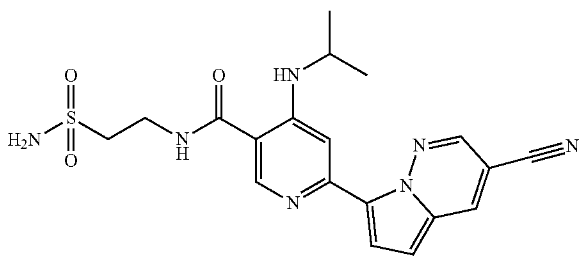 [SMILES: CC(C)Nc1cc(-c2ccc3cc(C#N)cnn23)ncc1C(=O)NCCS(N)(=O)=O] | 20 | 428.3 | 3 | 6-(3-cyanopyrrolo[1,2-b]pyridazin-7-yl)-4-(isopropylamino)-N-(2-sulfamoylethyl)nicotinamide |
| 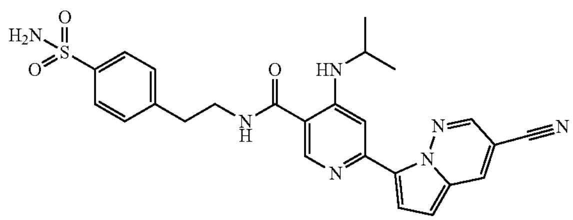 [SMILES: CC(C)Nc1cc(-c2ccc3cc(C#N)cnn23)ncc1C(=O)NCCc1ccc(S(N)(=O)=O)cc1] | 21 | 504.3 | 3 | 6-(3-cyanopyrrolo[1,2-b]pyridazin-7-yl)-4-(isopropylamino)-N-(4-sulfamoylphenethyl)nicotinamide |
| 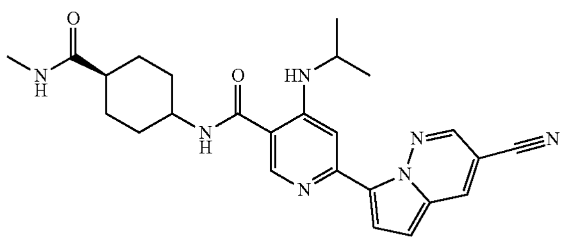 | 22 | 460.3 | 3 | 6-(3-cyanopyrrolo[1,2-b]pyridazin-7-yl)-4-(isopropylamino)-N-((1r,4r)-4-(methylcarbamoyl)cyclohexyl)nicotinamide |
| 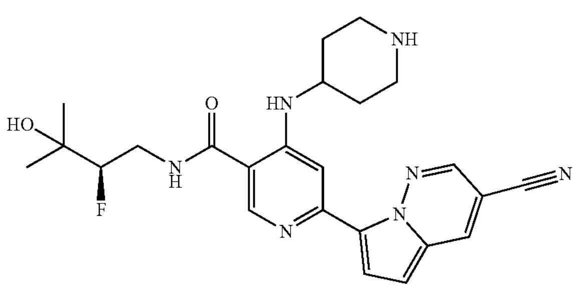 [SMILES: CC(C)(O)[C@H](F)CNC(=O)c1cnc(-c2ccc3cc(C#N)cnn23)cc1NC1CCNCC1] | 23 | 466.2 | 14 | (R)-6-(3-cyanopyrrolo[1,2-b]pyridazin-7-yl)-N-(2-fluoro-3-hydroxy-3-methylbutyl)-4-(piperidin-4-ylamino)nicotinamide |
| 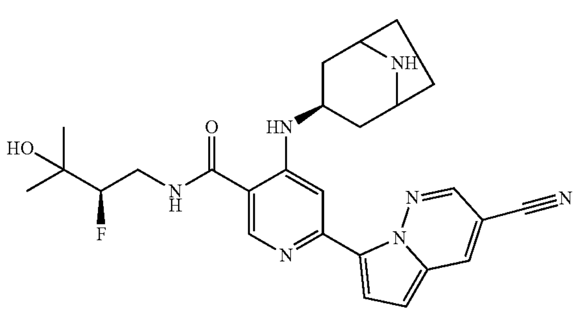 | 24 | 492.2 | 14 | 4-(((1R,3s,5S)-8-azabicyclo[3.2.1]octan-3-yl)amino)-6-(3-cyanopyrrolo[1,2-b]pyridazin-7-yl)-N-((R)-2-fluoro-3-hydroxy-3-methylbutyl)nicotinamide |

TABLE 1-continued

| Structure | compound | ES/MS m/z | procedure | Name |
|---|---|---|---|---|
| diastereomer 1 | 25 | 478.2 | 14 | 4-(3-azabicyclo[3.1.1]heptan-6-ylamino)-6-(3-cyanopyrrolo[1,2-b]pyridazin-7-yl)-N-((R)-2-fluoro-3-hydroxy-3-methylbutyl)nicotinamide |
| diastereomer 2 | 26 | 478.2 | 14 | 4-(3-azabicyclo[3.1.1]heptan-6-ylamino)-6-(3-cyanopyrrolo[1,2-b]pyridazin-7-yl)-N-((R)-2-fluoro-3-hydroxy-3-methylbutyl)nicotinamide |
| diastereomer 1 | 27 | 492.2 | 14 | 4-(3-azabicyclo[3.2.1]octan-8-ylamino)-6-(3-cyanopyrrolo[1,2-b]pyridazin-7-yl)-N-((R)-2-fluoro-3-hydroxy-3-methylbutyl)nicotinamide |
| diastereomer 2 | 28 | 292.2 | 14 | 4-(3-azabicyclo[3.2.1]octan-8-ylamino)-6-(3-cyano-pyrrolo[1,2-b]pyridazin-7-yl)-N-((R)-2-fluoro-3-hydroxy-3-methylbutyl)nicotinamide |

TABLE 1-continued

| Structure | compound | ES/MS m/z | procedure | Name |
|---|---|---|---|---|
| 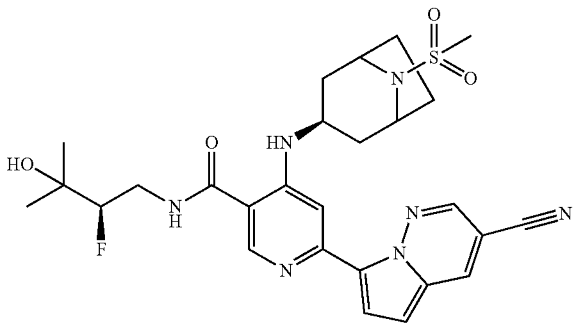 | 29 | 570.3 | 15 | 6-(3-cyanopyrrolo[1,2-b]pyridazin-7-yl)-N-((R)-2-fluoro-3-hydroxy-3-methylbutyl)-4-(((1R,3s,5S)-8-(methylsulfonyl)-8-azabicyclo[3.2.1]octan-3-yl)amino)nicotinamide |
| 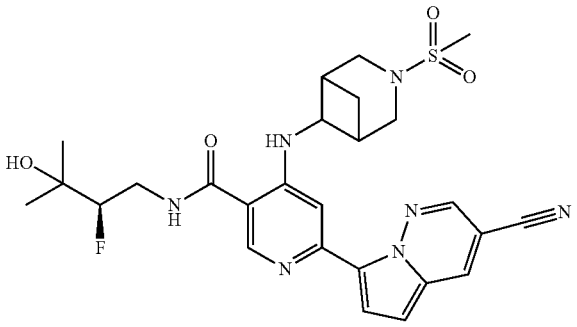 [SMILES: CC(C)(O)[C@H](F)CNC(=O)c1cnc(-c2ccc3cc(C#N)cnn23)cc1NC1C2CC1CN(S(C)(=O)=O)C2] | 30 | 556.2 | 15 | 6-(3-cyanopyrrolo[1,2-b]pyridazin-7-yl)-N-((R)-2-fluoro-3-hydroxy-3-methyl-butyl)-4-((3-(methylsulfonyl)-3-azabicyclo[3.1.1]heptan-6-yl)amino)nicotinamide |
| 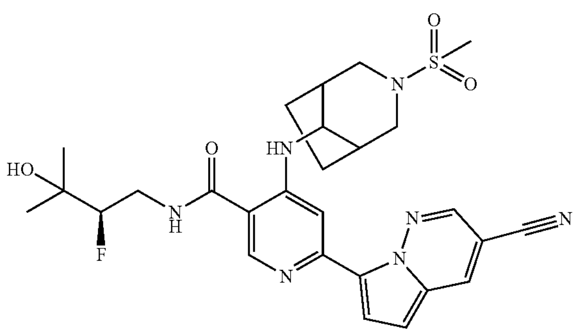 [SMILES: CC(C)(O)[C@H](F)CNC(=O)c1cnc(-c2ccc3cc(C#N)cnn23)cc1NC1C2CCC1CN(S(C)(=O)=O)C2] | 31 | 570.3 | 15 | 6-(3-cyanopyrrolo[1,2-b]pyridazin-7-yl)-N-((R)-2-fluoro-3-hydroxy-3-methylbutyl)-4-((3-(methylsulfonyl)-3-azabicyclo[3.2.1]octan-8-yl)amino)nicotinamide |
| 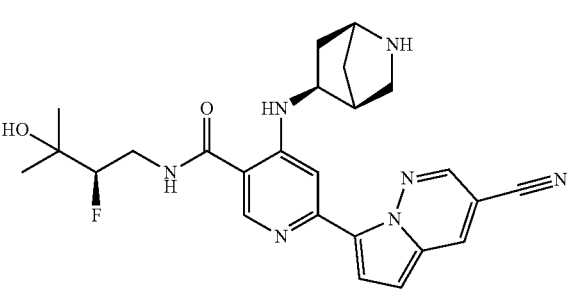 [SMILES: CC(C)(O)[C@H](F)CNC(=O)c1cnc(-c2ccc3cc(C#N)cnn23)cc1N[C@H]1C[C@@H]2C[C@H]1CN2] | 32 | 478.2 | 14 | 4-(((1S,4S,5S)-2-azabicyclo[2.2.1]heptan-5-yl)amino)-6-(3-cyano-pyrrolo[1,2-b]pyridazin-7-yl)-N-((R)-2-fluoro-3-hydroxy-3-methylbutyl)nicotinamide |
| 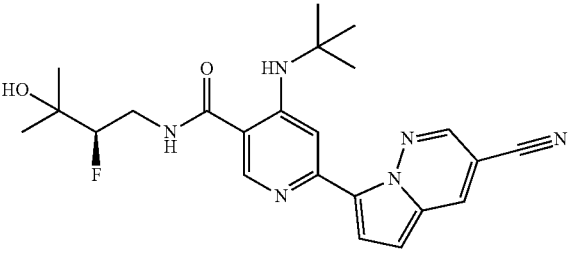 [SMILES: CC(C)(C)Nc1cc(-c2ccc3cc(C#N)cnn23)ncc1C(=O)NC[C@@H](F)C(C)(C)O] | 33 | 439.2 | 8 | (R)-4-(tert-butylamino)-6-(3-cyanopyrrolo[1,2-b]pyridazin-7-yl)-N-(2-fluoro-3-hydroxy-3-methylbutyl)nicotinamide |

TABLE 1-continued

| Structure | compound | ES/MS m/z | procedure | Name |
|---|---|---|---|---|
| 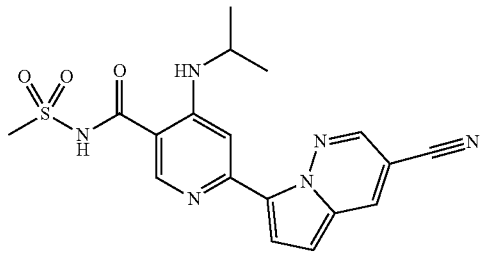 [SMILES: CC(C)Nc1cc(-c2ccc3cc(C#N)cnn23)ncc1C(=O)NS(C)(=O)=O] | 34 | 399.2 | 6 | 6-(3-cyanopyrrolo[1,2-b]pyridazin-7-yl)-4-(isopropylamino)-N-(methylsulfonyl)nicotinamide |
| 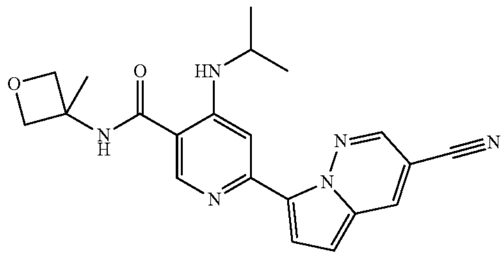 [SMILES: CC(C)Nc1cc(-c2ccc3cc(C#N)cnn23)ncc1C(=O)NC1(C)COC1] | 35 | 391.2 | 7 | 6-(3-cyanopyrrolo[1,2-b]pyridazin-7-yl)-4-(isopropylamino)-N-(3-methyloxetan-3-yl)nicotinamide |
| 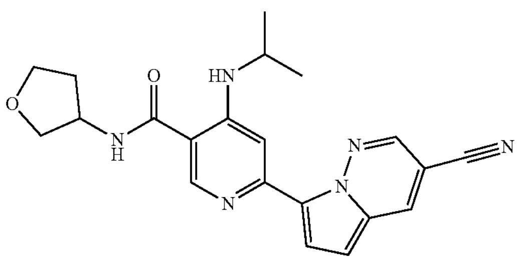 [SMILES: CC(C)Nc1cc(-c2ccc3cc(C#N)cnn23)ncc1C(=O)NC1CCOC1] | 36 | 391.3 | 6 | (S)-6-(3-cyanopyrrolo[1,2-b]pyridazin-7-yl)-4-(isopropylamino)-N-(tetrahydrofuran-3-yl)nicotinamide |
| 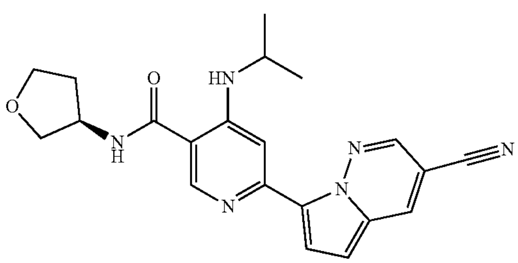 [SMILES: CC(C)Nc1cc(-c2ccc3cc(C#N)cnn23)ncc1C(=O)N[C@@H]1CCOC1] | 37 | 391.3 | 6 | (R)-6-(3-cyanopyrrolo[1,2-b]pyridazin-7-yl)-4-(isopropylamino)-N-(tetrahydrofuran-3-yl)nicotinamide |
| 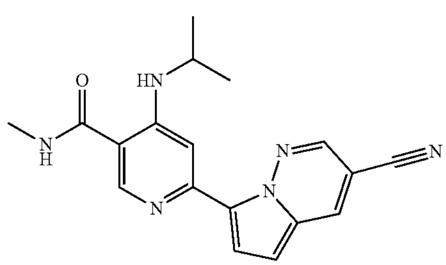 [SMILES: CNC(=O)c1cnc(-c2ccc3cc(C#N)cnn23)cc1NC(C)C] | 38 | 335.2 | 1 | 6-(3-cyanopyrrolo[1,2-b]pyridazin-7-yl)-4-(isopropylamino)-N-methylnicotinamide |
| 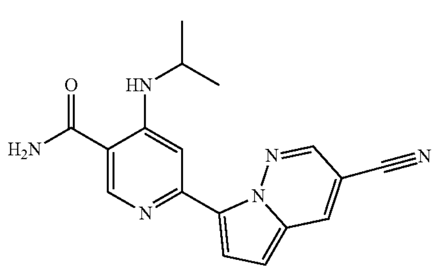 [SMILES: CC(C)Nc1cc(-c2ccc3cc(C#N)cnn23)ncc1C(N)=O] | 39 | 321.2 | 1 | 6-(3-cyanopyrrolo[1,2-b]pyridazin-7-yl)-4-(isopropylamino)nicotinamide |

TABLE 1-continued

| Structure | compound | ES/MS m/z | procedure | Name |
|---|---|---|---|---|
| 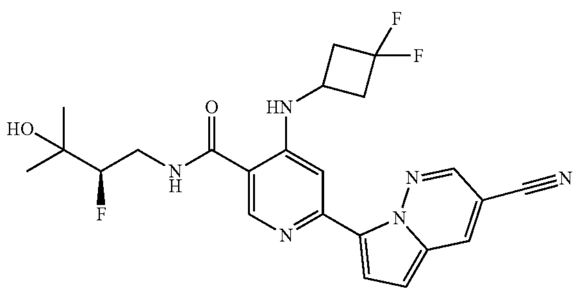 [SMILES: CC(C)(O)[C@H](F)CNC(=O)c1cnc(-c2ccc3cc(C#N)cnn23)cc1NC1CC(F)(F)C1] | 40 | 473.3 | 2 | (R)-6-(3-cyanopyrrolo[1,2-b]pyridazin-7-yl)-4-((3,3-difluorocyclobutyl)amino)-N-(2-fluoro-3-hydroxy-3-methylbutyl)nicotinamide |
| 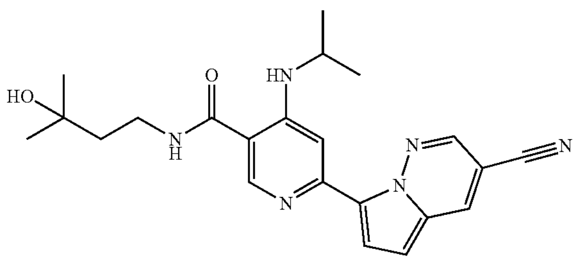 [SMILES: CC(C)Nc1cc(-c2ccc3cc(C#N)cnn23)ncc1C(=O)NCCC(C)(C)O] | 41 | 407.3 | 1 | 6-(3-cyanopyrrolo[1,2-b]pyridazin-7-yl)-N-(3-hydroxy-3-methylbutyl)-4-(isopropylamino)nicotinamide |
| 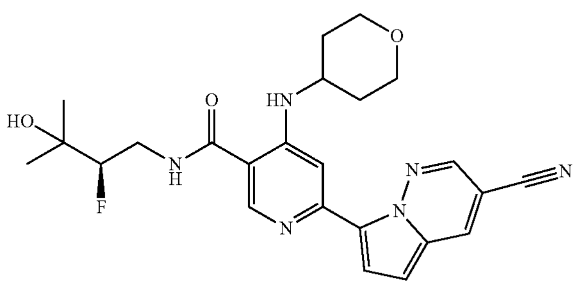 [SMILES: CC(C)(O)[C@H](F)CNC(=O)c1cnc(-c2ccc3cc(C#N)cnn23)cc1NC1CCOCC1] | 42 | 453.2 | 1 | (R)-6-(3-cyanopyrrolo[1,2-b]pyridazin-7-yl)-N-(2-fluoro-3-hydroxy-3-methylbutyl)-4-((tetrahydro-2H-pyran-4-yl)amino)nicotinamide |
| 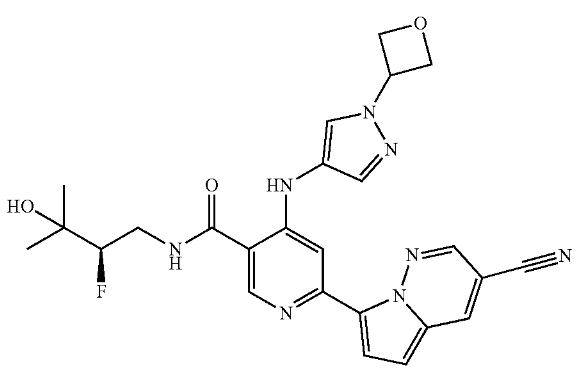 [SMILES: CC(C)(O)[C@H](F)CNC(=O)c1cnc(-c2ccc3cc(C#N)cnn23)cc1Nc1cnn(C2COC2)c1] | 43 | 505.3 | 1 | (R)-6-(3-cyanopyrrolo[1,2-b]pyridazin-7-yl)-N-(2-fluoro-3-hydroxy-3-methylbutyl)-4-((1-(oxetan-3-yl)-1H-pyrazol-4-yl)amino)nicotinamide |
| 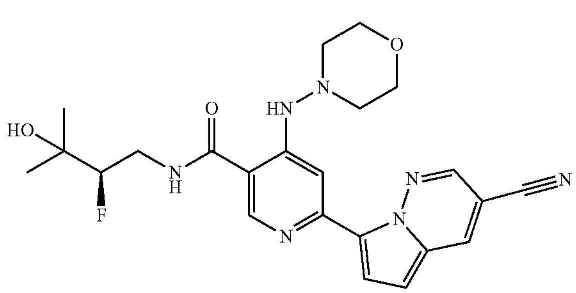 | 44 | 468.2 | 1 | (R)-6-(3-cyanopyrrolo[1,2-b]pyridazin-7-yl)-N-(2-fluoro-3-hydroxy-3-methylbutyl)-4-(morpholinoamino)nicotinamide |

TABLE 1-continued

| Structure | compound | ES/MS m/z | procedure | Name |
|---|---|---|---|---|
| (mixture) | 45 | 391.2 | 1 | 6-(3-cyanopyrrolo[1,2-b]pyridazin-7-yl)-N-(2-(hydroxymethyl)cyclopropyl)-4-(isopropylamino)nicotinamide |
| 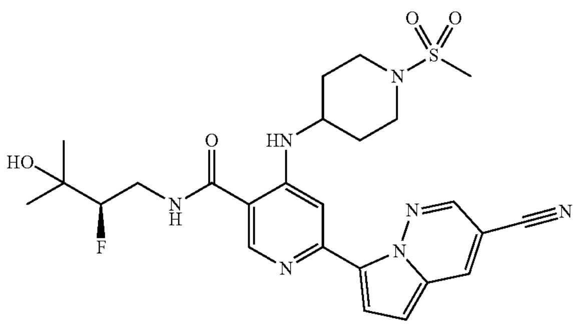 [SMILES: CC(C)(O)[C@H](F)CNC(=O)c1cnc(-c2ccc3cc(C#N)cnn23)cc1NC1CCN(S(C)(=O)=O)CC1] | 46 | 544.2 | 2 | (R)-6-(3-cyanopyrrolo[1,2-b]pyridazin-7-yl)-N-(2-fluoro-3-hydroxy-3-methylbutyl)-4-((1-(methylsulfonyl)piperidin-4-yl)amino)nicotinamide |
| 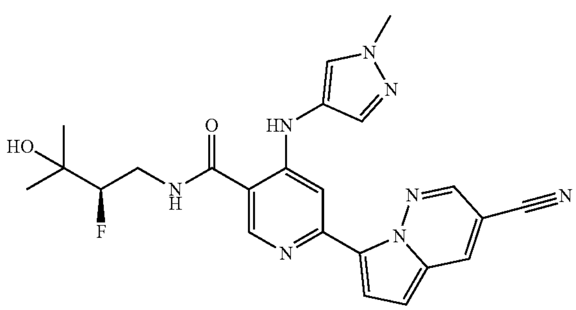 [SMILES: Cn1cc(Nc2cc(-c3ccc4cc(C#N)cnn34)ncc2C(=O)NC[C@@H](F)C(C)(C)O)cn1] | 47 | 463.3 | 2 | (R)-6-(3-cyanopyrrolo[1,2-b]pyridazin-7-yl)-N-(2-fluoro-3-hydroxy-3-methylbutyl)-4-((1-methyl-1H-pyrazol-4-yl)amino)nicotinamide |
| 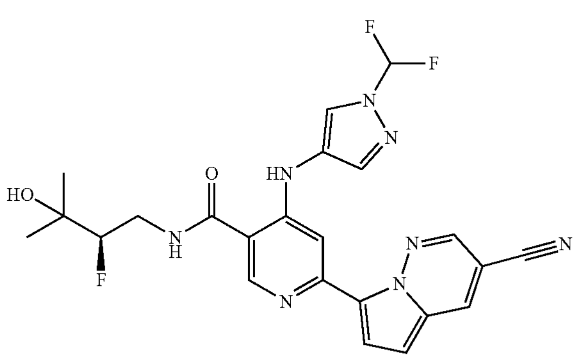 [SMILES: CC(C)(O)[C@H](F)CNC(=O)c1cnc(-c2ccc3cc(C#N)cnn23)cc1Nc1cnn(C(F)F)c1] | 48 | 499.3 | 2 | (R)-6-(3-cyanopyrrolo[1,2-b]pyridazin-7-yl)-4-((1-(difluoromethyl)-1H-pyrazol-4-yl)amino)-N-(2-fluoro-3-hydroxy-3-methylbutyl)nicotinamide |

TABLE 1-continued

| Structure | compound | ES/MS m/z | procedure | Name |
|---|---|---|---|---|
| 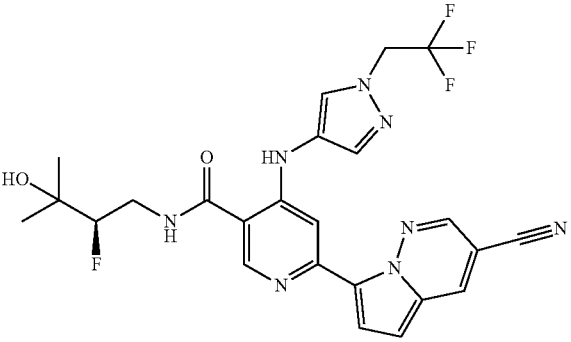 [SMILES: CC(C)(O)[C@H](F)CNC(=O)c1cnc(-c2ccc3cc(C#N)cnn23)cc1Nc1cnn(CC(F)(F)F)c1] | 49 | 531.3 | 2 | (R)-6-(3-cyanopyrrolo[1,2-b]pyridazin-7-yl)-N-(2-fluoro-3-hydroxy-3-methylbutyl)-4-((1-(2,2,2-trifluoroethyl)-1H-pyrazol-4-yl)amino)nicotinamide |
| 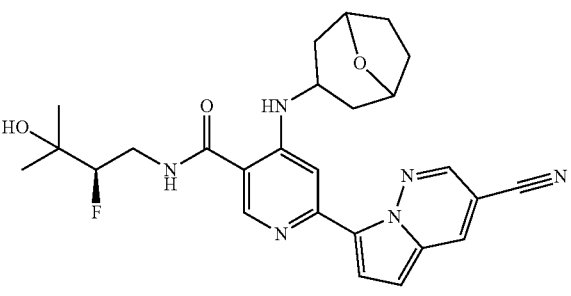 [SMILES: CC(C)(O)[C@H](F)CNC(=O)c1cnc(-c2ccc3cc(C#N)cnn23)cc1NC1CC2CCC(C1)O2] | 50 | 493.3 | 1 | 4-(8-oxabicyclo[3.2.1]octan-3-ylamino)-6-(3-cyanopyrrolo[1,2-b]pyridazin-7-yl)-N-((R)-2-fluoro-3-hydroxy-3-methylbutyl)nicotinamide |
| 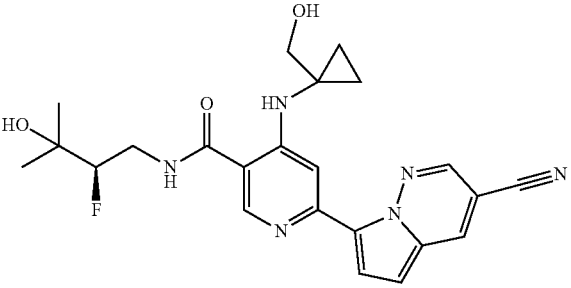 [SMILES: CC(C)(O)[C@H](F)CNC(=O)c1cnc(-c2ccc3cc(C#N)cnn23)cc1NC1(CO)CC1] | 51 | 453.2 | 1 | (R)-6-(3-cyanopyrrolo[1,2-b]pyridazin-7-yl)-N-(2-fluoro-3-hydroxy-3-methylbutyl)-4-((1-(hydroxymethyl)cyclopropyl)amino)nicotinamide |
| 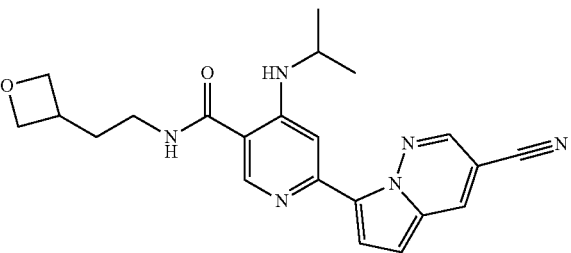 [SMILES: CC(C)Nc1cc(-c2ccc3cc(C#N)cnn23)ncc1C(=O)NCCC1COC1] | 52 | 405.3 | 1 | 6-(3-cyanopyrrolo[1,2-b]pyridazin-7-yl)-4-(isopropylamino)-N-(2-(oxetan-3-yl)ethyl)nicotinamide |
| 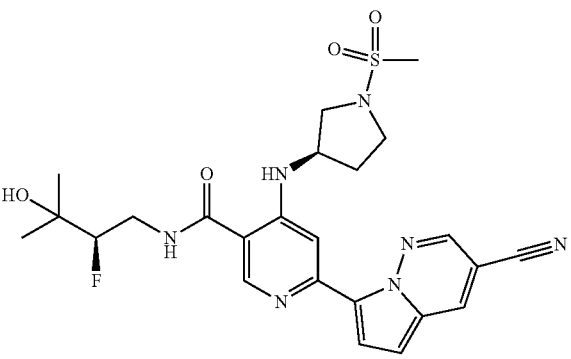 [SMILES: CC(C)(O)[C@H](F)CNC(=O)c1cnc(-c2ccc3cc(C#N)cnn23)cc1N[C@@H]1CCN(S(C)(=O)=O)C1] | 53 | 530.5 | 1 | 6-(3-cyanopyrrolo[1,2-b]pyridazin-7-yl)-N-((R)-2-fluoro-3-hydroxy-3-methylbutyl)-4-(((R)-1-(methylsulfonyl)pyrrolidin-3-yl)amino)nicotinamide |

TABLE 1-continued

| Structure | compound | ES/MS m/z | procedure | Name |
|---|---|---|---|---|
| 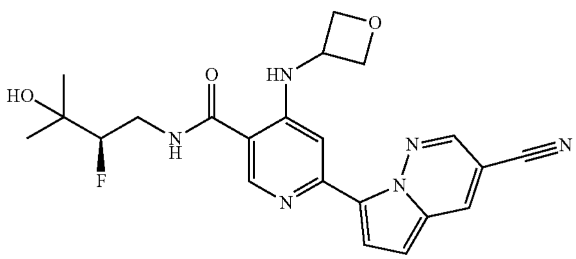 [SMILES: CC(C)(O)[C@H](F)CNC(=O)c1cnc(-c2ccc3cc(C#N)cnn23)cc1NC1COC1] | 54 | 439.3 | 1 | (R)-6-(3-cyanopyrrolo[1,2-b]pyridazin-7-yl)-N-(2-fluoro-3-hydroxy-3-methylbutyl)-4-(oxetan-3-ylamino)nicotinamide |
| 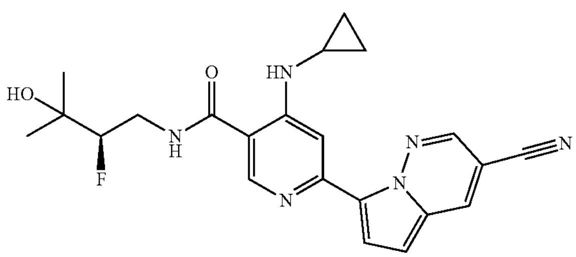 [SMILES: CC(C)(O)[C@H](F)CNC(=O)c1cnc(-c2ccc3cc(C#N)cnn23)cc1NC1CC1] | 55 | 423.4 | 1 | (R)-6-(3-cyanopyrrolo[1,2-b]pyridazin-7-yl)-4-(cyclopropylamino)-N-(2-fluoro-3-hydroxy-3-methylbutyl)nicotinamide |
| 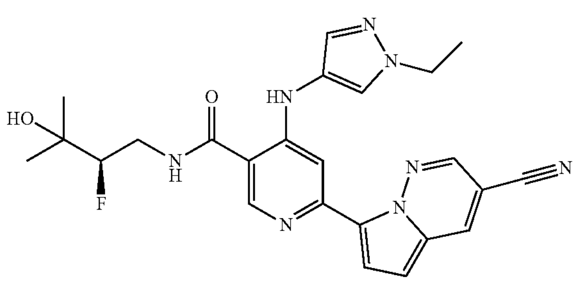 [SMILES: CCn1cc(Nc2cc(-c3ccc4cc(C#N)cnn34)ncc2C(=O)NC[C@@H](F)C(C)(C)O)cn1] | 56 | 477.5 | 1 | (R)-6-(3-cyanopyrrolo[1,2-b]pyridazin-7-yl)-4-((1-ethyl-1H-pyrazol-4-yl)amino)-N-(2-fluoro-3-hydroxy-3-methylbutyl)nicotinamide |
| 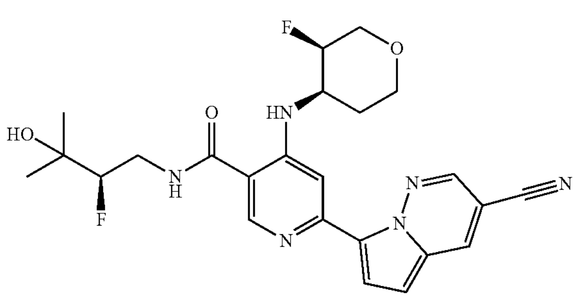 [SMILES: CC(C)(O)[C@H](F)CNC(=O)c1cnc(-c2ccc3cc(C#N)cnn23)cc1N[C@@H]1CCOC[C@@H]1F] | 57 | 485.3 | 2 | 6-(3-cyanopyrrolo[1,2-b]pyridazin-7-yl)-N-((R)-2-fluoro-3-hydroxy-3-methylbutyl)-4-(((3R,4R)-3-fluorotetrahydro-2H-pyran-4-yl)amino)nicotinamide |
| 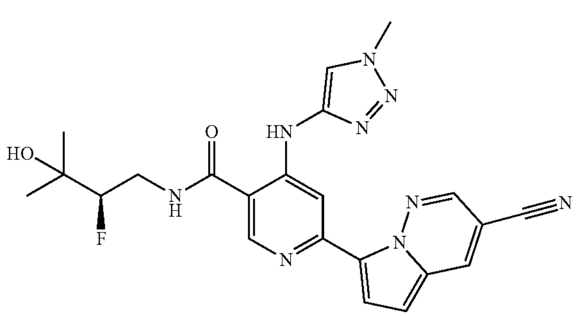 [SMILES: Cn1cc(Nc2cc(-c3ccc4cc(C#N)cnn34)ncc2C(=O)NC[C@@H](F)C(C)(C)O)nn1] | 58 | 464.2 | 2 | (R)-6-(3-cyanopyrrolo[1,2-b]pyridazin-7-yl)-N-(2-fluoro-3-hydroxy-3-methylbutyl)-4-((1-methyl-1H-1,2,3-triazol-4-yl)amino)nicotinamide |

TABLE 1-continued

| Structure | compound | ES/MS m/z | procedure | Name |
|---|---|---|---|---|
| 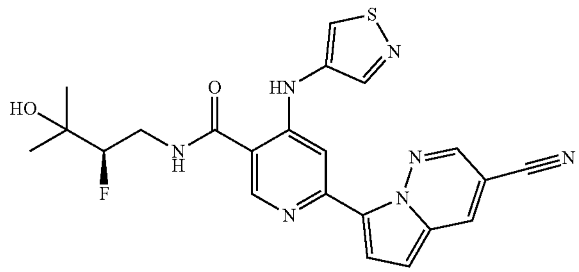 [SMILES: CC(C)(O)[C@H](F)CNC(=O)c1cnc(-c2ccc3cc(C#N)cnn23)cc1Nc1cnsc1] | 59 | 466.2 | 2 | (R)-6-(3-cyanopyrrolo[1,2-b]pyridazin-7-yl)-N-(2-fluoro-3-hydroxy-3-methylbutyl)-4-(isothiazol-4-ylamino)nicotinamide |
| 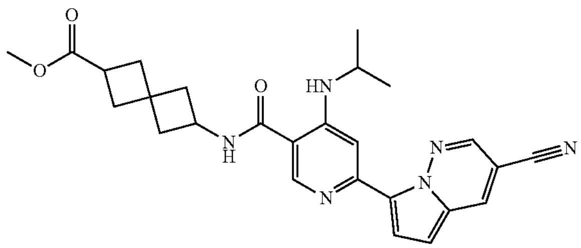 [SMILES: COC(=O)C1CC2(CC(NC(=O)c3cnc(-c4ccc5cc(C#N)cnn45)cc3NC(C)C)C2)C1] | 60 | 473.3 | 1 | methyl 6-(6-(3-cyano-pyrrolo[1,2-b]pyridazin-7-yl)-4-(isopropylamino)nicotinamido)spiro[3.3]heptane-2-carboxylate |
| 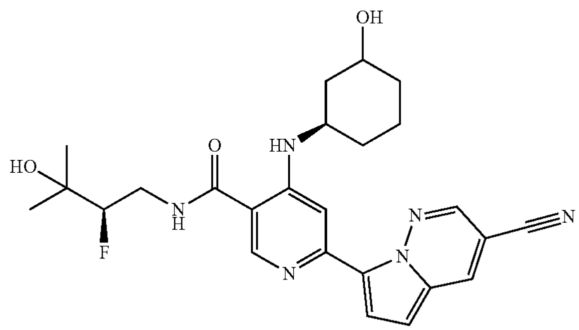 [SMILES: CC(C)(O)[C@H](F)CNC(=O)c1cnc(-c2ccc3cc(C#N)cnn23)cc1N[C@@H]1CCCC(O)C1] | 61 | 481.3 | 2 | 6-(3-cyanopyrrolo[1,2-b]pyridazin-7-yl)-N-((R)-2-fluoro-3-hydroxy-3-methylbutyl)-4-(((1R,3R)-3-hydroxycyclohexyl)amino)nicotinamide |
| 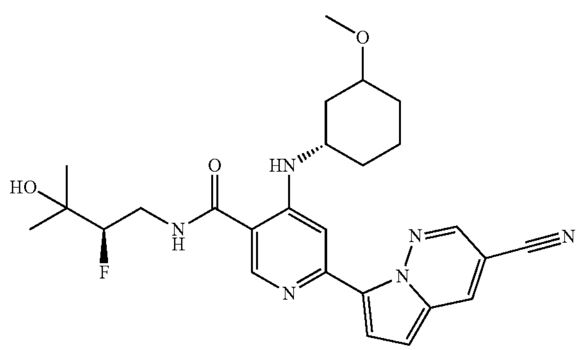 [SMILES: COC1CCC[C@H](Nc2cc(-c3ccc4cc(C#N)cnn34)ncc2C(=O)NC[C@@H](F)C(C)(C)O)C1] | 62 | 495.3 | 2 | 6-(3-cyanopyrrolo[1,2-b]pyridazin-7-yl)-N-((R)-2-fluoro-3-hydroxy-3-methylbutyl)-4-(((1S,3R)-3-methoxycyclohexyl)amino)nicotinamide |
| 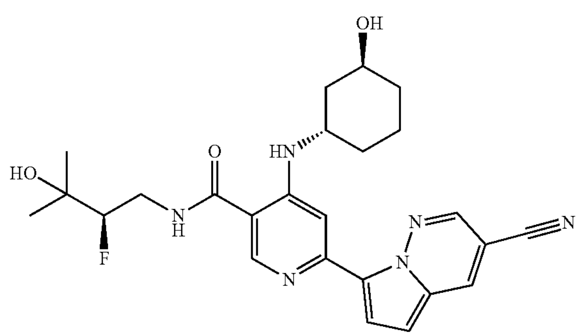 [SMILES: CC(C)(O)[C@H](F)CNC(=O)c1cnc(-c2ccc3cc(C#N)cnn23)cc1N[C@H]1CCC[C@H](O)C1] | 63 | 481.3 | 2 | 6-(3-cyanopyrrolo[1,2-b]pyridazin-7-yl)-N-((R)-2-fluoro-3-hydroxy-3-methylbutyl)-4-(((1S,3S)-3-hydroxycyclohexyl)amino)nicotinamide |

TABLE 1-continued

| Structure | compound | ES/MS m/z | procedure | Name |
|---|---|---|---|---|
| 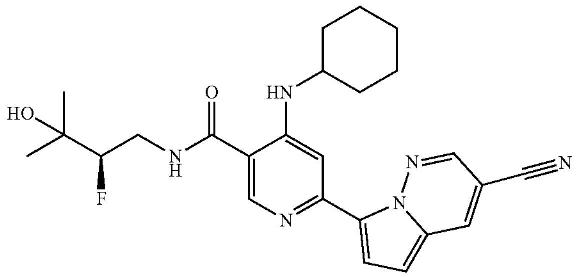 [SMILES: CC(C)(O)[C@H](F)CNC(=O)c1cnc(-c2ccc3cc(C#N)cnn23)cc1NC1CCCCC1] | 64 | 465.4 | 2* | (R)-6-(3-cyanopyrrolo[1,2-b]pyridazin-7-yl)-4-(cyclohexylamino)-N-(2-fluoro-3-hydroxy-3-methylbutyl)nicotinamide |
| 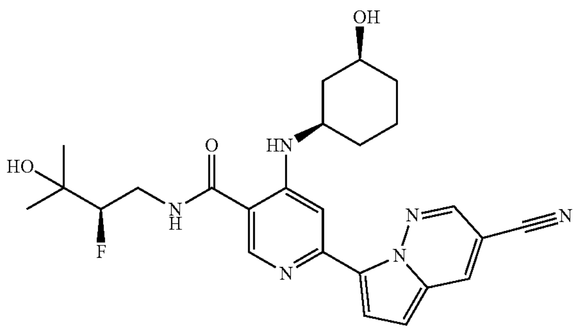 [SMILES: CC(C)(O)[C@H](F)CNC(=O)c1cnc(-c2ccc3cc(C#N)cnn23)cc1N[C@@H]1CCC[C@H](O)C1] | 65 | 481.3 | 2* | 6-(3-cyanopyrrolo[1,2-b]pyridazin-7-yl)-N-((R)-2-fluoro-3-hydroxy-3-methylbutyl)-4-(((1R,3S)-3-hydroxycyclohexyl)amino)nicotinamide |
| 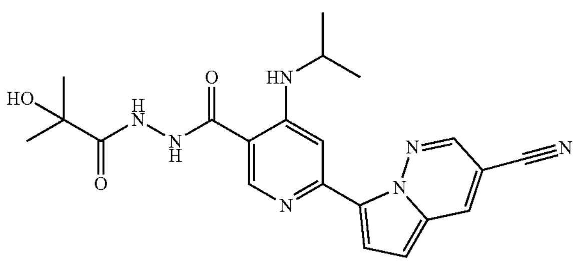 [SMILES: CC(C)Nc1cc(-c2ccc3cc(C#N)cnn23)ncc1C(=O)NNC(=O)C(C)(C)O] | 66 | 422.2 | 1 | 6-(3-cyanopyrrolo[1,2-b]pyridazin-7-yl)-N'-(2-hydroxy-2-methylpropanoyl)-4-(isopropylamino)nicotinohydrazide |
| 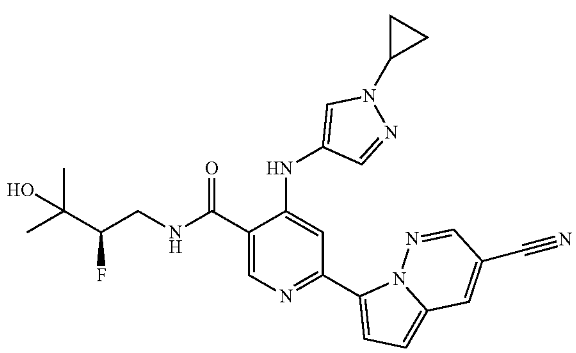 [SMILES: CC(C)(O)[C@H](F)CNC(=O)c1cnc(-c2ccc3cc(C#N)cnn23)cc1Nc1cnn(C2CC2)c1] | 67 | 489.3 | 2 | (R)-6-(3-cyanopyrrolo[1,2-b]pyridazin-7-yl)-4-((1-cyclopropyl-1H-pyrazol-4-yl)amino)-N-(2-fluoro-3-hydroxy-3-methylbutyl)nicotinamide |
| 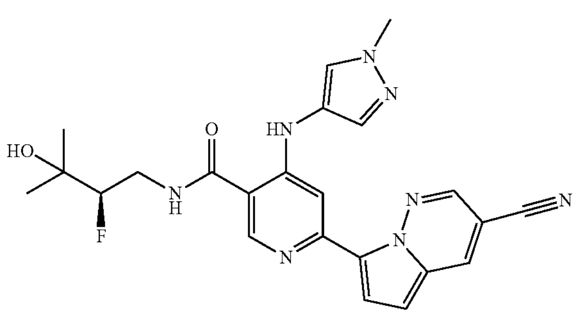 [SMILES: Cn1cc(Nc2cc(-c3ccc4cc(C#N)cnn34)ncc2C(=O)NC[C@@H](F)C(C)(C)O)cn1] | 68 | 463.2 | 2* | (R)-6-(3-cyanopyrrolo[1,2-b]pyridazin-7-yl)-N-(2-fluoro-3-hydroxy-3-methylbutyl)-4-((1-methyl-1H-imidazol-4-yl)amino)nicotinamide |

TABLE 1-continued

| Structure | compound | ES/MS m/z | procedure | Name |
|---|---|---|---|---|
| 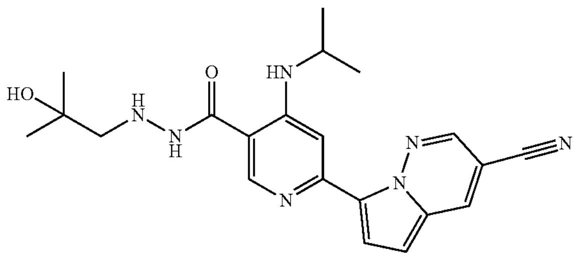 [SMILES: CC(C)Nc1cc(-c2ccc3cc(C#N)cnn23)ncc1C(=O)NNCC(C)(C)O] | 69 | 408.2 | 1 | 6-(3-cyanopyrrolo[1,2-b]pyridazin-7-yl)-N'-(2-hydroxy-2-methylpropyl)-4-(isopropylamino)nicotinohydrazide |
| 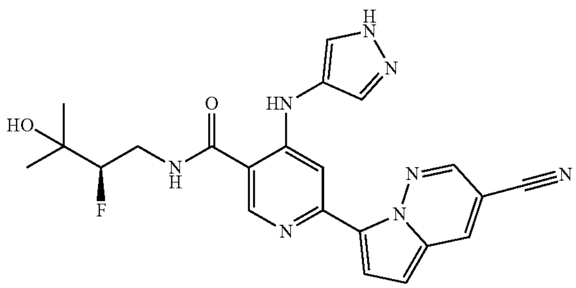 [SMILES: CC(C)(O)[C@H](F)CNC(=O)c1cnc(-c2ccc3cc(C#N)cnn23)cc1Nc1cn[nH]c1] | 70 | 449.2 | 2 | (R)-4-((1H-pyrazol-4-yl)amino)-6-(3-cyanopyrrolo[1,2-b]pyridazin-7-yl)-N-(2-fluoro-3-hydroxy-3-methylbutyl)nicotinamide |
| 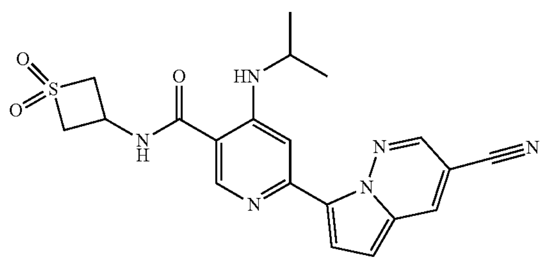 [SMILES: CC(C)Nc1cc(-c2ccc3cc(C#N)cnn23)ncc1C(=O)NC1CS(=O)(=O)C1] | 71 | 425.1 | 8 | 6-(3-cyanopyrrolo[1,2-b]pyridazin-7-yl)-N-(1,1-dioxidothietan-3-yl)-4-(isopropylamino)nicotinamide |
| 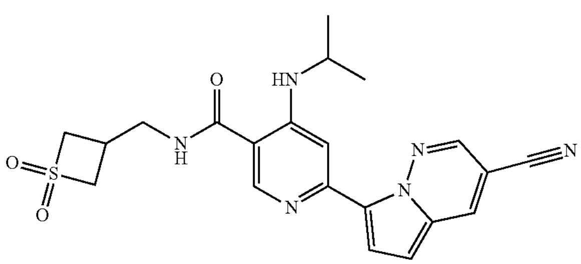 [SMILES: CC(C)Nc1cc(-c2ccc3cc(C#N)cnn23)ncc1C(=O)NCC1CS(=O)(=O)C1] | 72 | 439.2 | 8 | 6-(3-cyanopyrrolo[1,2-b]pyridazin-7-yl)-N-((1,1-dioxidothietan-3-yl)methyl)-4-(isopropylamino)nicotinamide |
| 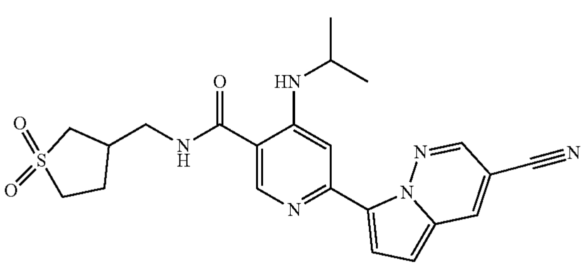 [SMILES: CC(C)Nc1cc(-c2ccc3cc(C#N)cnn23)ncc1C(=O)NCC1CCS(=O)(=O)C1] | 73 | 453.2 | 8 | 6-(3-cyanopyrrolo[1,2-b]pyridazin-7-yl)-N-((1,1-dioxidotetrahydrothiophen-3-yl)methyl)-4-(isopropylamino)nicotinamide |

TABLE 1-continued

| Structure | compound | ES/MS m/z | procedure | Name |
|---|---|---|---|---|
| 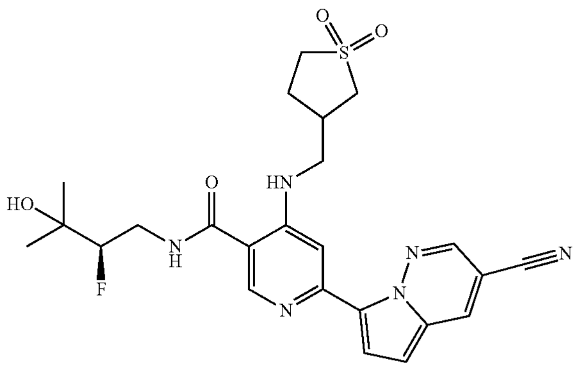 [SMILES: CC(C)(O)[C@H](F)CNC(=O)c1cnc(-c2ccc3cc(C#N)cnn23)cc1NCC1CCS(=O)(=O)C1] | 74 | 515.2 | 2 | 6-(3-cyanopyrrolo[1,2-b]pyridazin-7-yl)-4-(((1,1-dioxidotetrahydrothiophen-3-yl)methyl)amino)-N-((R)-2-fluoro-3-hydroxy-3-methylbutyl)nicotinamide |
| 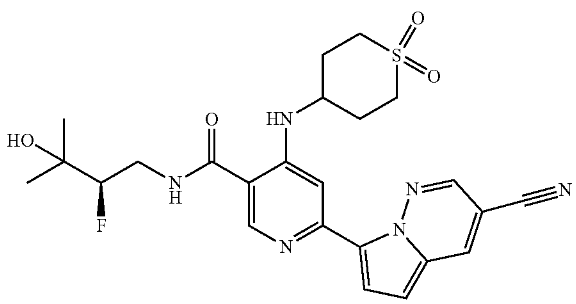 [SMILES: CC(C)(O)[C@H](F)CNC(=O)c1cnc(-c2ccc3cc(C#N)cnn23)cc1NC1CCS(=O)(=O)CC1] | 75 | 515.2 | 2 | (R)-6-(3-cyanopyrrolo[1,2-b]pyridazin-7-yl)-4-((1,1-dioxidotetrahydro-2H-thiopyran-4-yl)amino)-N-(2-fluoro-3-hydroxy-3-methylbutyl)nicotinamide |
| 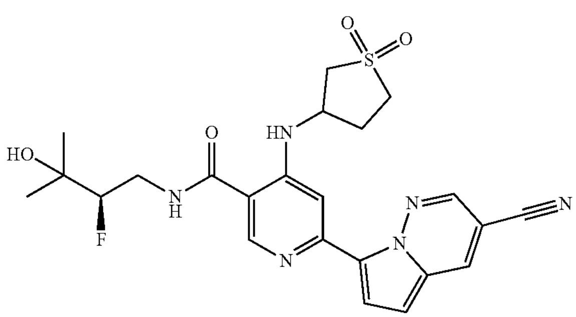 [SMILES: CC(C)(O)[C@H](F)CNC(=O)c1cnc(-c2ccc3cc(C#N)cnn23)cc1NC1CCS(=O)(=O)C1] | 76 | 501.2 | 2 | 6-(3-cyanopyrrolo[1,2-b]pyridazin-7-yl)-4-((1,1-dioxidotetrahydrothiophen-3-yl)amino)-N-((R)-2-fluoro-3-hydroxy-3-methylbutyl)nicotinamide |
| 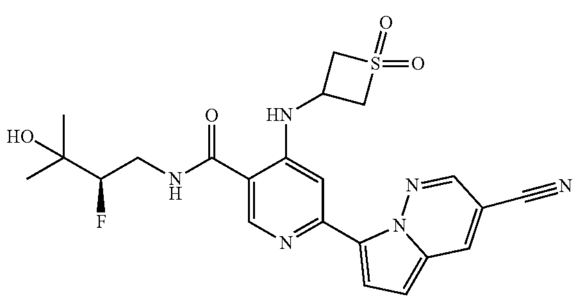 [SMILES: CC(C)(O)[C@H](F)CNC(=O)c1cnc(-c2ccc3cc(C#N)cnn23)cc1NC1CS(=O)(=O)C1] | 77 | 487.1 | 2 | (R)-6-(3-cyanopyrrolo[1,2-b]pyridazin-7-yl)-4-((1,1-dioxidothietan-3-yl)amino)-N-(2-fluoro-3-hydroxy-3-methylbutyl)nicotinamide |
| 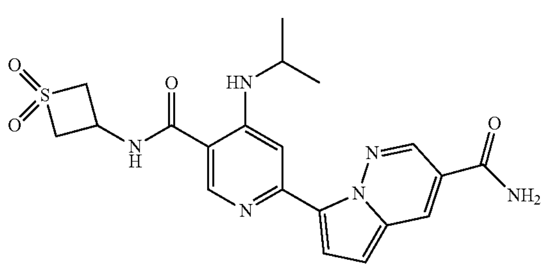 [SMILES: CC(C)Nc1cc(-c2ccc3cc(C(N)=O)cnn23)ncc1C(=O)NC1CS(=O)(=O)C1] | 78 | 443.2 | 9 | 7-(5-(((1,1-dioxidothietan-3-yl)carbamoyl)-4-(isopropylamino)pyridin-2-yl)pyrrolo[1,2-b]pyridazine-3-carboxamide |

TABLE 1-continued

| Structure | compound | ES/MS m/z | procedure | Name |
|---|---|---|---|---|
| 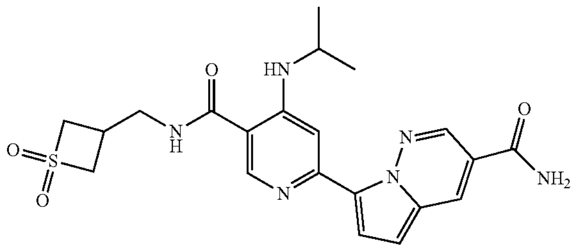 [SMILES: CC(C)Nc1cc(-c2ccc3cc(C(N)=O)cnn23)ncc1C(=O)NCC1CS(=O)(=O)C1] | 79 | 457.2 | 9 | 7-(5-(((1,1-dioxidothietan-3-yl)methyl)carbamoyl)-4-(isopropylamino)pyridin-2-yl)pyrrolo[1,2-b]pyridazine-3-carboxamide |
| 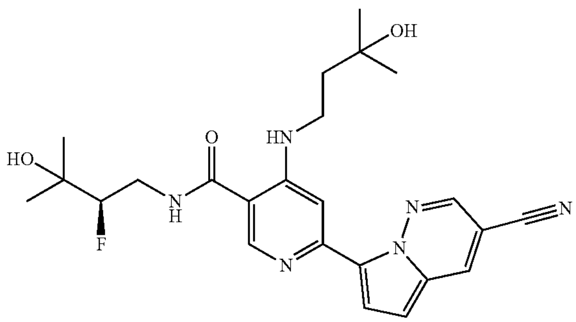 [SMILES: CC(C)(O)CCNc1cc(-c2ccc3cc(C#N)cnn23)ncc1C(=O)NC[C@@H](F)C(C)(C)O] | 80 | 469.3 | 1 | (R)-6-(3-cyanopyrrolo[1,2-b]pyridazin-7-yl)-N-(2-fluoro-3-hydroxy-3-methylbutyl)-4-((3-hydroxy-3-methylbutyl)amino)nicotinamide |
| 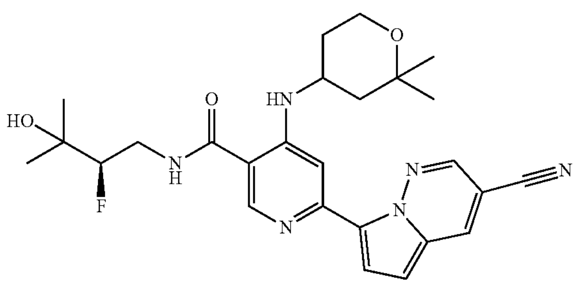 [SMILES: CC1(C)CC(Nc2cc(-c3ccc4cc(C#N)cnn34)ncc2C(=O)NC[C@@H](F)C(C)(C)O)CCO1] | 81 | 495.2 | 1 | 6-(3-cyanopyrrolo[1,2-b]pyridazin-7-yl)-4-((2,2-dimethyltetrahydro-2H-pyran-4-yl)amino)-N-((R)-2-fluoro-3-hydroxy-3-methylbutyl)nicotinamide |
| 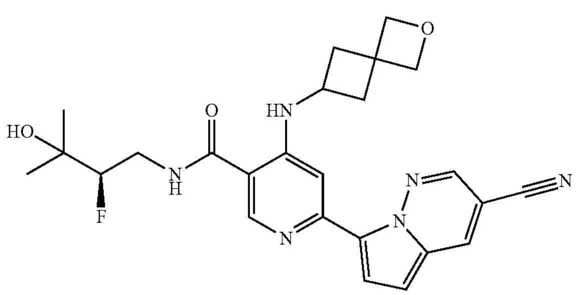 [SMILES: CC(C)(O)[C@H](F)CNC(=O)c1cnc(-c2ccc3cc(C#N)cnn23)cc1NC1CC2(COC2)C1] | 82 | 479.4 | 2 | (R)-4-(2-oxaspiro[3.3]heptan-6-ylamino)-6-(3-cyanopyrrolo[1,2-b]pyridazin-7-yl)-N-(2-fluoro-3-hydroxy-3-methylbutyl)nicotinamide |
| 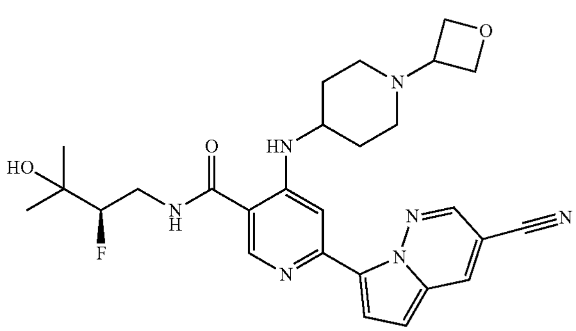 [SMILES: CC(C)(O)[C@H](F)CNC(=O)c1cnc(-c2ccc3cc(C#N)cnn23)cc1NC1CCN(C2COC2)CC1] | 83 | 522.4 | 2 | (R)-6-(3-cyanopyrrolo[1,2-b]pyridazin-7-yl)-N-(2-fluoro-3-hydroxy-3-methylbutyl)-4-((1-(oxetan-3-yl)piperidin-4-yl)amino)nicotinamide |

TABLE 1-continued

| Structure | compound | ES/MS m/z | procedure | Name |
|---|---|---|---|---|
| 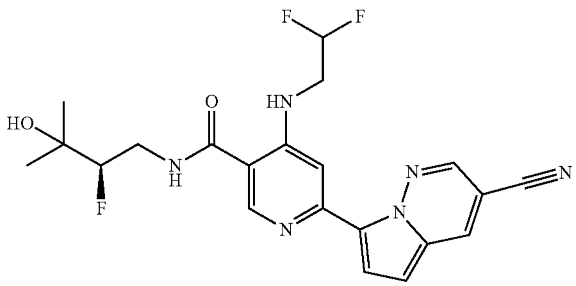 [SMILES: CC(C)(O)[C@H](F)CNC(=O)c1cnc(-c2ccc3cc(C#N)cnn23)cc1NCC(F)F] | 84 | 447.3 | 1 | (R)-6-(3-cyanopyrrolo[1,2-b]pyridazin-7-yl)-4-((2,2-difluoroethyl)amino)-N-(2-fluoro-3-hydroxy-3-methylbutyl)nicotinamide |
| 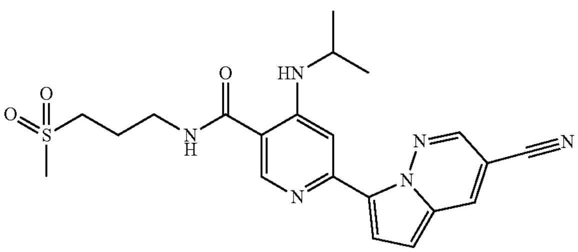 [SMILES: CC(C)Nc1cc(-c2ccc3cc(C#N)cnn23)ncc1C(=O)NCCCS(C)(=O)=O] | 85 | 441.3 | 3 | 6-(3-cyanopyrrolo[1,2-b]pyridazin-7-yl)-4-(isopropylamino)-N-(3-(methylsulfonyl)propyl)nicotinamide |
| 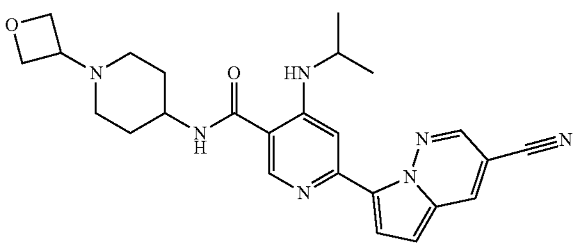 [SMILES: CC(C)Nc1cc(-c2ccc3cc(C#N)cnn23)ncc1C(=O)NC1CCN(C2COC2)CC1] | 86 | 460.4 | 3 | 6-(3-cyanopyrrolo[1,2-b]pyridazin-7-yl)-4-(isopropylamino)-N-(1-(oxetan-3-yl)piperidin-4-yl)nicotinamide |
| 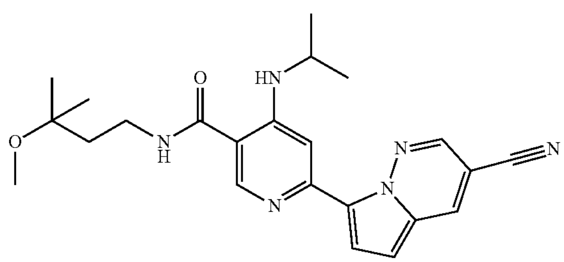 [SMILES: COC(C)(C)CCNC(=O)c1cnc(-c2ccc3cc(C#N)cnn23)cc1NC(C)C] | 87 | 421.4 | 3 | 6-(3-cyanopyrrolo[1,2-b]pyridazin-7-yl)-4-(isopropylamino)-N-(3-methoxy-3-methylbutyl)nicotinamide |
| 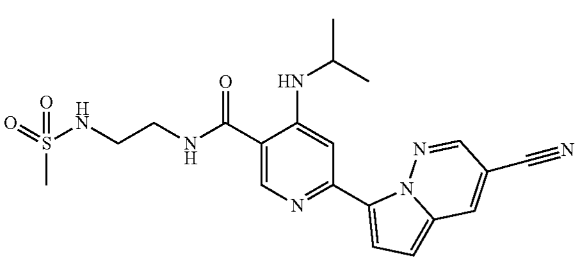 [SMILES: CC(C)Nc1cc(-c2ccc3cc(C#N)cnn23)ncc1C(=O)NCCNS(C)(=O)=O] | 88 | 442.3 | 3 | 6-(3-cyanopyrrolo[1,2-b]pyridazin-7-yl)-4-(isopropylamino)-N-(2-(methylsulfonamido)ethyl)nicotinamide |

TABLE 1-continued

| Structure | compound | ES/MS m/z | procedure | Name |
|---|---|---|---|---|
| 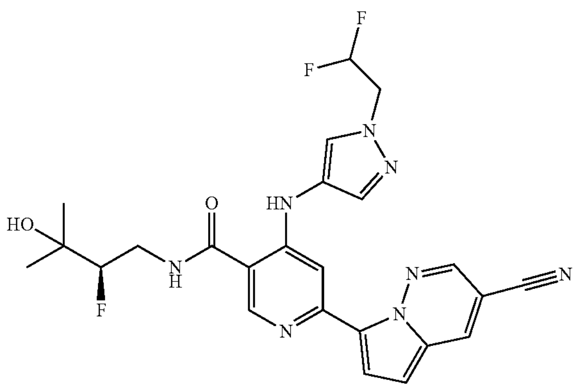 [SMILES: CC(C)(O)[C@H](F)CNC(=O)c1cnc(-c2ccc3cc(C#N)cnn23)cc1Nc1cnn(CC(F)F)c1] | 89 | 513.3 | 2 | (R)-6-(3-cyanopyrrolo[1,2-b]pyridazin-7-yl)-4-((1-(2,2-difluoroethyl)-1H-pyrazol-4-yl)amino)-N-(2-fluoro-3-hydroxy-3-methylbutyl)nicotinamide |
| 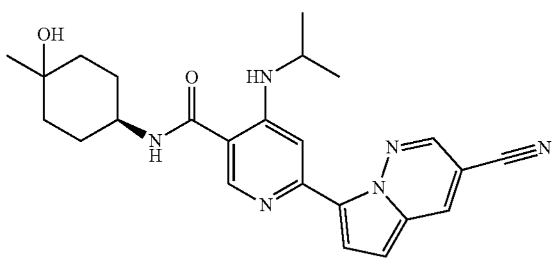 | 90 | 433.4 | 3 | 6-(3-cyanopyrrolo[1,2-b]pyridazin-7-yl)-N-((1s,4s)-4-hydroxy-4-methylcyclohexyl)-4-(isopropylamino)nicotinamide |
| 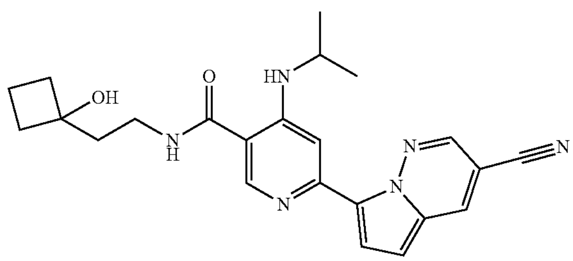 [SMILES: CC(C)Nc1cc(-c2ccc3cc(C#N)cnn23)ncc1C(=O)NCCC1(O)CCC1] | 91 | 419.4 | 3 | 6-(3-cyanopyrrolo[1,2-b]pyridazin-7-yl)-N-(2-(1-hydroxycyclobutyl)ethyl)-4-(isopropylamino)nicotinamide |
| 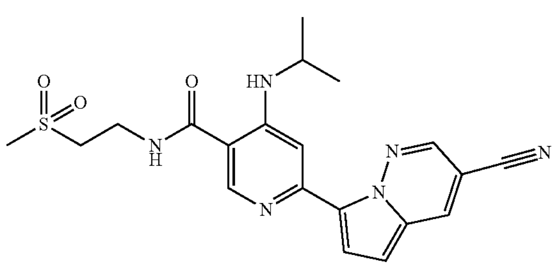 [SMILES: CC(C)Nc1cc(-c2ccc3cc(C#N)cnn23)ncc1C(=O)NCCS(C)(=O)=O] | 92 | 427.2 | 3 | 6-(3-cyanopyrrolo[1,2-b]pyridazin-7-yl)-4-(isopropylamino)-N-(2-(methylsulfonyl)ethyl)nicotinamide |
| 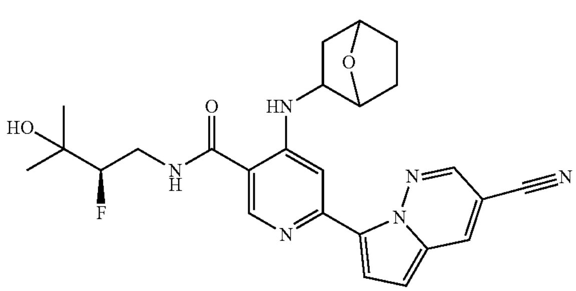 [SMILES: CC(C)(O)[C@H](F)CNC(=O)c1cnc(-c2ccc3cc(C#N)cnn23)cc1NC1CC2CCC1O2] | 93 | 479.3 | 2 | 4-(((1R,2R,4S)-7-oxabicyclo[2.2.1]heptan-2-yl)amino)-6-(3-cyanopyrrolo[1,2-b]pyridazin-7-yl)-N-((R)-2-fluoro-3-hydroxy-3-methylbutyl)nicotinamide |

TABLE 1-continued

| Structure | compound | ES/MS m/z | procedure | Name |
|---|---|---|---|---|
| 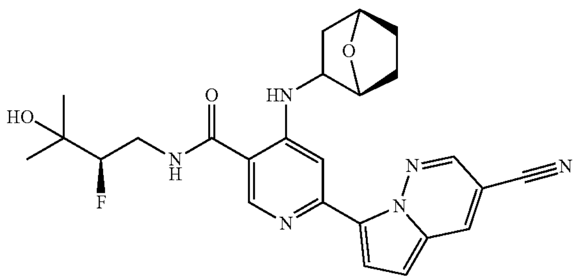 [SMILES: CC(C)(O)[C@H](F)CNC(=O)c1cnc(-c2ccc3cc(C#N)cnn23)cc1NC1C[C@H]2CC[C@@H]1O2] | 94 | 479.3 | 2 | 4-(((1S,2R,4R)-7-oxabicyclo[2.2.1]heptan-2-yl)amino)-6-(3-cyanopyrrolo[1,2-b]pyridazin-7-yl)-N-((R)-2-fluoro-3-hydroxy-3-methylbutyl)nicotinamide |
| 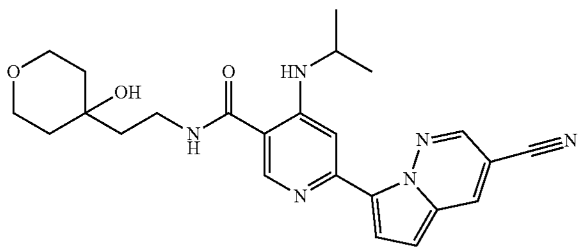 [SMILES: CC(C)Nc1cc(-c2ccc3cc(C#N)cnn23)ncc1C(=O)NCCC1(O)CCOCC1] | 95 | 449.3 | 3 | 6-(3-cyanopyrrolo[1,2-b]pyridazin-7-yl)-N-(2-(4-hydroxytetrahydro-2H-pyran-4-yl)ethyl)-4-(isopropylamino)nicotinamide |
| 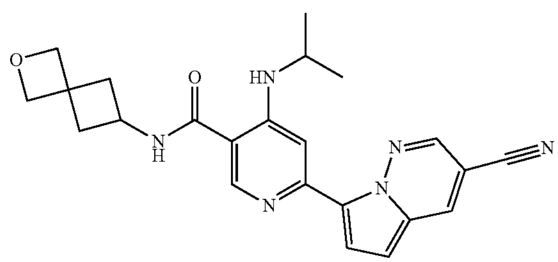 [SMILES: CC(C)Nc1cc(-c2ccc3cc(C#N)cnn23)ncc1C(=O)NC1CC2(COC2)C1] | 96 | 417.3 | 3 | 6-(3-cyanopyrrolo[1,2-b]pyridazin-7-yl)-4-(isopropylamino)-N-(2-oxaspiro[3.3]heptan-6-yl)nicotinamide |
| 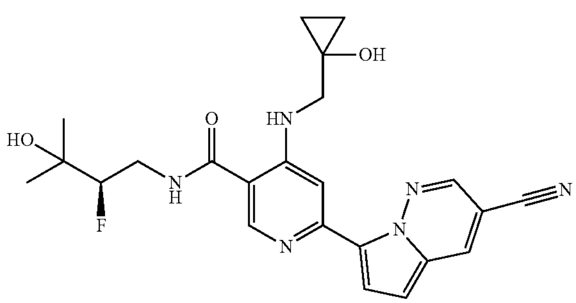 [SMILES: CC(C)(O)[C@H](F)CNC(=O)c1cnc(-c2ccc3cc(C#N)cnn23)cc1NCC1(O)CC1] | 97 | 453.3 | 1 | (R)-6-(3-cyanopyrrolo[1,2-b]pyridazin-7-yl)-N-(2-fluoro-3-hydroxy-3-methylbutyl)-4-(((1-hydroxycyclopropyl)methyl)amino)nicotinamide |
| 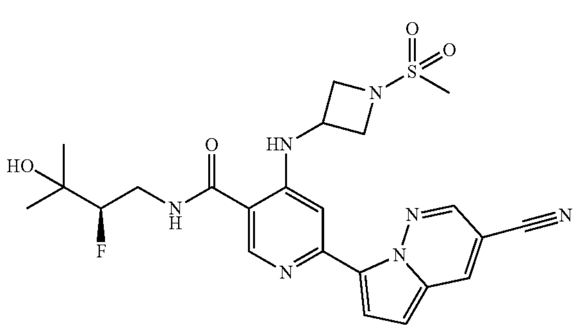 [SMILES: CC(C)(O)[C@H](F)CNC(=O)c1cnc(-c2ccc3cc(C#N)cnn23)cc1NC1CN(S(C)(=O)=O)C1] | 98 | 516.2 | 2 | (R)-6-(3-cyanopyrrolo[1,2-b]pyridazin-7-yl)-N-(2-fluoro-3-hydroxy-3-methylbutyl)-4-((1-(methylsulfonyl)azetidin-3-yl)amino)nicotinamide |

TABLE 1-continued

| Structure | compound | ES/MS m/z | procedure | Name |
|---|---|---|---|---|
| 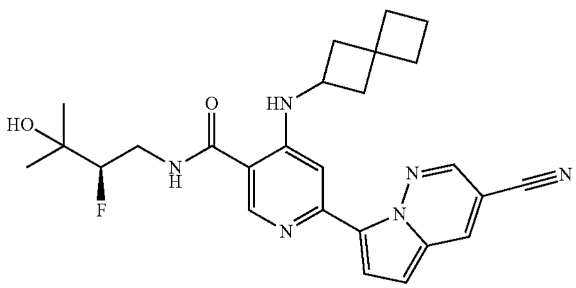 [SMILES: CC(C)(O)[C@H](F)CNC(=O)c1cnc(-c2ccc3cc(C#N)cnn23)cc1NC1CC2(CCC2)C1] | 99 | 477.4 | 1 | (R)-6-(3-cyanopyrrolo[1,2-b]pyridazin-7-yl)-N-(2-fluoro-3-hydroxy-3-methylbutyl)-4-(spiro[3.3]heptan-2-ylamino)nicotinamide |
| 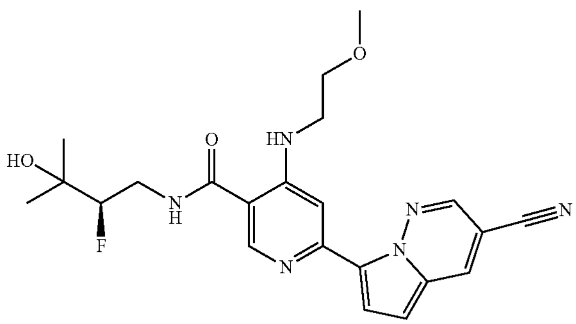 [SMILES: COCCNc1cc(-c2ccc3cc(C#N)cnn23)ncc1C(=O)NC[C@@H](F)C(C)(C)O] | 100 | 441.3 | 1 | (R)-6-(3-cyanopyrrolo[1,2-b]pyridazin-7-yl)-N-(2-fluoro-3-hydroxy-3-methylbutyl)-4-((2-methoxyethyl)amino)nicotinamide |
| 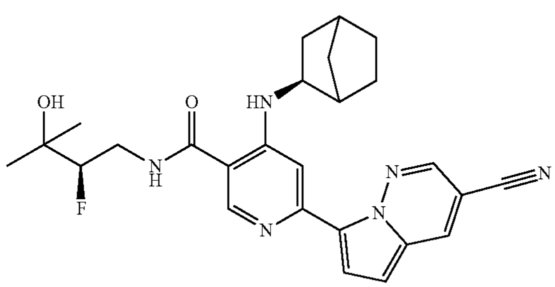 [SMILES: CC(C)(O)[C@H](F)CNC(=O)c1cnc(-c2ccc3cc(C#N)cnn23)cc1N[C@H]1CC2CCC1C2] | 101 | 477.4 | 1 | 4-(((1S,2S,4R)-bicyclo[2.2.1]heptan-2-yl)amino)-6-(3-cyanopyrrolo[1,2-b]pyridazin-7-yl)-N-((R)-2-fluoro-3-hydroxy-3-methylbutyl)nicotinamide |
| 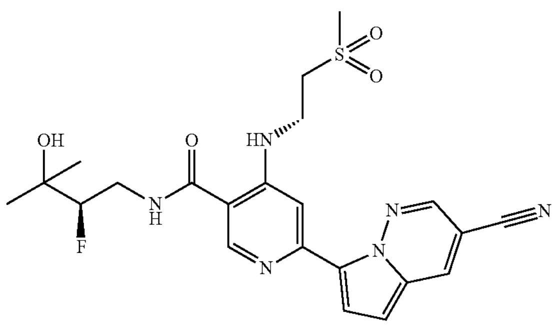 | 102 | 489.2 | 1 | (R)-6-(3-cyanopyrrolo[1,2-b]pyridazin-7-yl)-N-(2-fluoro-3-hydroxy-3-methylbutyl)-4-((2-(methylsulfonyl)ethyl)amino)nicotinamide |

TABLE 1-continued

| Structure | compound | ES/MS m/z | procedure | Name |
|---|---|---|---|---|
| 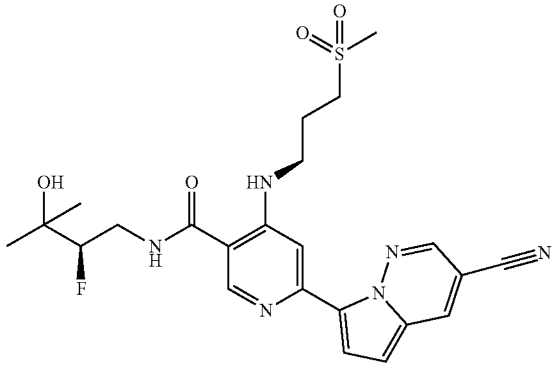 | 103 | 503.3 | 1 | (R)-6-(3-cyanopyrrolo[1,2-b]pyridazin-7-yl)-N-(2-fluoro-3-hydroxy-3-methylbutyl)-4-((3-(methylsulfonyl)propyl)amino)nicotinamide |
| 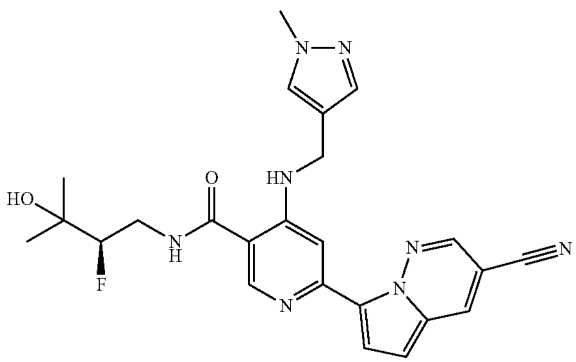 [SMILES: Cn1cc(CNc2cc(-c3ccc4cc(C#N)cnn34)ncc2C(=O)NC[C@@H](F)C(C)(C)O)cn1] | 104 | 477.2 | 2 | (R)-6-(3-cyanopyrrolo[1,2-b]pyridazin-7-yl)-N-(2-fluoro-3-hydroxy-3-methylbutyl)-4-(((1-methyl-1H-pyrazol-4-yl)methyl)amino)nicotinamide |
| 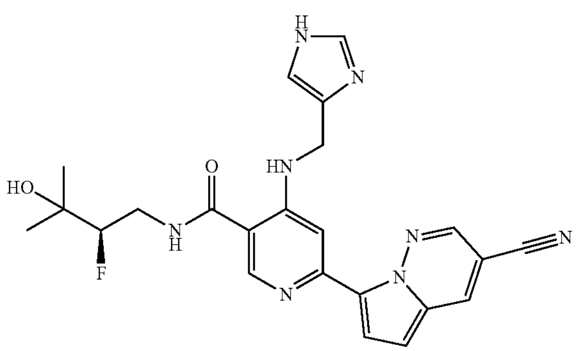 [SMILES: CC(C)(O)[C@H](F)CNC(=O)c1cnc(-c2ccc3cc(C#N)cnn23)cc1NCc1c[nH]cn1] | 105 | 463.2 | 2 | (R)-4-(((1H-imidazol-4-yl)methyl)amino)-6-(3-cyanopyrrolo[1,2-b]pyridazin-7-yl)-N-(2-fluoro-3-hydroxy-3-methylbutyl)nicotinamide |
| 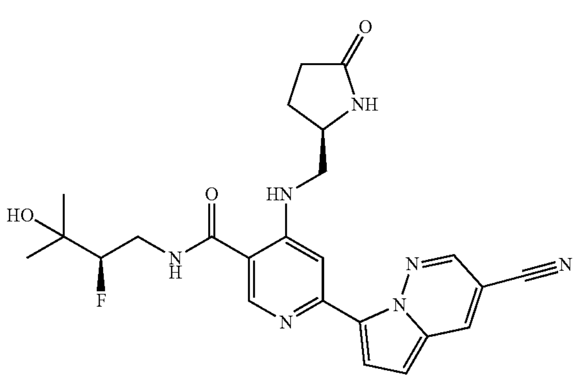 [SMILES: CC(C)(O)[C@H](F)CNC(=O)c1cnc(-c2ccc3cc(C#N)cnn23)cc1NC[C@H]1CCC(=O)N1] | 106 | 480.3 | 2 | 6-(3-cyanopyrrolo[1,2-b]pyridazin-7-yl)-N-((R)-2-fluoro-3-hydroxy-3-methylbutyl)-4-((((R)-5-oxopyrrolidin-2-yl)methyl)amino)nicotinamide |

TABLE 1-continued

| Structure | compound | ES/MS m/z | procedure | Name |
|---|---|---|---|---|
| 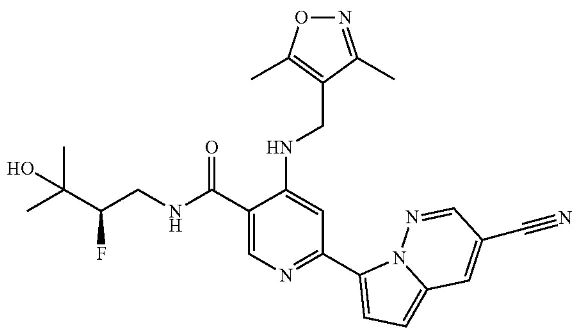 [SMILES: Cc1noc(C)c1CNc1cc(-c2ccc3cc(C#N)cnn23)ncc1C(=O)NC[C@@H](F)C(C)(C)O] | 107 | 492.2 | 2 | (R)-6-(3-cyanopyrrolo[1,2-b]pyridazin-7-yl)-4-(((3,5-dimethylisoxazol-4-yl)methyl)amino)-N-(2-fluoro-3-hydroxy-3-methylbutyl)nicotinamide |
| 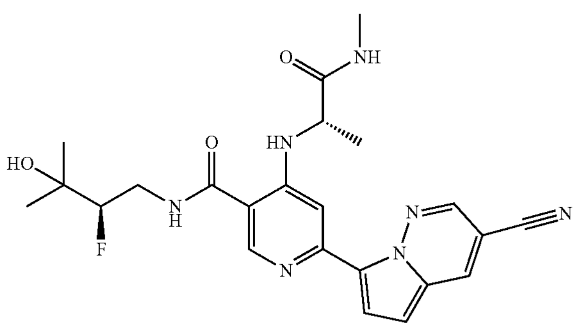 [SMILES: CNC(=O)[C@H](C)Nc1cc(-c2ccc3cc(C#N)cnn23)ncc1C(=O)NC[C@@H](F)C(C)(C)O] | 108 | 468.2 | 2 | 6-(3-cyanopyrrolo[1,2-b]pyridazin-7-yl)-N-((R)-2-fluoro-3-hydroxy-3-methylbutyl)-4-(((S)-1-(methylamino)-1-oxopropan-2-yl)amino)nicotinamide |
| 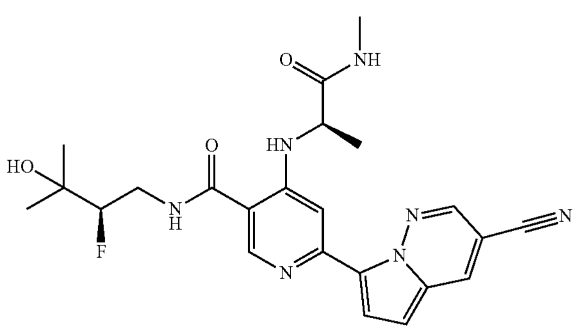 [SMILES: CNC(=O)[C@@H](C)Nc1cc(-c2ccc3cc(C#N)cnn23)ncc1C(=O)NC[C@@H](F)C(C)(C)O] | 109 | 468.2 | 2 | 6-(3-cyanopyrrolo[1,2-b]pyridazin-7-yl)-N-((R)-2-fluoro-3-hydroxy-3-methylbutyl)-4-(((R)-1-(methylamino)-1-oxopropan-2-yl)amino)nicotinamide |
| 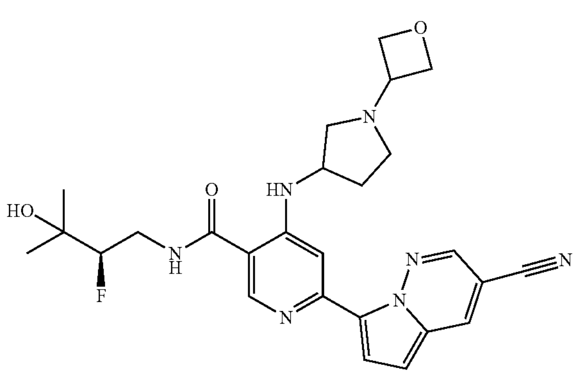 [SMILES: CC(C)(O)[C@H](F)CNC(=O)c1cnc(-c2ccc3cc(C#N)cnn23)cc1NC1CCN(C2COC2)C1] | 110 | 508.3 | 2 | 6-(3-cyanopyrrolo[1,2-b]pyridazin-7-yl)-N-((R)-2-fluoro-3-hydroxy-3-methylbutyl)-4-(((S)-1-(oxetan-3-yl)pyrrolidin-3-yl)amino)nicotinamide |

TABLE 1-continued

| Structure | compound | ES/MS m/z | procedure | Name |
|---|---|---|---|---|
| 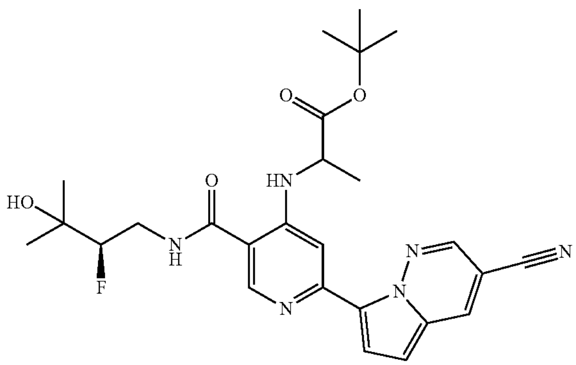 [SMILES: CC(Nc1cc(-c2ccc3cc(C#N)cnn23)ncc1C(=O)NC[C@@H](F)C(C)(C)O)C(=O)OC(C)(C)C] | 111 | 511.2 | 2 | tert-butyl (2-(3-cyano-pyrrolo[1,2-b]pyridazin-7-yl)-5-(((R)-2-fluoro-3-hydroxy-3-methylbutyl)carbamoyl)pyridin-4-yl)alaninate |
| 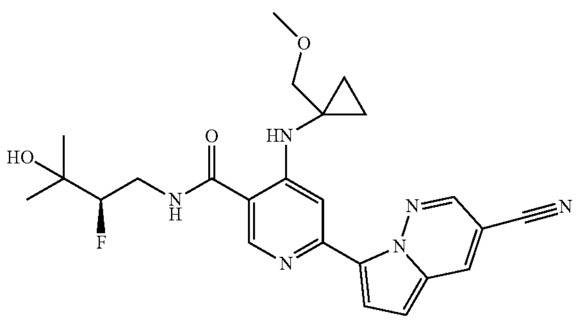 [SMILES: COCC1(Nc2cc(-c3ccc4cc(C#N)cnn34)ncc2C(=O)NC[C@@H](F)C(C)(C)O)CC1] | 112 | 467.4 | 2 | (R)-6-(3-cyano-pyrrolo[1,2-b]pyridazin-7-yl)-N-(2-fluoro-3-hydroxy-3-methylbutyl)-4-((1-(methoxymethyl)cyclopropyl)amino)nicotinanide |
| 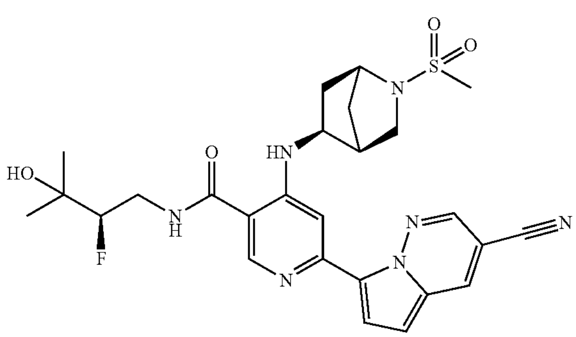 [SMILES: CC(C)(O)[C@H](F)CNC(=O)c1cnc(-c2ccc3cc(C#N)cnn23)cc1N[C@H]1C[C@@H]2C[C@H]1CN2S(C)(=O)=O] | 113 | 556.2 | 14 | 6-(3-cyanopyrrolo[1,2-b]pyridazin-7-yl)-N-((R)-2-fluoro-3-hydroxy-3-methylbutyl)-4-(((1S,4S,5S)-2-(methylsulfonyl)-2-azabicyclo[2.2.1]heptan-5-yl)amino)nicotinamide |
| 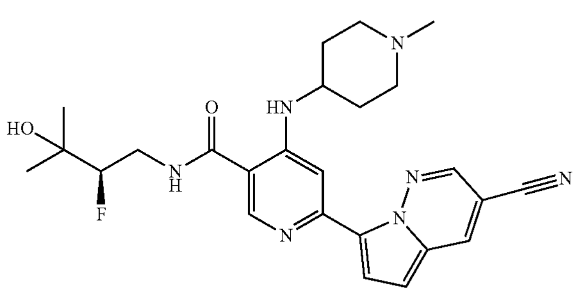 [SMILES: CN1CCC(Nc2cc(-c3ccc4cc(C#N)cnn34)ncc2C(=O)NC[C@@H](F)C(C)(C)O)CC1] | 114 | 480.3 | 2 | (R)-6-(3-cyanopyrrolo[1,2-b]pyridazin-7-yl)-N-(2-fluoro-3-hydroxy-3-methylbutyl)-4-((1-methylpiperidin-4-yl)amino)nicotinamide |

TABLE 1-continued

| Structure | compound | ES/MS m/z | procedure | Name |
|---|---|---|---|---|
| 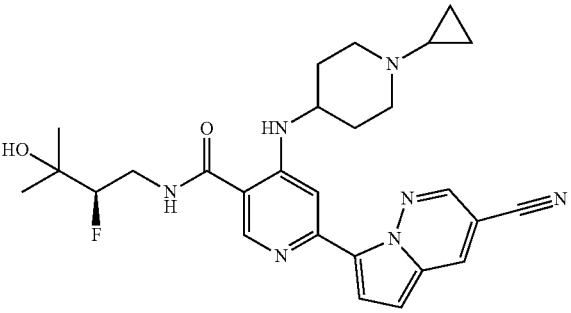 [SMILES: CC(C)(O)[C@H](F)CNC(=O)c1cnc(-c2ccc3cc(C#N)cnn23)cc1NC1CCN(C2CC2)CC1] | 115 | 506.4 | 8 | (R)-6-(3-cyanopyrrolo[1,2-b]pyridazin-7-yl)-4-((1-cyclopropylpiperidin-4-yl)amino)-N-(2-fluoro-3-hydroxy-3-methylbutyl)nicotinamide |
| 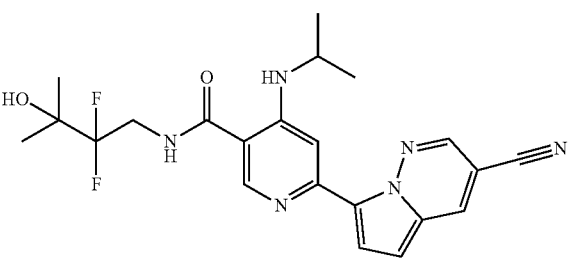 [SMILES: CC(C)Nc1cc(-c2ccc3cc(C#N)cnn23)ncc1C(=O)NCC(F)(F)C(C)(C)O] | 116 | 443.4 | 3 | 6-(3-cyanopyrrolo[1,2-b]pyridazin-7-yl)-N-(2,2-difluoro-3-hydroxy-3-methylbutyl)-4-(isopropylamino)nicotinamide |
| 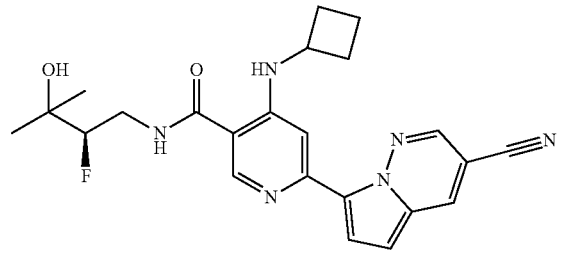 [SMILES: CC(C)(O)[C@H](F)CNC(=O)c1cnc(-c2ccc3cc(C#N)cnn23)cc1NC1CCC1] | 117 | 437.3 | 2 | (R)-6-(3-cyanopyrrolo[1,2-b]pyridazin-7-yl)-4-(cyclobutyl-amino)-N-(2-fluoro-3-hydroxy-3-methylbutyl)nicotinamide |
| 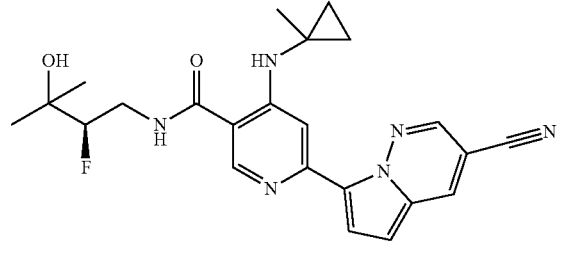 [SMILES: CC1(Nc2cc(-c3ccc4cc(C#N)cnn34)ncc2C(=O)NC[C@@H](F)C(C)(C)O)CC1] | 118 | 437.2 | 2 | (R)-6-(3-cyanopyrrolo[1,2-b]pyridazin-7-yl)-N-(2-fluoro-3-hydroxy-3-methylbutyl)-4-((1-methylcyclopropyl)amino)nicotinamide |
| 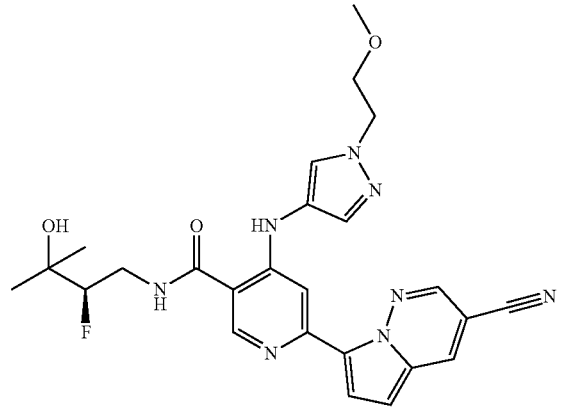 [SMILES: COCCn1cc(Nc2cc(-c3ccc4cc(C#N)cnn34)ncc2C(=O)NC[C@@H](F)C(C)(C)O)cn1] | 119 | 507.4 | 2 | (R)-6-(3-cyanopyrrolo[1,2-b]pyridazin-7-yl)-N-(2-fluoro-3-hydroxy-3-methylbutyl)-4-((1-(2-methoxyethyl)-1H-pyrazol-4-yl)amino)nicotinamide |

TABLE 1-continued

| Structure | compound | ES/MS m/z | procedure | Name |
|---|---|---|---|---|
| 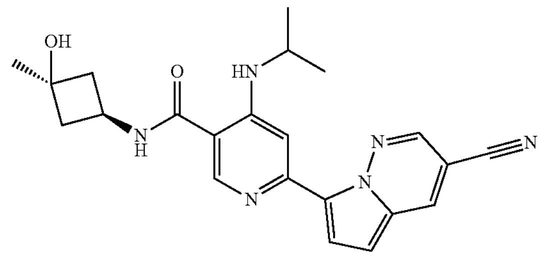 [SMILES: CC(C)Nc1cc(-c2ccc3cc(C#N)cnn23)ncc1C(=O)N[C@H]1C[C@@](C)(O)C1] | 120 | 405.4 | 3 | 6-(3-cyanopyrrolo[1,2-b]pyridazin-7-yl)-N-((1s,3s)-3-hydroxy-3-methylcyclobutyl)-4-(isopropylamino)nicotinamide |
| 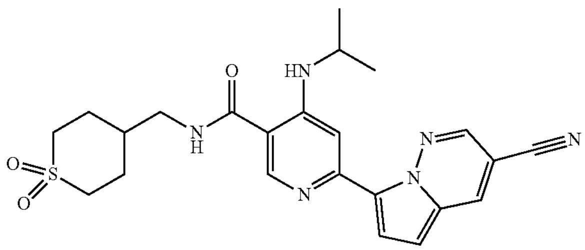 [SMILES: CC(C)Nc1cc(-c2ccc3cc(C#N)cnn23)ncc1C(=O)NCC1CCS(=O)(=O)CC1] | 121 | 467.2 | 1 | 6-(3-cyanopyrrolo[1,2-b]pyridazin-7-yl)-N-((1,1-dioxidotetrahydro-2H-thiopyran-4-yl)methyl)-4-(isopropylamino)nicotinamide |
| 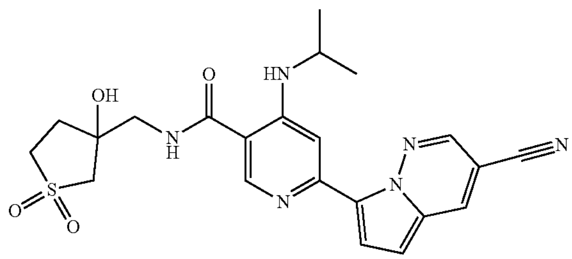 [SMILES: CC(C)Nc1cc(-c2ccc3cc(C#N)cnn23)ncc1C(=O)NCC1(O)CCS(=O)(=O)C1] | 122 | 469.1 | 23 | 6-(3-cyanopyrrolo[1,2-b]pyridazin-7-yl)-N-((3-hydroxy-1,1-dioxidotetrahydrothiophen-3-yl)methyl)-4-(isopropylamino)nicotinamide |
| 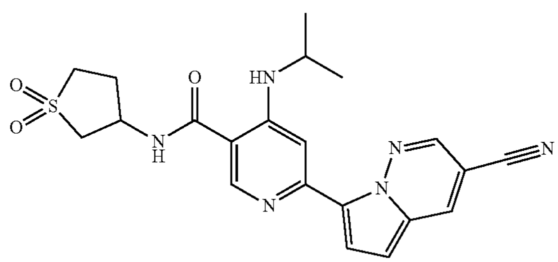 [SMILES: CC(C)Nc1cc(-c2ccc3cc(C#N)cnn23)ncc1C(=O)NC1CCS(=O)(=O)C1] | 123 | 439.1 | 23 | 6-(3-cyanopyrrolo[1,2-b]pyridazin-7-yl)-N-(1,1-dioxidotetrahydrothiophen-3-yl)-4-(isopropylamino)nicotinamide |
| 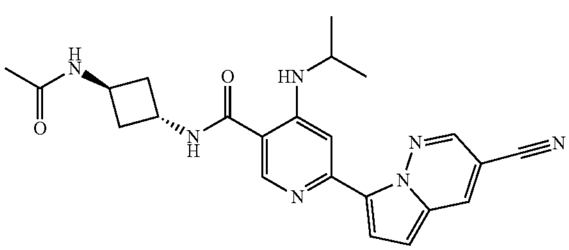 [SMILES: CC(=O)N[C@H]1C[C@H](NC(=O)c2cnc(-c3ccc4cc(C#N)cnn34)cc2NC(C)C)C1] | 124 | 432.3 | 12 | N-((1r,3r)-3-acetamidocyclobutyl)-6-(3-cyanopyrrolo[1,2-b]pyridazin-7-yl)-4-(isopropylamino)nicotinamide |
| 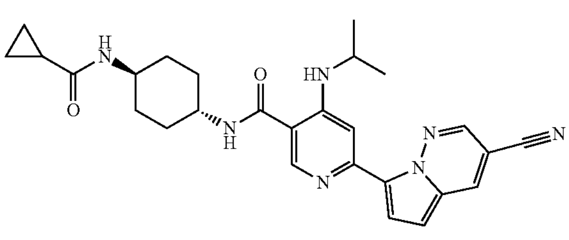 [SMILES: CC(C)Nc1cc(-c2ccc3cc(C#N)cnn23)ncc1C(=O)N[C@H]1CC[C@H](NC(=O)C2CC2)CC1] | 125 | 486.3 | 12 | 6-(3-cyanopyrrolo[1,2-b]pyridazin-7-yl)-N-((1r,4r)-4-(cyclopropanecarboxamido)cyclohexyl)-4-(isopropylamino)nicotinamide |

TABLE 1-continued

| Structure | compound | ES/MS m/z | procedure | Name |
|---|---|---|---|---|
| 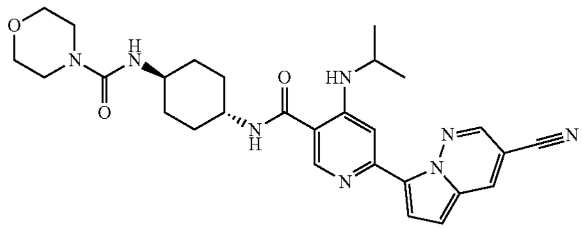 [SMILES: CC(C)Nc1cc(-c2ccc3cc(C#N)cnn23)ncc1C(=O)N[C@H]1CC[C@H](NC(=O)N2CCOCC2)CC1] | 126 | 531.3 | 12 | N-((1r,4r)-4-(6-(3-cyano-pyrrolo[1,2-b]pyridazin-7-yl)-4-(isopropylamino)nicotinamido)cyclohexyl)morpholine-4-carboxamide |
| 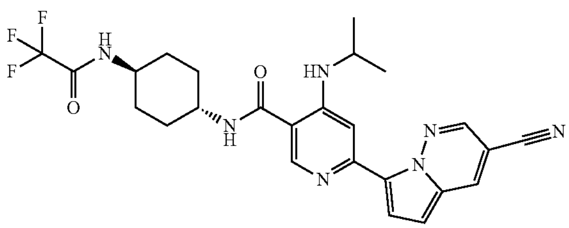 [SMILES: CC(C)Nc1cc(-c2ccc3cc(C#N)cnn23)ncc1C(=O)N[C@H]1CC[C@H](NC(=O)C(F)(F)F)CC1] | 127 | 514.2 | 12 | 6-(3-cyanopyrrolo[1,2-b]pyridazin-7-yl)-4-(isopropyl-amino)-N-((1r,4r)-4-(2,2,2-trifluoroacetamido)cyclohexyl)nicotinamide |
| 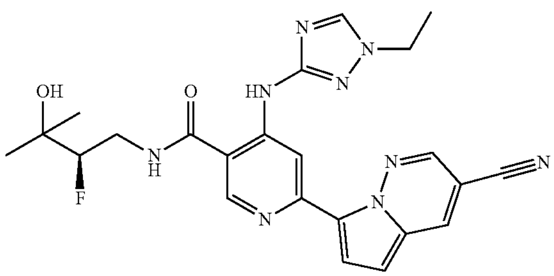 [SMILES: CCn1cnc(Nc2cc(-c3ccc4cc(C#N)cnn34)ncc2C(=O)NC[C@@H](F)C(C)(C)O)n1] | 128 | 478.2 | 2 | (R)-6-(3-cyanopyrrolo[1,2-b]pyridazin-7-yl)-4-((1-ethyl-1H-1,2,4-triazol-3-yl)amino)-N-(2-fluoro-3-hydroxy-3-methylbutyl)nicotinamide |
| 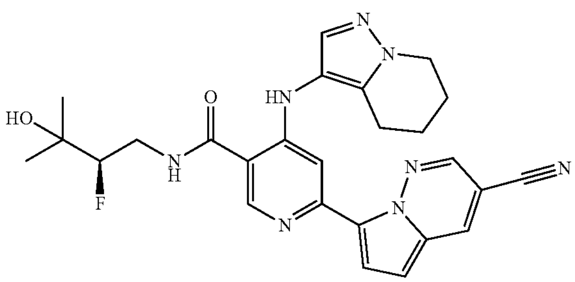 [SMILES: CC(C)(O)[C@H](F)CNC(=O)c1cnc(-c2ccc3cc(C#N)cnn23)cc1Nc1cnn2c1CCCC2] | 129 | 503.3 | 2 | (R)-6-(3-cyanopyrrolo[1,2-b]pyridazin-7-yl)-N-(2-fluoro-3-hydroxy-3-methylbutyl)-4-((4,5,6,7-tetrahydropyrazolo[1,5-a]pyridin-3-yl)amino)nicotinamide |
| 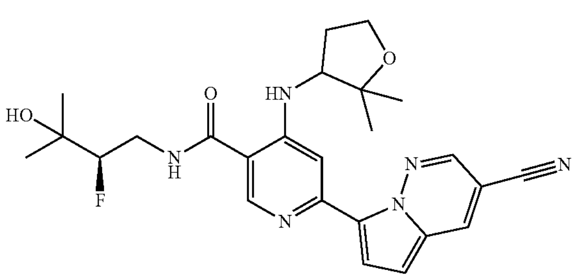 [SMILES: CC1(C)OCCC1Nc1cc(-c2ccc3cc(C#N)cnn23)ncc1C(=O)NC[C@@H](F)C(C)(C)O] | 130 | 481.3 | 2 | 6-(3-cyanopyrrolo[1,2-b]pyridazin-7-yl)-4-((2,2-dimethyltetrahydrofuran-3-yl)amino)-N-((R)-2-fluoro-3-hydroxy-3-methylbutyl)nicotinamide |
| 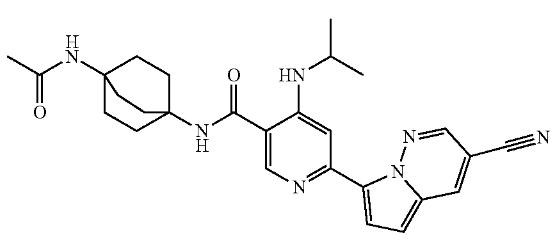 [SMILES: CC(=O)NC12CCC(NC(=O)c3cnc(-c4ccc5cc(C#N)cnn45)cc3NC(C)C)(CC1)CC2] | 131 | 486.3 | 12 | N-(4-acetamido-bicyclo[2.2.2]octan-1-yl)-6-(3-cyanopyrrolo[1,2-b]pyridazin-7-yl)-4-(isopropylamino)nicotinamide |

| compound | ES/MS m/z | procedure | Name |
|---|---|---|---|
| 132 | 444.2 | 12 | N-(3-acetamidobicyclo[1.1.1]pentan-1-yl)-6-(3-cyanopyrrolo[1,2-b]pyridazin-7-yl)-4-(isopropylamino)nicotinamide |
| 133 | 455.3 | 2 | (R)-6-(3-cyanopyrrolo[1,2-b]pyridazin-7-yl)-N-(2-fluoro-3-hydroxy-3-methylbutyl)-4-((3-methoxypropyl)amino)nicotinamide |
| 134 | 516.3 | 22 | 6-(3-cyanopyrrolo[1,2-b]pyridazin-7-yl)-4-(isopropylamino)-N-((1r,4r)-4-(3-methyloxetane-3-carboxamido)cyclohexyl)nicotinamide |
| 135 | 504.3 | 22 | 6-(3-cyanopyrrolo[1,2-b]pyridazin-7-yl)-N-((1r,4r)-4-(2-hydroxy-2-methylpropanamido)cyclohexyl)-4-(isopropylamino)nicotinamide |
| 136 | 469.4 | 2 | (R)-6-(3-cyanopyrrolo[1,2-b]pyridazin-7-yl)-N-(2-fluoro-3-hydroxy-3-methylbutyl)-4-((3-fluoro-3-methylcyclobutyl)amino)nicotinamide |

TABLE 1-continued

| Structure | compound | ES/ MS m/z | procedure | Name |
|---|---|---|---|---|
| 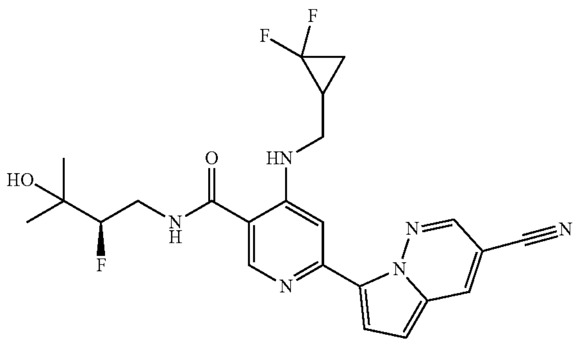 [SMILES: CC(C)(O)[C@H](F)CNC(=O)c1cnc(-c2ccc3cc(C#N)cnn23)cc1NCC1CC1(F)F] | 137 | 473.4 | 2 | 6-(3-cyanopyrrolo[1,2-b]pyridazin-7-yl)-4-(((2,2-difluorocyclopropyl)methyl)amino)-N-((R)-2-fluoro-3-hydroxy-3-methylbutyl)nicotinamide |
| 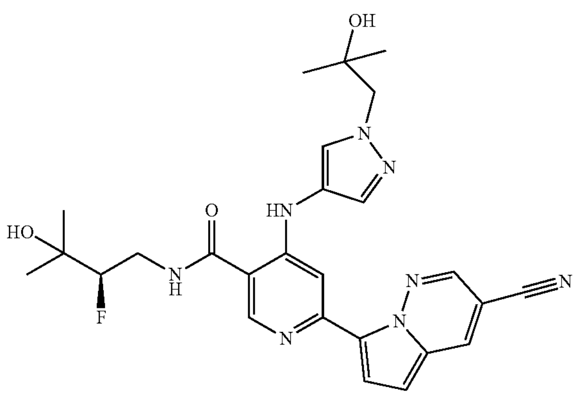 [SMILES: CC(C)(O)Cn1cc(Nc2cc(-c3ccc4cc(C#N)cnn34)ncc2C(=O)NC[C@@H](F)C(C)(C)O)cn1] | 138 | 521.3 | 2 | (R)-6-(3-cyanopyrrolo[1,2-b]pyridazin-7-yl)-N-(2-fluoro-3-hydroxy-3-methylbutyl)-4-((1-(2-hydroxy-2-methylpropyl)-1H-pyrazol-4-yl)amino)nicotinamide |
| 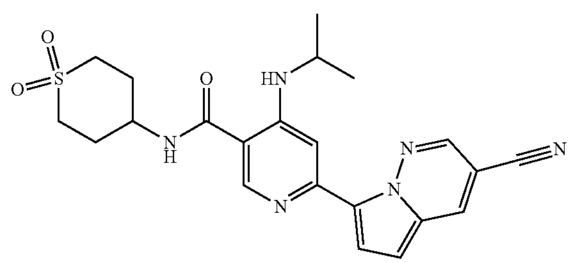 [SMILES: CC(C)Nc1cc(-c2ccc3cc(C#N)cnn23)ncc1C(=O)NC1CCS(=O)(=O)CC1] | 139 | 453.2 | 23 | 6-(3-cyanopyrrolo[1,2-b]pyridazin-7-yl)-N-(1,1-dioxidotetrahydro-2H-thiopyran-4-yl)-4-(isopropylamino)nicotinamide |
| 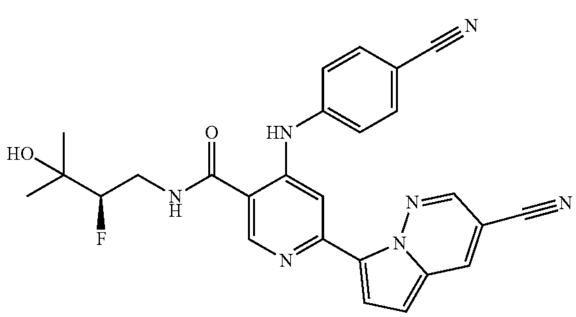 | 140 | 484.2 | 24 | (R)-4-((4-cyanophenyl)amino)-6-(3-cyanopyrrolo[1,2-b]pyridazin-7-yl)-N-(2-fluoro-3-hydroxy-3-methylbutyl)nicotinamide |

TABLE 1-continued

| Structure | compound | ES/MS m/z | procedure | Name |
|---|---|---|---|---|
| 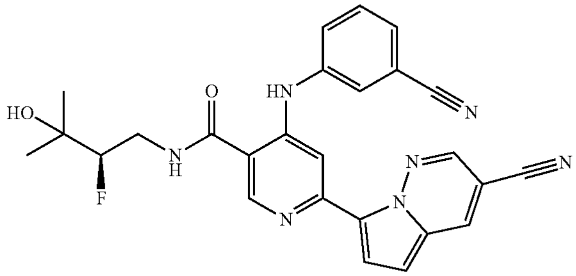 [SMILES: CC(C)(O)[C@H](F)CNC(=O)c1cnc(-c2ccc3cc(C#N)cnn23)cc1Nc1cccc(C#N)c1] | 141 | 484.2 | 24 | (R)-4-((3-cyanophenyl)amino)-6-(3-cyanopyrrolo[1,2-b]pyridazin-7-yl)-N-(2-fluoro-3-hydroxy-3-methylbutyl)nicotinamide |
| 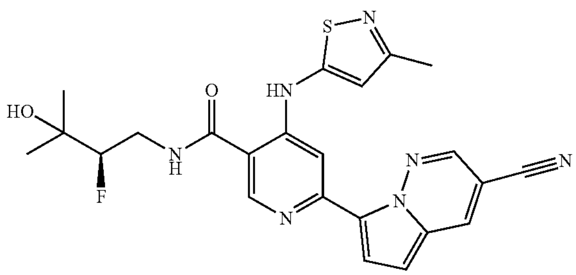 [SMILES: Cc1cc(Nc2cc(-c3ccc4cc(C#N)cnn34)ncc2C(=O)NC[C@@H](F)C(C)(C)O)sn1] | 142 | 481.1 | 21 | (R)-6-(3-cyanopyrrolo[1,2-b]pyridazin-7-yl)-N-(2-fluoro-3-hydroxy-3-methylbutyl)-4-((3-methyl-1,2,4-thiadiazol-5-yl)amino)nicotinamide |
| 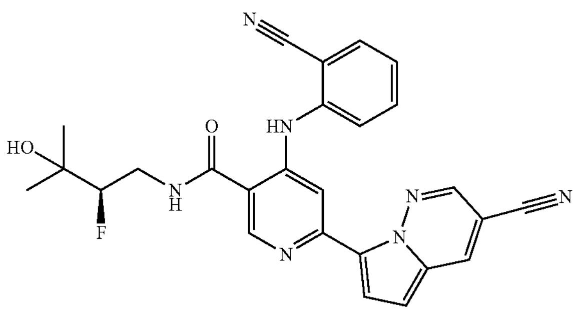 [SMILES: CC(C)(O)[C@H](F)CNC(=O)c1cnc(-c2ccc3cc(C#N)cnn23)cc1Nc1ccccc1C#N] | 143 | 484.3 | 24 | (R)-4-((2-cyanophenyl)amino)-6-(3-cyanopyrrolo[1,2-b]pyridazin-7-yl)-N-(2-fluoro-3-hydroxy-3-methylbutyl)nicotinamide |
| 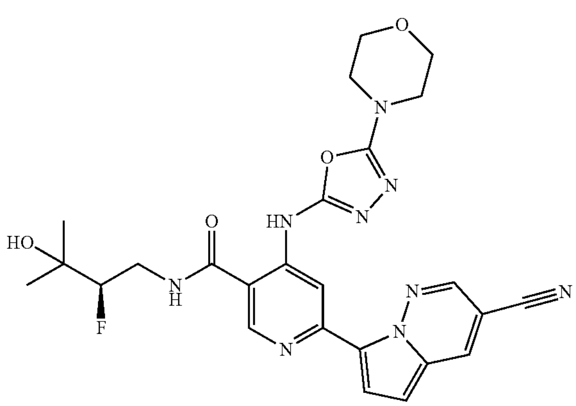 [SMILES: CC(C)(O)[C@H](F)CNC(=O)c1cnc(-c2ccc3cc(C#N)cnn23)cc1Nc1nnc(N2CCOCC2)o1] | 144 | 536.2 | 21 | (R)-6-(3-cyanopyrrolo[1,2-b]pyridazin-7-yl)-N-(2-fluoro-3-hydroxy-3-methylbutyl)-4-((5-morpholino-1,3,4-oxadiazol-2-yl)amino)nicotinamide |
| 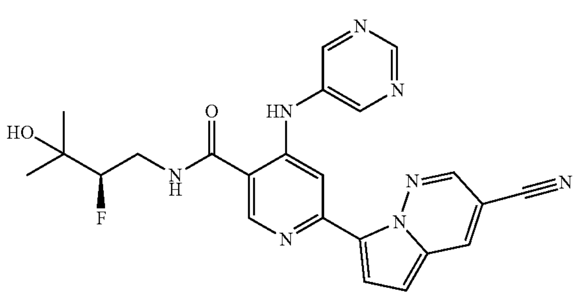 [SMILES: CC(C)(O)[C@H](F)CNC(=O)c1cnc(-c2ccc3cc(C#N)cnn23)cc1Nc1cncnc1] | 145 | 461.1 | 21 | (R)-6-(3-cyanopyrrolo[1,2-b]pyridazin-7-yl)-N-(2-fluoro-3-hydroxy-3-methylbutyl)-4-(pyrimidin-5-ylamino)nicotinamide |

TABLE 1-continued

| Structure | compound | ES/MS m/z | procedure | Name |
|---|---|---|---|---|
| 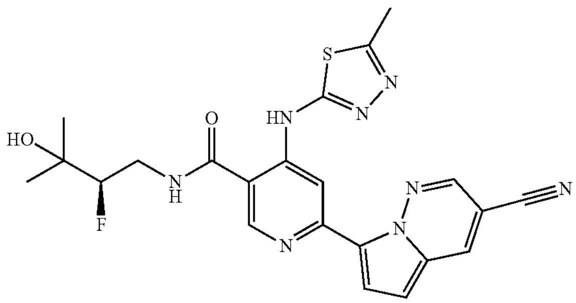 [SMILES: Cc1nnc(Nc2cc(-c3ccc4cc(C#N)cnn34)ncc2C(=O)NC[C@@H](F)C(C)(C)O)s1] | 146 | 481.1 | 21 | (R)-6-(3-cyanopyrrolo[1,2-b]pyridazin-7-yl)-N-(2-fluoro-3-hydroxy-3-methylbutyl)-4-((5-methyl-1,3,4-thiadiazol-2-yl)amino)nicotinamide |
| 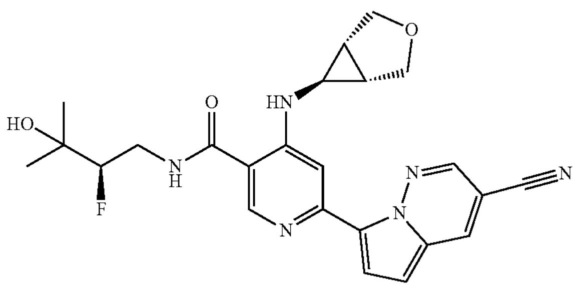 [SMILES: CC(C)(O)[C@H](F)CNC(=O)c1cnc(-c2ccc3cc(C#N)cnn23)cc1N[C@H]1[C@@H]2COC[C@@H]21] | 147 | 465.2 | 2 | 4-(((1R,5S,6r)-3-oxabicyclo[3.1.0]hexan-6-yl)amino)-6-(3-cyanopyrrolo[1,2-b]pyridazin-7-yl)-N-((R)-2-fluoro-3-hydroxy-3-methylbutyl)nicotinamide |
| 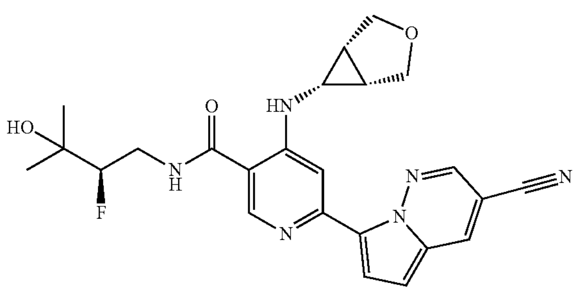 [SMILES: CC(C)(O)[C@H](F)CNC(=O)c1cnc(-c2ccc3cc(C#N)cnn23)cc1N[C@@H]1[C@@H]2COC[C@@H]21] | 148 | 465.3 | 2 | 4-(((1R,5S,6s)-3-oxabicyclo[3.1.0]hexan-6-yl)amino)-6-(3-cyanopyrrolo[1,2-b]pyridazin-7-yl)-N-((R)-2-fluoro-3-hydroxy-3-methylbutyl)nicotinamide |
| 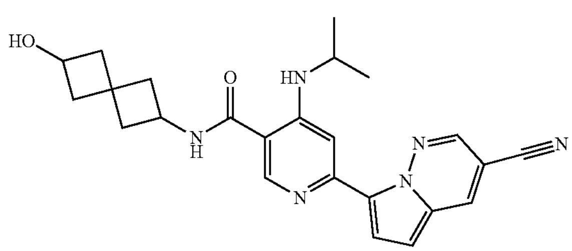 [SMILES: CC(C)Nc1cc(-c2ccc3cc(C#N)cnn23)ncc1C(=O)NC1CC2(CC(O)C2)C1] | 149 | 431.4 | 1 | 6-(3-cyanopyrrolo[1,2-b]pyridazin-7-yl)-N-(6-hydroxyspiro[3.3]heptan-2-yl)-4-(isopropylamino)nicotinamide |
| 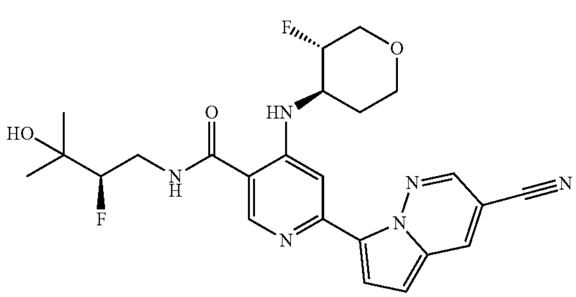 [SMILES: CC(C)(O)[C@H](F)CNC(=O)c1cnc(-c2ccc3cc(C#N)cnn23)cc1N[C@@H]1CCOC[C@H]1F] | 150 | 485.3 | 2 | 6-(3-cyanopyrrolo[1,2-b]pyridazin-7-yl)-N-((R)-2-fluoro-3-hydroxy-3-methylbutyl)-4-(((3S,4R)-3-fluorotetrahydro-2H-pyran-4-yl)amino)nicotinamide |

TABLE 1-continued

| Structure | compound | ES/MS m/z | procedure | Name |
|---|---|---|---|---|
| 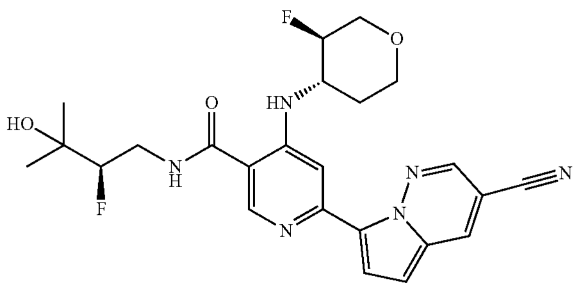 [SMILES: CC(C)(O)[C@H](F)CNC(=O)c1cnc(-c2ccc3cc(C#N)cnn23)cc1N[C@H]1CCOC[C@@H]1F] | 151 | 485.3 | 2 | 6-(3-cyanopyrrolo[1,2-b]pyridazin-7-yl)-N-((R)-2-fluoro-3-hydroxy-3-methylbutyl)-4-(((3R,4S)-3-fluorotetrahydro-2H-pyran-4-yl)amino)nicotinamide |
| 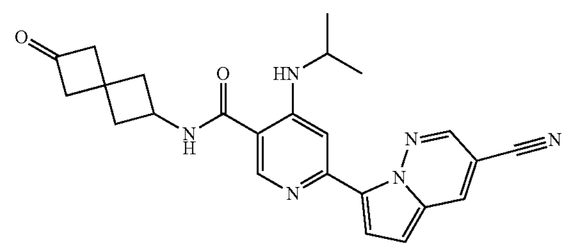 [SMILES: CC(C)Nc1cc(-c2ccc3cc(C#N)cnn23)ncc1C(=O)NC1CC2(CC(=O)C2)C1] | 152 | 429.3 | 19 | 6-(3-cyanopyrrolo[1,2-b]pyridazin-7-yl)-4-(isopropylamino)-N-(6-oxospiro[3.3]heptan-2-yl)nicotinamide |
| 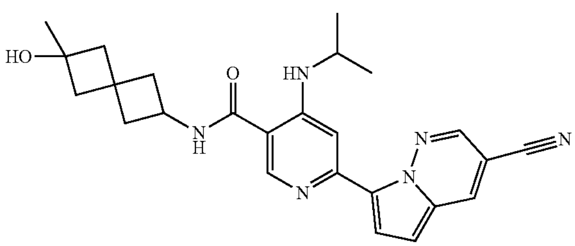 [SMILES: CC(C)Nc1cc(-c2ccc3cc(C#N)cnn23)ncc1C(=O)NC1CC2(C1)CC(C)(O)C2] | 153 | 445.3 | 20 | 6-(3-cyanopyrrolo[1,2-b]pyridazin-7-yl)-N-(6-hydroxy-6-methylspiro[3.3]heptan-2-yl)-4-(isopropylamino)nicotinamide |
| 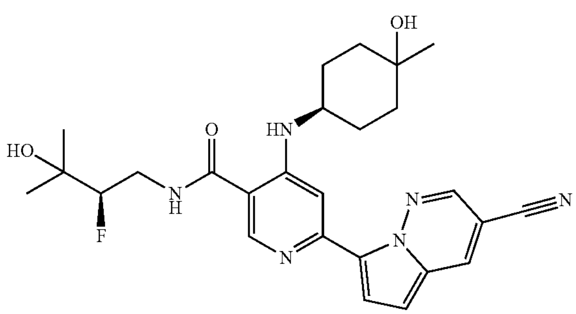 | 154 | 495.3 | 2 | 6-(3-cyanopyrrolo[1,2-b]pyridazin-7-yl)-N-((R)-2-fluoro-3-hydroxy-3-methylbutyl)-4-(((1s,4S)-4-hydroxy-4-methylcyclohexyl)amino)nicotinamide |
| 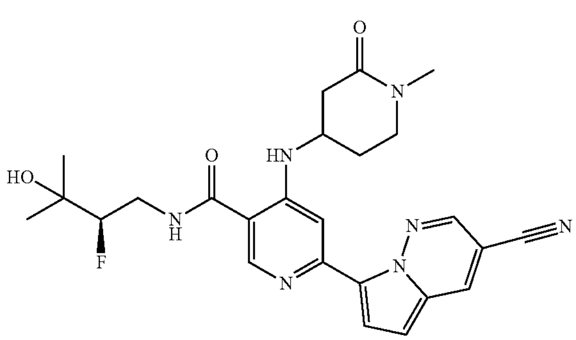 [SMILES: CN1CCC(Nc2cc(-c3ccc4cc(C#N)cnn34)ncc2C(=O)NC[C@@H](F)C(C)(C)O)CC1=O] | 155 | 494.3 | 2 | 6-(3-cyanopyrrolo[1,2-b]pyridazin-7-yl)-N-((R)-2-fluoro-3-hydroxy-3-methylbutyl)-4-((1-methyl-2-oxopiperidin-4-yl)amino)nicotinamide |

TABLE 1-continued

| Structure | compound | ES/MS m/z | procedure | Name |
|---|---|---|---|---|
| 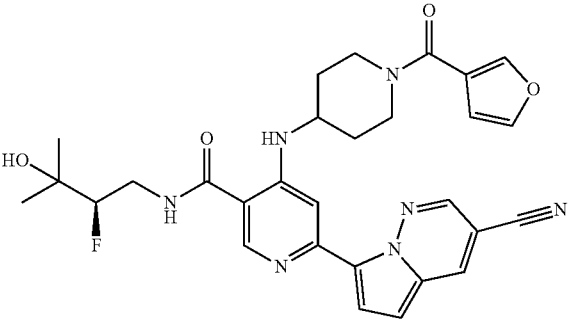 [SMILES: CC(C)(O)[C@H](F)CNC(=O)c1cnc(-c2ccc3cc(C#N)cnn23)cc1NC1CCN(C(=O)c2ccoc2)CC1] | 156 | 560.3 | 2 | (R)-6-(3-cyanopyrrolo[1,2-b]pyridazin-7-yl)-N-(2-fluoro-3-hydroxy-3-methylbutyl)-4-((1-(furan-3-carbonyl)piperidin-4-yl)amino)nicotinamide |
| 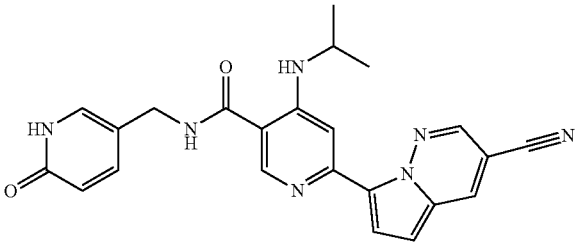 [SMILES: CC(C)Nc1cc(-c2ccc3cc(C#N)cnn23)ncc1C(=O)NCc1ccc(=O)[nH]c1] | 157 | 428.2 | 3 | 6-(3-cyanopyrrolo[1,2-b]pyridazin-7-yl)-4-(isopropylamino)-N-((6-oxo-1,6-dihydropyridin-3-yl)methyl)nicotinamide |
| 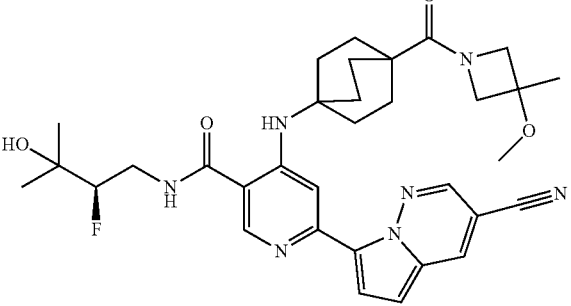 | 158 | 619.1 | 51 | (R)-6-(3-cyanopyrrolo[1,2-b]pyridazin 7-yl)-N-(2-fluoro-3-hydroxy-3-methylbutyl)-4-((4-(3-methoxy-3-methylazetidine-1-carbonyl)bicyclo[2.2.2]octan-1-yl)amino)nicotinamide |
| 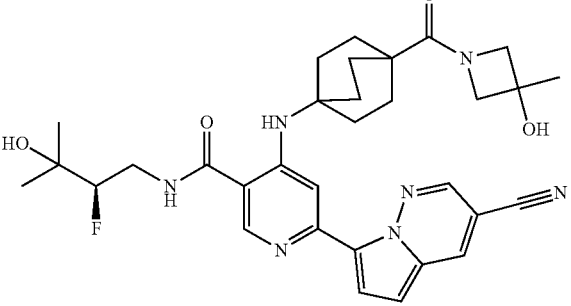 | 159 | 604.7 | 51 | (R)-6-(3-cyanopyrrolo[1,2-b]pyridazin-7-yl)-N-(2-fluoro-3-hydroxy-3-methylbutyl)-4-((4-(3-hydroxy-3-methylazetidine-1-carbonyl)bicyclo[2.2.2]octan-1-yl)amino)nicotinamide |
| 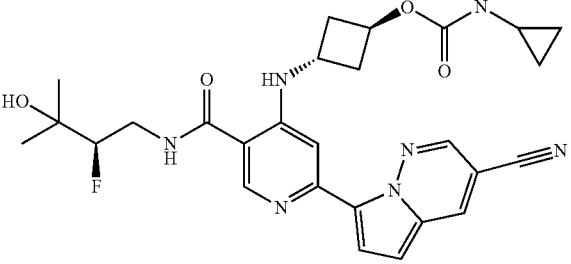 | 160 | 536.1 | 56 | (1R,3r)-3-((2-(3-cyanopyrrolo[1,2-b]pyridazin-7-yl)-5-(((R)-2-fluoro-3-hydroxy-3-methylbutyl)carbamoyl)pyridin-4-yl)amino)cyclobutyl cyclopropylcarbamate |

TABLE 1-continued

| Structure | compound | ES/MS m/z | procedure | Name |
|---|---|---|---|---|
| 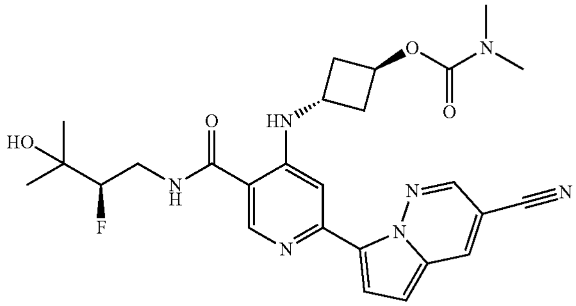 [SMILES: CN(C)C(=O)O[C@H]1C[C@H](Nc2cc(-c3ccc4cc(C#N)cnn34)ncc2C(=O)NC[C@@H](F)C(C)(C)O)C1] | 161 | 524.1 | 56 | (1R,3r)-3-((2-(3-cyano-pyrrolo[1,2-b]pyridazin-7-yl)-5-(((R)-2-fluoro-3-hydroxy-3-methylbutyl)carbamoyl)pyridin-4-yl)amino)cyclobutyl dimethylcarbamate |
| 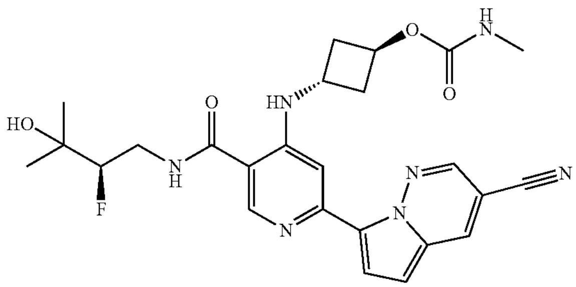 [SMILES: CNC(=O)O[C@H]1C[C@H](Nc2cc(-c3ccc4cc(C#N)cnn34)ncc2C(=O)NC[C@@H](F)C(C)(C)O)C1] | 162 | 510.2 | 56 | (1R,3r)-3-((2-(3-cyano-pyrrolo[1,2-b]pyridazin-7-yl)-5-(((R)-2-fluoro-3-hydroxy-3-methylbutyl)carbamoyl)pyridin-4-yl)amino)cyclobutyl methylcarbamate |
| 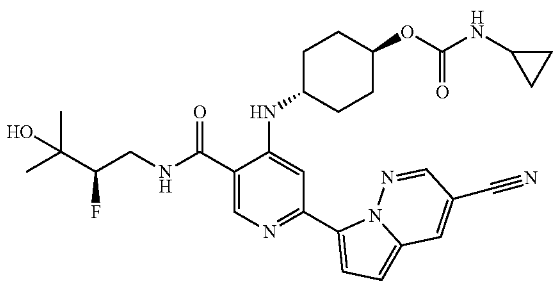 [SMILES: CC(C)(O)[C@H](F)CNC(=O)c1cnc(-c2ccc3cc(C#N)cnn23)cc1N[C@H]1CC[C@H](OC(=O)NC2CC2)CC1] | 163 | 564.1 | 56 | (1R,4r)-4-((2-(3-cyano-pyrrolo[1,2-b]pyridazin-7-yl)-5-(((R)-2-fluoro-3-hydroxy-3-methylbutyl)carbamoyl)pyridin-4-yl)amino)cyclohexyl cyclopropylcarbamate |
| 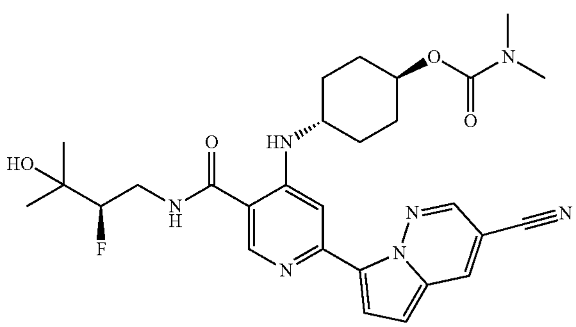 [SMILES: CN(C)C(=O)O[C@H]1CC[C@H](Nc2cc(-c3ccc4cc(C#N)cnn34)ncc2C(=O)NC[C@@H](F)C(C)(C)O)CC1] | 164 | 552.2 | 56 | (1R,4r)-4-((2-(3-cyano-pyrrolo[1,2-b]pyridazin-7-yl)-5-(((R)-2-fluoro-3-hydroxy-3-methylbutyl)carbamoyl)pyridin-4-yl)amino)cyclohexyl dimethylcarbamate |
| 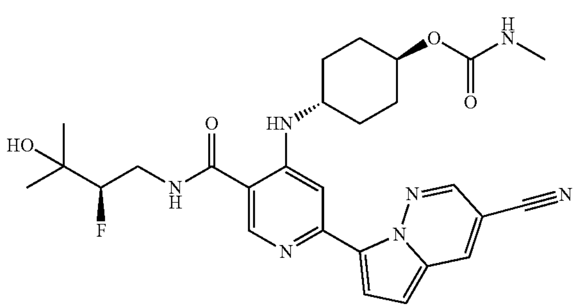 [SMILES: CNC(=O)O[C@H]1CC[C@H](Nc2cc(-c3ccc4cc(C#N)cnn34)ncc2C(=O)NC[C@@H](F)C(C)(C)O)CC1] | 165 | 538.1 | 56 | (1R,4r)-4-((2-(3-cyano-pyrrolo[1,2-b]pyridazin-7-yl)-5-(((R)-2-fluoro-3-hydroxy-3-methylbutyl)carbamoyl)pyridin-4-yl)amino)cyclohexyl methylcarbamate |

TABLE 1-continued

| Structure | compound | ES/MS m/z | procedure | Name |
|---|---|---|---|---|
| 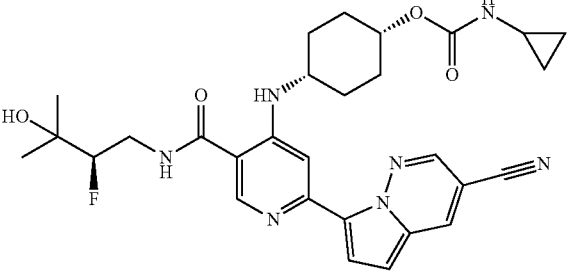 | 166 | 564.3 | 56 | (1S,4s)-4-((2-(3-cyano-pyrrolo[1,2-b]pyridazin-7-yl)-5-(((R)-2-fluoro-3-hydroxy-3-methylbutyl)carbamoyl)pyridin-4-yl)amino)cyclohexyl cyclopropylcarbamate |
| 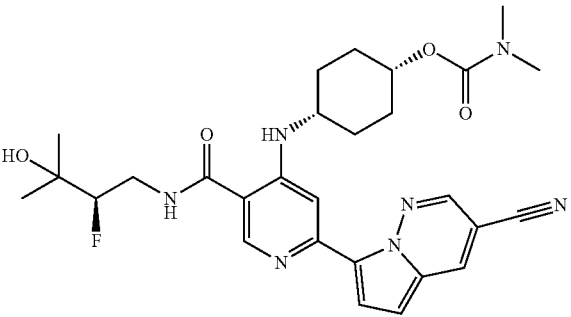 [SMILES: CN(C)C(=O)O[C@H]1CC[C@@H](Nc2cc(-c3ccc4cc(C#N)cnn34)ncc2C(=O)NC[C@@H](F)C(C)(C)O)CC1] | 167 | 552.2 | 56 | (1S,4s)-4-((2-(3-cyano-pyrrolo[1,2-b]pyridazin-7-yl)-5-(((R)-2-fluoro-3-hydroxy-3-methylbutyl)carbamoyl)pyridin-4-yl)amino)cyclohexyl dimethylcarbamate |
| 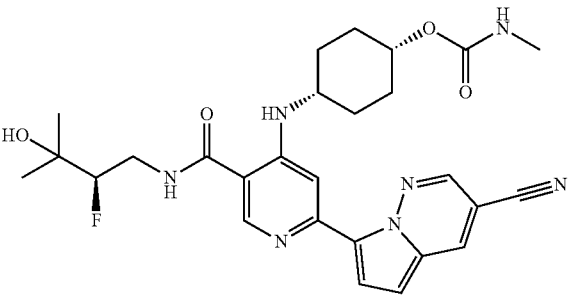 [SMILES: CNC(=O)O[C@H]1CC[C@@H](Nc2cc(-c3ccc4cc(C#N)cnn34)ncc2C(=O)NC[C@@H](F)C(C)(C)O)CC1] | 168 | 538.2 | 56 | (1S,4s)-4-((2-(3-cyano-pyrrolo[1,2-b]pyridazin-7-yl)-5-(((R)-2-fluoro-3-hydroxy-3-methylbutyl)carbamoyl)pyridin-4-yl)amino)cyclohexyl methylcarbamate |
| 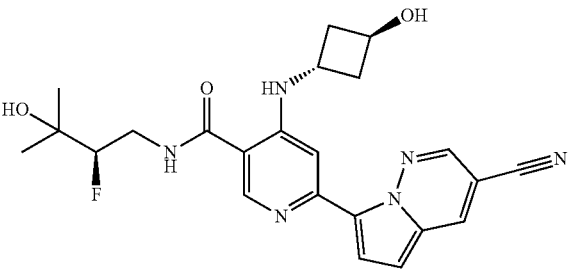 [SMILES: CC(C)(O)[C@H](F)CNC(=O)c1cnc(-c2ccc3cc(C#N)cnn23)cc1N[C@H]1C[C@H](O)C1] | 169 | 453.1 | 27 | 6-(3-cyanopyrrolo[1,2-b]pyridazin-7-yl)-N-((R)-2-fluoro-3-hydroxy-3-methylbutyl)-4-((((1r,3R)-3-hydroxycyclobutyl)amino)nicotinamide |
| 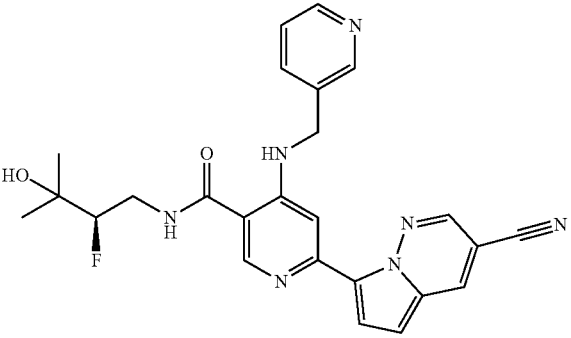 [SMILES: CC(C)(O)[C@H](F)CNC(=O)c1cnc(-c2ccc3cc(C#N)cnn23)cc1NCc1cccnc1] | 170 | 474.6 | 27 | (R)-6-(3-cyanopyrrolo[1,2-b]pyridazin-7-yl)-N-(2-fluoro-3-hydroxy-3-methylbutyl)-4-((pyridin-3-ylmethyl)amino)nicotinamide |

TABLE 1-continued

| Structure | compound | ES/MS m/z | procedure | Name |
|---|---|---|---|---|
| 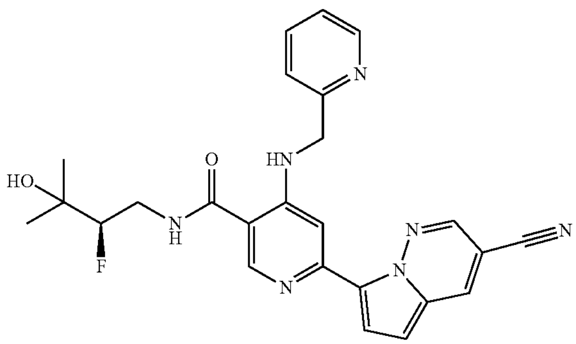 [SMILES: CC(C)(O)[C@H](F)CNC(=O)c1cnc(-c2ccc3cc(C#N)cnn23)cc1NCc1ccccn1] | 171 | 474.5 | 27 | (R)-6-(3-cyanopyrrolo[1,2-b]pyridazin-7-yl)-N-(2-fluoro-3-hydroxy-3-methylbutyl)-4-((pyridin-2-ylmethyl)amino)nicotinamide |
| 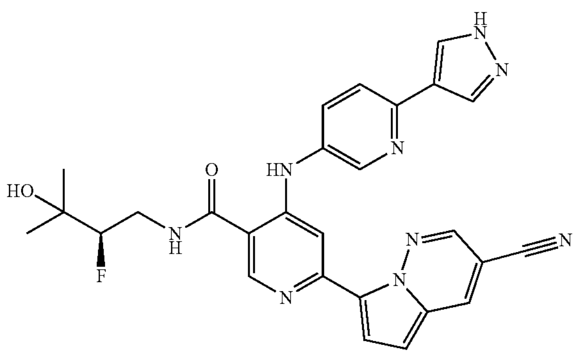 [SMILES: CC(C)(O)[C@H](F)CNC(=O)c1cnc(-c2ccc3cc(C#N)cnn23)cc1Nc1ccc(-c2cn[nH]c2)nc1] | 172 | 526.4 | 2 | (R)-4-((6-(1H-pyrazol-4-yl)pyridin-3-yl)amino)-6-(3-cyanopyrrolo[1,2-b]pyridazin-7-yl)-N-(2-fluoro-3-hydroxy-3-methylbutyl)nicotinamide |
| 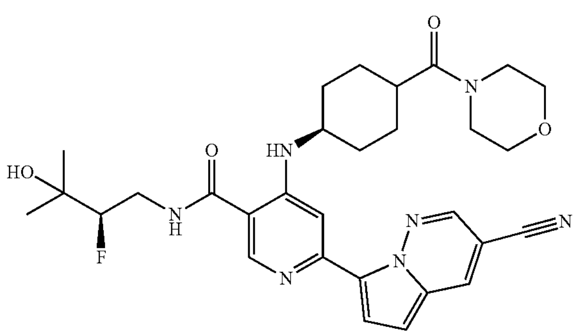 | 173 | 578.3 | 51 | 6-(3-cyanopyrrolo[1,2-b]pyridazin-7-yl)-N-((R)-2-fluoro-3-hydroxy-3-methylbutyl)-4-(((1r,4R)-4-(morpholine-4-carbonyl)cyclohexyl)amino)nicotinamide |
| 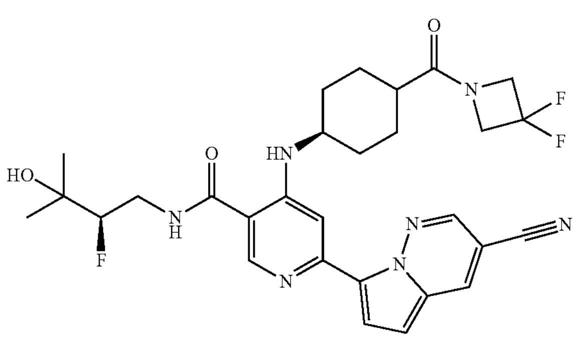 | 174 | 419.4 | 51 | 6-(3-cyanopyrrolo[1,2-b]pyridazin-7-yl)-4-(((1r,4R)-4-(3,3-difluoroazetidine-1-carbonyl)cyclohexyl)amino)-N-((R)-2-fluoro-3-hydroxy-3-methylbutyl)nicotinamide |

TABLE 1-continued

| Structure | compound | ES/MS m/z | procedure | Name |
|---|---|---|---|---|
| 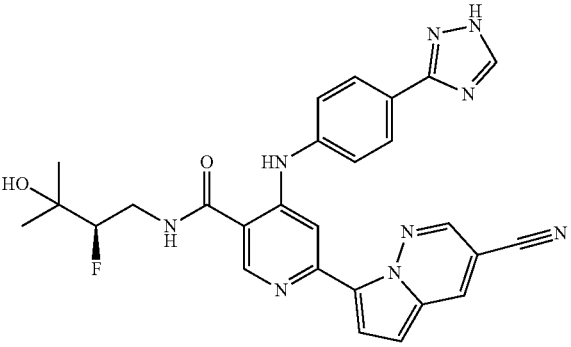 [SMILES: CC(C)(O)[C@H](F)CNC(=O)c1cnc(-c2ccc3cc(C#N)cnn23)cc1Nc1ccc(-c2nc[nH]n2)cc1] | 175 | 526.2 | 2 | (R)-4-((4-(1H-1,2,4-triazol-3-yl)phenyl)amino)-6-(3-cyanopyrrolo[1,2-b]pyridazin-7-yl)-N-(2-fluoro-3-hydroxy-3-methylbutyl)nicotinamide |
| 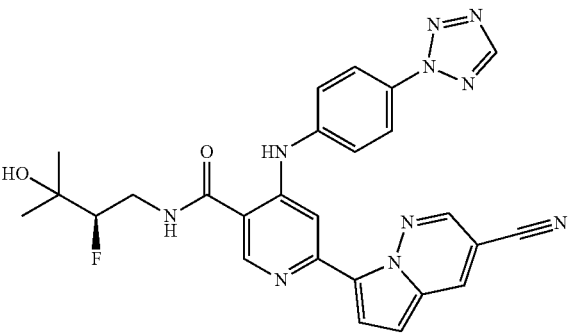 [SMILES: CC(C)(O)[C@H](F)CNC(=O)c1cnc(-c2ccc3cc(C#N)cnn23)cc1Nc1ccc(-n2ncnn2)cc1] | 176 | 527 | 27 | (R)-4-((4-(2H-tetrazol-2-yl)phenyl)amino)-6-(3-cyanopyrrolo[1,2-b]pyridazin-7-yl)-N-(2-fluoro-3-hydroxy-3-methylbutyl)nicotinamide |
| 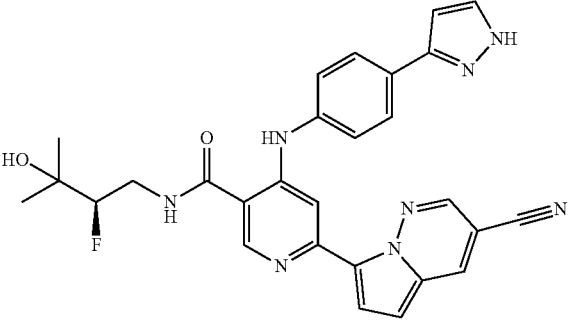 [SMILES: CC(C)(O)[C@H](F)CNC(=O)c1cnc(-c2ccc3cc(C#N)cnn23)cc1Nc1ccc(-c2cc[nH]n2)cc1] | 177 | 525.4 | 2 | (R)-4-((4-(1H-pyrazol-3-yl)phenyl)amino)-6-(3-cyanopyrrolo[1,2-b]pyridazin-7-yl)-N-(2-fluoro-3-hydroxy-3-methylbutyl)nicotinamide |
| 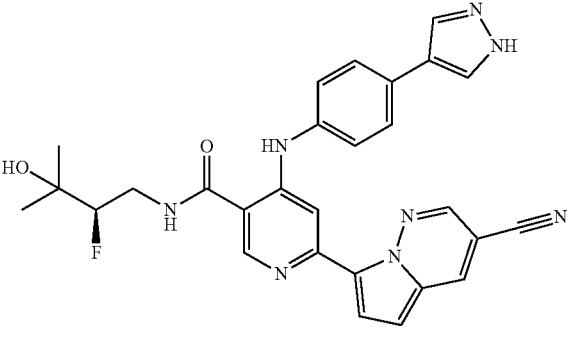 [SMILES: CC(C)(O)[C@H](F)CNC(=O)c1cnc(-c2ccc3cc(C#N)cnn23)cc1Nc1ccc(-c2cn[nH]c2)cc1] | 178 | 525.3 | 2 | (R)-4-((4-(1H-pyrazol-4-yl)phenyl)amino)-6-(3-cyanopyrrolo[1,2-b]pyridazin-7-yl)-N-(2-fluoro-3-hydroxy-3-methylbutyl)nicotinamide |

TABLE 1-continued

| Structure | compound | ES/MS m/z | procedure | Name |
|---|---|---|---|---|
| 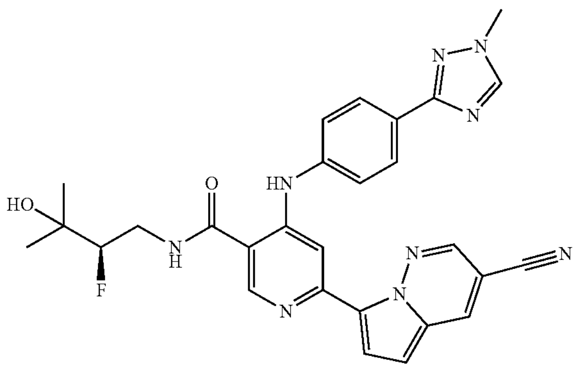 [SMILES: Cn1cnc(-c2ccc(Nc3cc(-c4ccc5cc(C#N)cnn45)ncc3C(=O)NC[C@@H](F)C(C)(C)O)cc2)n1] | 179 | 540.2 | 27 | (R)-6-(3-cyanopyrrolo[1,2-b]pyridazin-7-yl)-N-(2-fluoro-3-hydroxy-3-methylbutyl)-4-((4-(1-methyl-1H-1,2,4-triazol-3-yl)phenyl)amino)nicotinamide |
| 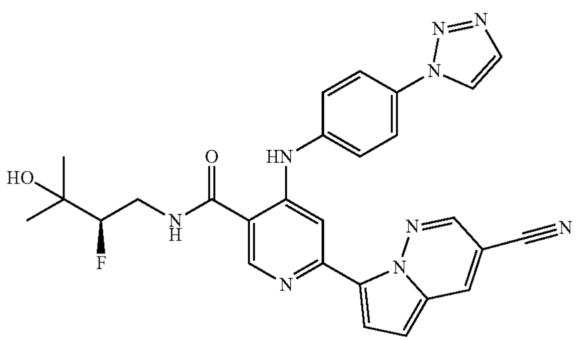 [SMILES: CC(C)(O)[C@H](F)CNC(=O)c1cnc(-c2ccc3cc(C#N)cnn23)cc1Nc1ccc(-n2ccnn2)cc1] | 180 | 526.1 | 27 | (R)-4-((4-(1H-1,2,3-triazol-1-yl)phenyl)amino)-6-(3-cyanopyrrolo[1,2-b]pyridazin-7-yl)-N-(2-fluoro-3-hydroxy-3-methylbutyl)nicotinamide |
| 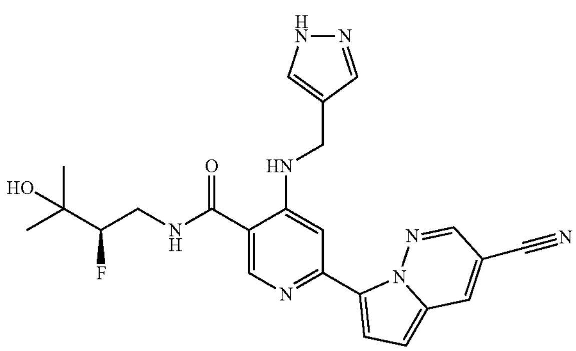 [SMILES: CC(C)(O)[C@H](F)CNC(=O)c1cnc(-c2ccc3cc(C#N)cnn23)cc1NCc1cn[nH]c1] | 181 | 462.9 | 27 | (R)-4-(((1H-pyrazol-4-yl)methyl)amino)-6-(3-cyanopyrrolo[1,2-b]pyridazin-7-yl)-N-(2-fluoro-3-hydroxy-3-methylbutyl)nicotinamide |
| 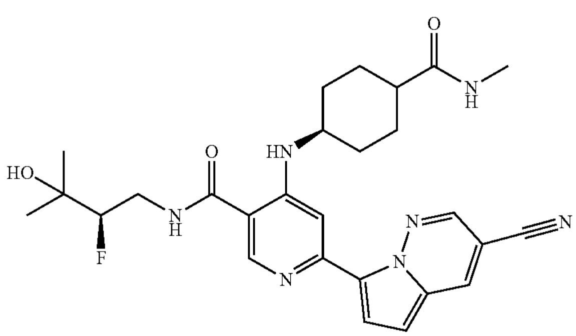 | 182 | 522.2 | 27 | 6-(3-cyanopyrrolo[1,2-b]pyridazin-7-yl)-N-((R)-2-fluoro-3-hydroxy-3-methylbutyl)-4-(((1r,4R)-4-(methylcarbamoyl)cyclohexyl)amino)nicotinamide |

TABLE 1-continued

| Structure | compound | ES/MS m/z | procedure | Name |
|---|---|---|---|---|
| 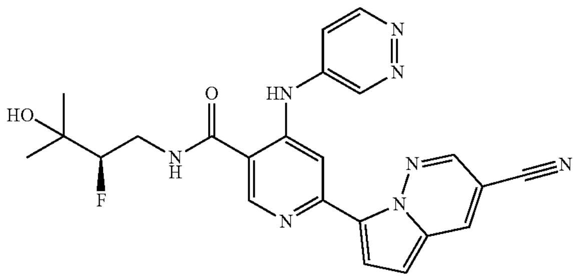 [SMILES: CC(C)(O)[C@H](F)CNC(=O)c1cnc(-c2ccc3cc(C#N)cnn23)cc1Nc1ccnnc1] | 183 | 461.1 | 27 | (R)-6-(3-cyanopyrrolo[1,2-b]pyridazin-7-yl)-N-(2-fluoro-3-hydroxy-3-methylbutyl)-4-(pyridazin-4-ylamino)nicotinamide |
| 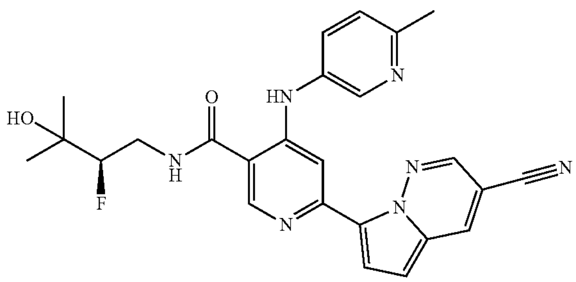 [SMILES: Cc1ccc(Nc2cc(-c3ccc4cc(C#N)cnn34)ncc2C(=O)NC[C@@H](F)C(C)(C)O)cn1] | 184 | 474.3 | 27 | (R)-6-(3-cyanopyrrolo[1,2-b]pyridazin-7-yl)-N-(2-fluoro-3-hydroxy-3-methylbutyl)-4-((6-methylpyridin-3-yl)amino)nicotinamide |
| 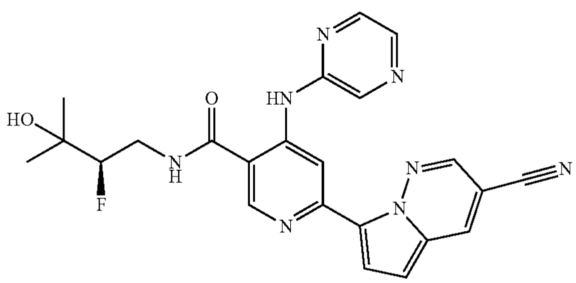 [SMILES: CC(C)(O)[C@H](F)CNC(=O)c1cnc(-c2ccc3cc(C#N)cnn23)cc1Nc1cnccn1] | 185 | 461.2 | 27 | (R)-6-(3-cyanopyrrolo[1,2-b]pyridazin-7-yl)-N-(2-fluoro-3-hydroxy-3-methylbutyl)-4-(pyrazin-2-ylamino)nicotinamide |
| 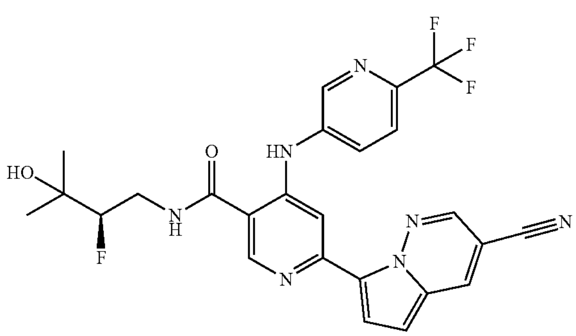 [SMILES: CC(C)(O)[C@H](F)CNC(=O)c1cnc(-c2ccc3cc(C#N)cnn23)cc1Nc1ccc(C(F)(F)F)nc1] | 186 | 528.3 | 27 | (R)-6-(3-cyanopyrrolo[1,2-b]pyridazin-7-yl)-N-(2-fluoro-3-hydroxy-3-methylbutyl)-4-((6-(trifluoromethyl)pyridin-3-yl)amino)nicotinamide |
| 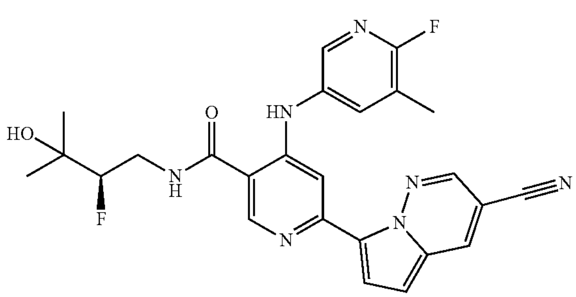 [SMILES: Cc1cc(Nc2cc(-c3ccc4cc(C#N)cnn34)ncc2C(=O)NC[C@@H](F)C(C)(C)O)cnc1F] | 187 | 492.2 | 27 | (R)-6-(3-cyanopyrrolo[1,2-b]pyridazin-7-yl)-N-(2-fluoro-3-hydroxy-3-methylbutyl)-4-((6-fluoro-5-methylpyridin-3-yl)amino)nicotinamide |

TABLE 1-continued

| Structure | compound | ES/MS m/z | procedure | Name |
|---|---|---|---|---|
| 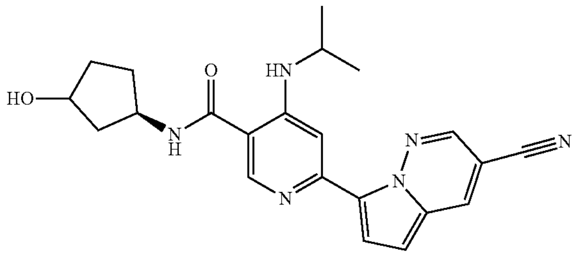 [SMILES: CC(C)Nc1cc(-c2ccc3cc(C#N)cnn23)ncc1C(=O)N[C@@H]1CCC(O)C1] | 188 | 405.3 | 43 | 6-(3-cyanopyrrolo[1,2-b]pyridazin-7-yl)-N-((1R,3R)-3-hydroxycyclopentyl)-4-(isopropylamino)nicotinamide |
| 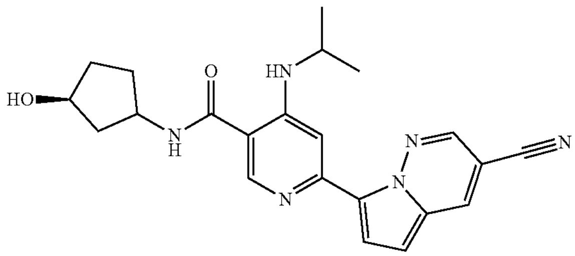 [SMILES: CC(C)Nc1cc(-c2ccc3cc(C#N)cnn23)ncc1C(=O)NC1CC[C@H](O)C1] | 189 | 405.3 | 43 | 6-(3-cyanopyrrolo[1,2-b]pyridazin-7-yl)-N-((1S,3S)-3-hydroxycyclopentyl)-4-(isopropylamino)nicotinamide |
| 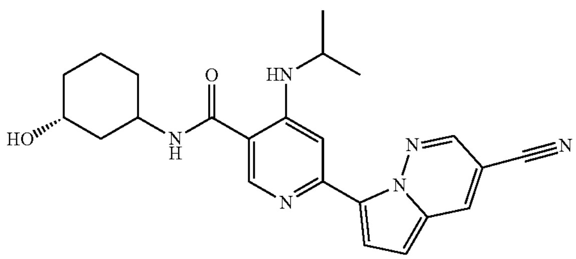 [SMILES: CC(C)Nc1cc(-c2ccc3cc(C#N)cnn23)ncc1C(=O)NC1CCC[C@@H](O)C1] | 190 | 419.4 | 1 | 6-(3-cyanopyrrolo[1,2-b]pyridazin-7-yl)-N-((1S,3R)-3-hydroxycyclohexyl)-4-(isopropylamino)nicotinamide |
| 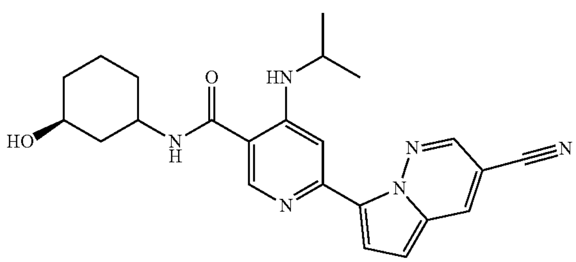 [SMILES: CC(C)Nc1cc(-c2ccc3cc(C#N)cnn23)ncc1C(=O)NC1CCC[C@H](O)C1] | 191 | 419.5 | 1 | 6-(3-cyanopyrrolo[1,2-b]pyridazin-7-yl)-N-((1S,3S)-3-hydroxycyclohexyl)-4-(isopropylamino)nicotinamide |
| 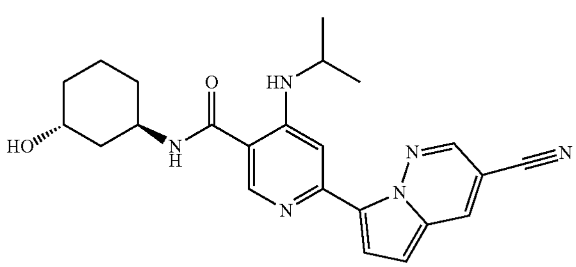 [SMILES: CC(C)Nc1cc(-c2ccc3cc(C#N)cnn23)ncc1C(=O)N[C@@H]1CCC[C@@H](O)C1] | 192 | 419.5 | 1 | 6-(3-cyanopyrrolo[1,2-b]pyridazin-7-yl)-N-((1R,3R)-3-hydroxycyclohexyl)-4-(isopropylamino)nicotinamide |
| 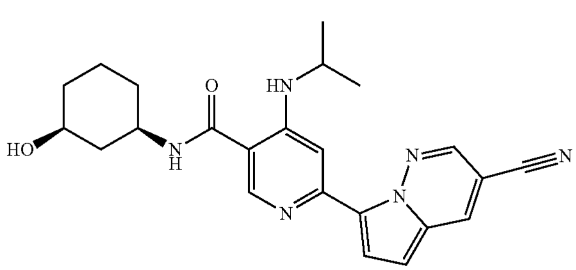 [SMILES: CC(C)Nc1cc(-c2ccc3cc(C#N)cnn23)ncc1C(=O)N[C@@H]1CCC[C@H](O)C1] | 193 | 419.4 | 1 | 6-(3-cyanopyrrolo[1,2-b]pyridazin-7-yl)-N-((1R,3S)-3-hydroxycyclohexyl)-4-(isopropylamino)nicotinamide |

TABLE 1-continued

| Structure | compound | ES/MS m/z | procedure | Name |
|---|---|---|---|---|
| 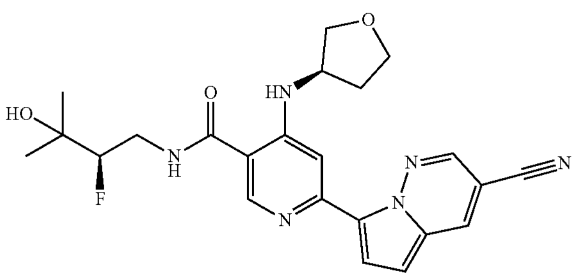 [SMILES: CC(C)(O)[C@H](F)CNC(=O)c1cnc(-c2ccc3cc(C#N)cnn23)cc1N[C@@H]1CCOC1] | 194 | 453.2 | 2 | 6-(3-cyanopyrrolo[1,2-b]pyridazin-7-yl)-N-((R)-2-fluoro-3-hydroxy-3-methylbutyl)-4-(((R)-tetrahydrofuran-3-yl)amino)nicotinamide |
| 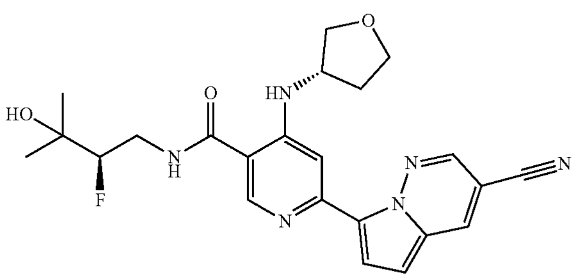 [SMILES: CC(C)(O)[C@H](F)CNC(=O)c1cnc(-c2ccc3cc(C#N)cnn23)cc1N[C@H]1CCOC1] | 195 | 453.2 | 2 | 6-(3-cyanopyrrolo[1,2-b]pyridazin-7-yl)-N-((R)-2-fluoro-3-hydroxy-3-methylbutyl)-4-(((S)-tetrahydrofuran-3-yl)amino)nicotinamide |
| 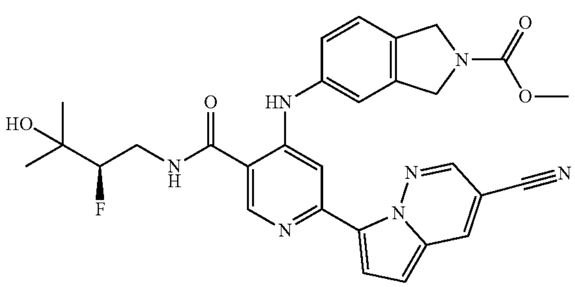 [SMILES: COC(=O)N1Cc2ccc(Nc3cc(-c4ccc5cc(C#N)cnn45)ncc3C(=O)NC[C@@H](F)C(C)(C)O)cc2C1] | 196 | 558.3 | 16 | (R)-methyl 5-((2-(3-cyanopyrrolo[1,2-b]pyridazin-7-yl)-5-((2-fluoro-3-hydroxy-3-methylbutyl)carbamoyl)pyridin-4-yl)amino)isoindoline-2-carboxylate |
| 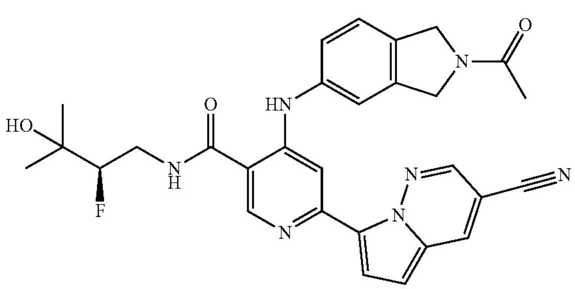 [SMILES: CC(=O)N1Cc2ccc(Nc3cc(-c4ccc5cc(C#N)cnn45)ncc3C(=O)NC[C@@H](F)C(C)(C)O)cc2C1] | 197 | 542.2 | 16 | (R)-4-((2-acetylisoindolin-5-yl)amino)-6-(3-cyanopyrrolo[1,2-b]pyridazin-7-yl)-N-(2-fluoro-3-hydroxy-3-methylbutyl)nicotinamide |
| 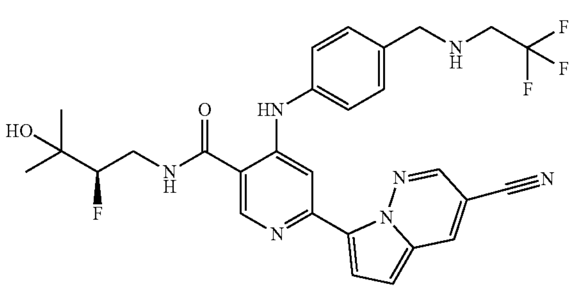 [SMILES: CC(C)(O)[C@H](F)CNC(=O)c1cnc(-c2ccc3cc(C#N)cnn23)cc1Nc1ccc(CNCC(F)(F)F)cc1] | 198 | 570.3 | 14 | (R)-6-(3-cyanopyrrolo[1,2-b]pyridazin-7-yl)-N-(2-fluoro-3-hydroxy-3-methylbutyl)-4-((4-(((2,2,2-trifluoroethyl)amino)methyl)phenyl)amino)nicotinamide |

TABLE 1-continued

| Structure | compound | ES/MS m/z | procedure | Name |
|---|---|---|---|---|
| 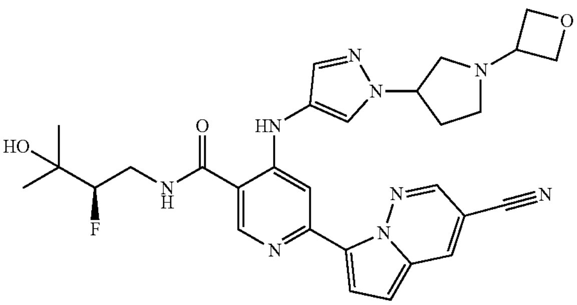 [SMILES: CC(C)(O)[C@H](F)CNC(=O)c1cnc(-c2ccc3cc(C#N)cnn23)cc1Nc1cnn(C2CCN(C3COC3)C2)c1] | 199 | 574.3 | 2 | 6-(3-cyanopyrrolo[1,2-b]pyridazin-7-yl)-N-((R)-2-fluoro-3-hydroxy-3-methylbutyl)-4-((1-((S)-1-(oxetan-3-yl)pyrrolidin-3-yl)-1H-pyrazol-4-yl)amino)nicotinamide |
| 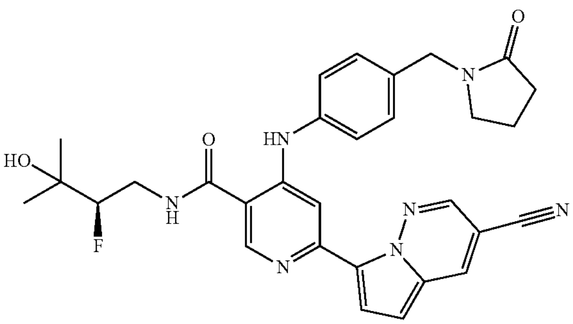 [SMILES: CC(C)(O)[C@H](F)CNC(=O)c1cnc(-c2ccc3cc(C#N)cnn23)cc1Nc1ccc(CN2CCCC2=O)cc1] | 200 | 556.3 | 2 | (R)-6-(3-cyanopyrrolo[1,2-b]pyridazin-7-yl)-N-(2-fluoro-3-hydroxy-3-methylbutyl)-4-((4-((2-oxopyrrolidin-1-yl)methyl)phenyl)amino)nicotinamide |
| 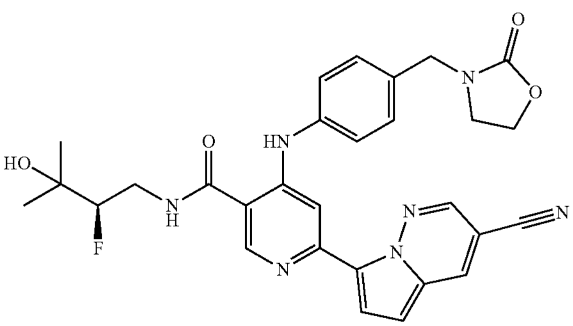 [SMILES: CC(C)(O)[C@H](F)CNC(=O)c1cnc(-c2ccc3cc(C#N)cnn23)cc1Nc1ccc(CN2CCOC2=O)cc1] | 201 | 558.2 | 2 | (R)-6-(3-cyanopyrrolo[1,2-b]pyridazin-7-yl)-N-(2-fluoro-3-hydroxy-3-methylbutyl)-4-((4-((2-oxooxazolidin-3-yl)methyl)phenyl)amino)nicotinamide |
| 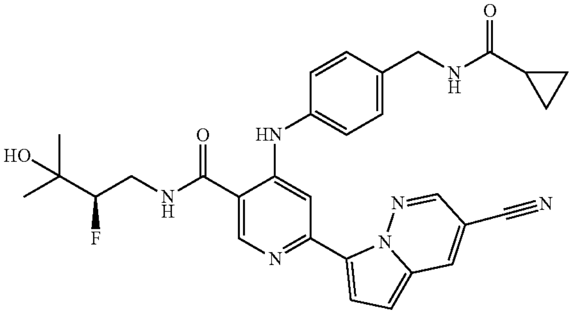 [SMILES: CC(C)(O)[C@H](F)CNC(=O)c1cnc(-c2ccc3cc(C#N)cnn23)cc1Nc1ccc(CNC(=O)C2CC2)cc1] | 202 | 556.3 | 16 | (R)-6-(3-cyanopyrrolo[1,2-b]pyridazin-7-yl)-4-((4-(cyclopropanecarboxamidomethyl)phenyl)amino)-N-(2-fluoro-3-hydroxy-3-methylbutyl)nicotinamide |

TABLE 1-continued

| Structure | compound | ES/MS m/z | procedure | Name |
|---|---|---|---|---|
| 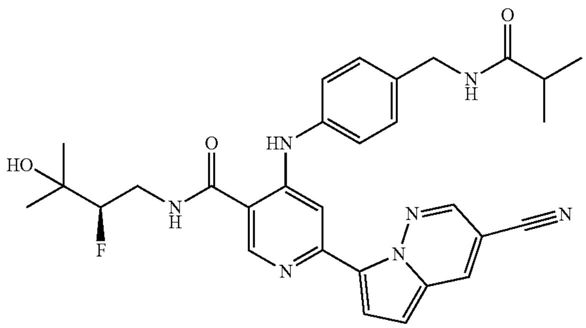 [SMILES: CC(C)C(=O)NCc1ccc(Nc2cc(-c3ccc4cc(C#N)cnn34)ncc2C(=O)NC[C@@H](F)C(C)(C)O)cc1] | 203 | 558.3 | 16 | (R)-6-(3-cyanopyrrolo[1,2-b]pyridazin-7-yl)-N-(2-fluoro-3-hydroxy-3-methylbutyl)-4-((4-(isobutyramidomethyl)phenyl)amino)nicotinamide |
| 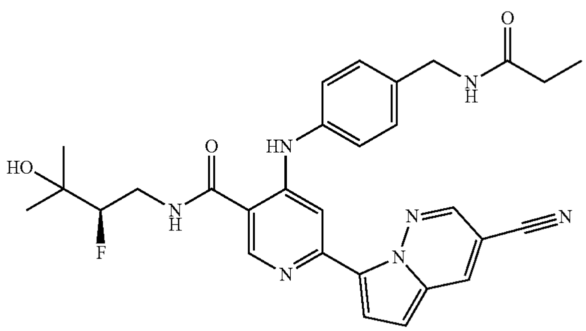 [SMILES: CCC(=O)NCc1ccc(Nc2cc(-c3ccc4cc(C#N)cnn34)ncc2C(=O)NC[C@@H](F)C(C)(C)O)cc1] | 204 | 544.3 | 16 | (R)-6-(3-cyanopyrrolo[1,2-b]pyridazin-7-yl)-N-(2-fluoro-3-hydroxy-3-methylbutyl)-4-((4-(propionamidomethyl)phenyl)amino)nicotinamide |
| 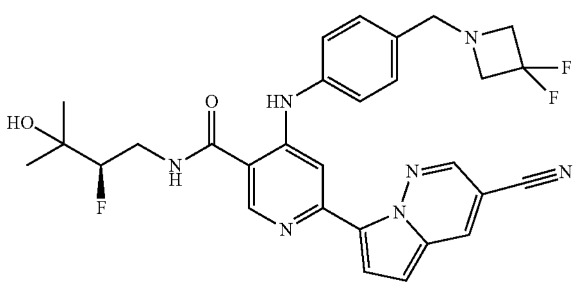 [SMILES: CC(C)(O)[C@H](F)CNC(=O)c1cnc(-c2ccc3cc(C#N)cnn23)cc1Nc1ccc(CN2CC(F)(F)C2)cc1] | 205 | 564.2 | 2 | (R)-6-(3-cyanopyrrolo[1,2-b]pyridazin-7-yl)-4-((4-((3,3-difluoroazetidin-1-yl)methyl)phenyl)amino)-N-(2-fluoro-3-hydroxy-3-methylbutyl)nicotinamide |
| 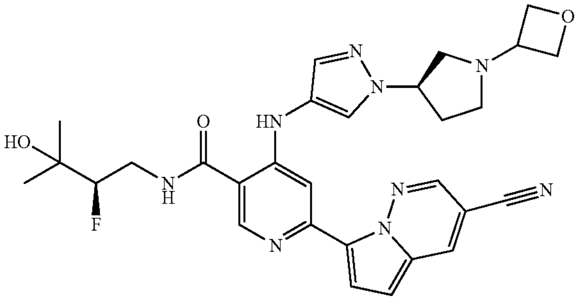 [SMILES: CC(C)(O)[C@H](F)CNC(=O)c1cnc(-c2ccc3cc(C#N)cnn23)cc1Nc1cnn([C@@H]2CCN(C3COC3)C2)c1] | 206 | 574.3 | 26 | 6-(3-cyanopyrrolo[1,2-b]pyridazin-7-yl)-N-((R)-2-fluoro-3-hydroxy-3-methylbutyl)-4-((1-((R)-1-(oxetan-3-yl)pyrrolidin-3-yl)-1H-pyrazol-4-yl)amino)nicotinamide |

TABLE 1-continued

| Structure | compound | ES/MS m/z | procedure | Name |
|---|---|---|---|---|
| 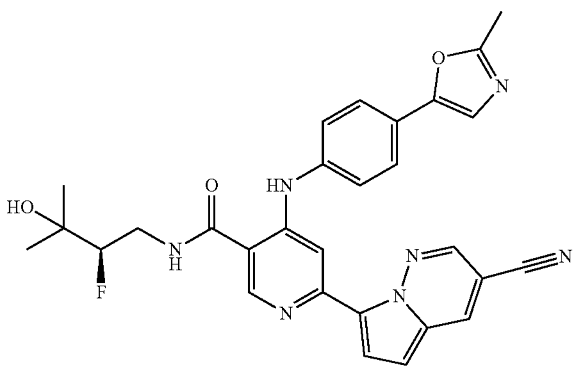 [SMILES: Cc1ncc(-c2ccc(Nc3cc(-c4ccc5cc(C#N)cnn45)ncc3C(=O)NC[C@@H](F)C(C)(C)O)cc2)o1] | 207 | 540.3 | 27 | (R)-6-(3-cyanopyrrolo[1,2-b]pyridazin-7-yl)-N-(2-fluoro-3-hydroxy-3-methylbutyl)-4-((4-(2-methyloxazol-5-yl)phenyl)amino)nicotinamide |
| 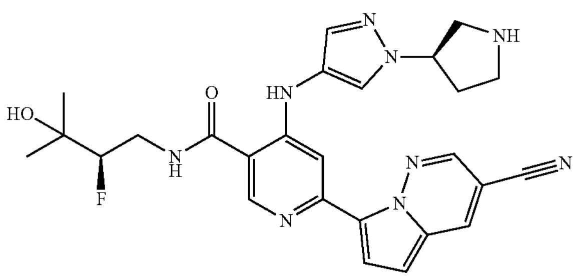 [SMILES: CC(C)(O)[C@H](F)CNC(=O)c1cnc(-c2ccc3cc(C#N)cnn23)cc1Nc1cnn([C@@H]2CCNC2)c1] | 208 | 518.2 | 14 | 6-(3-cyanopyrrolo[1,2-b]pyridazin-7-yl)-N-((R)-2-fluoro-3-hydroxy-3-methylbutyl)-4-((1-((R)-pyrrolidin-3-yl)-1H-pyrazol-4-yl)amino)nicotinamide |
| 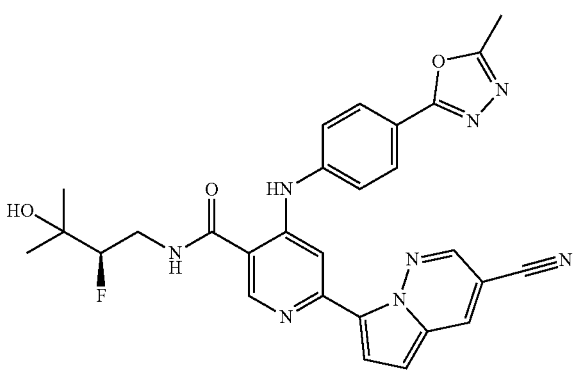 [SMILES: Cc1nnc(-c2ccc(Nc3cc(-c4ccc5cc(C#N)cnn45)ncc3C(=O)NC[C@@H](F)C(C)(C)O)cc2)o1] | 209 | 541.3 | 27 | (R)-6-(3-cyanopyrrolo[1,2-b]pyridazin-7-yl)-N-(2-fluoro-3-hydroxy-3-methylbutyl)-4-((4-(5-methyl-1,3,4-oxadiazol-2-yl)phenyl)amino)nicotinamide |
| 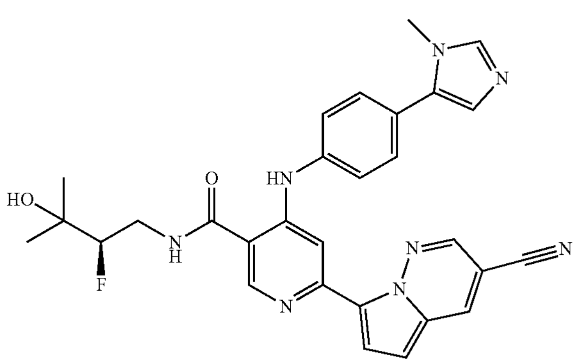 [SMILES: Cn1cncc1-c1ccc(Nc2cc(-c3ccc4cc(C#N)cnn34)ncc2C(=O)NC[C@@H](F)C(C)(C)O)cc1] | 210 | 539.2 | 2 | (R)-6-(3-cyanopyrrolo[1,2-b]pyridazin-7-yl)-N-(2-fluoro-3-hydroxy-3-methylbutyl)-4-((4-(1-methyl-1H-imidazol-5-yl)phenyl)amino)nicotinamide |

TABLE 1-continued

| Structure | compound | ES/MS m/z | procedure | Name |
|---|---|---|---|---|
| 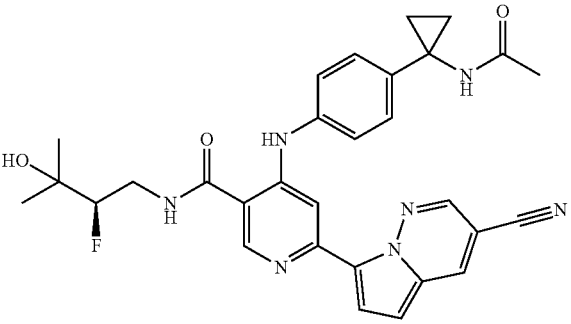 [SMILES: CC(=O)NC1(c2ccc(Nc3cc(-c4ccc5cc(C#N)cnn45)ncc3C(=O)NC[C@@H](F)C(C)(C)O)cc2)CC1] | 211 | 556.2 | 2 | (R)-4-((4-(1-acetamidocyclopropyl)phenyl)amino)-6-(3-cyanopyrrolo[1,2-b]pyridazin-7-yl)-N-(2-fluoro-3-hydroxy-3-methylbutyl)nicotinamide |
| 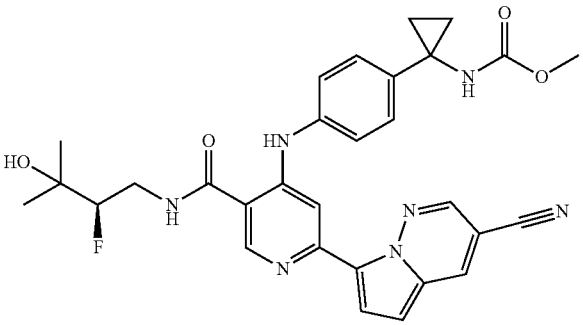 [SMILES: COC(=O)NC1(c2ccc(Nc3cc(-c4ccc5cc(C#N)cnn45)ncc3C(=O)NC[C@@H](F)C(C)(C)O)cc2)CC1] | 212 | 572.3 | 2 | (R)-methyl (1-(4-((2-(3-cyanopyrrolo[1,2-b]pyridazin-7-yl)-5-((2-fluoro-3-hydroxy-3-methylbutyl)carbamoyl)pyridin-4-yl)amino)phenyl)cyclopropyl)carbamate |
| 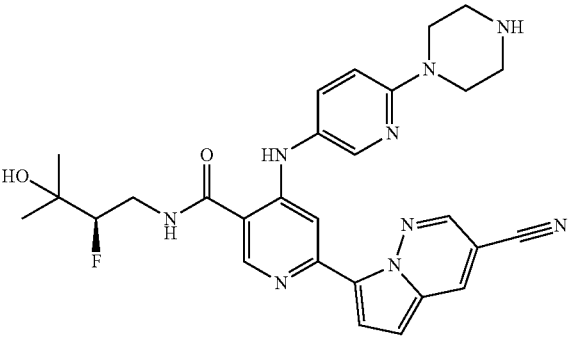 | 213 | 544.3 | 14 | (R)-6-(3-cyanopyrrolo[1,2-b]pyridazin-7-yl)-N-(2-fluoro-3-hydroxy-3-methylbutyl)-4-((6-(piperazin-1-yl)pyridin-3-yl)amino)nicotinamide |
| 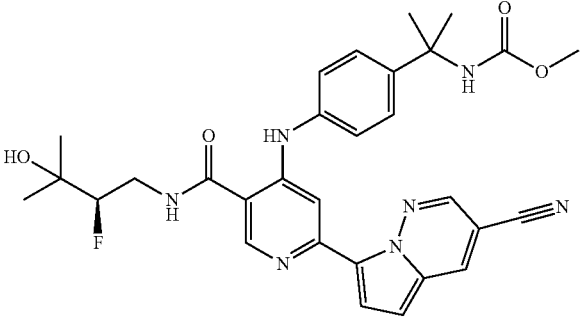 [SMILES: COC(=O)NC(C)(C)c1ccc(Nc2cc(-c3ccc4cc(C#N)cnn34)ncc2C(=O)NC[C@@H](F)C(C)(C)O)cc1] | 214 | 574.3 | 2 | (R)-methyl(2-(4-((2-(3-cyanopyrrolo[1,2-b]pyridazin-7-yl)-5-((2-fluoro-3-hydroxy-3-methylbutyl)carbamoyl)pyridin-4-yl)amino)phenyl)propan-2-yl)carbamate |

TABLE 1-continued

| Structure | compound | ES/MS m/z | procedure | Name |
|---|---|---|---|---|
| 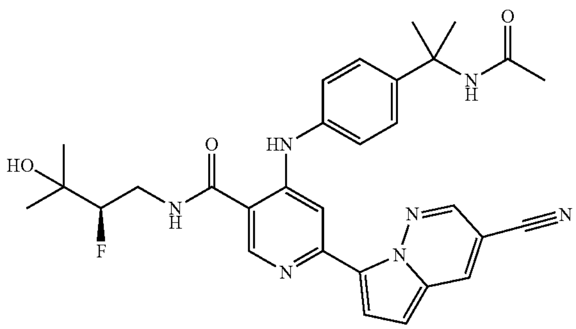 [SMILES: CC(=O)NC(C)(C)c1ccc(Nc2cc(-c3ccc4cc(C#N)cnn34)ncc2C(=O)NC[C@@H](F)C(C)(C)O)cc1] | 215 | 558.2 | 2 | (R)-4-((4-(2-acetamidopropan-2-yl)phenyl)amino)-6-(3-cyanopyrrolo[1,2-b]pyridazin-7-yl)-N-(2-fluoro-3-hydroxy-3-methylbutyl)nicotinamide |
| 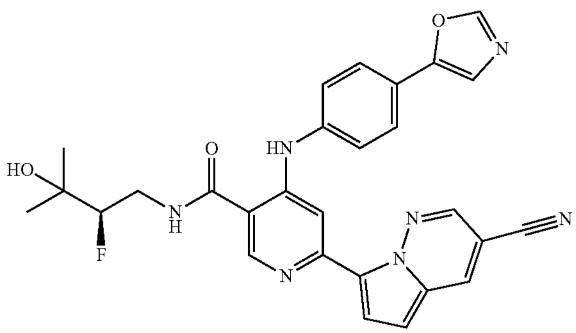 [SMILES: CC(C)(O)[C@H](F)CNC(=O)c1cnc(-c2ccc3cc(C#N)cnn23)cc1Nc1ccc(-c2cnco2)cc1] | 216 | 526.2 | 27 | (R)-6-(3-cyanopyrrolo[1,2-b]pyridazin-7-yl)-N-(2-fluoro-3-hydroxy-3-methylbutyl)-4-((4-(oxazol-5-yl)phenyl)amino)nicotinamide |
| 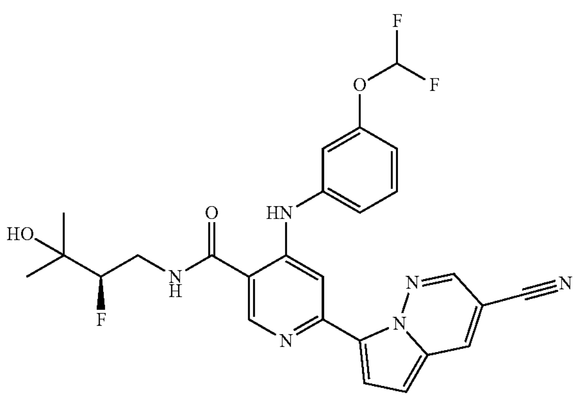 [SMILES: CC(C)(O)[C@H](F)CNC(=O)c1cnc(-c2ccc3cc(C#N)cnn23)cc1Nc1cccc(OC(F)F)c1] | 217 | 526.2 | 27 | (R)-6-(3-cyanopyrrolo[1,2-b]pyridazin-7-yl)-4-((5-(difluoromethoxy)pyridin-3-yl)amino)-N-(2-fluoro-3-hydroxy-3-methylbutyl)nicotinamide |
| 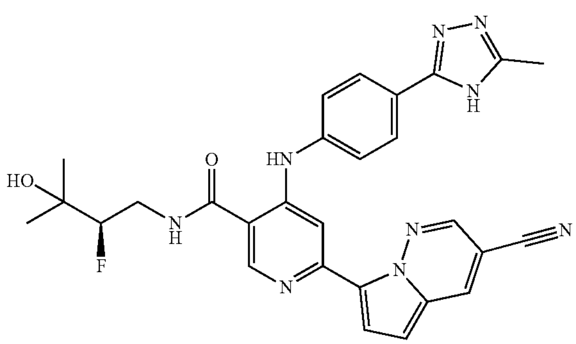 [SMILES: Cc1nnc(-c2ccc(Nc3cc(-c4ccc5cc(C#N)cnn45)ncc3C(=O)NC[C@@H](F)C(C)(C)O)cc2)[nH]1] | 218 | 540.3 | 2 | (R)-6-(3-cyanopyrrolo[1,2-b]pyridazin-7-yl)-N-(2-fluoro-3-hydroxy-3-methylbutyl)-4-((4-(5-methyl-4H-1,2,4-triazol-3-yl)phenyl)amino)nicotinamide |

TABLE 1-continued

| Structure | compound | ES/MS m/z | procedure | Name |
|---|---|---|---|---|
| 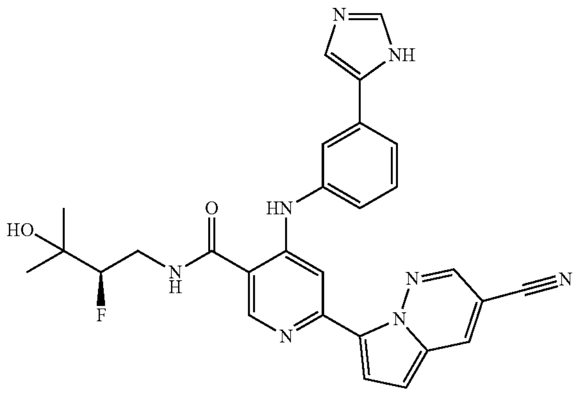 [SMILES: CC(C)(O)[C@H](F)CNC(=O)c1cnc(-c2ccc3cc(C#N)cnn23)cc1Nc1cccc(-c2cnc[nH]2)c1] | 219 | 525.2 | 2 | (R)-4-((3-(1H-imidazol-5-yl)phenyl)amino)-6-(3-cyanopyrrolo[1,2-b]pyridazin-7-yl)-N-(2-fluoro-3-hydroxy-3-methylbutyl)nicotinamide |
| 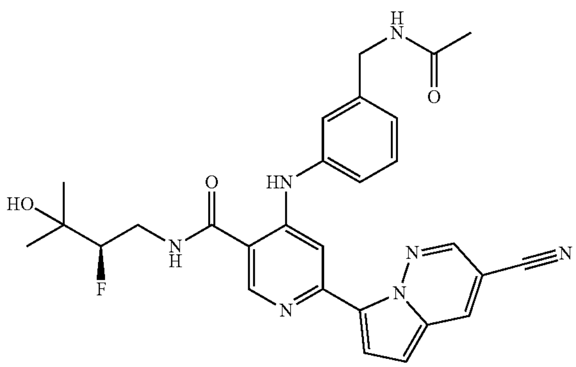 | 220 | 525.1 | 2 | (R)-4-((3-(acetamidomethyl)phenyl)amino)-6-(3-cyanopyrrolo[1,2-b]pyridazin-7-yl)-N-(2-fluoro-3-hydroxy-3-methylbutyl)nicotinamide |
| 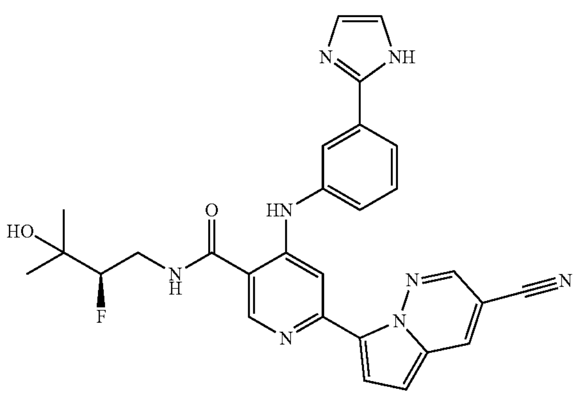 [SMILES: CC(C)(O)[C@H](F)CNC(=O)c1cnc(-c2ccc3cc(C#N)cnn23)cc1Nc1cccc(-c2ncc[nH]2)c1] | 221 | 525.1 | 2 | (R)-4-((3-(1H-imidazol-2-yl)phenyl)amino)-6-(3-cyanopyrrolo[1,2-b]pyridazin-7-yl)-N-(2-fluoro-3-hydroxy-3-methylbutyl)nicotinamide |
| 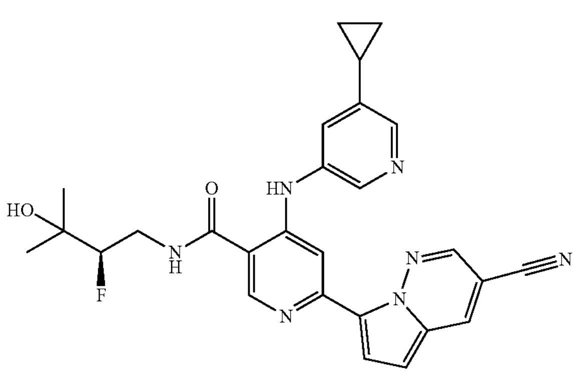 [SMILES: CC(C)(O)[C@H](F)CNC(=O)c1cnc(-c2ccc3cc(C#N)cnn23)cc1Nc1cncc(C2CC2)c1] | 222 | 500.2 | 27 | (R)-6-(3-cyanopyrrolo[1,2-b]pyridazin-7-yl)-4-((5-cyclopropylpyridin-3-yl)amino)-N-(2-fluoro-3-hydroxy-3-methylbutyl)nicotinamide |

US 10,336,762 B2

TABLE 1-continued

| Structure | compound | ES/ MS m/z | procedure | Name |
|---|---|---|---|---|
| 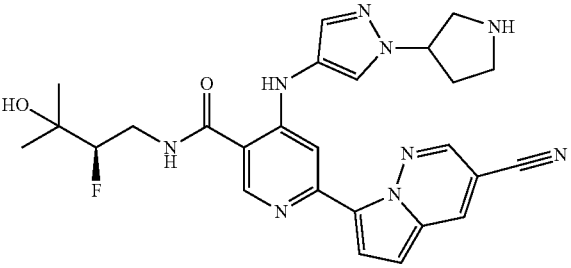 [SMILES: CC(C)(O)[C@H](F)CNC(=O)c1cnc(-c2ccc3cc(C#N)cnn23)cc1Nc1cnn(C2CCNC2)c1] | 223 | 518.2 | 14 | 6-(3-cyanopyrrolo[1,2-b]pyridazin-7-yl)-N-((R)-2-fluoro-3-hydroxy-3-methylbutyl)-4-((1-((S)-pyrrolidin-3-yl)-1H-pyrazol-4-yl)amino)nicotinamide |
| 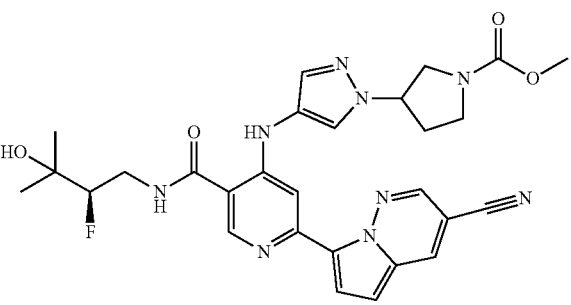 [SMILES: COC(=O)N1CCC(n2cc(Nc3cc(-c4ccc5cc(C#N)cnn45)ncc3C(=O)NC[C@@H](F)C(C)(C)O)cn2)C1] | 224 | 576.3 | 16 | (S)-methyl 3-(4-((2-(3-cyanopyrrolo[1,2-b]pyridazin-7-yl)-5-(((R)-2-fluoro-3-hydroxy-3-methylbutyl)carbamoyl)pyridin-4-yl)amino)-1H-pyrazol-1-yl)pyrrolidine-1-carboxylate |
| 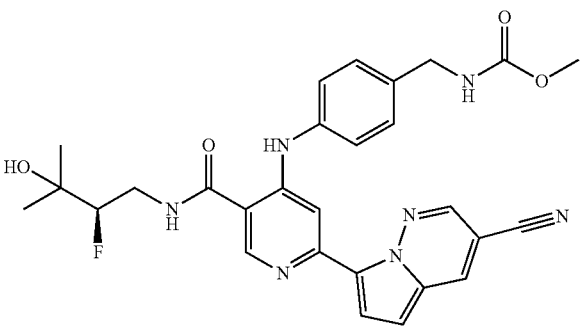 [SMILES: COC(=O)NCc1ccc(Nc2cc(-c3ccc4cc(C#N)cnn34)ncc2C(=O)NC[C@@H](F)C(C)(C)O)cc1] | 225 | 546.2 | 2 | (R)-methyl (4-((2-(3-cyano-pyrrolo[1,2-b]pyridazin-7-yl)-5-((2-fluoro-3-hydroxy-3-methylbutyl)carbamoyl)pyridin-4-yl)amino)benzyl)carbamate |
| 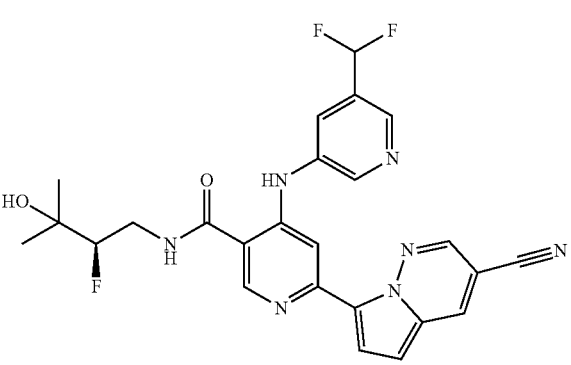 [SMILES: CC(C)(O)[C@H](F)CNC(=O)c1cnc(-c2ccc3cc(C#N)cnn23)cc1Nc1cncc(C(F)F)c1] | 226 | 510.2 | 27 | (R)-6-(3-cyanopyrrolo[1,2-b]pyridazin-7-yl)-4-((5-(difluoromethyl)pyridin-3-yl)amino)-N-(2-fluoro-3-hydroxy-3-methylbutyl)nicotinamide |

TABLE 1-continued

| Structure | compound | ES/MS m/z | procedure | Name |
|---|---|---|---|---|
| 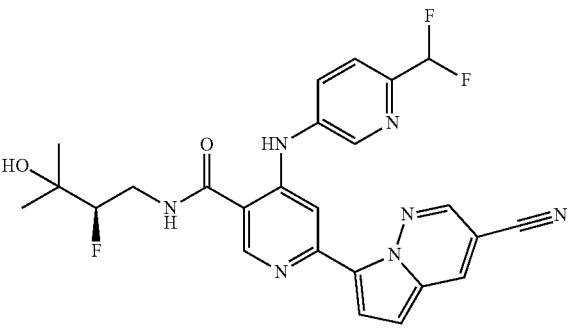 [SMILES: CC(C)(O)[C@H](F)CNC(=O)c1cnc(-c2ccc3cc(C#N)cnn23)cc1Nc1ccc(C(F)F)nc1] | 227 | 510.1 | 27 | (R)-6-(3-cyanopyrrolo[1,2-b]pyridazin-7-yl)-4-((6-(difluoromethyl)pyridin-3-yl)amino)-N-(2-fluoro-3-hydroxy-3-methylbutyl)nicotinamide |
| 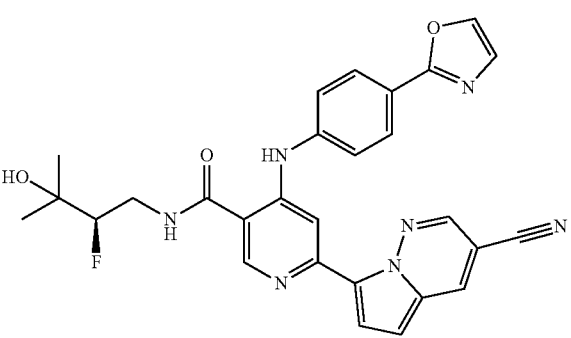 [SMILES: CC(C)(O)[C@H](F)CNC(=O)c1cnc(-c2ccc3cc(C#N)cnn23)cc1Nc1ccc(-c2ncco2)cc1] | 228 | 526.2 | 27 | (R)-6-(3-cyanopyrrolo[1,2-b]pyridazin-7-yl)-N-(2-fluoro-3-hydroxy-3-methylbutyl)-4-((4-(oxazol-2-yl)phenyl)amino)nicotinamide |
| 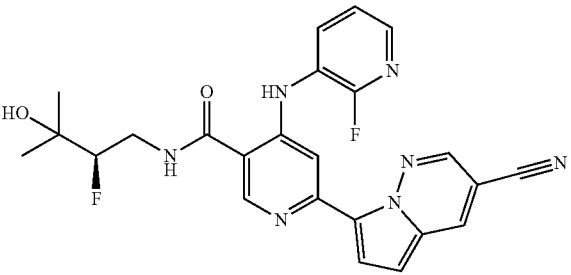 [SMILES: CC(C)(O)[C@H](F)CNC(=O)c1cnc(-c2ccc3cc(C#N)cnn23)cc1Nc1cccnc1F] | 229 | 478.1 | 27 | (R)-6-(3-cyanopyrrolo[1,2-b]pyridazin-7-yl)-N-(2-fluoro-3-hydroxy-3-methylbutyl)-4-((2-fluoropyridin-3-yl)amino)nicotinamide |
| 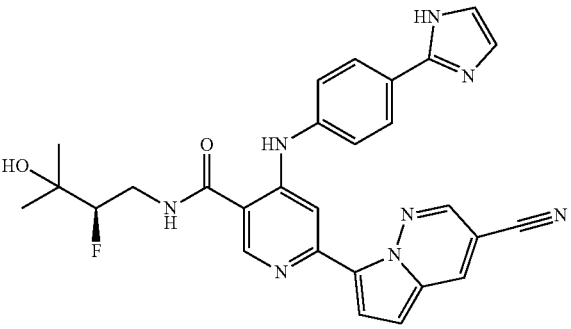 [SMILES: CC(C)(O)[C@H](F)CNC(=O)c1cnc(-c2ccc3cc(C#N)cnn23)cc1Nc1ccc(-c2ncc[nH]2)cc1] | 230 | 525.2 | 2 | (R)-4-((4-(1H-imidazol-2-yl)phenyl)amino)-6-(3-cyanopyrrolo[1,2-b]pyridazin-7-yl)-N-(2-fluoro-3-hydroxy-3-methylbutyl)nicotinamide |
| 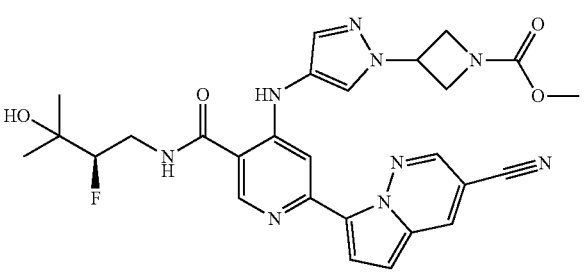 [SMILES: COC(=O)N1CC(n2cc(Nc3cc(-c4ccc5cc(C#N)cnn45)ncc3C(=O)NC[C@@H](F)C(C)(C)O)cn2)C1] | 231 | 562.2 | 16 | (R)-methyl 3-(4-((2-(3-cyanopyrrolo[1,2-b]pyridazin-7-yl)-5-((2-fluoro-3-hydroxy-3-methylbutyl)carbamoyl)pyridin-4-yl)amino)-1H-pyrazol-1-yl)azetidine-1-carboxylate |

TABLE 1-continued

| Structure | compound | ES/MS m/z | procedure | Name |
|---|---|---|---|---|
| 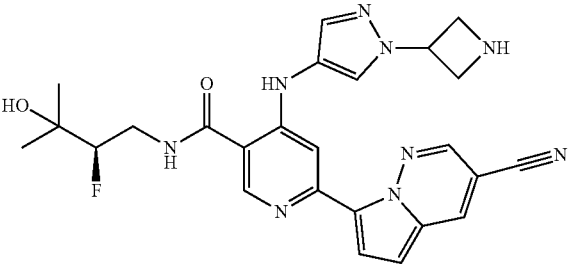 [SMILES: CC(C)(O)[C@H](F)CNC(=O)c1cnc(-c2ccc3cc(C#N)cnn23)cc1Nc1cnn(C2CNC2)c1] | 232 | 504.3 | 14 | (R)-4-((1-(azetidin-3-yl)-1H-pyrazol-4-yl)amino)-6-(3-cyanopyrrolo[1,2-b]pyridazin-7-yl)-N-(2-fluoro-3-hydroxy-3-methylbutyl)nicotinamide |
| 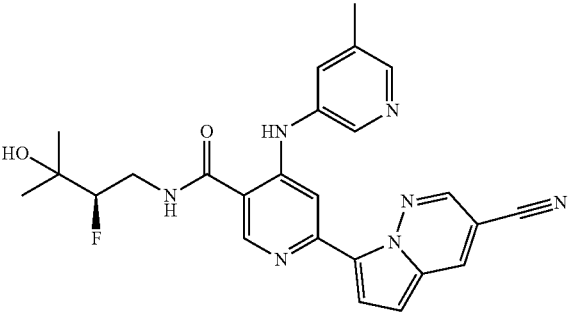 [SMILES: Cc1cncc(Nc2cc(-c3ccc4cc(C#N)cnn34)ncc2C(=O)NC[C@@H](F)C(C)(C)O)c1] | 233 | 474.1 | 27 | (R)-6-(3-cyanopyrrolo[1,2-b]pyridazin-7-yl)-N-(2-fluoro-3-hydroxy-3-methylbutyl)-4-((5-methylpyridin-3-yl)amino)nicotinamide |
| 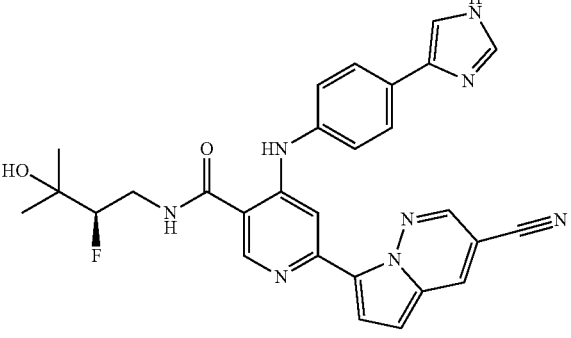 | 234 | 525.2 | 2 | (R)-4-((4-(1H-imidazol-4-yl)phenyl)amino)-6-(3-cyanopyrrolo[1,2-b]pyridazin-7-yl)-N-(2-fluoro-3-hydroxy-3-methylbutyl)nicotinamide |
| 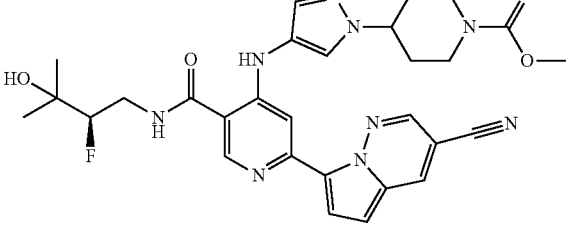 | 235 | 590.2 | 16 | (R)-methyl 4-(4-((2-(3-cyanopyrrolo[1,2-b]pyridazin-7-yl)-5-((2-fluoro-3-hydroxy-3-methylbutyl)carbamoyl)pyridin-4-yl)amino)-1H-pyrazol-1-yl)piperidine-1-carboxylate |
| 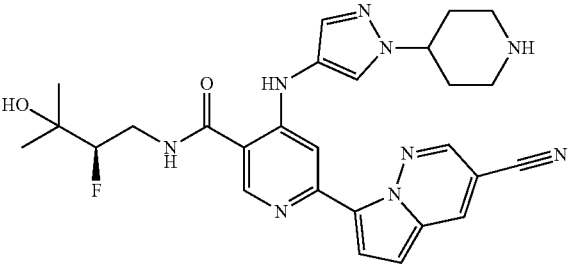 [SMILES: CC(C)(O)[C@H](F)CNC(=O)c1cnc(-c2ccc3cc(C#N)cnn23)cc1Nc1cnn(C2CCNCC2)c1] | 236 | 532.2 | 14 | (R)-6-(3-cyanopyrrolo[1,2-b]pyridazin-7-yl)-N-(2-fluoro-3-hydroxy-3-methylbutyl)-4-((1-(piperidin-4-yl)-1H-pyrazol-4-yl)amino)nicotinamide |

TABLE 1-continued

| Structure | compound | ES/ MS m/z | procedure | Name |
|---|---|---|---|---|
| 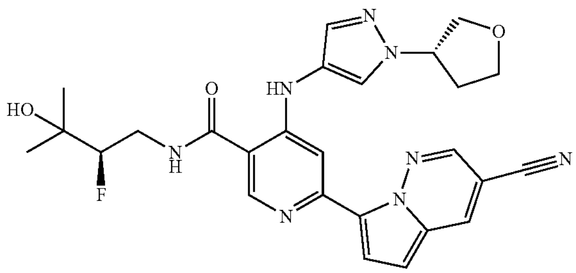 [SMILES: CC(C)(O)[C@H](F)CNC(=O)c1cnc(-c2ccc3cc(C#N)cnn23)cc1Nc1cnn([C@H]2CCOC2)c1] | 237 | 519.2 | 2 | 6-(3-cyanopyrrolo[1,2-b]pyridazin-7-yl)-N-((R)-2-fluoro-3-hydroxy-3-methylbutyl)-4-((1-((S)-tetrahydrofuran-3-yl)-1H-pyrazol-4-yl)amino)nicotinamide |
| 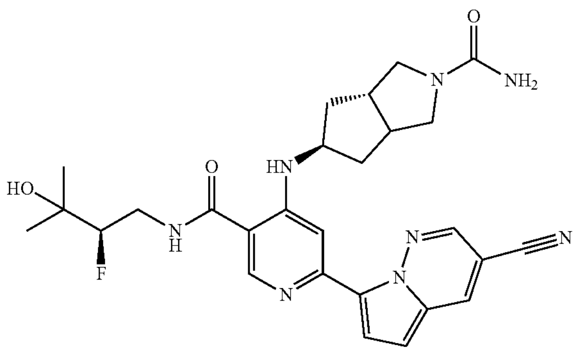 | 238 | 535.1 | 14 | (3aR,5s,6aS)-5-((2-(3-cyanopyrrolo[1,2-b]pyridazin-7-yl)-5-(((R)-2-fluoro-3-hydroxy-3-methylbutyl)carbamoyl)pyridin-4-yl)amino)hexahydrocyclopenta[c]pyrrole-2(1H)-carboxamide |
| 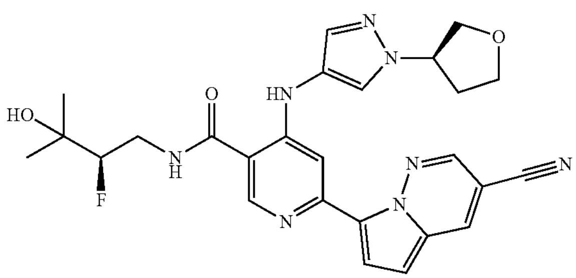 [SMILES: CC(C)(O)[C@H](F)CNC(=O)c1cnc(-c2ccc3cc(C#N)cnn23)cc1Nc1cnn([C@@H]2CCOC2)c1] | 239 | 519.2 | 2 | 6-(3-cyanopyrrolo[1,2-b]pyridazin-7-yl)-N-((R)-2-fluoro-3-hydroxy-3-methylbutyl)-4-((1-((R)-tetrahydrofuran-3-yl)-1H-pyrazol-4-yl)amino)nicotinamide |
| 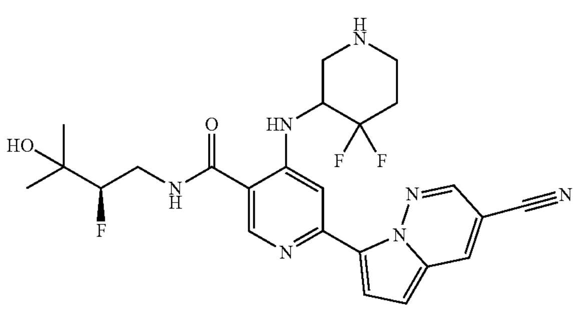 [SMILES: CC(C)(O)[C@H](F)CNC(=O)c1cnc(-c2ccc3cc(C#N)cnn23)cc1NC1CNCCC1(F)F] | 240 | 502.2 | 14 | 6-(3-cyanopyrrolo[1,2-b]pyridazin-7-yl)-4-(((R)-4,4-difluoropiperidin-3-yl)amino)-N-((R)-2-fluoro-3-hydroxy-3-methylbutyl)nicotinamide |
| 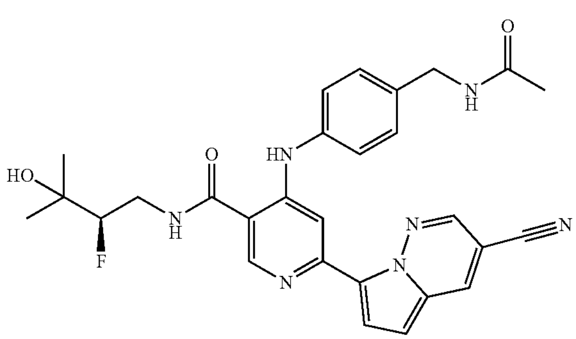 [SMILES: CC(=O)NCc1ccc(Nc2cc(-c3ccc4cc(C#N)cnn34)ncc2C(=O)NC[C@@H](F)C(C)(C)O)cc1] | 241 | 530.2 | 2 | (R)-4-((4-(acetamidomethyl)phenyl)amino)-6-(3-cyanopyrrolo[1,2-b]pyridazin-7-yl)-N-(2-fluoro-3-hydroxy-3-methylbutyl)nicotinamide |

TABLE 1-continued

| Structure | compound | ES/MS m/z | procedure | Name |
|---|---|---|---|---|
| 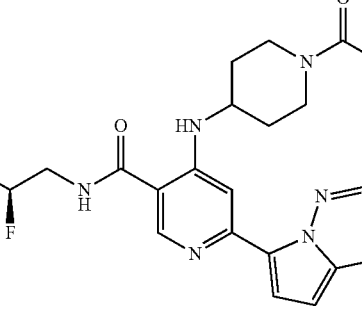 | 242 | 524.2 | 16 | (R)-methyl 4-((2-(3-cyano-pyrrolo[1,2-b]pyridazin-7-yl)-5-((2-fluoro-3-hydroxy-3-methylbutyl)carbamoyl)pyridin-4-yl)amino)piperidine-1-carboxylate |
| 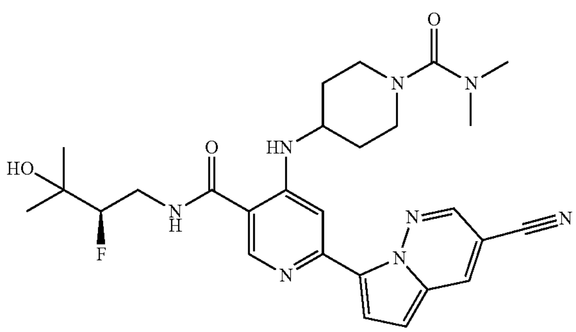 [SMILES: CN(C)C(=O)N1CCC(Nc2cc(-c3ccc4cc(C#N)cnn34)ncc2C(=O)NC[C@@H](F)C(C)(C)O)CC1] | 243 | 537.3 | 16 | (R)-6-(3-cyanopyrrolo[1,2-b]pyridazin-7-yl)-4-((1-(dimethylcarbamoyl)piperidin-4-yl)amino)-N-(2-fluoro-3-hydroxy-3-methylbutyl)nicotinamide |
| 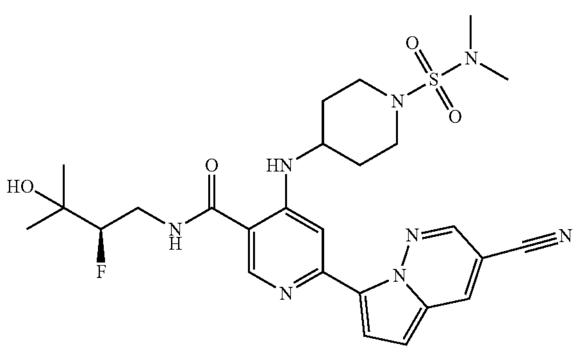 [SMILES: CN(C)S(=O)(=O)N1CCC(Nc2cc(-c3ccc4cc(C#N)cnn34)ncc2C(=O)NC[C@@H](F)C(C)(C)O)CC1] | 244 | 573.2 | 15 | (R)-6-(3-cyanopyrrolo[1,2-b]pyridazin-7-yl)-4-((1-(N,N-dimethylsulfamoyl)piperidin-4-yl)amino)-N-(2-fluoro-3-hydroxy-3-methylbutyl)nicotinamide |
| 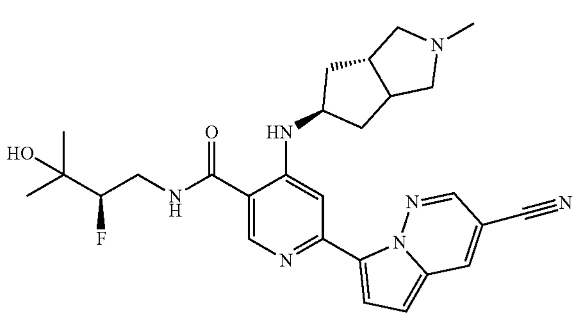 | 245 | 506.3 | 25 | 6-(3-cyanopyrrolo[1,2-b]pyridazin-7-yl)-N-((R)-2-fluoro-3-hydroxy-3-methylbutyl)-4-(((3aR,5s,6aS)-2-methyloctahydrocyclopenta[c]pyrrol-5-yl)amino)nicotinamide |

TABLE 1-continued

| Structure | compound | ES/MS m/z | procedure | Name |
|---|---|---|---|---|
| 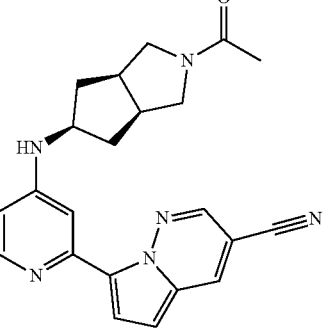 | 246 | 534.2 | 16 | 4-(((3aR,5r,6aS)-2-acetyl-octahydrocyclopenta[c]pyrrol-5-yl)amino)-6-(3-cyanopyrrolo[1,2-b]pyridazin-7-yl)-N-((R)-2-fluoro-3-hydroxy-3-methylbutyl)nicotinamide |
| 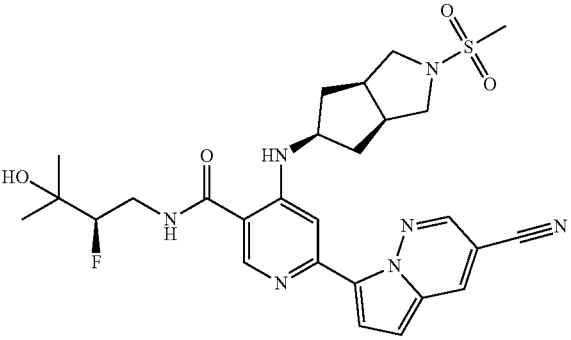 [SMILES: CC(C)(O)[C@H](F)CNC(=O)c1cnc(-c2ccc3cc(C#N)cnn23)cc1N[C@@H]1C[C@@H]2CN(S(C)(=O)=O)C[C@@H]2C1] | 247 | 570.2 | 15 | 6-(3-cyanopyrrolo[1,2-b]pyridazin-7-yl)-N-((R)-2-fluoro-3-hydroxy-3-methylbutyl)-4-(((3aR,5r,6aS)-2-(methylsulfonyl)octahydrocyclopenta[c]pyrrol-5-yl)amino)nicotinamide |
| 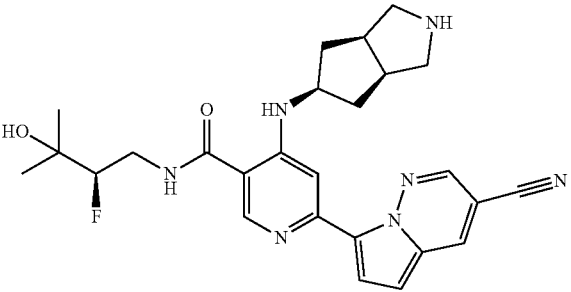 [SMILES: CC(C)(O)[C@H](F)CNC(=O)c1cnc(-c2ccc3cc(C#N)cnn23)cc1N[C@H]1C[C@H]2CNC[C@H]2C1] | 248 | 492.2 | 14 | 6-(3-cyanopyrrolo[1,2-b]pyridazin-7-yl)-N-((R)-2-fluoro-3-hydroxy-3-methylbutyl)-4-(((3aR,5r,6aS)-octahydrocyclopenta[c]pyrrol-5-yl)amino)nicotinamide |
| 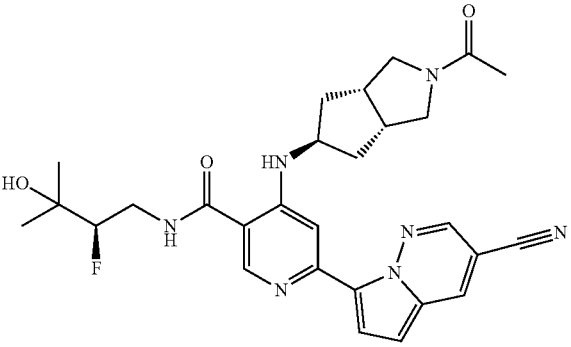 [SMILES: CC(=O)N1C[C@H]2C[C@H](Nc3cc(-c4ccc5cc(C#N)cnn45)ncc3C(=O)NC[C@@H](F)C(C)(C)O)C[C@H]2C1] | 249 | 534.2 | 16 | 4-(((3aR,5s,6aS)-2-acetyl-octahydrocyclopenta[c]pyrrol-5-yl)amino)-6-(3-cyanopyrrolo[1,2-b]pyridazin-7-yl)-N-((R)-2-fluoro-3-hydroxy-3-methylbutyl)nicotinamide |

TABLE 1-continued

| Structure | compound | ES/MS m/z | procedure | Name |
|---|---|---|---|---|
| 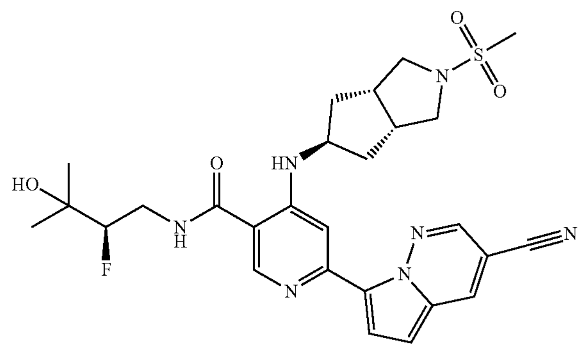 [SMILES: CC(C)(O)[C@H](F)CNC(=O)c1cnc(-c2ccc3cc(C#N)cnn23)cc1N[C@H]1C[C@@H]2CN(S(C)(=O)=O)C[C@@H]2C1] | 250 | 570.2 | 15 | 6-(3-cyanopyrrolo[1,2-b]pyridazin-7-yl)-N-((R)-2-fluoro-3-hydroxy-3-methylbutyl)-4-(((3aR,5s,6aS)-2-(methylsulfonyl)octahydrocyclopenta[c]pyrrol-5-yl)amino)nicotinamide |
| 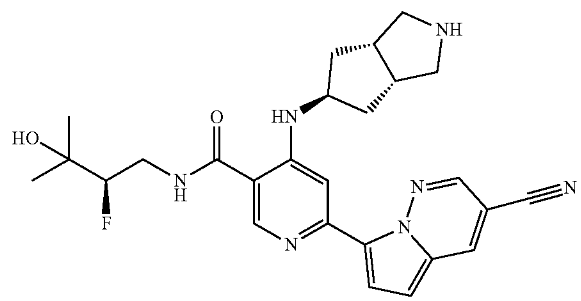 [SMILES: CC(C)(O)[C@H](F)CNC(=O)c1cnc(-c2ccc3cc(C#N)cnn23)cc1N[C@@H]1C[C@H]2CNC[C@H]2C1] | 251 | 492.2 | 14 | 6-(3-cyanopyrrolo[1,2-b]pyridazin-7-yl)-N-((R)-2-fluoro-3-hydroxy-3-methylbutyl)-4-(((3aR,5s,6aS)-octahydrocyclopenta[c]pyrrol-5-yl)amino)nicotinamide |
| 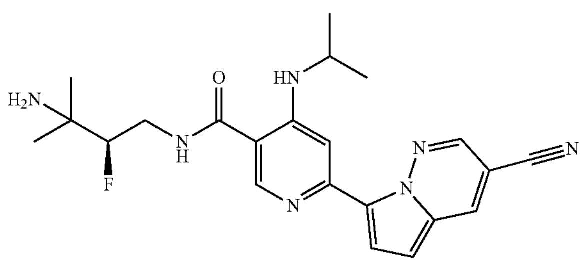 [SMILES: CC(C)Nc1cc(-c2ccc3cc(C#N)cnn23)ncc1C(=O)NC[C@@H](F)C(C)(C)N] | 252 | 406.2 | 12 | N-(3-amino-3-methylbutyl)-6-(3-cyanopyrrolo[1,2-b]pyridazin-7-yl)-4-(isopropylamino)nicotinamide |
| 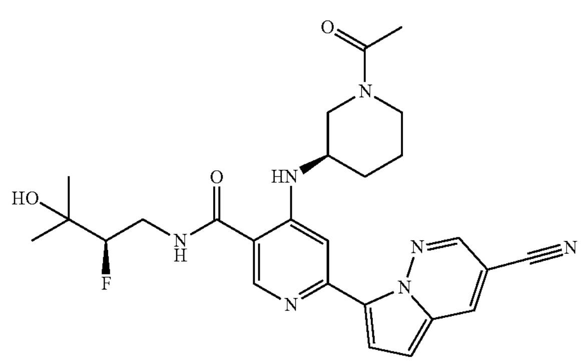 [SMILES: CC(=O)N1CCC[C@@H](Nc2cc(-c3ccc4cc(C#N)cnn34)ncc2C(=O)NC[C@@H](F)C(C)(C)O)C1] | 253 | 508.2 | 16 | 4-(((R)-1-acetylpiperidin-3-yl)amino)-6-(3-cyanopyrrolo[1,2-b]pyridazin-7-yl)-N-((R)-2-fluoro-3-hydroxy-3-methylbutyl)nicotinamide |

TABLE 1-continued

| Structure | compound | ES/MS m/z | procedure | Name |
|---|---|---|---|---|
| 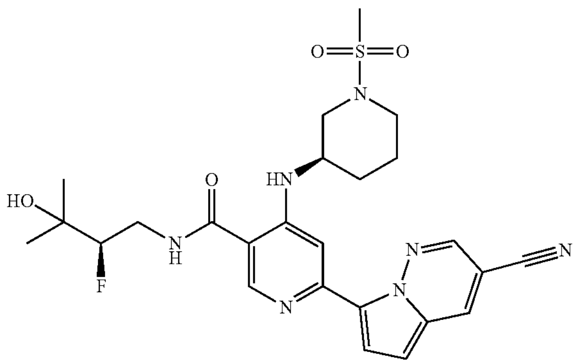 [SMILES: CC(C)(O)[C@H](F)CNC(=O)c1cnc(-c2ccc3cc(C#N)cnn23)cc1N[C@@H]1CCCN(S(C)(=O)=O)C1] | 254 | 544.2 | 15 | 6-(3-cyanopyrrolo[1,2-b]pyridazin-7-yl)-N-((R)-2-fluoro-3-hydroxy-3-methylbutyl)-4-(((R)-1-(methylsulfonyl)piperidin-3-yl)amino)nicotinamide |
| 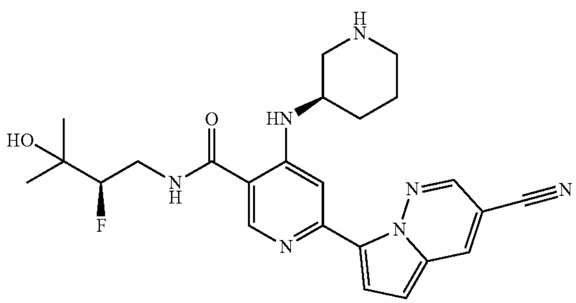 [SMILES: CC(C)(O)[C@H](F)CNC(=O)c1cnc(-c2ccc3cc(C#N)cnn23)cc1N[C@@H]1CCCNC1] | 255 | 466.2 | 14 | 6-(3-cyanopyrrolo[1,2-b]pyridazin-7-yl)-N-((R)-2-fluoro-3-hydroxy-3-methylbutyl)-4-(((R)-piperidin-3-yl)amino)nicotinamide |
| 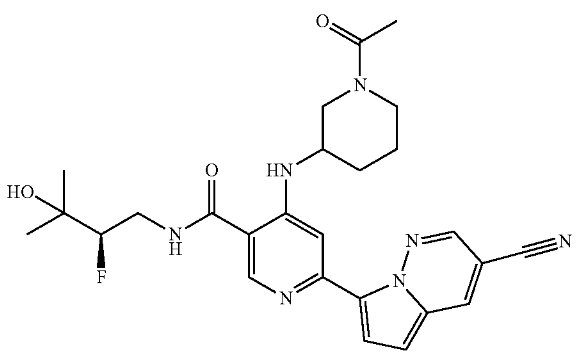 [SMILES: CC(=O)N1CCCC(Nc2cc(-c3ccc4cc(C#N)cnn34)ncc2C(=O)NC[C@@H](F)C(C)(C)O)C1] | 256 | 508.3 | 16 | 4-(((S)-1-acetylpiperidin-3-yl)amino)-6-(3-cyanopyrrolo[1,2-b]pyridazin-7-yl)-N-((R)-2-fluoro-3-hydroxy-3-methylbutyl)nicotinamide |
| 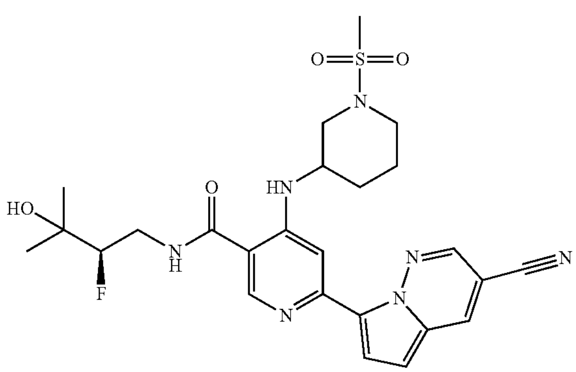 [SMILES: CC(C)(O)[C@H](F)CNC(=O)c1cnc(-c2ccc3cc(C#N)cnn23)cc1NC1CCCN(S(C)(=O)=O)C1] | 257 | 544.1 | 15 | 6-(3-cyanopyrrolo[1,2-b]pyridazin-7-yl)-N-((R)-2-fluoro-3-hydroxy-3-methylbutyl)-4-(((S)-1-(methylsulfonyl)piperidin-3-yl)amino)nicotinamide |

TABLE 1-continued

| Structure | compound | ES/MS m/z | procedure | Name |
|---|---|---|---|---|
| 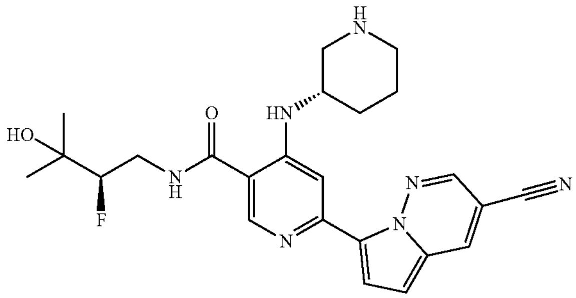 [SMILES: CC(C)(O)[C@H](F)CNC(=O)c1cnc(-c2ccc3cc(C#N)cnn23)cc1N[C@H]1CCCNC1] | 258 | 466.2 | 14 | 6-(3-cyanopyrrolo[1,2-b]pyridazin-7-yl)-N-((R)-2-fluoro-3-hydroxy-3-methylbutyl)-4-(((S)-piperidin-3-yl)amino)nicotinamide |
| 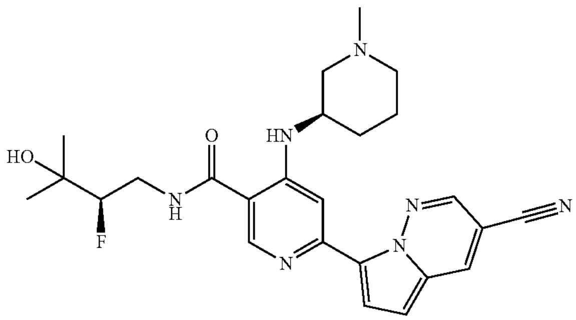 [SMILES: CN1CCC[C@@H](Nc2cc(-c3ccc4cc(C#N)cnn34)ncc2C(=O)NC[C@@H](F)C(C)(C)O)C1] | 259 | 480.2 | 2 | 6-(3-cyanopyrrolo[1,2-b]pyridazin-7-yl)-N-((R)-2-fluoro-3-hydroxy-3-methylbutyl)-4-(((R)-1-methylpiperidin-3-yl)amino)nicotinamide |
| 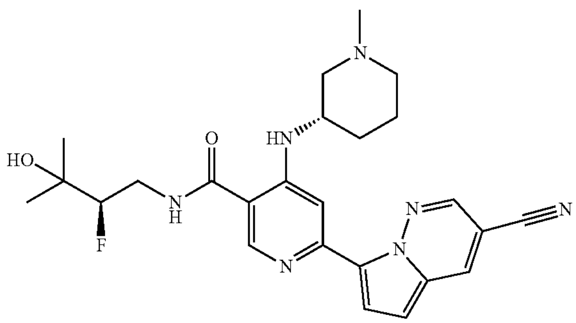 [SMILES: CN1CCC[C@H](Nc2cc(-c3ccc4cc(C#N)cnn34)ncc2C(=O)NC[C@@H](F)C(C)(C)O)C1] | 260 | 480.2 | 2 | 6-(3-cyanopyrrolo[1,2-b]pyridazin-7-yl)-N-((R)-2-fluoro-3-hydroxy-3-methylbutyl)-4-(((S)-1-methylpiperidin-3-yl)amino)nicotinamide |
| 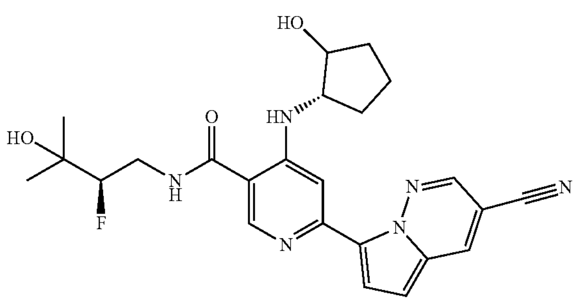 [SMILES: CC(C)(O)[C@H](F)CNC(=O)c1cnc(-c2ccc3cc(C#N)cnn23)cc1N[C@H]1CCCC1O] | 261 | 467.2 | 2 | 6-(3-cyanopyrrolo[1,2-b]pyridazin-7-yl)-N-((R)-2-fluoro-3-hydroxy-3-methylbutyl)-4-(((1S,2R)-2-hydroxycyclopentyl)amino)nicotinamide |
| 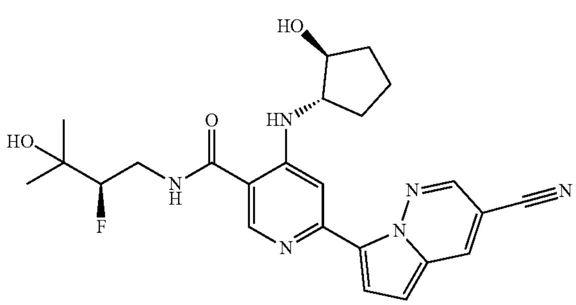 [SMILES: CC(C)(O)[C@H](F)CNC(=O)c1cnc(-c2ccc3cc(C#N)cnn23)cc1N[C@H]1CCC[C@@H]1O] | 262 | 467.2 | 2 | 6-(3-cyanopyrrolo[1,2-b]pyridazin-7-yl)-N-((R)-2-fluoro-3-hydroxy-3-methylbutyl)-4-(((1S,2S)-2-hydroxycyclopentyl)amino)nicotinamide |

TABLE 1-continued

| Structure | compound | ES/MS m/z | procedure | Name |
|---|---|---|---|---|
| 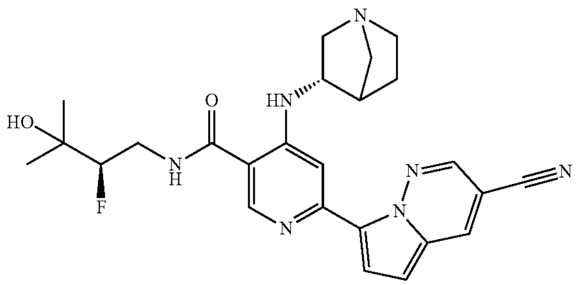 [SMILES: CC(C)(O)[C@H](F)CNC(=O)c1cnc(-c2ccc3cc(C#N)cnn23)cc1N[C@@H]1CN2CCC1C2] | 263 | 492.3 | 2 | 6-(3-cyanopyrrolo[1,2-b]pyridazin-7-yl)-N-((R)-2-fluoro-3-hydroxy-3-methylbutyl)-4-(((S)-quinuclidin-3-yl)amino)nicotinamide |
| 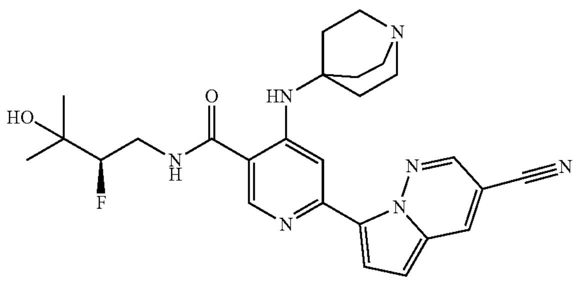 [SMILES: CC(C)(O)[C@H](F)CNC(=O)c1cnc(-c2ccc3cc(C#N)cnn23)cc1NC12CCN(CC1)CC2] | 264 | 492.1 | 2 | (R)-6-(3-cyanopyrrolo[1,2-b]pyridazin-7-yl)-N-(2-fluoro-3-hydroxy-3-methylbutyl)-4-(quinuclidin-4-ylamino)nicotinamide |
| 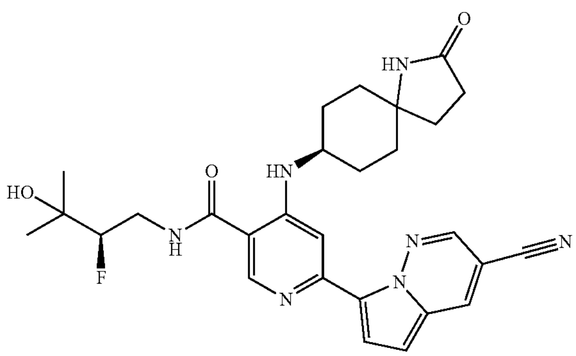 | 265 | 534.3 | 2 | 6-(3-cyanopyrrolo[1,2-b]pyridazin-7-yl)-N-((R)-2-fluoro-3-hydroxy-3-methylbutyl)-4-(((5S,8s)-2-oxo-1-azaspiro[4.5]decan-8-yl)amino)nicotinamide |
| 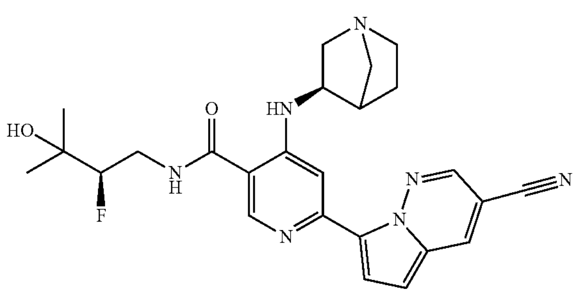 [SMILES: CC(C)(O)[C@H](F)CNC(=O)c1cnc(-c2ccc3cc(C#N)cnn23)cc1N[C@H]1CN2CCC1C2] | 266 | 492.3 | 2 | 6-(3-cyanopyrrolo[1,2-b]pyridazin-7-yl)-N-((R)-2-fluoro-3-hydroxy-3-methylbutyl)-4-(((R)-quinuclidin-3-yl)amino)nicotinamide |
| 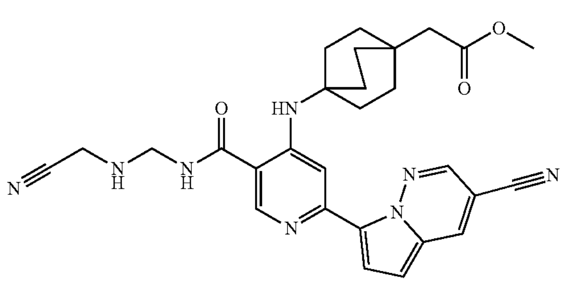 [SMILES: COC(=O)CC12CCC(Nc3cc(-c4ccc5cc(C#N)cnn45)ncc3C(=O)NCNCC#N)(CC1)CC2] | 267 | 499.3 | 40 | methyl (4-((5-((cyanomethyl)carbamoyl)-2-(3-cyanopyrrolo[1,2-b]pyridazin-7-yl)pyridin-4-yl)amino)bicyclo[2.2.2]octan-1-yl)carbamate |

TABLE 1-continued

| Structure | compound | ES/MS m/z | procedure | Name |
|---|---|---|---|---|
| 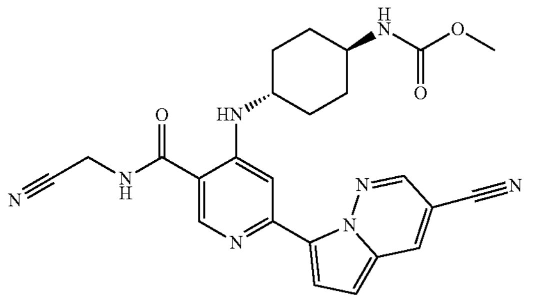 [SMILES: COC(=O)N[C@H]1CC[C@H](Nc2cc(-c3ccc4cc(C#N)cnn34)ncc2C(=O)NCC#N)CC1] | 268 | 473.3 | 40 | methyl ((1r,4r)-4-((5-((cyanomethyl)carbamoyl)-2-(3-cyanopyrrolo[1,2-b]pyridazin-7-yl)pyridin-4-yl)amino)cyclohexyl)carbamate |
| 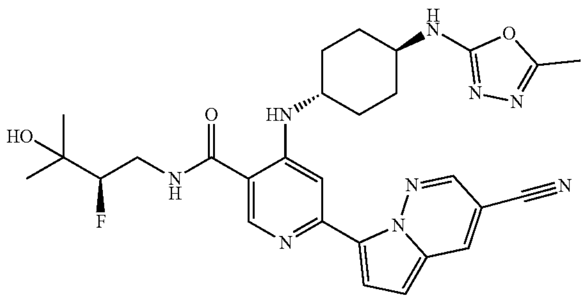 [SMILES: Cc1nnc(N[C@H]2CC[C@H](Nc3cc(-c4ccc5cc(C#N)cnn45)ncc3C(=O)NC[C@@H](F)C(C)(C)O)CC2)o1] | 269 | 562.3 | 39 | 6-(3-cyanopyrrolo[1,2-b]pyridazin-7-yl)-N-((R)-2-fluoro-3-hydroxy-3-methylbutyl)-4-(((1r,4R)-4-((5-methyl-1,3,4-oxadiazol-2-yl)amino)cyclohexyl)amino)nicotinamide |
| 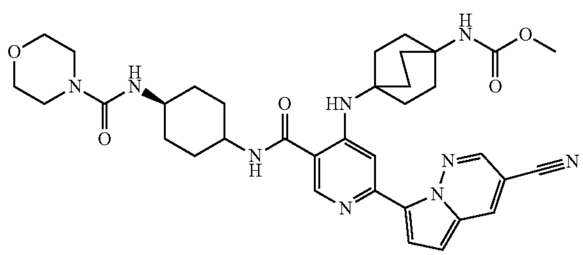 | 270 | 670.3 | 13 | methyl (4-((2-(3-cyano-pyrrolo[1,2-b]pyridazin-7-yl)-5-((4-(morpholine-4-carboxamido)cyclohexyl)carbamoyl)pyridin-4-yl)amino)bicyclo[2.2.2]octan-1-yl)carbamate |
| 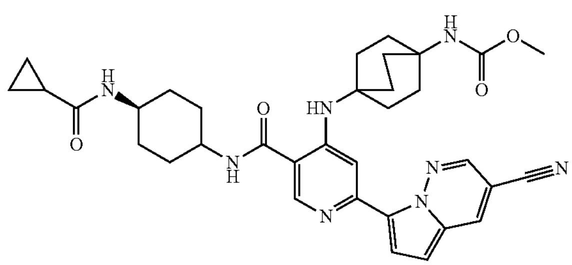 | 271 | 625.4 | 13 | methyl (4-((2-(3-cyano-pyrrolo[1,2-b]pyridazin-7-yl)-5-((4-(cyclopropane-carboxamido)cyclohexyl)carbamoyl)pyridin-4-yl)amino)bicyclo[2.2.2]octan-1-yl)carbamate |
| 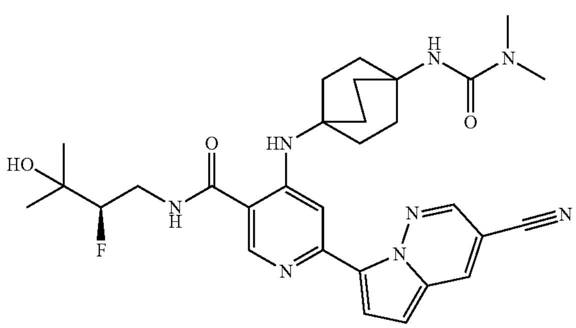 [SMILES: CN(C)C(=O)NC12CCC(Nc3cc(-c4ccc5cc(C#N)cnn45)ncc3C(=O)NC[C@@H](F)C(C)(C)O)(CC1)CC2] | 272 | 577.3 | 31 | (R)-6-(3-cyanopyrrolo[1,2-b]pyridazin-7-yl)-4-((4-(3,3-dimethylureido)bicyclo[2.2.2]octan-1-yl)amino)-N-(2-fluoro-3-hydroxy-3-methylbutyl)nicotinamide |

TABLE 1-continued

| Structure | compound | ES/MS m/z | procedure | Name |
|---|---|---|---|---|
| 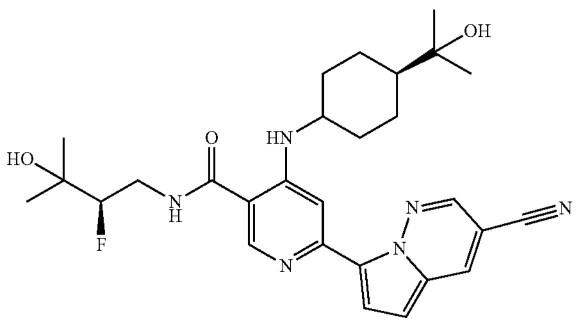 | 273 | 523.5 | 2 | 6-(3-cyanopyrrolo[1,2-b]pyridazin-7-yl)-N-((R)-2-fluoro-3-hydroxy-3-methylbutyl)-4-(((1r,4R)-4-(2-hydroxypropan-2-yl)cyclohexyl)amino)nicotinamide |
| 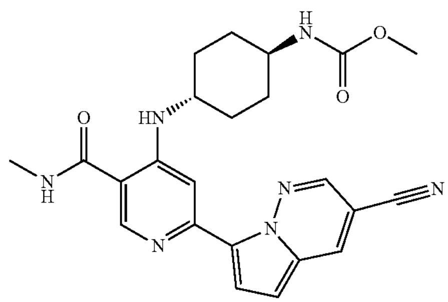 [SMILES: CNC(=O)c1cnc(-c2ccc3cc(C#N)cnn23)cc1N[C@H]1CC[C@H](NC(=O)OC)CC1] | 274 | 448.3 | 2 | methyl ((1r,4r)-4-((2-(3-cyanopyrrolo[1,2-b]pyridazin-7-yl)-5-(methylcarbamoyl)pyridin-4-yl)amino)cyclohexyl)carbamate |
| 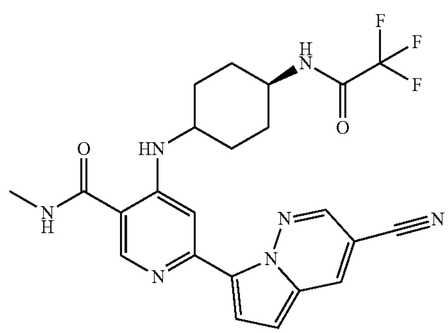 | 275 | 486.4 | 2 | 6-(3-cyanopyrrolo[1,2-b]pyridazin-7-yl)-N-methyl-4-(((1r,4r)-4-(2,2,2-trifluoroacetamido)cyclohexyl)amino)nicotinamide |
| 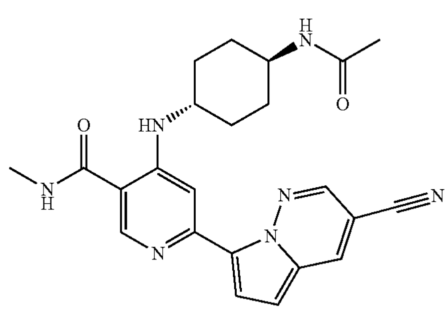 [SMILES: CNC(=O)c1cnc(-c2ccc3cc(C#N)cnn23)cc1N[C@H]1CC[C@H](NC(C)=O)CC1] | 276 | 432.3 | 2 | 4-(((1r,4r)-4-acetamidocyclohexyl)amino)-6-(3-cyano-pyrrolo[1,2-b]pyridazin-7-yl)-N-methylnicotinamide |
| 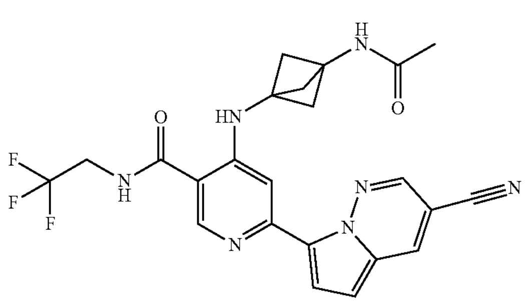 [SMILES: CC(=O)NC12CC(Nc3cc(-c4ccc5cc(C#N)cnn45)ncc3C(=O)NCC(F)(F)F)(C1)C2] | 277 | 484.3 | 2 | 4-((3-acetamido-bicyclo[1.1.1]pentan-1-yl)amino)-6-(3-cyano-pyrrolo[1,2-b]pyridazin-7-yl)-N-(2,2,2-trifluoroethyl)nicotinamide |

TABLE 1-continued

| Structure | compound | ES/ MS m/z | procedure | Name |
|---|---|---|---|---|
| 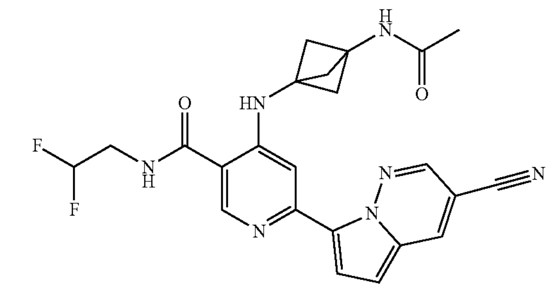 [SMILES: CC(=O)NC12CC(Nc3cc(-c4ccc5cc(C#N)cnn45)ncc3C(=O)NCC(F)F)(C1)C2] | 278 | 466.3 | 2 | 4-((3-acetamido-bicyclo[1.1.1]pentan-1-yl)amino)-6-(3-cyano-pyrrolo[1,2-b]pyridazin-7-yl)-N-(2,2-difluoroethyl) nicotinamide |
| 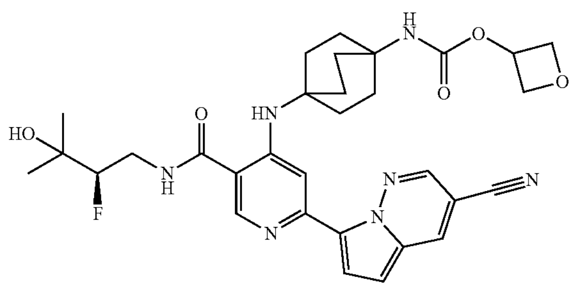 [SMILES: CC(C)(O)[C@H](F)CNC(=O)c1cnc(-c2ccc3cc(C#N)cnn23)cc1NC12CCC(NC(=O)OC3COC3)(CC1)CC2] | 279 | 606.3 | 29 | (R)-oxetan-3-yl (4-((2-(3-cyanopyrrolo[1,2-b] pyridazin-7-yl)-5-((2-fluoro-3-hydroxy-3-methylbutyl)carbamoyl) pyridin-4-yl)amino) bicyclo[2.2.2]octan-1-yl)carbamate |
| 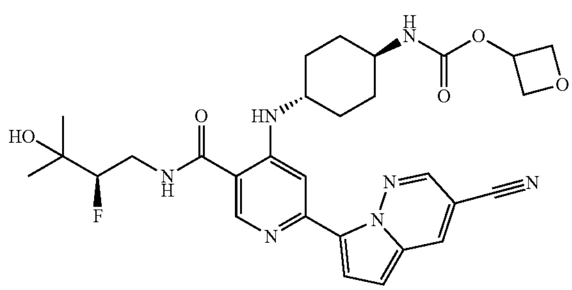 [SMILES: CC(C)(O)[C@H](F)CNC(=O)c1cnc(-c2ccc3cc(C#N)cnn23)cc1N[C@H]1CC[C@H](NC(=O)OC2COC2)CC1] | 280 | 580.3 | 29 | oxetan-3-yl ((1R,4r)-4-((2-(3-cyanopyrrolo[1,2-b]pyridazin-7-yl)-5-(((R)-2-fluoro-3-hydroxy-3-methylbutyl)carbamoyl) pyridin-4-yl)amino)cyclo-hexyl)carbamate |
| 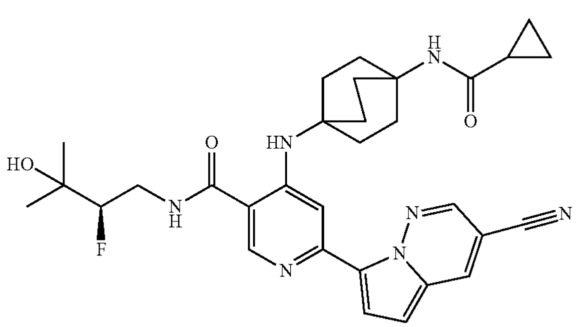 [SMILES: CC(C)(O)[C@H](F)CNC(=O)c1cnc(-c2ccc3cc(C#N)cnn23)cc1NC12CCC(NC(=O)C3CC3)(CC1)CC2] | 281 | 574.4 | 29 | (R)-6-(3-cyanopyrrolo[1,2-b]pyridazin-7-yl)-4-((4-(cyclopropanecarboxamido) bicyclo[2.2.2]octan-1-yl) amino)-N-(2-fluoro-3-hydroxy-3-methylbutyl) nicotinamide |
| 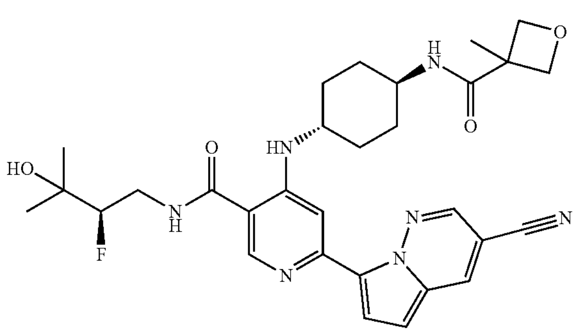 [SMILES: CC1(C(=O)N[C@H]2CC[C@H](Nc3cc(-c4ccc5cc(C#N)cnn45)ncc3C(=O)NC[C@@H](F)C(C)(C)O)CC2)COC1] | 282 | 578.3 | 33 | 6-(3-cyanopyrrolo[1,2-b]pyridazin-7-yl)-N-((R)-2-fluoro-3-hydroxy-3-methylbutyl)-4-(((1r,4R)-4-(3-methyloxetane-3-carboxamido)cyclohexyl) amino)nicotinamide |

TABLE 1-continued

| Structure | compound | ES/MS m/z | procedure | Name |
|---|---|---|---|---|
| 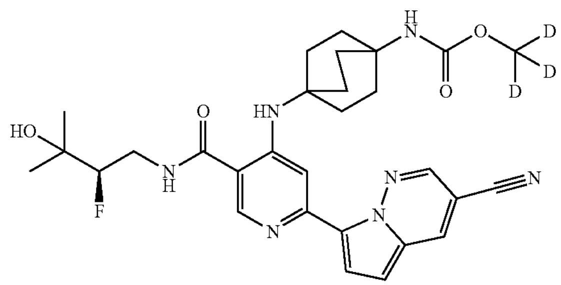 [SMILES: [2H]C([2H])([2H])OC(=O)NC12CCC(Nc3cc(-c4ccc5cc(C#N)cnn45)ncc3C(=O)NC[C@@H](F)C(C)(C)O)(CC1)CC2] | 283 | 567.5 | 2 | methyl-d3 (R)-(4-((2-(3-cyanopyrrolo[1,2-b]pyridazin-7-yl)-5-((2-fluoro-3-hydroxy-3-methylbutyl)carbamoyl)pyridin-4-yl)amino)bicyclo[2.2.2]octan-1-yl)carbamate |
| 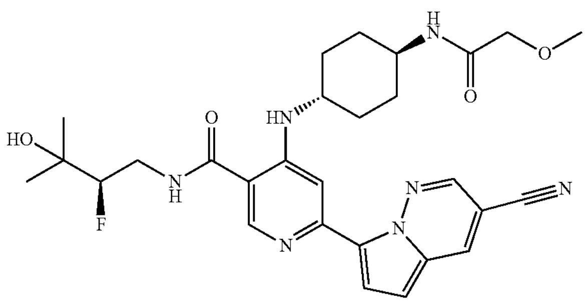 [SMILES: COCC(=O)N[C@H]1CC[C@H](Nc2cc(-c3ccc4cc(C#N)cnn34)ncc2C(=O)NC[C@@H](F)C(C)(C)O)CC1] | 284 | 552.3 | 29 | 6-(3-cyanopyrrolo[1,2-b]pyridazin-7-yl)-N-((R)-2-fluoro-3-hydroxy-3-methylbutyl)-4-(((1r,4R)-4-(2-methoxyacetamido)cyclohexyl)amino)nicotinamide |
| 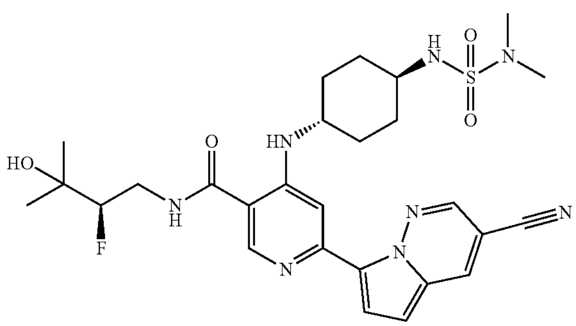 [SMILES: CN(C)S(=O)(=O)N[C@H]1CC[C@H](Nc2cc(-c3ccc4cc(C#N)cnn34)ncc2C(=O)NC[C@@H](F)C(C)(C)O)CC1] | 285 | 587.3 | 32 | 6-(3-cyanopyrrolo[1,2-b]pyridazin-7-yl)-4-(((1r,4R)-4-(N,N-dimethylsulfamoyl)amino)cyclohexyl)amino)-N-((R)-2-fluoro-3-hydroxy-3-methylbutyl)nicotinamide |
| 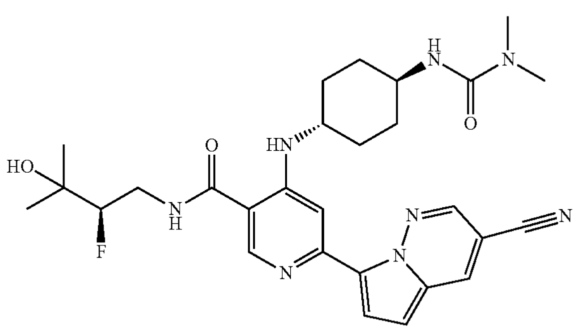 [SMILES: CN(C)C(=O)N[C@H]1CC[C@H](Nc2cc(-c3ccc4cc(C#N)cnn34)ncc2C(=O)NC[C@@H](F)C(C)(C)O)CC1] | 286 | 551.3 | 31 | 6-(3-cyanopyrrolo[1,2-b]pyridazin-7-yl)-4-(((1r,4R)-4-(3,3-dimethylureido)cyclohexyl)amino)-N-((R)-2-fluoro-3-hydroxy-3-methylbutyl)nicotinamide |
| 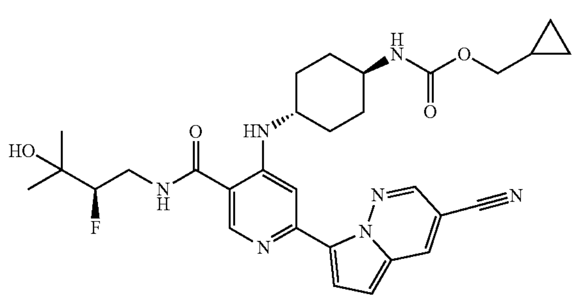 [SMILES: CC(C)(O)[C@H](F)CNC(=O)c1cnc(-c2ccc3cc(C#N)cnn23)cc1N[C@H]1CC[C@H](NC(=O)OCC2CC2)CC1] | 287 | 578.4 | 29 | cyclopropylmethyl ((1R,4r)-4-((2-(3-cyanopyrrolo[1,2-b]pyridazin-7-yl)-5-(((R)-2-fluoro-3-hydroxy-3-methylbutyl)carbamoyl)pyridin-4-yl)amino)cyclohexyl)carbamate |

TABLE 1-continued

| Structure | compound | ES/ MS m/z | procedure | Name |
|---|---|---|---|---|
| 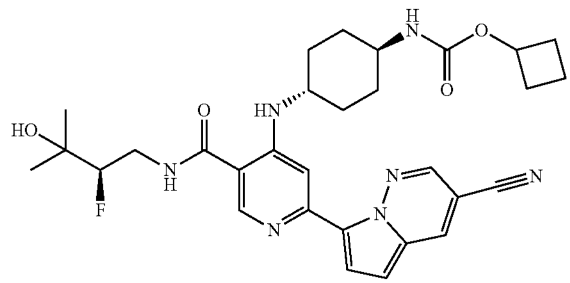 [SMILES: CC(C)(O)[C@H](F)CNC(=O)c1cnc(-c2ccc3cc(C#N)cnn23)cc1N[C@H]1CC[C@H](NC(=O)OC2CCC2)CC1] | 288 | 578.4 | 29 | cyclobutyl ((1R,4r)-4-((2-(3-cyanopyrrolo[1,2-b]pyridazin-7-yl)-5-(((R)-2-fluoro-3-hydroxy-3-methylbutyl)carbamoyl)pyridin-4-yl)amino)cyclohexyl)carbamate |
| 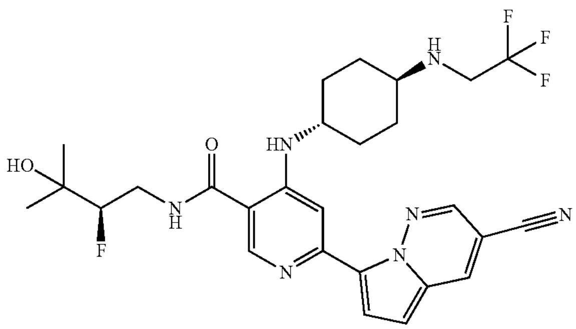 [SMILES: CC(C)(O)[C@H](F)CNC(=O)c1cnc(-c2ccc3cc(C#N)cnn23)cc1N[C@H]1CC[C@H](NCC(F)(F)F)CC1] | 289 | 562.2 | 34 | 6-(3-cyanopyrrolo[1,2-b]pyridazin-7-yl)-N-((R)-2-fluoro-3-hydroxy-3-methylbutyl)-4-(((1r,4R)-4-((2,2,2-trifluoroethyl)amino)cyclohexyl)amino)nicotinamide |
| 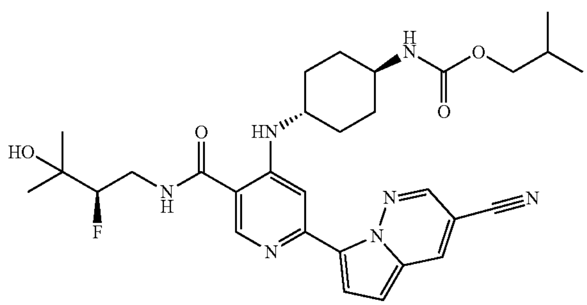 [SMILES: CC(C)COC(=O)N[C@H]1CC[C@H](Nc2cc(-c3ccc4cc(C#N)cnn34)ncc2C(=O)NC[C@@H](F)C(C)(C)O)CC1] | 290 | 580.3 | 29 | isobutyl ((1R,4r)-4-((2-(3-cyanopyrrolo[1,2-b]pyridazin-7-yl)-5-(((R)-2-fluoro-3-hydroxy-3-methylbutyl)carbamoyl)pyridin-4-yl)amino)cyclohexyl)carbamate |
| 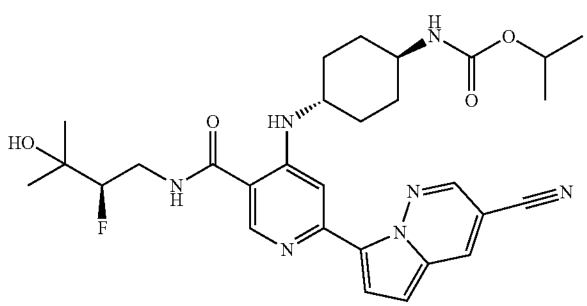 [SMILES: CC(C)OC(=O)N[C@H]1CC[C@H](Nc2cc(-c3ccc4cc(C#N)cnn34)ncc2C(=O)NC[C@@H](F)C(C)(C)O)CC1] | 291 | 566.3 | 29 | isopropyl ((1R,4r)-4-((2-(3-cyanopyrrolo[1,2-b]pyridazin-7-yl)-5-(((R)-2-fluoro-3-hydroxy-3-methylbutyl)carbamoyl)pyridin-4-yl)amino)cyclohexyl)carbamate |
| 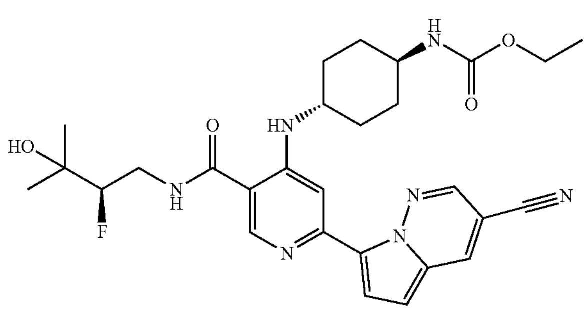 [SMILES: CCOC(=O)N[C@H]1CC[C@H](Nc2cc(-c3ccc4cc(C#N)cnn34)ncc2C(=O)NC[C@@H](F)C(C)(C)O)CC1] | 292 | 552.3 | 29 | ethyl ((1R,4r)-4-((2-(3-cyanopyrrolo[1,2-b]pyridazin-7-yl)-5-(((R)-2-fluoro-3-hydroxy-3-methylbutyl)carbamoyl)pyridin-4-yl)amino)cyclohexyl)carbamate |

TABLE 1-continued

| Structure | compound | ES/MS m/z | procedure | Name |
|---|---|---|---|---|
| 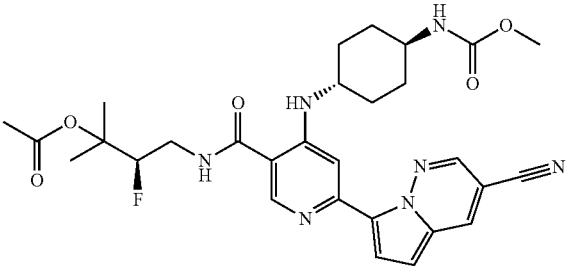 [SMILES: COC(=O)N[C@H]1CC[C@H](Nc2cc(-c3ccc4cc(C#N)cnn34)ncc2C(=O)NC[C@@H](F)C(C)(C)OC(C)=O)CC1] | 293 | 580.3 | 35 | (R)-4-(6-(3-cyano-pyrrolo[1,2-b]pyridazin-7-yl)-4-(((1r,4R)-4-((methoxycarbonyl)amino)cyclohexyl)amino)nicotinamido)-3-fluoro-2-methylbutan-2-yl acetate |
| 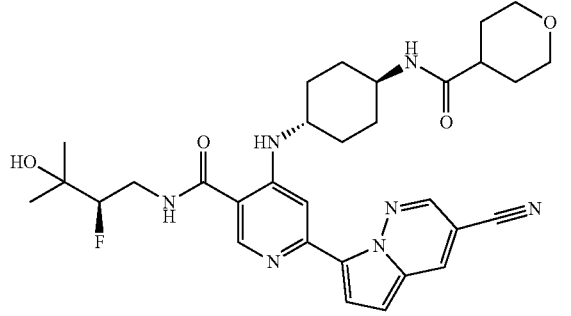 [SMILES: CC(C)(O)[C@H](F)CNC(=O)c1cnc(-c2ccc3cc(C#N)cnn23)cc1N[C@H]1CC[C@H](NC(=O)C2CCOCC2)CC1] | 294 | 592.3 | 29 | 6-(3-cyanopyrrolo[1,2-b]pyridazin-7-yl)-N-((R)-2-fluoro-3-hydroxy-3-methylbutyl)-4-(((1r,4R)-4-(tetrahydro-2H-pyran-4-carboxamido)cyclohexyl)amino)nicotinamide |
| 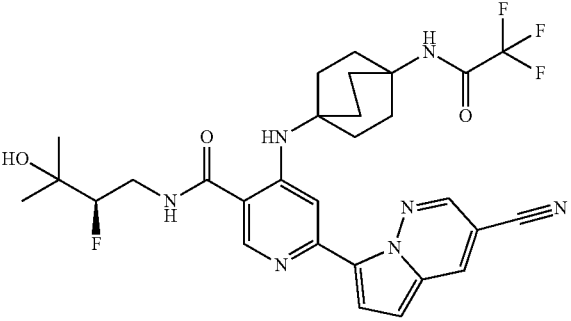 [SMILES: CC(C)(O)[C@H](F)CNC(=O)c1cnc(-c2ccc3cc(C#N)cnn23)cc1NC12CCC(NC(=O)C(F)(F)F)(CC1)CC2] | 295 | 602.3 | 29 | (R)-6-(3-cyanopyrrolo[1,2-b]pyridazin-7-yl)-N-(2-fluoro-3-hydroxy-3-methylbutyl)-4-((4-(2,2,2-trifluoroacetamido)bicyclo[2.2.2]octan-1-yl)amino)nicotinamide |
| 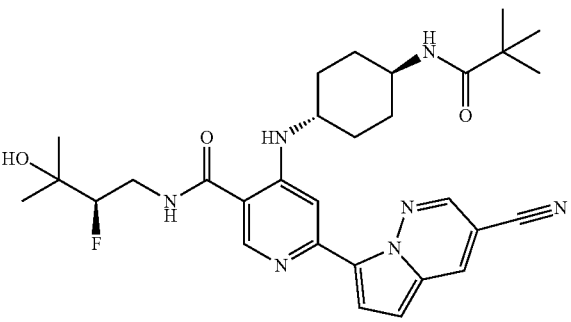 [SMILES: CC(C)(C)C(=O)N[C@H]1CC[C@H](Nc2cc(-c3ccc4cc(C#N)cnn34)ncc2C(=O)NC[C@@H](F)C(C)(C)O)CC1] | 296 | 564.3 | 29 | 6-(3-cyanopyrrolo[1,2-b]pyridazin-7-yl)-N-((R)-2-fluoro-3-hydroxy-3-methylbutyl)-4-(((1r,4R)-4-pivalamidocyclohexyl)amino)nicotinamide |
| 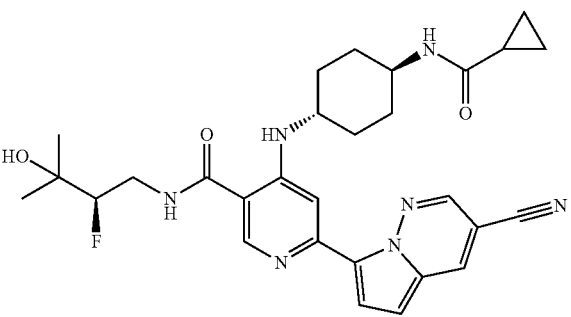 [SMILES: CC(C)(O)[C@H](F)CNC(=O)c1cnc(-c2ccc3cc(C#N)cnn23)cc1N[C@H]1CC[C@H](NC(=O)C2CC2)CC1] | 297 | 548.2 | 29 | 6-(3-cyanopyrrolo[1,2-b]pyridazin-7-yl)-4-(((1r,4R)-4-(cyclopropanecarboxamido)cyclohexyl)amino)-N-((R)-2-fluoro-3-hydroxy-3-methylbutyl)nicotinamide |

TABLE 1-continued

| Structure | compound | ES/MS m/z | procedure | Name |
|---|---|---|---|---|
| 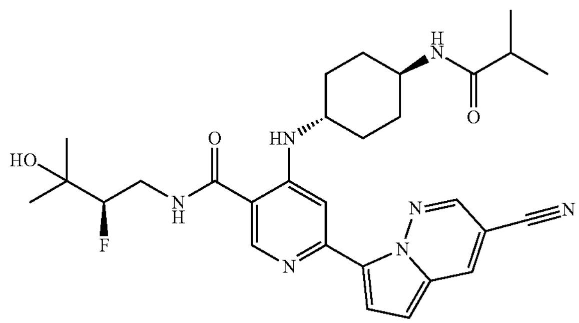 [SMILES: CC(C)C(=O)N[C@H]1CC[C@H](Nc2cc(-c3ccc4cc(C#N)cnn34)ncc2C(=O)NC[C@@H](F)C(C)(C)O)CC1] | 298 | 550.3 | 29 | 6-(3-cyanopyrrolo[1,2-b]pyridazin-7-yl)-N-((R)-2-fluoro-3-hydroxy-3-methylbutyl)-4-(((1r,4R)-4-isobutyramidocyclohexyl)amino)nicotinamide |
| 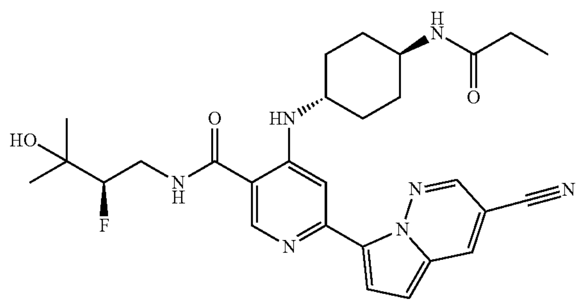 [SMILES: CCC(=O)N[C@H]1CC[C@H](Nc2cc(-c3ccc4cc(C#N)cnn34)ncc2C(=O)NC[C@@H](F)C(C)(C)O)CC1] | 299 | 536.3 | 29 | 6-(3-cyanopyrrolo[1,2-b]pyridazin-7-yl)-N-((R)-2-fluoro-3-hydroxy-3-methyl-butyl)-4-(((1r,4R)-4-propionamidocyclohexyl)amino)nicotinamide |
| 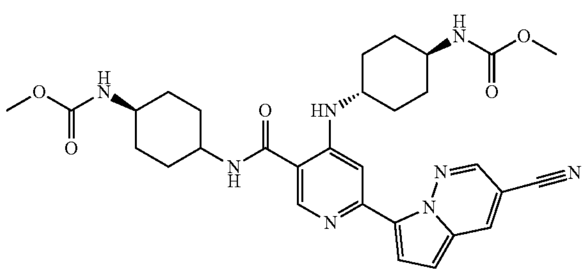 | 300 | 589.3 | 36 | methyl ((1R,4r)-4-(6-(3-cyanopyrrolo[1,2-b]pyridazin-7-yl)-4-(((1r,4R)-4-((methoxycarbonyl)amino)cyclohexyl)amino)nicotinamido)cyclohexyl)carbamate |
| 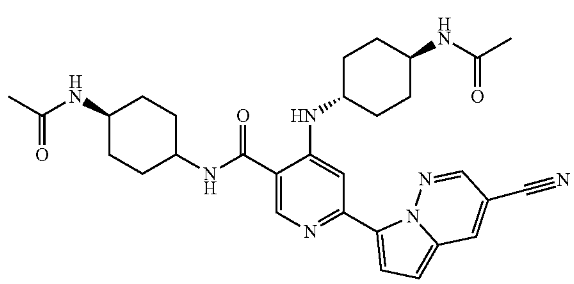 | 301 | 557.2 | 36 | N-((1r,4R)-4-acetamidocyclohexyl)-4-(((1r,4R)-4-acetamidocyclohexyl)amino)-6-(3-cyanopyrrolo[1,2-b]pyridazin-7-yl)nicotinamide |
| 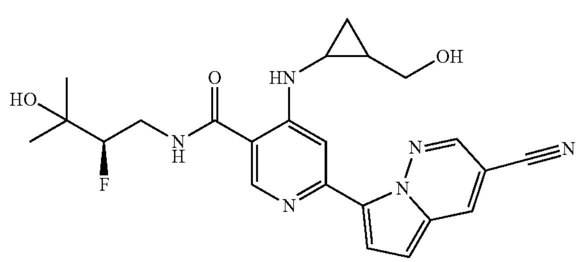 [SMILES: CC(C)(O)[C@H](F)CNC(=O)c1cnc(-c2ccc3cc(C#N)cnn23)cc1NC1CC1CO] | 302 | 453.3 | 37 | 6-(3-cyanopyrrolo[1,2-b]pyridazin-7-yl)-N-((R)-2-fluoro-3-hydroxy-3-methylbutyl)-4-((2-(hydroxymethyl)cyclopropyl)amino)nicotinamide |

| compound | ES/MS m/z | procedure | Name |
|---|---|---|---|
| 303 | 453.3 | 37 | 6-(3-cyanopyrrolo[1,2-b]pyridazin-7-yl)-N-((R)-2-fluoro-3-hydroxy-3-methylbutyl)-4-((2-(hydroxymethyl)cyclopropyl)amino)nicotinamide |
| 304 | 606.3 | 2 | (R)-tert-butyl (4-((2-(3-cyanopyrrolo[1,2-b]pyridazin-7-yl)-5-((2-fluoro-3-hydroxy-3-methylbutyl)carbamoyl)pyridin-4yl)amino)bicyclo[2.2.2]octan-1-yl)carbamate |
| 305 | 580.2 | 2 | tert-butyl ((1R,4r)-4-((2-(3-cyanopyrrolo[1,2-b]pyridazin-7-yl-5-(((R)-2-fluoro-3-hydroxy-3-methylbutyl)carbamoyl)pyridin-4-yl)amino)cyclohexyl)carbamate |
| 306 | 508.2 | 29 | 4-(((1R,3R)-3-acetamidocyclopentyl)amino)-6-(3-cyanopyrrolo[1,2-b]pyridazin-7-yl)-N-((R)-2-fluoro-3-hydroxy-3-methylbutyl)nicotinamide |
| 307 | 508.2 | 29 | 4-(((1R,3S)-3-acetamidocyclopentyl)amino)-6-(3-cyanopyrrolo[1,2-b]pyridazin-7-yl)-N-((R)-2-fluoro-3-hydroxy-3-methylbutyl)nicotinamide |

TABLE 1-continued

| Structure | compound | ES/MS m/z | procedure | Name |
|---|---|---|---|---|
| 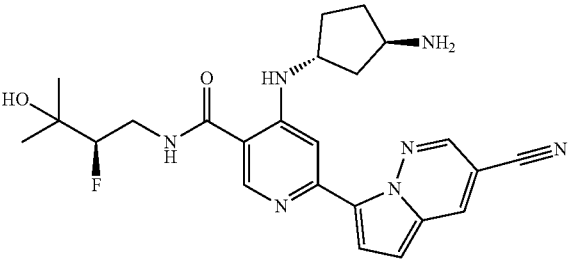 [SMILES: CC(C)(O)[C@H](F)CNC(=O)c1cnc(-c2ccc3cc(C#N)cnn23)cc1N[C@@H]1CC[C@@H](N)C1] | 308 | 466.2 | 28 | 4-(((1R,3R)-3-aminocyclopentyl)amino)-6-(3-cyanopyrrolo[1,2-b]pyridazin-7-yl)-N-((R)-2-fluoro-3-hydroxy-3-methylbutyl)nicotinamide |
| 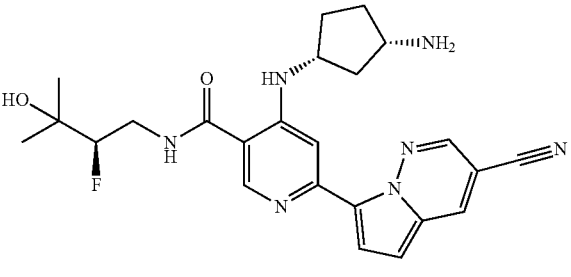 [SMILES: CC(C)(O)[C@H](F)CNC(=O)c1cnc(-c2ccc3cc(C#N)cnn23)cc1N[C@@H]1CC[C@H](N)C1] | 309 | 466.2 | 28 | 4-(((1R,3S)-3-aminocyclopentyl)amino)-6-(3-cyanopyrrolo[1,2-b]pyridazin-7-yl)-N-((R)-2-fluoro-3-hydroxy-3-methylbutyl)nicotinamide |
| 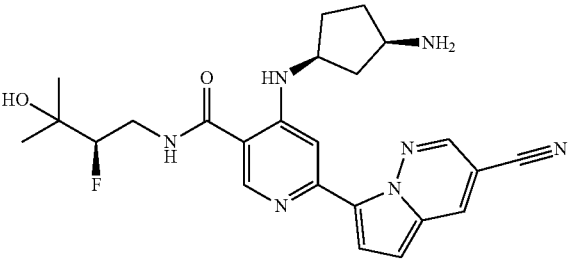 [SMILES: CC(C)(O)[C@H](F)CNC(=O)c1cnc(-c2ccc3cc(C#N)cnn23)cc1N[C@H]1CC[C@@H](N)C1] | 310 | 466.2 | 28 | 4-(((1S,3R)-3-aminocyclopentyl)amino)-6-(3-cyanopyrrolo[1,2-b]pyridazin-7-yl)-N-((R)-2-fluoro-3-hydroxy-3-methylbutyl)nicotinamide |
| 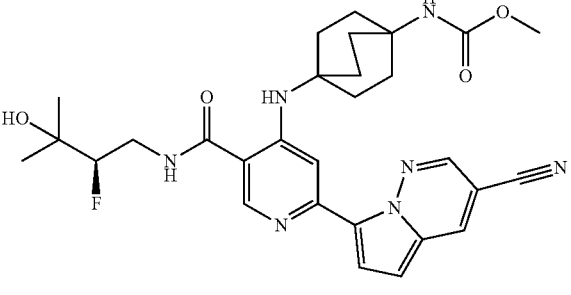 | 311 | 564.3 | 29 | (R)-methyl (4-((2-(3-cyanopyrrolo[1,2-b]pyridazin-7-yl)-5-((2-fluoro-3-hydroxy-3-methylbutyl)carbamoyl)pyridin-4-yl)amino)bicyclo[2.2.2]octan-1-yl)carbamate |
| 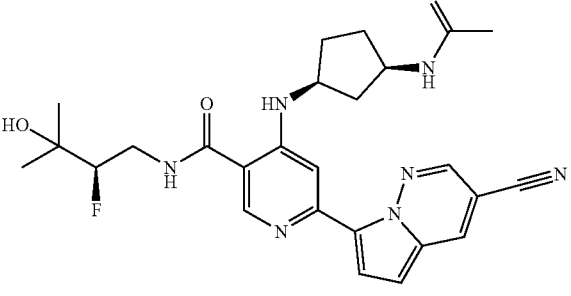 | 312 | 508.2 | 29 | 4-(((1S,3R)-3-acetamidocyclopentyl)amino)-6-(3-cyanopyrrolo[1,2-b]pyridazin-7-yl)-N-((R)-2-fluoro-3-hydroxy-3-methylbutyl)nicotinamide |

TABLE 1-continued

| Structure | compound | ES/ MS m/z | procedure | Name |
|---|---|---|---|---|
| 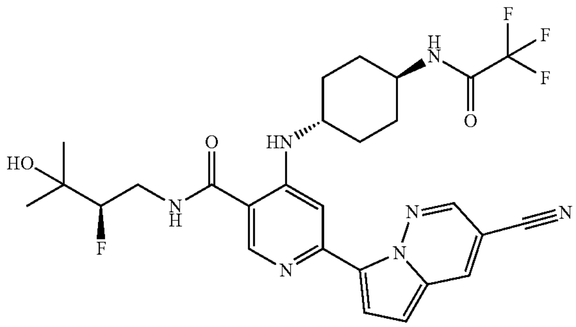 [SMILES: CC(C)(O)[C@H](F)CNC(=O)c1cnc(-c2ccc3cc(C#N)cnn23)cc1N[C@H]1CC[C@H](NC(=O)C(F)(F)F)CC1] | 313 | 576.2 | 29 | 6-(3-cyanopyrrolo[1,2-b]pyridazin-7-yl)-N-((R)-2-fluoro-3-hydroxy-3-methylbutyl)-4-(((1r,4R)-4-(2,2,2-trifluoroacetamido)cyclohexyl)amino)nicotinamide |
| 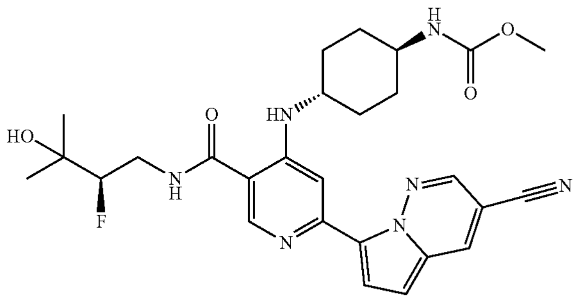 [SMILES: COC(=O)N[C@H]1CC[C@H](Nc2cc(-c3ccc4cc(C#N)cnn34)ncc2C(=O)NC[C@@H](F)C(C)(C)O)CC1] | 314 | 538.2 | 29 | methyl ((1R,4r)-4-((2-(3-cyanopyrrolo[1,2-b]pyridazin-7-yl)-5-(((R)-2-fluoro-3-hydroxy-3-methylbutyl)carbamoyl)pyridin-4-yl)amino)cyclohexyl)carbamate |
| 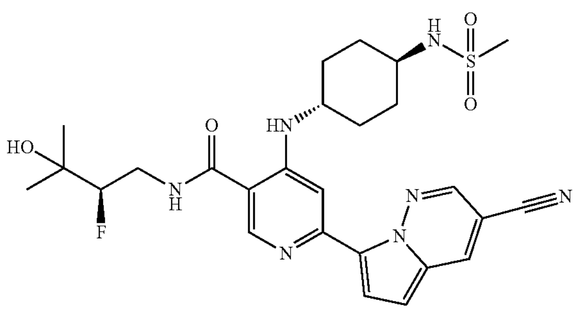 [SMILES: CC(C)(O)[C@H](F)CNC(=O)c1cnc(-c2ccc3cc(C#N)cnn23)cc1N[C@H]1CC[C@H](NS(C)(=O)=O)CC1] | 315 | 558.2 | 30 | 6-(3-cyanopyrrolo[1,2-b]pyridazin-7-yl)-N-((R)-2-fluoro-3-hydroxy-3-methylbutyl)-4-(((1r,4R)-4-(methylsulfonamido)cyclohexyl)amino)nicotinamide |
| 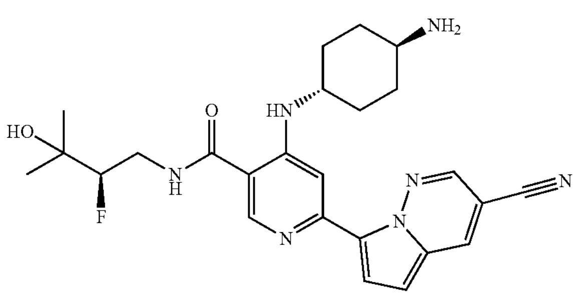 [SMILES: CC(C)(O)[C@H](F)CNC(=O)c1cnc(-c2ccc3cc(C#N)cnn23)cc1N[C@H]1CC[C@H](N)CC1] | 316 | 480.2 | 28 | 4-(((1r,4R)-4-aminocyclohexyl)amino)-6-(3-cyanopyrrolo[1,2-b]pyridazin-7-yl)-N-((R)-2-fluoro-3-hydroxy-3-methylbutyl)nicotinamide |
| 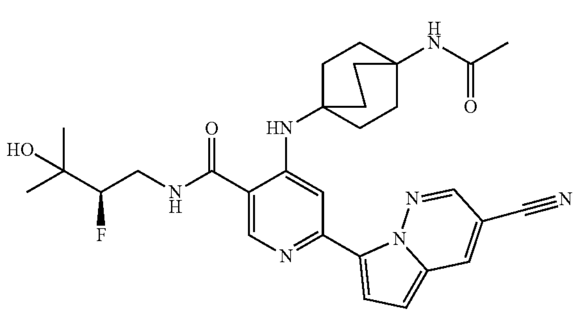 [SMILES: CC(=O)NC12CCC(Nc3cc(-c4ccc5cc(C#N)cnn45)ncc3C(=O)NC[C@@H](F)C(C)(C)O)(CC1)CC2] | 317 | 548.3 | 29 | (R)-4-((4-acetamidobicyclo[2.2.2]octan-1-yl)amino)-6-(3-cyanopyrrolo[1,2-b]pyridazin-7-yl)-N-(2-fluoro-3-hydroxy-3-methylbutyl)nicotinamide |

TABLE 1-continued

| Structure | compound | ES/MS m/z | procedure | Name |
|---|---|---|---|---|
| 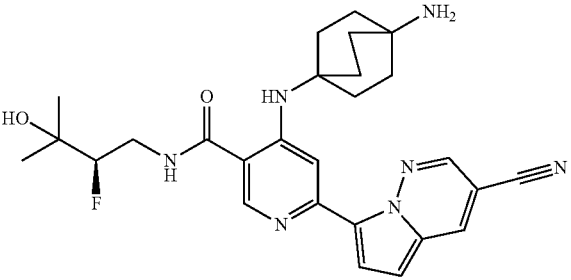 | 318 | 506.3 | 28 | (R)-4-((4-amino-bicyclo[2.2.2]octan-1-yl)amino)-6-(3-cyano-pyrrolo[1,2-b]pyridazin-7-yl)-N-(2-fluoro-3-hydroxy-3-methylbutyl)nicotinamide |
| 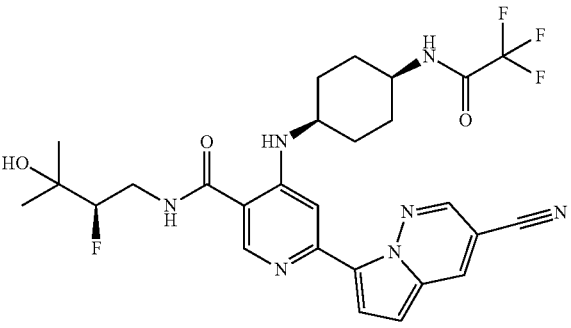 [SMILES: CC(C)(O)[C@H](F)CNC(=O)c1cnc(-c2ccc3cc(C#N)cnn23)cc1N[C@H]1CC[C@@H](NC(=O)C(F)(F)F)CC1] | 319 | 576.2 | 29 | 6-(3-cyanopyrrolo[1,2-b]pyridazin-7-yl)-N-((R)-2-fluoro-3-hydroxy-3-methyl-butyl)-4-(((1s,4S)-4-(2,2,2-trifluoroacetamido)cyclo-hexyl)amino)nicotinamide |
| 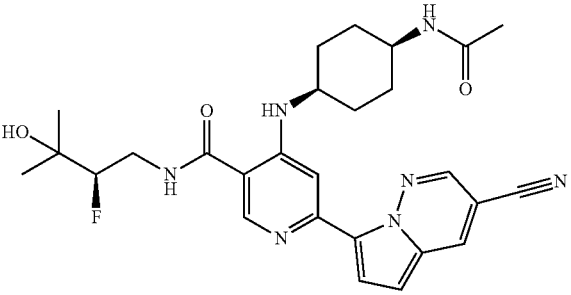 [SMILES: CC(=O)N[C@H]1CC[C@@H](Nc2cc(-c3ccc4cc(C#N)cnn34)ncc2C(=O)NC[C@@H](F)C(C)(C)O)CC1] | 320 | 522.3 | 29 | 4-(((1s,4S)-4-acetamidocyclohexyl)amino)-6-(3-cyano-pyrrolo[1,2-b]pyridazin-7-yl)-N-((R)-2-fluoro-3-hydroxy-3-methylbutyl)nicotinamide |
| 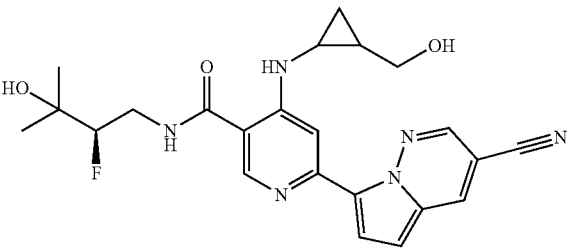 [SMILES: CC(C)(O)[C@H](F)CNC(=O)c1cnc(-c2ccc3cc(C#N)cnn23)cc1NC1CC1CO]  mixture | 321 | 453.3 | 2 | 6-(3-cyanopyrrolo[1,2-b]pyridazin-7-yl)-N-((R)-2-fluoro-3-hydroxy-3-methylbutyl)-4-((2-(hydroxymethyl)cyclo-propyl)amino)nicotinamide |
| 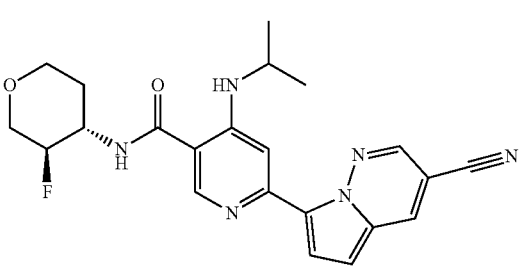 [SMILES: CC(C)Nc1cc(-c2ccc3cc(C#N)cnn23)ncc1C(=O)N[C@H]1CCOC[C@@H]1F] | 322 | 423.2 | 3 | 6-(3-cyanopyrrolo[1,2-b]pyridazin-7-yl)-N-((3R,4S)-3-fluorotetrahydro-2H-pyran-4-yl)-4-(isopropylamino)nicotinamide |

TABLE 1-continued

| Structure | compound | ES/MS m/z | procedure | Name |
|---|---|---|---|---|
| 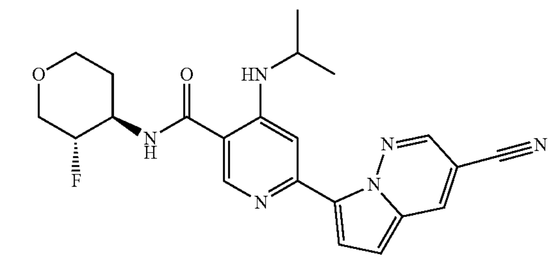 [SMILES: CC(C)Nc1cc(-c2ccc3cc(C#N)cnn23)ncc1C(=O)N[C@@H]1CCOC[C@H]1F] | 323 | 423.2 | 3 | 6-(3-cyanopyrrolo[1,2-b]pyridazin-7-yl)-N-((3S,4R)-3-fluoro-tetrahydro-2H-pyran-4-yl)-4-(isopropylamino)nicotinamide |
| 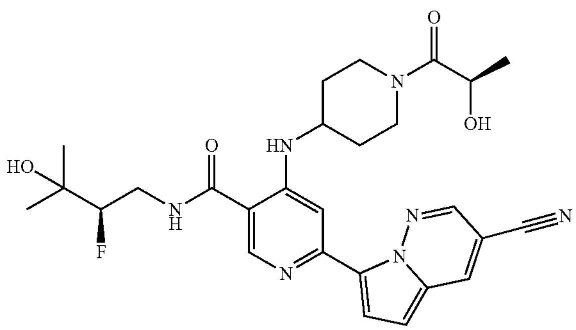 [SMILES: C[C@@H](O)C(=O)N1CCC(Nc2cc(-c3ccc4cc(C#N)cnn34)ncc2C(=O)NC[C@@H](F)C(C)(C)O)CC1] | 324 | 538.2 | 38 | 6-(3-cyanopyrrolo[1,2-b]pyridazin-7-yl)-N-((R)-2-fluoro-3-hydroxy-3-methylbutyl)-4-((1-((R)-2-hydroxy-propanoyl)piperidin-4-yl)amino)nicotinamide |
| 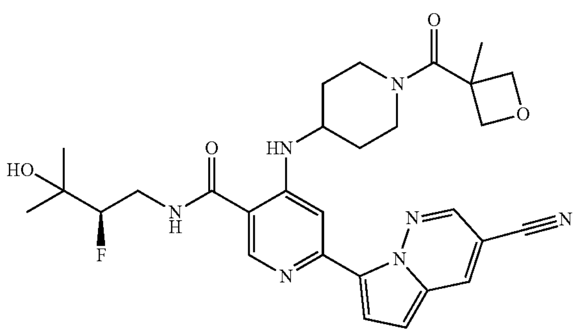 [SMILES: CC1(C(=O)N2CCC(Nc3cc(-c4ccc5cc(C#N)cnn45)ncc3C(=O)NC[C@@H](F)C(C)(C)O)CC2)COC1] | 325 | 564.3 | 38 | (R)-6-(3-cyanopyrrolo[1,2-b]pyridazin-7-yl)-N-(2-fluoro-3-hydroxy-3-methylbutyl)-4-((1-(3-methyloxetane-3-carbonyl)piperidin-4-yl)amino)nicotinamide |
| 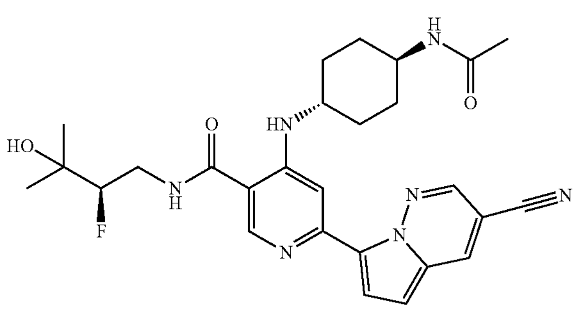 [SMILES: CC(=O)N[C@H]1CC[C@H](Nc2cc(-c3ccc4cc(C#N)cnn34)ncc2C(=O)NC[C@@H](F)C(C)(C)O)CC1] | 326 | 522.3 | 29 | 4-(((1r,4R)-4-acetamidocyclohexyl)amino)-6-(3-cyano-pyrrolo[1,2-b]pyridazin-7-yl)-N-((R)-2-fluoro-3-hydroxy-3-methylbutyl)nicotinamide |
| 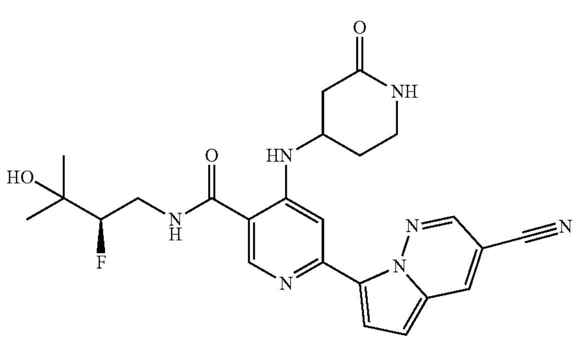 [SMILES: CC(C)(O)[C@H](F)CNC(=O)c1cnc(-c2ccc3cc(C#N)cnn23)cc1NC1CCNC(=O)C1] | 327 | 480.2 | 2 | 6-(3-cyanopyrrolo[1,2-b]pyridazin-7-yl)-N-((R)-2-fluoro-3-hydroxy-3-methylbutyl)-4-((2-oxo-piperidin-4-yl)amino)nicotinamide |

TABLE 1-continued

| Structure | compound | ES/MS m/z | procedure | Name |
|---|---|---|---|---|
| 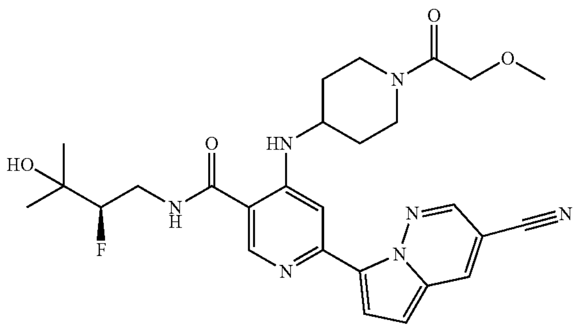 [SMILES: COCC(=O)N1CCC(Nc2cc(-c3ccc4cc(C#N)cnn34)ncc2C(=O)NC[C@@H](F)C(C)(C)O)CC1] | 328 | 538.3 | 2 | (R)-6-(3-cyanopyrrolo[1,2-b]pyridazin-7-yl)-N-(2-fluoro-3-hydroxy-3-methylbutyl)-4-((1-(2-methoxyacetyl)piperidin-4-yl)amino)nicotinamide |
| 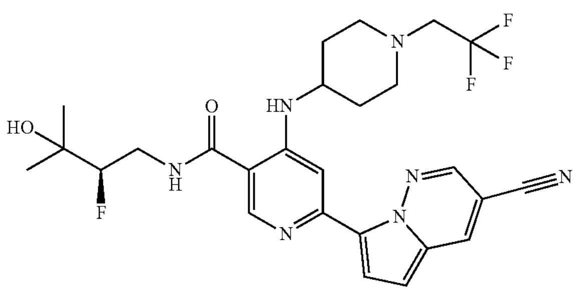 [SMILES: CC(C)(O)[C@H](F)CNC(=O)c1cnc(-c2ccc3cc(C#N)cnn23)cc1NC1CCN(CC(F)(F)F)CC1] | 329 | 548.3 | 2 | (R)-6-(3-cyanopyrrolo[1,2-b]pyridazin-7-yl)-N-(2-fluoro-3-hydroxy-3-methylbutyl)-4-((1-(2,2,2-trifluoroethyl)piperidin-4-yl)amino)nicotinamide |
| 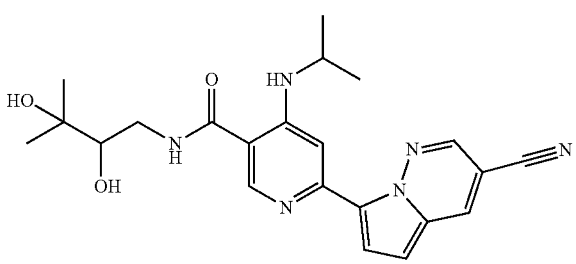 [SMILES: CC(C)Nc1cc(-c2ccc3cc(C#N)cnn23)ncc1C(=O)NCC(O)C(C)(C)O] | 330 | 423.4 | 49 | 6-(3-cyanopyrrolo[1,2-b]pyridazin-7-yl)-N-(2,3-dihydroxy-3-methylbutyl)-4-(isopropylamino)nicotinamide |
| 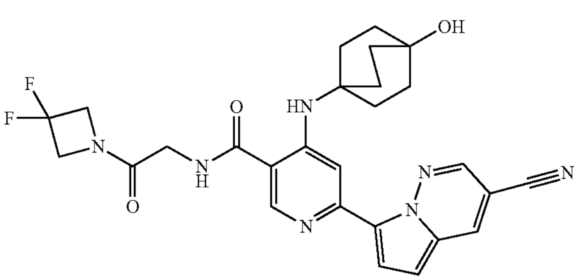 | 331 | 536.3 | 49 | 6-(3-cyanopyrrolo[1,2-b]pyridazin-7-yl)-N-(2-(3,3-difluoroazetidin-1-yl)-2-oxoethyl)-4-((4-hydroxybicyclo[2.2.2]octan-1-yl)amino)nicotinamide |
| 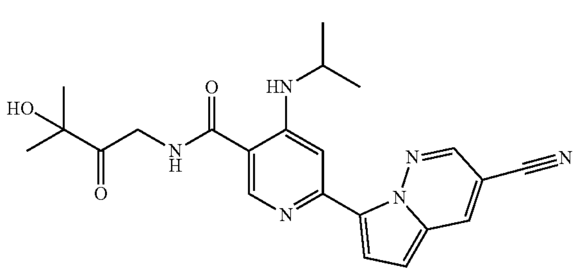 [SMILES: CC(C)Nc1cc(-c2ccc3cc(C#N)cnn23)ncc1C(=O)NCC(=O)C(C)(C)O] | 332 | 421.3 | 1 | 6-(3-cyanopyrrolo[1,2-b]pyridazin-7-yl)-N-(3-hydroxy-3-methyl-2-oxobutyl)-4-(isopropylamino)nicotinamide |

TABLE 1-continued

| Structure | compound | ES/MS m/z | procedure | Name |
|---|---|---|---|---|
| 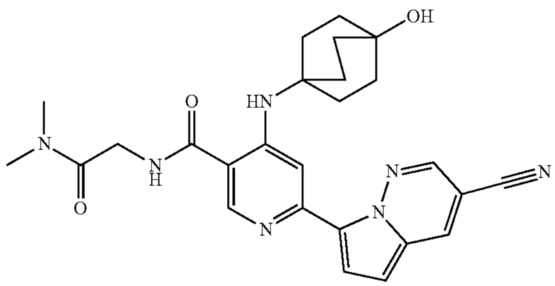 [SMILES: CN(C)C(=O)CNC(=O)c1cnc(-c2ccc3cc(C#N)cnn23)cc1NC12CCC(O)(CC1)CC2] | 333 | 488.3 | 49 | 6-(3-cyanopyrrolo[1,2-b]pyridazin-7-yl)-N-(2-(dimethylamino)-2-oxoethyl)-4-((4-hydroxybicyclo[2.2.2]octan-1-yl)amino)nicotinamide |
| 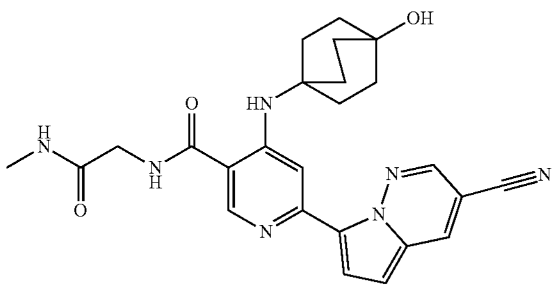 [SMILES: CNC(=O)CNC(=O)c1cnc(-c2ccc3cc(C#N)cnn23)cc1NC12CCC(O)(CC1)CC2] | 334 | 474.3 | 49 | 6-(3-cyanopyrrolo[1,2-b]pyridazin-7-yl)-4-((4-hydroxybicyclo[2.2.2]octan-1-yl)amino)-N-(2-(methylamino)-2-oxoethyl)nicotinamide |
| 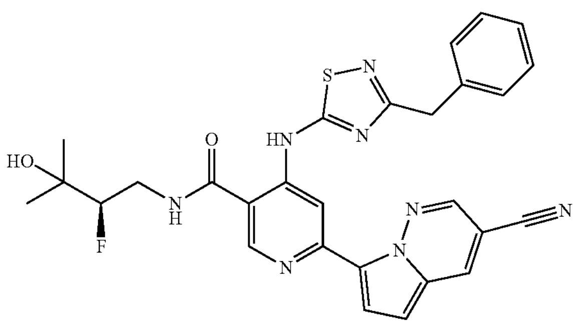 [SMILES: CC(C)(O)[C@H](F)CNC(=O)c1cnc(-c2ccc3cc(C#N)cnn23)cc1Nc1nc(Cc2ccccc2)ns1] | 335 | 557.3 | 47 | (R)-4-((3-benzyl-1,2,4-thiadiazol-5-yl)amino)-6-(3-cyanopyrrolo[1,2-b]pyridazin-7-yl)-N-(2-fluoro-3-hydroxy-3-methylbutyl)nicotinamide |
| 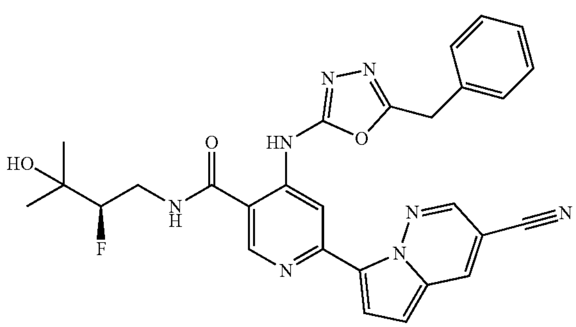 [SMILES: CC(C)(O)[C@H](F)CNC(=O)c1cnc(-c2ccc3cc(C#N)cnn23)cc1Nc1nnc(Cc2ccccc2)o1] | 336 | 541.2 | 47 | (R)-4-((5-benzyl-1,3,4-oxadiazol-2-yl)amino)-6-(3-cyanopyrrolo[1,2-b]pyridazin-7-yl)-N-(2-fluoro-3-hydroxy-3-methylbutyl)nicotinamide |
| 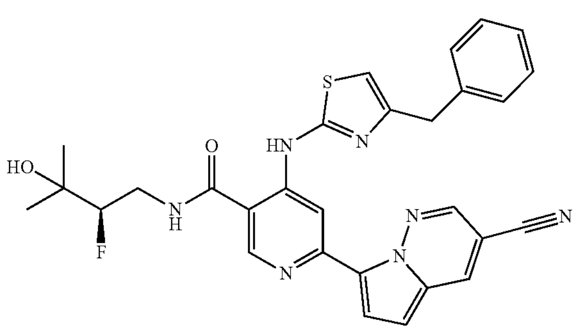 [SMILES: CC(C)(O)[C@H](F)CNC(=O)c1cnc(-c2ccc3cc(C#N)cnn23)cc1Nc1nc(Cc2ccccc2)cs1] | 337 | 556.2 | 47 | (R)-4-((4-benzylthiazol-2-yl)amino)-6-(3-cyanopyrrolo[1,2-b]pyridazin-7-yl)-N-(2-fluoro-3-hydroxy-3-methylbutyl)nicotinamide |

TABLE 1-continued

| Structure | compound | ES/ MS m/z | procedure | Name |
|---|---|---|---|---|
| 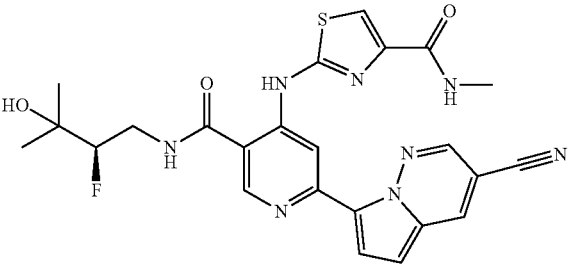 [SMILES: CNC(=O)c1csc(Nc2cc(-c3ccc4cc(C#N)cnn34)ncc2C(=O)NC[C@@H](F)C(C)(C)O)n1] | 338 | 523.1 | 48 | (R)-2-((2-(3-cyano-pyrrolo[1,2-b]pyridazin-7-yl)-5-((2-fluoro-3-hydroxy-3-methylbutyl)carbamoyl)pyridin-4-yl)amino)-N-methyl-thiazole-4-carboxamide |
| 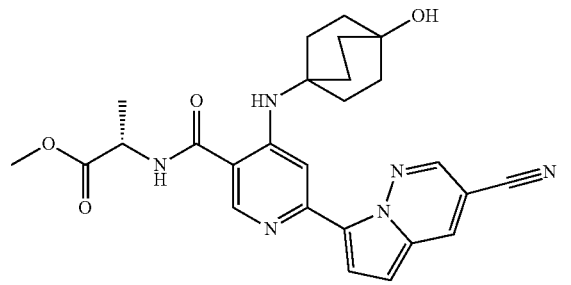 [SMILES: COC(=O)[C@H](C)NC(=O)c1cnc(-c2ccc3cc(C#N)cnn23)cc1NC12CCC(O)(CC1)CC2] | 339 | 489.4 | 1 | methyl (6-(3-cyano-pyrrolo[1,2-b]pyridazin-7-yl)-4-((4-hydroxy-bicyclo[2.2.2]octan-1-yl)amino)nicotinoyl)-L-alaninate |
| 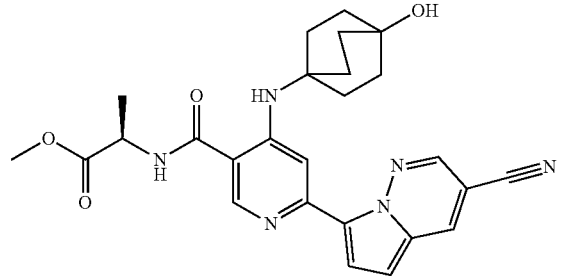 [SMILES: COC(=O)[C@@H](C)NC(=O)c1cnc(-c2ccc3cc(C#N)cnn23)cc1NC12CCC(O)(CC1)CC2] | 340 | 489.3 | 1 | methyl (6-(3-cyano-pyrrolo[1,2-b]pyridazin-7-yl)-4-((4-hydroxy-bicyclo[2.2.2]octan-1-yl)amino)nicotinoyl)-D-alaninate |
| 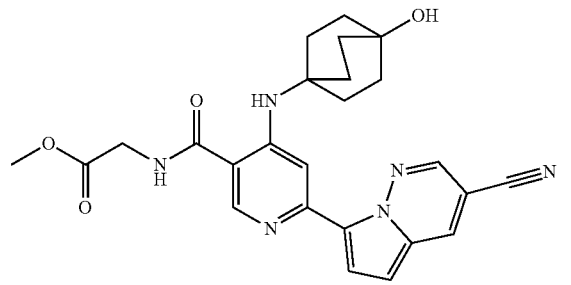 [SMILES: COC(=O)CNC(=O)c1cnc(-c2ccc3cc(C#N)cnn23)cc1NC12CCC(O)(CC1)CC2] | 341 | 475.3 | 1 | methyl (6-(3-cyano-pyrrolo[1,2-b]pyridazin-7-yl)-4-((4-hydroxy-bicyclo[2.2.2]octan-1-yl)amino)nicotinoyl) glycinate |
| 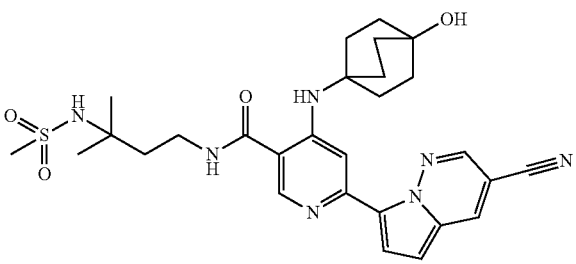 [SMILES: CC(C)(CCNC(=O)c1cnc(-c2ccc3cc(C#N)cnn23)cc1NC12CCC(O)(CC1)CC2)NS(C)(=O)=O] | 342 | 566.3 | 15 | 6-(3-cyanopyrrolo[1,2-b]pyridazin-7-yl)-4-((4-hydroxybicyclo[2.2.2]octan-1-yl)amino)-N-(3-methyl-3-(methyl-sulfonamido)butyl)nicotinamide |

TABLE 1-continued

| Structure | compound | ES/MS m/z | procedure | Name |
|---|---|---|---|---|
| 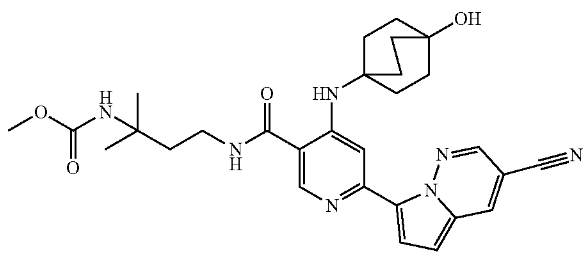 [SMILES: COC(=O)NC(C)(C)CCNC(=O)c1cnc(-c2ccc3cc(C#N)cnn23)cc1NC12CCC(O)(CC1)CC2] | 343 | 546.4 | 46 | methyl (4-(6-(3-cyanopyrrolo[1,2-b]pyridazin-7-yl)-4-((4-hydroxybicyclo[2.2.2]octan-1-yl)amino)nicotinamido)-2-methylbutan-2-yl)carbamate |
| 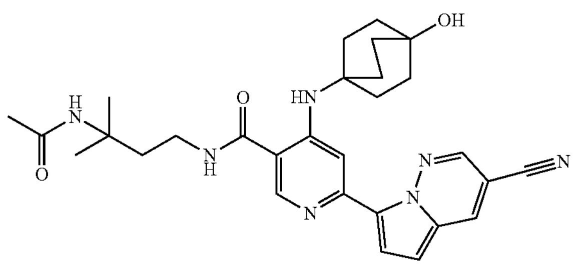 [SMILES: CC(=O)NC(C)(C)CCNC(=O)c1cnc(-c2ccc3cc(C#N)cnn23)cc1NC12CCC(O)(CC1)CC2] | 344 | 530.4 | 13 | N-(3-acetamido-3-methylbutyl)-6-(3-cyanopyrrolo[1,2-b]pyridazin-7-yl)-4-((4-hydroxybicyclo[2.2.2]octan-1-yl)amino)nicotinamide |
| 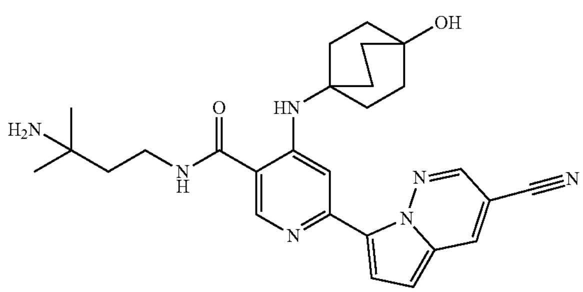 [SMILES: CC(C)(N)CCNC(=O)c1cnc(-c2ccc3cc(C#N)cnn23)cc1NC12CCC(O)(CC1)CC2] | 345 | 488.6 | 45 | N-(3-amino-3-methylbutyl)-6-(3-cyanopyrrolo[1,2-b]pyridazin-7-yl)-4-((4-hydroxybicyclo[2.2.2]octan-1-yl)amino)nicotinamide |
| 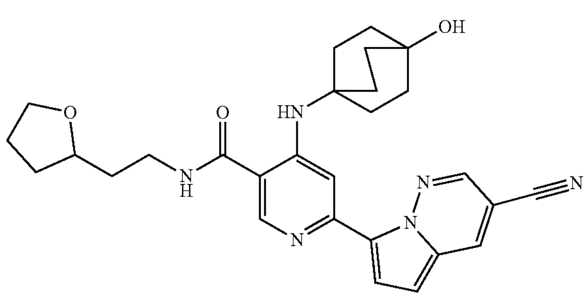 [SMILES: N#Cc1cnn2c(-c3cc(NC45CCC(O)(CC4)CC5)c(C(=O)NCCC4CCCO4)cn3)ccc2c1] | 346 | 501.5 | 1 | 6-(3-cyanopyrrolo[1,2-b]pyridazin-7-yl)-4-((4-hydroxybicyclo[2.2.2]octan-1-yl)amino)-N-(2-(tetrahydrofuran-2-yl)ethyl)nicotinamide |
| 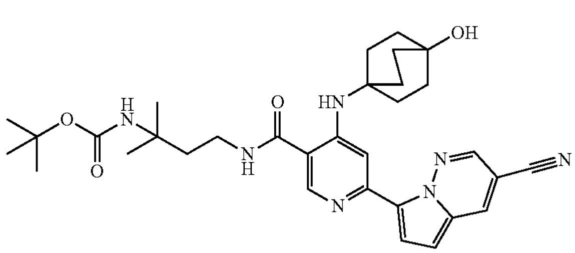 [SMILES: CC(C)(CCNC(=O)c1cnc(-c2ccc3cc(C#N)cnn23)cc1NC12CCC(O)(CC1)CC2)NC(=O)OC(C)(C)C] | 347 | 588.4 | 1 | tert-butyl (4-(6-(3-cyanopyrrolo[1,2-b]pyridazin-7-yl)-4-((4-hydroxybicyclo[2.2.2]octan-1-yl)amino)nicotinamido)-2-methylbutan-2-yl)carbamate |

TABLE 1-continued

| Structure | compound | ES/ MS m/z | procedure | Name |
|---|---|---|---|---|
| 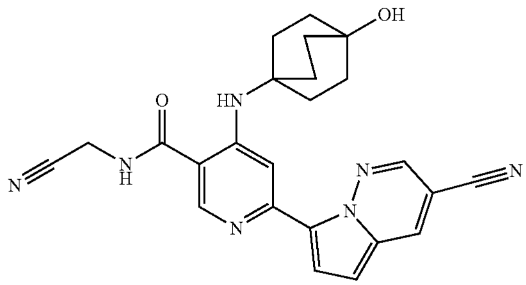 [SMILES: N#CCNC(=O)c1cnc(-c2ccc3cc(C#N)cnn23)cc1NC12CCC(O)(CC1)CC2] | 348 | 442.2 | 1 | N-(cyanomethyl)-6-(3-cyanopyrrolo[1,2-b]pyridazin-7-yl)-4-((4-hydroxybicyclo[2.2.2]octan-1-yl)amino)nicotinamide |
| 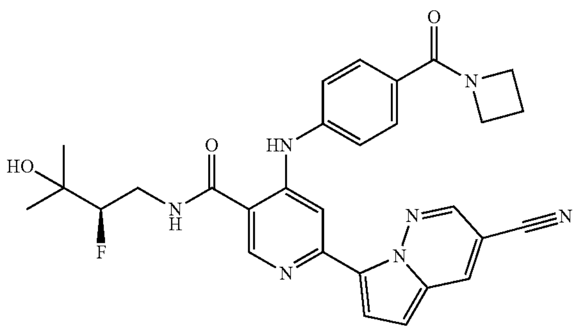 [SMILES: CC(C)(O)[C@H](F)CNC(=O)c1cnc(-c2ccc3cc(C#N)cnn23)cc1Nc1ccc(C(=O)N2CCC2)cc1] | 349 | 542.3 | 51 | (R)-4-((4-(azetidine-1-carbonyl)phenyl)amino)-6-(3-cyanopyrrolo[1,2-b]pyridazin-7-yl)-N-(2-fluoro-3-hydroxy-3-methylbutyl)nicotinamide |
| 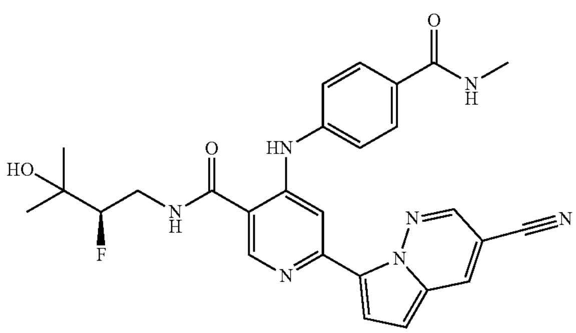 | 350 | 477.5 | 51 | (R)-6-(3-cyanopyrrolo[1,2-b]pyridazin-7-yl)-N-(2-fluoro-3-hydroxy-3-methylbutyl)-4-((4-(methylcarbamoyl)phenyl)amino)nicotinamide |
| 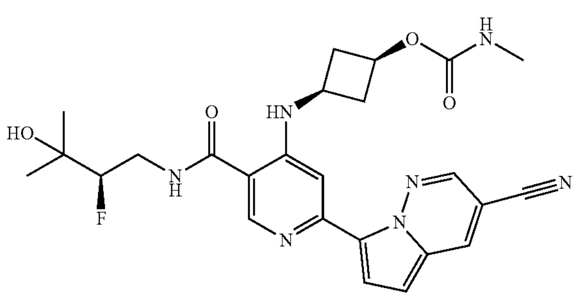 [SMILES: CNC(=O)O[C@H]1C[C@@H](Nc2cc(-c3ccc4cc(C#N)cnn34)ncc2C(=O)NC[C@@H](F)C(C)(C)O)C1] | 351 | 510.3 | 44 | (1S,3s)-3-((2-(3-cyanopyrrolo[1,2-b]pyridazin-7-yl)-5-(((R)-2-fluoro-3-hydroxy-3-methylbutyl)carbamoyl)pyridin-4-yl)amino)cyclobutyl methylcarbamate |
| 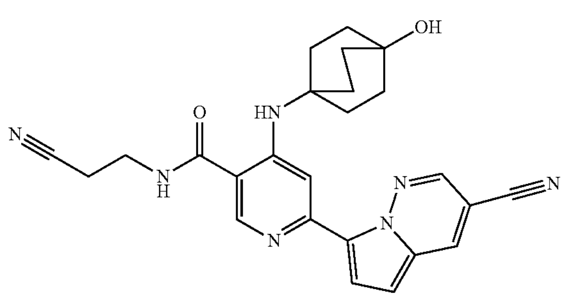 [SMILES: N#CCCNC(=O)c1cnc(-c2ccc3cc(C#N)cnn23)cc1NC12CCC(O)(CC1)CC2] | 352 | 456.3 | 1 | N-(2-cyanoethyl)-6-(3-cyanopyrrolo[1,2-b]pyridazin-7-yl)-4-((4-hydroxybicyclo[2.2.2]octan-1-yl)amino)nicotinamide |

TABLE 1-continued

| Structure | compound | ES/MS m/z | procedure | Name |
|---|---|---|---|---|
| 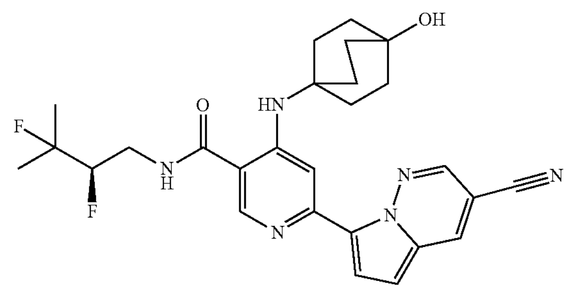 [SMILES: CC(C)(F)[C@H](F)CNC(=O)c1cnc(-c2ccc3cc(C#N)cnn23)cc1NC12CCC(O)(CC1)CC2] | 353 | 509.3 | 1 | (R)-6-(3-cyanopyrrolo[1,2-b]pyridazin-7-yl)-N-(2,3-difluoro-3-methylbutyl)-4-((4-hydroxybicyclo[2.2.2]octan-1-yl)amino)nicotinamide |
| 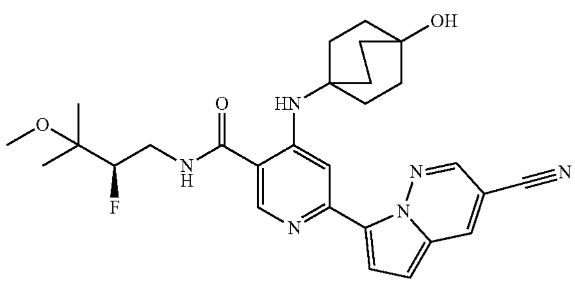 [SMILES: COC(C)(C)[C@H](F)CNC(=O)c1cnc(-c2ccc3cc(C#N)cnn23)cc1NC12CCC(O)(CC1)CC2] | 354 | 521.3 | 1 | (R)-6-(3-cyanopyrrolo[1,2-b]pyridazin-7-yl)-N-(2-fluoro-3-methoxy-3-methylbutyl)-4-((4-hydroxybicyclo[2.2.2]octan-1-yl)amino)nicotinamide |
| 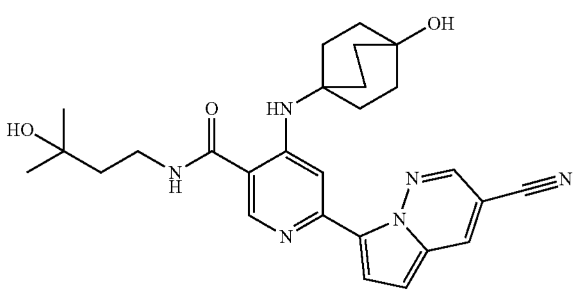 [SMILES: CC(C)(O)CCNC(=O)c1cnc(-c2ccc3cc(C#N)cnn23)cc1NC12CCC(O)(CC1)CC2] | 355 | 489.4 | 1 | 6-(3-cyanopyrrolo[1,2-b]pyridazin-7-yl)-N-(3-hydroxy-3-methylbutyl)-4-((4-hydroxybicyclo[2.2.2]octan-1-yl)amino)nicotinamide |
| 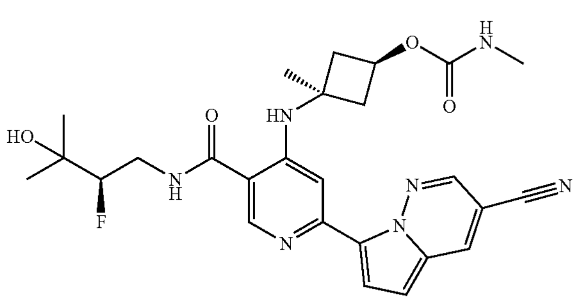 [SMILES: CNC(=O)O[C@H]1C[C@@](C)(Nc2cc(-c3ccc4cc(C#N)cnn34)ncc2C(=O)NC[C@@H](F)C(C)(C)O)C1] | 356 | 524.3 | 56 | (1S,3s)-3-((2-(3-cyano-pyrrolo[1,2-b]pyridazin-7-yl)-5-(((R)-2-fluoro-3-hydroxy-3-methylbutyl)carbamoyl)pyridin-4-yl)amino)-3-methylcyclobutylmethylcarbamate |
| 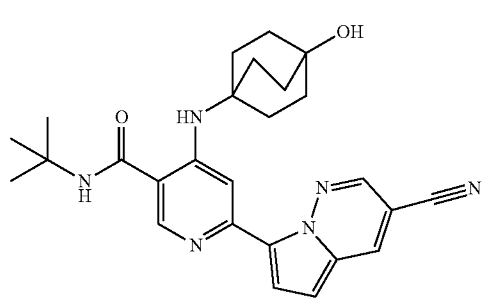 [SMILES: CC(C)(C)NC(=O)c1cnc(-c2ccc3cc(C#N)cnn23)cc1NC12CCC(O)(CC1)CC2] | 357 | 459.5 | 2 | N-(tert-butyl)-6-(3-cyano-pyrrolo[1,2-b]pyridazin-7-yl)-4-((4-hydroxybicyclo[2.2.2]octan-1-yl)amino)nicotinamide |

TABLE 1-continued

| Structure | compound | ES/MS m/z | procedure | Name |
|---|---|---|---|---|
| 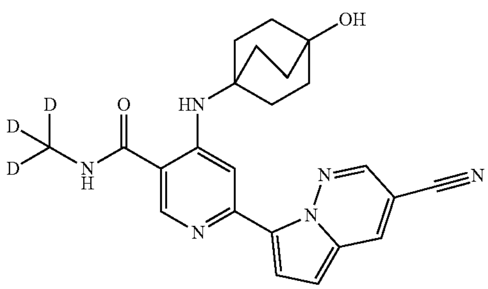 [SMILES: [2H]C([2H])([2H])NC(=O)c1cnc(-c2ccc3cc(C#N)cnn23)cc1NC12CCC(O)(CC1)CC2] | 358 | 420.3 | 2 | 6-(3-cyanopyrrolo[1,2-b]pyridazin-7-yl)-4-((4-hydroxybicyclo[2.2.2]octan-1-yl)amino)-N-(methyl-d3)nicotinamide |
| 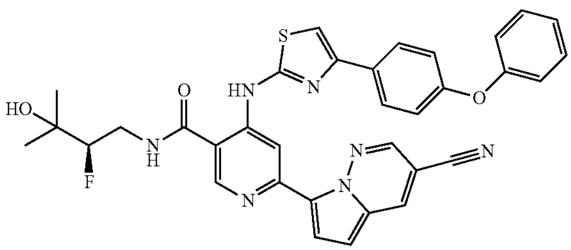 [SMILES: CC(C)(O)[C@H](F)CNC(=O)c1cnc(-c2ccc3cc(C#N)cnn23)cc1Nc1nc(-c2ccc(Oc3ccccc3)cc2)cs1] | 359 | 634.3 | 27 | (R)-6-(3-cyanopyrrolo[1,2-b]pyridazin-7-yl)-N-(2-fluoro-3-hydroxy-3-methylbutyl)-4-((4-(4-phenoxyphenyl)thiazol-2-yl)amino)nicotinamide |
| 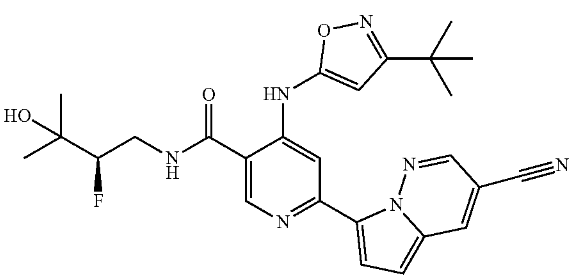 [SMILES: CC(C)(C)c1cc(Nc2cc(-c3ccc4cc(C#N)cnn34)ncc2C(=O)NC[C@@H](F)C(C)(C)O)on1] | 360 | 399.4 | 27 | (R)-4-((3-(tert-butyl)isoxazol-5-yl)amino)-6-(3-cyanopyrrolo[1,2-b]pyridazin-7-yl)-N-(2-fluoro-3-hydroxy-3-methyl-butyl)nicotinamide |
| 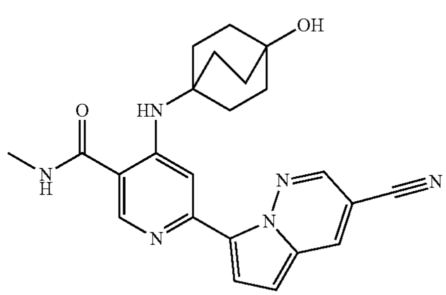 [SMILES: CNC(=O)c1cnc(-c2ccc3cc(C#N)cnn23)cc1NC12CCC(O)(CC1)CC2] | 361 | 417.3 | 1 | 6-(3-cyanopyrrolo[1,2-b]pyridazin-7-yl)-4-((4-hydroxybicyclo[2.2.2]octan-1-yl)amino)-N-methylnicotinamide |
| 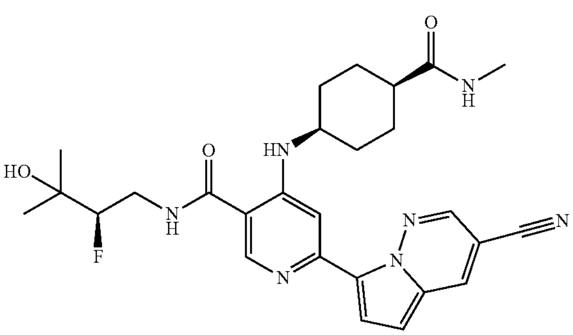 [SMILES: CNC(=O)[C@H]1CC[C@@H](Nc2cc(-c3ccc4cc(C#N)cnn34)ncc2C(=O)NC[C@@H](F)C(C)(C)O)CC1] | 362 | 522.3 | 51 | 6-(3-cyanopyrrolo[1,2-b]pyridazin-7-yl)-N-((R)-2-fluoro-3-hydroxy-3-methylbutyl)-4-(((1s,4S)-4-(methylcarbamoyl)cyclohexyl)amino)nicotinamide |

TABLE 1-continued

| Structure | compound | ES/MS m/z | procedure | Name |
|---|---|---|---|---|
| 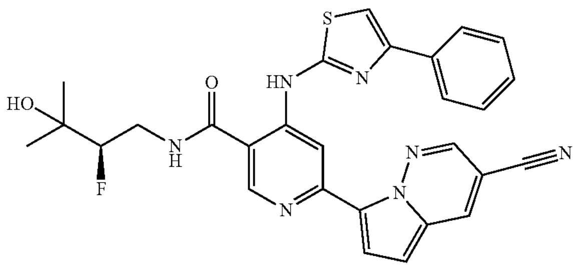 [SMILES: CC(C)(O)[C@H](F)CNC(=O)c1cnc(-c2ccc3cc(C#N)cnn23)cc1Nc1nc(-c2ccccc2)cs1] | 363 | 542.1 | 27 | (R)-6-(3-cyanopyrrolo[1,2-b]pyridazin-7-yl)-N-(2-fluoro-3-hydroxy-3-methylbutyl)-4-((4-phenyl-thiazol-2-yl)amino)nicotinamide |
| 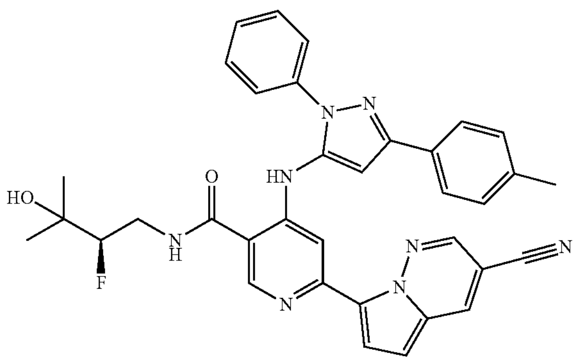 [SMILES: Cc1ccc(-c2cc(Nc3cc(-c4ccc5cc(C#N)cnn45)ncc3C(=O)NC[C@@H](F)C(C)(C)O)n(-c3ccccc3)n2)cc1] | 364 | 615.3 | 27 | (R)-6-(3-cyanopyrrolo[1,2-b]pyridazin-7-yl)-N-(2-fluoro-3-hydroxy-3-methylbutyl)-4-((1-phenyl-3-(p-tolyl)-1H-pyrazol-5-yl)amino)nicotinamide |
| 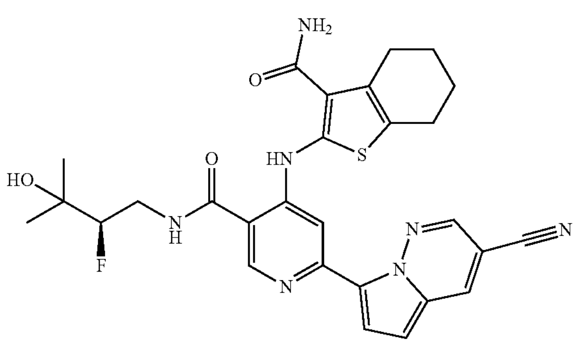 [SMILES: CC(C)(O)[C@H](F)CNC(=O)c1cnc(-c2ccc3cc(C#N)cnn23)cc1Nc1sc2c(c1C(N)=O)CCCC2] | 365 | 562.1 | 27 | (R)-4-((3-carbamoyl-4,5,6,7-tetrahydrobenzo[b]thiophen-2-yl)amino)-6-(3-cyanopyrrolo[1,2-b]pyridazin-7-yl)-N-(2-fluoro-3-hydroxy-3-methylbutyl)nicotinamide |
| 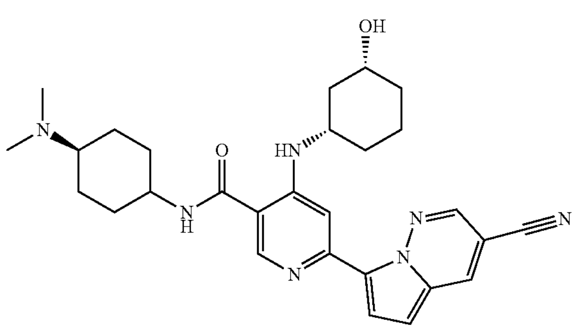 | 366 | 502.3 | 43 | 6-(3-cyanopyrrolo[1,2-b]pyridazin-7-yl)-N-((1r,4S)-4-(dimethylamino)cyclohexyl)-4-(((1S,3R)-3-hydroxycyclohexyl)amino)nicotinamide |

TABLE 1-continued

| Structure | compound | ES/MS m/z | procedure | Name |
|---|---|---|---|---|
| 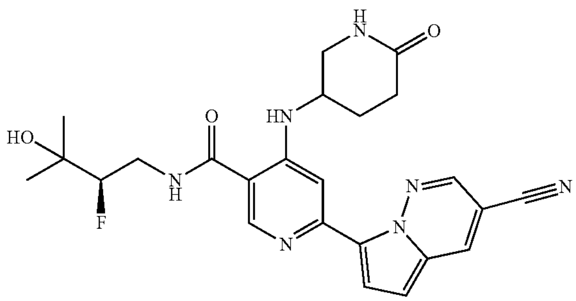 [SMILES: CC(C)(O)[C@H](F)CNC(=O)c1cnc(-c2ccc3cc(C#N)cnn23)cc1NC1CCC(=O)NC1] | 367 | 373.1 | 2 | 6-(3-cyanopyrrolo[1,2-b]pyridazin-7-yl)-N-((R)-2-fluoro-3-hydroxy-3-methylbutyl)-4-((6-oxopiperidin-3-yl)amino)nicotinamide |
| 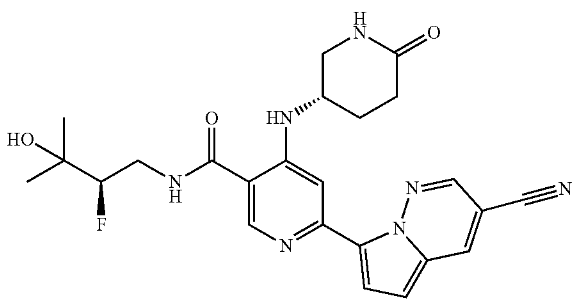 [SMILES: CC(C)(O)[C@H](F)CNC(=O)c1cnc(-c2ccc3cc(C#N)cnn23)cc1N[C@H]1CCC(=O)NC1] | 368 | 373.1 | 2 | 6-(3-cyanopyrrolo[1,2-b]pyridazin-7-yl)-N-((R)-2-fluoro-3-hydroxy-3-methylbutyl)-4-(((S)-6-oxopiperidin-3-yl)amino)nicotinamide |
| 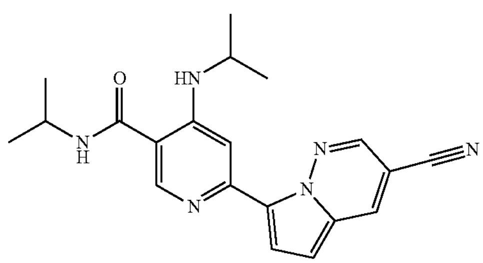 [SMILES: CC(C)NC(=O)c1cnc(-c2ccc3cc(C#N)cnn23)cc1NC(C)C] | 369 | 363.3 | 43 | 6-(3-cyanopyrrolo[1,2-b]pyridazin-7-yl)-N-isopropyl-4-(isopropylamino)nicotinamide |
| 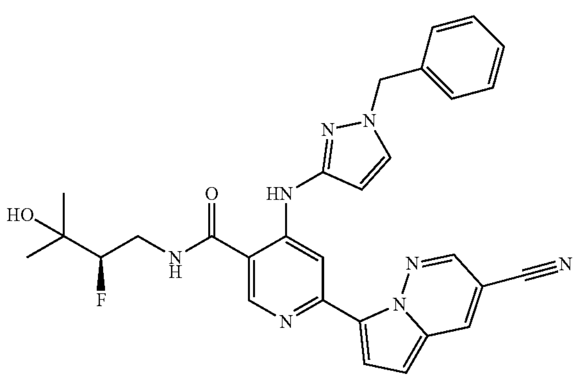 [SMILES: CC(C)(O)[C@H](F)CNC(=O)c1cnc(-c2ccc3cc(C#N)cnn23)cc1Nc1ccn(Cc2ccccc2)n1] | 370 | 539.2 | 2 | (R)-4-((1-benzyl-1H-pyrazol-3-yl)amino)-6-(3-cyanopyrrolo[1,2-b]pyridazin-7-yl)-N-(2-fluoro-3-hydroxy-3-methylbutyl)nicotinamide |
| 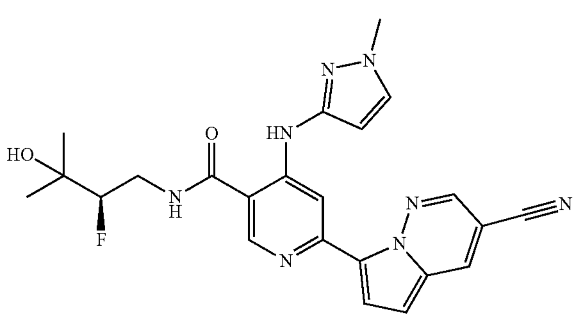 [SMILES: Cn1ccc(Nc2cc(-c3ccc4cc(C#N)cnn34)ncc2C(=O)NC[C@@H](F)C(C)(C)O)n1] | 371 | 463.2 | 2 | (R)-6-(3-cyanopyrrolo[1,2-b]pyridazin-7-yl)-N-(2-fluoro-3-hydroxy-3-methylbutyl)-4-((1-methyl-1H-pyrazol-3-yl)amino)nicotinamide |

TABLE 1-continued

| Structure | compound | ES/MS m/z | procedure | Name |
|---|---|---|---|---|
| 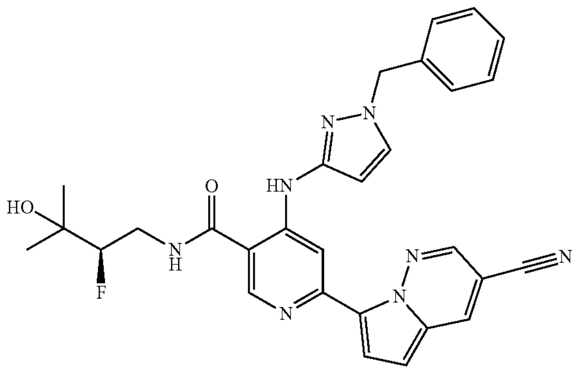 [SMILES: CC(C)(O)[C@H](F)CNC(=O)c1cnc(-c2ccc3cc(C#N)cnn23)cc1Nc1ccn(Cc2ccccc2)n1] | 372 | 539.4 | 2 | (R)-4-((1-benzyl-1H-pyrazol-4-yl)amino)-6-(3-cyanopyrrolo[1,2-b]pyridazin-7-yl)-N-(2-fluoro-3-hydroxy-3-methylbutyl)nicotinamide |
| 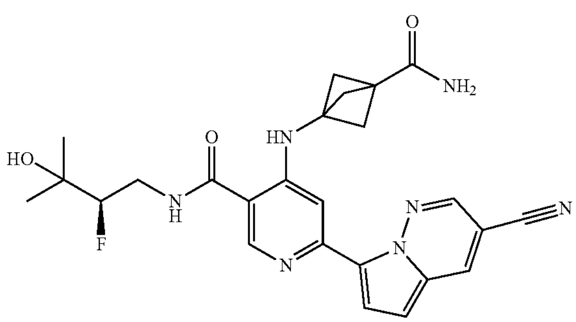 [SMILES: CC(C)(O)[C@H](F)CNC(=O)c1cnc(-c2ccc3cc(C#N)cnn23)cc1NC12CC(C(N)=O)(C1)C2] | 373 | 492.1 | 42 | (R)-4-((3-carbamoyl-bicyclo[1.1.1]pentan-1-yl)amino)-6-(3-cyano-pyrrolo[1,2-b]pyridazin-7-yl)-N-(2-fluoro-3-hydroxy-3-methylbutyl)nicotinamide |
| 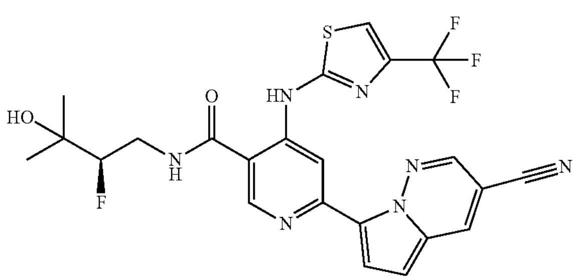 [SMILES: CC(C)(O)[C@H](F)CNC(=O)c1cnc(-c2ccc3cc(C#N)cnn23)cc1Nc1nc(C(F)(F)F)cs1] | 374 | 534.1 | 41 | (R)-6-(3-cyanopyrrolo[1,2-b]pyridazin-7-yl)-N-(2-fluoro-3-hydroxy-3-methylbutyl)-4-((4-(trifluoromethyl)thiazol-2-yl)amino)nicotinamide |
| 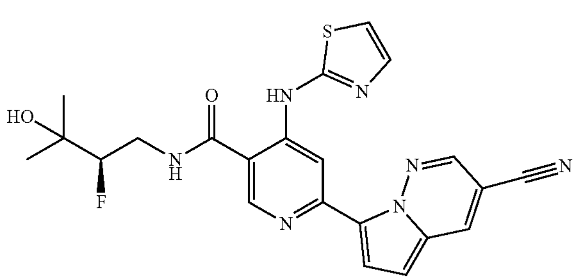 [SMILES: CC(C)(O)[C@H](F)CNC(=O)c1cnc(-c2ccc3cc(C#N)cnn23)cc1Nc1nccs1] | 375 | 466.1 | 41 | (R)-6-(3-cyanopyrrolo[1,2-b]pyridazin-7-yl)-N-(2-fluoro-3-hydroxy-3-methylbutyl)-4-(thiazol-2-ylamino)nicotinamide |

TABLE 1-continued

| compound | ES/MS m/z | procedure | Name |
|---|---|---|---|
| 376 | 546.1 | 41 | (R)-6-(3-cyanopyrrolo[1,2-b]pyridazin-7-yl)-N-(2-fluoro-3-hydroxy-3-methylbutyl)-4-((6-methoxybenzo[d]thiazol-2-yl)amino)nicotinamide |
| 377 | 516.1 | 41 | (R)-4-(benzo[d]thiazol-2-ylamino)-6-(3-cyano-pyrrolo[1,2-b]pyridazin-7-yl)-N-(2-fluoro-3-hydroxy-3-methylbutyl)nicotinamide |
| 378 | 474.3 | 2 | (R)-4-((3-cyano-bicyclo[1.1.1]pentan-1-yl)amino)-6-(3-cyano-pyrrolo[1,2-b]pyridazin-7-yl)-N-(2-fluoro-3-hydroxy-3-methylbutyl)nicotinamide |
| 379 | 397.3 | 2 | (R)-6-(3-cyanopyrrolo[1,2-b]pyridazin-7-yl)-N-(2-fluoro-3-hydroxy-3-methylbutyl)-4-(methyl-amino)nicotinamide |
| 380 | 412.3 | 1 | N-(3-cyanobicyclo[1.1.1]pentan-1-yl)-6-(3-cyano-pyrrolo[1,2-b]pyridazin-7-yl)-4-(isopropylamino)nicotinamide |

TABLE 1-continued

| Structure | compound | ES/MS m/z | procedure | Name |
|---|---|---|---|---|
| 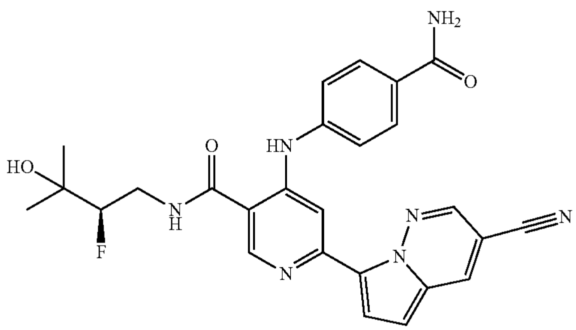 [SMILES: CC(C)(O)[C@H](F)CNC(=O)c1cnc(-c2ccc3cc(C#N)cnn23)cc1Nc1ccc(C(N)=O)cc1] | 381 | 502.3 | 65 | (R)-4-((4-carbamoylphenyl)amino)-6-(3-cyanopyrrolo[1,2-b]pyridazin-7-yl)-N-(2-fluoro-3-hydroxy-3-methylbutyl)nicotinamide |
| 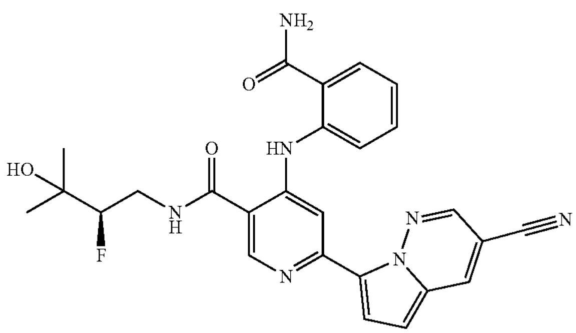 [SMILES: CC(C)(O)[C@H](F)CNC(=O)c1cnc(-c2ccc3cc(C#N)cnn23)cc1Nc1ccccc1C(N)=O] | 382 | 502.2 | 65 | (R)-4-((2-carbamoylphenyl)amino)-6-(3-cyanopyrrolo[1,2-b]pyridazin-7-yl)-N-(2-fluoro-3-hydroxy-3-methylbutyl)nicotinamide |
| 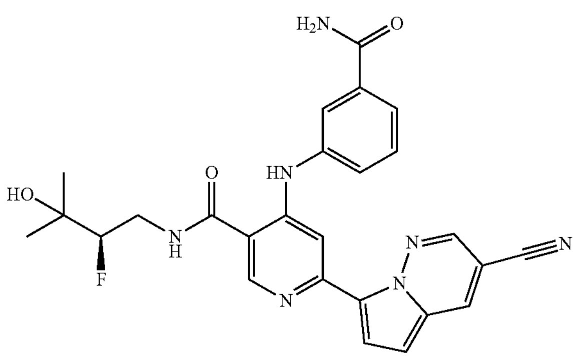 [SMILES: CC(C)(O)[C@H](F)CNC(=O)c1cnc(-c2ccc3cc(C#N)cnn23)cc1Nc1cccc(C(N)=O)c1] | 383 | 502.2 | 65 | (R)-4-((3-carbamoylphenyl)amino)-6-(3-cyanopyrrolo[1,2-b]pyridazin-7-yl)-N-(2-fluoro-3-hydroxy-3-methylbutyl)nicotinamide |
| 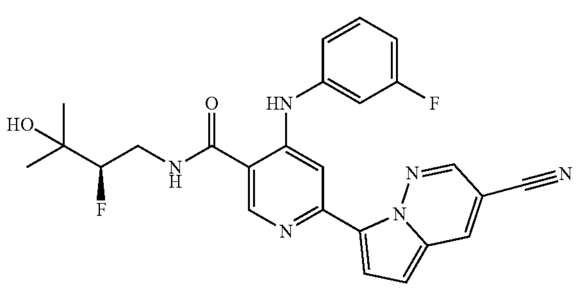 [SMILES: CC(C)(O)[C@H](F)CNC(=O)c1cnc(-c2ccc3cc(C#N)cnn23)cc1Nc1cccc(F)c1] | 384 | 477.2 | 24 | (R)-6-(3-cyanopyrrolo[1,2-b]pyridazin-7-yl)-N-(2-fluoro-3-hydroxy-3-methylbutyl)-4-((3-fluorophenyl)amino)nicotinamide |

TABLE 1-continued

| Structure | compound | ES/ MS m/z | procedure | Name |
|---|---|---|---|---|
| 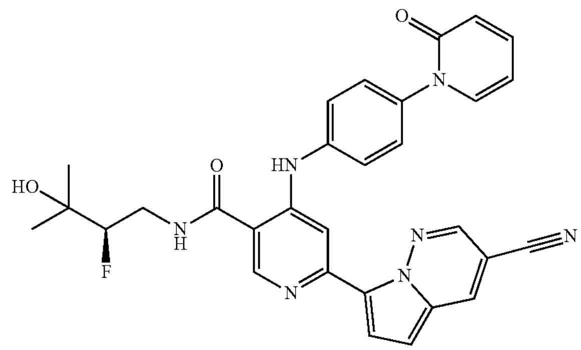 [SMILES: CC(C)(O)[C@H](F)CNC(=O)c1cnc(-c2ccc3cc(C#N)cnn23)cc1Nc1ccc(-n2ccccc2=O)cc1] | 385 | 552.3 | 2 | (R)-6-(3-cyanopyrrolo[1,2-b]pyridazin-7-yl)-N-(2-fluoro-3-hydroxy-3-methylbutyl)-4-((4-(2-oxopyridin-1(2H)-yl)phenyl)amino)nicotinamide |
| 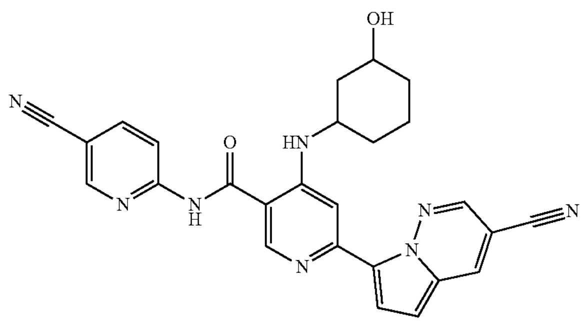 [SMILES: N#Cc1ccc(NC(=O)c2cnc(-c3ccc4cc(C#N)cnn34)cc2NC2CCCC(O)C2)nc1] | 386 | 479.3 | 55 | N-(5-cyanopyridin-2-yl)-6-(3-cyanopyrrolo[1,2-b]pyridazin-7-yl)-4-(((1S,3R)-3-hydroxycyclohexyl)amino)nicotinamide |
| 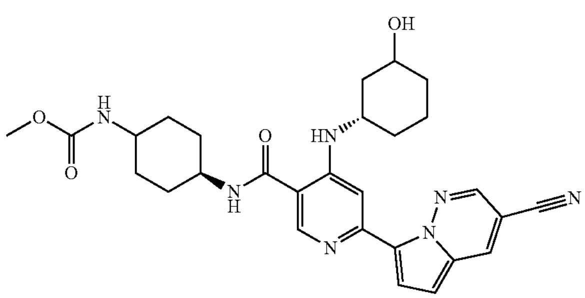 | 387 | 532.4 | 1 | methyl ((1S,4r)-4-(6-(3-cyanopyrrolo[1,2-b]pyridazin-7-yl)-4-(((1S,3R)-3-hydroxy-cyclohexyl)amino)nicotinamido)cyclohexyl)carbamate |
| 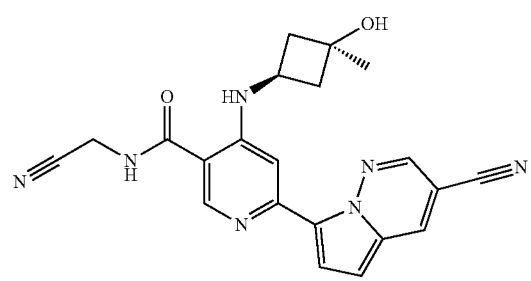 [SMILES: C[C@]1(O)C[C@@H](Nc2cc(-c3ccc4cc(C#N)cnn34)ncc2C(=O)NCC#N)C1] | 388 | 402.3 | 2 | N-(cyanomethyl)-6-(3-cyanopyrrolo[1,2-b]pyridazin-7-yl)-4-(((1s,3s)-3-hydroxy-3-methylcyclobutyl)amino)nicotinamide |
| 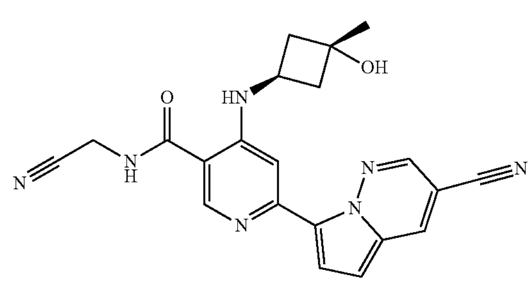 [SMILES: C[C@]1(O)C[C@H](Nc2cc(-c3ccc4cc(C#N)cnn34)ncc2C(=O)NCC#N)C1] | 389 | 402.4 | 2 | N-(cyanomethyl)-6-(3-cyanopyrrolo[1,2-b]pyridazin-7-yl)-4-(((1r,3r)-3-hydroxy-3-methylcyclobutyl)amino)nicotinamide |

TABLE 1-continued

| Structure | compound | ES/MS m/z | procedure | Name |
|---|---|---|---|---|
| 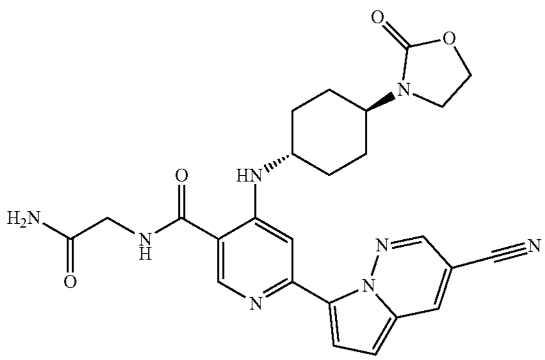 [SMILES: N#Cc1cnn2c(-c3cc(N[C@H]4CC[C@H](N5CCOC5=O)CC4)c(C(=O)NCC(N)=O)cn3)ccc2c1] | 390 | 503.3 | 50 | N-(2-amino-2-oxoethyl)-6-(3-cyanopyrrolo[1,2-b]pyridazin-7-yl)-4-(((1r,4r)-4-(2-oxooxazolidin-3-yl)cyclohexyl)amino)nicotinamide |
| 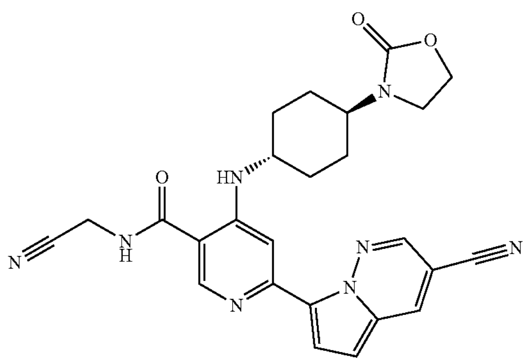 [SMILES: N#CCNC(=O)c1cnc(-c2ccc3cc(C#N)cnn23)cc1N[C@H]1CC[C@H](N2CCOC2=O)CC1] | 391 | 485.3 | 50 | N-(cyanomethyl)-6-(3-cyanopyrrolo[1,2-b]pyridazin-7-yl)-4-(((1r,4r)-4-(2-oxooxazolidin-3-yl)cyclohexyl)amino)nicotinamide |
| 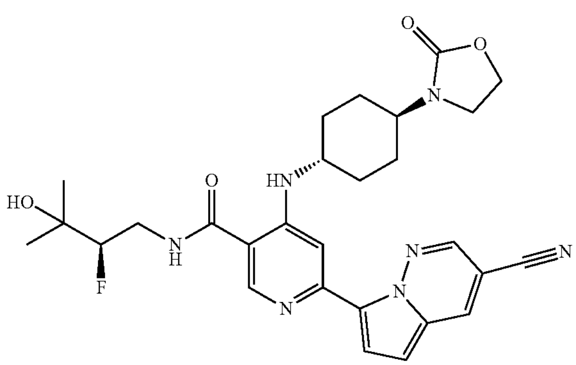 [SMILES: CC(C)(O)[C@H](F)CNC(=O)c1cnc(-c2ccc3cc(C#N)cnn23)cc1N[C@H]1CC[C@H](N2CCOC2=O)CC1] | 392 | 550.4 | 50 | 6-(3-cyanopyrrolo[1,2-b]pyridazin-7-yl)-N-((R)-2-fluoro-3-hydroxy-3-methylbutyl)-4-(((1r,4R)-4-(2-oxooxazolidin-3-yl)cyclohexyl)amino)nicotinamide |
| 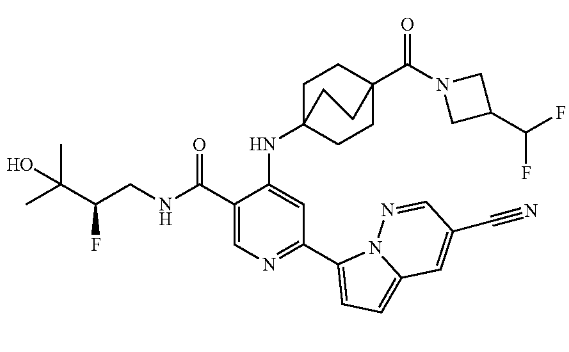 [SMILES: CC(C)(O)[C@H](F)CNC(=O)c1cnc(-c2ccc3cc(C#N)cnn23)cc1NC12CCC(C(=O)N3CC(C(F)F)C3)(CC1)CC2] | 393 | 624.3 | 51 | (R)-6-(3-cyanopyrrolo[1,2-b]pyridazin-7-yl)-4-((4-(3-(difluoromethyl)azetidine-1-carbonyl)bicyclo[2.2.2]octan-1-yl)amino)-N-(2-fluoro-3-hydroxy-3-methylbutyl)nicotinamide |

TABLE 1-continued

| Structure | compound | ES/MS m/z | procedure | Name |
|---|---|---|---|---|
| 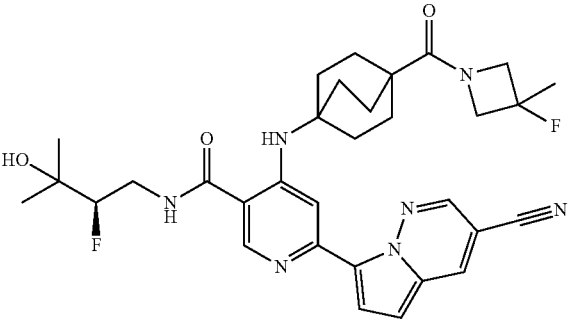 [SMILES: CC1(F)CN(C(=O)C23CCC(Nc4cc(-c5ccc6cc(C#N)cnn56)ncc4C(=O)NC[C@@H](F)C(C)(C)O)(CC2)CC3)C1] | 394 | 606.4 | 51 | (R)-6-(3-cyanopyrrolo[1,2-b]pyridazin-7-yl)-N-(2-fluoro-3-hydroxy-3-methylbutyl)-4-((4-(3-fluoro-3-methylazetidine-1-carbonyl)bicyclo[2.2.2]octan-1-yl)amino)nicotinamide |
| 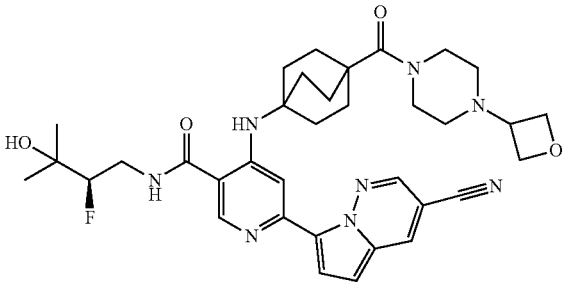 [SMILES: CC(C)(O)[C@H](F)CNC(=O)c1cnc(-c2ccc3cc(C#N)cnn23)cc1NC12CCC(C(=O)N3CCN(C4COC4)CC3)(CC1)CC2] | 395 | 659.4 | 51 | (R)-6-(3-cyanopyrrolo[1,2-b]pyridazin-7-yl)-N-(2-fluoro-3-hydroxy-3-methylbutyl)-4-((4-(4-(oxetan-3-yl)piperazine-1-carbonyl)bicyclo[2.2.2]octan-1-yl)amino)nicotinamide |
| 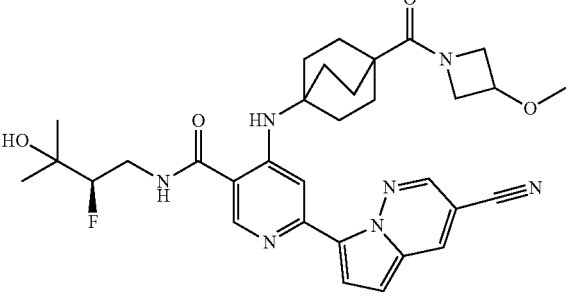 | 396 | 604.4 | 51 | (R)-6-(3-cyanopyrrolo[1,2-b]pyridazin-7-yl)-N-(2-fluoro-3-hydroxy-3-methylbutyl)-4-((4-(3-methoxyazetidine-1-carbonyl)bicyclo[2.2.2]octan-1-yl)amino)nicotinamide |
| 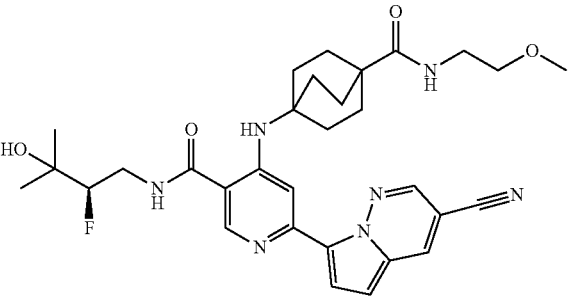 [SMILES: COCCNC(=O)C12CCC(Nc3cc(-c4ccc5cc(C#N)cnn45)ncc3C(=O)NC[C@@H](F)C(C)(C)O)(CC1)CC2] | 397 | 592.4 | 51 | (R)-6-(3-cyanopyrrolo[1,2-b]pyridazin-7-yl)-N-(2-fluoro-3-hydroxy-3-methylbutyl)-4-((4-((2-methoxyethyl)carbamoyl)bicyclo[2.2.2]octan-1-yl)amino)nicotinamide |
| 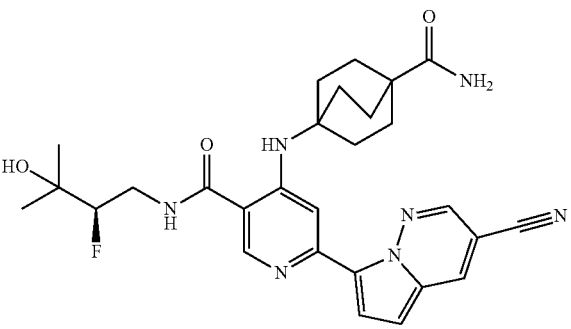 [SMILES: CC(C)(O)[C@H](F)CNC(=O)c1cnc(-c2ccc3cc(C#N)cnn23)cc1NC12CCC(C(N)=O)(CC1)CC2] | 398 | 534.5 | 51 | (R)-4-((4-carbamoylbicyclo[2.2.2]octan-1-yl)amino)-6-(3-cyanopyrrolo[1,2-b]pyridazin-7-yl)-N-(2-fluoro-3-hydroxy-3-methyl-butyl)nicotinamide |

TABLE 1-continued

| Structure | compound | ES/MS m/z | procedure | Name |
|---|---|---|---|---|
| 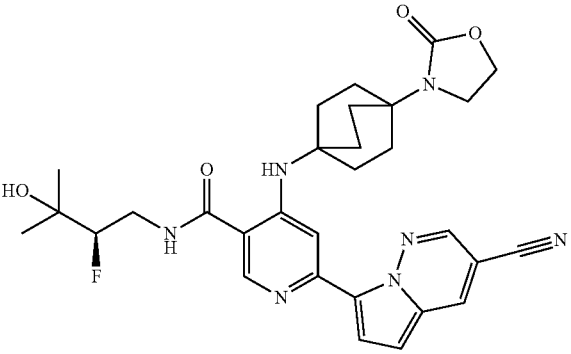 [SMILES: CC(C)(O)[C@H](F)CNC(=O)c1cnc(-c2ccc3cc(C#N)cnn23)cc1NC12CCC(N3CCOC3=O)(CC1)CC2] | 399 | 576.4 | 50 | (R)-6-(3-cyanopyrrolo[1,2-b]pyridazin-7-yl)-N-(2-fluoro-3-hydroxy-3-methylbutyl)-4-((4-(2-oxooxazolidin-3-yl)bicyclo[2.2.2]octan-1-yl)amino)nicotinamide |
| 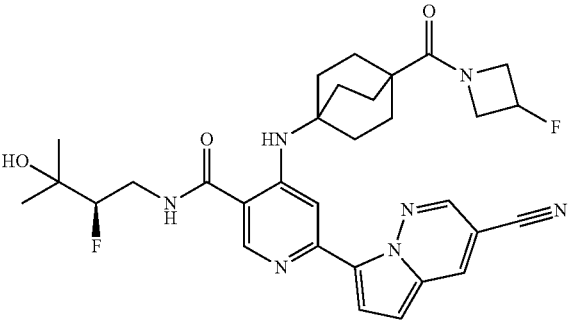 [SMILES: CC(C)(O)[C@H](F)CNC(=O)c1cnc(-c2ccc3cc(C#N)cnn23)cc1NC12CCC(C(=O)N3CC(F)C3)(CC1)CC2] | 400 | 592.4 | 51 | (R)-6-(3-cyanopyrrolo[1,2-b]pyridazin-7-yl)-N-(2-fluoro-3-hydroxy-3-methylbutyl)-4-((4-(3-fluoroazetidine-1-carbonyl)bicyclo[2.2.2]octan-1-yl)amino)nicotinamide |
| 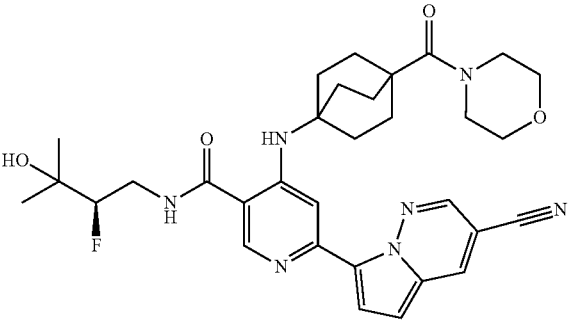 [SMILES: CC(C)(O)[C@H](F)CNC(=O)c1cnc(-c2ccc3cc(C#N)cnn23)cc1NC12CCC(C(=O)N3CCOCC3)(CC1)CC2] | 401 | 604.4 | 51 | (R)-6-(3-cyanopyrrolo[1,2-b]pyridazin-7-yl)-N-(2-fluoro-3-hydroxy-3-methylbutyl)-4-((4-(morpholine-4-carbonyl)bicyclo[2.2.2]octan-1-yl)amino)nicotinamide |
| 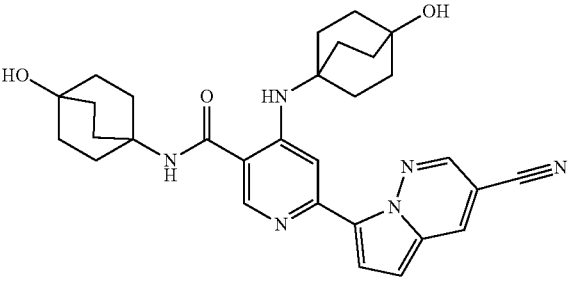 [SMILES: N#Cc1cnn2c(-c3cc(NC45CCC(O)(CC4)CC5)c(C(=O)NC45CCC(O)(CC4)CC5)cn3)ccc2c1] | 402 | 527.4 | 1 | 6-(3-cyanopyrrolo[1,2-b]pyridazin-7-yl)-N-(4-hydroxybicyclo[2.2.2]octan-1-yl)-4-((4-hydroxybicyclo[2.2.2]octan-1-yl)amino)nicotinamide |

TABLE 1-continued

| Structure | compound | ES/MS m/z | procedure | Name |
|---|---|---|---|---|
| 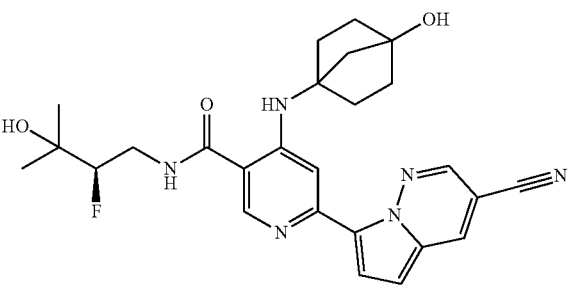 [SMILES: CC(C)(O)[C@H](F)CNC(=O)c1cnc(-c2ccc3cc(C#N)cnn23)cc1NC12CCC(O)(CC1)C2] | 403 | 493.4 | 2 | (R)-6-(3-cyanopyrrolo[1,2-b]pyridazin-7-yl)-N-(2-fluoro-3-hydroxy-3-methylbutyl)-4-((4-hydroxybicyclo[2.2.1]heptan-1-yl)amino)nicotinamide |
| 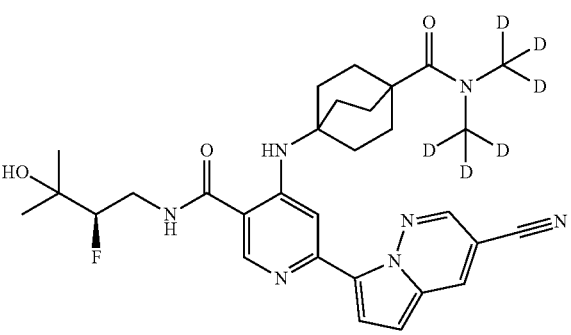 [SMILES: [2H]C([2H])([2H])N(C(=O)C12CCC(Nc3cc(-c4ccc5cc(C#N)cnn45)ncc3C(=O)NC[C@@H](F)C(C)(C)O)(CC1)CC2)C([2H])([2H])[2H]] | 404 | 568.5 | 51 | (R)-4-((4-(bis(methyl-d3)carbamoyl)bicyclo[2.2.2]octan-1-yl)amino)-6-(3-cyanopyrrolo[1,2-b]pyridazin-7-yl)-N-(2-fluoro-3-hydroxy-3-methylbutyl)nicotinamide |
| 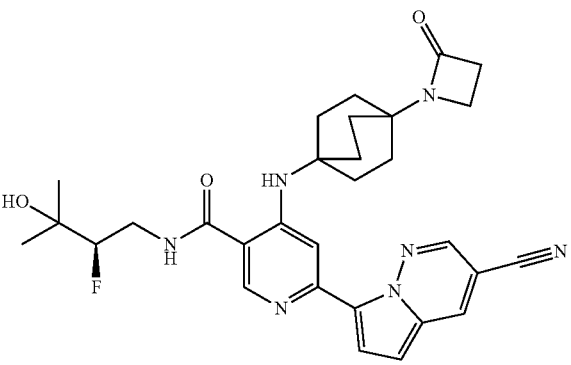 [SMILES: CC(C)(O)[C@H](F)CNC(=O)c1cnc(-c2ccc3cc(C#N)cnn23)cc1NC12CCC(N3CCC3=O)(CC1)CC2] | 405 | 560.5 | 52 | (R)-6-(3-cyanopyrrolo[1,2-b]pyridazin-7-yl)-N-(2-fluoro-3-hydroxy-3-methylbutyl)-4-((4-(2-oxoazetidin-1-yl)bicyclo[2.2.2]octan-1-yl)amino)nicotinamide |
| 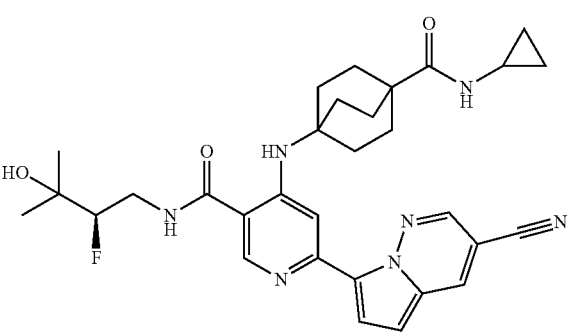 [SMILES: CC(C)(O)[C@H](F)CNC(=O)c1cnc(-c2ccc3cc(C#N)cnn23)cc1NC12CCC(C(=O)NC3CC3)(CC1)CC2] | 406 | 574.4 | 51 | (R)-6-(3-cyanopyrrolo[1,2-b]pyridazin-7-yl)-4-((4-(cyclopropylcarbamoyl)bicyclo[2.2.2]octan-1-yl)amino)-N-(2-fluoro-3-hydroxy-3-methylbutyl)nicotinamide |

TABLE 1-continued

| Structure | compound | ES/MS m/z | procedure | Name |
|---|---|---|---|---|
| 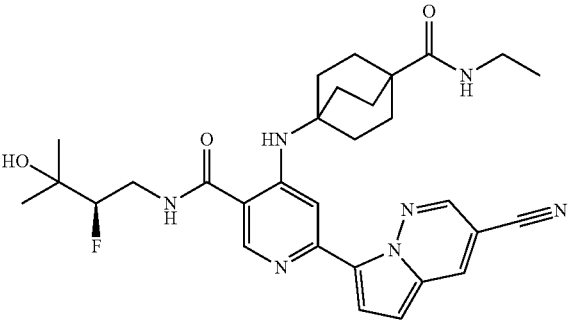 [SMILES: CCNC(=O)C12CCC(Nc3cc(-c4ccc5cc(C#N)cnn45)ncc3C(=O)NC[C@@H](F)C(C)(C)O)(CC1)CC2] | 407 | 562.5 | 51 | (R)-6-(3-cyanopyrrolo[1,2-b]pyridazin-7-yl)-4-((4-(ethylcarbamoyl)bicyclo[2.2.2]octan-1-yl)amino)-N-(2-fluoro-3-hydroxy-3-methylbutyl)nicotinamide |
| 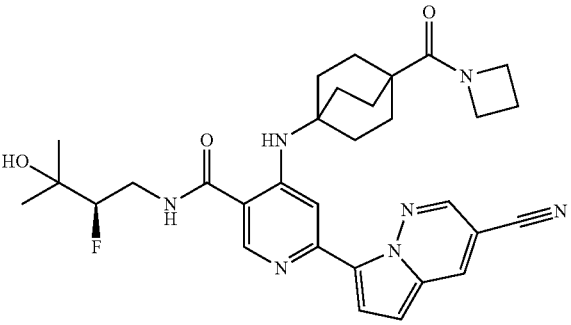 [SMILES: CC(C)(O)[C@H](F)CNC(=O)c1cnc(-c2ccc3cc(C#N)cnn23)cc1NC12CCC(C(=O)N3CCC3)(CC1)CC2] | 408 | 574.5 | 51 | (R)-4-((4-(azetidine-1-carbonyl)bicyclo[2.2.2]octan-1-yl)amino)-6-(3-cyanopyrrolo[1,2-b]pyridazin-7-yl)-N-(2-fluoro-3-hydroxy-3-methylbutyl)nicotinamide |
| 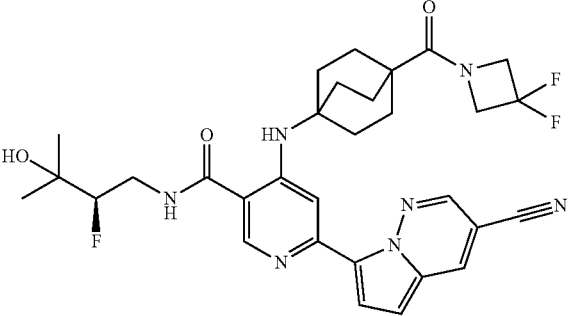 [SMILES: CC(C)(O)[C@H](F)CNC(=O)c1cnc(-c2ccc3cc(C#N)cnn23)cc1NC12CCC(C(=O)N3CC(F)(F)C3)(CC1)CC2] | 409 | 610.5 | 51 | (R)-6-(3-cyanopyrrolo[1,2-b]pyridazin-7-yl)-4-((4-(3,3-difluoroazetidine-1-carbonyl)bicyclo[2.2.2]octan-1-yl)amino)-N-(2-fluoro-3-hydroxy-3-methylbutyl)nicotinamide |
| 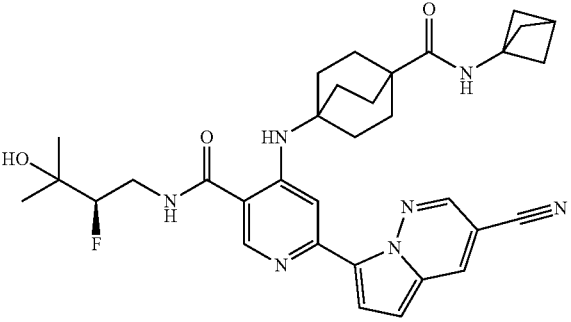 [SMILES: CC(C)(O)[C@H](F)CNC(=O)c1cnc(-c2ccc3cc(C#N)cnn23)cc1NC12CCC(C(=O)NC34CC(C3)C4)(CC1)CC2] | 410 | 600.7 | 51 | (R)-4-((4-(bicyclo[1.1.1]pentan-1-ylcarbamoyl)bicyclo[2.2.2]octan-1-yl)amino)-6-(3-cyanopyrrolo[1,2-b]pyridazin-7-yl)-N-(2-fluoro-3-hydroxy-3-methylbutyl)nicotinamide |

TABLE 1-continued

| Structure | compound | ES/MS m/z | procedure | Name |
|---|---|---|---|---|
| 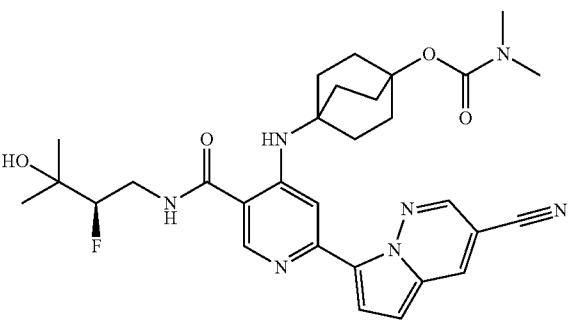 [SMILES: CN(C)C(=O)OC12CCC(Nc3cc(-c4ccc5cc(C#N)cnn45)ncc3C(=O)NC[C@@H](F)C(C)(C)O)(CC1)CC2] | 411 | 578.5 | 56 | (R)-4-((2-(3-cyano-pyrrolo[1,2-b]pyridazin-7-yl)-5-((2-fluoro-3-hydroxy-3-methylbutyl)carbamoyl)pyridin-4-yl)amino)bicyclo[2.2.2]octan-1-yl dimethylcarbamate |
| 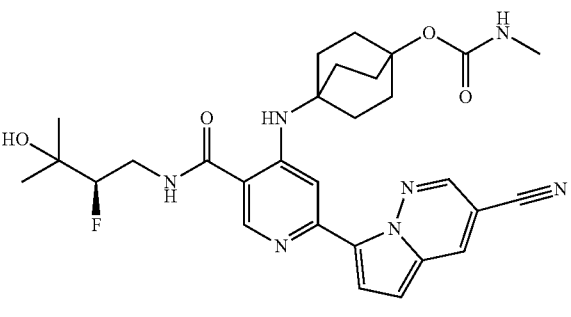 [SMILES: CNC(=O)OC12CCC(Nc3cc(-c4ccc5cc(C#N)cnn45)ncc3C(=O)NC[C@@H](F)C(C)(C)O)(CC1)CC2] | 412 | 564.5 | 56 | (R)-4-((2-(3-cyano-pyrrolo[1,2-b]pyridazin-7-yl)-5-((2-fluoro-3-hydroxy-3-methylbutyl)carbamoyl)pyridin-4-yl)amino)bicyclo[2.2.2]octan-1-yl methylcarbamate |
| 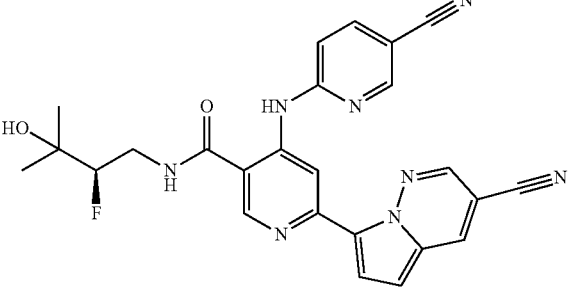 | 413 | 485.2 | 27 | (R)-4-((5-cyanopyridin-2-yl)amino)-6-(3-cyano-pyrrolo[1,2-b]pyridazin-7-yl)-N-(2-fluoro-3-hydroxy-3-methylbutyl)nicotinamide |
| 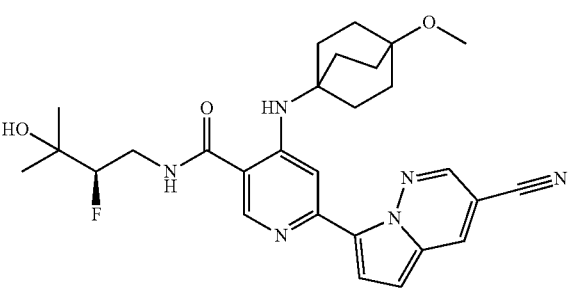 [SMILES: COC12CCC(Nc3cc(-c4ccc5cc(C#N)cnn45)ncc3C(=O)NC[C@@H](F)C(C)(C)O)(CC1)CC2] | 414 | 521.2 | 54 | (R)-6-(3-cyanopyrrolo[1,2-b]pyridazin-7-yl)-N-(2-fluoro-3-hydroxy-3-methylbutyl)-4-((4-methoxybicyclo[2.2.2]octan-1-yl)amino)nicotinamide |
| 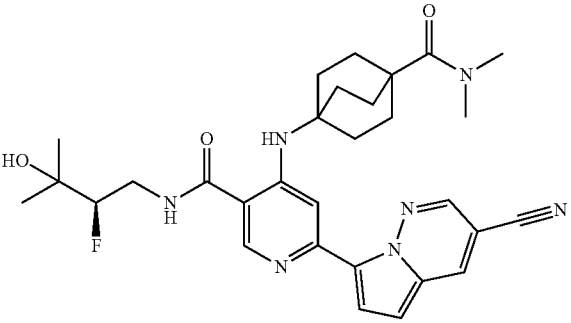 [SMILES: CN(C)C(=O)C12CCC(Nc3cc(-c4ccc5cc(C#N)cnn45)ncc3C(=O)NC[C@@H](F)C(C)(C)O)(CC1)CC2] | 415 | 562.4 | 51 | (R)-6-(3-cyanopyrrolo[1,2-b]pyridazin-7-yl)-4-((4-(dimethylcarbamoyl)bicyclo[2.2.2]octan-1-yl)amino)-N-(2-fluoro-3-hydroxy-3-methylbutyl)nicotinamide |

TABLE 1-continued

| Structure | compound | ES/MS m/z | procedure | Name |
|---|---|---|---|---|
| 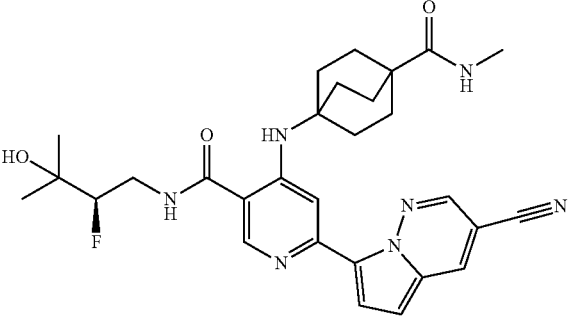 [SMILES: CNC(=O)C12CCC(Nc3cc(-c4ccc5cc(C#N)cnn45)ncc3C(=O)NC[C@@H](F)C(C)(C)O)(CC1)CC2] | 416 | 548.4 | 51 | (R)-6-(3-cyanopyrrolo[1,2-b]pyridazin-7-yl)-N-(2-fluoro-3-hydroxy-3-methylbutyl)-4-((4-(methylcarbamoyl)bicyclo[2.2.2]octan-1-yl)amino)nicotinamide |
| 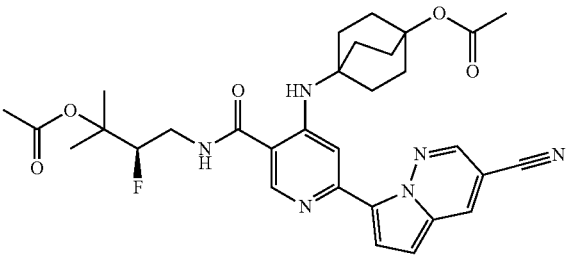 [SMILES: CC(=O)OC12CCC(Nc3cc(-c4ccc5cc(C#N)cnn45)ncc3C(=O)NC[C@@H](F)C(C)(C)OC(C)=O)(CC1)CC2] | 417 | 591.4 | 53 | (R)-4-((5-((3-acetoxy-2-fluoro-3-methylbutyl)carbamoyl)-2-(3-cyanopyrrolo[1,2-b]pyridazin-7-yl)pyridin-4-yl)amino)bicyclo[2.2.2]octan-1-yl acetate |
| 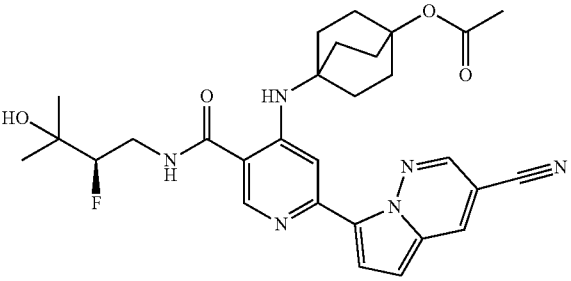 [SMILES: CC(=O)OC12CCC(Nc3cc(-c4ccc5cc(C#N)cnn45)ncc3C(=O)NC[C@@H](F)C(C)(C)O)(CC1)CC2] | 418 | 549.4 | 53 | (R)-4-((2-(3-cyanopyrrolo[1,2-b]pyridazin-7-yl)-5-((2-fluoro-3-hydroxy-3-methylbutyl)carbamoyl)pyridin-4-yl)amino)bicyclo[2.2.2]octan-1-yl acetate |
| 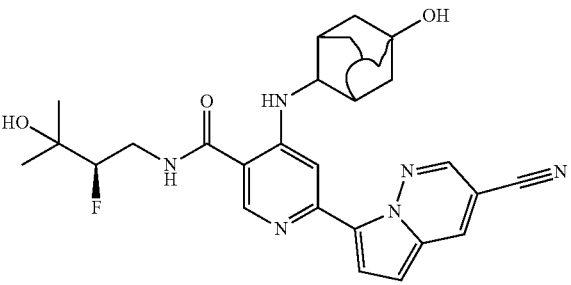 | 419 | 533.4 | 2 | 6-(3-cyanopyrrolo[1,2-b]pyridazin-7-yl)-N-((R)-2-fluoro-3-hydroxy-3-methylbutyl)-4-((5-hydroxyadamantan-2-yl)amino)nicotinamide |
| 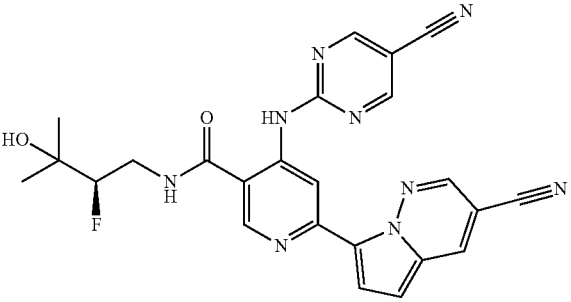 [SMILES: CC(C)(O)[C@H](F)CNC(=O)c1cnc(-c2ccc3cc(C#N)cnn23)cc1Nc1ncc(C#N)cn1] | 420 | 486.1 | 27 | (R)-4-((5-cyanopyrimidin-2-yl)amino)-6-(3-cyanopyrrolo[1,2-b]pyridazin-7-yl)-N-(2-fluoro-3-hydroxy-3-methylbutyl)nicotinamide |

TABLE 1-continued

| Structure | compound | ES/MS m/z | procedure | Name |
|---|---|---|---|---|
| 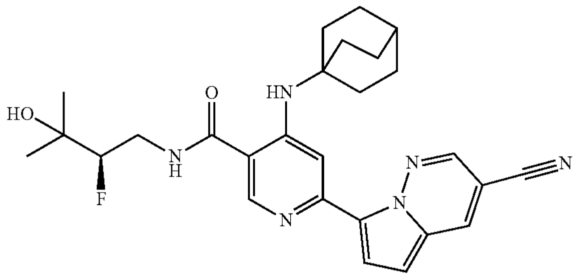 [SMILES: CC(C)(O)[C@H](F)CNC(=O)c1cnc(-c2ccc3cc(C#N)cnn23)cc1NC12CCC(CC1)CC2] | 421 | 491.3 | 2 | (R)-4-(bicyclo[2.2.2]octan-1-ylamino)-6-(3-cyanopyrrolo[1,2-b]pyridazin-7-yl)-N-(2-fluoro-3-hydroxy-3-methylbutyl)nicotinamide |
| 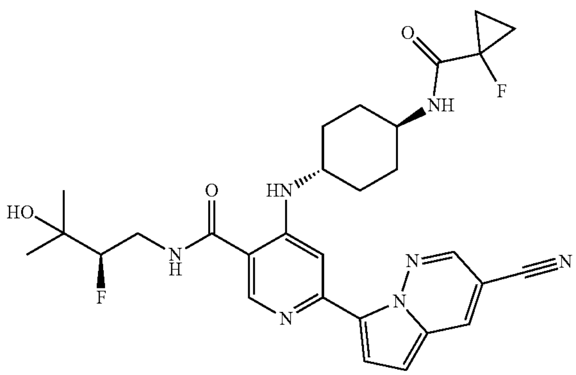 | 422 | 566.3 | 16 | 6-(3-cyanopyrrolo[1,2-b]pyridazin-7-yl)-N-((R)-2-fluoro-3-hydroxy-3-methylbutyl)-4-(((1r,4R)-4-(1-fluorocyclopropane-1-carboxamido)cyclohexyl)amino)nicotinamide |
| 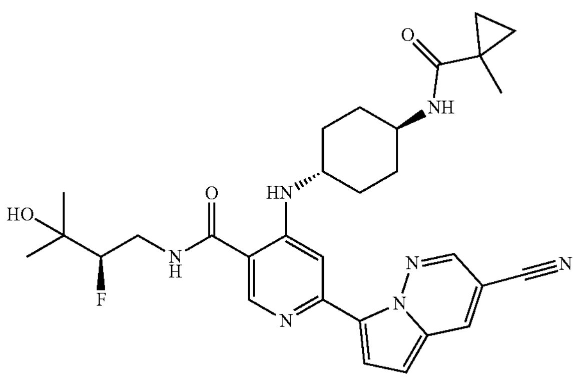 [SMILES: CC1(C(=O)N[C@H]2CC[C@H](Nc3cc(-c4ccc5cc(C#N)cnn45)ncc3C(=O)NC[C@@H](F)C(C)(C)O)CC2)CC1] | 423 | 562.3 | 16 | 6-(3-cyanopyrrolo[1,2-b]pyridazin-7-yl)-N-((R)-2-fluoro-3-hydroxy-3-methylbutyl)-4-(((1r,4R)-4-(1-methylcyclopropane-1-carboxamido)cyclohexyl)amino)nicotinamide |
| 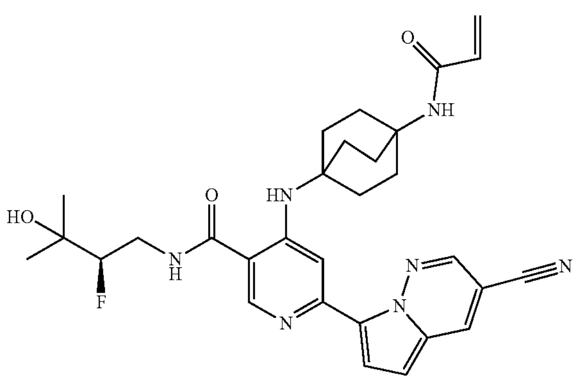 [SMILES: C=CC(=O)NC12CCC(Nc3cc(-c4ccc5cc(C#N)cnn45)ncc3C(=O)NC[C@@H](F)C(C)(C)O)(CC1)CC2] | 424 | 560.3 | 16 | (R)-4-((4-acrylamidobicyclo[2.2.2]octan-1-yl)amino)-6-(3-cyanopyrrolo[1,2-b]pyridazin-7-yl)-N-(2-fluoro-3-hydroxy-3-methylbutyl)nicotinamide |

TABLE 1-continued

| Structure | compound | ES/MS m/z | procedure | Name |
|---|---|---|---|---|
| 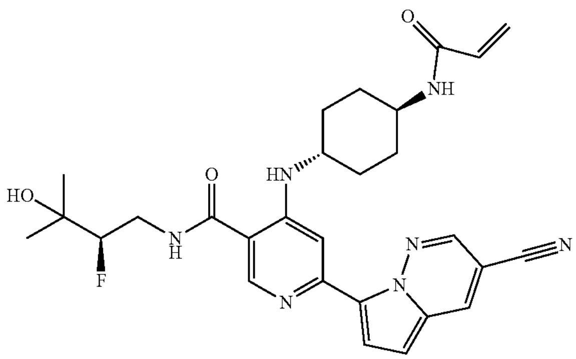 [SMILES: C=CC(=O)N[C@H]1CC[C@H](Nc2cc(-c3ccc4cc(C#N)cnn34)ncc2C(=O)NC[C@@H](F)C(C)(C)O)CC1] | 425 | 534.3 | 16 | 4-(((1r,4R)-4-acrylamidocyclohexyl)amino)-6-(3-cyanopyrrolo[1,2-b]pyridazin-7-yl)-N-((R)-2-fluoro-3-hydroxy-3-methylbutyl)nicotinamide |
| 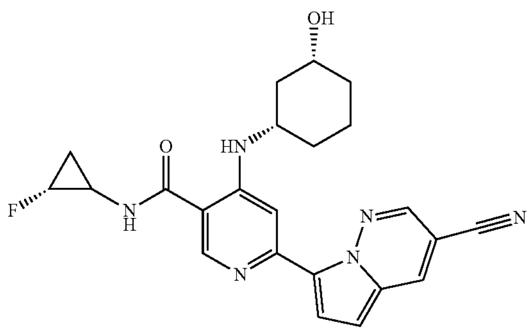 [SMILES: N#Cc1cnn2c(-c3cc(N[C@H]4CCC[C@@H](O)C4)c(C(=O)NC4C[C@H]4F)cn3)ccc2c1] | 426 | 435.2 | 3 | 6-(3-cyanopyrrolo[1,2-b]pyridazin-7-yl)-N-((2R)-2-fluorocyclopropyl)-4-(((1S,3R)-3-hydroxycyclohexyl)amino)nicotinamide |
| 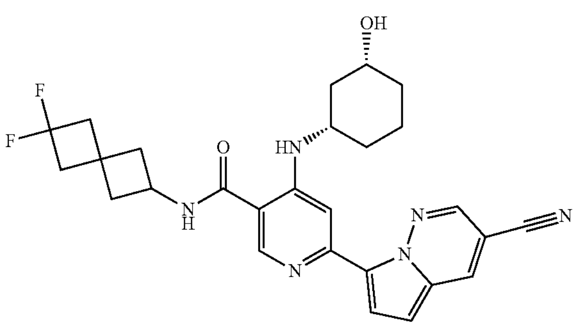 [SMILES: N#Cc1cnn2c(-c3cc(N[C@H]4CCC[C@@H](O)C4)c(C(=O)NC4CC5(C4)CC(F)(F)C5)cn3)ccc2c1] | 427 | 507.3 | 3 | 6-(3-cyanopyrrolo[1,2-b]pyridazin-7-yl)-N-(6,6-difluorospiro[3.3]heptan-2-yl)-4-(((1S,3R)-3-hydroxycyclohexyl)amino)nicotinamide |
| 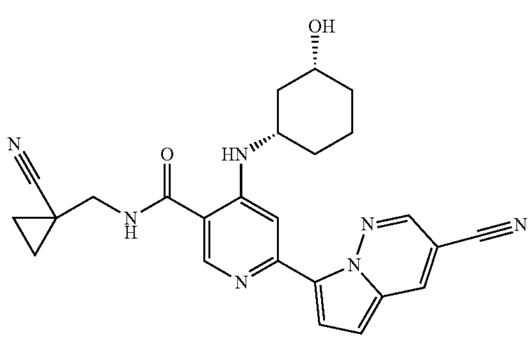 [SMILES: N#Cc1cnn2c(-c3cc(N[C@H]4CCC[C@@H](O)C4)c(C(=O)NCC4(C#N)CC4)cn3)ccc2c1] | 428 | 456.3 | 3 | N-((1-cyanocyclopropyl)methyl)-6-(3-cyanopyrrolo[1,2-b]pyridazin-7-yl)-4-(((1S,3R)-3-hydroxycyclohexyl)amino)nicotinamide |

TABLE 1-continued

| Structure | compound | ES/MS m/z | procedure | Name |
|---|---|---|---|---|
| 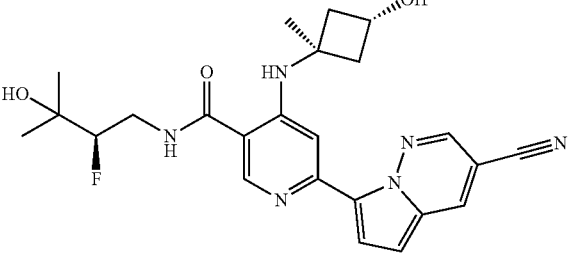 | 429 | 467.2 | 2 | 6-(3-cyanopyrrolo[1,2-b]pyridazin-7-yl)-N-((R)-2-fluoro-3-hydroxy-3-methylbutyl)-4-(((1r,3R)-3-hydroxy-1-methylcyclobutyl)amino)nicotinamide |
| 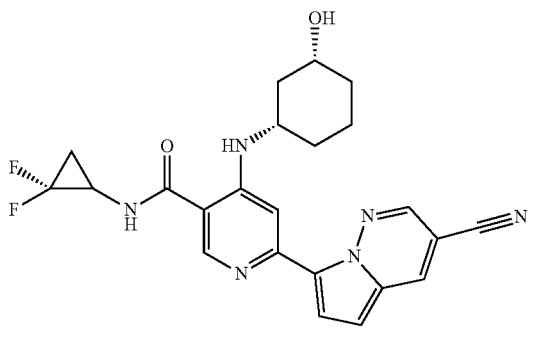 | 430 | 453.2 | 3 | 6-(3-cyanopyrrolo[1,2-b]pyridazin-7-yl)-N-(2,2-difluorocyclopropyl)-4-(((1S,3R)-3-hydroxycyclohexyl)amino)nicotinamide |
| 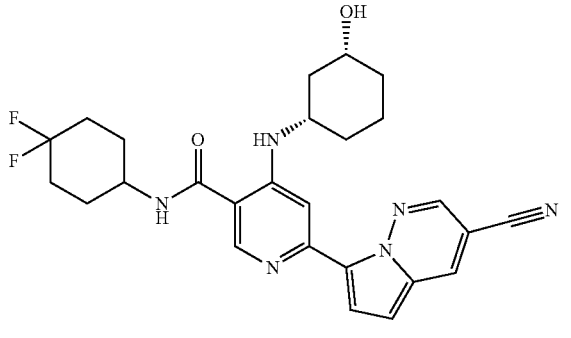 [SMILES: N#Cc1cnn2c(-c3cc(N[C@H]4CCC[C@@H](O)C4)c(C(=O)NC4CCC(F)(F)CC4)cn3)ccc2c1] | 431 | 495.4 | 3 | 6-(3-cyanopyrrolo[1,2-b]pyridazin-7-yl)-N-(4,4-difluorocyclohexyl)-4-(((1S,3R)-3-hydroxycyclohexyl)amino)nicotinamide |
| 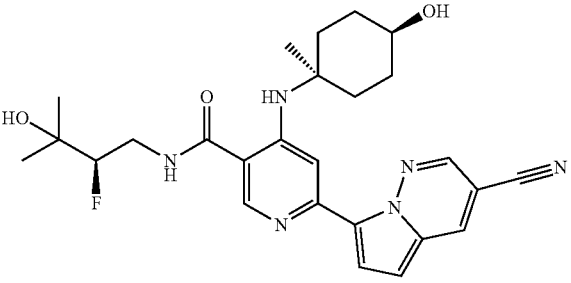 [SMILES: CC(C)(O)[C@H](F)CNC(=O)c1cnc(-c2ccc3cc(C#N)cnn23)cc1N[C@]1(C)CC[C@H](O)CC1] | 432 | 495.2 | 2 | 6-(3-cyanopyrrolo[1,2-b]pyridazin-7-yl)-N-((R)-2-fluoro-3-hydroxy-3-methylbutyl)-4-(((1s,4S)-4-hydroxy-1-methylcyclohexyl)amino)nicotinamide |
| 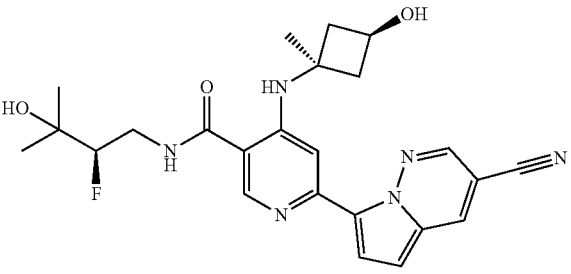 [SMILES: CC(C)(O)[C@H](F)CNC(=O)c1cnc(-c2ccc3cc(C#N)cnn23)cc1N[C@]1(C)C[C@H](O)C1] | 433 | 467.3 | 2 | 6-(3-cyanopyrrolo[1,2-b]pyridazin-7-yl)-N-((R)-2-fluoro-3-hydroxy-3-methylbutyl)-4-(((1s,3S)-3-hydroxy-1-methylcyclobutyl)amino)nicotinamide |

TABLE 1-continued

| Structure | compound | ES/MS m/z | procedure | Name |
|---|---|---|---|---|
| 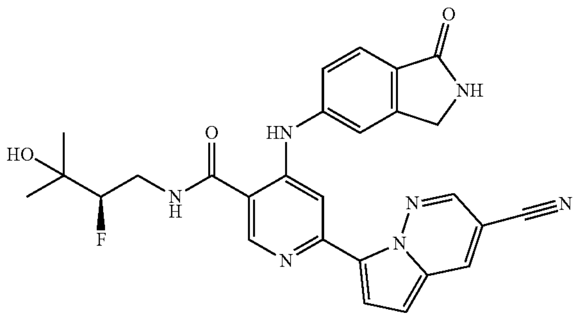 [SMILES: CC(C)(O)[C@H](F)CNC(=O)c1cnc(-c2ccc3cc(C#N)cnn23)cc1Nc1ccc2c(c1)CNC2=O] | 434 | 514.2 | 27 | (R)-6-(3-cyanopyrrolo[1,2-b]pyridazin-7-yl)-N-(2-fluoro-3-hydroxy-3-methylbutyl)-4-((1-oxoisoindolin-5-yl)amino)nicotinamide |
| 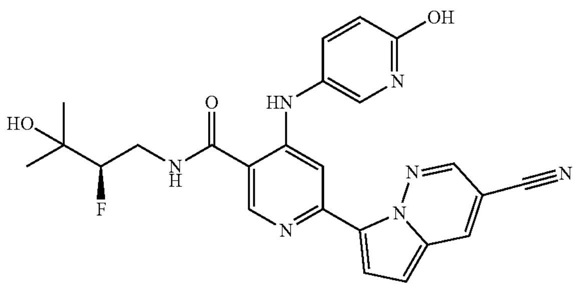 [SMILES: CC(C)(O)[C@H](F)CNC(=O)c1cnc(-c2ccc3cc(C#N)cnn23)cc1Nc1ccc(O)nc1] | 435 | 476.1 | 27 | (R)-6-(3-cyanopyrrolo[1,2-b]pyridazin-7-yl)-N-(2-fluoro-3-hydroxy-3-methylbutyl)-4-((6-hydroxypyridin-3-yl)amino)nicotinamide |
| 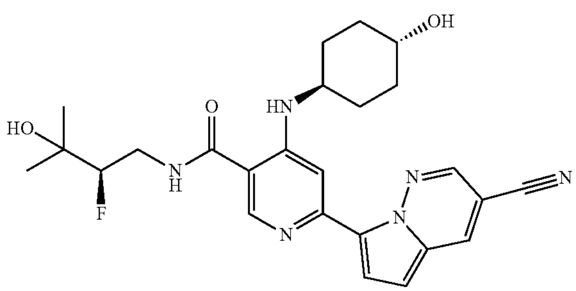 [SMILES: CC(C)(O)[C@H](F)CNC(=O)c1cnc(-c2ccc3cc(C#N)cnn23)cc1N[C@H]1CC[C@H](O)CC1] | 436 | 481.2 | 2 | 6-(3-cyanopyrrolo[1,2-b]pyridazin-7-yl)-N-((R)-2-fluoro-3-hydroxy-3-methylbutyl)-4-(((1r,4R)-4-hydroxycyclohexyl)amino)nicotinamide |
| 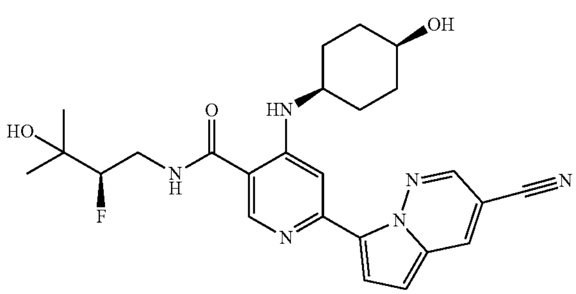 [SMILES: CC(C)(O)[C@H](F)CNC(=O)c1cnc(-c2ccc3cc(C#N)cnn23)cc1N[C@H]1CC[C@@H](O)CC1] | 437 | 481.3 | 2 | 6-(3-cyanopyrrolo[1,2-b]pyridazin-7-yl)-N-((R)-2-fluoro-3-hydroxy-3-methylbutyl)-4-(((1s,4S)-4-hydroxycyclohexyl)amino)nicotinamide |
| 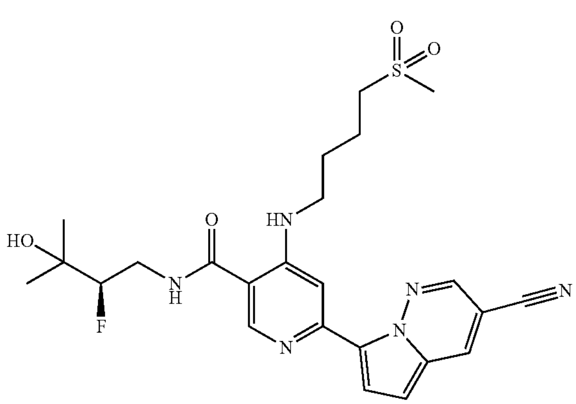 [SMILES: CC(C)(O)[C@H](F)CNC(=O)c1cnc(-c2ccc3cc(C#N)cnn23)cc1NCCCCS(C)(=O)=O] | 438 | 517.2 | 2 | (R)-6-(3-cyanopyrrolo[1,2-b]pyridazin-7-yl)-N-(2-fluoro-3-hydroxy-3-methylbutyl)-4-((4-(methylsulfonyl)butyl)amino)nicotinamide |

TABLE 1-continued

| Structure | compound | ES/ MS m/z | procedure | Name |
|---|---|---|---|---|
| 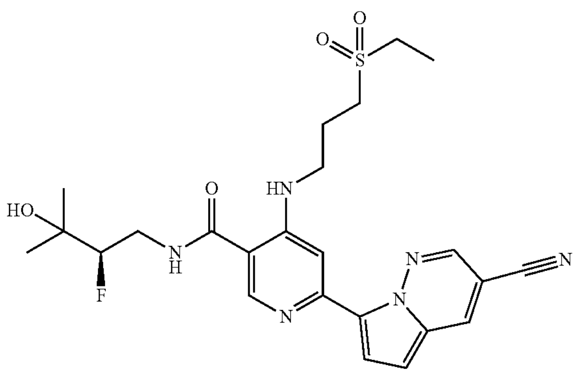 [SMILES: CCS(=O)(=O)CCCNc1cc(-c2ccc3cc(C#N)cnn23)ncc1C(=O)NC[C@@H](F)C(C)(C)O] | 439 | 517.3 | 2 | (R)-6-(3-cyanopyrrolo[1,2-b]pyridazin-7-yl)-4-((3-(ethylsulfonyl)propyl)amino)-N-(2-fluoro-3-hydroxy-3-methylbutyl)nicotinamide |
| 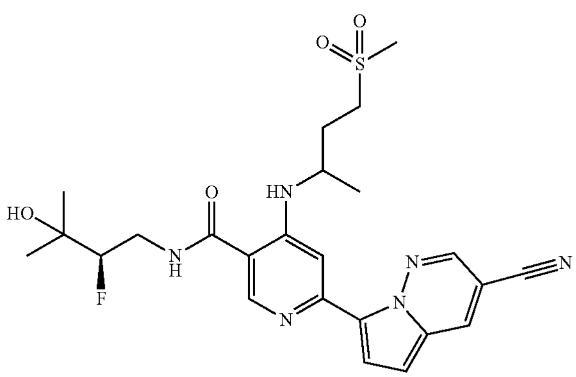 [SMILES: CC(CCS(C)(=O)=O)Nc1cc(-c2ccc3cc(C#N)cnn23)ncc1C(=O)NC[C@@H](F)C(C)(C)O] | 440 | 517.2 | 2 | 6-(3-cyanopyrrolo[1,2-b]pyridazin-7-yl)-N-((R)-2-fluoro-3-hydroxy-3-methylbutyl)-4-((4-(methylsulfonyl)butan-2-yl)amino)nicotinamide |
| 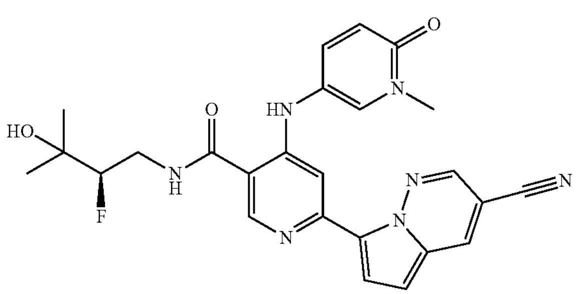 | 441 | 490.2 | 27 | (R)-6-(3-cyanopyrrolo[1,2-b]pyridazin-7-yl)-N-(2-fluoro-3-hydroxy-3-methylbutyl)-4-((1-methyl-6-oxo-1,6-dihydropyridin-3-yl)amino)nicotinamide |
| 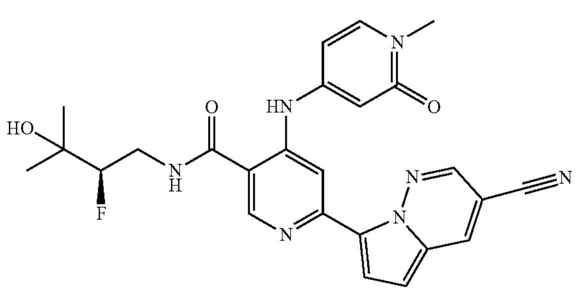 | 442 | 490.1 | 27 | (R)-6-(3-cyanopyrrolo[1,2-b]pyridazin-7-yl)-N-(2-fluoro-3-hydroxy-3-methylbutyl)-4-((1-methyl-2-oxo-1,2-dihydropyridin-4-yl)amino)nicotinamide |

TABLE 1-continued

| Structure | compound | ES/MS m/z | procedure | Name |
|---|---|---|---|---|
| 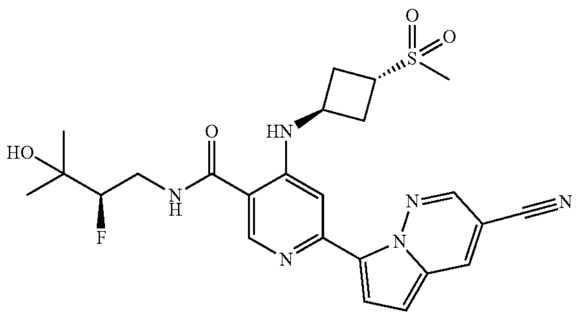 [SMILES: CC(C)(O)[C@H](F)CNC(=O)c1cnc(-c2ccc3cc(C#N)cnn23)cc1N[C@H]1C[C@H](S(C)(=O)=O)C1] | 443 | 515.2 | 2 | 6-(3-cyanopyrrolo[1,2-b]pyridazin-7-yl)-N-((R)-2-fluoro-3-hydroxy-3-methylbutyl)-4-(((1r,3R)-3-(methylsulfonyl)cyclobutyl)amino)nicotinamide |
| 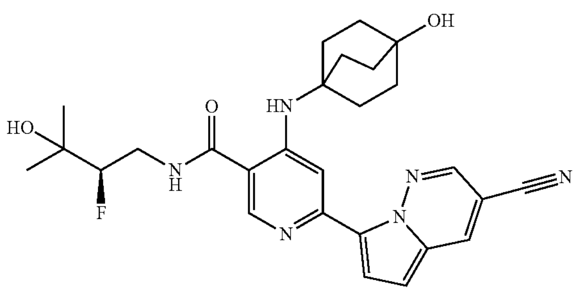 [SMILES: CC(C)(O)[C@H](F)CNC(=O)c1cnc(-c2ccc3cc(C#N)cnn23)cc1NC12CCC(O)(CC1)CC2] | 444 | 507.3 | 2 | (R)-6-(3-cyanopyrrolo[1,2-b]pyridazin-7-yl)-N-(2-fluoro-3-hydroxy-3-methylbutyl)-4-((4-hydroxybicyclo[2.2.2]octan-1-yl)amino)nicotinamide |
| 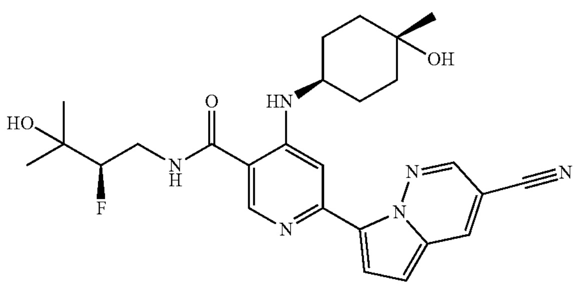 [SMILES: CC(C)(O)[C@H](F)CNC(=O)c1cnc(-c2ccc3cc(C#N)cnn23)cc1N[C@H]1CC[C@](C)(O)CC1] | 445 | 495.3 | 2 | 6-(3-cyanopyrrolo[1,2-b]pyridazin-7-yl)-N-((R)-2-fluoro-3-hydroxy-3-methylbutyl)-4-(((1r,4R)-4-hydroxy-4-methylcyclohexyl)amino)nicotinamide |
| 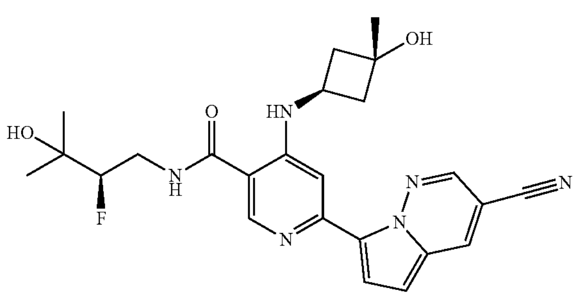 [SMILES: CC(C)(O)[C@H](F)CNC(=O)c1cnc(-c2ccc3cc(C#N)cnn23)cc1N[C@H]1C[C@](C)(O)C1] | 446 | 467.3 | 2 | 6-(3-cyanopyrrolo[1,2-b]pyridazin-7-yl)-N-((R)-2-fluoro-3-hydroxy-3-methylbutyl)-4-(((1r,3R)-3-hydroxy-3-methylcyclobutyl)amino)nicotinamide |
| 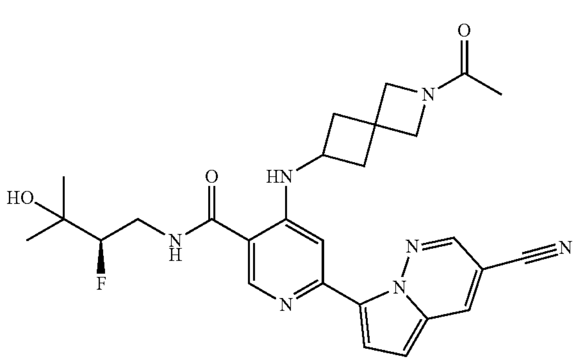 [SMILES: CC(=O)N1CC2(CC(Nc3cc(-c4ccc5cc(C#N)cnn45)ncc3C(=O)NC[C@@H](F)C(C)(C)O)C2)C1] | 447 | 520.3 | 16 | (R)-4-((2-acetyl-2-azaspiro[3.3]heptan-6-yl)amino)-6-(3-cyano-pyrrolo[1,2-b]pyridazin-7-yl)-N-(2-fluoro-3-hydroxy-3-methylbutyl)nicotinamide |

TABLE 1-continued

| Structure | compound | ES/MS m/z | procedure | Name |
|---|---|---|---|---|
| 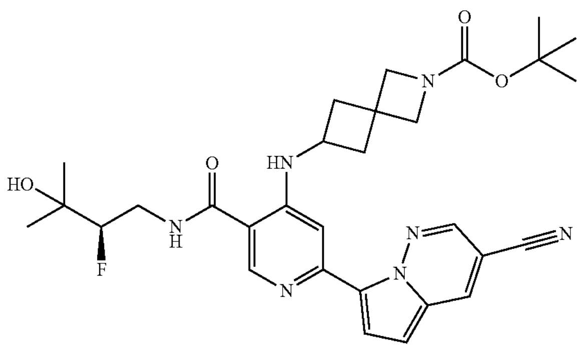 [SMILES: CC(C)(C)OC(=O)N1CC2(CC(Nc3cc(-c4ccc5cc(C#N)cnn45)ncc3C(=O)NC[C@@H](F)C(C)(C)O)C2)C1] | 448 | 578.5 | 2 | (R)-tert-butyl 6-((2-(3-cyanopyrrolo[1,2-b]pyridazin-7-yl)-5-((2-fluoro-3-hydroxy-3-methylbutyl)carbamoyl)pyridin-4-yl)amino)-2-azaspiro[3.3]heptane-2-carboxylate |
| 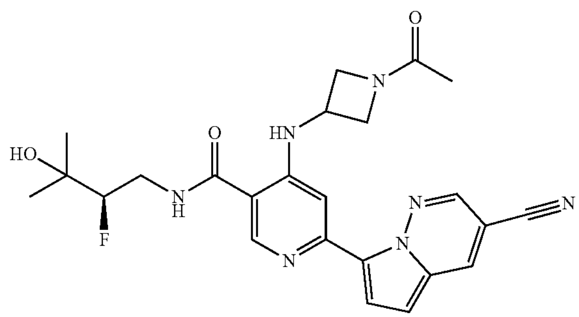 [SMILES: CC(=O)N1CC(Nc2cc(-c3ccc4cc(C#N)cnn34)ncc2C(=O)NC[C@@H](F)C(C)(C)O)C1] | 449 | 480.3 | 16 | (R)-4-((1-acetylazetidin-3-yl)amino)-6-(3-cyanopyrrolo[1,2-b]pyridazin-7-yl)-N-(2-fluoro-3-hydroxy-3-methylbutyl)nicotinamide |
| 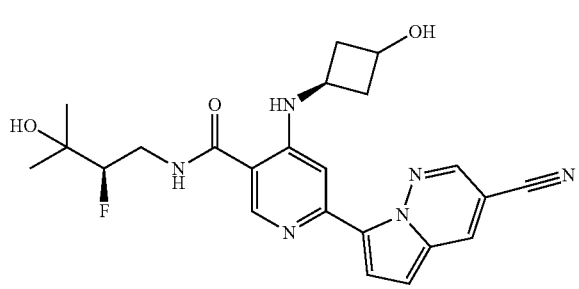 | 450 | 467.3 | 2 | 6-(3-cyanopyrrolo[1,2-b]pyridazin-7-yl)-N-((R)-2-fluoro-3-hydroxy-3-methylbutyl)-4-(((1s,3S)-3-hydroxy-3-methylcyclobutyl)amino)nicotinamide |
| 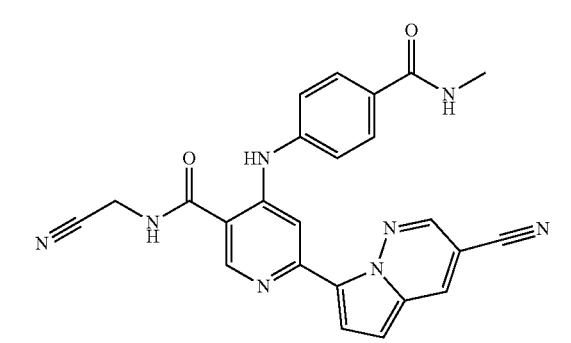 [SMILES: CNC(=O)c1ccc(Nc2cc(-c3ccc4cc(C#N)cnn34)ncc2C(=O)NCC#N)cc1] | 451 | 451.3 | 51 | N-(cyanomethyl)-6-(3-cyanopyrrolo[1,2-b]pyridazin-7-yl)-4-((4-(methylcarbamoyl)phenyl)amino)nicotinamide |

TABLE 1-continued

| Structure | compound | ES/MS m/z | procedure | Name |
|---|---|---|---|---|
| 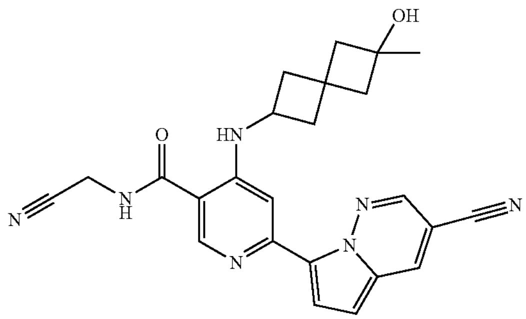 [SMILES: CC1(O)CC2(CC(Nc3cc(-c4ccc5cc(C#N)cnn45)ncc3C(=O)NCC#N)C2)C1] | 452 | 442.4 | 60 | N-(cyanomethyl)-6-(3-cyanopyrrolo[1,2-b]pyridazin-7-yl)-4-((6-hydroxy-6-methyl-spiro[3.3]heptan-2-yl)amino)nicotinamide |
| 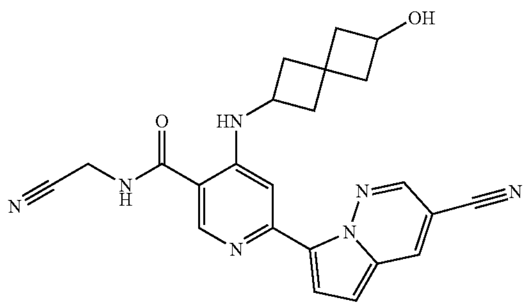 [SMILES: N#CCNC(=O)c1cnc(-c2ccc3cc(C#N)cnn23)cc1NC1CC2(CC(O)C2)C1] | 453 | 428.5 | 2 | N-(cyanomethyl)-6-(3-cyanopyrrolo[1,2-b]pyridazin-7-yl)-4-((6-hydroxyspiro[3.3]heptan-2-yl)amino)nicotinamide |
| 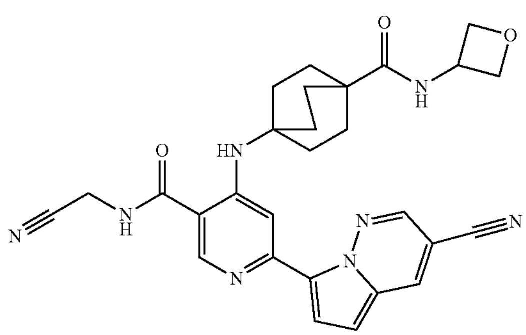 [SMILES: N#CCNC(=O)c1cnc(-c2ccc3cc(C#N)cnn23)cc1NC12CCC(C(=O)NC3COC3)(CC1)CC2] | 454 | 525.4 | 51 | N-(cyanomethyl)-6-(3-cyanopyrrolo[1,2-b]pyridazin-7-yl)-4-((4-(oxetan-3-ylcarbamoyl)bicyclo[2.2.2]octan-1-yl)amino)nicotinamide |
| 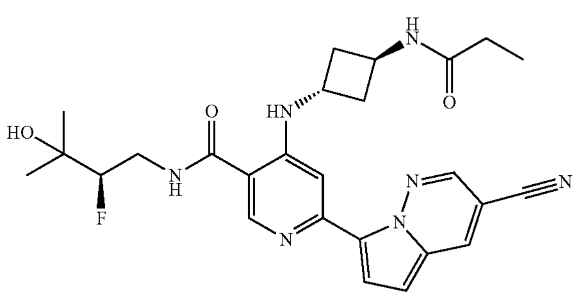 [SMILES: CCC(=O)N[C@H]1C[C@H](Nc2cc(-c3ccc4cc(C#N)cnn34)ncc2C(=O)NC[C@@H](F)C(C)(C)O)C1] | 455 | 510.3 | 16 | methyl ((1R,3r)-3-((2-(3-cyanopyrrolo[1,2-b]pyridazin-7-yl)-5-(((R)-2-fluoro-3-hydroxy-3-methylbutyl)carbamoyl)pyridin-4-yl)amino)cyclobutyl)carbamate |
| 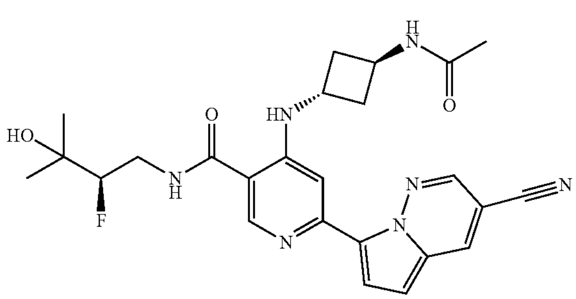 [SMILES: CC(=O)N[C@H]1C[C@H](Nc2cc(-c3ccc4cc(C#N)cnn34)ncc2C(=O)NC[C@@H](F)C(C)(C)O)C1] | 456 | 494.4 | 16 | 4-(((1r,3R)-3-acetamidocyclobutyl)amino)-6-(3-cyanopyrrolo[1,2-b]pyridazin-7-yl)-N-((R)-2-fluoro-3-hydroxy-3-methylbutyl)nicotinamide |

TABLE 1-continued

| Structure | compound | ES/MS m/z | procedure | Name |
|---|---|---|---|---|
| 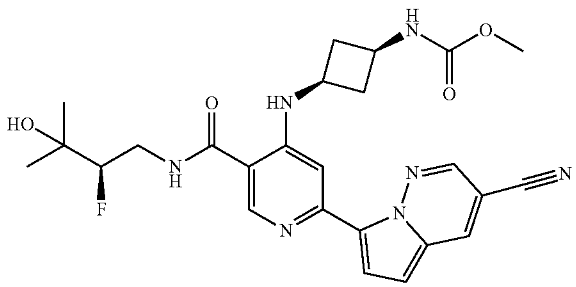 [SMILES: COC(=O)N[C@H]1C[C@@H](Nc2cc(-c3ccc4cc(C#N)cnn34)ncc2C(=O)NC[C@@H](F)C(C)(C)O)C1] | 457 | 510.4 | 16 | methyl ((1S,3s)-3-((2-(3-cyanopyrrolo[1,2-b]pyridazin-7-yl)-5-(((R)-2-fluoro-3-hydroxy-3-methylbutyl)carbamoyl)pyridin-4-yl)amino)cyclobutyl)carbamate |
| 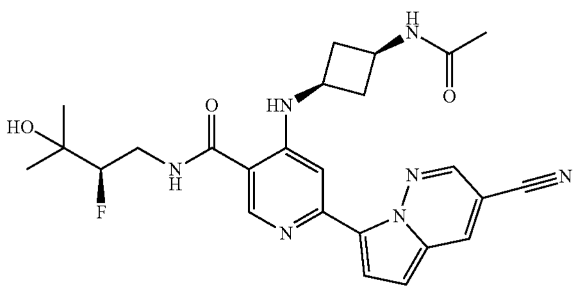 [SMILES: CC(=O)N[C@H]1C[C@@H](Nc2cc(-c3ccc4cc(C#N)cnn34)ncc2C(=O)NC[C@@H](F)C(C)(C)O)C1] | 458 | 494.3 | 16 | 4-(((1s,3S)-3-acetamidocyclobutyl)amino)-6-(3-cyanopyrrolo[1,2-b]pyridazin-7-yl)-N-((R)-2-fluoro-3-hydroxy-3-methylbutyl)nicotinamide |
| 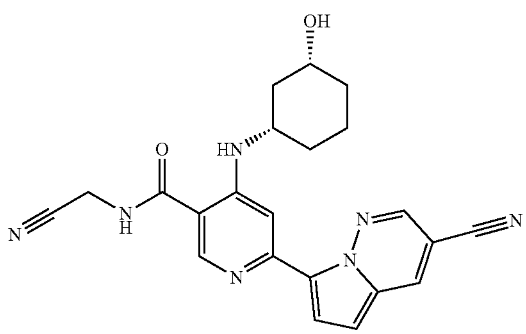 [SMILES: N#CCNC(=O)c1cnc(-c2ccc3cc(C#N)cnn23)cc1N[C@H]1CCC[C@@H](O)C1] | 459 | 416.3 | 2 | N-(cyanomethyl)-6-(3-cyanopyrrolo[1,2-b]pyridazin-7-yl)-4-(((1S,3R)-3-hydroxycyclohexyl)amino)nicotinamide |
| 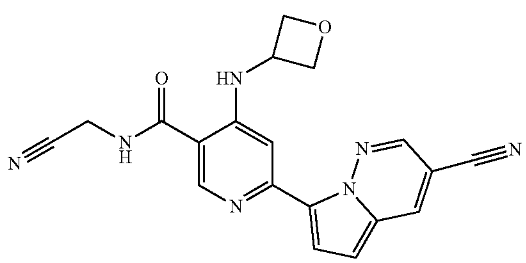 [SMILES: N#CCNC(=O)c1cnc(-c2ccc3cc(C#N)cnn23)cc1NC1COC1] | 460 | 374.2 | 2 | N-(cyanomethyl)-6-(3-cyanopyrrolo[1,2-b]pyridazin-7-yl)-4-(oxetan-3-ylamino)nicotinamide |
| 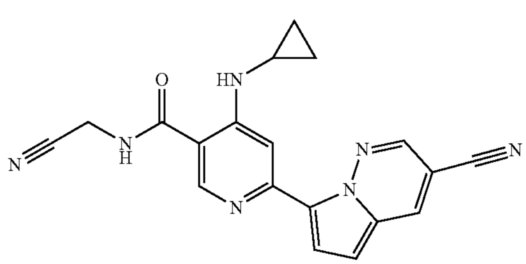 [SMILES: N#CCNC(=O)c1cnc(-c2ccc3cc(C#N)cnn23)cc1NC1CC1] | 461 | 358.3 | 2 | N-(cyanomethyl)-6-(3-cyanopyrrolo[1,2-b]pyridazin-7-yl)-4-(cyclopropylamino)nicotinamide |

TABLE 1-continued

| Structure | compound | ES/MS m/z | procedure | Name |
|---|---|---|---|---|
| 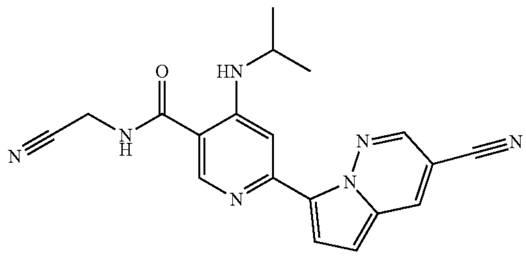 [SMILES: CC(C)Nc1cc(-c2ccc3cc(C#N)cnn23)ncc1C(=O)NCC#N] | 462 | 360.3 | 2 | N-(cyanomethyl)-6-(3-cyanopyrrolo[1,2-b]pyridazin-7-yl)-4-(isopropylamino)nicotinamide |
| 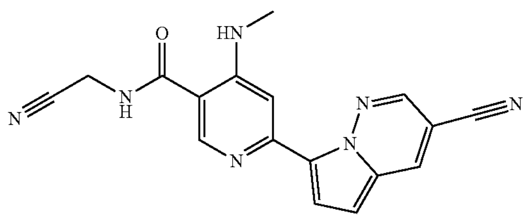 [SMILES: CNc1cc(-c2ccc3cc(C#N)cnn23)ncc1C(=O)NCC#N] | 463 | 332.2 | 2 | N-(cyanomethyl)-6-(3-cyanopyrrolo[1,2-b]pyridazin-7-yl)-4-(methylamino)nicotinamide |
| 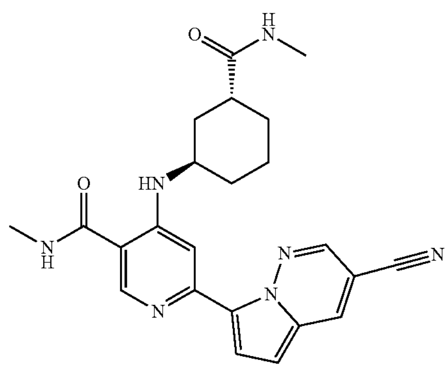 [SMILES: CNC(=O)c1cnc(-c2ccc3cc(C#N)cnn23)cc1N[C@@H]1CCC[C@@H](C(=O)NC)C1] | 464 | 432.4 | 51 | 6-(3-cyanopyrrolo[1,2-b]pyridazin-7-yl)-N-methyl-4-(((1R,3R)-3-(methylcarbamoyl)cyclohexyl)amino)nicotinamide |
| 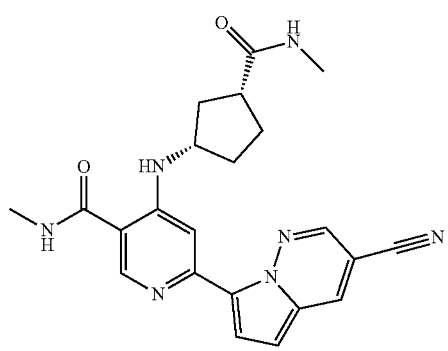 [SMILES: CNC(=O)c1cnc(-c2ccc3cc(C#N)cnn23)cc1N[C@H]1CC[C@@H](C(=O)NC)C1] | 465 | 418.3 | 51 | 6-(3-cyanopyrrolo[1,2-b]pyridazin-7-yl)-N-methyl-4-(((1S,3R)-3-(methylcarbamoyl)cyclopentyl)amino)nicotinamide |
| 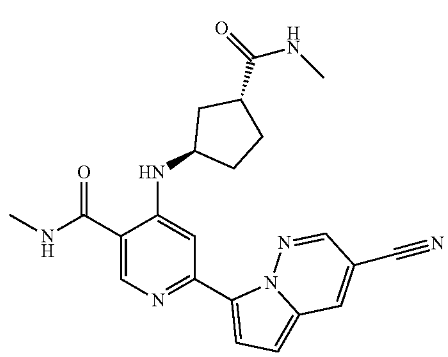 [SMILES: CNC(=O)c1cnc(-c2ccc3cc(C#N)cnn23)cc1N[C@@H]1CC[C@@H](C(=O)NC)C1] | 466 | 418.4 | 51 | 6-(3-cyanopyrrolo[1,2-b]pyridazin-7-yl)-N-methyl-4-(((1R,3R)-3-(methylcarbamoyl)cyclopentyl)amino)nicotinamide |

TABLE 1-continued

| Structure | compound | ES/MS m/z | procedure | Name |
|---|---|---|---|---|
| 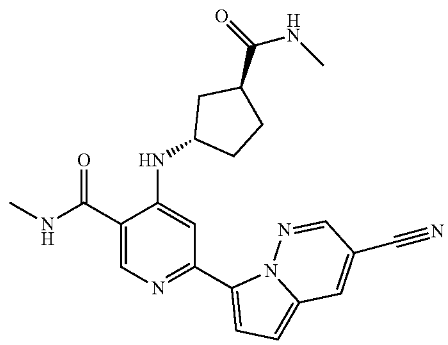 [SMILES: CNC(=O)c1cnc(-c2ccc3cc(C#N)cnn23)cc1N[C@H]1CC[C@H](C(=O)NC)C1] | 467 | 418.3 | 51 | 6-(3-cyanopyrrolo[1,2-b]pyridazin-7-yl)-N-methyl-4-(((1S,3S)-3-(methylcarbamoyl)cyclopentyl)amino)nicotinamide |
| 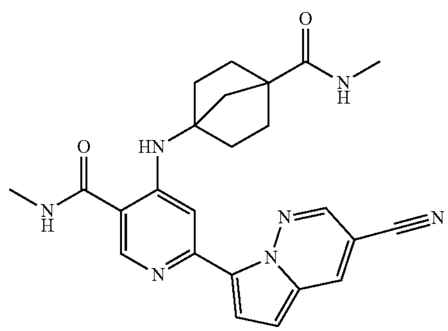 [SMILES: CNC(=O)c1cnc(-c2ccc3cc(C#N)cnn23)cc1NC12CCC(C(=O)NC)(CC1)C2] | 468 | 444.4 | 51 | 6-(3-cyanopyrrolo[1,2-b]pyridazin-7-yl)-N-methyl-4-((4-(methylcarbamoyl)bicyclo[2.2.1]heptan-1-yl)amino)nicotinamide |
| 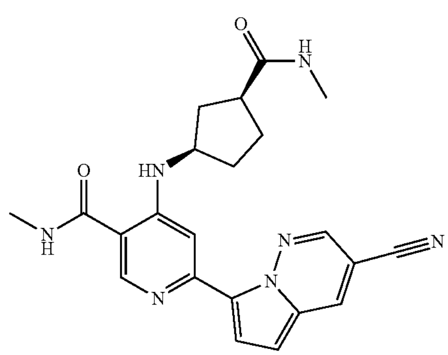 [SMILES: CNC(=O)c1cnc(-c2ccc3cc(C#N)cnn23)cc1N[C@@H]1CC[C@H](C(=O)NC)C1] | 469 | 418.3 | 51 | 6-(3-cyanopyrrolo[1,2-b]pyridazin-7-yl)-N-methyl-4-(((1R,3S)-3-(methylcarbamoyl)cyclopentyl)amino)nicotinamide |
| 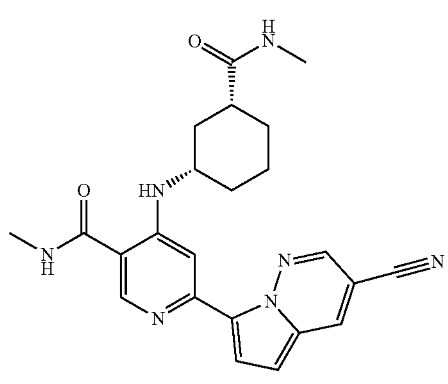 [SMILES: CNC(=O)c1cnc(-c2ccc3cc(C#N)cnn23)cc1N[C@H]1CCC[C@@H](C(=O)NC)C1] | 470 | 432.4 | 51 | 6-(3-cyanopyrrolo[1,2-b]pyridazin-7-yl)-N-methyl-4-(((1S,3R)-3-(methylcarbamoyl)cyclohexyl)amino)nicotinamide |

TABLE 1-continued

| Structure | compound | ES/MS m/z | procedure | Name |
|---|---|---|---|---|
| 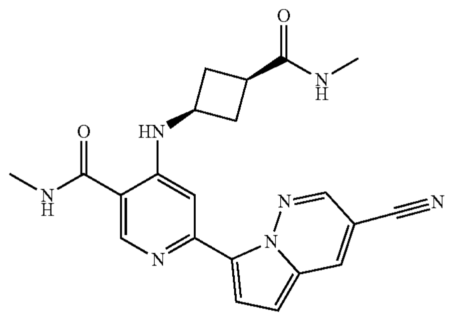 [SMILES: CNC(=O)c1cnc(-c2ccc3cc(C#N)cnn23)cc1N[C@H]1C[C@@H](C(=O)NC)C1] | 471 | 404.3 | 51 | 6-(3-cyanopyrrolo[1,2-b]pyridazin-7-yl)-N-methyl-4-(((1s,3s)-3-(methylcarbamoyl)cyclobutyl)amino)nicotinamide |
| 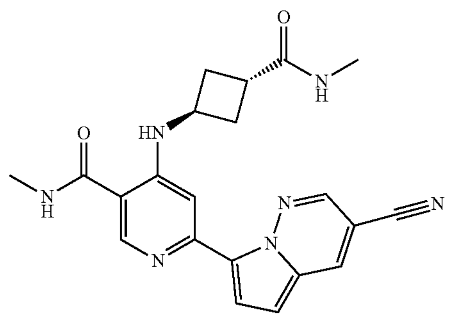 [SMILES: CNC(=O)c1cnc(-c2ccc3cc(C#N)cnn23)cc1N[C@H]1C[C@H](C(=O)NC)C1] | 472 | 404.2 | 51 | 6-(3-cyanopyrrolo[1,2-b]pyridazin-7-yl)-N-methyl-4-(((1r,3r)-3-(methylcarbamoyl)cyclobutyl)amino)nicotinamide |
| 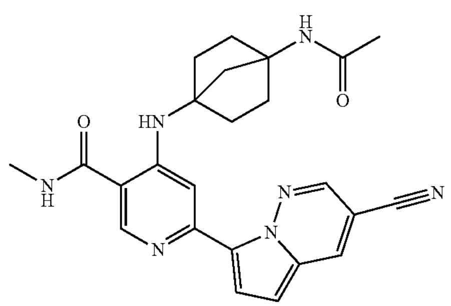 [SMILES: CNC(=O)c1cnc(-c2ccc3cc(C#N)cnn23)cc1NC12CCC(NC(C)=O)(CC1)C2] | 473 | 444.3 | 16 | 4-((4-acetamidobicyclo[2.2.1]heptan-1-yl)amino)-6-(3-cyano-pyrrolo[1,2-b]pyridazin-7-yl)-N-methylnicotinamide |
| 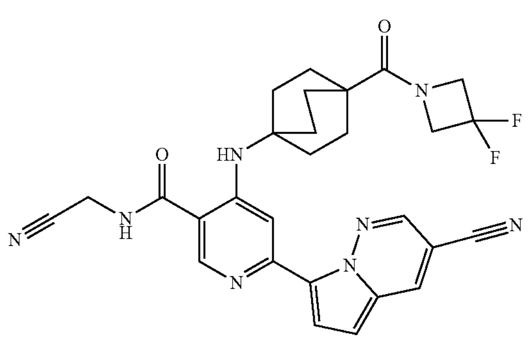 [SMILES: N#CCNC(=O)c1cnc(-c2ccc3cc(C#N)cnn23)cc1NC12CCC(C(=O)N3CC(F)(F)C3)(CC1)CC2] | 474 | 545.4 | 51 | N-(cyanomethyl)-6-(3-cyanopyrrolo[1,2-b]pyridazin-7-yl)-4-((4-(3,3-difluoroazetidine-1-carbonyl)bicyclo[2.2.2]octan-1-yl)amino)nicotinamide |

TABLE 1-continued

| Structure | compound | ES/MS m/z | procedure | Name |
|---|---|---|---|---|
| 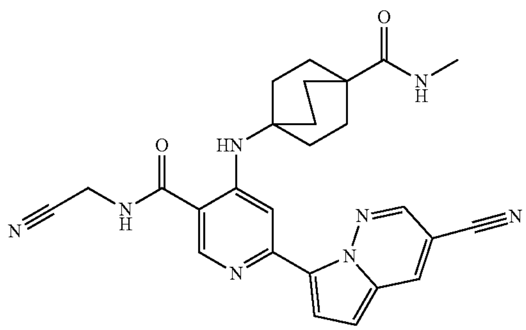 [SMILES: CNC(=O)C12CCC(Nc3cc(-c4ccc5cc(C#N)cnn45)ncc3C(=O)NCC#N)(CC1)CC2] | 475 | 483.4 | 51 | N-(cyanomethyl)-6-(3-cyanopyrrolo[1,2-b]pyridazin-7-yl)-4-((4-(methylcarbamoyl)bicyclo[2.2.2]octan-1-yl)amino)nicotinamide |
| 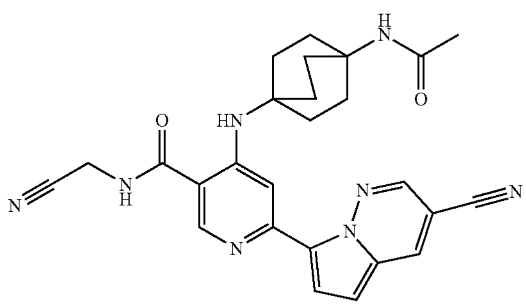 [SMILES: CC(=O)NC12CCC(Nc3cc(-c4ccc5cc(C#N)cnn45)ncc3C(=O)NCC#N)(CC1)CC2] | 476 | 483.5 | 16 | 4-((4-acetamido-bicyclo[2.2.2]octan-1-yl)amino)-N-(cyanomethyl)-6-(3-cyano-pyrrolo[1,2-b]pyridazin-7-yl)nicotinamide |
| 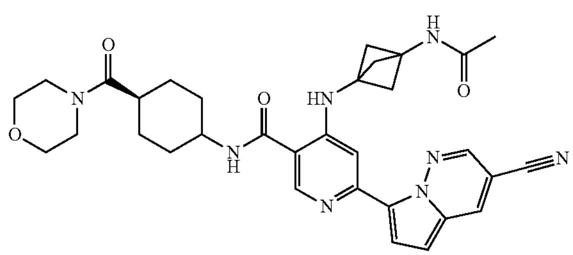 | 477 | 597.4 | 64 | 4-((3-acetamido-bicyclo[1.1.1]pentan-1-yl)amino)-6-(3-cyano-pyrrolo[1,2-b]pyridazin-7-yl)-N-((1r,4r)-4-(morpholine-4-carbonyl)cyclohexyl)nicotinamide |
| 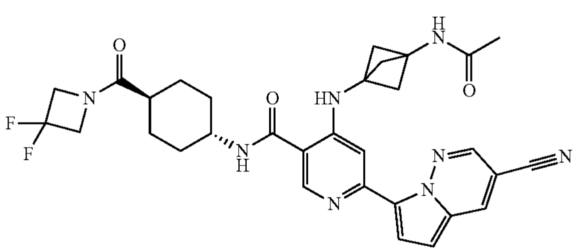 [SMILES: CC(=O)NC12CC(Nc3cc(-c4ccc5cc(C#N)cnn45)ncc3C(=O)N[C@H]3CC[C@H](C(=O)N4CC(F)(F)C4)CC3)(C1)C2] | 478 | 603.3 | 64 | 4-((3-acetamido-bicyclo[1.1.1]pentan-1-yl)amino)-6-(3-cyano-pyrrolo[1,2-b]pyridazin-7-yl)-N-((1r,4r)-4-(3,3-difluoroazetidine-1-carbonyl)cyclohexyl)nicotinamide |
| 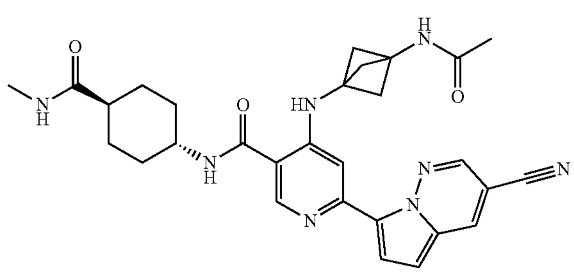 [SMILES: CNC(=O)[C@H]1CC[C@H](NC(=O)c2cnc(-c3ccc4cc(C#N)cnn34)cc2NC23CC(NC(C)=O)(C2)C3)CC1] | 479 | 541.3 | 64 | 4-((3-acetamido-bicyclo[1.1.1]pentan-1-yl)amino)-6-(3-cyano-pyrrolo[1,2-b]pyridazin-7-yl)-N-((1r,4r)-4-(methylcarbamoyl)cyclohexyl)nicotinamide |

TABLE 1-continued

| Structure | compound | ES/ MS m/z | procedure | Name |
|---|---|---|---|---|
| 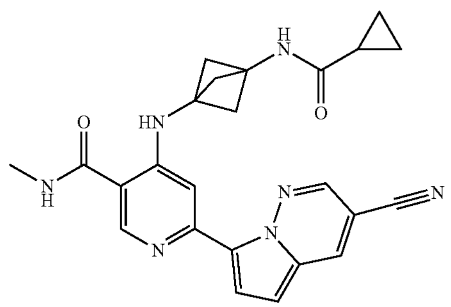 [SMILES: CNC(=O)c1cnc(-c2ccc3cc(C#N)cnn23)cc1NC12CC(NC(=O)C3CC3)(C1)C2] | 480 | 442.4 | 16 | 6-(3-cyanopyrrolo[1,2-b]pyridazin-7-yl)-4-((3-(cyclopropanecarboxamido)bicyclo[1.1.1]pentan-1-yl)amino)-N-methylnicotinamide |
| 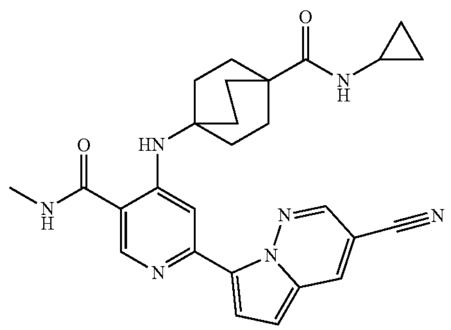 [SMILES: CNC(=O)c1cnc(-c2ccc3cc(C#N)cnn23)cc1NC12CCC(C(=O)NC3CC3)(CC1)CC2] | 481 | 484.4 | 51 | 6-(3-cyanopyrrolo[1,2-b]pyridazin-7-yl)-4-((4-(cyclopropylcarbamoyl)bicyclo[2.2.2]octan-1-yl)amino)-N-methylnicotinamide |
| 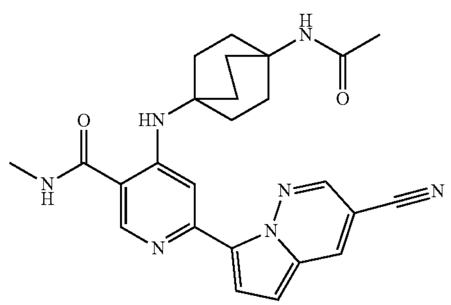 [SMILES: CNC(=O)c1cnc(-c2ccc3cc(C#N)cnn23)cc1NC12CCC(NC(C)=O)(CC1)CC2] | 482 | 458.4 | 16 | 4-((4-acetamidobicyclo[2.2.2]octan-1-yl)amino)-6-(3-cyanopyrrolo[1,2-b]pyridazin-7-yl)-N-methylnicotinamide |
| 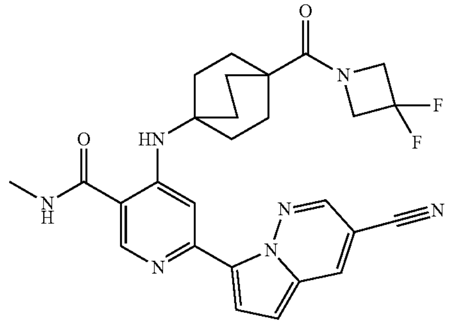 [SMILES: CNC(=O)c1cnc(-c2ccc3cc(C#N)cnn23)cc1NC12CCC(C(=O)N3CC(F)(F)C3)(CC1)CC2] | 483 | 520.4 | 51 | 6-(3-cyanopyrrolo[1,2-b]pyridazin-7-yl)-4-((4-(3,3-difluoroazetidine-1-carbonyl)bicyclo[2.2.2]octan-1-yl)amino)-N-methylnicotinamide |

TABLE 1-continued

| Structure | compound | ES/MS m/z | procedure | Name |
|---|---|---|---|---|
| 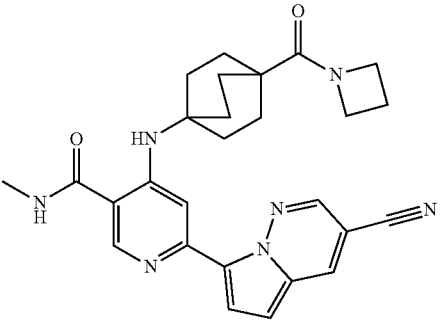 [SMILES: CNC(=O)c1cnc(-c2ccc3cc(C#N)cnn23)cc1NC12CCC(C(=O)N3CCC3)(CC1)CC2] | 484 | 484.4 | 51 | 4-((4-(azetidine-1-carbonyl)bicyclo[2.2.2]octan-1-yl)amino)-6-(3-cyanopyrrolo[1,2-b]pyridazin-7-yl)-N-methyl-nicotinamide |
| 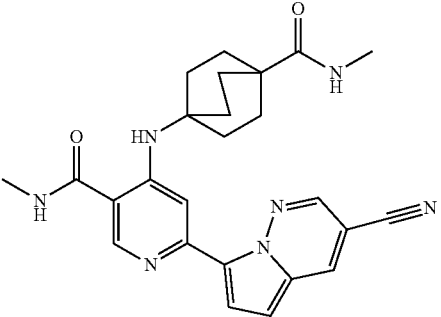 [SMILES: CNC(=O)c1cnc(-c2ccc3cc(C#N)cnn23)cc1NC12CCC(C(=O)NC)(CC1)CC2] | 485 | 458.4 | 51 | 6-(3-cyanopyrrolo[1,2-b]pyridazin-7-yl)-N-methyl-4-((4-(methylcarbamoyl)bicyclo[2.2.2]octan-1-yl)amino)nicotinamide |
| 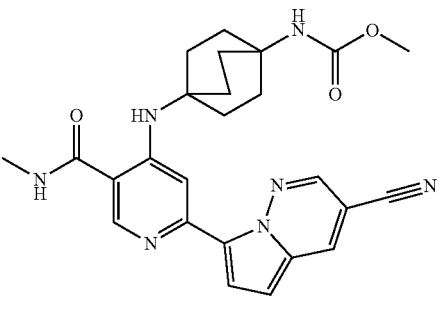 [SMILES: CNC(=O)c1cnc(-c2ccc3cc(C#N)cnn23)cc1NC12CCC(NC(=O)OC)(CC1)CC2] | 486 | 474.3 | 16 | methyl (4-((2-(3-cyano-pyrrolo[1,2-b]pyridazin-7-yl)-5-(methylcarbamoyl)pyridin-4-yl)amino)bicyclo[2.2.2]octan-1-yl)carbamate |
| 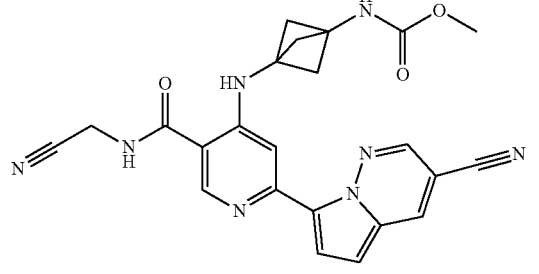 | 487 | 457.2 | 16 | methyl (3-((5-((cyanomethyl)carbamoyl)-2-(3-cyanopyrrolo[1,2-b]pyridazin-7-yl)pyridin-4-yl)amino)bicyclo[1.1.1]pentan-1-yl)carbamate |
| 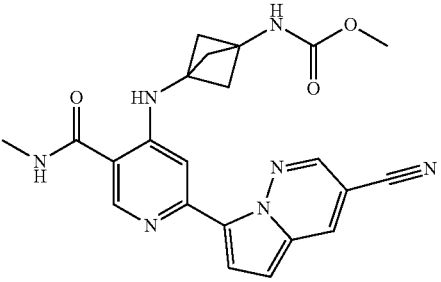 [SMILES: CNC(=O)c1cnc(-c2ccc3cc(C#N)cnn23)cc1NC12CC(NC(=O)OC)(C1)C2] | 488 | 432.3 | 16 | methyl (3-((2-(3-cyano-pyrrolo[1,2-b]pyridazin-7-yl)-5-(methylcarbamoyl)pyridin-4-yl)amino)bicyclo[1.1.1]pentan-1-yl)carbamate |

TABLE 1-continued

| Structure | compound | ES/MS m/z | procedure | Name |
|---|---|---|---|---|
| 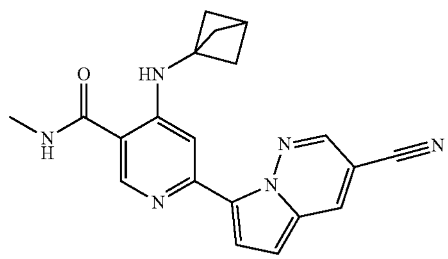 [SMILES: CNC(=O)c1cnc(-c2ccc3cc(C#N)cnn23)cc1NC12CC(C1)C2] | 489 | 359.2 | 2 | 4-(bicyclo[1.1.1]pentan-1-ylamino)-6-(3-cyanopyrrolo[1,2-b]pyridazin-7-yl)-N-methylnicotinamide |
| 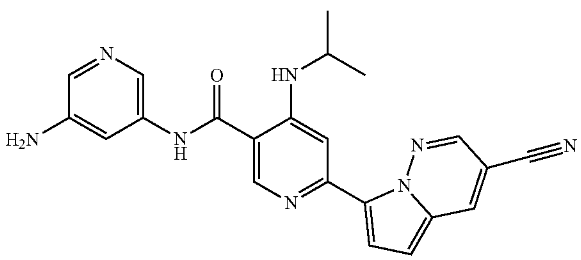 [SMILES: CC(C)Nc1cc(-c2ccc3cc(C#N)cnn23)ncc1C(=O)Nc1cncc(N)c1] | 490 | 413.3 | 1 | N-(5-aminopyridin-3-yl)-6-(3-cyanopyrrolo[1,2-b]pyridazin-7-yl)-4-isopropylamino)nicotinamide |
| 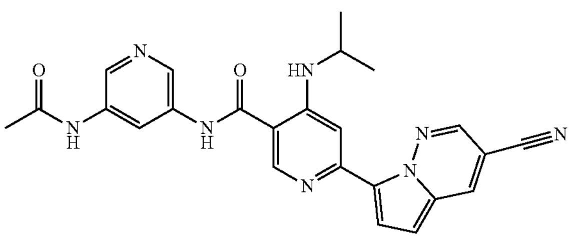 [SMILES: CC(=O)Nc1cncc(NC(=O)c2cnc(-c3ccc4cc(C#N)cnn34)cc2NC(C)C)c1] | 491 | 455.3 | 63 | N-(5-acetamidopyridin-3-yl)-6-(3-cyanopyrrolo[1,2-b]pyridazin-7-yl)-4-(isopropylamino)nicotinamide |
| 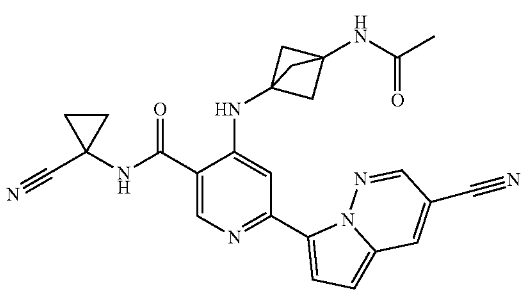 [SMILES: CC(=O)NC12CC(Nc3cc(-c4ccc5cc(C#N)cnn45)ncc3C(=O)NC3(C#N)CC3)(C1)C2] | 492 | 467.5 | 1 | 4-((3-acetamidobicyclo[1.1.1]pentan-1-yl)amino)-N-(1-cyanocyclopropyl)-6-(3-cyanopyrrolo[1,2-b]pyridazin-7-yl)nicotinamide |
| 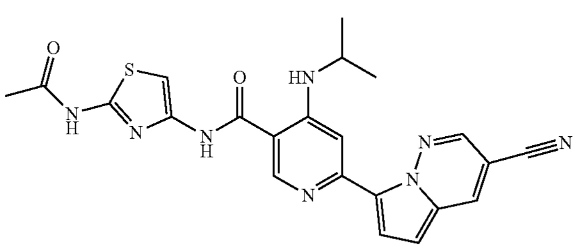 [SMILES: CC(=O)Nc1nc(NC(=O)c2cnc(-c3ccc4cc(C#N)cnn34)cc2NC(C)C)cs1] | 493 | 461.3 | 63 | N-(2-acetamidothiazol-4-yl)-6-(3-cyanopyrrolo[1,2-b]pyridazin-7-yl)-4-(isopropylamino)nicotinamide |

TABLE 1-continued

| Structure | compound | ES/MS m/z | procedure | Name |
|---|---|---|---|---|
| 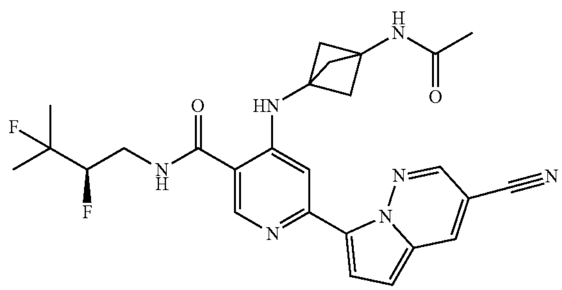 [SMILES: CC(=O)NC12CC(Nc3cc(-c4ccc5cc(C#N)cnn45)ncc3C(=O)NC[C@@H](F)C(C)(C)F)(C1)C2] | 494 | 508.3 | 1 | (R)-4-((3-acetamidobicyclo[1.1.1]pentan-1-yl)amino)-6-(3-cyanopyrrolo[1,2-b]pyridazin-7-yl)-N-(2,3-difluoro-3-methylbutyl)nicotinamide |
| 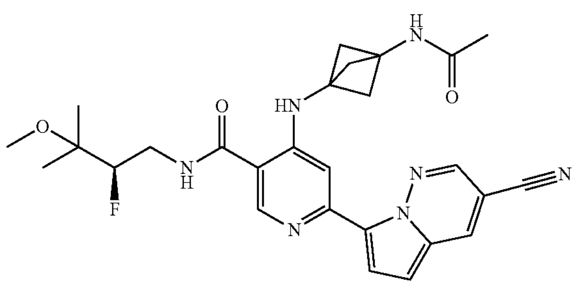 [SMILES: COC(C)(C)[C@H](F)CNC(=O)c1cnc(-c2ccc3cc(C#N)cnn23)cc1NC12CC(NC(C)=O)(C1)C2] | 495 | 520.2 | 1 | (R)-4-((3-acetamidobicyclo[1.1.1]pentan-1-yl)amino)-6-(3-cyanopyrrolo[1,2-b]pyridazin-7-yl)-N-(2-fluoro-3-methoxy-3-methylbutyl)nicotinamide |
| 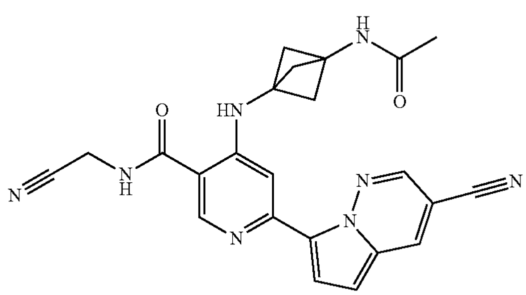 [SMILES: CC(=O)NC12CC(Nc3cc(-c4ccc5cc(C#N)cnn45)ncc3C(=O)NCC#N)(C1)C2] | 496 | 441.2 | 1 | 4-((3-acetamidobicyclo[1.1.1]pentan-1-yl)amino)-N-(cyanomethyl)-6-(3-cyanopyrrolo[1,2-b]pyridazin-7-yl)nicotinamide |
| 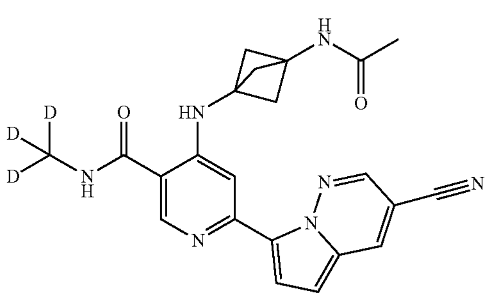 [SMILES: [2H]C([2H])([2H])NC(=O)c1cnc(-c2ccc3cc(C#N)cnn23)cc1NC12CC(NC(C)=O)(C1)C2] | 497 | 419.2 | 1 | 4-((3-acetamidobicyclo[1.1.1]pentan-1-yl)amino)-6-(3-cyanopyrrolo[1,2-b]pyridazin-7-yl)-N-(methyl-d3)nicotinamide |
| 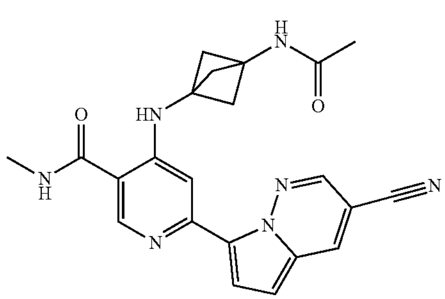 [SMILES: CNC(=O)c1cnc(-c2ccc3cc(C#N)cnn23)cc1NC12CC(NC(C)=O)(C1)C2] | 498 | 416.1 | 1 | 4-((3-acetamidobicyclo[1.1.1]pentan-1-yl)amino)-6-(3-cyanopyrrolo[1,2-b]pyridazin-7-yl)-N-methyl-nicotinamide |

TABLE 1-continued

| Structure | compound | ES/ MS m/z | procedure | Name |
|---|---|---|---|---|
| 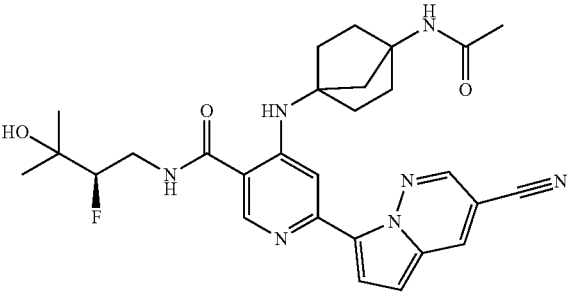 [SMILES: CC(=O)NC12CCC(Nc3cc(-c4ccc5cc(C#N)cnn45)ncc3C(=O)NC[C@@H](F)C(C)(C)O)(CC1)C2] | 499 | 534.2 | 16 | (R)-4-((4-acetamidobicyclo[2.2.1]heptan-1-yl)amino)-6-(3-cyanopyrrolo[1,2-b]pyridazin-7-yl)-N-(2-fluoro-3-hydroxy-3-methylbutyl)nicotinamide |
| 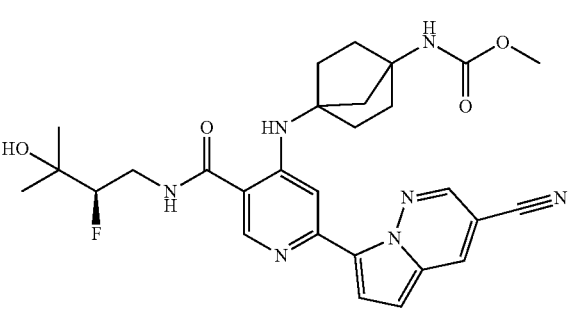 [SMILES: COC(=O)NC12CCC(Nc3cc(-c4ccc5cc(C#N)cnn45)ncc3C(=O)NC[C@@H](F)C(C)(C)O)(CC1)C2] | 500 | 550.3 | 16 | (R)-methyl (4-((2-(3-cyano-pyrrolo[1,2-b]pyridazin-7-yl)-5-((2-fluoro-3-hydroxy-3-methylbutyl)carbamoyl)pyridin-4-yl)amino)bicyclo[2.2.1]heptan-1-yl)carbamate |
| 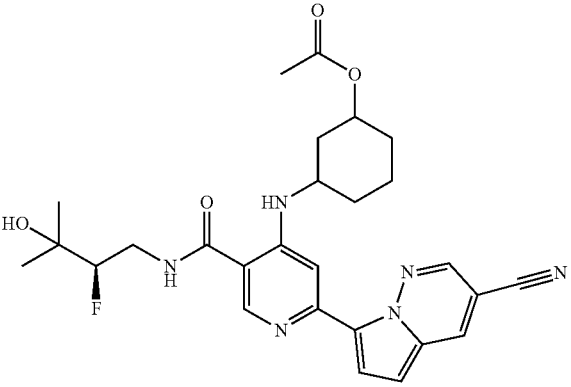 [SMILES: CC(=O)OC1CCCC(Nc2cc(-c3ccc4cc(C#N)cnn34)ncc2C(=O)NC[C@@H](F)C(C)(C)O)C1] | 501 | 523.3 | 62 | (1R,3S)-3-((2-(3-cyano-pyrrolo[1,2-b]pyridazin-7-yl)-5-(((R)-2-fluoro-3-hydroxy-3-methylbutyl)carbamoyl)pyridin-4-yl)amino)cyclohexyl acetate |
| 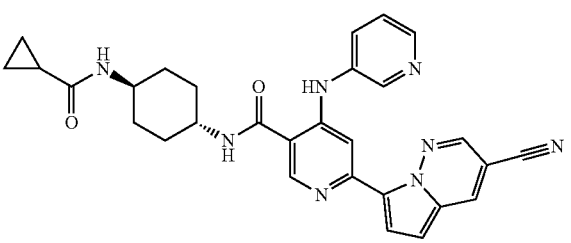 [SMILES: N#Cc1cnn2c(-c3cc(Nc4cccnc4)c(C(=O)N[C@H]4CC[C@H](NC(=O)C5CC5)CC4)cn3)ccc2c1] | 502 | 521.2 | 13 | 6-(3-cyanopyrrolo[1,2-b]pyridazin-7-yl)-N-((1r,4r)-4-(cyclopropane-carboxamido)cyclohexyl)-4-(pyridin-3-ylamino)nicotinamide |
| 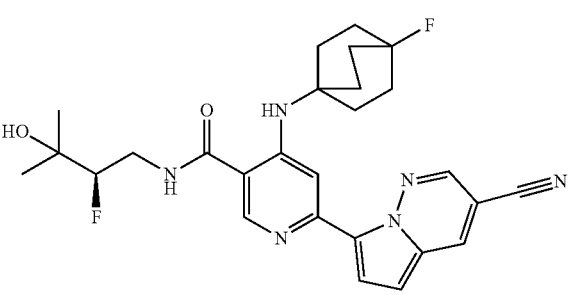 [SMILES: CC(C)(O)[C@H](F)CNC(=O)c1cnc(-c2ccc3cc(C#N)cnn23)cc1NC12CCC(F)(CC1)CC2] | 503 | 509.3 | 2 | (R)-6-(3-cyanopyrrolo[1,2-b]pyridazin-7-yl)-N-(2-fluoro-3-hydroxy-3-methylbutyl)-4-((4-fluorobicyclo[2.2.2]octan-1-yl)amino)nicotinamide |

TABLE 1-continued

| Structure | compound | ES/MS m/z | procedure | Name |
|---|---|---|---|---|
| 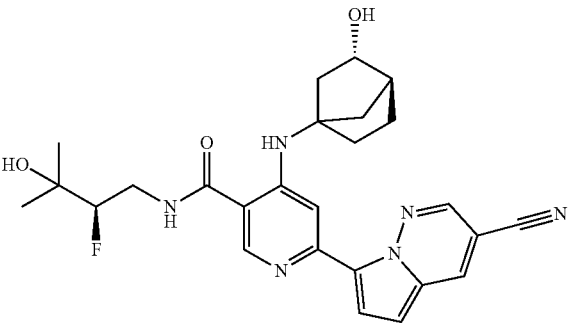 [SMILES: CC(C)(O)[C@H](F)CNC(=O)c1cnc(-c2ccc3cc(C#N)cnn23)cc1NC12CC[C@@H](C1)[C@@H](O)C2] | 504 | 493.2 | 2 | 6-(3-cyanopyrrolo[1,2-b]pyridazin-7-yl)-N-((R)-2-fluoro-3-hydroxy-3-methyl butyl)-4-(((1S,3S,4S)-3-hydroxybicyclo[2.2.1]heptan-1-yl)amino)nicotinamide |
| 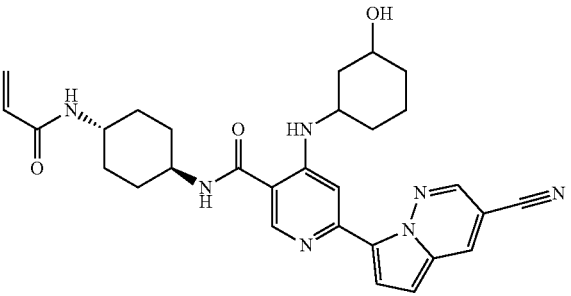 [SMILES: C=CC(=O)N[C@H]1CC[C@H](NC(=O)c2cnc(-c3ccc4cc(C#N)cnn34)cc2NC2CCCC(O)C2)CC1] | 505 | 528.3 | 61 | N-((1r,4S)-4-acrylamido-cyclohexyl)-6-(3-cyano-pyrrolo[1,2-b]pyridazin-7-yl)-4-(((1S,3R)-3-hydroxycyclohexyl)amino)nicotinamide |
| 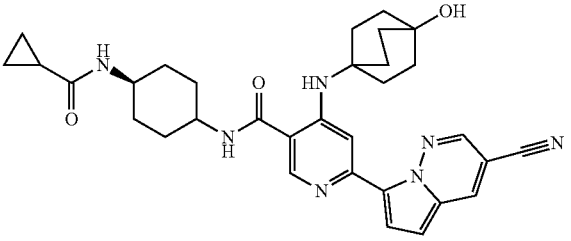 | 506 | 568.3 | 13 | 6-(3-cyanopyrrolo[1,2-b]pyridazin-7-yl)-N-((1r,4r)-4-(cyclopropane-carboxamido)cyclohexyl)-4-((4-hydroxybicyclo[2.2.2]octan-1-yl)amino)nicotinamide |
| 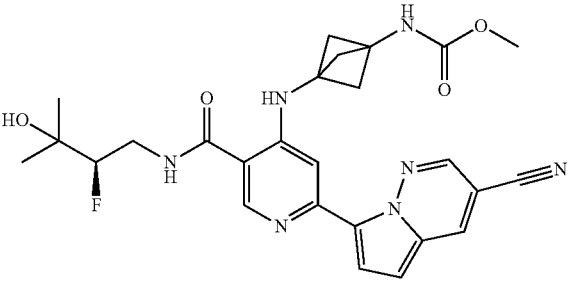 [SMILES: COC(=O)NC12CC(Nc3cc(-c4ccc5cc(C#N)cnn45)ncc3C(=O)NC[C@@H](F)C(C)(C)O)(C1)C2] | 507 | 522.3 | 16 | (R)-methyl (3-((2-(3-cyanopyrrolo[1,2-b]pyridazin-7-yl)-5-((2-fluoro-3-hydroxy-3-methylbutyl)carbamoyl)pyridin-4-yl)amino)bicyclo[1.1.1]pentan-1-yl)carbamate |
| 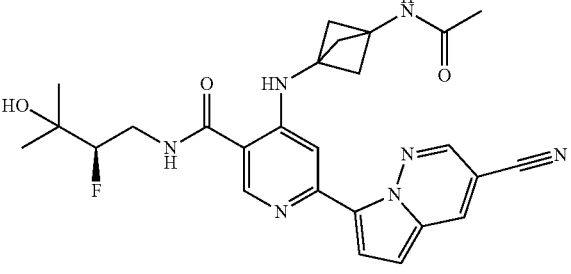 | 508 | 506.2 | 16 | (R)-4-((3-acetamidobicyclo[1.1.1]pentan-1-yl)amino)-6-(3-cyanopyrrolo[1,2-b]pyridazin-7-yl)-N-(2-fluoro-3-hydroxy-3-methyl-butyl)nicotinamide |

TABLE 1-continued

| Structure | compound | ES/MS m/z | procedure | Name |
|---|---|---|---|---|
| 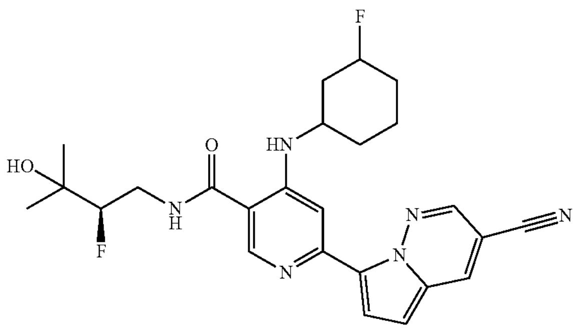 [SMILES: CC(C)(O)[C@H](F)CNC(=O)c1cnc(-c2ccc3cc(C#N)cnn23)cc1NC1CCCC(F)C1] | 509 | 483.4 | 1 | 6-(3-cyanopyrrolo[1,2-b]pyridazin-7-yl)-N-((R)-2-fluoro-3-hydroxy-3-methylbutyl)-4-(((1S)-3-fluorocyclohexyl)amino)nicotinamide |
| 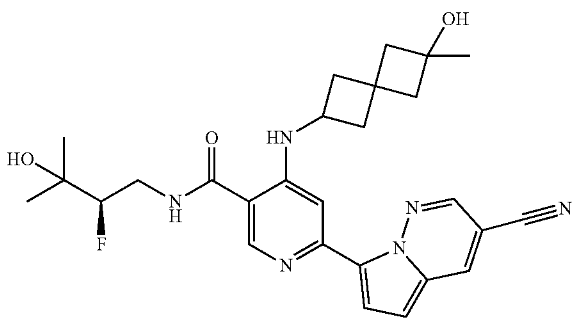 [SMILES: CC1(O)CC2(CC(Nc3cc(-c4ccc5cc(C#N)cnn45)ncc3C(=O)NC[C@@H](F)C(C)(C)O)C2)C1] | 510 | 507.3 | 60 | (R)-6-(3-cyanopyrrolo[1,2-b]pyridazin-7-yl)-N-(2-fluoro-3-hydroxy-3-methylbutyl)-4-((6-hydroxy-6-methylspiro[3.3]heptan-2-yl)amino)nicotinamide |
| 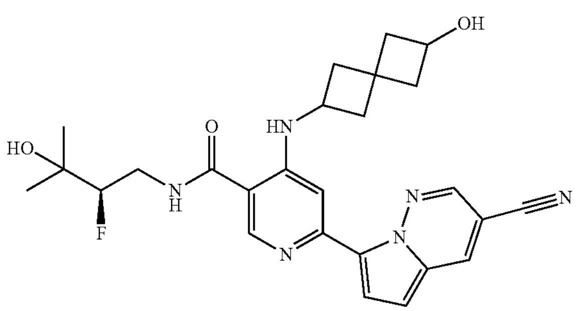 [SMILES: CC(C)(O)[C@H](F)CNC(=O)c1cnc(-c2ccc3cc(C#N)cnn23)cc1NC1CC2(CC(O)C2)C1] | 511 | 493.3 | 2 | (R)-6-(3-cyano-pyrrolo[1,2-b]pyridazin-7-yl)-N-(2-fluoro-3-hydroxy-3-methylbutyl)-4-((6-hydroxyspiro[3.3]heptan-2-yl)amino)nicotinamide |
| 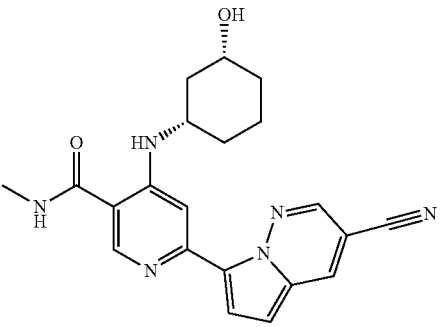 [SMILES: CNC(=O)c1cnc(-c2ccc3cc(C#N)cnn23)cc1N[C@H]1CCC[C@@H](O)C1] | 512 | 391.2 | 1 | 6-(3-cyanopyrrolo[1,2-b]pyridazin-7-yl)-4-(((1S,3R)-3-hydroxy-cyclohexyl)amino)-N-methylnicotinamide |

TABLE 1-continued

| Structure | compound | ES/MS m/z | procedure | Name |
|---|---|---|---|---|
| 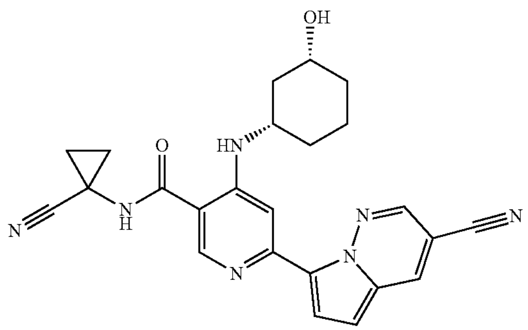 [SMILES: N#Cc1cnn2c(-c3cc(N[C@H]4CCC[C@@H](O)C4)c(C(=O)NC4(C#N)CC4)cn3)ccc2c1] | 513 | 442.3 | 1 | N-(1-cyanocyclopropyl)-6-(3-cyanopyrrolo[1,2-b]pyridazin-7-yl)-4-((((1S,3R)-3-hydroxy-cyclohexyl)amino)nicotinamide |
| 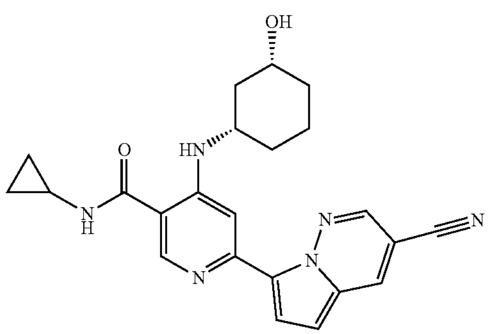 [SMILES: N#Cc1cnn2c(-c3cc(N[C@H]4CCC[C@@H](O)C4)c(C(=O)NC4CC4)cn3)ccc2c1] | 514 | 417.3 | 1 | 6-(3-cyanopyrrolo[1,2-b]pyridazin-7-yl)-N-cyclopropyl-4-((((1S,3R)-3-hydroxy-cyclohexyl)amino)nicotinamide |
| diasteromer 1 | 515 | 543.3 | 59 | 6-(3-cyanopyrrolo[1,2-b]pyridazin-7-yl)-N-((R)-2-fluoro-3-hydroxy-3-methylbutyl)-4-((3-(methylsulfonyl)cyclo-hexyl)amino)nicotinamide |
| diastereomers 2,3 | 516 | 543.4 | 59 | 6-(3-cyanopyrrolo[1,2-b]pyridazin-7-yl)-N-((R)-2-fluoro-3-hydroxy-3-methylbutyl)-4-((3-(methylsulfonyl)cyclo-hexyl)amino)nicotinamide |

TABLE 1-continued

| Structure | compound | ES/MS m/z | procedure | Name |
|---|---|---|---|---|
| 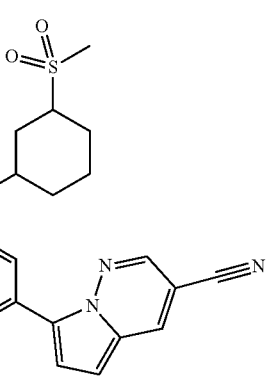<br>diastereomer 1 | 517 | 543.5 | 59 | 6-(3-cyanopyrrolo[1,2-b]pyridazin-7-yl)-N-((R)-2-fluoro-3-hydroxy-3-methylbutyl)-4-((3-(methylsulfonyl)cyclohexyl)amino)nicotinamide |
| 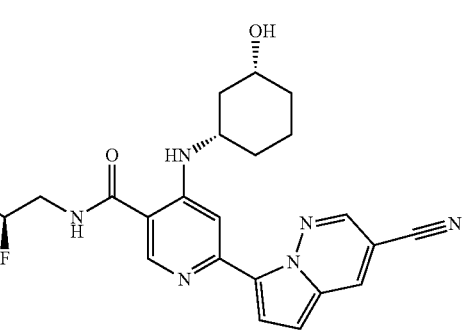 | 518 | 495.4 | 1 | 6-(3-cyanopyrrolo[1,2-b]pyridazin-7-yl)-N-((R)-2-fluoro-3-methoxy-3-methylbutyl)-4-(((1S,3R)-3-hydroxycyclohexyl)amino)nicotinamide |
| 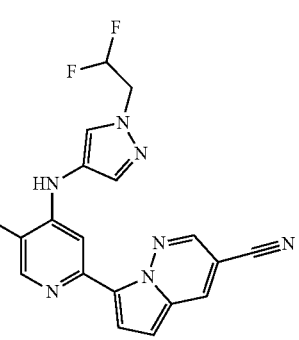 | 519 | 574.3 | 13 | 6-(3-cyanopyrrolo[1,2-b]pyridazin-7-yl)-N-((1r,4r)-4-(cyclopropanecarboxamido)cyclohexyl)-4-((1-(2,2-difluoroethyl)-1H-pyrazol-4-yl)amino)nicotinamide |
| 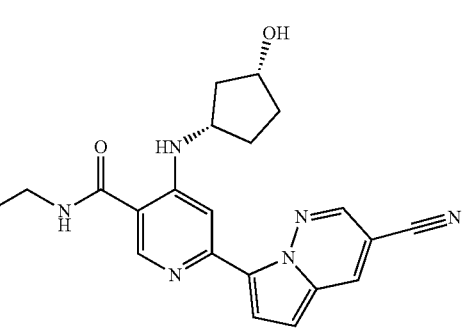 | 520 | 467.3 | 2 | 6-(3-cyanopyrrolo[1,2-b]pyridazin-7-yl)-N-((R)-2-fluoro-3-hydroxy-3-methylbutyl)-4-(((1S,3R)-3-hydroxycyclopentyl)amino)nicotinamide |

TABLE 1-continued

| Structure | compound | ES/MS m/z | procedure | Name |
|---|---|---|---|---|
| 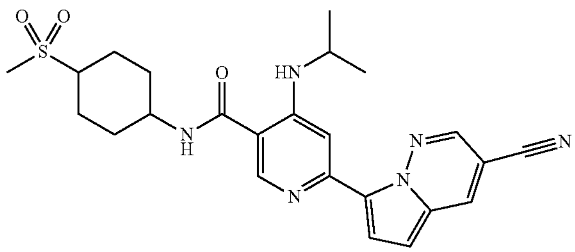 [SMILES: CC(C)Nc1cc(-c2ccc3cc(C#N)cnn23)ncc1C(=O)NC1CCC(S(C)(=O)=O)CC1] | 521 | 481.3 | 1 | 6-(3-cyanopyrrolo[1,2-b]pyridazin-7-yl)-4-(isopropylamino)-N-(4-(methylsulfonyl)cyclohexyl)nicotinamide |
| 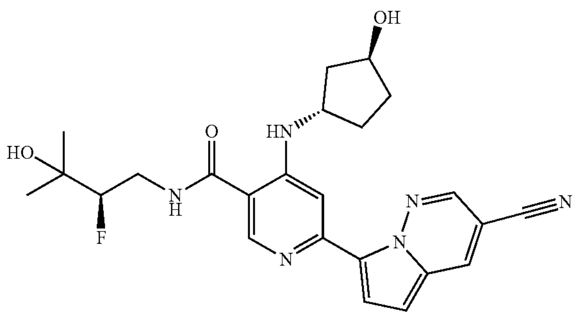 [SMILES: CC(C)(O)[C@H](F)CNC(=O)c1cnc(-c2ccc3cc(C#N)cnn23)cc1N[C@H]1CC[C@H](O)C1] | 522 | 467.2 | 2 | 6-(3-cyanopyrrolo[1,2-b]pyridazin-7-yl)-N-((R)-2-fluoro-3-hydroxy-3-methylbutyl)-4-(((1S,3S)-3-hydroxycyclopentyl)amino)nicotinamide |
| 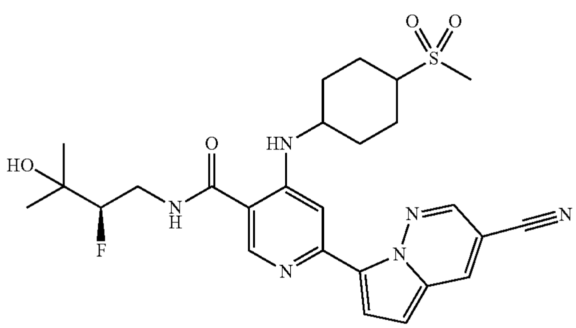 [SMILES: CC(C)(O)[C@H](F)CNC(=O)c1cnc(-c2ccc3cc(C#N)cnn23)cc1NC1CCC(S(C)(=O)=O)CC1] | 523 | 543.2 | 2 | (R)-6-(3-cyanopyrrolo[1,2-b]pyridazin-7-yl)-N-(2-fluoro-3-hydroxy-3-methylbutyl)-4-((4-(methylsulfonyl)cyclohexyl)amino)nicotinamide |
| 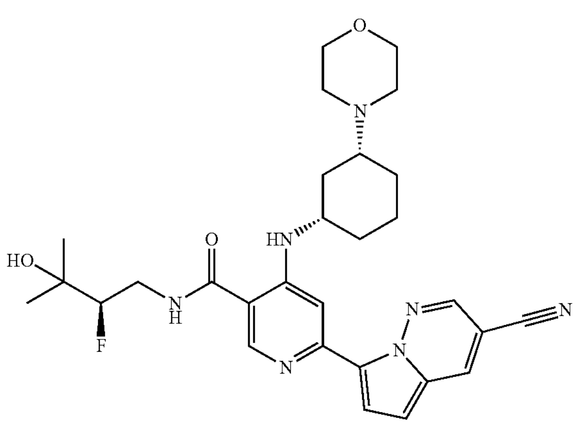 [SMILES: CC(C)(O)[C@H](F)CNC(=O)c1cnc(-c2ccc3cc(C#N)cnn23)cc1N[C@H]1CCC[C@@H](N2CCOCC2)C1] | 524 | 550.3 | 58 | 6-(3-cyanopyrrolo[1,2-b]pyridazin-7-yl)-N-((R)-2-fluoro-3-hydroxy-3-methylbutyl)-4-(((1S,3R)-3-morpholinocyclohexyl)amino)nicotinamide |

TABLE 1-continued

| Structure | compound | ES/MS m/z | procedure | Name |
|---|---|---|---|---|
| 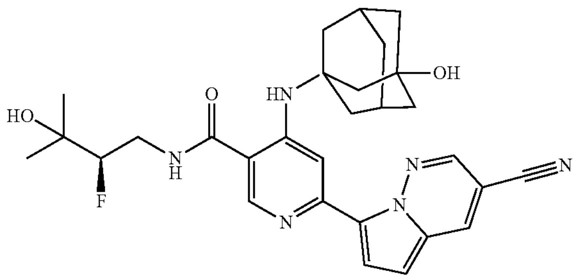 | 525 | 533.3 | 2 | 6-(3-cyanopyrrolo[1,2-b]pyridazin-7-yl)-N-((R)-2-fluoro-3-hydroxy-3-methylbutyl)-4-(((1s,3S)-3-hydroxyadamantan-1-yl)amino)nicotinamide |
| 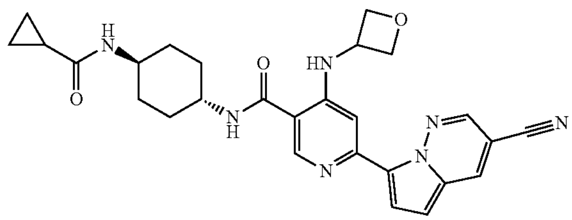 [SMILES: N#Cc1cnn2c(-c3cc(NC4COC4)c(C(=O)N[C@H]4CC[C@H](NC(=O)C5CC5)CC4)cn3)ccc2c1] | 526 | 500.2 | 13 | 6-(3-cyanopyrrolo[1,2-b]pyridazin-7-yl)-N-((1r,4r)-4-(cyclopropane-carboxamido)cyclohexyl)-4-(oxetan-3-ylamino)nicotinamide |
| 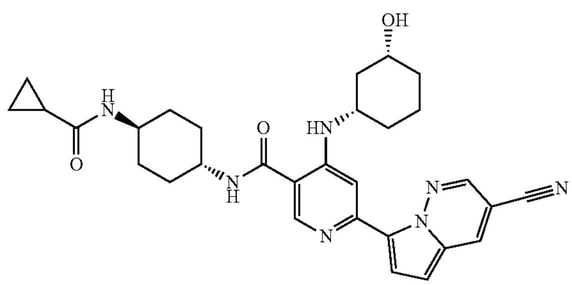 [SMILES: N#Cc1cnn2c(-c3cc(N[C@H]4CCC[C@@H](O)C4)c(C(=O)N[C@H]4CC[C@H](NC(=O)C5CC5)CC4)cn3)ccc2c1] | 527 | 542.3 | 13 | 6-(3-cyanopyrrolo[1,2-b]pyridazin-7-yl)-N-((1r,4S)-4-(cyclopropane-carboxamido)cyclohexyl)-4-((((1S,3R)-3-hydroxycyclohexyl)amino)nicotinamide |
| diastereomer 1 | 528 | 495.4 | 57 | 6-(3-cyanopyrrolo[1,2-b]pyridazin-7-yl)-N-((R)-2-fluoro-3-hydroxy-3-methylbutyl)-4-((3-hydroxy-3-methylcyclohexyl)amino)nicotinamide |
| diastereomer 2 | 529 | 495.4 | 57 | 6-(3-cyanopyrrolo[1,2-b]pyridazin-7-yl)-N-((R)-2-fluoro-3-hydroxy-3-methylbutyl)-4-((3-hydroxy-3-methylcyclohexyl)amino)nicotinamide |

TABLE 1-continued

| Structure | compound | ES/MS m/z | procedure | Name |
|---|---|---|---|---|
| 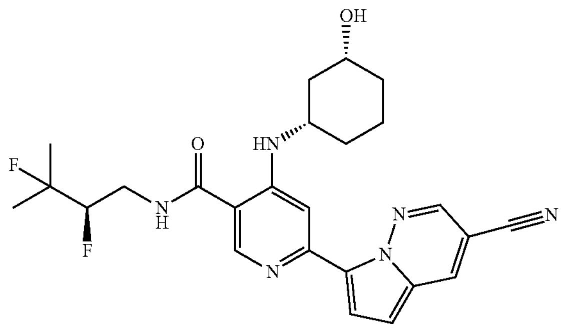 [SMILES: CC(C)(F)[C@H](F)CNC(=O)c1cnc(-c2ccc3cc(C#N)cnn23)cc1N[C@H]1CCC[C@@H](O)C1] | 530 | 483.6 | 1 | 6-(3-cyanopyrrolo[1,2-b]pyridazin-7-yl)-N-((R)-2,3-difluoro-3-methylbutyl)-4-(((1S,3R)-3-hydroxycyclohexyl)amino)nicotinamide |
| 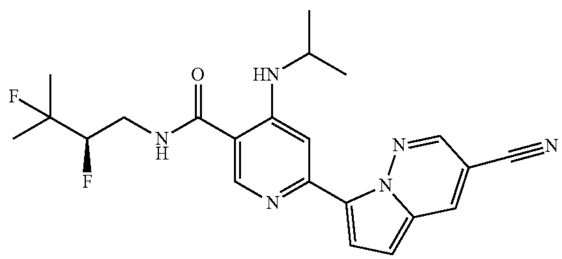 [SMILES: CC(C)Nc1cc(-c2ccc3cc(C#N)cnn23)ncc1C(=O)NC[C@@H](F)C(C)(C)F] | 531 | 427.5 | 1 | (R)-6-(3-cyanopyrrolo[1,2-b]pyridazin-7-yl)-N-(2,3-difluoro-3-methylbutyl)-4-(isopropylamino)nicotinamide |
| 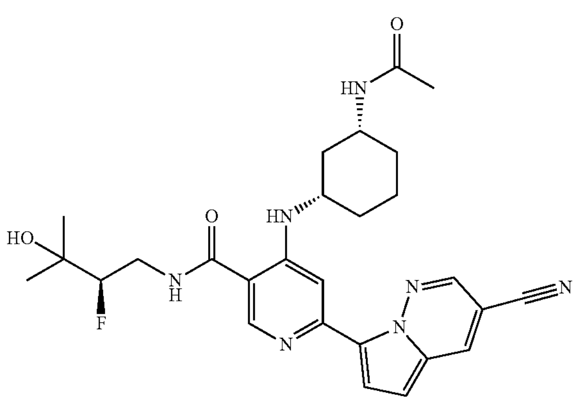 [SMILES: CC(=O)N[C@@H]1CCC[C@H](Nc2cc(-c3ccc4cc(C#N)cnn34)ncc2C(=O)NC[C@@H](F)C(C)(C)O)C1] | 532 | 522.3 | 16 | 4-(((1S,3R)-3-acetamidocyclohexyl)amino)-6-(3-cyano-pyrrolo[1,2-b]pyridazin-7-yl)-N-((R)-2-fluoro-3-hydroxy-3-methylbutyl)nicotinamide |
| 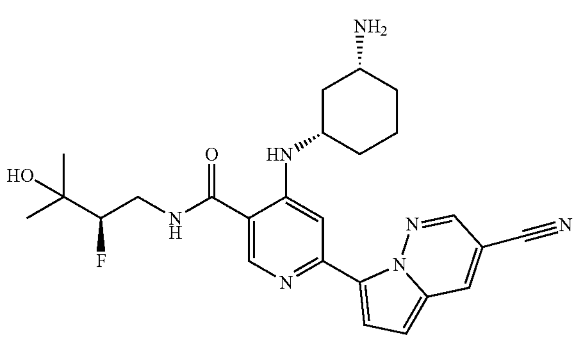 | 533 | 480.3 | 14 | 4-(((1S,3R)-3-aminocyclohexyl)amino)-6-(3-cyanopyrrolo[1,2-b]pyridazin-7-yl)-N-((R)-2-fluoro-3-hydroxy-3-methylbutyl)nicotinamide |

TABLE 1-continued

| Structure | compound | ES/MS m/z | procedure | Name |
|---|---|---|---|---|
| 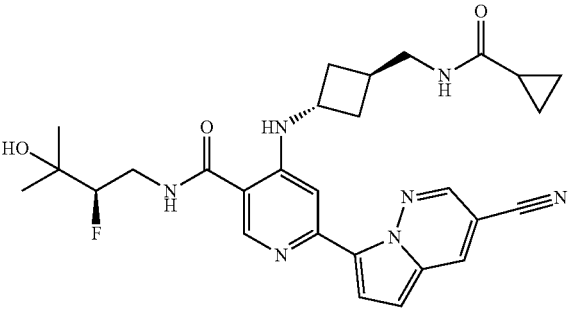 [SMILES: CC(C)(O)[C@H](F)CNC(=O)c1cnc(-c2ccc3cc(C#N)cnn23)cc1N[C@H]1C[C@H](CNC(=O)C2CC2)C1] | 534 | 534.4 | 28 | 6-(3-cyanopyrrolo[1,2-b]pyridazin-7-yl)-4-(((1r,3R)-3-(cyclopropane-carboxamidomethyl)cyclobutyl)amino)-N-((R)-2-fluoro-3-hydroxy-3-methylbutyl)nicotinamide |
| 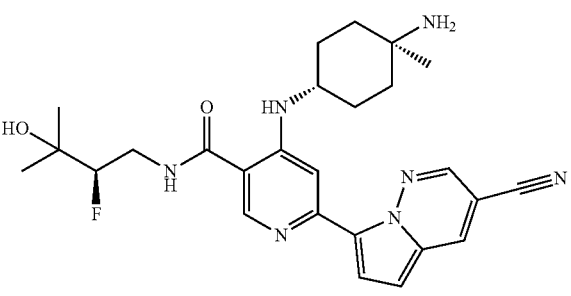 [SMILES: CC(C)(O)[C@H](F)CNC(=O)c1cnc(-c2ccc3cc(C#N)cnn23)cc1N[C@H]1CC[C@](C)(N)CC1] | 535 | 494.3 | 66 | 4-(((1r,4R)-4-amino-4-methylcyclohexyl)amino)-6-(3-cyanopyrrolo[1,2-b]pyridazin-7-yl)-N-((R)-2-fluoro-3-hydroxy-3-methylbutyl)nicotinamide |
| 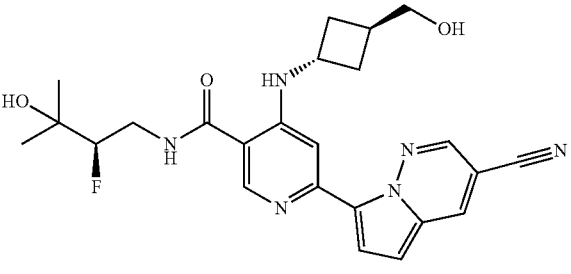 [SMILES: CC(C)(O)[C@H](F)CNC(=O)c1cnc(-c2ccc3cc(C#N)cnn23)cc1N[C@H]1C[C@H](CO)C1] | 536 | 467.4 | 2 | 6-(3-cyanopyrrolo[1,2-b]pyridazin-7-yl)-N-((R)-2-fluoro-3-hydroxy-3-methylbutyl)-4-(((1r,3R)-3-(hydroxymethyl)cyclobutyl)amino)nicotinamide |
| 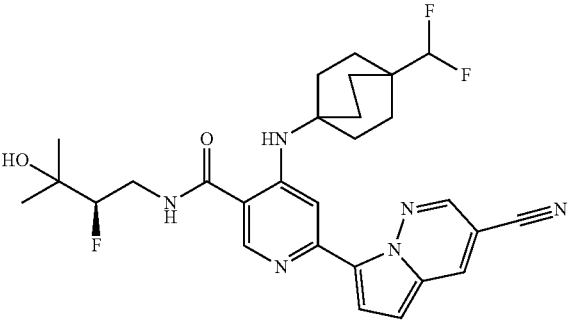 [SMILES: CC(C)(O)[C@H](F)CNC(=O)c1cnc(-c2ccc3cc(C#N)cnn23)cc1NC12CCC(C(F)F)(CC1)CC2] | 537 | 541.3 | 2 | (R)-6-(3-cyanopyrrolo[1,2-b]pyridazin-7-yl)-4-((4-(difluoromethyl)bicyclo[2.2.2]octan-1-yl)amino)-N-(2-fluoro-3-hydroxy-3-methylbutyl)nicotinamide |
| 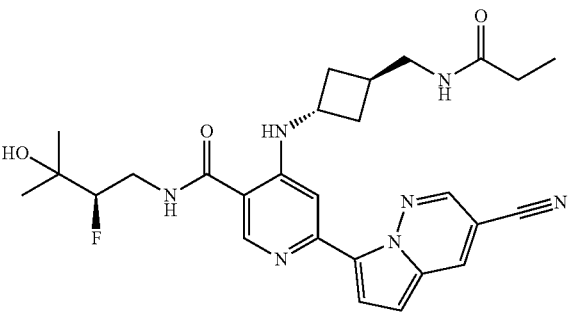 [SMILES: CCC(=O)NC[C@H]1C[C@H](Nc2cc(-c3ccc4cc(C#N)cnn34)ncc2C(=O)NC[C@@H](F)C(C)(C)O)C1] | 538 | 522.3 | 28 | 6-(3-cyanopyrrolo[1,2-b]pyridazin-7-yl)-N-((R)-2-fluoro-3-hydroxy-3-methylbutyl)-4-(((1r,3R)-3-(propionamidomethyl)cyclobutyl)amino)nicotinamide |

TABLE 1-continued

| Structure | compound | ES/MS m/z | procedure | Name |
|---|---|---|---|---|
| 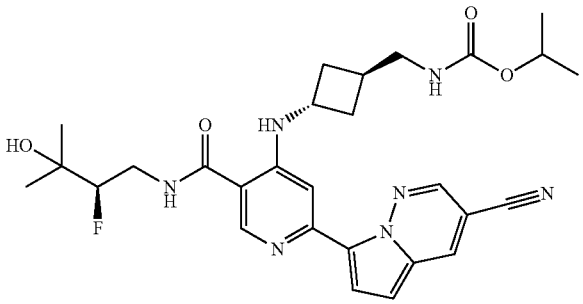 [SMILES: CC(C)OC(=O)NC[C@H]1C[C@H](Nc2cc(-c3ccc4cc(C#N)cnn34)ncc2C(=O)NC[C@@H](F)C(C)(C)O)C1] | 539 | 552.5 | 35 | isopropyl (((1R,3r)-3-((2-(3-cyanopyrrolo[1,2-b]pyridazin-7-yl)-5-(((R)-2-fluoro-3-hydroxy-3-methylbutyl)carbamoyl)pyridin-4-yl)amino)cyclobutyl)methyl)carbamate |
| 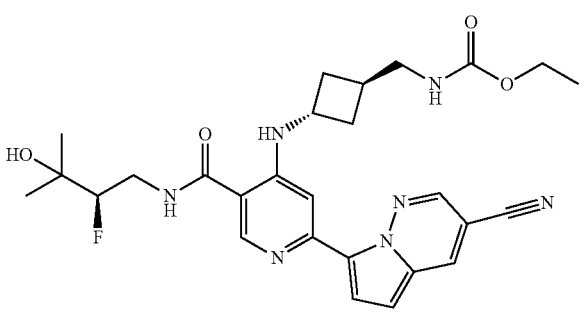 [SMILES: CCOC(=O)NC[C@H]1C[C@H](Nc2cc(-c3ccc4cc(C#N)cnn34)ncc2C(=O)NC[C@@H](F)C(C)(C)O)C1] | 540 | 538.4 | 35 | ethyl (((1R,3r)-3-((2-(3-cyanopyrrolo[1,2-b]pyridazin-7-yl)-5-(((R)-2-fluoro-3-hydroxy-3-methylbutyl)carbamoyl)pyridin-4-yl)amino)cyclobutyl)methyl)carbamate |
| 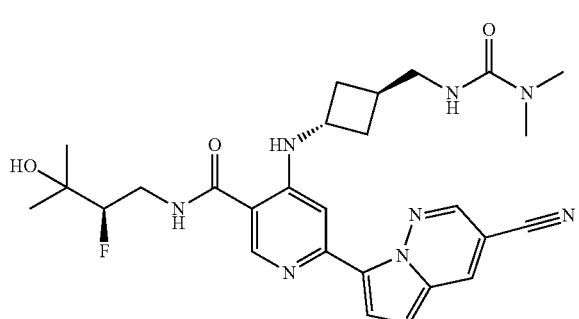 | 541 | 537.4 | 31 | 6-(3-cyanopyrrolo[1,2-b]pyridazin-7-yl)-4-(((1r,3R)-3-((3,3-dimethylureido)methyl)cyclobutyl)amino)-N-((R)-2-fluoro-3-hydroxy-3-methylbutyl)nicotinamide |
| 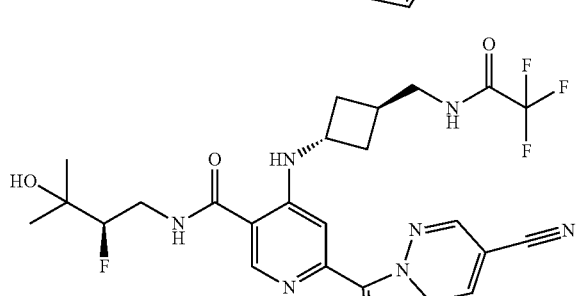 | 542 | 562.3 | 67 | 6-(3-cyanopyrrolo[1,2-b]pyridazin-7-yl)-N-((R)-2-fluoro-3-hydroxy-3-methylbutyl)-4-(((1r,3R)-3-((2,2,2-trifluoroacetamido)methyl)cyclobutyl)amino)nicotinamide |
| 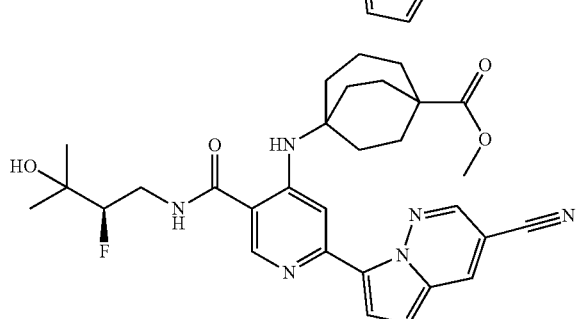 | 543 | 563.4 | 2 | (R)-methyl 5-((2-(3-cyanopyrrolo[1,2-b]pyridazin-7-yl)-5-((2-fluoro-3-hydroxy-3-methylbutyl)carbamoyl)pyridin-4-yl)amino)bicyclo[3.2.2]nonane-1-carboxylate |

TABLE 1-continued

| Structure | compound | ES/MS m/z | procedure | Name |
|---|---|---|---|---|
| 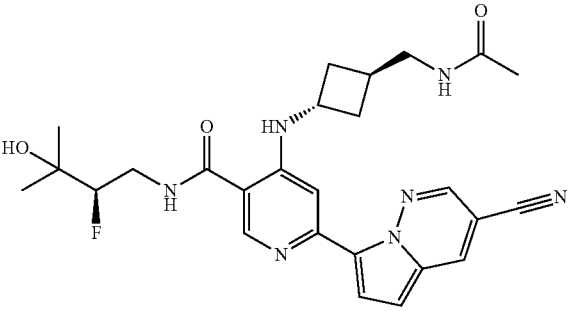 [SMILES: CC(=O)NC[C@H]1C[C@H](Nc2cc(-c3ccc4cc(C#N)cnn34)ncc2C(=O)NC[C@@H](F)C(C)(C)O)C1] | 544 | 508.3 | 28 | 4-(((1r,3R)-3-(acetamidomethyl)cyclobutyl)amino)-6-(3-cyanopyrrolo[1,2-b]pyridazin-7-yl)-N-((R)-2-fluoro-3-hydroxy-3-methylbutyl)nicotinamide |
| 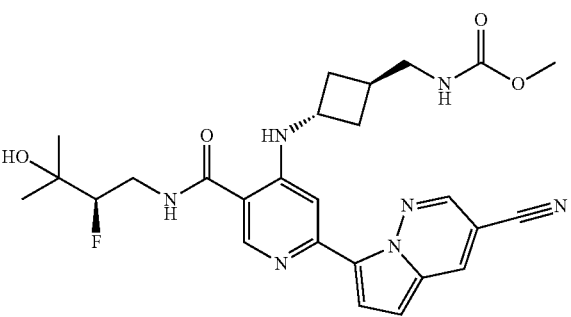 [SMILES: COC(=O)NC[C@H]1C[C@H](Nc2cc(-c3ccc4cc(C#N)cnn34)ncc2C(=O)NC[C@@H](F)C(C)(C)O)C1] | 545 | 524.3 | 68 | methyl (((1R,3r)-3-((2-(3-cyanopyrrolo[1,2-b]pyridazin-7-yl)-5-(((R)-2-fluoro-3-hydroxy-3-methylbutyl)carbamoyl)pyridin-4-yl)amino)cyclobutyl)methyl)carbamate |
| 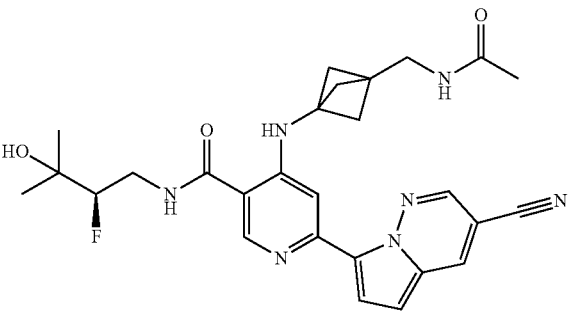 [SMILES: CC(=O)NCC12CC(Nc3cc(-c4ccc5cc(C#N)cnn45)ncc3C(=O)NC[C@@H](F)C(C)(C)O)(C1)C2] | 546 | 520.2 | 28 | (R)-4-((3-(acetamidomethyl)bicyclo[1.1.1]pentan-1-yl)amino)-6-(3-cyanopyrrolo[1,2-b]pyridazin-7-yl)-N-(2-fluoro-3-hydroxy-3-methylbutyl)nicotinamide |
| 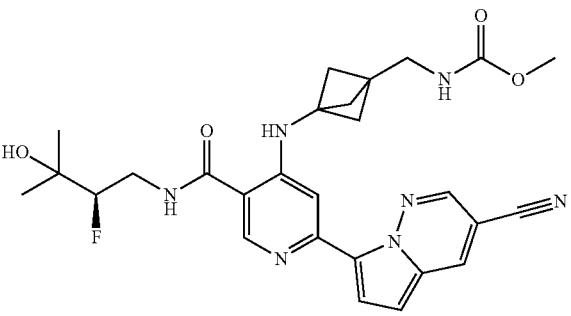 [SMILES: COC(=O)NCC12CC(Nc3cc(-c4ccc5cc(C#N)cnn45)ncc3C(=O)NC[C@@H](F)C(C)(C)O)(C1)C2] | 547 | 536.2 | 68 | (R)-methyl ((3-((2-(3-cyanopyrrolo[1,2-b]pyridazin-7-yl)-5-((2-fluoro-3-hydroxy-3-methylbutyl)carbamoyl)pyridin-4-yl)amino)bicyclo[1.1.1]pentan-1-yl)methyl)carbamate |

TABLE 1-continued

| Structure | compound | ES/MS m/z | procedure | Name |
|---|---|---|---|---|
| 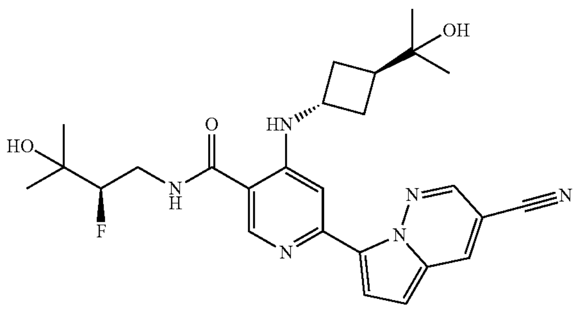 [SMILES: CC(C)(O)[C@H](F)CNC(=O)c1cnc(-c2ccc3cc(C#N)cnn23)cc1N[C@H]1C[C@H](C(C)(C)O)C1] | 548 | 495.4 | 2 | 6-(3-cyanopyrrolo[1,2-b]pyridazin-7-yl)-N-((R)-2-fluoro-3-hydroxy-3-methylbutyl)-4-(((1r,3R)-3-(2-hydroxypropan-2-yl)cyclobutyl)amino)nicotinamide |
| 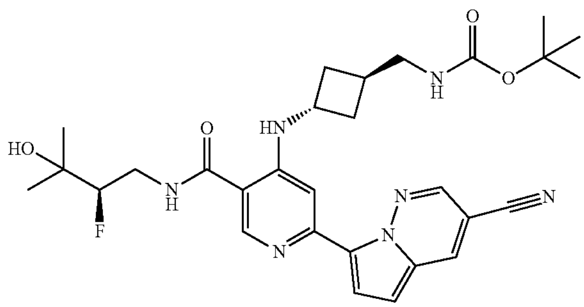 [SMILES: CC(C)(C)OC(=O)NC[C@H]1C[C@H](Nc2cc(-c3ccc4cc(C#N)cnn34)ncc2C(=O)NC[C@@H](F)C(C)(C)O)C1] | 549 | 566.2 | 2 | tert-butyl (((1R,3r)-3-((2-(3-cyanopyrrolo[1,2-b]pyridazin-7-yl)-5-(((R)-2-fluoro-3-hydroxy-3-methylbutyl)carbamoyl)pyridin-4-yl)amino)cyclobutyl)methyl)carbamate |
| 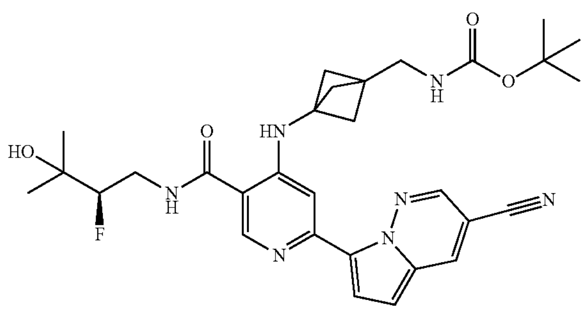 [SMILES: CC(C)(C)OC(=O)NCC12CC(Nc3cc(-c4ccc5cc(C#N)cnn45)ncc3C(=O)NC[C@@H](F)C(C)(C)O)(C1)C2] | 550 | 578.3 | 2 | (R)-tert-butyl ((3-((2-(3-cyanopyrrolo[1,2-b]pyridazin-7-yl)-5-((2-fluoro-3-hydroxy-3-methylbutyl)carbamoyl)pyridin-4-yl)amino)bicyclo[1.1.1]pentan-1-yl)methyl)carbamate |
| 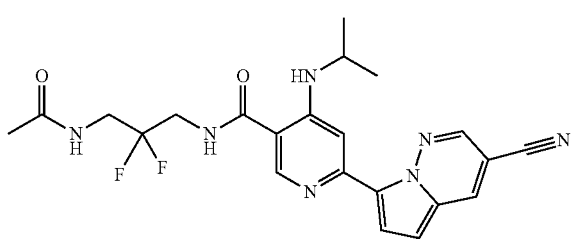 [SMILES: CC(=O)NCC(F)(F)CNC(=O)c1cnc(-c2ccc3cc(C#N)cnn23)cc1NC(C)C] | 551 | 456.3 | 69 | N-(3-acetamido-2,2-difluoropropyl)-6-(3-cyanopyrrolo[1,2-b]pyridazin-7-yl)-4-(isopropylamino)nicotinamide |
| 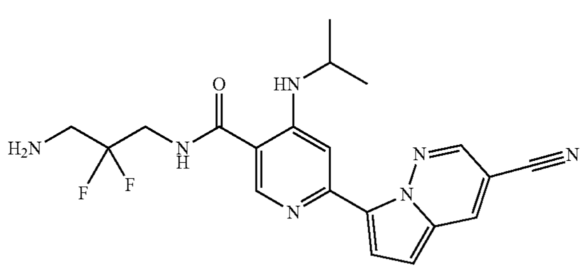 [SMILES: CC(C)Nc1cc(-c2ccc3cc(C#N)cnn23)ncc1C(=O)NCC(F)(F)CN] | 552 | 414.3 | 69 | N-(3-amino-2,2-difluoropropyl)-6-(3-cyanopyrrolo[1,2-b]pyridazin-7-yl)-4-(isopropylamino)nicotinamide |

TABLE 1-continued

| Structure | compound | ES/MS m/z | procedure | Name |
|---|---|---|---|---|
| 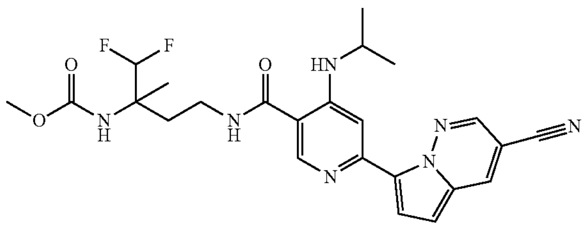 [SMILES: COC(=O)NC(C)(CCNC(=O)c1cnc(-c2ccc3cc(C#N)cnn23)cc1NC(C)C)C(F)F] | 553 | 500.3 | 68 | methyl (4-(6-(3-cyano-pyrrolo[1,2-b]pyridazin-7-yl)-4-(isopropylamino)nicotinamido)-1,1-difluoro-2-methylbutan-2-yl)carbamate |
| 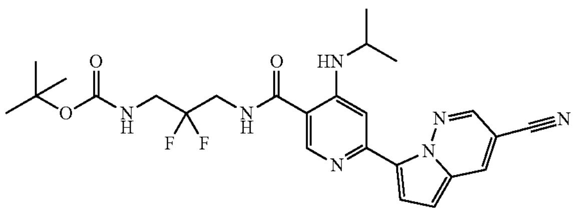 [SMILES: CC(C)Nc1cc(-c2ccc3cc(C#N)cnn23)ncc1C(=O)NCC(F)(F)CNC(=O)OC(C)(C)C] | 554 | 514.4 | 1 | tert-butyl (3-(6-(3-cyano-pyrrolo[1,2-b]pyridazin-7-yl)-4-(isopropylamino)nicotinamido)-2,2-difluoropropyl)carbamate |
| 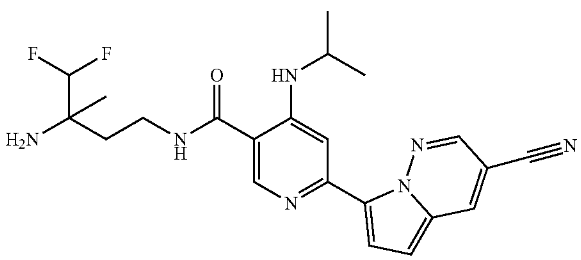 [SMILES: CC(C)Nc1cc(-c2ccc3cc(C#N)cnn23)ncc1C(=O)NCCC(C)(N)C(F)F] | 555 | 442.3 | 1 | N-(3-amino-4,4-difluoro-3-methylbutyl)-6-(3-cyano-pyrrolo[1,2-b]pyridazin-7-yl)-4-(isopropylamino)nicotinamide |
| 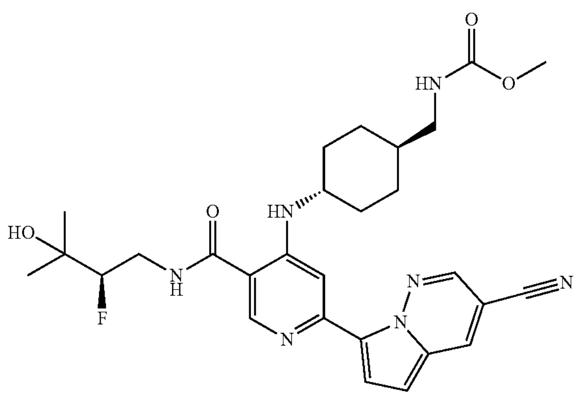 [SMILES: COC(=O)NC[C@H]1CC[C@H](Nc2cc(-c3ccc4cc(C#N)cnn34)ncc2C(=O)NC[C@@H](F)C(C)(C)O)CC1] | 556 | 552.3 | 68 | methyl (((1R,4r)-4-((2-(3-cyanopyrrolo[1,2-b]pyridazin-7-yl)-5-(((R)-2-fluoro-3-hydroxy-3-methylbutyl)carbamoyl)pyridin-4-yl)amino)cyclohexyl)methyl)carbamate |
| 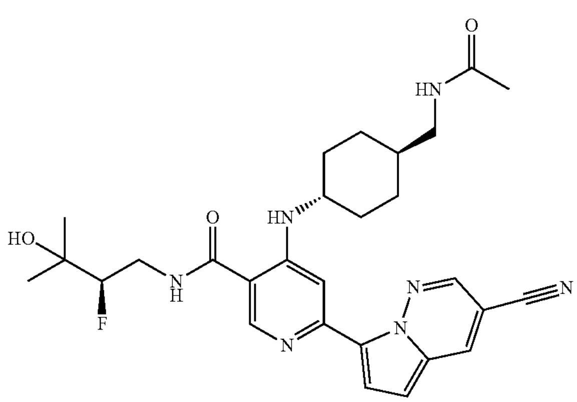 [SMILES: CC(=O)NC[C@H]1CC[C@H](Nc2cc(-c3ccc4cc(C#N)cnn34)ncc2C(=O)NC[C@@H](F)C(C)(C)O)CC1] | 557 | 536.3 | 28 | 4-(((1r,4R)-4-(acetamidomethyl)cyclohexyl)amino)-6-(3-cyano-pyrrolo[1,2-b]pyridazin-7-yl)-N-((R)-2-fluoro-3-hydroxy-3-methylbutyl)nicotinamide |

TABLE 1-continued

| Structure | compound | ES/MS m/z | procedure | Name |
|---|---|---|---|---|
| 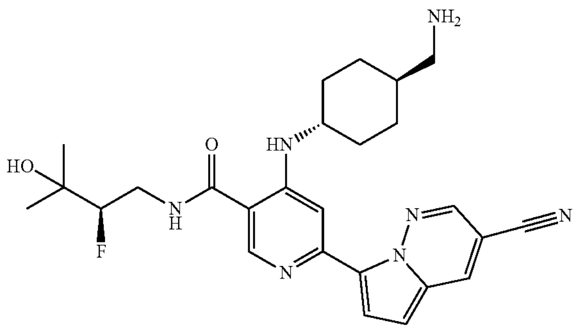 [SMILES: CC(C)(O)[C@H](F)CNC(=O)c1cnc(-c2ccc3cc(C#N)cnn23)cc1N[C@H]1CC[C@H](CN)CC1] | 558 | 494.2 | 68 | 4-(((1r,4R)-4-(aminomethyl)cyclohexyl)amino)-6-(3-cyanopyrrolo[1,2-b]pyridazin-7-yl)-N-((R)-2-fluoro-3-hydroxy-3-methylbutyl)nicotinamide |
| 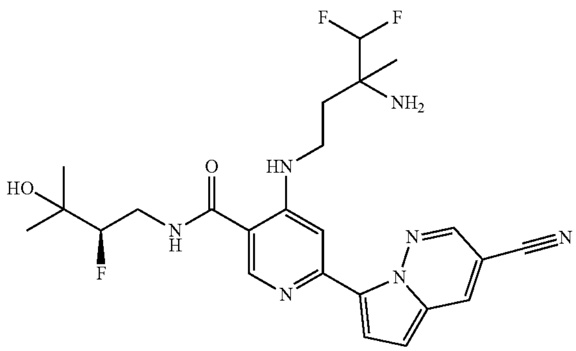 [SMILES: CC(N)(CCNc1cc(-c2ccc3cc(C#N)cnn23)ncc1C(=O)NC[C@@H](F)C(C)(C)O)C(F)F] | 559 | 504.2 | 1 | 4-((3-amino-4,4-difluoro-3-methylbutyl)amino)-6-(3-cyanopyrrolo[1,2-b]pyridazin-7-yl)-N-((R)-2-fluoro-3-hydroxy-3-methylbutyl)nicotinamide |
| 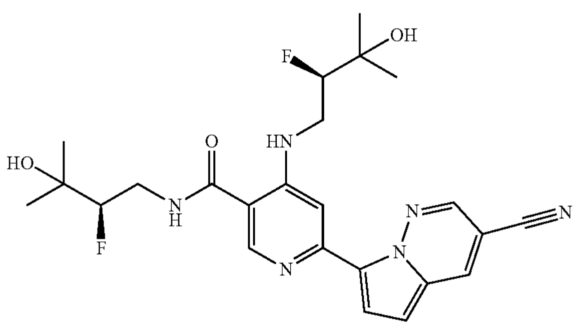 [SMILES: CC(C)(O)[C@H](F)CNC(=O)c1cnc(-c2ccc3cc(C#N)cnn23)cc1NC[C@@H](F)C(C)(C)O] | 560 | 487.6 | 1 | 6-(3-cyanopyrrolo[1,2-b]pyridazin-7-yl)-N-((R)-2-fluoro-3-hydroxy-3-methylbutyl)-4-(((R)-2-fluoro-3-hydroxy-3-methylbutyl)amino)nicotinamide |
| 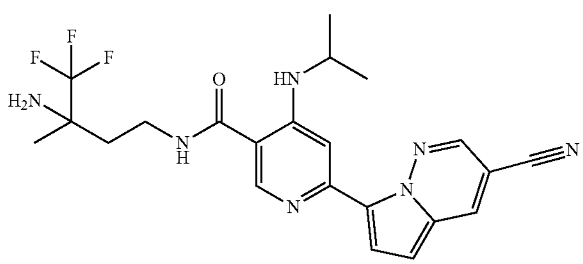 [SMILES: CC(C)Nc1cc(-c2ccc3cc(C#N)cnn23)ncc1C(=O)NCCC(C)(N)C(F)(F)F] | 561 | 460.4 | 1 | N-(3-amino-4,4,4-trifluoro-3-methylbutyl)-6-(3-cyanopyrrolo[1,2-b]pyridazin-7-yl)-4-(isopropylamino)nicotinamide |
| 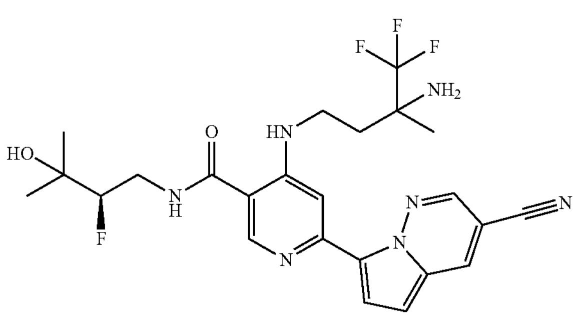 [SMILES: CC(C)(O)[C@H](F)CNC(=O)c1cnc(-c2ccc3cc(C#N)cnn23)cc1NCCC(C)(N)C(F)(F)F] | 562 | 522.4 | 1 | 4-((3-amino-4,4,4-trifluoro-3-methylbutyl)amino)-6-(3-cyanopyrrolo[1,2-b]pyridazin-7-yl)-N-((R)-2-fluoro-3-hydroxy-3-methylbutyl)nicotinamide |

TABLE 1-continued

| Structure | compound | ES/MS m/z | procedure | Name |
|---|---|---|---|---|
| 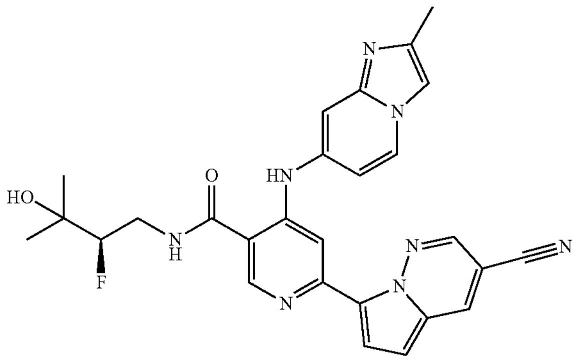 [SMILES: Cc1cn2ccc(Nc3cc(-c4ccc5cc(C#N)cnn45)ncc3C(=O)NC[C@@H](F)C(C)(C)O)cc2n1] | 563 | 513.2 | 2 | (R)-6-(3-cyanopyrrolo[1,2-b]pyridazin-7-yl)-N-(2-fluoro-3-hydroxy-3-methylbutyl)-4-((2-methylimidazo[1,2-a]pyridin-7-yl)amino)nicotinamide |
| 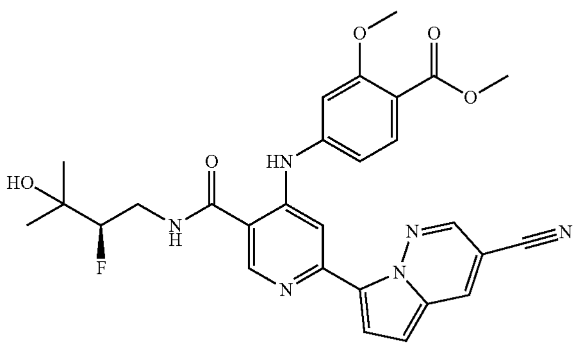 [SMILES: COC(=O)c1ccc(Nc2cc(-c3ccc4cc(C#N)cnn34)ncc2C(=O)NC[C@@H](F)C(C)(C)O)cc1OC] | 564 | 548.2 | 27 | (R)-methyl 4-((2-(3-cyanopyrrolo[1,2-b]pyridazin-7-yl)-5-((2-fluoro-3-hydroxy-3-methylbutyl)carbamoyl)pyridin-4-yl)amino)-2-methoxybenzoate |
| 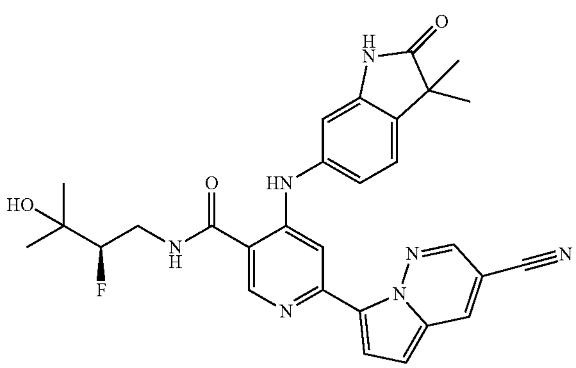 [SMILES: CC1(C)C(=O)Nc2cc(Nc3cc(-c4ccc5cc(C#N)cnn45)ncc3C(=O)NC[C@@H](F)C(C)(C)O)ccc21] | 565 | 542.4 | 2 | (R)-6-(3-cyanopyrrolo[1,2-b]pyridazin-7-yl)-4-((3,3-dimethyl-2-oxoindolin-6-yl)amino)-N-(2-fluoro-3-hydroxy-3-methylbutyl)nicotinamide |
| 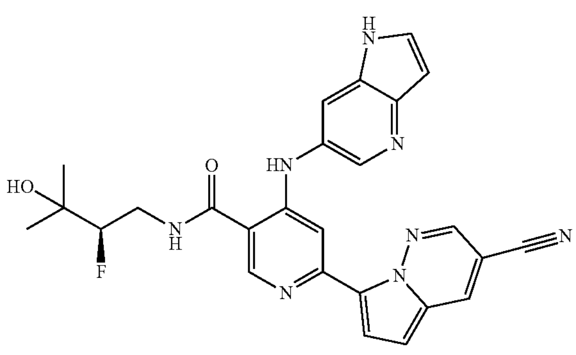 | 566 | 499.3 | 2 | (R)-4-((1H-pyrrolo[3,2-b]pyridin-6-yl)amino)-6-(3-cyanopyrrolo[1,2-b]pyridazin-7-yl)-N-(2-fluoro-3-hydroxy-3-methylbutyl)nicotinamide |

TABLE 1-continued

| Structure | compound | ES/MS m/z | procedure | Name |
|---|---|---|---|---|
| 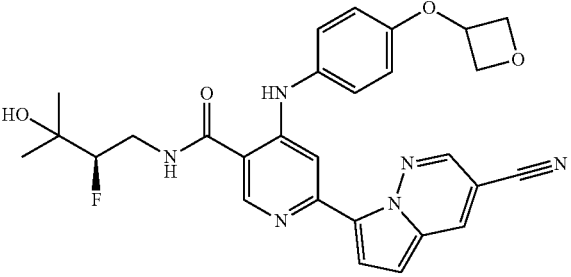 [SMILES: CC(C)(O)[C@H](F)CNC(=O)c1cnc(-c2ccc3cc(C#N)cnn23)cc1Nc1ccc(OC2COC2)cc1] | 567 | 532.3 | 2 | (R)-6-(3-cyanopyrrolo[1,2-b]pyridazin-7-yl)-N-(2-fluoro-3-hydroxy-3-methylbutyl)-4-((4-(oxetan-3-yloxy)phenyl)amino)nicotinamide |
| 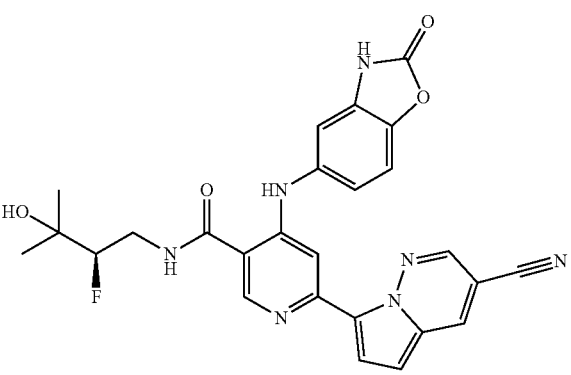 | 568 | 517.2 | 2 | (R)-6-(3-cyanopyrrolo[1,2-b]pyridazin-7-yl)-N-(2-fluoro-3-hydroxy-3-methylbutyl)-4-((2-oxo-2,3-dihydrobenzo[d]oxazol-5-yl)amino)nicotinamide |
| 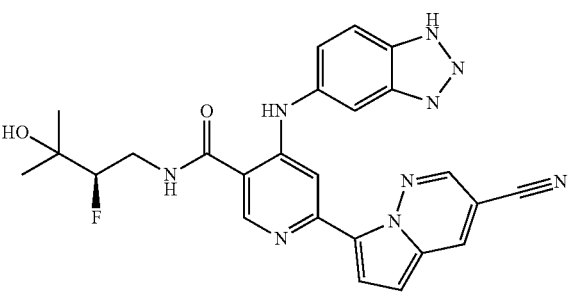 [SMILES: CC(C)(O)[C@H](F)CNC(=O)c1cnc(-c2ccc3cc(C#N)cnn23)cc1Nc1ccc2c(c1)NNN2] | 569 | 501.3 | 2 | (R)-4-((1H-benzo[d][1,2,3]triazol-5-yl)amino)-6-(3-cyanopyrrolo[1,2-b]pyridazin-7-yl)-N-(2-fluoro-3-hydroxy-3-methylbutyl)nicotinamide |
| 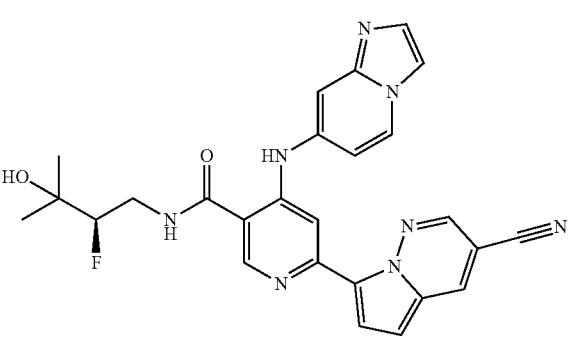 [SMILES: CC(C)(O)[C@H](F)CNC(=O)c1cnc(-c2ccc3cc(C#N)cnn23)cc1Nc1ccn2ccnc2c1] | 570 | 500.2 | 2 | (R)-6-(3-cyanopyrrolo[1,2-b]pyridazin-7-yl)-N-(2-fluoro-3-hydroxy-3-methylbutyl)-4-(imidazo[1,2-a]pyridin-7-ylamino)nicotinamide |

TABLE 1-continued

| Structure | compound | ES/MS m/z | procedure | Name |
|---|---|---|---|---|
| 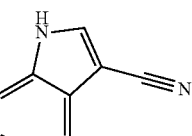 | 571 | 524.2 | 2 | (R)-4-((3-cyano-1H-indol-6-yl)amino)-6-(3-cyano-pyrrolo[1,2-b]pyridazin-7-yl)-N-(2-fluoro-3-hydroxy-3-methylbutyl)nicotinamide |
| 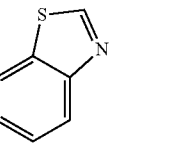 | 572 | 516.3 | 2 | (R)-4-(benzo[d]thiazol-6-ylamino)-6-(3-cyano-pyrrolo[1,2-b]pyridazin-7-yl)-N-(2-fluoro-3-hydroxy-3-methylbutyl)nicotinamide |
| 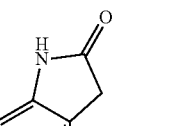 | 573 | 515.2 | 2 | (R)-6-(3-cyanopyrrolo[1,2-b]pyridazin-7-yl)-N-(2-fluoro-3-hydroxy-3-methyl-butyl)-4-((2-oxoindolin-6-yl)amino)nicotinamide |
| 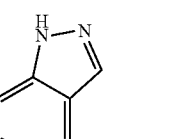 | 574 | 500.3 | 2 | (R)-4-((1H-indazol-6-yl)amino)-6-(3-cyano-pyrrolo[1,2-b]pyridazin-7-yl)-N-(2-fluoro-3-hydroxy-3-methylbutyl)nicotinamide |

TABLE 1-continued

| Structure | compound | ES/MS m/z | procedure | Name |
|---|---|---|---|---|
| 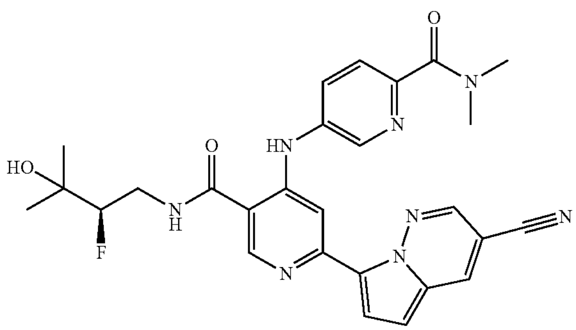 [SMILES: CN(C)C(=O)c1ccc(Nc2cc(-c3ccc4cc(C#N)cnn34)ncc2C(=O)NC[C@@H](F)C(C)(C)O)cn1] | 575 | 532.2 | 27 | (R)-5-((2-(3-cyano-pyrrolo[1,2-b]pyridazin-7-yl)-5-((2-fluoro-3-hydroxy-3-methylbutyl)carbamoyl)pyridin-4-yl)amino)-N,N-dimethyl-picolinamide |
| 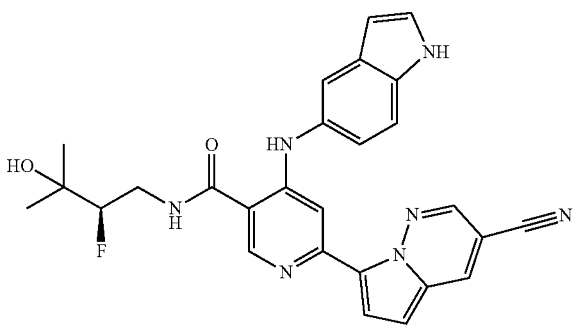 [SMILES: CC(C)(O)[C@H](F)CNC(=O)c1cnc(-c2ccc3cc(C#N)cnn23)cc1Nc1ccc2[nH]ccc2c1] | 576 | 499.2 | 2 | (R)-4-((1H-indol-5-yl)amino)-6-(3-cyano-pyrrolo[1,2-b]pyridazin-7-yl)-N-(2-fluoro-3-hydroxy-3-methylbutyl)nicotinamide |
| 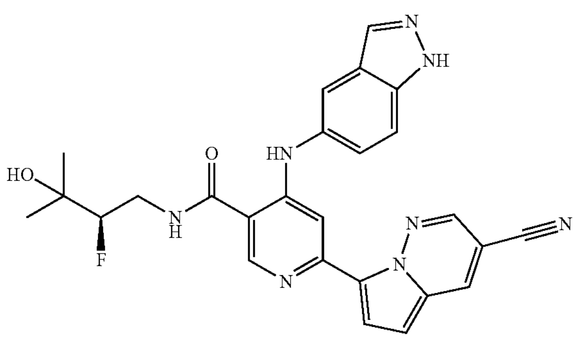 [SMILES: CC(C)(O)[C@H](F)CNC(=O)c1cnc(-c2ccc3cc(C#N)cnn23)cc1Nc1ccc2[nH]ncc2c1] | 577 | 500.2 | 2 | (R)-4-((1H-indazol-5-yl)amino)-6-(3-cyano-pyrrolo[1,2-b]pyridazin-7-yl)-N-(2-fluoro-3-hydroxy-3-methylbutyl)nicotinamide |
| 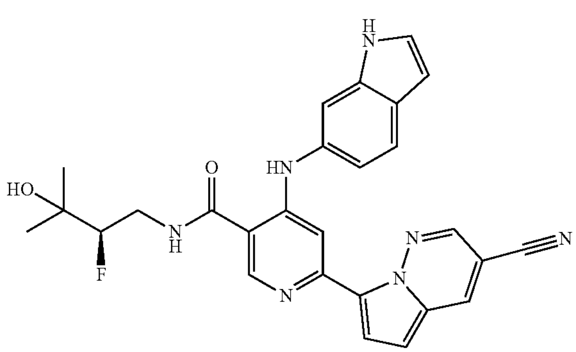 | 578 | 499.2 | 2 | (R)-4-((1H-indol-6-yl)amino)-6-(3-cyano-pyrrolo[1,2-b]pyridazin-7-yl)-N-(2-fluoro-3-hydroxy-3-methylbutyl)nicotinamide |

TABLE 1-continued

| Structure | compound | ES/MS m/z | procedure | Name |
|---|---|---|---|---|
| 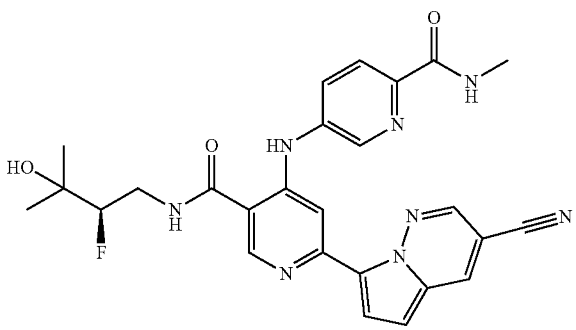 [SMILES: CNC(=O)c1ccc(Nc2cc(-c3ccc4cc(C#N)cnn34)ncc2C(=O)NC[C@@H](F)C(C)(C)O)cn1] | 579 | 518.3 | 27 | (R)-5-((2-(3-cyano-pyrrolo[1,2-b]pyridazin-7-yl)-5-((2-fluoro-3-hydroxy-3-methylbutyl)carbamoyl)pyridin-4-yl)amino)-N-methylpicolinamide |
| 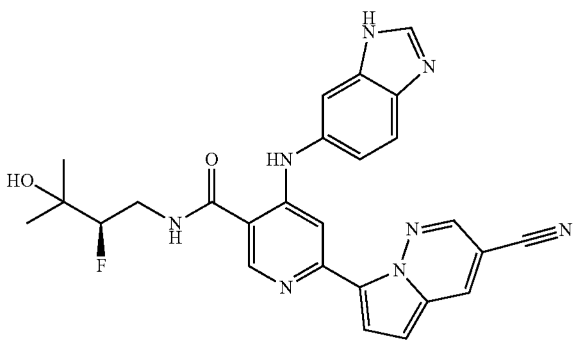 [SMILES: CC(C)(O)[C@H](F)CNC(=O)c1cnc(-c2ccc3cc(C#N)cnn23)cc1Nc1ccc2nc[nH]c2c1] | 580 | 500.2 | 2 | (R)-4-((1H-benzo[d]imidazol-6-yl)amino)-6-(3-cyanopyrrolo[1,2-b]pyridazin-7-yl)-N-(2-fluoro-3-hydroxy-3-methylbutyl)nicotinamide |
| 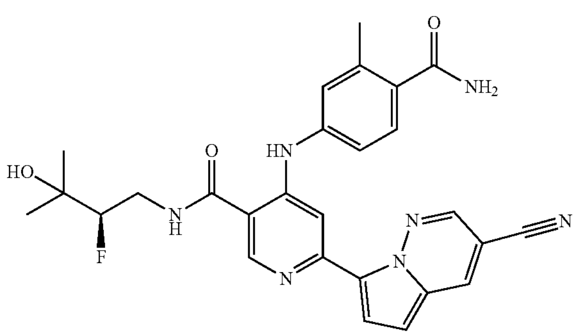 [SMILES: Cc1cc(Nc2cc(-c3ccc4cc(C#N)cnn34)ncc2C(=O)NC[C@@H](F)C(C)(C)O)ccc1C(N)=O] | 581 | 517.3 | 27 | (R)-4-((4-carbamoyl-3-methylphenyl)amino)-6-(3-cyanopyrrolo[1,2-b]pyridazin-7-yl)-N-(2-fluoro-3-hydroxy-3-methylbutyl)nicotinamide |
| 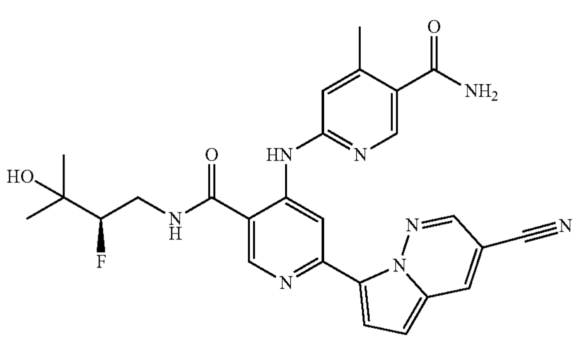 [SMILES: Cc1cc(Nc2cc(-c3ccc4cc(C#N)cnn34)ncc2C(=O)NC[C@@H](F)C(C)(C)O)ncc1C(N)=O] | 582 | 518.1 | 27 | (R)-4-((5-carbamoyl-4-methylpyridin-2-yl)amino)-6-(3-cyanopyrrolo[1,2-b]pyridazin-7-yl)-N-(2-fluoro-3-hydroxy-3-methylbutyl)nicotinamide |

TABLE 1-continued

| Structure | compound | ES/MS m/z | procedure | Name |
|---|---|---|---|---|
| 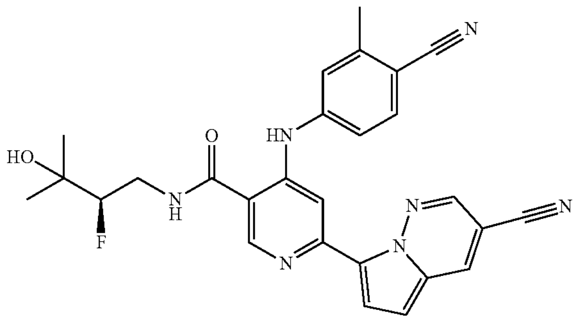 [SMILES: Cc1cc(Nc2cc(-c3ccc4cc(C#N)cnn34)ncc2C(=O)NC[C@@H](F)C(C)(C)O)ccc1C#N] | 583 | 499.2 | 27 | (R)-4-((4-cyano-3-methylphenyl)amino)-6-(3-cyanopyrrolo[1,2-b]pyridazin-7-yl)-N-(2-fluoro-3-hydroxy-3-methylbutyl)nicotinamide |
| 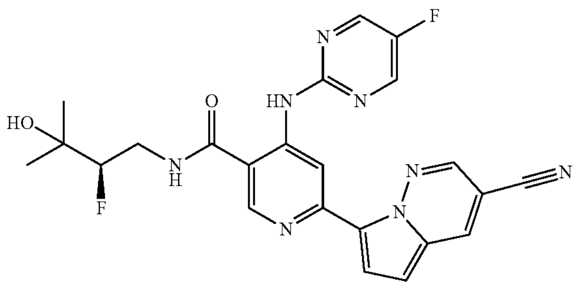 [SMILES: CC(C)(O)[C@H](F)CNC(=O)c1cnc(-c2ccc3cc(C#N)cnn23)cc1Nc1ncc(F)cn1] | 584 | 480.1 | 27 | (R)-6-(3-cyanopyrrolo[1,2-b]pyridazin-7-yl)-N-(2-fluoro-3-hydroxy-3-methylbutyl)-4-((5-fluoropyrimidin-2-yl)amino)nicotinamide |
| 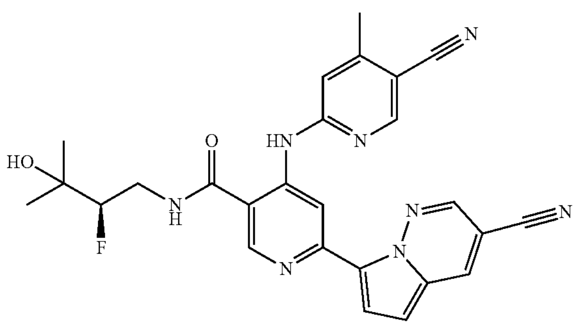 [SMILES: Cc1cc(Nc2cc(-c3ccc4cc(C#N)cnn34)ncc2C(=O)NC[C@@H](F)C(C)(C)O)ncc1C#N] | 585 | 500.2 | 27 | (R)-4-((5-cyano-4-methylpyridin-2-yl)amino)-6-(3-cyanopyrrolo[1,2-b]pyridazin-7-yl)-N-(2-fluoro-3-hydroxy-3-methylbutyl)nicotinamide |
| 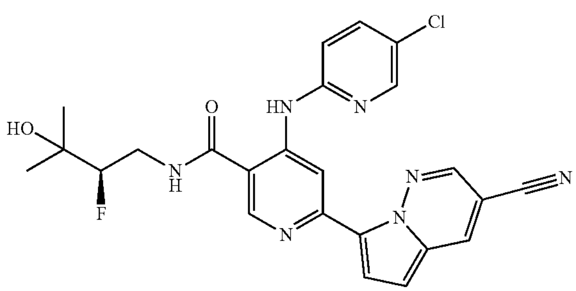 [SMILES: CC(C)(O)[C@H](F)CNC(=O)c1cnc(-c2ccc3cc(C#N)cnn23)cc1Nc1ccc(Cl)cn1] | 586 | 496.1 | 27 | (R)-4-((5-chloropyridin-2-yl)amino)-6-(3-cyanopyrrolo[1,2-b]pyridazin-7-yl)-N-(2-fluoro-3-hydroxy-3-methylbutyl)nicotinamide |
| 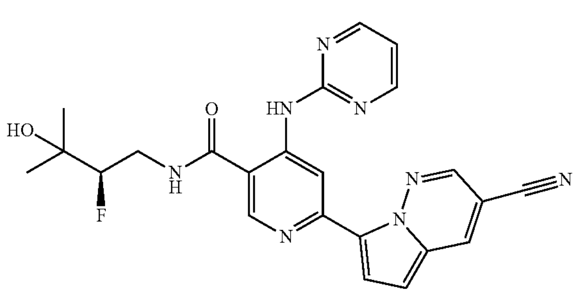 [SMILES: CC(C)(O)[C@H](F)CNC(=O)c1cnc(-c2ccc3cc(C#N)cnn23)cc1Nc1ncccn1] | 587 | 462.1 | 27 | (R)-6-(3-cyanopyrrolo[1,2-b]pyridazin-7-yl)-N-(2-fluoro-3-hydroxy-3-methylbutyl)-4-(pyrimidin-2-ylamino)nicotinamide |

TABLE 1-continued

| Structure | compound | ES/MS m/z | procedure | Name |
|---|---|---|---|---|
| 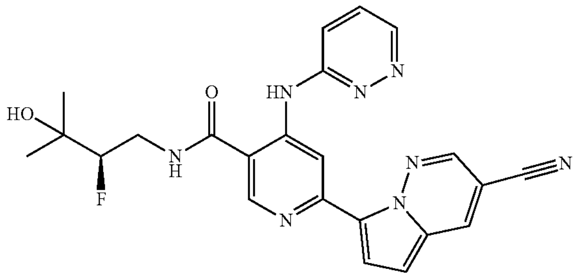 [SMILES: CC(C)(O)[C@H](F)CNC(=O)c1cnc(-c2ccc3cc(C#N)cnn23)cc1Nc1cccnn1] | 588 | 462 | 27 | (R)-6-(3-cyanopyrrolo[1,2-b]pyridazin-7-yl)-N-(2-fluoro-3-hydroxy-3-methylbutyl)-4-(pyridazin-3-ylamino)nicotinamide |
| 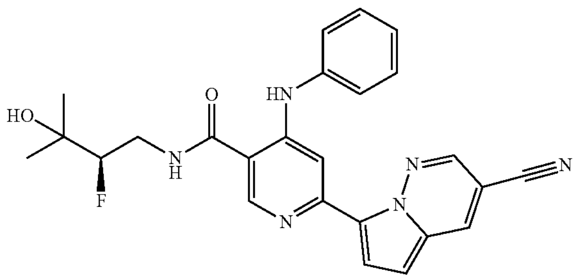 [SMILES: CC(C)(O)[C@H](F)CNC(=O)c1cnc(-c2ccc3cc(C#N)cnn23)cc1Nc1ccccc1] | 589 | 460.2 | 27 | (R)-6-(3-cyanopyrrolo[1,2-b]pyridazin-7-yl)-N-(2-fluoro-3-hydroxy-3-methylbutyl)-4-(phenylamino)nicotinamide |
| 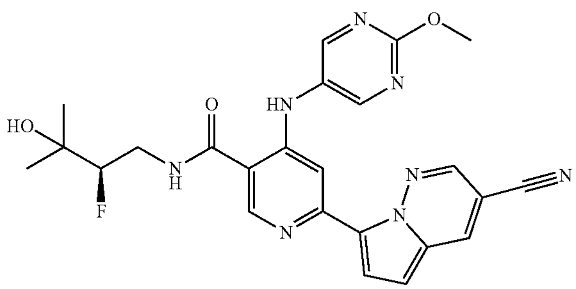 [SMILES: COc1ncc(Nc2cc(-c3ccc4cc(C#N)cnn34)ncc2C(=O)NC[C@@H](F)C(C)(C)O)cn1] | 590 | 492.1 | 27 | (R)-6-(3-cyanopyrrolo[1,2-b]pyridazin-7-yl)-N-(2-fluoro-3-hydroxy-3-methylbutyl)-4-((2-methoxypyrimidin-5-yl)amino)nicotinamide |
| 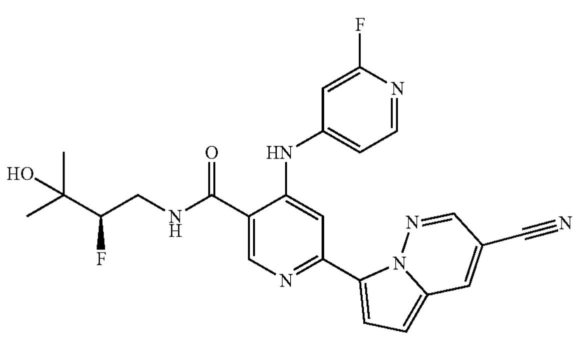 [SMILES: CC(C)(O)[C@H](F)CNC(=O)c1cnc(-c2ccc3cc(C#N)cnn23)cc1Nc1ccnc(F)c1] | 591 | 479.1 | 27 | (R)-6-(3-cyanopyrrolo[1,2-b]pyridazin-7-yl)-N-(2-fluoro-3-hydroxy-3-methylbutyl)-4-((2-fluoropyridin-4-yl)amino)nicotinamide |
| 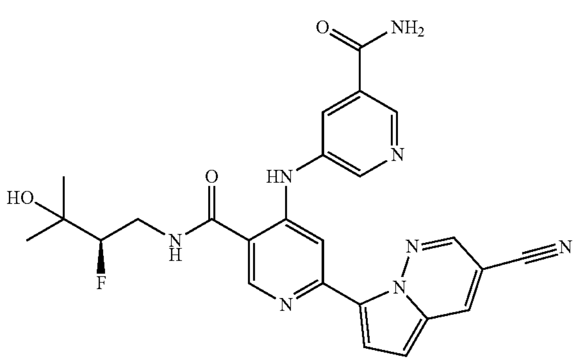 [SMILES: CC(C)(O)[C@H](F)CNC(=O)c1cnc(-c2ccc3cc(C#N)cnn23)cc1Nc1cncc(C(N)=O)c1] | 592 | 504.2 | 27 | (R)-4-((5-carbamoylpyridin-3-yl)amino)-6-(3-cyanopyrrolo[1,2-b]pyridazin-7-yl)-N-(2-fluoro-3-hydroxy-3-methylbutyl)nicotinamide |

TABLE 1-continued

| Structure | compound | ES/ MS m/z | procedure | Name |
|---|---|---|---|---|
| 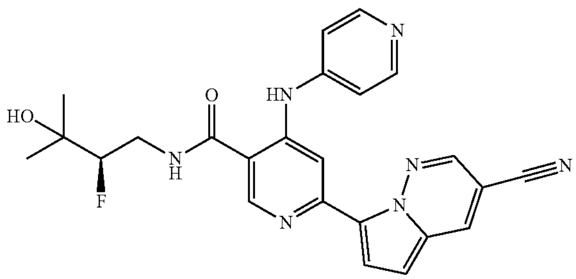 [SMILES: CC(C)(O)[C@H](F)CNC(=O)c1cnc(-c2ccc3cc(C#N)cnn23)cc1Nc1ccncc1] | 593 | 461.1 | 27 | (R)-6-(3-cyano-pyrrolo[1,2-b]pyridazin-7-yl)-N-(2-fluoro-3-hydroxy-3-methylbutyl)-4-(pyridin-4-ylamino) nicotinamide |
| 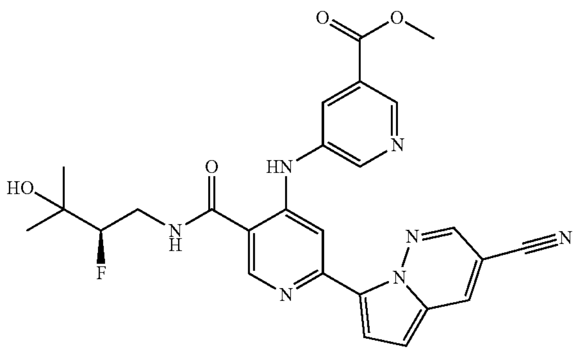 [SMILES: COC(=O)c1cncc(Nc2cc(-c3ccc4cc(C#N)cnn34)ncc2C(=O)NC[C@@H](F)C(C)(C)O)c1] | 594 | 519.1 | 27 | (R)-methyl 5-((2-(3-cyanopyrrolo[1,2-b]pyridazin-7-yl)-5-((2-fluoro-3-hydroxy-3-methylbutyl)carbamoyl)pyridin-4-yl)amino) nicotinate |
| 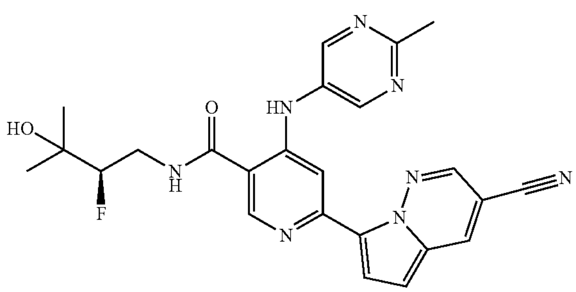 [SMILES: Cc1ncc(Nc2cc(-c3ccc4cc(C#N)cnn34)ncc2C(=O)NC[C@@H](F)C(C)(C)O)cn1] | 595 | 476.2 | 27 | (R)-6-(3-cyano-pyrrolo[1,2-b]pyridazin-7-yl)-N-(2-fluoro-3-hydroxy-3-methylbutyl)-4-((2-methylpyrimidin-5-yl)amino)nicotinamide |
| 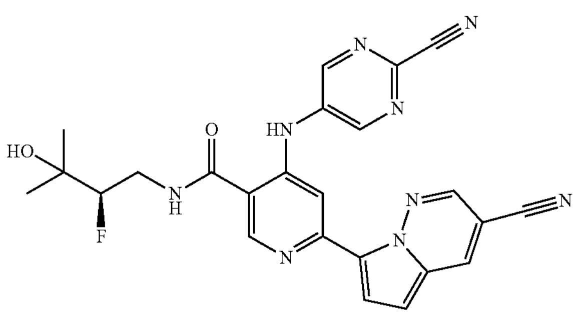 [SMILES: CC(C)(O)[C@H](F)CNC(=O)c1cnc(-c2ccc3cc(C#N)cnn23)cc1Nc1cnc(C#N)nc1] | 596 | 486.1 | 27 | (R)-4-((2-cyano-pyrimidin-5-yl)amino)-6-(3-cyanopyrrolo[1,2-b]pyridazin-7-yl)-N-(2-fluoro-3-hydroxy-3-methylbutyl) nicotinamide |
| 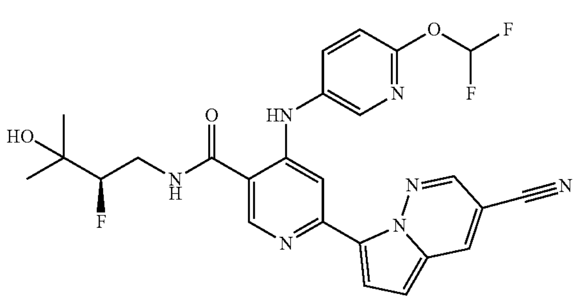 [SMILES: CC(C)(O)[C@H](F)CNC(=O)c1cnc(-c2ccc3cc(C#N)cnn23)cc1Nc1ccc(OC(F)F)nc1] | 597 | 527.2 | 27 | (R)-6-(3-cyano-pyrrolo[1,2-b]pyridazin-7-yl)-4-((6-(difluoro-methoxy)pyridin-3-yl)amino)-N-(2-fluoro-3-hydroxy-3-methylbutyl) nicotinamide |

TABLE 1-continued

| Structure | compound | ES/ MS m/z | procedure | Name |
|---|---|---|---|---|
| 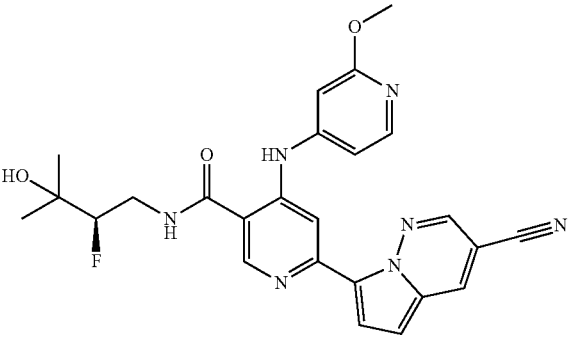 [SMILES: COc1cc(Nc2cc(-c3ccc4cc(C#N)cnn34)ncc2C(=O)NC[C@@H](F)C(C)(C)O)ccn1] | 598 | 491.1 | 27 | (R)-6-(3-cyano-pyrrolo[1,2-b]pyridazin-7-yl)-N-(2-fluoro-3-hydroxy-3-methyl-butyl)-4-((2-methoxy-pyridin-4-yl)amino) nicotinamide |
| 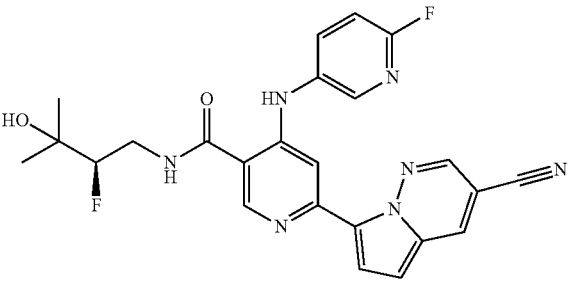 [SMILES: CC(C)(O)[C@H](F)CNC(=O)c1cnc(-c2ccc3cc(C#N)cnn23)cc1Nc1ccc(F)nc1] | 599 | 479.1 | 27 | (R)-6-(3-cyano-pyrrolo[1,2-b]pyridazin-7-yl)-N-(2-fluoro-3-hydroxy-3-methyl butyl)-4-((6-fluoro-pyridin-3-yl)amino) nicotinamide |
| 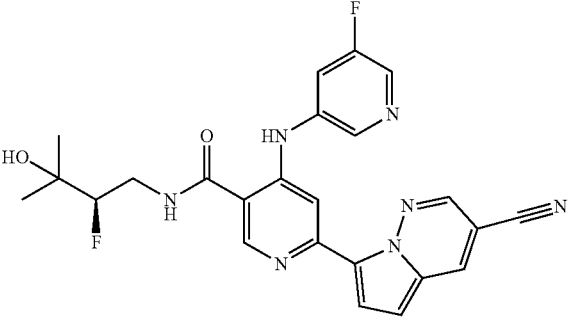 [SMILES: CC(C)(O)[C@H](F)CNC(=O)c1cnc(-c2ccc3cc(C#N)cnn23)cc1Nc1cncc(F)c1] | 600 | 479.2 | 27 | (R)-6-(3-cyano-pyrrolo[1,2-b]pyridazin-7-yl)-N-(2-fluoro-3-hydroxy-3-methylbutyl)-4-((5-fluoropyridin-3-yl)amino)nicotinamide |
| 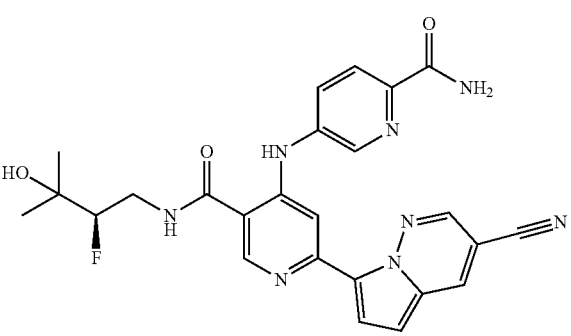 [SMILES: CC(C)(O)[C@H](F)CNC(=O)c1cnc(-c2ccc3cc(C#N)cnn23)cc1Nc1ccc(C(N)=O)nc1] | 601 | 504.2 | 27 | (R)-5-((2-(3-cyano-pyrrolo[1,2-b]pyridazin-7-yl)-5-((2-fluoro-3-hydroxy-3-methylbutyl)carbamoyl) pyridin-4-yl)amino) picolinamide |
| 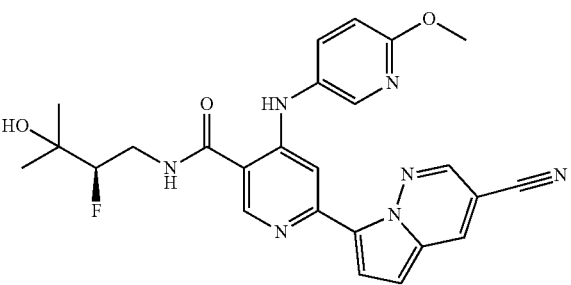 [SMILES: COc1ccc(Nc2cc(-c3ccc4cc(C#N)cnn34)ncc2C(=O)NC[C@@H](F)C(C)(C)O)cn1] | 602 | 490.5 | 27 | (R)-6-(3-cyanopyrrolo[1,2-b]pyridazin-7-yl)-N-(2-fluoro-3-hydroxy-3-methylbutyl)-4-((6-methoxy-pyridin-3-yl)amino) nicotinamide |

TABLE 1-continued

| Structure | compound | ES/ MS m/z | procedure | Name |
|---|---|---|---|---|
| 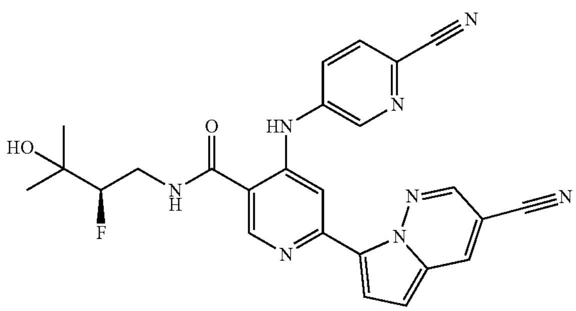 [SMILES: CC(C)(O)[C@H](F)CNC(=O)c1cnc(-c2ccc3cc(C#N)cnn23)cc1Nc1ccc(C#N)nc1] | 603 | 485.2 | 27 | (R)-4-((6-cyanopyridin-3-yl)amino)-6-(3-cyanopyrrolo[1,2-b]pyridazin-7-yl)-N-(2-fluoro-3-hydroxy-3-methylbutyl)nicotinamide |
| 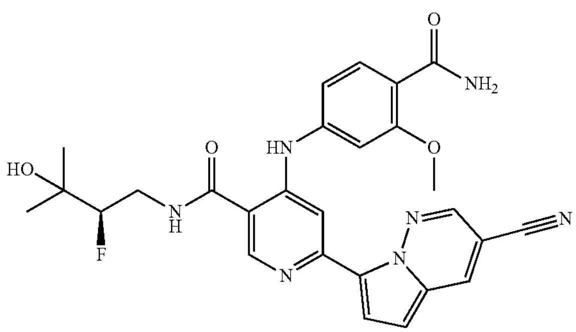 [SMILES: COc1cc(Nc2cc(-c3ccc4cc(C#N)cnn34)ncc2C(=O)NC[C@@H](F)C(C)(C)O)ccc1C(N)=O] | 604 | 532.2 | 27 | (R)-4-((4-carbamoyl-3-methoxyphenyl)amino)-6-(3-cyanopyrrolo[1,2-b]pyridazin-7-yl)-N-(2-fluoro-3-hydroxy-3-methylbutyl)nicotinamide |
| 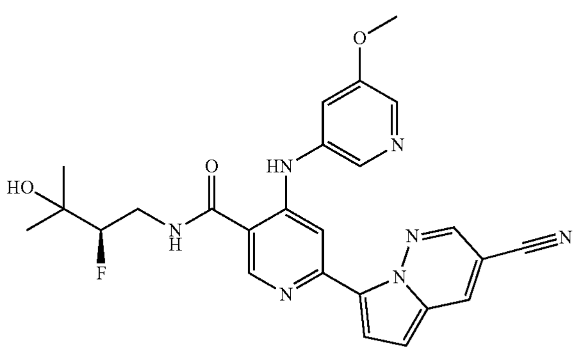 [SMILES: COc1cncc(Nc2cc(-c3ccc4cc(C#N)cnn34)ncc2C(=O)NC[C@@H](F)C(C)(C)O)c1] | 605 | 490.3 | 27 | (R)-6-(3-cyanopyrrolo[1,2-b]pyridazin-7-yl)-N-(2-fluoro-3-hydroxy-3-methylbutyl)-4-((5-methoxypyridin-3-yl)amino)nicotinamide |
| 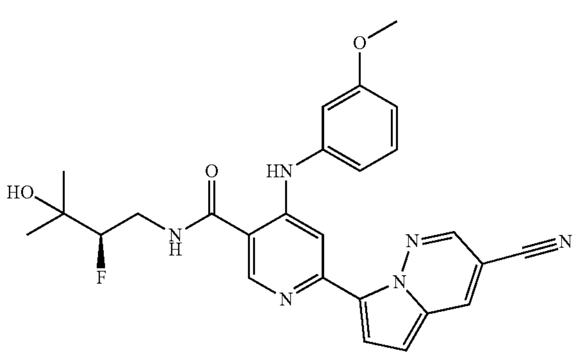 [SMILES: COc1cccc(Nc2cc(-c3ccc4cc(C#N)cnn34)ncc2C(=O)NC[C@@H](F)C(C)(C)O)c1] | 606 | 489.3 | 27 | (R)-6-(3-cyanopyrrolo[1,2-b]pyridazin-7-yl)-N-(2-fluoro-3-hydroxy-3-methylbutyl)-4-((3-methoxyphenyl)amino)nicotinamide |

TABLE 1-continued

| Structure | compound | ES/MS m/z | procedure | Name |
|---|---|---|---|---|
| 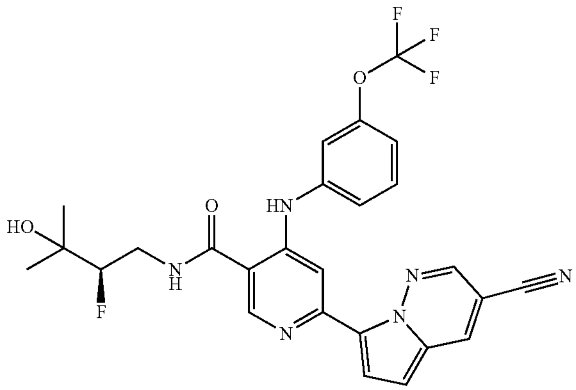 [SMILES: CC(C)(O)[C@H](F)CNC(=O)c1cnc(-c2ccc3cc(C#N)cnn23)cc1Nc1cccc(OC(F)(F)F)c1] | 607 | 543.3 | 27 | (R)-6-(3-cyanopyrrolo[1,2-b]pyridazin-7-yl)-N-(2-fluoro-3-hydroxy-3-methylbutyl)-4-((3-(trifluoromethoxy)phenyl)amino)nicotinamide |
| 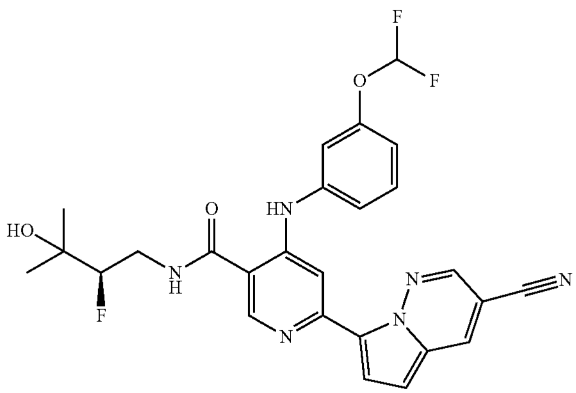 [SMILES: CC(C)(O)[C@H](F)CNC(=O)c1cnc(-c2ccc3cc(C#N)cnn23)cc1Nc1cccc(OC(F)F)c1] | 608 | 525.2 | 27 | (R)-6-(3-cyanopyrrolo[1,2-b]pyridazin-7-yl)-4-((3-(difluoromethoxy)phenyl)amino)-N-(2-fluoro-3-hydroxy-3-methylbutyl)nicotinamide |
| 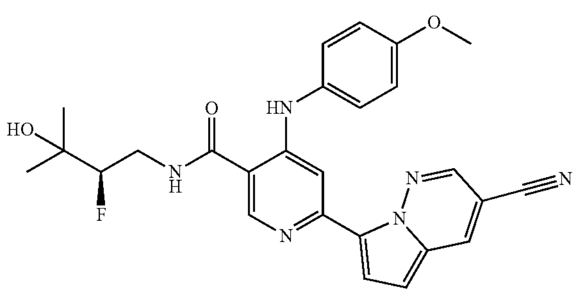 [SMILES: COc1ccc(Nc2cc(-c3ccc4cc(C#N)cnn34)ncc2C(=O)NC[C@@H](F)C(C)(C)O)cc1] | 609 | 489.3 | 27 | (R)-6-(3-cyanopyrrolo[1,2-b]pyridazin-7-yl)-N-(2-fluoro-3-hydroxy-3-methylbutyl)-4-((4-methoxyphenyl)amino)nicotinamide |
| 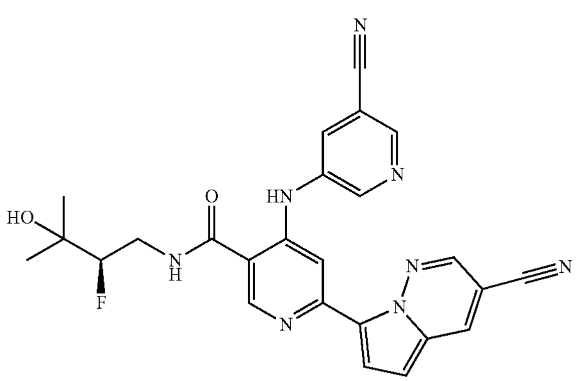 [SMILES: CC(C)(O)[C@H](F)CNC(=O)c1cnc(-c2ccc3cc(C#N)cnn23)cc1Nc1cncc(C#N)c1] | 610 | 485.1 | 27 | (R)-4-((5-cyanopyridin-3-yl)amino)-6-(3-cyanopyrrolo[1,2-b]pyridazin-7-yl)-N-(2-fluoro-3-hydroxy-3-methylbutyl)nicotinamide |

TABLE 1-continued

| Structure | compound | ES/MS m/z | procedure | Name |
|---|---|---|---|---|
| 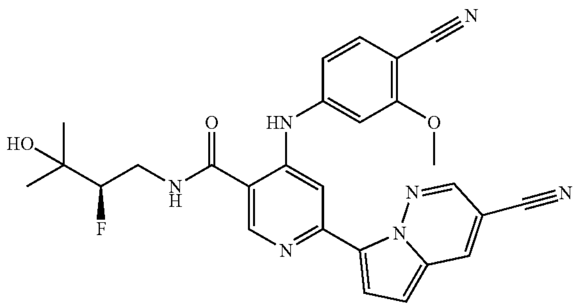 [SMILES: COc1cc(Nc2cc(-c3ccc4cc(C#N)cnn34)ncc2C(=O)NC[C@@H](F)C(C)(C)O)ccc1C#N] | 611 | 514.2 | 27 | (R)-4-((4-cyano-3-methoxyphenyl)amino)-6-(3-cyanopyrrolo[1,2-b]pyridazin-7-yl)-N-(2-fluoro-3-hydroxy-3-methylbutyl)nicotinamide |
| 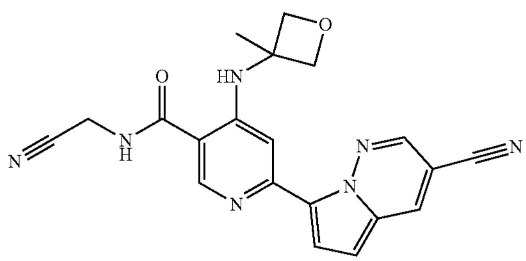 [SMILES: CC1(Nc2cc(-c3ccc4cc(C#N)cnn34)ncc2C(=O)NCC#N)COC1] | 612 | 388.3 | 2 | N-(cyanomethyl)-6-(3-cyanopyrrolo[1,2-b]pyridazin-7-yl)-4-((3-methyloxetan-3-yl)amino)nicotinamide |
| 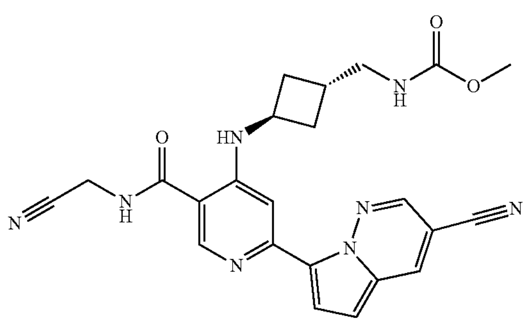 [SMILES: COC(=O)NC[C@H]1C[C@H](Nc2cc(-c3ccc4cc(C#N)cnn34)ncc2C(=O)NCC#N)C1] | 613 | 459.3 | 68 | methyl (((1r,3r)-3-((5-((cyanomethyl)carbamoyl)-2-(3-cyanopyrrolo[1,2-b]pyridazin-7-yl)pyridin-4-yl)amino)cyclobutyl)methyl)carbamate |
| 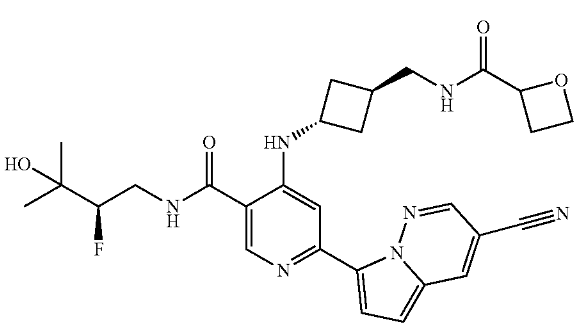 [SMILES: CC(C)(O)[C@H](F)CNC(=O)c1cnc(-c2ccc3cc(C#N)cnn23)cc1N[C@H]1C[C@H](CNC(=O)C2CCO2)C1] | 614 | 550.3 | 33 | 6-(3-cyanopyrrolo[1,2-b]pyridazin-7-yl)-N-((R)-2-fluoro-3-hydroxy-3-methylbutyl)-4-(((1r,3R)-3-((oxetane-2-carboxamido)methyl)cyclobutyl)amino)nicotinamide |

TABLE 1-continued

| Structure | compound | ES/MS m/z | procedure | Name |
|---|---|---|---|---|
| 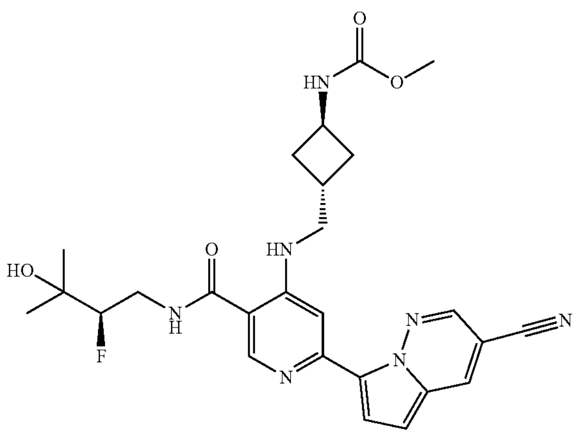 [SMILES: COC(=O)N[C@H]1C[C@H](CNc2cc(-c3ccc4cc(C#N)cnn34)ncc2C(=O)NC[C@@H](F)C(C)(C)O)C1] | 615 | 524.4 | 68 | methyl ((1R,3r)-3-(((2-(3-cyanopyrrolo[1,2-b]pyridazin-7-yl)-5-(((R)-2-fluoro-3-hydroxy-3-methylbutyl)carbamoyl)pyridin-4-yl)amino)methyl)cyclobutyl)carbamate |
| 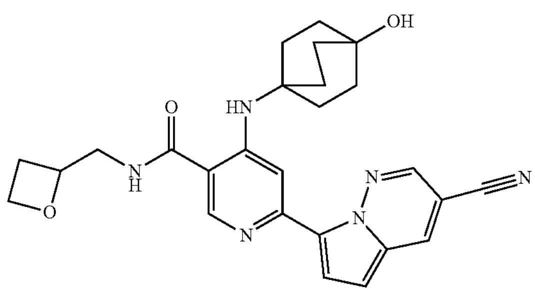 [SMILES: N#Cc1cnn2c(-c3cc(NC45CCC(O)(CC4)CC5)c(C(=O)NCC4CCO4)cn3)ccc2c1] | 616 | 473.3 | 3 | 6-(3-cyanopyrrolo[1,2-b]pyridazin-7-yl)-4-((4-hydroxybicyclo[2.2.2]octan-1-yl)amino)-N-(oxetan-2-ylmethyl)nicotinamide |
| 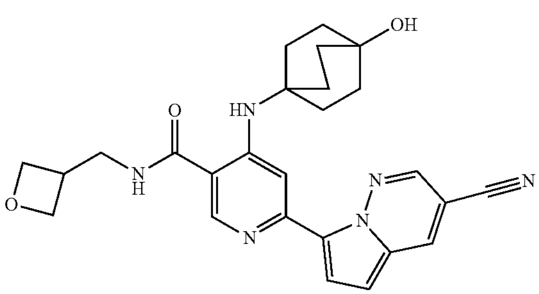 [SMILES: N#Cc1cnn2c(-c3cc(NC45CCC(O)(CC4)CC5)c(C(=O)NCC4COC4)cn3)ccc2c1] | 617 | 473.3 | 3 | 6-(3-cyanopyrrolo[1,2-b]pyridazin-7-yl)-4-((4-hydroxybicyclo[2.2.2]octan-1-yl)amino)-N-(oxetan-3-ylmethyl)nicotinamide |
| 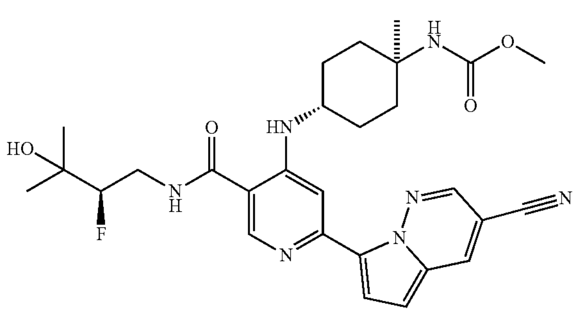 [SMILES: COC(=O)N[C@]1(C)CC[C@@H](Nc2cc(-c3ccc4cc(C#N)cnn34)ncc2C(=O)NC[C@@H](F)C(C)(C)O)CC1] | 618 | 553.3 | 35 | methyl ((1R,4r)-4-((2-(3-cyanopyrrolo[1,2-b]pyridazin-7-yl)-5-(((R)-2-fluoro-3-hydroxy-3-methylbutyl)carbamoyl)pyridin-4-yl)amino)-1-methylcyclohexyl)carbamate |

TABLE 1-continued

| compound | ES/MS m/z | procedure | Name |
|---|---|---|---|
| 619 | 553.4 | 35 | methyl ((1S,4s)-4-((2-(3-cyanopyrrolo[1,2-b]pyridazin-7-yl)-5-(((R)-2-fluoro-3-hydroxy-3-methylbutyl)carbamoyl)pyridin-4-yl)amino)-1-methylcyclohexyl)carbamate |
| 620 | 538.3 | 70 | methyl (((1R,3r)-3-((2-(3-cyanopyrrolo[1,2-b]pyridazin-7-yl)-5-(((R)-2-fluoro-3-hydroxy-3-methylbutyl)carbamoyl)pyridin-4-yl)amino)cyclobutyl)methyl)(methyl)carbamate |
| 621 | 484.3 | 1 | 6-(3-cyanopyrrolo[1,2-b]pyridazin-7-yl)-4-((4-hydroxybicyclo[2.2.2]octan-1-yl)amino)-N-(oxazol-2-ylmethyl)nicotinamide |
| 622 | 542.4 | 71 | 6-(3-cyanopyrrolo[1,2-b]pyridazin-7-yl)-4-((4-hydroxybicyclo[2.2.2]octan-1-yl)amino)-N-((4-(2-hydroxypropan-2-yl)oxazol-2-yl)methyl)nicotinamide |
| 623 | 441.3 | 3 | 6-(3-cyanopyrrolo[1,2-b]pyridazin-7-yl)-4-((4-hydroxybicyclo[2.2.2]octan-1-yl)amino)-N-(prop-2-yn-1-yl)nicotinamide |

TABLE 1-continued

| Structure | compound | ES/MS m/z | procedure | Name |
|---|---|---|---|---|
| 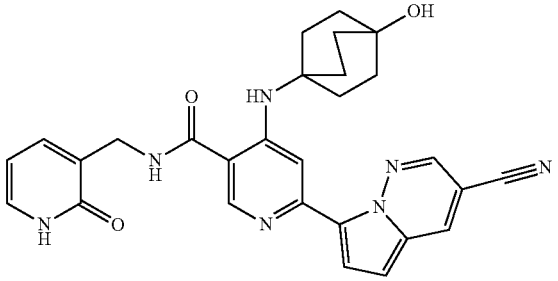 [SMILES: N#Cc1cnn2c(-c3cc(NC45CCC(O)(CC4)CC5)c(C(=O)NCc4ccc[nH]c4=O)cn3)ccc2c1] | 624 | 510.3 | 3 | 6-(3-cyanopyrrolo[1,2-b]pyridazin-7-yl)-4-((4-hydroxybicyclo[2.2.2]octan-1-yl)amino)-N-((2-oxo-1,2-dihydro-pyridin-3-yl)methyl)nicotinamide |
| 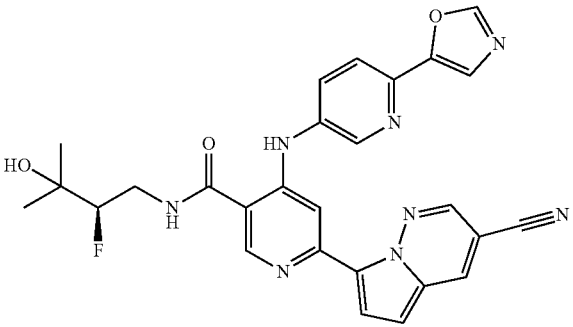 | 625 | 527.2 | 27 | (R)-6-(3-cyanopyrrolo[1,2-b]pyridazin-7-yl)-N-(2-fluoro-3-hydroxy-3-methylbutyl)-4-((6-(oxazol-5-yl)pyridin-3-yl)amino)nicotinamide |
| 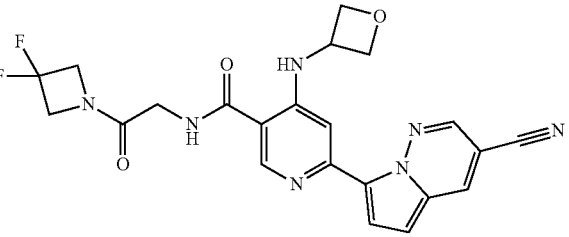 | 626 | 468.2 | 49 | 6-(3-cyanopyrrolo[1,2-b]pyridazin-7-yl)-N-(2-(3,3-difluoroazetidin-1-yl)-2-oxoethyl)-4-(oxetan-3-ylamino)nicotinamide |
| 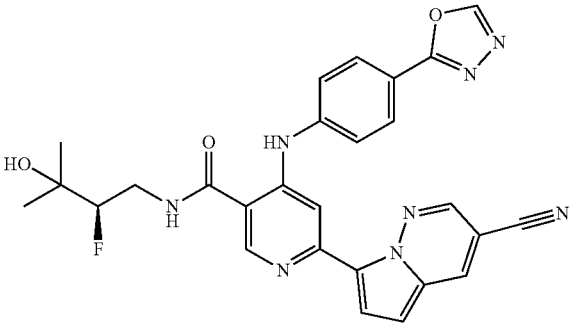 | 627 | 527.3 | 27 | (R)-4-((4-(1,3,4-oxadiazol-2-yl)phenyl)amino)-6-(3-cyanopyrrolo[1,2-b]pyridazin-7-yl)-N-(2-fluoro-3-hydroxy-3-methylbutyl)nicotinamide |
| 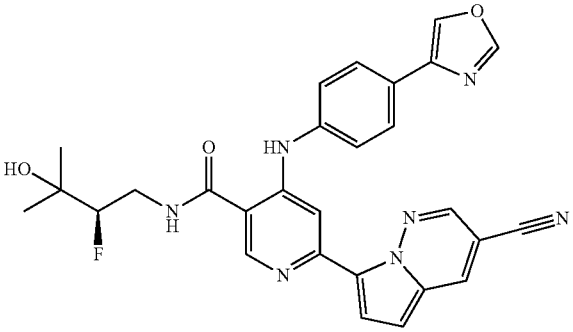 [SMILES: CC(C)(O)[C@H](F)CNC(=O)c1cnc(-c2ccc3cc(C#N)cnn23)cc1Nc1ccc(-c2cocn2)cc1] | 628 | 526.3 | 27 | (R)-6-(3-cyanopyrrolo[1,2-b]pyridazin-7-yl)-N-(2-fluoro-3-hydroxy-3-methyl-butyl)-4-((4-(oxazol-4-yl)phenyl)amino)nicotinamide |

TABLE 1-continued

| Structure | compound | ES/MS m/z | procedure | Name |
|---|---|---|---|---|
| 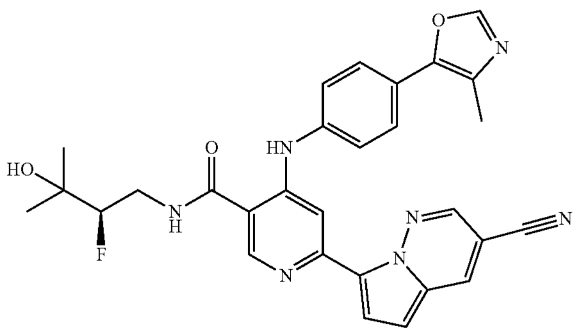 | 629 | 540.5 | 27 | (R)-6-(3-cyanopyrrolo[1,2-b]pyridazin-7-yl)-N-(2-fluoro-3-hydroxy-3-methylbutyl)-4-((4-(4-methyloxazol-5-yl)phenyl)amino)nicotinamide |
| 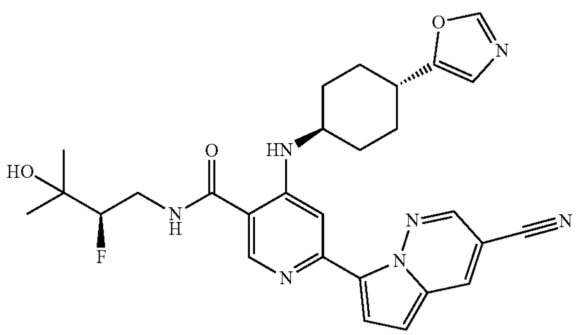 [SMILES: CC(C)(O)[C@H](F)CNC(=O)c1cnc(-c2ccc3cc(C#N)cnn23)cc1N[C@H]1CC[C@H](c2cnco2)CC1] | 630 | 532.6 | 2 | 6-(3-cyanopyrrolo[1,2-b]pyridazin-7-yl)-N-((R)-2-fluoro-3-hydroxy-3-methylbutyl)-4-(((1r,4R)-4-(oxazol-5-yl)cyclohexyl)amino)nicotinamide |
| 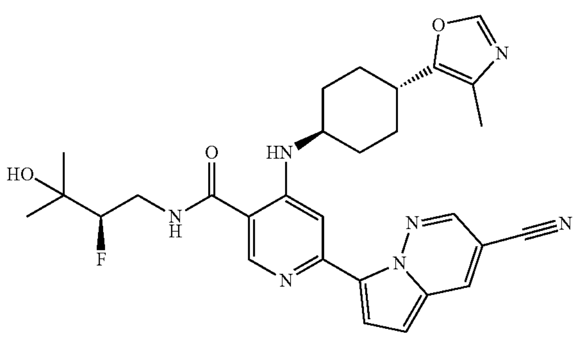 [SMILES: Cc1ncoc1[C@H]1CC[C@H](Nc2cc(-c3ccc4cc(C#N)cnn34)ncc2C(=O)NC[C@@H](F)C(C)(C)O)CC1] | 631 | 546.6 | 2 | 6-(3-cyanopyrrolo[1,2-b]pyridazin-7-yl)-N-((R)-2-fluoro-3-hydroxy-3-methylbutyl)-4-(((1r,4R)-4-(4-methyloxazol-5-yl)cyclohexyl)amino)nicotinamide |
| 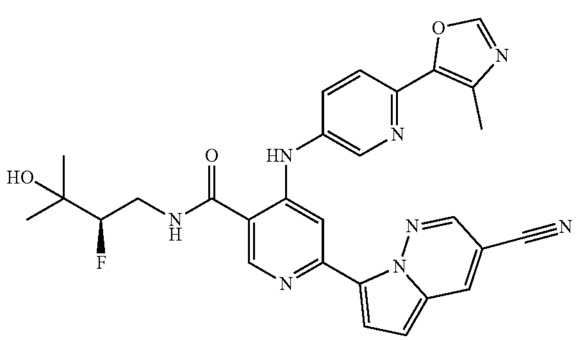 [SMILES: Cc1ncoc1-c1ccc(Nc2cc(-c3ccc4cc(C#N)cnn34)ncc2C(=O)NC[C@@H](F)C(C)(C)O)cn1] | 632 | 541.5 | 27 | (R)-6-(3-cyanopyrrolo[1,2-b]pyridazin-7-yl)-N-(2-fluoro-3-hydroxy-3-methylbutyl)-4-((6-(4-methyloxazol-5-yl)pyridin-3-yl)amino)nicotinamide |

TABLE 1-continued

| Structure | compound | ES/MS m/z | procedure | Name |
|---|---|---|---|---|
| 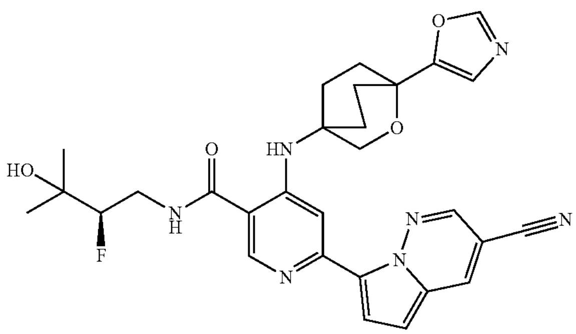 [SMILES: CC(C)(O)[C@H](F)CNC(=O)c1cnc(-c2ccc3cc(C#N)cnn23)cc1NC12CCC(c3cnco3)(CC1)OC2] | 633 | 560.6 | 2 | (R)-6-(3-cyanopyrrolo[1,2-b]pyridazin-7-yl)-N-(2-fluoro-3-hydroxy-3-methylbutyl)-4-((1-(oxazol-5-yl)-2-oxabicyclo[2.2.2]octan-4-yl)amino)nicotinamide |
| 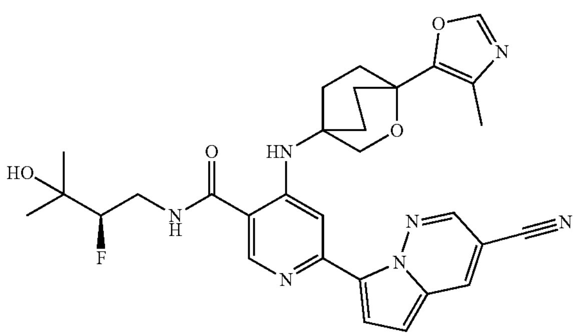 [SMILES: Cc1ncoc1C12CCC(Nc3cc(-c4ccc5cc(C#N)cnn45)ncc3C(=O)NC[C@@H](F)C(C)(C)O)(CC1)CO2] | 634 | 574.6 | 2 | (R)-6-(3-cyanopyrrolo[1,2-b]pyridazin-7-yl)-N-(2-fluoro-3-hydroxy-3-methylbutyl)-4-((1-(4-methyloxazol-5-yl)-2-oxabicyclo[2.2.2]octan-4-yl)amino)nicotinamide |
| 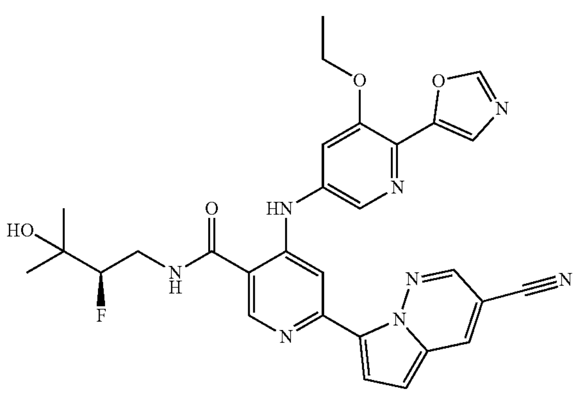 [SMILES: CCOc1cc(Nc2cc(-c3ccc4cc(C#N)cnn34)ncc2C(=O)NC[C@@H](F)C(C)(C)O)cnc1-c1cnco1] | 635 | 571.6 | 27 | (R)-6-(3-cyanopyrrolo[1,2-b]pyridazin-7-yl)-4-((5-ethoxy-6-(oxazol-5-yl)pyridin-3-yl)amino)-N-(2-fluoro-3-hydroxy-3-methylbutyl)nicotinamide |
| mixture | 636 | 518.4 | 2 | (R)-6-(3-cyanopyrrolo[1,2-b]pyridazin-7-yl)-N-(2-fluoro-3-hydroxy-3-methylbutyl)-4-((3-(oxazol-5-ylmethyl)cyclobutyl)amino)nicotinamide |

TABLE 1-continued

| Structure | compound | ES/MS m/z | procedure | Name |
|---|---|---|---|---|
| 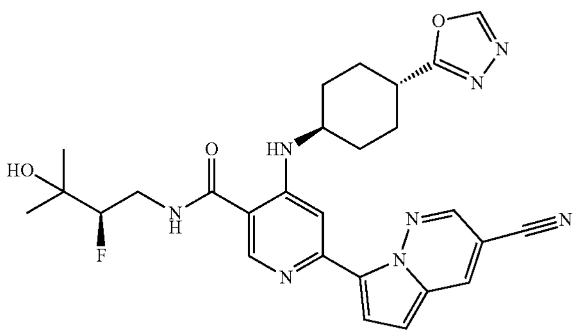 | 637 | 533.3 | 2 | 4-(((1r,4R)-4-(1,3,4-oxadiazol-2-yl)cyclohexyl)amino)-6-(3-cyanopyrrolo[1,2-b]pyridazin-7-yl)-N-((R)-2-fluoro-3-hydroxy-3-methylbutyl)nicotinamide |
| Diastereomer 1 | 638 | 518.4 | 72 | (R)-6-(3-cyanopyrrolo[1,2-b]pyridazin-7-yl)-N-(2-fluoro-3-hydroxy-3-methylbutyl)-4-((3-(oxazol-5-ylmethyl)cyclobutyl)amino)nicotinamide |
| 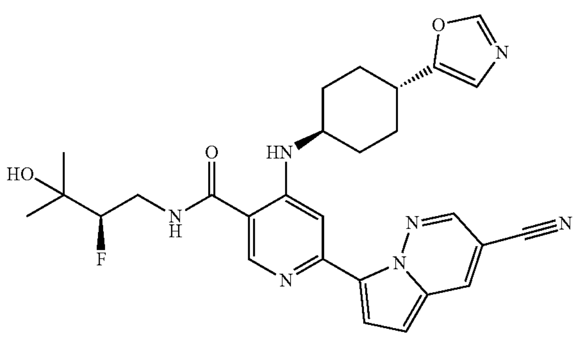 [SMILES: CC(C)(O)[C@H](F)CNC(=O)c1cnc(-c2ccc3cc(C#N)cnn23)cc1N[C@H]1CC[C@H](c2cnco2)CC1] | 639 | 534.5 | 2 | 6-(3-cyanopyrrolo[1,2-b]pyridazin-7-yl)-N-((R)-2-fluoro-3-hydroxy-3-methylbutyl)-4-(((3R,6S)-6-(oxazol-5-yl)tetrahydro-2H-pyran-3-yl)amino)nicotinamide |
| Diastereomer 2 | 640 | 518.4 | 72 | (R)-6-(3-cyanopyrrolo[1,2-b]pyridazin-7-yl)-N-(2-fluoro-3-hydroxy-3-methylbutyl)-4-((3-(oxazol-5-ylmethyl)cyclobutyl)amino)nicotinamide |

TABLE 1-continued

| Structure | compound | ES/MS m/z | procedure | Name |
|---|---|---|---|---|
| 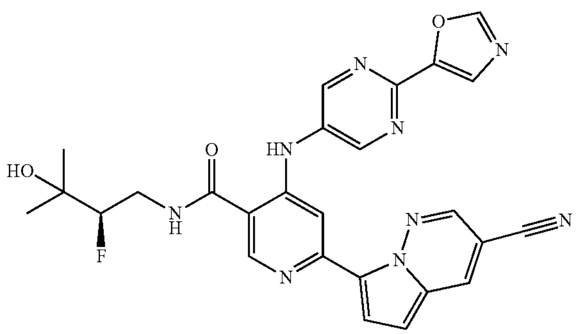 [SMILES: CC(C)(O)[C@H](F)CNC(=O)c1cnc(-c2ccc3cc(C#N)cnn23)cc1Nc1cnc(-c2cnco2)nc1] | 641 | 528.1 | 27 | (R)-6-(3-cyanopyrrolo[1,2-b]pyridazin-7-yl)-N-(2-fluoro-3-hydroxy-3-methylbutyl)-4-((2-(oxazol-5-yl)pyrimidin-5-yl)amino)nicotinamide |
| 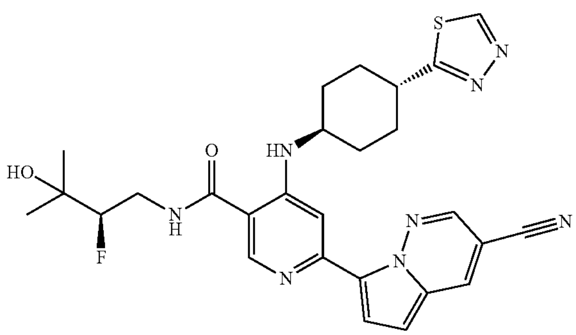 [SMILES: CC(C)(O)[C@H](F)CNC(=O)c1cnc(-c2ccc3cc(C#N)cnn23)cc1N[C@H]1CC[C@H](c2nncs2)CC1] | 642 | 550.3 | 2 | 4-(((1r,4R)-4-(1,3,4-thiadiazol-2-yl)cyclohexyl)amino)-6-(3-cyanopyrrolo[1,2-b]pyridazin-7-yl)-N-((R)-2-fluoro-3-hydroxy-3-methylbutyl)nicotinamide |
| 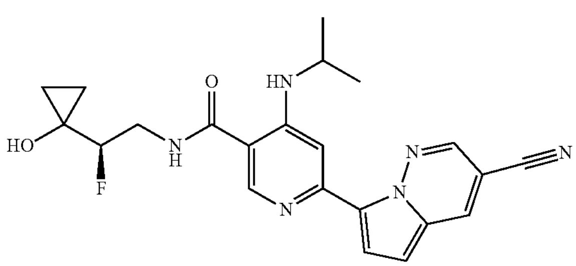 [SMILES: CC(C)Nc1cc(-c2ccc3cc(C#N)cnn23)ncc1C(=O)NC[C@@H](F)C1(O)CC1] | 643 | 423.3 | 1 | (R)-6-(3-cyanopyrrolo[1,2-b]pyridazin-7-yl)-N-(2-fluoro-2-(1-hydroxycyclopropyl)ethyl)-4-(isopropylamino)nicotinamide |
| mixture | 644 | 546.5 | 2 | (R)-6-(3-cyanopyrrolo[1,2-b]pyridazin-7-yl)-N-(2-fluoro-3-hydroxy-3-methylbutyl)-4-((4-(2-methyloxazol-5-yl)cyclohexyl)amino)nicotinamide |

TABLE 1-continued

| Structure | compound | ES/MS m/z | procedure | Name |
|---|---|---|---|---|
| 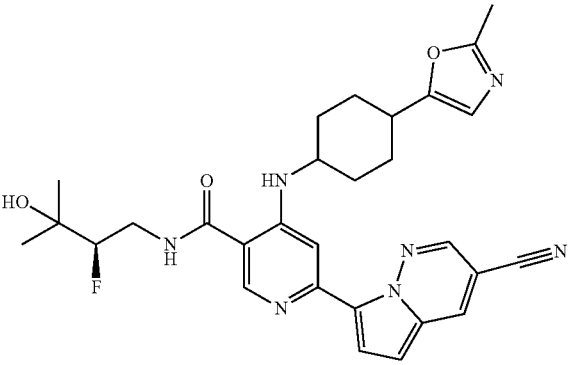 [SMILES: Cc1ncc(C2CCC(Nc3cc(-c4ccc5cc(C#N)cnn45)ncc3C(=O)NC[C@@H](F)C(C)(C)O)CC2)o1]<br>Diastereomer 1 | 645 | 546.5 | 73 | (R)-6-(3-cyanopyrrolo[1,2-b]pyridazin-7-yl)-N-(2-fluoro-3-hydroxy-3-methylbutyl)-4-((4-(2-methyloxazol-5-yl)cyclohexyl)amino)nicotinamide |
| 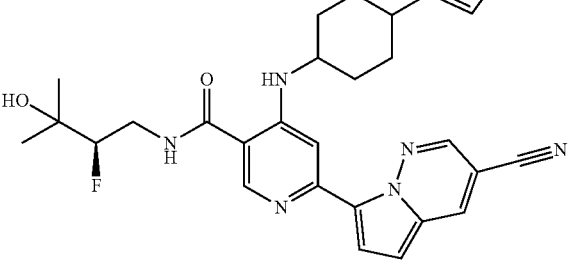<br>Diastereomer 2 | 646 | 546.4 | 73 | (R)-6-(3-cyanopyrrolo[1,2-b]pyridazin-7-yl)-N-(2-fluoro-3-hydroxy-3-methylbutyl)-4-((4-(2-methyloxazol-5-yl)cyclohexyl)amino)nicotinamide |
| 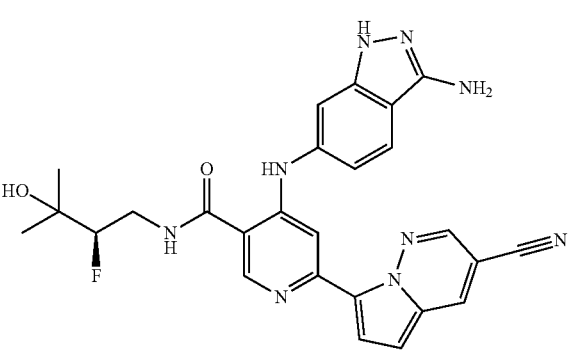 [SMILES: CC(C)(O)[C@H](F)CNC(=O)c1cnc(-c2ccc3cc(C#N)cnn23)cc1Nc1ccc2c(N)n[nH]c2c1] | 647 | 514.3 | 2 | (R)-4-((3-amino-1H-indazol-6-yl)amino)-6-(3-cyanopyrrolo[1,2-b]pyridazin-7-yl)-N-(2-fluoro-3-hydroxy-3-methyl-butyl)nicotinamide |
| 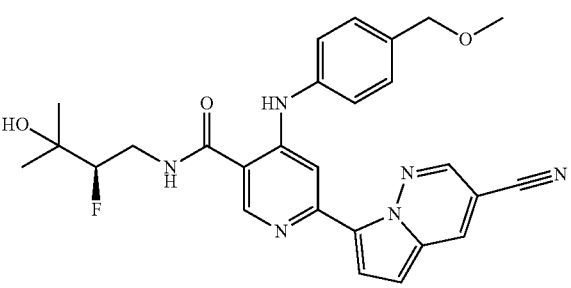 [SMILES: COCc1ccc(Nc2cc(-c3ccc4cc(C#N)cnn34)ncc2C(=O)NC[C@@H](F)C(C)(C)O)cc1] | 648 | 503.3 | 2 | (R)-6-(3-cyanopyrrolo[1,2-b]pyridazin-7-yl)-N-(2-fluoro-3-hydroxy-3-methylbutyl)-4-((4-(methoxymethyl)phenyl)amino)nicotinamide |

TABLE 1-continued

| compound | ES/MS m/z | procedure | Name |
|---|---|---|---|
| 649 | 532.2 | 2 | (R)-6-(3-cyanopyrrolo[1,2-b]pyridazin-7-yl)-N-(2-fluoro-3-hydroxy-3-methylbutyl)-4-((6-(oxetan-3-yloxy)pyridin-3-yl)amino)nicotinamide |
| 650 | 514.3 | 2 | (R)-6-(3-cyanopyrrolo[1,2-b]pyridazin-7-yl)-N-(2-fluoro-3-hydroxy-3-methylbutyl)-4-((2-oxoindolin-5-yl)amino)nicotinamide |
| 651 | 539.3 | 2 | (R)-6-(3-cyanopyrrolo[1,2-b]pyridazin-7-yl)-4-((2,2-difluorobenzo[d][1,3]dioxol-5-yl)amino)-N-(2-fluoro-3-hydroxy-3-methylbutyl)nicotinamide |
| 652 | 556.4 | 2 | (R)-6-(3-cyanopyrrolo[1,2-b]pyridazin-7-yl)-N-(2-fluoro-3-hydroxy-3-methylbutyl)-4-((1,3,3-trimethyl-2-oxoindolin-6-yl)amino)nicotinamide |

TABLE 1-continued

| Structure | compound | ES/MS m/z | procedure | Name |
|---|---|---|---|---|
| 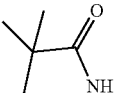 | 653 | 542.3 | 2 | (R)-6-(3-cyanopyrrolo[1,2-b]pyridazin-7-yl)-4-((3,3-dimethyl-2-oxoindolin-5-yl)amino)-N-(2-fluoro-3-hydroxy-3-methylbutyl)nicotinamide |
| 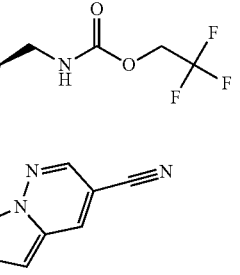 | 654 | 593.3 | 67 | 2,2,2-trifluoroethyl (((1R,3r)-3-((2-(3-cyanopyrrolo[1,2-b]pyridazin-7-yl)-5-(((R)-2-fluoro-3-hydroxy-3-methylbutyl)carbamoyl)pyridin-4-yl)amino)cyclobutyl)methyl)carbamate |
| 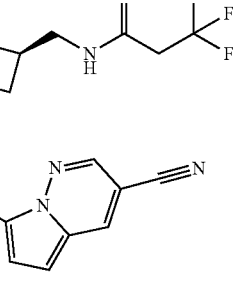 | 655 | 576.3 | 67 | 6-(3-cyanopyrrolo[1,2-b]pyridazin-7-yl)-N-((R)-2-fluoro-3-hydroxy-3-methylbutyl)-4-(((1r,3R)-3-((3,3,3-trifluoropropanamido)methyl)cyclobutyl)amino)nicotinamide |
| 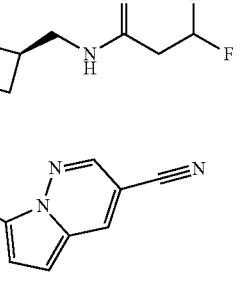 | 656 | 558.4 | 67 | 6-(3-cyanopyrrolo[1,2-b]pyridazin-7-yl)-4-(((1r,3R)-3-((3,3-difluoropropanamido)methyl)cyclobutyl)amino)-N-((R)-2-fluoro-3-hydroxy-3-methylbutyl)nicotinamide |
| 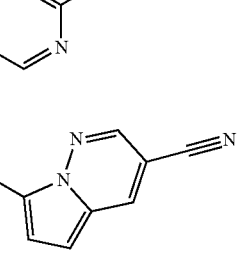 | 657 | 475.2 | 2 | (R)-4-((6-aminopyridin-3-yl)amino)-6-(3-cyanopyrrolo[1,2-b]pyridazin-7-yl)-N-(2-fluoro-3-hydroxy-3-methylbutyl)nicotinamide |

TABLE 1-continued

| Structure | compound | ES/MS m/z | procedure | Name |
|---|---|---|---|---|
| 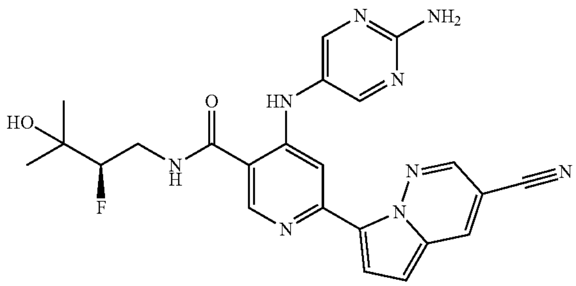 [SMILES: CC(C)(O)[C@H](F)CNC(=O)c1cnc(-c2ccc3cc(C#N)cnn23)cc1Nc1cnc(N)nc1] | 658 | 476.3 | 2 | (R)-4-((2-aminopyrimidin-5-yl)amino)-6-(3-cyanopyrrolo[1,2-b]pyridazin-7-yl)-N-(2-fluoro-3-hydroxy-3-methylbutyl)nicotinamide |
| 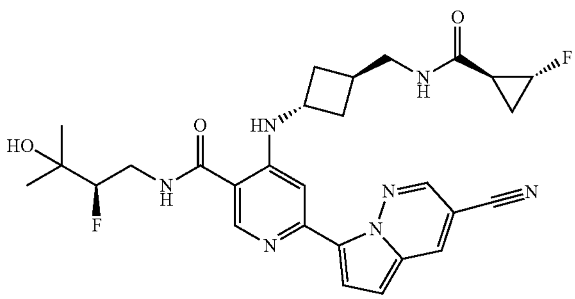 [SMILES: CC(C)(O)[C@H](F)CNC(=O)c1cnc(-c2ccc3cc(C#N)cnn23)cc1N[C@H]1C[C@H](CNC(=O)[C@@H]2C[C@H]2F)C1] | 659 | 552.4 | 67 | 6-(3-cyanopyrrolo[1,2-b]pyridazin-7-yl)-N-((R)-2-fluoro-3-hydroxy-3-methylbutyl)-4-(((1S,3R)-3-(((1S,2R)-2-fluorocyclopropane-1-carboxamido)methyl)cyclobutyl)amino)nicotinamide |
| 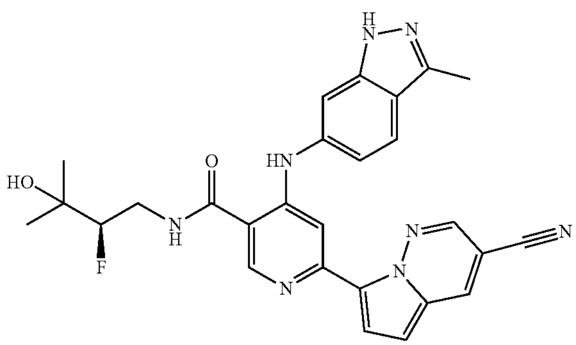 [SMILES: Cc1n[nH]c2cc(Nc3cc(-c4ccc5cc(C#N)cnn45)ncc3C(=O)NC[C@@H](F)C(C)(C)O)ccc12] | 660 | 513.2 | 2 | (R)-6-(3-cyanopyrrolo[1,2-b]pyridazin-7-yl)-N-(2-fluoro-3-hydroxy-3-methylbutyl)-4-((3-methyl-1H-indazol-6-yl)amino)nicotinamide |
| 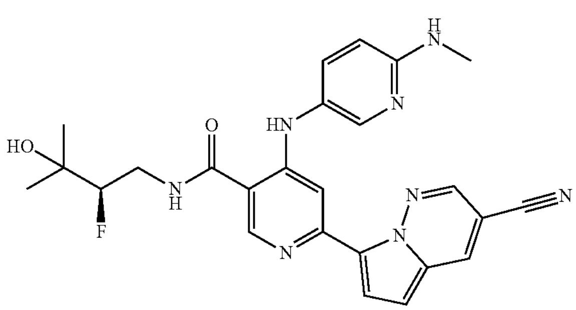 [SMILES: CNc1ccc(Nc2cc(-c3ccc4cc(C#N)cnn34)ncc2C(=O)NC[C@@H](F)C(C)(C)O)cn1] | 661 | 489.3 | 2 | (R)-6-(3-cyanopyrrolo[1,2-b]pyridazin-7-yl)-N-(2-fluoro-3-hydroxy-3-methylbutyl)-4-((6-(methylamino)pyridin-3-yl)amino)nicotinamide |
| 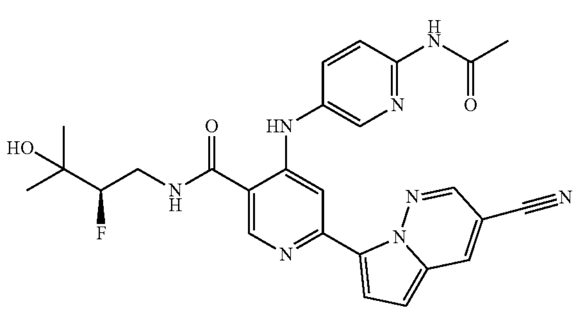 [SMILES: CC(=O)Nc1ccc(Nc2cc(-c3ccc4cc(C#N)cnn34)ncc2C(=O)NC[C@@H](F)C(C)(C)O)cn1] | 662 | 517.2 | 2 | (R)-4-((6-acetamidopyridin-3-yl)amino)-6-(3-cyanopyrrolo[1,2-b]pyridazin-7-yl)-N-(2-fluoro-3-hydroxy-3-methylbutyl)nicotinamide |

TABLE 1-continued

| Structure | compound | ES/MS m/z | procedure | Name |
|---|---|---|---|---|
| 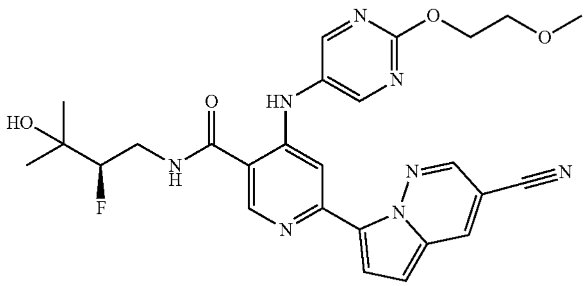 [SMILES: COCCOc1ncc(Nc2cc(-c3ccc4cc(C#N)cnn34)ncc2C(=O)NC[C@@H](F)C(C)(C)O)cn1] | 663 | 535.3 | 2 | (R)-6-(3-cyanopyrrolo[1,2-b]pyridazin-7-yl)-N-(2-fluoro-3-hydroxy-3-methylbutyl)-4-((2-(2-methoxyethoxy)pyrimidin-5-yl)amino)nicotinamide |
| 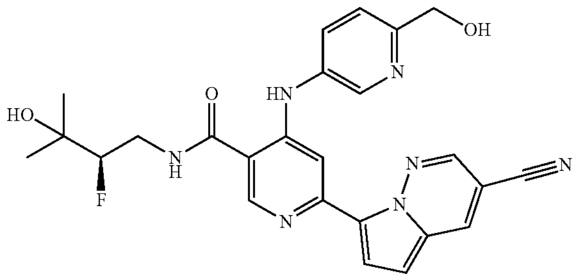 [SMILES: CC(C)(O)[C@H](F)CNC(=O)c1cnc(-c2ccc3cc(C#N)cnn23)cc1Nc1ccc(CO)nc1] | 664 | 490.3 | 2 | (R)-6-(3-cyanopyrrolo[1,2-b]pyridazin-7-yl)-N-(2-fluoro-3-hydroxy-3-methylbutyl)-4-((6-(hydroxymethyl)pyridin-3-yl)amino)nicotinamide |
| 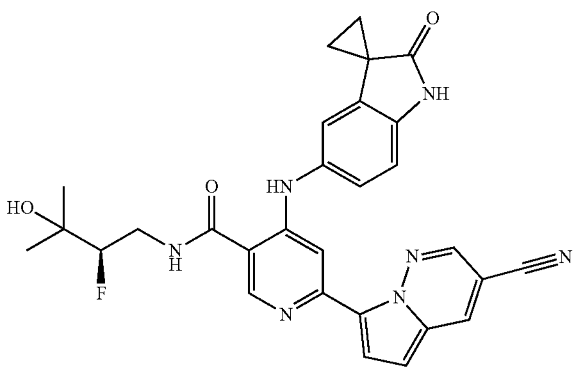 [SMILES: CC(C)(O)[C@H](F)CNC(=O)c1cnc(-c2ccc3cc(C#N)cnn23)cc1Nc1ccc2c(c1)C1(CC1)C(=O)N2] | 665 | 540.3 | 2 | (R)-6-(3-cyanopyrrolo[1,2-b]pyridazin-7-yl)-N-(2-fluoro-3-hydroxy-3-methylbutyl)-4-((2'-oxospiro[cyclopropane-1,3'-indolin]-5'-yl)amino)nicotinamide |
| 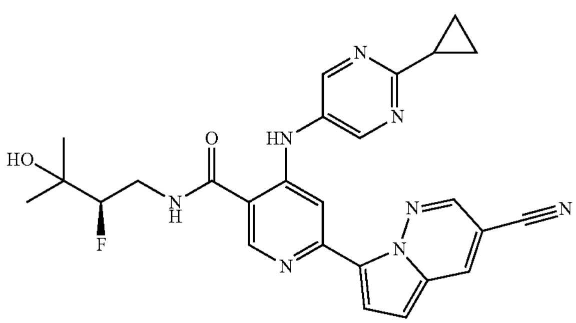 [SMILES: CC(C)(O)[C@H](F)CNC(=O)c1cnc(-c2ccc3cc(C#N)cnn23)cc1Nc1cnc(C2CC2)nc1] | 666 | 501.3 | 2 | (R)-6-(3-cyanopyrrolo[1,2-b]pyridazin-7-yl)-4-((2-cyclopropylpyrimidin-5-yl)amino)-N-(2-fluoro-3-hydroxy-3-methylbutyl)nicotinamide |
| 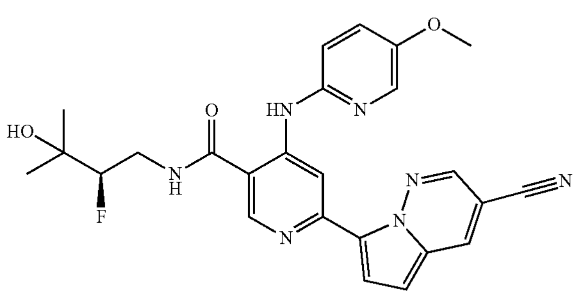 [SMILES: COc1ccc(Nc2cc(-c3ccc4cc(C#N)cnn34)ncc2C(=O)NC[C@@H](F)C(C)(C)O)nc1] | 667 | 490.2 | 27 | (R)-6-(3-cyanopyrrolo[1,2-b]pyridazin-7-yl)-N-(2-fluoro-3-hydroxy-3-methylbutyl)-4-((5-methoxypyridin-2-yl)amino)nicotinamide |

TABLE 1-continued

| Structure | compound | ES/MS m/z | procedure | Name |
|---|---|---|---|---|
| 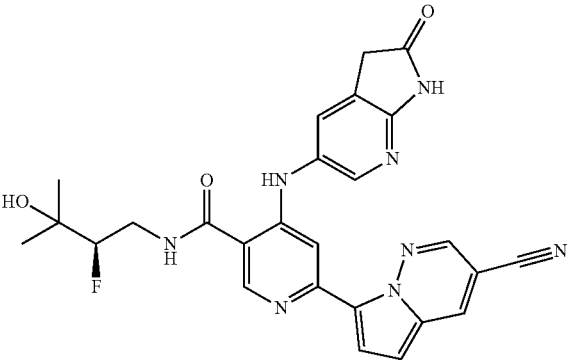 [SMILES: CC(C)(O)[C@H](F)CNC(=O)c1cnc(-c2ccc3cc(C#N)cnn23)cc1Nc1cnc2c(c1)CC(=O)N2] | 668 | 515.3 | 2 | (R)-6-(3-cyanopyrrolo[1,2-b]pyridazin-7-yl)-N-(2-fluoro-3-hydroxy-3-methylbutyl)-4-((2-oxo-2,3-dihydro-1H-pyrrolo[2,3-b]pyridin-5-yl)amino)nicotinamide |
| 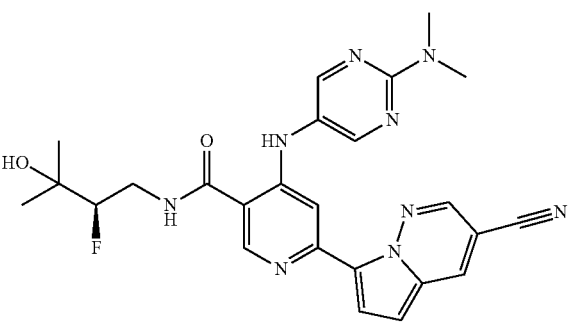 [SMILES: CN(C)c1ncc(Nc2cc(-c3ccc4cc(C#N)cnn34)ncc2C(=O)NC[C@@H](F)C(C)(C)O)cn1] | 669 | 504.5 | 2 | (R)-6-(3-cyanopyrrolo[1,2-b]pyridazin-7-yl)-4-((2-(dimethylamino)pyrimidin-5-yl)amino)-N-(2-fluoro-3-hydroxy-3-methylbutyl)nicotinamide |
| 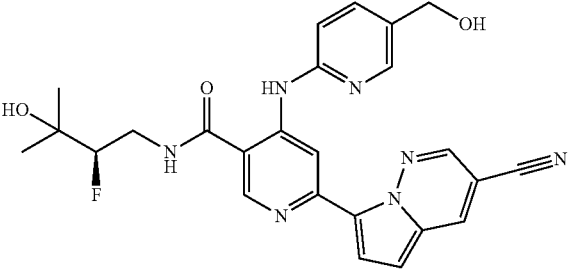 [SMILES: CC(C)(O)[C@H](F)CNC(=O)c1cnc(-c2ccc3cc(C#N)cnn23)cc1Nc1ccc(CO)cn1] | 670 | 490 | 27 | (R)-6-(3-cyanopyrrolo[1,2-b]pyridazin-7-yl)-N-(2-fluoro-3-hydroxy-3-methylbutyl)-4-((5-(hydroxymethyl)pyridin-2-yl)amino)nicotinamide |
| 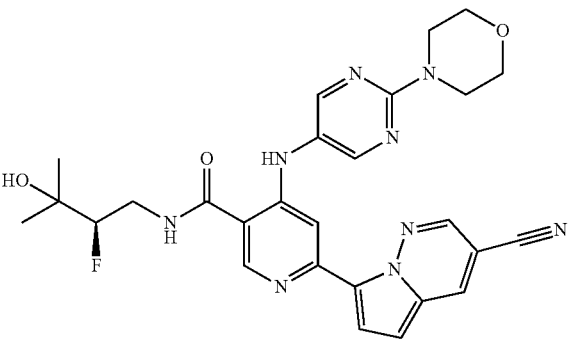 [SMILES: CC(C)(O)[C@H](F)CNC(=O)c1cnc(-c2ccc3cc(C#N)cnn23)cc1Nc1cnc(N2CCOCC2)nc1] | 671 | 490.4 | 27 | (R)-6-(3-cyanopyrrolo[1,2-b]pyridazin-7-yl)-N-(2-fluoro-3-hydroxy-3-methylbutyl)-4-((2-morpholinopyrimidin-5-yl)amino)nicotinamide |

TABLE 1-continued

| Structure | compound | ES/MS m/z | procedure | Name |
|---|---|---|---|---|
| (mixture) | 672 | 500.3 | 27 | 6-(3-cyanopyrrolo[1,2-b]pyridazin-7-yl)-4-((6,7-dihydro-5H-cyclopenta[c]pyridin-6-yl)amino)-N-((R)-2-fluoro-3-hydroxy-3-methylbutyl)nicotinamide |
| 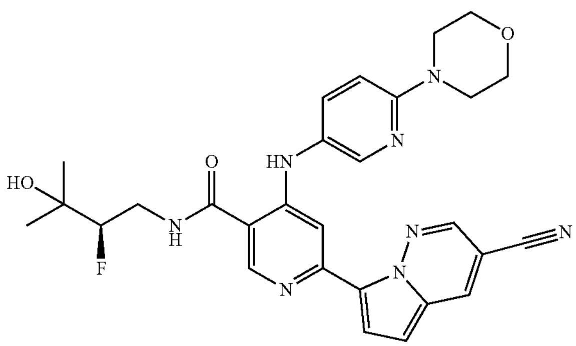 [SMILES: CC(C)(O)[C@H](F)CNC(=O)c1cnc(-c2ccc3cc(C#N)cnn23)cc1Nc1ccc(N2CCOCC2)nc1] | 673 | 545.4 | 27 | (R)-6-(3-cyanopyrrolo[1,2-b]pyridazin-7-yl)-N-(2-fluoro-3-hydroxy-3-methylbutyl)-4-((6-morpholinopyridin-3-yl)amino)nicotinamide |
| 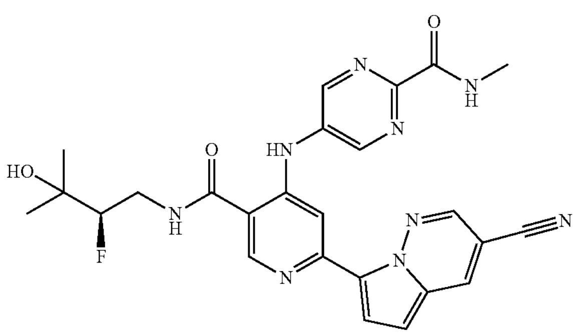 [SMILES: CNC(=O)c1ncc(Nc2cc(-c3ccc4cc(C#N)cnn34)ncc2C(=O)NC[C@@H](F)C(C)(C)O)cn1] | 674 | 518.2 | 27 | (R)-5-((2-(3-cyanopyrrolo[1,2-b]pyridazin-7-yl)-5-((2-fluoro-3-hydroxy-3-methylbutyl)carbamoyl)pyridin-4-yl)amino)-N-methylpyrimidine-2-carboxamide |
| 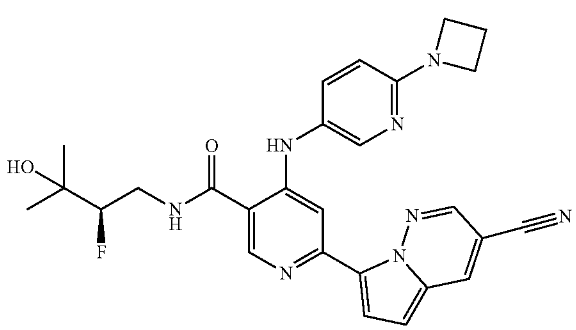 [SMILES: CC(C)(O)[C@H](F)CNC(=O)c1cnc(-c2ccc3cc(C#N)cnn23)cc1Nc1ccc(N2CCC2)nc1] | 675 | 515.3 | 27 | (R)-4-((6-(azetidin-1-yl)pyridin-3-yl)amino)-6-(3-cyanopyrrolo[1,2-b]pyridazin-7-yl)-N-(2-fluoro-3-hydroxy-3-methylbutyl)nicotinamide |

TABLE 1-continued

| Structure | compound | ES/MS m/z | procedure | Name |
|---|---|---|---|---|
| 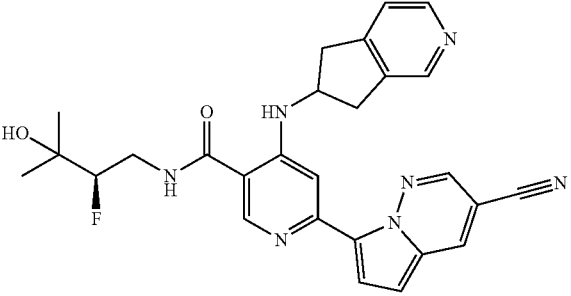 [SMILES: CC(C)(O)[C@H](F)CNC(=O)c1cnc(-c2ccc3cc(C#N)cnn23)cc1NC1Cc2ccncc2C1] diastereomer 1 | 676 | 500.4 | 88 | 6-(3-cyanopyrrolo[1,2-b]pyridazin-7-yl)-4-((6,7-dihydro-5H-cyclopenta[c]pyridin-6-yl)amino)-N-((R)-2-fluoro-3-hydroxy-3-methylbutyl)nicotinamide |
| 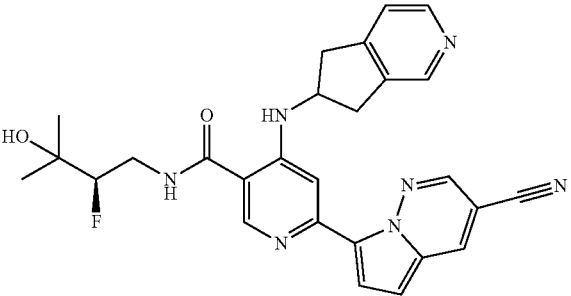 [SMILES: CC(C)(O)[C@H](F)CNC(=O)c1cnc(-c2ccc3cc(C#N)cnn23)cc1NC1Cc2ccncc2C1] diastereomer 2 | 677 | 500.3 | 88 | 6-(3-cyanopyrrolo[1,2-b]pyridazin-7-yl)-4-((6,7-dihydro-5H-cyclopenta[c]pyridin-6-yl)amino)-N-((R)-2-fluoro-3-hydroxy-3-methylbutyl)nicotinamide |
| 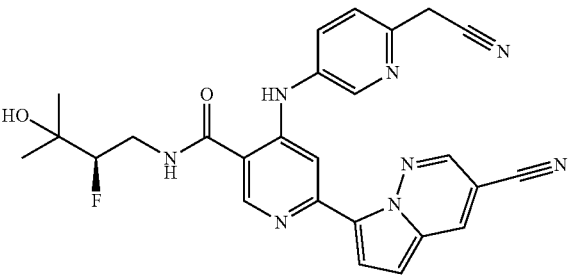 [SMILES: CC(C)(O)[C@H](F)CNC(=O)c1cnc(-c2ccc3cc(C#N)cnn23)cc1Nc1ccc(CC#N)nc1] | 678 | 499.4 | 27 | (R)-4-((6-(cyanomethyl)pyridin-3-yl)amino)-6-(3-cyanopyrrolo[1,2-b]pyridazin-7-yl)-N-(2-fluoro-3-hydroxy-3-methylbutyl)nicotinamide |
| 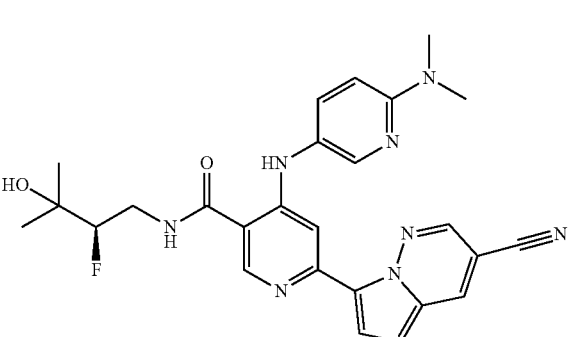 | 679 | 503.4 | 27 | (R)-6-(3-cyanopyrrolo[1,2-b]pyridazin-7-yl)-4-((6-(dimethylamino)pyridin-3-yl)amino)-N-(2-fluoro-3-hydroxy-3-methylbutyl)nicotinamide |

TABLE 1-continued

| Structure | compound | ES/ MS m/z | procedure | Name |
|---|---|---|---|---|
| 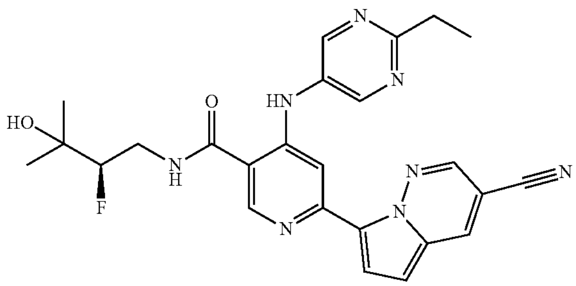 [SMILES: CCc1ncc(Nc2cc(-c3ccc4cc(C#N)cnn34)ncc2C(=O)NC[C@@H](F)C(C)(C)O)cn1] | 680 | 489.4 | 27 | (R)-6-(3-cyanopyrrolo[1,2-b]pyridazin-7-yl)-4-((2-ethylpyrimidin-5-yl)amino)-N-(2-fluoro-3-hydroxy-3-methylbutyl)nicotinamide |
| 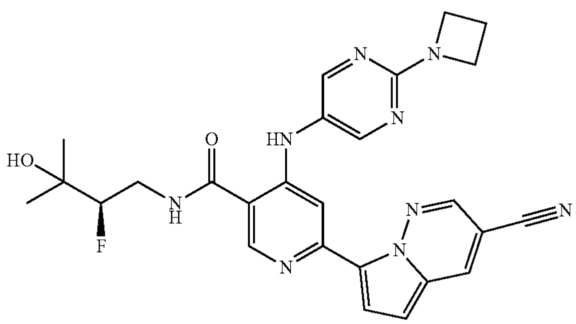 [SMILES: CC(C)(O)[C@H](F)CNC(=O)c1cnc(-c2ccc3cc(C#N)cnn23)cc1Nc1cnc(N2CCC2)nc1] | 681 | 516.3 | 27 | (R)-4-((2-(azetidin-1-yl)pyrimidin-5-yl)amino)-6-(3-cyanopyrrolo[1,2-b]pyridazin-7-yl)-N-(2-fluoro-3-hydroxy-3-methylbutyl)nicotinamide |
| 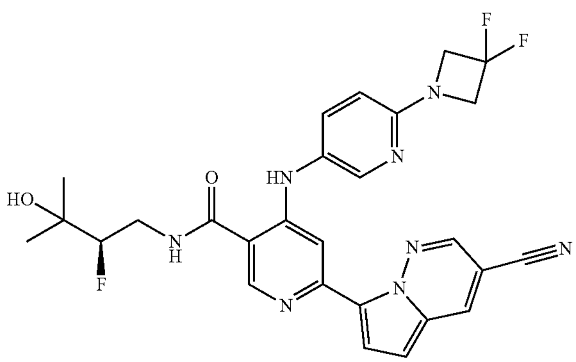 [SMILES: CC(C)(O)[C@H](F)CNC(=O)c1cnc(-c2ccc3cc(C#N)cnn23)cc1Nc1ccc(N2CC(F)(F)C2)nc1] | 682 | 551.3 | 27 | (R)-6-(3-cyanopyrrolo[1,2-b]pyridazin-7-yl)-4-((6-(3,3-difluoroazetidin-1-yl)pyridin-3-yl)amino)-N-(2-fluoro-3-hydroxy-3-methylbutyl)nicotinamide |
| 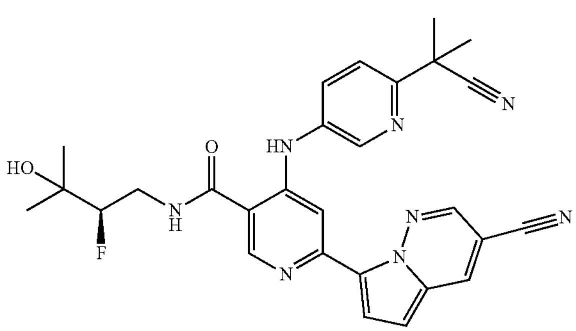 [SMILES: CC(C)(C#N)c1ccc(Nc2cc(-c3ccc4cc(C#N)cnn34)ncc2C(=O)NC[C@@H](F)C(C)(C)O)cn1] | 683 | 527.6 | 27 | (R)-4-((6-(2-cyanopropan-2-yl)pyridin-3-yl)amino)-6-(3-cyanopyrrolo[1,2-b]pyridazin-7-yl)-N-(2-fluoro-3-hydroxy-3-methylbutyl)nicotinamide |

TABLE 1-continued

| Structure | compound | ES/MS m/z | procedure | Name |
|---|---|---|---|---|
| 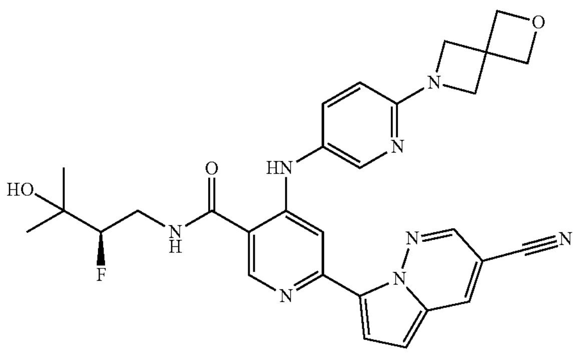 [SMILES: CC(C)(O)[C@H](F)CNC(=O)c1cnc(-c2ccc3cc(C#N)cnn23)cc1Nc1ccc(N2CC3(COC3)C2)nc1] | 684 | 557.4 | 27 | (R)-4-((6-(2-oxa-6-azaspiro[3.3]heptan-6-yl)pyridin-3-yl)amino)-6-(3-cyanopyrrolo[1,2-b]pyridazin-7-yl)-N-(2-fluoro-3-hydroxy-3-methylbutyl)nicotinamide |
| 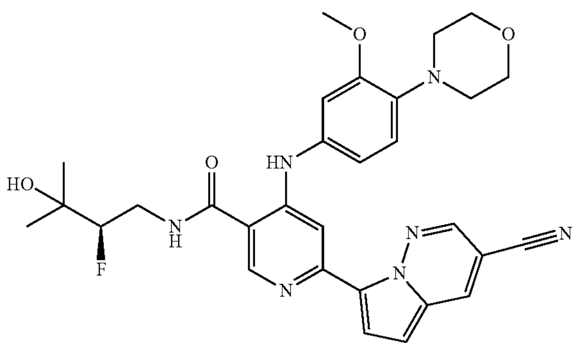 [SMILES: COc1cc(Nc2cc(-c3ccc4cc(C#N)cnn34)ncc2C(=O)NC[C@@H](F)C(C)(C)O)ccc1N1CCOCC1] | 685 | 574.6 | 2 | (R)-6-(3-cyanopyrrolo[1,2-b]pyridazin-7-yl)-N-(2-fluoro-3-hydroxy-3-methylbutyl)-4-((3-methoxy-4-morpholino-phenyl)amino)nicotinamide |
| 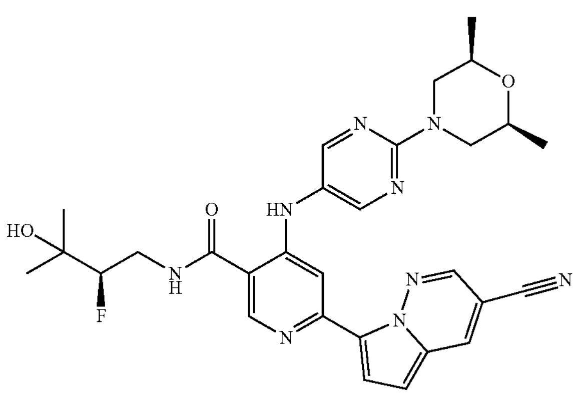 [SMILES: C[C@@H]1CN(c2ncc(Nc3cc(-c4ccc5cc(C#N)cnn45)ncc3C(=O)NC[C@@H](F)C(C)(C)O)cn2)C[C@H](C)O1] | 686 | 574.6 | 27 | 6-(3-cyanopyrrolo[1,2-b]pyridazin-7-yl)-4-((2-((2S,6R)-2,6-dimethyl-morpholino)pyrimidin-5-yl)amino)-N-((R)-2-fluoro-3-hydroxy-3-methylbutyl)nicotinamide |
| 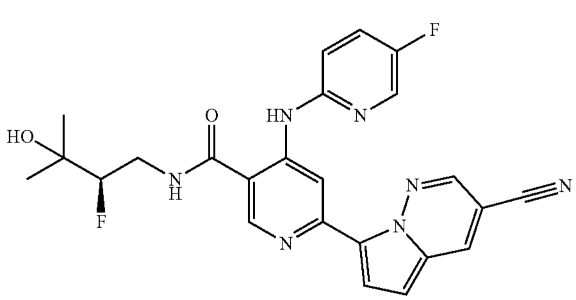 | 687 | 478.3 | 27 | (R)-6-(3-cyanopyrrolo[1,2-b]pyridazin-7-yl)-N-(2-fluoro-3-hydroxy-3-methylbutyl)-4-((5-fluoro-pyridin-2-yl)amino)nicotinamide |

TABLE 1-continued

| Structure | compound | ES/ MS m/z | procedure | Name |
|---|---|---|---|---|
| 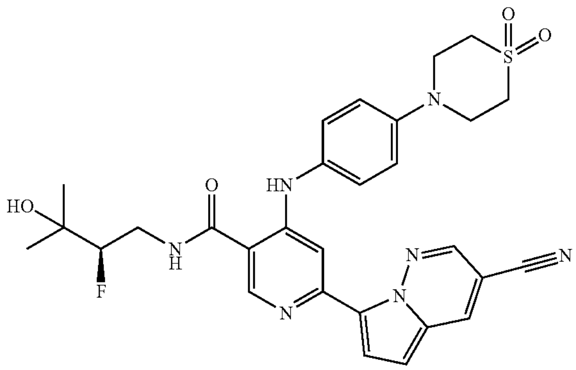 [SMILES: CC(C)(O)[C@H](F)CNC(=O)c1cnc(-c2ccc3cc(C#N)cnn23)cc1Nc1ccc(N2CCS(=O)(=O)CC2)cc1] | 688 | 592.3 | 2 | (R)-6-(3-cyanopyrrolo[1,2-b]pyridazin-7-yl)-4-((4-(1,1-dioxidothiomorpholino)phenyl)amino)-N-(2-fluoro-3-hydroxy-3-methylbutyl)nicotinamide |
| 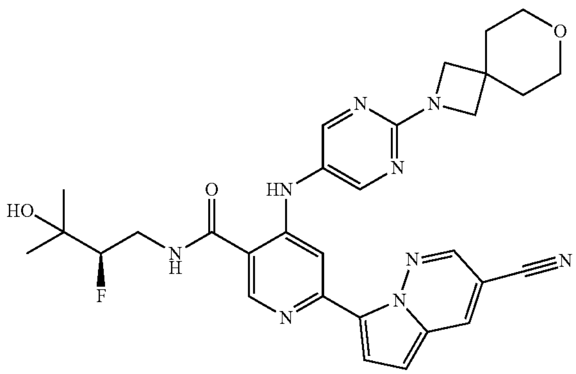 [SMILES: CC(C)(O)[C@H](F)CNC(=O)c1cnc(-c2ccc3cc(C#N)cnn23)cc1Nc1cnc(N2CC3(CCOCC3)C2)nc1] | 689 | 586.4 | 2 | (R)-4-((2-(7-oxa-2-azaspiro[3.5]nonan-2-yl)pyrimidin-5-yl)amino)-6-(3-cyanopyrrolo[1,2-b]pyridazin-7-yl)-N-(2-fluoro-3-hydroxy-3-methylbutyl)nicotinamide |
| diastereomer 1 | 690 | 564.4 | 2 | (R)-6-(3-cyanopyrrolo[1,2-b]pyridazin-7-yl)-N-(2-fluoro-3-hydroxy-3-methylbutyl)-4-((4-methyl-4-morpholinocyclohexyl)amino)nicotinamide |
| diastereomer 2 | 691 | 564.6 | 2 | (R)-6-(3-cyanopyrrolo[1,2-b]pyridazin-7-yl)-N-(2-fluoro-3-hydroxy-3-methylbutyl)-4-((4-methyl-4-morpholinocyclohexyl)amino)nicotinamide |

TABLE 1-continued

| Structure | compound | ES/MS m/z | procedure | Name |
|---|---|---|---|---|
| 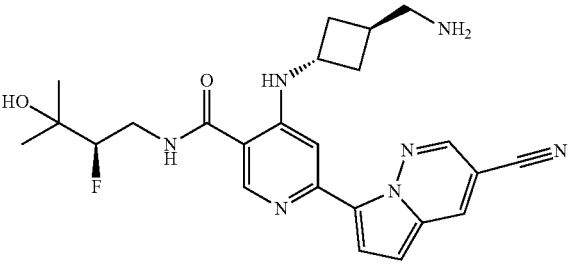 [SMILES: CC(C)(O)[C@H](F)CNC(=O)c1cnc(-c2ccc3cc(C#N)cnn23)cc1N[C@H]1C[C@H](CN)C1] | 692 | 466.3 | 67 | 4-(((1r,3R)-3-(aminomethyl)cyclobutyl)amino)-6-(3-cyanopyrrolo[1,2-b]pyridazin-7-yl)-N-((R)-2-fluoro-3-hydroxy-3-methylbutyl)nicotinamide |
| 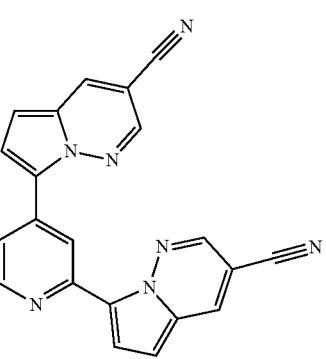 | 693 | 509.2 | 2 | (R)-4,6-bis(3-cyanopyrrolo[1,2-b]pyridazin-7-yl)-N-(2-fluoro-3-hydroxy-3-methylbutyl)nicotinamide |
| 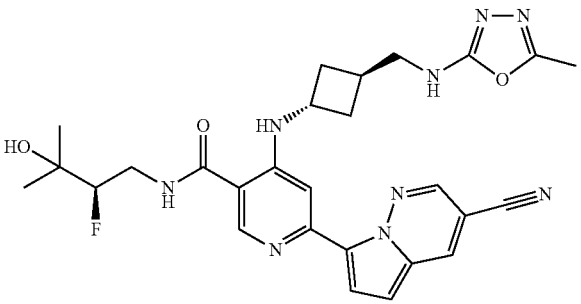 [SMILES: Cc1nnc(NC[C@H]2C[C@H](Nc3cc(-c4ccc5cc(C#N)cnn45)ncc3C(=O)NC[C@@H](F)C(C)(C)O)C2)o1] | 694 | 548.3 | 74 | 6-(3-cyanopyrrolo[1,2-b]pyridazin-7-yl)-N-((R)-2-fluoro-3-hydroxy-3-methylbutyl)-4-(((1r,3R)-3-(((5-methyl-1,3,4-oxadiazol-2-yl)amino)methyl)cyclobutyl)amino)nicotinamide |
| 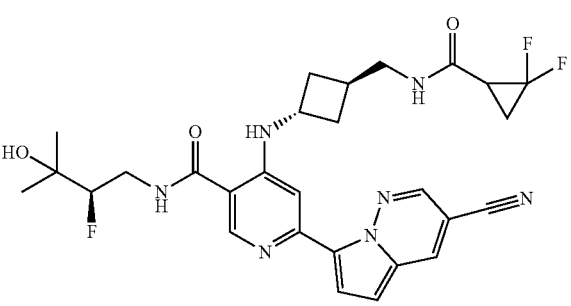 [SMILES: CC(C)(O)[C@H](F)CNC(=O)c1cnc(-c2ccc3cc(C#N)cnn23)cc1N[C@H]1C[C@H](CNC(=O)C2CC2(F)F)C1] | 695 | 570.4 | 33 | 6-(3-cyanopyrrolo[1,2-b]pyridazin-7-yl)-4-(((1R,3R)-3-(((R)-2,2-difluorocyclopropane-1-carboxamido)methyl)cyclobutyl)amino)-N-((R)-2-fluoro-3-hydroxy-3-methylbutyl)nicotinamide |
| 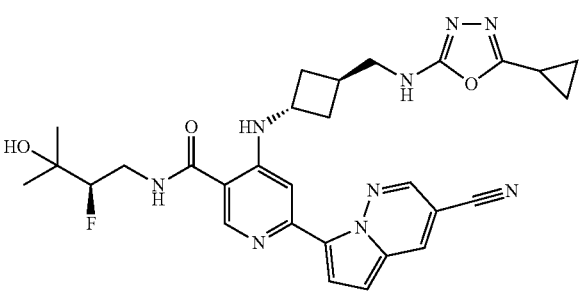 [SMILES: CC(C)(O)[C@H](F)CNC(=O)c1cnc(-c2ccc3cc(C#N)cnn23)cc1N[C@H]1C[C@H](CNc2nnc(C3CC3)o2)C1] | 696 | 574.3 | 74 | 6-(3-cyanopyrrolo[1,2-b]pyridazin-7-yl)-4-(((1r,3R)-3-(((5-cyclopropyl-1,3,4-oxadiazol-2-yl)amino)methyl)cyclobutyl)amino)-N-((R)-2-fluoro-3-hydroxy-3-methylbutyl)nicotinamide |

TABLE 1-continued

| Structure | compound | ES/MS m/z | procedure | Name |
|---|---|---|---|---|
| 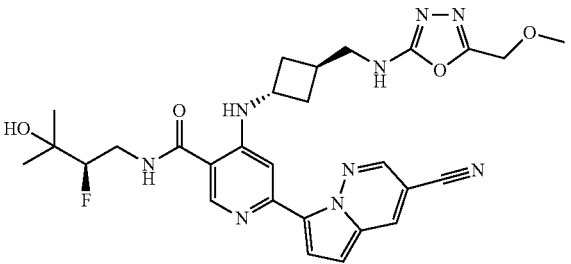 [SMILES: COCc1nnc(NC[C@H]2C[C@H](Nc3cc(-c4ccc5cc(C#N)cnn45)ncc3C(=O)NC[C@@H](F)C(C)(C)O)C2)o1] | 697 | 578.3 | 74 | 6-(3-cyanopyrrolo[1,2-b]pyridazin-7-yl)-N-((R)-2-fluoro-3-hydroxy-3-methylbutyl)-4-(((1r,3R)-3-(((5-(methoxymethyl)-1,3,4-oxadiazol-2-yl)amino)methyl)cyclobutyl)amino)nicotinamide |
| 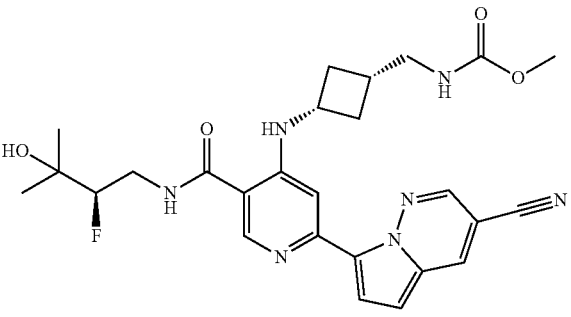 [SMILES: COC(=O)NC[C@H]1C[C@@H](Nc2cc(-c3ccc4cc(C#N)cnn34)ncc2C(=O)NC[C@@H](F)C(C)(C)O)C1] | 698 | 524.3 | 68 | methyl (((1S,3s)-3-((2-(3-cyanopyrrolo[1,2-b]pyridazin-7-yl)-5-(((R)-2-fluoro-3-hydroxy-3-methylbutyl)carbamoyl)pyridin-4-yl)amino)cyclobutyl)methyl)carbamate |
| 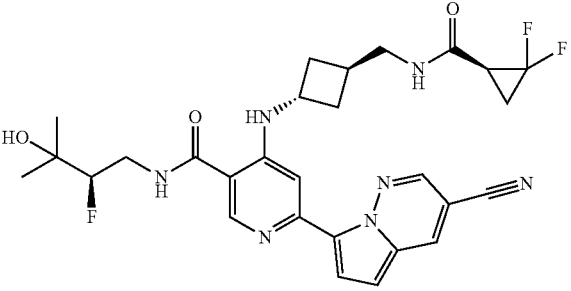 [SMILES: CC(C)(O)[C@H](F)CNC(=O)c1cnc(-c2ccc3cc(C#N)cnn23)cc1N[C@H]1C[C@H](CNC(=O)[C@@H]2CC2(F)F)C1] | 699 | 570.3 | 33 | 6-(3-cyanopyrrolo[1,2-b]pyridazin-7-yl)-4-(((1S,3R)-3-(((S)-2,2-difluorocyclopropane-1-carboxamido)methyl)cyclobutyl)amino)-N-((R)-2-fluoro-3-hydroxy-3-methylbutyl)nicotinamide |
| 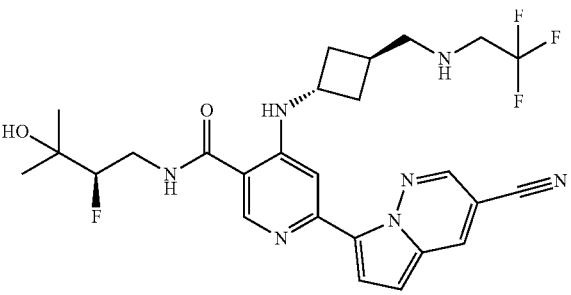 [SMILES: CC(C)(O)[C@H](F)CNC(=O)c1cnc(-c2ccc3cc(C#N)cnn23)cc1N[C@H]1C[C@H](CNCC(F)(F)F)C1] | 700 | 548.3 | 75 | 6-(3-cyanopyrrolo[1,2-b]pyridazin-7-yl)-N-((R)-2-fluoro-3-hydroxy-3-methylbutyl)-4-(((1r,3R)-3-(((2,2,2-trifluoroethyl)amino)methyl)cyclobutyl)amino)nicotinamide |
| 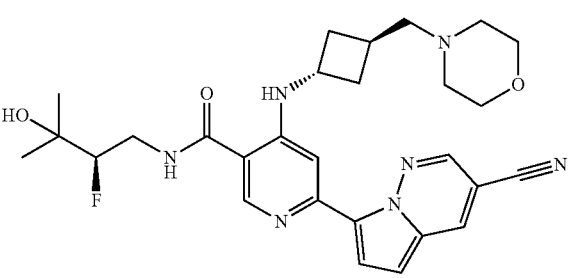 [SMILES: CC(C)(O)[C@H](F)CNC(=O)c1cnc(-c2ccc3cc(C#N)cnn23)cc1N[C@H]1C[C@H](CN2CCOCC2)C1] | 701 | 536.3 | 75 | 6-(3-cyanopyrrolo[1,2-b]pyridazin-7-yl)-N-((R)-2-fluoro-3-hydroxy-3-methylbutyl)-4-(((1r,3R)-3-(morpholinomethyl)cyclobutyl)amino)nicotinamide |

TABLE 1-continued

| Structure | compound | ES/MS m/z | procedure | Name |
|---|---|---|---|---|
| 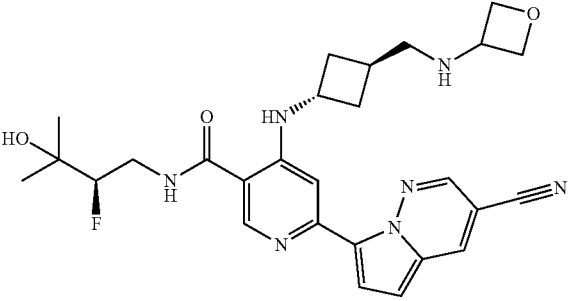 [SMILES: CC(C)(O)[C@H](F)CNC(=O)c1cnc(-c2ccc3cc(C#N)cnn23)cc1N[C@H]1C[C@H](CNC2COC2)C1] | 702 | 522.3 | 76 | 6-(3-cyanopyrrolo[1,2-b]pyridazin-7-yl)-N-((R)-2-fluoro-3-hydroxy-3-methylbutyl)-4-(((1r)3R)-3-((oxetan-3-ylamino)methyl)cyclobutyl)amino)nicotinamide |
| 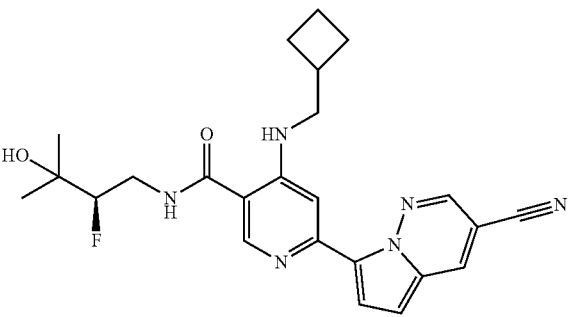 [SMILES: CC(C)(O)[C@H](F)CNC(=O)c1cnc(-c2ccc3cc(C#N)cnn23)cc1NCC1CCC1] | 703 | 451.4 | 2 | (R)-6-(3-cyano-pyrrolo[1,2-b]pyridazin-7-yl)-4-((cyclobutyl-methyl)amino)-N-(2-fluoro-3-hydroxy-3-methylbutyl)nicotinamide |
| 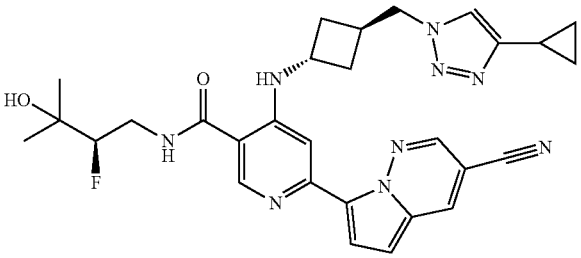 [SMILES: CC(C)(O)[C@H](F)CNC(=O)c1cnc(-c2ccc3cc(C#N)cnn23)cc1N[C@H]1C[C@H](Cn2cc(C3CC3)nn2)C1] | 704 | 558.2 | 77 | 6-(3-cyanopyrrolo[1,2-b]pyridazin-7-yl)-4-(((1r,3R)-3-((4-cyclopropyl-1H-1,2,3-triazol-1-yl)methyl)cyclobutyl)amino)-N-((R)-2-fluoro-3-hydroxy-3-methylbutyl)nicotinamide |
| 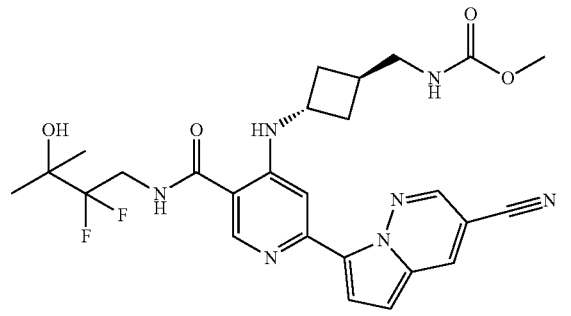 [SMILES: COC(=O)NC[C@H]1C[C@H](Nc2cc(-c3ccc4cc(C#N)cnn34)ncc2C(=O)NCC(F)(F)C(C)(C)O)C1] | 705 | 542.2 | 1 | methyl (((1r,3r)-3-((2-(3-cyanopyrrolo[1,2-b]pyridazin-7-yl)-5-((2,2-difluoro-3-hydroxy-3-methylbutyl)carbamoyl)pyridin-4-yl)amino)cyclobutyl)methyl)carbamate |
| 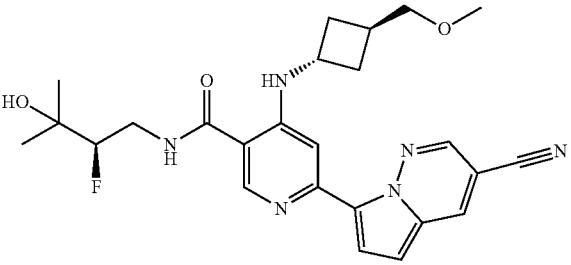 [SMILES: COC[C@H]1C[C@H](Nc2cc(-c3ccc4cc(C#N)cnn34)ncc2C(=O)NC[C@@H](F)C(C)(C)O)C1] | 706 | 481.3 | 78 | 6-(3-cyanopyrrolo[1,2-b]pyridazin-7-yl)-N-((R)-2-fluoro-3-hydroxy-3-methylbutyl)-4-(((1r3R)-3-(methoxymethyl)cyclobutyl)amino)nicotinamide |

TABLE 1-continued

| Structure | compound | ES/MS m/z | procedure | Name |
|---|---|---|---|---|
| 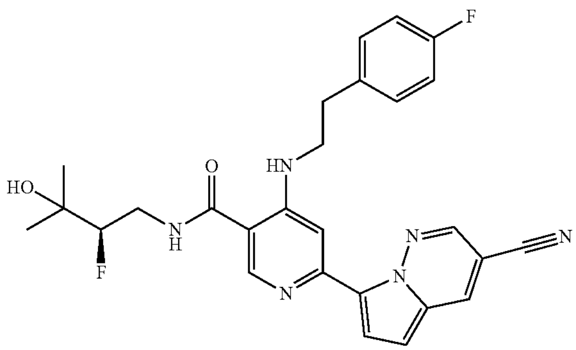 [SMILES: CC(C)(O)[C@H](F)CNC(=O)c1cnc(-c2ccc3cc(C#N)cnn23)cc1NCCc1ccc(F)cc1] | 707 | 505.4 | 2 | (R)-6-(3-cyanopyrrolo[1,2-b]pyridazin-7-yl)-N-(2-fluoro-3-hydroxy-3-methylbutyl)-4-((4-fluorophenethyl)amino)nicotinamide |
| 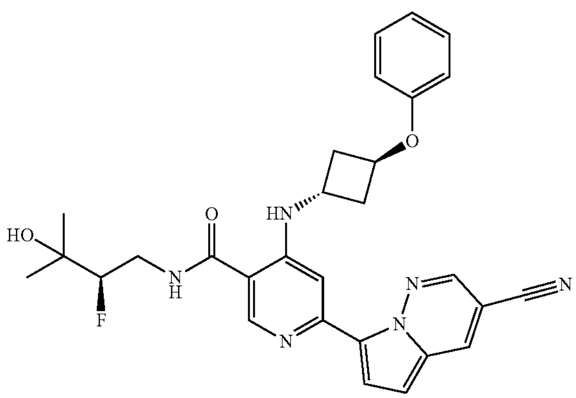 [SMILES: CC(C)(O)[C@H](F)CNC(=O)c1cnc(-c2ccc3cc(C#N)cnn23)cc1N[C@H]1C[C@H](Oc2ccccc2)C1] | 708 | 529.4 | 2 | 6-(3-cyanopyrrolo[1,2-b]pyridazin-7-yl)-N-((R)-2-fluoro-3-hydroxy-3-methylbutyl)-4-(((1r,3R)-3-phenoxycyclobutyl)amino)nicotinamide |
| 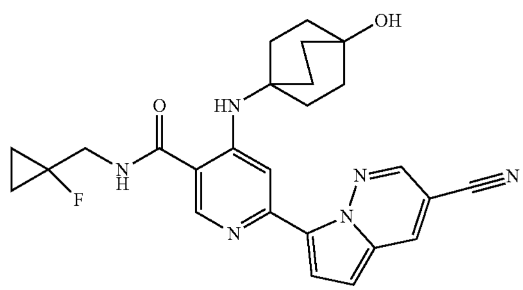 [SMILES: N#Cc1cnn2c(-c3cc(NC45CCC(O)(CC4)CC5)c(C(=O)NCC4(F)CC4)cn3)ccc2c1] | 709 | 475.4 | 3 | 6-(3-cyanopyrrolo[1,2-b]pyridazin-7-yl)-N-((1-fluorocyclopropyl)methyl)-4-((4-hydroxybicyclo[2.2.2]octan-1-yl)amino)nicotinamide |
| 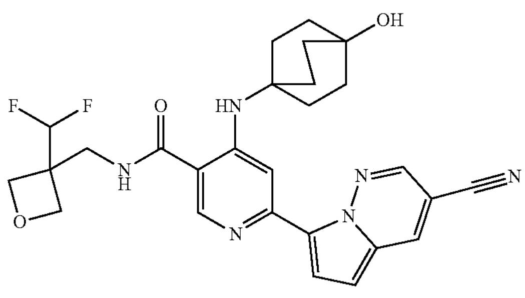 [SMILES: N#Cc1cnn2c(-c3cc(NC45CCC(O)(CC4)CC5)c(C(=O)NCC4(C(F)F)COC4)cn3)ccc2c1] | 710 | 523.3 | 3 | 6-(3-cyanopyrrolo[1,2-b]pyridazin-7-yl)-N-((3-(difluoromethyl)oxetan-3-yl)methyl)-4-((4-hydroxybicyclo[2.2.2]octan-1-yl)amino)nicotinamide |

TABLE 1-continued

| Structure | compound | ES/MS m/z | procedure | Name |
|---|---|---|---|---|
| 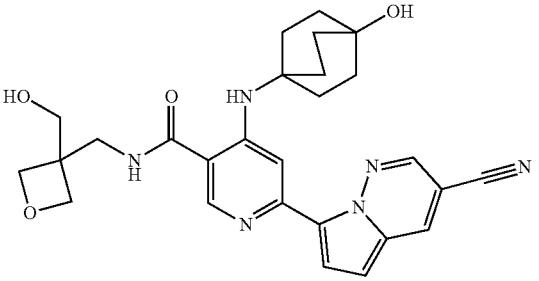 [SMILES: N#Cc1cnn2c(-c3cc(NC45CCC(O)(CC4)CC5)c(C(=O)NCC4(CO)COC4)cn3)ccc2c1] | 711 | 503.3 | 3 | 6-(3-cyanopyrrolo[1,2-b]pyridazin-7-yl)-4-((4-hydroxybicyclo[2.2.2]octan-1-yl)amino)-N-((3-(hydroxymethyl)oxetan-3-yl)methyl)nicotinamide |
| 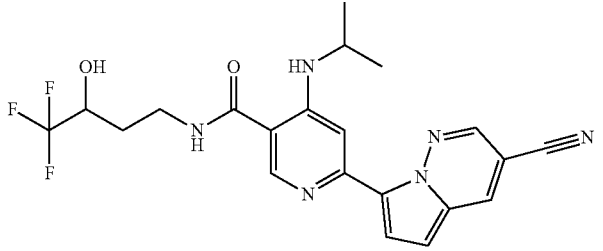 [SMILES: CC(C)Nc1cc(-c2ccc3cc(C#N)cnn23)ncc1C(=O)NCCC(O)C(F)(F)F] | 712 | 447.3 | 3 | 6-(3-cyanopyrrolo[1,2-b]pyridazin-7-yl)-4-(isopropylamino)-N-(4,4,4-trifluoro-3-hydroxybutyl)nicotinamide |
| 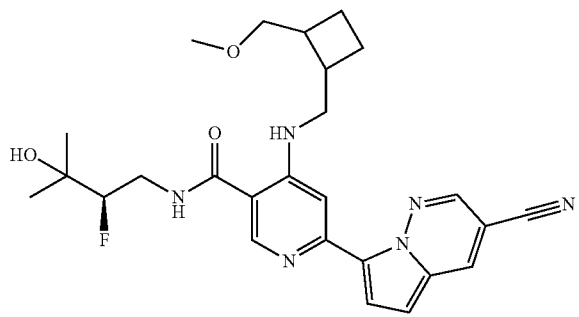 [SMILES: COCC1CCC1CNc1cc(-c2ccc3cc(C#N)cnn23)ncc1C(=O)NC[C@@H](F)C(C)(C)O] | 713 | 495.4 | 2 | 6-(3-cyanopyrrolo[1,2-b]pyridazin-7-yl)-N-((R)-2-fluoro-3-hydroxy-3-methylbutyl)-4-(((2-(methoxymethyl)cyclobutyl)methyl)amino)nicotinamide |
| 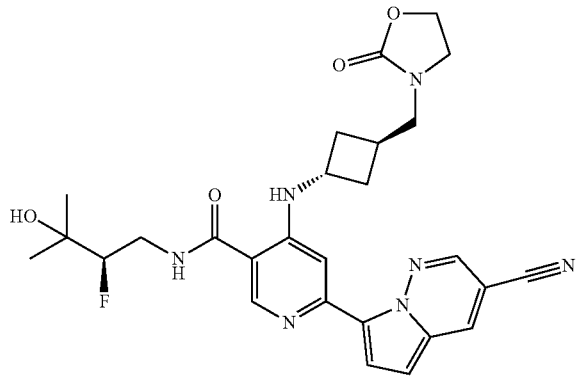 [SMILES: CC(C)(O)[C@H](F)CNC(=O)c1cnc(-c2ccc3cc(C#N)cnn23)cc1N[C@H]1C[C@H](CN2CCOC2=O)C1] | 714 | 536.5 | 50 | 6-(3-cyanopyrrolo[1,2-b]pyridazin-7-yl)-N-((R)-2-fluoro-3-hydroxy-3-methylbutyl)-4-(((1r,3R)-3-((2-oxooxazolidin-3-yl)methyl)cyclobutyl)amino)nicotinamide |
| 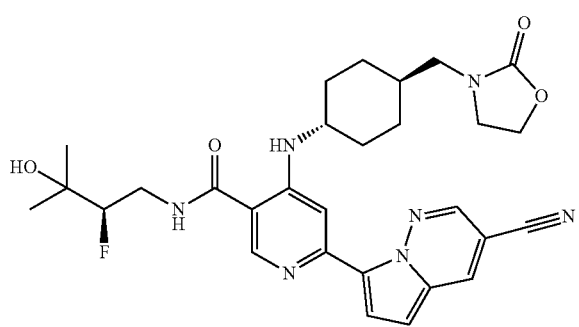 [SMILES: CC(C)(O)[C@H](F)CNC(=O)c1cnc(-c2ccc3cc(C#N)cnn23)cc1N[C@H]1CC[C@H](CN2CCOC2=O)CC1] | 715 | 564.5 | 50 | 6-(3-cyanopyrrolo[1,2-b]pyridazin-7-yl)-N-((R)-2-fluoro-3-hydroxy-3-methylbutyl)-4-(((1r,4R)-4-((2-oxooxazolidin-3-yl)methyl)cyclohexyl)amino)nicotinamide |

TABLE 1-continued

| Structure | compound | ES/MS m/z | procedure | Name |
|---|---|---|---|---|
| 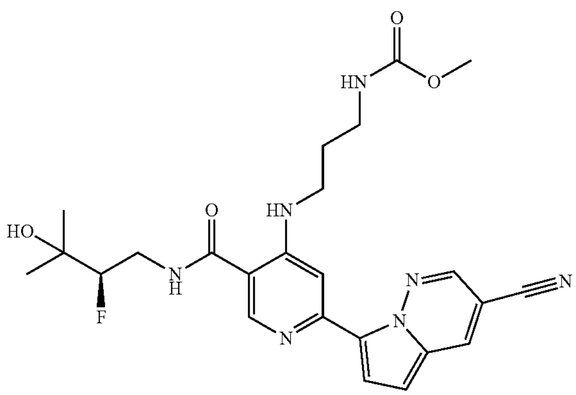 [SMILES: COC(=O)NCCCNc1cc(-c2ccc3cc(C#N)cnn23)ncc1C(=O)NC[C@@H](F)C(C)(C)O] | 716 | 498.4 | 35 | (R)-methyl (3-((2-(3-cyanopyrrolo[1,2-b]pyridazin-7-yl)-5-((2-fluoro-3-hydroxy-3-methylbutyl)carbamoyl)pyridin-4-yl)amino)propyl)carbamate |
| 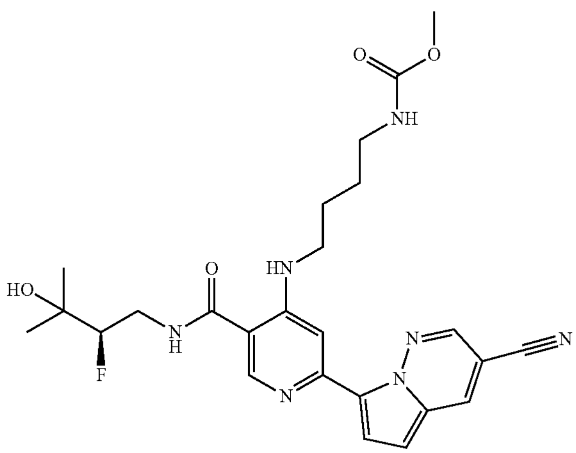 [SMILES: COC(=O)NCCCCNc1cc(-c2ccc3cc(C#N)cnn23)ncc1C(=O)NC[C@@H](F)C(C)(C)O] | 717 | 512.6 | 35 | (R)-methyl (4-((2-(3-cyano-pyrrolo[1,2-b]pyridazin-7-yl)-5-((2-fluoro-3-hydroxy-3-methylbutyl)carbamoyl)pyridin-4-yl)amino)butyl)carbamate |
| 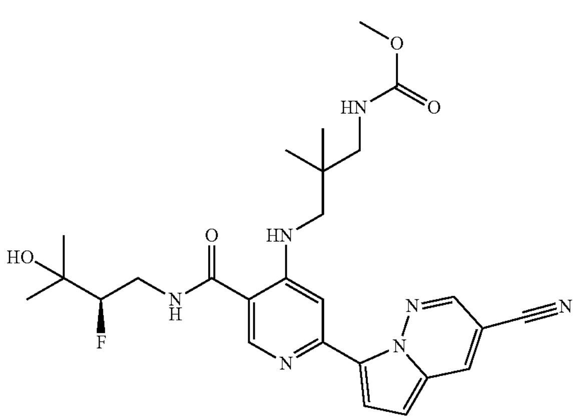 [SMILES: COC(=O)NCC(C)(C)CNc1cc(-c2ccc3cc(C#N)cnn23)ncc1C(=O)NC[C@@H](F)C(C)(C)O] | 718 | 526.5 | 35 | (R)-methyl (3-((2-(3-cyano-pyrrolo[1,2-b]pyridazin-7-yl)-5-((2-fluoro-3-hydroxy-3-methylbutyl)carbamoyl)pyridin-4-yl)amino)-2,2-dimethylpropyl)carbamate |

TABLE 1-continued

| Structure | compound | ES/ MS m/z | procedure | Name |
|---|---|---|---|---|
| 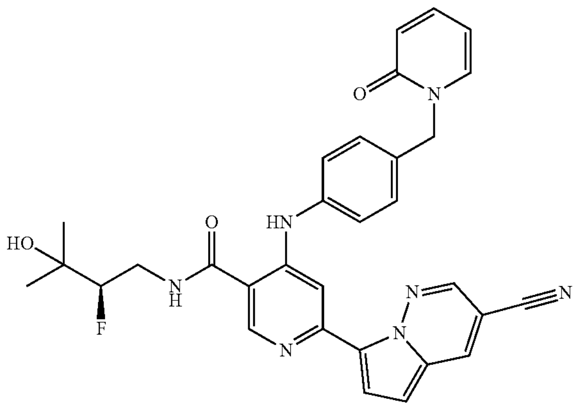 [SMILES: CC(C)(O)[C@H](F)CNC(=O)c1cnc(-c2ccc3cc(C#N)cnn23)cc1Nc1ccc(Cn2ccccc2=O)cc1] | 719 | 566.3 | 27 | (R)-6-(3-cyanopyrrolo[1,2-b]pyridazin-7-yl)-N-(2-fluoro-3-hydroxy-3-methylbutyl)-4-((4-((2-oxopyridin-1(2H)-yl)methyl)phenyl)amino)nicotinamide |
| 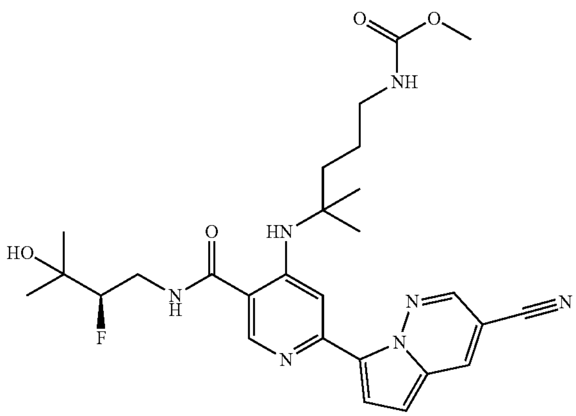 [SMILES: COC(=O)NCCCC(C)(C)Nc1cc(-c2ccc3cc(C#N)cnn23)ncc1C(=O)NC[C@@H](F)C(C)(C)O] | 720 | 540.4 | 35 | (R)-methyl (4-((2-(3-cyano-pyrrolo[1,2-b]pyridazin-7-yl)-5-((2-fluoro-3-hydroxy-3-methylbutyl)carbamoyl)pyridin-4-yl)amino)-4-methylpentyl)carbamate |
| 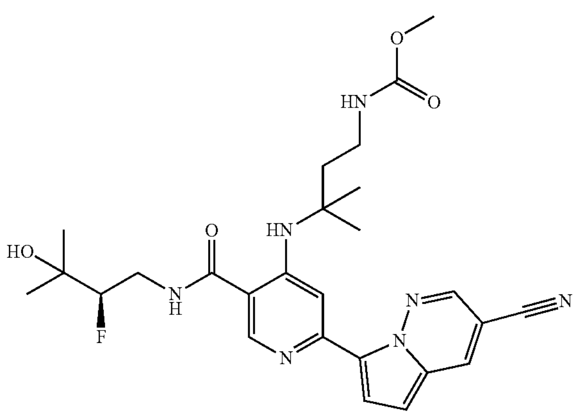 [SMILES: COC(=O)NCCC(C)(C)Nc1cc(-c2ccc3cc(C#N)cnn23)ncc1C(=O)NC[C@@H](F)C(C)(C)O] | 721 | 526.5 | 35 | (R)-methyl (3-((2-(3-cyano-pyrrolo[1,2-b]pyridazin-7-yl)-5-((2-fluoro-3-hydroxy-3-methylbutyl)carbamoyl)pyridin-4-yl)amino)-3-methylbutyl)carbamate |
| 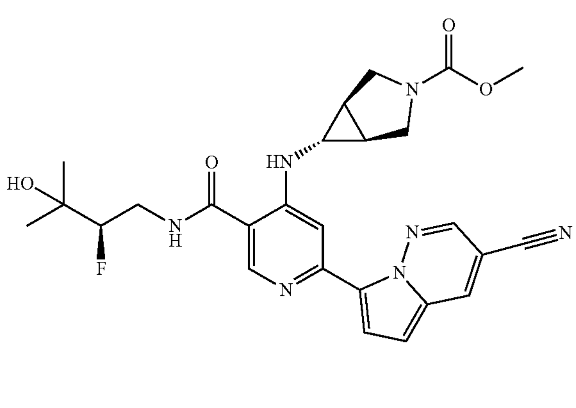 [SMILES: COC(=O)N1C[C@@H]2[C@H](C1)[C@H]2Nc1cc(-c2ccc3cc(C#N)cnn23)ncc1C(=O)NC[C@@H](F)C(C)(C)O] | 722 | 522.3 | 35 | (1R,5S,6s)-methyl 6-((2-(3-cyanopyrrolo[1,2-b]pyridazin-7-yl)-5-(((R)-2-fluoro-3-hydroxy-3-methyl-butyl)carbamoyl)pyridin-4-yl)amino)-3-aza-bicyclo[3.1.0]hexane-3-carboxylate |

TABLE 1-continued

| Structure | compound | ES/MS m/z | procedure | Name |
|---|---|---|---|---|
| 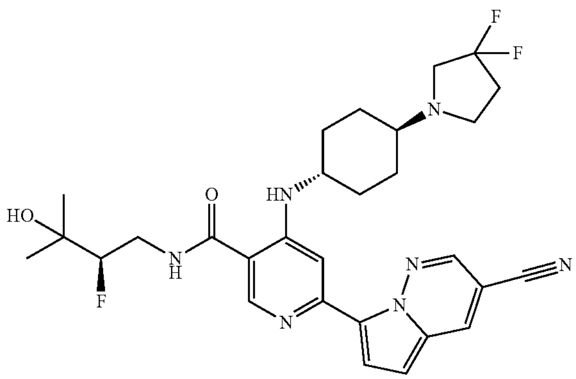 [SMILES: CC(C)(O)[C@H](F)CNC(=O)c1cnc(-c2ccc3cc(C#N)cnn23)cc1N[C@H]1CC[C@H](N2CCC(F)(F)C2)CC1] | 723 | 570.4 | 2 | 6-(3-cyanopyrrolo[1,2-b]pyridazin-7-yl)-4-(((1r,4R)-4-(3,3-difluoropyrrolidin-1-yl)cyclohexyl)amino)-N-((R)-2-fluoro-3-hydroxy-3-methylbutyl)nicotinamide |
| 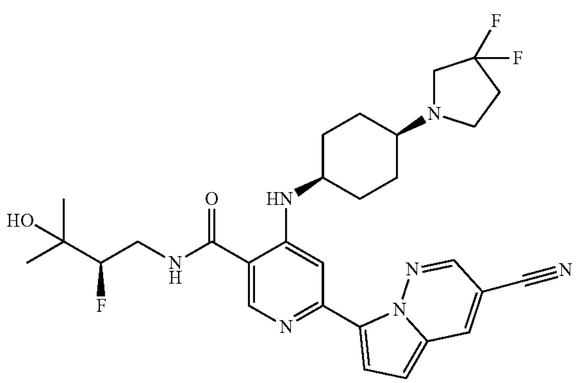 [SMILES: CC(C)(O)[C@H](F)CNC(=O)c1cnc(-c2ccc3cc(C#N)cnn23)cc1N[C@H]1CC[C@@H](N2CCC(F)(F)C2)CC1] | 724 | 570.3 | 2 | 6-(3-cyanopyrrolo[1,2-b]pyridazin-7-yl)-4-(((1s,4S)-4-(3,3-difluoropyrrolidin-1-yl)cyclohexyl)amino)-N-((R)-2-fluoro-3-hydroxy-3-methylbutyl)nicotinamide |
| 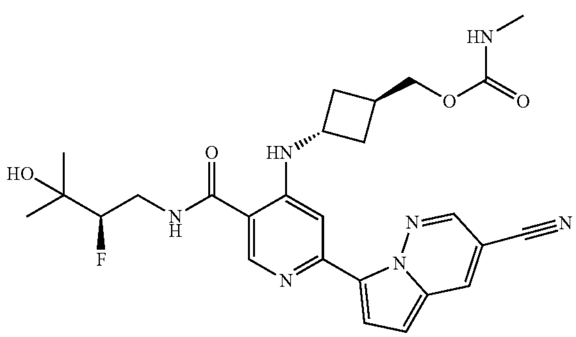 [SMILES: CNC(=O)OC[C@H]1C[C@H](Nc2cc(-c3ccc4cc(C#N)cnn34)ncc2C(=O)NC[C@@H](F)C(C)(C)O)C1] | 725 | 524.4 | 56 | ((1R,3r)-3-((2-(3-cyanopyrrolo[1,2-b]pyridazin-7-yl)-5-(((R)-2-fluoro-3-hydroxy-3-methylbutyl)carbamoyl)pyridin-4-yl)amino)cyclobutyl)methyl methylcarbamate |
| 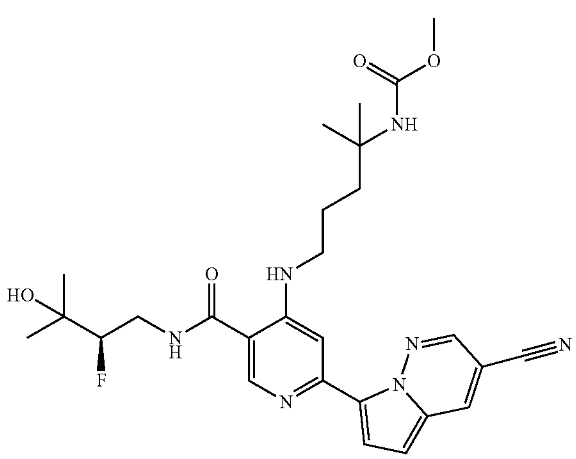 [SMILES: COC(=O)NC(C)(C)CCCNc1cc(-c2ccc3cc(C#N)cnn23)ncc1C(=O)NC[C@@H](F)C(C)(C)O] | 726 | 540.3 | 35 | (R)-methyl (5-((2-(3-cyanopyrrolo[1,2-b]pyridazin-7-yl)-5-((2-fluoro-3-hydroxy-3-methylbutyl)carbamoyl)pyridin-4-yl)amino)-2-methylpentan-2-yl)carbamate |

TABLE 1-continued

| Structure | compound | ES/MS m/z | procedure | Name |
|---|---|---|---|---|
| 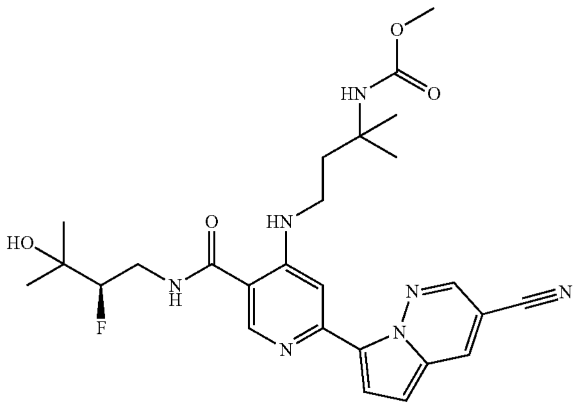 [SMILES: COC(=O)NC(C)(C)CCNc1cc(-c2ccc3cc(C#N)cnn23)ncc1C(=O)NC[C@@H](F)C(C)(C)O] | 727 | 526.4 | 35 | (R)-methyl (4-((2-(3-cyanopyrrolo[1,2-b]pyridazin-7-yl)-5-((2-fluoro-3-hydroxy-3-methylbutyl)carbamoyl)pyridin-4-yl)amino)-2-methylbutan-2-yl)carbamate |
| 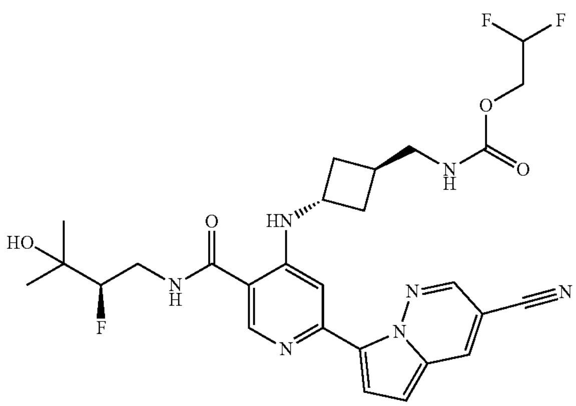 [SMILES: CC(C)(O)[C@H](F)CNC(=O)c1cnc(-c2ccc3cc(C#N)cnn23)cc1N[C@H]1C[C@H](CNC(=O)OCC(F)F)C1] | 728 | 574.7 | 68 | 2,2-difluoroethyl (((1R,3r)-3-((2-(3-cyanopyrrolo[1,2-b]pyridazin-7-yl)-5-(((R)-2-fluoro-3-hydroxy-3-methylbutyl)carbamoyl)pyridin-4-yl)amino)cyclobutyl)methyl)carbamate |
| 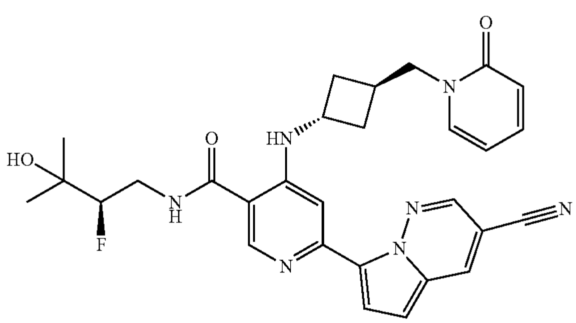 [SMILES: CC(C)(O)[C@H](F)CNC(=O)c1cnc(-c2ccc3cc(C#N)cnn23)cc1N[C@H]1C[C@H](Cn2ccccc2=O)C1] | 729 | 544.4 | 2 | 6-(3-cyanopyrrolo[1,2-b]pyridazin-7-yl)-N-((R)-2-fluoro-3-hydroxy-3-methylbutyl)-4-(((1r,3R)-3-((2-oxopyridin-1(2H)-yl)methyl)cyclobutyl)amino)nicotinamide |
| 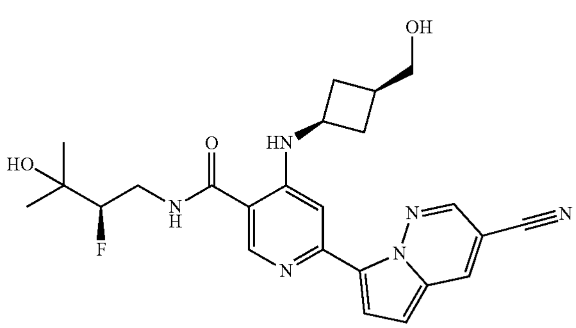 [SMILES: CC(C)(O)[C@H](F)CNC(=O)c1cnc(-c2ccc3cc(C#N)cnn23)cc1N[C@H]1C[C@@H](CO)C1] | 730 | 467.4 | 2 | 6-(3-cyanopyrrolo[1,2-b]pyridazin-7-yl)-N-((R)-2-fluoro-3-hydroxy-3-methylbutyl)-4-(((1s,3S)-3-hydroxymethyl)cyclobutyl)amino)nicotinamide |

TABLE 1-continued

| Structure | compound | ES/MS m/z | procedure | Name |
|---|---|---|---|---|
| 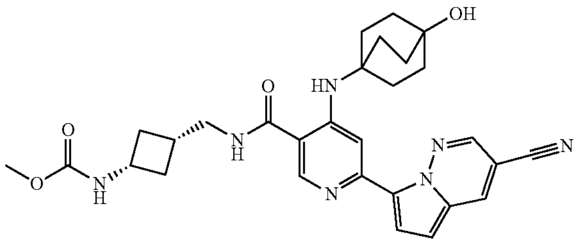 [SMILES: COC(=O)N[C@H]1C[C@@H](CNC(=O)c2cnc(-c3ccc4cc(C#N)cnn34)cc2NC23CCC(O)(CC2)CC3)C1] | 731 | 544.5 | 46 | methyl ((1s,3s)-3-((6-(3-cyanopyrrolo[1,2-b]pyridazin-7-yl)-4-((4-hydroxybicyclo[2.2.2]octan-1-yl)amino)nicotin-amido)methyl)cyclobutyl)carbamate |
| 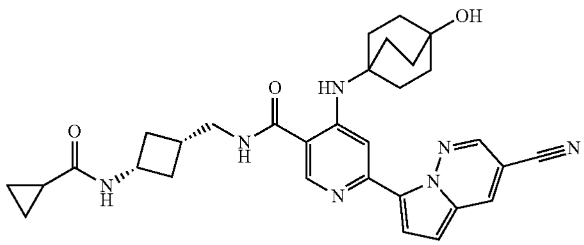 [SMILES: N#Cc1cnn2c(-c3cc(NC45CCC(O)(CC4)CC5)c(C(=O)NC[C@H]4C[C@@H](NC(=O)C5CC5)C4)cn3)ccc2c1] | 732 | 554.6 | 22 | 6-(3-cyanopyrrolo[1,2-b]pyridazin-7-yl)-N-(((1s,3s)-3-(cyclopropane-carboxamido)cyclobutyl)methyl)-4-((4-hydroxy-bicyclo[2.2.2]octan-1-yl)amino)nicotinamide |
| 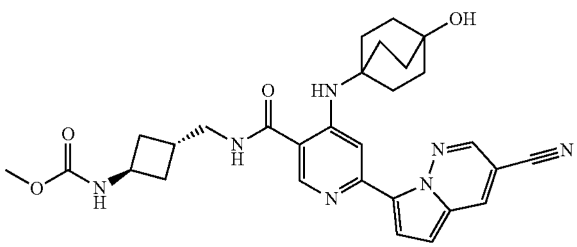 [SMILES: COC(=O)N[C@H]1C[C@H](CNC(=O)c2cnc(-c3ccc4cc(C#N)cnn34)cc2NC23CCC(O)(CC2)CC3)C1] | 733 | 544.4 | 46 | methyl ((1r,3r)-3-((6-(3-cyanopyrrolo[1,2-b]pyridazin-7-yl)-4-((4-hydroxybicyclo[2.2.2]octan-1-yl)amino)nicotin-amido)methyl)cyclobutyl)carbamate |
| 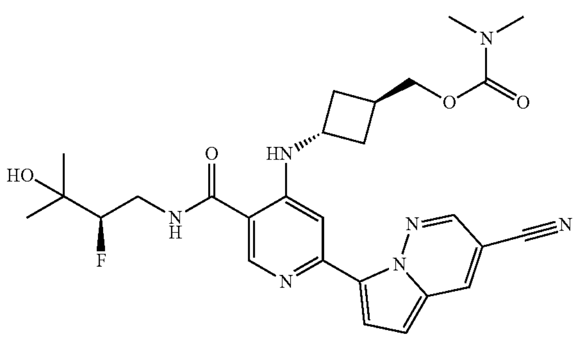 [SMILES: CN(C)C(=O)OC[C@H]1C[C@H](Nc2cc(-c3ccc4cc(C#N)cnn34)ncc2C(=O)NC[C@@H](F)C(C)(C)O)C1] | 734 | 538.6 | 56 | ((1R,3r)-3-((2-(3-cyanopyrrolo[1,2-b]pyridazin-7-yl)-5-(((R)-2-fluoro-3-hydroxy-3-methylbutyl)carbamoyl)pyridin-4-yl)amino)cyclobutyl)methyldimethyl-carbamate |
| 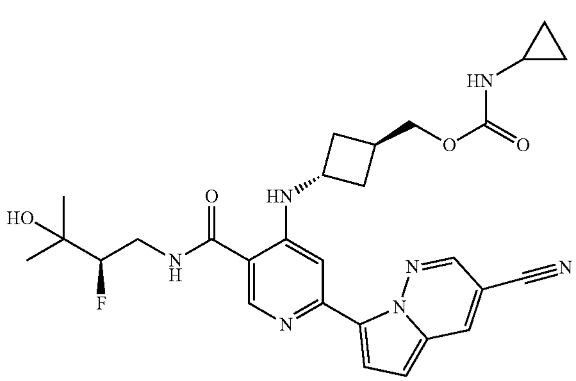 [SMILES: CC(C)(O)[C@H](F)CNC(=O)c1cnc(-c2ccc3cc(C#N)cnn23)cc1N[C@H]1C[C@H](COC(=O)NC2CC2)C1] | 735 | 550.3 | 56 | ((1R,3r)-3-((2-(3-cyano-pyrrolo[1,2-b]pyridazin-7-yl)-5-(((R)-2-fluoro-3-hydroxy-3-methylbutyl)carbamoyl)pyridin-4-yl)amino)cyclobutyl)methyl cyclopropylcarbamate |

TABLE 1-continued

| Structure | compound | ES/MS m/z | procedure | Name |
|---|---|---|---|---|
| 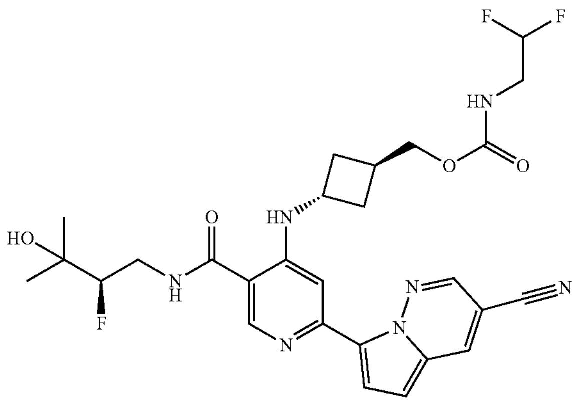 [SMILES: CC(C)(O)[C@H](F)CNC(=O)c1cnc(-c2ccc3cc(C#N)cnn23)cc1N[C@H]1C[C@H](COC(=O)NCC(F)F)C1] | 736 | 574.4 | 56 | ((1R,3r)-3-((2-(3-cyanopyrrolo[1,2-b]pyridazin-7-yl)-5-(((R)-2-fluoro-3-hydroxy-3-methylbutyl)carbamoyl)pyridin-4-yl)amino)cyclobutyl)methyl (2,2-difluoroethyl)carbamate |
| 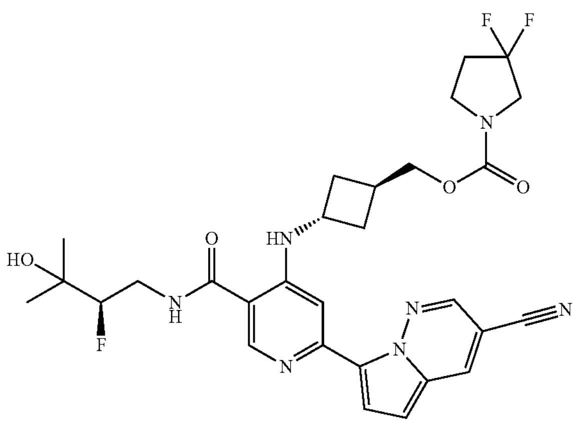 [SMILES: CC(C)(O)[C@H](F)CNC(=O)c1cnc(-c2ccc3cc(C#N)cnn23)cc1N[C@H]1C[C@H](COC(=O)N2CCC(F)(F)C2)C1] | 737 | 600.4 | 56 | ((1R,3r)-3-((2-(3-cyanopyrrolo[1,2-b]pyridazin-7-yl)-5-(((R)-2-fluoro-3-hydroxy-3-methylbutyl)carbamoyl)pyridin-4-yl)amino)cyclobutyl)methyl 3,3-difluoropyrrolidine-1-carboxylate |
| 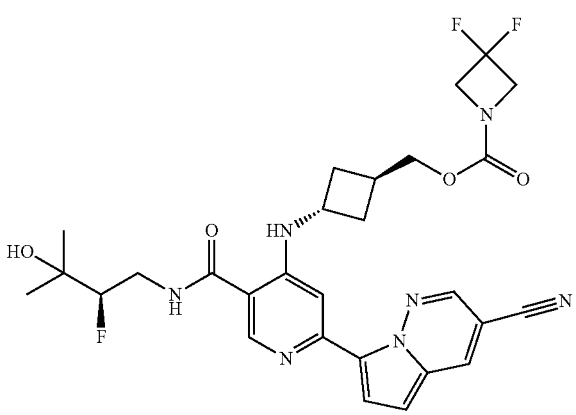 [SMILES: CC(C)(O)[C@H](F)CNC(=O)c1cnc(-c2ccc3cc(C#N)cnn23)cc1N[C@H]1C[C@H](COC(=O)N2CC(F)(F)C2)C1] | 738 | 586.6 | 56 | ((1R,3r)-3-((2-(3-cyanopyrrolo[1,2-b]pyridazin-7-yl)-5-(((R)-2-fluoro-3-hydroxy-3-methylbutyl)carbamoyl)pyridin-4-yl)amino)cyclobutyl)methyl 3,3-difluoroazetidine-1-carboxylate |
| 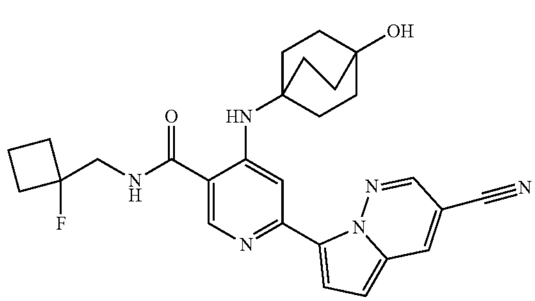 [SMILES: N#Cc1cnn2c(-c3cc(NC45CCC(O)(CC4)CC5)c(C(=O)NCC4(F)CCC4)cn3)ccc2c1] | 739 | 489.4 | 49 | 6-(3-cyanopyrrolo[1,2-b]pyridazin-7-yl)-N-((1-fluorocyclobutyl)methyl)-4-((4-hydroxybicyclo[2.2.2]octan-1-yl)amino)nicotinamide |

TABLE 1-continued

| Structure | compound | ES/MS m/z | procedure | Name |
|---|---|---|---|---|
| 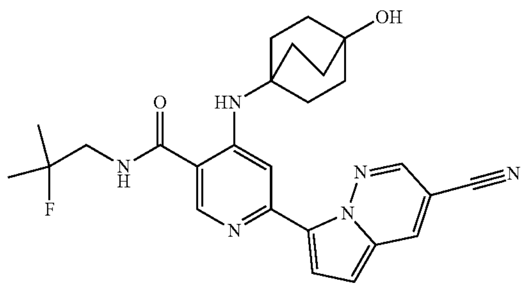 [SMILES: CC(C)(F)CNC(=O)c1cnc(-c2ccc3cc(C#N)cnn23)cc1NC12CCC(O)(CC1)CC2] | 740 | 477.3 | 49 | 6-(3-cyanopyrrolo[1,2-b]pyridazin-7-yl)-N-(2-fluoro-2-methylpropyl)-4-((4-hydroxybicyclo[2.2.2]octan-1-yl)amino)nicotinamide |
| 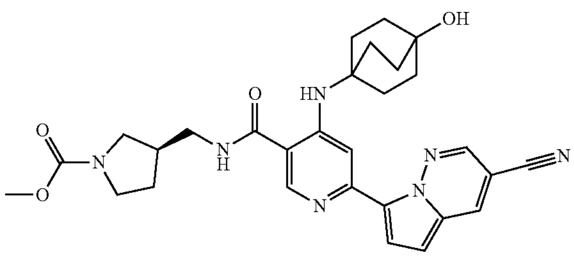 [SMILES: COC(=O)N1CC[C@H](CNC(=O)c2cnc(-c3ccc4cc(C#N)cnn34)cc2NC23CCC(O)(CC2)CC3)C1] | 741 | 544.7 | 46 | (R)-methyl 3-((6-(3-cyano-pyrrolo[1,2-b]pyridazin-7-yl)-4-((4-hydroxybicyclo[2.2.2]octan-1-yl)amino)nicotinamido)methyl)pyrrolidine-1-carboxylate |
| 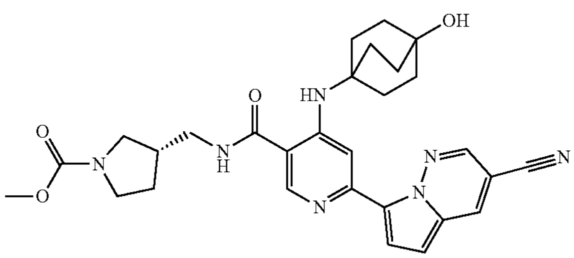 [SMILES: COC(=O)N1CC[C@@H](CNC(=O)c2cnc(-c3ccc4cc(C#N)cnn34)cc2NC23CCC(O)(CC2)CC3)C1] | 742 | 544.5 | 46 | (S)-methyl 3-((6-(3-cyano-pyrrolo[1,2-b]pyridazin-7-yl)-4-((4-hydroxy-bicyclo[2.2.2]octan-1-yl)amino)nicotinamido)methyl)pyrrolidine-1-carboxylate |
| 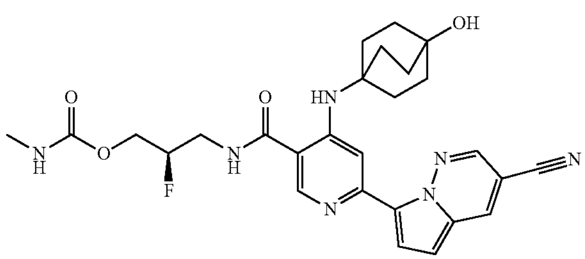 [SMILES: CNC(=O)OC[C@H](F)CNC(=O)c1cnc(-c2ccc3cc(C#N)cnn23)cc1NC12CCC(O)(CC1)CC2] | 743 | 536.4 | 49 | (R)-3-(6-(3-cyano-pyrrolo[1,2-b]pyridazin-7-yl)-4-((4-hydroxy-bicyclo[2.2.2]octan-1-yl)amino)nicotinamido)-2-fluoropropyl methylcarbamate |
| 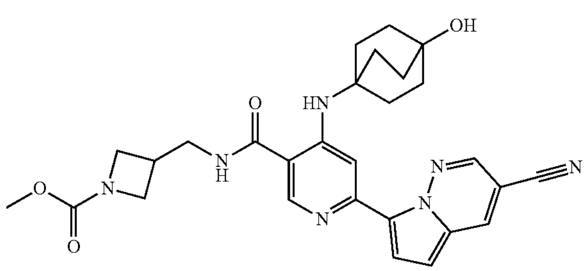 [SMILES: COC(=O)N1CC(CNC(=O)c2cnc(-c3ccc4cc(C#N)cnn34)cc2NC23CCC(O)(CC2)CC3)C1] | 744 | 530.4 | 46 | methyl 3-((6-(3-cyano-pyrrolo[1,2-b]pyridazin-7-yl)-4-((4-hydroxy-bicyclo[2.2.2]octan-1-yl)amino)nicotinamido)methyl)azetidine-1-carboxylate |

TABLE 1-continued

| Structure | compound | ES/MS m/z | procedure | Name |
|---|---|---|---|---|
| 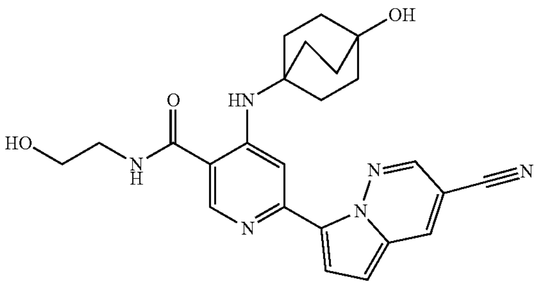 [SMILES: N#Cc1cnn2c(-c3cc(NC45CCC(O)(CC4)CC5)c(C(=O)NCCO)cn3)ccc2c1] | 745 | 447.3 | 49 | 6-(3-cyanopyrrolo[1,2-b]pyridazin-7-yl)-4-((4-hydroxybicyclo[2.2.2]octan-1-yl)amino)-N-(2-hydroxyethyl)nicotinamide |
| 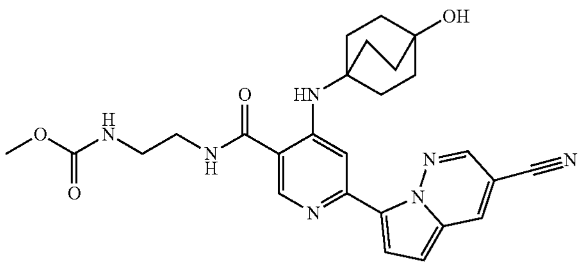 [SMILES: COC(=O)NCCNC(=O)c1cnc(-c2ccc3cc(C#N)cnn23)cc1NC12CCC(O)(CC1)CC2] | 746 | 504.5 | 46 | methyl (2-(6-(3-cyanopyrrolo[1,2-b]pyridazin-7-yl)-4-((4-hydroxybicyclo[2.2.2]octan-1-yl)amino)nicotinamido)ethyl)carbamate |
| 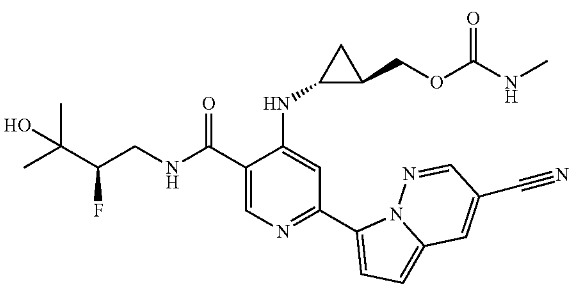 [SMILES: CNC(=O)OC[C@@H]1C[C@H]1Nc1cc(-c2ccc3cc(C#N)cnn23)ncc1C(=O)NC[C@@H](F)C(C)(C)O] | 747 | 510.5 | 56 | ((1R,2R)-2-((2-(3-cyanopyrrolo[1,2-b]pyridazin-7-yl)-5-(((R)-2-fluoro-3-hydroxy-3-methylbutyl)carbamoyl)pyridin-4-yl)amino)cyclopropyl)methylmethylcarbamate |
| 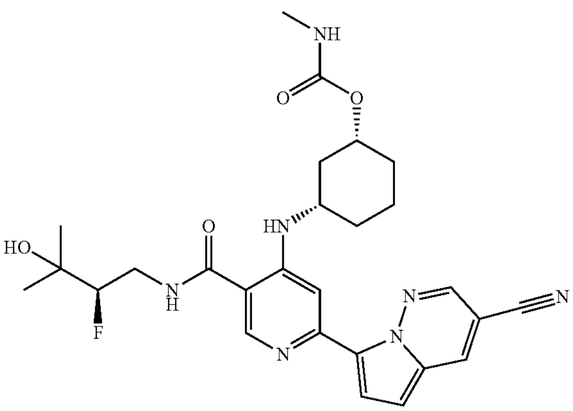 [SMILES: CNC(=O)O[C@@H]1CCC[C@H](Nc2cc(-c3ccc4cc(C#N)cnn34)ncc2C(=O)NC[C@@H](F)C(C)(C)O)C1] | 748 | 538.4 | 56 | (1R,3S)-3-((2-(3-cyanopyrrolo[1,2-b]pyridazin-7-yl)-5-(((R)-2-fluoro-3-hydroxy-3-methylbutyl)carbamoyl)pyridin-4-yl)amino)cyclohexyl methylcarbamate |
| 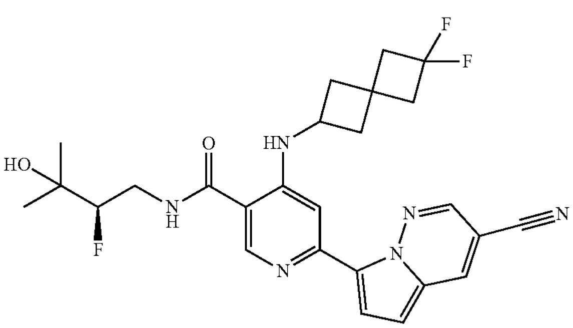 [SMILES: CC(C)(O)[C@H](F)CNC(=O)c1cnc(-c2ccc3cc(C#N)cnn23)cc1NC1CC2(C1)CC(F)(F)C2] | 749 | 513.5 | 2 | (R)-6-(3-cyanopyrrolo[1,2-b]pyridazin-7-yl)-4-((6,6-difluorospiro[3.3]heptan-2-yl)amino)-N-(2-fluoro-3-hydroxy-3-methylbutyl)nicotinamide |

TABLE 1-continued

| Structure | compound | ES/MS m/z | procedure | Name |
|---|---|---|---|---|
| 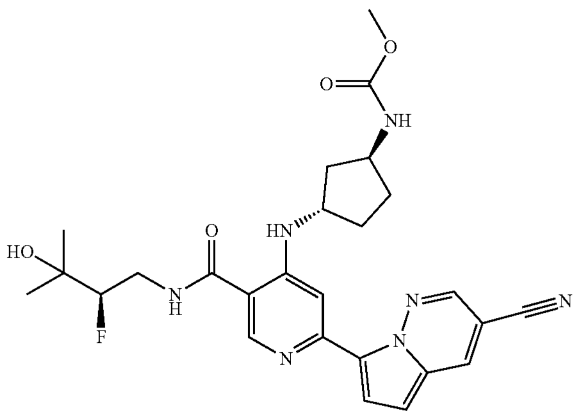 [SMILES: COC(=O)N[C@H]1CC[C@H](Nc2cc(-c3ccc4cc(C#N)cnn34)ncc2C(=O)NC[C@@H](F)C(C)(C)O)C1] | 750 | 524.5 | 35 | methyl ((1S,3S)-3-((2-(3-cyanopyrrolo[1,2-b]pyridazin-7-yl)-5-(((R)-2-fluoro-3-hydroxy-3-methylbutyl)carbamoyl)pyridin-4-yl)amino)cyclopentyl)carbamate |
| 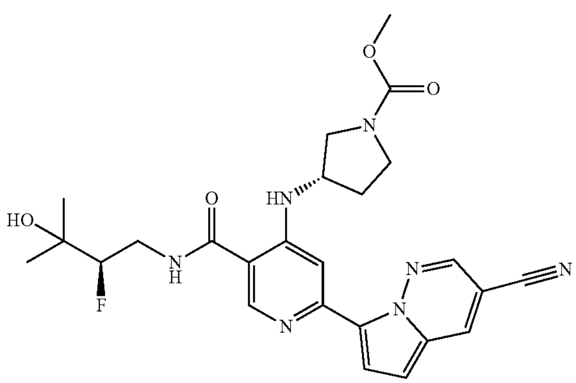 [SMILES: COC(=O)N1CC[C@H](Nc2cc(-c3ccc4cc(C#N)cnn34)ncc2C(=O)NC[C@@H](F)C(C)(C)O)C1] | 751 | 510.3 | 35 | (S)-methyl 3-((2-(3-cyanopyrrolo[1,2-b]pyridazin-7-yl)-5-(((R)-2-fluoro-3-hydroxy-3-methylbutyl)carbamoyl)pyridin-4-yl)amino)pyrrolidine-1-carboxylate |
| 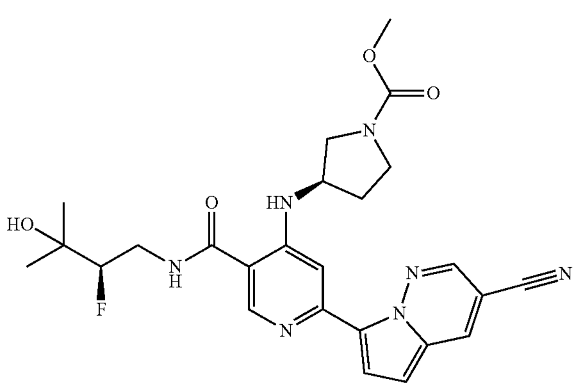 [SMILES: COC(=O)N1CC[C@@H](Nc2cc(-c3ccc4cc(C#N)cnn34)ncc2C(=O)NC[C@@H](F)C(C)(C)O)C1] | 752 | 510.3 | 35 | (R)-methyl 3-((2-(3-cyanopyrrolo[1,2-b]pyridazin-7-yl)-5-(((R)-2-fluoro-3-hydroxy-3-methylbutyl)carbamoyl)pyridin-4-yl)amino)pyrrolidine-1-carboxylate |
| 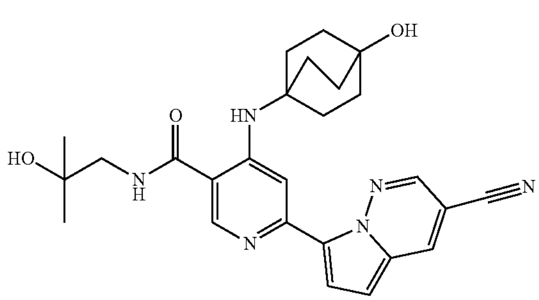 [SMILES: CC(C)(O)CNC(=O)c1cnc(-c2ccc3cc(C#N)cnn23)cc1NC12CCC(O)(CC1)CC2] | 753 | 475.3 | 49 | 6-(3-cyanopyrrolo[1,2-b]pyridazin-7-yl)-N-(2-hydroxy-2-methylpropyl)-4-((4-hydroxybicyclo[2.2.2]octan-1-yl)amino)nicotinamide |

TABLE 1-continued

| Structure | compound | ES/MS m/z | procedure | Name |
|---|---|---|---|---|
| mixture | 754 | 550.4 | 35 | (R)-methyl (6-((2-(3-cyanopyrrolo[1,2-b]pyridazin-7-yl)-5-((2-fluoro-3-hydroxy-3-methylbutyl)carbamoyl)pyridin-4-yl)amino)spiro[3.3]heptan-2-yl)carbamate |
| 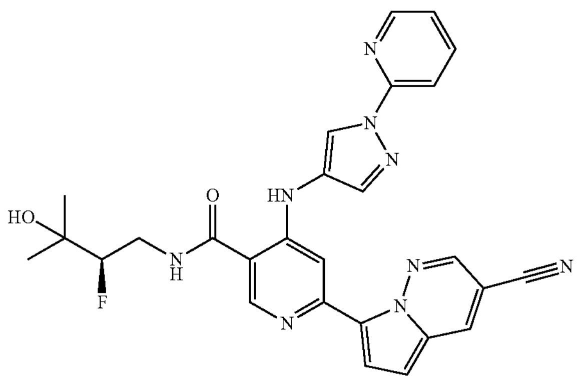 [SMILES: CC(C)(O)[C@H](F)CNC(=O)c1cnc(-c2ccc3cc(C#N)cnn23)cc1Nc1cnn(-c2ccccn2)c1] | 755 | 526.3 | 27 | (R)-6-(3-cyanopyrrolo[1,2-b]pyridazin-7-yl)-N-(2-fluoro-3-hydroxy-3-methylbutyl)-4-((1-(pyridin-2-yl)-1H-pyrazol-4-yl)amino)nicotinamide |
| diastereomer 1 | 756 | 550.4 | 86 | (R)-methyl (6-((2-(3-cyanopyrrolo[1,2-b]pyridazin-7-yl)-5-((2-fluoro-3-hydroxy-3-methylbutyl)carbamoyl)pyridin-4-yl)amino)spiro[3.3]heptan-2-yl)carbamate |
| diastereomer 2 | 757 | 550.4 | 86 | (R)-methyl (6-((2-(3-cyanopyrrolo[1,2-b]pyridazin-7-yl)-5-((2-fluoro-3-hydroxy-3-methylbutyl)carbamoyl)pyridin-4-yl)amino)spiro[3.3]heptan-2-yl)carbamate |

TABLE 1-continued

| Structure | compound | ES/MS m/z | procedure | Name |
|---|---|---|---|---|
| mixture | 758 | 542.3 | 1 | (R)-methyl ((3-((2-(3-cyanopyrrolo[1,2-b]pyridazin-7-yl)-5-((2-fluoro-3-hydroxy-3-methylbutyl)carbamoyl)pyridin-4-yl)amino)-1-fluorocyclobutyl)methyl)carbamate |
| diastereomer 1 | 759 | 540.2 | 2 | (R)-methyl ((3-((2-(3-cyanopyrrolo[1,2-b]pyridazin-7-yl)-5-((2-fluoro-3-hydroxy-3-methylbutyl)carbamoyl)pyridin-4-yl)amino)-1-hydroxycyclobutyl)methyl)carbamate |
| diastereomer 2 | 760 | 540.3 | 2 | (R)-methyl ((3-((2-(3-cyanopyrrolo[1,2-b]pyridazin-7-yl)-5-((2-fluoro-3-hydroxy-3-methylbutyl)carbamoyl)pyridin-4-yl)amino)-1-hydroxycyclobutyl)methyl)carbamate |
| 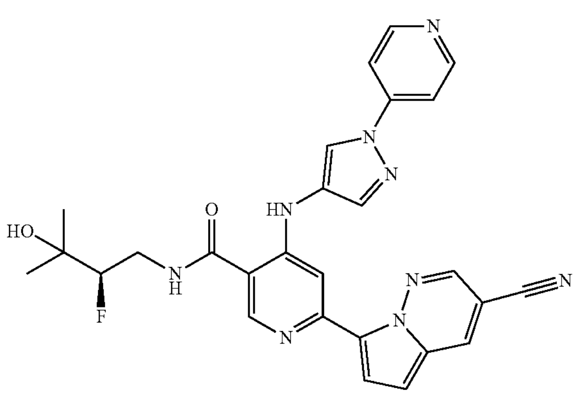 [SMILES: CC(C)(O)[C@H](F)CNC(=O)c1cnc(-c2ccc3cc(C#N)cnn23)cc1Nc1cnn(-c2ccncc2)c1] | 761 | 526.3 | 27 | (R)-6-(3-cyanopyrrolo[1,2-b]pyridazin-7-yl)-N-(2-fluoro-3-hydroxy-3-methylbutyl)-4-((1-(pyridin-4-yl)-1H-pyrazol-4-yl)amino)nicotinamide |

TABLE 1-continued

| compound | ES/MS m/z | procedure | Name |
|---|---|---|---|
| 762 | 526.4 | 27 | (R)-4-((4-(1H-1,2,4-triazol-1-yl)phenyl)amino)-6-(3-cyanopyrrolo[1,2-b]pyridazin-7-yl)-N-(2-fluoro-3-hydroxy-3-methylbutyl)nicotinamide |
| 763 | 508.3 | 1 | (R)-6-(3-cyanopyrrolo[1,2-b]pyridazin-7-yl)-N-(2-fluoro-3-hydroxy-3-methylbutyl)-4-((6-oxo-5-oxa-7-azaspiro[3.4]octan-2-yl)amino)nicotinamide |
| 764 | 542.4 | 87 | (R)-methyl ((3-((2-(3-cyanopyrrolo[1,2-b]pyridazin-7-yl)-5-((2-fluoro-3-hydroxy-3-methylbutyl)carbamoyl)pyridin-4-yl)amino)-1-fluorocyclobutyl)methyl)carbamate |
| 765 | 542.4 | 87 | (R)-methyl ((3-((2-(3-cyanopyrrolo[1,2-b]pyridazin-7-yl)-5-((2-fluoro-3-hydroxy-3-methylbutyl)carbamoyl)pyridin-4-yl)amino)-1-fluorocyclobutyl)methyl)carbamate | diastereomer 1 (compound 764)

diastereomer 2 (compound 765)

TABLE 1-continued

| Structure | compound | ES/MS m/z | procedure | Name |
|---|---|---|---|---|
| 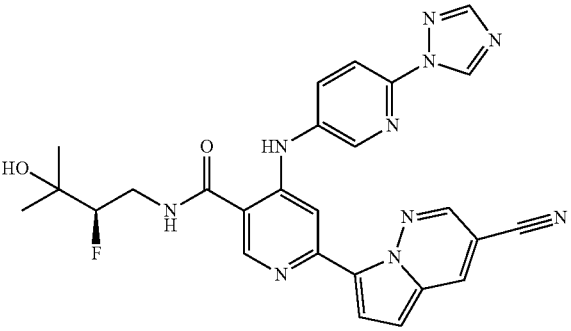 [SMILES: CC(C)(O)[C@H](F)CNC(=O)c1cnc(-c2ccc3cc(C#N)cnn23)cc1Nc1ccc(-n2cncn2)nc1] | 766 | 527.3 | 27 | (R)-4-((6-(1H-1,2,4-triazol-1-yl)pyridin-3-yl)amino)-6-(3-cyanopyrrolo[1,2-b]pyridazin-7-yl)-N-(2-fluoro-3-hydroxy-3-methylbutyl)nicotinamide |
| 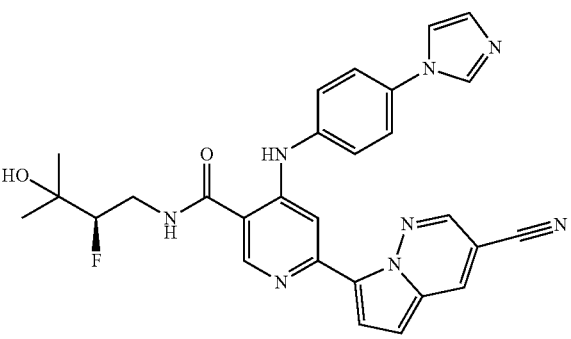 [SMILES: CC(C)(O)[C@H](F)CNC(=O)c1cnc(-c2ccc3cc(C#N)cnn23)cc1Nc1ccc(-n2ccnc2)cc1] | 767 | 525.3 | 27 | (R)-4-((4-(1H-imidazol-1-yl)phenyl)amino)-6-(3-cyanopyrrolo[1,2-b]pyridazin-7-yl)-N-(2-fluoro-3-hydroxy-3-methylbutyl)nicotinamide |
| 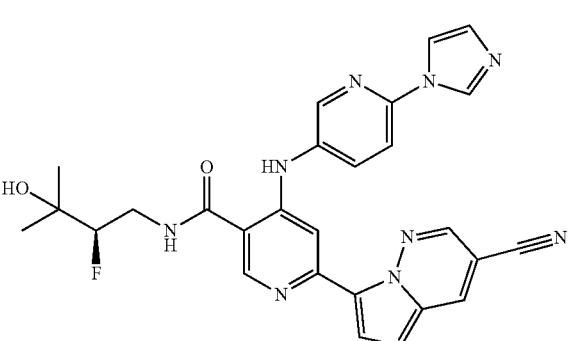 | 768 | 526.4 | 27 | (R)-4-((6-(1H-imidazol-1-yl)pyridin-3-yl)amino)-6-(3-cyanopyrrolo[1,2-b]pyridazin-7-yl)-N-(2-fluoro-3-hydroxy-3-methylbutyl)nicotinamide |
| 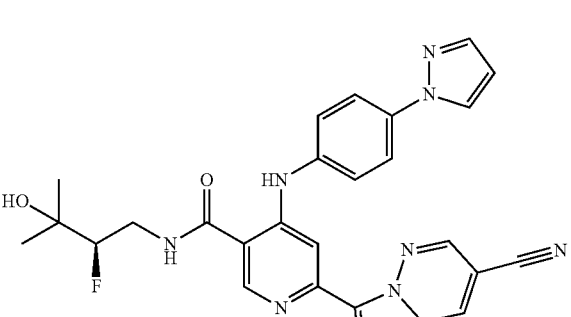 | 769 | 525.3 | 27 | (R)-4-((4-(1H-pyrazol-1-yl)phenyl)amino)-6-(3-cyanopyrrolo[1,2-b]pyridazin-7-yl)-N-(2-fluoro-3-hydroxy-3-methylbutyl)nicotinamide |

TABLE 1-continued

| Structure | compound | ES/MS m/z | procedure | Name |
|---|---|---|---|---|
| 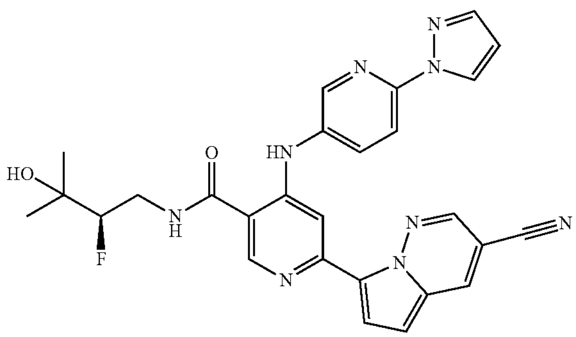 [SMILES: CC(C)(O)[C@H](F)CNC(=O)c1cnc(-c2ccc3cc(C#N)cnn23)cc1Nc1ccc(-n2cccn2)nc1] | 770 | 526.3 | 27 | (R)-4-((6-(1H-pyrazol-1-yl)pyridin-3-yl)amino)-6-(3-cyanopyrrolo[1,2-b]pyridazin-7-yl)-N-(2-fluoro-3-hydroxy-3-methylbutyl)nicotinamide |
| 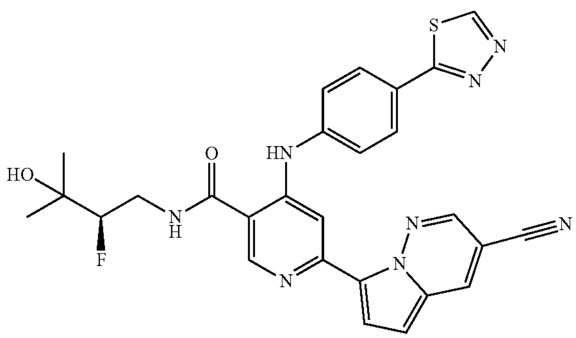 [SMILES: CC(C)(O)[C@H](F)CNC(=O)c1cnc(-c2ccc3cc(C#N)cnn23)cc1Nc1ccc(-c2nncs2)cc1] | 771 | 543.3 | 27 | (R)-4-((4-(1,3,4-thiadiazol-2-yl)phenyl)amino)-6-(3-cyanopyrrolo[1,2-b]pyridazin-7-yl)-N-(2-fluoro-3-hydroxy-3-methylbutyl)nicotinamide |
| 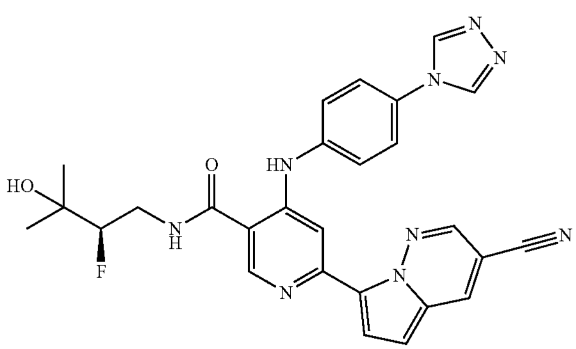 [SMILES: CC(C)(O)[C@H](F)CNC(=O)c1cnc(-c2ccc3cc(C#N)cnn23)cc1Nc1ccc(-n2cnnc2)cc1] | 772 | 526.2 | 27 | (R)-4-((4-(4H-1,2,4-triazol-4-yl)phenyl)amino)-6-(3-cyanopyrrolo[1,2-b]pyridazin-7-yl)-N-(2-fluoro-3-hydroxy-3-methylbutyl)nicotinamide |
| 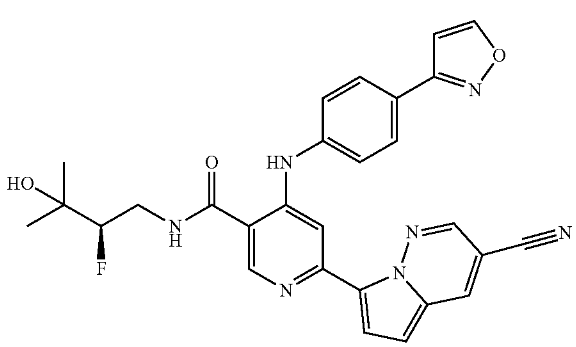 [SMILES: CC(C)(O)[C@H](F)CNC(=O)c1cnc(-c2ccc3cc(C#N)cnn23)cc1Nc1ccc(-c2ccon2)cc1] | 773 | 526.3 | 27 | (R)-6-(3-cyanopyrrolo[1,2-b]pyridazin-7-yl)-N-(2-fluoro-3-hydroxy-3-methylbutyl)-4-((4-(isoxazol-3-yl)phenyl)amino)nicotinamide |

TABLE 1-continued

| Structure | compound | ES/MS m/z | procedure | Name |
|---|---|---|---|---|
| 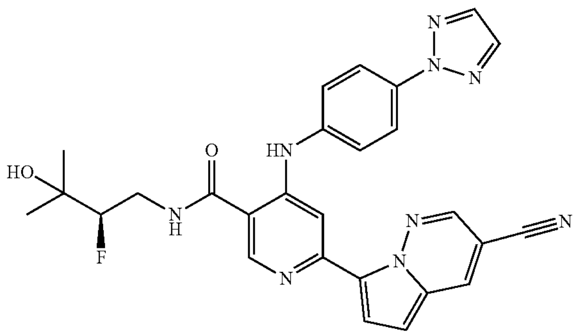 [SMILES: CC(C)(O)[C@H](F)CNC(=O)c1cnc(-c2ccc3cc(C#N)cnn23)cc1Nc1ccc(-n2nccn2)cc1] | 774 | 526.3 | 27 | (R)-4-((4-(2H-1,2,3-triazol-2-yl)phenyl)amino)-6-(3-cyanopyrrolo[1,2-b]pyridazin-7-yl)-N-(2-fluoro-3-hydroxy-3-methylbutyl)nicotinamide |
| 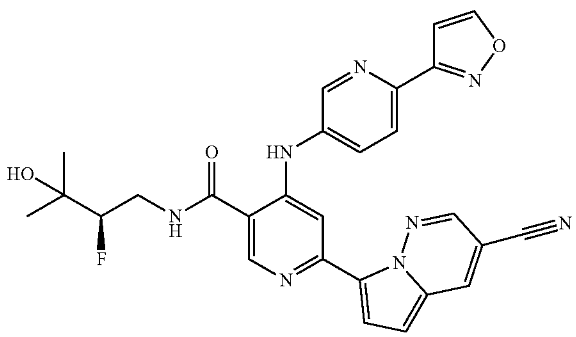 [SMILES: CC(C)(O)[C@H](F)CNC(=O)c1cnc(-c2ccc3cc(C#N)cnn23)cc1Nc1ccc(-c2ccon2)nc1] | 775 | 527.3 | 27 | (R)-6-(3-cyanopyrrolo[1,2-b]pyridazin-7-yl)-N-(2-fluoro-3-hydroxy-3-methylbutyl)-4-((6-(isoxazol-3-yl)pyridin-3-yl)amino)nicotinamide |
| 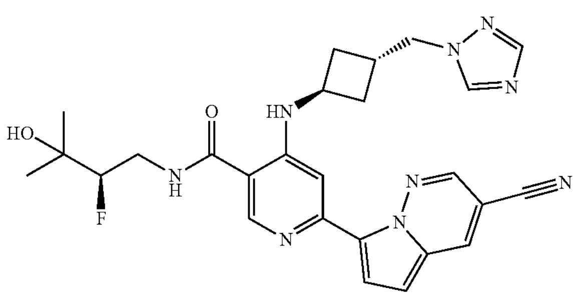 [SMILES: CC(C)(O)[C@H](F)CNC(=O)c1cnc(-c2ccc3cc(C#N)cnn23)cc1N[C@H]1C[C@H](Cn2cncn2)C1] | 776 | 518.3 | 1 | 4-(((1r,3R)-3-((1H-1,2,4-triazol-1-yl)methyl)cyclobutyl)amino)-6-(3-cyanopyrrolo[1,2-b]pyridazin-7-yl)-N-((R)-2-fluoro-3-hydroxy-3-methylbutyl)nicotinamide |
| 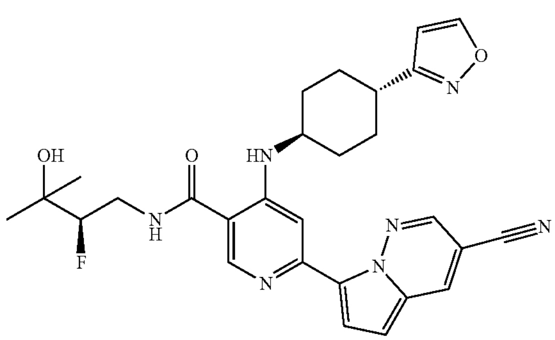 [SMILES: CC(C)(O)[C@H](F)CNC(=O)c1cnc(-c2ccc3cc(C#N)cnn23)cc1N[C@H]1CC[C@H](c2ccon2)CC1] | 777 | 532.3 | 2 | 6-(3-cyanopyrrolo[1,2-b]pyridazin-7-yl)-N-((R)-2-fluoro-3-hydroxy-3-methylbutyl)-4-(((1r,4R)-4-(isoxazol-3-yl)cyclohexyl)amino)nicotinamide |

TABLE 1-continued

| Structure | compound | ES/MS m/z | procedure | Name |
|---|---|---|---|---|
| 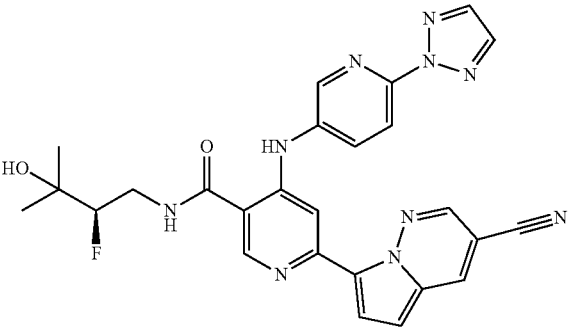 [SMILES: CC(C)(O)[C@H](F)CNC(=O)c1cnc(-c2ccc3cc(C#N)cnn23)cc1Nc1ccc(-n2nccn2)nc1] | 778 | 527.2 | 27 | (R)-4-((6-(2H-1,2,3-triazol-2-yl)pyridin-3-yl)amino)-6-(3-cyanopyrrolo[1,2-b]pyridazin-7-yl)-N-(2-fluoro-3-hydroxy-3-methyl-butyl)nicotinamide |
| 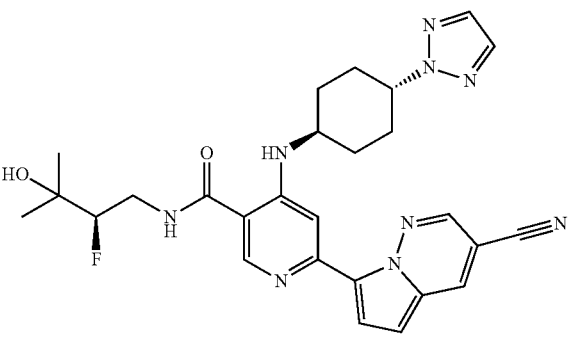 [SMILES: CC(C)(O)[C@H](F)CNC(=O)c1cnc(-c2ccc3cc(C#N)cnn23)cc1N[C@H]1CC[C@H](n2nccn2)CC1] | 779 | 532.4 | 1 | 4-(((1r,4R)-4-(1H-1,2,4-triazol-1-yl)cyclohexyl)amino)-6-(3-cyano-pyrrolo[1,2-b]pyridazin-7-yl)-N-((R)-2-fluoro-3-hydroxy-3-methylbutyl)nicotinamide |
| 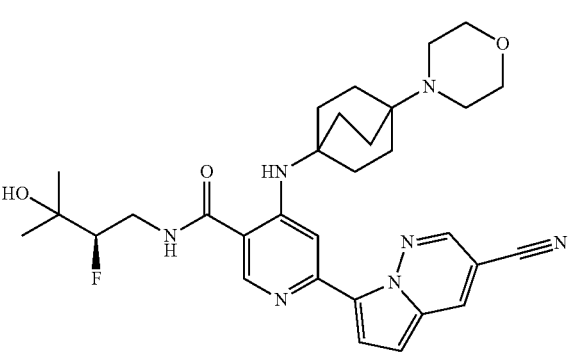 [SMILES: CC(C)(O)[C@H](F)CNC(=O)c1cnc(-c2ccc3cc(C#N)cnn23)cc1NC12CCC(N3CCOCC3)(CC1)CC2] | 780 | 576.4 | 1 | (R)-6-(3-cyanopyrrolo[1,2-b]pyridazin-7-yl)-N-(2-fluoro-3-hydroxy-3-methylbutyl)-4-((4-morpholino bicyclo[2.2.2]octan-1-yl)amino)nicotinamide |
| 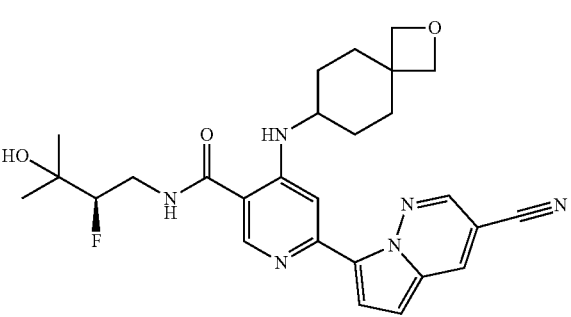 [SMILES: CC(C)(O)[C@H](F)CNC(=O)c1cnc(-c2ccc3cc(C#N)cnn23)cc1NC1CCC2(CC1)COC2] | 781 | 507.5 | 2 | (R)-4-(2-oxaspiro[3.5]nonan-7-ylamino)-6-(3-cyanopyrrolo[1,2-b]pyridazin-7-yl)-N-(2-fluoro-3-hydroxy-3-methyl-butyl)nicotinamide |

TABLE 1-continued

| Structure | compound | ES/MS m/z | procedure | Name |
|---|---|---|---|---|
| 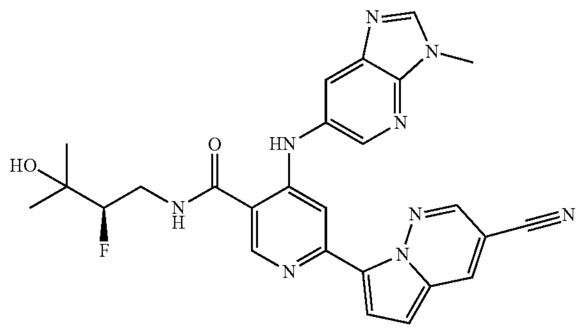 [SMILES: Cn1cnc2cc(Nc3cc(-c4ccc5cc(C#N)cnn45)ncc3C(=O)NC[C@@H](F)C(C)(C)O)cnc21] | 782 | 514.2 | 27 | (R)-6-(3-cyanopyrrolo[1,2-b]pyridazin-7-yl)-N-(2-fluoro-3-hydroxy-3-methylbutyl)-4-((3-methyl-3H-imidazo[4,5-b]pyridin-6-yl)amino)nicotinamide |
| 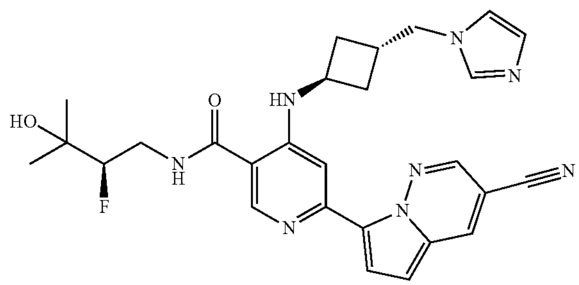 [SMILES: CC(C)(O)[C@H](F)CNC(=O)c1cnc(-c2ccc3cc(C#N)cnn23)cc1N[C@H]1C[C@H](Cn2ccnc2)C1] | 783 | 517.3 | 1 | 4-(((1r,3R)-3-((1H-imidazol-1-yl)methyl)cyclobutyl)amino)-6-(3-cyanopyrrolo[1,2-b]pyridazin-7-yl)-N-((R)-2-fluoro-3-hydroxy-3-methylbutyl)nicotinamide |
| 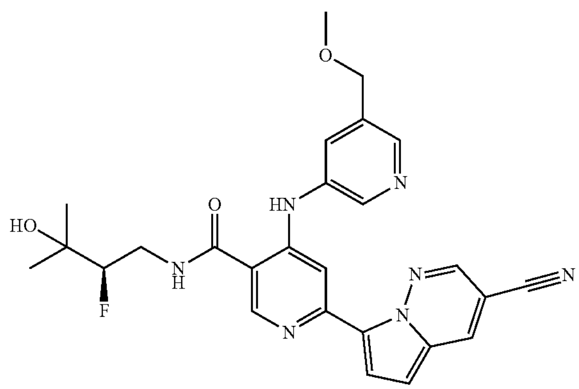 [SMILES: COCc1cncc(Nc2cc(-c3ccc4cc(C#N)cnn34)ncc2C(=O)NC[C@@H](F)C(C)(C)O)c1] | 784 | 504.3 | 27 | (R)-6-(3-cyanopyrrolo[1,2-b]pyridazin-7-yl)-N-(2-fluoro-3-hydroxy-3-methylbutyl)-4-((5-(methoxymethyl)pyridin-3-yl)amino)nicotinamide |
| 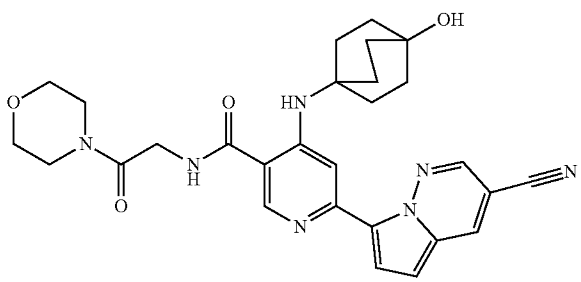 [SMILES: N#Cc1cnn2c(-c3cc(NC45CCC(O)(CC4)CC5)c(C(=O)NCC(=O)N4CCOCC4)cn3)ccc2c1] | 785 | 530.3 | 49 | 6-(3-cyanopyrrolo[1,2-b]pyridazin-7-yl)-4-((4-hydroxybicyclo[2.2.2]octan-1-yl)amino)-N-(2-morpholino-2-oxoethyl)nicotinamide |
| 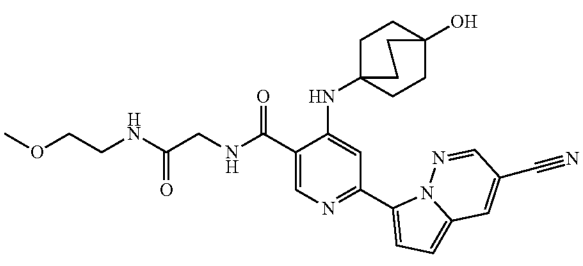 [SMILES: COCCNC(=O)CNC(=O)c1cnc(-c2ccc3cc(C#N)cnn23)cc1NC12CCC(O)(CC1)CC2] | 786 | 518.6 | 49 | 6-(3-cyanopyrrolo[1,2-b]pyridazin-7-yl)-4-((4-hydroxybicyclo[2.2.2]octan-1-yl)amino)-N-(2-((2-methoxyethyl)amino)-2-oxoethyl)nicotinamide |

TABLE 1-continued

| Structure | compound | ES/MS m/z | procedure | Name |
|---|---|---|---|---|
| 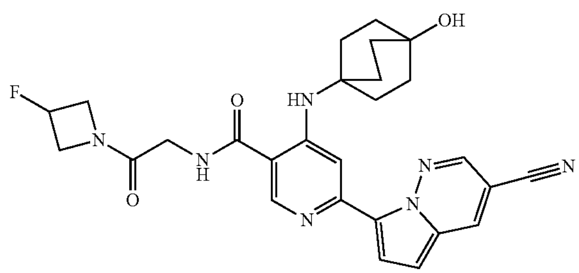 [SMILES: N#Cc1cnn2c(-c3cc(NC45CCC(O)(CC4)CC5)c(C(=O)NCC(=O)N4CC(F)C4)cn3)ccc2c1] | 787 | 518.3 | 49 | 6-(3-cyanopyrrolo[1,2-b]pyridazin-7-yl)-N-(2-(3-fluoroazetidin-1-yl)-2-oxoethyl)-4-((4-hydroxybicyclo[2.2.2]octan-1-yl)amino)nicotinamide |
| 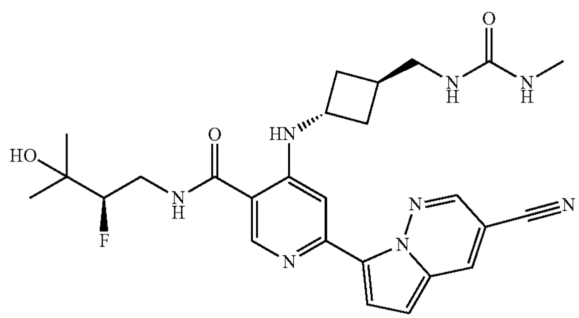 [SMILES: CNC(=O)NC[C@H]1C[C@H](Nc2cc(-c3ccc4cc(C#N)cnn34)ncc2C(=O)NC[C@@H](F)C(C)(C)O)C1] | 788 | 523.4 | 67 | 6-(3-cyanopyrrolo[1,2-b]pyridazin-7-yl)-N-((R)-2-fluoro-3-hydroxy-3-methylbutyl)-4-(((1r,3R)-3-((3-methylureido)methyl)cyclobutyl)amino)nicotinamide |
| 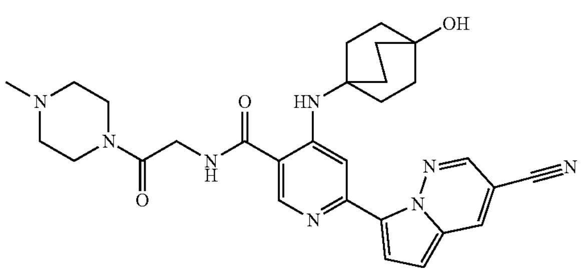 [SMILES: CN1CCN(C(=O)CNC(=O)c2cnc(-c3ccc4cc(C#N)cnn34)cc2NC23CCC(O)(CC2)CC3)CC1] | 789 | 543.3 | 49 | 6-(3-cyanopyrrolo[1,2-b]pyridazin-7-yl)-4-((4-hydroxybicyclo[2.2.2]octan-1-yl)amino)-N-(2-(4-methylpiperazin-1-yl)-2-oxoethyl)nicotinamide |
| 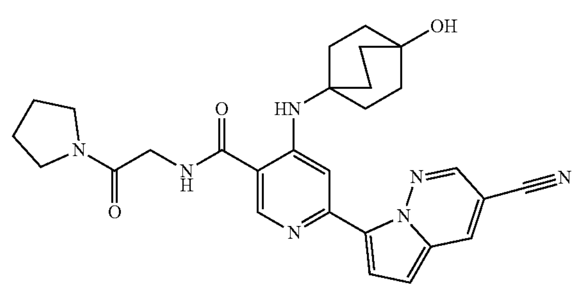 [SMILES: N#Cc1cnn2c(-c3cc(NC45CCC(O)(CC4)CC5)c(C(=O)NCC(=O)N4CCCC4)cn3)ccc2c1] | 790 | 514.4 | 49 | 6-(3-cyanopyrrolo[1,2-b]pyridazin-7-yl)-4-((4-hydroxybicyclo[2.2.2]octan-1-yl)amino)-N-(2-oxo-2-(pyrrolidin-1-yl)ethyl)nicotinamide |
| 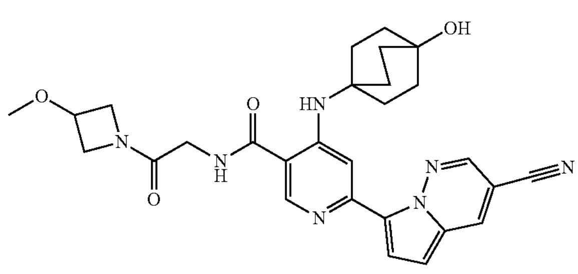 [SMILES: COC1CN(C(=O)CNC(=O)c2cnc(-c3ccc4cc(C#N)cnn34)cc2NC23CCC(O)(CC2)CC3)C1] | 791 | 530.3 | 49 | 6-(3-cyanopyrrolo[1,2-b]pyridazin-7-yl)-4-((4-hydroxybicyclo[2.2.2]octan-1-yl)amino)-N-(2-(3-methoxyazetidin-1-yl)-2-oxoethyl)nicotinamide |

TABLE 1-continued

| Structure | compound | ES/MS m/z | procedure | Name |
|---|---|---|---|---|
| 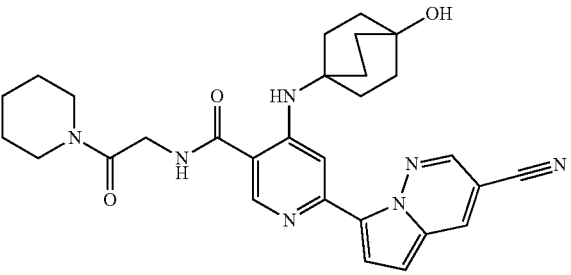 [SMILES: N#Cc1cnn2c(-c3cc(NC45CCC(O)(CC4)CC5)c(C(=O)NCC(=O)N4CCCCC4)cn3)ccc2c1] | 792 | 528.3 | 49 | 6-(3-cyanopyrrolo[1,2-b]pyridazin-7-yl)-4-((4-hydroxybicyclo[2.2.2]octan-1-yl)amino)-N-(2-oxo-2-(piperidin-1-yl)ethyl)nicotinamide |
| 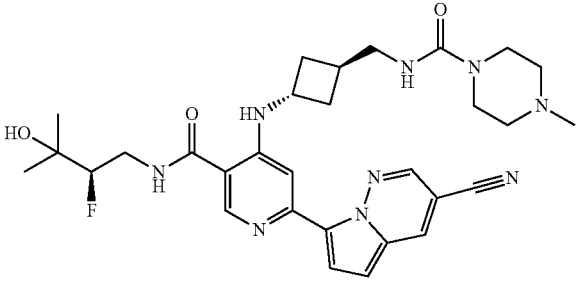 [SMILES: CN1CCN(C(=O)NC[C@H]2C[C@H](Nc3cc(-c4ccc5cc(C#N)cnn45)ncc3C(=O)NC[C@@H](F)C(C)(C)O)C2)CC1] | 793 | 592.4 | 81 | N-(((1R,3r)-3-((2-(3-cyanopyrrolo[1,2-b]pyridazin-7-yl)-5-(((R)-2-fluoro-3-hydroxy-3-methylbutyl)carbamoyl)pyridin-4-yl)amino)cyclobutyl)methyl)-4-methylpiperazine-1-carboxamide |
| 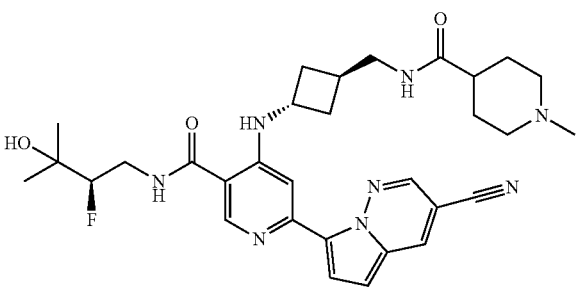 [SMILES: CN1CCC(C(=O)NC[C@H]2C[C@H](Nc3cc(-c4ccc5cc(C#N)cnn45)ncc3C(=O)NC[C@@H](F)C(C)(C)O)C2)CC1] | 794 | 591.4 | 33 | 6-(3-cyanopyrrolo[1,2-b]pyridazin-7-yl)-N-((R)-2-fluoro-3-hydroxy-3-methylbutyl)-4-(((1r,3R)-3-((1-methylpiperidine-4-carboxamido)methyl)cyclobutyl)amino)nicotinamide |
| 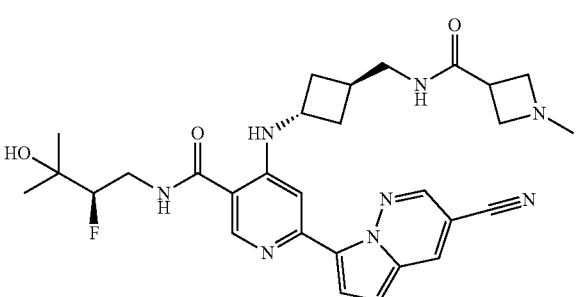 | 795 | 564.4 | 33 | 6-(3-cyanopyrrolo[1,2-b]pyridazin-7-yl)-N-((R)-2-fluoro-3-hydroxy-3-methylbutyl)-4-(((1r,3R)-3-((1-methylazetidine-3-carboxamido)methyl)cyclobutyl)amino)nicotinamide |
| 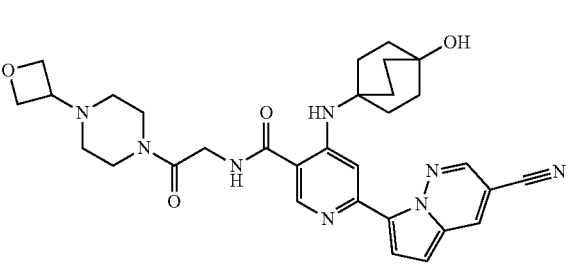 [SMILES: N#Cc1cnn2c(-c3cc(NC45CCC(O)(CC4)CC5)c(C(=O)NCC(=O)N4CCN(C5COC5)CC4)cn3)ccc2c1] | 796 | 585.3 | 49 | 6-(3-cyanopyrrolo[1,2-b]pyridazin-7-yl)-4-((4-hydroxybicyclo[2.2.2]octan-1-yl)amino)-N-(2-(4-(oxetan-3-yl)piperazin-1-yl)-2-oxoethyl)nicotinamide |

TABLE 1-continued

| Structure | compound | ES/MS m/z | procedure | Name |
|---|---|---|---|---|
| 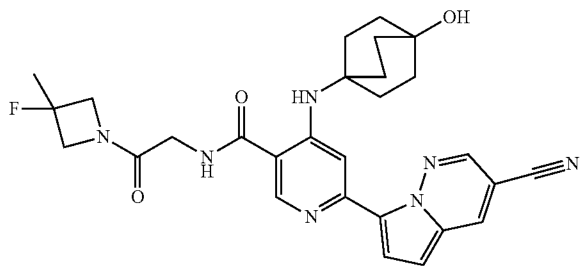 [SMILES: CC1(F)CN(C(=O)CNC(=O)c2cnc(-c3ccc4cc(C#N)cnn34)cc2NC23CCC(O)(CC2)CC3)C1] | 797 | 425.6 | 49 | 6-(3-cyanopyrrolo[1,2-b]pyridazin-7-yl)-N-(2-(3-fluoro-3-methyl-azetidin-1-yl)-2-oxoethyl)-4-((4-hydroxybicyclo[2.2.2]octan-1-yl)amino)nicotinamide |
| 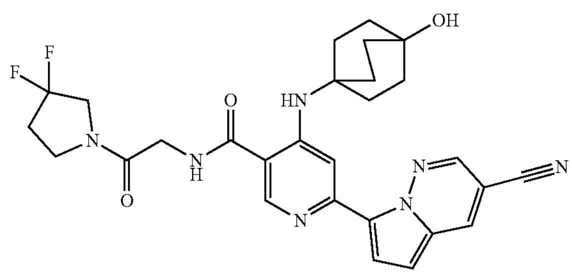 [SMILES: N#Cc1cnn2c(-c3cc(NC45CCC(O)(CC4)CC5)c(C(=O)NCC(=O)N4CCC(F)(F)C4)cn3)ccc2c1] | 798 | 550.4 | 49 | 6-(3-cyanopyrrolo[1,2-b]pyridazin-7-yl)-N-(2-(3,3-difluoropyrrolidin-1-yl)-2-oxoethyl)-4-((4-hydroxybicyclo[2.2.2]octan-1-yl)amino)nicotinamide |
| 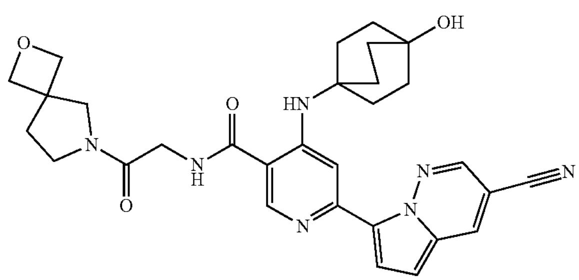 [SMILES: N#Cc1cnn2c(-c3cc(NC45CCC(O)(CC4)CC5)c(C(=O)NCC(=O)N4CCC5(COC5)C4)cn3)ccc2c1] | 799 | 556.3 | 49 | 6-(3-cyanopyrrolo[1,2-b]pyridazin-7-yl)-4-((4-hydroxybicyclo[2.2.2]octan-1-yl)amino)-N-(2-oxo-2-(2-oxa-6-azaspiro[3.4]octan-6-yl)ethyl)nicotinamide |
| 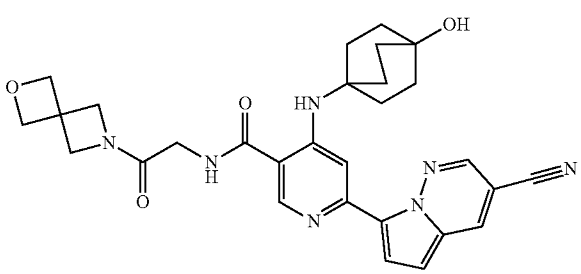 [SMILES: N#Cc1cnn2c(-c3cc(NC45CCC(O)(CC4)CC5)c(C(=O)NCC(=O)N4CC5(COC5)C4)cn3)ccc2c1] | 800 | 541.4 | 49 | 6-(3-cyanopyrrolo[1,2-b]pyridazin-7-yl)-4-((4-hydroxybicyclo[2.2.2]octan-1-yl)amino)-N-(2-oxo-2-(2-oxa-6-azaspiro[3.3]heptan-6-yl)ethyl)nicotinamide |
| 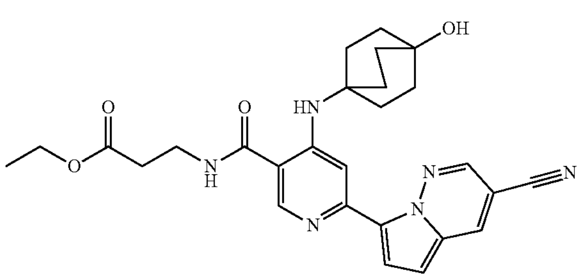 [SMILES: CCOC(=O)CCNC(=O)c1cnc(-c2ccc3cc(C#N)cnn23)cc1NC12CCC(O)(CC1)CC2] | 801 | 503.7 | 49 | ethyl 3-(6-(3-cyano-pyrrolo[1,2-b]pyridazin-7-yl)-4-((4-hydroxybicyclo[2.2.2]octan-1-yl)amino)nicotinamido)propanoate |

TABLE 1-continued

| Structure | compound | ES/MS m/z | procedure | Name |
|---|---|---|---|---|
| 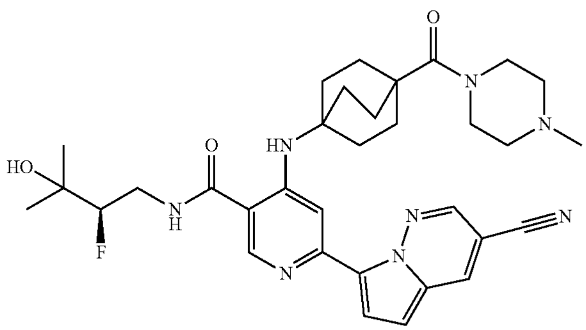 [SMILES: CN1CCN(C(=O)C23CCC(Nc4cc(-c5ccc6cc(C#N)cnn56)ncc4C(=O)NC[C@@H](F)C(C)(C)O)(CC2)CC3)CC1] | 802 | 617.4 | 51 | (R)-6-(3-cyanopyrrolo[1,2-b]pyridazin-7-yl)-N-(2-fluoro-3-hydroxy-3-methylbutyl)-4-((4-(4-methylpiperazine-1-carbonyl)bicyclo[2.2.2]octan-1-yl)amino)nicotinamide |
| 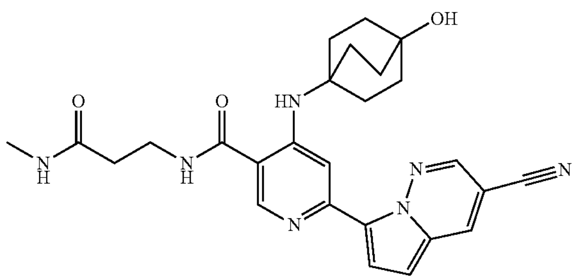 [SMILES: CNC(=O)CCNC(=O)c1cnc(-c2ccc3cc(C#N)cnn23)cc1NC12CCC(O)(CC1)CC2] | 803 | 488.5 | 82 | 6-(3-cyanopyrrolo[1,2-b]pyridazin-7-yl)-4-((4-hydroxybicyclo[2.2.2]octan-1-yl)amino)-N-(3-(methylamino)-3-oxopropyl)nicotinamide |
| 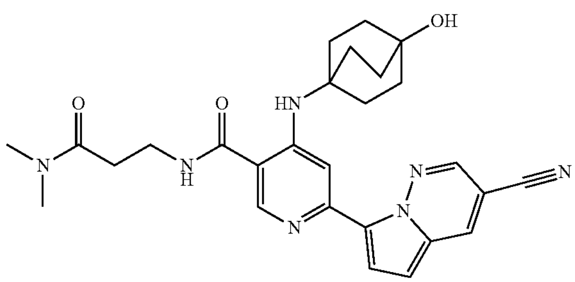 [SMILES: CN(C)C(=O)CCNC(=O)c1cnc(-c2ccc3cc(C#N)cnn23)cc1NC12CCC(O)(CC1)CC2] | 804 | 502.5 | 82 | 6-(3-cyanopyrrolo[1,2-b]pyridazin-7-yl)-N-(3-(dimethylamino)-3-oxopropyl)-4-((4-hydroxybicyclo[2.2.2]octan-1-yl)amino)nicotinamide |
| 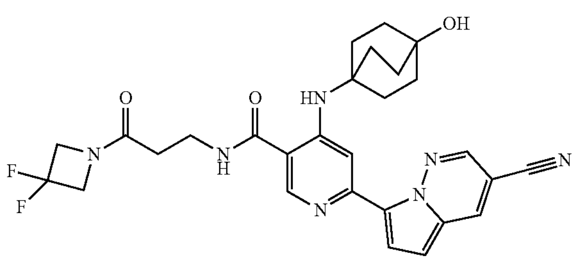 [SMILES: N#Cc1cnn2c(-c3cc(NC45CCC(O)(CC4)CC5)c(C(=O)NCCC(=O)N4CC(F)(F)C4)cn3)ccc2c1] | 805 | 550.7 | 82 | 6-(3-cyanopyrrolo[1,2-b]pyridazin-7-yl)-N-(3-(3,3-difluoroazetidin-1-yl)-3-oxopropyl)-4-((4-hydroxybicyclo[2.2.2]octan-1-yl)amino)nicotinamide |
| 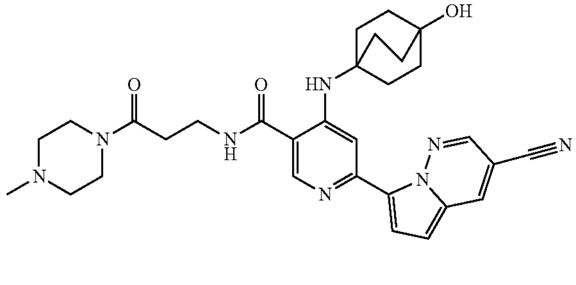 [SMILES: CN1CCN(C(=O)CCNC(=O)c2cnc(-c3ccc4cc(C#N)cnn34)cc2NC23CCC(O)(CC2)CC3)CC1] | 806 | 557.4 | 82 | 6-(3-cyanopyrrolo[1,2-b]pyridazin-7-yl)-4-((4-hydroxybicyclo[2.2.2]octan-1-yl)amino)-N-(3-(4-methylpiperazin-1-yl)-3-oxopropyl)nicotinamide |

TABLE 1-continued

| Structure | compound | ES/MS m/z | procedure | Name |
|---|---|---|---|---|
| 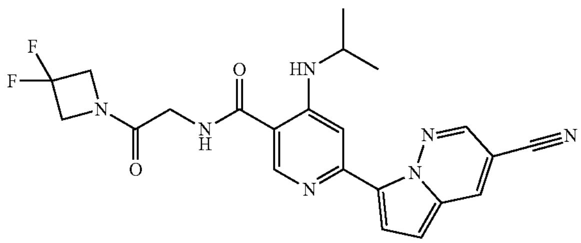 [SMILES: CC(C)Nc1cc(-c2ccc3cc(C#N)cnn23)ncc1C(=O)NCC(=O)N1CC(F)(F)C1] | 807 | 454.5 | 3 | 6-(3-cyanopyrrolo[1,2-b]pyridazin-7-yl)-N-(2-(3,3-difluoroazetidin-1-yl)-2-oxoethyl)-4-(isopropylamino)nicotinamide |
| 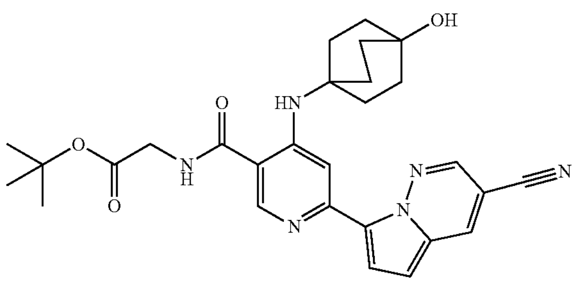 [SMILES: CC(C)(C)OC(=O)CNC(=O)c1cnc(-c2ccc3cc(C#N)cnn23)cc1NC12CCC(O)(CC1)CC2] | 808 | 517.3 | 3 | tert-butyl (6-(3-cyanopyrrolo[1,2-b]pyridazin-7-yl)-4-((4-hydroxybicyclo[2.2.2]octan-1-yl)amino)nicotinoyl)glycinate |
| 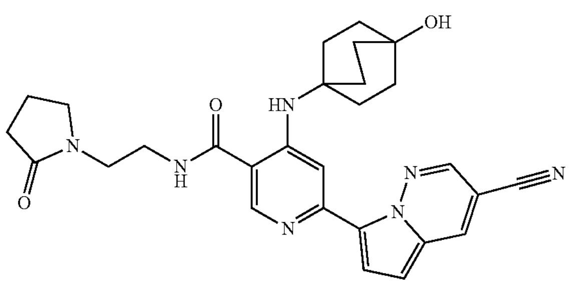 [SMILES: N#Cc1cnn2c(-c3cc(NC45CCC(O)(CC4)CC5)c(C(=O)NCCN4CCCC4=O)cn3)ccc2c1] | 809 | 514.4 | 3 | 6-(3-cyanopyrrolo[1,2-b]pyridazin-7-yl)-4-((4-hydroxybicyclo[2.2.2]octan-1-yl)amino)-N-(2-(2-oxopyrrolidin-1-yl)ethyl)nicotinamide |
| 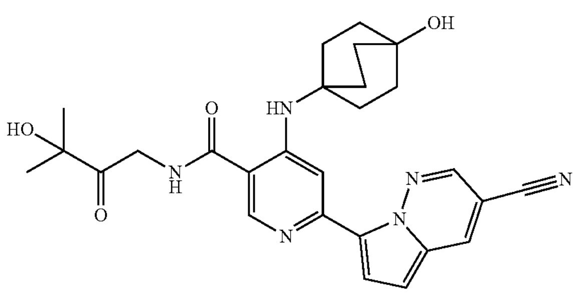 [SMILES: CC(C)(O)C(=O)CNC(=O)c1cnc(-c2ccc3cc(C#N)cnn23)cc1NC12CCC(O)(CC1)CC2] | 810 | 503.3 | 3 | 6-(3-cyanopyrrolo[1,2-b]pyridazin-7-yl)-N-(3-hydroxy-3-methyl-2-oxobutyl)-4-((4-hydroxybicyclo[2.2.2]octan-1-yl)amino)nicotinamide |
| 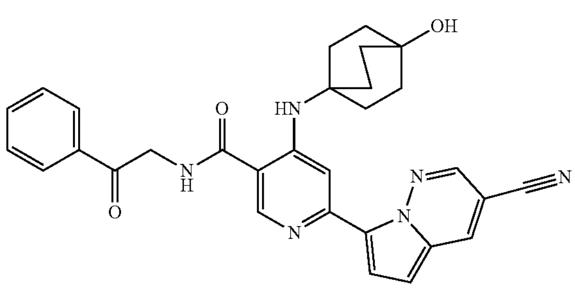 [SMILES: N#Cc1cnn2c(-c3cc(NC45CCC(O)(CC4)CC5)c(C(=O)NCC(=O)c4ccccc4)cn3)ccc2c1] | 811 | 521.4 | 3 | 6-(3-cyanopyrrolo[1,2-b]pyridazin-7-yl)-4-((4-hydroxybicyclo[2.2.2]octan-1-yl)amino)-N-(2-oxo-2-phenylethyl)nicotinamide |

TABLE 1-continued

| Structure | compound | ES/MS m/z | procedure | Name |
|---|---|---|---|---|
| 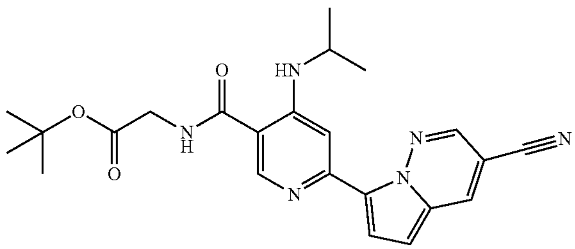 [SMILES: CC(C)Nc1cc(-c2ccc3cc(C#N)cnn23)ncc1C(=O)NCC(=O)OC(C)(C)C] | 812 | 435.4 | 3 | tert-butyl (6-(3-cyanopyrrolo[1,2-b]pyridazin-7-yl)-4-(isopropylamino)nicotinoyl)glycinate |
| 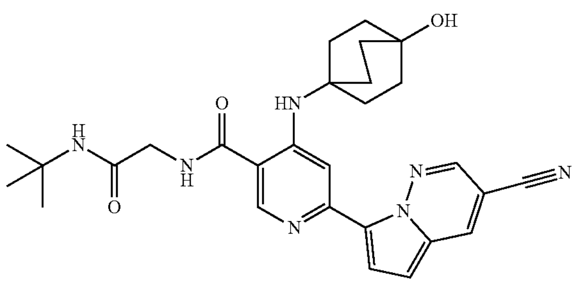 [SMILES: CC(C)(C)NC(=O)CNC(=O)c1cnc(-c2ccc3cc(C#N)cnn23)cc1NC12CCC(O)(CC1)CC2] | 813 | 516.3 | 3 | N-(2-(tert-butylamino)-2-oxoethyl)-6-(3-cyanopyrrolo[1,2-b]pyridazin-7-yl)-4-((4-hydroxybicyclo[2.2.2]octan-1-yl)amino)nicotinamide |
| 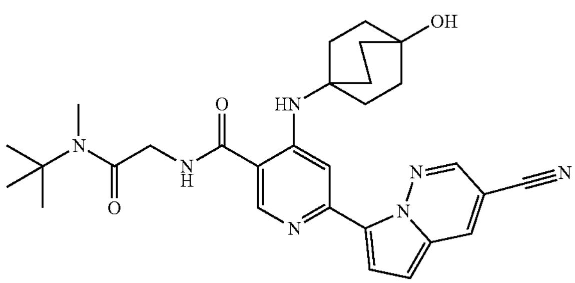 [SMILES: CN(C(=O)CNC(=O)c1cnc(-c2ccc3cc(C#N)cnn23)cc1NC12CCC(O)(CC1)CC2)C(C)(C)C] | 814 | 530.7 | 3 | N-(2-(tert-butyl(methyl)amino)-2-oxoethyl)-6-(3-cyanopyrrolo[1,2-b]pyridazin-7-yl)-4-((4-hydroxybicyclo[2.2.2]octan-1-yl)amino)nicotinamide |
| 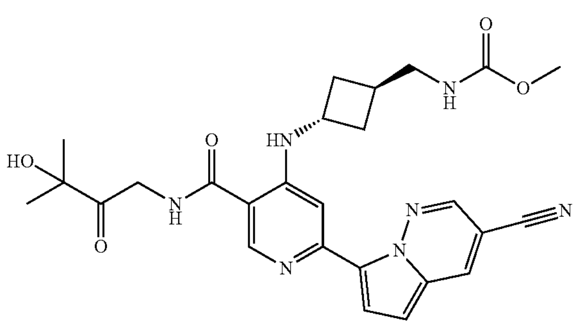 [SMILES: COC(=O)NC[C@H]1C[C@H](Nc2cc(-c3ccc4cc(C#N)cnn34)ncc2C(=O)NCC(=O)C(C)(C)O)C1] | 815 | 520.3 | 3 | methyl (((1r,3r)-3-((2-(3-cyanopyrrolo[1,2-b]pyridazin-7-yl)-5-((3-hydroxy-3-methyl-2-oxobutyl)carbamoyl)pyridin-4-yl)amino)cyclobutyl)methyl)carbamate |
| 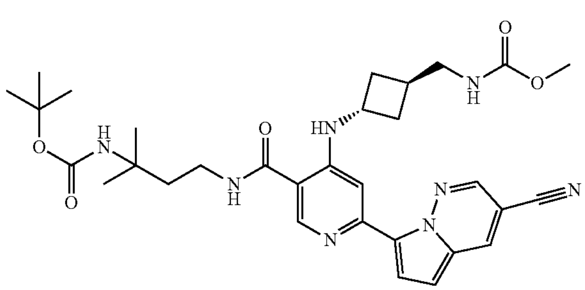 [SMILES: COC(=O)NC[C@H]1C[C@H](Nc2cc(-c3ccc4cc(C#N)cnn34)ncc2C(=O)NCCC(C)(C)NC(=O)OC(C)(C)C)C1] | 816 | 605.4 | 3 | methyl (((1r,3r)-3-((5-((3-((tert-butoxycarbonyl)amino)-3-methylbutyl)carbamoyl)-2-(3-cyanopyrrolo[1,2-b]pyridazin-7-yl)pyridin-4-yl)amino)cyclobutyl)methyl)carbamate |

TABLE 1-continued

| Structure | compound | ES/MS m/z | procedure | Name |
|---|---|---|---|---|
| 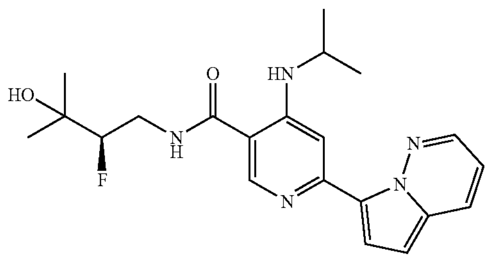 [SMILES: CC(C)Nc1cc(-c2ccc3cccnn23)ncc1C(=O)NC[C@@H](F)C(C)(C)O] | 817 | 400.6 | 2 | (R)-N-(2-fluoro-3-hydroxy-3-methylbutyl)-4-(isopropylamino)-6-(pyrrolo[1,2-b]pyridazin-7-yl)nicotinamide |
| 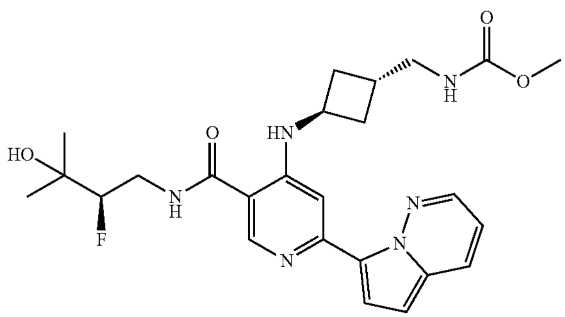 [SMILES: COC(=O)NC[C@H]1C[C@H](Nc2cc(-c3ccc4cccnn34)ncc2C(=O)NC[C@@H](F)C(C)(C)O)C1] | 818 | 499.4 | 2 | methyl (((1R,3r)-3-((5-(((R)-2-fluoro-3-hydroxy-3-methylbutyl)carbamoyl)-2-(pyrrolo[1,2-b]pyridazin-7-yl)pyridin-4-yl)amino)cyclobutyl)methyl)carbamate |
| 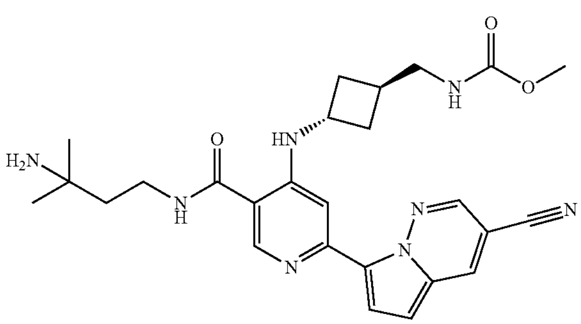 [SMILES: COC(=O)NC[C@H]1C[C@H](Nc2cc(-c3ccc4cc(C#N)cnn34)ncc2C(=O)NCCC(C)(C)N)C1] | 819 | 505.4 | 45 | methyl (((1r,3r)-3-((5-((3-amino-3-methylbutyl)carbamoyl)-2-(3-cyanopyrrolo[1,2-b]pyridazin-7-yl)pyridin-4-yl)amino)cyclobutyl)methyl)carbamate |
| 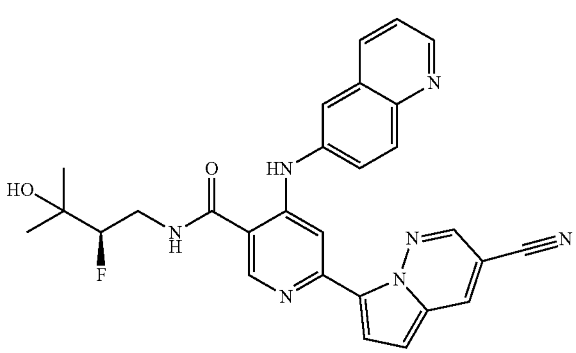 [SMILES: CC(C)(O)[C@H](F)CNC(=O)c1cnc(-c2ccc3cc(C#N)cnn23)cc1Nc1ccc2ncccc2c1] | 820 | 510.3 | 2 | (R)-6-(3-cyanopyrrolo[1,2-b]pyridazin-7-yl)-N-(2-fluoro-3-hydroxy-3-methylbutyl)-4-(quinolin-6-ylamino)nicotinamide |

TABLE 1-continued

| Structure | compound | ES/MS m/z | procedure | Name |
|---|---|---|---|---|
| 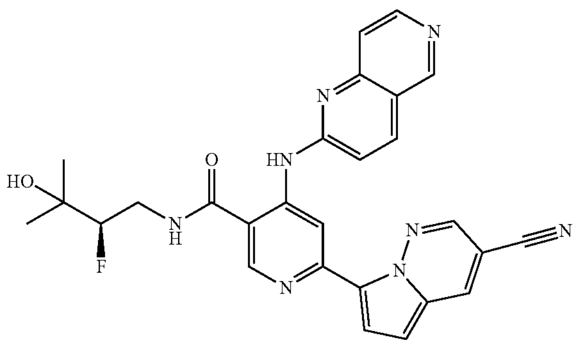 [SMILES: CC(C)(O)[C@H](F)CNC(=O)c1cnc(-c2ccc3cc(C#N)cnn23)cc1Nc1ccc2cnccc2n1] | 821 | 511.2 | 2 | (R)-4-((1,6-naphthyridin-2-yl)amino)-6-(3-cyanopyrrolo[1,2-b]pyridazin-7-yl)-N-(2-fluoro-3-hydroxy-3-methylbutyl)nicotinamide |
| 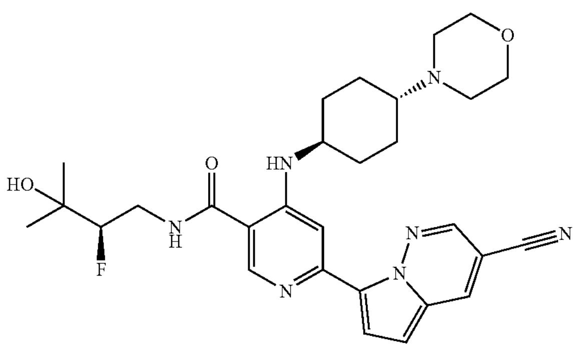 [SMILES: CC(C)(O)[C@H](F)CNC(=O)c1cnc(-c2ccc3cc(C#N)cnn23)cc1N[C@H]1CC[C@H](N2CCOCC2)CC1] | 822 | 550.5 | 2 | 6-(3-cyanopyrrolo[1,2-b]pyridazin-7-yl)-N-((R)-2-fluoro-3-hydroxy-3-methylbutyl)-4-(((1r,4R)-4-morpholinocyclohexyl)amino)nicotinamide |
| 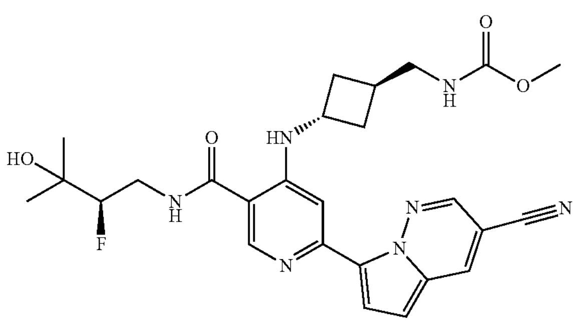 [SMILES: COC(=O)NC[C@H]1C[C@H](Nc2cc(-c3ccc4cc(C#N)cnn34)ncc2C(=O)NC[C@@H](F)C(C)(C)O)C1] | 823 | 538.4 | 29 | 6-(3-cyanopyrrolo[1,2-b]pyridazin-7-yl)-N-((R)-2-fluoro-3-hydroxy-3-methylbutyl)-4-(((1r,3R)-3-((2-methoxyacetamido)methyl)cyclobutyl)amino)nicotinamide |
| 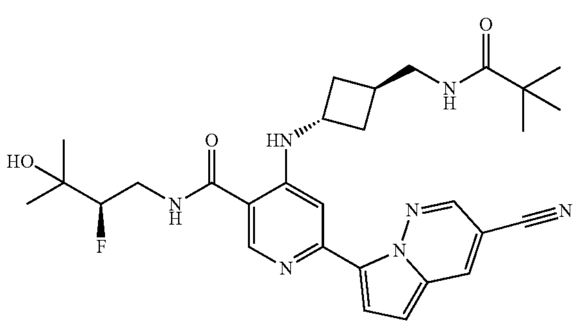 [SMILES: CC(C)(C)C(=O)NC[C@H]1C[C@H](Nc2cc(-c3ccc4cc(C#N)cnn34)ncc2C(=O)NC[C@@H](F)C(C)(C)O)C1] | 824 | 550.8 | 29 | 6-(3-cyanopyrrolo[1,2-b]pyridazin-7-yl)-N-((R)-2-fluoro-3-hydroxy-3-methylbutyl)-4-(((1r,3R)-3-(pivalamidomethyl)cyclobutyl)amino)nicotinamide |

TABLE 1-continued

| Structure | compound | ES/MS m/z | procedure | Name |
|---|---|---|---|---|
| 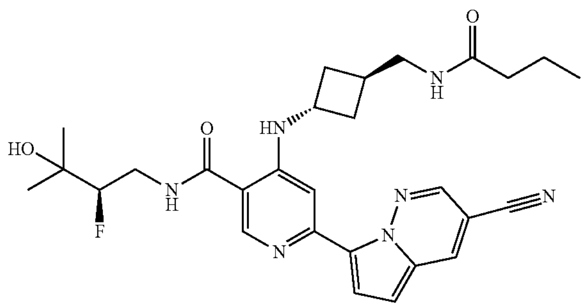 | 825 | 536.8 | 29 | 4-(((1r,3R)-3-(butyramidomethyl)cyclobutyl)amino)-6-(3-cyanopyrrolo[1,2-b]pyridazin-7-yl)-N-((R)-2-fluoro-3-hydroxy-3-methylbutyl)nicotinamide |
| 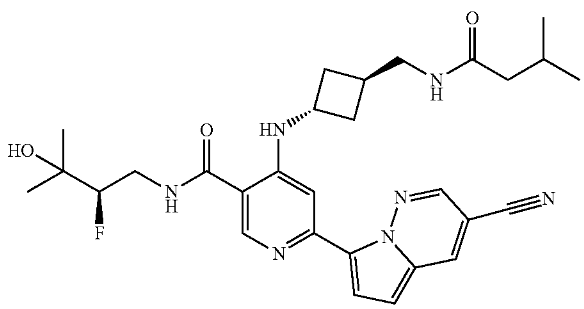 [SMILES: CC(C)CC(=O)NC[C@H]1C[C@H](Nc2cc(-c3ccc4cc(C#N)cnn34)ncc2C(=O)NC[C@@H](F)C(C)(C)O)C1] | 826 | 550.8 | 29 | 6-(3-cyanopyrrolo[1,2-b]pyridazin-7-yl)-N-((R)-2-fluoro-3-hydroxy-3-methylbutyl)-4-(((1r,3R)-3-((3-methylbutanamido)methyl)cyclobutyl)amino)nicotinamide |
| 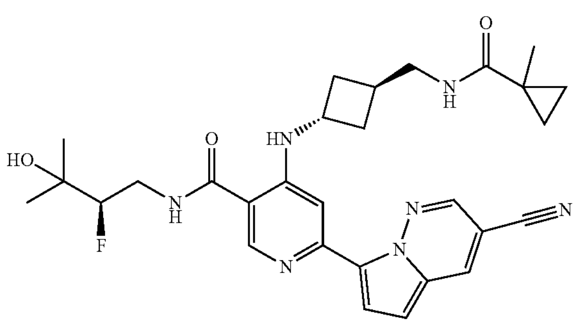 [SMILES: CC1(C(=O)NC[C@H]2C[C@H](Nc3cc(-c4ccc5cc(C#N)cnn45)ncc3C(=O)NC[C@@H](F)C(C)(C)O)C2)CC1] | 827 | 548.8 | 29 | 6-(3-cyanopyrrolo[1,2-b]pyridazin-7-yl)-N-((R)-2-fluoro-3-hydroxy-3-methylbutyl)-4-(((1r,3R)-3-((1-methylcyclopropane-1-carboxamido)methyl)cyclobutyl)amino)nicotinamide |
| 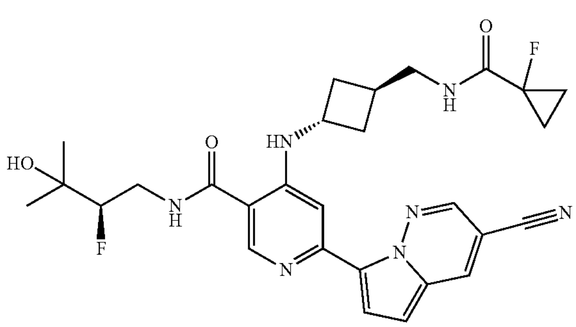 [SMILES: CC(C)(O)[C@H](F)CNC(=O)c1cnc(-c2ccc3cc(C#N)cnn23)cc1N[C@H]1C[C@H](CNC(=O)C2(F)CC2)C1] | 828 | 552.8 | 29 | 6-(3-cyanopyrrolo[1,2-b]pyridazin-7-yl)-N-((R)-2-fluoro-3-hydroxy-3-methylbutyl)-4-(((1r,3R)-3-((1-fluorocyclopropane-1-carboxamido)methyl)cyclobutyl)amino)nicotinamide |

TABLE 1-continued

| Structure | compound | ES/MS m/z | procedure | Name |
|---|---|---|---|---|
| 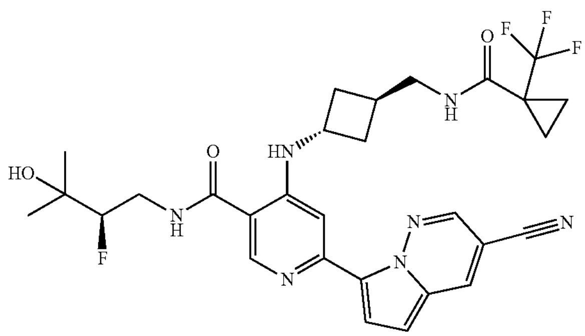 [SMILES: CC(C)(O)[C@H](F)CNC(=O)c1cnc(-c2ccc3cc(C#N)cnn23)cc1N[C@H]1C[C@H](CNC(=O)C2(C(F)(F)F)CC2)C1] | 829 | 602.8 | 29 | 6-(3-cyanopyrrolo[1,2-b]pyridazin-7-yl)-N-((R)-2-fluoro-3-hydroxy-3-methylbutyl)-4-(((1r,3R)-3-((1-(trifluoromethyl)cyclopropane-1-carboxamido)methyl)cyclobutyl)amino)nicotinamide |
| 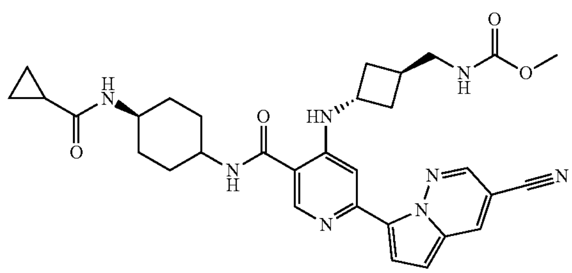 | 830 | 585.8 | 79 | methyl (((1R,3r)-3-((2-(3-cyanopyrrolo[1,2-b]pyridazin-7-yl)-5-(((1r,4R)-4-(cyclopropanecarboxamido)cyclohexyl)carbamoyl)pyridin-4-yl)amino)cyclobutyl)methyl)carbamate |
| 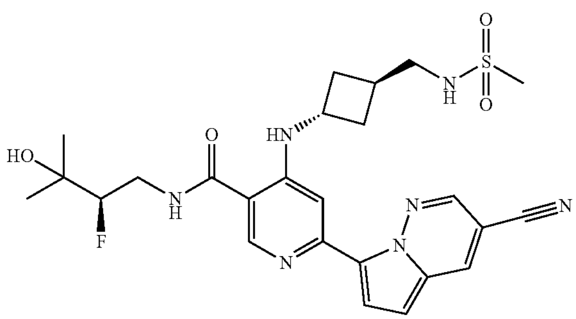 [SMILES: CC(C)(O)[C@H](F)CNC(=O)c1cnc(-c2ccc3cc(C#N)cnn23)cc1N[C@H]1C[C@H](CNS(C)(=O)=O)C1] | 831 | 544.3 | 29 | 6-(3-cyanopyrrolo[1,2-b]pyridazin-7-yl)-N-((R)-2-fluoro-3-hydroxy-3-methylbutyl)-4-(((1r,3R)-3-(methylsulfonamidomethyl)cyclobutyl)amino)nicotinamide |
| 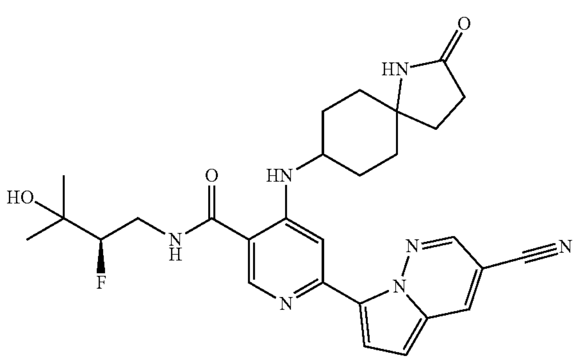 [SMILES: CC(C)(O)[C@H](F)CNC(=O)c1cnc(-c2ccc3cc(C#N)cnn23)cc1NC1CCC2(CCC(=O)N2)CC1] | 832 | 534.4 | 47 | 6-(3-cyanopyrrolo[1,2-b]pyridazin-7-yl)-N-((R)-2-fluoro-3-hydroxy-3-methylbutyl)-4-(((5R,8r)-2-oxo-1-azaspiro[4.5]decan-8-yl)amino)nicotinamide |

TABLE 1-continued

| Structure | compound | ES/ MS m/z | procedure | Name |
|---|---|---|---|---|
| 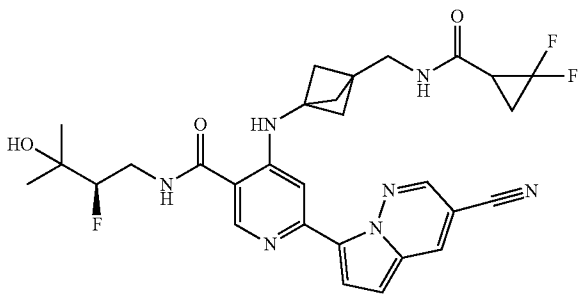 [SMILES: CC(C)(O)[C@H](F)CNC(=O)c1cnc(-c2ccc3cc(C#N)cnn23)cc1NC12CC(CNC(=O)C3CC3(F)F)(C1)C2] | 833 | 582.3 | 33 | 6-(3-cyanopyrrolo[1,2-b]pyridazin-7-yl)-4-((3-(((R)-2,2-difluorocyclopropane-1-carboxamido)methyl)bicyclo[1.1.1]pentan-1-yl)amino)-N-((R)-2-fluoro-3-hydroxy-3-methylbutyl)nicotinamide |
| 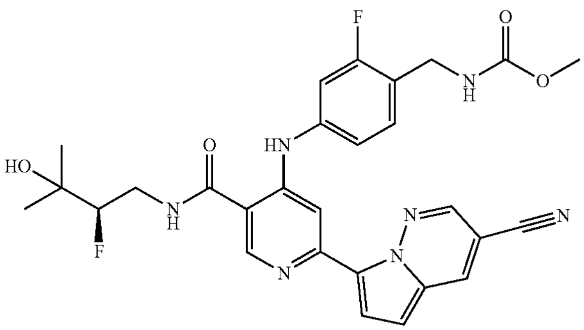 [SMILES: COC(=O)NCc1ccc(Nc2cc(-c3ccc4cc(C#N)cnn34)ncc2C(=O)NC[C@@H](F)C(C)(C)O)cc1F] | 834 | 564.3 | 29 | (R)-methyl (4-((2-(3-cyanopyrrolo[1,2-b]pyridazin-7-yl)-5-((2-fluoro-3-hydroxy-3-methylbutyl)carbamoyl)pyridin-4-yl)amino)-2-fluorobenzyl)carbamate |
| 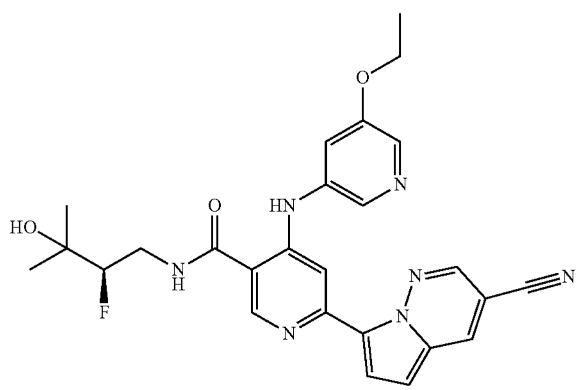 [SMILES: CCOc1cncc(Nc2cc(-c3ccc4cc(C#N)cnn34)ncc2C(=O)NC[C@@H](F)C(C)(C)O)c1] | 835 | 504.4 | 47 | (R)-6-(3-cyanopyrrolo[1,2-b]pyridazin-7-yl)-4-((5-ethoxypyridin-3-yl)amino)-N-(2-fluoro-3-hydroxy-3-methylbutyl)nicotinamide |
| 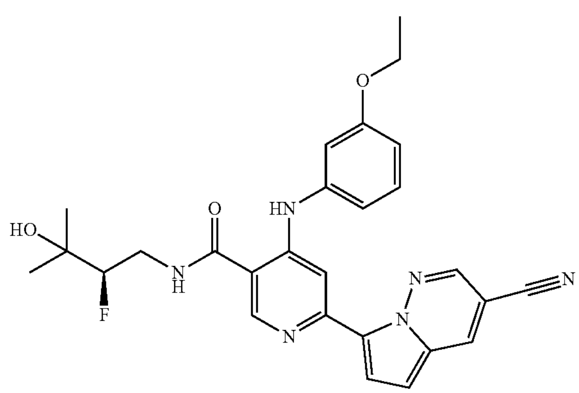 | 836 | 503.5 | 47 | (R)-6-(3-cyanopyrrolo[1,2-b]pyridazin-7-yl)-4-((3-ethoxyphenyl)amino)-N-(2-fluoro-3-hydroxy-3-methylbutyl)nicotinamide |

TABLE 1-continued

| Structure | compound | ES/MS m/z | procedure | Name |
|---|---|---|---|---|
| 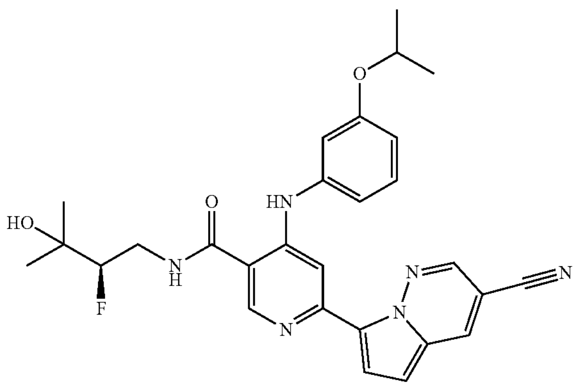 | 837 | 517.4 | 47 | (R)-6-(3-cyanopyrrolo[1,2-b]pyridazin-7-yl)-N-(2-fluoro-3-hydroxy-3-methylbutyl)-4-((3-isopropoxyphenyl)amino)nicotinamide |
| 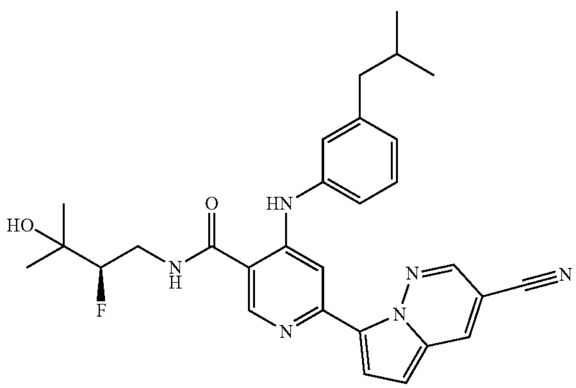 | 838 | 515.4 | 47 | (R)-6-(3-cyanopyrrolo[1,2-b]pyridazin-7-yl)-N-(2-fluoro-3-hydroxy-3-methylbutyl)-4-((3-isobutylphenyl)amino)nicotinamide |
| 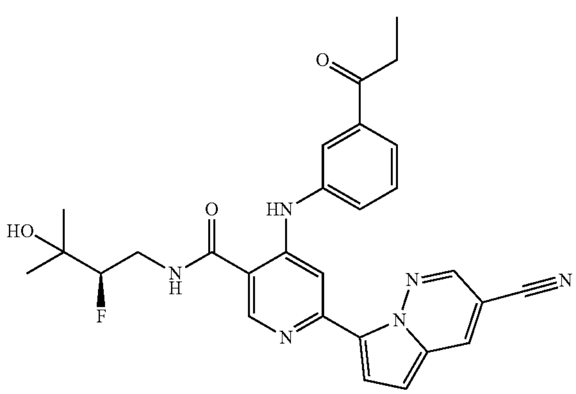 [SMILES: CCC(=O)c1cccc(Nc2cc(-c3ccc4cc(C#N)cnn34)ncc2C(=O)NC[C@@H](F)C(C)(C)O)c1] | 839 | 515.3 | 47 | (R)-6-(3-cyanopyrrolo[1,2-b]pyridazin-7-yl)-N-(2-fluoro-3-hydroxy-3-methylbutyl)-4-((3-propionylphenyl)amino)nicotinamide |
| 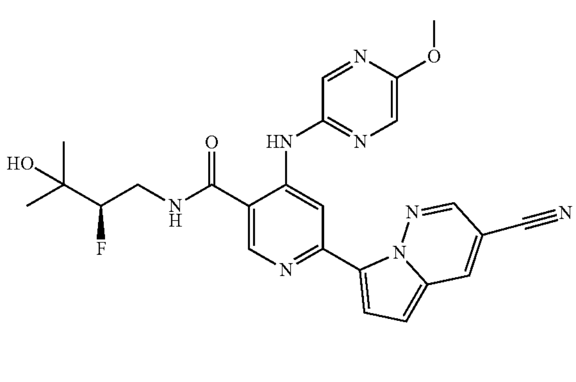 [SMILES: COc1cnc(Nc2cc(-c3ccc4cc(C#N)cnn34)ncc2C(=O)NC[C@@H](F)C(C)(C)O)cn1] | 840 | 491.2 | 47 | (R)-6-(3-cyanopyrrolo[1,2-b]pyridazin-7-yl)-N-(2-fluoro-3-hydroxy-3-methylbutyl)-4-((5-methoxypyrazin-2-yl)amino)nicotinamide |

TABLE 1-continued

| Structure | compound | ES/ MS m/z | procedure | Name |
|---|---|---|---|---|
| 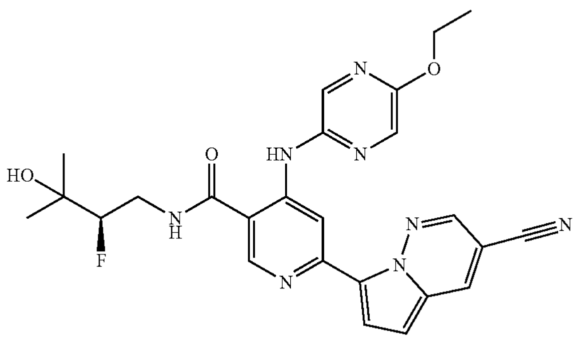 [SMILES: CCOc1cnc(Nc2cc(-c3ccc4cc(C#N)cnn34)ncc2C(=O)NC[C@@H](F)C(C)(C)O)cn1] | 841 | 505.3 | 47 | (R)-6-(3-cyanopyrrolo[1,2-b]pyridazin-7-yl)-4-((5-ethoxypyrazin-2-yl)amino)-N-(2-fluoro-3-hydroxy-3-methylbutyl)nicotinamide |
| 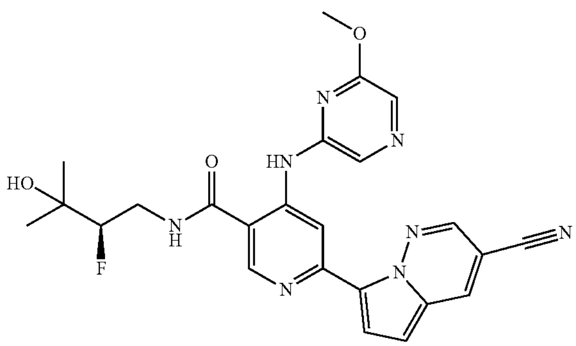 [SMILES: COc1cncc(Nc2cc(-c3ccc4cc(C#N)cnn34)ncc2C(=O)NC[C@@H](F)C(C)(C)O)n1] | 842 | 491.2 | 47 | (R)-6-(3-cyanopyrrolo[1,2-b]pyridazin-7-yl)-N-(2-fluoro-3-hydroxy-3-methylbutyl)-4-((6-methoxypyrazin-2-yl)amino)nicotinamide |
| 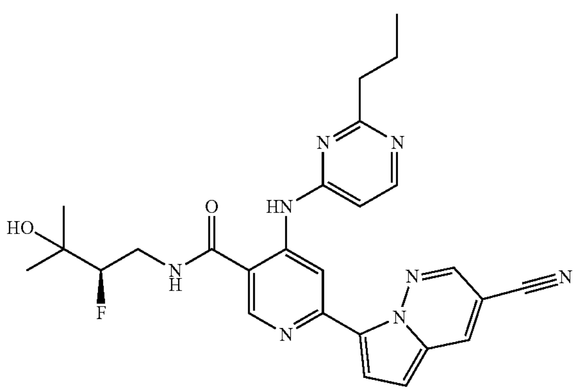 | 843 | 503.3 | 47 | (R)-6-(3-cyanopyrrolo[1,2-b]pyridazin-7-yl)-N-(2-fluoro-3-hydroxy-3-methylbutyl)-4-((2-propyl-pyrimidin-4-yl)amino)nicotinamide |
| 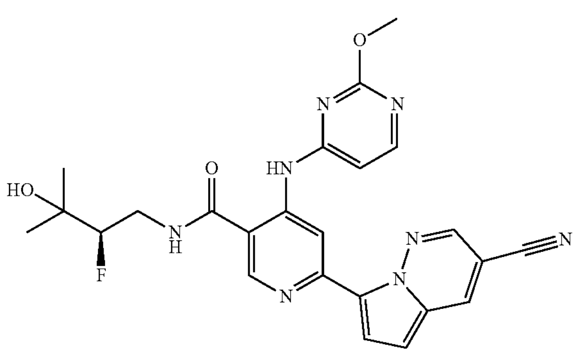 [SMILES: COc1nccc(Nc2cc(-c3ccc4cc(C#N)cnn34)ncc2C(=O)NC[C@@H](F)C(C)(C)O)n1] | 844 | 491.3 | 47 | (R)-6-(3-cyanopyrrolo[1,2-b]pyridazin-7-yl)-N-(2-fluoro-3-hydroxy-3-methylbutyl)-4-((2-methoxypyrimidin-4-yl)amino)nicotinamide |

TABLE 1-continued

| Structure | compound | ES/MS m/z | procedure | Name |
|---|---|---|---|---|
| 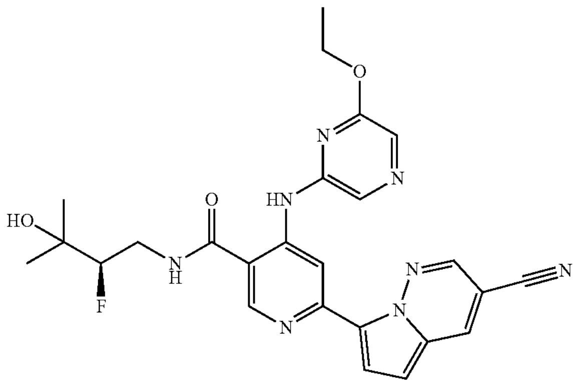 | 845 | 505.4 | 47 | (R)-6-(3-cyanopyrrolo[1,2-b]pyridazin-7-yl)-4-((6-ethoxypyrazin-2-yl)amino)-N-(2-fluoro-3-hydroxy-3-methylbutyl)nicotinamide |
| 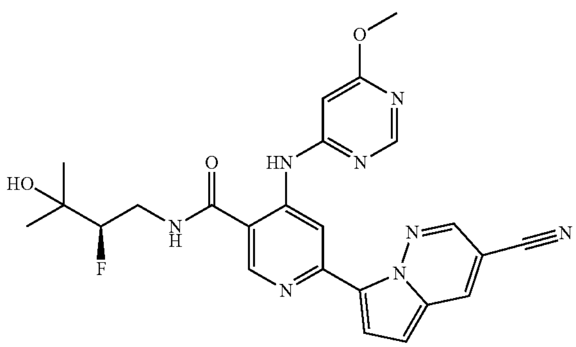 [SMILES: COc1cc(Nc2cc(-c3ccc4cc(C#N)cnn34)ncc2C(=O)NC[C@@H](F)C(C)(C)O)ncn1] | 846 | 491.2 | 47 | (R)-6-(3-cyanopyrrolo[1,2-b]pyridazin-7-yl)-N-(2-fluoro-3-hydroxy-3-methylbutyl)-4-((6-methoxy-pyrimidin-4-yl)amino)nicotinamide |
| 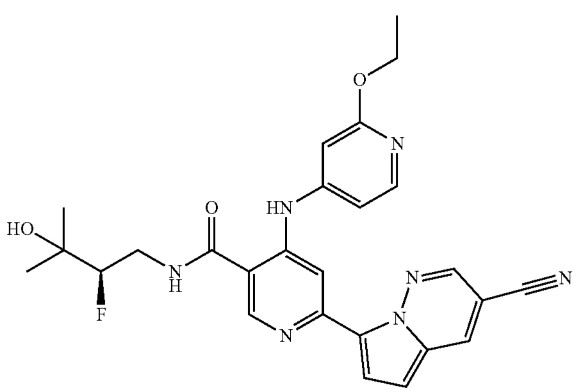 | 847 | 504.3 | 47 | (R)-6-(3-cyanopyrrolo[1,2-b]pyridazin-7-yl)-4-((2-ethoxypyridin-4-yl)amino)-N-(2-fluoro-3-hydroxy-3-methylbutyl)nicotinamide |
| 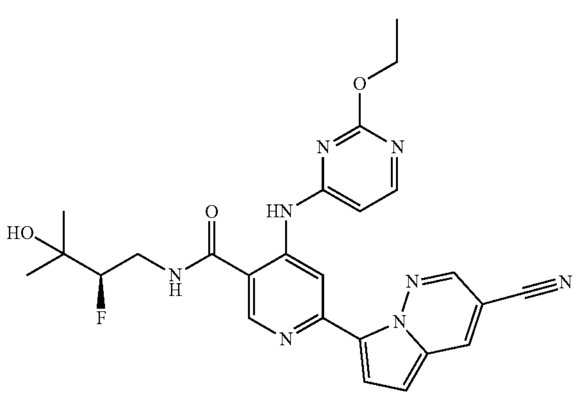 [SMILES: CCOc1nccc(Nc2cc(-c3ccc4cc(C#N)cnn34)ncc2C(=O)NC[C@@H](F)C(C)(C)O)n1] | 848 | 505.4 | 47 | (R)-6-(3-cyanopyrrolo[1,2-b]pyridazin-7-yl)-4-((2-ethoxypyrimidin-4-yl)amino)-N-(2-fluoro-3-hydroxy-3-methylbutyl)nicotinamide |

TABLE 1-continued

| Structure | compound | ES/MS m/z | procedure | Name |
|---|---|---|---|---|
| 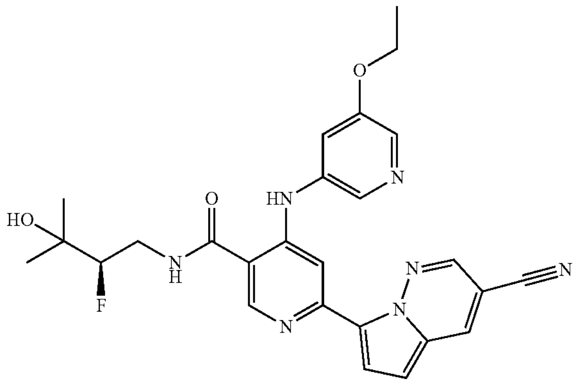 [SMILES: CCOc1cncc(Nc2cc(-c3ccc4cc(C#N)cnn34)ncc2C(=O)NC[C@@H](F)C(C)(C)O)c1] | 849 | 518.3 | 47 | (R)-6-(3-cyanopyrrolo[1,2-b]pyridazin-7-yl)-N-(2-fluoro-3-hydroxy-3-methylbutyl)-4-((5-propoxy-pyridin-3-yl)amino)nicotinamide |
| 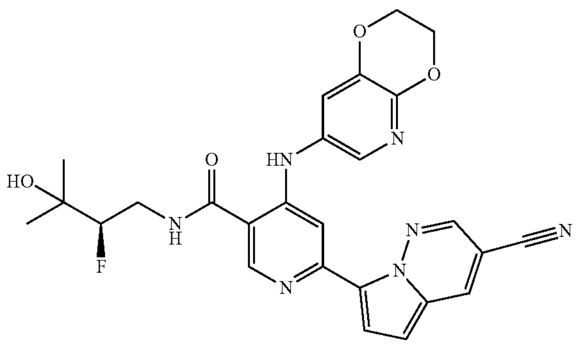 [SMILES: CC(C)(O)[C@H](F)CNC(=O)c1cnc(-c2ccc3cc(C#N)cnn23)cc1Nc1cnc2c(c1)OCCO2] | 850 | 518.3 | 47 | (R)-6-(3-cyanopyrrolo[1,2-b]pyridazin-7-yl)-4-((2,3-dihydro-[1,4]dioxino[2,3-b]pyridin-7-yl)amino)-N-(2-fluoro-3-hydroxy-3-methylbutyl)nicotinamide |
| 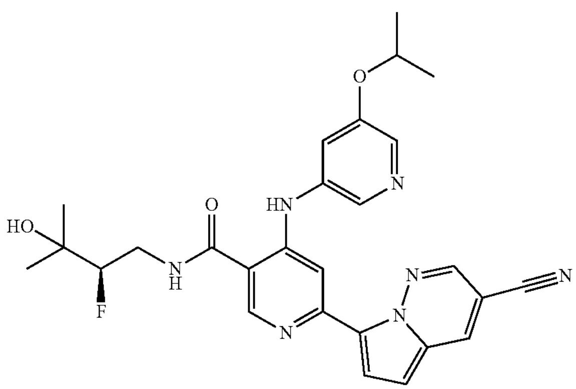 [SMILES: CC(C)Oc1cncc(Nc2cc(-c3ccc4cc(C#N)cnn34)ncc2C(=O)NC[C@@H](F)C(C)(C)O)c1] | 851 | 518.3 | 47 | (R)-6-(3-cyanopyrrolo[1,2-b]pyridazin-7-yl)-N-(2-fluoro-3-hydroxy-3-methylbutyl)-4-((5-isopropoxypyridin-3-yl)amino)nicotinamide |
| 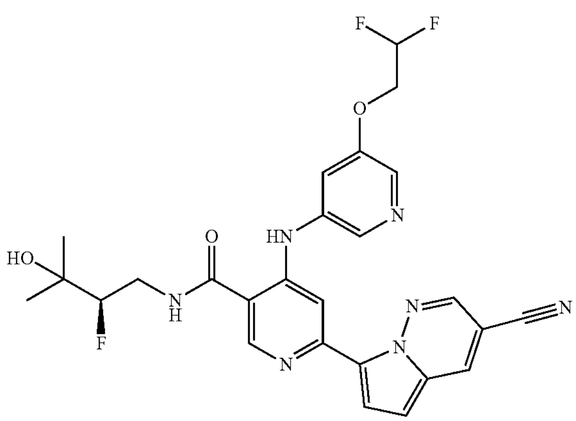 [SMILES: CC(C)(O)[C@H](F)CNC(=O)c1cnc(-c2ccc3cc(C#N)cnn23)cc1Nc1cncc(OCC(F)F)c1] | 852 | 540.3 | 47 | (R)-6-(3-cyanopyrrolo[1,2-b]pyridazin-7-yl)-4-((5-(2,2-difluoroethoxy)pyridin-3-yl)amino)-N-(2-fluoro-3-hydroxy-3-methylbutyl)nicotinamide |

TABLE 1-continued

| Structure | compound | ES/MS m/z | procedure | Name |
|---|---|---|---|---|
| 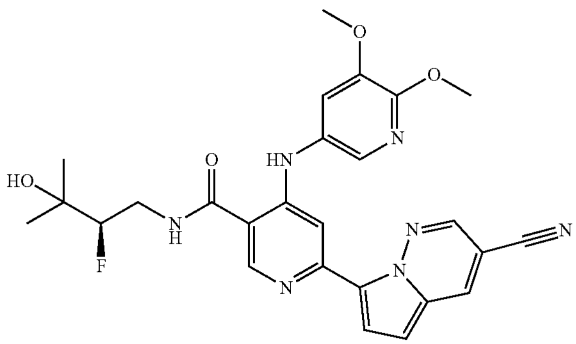 [SMILES: COc1cc(Nc2cc(-c3ccc4cc(C#N)cnn34)ncc2C(=O)NC[C@@H](F)C(C)(C)O)cnc1OC] | 853 | 520.3 | 47 | (R)-6-(3-cyanopyrrolo[1,2-b]pyridazin-7-yl)-4-((5,6-dimethoxypyridin-3-yl)amino)-N-(2-fluoro-3-hydroxy-3-methylbutyl)nicotinamide |
| 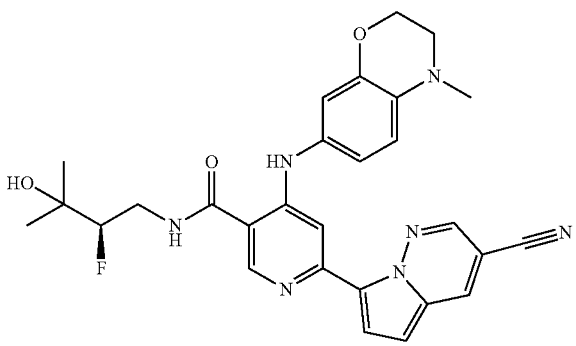 [SMILES: CN1CCOc2cc(Nc3cc(-c4ccc5cc(C#N)cnn45)ncc3C(=O)NC[C@@H](F)C(C)(C)O)ccc21] | 854 | 530.3 | 47 | (R)-6-(3-cyanopyrrolo[1,2-b]pyridazin-7-yl)-N-(2-fluoro-3-hydroxy-3-methylbutyl)-4-((4-methyl-3,4-dihydro-2H-benzo[b][1,4]oxazin-7-yl)amino)nicotinamide |
| 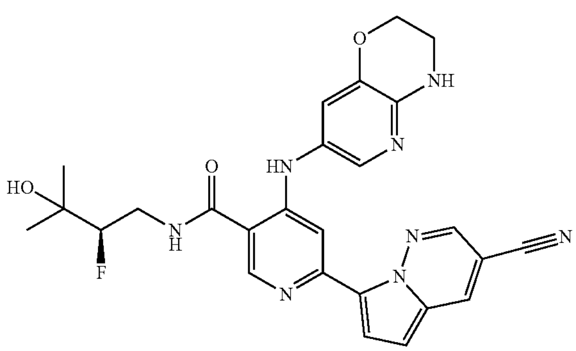 [SMILES: CC(C)(O)[C@H](F)CNC(=O)c1cnc(-c2ccc3cc(C#N)cnn23)cc1Nc1cnc2c(c1)OCCN2] | 855 | 517.3 | 47 | (R)-6-(3-cyanopyrrolo[1,2-b]pyridazin-7-yl)-4-((3,4-dihydro-2H-pyrido[3,2-b][1,4]oxazin-7-yl)amino)-N-(2-fluoro-3-hydroxy-3-methylbutyl)nicotinamide |
| 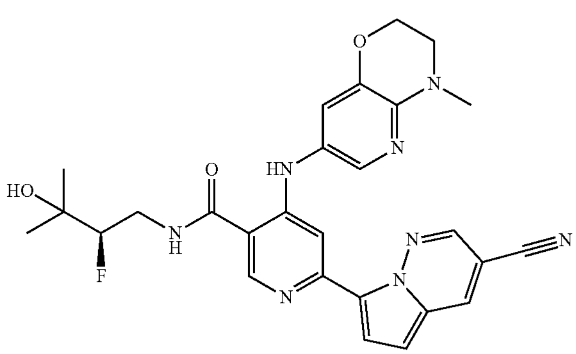 [SMILES: CN1CCOc2cc(Nc3cc(-c4ccc5cc(C#N)cnn45)ncc3C(=O)NC[C@@H](F)C(C)(C)O)cnc21] | 856 | 531.3 | 47 | (R)-6-(3-cyanopyrrolo[1,2-b]pyridazin-7-yl)-N-(2-fluoro-3-hydroxy-3-methylbutyl)-4-((4-methyl-3,4-dihydro-2H-pyrido[3,2-b][1,4]oxazin-7-yl)amino)nicotinamide |

| Structure | compound | ES/MS m/z | procedure | Name |
|---|---|---|---|---|
| 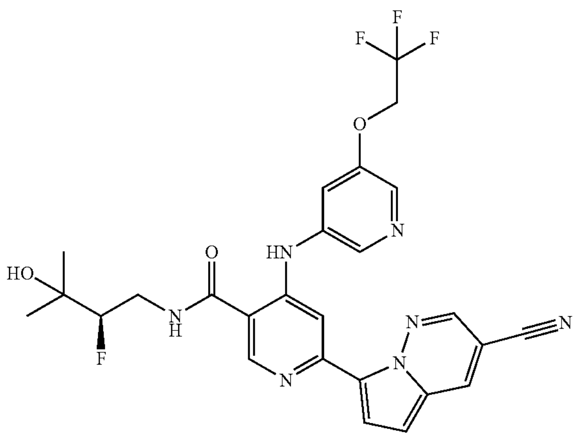 [SMILES: CC(C)(O)[C@H](F)CNC(=O)c1cnc(-c2ccc3cc(C#N)cnn23)cc1Nc1cncc(OCC(F)(F)F)c1] | 857 | 558.4 | 47 | (R)-6-(3-cyanopyrrolo[1,2-b]pyridazin-7-yl)-N-(2-fluoro-3-hydroxy-3-methylbutyl)-4-((5-(2,2,2-trifluoroethoxy)pyridin-3-yl)amino)nicotinamide |
| 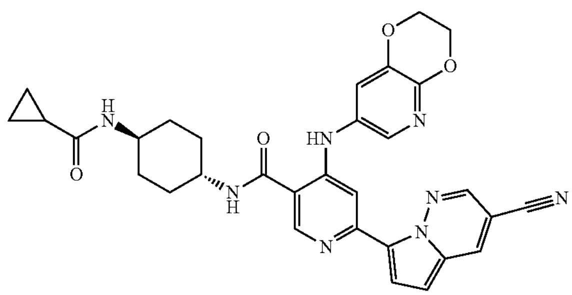 [SMILES: N#Cc1cnn2c(-c3cc(Nc4cnc5c(c4)OCCO5)c(C(=O)N[C@H]4CC[C@H](NC(=O)C5CC5)CC4)cn3)ccc2c1] | 858 | 579.3 | 79 | 6-(3-cyanopyrrolo[1,2-b]pyridazin-7-yl)-N-((1r,4r)-4-(cyclopropanecarboxamido)cyclohexyl)-4-((2,3-dihydro-[1,4]dioxino[2,3-b]pyridin-7-yl)amino)nicotinamide |
| 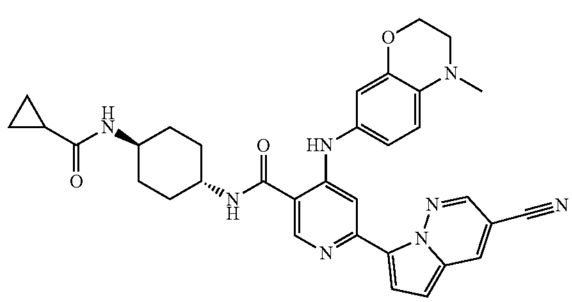 [SMILES: CN1CCOc2cc(Nc3cc(-c4ccc5cc(C#N)cnn45)ncc3C(=O)N[C@H]3CC[C@H](NC(=O)C4CC4)CC3)ccc21] | 859 | 591.4 | 79 | 6-(3-cyanopyrrolo[1,2-b]pyridazin-7-yl)-N-((1r,4r)-4-(cyclopropanecarboxamido)cyclohexyl)-4-((4-methyl-3,4-dihydro-2H-benzo[b][1,4]oxazin-7-yl)amino)nicotinamide |
| 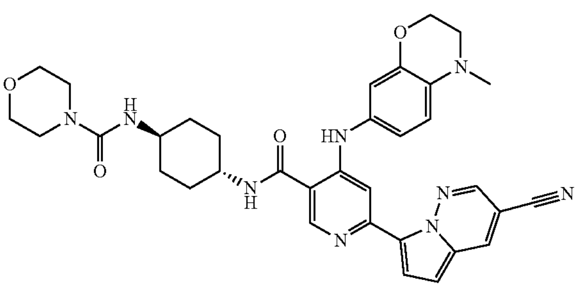 [SMILES: CN1CCOc2cc(Nc3cc(-c4ccc5cc(C#N)cnn45)ncc3C(=O)N[C@H]3CC[C@H](NC(=O)N4CCOCC4)CC3)ccc21] | 860 | 636.3 | 79 | N-((1r,4r)-4-(6-(3-cyanopyrrolo[1,2-b]pyridazin-7-yl)-4-((4-methyl-3,4-dihydro-2H-benzo[b][1,4]oxazin-7-yl)amino)nicotinamido)cyclohexyl)morpholine-4-carboxamide |

TABLE 1-continued

| Structure | compound | ES/MS m/z | procedure | Name |
|---|---|---|---|---|
| 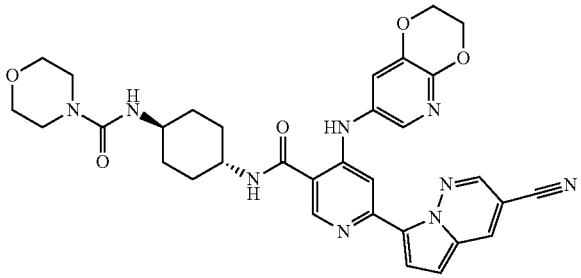 [SMILES: N#Cc1cnn2c(-c3cc(Nc4cnc5c(c4)OCCO5)c(C(=O)N[C@H]4CC[C@H](NC(=O)N5CCOCC5)CC4)cn3)ccc2c1] | 861 | 624.3 | 79 | N-((1r,4r)-4-(6-(3-cyano-pyrrolo[1,2-b]pyridazin-7-yl)-4-((2,3-dihydro-[1,4]dioxino[2,3-b]pyridin-7-yl)amino)nicotinamido)cyclohexyl)morpholine-4-carboxamide |
| 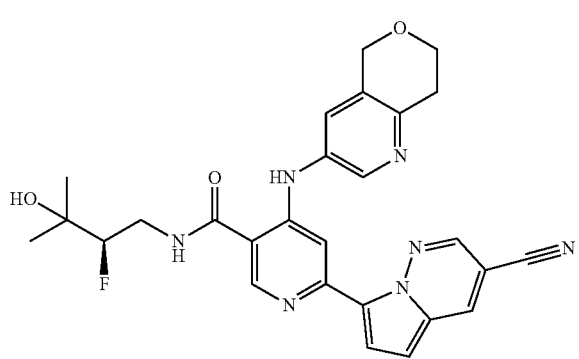 [SMILES: CC(C)(O)[C@H](F)CNC(=O)c1cnc(-c2ccc3cc(C#N)cnn23)cc1Nc1cnc2c(c1)COCC2] | 862 | 516.4 | 47 | (R)-6-(3-cyanopyrrolo[1,2-b]pyridazin-7-yl)-4-((7,8-dihydro-5H-pyrano[4,3-b]pyridin-3-yl)amino)-N-(2-fluoro-3-hydroxy-3-methylbutyl)nicotinamide |
| 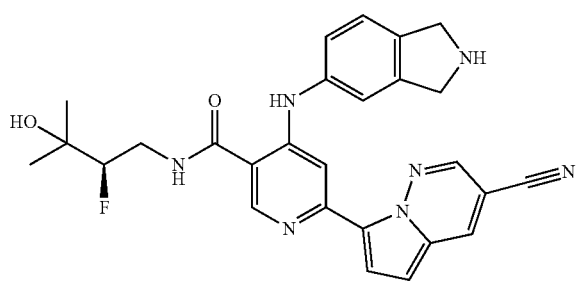 [SMILES: CC(C)(O)[C@H](F)CNC(=O)c1cnc(-c2ccc3cc(C#N)cnn23)cc1Nc1ccc2c(c1)CNC2] | 863 | 500.2 | 28 | (R)-6-(3-cyanopyrrolo[1,2-b]pyridazin-7-yl)-N-(2-fluoro-3-hydroxy-3-methylbutyl)-4-(isoindolin-5-ylamino)nicotinamide |
| 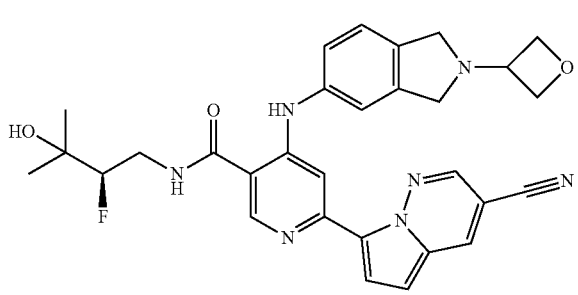 [SMILES: CC(C)(O)[C@H](F)CNC(=O)c1cnc(-c2ccc3cc(C#N)cnn23)cc1Nc1ccc2c(c1)CN(C1COC1)C2] | 864 | 556.3 | 26 | (R)-6-(3-cyanopyrrolo[1,2-b]pyridazin-7-yl)-N-(2-fluoro-3-hydroxy-3-methylbutyl)-4-((2-(oxetan-3-yl)isoindolin-5-yl)amino)nicotinamide |
| 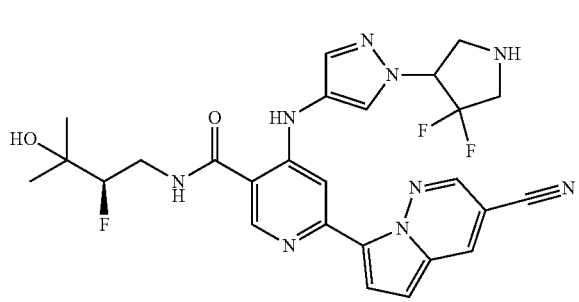 [SMILES: CC(C)(O)[C@H](F)CNC(=O)c1cnc(-c2ccc3cc(C#N)cnn23)cc1Nc1cnn(C2CNCC2(F)F)c1] | 865 | 554.3 | 28 | 6-(3-cyanopyrrolo[1,2-b]pyridazin-7-yl)-4-((1-(4,4-difluoropyrrolidin-3-yl)-1H-pyrazol-4-yl)amino)-N-((R)-2-fluoro-3-hydroxy-3-methylbutyl)nicotinamide |

TABLE 1-continued

| Structure | compound | ES/MS m/z | procedure | Name |
|---|---|---|---|---|
| 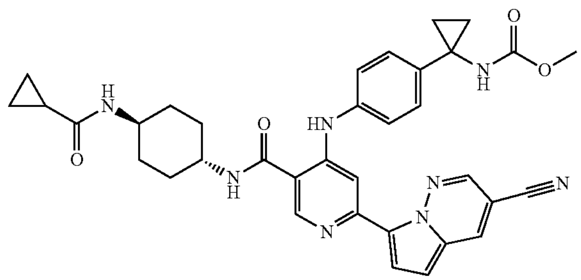 [SMILES: COC(=O)NC1(c2ccc(Nc3cc(-c4ccc5cc(C#N)cnn45)ncc3C(=O)N[C@H]3CC[C@H](NC(=O)C4CC4)CC3)cc2)CC1] | 866 | 633.3 | 13 | methyl (1-(4-((2-(3-cyanopyrrolo[1,2-b]pyridazin-7-yl)-5-(((1r,4r)-4-(cyclopropanecarboxamido)cyclohexyl)carbamoyl)pyridin-4-yl)amino)phenyl)cyclopropyl)carbamate |
| 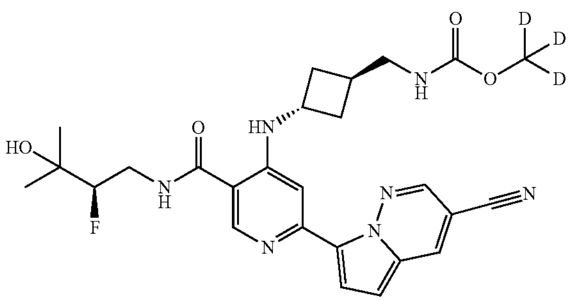 [SMILES: [2H]C([2H])([2H])OC(=O)NC[C@H]1C[C@H](Nc2cc(-c3ccc4cc(C#N)cnn34)ncc2C(=O)NC[C@@H](F)C(C)(C)O)C1] | 867 | 527.3 | 35 | methyl-d3 (((1R,3r)-3-((2-(3-cyanopyrrolo[1,2-b]pyridazin-7-yl)-5-(((R)-2-fluoro-3-hydroxy-3-methylbutyl)carbamoyl)pyridin-4-yl)amino)cyclobutyl)methyl)carbamate |
| diastereomer 1 | 868 | 554.3 | 37 | 6-(3-cyanopyrrolo[1,2-b]pyridazin-7-yl)-4-((1-(4,4-difluoropyrrolidin-3-yl)-1H-pyrazol-4-yl)amino)-N-((R)-2-fluoro-3-hydroxy-3-methylbutyl)nicotinamide |
| diastereomer 2 | 869 | 554.2 | 37 | 6-(3-cyanopyrrolo[1,2-b]pyridazin-7-yl)-4-((1-(4,4-difluoropyrrolidin-3-yl)-1H-pyrazol-4-yl)amino)-N-((R)-2-fluoro-3-hydroxy-3-methylbutyl)nicotinamide |

TABLE 1-continued

| Structure | compound | ES/MS m/z | procedure | Name |
|---|---|---|---|---|
| 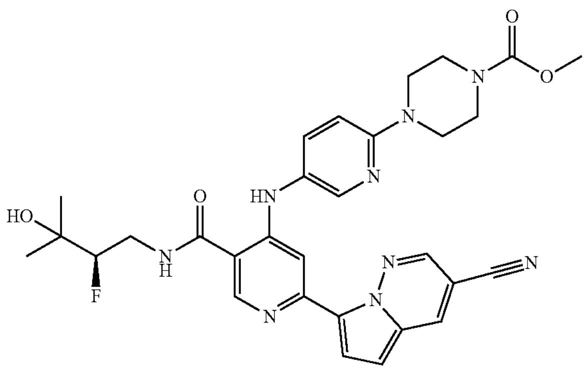 [SMILES: COC(=O)N1CCN(c2ccc(Nc3cc(-c4ccc5cc(C#N)cnn45)ncc3C(=O)NC[C@@H](F)C(C)(C)O)cn2)CC1] | 870 | 602.3 | 35 | (R)-methyl 4-(5-((2-(3-cyanopyrrolo[1,2-b]pyridazin-7-yl)-5-((2-fluoro-3-hydroxy-3-methylbutyl)carbamoyl)pyridin-4-yl)amino)pyridin-2-yl)piperazine-1-carboxylate |
| 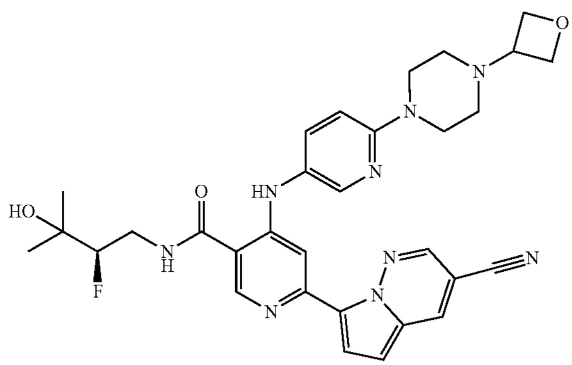 [SMILES: CC(C)(O)[C@H](F)CNC(=O)c1cnc(-c2ccc3cc(C#N)cnn23)cc1Nc1ccc(N2CCN(C3COC3)CC2)nc1] | 871 | 600.3 | 2 | (R)-6-(3-cyanopyrrolo[1,2-b]pyridazin-7-yl)-N-(2-fluoro-3-hydroxy-3-methylbutyl)-4-((6-(4-(oxetan-3-yl)piperazin-1-yl)pyridin-3-yl)amino)nicotinamide |
| 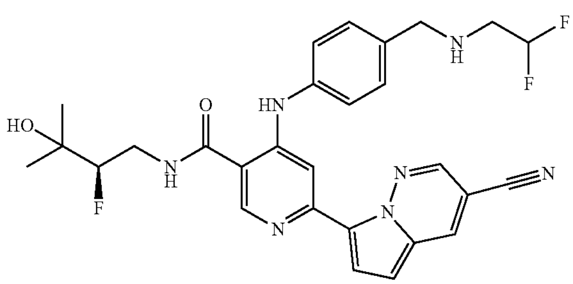 [SMILES: CC(C)(O)[C@H](F)CNC(=O)c1cnc(-c2ccc3cc(C#N)cnn23)cc1Nc1ccc(CNCC(F)F)cc1] | 872 | 552.3 | 28 | (R)-6-(3-cyanopyrrolo[1,2-b]pyridazin-7-yl)-4-((4-(((2,2-difluoroethyl)amino)methyl)phenyl)amino)-N-(2-fluoro-3-hydroxy-3-methylbutyl)nicotinamide |
| 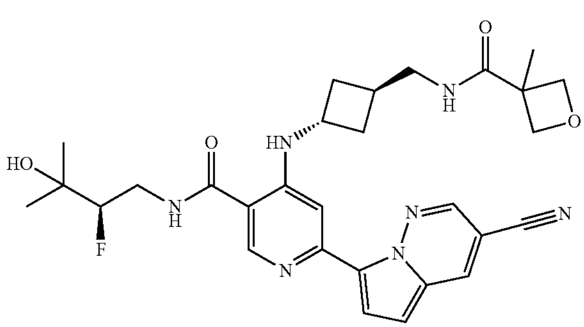 [SMILES: CC1(C(=O)NC[C@H]2C[C@H](Nc3cc(-c4ccc5cc(C#N)cnn45)ncc3C(=O)NC[C@@H](F)C(C)(C)O)C2)COC1] | 873 | 564.3 | 38 | 6-(3-cyanopyrrolo[1,2-b]pyridazin-7-yl)-N-((R)-2-fluoro-3-hydroxy-3-methylbutyl)-4-(((1r,3R)-3-((3-methyloxetane-3-carboxamido)methyl)cyclobutyl)amino)nicotinamide |

TABLE 1-continued

| Structure | compound | ES/ MS m/z | procedure | Name |
|---|---|---|---|---|
| 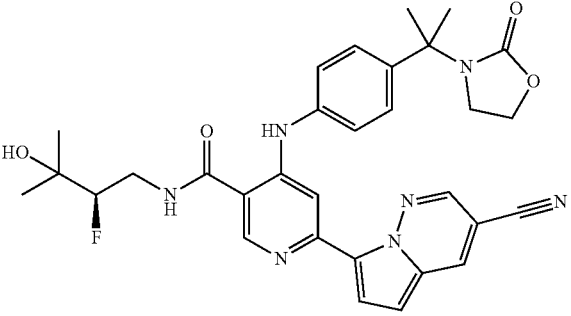 | 874 | 586.2 | 2 | (R)-6-(3-cyanopyrrolo[1,2-b]pyridazin-7-yl)-N-(2-fluoro-3-hydroxy-3-methylbutyl)-4-((4-(2-(2-oxooxazolidin-3-yl)propan-2-yl)phenyl)amino)nicotinamide |
| 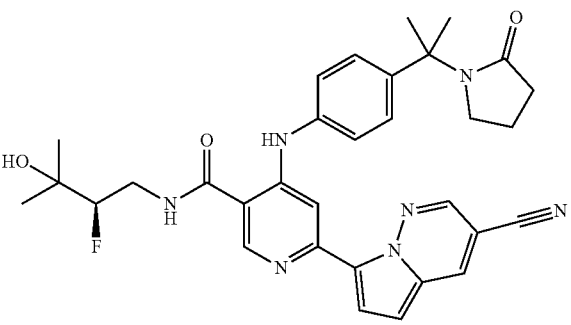 [SMILES: CC(C)(O)[C@H](F)CNC(=O)c1cnc(-c2ccc3cc(C#N)cnn23)cc1Nc1ccc(C(C)(C)N2CCCC2=O)cc1] | 875 | 584.3 | 2 | (R)-6-(3-cyanopyrrolo[1,2-b]pyridazin-7-yl)-N-(2-fluoro-3-hydroxy-3-methyl-butyl)-4-((4-(2-(2-oxo-pyrrolidin-1-yl)propan-2-yl)phenyl)amino)nicotinamide |
| 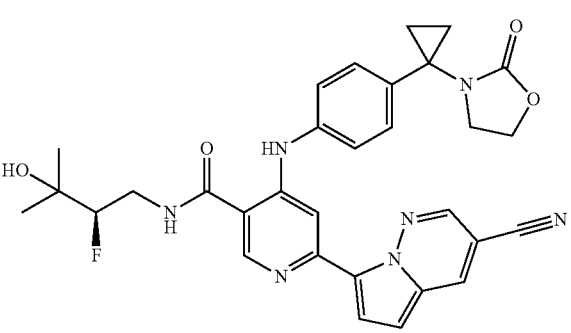 [SMILES: CC(C)(O)[C@H](F)CNC(=O)c1cnc(-c2ccc3cc(C#N)cnn23)cc1Nc1ccc(C2(N3CCOC3=O)CC2)cc1] | 876 | 584.3 | 2 | (R)-6-(3-cyanopyrrolo[1,2-b]pyridazin-7-yl)-N-(2-fluoro-3-hydroxy-3-methylbutyl)-4-((4-(1-(2-oxooxazolidin-3-yl)cyclopropyl)phenyl)amino)nicotinamide |
| 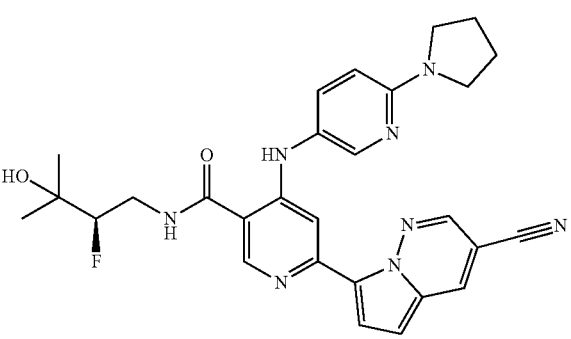 [SMILES: CC(C)(O)[C@H](F)CNC(=O)c1cnc(-c2ccc3cc(C#N)cnn23)cc1Nc1ccc(N2CCCC2)nc1] | 877 | 529.3 | 2 | (R)-6-(3-cyano-pyrrolo[1,2-b]pyridazin-7-yl)-N-(2-fluoro-3-hydroxy-3-methylbutyl)-4-((6-(pyrrolidin-1-yl)pyridin-3-yl)amino)nicotinamide |

TABLE 1-continued

| Structure | compound | ES/MS m/z | procedure | Name |
|---|---|---|---|---|
| 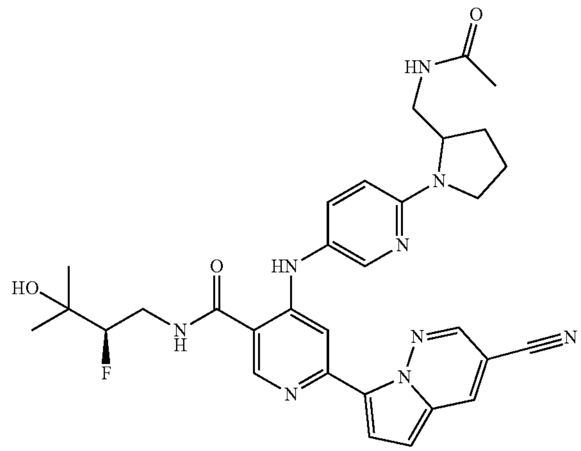 [SMILES: CC(=O)NCC1CCCN1c1ccc(Nc2cc(-c3ccc4cc(C#N)cnn34)ncc2C(=O)NC[C@@H](F)C(C)(C)O)cn1] | 878 | 600.3 | 16 | 4-((6-((S)-2-(acetamidomethyl)pyrrolidin-1-yl)pyridin-3-yl)amino)-6-(3-cyanopyrrolo[1,2-b]pyridazin-7-yl)-N-((R)-2-fluoro-3-hydroxy-3-methylbutyl)nicotinamide |
| 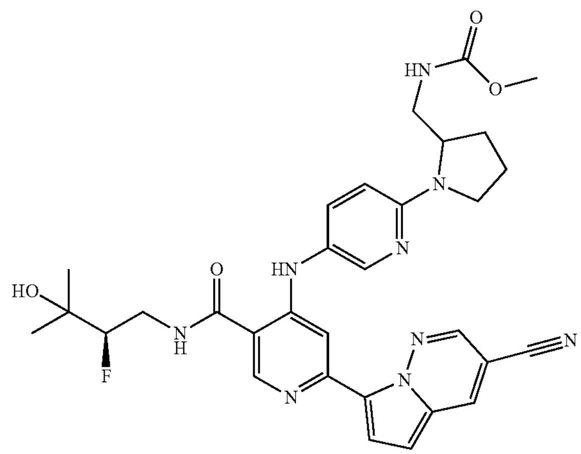 [SMILES: COC(=O)NCC1CCCN1c1ccc(Nc2cc(-c3ccc4cc(C#N)cnn34)ncc2C(=O)NC[C@@H](F)C(C)(C)O)cn1] | 879 | 616.3 | 35 | methyl (((S)-1-(5-((2-(3-cyanopyrrolo[1,2-b]pyridazin-7-yl)-5-(((R)-2-fluoro-3-hydroxy-3-methylbutyl)carbamoyl)pyridin-4-yl)amino)pyridin-2-yl)pyrrolidin-2-yl)methyl)carbamate |
| 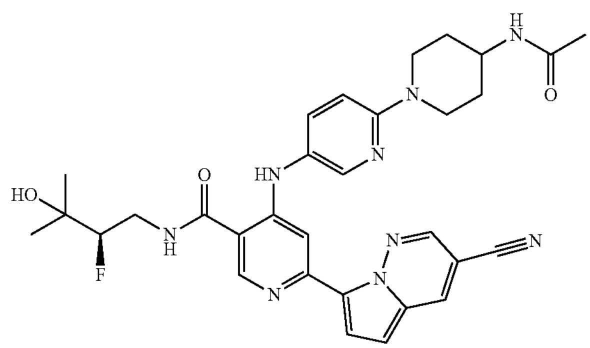 [SMILES: CC(=O)NC1CCN(c2ccc(Nc3cc(-c4ccc5cc(C#N)cnn45)ncc3C(=O)NC[C@@H](F)C(C)(C)O)cn2)CC1] | 880 | 600.3 | 16 | (R)-4-((6-(4-acetamido-piperidin-1-yl)pyridin-3-yl)amino)-6-(3-cyanopyrrolo[1,2-b]pyridazin-7-yl)-N-(2-fluoro-3-hydroxy-3-methylbutyl)nicotinamide |
| 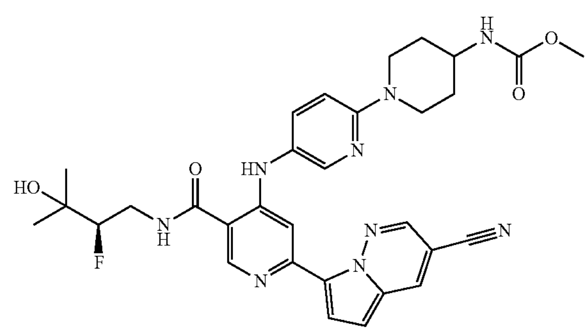 [SMILES: COC(=O)NC1CCN(c2ccc(Nc3cc(-c4ccc5cc(C#N)cnn45)ncc3C(=O)NC[C@@H](F)C(C)(C)O)cn2)CC1] | 881 | 616.3 | 35 | (R)-methyl (1-(5-((2-(3-cyanopyrrolo[1,2-b]pyridazin-7-yl)-5-((2-fluoro-3-hydroxy-3-methylbutyl)carbamoyl)pyridin-4-yl)amino)pyridin-2-yl)piperidin-4-yl)carbamate |

TABLE 1-continued

| Structure | compound | ES/MS m/z | procedure | Name |
|---|---|---|---|---|
| 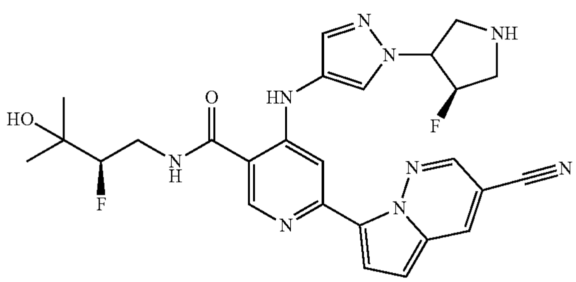 [SMILES: CC(C)(O)[C@H](F)CNC(=O)c1cnc(-c2ccc3cc(C#N)cnn23)cc1Nc1cnn(C2CNC[C@H]2F)c1] | 882 | 536.2 | 28 | 6-(3-cyanopyrrolo[1,2-b]pyridazin-7-yl)-N-((R)-2-fluoro-3-hydroxy-3-methylbutyl)-4-((1-((3R,4R)-4-fluoropyrrolidin-3-yl)-1H-pyrazol-4-yl)amino)nicotinamide |
| 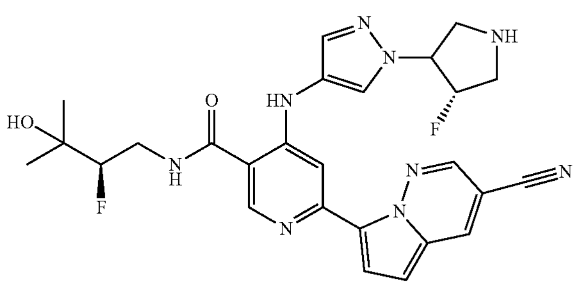 [SMILES: CC(C)(O)[C@H](F)CNC(=O)c1cnc(-c2ccc3cc(C#N)cnn23)cc1Nc1cnn(C2CNC[C@@H]2F)c1] | 883 | 536.2 | 28 | 6-(3-cyanopyrrolo[1,2-b]pyridazin-7-yl)-N-((R)-2-fluoro-3-hydroxy-3-methylbutyl)-4-((1-((3R,4S)-4-fluoropyrrolidin-3-yl)-1H-pyrazol-4-yl)amino)nicotinamide |
| 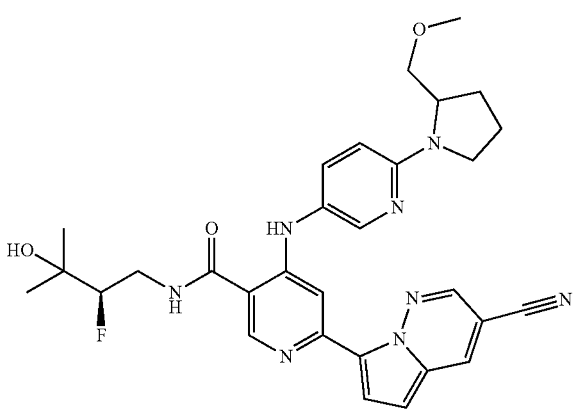 [SMILES: COCC1CCCN1c1ccc(Nc2cc(-c3ccc4cc(C#N)cnn34)ncc2C(=O)NC[C@@H](F)C(C)(C)O)cn1] | 884 | 573.3 | 2 | 6-(3-cyanopyrrolo[1,2-b]pyridazin-7-yl)-N-((R)-2-fluoro-3-hydroxy-3-methylbutyl)-4-((6-((S)-2-(methoxymethyl)pyrrolidin-1-yl)pyridin-3-yl)amino)nicotinamide |
| 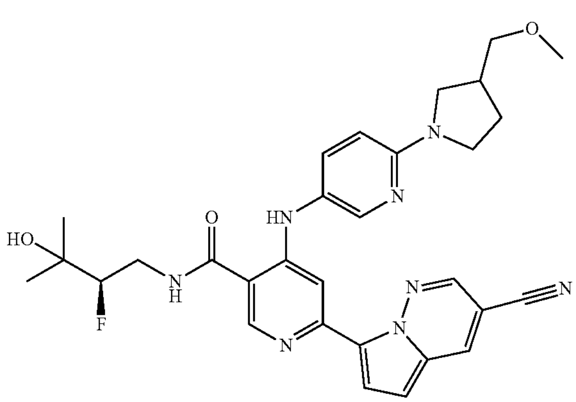 [SMILES: COCC1CCN(c2ccc(Nc3cc(-c4ccc5cc(C#N)cnn45)ncc3C(=O)NC[C@@H](F)C(C)(C)O)cn2)C1] | 885 | 573.3 | 2 | 6-(3-cyanopyrrolo[1,2-b]pyridazin-7-yl)-N-((R)-2-fluoro-3-hydroxy-3-methylbutyl)-4-((6-((R)-3-(methoxymethyl)pyrrolidin-1-yl)pyridin-3-yl)amino)nicotinamide |

TABLE 1-continued

| Structure | compound | ES/MS m/z | procedure | Name |
|---|---|---|---|---|
| 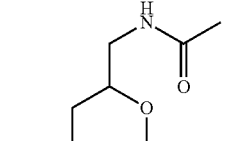 | 886 | 616.3 | 16 | 4-((6-((S)-2-(acetamidomethyl)morpholino)pyridin-3-yl)amino)-6-(3-cyanopyrrolo[1,2-b]pyridazin-7-yl)-N-((R)-2-fluoro-3-hydroxy-3-methylbutyl)nicotinamide |
| 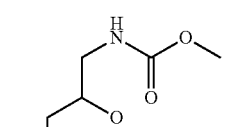 | 887 | 632.3 | 35 | methyl (((S)-4-(5-((2-(3-cyanopyrrolo[1,2-b]pyridazin-7-yl)-5-(((R)-2-fluoro-3-hydroxy-3-methylbutyl)carbamoyl)pyridin-4-yl)amino)pyridin-2-yl)morpholin-2-yl)methyl)carbamate |
| 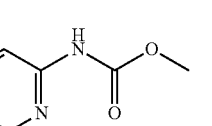 | 888 | 533.2 | 80 | (R)-methyl (5-((2-(3-cyanopyrrolo[1,2-b]pyridazin-7-yl)-5-((2-fluoro-3-hydroxy-3-methylbutyl)carbamoyl)pyridin-4-yl)amino)pyridin-2-yl)carbamate |
| 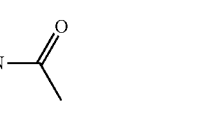 | 889 | 494.4 | 16 | 4-((((S)-1-acetylazetidin-2-yl)methyl)amino)-6-(3-cyanopyrrolo[1,2-b]pyridazin-7-yl)-N-((R)-2-fluoro-3-hydroxy-3-methylbutyl)nicotinamide |

TABLE 1-continued

| Structure | compound | ES/ MS m/z | procedure | Name |
|---|---|---|---|---|
| 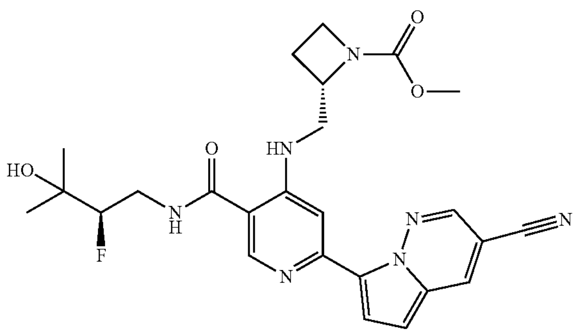 [SMILES: COC(=O)N1CC[C@H]1CNc1cc(-c2ccc3cc(C#N)cnn23)ncc1C(=O)NC[C@@H](F)C(C)(C)O] | 890 | 510.4 | 35 | (S)-methyl 2-(((2-(3-cyanopyrrolo[1,2-b]pyridazin-7-yl)-5-(((R)-2-fluoro-3-hydroxy-3-methylbutyl)carbamoyl)pyridin-4-yl)amino)methyl)azetidine-1-carboxylate |
| 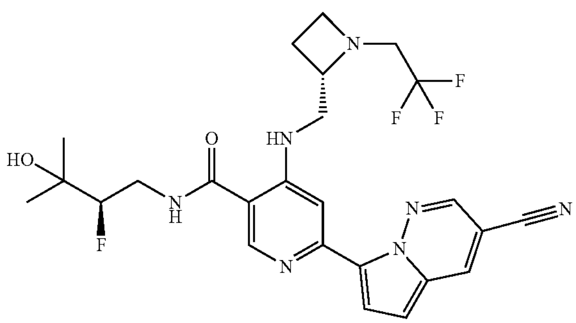 [SMILES: CC(C)(O)[C@H](F)CNC(=O)c1cnc(-c2ccc3cc(C#N)cnn23)cc1NC[C@@H]1CCN1CC(F)(F)F] | 891 | 534.3 | 34 | 6-(3-cyanopyrrolo[1,2-b]pyridazin-7-yl)-N-((R)-2-fluoro-3-hydroxy-3-methylbutyl)-4-((((S)-1-(2,2,2-trifluoroethyl)azetidin-2-yl)methyl)amino)nicotinamide |
| 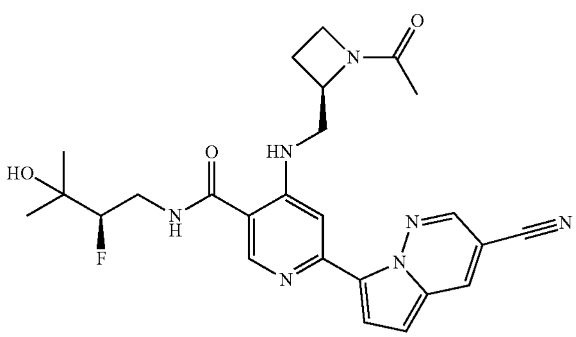 [SMILES: CC(=O)N1CC[C@@H]1CNc1cc(-c2ccc3cc(C#N)cnn23)ncc1C(=O)NC[C@@H](F)C(C)(C)O] | 892 | 494.2 | 16 | 4-((((R)-1-acetylazetidin-2-yl)methyl)amino)-6-(3-cyanopyrrolo[1,2-b]pyridazin-7-yl)-N-((R)-2-fluoro-3-hydroxy-3-methylbutyl)nicotinamide |
| 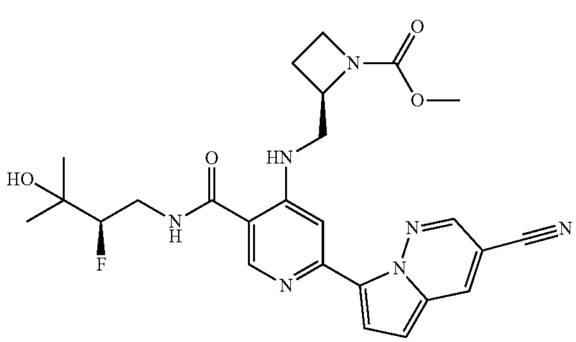 [SMILES: COC(=O)N1CC[C@@H]1CNc1cc(-c2ccc3cc(C#N)cnn23)ncc1C(=O)NC[C@@H](F)C(C)(C)O] | 893 | 510.3 | 35 | (R)-methyl 2-(((2-(3-cyanopyrrolo[1,2-b]pyridazin-7-yl)-5-(((R)-2-fluoro-3-hydroxy-3-methylbutyl)carbamoyl)pyridin-4-yl)amino)methyl)azetidine-1-carboxylate |

TABLE 1-continued

| Structure | compound | ES/MS m/z | procedure | Name |
|---|---|---|---|---|
| 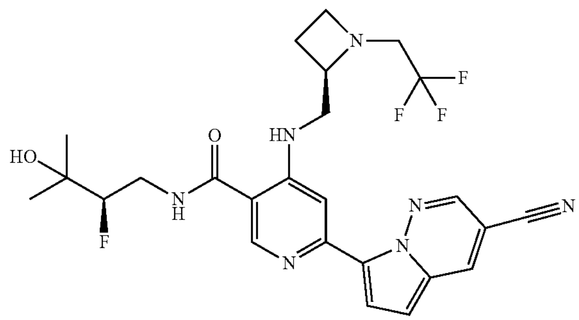 [SMILES: CC(C)(O)[C@H](F)CNC(=O)c1cnc(-c2ccc3cc(C#N)cnn23)cc1NC[C@H]1CCN1CC(F)(F)F] | 894 | 534.2 | 34 | 6-(3-cyanopyrrolo[1,2-b]pyridazin-7-yl)-N-((R)-2-fluoro-3-hydroxy-3-methylbutyl)-4-((((R)-1-(2,2,2-trifluoroethyl)azetidin-2-yl)methyl)amino)nicotinamide |
| 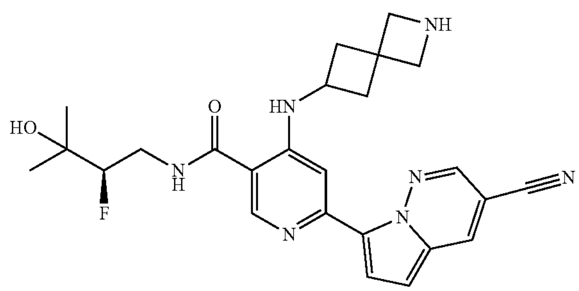 [SMILES: CC(C)(O)[C@H](F)CNC(=O)c1cnc(-c2ccc3cc(C#N)cnn23)cc1NC1CC2(CNC2)C1] | 895 | 478.3 | 14 | (R)-4-(2-azaspiro[3.3]heptan-6-ylamino)-6-(3-cyanopyrrolo[1,2-b]pyridazin-7-yl)-N-(2-fluoro-3-hydroxy-3-methyl-butyl)nicotinamide |
| 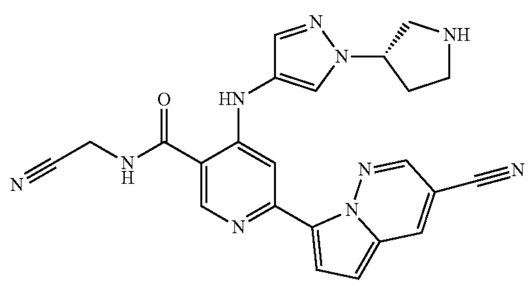 [SMILES: N#CCNC(=O)c1cnc(-c2ccc3cc(C#N)cnn23)cc1Nc1cnn([C@H]2CCNC2)c1] | 896 | 453.2 | 14 | (S)-N-(cyanomethyl)-6-(3-cyanopyrrolo[1,2-b]pyridazin-7-yl)-4-((1-(pyrrolidin-3-yl)-1H-pyrazol-4-yl)amino)nicotinamide |
| 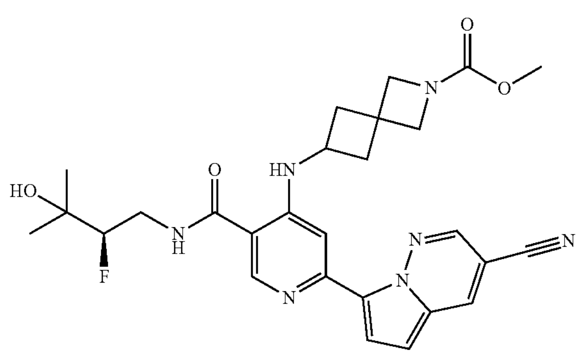 [SMILES: COC(=O)N1CC2(CC(Nc3cc(-c4ccc5cc(C#N)cnn45)ncc3C(=O)NC[C@@H](F)C(C)(C)O)C2)C1] | 897 | 536.3 | 35 | (R)-methyl 6-((2-(3-cyano-pyrrolo[1,2-b]pyridazin-7-yl)-5-((2-fluoro-3-hydroxy-3-methylbutyl)carbamoyl)pyridin-4-yl)amino)-2-azaspiro[3.3]heptane-2-carboxylate |
| 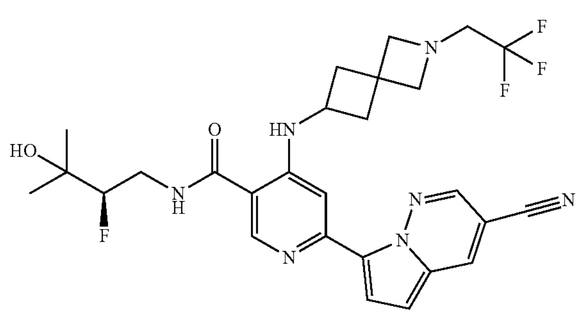 [SMILES: CC(C)(O)[C@H](F)CNC(=O)c1cnc(-c2ccc3cc(C#N)cnn23)cc1NC1CC2(C1)CN(CC(F)(F)F)C2] | 898 | 560.3 | 34 | (R)-6-(3-cyanopyrrolo[1,2-b]pyridazin-7-yl)-N-(2-fluoro-3-hydroxy-3-methylbutyl)-4-((2-(2,2,2-trifluoroethyl)-2-aza-spiro[3.3]heptan-6-yl)amino)nicotinamide |

TABLE 1-continued

| Structure | compound | ES/ MS m/z | procedure | Name |
|---|---|---|---|---|
| 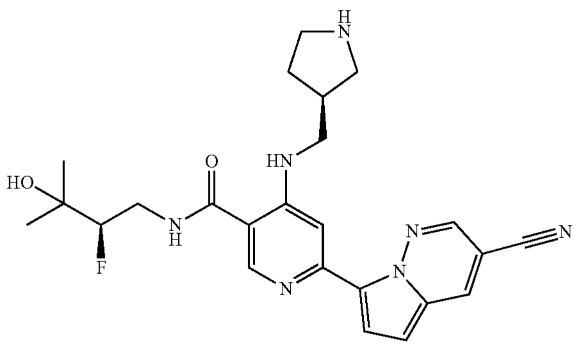 [SMILES: CC(C)(O)[C@H](F)CNC(=O)c1cnc(-c2ccc3cc(C#N)cnn23)cc1NC[C@H]1CCNC1] | 899 | 466.2 | 14 | 6-(3-cyanopyrrolo[1,2-b]pyridazin-7-yl)-N-((R)-2-fluoro-3-hydroxy-3-methylbutyl)-4-((((S)-pyrrolidin-3-yl)methyl)amino)nicotinamide |
| 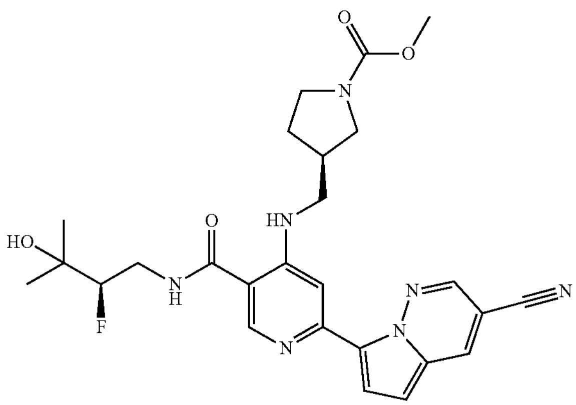 [SMILES: COC(=O)N1CC[C@H](CNc2cc(-c3ccc4cc(C#N)cnn34)ncc2C(=O)NC[C@@H](F)C(C)(C)O)C1] | 900 | 524.2 | 35 | (R)-methyl 3-(((2-(3-cyanopyrrolo[1,2-b]pyridazin-7-yl)-5-(((R)-2-fluoro-3-hydroxy-3-methylbutyl)carbamoyl)pyridin-4-yl)amino)methyl)pyrrolidine-1-carboxylate |
| 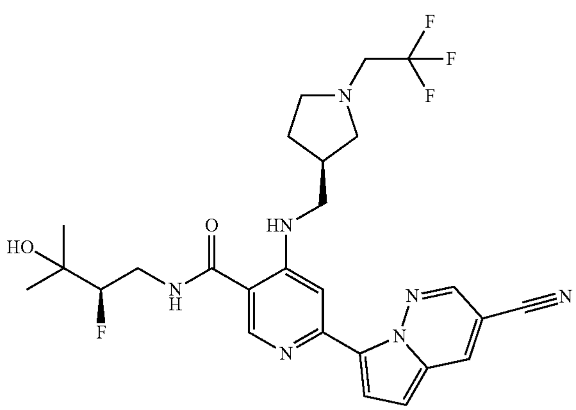 [SMILES: CC(C)(O)[C@H](F)CNC(=O)c1cnc(-c2ccc3cc(C#N)cnn23)cc1NC[C@H]1CCN(CC(F)(F)F)C1] | 901 | 548.3 | 34 | 6-(3-cyanopyrrolo[1,2-b]pyridazin-7-yl)-N-((R)-2-fluoro-3-hydroxy-3-methylbutyl)-4-((((R)-1-(2,2,2-trifluoroethyl)pyrrolidin-3-yl)methyl)amino)nicotinamide |
| 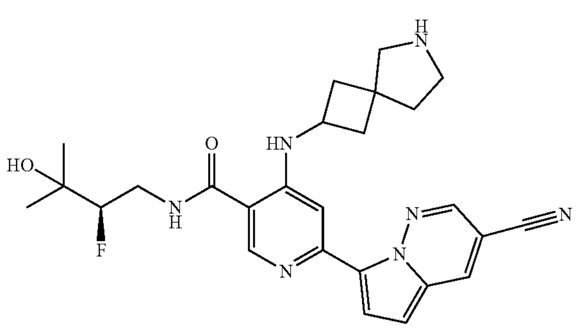 [SMILES: CC(C)(O)[C@H](F)CNC(=O)c1cnc(-c2ccc3cc(C#N)cnn23)cc1NC1CC2(CCNC2)C1] | 902 | 492.3 | 14 | (R)-4-(6-azaspiro[3.4]octan-2-ylamino)-6-(3-cyanopyrrolo[1,2-b]pyridazin-7-yl)-N-(2-fluoro-3-hydroxy-3-methylbutyl)nicotinamide |

TABLE 1-continued

| Structure | compound | ES/ MS m/z | procedure | Name |
|---|---|---|---|---|
| 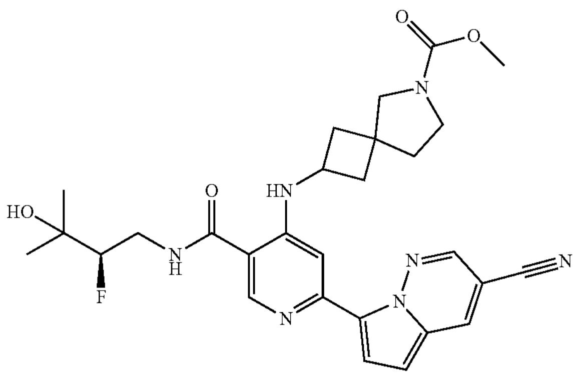 [SMILES: COC(=O)N1CCC2(CC(Nc3cc(-c4ccc5cc(C#N)cnn45)ncc3C(=O)NC[C@@H](F)C(C)(C)O)C2)C1] | 903 | 550.3 | 35 | (R)-methyl 2-((2-(3-cyano-pyrrolo[1,2-b]pyridazin-7-yl)-5-((2-fluoro-3-hydroxy-3-methylbutyl)carbamoyl)pyridin-4-yl)amino)-6-azaspiro[3.4]octane-6-carboxylate |
| 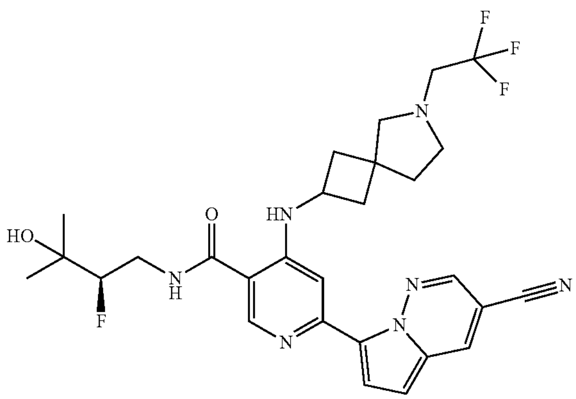 [SMILES: CC(C)(O)[C@H](F)CNC(=O)c1cnc(-c2ccc3cc(C#N)cnn23)cc1NC1CC2(CCN(CC(F)(F)F)C2)C1] | 904 | 574.3 | 34 | (R)-6-(3-cyanopyrrolo[1,2-b]pyridazin-7-yl)-N-(2-fluoro-3-hydroxy-3-methylbutyl)-4-((6-(2,2,2-trifluoroethyl)-6-azaspiro[3.4]octan-2-yl)amino)nicotinamide |
| 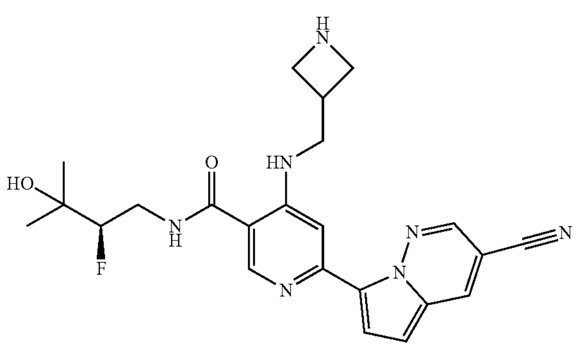 [SMILES: CC(C)(O)[C@H](F)CNC(=O)c1cnc(-c2ccc3cc(C#N)cnn23)cc1NCC1CNC1] | 905 | 452.2 | 14 | (R)-4-((azetidin-3-yl-methyl)amino)-6-(3-cyanopyrrolo[1,2-b]pyridazin-7-yl)-N-(2-fluoro-3-hydroxy-3-methylbutyl)nicotinamide |
| 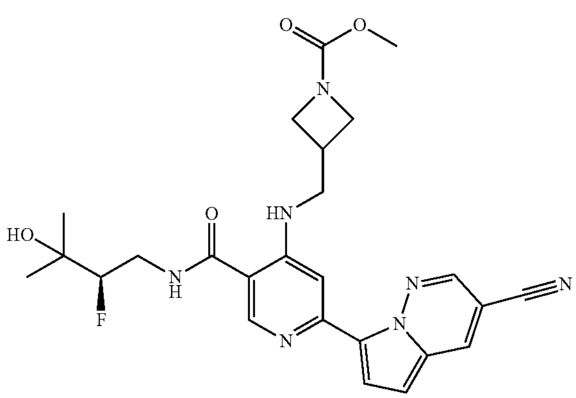 [SMILES: COC(=O)N1CC(CNc2cc(-c3ccc4cc(C#N)cnn34)ncc2C(=O)NC[C@@H](F)C(C)(C)O)C1] | 906 | 510.2 | 35 | (R)-methyl 3-(((2-(3-cyanopyrrolo[1,2-b]pyridazin-7-yl)-5-((2-fluoro-3-hydroxy-3-methylbutyl)carbamoyl)pyridin-4-yl)amino)methyl)azetidine-1-carboxylate |

TABLE 1-continued

| Structure | compound | ES/MS m/z | procedure | Name |
|---|---|---|---|---|
| 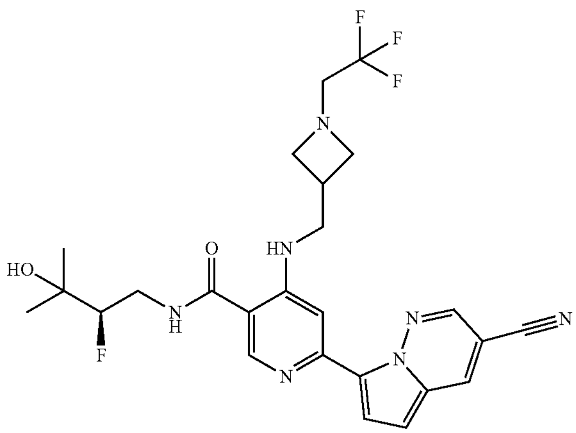 [SMILES: CC(C)(O)[C@H](F)CNC(=O)c1cnc(-c2ccc3cc(C#N)cnn23)cc1NCC1CN(CC(F)(F)F)C1] | 907 | 534.3 | 34 | (R)-6-(3-cyanopyrrolo[1,2-b]pyridazin-7-yl)-N-(2-fluoro-3-hydroxy-3-methylbutyl)-4-(((1-(2,2,2-trifluoroethyl)azetidin-3-yl)methyl)amino)nicotinamide |
| 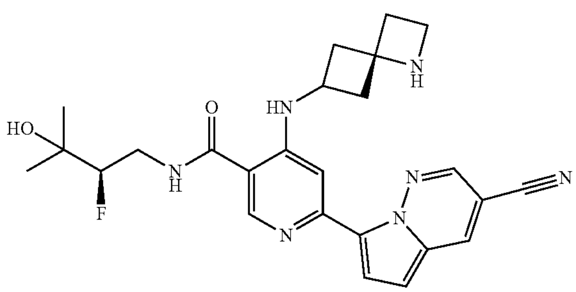 | 908 | 478.2 | 14 | 4-(((4S,6r)-1-azaspiro[3.3]heptan-6-yl)amino)-6-(3-cyanopyrrolo[1,2-b]pyridazin-7-yl)-N-((R)-2-fluoro-3-hydroxy-3-methylbutyl)nicotinamide |
| 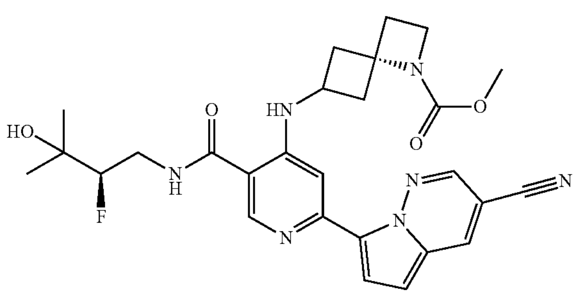 | 909 | 536.2 | 35 | (4S,6r)-methyl 6-((2-(3-cyanopyrrolo[1,2-b]pyridazin-7-yl)-5-(((R)-2-fluoro-3-hydroxy-3-methylbutyl)carbamoyl)pyridin-4-yl)amino)-1-azaspiro[3.3]heptane-1-carboxylate |
| 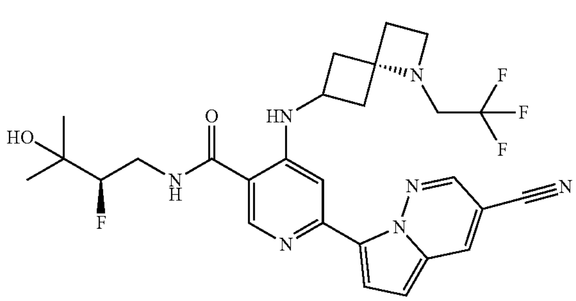 | 910 | 560.2 | 34 | 6-(3-cyanopyrrolo[1,2-b]pyridazin-7-yl)-N-((R)-2-fluoro-3-hydroxy-3-methylbutyl)-4-(((4S,6r)-1-(2,2,2-trifluoroethyl)-1-azaspiro[3.3]heptan-6-yl)amino)nicotinamide |

TABLE 1-continued

| Structure | compound | ES/MS m/z | procedure | Name |
|---|---|---|---|---|
| 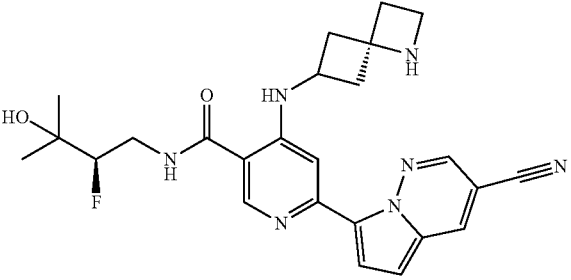 | 911 | 478.3 | 14 | 4-(((4R,6s)-1-azaspiro[3.3]heptan-6-yl)amino)-6-(3-cyanopyrrolo[1,2-b]pyridazin-7-yl)-N-((R)-2-fluoro-3-hydroxy-3-methylbutyl)nicotinamide |
| 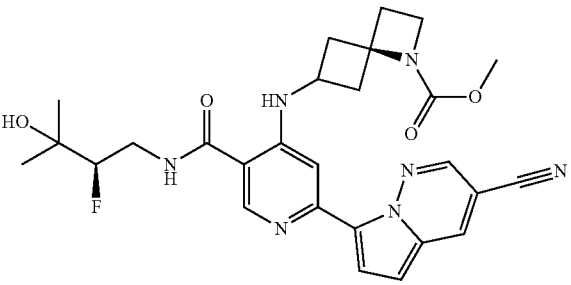 | 912 | 536.3 | 35 | (4R,6s)-methyl 6-((2-(3-cyanopyrrolo[1,2-b]pyridazin-7-yl)-5-(((R)-2-fluoro-3-hydroxy-3-methylbutyl)carbamoyl)pyridin-4-yl)amino)-1-azaspiro[3.3]heptane-1-carboxylate |
| 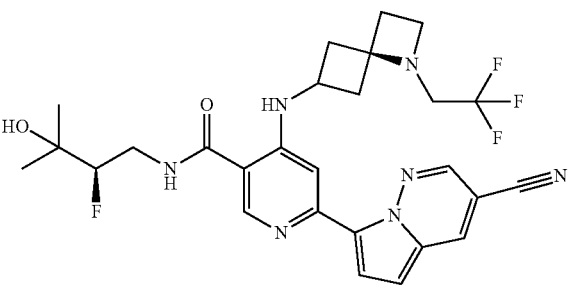 | 913 | 560.3 | 34 | 6-(3-cyanopyrrolo[1,2-b]pyridazin-7-yl)-N-((R)-2-fluoro-3-hydroxy-3-methylbutyl)-4-(((4R,6s)-1-(2,2,2-trifluoroethyl)-1-azaspiro[3.3]heptan-6-yl)amino)nicotinamide |
| 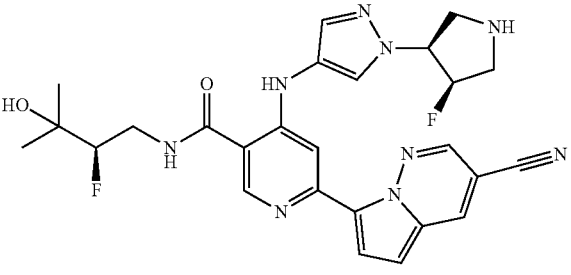 [SMILES: CC(C)(O)[C@H](F)CNC(=O)c1cnc(-c2ccc3cc(C#N)cnn23)cc1Nc1cnn([C@H]2CNC[C@H]2F)c1] | 914 | 536.2 | 14 | 6-(3-cyanopyrrolo[1,2-b]pyridazin-7-yl)-N-((R)-2-fluoro-3-hydroxy-3-methylbutyl)-4-((1-((3S,4R)-4-fluoropyrrolidin-3-yl)-1H-pyrazol-4-yl)amino)nicotinamide |

TABLE 1-continued

| Structure | compound | ES/MS m/z | procedure | Name |
|---|---|---|---|---|
| 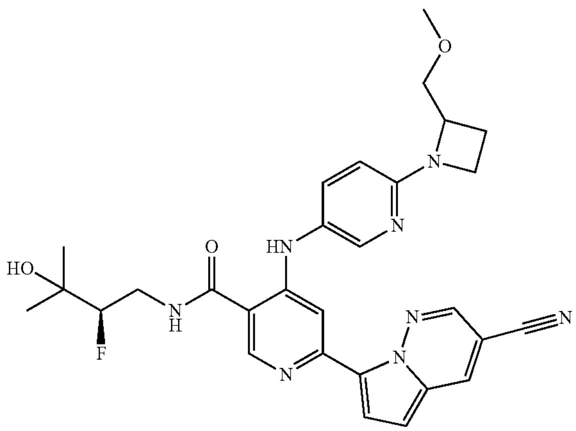 [SMILES: COCC1CCN1c1ccc(Nc2cc(-c3ccc4cc(C#N)cnn34)ncc2C(=O)NC[C@@H](F)C(C)(C)O)cn1] | 915 | 559.3 | 2 | 6-(3-cyanopyrrolo[1,2-b]pyridazin-7-yl)-N-((R)-2-fluoro-3-hydroxy-3-methylbutyl)-4-((6-((S)-2-(methoxymethyl)azetidin-1-yl)pyridin-3-yl)amino)nicotinamide |
| 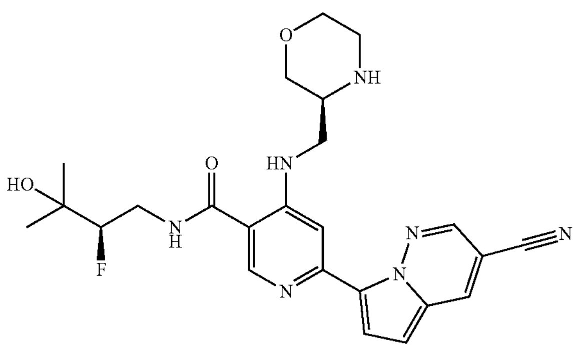 [SMILES: CC(C)(O)[C@H](F)CNC(=O)c1cnc(-c2ccc3cc(C#N)cnn23)cc1NC[C@H]1COCCN1] | 916 | 482.3 | 14 | 6-(3-cyanopyrrolo[1,2-b]pyridazin-7-yl)-N-((R)-2-fluoro-3-hydroxy-3-methylbutyl)-4-((((S)-morpholin-3-yl)methyl)amino)nicotinamide |
| 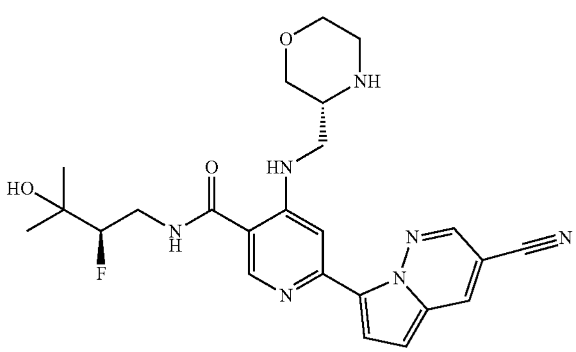 [SMILES: CC(C)(O)[C@H](F)CNC(=O)c1cnc(-c2ccc3cc(C#N)cnn23)cc1NC[C@@H]1COCCN1] | 917 | 482.3 | 14 | 6-(3-cyanopyrrolo[1,2-b]pyridazin-7-yl)-N-((R)-2-fluoro-3-hydroxy-3-methylbutyl)-4-((((R)-morpholin-3-yl)methyl)amino)nicotinamide |
| 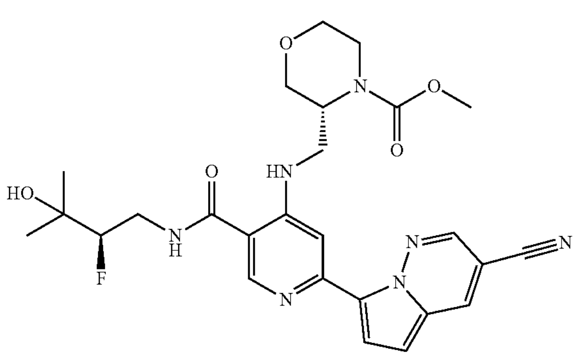 [SMILES: COC(=O)N1CCOC[C@H]1CNc1cc(-c2ccc3cc(C#N)cnn23)ncc1C(=O)NC[C@@H](F)C(C)(C)O] | 918 | 540.3 | 35 | (R)-methyl 3-(((2-(3-cyanopyrrolo[1,2-b]pyridazin-7-yl)-5-(((R)-2-fluoro-3-hydroxy-3-methylbutyl)carbamoyl)pyridin-4-yl)amino)methyl)morpholine-4-carboxylate |

TABLE 1-continued

| Structure | compound | ES/MS m/z | procedure | Name |
|---|---|---|---|---|
| 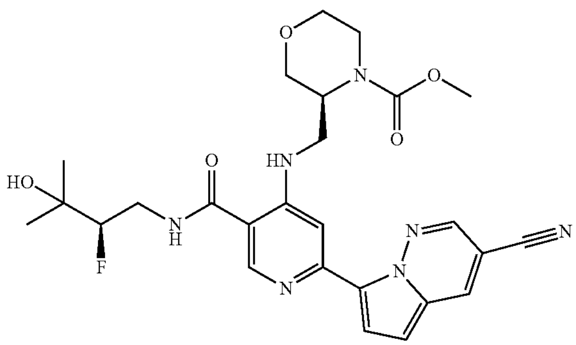 [SMILES: COC(=O)N1CCOC[C@@H]1CNc1cc(-c2ccc3cc(C#N)cnn23)ncc1C(=O)NC[C@@H](F)C(C)(C)O] | 919 | 540.3 | 35 | (S)-methyl 3-(((2-(3-cyano-pyrrolo[1,2-b]pyridazin-7-yl)-5-(((R)-2-fluoro-3-hydroxy-3-methylbutyl)carbamoyl)pyridin-4-yl)amino)methyl)morpholine-4-carboxylate |
| 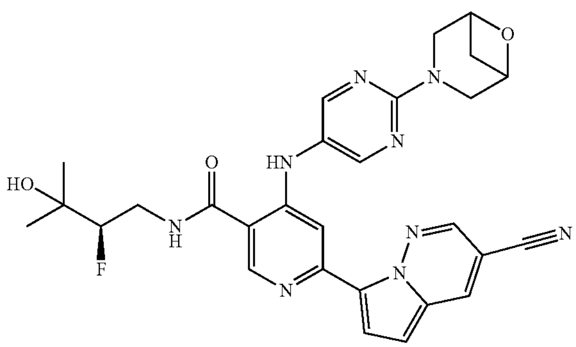 [SMILES: CC(C)(O)[C@H](F)CNC(=O)c1cnc(-c2ccc3cc(C#N)cnn23)cc1Nc1cnc(N2CC3CC(C2)O3)nc1] | 920 | 558.2 | 2 | 4-((2-(6-oxa-3-aza-bicyclo[3.1.1]heptan-3-yl)pyrimidin-5-yl)amino)-6-(3-cyanopyrrolo[1,2-b]pyridazin-7-yl)-N-((R)-2-fluoro-3-hydroxy-3-methyl-butyl)nicotinamide |
| 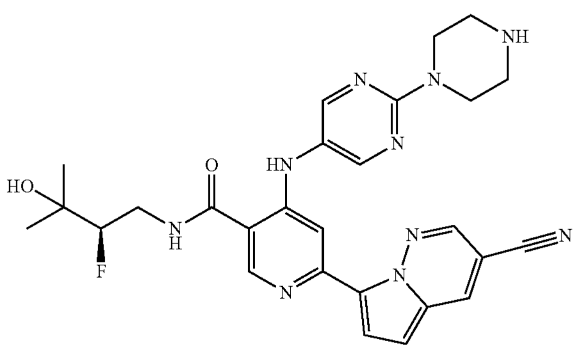 [SMILES: CC(C)(O)[C@H](F)CNC(=O)c1cnc(-c2ccc3cc(C#N)cnn23)cc1Nc1cnc(N2CCNCC2)nc1] | 921 | 545.2 | 14 | (R)-6-(3-cyanopyrrolo[1,2-b]pyridazin-7-yl)-N-(2-fluoro-3-hydroxy-3-methyl-butyl)-4-((2-(piperazin-1-yl)pyrimidin-5-yl)amino)nicotinamide |
| 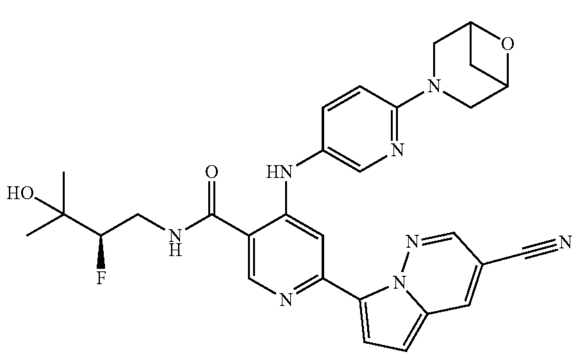 [SMILES: CC(C)(O)[C@H](F)CNC(=O)c1cnc(-c2ccc3cc(C#N)cnn23)cc1Nc1ccc(N2CC3CC(C2)O3)nc1] | 922 | 557.2 | 2 | 4-((6-(6-oxa-3-azabicyclo[3.1.1]heptan-3-yl)pyridin-3-yl)amino)-6-(3-cyanopyrrolo[1,2-b]pyridazin-7-yl)-N-((R)-2-fluoro-3-hydroxy-3-methylbutyl)nicotinamide |

TABLE 1-continued

| Structure | compound | ES/MS m/z | procedure | Name |
|---|---|---|---|---|
| 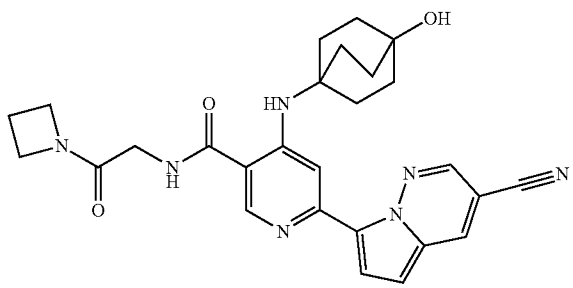 [SMILES: N#Cc1cnn2c(-c3cc(NC45CCC(O)(CC4)CC5)c(C(=O)NCC(=O)N4CCC4)cn3)ccc2c1] | 923 | 500.3 | 49 | N-(2-(azetidin-1-yl)-2-oxoethyl)-6-(3-cyanopyrrolo[1,2-b]pyridazin-7-yl)-4-((4-hydroxybicyclo[2.2.2]octan-1-yl)amino)nicotinamide |
| 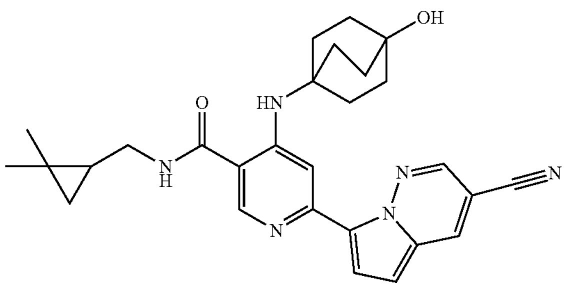 [SMILES: CC1(C)CC1CNC(=O)c1cnc(-c2ccc3cc(C#N)cnn23)cc1NC12CCC(O)(CC1)CC2] | 924 | 485.6 | 49 | 6-(3-cyanopyrrolo[1,2-b]pyridazin-7-yl)-N-((2,2-dimethylcyclopropyl)methyl)-4-((4-hydroxybicyclo[2.2.2]octan-1-yl)amino)nicotinamide |
| 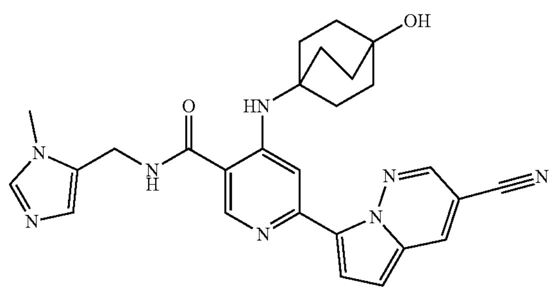 [SMILES: Cn1cncc1CNC(=O)c1cnc(-c2ccc3cc(C#N)cnn23)cc1NC12CCC(O)(CC1)CC2] | 925 | 497.3 | 49 | 6-(3-cyanopyrrolo[1,2-b]pyridazin-7-yl)-4-((4-hydroxybicyclo[2.2.2]octan-1-yl)amino)-N-((1-methyl-1H-imidazol-5-yl)methyl)nicotinamide |
| 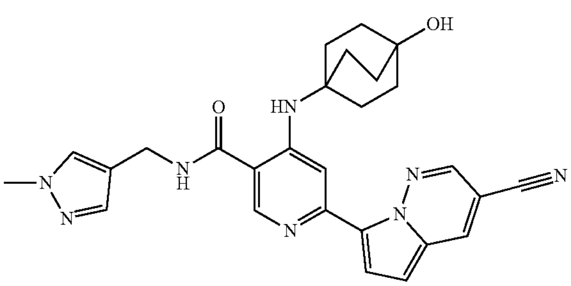 [SMILES: Cn1cc(CNC(=O)c2cnc(-c3ccc4cc(C#N)cnn34)cc2NC23CCC(O)(CC2)CC3)cn1] | 926 | 497.4 | 49 | 6-(3-cyanopyrrolo[1,2-b]pyridazin-7-yl)-4-((4-hydroxybicyclo[2.2.2]octan-1-yl)amino)-N-((1-methyl-1H-pyrazol-4-yl)methyl)nicotinamide |
| 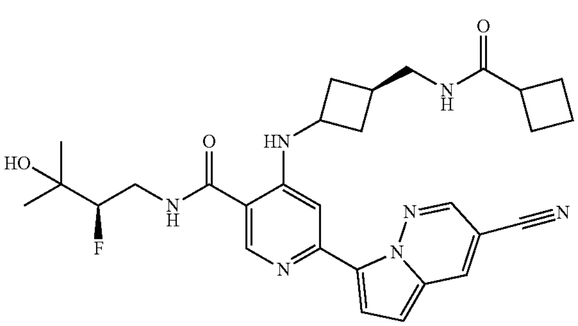 | 927 | 548.7 | 33 | 6-(3-cyanopyrrolo[1,2-b]pyridazin-7-yl)-4-(((1r,3R)-3-(cyclobutanecarboxamidomethyl)cyclobutyl)amino)-N-((R)-2-fluoro-3-hydroxy-3-methylbutyl)nicotinamide |

TABLE 1-continued

| Structure | compound | ES/MS m/z | procedure | Name |
|---|---|---|---|---|
| 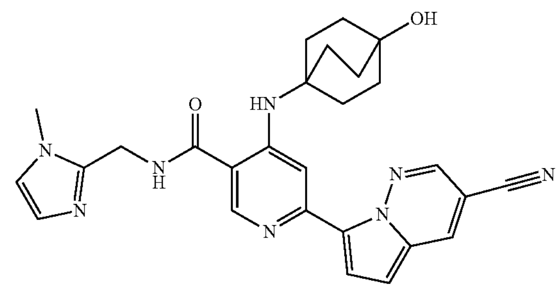 [SMILES: Cn1ccnc1CNC(=O)c1cnc(-c2ccc3cc(C#N)cnn23)cc1NC12CCC(O)(CC1)CC2] | 928 | 497.3 | 49 | 6-(3-cyanopyrrolo[1,2-b]pyridazin-7-yl)-4-((4-hydroxybicyclo[2.2.2]octan-1-yl)amino)-N-((1-methyl-1H-imidazol-2-yl)methyl)nicotinamide |
| 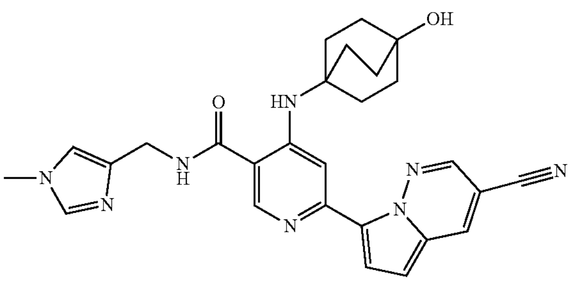 [SMILES: Cn1cnc(CNC(=O)c2cnc(-c3ccc4cc(C#N)cnn34)cc2NC23CCC(O)(CC2)CC3)c1] | 929 | 497.3 | 49 | 6-(3-cyanopyrrolo[1,2-b]pyridazin-7-yl)-4-((4-hydroxybicyclo[2.2.2]octan-1-yl)amino)-N-((1-methyl-1H-imidazol-4-yl)methyl)nicotinamide |
| 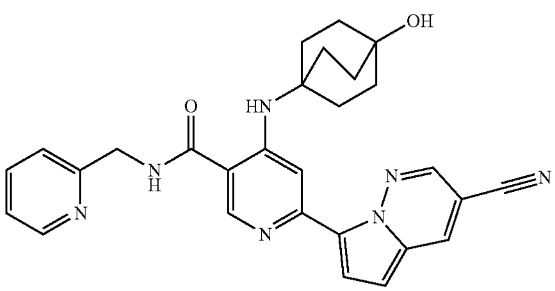 [SMILES: N#Cc1cnn2c(-c3cc(NC45CCC(O)(CC4)CC5)c(C(=O)NCc4ccccn4)cn3)ccc2c1] | 930 | 494.5 | 49 | 6-(3-cyanopyrrolo[1,2-b]pyridazin-7-yl)-4-((4-hydroxybicyclo[2.2.2]octan-1-yl)amino)-N-(pyridin-2-ylmethyl)nicotinamide |
| 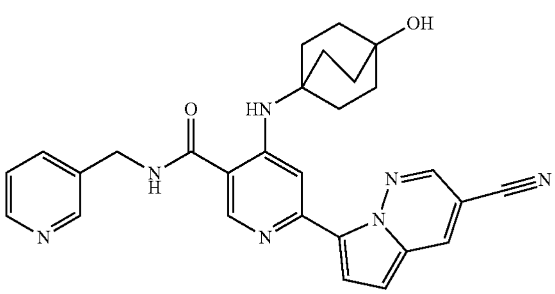 [SMILES: N#Cc1cnn2c(-c3cc(NC45CCC(O)(CC4)CC5)c(C(=O)NCc4cccnc4)cn3)ccc2c1] | 931 | 494.4 | 49 | 6-(3-cyanopyrrolo[1,2-b]pyridazin-7-yl)-4-((4-hydroxybicyclo[2.2.2]octan-1-yl)amino)-N-(pyridin-3-ylmethyl)nicotinamide |
| 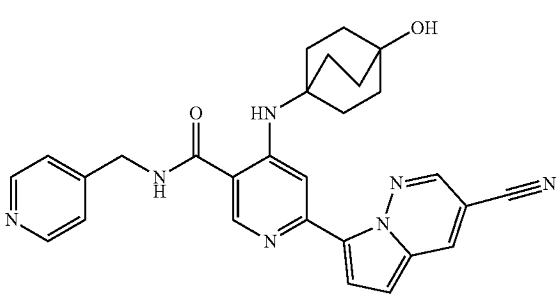 [SMILES: N#Cc1cnn2c(-c3cc(NC45CCC(O)(CC4)CC5)c(C(=O)NCc4ccncc4)cn3)ccc2c1] | 932 | 494.4 | 49 | 6-(3-cyanopyrrolo[1,2-b]pyridazin-7-yl)-4-((4-hydroxybicyclo[2.2.2]octan-1-yl)amino)-N-(pyridin-4-ylmethyl)nicotinamide |

TABLE 1-continued

| Structure | compound | ES/MS m/z | procedure | Name |
|---|---|---|---|---|
| 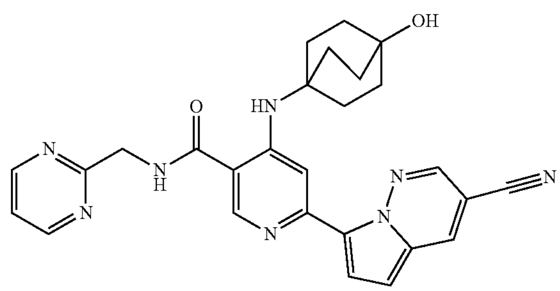 [SMILES: N#Cc1cnn2c(-c3cc(NC45CCC(O)(CC4)CC5)c(C(=O)NCc4ncccn4)cn3)ccc2c1] | 933 | 395.3 | 49 | 6-(3-cyanopyrrolo[1,2-b]pyridazin-7-yl)-4-((4-hydroxybicyclo[2.2.2]octan-1-yl)amino)-N-(pyrimidin-2-ylmethyl)nicotinamide |
| 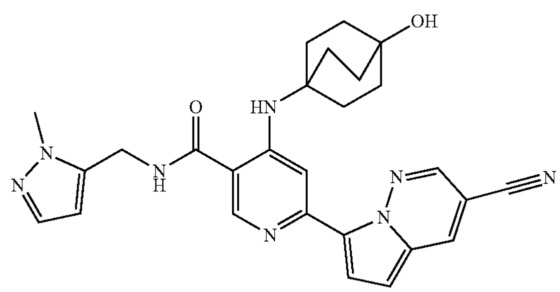 [SMILES: Cn1nccc1CNC(=O)c1cnc(-c2ccc3cc(C#N)cnn23)cc1NC12CCC(O)(CC1)CC2] | 934 | 497.5 | 49 | 6-(3-cyanopyrrolo[1,2-b]pyridazin-7-yl)-4-((4-hydroxybicyclo[2.2.2]octan-1-yl)amino)-N-((1-methyl-1H-pyrazol-5-yl)methyl)nicotinamide |
| 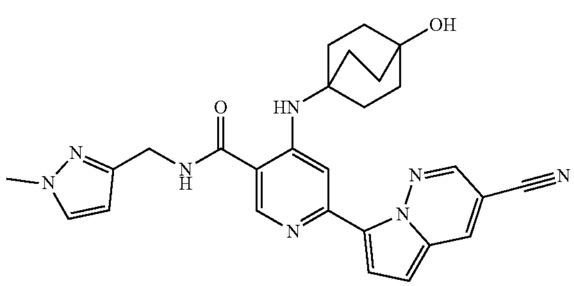 [SMILES: Cn1ccc(CNC(=O)c2cnc(-c3ccc4cc(C#N)cnn34)cc2NC23CCC(O)(CC2)CC3)n1] | 935 | 497.6 | 49 | 6-(3-cyanopyrrolo[1,2-b]pyridazin-7-yl)-4-((4-hydroxybicyclo[2.2.2]octan-1-yl)amino)-N-((1-methyl-1H-pyrazol-3-yl)methyl)nicotinamide |
| 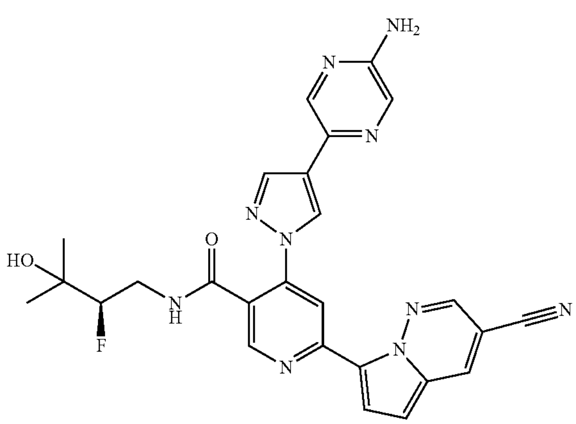 [SMILES: CC(C)(O)[C@H](F)CNC(=O)c1cnc(-c2ccc3cc(C#N)cnn23)cc1-n1cc(-c2cnc(N)cn2)cn1] | 936 | 527.1 | 2 | (R)-4-(4-(5-aminopyrazin-2-yl)-1H-pyrazol-1-yl)-6-(3-cyanopyrrolo[1,2-b]pyridazin-7-yl)-N-(2-fluoro-3-hydroxy-3-methylbutyl)nicotinamide |

TABLE 1-continued

| Structure | compound | ES/MS m/z | procedure | Name |
|---|---|---|---|---|
| 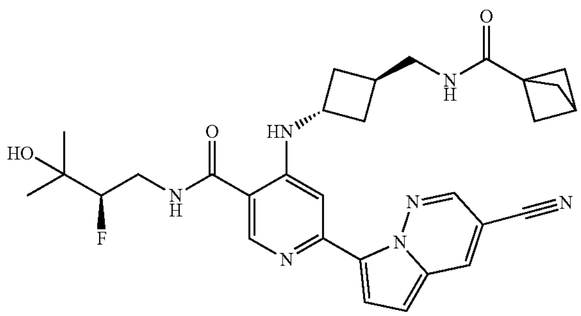 [SMILES: CC(C)(O)[C@H](F)CNC(=O)c1cnc(-c2ccc3cc(C#N)cnn23)cc1N[C@H]1C[C@H](CNC(=O)C23CC(C2)C3)C1] | 937 | 560.4 | 33 | 4-(((1r,3R)-3-((bicyclo[1.1.1]pentane-1-carboxamido)methyl)cyclobutyl)amino)-6-(3-cyanopyrrolo[1,2-b]pyridazin-7-yl)-N-((R)-2-fluoro-3-hydroxy-3-methylbutyl)nicotinamide |
| 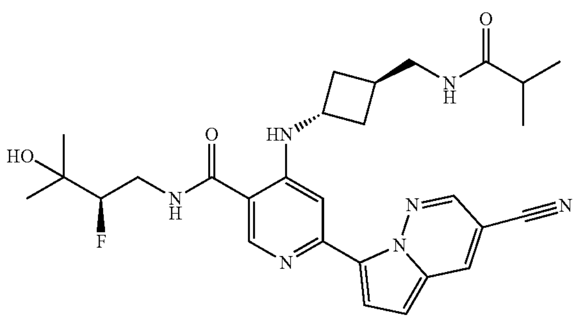 [SMILES: CC(C)C(=O)NC[C@H]1C[C@H](Nc2cc(-c3ccc4cc(C#N)cnn34)ncc2C(=O)NC[C@@H](F)C(C)(C)O)C1] | 938 | 536.3 | 67 | 6-(3-cyanopyrrolo[1,2-b]pyridazin-7-yl)-N-((R)-2-fluoro-3-hydroxy-3-methylbutyl)-4-(((1r,3R)-3-(isobutyramidomethyl)cyclobutyl)amino)nicotinamide |
| 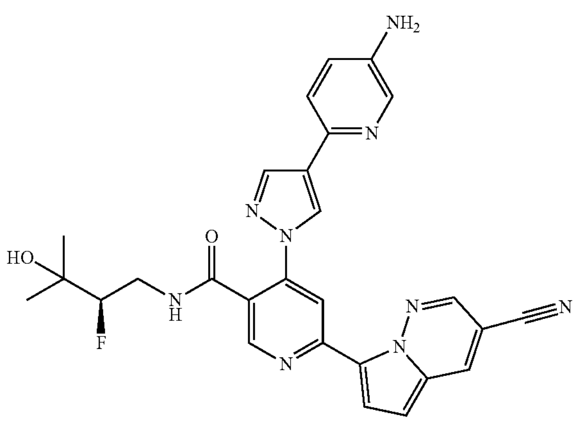 [SMILES: CC(C)(O)[C@H](F)CNC(=O)c1cnc(-c2ccc3cc(C#N)cnn23)cc1-n1cc(-c2ccc(N)cn2)cn1] | 939 | 526.1 | 2 | (R)-4-(4-(5-aminopyridin-2-yl)-1H-pyrazol-1-yl)-6-(3-cyanopyrrolo[1,2-b]pyridazin-7-yl)-N-(2-fluoro-3-hydroxy-3-methyl-butyl)nicotinamide |
| 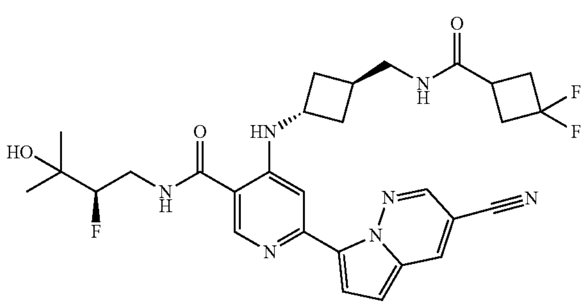 [SMILES: CC(C)(O)[C@H](F)CNC(=O)c1cnc(-c2ccc3cc(C#N)cnn23)cc1N[C@H]1C[C@H](CNC(=O)C2CC(F)(F)C2)C1] | 940 | 584.4 | 33 | 6-(3-cyanopyrrolo[1,2-b]pyridazin-7-yl)-4-(((1r,3R)-3-((3,3-difluorocyclobutane-1-carboxamido)methyl)cyclobutyl)amino)-N-((R)-2-fluoro-3-hydroxy-3-methylbutyl)nicotinamide |

TABLE 1-continued

| Structure | compound | ES/MS m/z | procedure | Name |
|---|---|---|---|---|
| 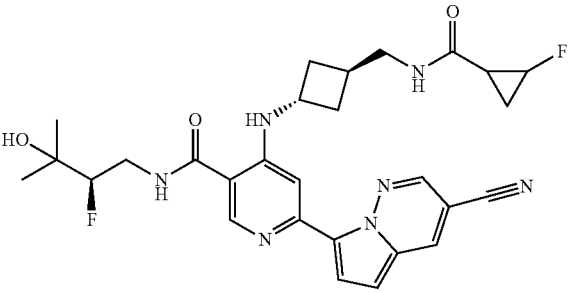 [SMILES: CC(C)(O)[C@H](F)CNC(=O)c1cnc(-c2ccc3cc(C#N)cnn23)cc1N[C@H]1C[C@H](CNC(=O)C2CC2F)C1] | 941 | 552.4 | 33 | 6-(3-cyanopyrrolo[1,2-b]pyridazin-7-yl)-N-((R)-2-fluoro-3-hydroxy-3-methylbutyl)-4-(((1R,3R)-3-((((1R,2R)-2-fluorocyclopropane-1-carboxamido)methyl)cyclobutyl)amino)nicotinamide |
| 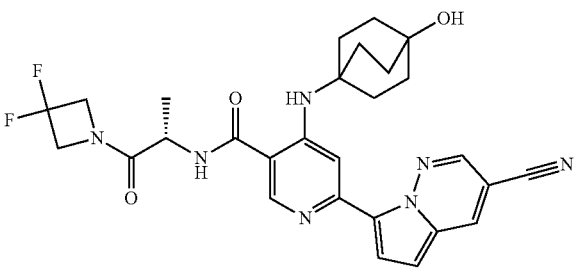 [SMILES: C[C@H](NC(=O)c1cnc(-c2ccc3cc(C#N)cnn23)cc1NC12CCC(O)(CC1)CC2)C(=O)N1CC(F)(F)C1] | 942 | 550.3 | 49 | (S)-6-(3-cyanopyrrolo[1,2-b]pyridazin-7-yl)-N-(1-(3,3-difluoroazetidin-1-yl)-1-oxopropan-2-yl)-4-((4-hydroxybicyclo[2.2.2]octan-1-yl)amino)nicotinamide |
| 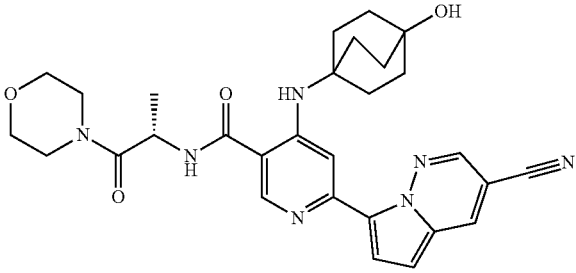 [SMILES: C[C@H](NC(=O)c1cnc(-c2ccc3cc(C#N)cnn23)cc1NC12CCC(O)(CC1)CC2)C(=O)N1CCOCC1] | 943 | 544.3 | 49 | (S)-6-(3-cyano-pyrrolo[1,2-b]pyridazin-7-yl)-4-((4-hydroxy-bicyclo[2.2.2]octan-1-yl)amino)-N-(1-morpholino-1-oxopropan-2-yl)nicotinamide |
| 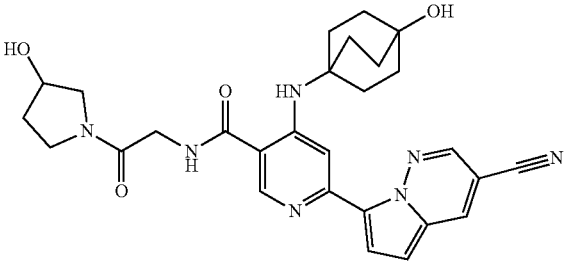 [SMILES: N#Cc1cnn2c(-c3cc(NC45CCC(O)(CC4)CC5)c(C(=O)NCC(=O)N4CCC(O)C4)cn3)ccc2c1] | 944 | 530.2 | 49 | (S)-6-(3-cyano-pyrrolo[1,2-b]pyridazin-7-yl)-4-((4-hydroxy-bicyclo[2.2.2]octan-1-yl)amino)-N-(2-(3-hydroxypyrrolidin-1-yl)-2-oxoethyl)nicotinamide |
| 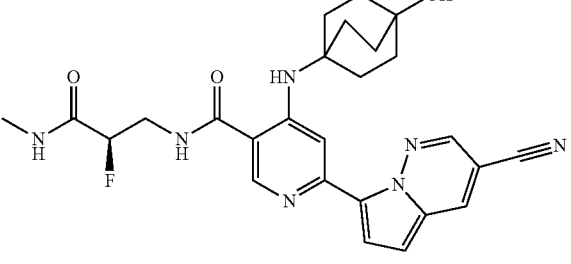 | 945 | 506.3 | 49 | (R)-6-(3-cyanopyrrolo[1,2-b]pyridazin-7-yl)-N-(2-fluoro-3-(methylamino)-3-oxopropyl)-4-((4-hydroxybicyclo[2.2.2]octan-1-yl)amino)nicotinamide |

TABLE 1-continued

| Structure | compound | ES/MS m/z | procedure | Name |
|---|---|---|---|---|
| 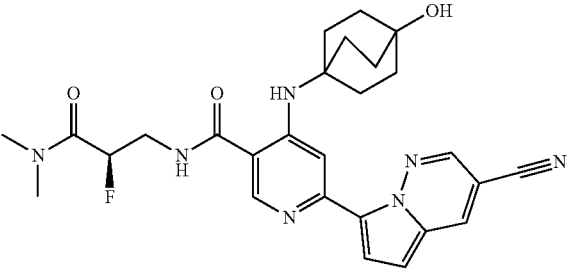 [SMILES: CN(C)C(=O)[C@H](F)CNC(=O)c1cnc(-c2ccc3cc(C#N)cnn23)cc1NC12CCC(O)(CC1)CC2] | 946 | 520.3 | 49 | (R)-6-(3-cyanopyrrolo[1,2-b]pyridazin-7-yl)-N-(3-(dimethylamino)-2-fluoro-3-oxopropyl)-4-((4-hydroxybicyclo[2.2.2]octan-1-yl)amino)nicotinamide |
| 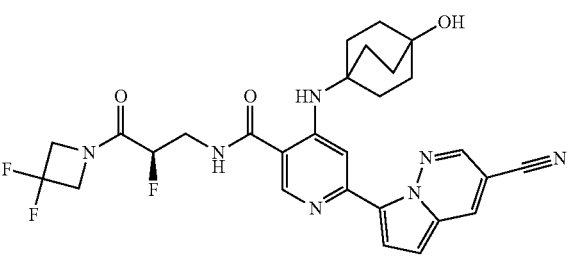 [SMILES: N#Cc1cnn2c(-c3cc(NC45CCC(O)(CC4)CC5)c(C(=O)NC[C@@H](F)C(=O)N4CC(F)(F)C4)cn3)ccc2c1] | 947 | 568.3 | 49 | (R)-6-(3-cyanopyrrolo[1,2-b]pyridazin-7-yl)-N-(3-(3,3-difluoroazetidin-1-yl)-2-fluoro-3-oxopropyl)-4-((4-hydroxybicyclo[2.2.2]octan-1-yl)amino)nicotinamide |
| 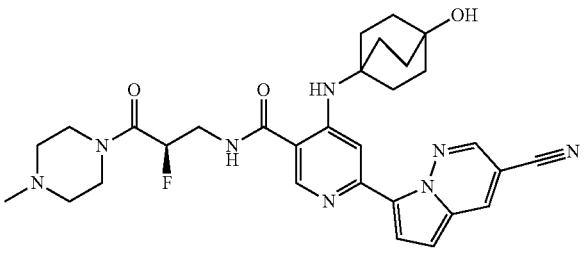 [SMILES: CN1CCN(C(=O)[C@H](F)CNC(=O)c2cnc(-c3ccc4cc(C#N)cnn34)cc2NC23CCC(O)(CC2)CC3)CC1] | 948 | 575.3 | 49 | (R)-6-(3-cyanopyrrolo[1,2-b]pyridazin-7-yl)-N-(2-fluoro-3-(4-methylpiperazin-1-yl)-3-oxopropyl)-4-((4-hydroxybicyclo[2.2.2]octan-1-yl)amino)nicotinamide |
| 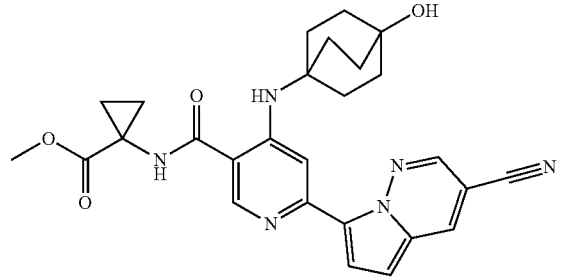 [SMILES: COC(=O)C1(NC(=O)c2cnc(-c3ccc4cc(C#N)cnn34)cc2NC23CCC(O)(CC2)CC3)CC1] | 949 | 501.4 | 3 | methyl 1-(6-(3-cyano-pyrrolo[1,2-b]pyridazin-7-yl)-4-((4-hydroxy-bicyclo[2.2.2]octan-1-yl)amino)nicotinamido)cyclopropane-1-carboxylate |
| 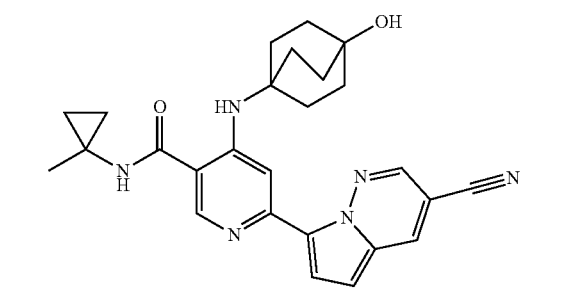 [SMILES: CC1(NC(=O)c2cnc(-c3ccc4cc(C#N)cnn34)cc2NC23CCC(O)(CC2)CC3)CC1] | 950 | 457.5 | 3 | 6-(3-cyanopyrrolo[1,2-b]pyridazin-7-yl)-4-((4-hydroxybicyclo[2.2.2]octan-1-yl)amino)-N-(1-methylcyclopropyl)nicotinamide |

| Structure | compound | ES/MS m/z | procedure | Name |
|---|---|---|---|---|
| 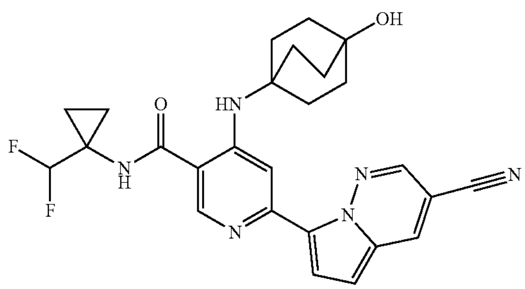 [SMILES: N#Cc1cnn2c(-c3cc(NC45CCC(O)(CC4)CC5)c(C(=O)NC4(C(F)F)CC4)cn3)ccc2c1] | 951 | 493.4 | 3 | 6-(3-cyanopyrrolo[1,2-b]pyridazin-7-yl)-N-(1-(difluoromethyl)cyclopropyl)-4-((4-hydroxybicyclo[2.2.2]octan-1-yl)amino)nicotinamide |
| 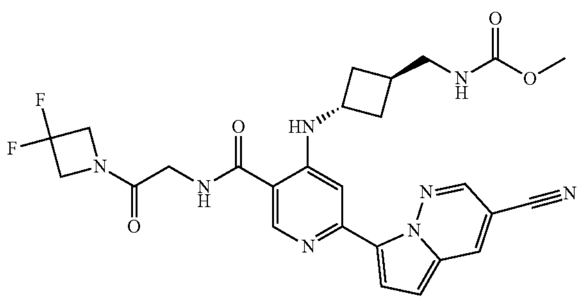 [SMILES: COC(=O)NC[C@H]1C[C@H](Nc2cc(-c3ccc4cc(C#N)cnn34)ncc2C(=O)NCC(=O)N2CC(F)(F)C2)C1] | 952 | 553.2 | 3 | methyl (((1r,3r)-3-((2-(3-cyanopyrrolo[1,2-b]pyridazin-7-yl)-5-((2-(3,3-difluoroazetidin-1-yl)-2-oxoethyl)carbamoyl)pyridin-4-yl)amino)cyclobutyl)methyl)carbamate |
| 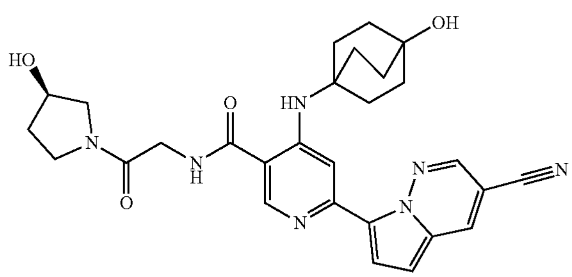 [SMILES: N#Cc1cnn2c(-c3cc(NC45CCC(O)(CC4)CC5)c(C(=O)NCC(=O)N4CC[C@@H](O)C4)cn3)ccc2c1] | 953 | 530.3 | 49 | (R)-6-(3-cyanopyrrolo[1,2-b]pyridazin-7-yl)-4-((4-hydroxybicyclo[2.2.2]octan-1-yl)amino)-N-(2-(3-hydroxypyrrolidin-1-yl)-2-oxoethyl)nicotinamide |
| 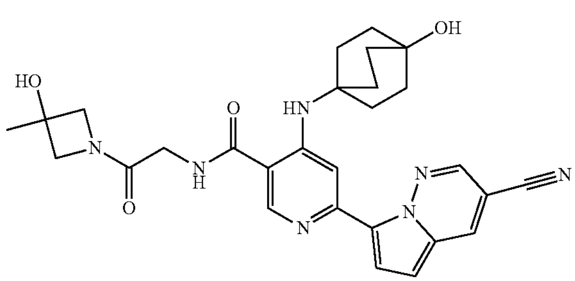 [SMILES: CC1(O)CN(C(=O)CNC(=O)c2cnc(-c3ccc4cc(C#N)cnn34)cc2NC23CCC(O)(CC2)CC3)C1] | 954 | 530.3 | 49 | 6-(3-cyanopyrrolo[1,2-b]pyridazin-7-yl)-N-(2-(3-hydroxy-3-methylazetidin-1-yl)-2-oxoethyl)-4-((4-hydroxybicyclo[2.2.2]octan-1-yl)amino)nicotinamide |
| 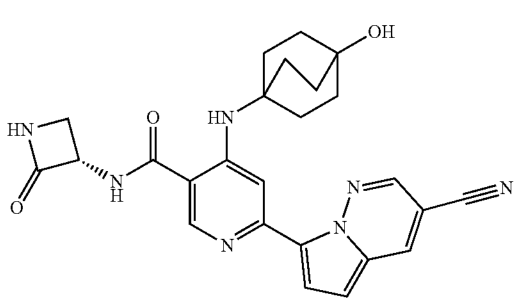 [SMILES: N#Cc1cnn2c(-c3cc(NC45CCC(O)(CC4)CC5)c(C(=O)N[C@H]4CNC4=O)cn3)ccc2c1] | 955 | 472.2 | 3 | (S)-6-(3-cyanopyrrolo[1,2-b]pyridazin-7-yl)-4-((4-hydroxybicyclo[2.2.2]octan-1-yl)amino)-N-(2-oxoazetidin-3-yl)nicotinamide |

TABLE 1-continued

| Structure | compound | ES/MS m/z | procedure | Name |
|---|---|---|---|---|
| 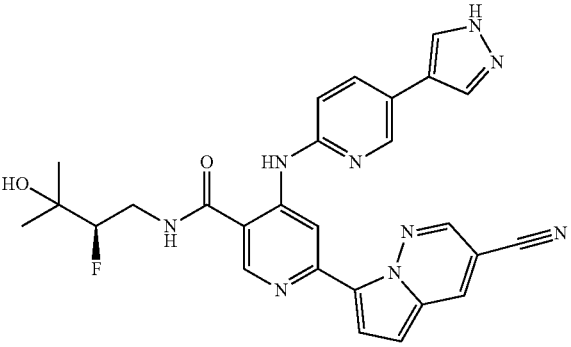 [SMILES: CC(C)(O)[C@H](F)CNC(=O)c1cnc(-c2ccc3cc(C#N)cnn23)cc1Nc1ccc(-c2cn[nH]c2)cn1] | 956 | 526.2 | 84 | (R)-4-((5-(1H-pyrazol-4-yl)pyridin-2-yl)amino)-6-(3-cyanopyrrolo[1,2-b]pyridazin-7-yl)-N-(2-fluoro-3-hydroxy-3-methyl-butyl)nicotinamide |
| 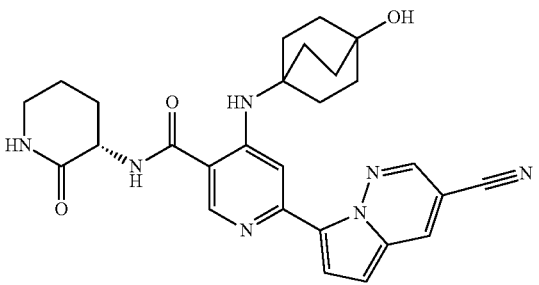 [SMILES: N#Cc1cnn2c(-c3cc(NC45CCC(O)(CC4)CC5)c(C(=O)N[C@H]4CCCNC4=O)cn3)ccc2c1] | 957 | 500.4 | 3 | (S)-6-(3-cyanopyrrolo[1,2-b]pyridazin-7-yl)-4-((4-hydroxybicyclo[2.2.2]octan-1-yl)amino)-N-(2-oxo-piperidin-3-yl)nicotinamide |
| 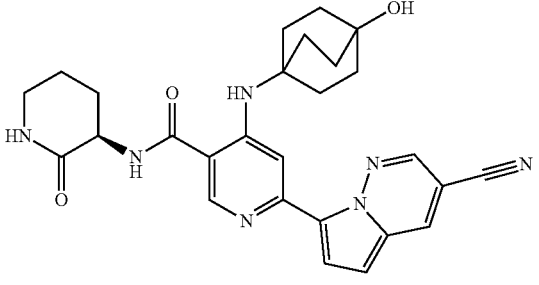 [SMILES: N#Cc1cnn2c(-c3cc(NC45CCC(O)(CC4)CC5)c(C(=O)N[C@@H]4CCCNC4=O)cn3)ccc2c1] | 958 | 500.3 | 3 | (R)-6-(3-cyanopyrrolo[1,2-b]pyridazin-7-yl)-4-((4-hydroxybicyclo[2.2.2]octan-1-yl)amino)-N-(2-oxo-piperidin-3-yl)nicotinamide |
| 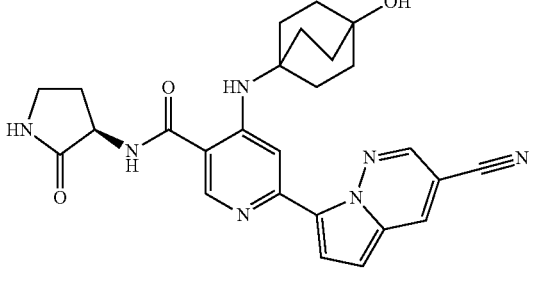 | 959 | 486.3 | 3 | (R)-6-(3-cyanopyrrolo[1,2-b]pyridazin-7-yl)-4-((4-hydroxybicyclo[2.2.2]octan-1-yl)amino)-N-(2-oxo-pyrrolidin-3-yl)nicotinamide |
| 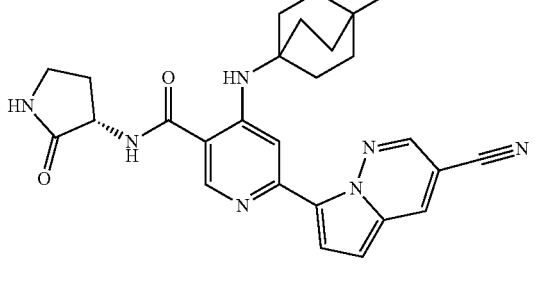 | 960 | 486.3 | 3 | (S)-6-(3-cyanopyrrolo[1,2-b]pyridazin-7-yl)-4-((4-hydroxybicyclo[2.2.2]octan-1-yl)amino)-N-(2-oxo-pyrrolidin-3-yl)nicotinamide |

TABLE 1-continued

| Structure | compound | ES/ MS m/z | procedure | Name |
|---|---|---|---|---|
| 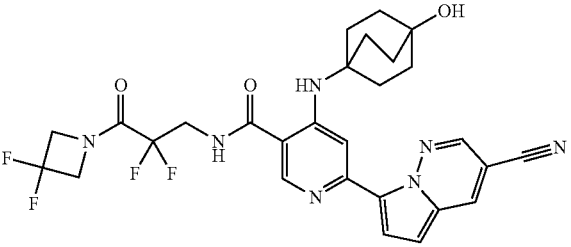 [SMILES: N#Cc1cnn2c(-c3cc(NC45CCC(O)(CC4)CC5)c(C(=O)NCC(F)(F)C(=O)N4CC(F)(F)C4)cn3)ccc2c1] | 961 | 586.3 | 49 | 6-(3-cyanopyrrolo[1,2-b]pyridazin-7-yl)-N-(3-(3,3-difluoroazetidin-1-yl)-2,2-difluoro-3-oxopropyl)-4-((4-hydroxybicyclo[2.2.2]octan-1-yl)amino)nicotinamide |
| 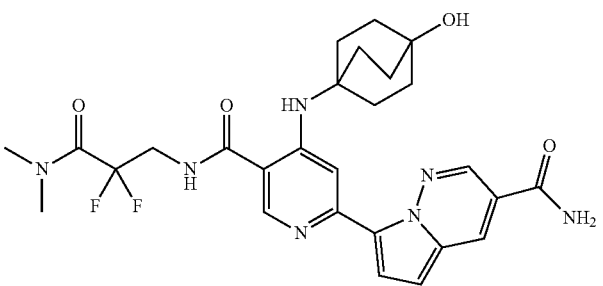 [SMILES: CN(C)C(=O)C(F)(F)CNC(=O)c1cnc(-c2ccc3cc(C(N)=O)cnn23)cc1NC12CCC(O)(CC1)CC2] | 962 | 556.2 | 85 | 7-(5-((3-(dimethylamino)-2,2-difluoro-3-oxopropyl)carbamoyl)-4-((4-hydroxybicyclo[2.2.2]octan-1-yl)amino)pyridin-2-yl)pyrrolo[1,2-b]pyridazine-3-carboxamide |
| 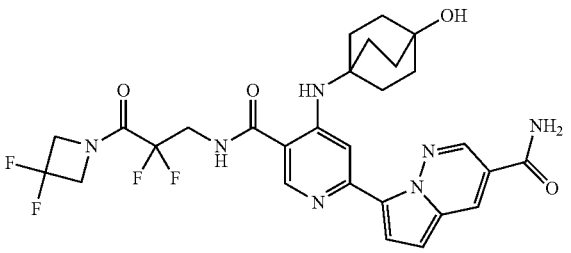 [SMILES: NC(=O)c1cnn2c(-c3cc(NC45CCC(O)(CC4)CC5)c(C(=O)NCC(F)(F)C(=O)N4CC(F)(F)C4)cn3)ccc2c1] | 963 | 604.2 | 85 | 7-(5-((3-(3,3-difluoroazetidin-1-yl)-2,2-difluoro-3-oxopropyl)carbamoyl)-4-((4-hydroxybicyclo[2.2.2]octan-1-yl)amino)pyridin-2-yl)pyrrolo[1,2-b]pyridazine-3-carboxamide |
| 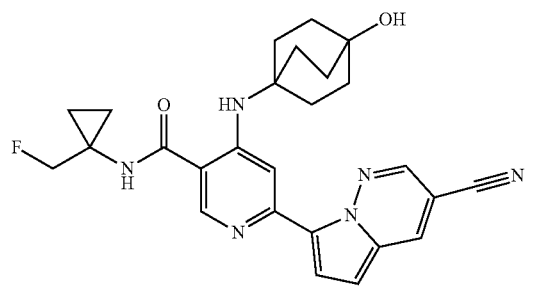 [SMILES: N#Cc1cnn2c(-c3cc(NC45CCC(O)(CC4)CC5)c(C(=O)NC4(CF)CC4)cn3)ccc2c1] | 964 | 475.3 | 3 | 6-(3-cyanopyrrolo[1,2-b]pyridazin-7-yl)-N-(1-(fluoromethyl)cyclopropyl)-4-((4-hydroxybicyclo[2.2.2]octan-1-yl)amino)nicotinamide |
| 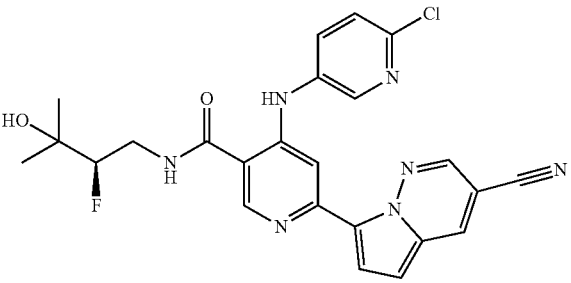 | 965 | 494.3 | 83 | (R)-4-((6-chloropyridin-3-yl)amino)-6-(3-cyanopyrrolo[1,2-b]pyridazin-7-yl)-N-(2-fluoro-3-hydroxy-3-methylbutyl)nicotinamide |

TABLE 1-continued

| Structure | compound | ES/MS m/z | procedure | Name |
|---|---|---|---|---|
| 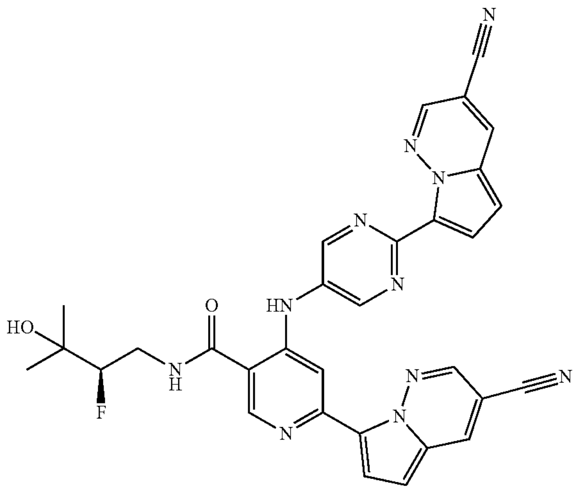 [SMILES: CC(C)(O)[C@H](F)CNC(=O)c1cnc(-c2ccc3cc(C#N)cnn23)cc1Nc1cnc(-c2ccc3cc(C#N)cnn23)nc1] | 966 | 602.3 | 83 | (R)-6-(3-cyanopyrrolo[1,2-b]pyridazin-7-yl)-4-((2-(3-cyanopyrrolo[1,2-b]pyridazin-7-yl)pyrimidin-5-yl)amino)-N-(2-fluoro-3-hydroxy-3-methylbutyl) nicotinamide |
| 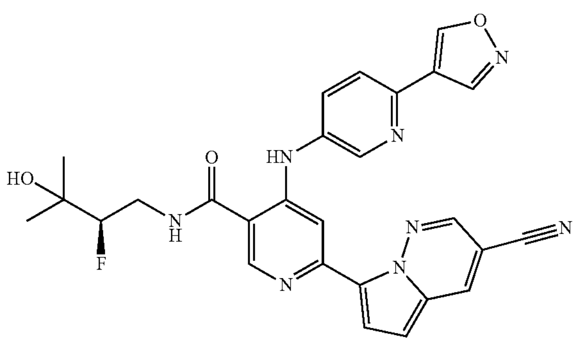 [SMILES: CC(C)(O)[C@H](F)CNC(=O)c1cnc(-c2ccc3cc(C#N)cnn23)cc1Nc1ccc(-c2cnoc2)nc1] | 967 | 527.2 | 84 | (R)-6-(3-cyanopyrrolo[1,2-b]pyridazin-7-yl)-N-(2-fluoro-3-hydroxy-3-methylbutyl)-4-((6-(isoxazol-4-yl)pyridin-3-yl)amino) nicotinamide |
| 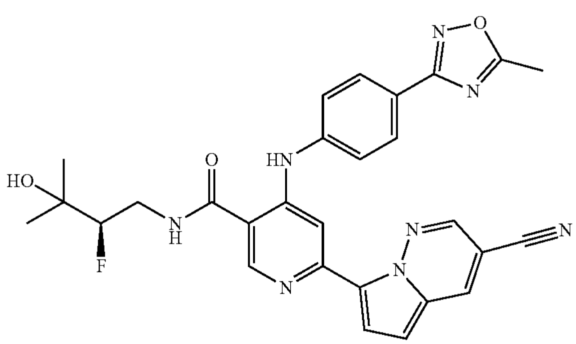 [SMILES: Cc1nc(-c2ccc(Nc3cc(-c4ccc5cc(C#N)cnn45)ncc3C(=O)NC[C@@H](F)C(C)(C)O)cc2)no1] | 968 | 541.4 | 2 | (R)-6-(3-cyanopyrrolo[1,2-b]pyridazin-7-yl)-N-(2-fluoro-3-hydroxy-3-methylbutyl)-4-((4-(5-methyl-1,2,4-oxadiazol-3-yl)phenyl)amino) nicotinamide |
| 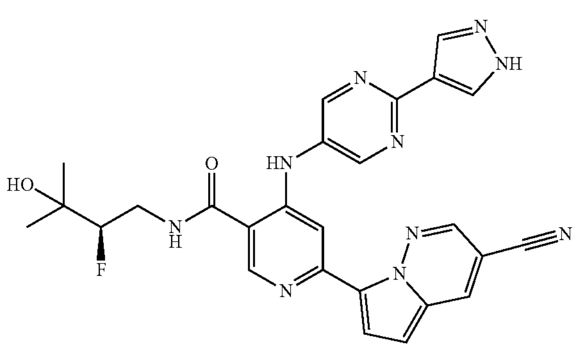 [SMILES: CC(C)(O)[C@H](F)CNC(=O)c1cnc(-c2ccc3cc(C#N)cnn23)cc1Nc1cnc(-c2cn[nH]c2)nc1] | 969 | 527.2 | 2 | (R)-4-((2-(1H-pyrazol-4-yl)pyrimidin-5-yl)amino)-6-(3-cyanopyrrolo[1,2-b]pyridazin-7-yl)-N-(2-fluoro-3-hydroxy-3-methyl-butyl)nicotinamide |

TABLE 1-continued

| Structure | compound | ES/MS m/z | procedure | Name |
|---|---|---|---|---|
| 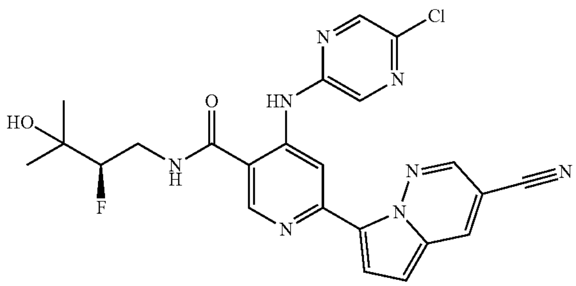 | 970 | 495.3 | 83 | (R)-4-((5-chloropyrazin-2-yl)amino)-6-(3-cyano-pyrrolo[1,2-b]pyridazin-7-yl)-N-(2-fluoro-3-hydroxy-3-methylbutyl)nicotinamide |
| 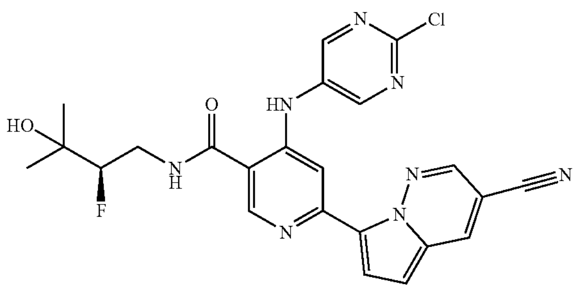 [SMILES: CC(C)(O)[C@H](F)CNC(=O)c1cnc(-c2ccc3cc(C#N)cnn23)cc1Nc1cnc(Cl)nc1] | 971 | 495.2 | 83 | (R)-4-((2-chloropyrimidin-5-yl)amino)-6-(3-cyano-pyrrolo[1,2-b]pyridazin-7-yl)-N-(2-fluoro-3-hydroxy-3-methylbutyl)nicotinamide |
| 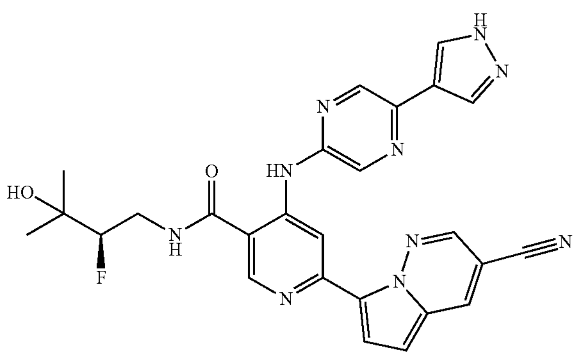 [SMILES: CC(C)(O)[C@H](F)CNC(=O)c1cnc(-c2ccc3cc(C#N)cnn23)cc1Nc1cnc(-c2cn[nH]c2)cn1] | 972 | 527.2 | 84 | (R)-4-((5-(1H-pyrazol-4-yl)pyrazin-2-yl)amino)-6-(3-cyanopyrrolo[1,2-b]pyridazin-7-yl)-N-(2-fluoro-3-hydroxy-3-methyl-butyl)nicotinamide |
| 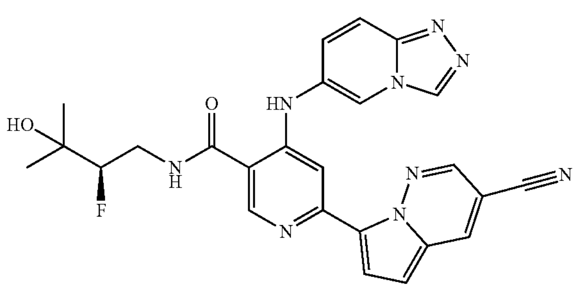 [SMILES: CC(C)(O)[C@H](F)CNC(=O)c1cnc(-c2ccc3cc(C#N)cnn23)cc1Nc1ccc2nncn2c1] | 973 | 500.2 | 2 | (R)-4-([1,2,4]triazolo[4,3-a]pyridin-6-ylamino)-6-(3-cyanopyrrolo[1,2-b]pyridazin-7-yl)-N-(2-fluoro-3-hydroxy-3-methylbutyl)nicotinamide |
| 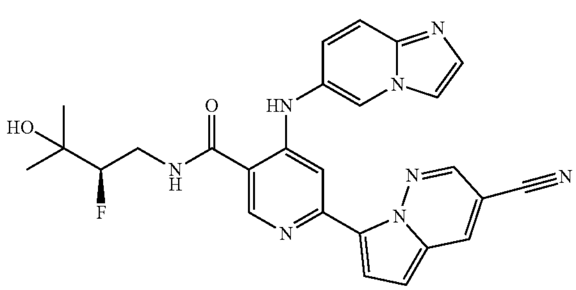 | 974 | 499.2 | 2 | (R)-6-(3-cyanopyrrolo[1,2-b]pyridazin-7-yl)-N-(2-fluoro-3-hydroxy-3-methylbutyl)-4-(imidazo[1,2-a]pyridin-6-ylamino)nicotinamide |

TABLE 1-continued

| Structure | compound | ES/MS m/z | procedure | Name |
|---|---|---|---|---|
| 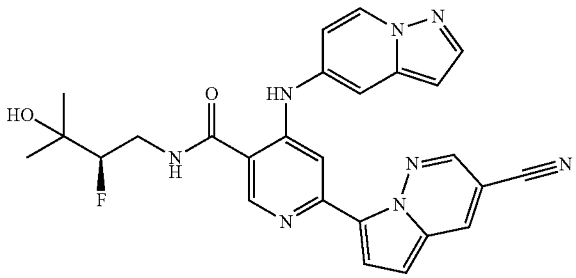 [SMILES: CC(C)(O)[C@H](F)CNC(=O)c1cnc(-c2ccc3cc(C#N)cnn23)cc1Nc1ccn2nccc2c1] | 975 | 499.3 | 2 | (R)-6-(3-cyanopyrrolo[1,2-b]pyridazin-7-yl)-N-(2-fluoro-3-hydroxy-3-methyl-butyl)-4-(pyrazolo[1,5-a]pyridin-5-ylamino)nicotinamide |

1H NMR

Proton NMR data is shown in table 2.

TABLE 2

| compound | 1H-NMR |
|---|---|
| 1 | 1H NMR (400 MHz, Acetonitrile-d3) δ 9.76 (s, 1H), 8.64 (s, 1H), 8.62 (d, J = 2.2 Hz, 1H), 8.58 (d, J = 2.2 Hz, 1H), 8.00 (d, J = 5.1 Hz, 1H), 7.77 (s, 1H), 7.42 (s, 1H), 7.16 (d, J = 5.1 Hz, 1H), 4.86 (d, J = 6.5 Hz, 2H), 4.72 (d, J = 6.5 Hz, 2H), 1.83 (s, 3H), 1.27 (d, J = 2.0 Hz, 6H). |
| 2 | 1H NMR (400 MHz, Methanol-d4) δ 8.76 (d, J = 2.2 Hz, 1H), 8.67 (d, J = 2.2 Hz, 1H), 8.54 (s, 1H), 8.01 (d, J = 5.0 Hz, 1H), 7.86 (s, 1H), 7.21 (d, J = 5.1 Hz, 1H), 4.61-4.28 (m, 1H), 4.14-3.75 (m, 3H), 3.48 (td, J = 15.6, 15.2, 9.4 Hz, 1H), 2.32 (d, J = 12.5 Hz, 1H), 2.00 (d, J = 37.3 Hz, 3H), 1.70-1.34 (m, 4H), 1.29 (d, J = 1.6 Hz, 6H). |
| 3 | 1H NMR (400 MHz, Chloroform-d) δ 9.99 (d, J = 7.5 Hz, 1H), 9.03 (s, 1H), 8.45 (d, J = 2.2 Hz, 1H), 8.32 (d, J = 2.1 Hz, 1H), 8.10 (d, J = 5.1 Hz, 1H), 7.93 (s, 1H), 7.69 (d, J = 7.6 Hz, 1H), 7.09 (d, J = 5.0 Hz, 1H), 3.93 (h, J = 6.4 Hz, 1H), 3.89-3.77 (m, 1H), 2.08 (d, J = 12.2 Hz, 2H), 1.93 (d, J = 12.5 Hz, 2H), 1.43 (d, J = 6.4 Hz, 6H), 1.40-1.21 (m, 3H), 1.19 (s, 6H). |
| 4 | 1H NMR (400 MHz, Methanol-d4) δ 8.77 (d, J = 2.3 Hz, 1H), 8.77 (s, 1H), 8.71 (d, J = 2.2 Hz, 1H), 8.62 (dd, J = 4.9, 1.4 Hz, 1H), 8.57 (d, J = 2.2 Hz, 1H), 8.22 (s, 1H), 8.08 (ddd, J = 8.2, 2.6, 1.4 Hz, 1H), 7.84 (d, J = 5.1 Hz, 1H), 7.73 (ddd, J = 8.2, 4.9, 0.8 Hz, 1H), 7.16 (d, J = 5.0 Hz, 1H), 4.47 (ddd, J = 49.0, 9.3, 2.1 Hz, 1H), 3.99 (ddd, J = 36.4, 14.5, 2.1 Hz, 1H), 3.62-3.45 (m, 1H), 1.30 (d, J = 1.6 Hz, 6H). |
| 5 | 1H NMR (400 MHz, Methanol-d4) δ 8.74 (d, J = 2.2 Hz, 1H), 8.65 (d, J = 2.2 Hz, 1H), 8.53 (s, 1H), 7.97 (d, J = 5.0 Hz, 1H), 7.81 (s, 1H), 7.20 (d, J = 5.1 Hz, 1H), 4.44-4.28 (m, 1H), 4.13 (hept, J = 6.5 Hz, 1H), 2.62-2.48 (m, 1H), 2.37-2.20 (m, 2H), 2.18-1.93 (m, 5H), 1.90-1.78 (m, 1H), 1.39 (d, J = 6.4 Hz, 6H), 1.08 (s, 3H), 1.07 (s, 3H). |
| 6 | 1H NMR (400 MHz, Methanol-d4) δ 8.74 (d, J = 2.2 Hz, 1H), 8.65 (d, J = 2.2 Hz, 1H), 8.55 (s, 1H), 7.98 (d, J = 5.0 Hz, 1H), 7.84 (s, 1H), 7.20 (d, J = 5.1 Hz, 1H), 4.12 (ddt, J = 15.2, 11.0, 5.3 Hz, 2H), 4.05-3.94 (m, 2H), 3.53 (td, J = 11.8, 2.1 Hz, 2H), 1.99-1.88 (m, 2H), 1.67 (qd, J = 11.9, 4.4 Hz, 2H), 1.39 (d, J = 6.4 Hz, 6H). |
| 7 | 1H NMR (400 MHz, Methanol-d4) δ 8.63 (s, 1H), 8.55 (d, J = 2.2 Hz, 1H), 8.48 (d, J = 2.2 Hz, 1H), 8.13 (s, 1H), 7.80 (d, J = 4.8 Hz, 1H), 7.08 (d, J = 4.9 Hz, 1H), 5.09 (dt, J = 7.7, 6.7 Hz, 1H), 4.93 (t, J = 7.0 Hz, 2H), 4.72 (t, J = 6.6 Hz, 2H), 3.87 (p, J = 6.3 Hz, 1H), 1.33 (d, J = 6.3 Hz, 6H). |
| 8 | 1H NMR (400 MHz, Methanol-d4) δ 8.75 (d, J = 2.2 Hz, 1H), 8.69 (d, J = 2.1 Hz, 1H), 8.64 (s, 1H), 8.04 (d, J = 5.1 Hz, 1H), 7.87 (s, 1H), 7.22 (d, J = 5.1 Hz, 1H), 4.84-4.68 (m, 1H), 4.42 (ddd, J = 49.0, 9.4, 2.1 Hz, 1H), 4.07-3.72 (m, 2H), 3.61-3.40 (m, 2H), 2.99 (dd, J = 17.1, 8.0 Hz, 1H), 2.48 (dd, J = 17.1, 4.7 Hz, 1H), 1.28 (d, J = 1.7 Hz, 6H). |
| 9 | 1H NMR (400 MHz, Methanol-d4) δ 8.91 (d, J = 2.2 Hz, 1H), 8.68 (d, J = 2.3 Hz, 1H), 8.55 (s, 1H), 7.97 (d, J = 5.0 Hz, 1H), 7.80 (s, 1H), 7.11 (d, J = 5.0 Hz, 1H), 4.15 (p, J = 6.4 Hz, 1H), 3.54 (qd, J = 13.7, 6.4 Hz, 2H), 3.26-3.02 (m, 2H), 2.97-2.73 (m, 2H), 2.50-2.29 (m, 1H), 2.08-1.81 (m, 1H), 1.40 (d, J = 6.4 Hz, 6H). |
| 10 | 1H NMR (400 MHz, Methanol-d4) δ 8.84 (s, 1H), 8.55 (d, J = 11.5 Hz, 2H), 8.34 (s, 1H), 7.78 (s, 1H), 7.11 (d, J = 5.0 Hz, 1H), 4.51-4.27 (m, 2H), 3.95 (m, 1H), 3.50 (td, J = 14.8, 9.4 Hz, 1H), 3.13 (s, 3H), 1.27 (d, J = 6.4 Hz, 6H). |
| 11 | 1H NMR (400 MHz, Methanol-d4) δ 8.73 (d, J = 2.2 Hz, 1H), 8.62 (d, J = 2.2 Hz, 1H), 8.56 (s, 1H), 7.87 (s, 1H), 7.83 (d, J = 5.0 Hz, 1H), 7.19 (d, J = 5.0 Hz, 1H), 4.42 (ddd, J = 49.1, 9.3, 2.2 Hz, 1H), 4.10-3.80 (m, 1H), 3.60-3.38 (m, 1H), 1.28 (d, J = 1.6 Hz, 6H). |

TABLE 2-continued

| compound | 1H-NMR |
|---|---|
| 12 | 1H NMR (400 MHz, Methanol-d4) δ 8.75 (d, J = 2.2 Hz, 1H), 8.66 (d, J = 2.2 Hz, 1H), 8.57 (s, 1H), 8.00 (d, J = 5.0 Hz, 1H), 7.86 (s, 1H), 7.21 (d, J = 5.0 Hz, 1H), 4.15 (hept, J = 6.2 Hz, 1H), 3.89 (d, J = 9.7 Hz, 1H), 3.14 (s, 1H), 2.15 (d, J = 10.2 Hz, 4H), 1.69-1.45 (m, 4H), 1.40 (d, J = 6.3 Hz, 6H). |
| 13 | 1H NMR (400 MHz, Methanol-d4) δ 8.75 (d, J = 2.2 Hz, 1H), 8.66 (d, J = 2.2 Hz, 1H), 8.54 (s, 1H), 7.99 (d, J = 5.0 Hz, 1H), 7.84 (s, 1H), 7.21 (d, J = 5.0 Hz, 1H), 4.15 (hept, J = 6.9, 6.4 Hz, 1H), 3.94-3.81 (m, 1H), 3.73-3.58 (m, 1H), 2.11-1.96 (m, 4H), 1.93 (s, 3H), 1.59-1.45 (m, 2H), 1.45-1.36 (m, 8H). |
| 14 | 1H NMR (400 MHz, Methanol-d4) δ 8.76 (d, J = 2.2 Hz, 1H), 8.70 (d, J = 0.8 Hz, 1H), 8.66 (d, J = 2.2 Hz, 1H), 8.02 (d, J = 5.1 Hz, 1H), 7.78 (s, 1H), 7.22 (d, J = 5.1 Hz, 1H), 4.43 (ddd, J = 49.1, 9.3, 2.2 Hz, 1H), 4.36-4.26 (m, 1H), 4.16 (s, 2H), 3.93 (ddd, J = 36.2, 14.6, 2.2 Hz, 1H), 3.64-3.49 (m, 1H), 2.62-2.50 (m, 2H), 2.47-2.37 (m, 2H), 2.33-2.19 (m, 4H), 1.30 (d, J = 1.7 Hz, 6H). |
| 15 | 1H NMR (400 MHz, Methanol-d4) δ 8.75 (d, J = 2.1 Hz, 1H), 8.68 (d, J = 2.2 Hz, 1H), 8.63 (s, 1H), 8.00 (d, J = 5.1 Hz, 1H), 7.78 (s, 1H), 7.21 (d, J = 5.1 Hz, 1H), 4.51-4.31 (m, 3H), 4.24 (t, J = 6.4 Hz, 1H), 3.94 (ddd, J = 36.2, 14.6, 2.2 Hz, 1H), 3.59-3.45 (m, 1H), 3.00 (s, 3H), 2.48 (dd, J = 13.0, 7.7 Hz, 2H), 2.31-2.11 (m, 4H), 2.05 (d, J = 14.6 Hz, 2H), 1.30 (d, J = 1.7 Hz, 6H). |
| 16 | 1H NMR (400 MHz, Methanol-d4) δ 8.76 (d, J = 2.2 Hz, 1H), 8.68 (d, J = 2.2 Hz, 1H), 8.60 (s, 1H), 8.05 (d, J = 5.1 Hz, 1H), 7.91 (s, 1H), 7.22 (d, J = 5.1 Hz, 1H), 4.52-4.31 (m, 2H), 4.22-4.11 (m, 1H), 3.93 (dd, J = 34.6, 14.4 Hz, 2H), 3.58-3.38 (m, 2H), 3.17-3.04 (m, 1H), 2.16 (s, 4H), 1.80-1.53 (m, 2H), 1.29 (d, J = 1.6 Hz, 6H). |
| 17 | 1H NMR (400 MHz, Methanol-d4) δ 9.13 (s, 1H), 8.81-8.75 (m, 1H), 8.53 (s, 1H), 7.97 (d, J = 5.0 Hz, 1H), 7.76 (s, 1H), 7.10 (d, J = 5.0 Hz, 1H), 4.43 (ddd, J = 49.1, 9.4, 2.1 Hz, 1H), 4.16 (p, J = 6.3 Hz, 1H), 3.93 (ddd, J = 36.3, 14.6, 2.1 Hz, 1H), 3.49 (td, J = 15.3, 9.3 Hz, 1H), 1.41 (d, J = 6.4 Hz, 6H), 1.29 (d, J = 1.6 Hz, 6H). |
| 18 | 1H NMR (400 MHz, Methanol-d4) δ 8.74 (d, J = 2.2 Hz, 1H), 8.65 (d, J = 2.2 Hz, 1H), 8.49 (s, 1H), 7.98 (d, J = 5.1 Hz, 1H), 7.84 (s, 1H), 7.20 (d, J = 5.0 Hz, 1H), 4.15 (p, J = 6.4 Hz, 1H), 3.54 (d, J = 6.6 Hz, 2H), 2.83-2.71 (m, 1H), 1.40 (d, J = 6.4 Hz, 6H), 1.38-1.26 (m, 1H), 0.94-0.79 (m, 2H). |
| 19 | 1H NMR (400 MHz, Methanol-d4) δ 8.74 (d, J = 2.2 Hz, 1H), 8.65 (d, J = 2.1 Hz, 1H), 8.49 (s, 1H), 7.98 (d, J = 5.0 Hz, 1H), 7.84 (s, 1H), 7.20 (d, J = 5.1 Hz, 1H), 4.15 (p, J = 6.4 Hz, 1H), 3.54 (d, J = 6.6 Hz, 2H), 2.77 (dt, J = 7.6, 4.0 Hz, 1H), 1.40 (d, J = 6.4 Hz, 6H), 1.36-1.29 (m, 1H), 0.95-0.82 (m, 2H). |
| 20 | 1H NMR (400 MHz, Chloroform-d) δ 9.77 (d, J = 7.5 Hz, 1H), 9.17 (s, 1H), 8.98 (s, 1H), 8.49 (d, J = 2.1 Hz, 1H), 8.32 (d, J = 2.1 Hz, 1H), 8.03 (d, J = 5.0 Hz, 1H), 7.78 (s, 1H), 7.09 (d, J = 5.0 Hz, 1H), 4.02-3.89 (m, 3H), 3.49-3.39 (m, 2H), 1.44 (d, J = 6.4 Hz, 6H). |
| 21 | 1H NMR (400 MHz, Chloroform-d) δ 9.89 (d, J = 7.4 Hz, 1H), 8.80 (s, 1H), 8.46 (d, J = 2.1 Hz, 1H), 8.32 (d, J = 2.1 Hz, 1H), 8.11-7.98 (m, 2H), 7.88 (s, 1H), 7.84 (d, J = 8.1 Hz, 2H), 7.34 (d, J = 8.0 Hz, 2H), 7.08 (d, J = 5.1 Hz, 1H), 4.04-3.88 (m, 1H), 3.70 (d, J = 6.3 Hz, 2H), 2.99 (t, J = 6.5 Hz, 2H), 1.45 (d, J = 6.3 Hz, 6H). |
| 22 | 1H NMR (400 MHz, Chloroform-d) δ 10.02 (d, J = 7.4 Hz, 1H), 9.10 (s, 1H), 8.45 (d, J = 2.1 Hz, 1H), 8.32 (d, J = 2.1 Hz, 1H), 8.10 (d, J = 5.1 Hz, 1H), 7.99 (d, J = 7.7 Hz, 1H), 7.94 (s, 1H), 7.08 (d, J = 5.0 Hz, 1H), 5.72-5.56 (m, 1H), 3.93 (dq, J = 13.2, 6.6 Hz, 2H), 2.81 (d, J = 4.7 Hz, 3H), 2.16-2.00 (m, 3H), 1.95 (d, J = 13.4 Hz, 2H), 1.64 (q, J = 12.5, 12.0 Hz, 2H), 1.43 (d, J = 6.4 Hz, 7H). |
| 23 | 1H NMR (400 MHz, Methanol-d4) δ 8.76 (d, J = 2.2 Hz, 1H), 8.67 (d, J = 2.1 Hz, 1H), 8.66 (s, 1H), 8.04 (d, J = 5.1 Hz, 1H), 7.90 (s, 1H), 7.22 (d, J = 5.0 Hz, 1H), 4.52-4.33 (m, 1H), 4.28-4.17 (m, 1H), 4.02-3.83 (m, 1H), 3.60-3.49 (m, 3H), 3.29-3.22 (m, 1H), 2.43-2.31 (m, 2H), 1.99-1.83 (m, 2H), 1.30 (d, J = 1.7 Hz, 6H). |
| 24 | 1H NMR (400 MHz, Methanol-d4) δ 8.77 (d, J = 2.2 Hz, 1H), 8.68 (d, J = 2.2 Hz, 1H), 8.65 (s, 1H), 8.05-8.00 (m, 2H), 7.23 (d, J = 5.1 Hz, 1H), 4.50-4.32 (m, 2H), 4.22 (s, 2H), 4.01-3.82 (m, 1H), 3.59-3.44 (m, 1H), 2.49-2.39 (m, 2H), 2.35-2.18 (m, 4H), 1.94 (t, J = 12.7 Hz, 2H), 1.29 (d, J = 1.6 Hz, 6H). |
| 25 | 1H NMR (400 MHz, Methanol-d4) δ 8.77 (d, J = 2.2 Hz, 1H), 8.69 (s, 1H), 8.66 (d, J = 2.2 Hz, 1H), 8.08 (d, J = 5.1 Hz, 1H), 8.01 (s, 1H), 7.22 (d, J = 5.1 Hz, 1H), 4.95-4.86 (m, 1H), 4.43 (ddd, J = 48.9, 9.3, 2.1 Hz, 1H), 4.04-3.84 (m, 1H), 3.74 (dd, J = 13.4, 8.0 Hz, 1H), 3.61-3.46 (m, 2H), 3.15 (dd, J = 13.8, 2.6 Hz, 1H), 2.77 (t, J = 11.8 Hz, 1H), 1.86-1.74 (m, 1H), 1.71-1.61 (m, 1H), 1.30 (d, J = 1.8 Hz, 6H), 1.18-1.04 (m, 1H), 0.91 (q, J = 5.7 Hz, 1H). |
| 26 | 1H NMR (400 MHz, Methanol-d4) δ 8.83-8.57 (m, 3H), 8.01 (d, J = 5.1 Hz, 1H), 7.99 (s, 1H), 7.50-7.05 (m, 2H), 4.57-4.48 (m, 2H), 4.45-4.34 (m, 1H), 4.05-3.94 (m, 1H), 3.96-3.84 (m, 1H), 3.73 (dd, J = 13.6, 7.5 Hz, 1H), 3.63-3.45 (m, 1H), 3.23 (s, 1H), 1.63-1.38 (m, 2H), 1.38-1.26 (m, 6H), 1.21 (td, J = 9.0, 5.8 Hz, 1H), 0.76 (q, J = 5.7 Hz, 1H).; 1H NMR (400 MHz, Methanol-d4) δ 8.77 (d, J = 2.2 Hz, 1H), 8.69 (s, 1H), 8.66 (d, J = 2.2 Hz, 1H), 8.08 (d, J = 5.1 Hz, 1H), 8.01 (s, 1H), 7.22 (d, J = 5.1 Hz, 1H), 4.95-4.86 (m, 1H), 4.43 (ddd, J = 48.9, 9.3, 2.1 Hz, 1H), 4.04-3.84 (m, 1H), 3.74 (dd, J = 13.4, 8.0 Hz, 1H), 3.61-3.46 (m, 2H), 3.15 (dd, J = 13.8, 2.6 Hz, 1H), 2.77 (t, J = 11.8 Hz, 1H), 1.86-1.74 (m, 1H), 1.71-1.61 (m, 1H), 1.30 (d, J = 1.8 Hz, 6H), 1.18-1.04 (m, 1H), 0.91 (q, J = 5.7 Hz, 1H). |
| 27 | 1H NMR (400 MHz, Methanol-d4) δ 8.76 (d, J = 2.1 Hz, 1H), 8.68 (s, 1H), 8.66 (d, J = 2.2 Hz, 1H), 8.02 (d, J = 5.0 Hz, 1H), 7.99 (s, 1H), 7.23 (d, J = 5.1 Hz, 1H), 4.42 (ddd, J = 49.0, 9.3, 2.1 Hz, 1H), 4.27 (s, 1H), 4.00-3.81 (m, 1H), 3.58-3.44 (m, 3H), 3.43-3.36 (m, 2H), 2.71 (s, 2H), 2.27-2.12 (m, 2H), 2.02-1.86 (m, 2H), 1.29 (d, J = 1.7 Hz, 6H). |

TABLE 2-continued

| compound | 1H-NMR |
|---|---|
| 28 | 1H NMR (400 MHz, Methanol-d4) δ 8.75 (d, J = 2.2 Hz, 1H), 8.74 (s, 1H), 8.66 (d, J = 2.2 Hz, 1H), 8.04 (d, J = 5.1 Hz, 1H), 7.98 (s, 1H), 7.21 (d, J = 5.1 Hz, 1H), 4.45 (dd, J = 49.1, 7.2 Hz, 1H), 4.17 (t, J = 5.0 Hz, 1H), 3.94 (ddd, J = 35.8, 14.4, 1.8 Hz, 1H), 3.58 (td, J = 15.6, 9.4 Hz, 1H), 3.39 (d, J = 13.7 Hz, 2H), 3.23 (d, J = 13.6 Hz, 2H), 2.71 (s, 2H), 2.35-2.22 (m, 2H), 2.03-1.91 (m, 2H), 1.30 (d, J = 1.7 Hz, 6H).; 1H NMR (400 MHz, Methanol-d4) δ 8.76 (d, J = 2.1 Hz, 1H), 8.68 (d, J = 2.2 Hz, 1H), 8.02 (d, J = 5.0 Hz, 1H), 7.99 (s, 1H), 7.23 (d, J = 5.1 Hz, 1H), 4.42 (ddd, J = 49.0, 9.3, 2.1 Hz, 1H), 4.27 (s, 1H), 4.00-3.81 (m, 1H), 3.58-3.44 (m, 3H), 3.43-3.36 (m, 2H), 2.71 (s, 2H), 2.27-2.12 (m, 2H), 2.02-1.86 (m, 2H), 1.29 (d, J = 1.7 Hz, 6H). |
| 29 | 1H NMR (400 MHz, Methanol-d4) δ 8.76 (d, J = 2.2 Hz, 1H), 8.68 (d, J = 2.2 Hz, 1H), 8.58 (s, 1H), 8.02 (s, 1H), 7.99 (d, J = 5.1 Hz, 1H), 7.23 (d, J = 5.1 Hz, 1H), 4.51-4.29 (m, 4H), 3.93 (dd, J = 35.7, 15.2 Hz, 1H), 3.56-3.40 (m, 2H), 3.02 (s, 3H), 2.33-2.17 (m, 3H), 2.07 (t, J = 7.2 Hz, 2H), 1.94-1.80 (m, 2H), 1.29 (d, J = 1.6 Hz, 6H). |
| 30 | 1H NMR (400 MHz, Methanol-d4) δ 8.75 (d, J = 2.2 Hz, 1H), 8.71-8.67 (m, 1H), 8.63-8.59 (m, 1H), 8.00 (dd, J = 5.6, 3.2 Hz, 2H), 7.22 (d, J = 5.1 Hz, 1H), 4.63-4.31 (m, 2H), 3.96 (ddd, J = 35.8, 14.7, 4.6 Hz, 1H), 3.83-3.59 (m, 1H), 3.59-3.44 (m, 2H), 2.92-2.85 (m, 3H), 1.75 (dt, J = 15.1, 8.2 Hz, 1H), 1.62-1.42 (m, 1H), 1.30 (d, J = 1.7 Hz, 8H), 1.07-0.80 (m, 1H), 0.78-0.63 (m, 1H). |
| 31 | 1H NMR (400 MHz, Methanol-d4) δ 8.76 (d, J = 2.2 Hz, 1H), 8.69-8.66 (m, 2H), 8.05 (d, J = 5.1 Hz, 1H), 7.93 (s, 1H), 7.22 (d, J = 5.0 Hz, 1H), 4.43 (ddd, J = 49.1, 9.3, 2.1 Hz, 1H), 4.16 (t, J = 4.7 Hz, 1H), 4.04-3.85 (m, 1H), 3.62-3.51 (m, 1H), 3.51-3.43 (m, 2H), 3.20 (dd, J = 11.9, 4.8 Hz, 2H), 2.95-2.90 (m, 3H), 2.59 (s, 2H), 2.12-2.02 (m, 2H), 1.96-1.87 (m, 2H), 1.29 (d, J = 1.7 Hz, 6H). |
| 32 | 1H NMR (400 MHz, Methanol-d4) δ 8.77 (d, J = 2.2 Hz, 1H), 8.72-8.65 (m, 2H), 8.05 (d, J = 5.1 Hz, 1H), 7.92 (s, 1H), 7.23 (d, J = 5.1 Hz, 1H), 4.53-4.35 (m, 2H), 4.20 (s, 1H), 3.94 (ddd, J = 36.5, 14.5, 2.1 Hz, 1H), 3.64-3.50 (m, 1H), 3.47-3.39 (m, 1H), 3.27-3.19 (m, 2H), 2.65 (ddd, J = 14.8, 11.0, 3.6 Hz, 1H), 2.17 (d, J = 11.8 Hz, 1H), 2.02 (d, J = 11.9 Hz, 1H), 1.68 (dt, J = 14.9, 4.0 Hz, 1H), 1.30 (d, J = 1.7 Hz, 6H). |
| 33 | 1H NMR (400 MHz, Methanol-d4) δ 8.76 (d, J = 2.2 Hz, 1H), 8.70 (d, J = 2.2 Hz, 1H), 8.55 (s, 1H), 8.30 (s, 1H), 7.92 (d, J = 5.1 Hz, 1H), 7.22 (d, J = 5.1 Hz, 1H), 4.42 (ddd, J = 49.1, 9.4, 2.1 Hz, 1H), 3.93 (ddd, J = 36.6, 14.6, 2.1 Hz, 1H), 3.55-3.42 (m, 1H), 1.63 (s, 9H), 1.29 (d, J = 1.7 Hz, 6H). |
| 34 | 1H NMR (400 MHz, Methanol-d4) δ 8.77 (s, 1H), 8.73 (d, J = 2.2 Hz, 1H), 8.65 (d, J = 2.2 Hz, 1H), 7.98 (d, J = 5.1 Hz, 1H), 7.83 (s, 1H), 7.20 (d, J = 5.0 Hz, 1H), 4.16 (p, J = 6.5 Hz, 1H), 3.25 (s, 3H), 1.41 (d, J = 6.4 Hz, 6H). |
| 35 | 1H NMR (400 MHz, Methanol-d4) δ 8.63 (s, 1H), 8.55 (d, J = 2.2 Hz, 1H), 8.48 (d, J = 2.3 Hz, 1H), 8.15 (s, 1H), 7.79 (d, J = 4.9 Hz, 1H), 7.08 (d, J = 4.8 Hz, 1H), 4.40 (d, J = 8.2 Hz, 1H), 4.00 (d, J = 8.2 Hz, 1H), 3.92 (p, J = 6.4 Hz, 1H), 3.64-3.49 (m, 2H), 1.37 (d, J = 6.4 Hz, 6H), 1.34 (s, 3H). |
| 36 | 1H NMR (400 MHz, Methanol-d4) δ 8.74 (d, J = 2.2 Hz, 1H), 8.65 (d, J = 2.2 Hz, 1H), 8.57 (s, 1H), 7.98 (d, J = 5.0 Hz, 1H), 7.84 (s, 1H), 7.20 (d, J = 5.1 Hz, 1H), 4.58 (ddd, J = 9.6, 7.5, 3.8 Hz, 1H), 4.15 (p, J = 6.4 Hz, 1H), 4.05-3.90 (m, 2H), 3.84 (td, J = 8.3, 5.8 Hz, 1H), 3.77 (dd, J = 9.3, 3.5 Hz, 1H), 2.39-2.26 (m, 1H), 2.09-1.90 (m, 1H), 1.40 (d, J = 6.4 Hz, 6H). |
| 37 | 1H NMR (400 MHz, Methanol-d4) δ 8.74 (d, J = 2.2 Hz, 1H), 8.65 (d, J = 2.2 Hz, 1H), 8.57 (s, 1H), 7.98 (d, J = 5.1 Hz, 1H), 7.84 (s, 1H), 7.20 (d, J = 5.1 Hz, 1H), 4.58 (dq, J = 9.7, 3.8 Hz, 1H), 4.15 (p, J = 6.4 Hz, 1H), 4.08-3.89 (m, 2H), 3.84 (td, J = 8.4, 5.9 Hz, 1H), 3.77 (dd, J = 9.3, 3.5 Hz, 1H), 2.33 (dtd, J = 13.0, 8.0, 6.7 Hz, 1H), 2.11-1.91 (m, 1H), 1.40 (d, J = 6.5 Hz, 6H). |
| 38 | 1H NMR (400 MHz, DMSO-d6) δ 8.81 (d, J = 2.2 Hz, 1H), 8.68 (d, J = 2.3 Hz, 1H), 8.62 (s, 1H), 8.49 (dd, J = 13.9, 6.1 Hz, 2H), 8.04 (s, 1H), 7.80 (d, J = 4.8 Hz, 1H), 7.08 (d, J = 4.7 Hz, 1H), 3.76 (h, J = 6.4 Hz, 1H), 2.75 (d, J = 4.4 Hz, 3H), 1.25 (d, J = 6.4 Hz, 6H). |
| 39 | 1H NMR (400 MHz, DMSO-d6) δ 8.81 (d, J = 2.2 Hz, 1H), 8.72 (d, J = 7.2 Hz, 1H), 8.69 (d, J = 2.0 Hz, 2H), 8.04 (s, 2H), 7.81 (d, J = 4.8 Hz, 1H), 7.33 (s, 1H), 7.08 (d, J = 4.8 Hz, 1H), 3.76 (h, J = 6.4 Hz, 1H), 1.25 (d, J = 6.3 Hz, 6H). |
| 40 | 1H NMR (400 MHz, Methanol-d4) δ 8.75 (d, J = 2.2 Hz, 1H), 8.69 (d, J = 2.1 Hz, 1H), 8.61 (s, 1H), 8.03 (d, J = 5.1 Hz, 1H), 7.72 (s, 1H), 7.21 (d, J = 5.1 Hz, 1H), 4.53-4.29 (m, 2H), 3.95 (ddd, J = 36.3, 14.6, 2.1 Hz, 1H), 3.60-3.40 (m, 1H), 3.25 (s, 1H), 2.88-2.69 (m, 1H), 1.29 (d, J = 1.6 Hz, 6H). 2 protons obscured by solvent peaks. |
| 41 | 1H NMR (400 MHz, Methanol-d4) δ 8.74 (d, J = 2.1 Hz, 1H), 8.65 (d, J = 2.2 Hz, 1H), 8.48 (s, 1H), 7.99 (d, J = 5.1 Hz, 1H), 7.82 (s, 1H), 7.20 (d, J = 5.1 Hz, 1H), 4.15 (p, J = 6.4 Hz, 1H), 3.55-3.45 (m, 2H), 1.83-1.72 (m, 2H), 1.40 (d, J = 6.4 Hz, 6H), 1.27 (s, 6H). |
| 42 | 1H NMR (400 MHz, Methanol-d4) δ 8.75 (d, J = 2.2 Hz, 1H), 8.67 (d, J = 2.2 Hz, 1H), 8.59 (s, 1H), 8.03 (d, J = 5.1 Hz, 1H), 7.88 (s, 1H), 7.21 (d, J = 5.1 Hz, 1H), 4.42 (ddd, J = 49.0, 9.4, 2.0 Hz, 1H), 4.18-4.08 (m, 1H), 4.04-3.83 (m, 3H), 3.66 (t, J = 10.5 Hz, 2H), 3.56-3.41 (m, 1H), 2.10 (d, J = 12.8 Hz, 2H), 1.80-1.65 (m, 2H), 1.29 (d, J = 1.6 Hz, 6H). |
| 43 | 1H NMR (400 MHz, Methanol-d4) δ 8.73 (d, J = 2.2 Hz, 1H), 8.68 (s, 1H), 8.62 (d, J = 2.2 Hz, 1H), 8.12 (d, J = 0.8 Hz, 1H), 8.10 (s, 1H), 7.84 (d, J = 5.0 Hz, 2H), 7.18 (d, J = 5.1 Hz, 1H), 5.67-5.58 (m, 1H), 5.26-5.00 (m, 4H), 4.46 (ddd, J = 49.0, 9.4, 2.1 Hz, 1H), 4.09-3.84 (m, 1H), 3.64-3.43 (m, 1H), 1.29 (d, J = 1.7 Hz, 6H). |

TABLE 2-continued

| compound | 1H-NMR |
|---|---|
| 44 | 1H NMR (400 MHz, Methanol-d4) δ 8.59 (d, J = 2.2 Hz, 1H), 8.34 (d, J = 2.2 Hz, 1H), 8.12 (s, 1H), 7.43 (d, J = 4.8 Hz, 1H), 7.32 (s, 1H), 7.08 (d, J = 4.8 Hz, 1H), 4.27-4.06 (m, 1H), 3.99-3.78 (m, 4H), 3.79-3.60 (m, 1H), 3.56-3.49 (m, 1H), 2.96 (s, 4H), 1.20 (d, J = 2.0 Hz, 6H). |
| 45 | 1H NMR (400 MHz, Methanol-d4) δ 8.74 (d, J = 2.2 Hz, 1H), 8.65 (d, J = 2.2 Hz, 1H), 8.49 (s, 1H), 7.98 (d, J = 5.1 Hz, 1H), 7.84 (s, 1H), 7.20 (d, J = 5.0 Hz, 1H), 4.15 (p, J = 6.4 Hz, 1H), 3.54 (d, J = 6.5 Hz, 2H), 2.81-2.72 (m, 1H), 1.40 (d, J = 6.4 Hz, 6H), 1.37-1.28 (m, 1H), 0.95-0.79 (m, 2H). |
| 46 | 1H NMR (400 MHz, Methanol-d4) δ 8.75 (d, J = 2.2 Hz, 1H), 8.68 (d, J = 2.2 Hz, 1H), 8.59 (s, 1H), 8.02 (d, J = 5.1 Hz, 1H), 7.90 (s, 1H), 7.21 (d, J = 5.1 Hz, 1H), 4.55-4.29 (m, 1H), 4.14-4.01 (m, 1H), 4.01-3.85 (m, 1H), 3.78-3.67 (m, 1H), 3.58-3.42 (m, 1H), 3.20-3.08 (m, 2H), 2.91 (s, 3H), 2.32-2.14 (m, 2H), 1.91-1.71 (m, 2H), 1.28 (d, J = 1.6 Hz, 6H). |
| 47 | 1H NMR (400 MHz, Methanol-d4) δ 8.72 (d, J = 2.2 Hz, 1H), 8.66 (s, 1H), 8.60 (d, J = 2.2 Hz, 1H), 8.08 (s, 1H), 7.90 (s, 1H), 7.83 (d, J = 5.1 Hz, 1H), 7.69 (d, J = 0.9 Hz, 1H), 7.17 (d, J = 5.1 Hz, 1H), 4.55-4.35 (m, 1H), 4.04-3.91 (m, 1H), 3.98 (s, 3H), 3.61-3.43 (m, 1H), 1.29 (d, J = 1.7 Hz, 6H). |
| 48 | 1H NMR (400 MHz, Methanol-d4) δ 8.71 (d, J = 2.2 Hz, 1H), 8.70 (s, 1H), 8.52 (d, J = 2.2 Hz, 1H), 8.44 (s, 1H), 8.19 (s, 1H), 7.97 (s, 1H), 7.86 (d, J = 5.1 Hz, 1H), 7.58 (t, J = 59.6 Hz, 1H), 7.18 (d, J = 5.1 Hz, 1H), 4.58-4.36 (m, 1H), 4.07-3.88 (m, 1H), 3.66-3.42 (m, 1H), 1.30 (d, J = 1.7 Hz, 6H). |
| 49 | 1H NMR (400 MHz, Methanol-d4) δ 8.72 (d, J = 2.2 Hz, 1H), 8.68 (s, 1H), 8.55 (d, J = 2.2 Hz, 1H), 8.10 (d, J = 6.8 Hz, 1H), 8.10 (s, 1H), 7.83 (s, 1H), 7.81 (d, J = 5.1 Hz, 1H), 7.18 (d, J = 5.0 Hz, 1H), 5.06 (q, J = 8.7 Hz, 2H), 4.46 (ddd, J = 49.1, 9.4, 2.1 Hz, 1H), 4.10-3.85 (m, 1H), 3.61-3.42 (m, 1H), 1.29 (d, J = 1.7 Hz, 6H). |
| 50 | 1H NMR (400 MHz, Methanol-d4) δ 8.74 (d, J = 2.2 Hz, 1H), 8.66 (d, J = 2.1 Hz, 1H), 8.62 (s, 1H), 7.98 (d, J = 5.1 Hz, 1H), 7.74 (s, 1H), 7.20 (d, J = 5.1 Hz, 1H), 4.45 (s, 2H), 4.42 (ddd, J = 49.1, 9.4, 2.1 Hz, 1H), 4.19 (t, J = 6.2 Hz, 1H), 3.94 (ddd, J = 36.3, 14.6, 2.2 Hz, 1H), 3.66-3.43 (m, 1H), 2.50-2.31 (m, 2H), 2.23-2.03 (m, 4H), 1.85 (d, J = 14.8 Hz, 2H), 1.29 (d, J = 1.7 Hz, 6H). |
| 51 | 1H NMR (400 MHz, Methanol-d4) δ 8.75 (d, J = 2.2 Hz, 1H), 8.68 (d, J = 2.2 Hz, 1H), 8.55 (s, 1H), 8.35 (s, 1H), 7.91 (d, J = 5.1 Hz, 1H), 7.21 (d, J = 5.1 Hz, 1H), 4.42 (ddd, J = 49.1, 9.3, 2.1 Hz, 1H), 3.93 (ddd, J = 36.4, 14.6, 2.1 Hz, 1H), 3.74 (s, 2H), 3.56-3.38 (m, 1H), 1.28 (d, J = 1.7 Hz, 6H), 1.20-1.14 (m, 2H), 1.06-0.99 (m, 2H). |
| 52 | 1H NMR (400 MHz, Methanol-d4) δ 8.75 (d, J = 2.2 Hz, 1H), 8.66 (d, J = 2.1 Hz, 1H), 8.50 (s, 1H), 7.99 (dd, J = 4.9, 1.8 Hz, 1H), 7.83 (s, 1H), 7.20 (d, J = 5.1 Hz, 1H), 4.83 (dd, J = 7.8, 6.0 Hz, 1H), 4.45 (t, J = 6.2 Hz, 1H), 4.15 (p, J = 6.5 Hz, 1H), 3.66-3.57 (m, 1H), 3.59-3.42 (m, 1H), 3.35 (t, J = 7.1 Hz, 1H), 3.20-3.01 (m, 1H), 2.02 (q, J = 7.3 Hz, 2H), 1.84-1.61 (m, 1H), 1.40 (dd, J = 6.4, 1.4 Hz, 8H). |
| 53 | 1H NMR (400 MHz, Methanol-d4) δ 8.76 (d, J = 2.2 Hz, 1H), 8.68 (d, J = 2.1 Hz, 1H), 8.63 (s, 1H), 8.04 (d, J = 5.0 Hz, 1H), 7.91 (s, 1H), 7.22 (d, J = 5.1 Hz, 1H), 4.68-4.61 (m, 1H), 4.51-4.31 (m, 1H), 4.02-3.86 (m, 1H), 3.82 (dd, J = 10.6, 5.7 Hz, 1H), 3.64-3.40 (m, 4H), 2.97 (s, 3H), 2.52 (td, J = 14.1, 7.6 Hz, 1H), 2.21 (dt, J = 12.7, 6.1 Hz, 1H), 1.28 (d, J = 1.6 Hz, 6H). |
| 54 | 1H NMR (400 MHz, Methanol-d4) δ 8.75 (d, J = 2.2 Hz, 1H), 8.69 (d, J = 2.1 Hz, 1H), 8.62 (s, 1H), 8.00 (d, J = 5.2 Hz, 1H), 7.62 (s, 1H), 7.21 (d, J = 5.0 Hz, 1H), 5.18-5.08 (m, 3H), 4.76-4.71 (m, 2H), 4.44 (dd, J = 48.6, 8.1 Hz, 1H), 4.12-3.84 (m, 1H), 3.58-3.43 (m, 1H), 1.29 (d, J = 1.6 Hz, 6H). |
| 55 | 1H NMR (400 MHz, Methanol-d4) δ 8.76 (d, J = 2.1 Hz, 1H), 8.69 (d, J = 2.2 Hz, 1H), 8.56 (s, 1H), 8.24 (s, 1H), 7.99 (d, J = 5.1 Hz, 1H), 7.22 (d, J = 5.1 Hz, 1H), 4.51-4.31 (m, 1H), 4.07-3.80 (m, 1H), 3.54-3.39 (m, 1H), 2.87 (tt, J = 7.2, 3.8 Hz, 1H), 1.28 (d, J = 1.6 Hz, 6H), 1.15-1.06 (m, 2H), 0.83-0.74 (m, 2H). |
| 56 | 1H NMR (400 MHz, Methanol-d4) δ 8.72 (d, J = 2.2 Hz, 1H), 8.66 (s, 1H), 8.59 (d, J = 2.2 Hz, 1H), 8.10 (s, 1H), 7.96 (d, J = 0.9 Hz, 1H), 7.82 (d, J = 5.0 Hz, 1H), 7.72 (d, J = 0.9 Hz, 1H), 7.17 (d, J = 5.0 Hz, 1H), 4.55-4.36 (m, 1H), 4.27 (q, J = 7.2 Hz, 2H), 4.08-3.79 (m, 1H), 3.59-3.44 (m, 1H), 1.52 (t, J = 7.3 Hz, 3H), 1.29 (d, J = 1.6 Hz, 6H). |
| 57 | 1H NMR (400 MHz, Methanol-d4) δ 8.76 (d, J = 2.1 Hz, 1H), 8.67 (d, J = 2.2 Hz, 1H), 8.64 (s, 1H), 8.06 (d, J = 5.1 Hz, 1H), 7.88 (s, 1H), 7.21 (d, J = 5.1 Hz, 1H), 4.52-4.29 (m, 2H), 4.18 (t, J = 12.8 Hz, 1H), 4.08-3.84 (m, 2H), 3.82-3.63 (m, 2H), 3.55-3.40 (m, 1H), 2.11-1.91 (m, 2H), 1.29 (d, J = 1.6 Hz, 6H). |
| 58 | 1H NMR (400 MHz, Methanol-d4) δ 8.75 (s, 1H), 8.72 (d, J = 2.1 Hz, 1H), 8.66 (s, 1H), 8.63 (d, J = 2.2 Hz, 1H), 8.08 (s, 1H), 7.89 (d, J = 5.1 Hz, 1H), 7.18 (d, J = 5.0 Hz, 1H), 4.47 (ddd, J = 49.1, 9.3, 2.1 Hz, 1H), 4.20 (s, 3H), 3.98 (ddd, J = 36.3, 14.6, 2.2 Hz, 1H), 3.68-3.45 (m, 1H), 1.30 (d, J = 1.7 Hz, 6H). |
| 59 | 1H NMR (400 MHz, Methanol-d4) δ 9.06 (s, 1H), 8.73 (s, 1H), 8.72 (d, J = 2.1 Hz, 1H), 8.69 (s, 1H), 8.60 (d, J = 2.2 Hz, 1H), 8.19 (s, 1H), 7.86 (d, J = 5.1 Hz, 1H), 7.17 (d, J = 5.1 Hz, 1H), 4.47 (ddd, J = 49.0, 9.4, 2.1 Hz, 1H), 3.99 (ddd, J = 36.4, 14.6, 2.1 Hz, 1H), 3.62-3.45 (m, 1H), 1.30 (d, J = 1.7 Hz, 6H). |
| 60 | 1H NMR (400 MHz, Methanol-d4) δ 8.74 (d, J = 2.2 Hz, 1H), 8.65 (d, J = 2.1 Hz, 1H), 8.53 (s, 1H), 7.98 (d, J = 5.0 Hz, 1H), 7.82 (s, 1H), 7.20 (d, J = 5.1 Hz, 1H), 4.33 (p, J = 8.2 Hz, 1H), 4.13 (hept, J = 6.4 Hz, 1H), 3.66 (s, 3H), 3.09 (p, J = 8.3 Hz, 1H), 2.63-2.51 (m, 1H), 2.48-2.18 (m, 5H), 2.16-2.01 (m, 2H), 1.39 (d, J = 6.4 Hz, 6H). |

TABLE 2-continued

| compound | 1H-NMR |
|---|---|
| 61 | 1H NMR (400 MHz, Methanol-d4) δ 8.74 (d, J = 2.2 Hz, 1H), 8.65 (d, J = 2.2 Hz, 1H), 8.57 (s, 1H), 8.02 (d, J = 5.1 Hz, 1H), 7.91 (s, 1H), 7.21 (d, J = 5.1 Hz, 1H), 4.42 (ddd, J = 49.0, 9.3, 2.2 Hz, 1H), 4.29-4.17 (m, 1H), 4.11 (s, 1H), 3.92 (ddd, J = 36.3, 14.5, 2.1 Hz, 1H), 3.58-3.39 (m, 1H), 2.14-1.84 (m, 3H), 1.82-1.52 (m, 5H), 1.28 (d, J = 1.6 Hz, 6H). |
| 62 | 1H NMR (400 MHz, Methanol-d4) δ 8.74 (d, J = 2.2 Hz, 1H), 8.64 (d, J = 2.2 Hz, 1H), 8.50 (s, 1H), 7.99 (d, J = 5.0 Hz, 1H), 7.80 (s, 1H), 7.20 (d, J = 5.1 Hz, 1H), 4.42 (ddd, J = 49.1, 9.3, 2.0 Hz, 1H), 4.06 (s, 1H), 3.94 (dd, J = 36.5, 14.3 Hz, 1H), 3.64-3.42 (m, 2H), 3.40 (s, 3H), 2.21 (d, J = 13.3 Hz, 1H), 2.05-1.79 (m, 3H), 1.76-1.41 (m, 4H), 1.29 (d, J = 1.7 Hz, 6H). |
| 63 | 1H NMR (400 MHz, Methanol-d4) δ 8.74 (d, J = 2.2 Hz, 1H), 8.65 (d, J = 2.2 Hz, 1H), 8.56 (s, 1H), 8.01 (d, J = 5.1 Hz, 1H), 7.90 (s, 1H), 7.21 (d, J = 5.0 Hz, 1H), 4.53-4.31 (m, 1H), 4.29-4.17 (m, 1H), 4.10 (s, 1H), 4.01-3.82 (m, 1H), 3.58-3.41 (m, 1H), 2.10-1.83 (m, 3H), 1.83-1.52 (m, 5H), 1.28 (d, J = 1.7 Hz, 6H). |
| 64 | 1H NMR (400 MHz, Methanol-d4) δ 8.74 (d, J = 2.2 Hz, 1H), 8.65 (d, J = 2.2 Hz, 1H), 8.55 (s, 1H), 7.99 (d, J = 5.0 Hz, 1H), 7.85 (s, 1H), 7.20 (d, J = 5.1 Hz, 1H), 4.42 (ddd, J = 49.1, 9.4, 2.1 Hz, 1H), 4.08-3.80 (m, 2H), 3.61-3.39 (m, 1H), 2.08 (d, J = 12.0 Hz, 2H), 1.82 (d, J = 11.9 Hz, 2H), 1.74-1.34 (m, 6H), 1.29 (d, J = 1.7 Hz, 6H). |
| 65 | 1H NMR (400 MHz, Methanol-d4) δ 8.74 (d, J = 2.2 Hz, 1H), 8.66 (d, J = 2.2 Hz, 1H), 8.53 (s, 1H), 7.99 (d, J = 5.1 Hz, 1H), 7.85 (s, 1H), 7.20 (d, J = 5.1 Hz, 1H), 4.42 (ddd, J = 49.1, 9.3, 2.1 Hz, 1H), 4.06-3.76 (m, 3H), 3.58-3.38 (m, 1H), 2.31 (d, J = 12.3 Hz, 1H), 2.12-1.85 (m, 4H), 1.61-1.33 (m, 3H), 1.28 (d, J = 1.7 Hz, 6H). |
| 66 | 1H NMR (400 MHz, Methanol-d4) δ 8.75 (d, J = 2.2 Hz, 1H), 8.67 (d, J = 2.2 Hz, 1H), 8.59 (s, 1H), 8.01 (d, J = 5.1 Hz, 1H), 7.86 (s, 1H), 7.21 (d, J = 5.0 Hz, 1H), 4.18 (hept, J = 6.4 Hz, 1H), 1.47 (s, 6H), 1.40 (d, J = 6.4 Hz, 6H). |
| 67 | 1H NMR (400 MHz, Methanol-d4) δ 8.63 (d, J = 3.0 Hz, 1H), 8.49 (dd, J = 2.3, 1.1 Hz, 1H), 8.38-8.27 (m, 2H), 7.80 (dd, J = 10.9, 0.9 Hz, 1H), 7.77 (dd, J = 4.9, 1.2 Hz, 1H), 7.62 (dd, J = 12.7, 0.9 Hz, 1H), 7.02 (d, J = 4.9 Hz, 1H), 6.35-5.87 (m, 1H), 5.33-5.17 (m, 1H), 4.46 (ddd, J = 48.8, 9.0, 2.0 Hz, 1H), 4.11-3.81 (m, 1H), 3.60-3.44 (m, 1H), 1.91 (s, 1H), 1.30 (d, J = 1.6 Hz, 7H), 1.19-1.03 (m, 2H). |
| 68 | 1H NMR (400 MHz, Methanol-d4) δ 8.78-8.68 (m, 2H), 8.63 (d, J = 2.2 Hz, 1H), 8.40 (s, 1H), 7.91 (s, 1H), 7.87 (d, J = 5.1 Hz, 1H), 7.34 (d, J = 1.5 Hz, 1H), 7.18 (d, J = 5.1 Hz, 1H), 4.45 (ddd, J = 49.1, 9.3, 2.1 Hz, 1H), 3.97 (ddd, J = 36.4, 14.6, 2.2 Hz, 1H), 3.86 (s, 3H), 3.52 (ddd, J = 16.0, 14.5, 9.3 Hz, 1H), 1.29 (d, J = 1.6 Hz, 6H). |
| 69 | 1H NMR (400 MHz, Methanol-d4) δ 8.74 (d, J = 2.2 Hz, 1H), 8.66 (d, J = 2.1 Hz, 1H), 8.47 (s, 1H), 7.99 (d, J = 5.1 Hz, 1H), 7.81 (s, 1H), 7.20 (d, J = 5.0 Hz, 1H), 4.16 (p, J = 6.4 Hz, 1H), 2.91 (s, 2H), 1.40 (d, J = 6.4 Hz, 6H), 1.29 (s, 6H). |
| 70 | 1H NMR (400 MHz, Methanol-d4) δ 8.72 (d, J = 2.2 Hz, 1H), 8.66 (s, 1H), 8.59 (d, J = 2.2 Hz, 1H), 8.09 (s, 1H), 7.89 (s, 2H), 7.81 (d, J = 5.1 Hz, 1H), 7.17 (d, J = 5.2 Hz, 1H), 4.46 (dd, J = 48.9, 8.1 Hz, 1H), 3.98 (dd, J = 36.8, 14.5 Hz, 1H), 3.59-3.44 (m, 1H), 1.30 (d, J = 1.6 Hz, 6H). |
| 71 | 1H NMR (400 MHz, Methanol-d4) δ 8.74 (d, J = 2.2 Hz, 1H), 8.71-8.55 (m, 2H), 7.99 (d, J = 5.0 Hz, 1H), 7.88 (s, 1H), 7.20 (d, J = 5.0 Hz, 1H), 4.72-4.51 (m, 3H), 4.30-4.21 (m, 2H), 4.15 (hept, J = 6.3 Hz, 1H), 1.40 (d, J = 6.4 Hz, 6H). |
| 72 | 1H NMR (400 MHz, Methanol-d4) δ 8.74 (d, J = 2.2 Hz, 1H), 8.65 (d, J = 2.2 Hz, 1H), 8.57 (s, 1H), 7.99 (d, J = 5.1 Hz, 1H), 7.85 (s, 1H), 7.20 (d, J = 5.0 Hz, 1H), 4.38-4.21 (m, 2H), 4.15 (p, J = 6.4 Hz, 1H), 4.08-3.89 (m, 2H), 3.69 (d, J = 6.6 Hz, 2H), 2.92 (qd, J = 9.9, 5.9 Hz, 1H), 1.40 (d, J = 6.4 Hz, 6H). |
| 73 | 1H NMR (400 MHz, Methanol-d4) δ 8.74 (d, J = 2.2 Hz, 1H), 8.66 (d, J = 2.2 Hz, 1H), 8.56 (s, 1H), 7.99 (d, J = 5.0 Hz, 1H), 7.85 (s, 1H), 7.20 (d, J = 5.1 Hz, 1H), 4.15 (p, J = 6.4 Hz, 1H), 3.54 (qd, J = 13.7, 6.4 Hz, 2H), 3.26-3.03 (m, 2H), 2.96-2.66 (m, 2H), 2.51-2.30 (m, 1H), 2.10-1.83 (m, 1H), 1.40 (d, J = 6.4 Hz, 6H). |
| 74 | 1H NMR (400 MHz, Methanol-d4) δ 8.75 (d, J = 2.2 Hz, 1H), 8.67 (d, J = 2.2 Hz, 1H), 8.57 (s, 1H), 8.02 (d, J = 5.1 Hz, 1H), 7.89 (s, 1H), 7.21 (d, J = 5.0 Hz, 1H), 4.57-4.31 (m, 1H), 3.94 (dd, J = 36.1, 14.6 Hz, 1H), 3.75 (qd, J = 14.1, 6.4 Hz, 2H), 3.58-3.42 (m, 1H), 3.44-3.21 (m, 2H), 3.22-3.06 (m, 1H), 3.05-2.81 (m, 2H), 2.57-2.44 (m, 1H), 2.19-1.92 (m, 1H), 1.29 (d, J = 1.7 Hz, 6H). |
| 75 | 1H NMR (400 MHz, Methanol-d4) δ 8.76 (d, J = 2.2 Hz, 1H), 8.68 (d, J = 2.2 Hz, 1H), 8.62 (s, 1H), 8.04 (d, J = 5.1 Hz, 1H), 7.88 (s, 1H), 7.22 (d, J = 5.0 Hz, 1H), 4.43 (ddd, J = 48.9, 9.3, 2.1 Hz, 1H), 4.24 (t, J = 10.3 Hz, 1H), 4.05-3.82 (m, 1H), 3.60-3.45 (m, 1H), 3.43-3.32 (m, 2H), 3.20 (d, J = 14.5 Hz, 2H), 2.47 (d, J = 13.8 Hz, 2H), 2.33 (t, J = 11.1 Hz, 2H), 1.29 (d, J = 1.7 Hz, 6H). |
| 76 | 1H NMR (400 MHz, Methanol-d4) δ 8.76 (d, J = 2.2 Hz, 1H), 8.68 (d, J = 2.2 Hz, 1H), 8.64 (s, 1H), 8.06 (d, J = 5.1 Hz, 1H), 7.90 (s, 1H), 7.22 (d, J = 5.1 Hz, 1H), 4.96-4.75 (m, 1H), 4.43 (ddd, J = 49.1, 9.3, 2.1 Hz, 1H), 3.94 (dd, J = 36.3, 14.7 Hz, 1H), 3.73 (dd, J = 13.7, 7.5 Hz, 1H), 3.61-3.16 (m, 4H), 2.80 (td, J = 13.7, 6.1 Hz, 1H), 2.44 (dq, J = 15.2, 8.0 Hz, 1H), 1.29 (d, J = 1.6 Hz, 6 H). |
| 77 | 1H NMR (400 MHz, Methanol-d4) δ 8.75 (d, J = 2.2 Hz, 1H), 8.72-8.64 (m, 2H), 8.04 (d, J = 5.0 Hz, 1H), 7.78 (s, 1H), 7.21 (d, J = 5.1 Hz, 1H), 4.82-4.71 (m, 3H), 4.59-4.20 (m, 3H), 4.06-3.85 (m, 1H), 3.61-3.40 (m, 1H), 1.29 (d, J = 1.6 Hz, 6H). |

TABLE 2-continued

| compound | 1H-NMR |
|---|---|
| 78 | 1H NMR (400 MHz, Methanol-d4) δ 8.92 (d, J = 2.3 Hz, 1H), 8.68 (d, J = 2.2 Hz, 1H), 8.61 (s, 1H), 7.98 (d, J = 5.0 Hz, 1H), 7.84 (s, 1H), 7.12 (d, J = 5.0 Hz, 1H), 4.75-4.47 (m, 3H), 4.33-4.21 (m, 2H), 4.16 (p, J = 6.3 Hz, 1H), 1.40 (d, J = 6.4 Hz, 6H). |
| 79 | 1H NMR (400 MHz, Methanol-d4) δ 8.92 (d, J = 2.3 Hz, 1H), 8.68 (d, J = 2.3 Hz, 1H), 8.54 (s, 1H), 7.98 (d, J = 5.0 Hz, 1H), 7.81 (s, 1H), 7.12 (d, J = 5.0 Hz, 1H), 4.30 (dd, J = 14.3, 9.9 Hz, 2H), 4.16 (p, J = 6.4 Hz, 1H), 4.00 (dd, J = 14.5, 5.5 Hz, 2H), 3.69 (d, J = 6.5 Hz, 2H), 3.00-2.82 (m, 1H), 1.40 (d, J = 6.4 Hz, 6H). |
| 80 | 1H NMR (400 MHz, Methanol-d4) δ 8.74 (d, J = 2.2 Hz, 1H), 8.64 (d, J = 2.1 Hz, 1H), 8.51 (s, 1H), 7.99 (d, J = 5.1 Hz, 1H), 7.86 (s, 1H), 7.20 (d, J = 5.1 Hz, 1H), 4.42 (ddd, J = 49.0, 9.4, 2.1 Hz, 1H), 3.92 (ddd, J = 36.3, 14.5, 2.2 Hz, 1H), 3.73-3.63 (m, 2H), 3.56-3.39 (m, 1H), 1.98-1.85 (m, 2H), 1.39-1.23 (m, 12H). |
| 81 | 1H NMR (400 MHz, Methanol-d4) δ 8.75 (d, J = 2.2 Hz, 1H), 8.64 (d, J = 2.2 Hz, 1H), 8.57 (s, 1H), 8.00 (d, J = 5.1 Hz, 1H), 7.95 (s, 1H), 7.21 (d, J = 5.1 Hz, 1H), 4.49-4.36 (m, 1H), 4.29-4.20 (m, 1H), 4.01-3.76 (m, 3H), 3.56-3.40 (m, 1H), 2.16-2.01 (m, 2H), 1.61 (td, J = 12.0, 5.2 Hz, 1H), 1.51 (t, J = 12.4 Hz, 1H), 1.41 (s, 3H), 1.28 (d, J = 1.7 Hz, 9H). |
| 82 | 1H NMR (400 MHz, Methanol-d4) δ 8.56 (d, J = 6.7 Hz, 3H), 7.99 (s, 1H), 7.80 (d, J = 4.9 Hz, 1H), 7.07 (d, J = 4.9 Hz, 1H), 4.68 (s, 2H), 4.41 (ddd, J = 48.9, 9.2, 2.3 Hz, 1H), 4.03-3.92 (m, 1H), 3.92-3.77 (m, 1H), 3.57-3.40 (m, 1H), 3.00-2.79 (m, 2H), 2.32-2.17 (m, 2H), 1.28 (d, J = 1.7 Hz, 7H). |
| 83 | 1H NMR (400 MHz, Methanol-d4) δ 8.76 (d, J = 2.2 Hz, 1H), 8.69-8.63 (m, 2H), 8.03 (d, J = 5.1 Hz, 1H), 7.90 (s, 1H), 7.22 (d, J = 5.0 Hz, 1H), 4.91 (t, J = 7.7 Hz, 3H), 4.81 (dd, J = 8.2, 5.6 Hz, 2H), 4.54-4.31 (m, 2H), 4.22 (s, 1H), 4.05-3.81 (m, 1H), 3.60-3.48 (m, 2H), 3.20-3.02 (m, 2H), 2.43 (d, J = 13.8 Hz, 2H), 2.12-1.84 (m, 2H), 1.29 (d, J = 1.7 Hz, 6H). |
| 84 | 1H NMR (400 MHz, Methanol-d4) δ 8.76 (d, J = 2.1 Hz, 1H), 8.66 (d, J = 2.2 Hz, 1H), 8.62 (s, 1H), 8.04 (d, J = 5.0 Hz, 1H), 7.94 (s, 1H), 7.21 (d, J = 5.1 Hz, 1H), 6.20 (tt, J = 55.0, 3.3 Hz, 1H), 4.43 (ddd, J = 49.1, 9.4, 2.1 Hz, 1H), 4.09 (td, J = 15.4, 3.3 Hz, 2H), 3.95 (ddd, J = 36.4, 14.6, 2.1 Hz, 1H), 3.49 (ddd, J = 15.9, 14.5, 9.4 Hz, 1H), 1.29 (d, J = 1.7 Hz, 6H). |
| 85 | 1H NMR (400 MHz, Methanol-d4) δ 8.74 (d, J = 2.1 Hz, 1H), 8.65 (d, J = 2.1 Hz, 1H), 8.55 (s, 1H), 7.98 (d, J = 5.0 Hz, 1H), 7.84 (s, 1H), 7.20 (d, J = 5.1 Hz, 1H), 4.15 (p, J = 6.4 Hz, 1H), 3.54 (t, J = 6.9 Hz, 2H), 3.24 (dd, J = 8.9, 6.5 Hz, 2H), 2.99 (s, 3H), 2.14 (dq, J = 9.4, 7.0 Hz, 2H), 1.40 (d, J = 6.4 Hz, 6H). |
| 86 | 1H NMR (400 MHz, Methanol-d4) δ 8.74 (d, J = 2.1 Hz, 1H), 8.70-8.55 (m, 2H), 7.99 (d, J = 5.1 Hz, 1H), 7.86 (s, 1H), 7.21 (d, J = 5.1 Hz, 1H), 4.88 (t, J = 7.7 Hz, 2H), 4.42 (d, J = 9.4 Hz, 1H), 4.16 (td, J = 13.8, 12.7, 7.5 Hz, 2H), 3.69-3.43 (m, 2H), 3.18-2.92 (m, 2H), 2.31 (d, J = 13.2 Hz, 2H), 2.00 (d, J = 16.6 Hz, 2H), 1.39 (d, J = 6.4 Hz, 6H). |
| 87 | 1H NMR (400 MHz, Methanol-d4) δ 8.74 (d, J = 2.2 Hz, 1H), 8.65 (d, J = 2.2 Hz, 1H), 8.49 (s, 1H), 7.99 (d, J = 5.1 Hz, 1H), 7.82 (s, 1H), 7.20 (d, J = 5.1 Hz, 1H), 4.15 (p, J = 6.4 Hz, 1H), 3.51-3.37 (m, 2H), 3.25 (s, 3H), 1.91-1.75 (m, 2H), 1.40 (d, J = 6.4 Hz, 6H), 1.24 (s, 6H). |
| 88 | 1H NMR (400 MHz, Methanol-d4) δ 8.74 (d, J = 2.2 Hz, 1H), 8.65 (d, J = 2.1 Hz, 1H), 8.55 (s, 1H), 7.98 (d, J = 5.0 Hz, 1H), 7.83 (s, 1H), 7.20 (d, J = 5.0 Hz, 1H), 4.14 (p, J = 6.4 Hz, 1H), 3.55-3.44 (m, 2H), 2.96 (s, 3H), 1.39 (d, J = 6.4 Hz, 6H). |
| 89 | 1H NMR (400 MHz, Methanol-d4) δ 8.72 (d, J = 2.2 Hz, 1H), 8.68 (s, 1H), 8.57 (J = 2.2 Hz, 1H), 8.12 (s, 1H), 8.05 (s, 1H), 7.82 (d, J = 5.1 Hz, 1H), 7.78 (d, J = 0.8 Hz, 1H), 7.18 (d, J = 5.1 Hz, 1H), 6.29 (tt, J = 55.0, 3.6 Hz, 1H), 4.67 (td, J = 14.7, 3.6 Hz, 2H), 4.46 (ddd, J = 49.0, 9.3, 2.1 Hz, 1H), 3.98 (ddd, J = 36.5, 14.6, 2.1 Hz, 1H), 3.52 (ddd, J = 16.0, 14.5, 9.3 Hz, 1H), 1.29 (d, J = 1.7 Hz, 6H). |
| 90 | 1H NMR (400 MHz, Methanol-d4) δ 8.74 (d, J = 2.2 Hz, 1H), 8.65 (d, J = 2.2 Hz, 1H), 8.57 (d, J = 7.5 Hz, 1H), 8.53 (s, 1H), 7.99 (d, J = 5.1 Hz, 1H), 7.82 (s, 1H), 7.20 (d, J = 5.1 Hz, 1H), 4.14 (p, J = 6.4 Hz, 1H), 3.85 (d, J = 8.1 Hz, 1H), 1.86-1.66 (m, 6H), 1.53 (dt, J = 13.4, 8.4 Hz, 2H), 1.46-1.30 (m, 6H), 1.23 (s, 3H). |
| 91 | 1H NMR (400 MHz, Methanol-d4) δ 8.74 (d, J = 2.2 Hz, 1H), 8.65 (d, J = 2.1 Hz, 1H), 8.49 (s, 1H), 7.99 (d, J = 5.0 Hz, 1H), 7.82 (s, 1H), 7.20 (d, J = 5.0 Hz, 1H), 4.15 (p, J = 6.3 Hz, 1H), 3.55-3.43 (m, 2H), 2.21-2.02 (m, 4H), 1.98-1.86 (m, 2H), 1.79 (dtd, J = 11.2, 8.6, 4.0 Hz, 1H), 1.65-1.53 (m, 1H), 1.45-1.35 (m, 6H). |
| 92 | 1H NMR (400 MHz, Methanol-d4) δ 8.74 (d, J = 2.2 Hz, 1H), 8.65 (d, J = 2.2 Hz, 1H), 8.50 (s, 1H), 7.99 (d, J = 5.1 Hz, 1H), 7.83 (s, 1H), 7.20 (d, J = 5.1 Hz, 1H), 4.15 (p, J = 6.4 Hz, 1H), 3.88 (dd, J = 6.9, 5.8 Hz, 2H), 3.46 (t, J = 6.4 Hz, 2H), 3.06 (s, 3H), 1.40 (d, J = 6.4 Hz, 6H). |
| 93 | 1H NMR (400 MHz, Methanol-d4) δ 8.61-8.51 (m, 2H), 8.48 (d, J = 2.2 Hz, 1H), 8.13 (s, 1H), 7.82 (d, J = 4.9 Hz, 1H), 7.07 (d, J = 4.9 Hz, 1H), 4.69 (t, J = 4.9 Hz, 1H), 4.55 (d, J = 5.2 Hz, 1H), 4.42 (ddt, J = 49.0, 9.1, 2.6 Hz, 1H), 3.97-3.74 (m, 2H), 3.54-3.38 (m, 1H), 2.24 (dd, J = 12.6, 7.7 Hz, 1H), 1.86-1.54 (m, 4H), 1.39-1.18 (m, 7H). |
| 94 | 1H NMR (400 MHz, Methanol-d4) δ 8.59 (s, 1H), 8.52 (dd, J = 11.9, 2.3 Hz, 2H), 8.16 (s, 1H), 7.81 (d, J = 4.9 Hz, 1H), 7.06 (d, J = 4.9 Hz, 1H), 4.89 (t, J = 4.8 Hz, 1H), 4.65 (t, J = 5.3 Hz, 1H), 4.43 (ddd, J = 48.9, 9.2, 2.3 Hz, 1H), 4.02 (dt, J = 9.8, 4.3 Hz, 1H), 3.88 (ddd, J = 35.4, 14.5, 2.3 Hz, 1H), 3.56-3.43 (m, 1H), 2.53-2.38 (m, 1H), 2.10-1.98 (m, 1H), 1.79 (dt, J = 12.2, 4.0 Hz, 1H), 1.67 (tt, J = 9.5, 4.3 Hz, 2H), 1.29 (d, J = 1.7 Hz, 7H). |
| 95 | 1H NMR (400 MHz, Methanol-d4) δ 8.43 (s, 1H), 8.40-8.33 (m, 2H), 8.02 (s, 1H), 7.75 (d, J = 4.9 Hz, 1H), 7.02 (d, J = 4.9 Hz, 1H), 3.89-3.63 (m, 5H), 3.54-3.44 (m, 2H), 1.85-1.76 (m, 2H), 1.75-1.54 (m, 4H), 1.33 (d, J = 6.3 Hz, 6H). |

TABLE 2-continued

| compound | 1H-NMR |
|---|---|
| 96 | 1H NMR (400 MHz, Methanol-d4) δ 8.56-8.48 (m, 2H), 8.44 (d, J = 2.2 Hz, 1H), 8.08 (s, 1H), 7.76 (d, J = 4.8 Hz, 1H), 7.04 (d, J = 4.8 Hz, 1H), 4.78 (s, 2H), 4.65 (s, 2H), 4.27 (p, J = 8.2 Hz, 1H), 3.84 (p, J = 6.4 Hz, 1H), 2.70 (ddt, J = 9.7, 7.8, 2.4 Hz, 2H), 2.34-2.26 (m, 2H), 1.32 (d, J = 6.3 Hz, 7H). |
| 97 | 1H NMR (400 MHz, Methanol-d4) δ 8.53 (s, 1H), 8.48 (d, J = 2.2 Hz, 1H), 8.43 (d, J = 2.3 Hz, 1H), 8.10 (s, 1H), 7.77 (d, J = 4.9 Hz, 1H), 7.04 (d, J = 4.8 Hz, 1H), 4.43 (ddd, J = 48.9, 9.0, 2.3 Hz, 1H), 3.89 (ddd, J = 35.3, 14.5, 2.3 Hz, 1H), 3.56-3.37 (m, 3H), 1.28 (d, J = 1.6 Hz, 6H), 0.86-0.68 (m, 4H). |
| 98 | 1H NMR (400 MHz, Methanol-d4) δ 8.75 (d, J = 2.2 Hz, 1H), 8.70 (d, J = 2.2 Hz, 1H), 8.64 (s, 1H), 8.02 (d, J = 5.1 Hz, 1H), 7.72 (s, 1H), 7.21 (d, J = 5.1 Hz, 1H), 4.80-4.77 (m, 1H), 4.55-4.27 (m, 3H), 4.12-3.85 (m, 3H), 3.61-3.39 (m, 1H), 3.03 (s, 3H), 1.29 (d, J = 1.6 Hz, 6H). |
| 99 | 1H NMR (400 MHz, Methanol-d4) δ 8.74 (d, J = 2.2 Hz, 1H), 8.67 (d, J = 2.1 Hz, 1H), 8.55 (s, 1H), 7.98 (d, J = 5.0 Hz, 1H), 7.68 (s, 1H), 7.20 (d, J = 5.1 Hz, 1H), 4.42 (ddd, J = 49.0, 9.3, 2.1 Hz, 1H), 4.22 (p, J = 7.6 Hz, 1H), 3.92 (ddd, J = 36.4, 14.5, 2.1 Hz, 1H), 3.48 (ddd, J = 16.1, 14.5, 9.3 Hz, 1H), 2.72 (ddt, J = 9.4, 7.5, 2.4 Hz, 2H), 2.26-2.11 (m, 2H), 2.11-1.99 (m, 4H), 1.99-1.82 (m, 2H), 1.28 (d, J = 1.7 Hz, 6H). |
| 100 | 1H NMR (400 MHz, Methanol-d4) δ 8.73 (d, J = 2.2 Hz, 1H), 8.64 (d, J = 2.2 Hz, 1H), 8.55 (s, 1H), 7.98 (d, J = 5.0 Hz, 1H), 7.86 (s, 1H), 7.20 (d, J = 5.0 Hz, 1H), 4.42 (ddd, J = 49.0, 9.4, 2.2 Hz, 1H), 3.93 (ddd, J = 36.4, 14.5, 2.1 Hz, 1H), 3.72 (s, 4H), 3.55-3.44 (m, 1H), 3.42 (s, 3H), 1.29 (d, J = 1.7 Hz, 6H). |
| 101 | 1H NMR (400 MHz, Methanol-d4) δ 8.74 (d, J = 2.1 Hz, 1H), 8.66 (d, J = 2.2 Hz, 1H), 8.57 (s, 1H), 7.96 (d, J = 5.1 Hz, 1H), 7.87 (s, 1H), 7.21 (d, J = 5.1 Hz, 1H), 4.41 (ddd, J = 49.1, 9.4, 2.1 Hz, 1H), 3.92 (ddd, J = 36.5, 14.6, 2.1 Hz, 1H), 3.74 (dd, J = 7.9, 3.2 Hz, 1H), 3.58-3.41 (m, 1H), 2.44 (t, J = 5.0 Hz, 2H), 2.15-2.00 (m, 1H), 1.80-1.21 (m, 13H). |
| 102 | 1H NMR (400 MHz, Methanol-d4) δ 8.74 (d, J = 2.2 Hz, 1H), 8.65 (d, J = 2.2 Hz, 1H), 8.58 (s, 1H), 8.03 (d, J = 5.1 Hz, 1H), 7.97 (s, 1H), 7.21 (d, J = 5.1 Hz, 1H), 4.42 (ddd, J = 49.1, 9.4, 2.2 Hz, 1H), 4.10 (t, J = 6.5 Hz, 2H), 4.02-3.84 (m, 1H), 3.61 (t, J = 6.5 Hz, 2H), 3.48 (ddd, J = 16.2, 14.5, 9.4 Hz, 1H), 3.09 (s, 3H), 1.28 (d, J = 1.7 Hz, 6H). |
| 103 | 1H NMR (400 MHz, Methanol-d4) δ 8.74 (d, J = 2.2 Hz, 1H), 8.67 (d, J = 2.2 Hz, 1H), 8.55 (s, 1H), 8.03 (d, J = 5.0 Hz, 1H), 7.90 (s, 1H), 7.20 (d, J = 5.1 Hz, 1H), 4.43 (ddd, J = 48.9, 9.3, 2.2 Hz, 1H), 4.05-3.83 (m, 1H), 3.83-3.69 (m, 2H), 3.49 (ddd, J = 16.2, 14.5, 9.3 Hz, 1H), 3.04 (s, 3H), 2.27 (p, J = 7.3 Hz, 2H), 1.29 (d, J = 1.7 Hz, 6H). |
| 104 | 1H NMR (400 MHz, DMSO-d6) δ 9.06 (s, 1H), 8.96 (s, 1H), 8.86 (d, J = 2.3 Hz, 1H), 8.60 (s, 1H), 8.04 (s, 1H), 7.98 (d, J = 5.0 Hz, 1H), 7.76 (s, 1H), 7.51 (s, 1H), 7.21 (d, J = 4.9 Hz, 1H), 4.84 (s, 1H), 4.51 (s, 2H), 4.33 (dd, J = 49.3, 9.2 Hz, 1H), 3.79 (s, 4H), 1.15 (d, J = 5.0 Hz, 7H). |
| 105 | 1H NMR (400 MHz, DMSO-d6) δ 8.88 (s, 2H), 8.74 (s, 1H), 8.70 (s, 1H), 7.97 (s, 1H), 7.85 (s, 1H), 7.72 (s, 1H), 7.12 (s, 1H), 4.85 (s, 1H), 4.66 (s, 2H), 4.42 (d, J = 9.3 Hz, 1H), 4.29 (d, J = 9.1 Hz, 1H), 1.16 (d, J = 4.3 Hz, 8H). |
| 106 | 1H NMR (400 MHz, DMSO-d6) δ 8.82 (d, J = 2.3 Hz, 1H), 8.72 (d, J = 2.3 Hz, 1H), 8.72-8.60 (m, 2H), 8.12 (s, 1H), 7.84 (s, 1H), 7.81 (d, J = 4.8 Hz, 1H), 7.09 (d, J = 4.8 Hz, 1H), 4.82 (s, 1H), 4.35 (ddd, J = 49.5, 9.1, 1.5 Hz, 1H), 3.89-3.79 (m, 2H), 3.80-3.60 (m, 1H), 3.46-3.29 (m, 2H), 2.33-2.03 (m, 3H), 1.86-1.74 (m, 1H), 1.15 (d, J = 4.3 Hz, 6H). |
| 107 | 1H NMR (400 MHz, DMSO-d6) δ 9.46 (s, 1H), 9.11 (s, 1H), 8.96 (d, J = 2.2 Hz, 1H), 8.74 (d, J = 2.2 Hz, 1H), 8.63 (s, 1H), 7.94 (d, J = 5.0 Hz, 1H), 7.86 (s, 1H), 7.21 (d, J = 5.0 Hz, 1H), 4.51 (d, J = 5.6 Hz, 2H), 4.34 (ddd, J = 49.3, 9.5, 2.0 Hz, 1H), 3.90-3.59 (m, 1H), 3.48-3.24 (m, 1H), 2.41 (s, 3H), 2.22 (s, 3H), 1.15 (d, J = 5.5 Hz, 6H). |
| 108 | |
| 109 | 1H NMR (400 MHz, Methanol-d4) δ 8.74 (d, J = 2.2 Hz, 1H), 8.68-8.57 (m, 1H), 8.27 (s, 1H), 7.92 (d, J = 5.0 Hz, 1H), 7.80 (s, 1H), 7.21 (d, J = 5.0 Hz, 1H), 4.57-4.30 (m, 2H), 3.93 (d, J = 35.5 Hz, 2H), 3.49 (d, J = 9.9 Hz, 2H), 2.94-2.71 (m, 3H), 1.61 (d, J = 6.9 Hz, 2H), 1.29 (d, J = 4 Hz). |
| 110 | 1H NMR (400 MHz, Methanol-d4) δ 8.76 (d, J = 2.2 Hz, 1H), 8.69-8.63 (m, 2H), 8.05 (d, J = 4.8 Hz, 1H), 7.88 (s, 1H), 7.22 (d, J = 5.1 Hz, 1H), 4.91 (t, J = 7.6 Hz, 2H), 4.73 (dd, J = 8.2, 4.4 Hz, 2H), 4.52-4.28 (m, 3H), 3.80-3.40 (m, 5H), 2.76 (dd, J = 13.9, 7.0 Hz, 2H), 2.24 (s, 2H), 1.29 (d, J = 1.7 Hz, 6H). |
| 111 | |
| 112 | 1H NMR (400 MHz, Methanol-d4) δ 8.78 (d, J = 2.2 Hz, 1H), 8.71 (d, J = 2.2 Hz, 1H), 8.58 (s, 1H), 8.41 (s, 1H), 7.91 (d, J = 5.1 Hz, 1H), 7.25 (d, J = 5.0 Hz, 1H), 4.45 (ddd, J = 49.0, 9.4, 2.1 Hz, 1H), 3.96 (ddd, J = 36.7, 14.5, 2.1 Hz, 1H), 3.63 (s, 2H), 3.56-3.44 (m, 1H), 3.37 (s, 3H), 1.31 (d, J = 1.7 Hz, 6H), 1.26-1.19 (m, 2H), 1.12-1.05 (m, 2H). |
| 113 | 1H NMR (400 MHz, Methanol-d4) δ 8.76 (d, J = 2.2 Hz, 1H), 8.69 (d, J = 2.2 Hz, 1H), 8.63 (s, 1H), 8.03 (d, J = 5.0 Hz, 1H), 7.89 (s, 1H), 7.22 (d, J = 5.0 Hz, 1H), 4.56-4.34 (m, 2H), 4.26 (s, 1H), 4.06-3.85 (m, 1H), 3.58-3.42 (m, 2H), 3.38-3.35 (m, 1H), 3.21-3.15 (m, 1H), 2.96 (s, 3H), 2.57-2.42 (m, 1H), 2.04-1.84 (m, 2H), 1.78-1.66 (m, 1H), 1.30 (d, J = 1.6 Hz, 6H). |

TABLE 2-continued

| compound | 1H-NMR |
|---|---|
| 114 | 1H NMR (400 MHz, Methanol-d4) δ 8.77 (d, J = 2.2 Hz, 1H), 8.68 (d, J = 2.2 Hz, 1H), 8.65 (s, 1H), 8.05 (d, J = 5.0 Hz, 1H), 7.91 (s, 1H), 7.23 (d, J = 5.1 Hz, 1H), 4.43 (dd, J = 49.1, 9.1 Hz, 1H), 4.26-4.10 (m, 1H), 3.93 (dd, J = 36.2, 14.4 Hz, 1H), 3.75-3.63 (m, 2H), 3.60-3.44 (m, 1H), 2.97 (s, 3H), 2.45 (d, J = 14.6 Hz, 2H), 2.28 (s, 1H), 2.01-1.86 (m, 2H), 1.33-1.27 (m, 7H). |
| 115 | 1H NMR (400 MHz, Methanol-d4) δ 8.78 (d, J = 2.1 Hz, 1H), 8.69 (d, J = 2.2 Hz, 1H), 8.66 (s, 1H), 8.05 (d, J = 5.1 Hz, 1H), 7.92 (s, 1H), 7.24 (d, J = 5.0 Hz, 1H), 4.43 (dd, J = 49.0, 9.3 Hz, 1H), 4.32-4.16 (m, 2H), 4.03-3.69 (m, 2H), 3.63-3.38 (m, 2H), 2.96-2.85 (m, 1H), 2.52-2.34 (m, 2H), 2.19-1.80 (m, 2H), 1.29 (d, J = 1.7 Hz, 7H), 1.05 (s, 2H), 1.04 (s, 2H). |
| 116 | 1H NMR (400 MHz, Methanol-d4) δ 8.74 (d, J = 2.2 Hz, 1H), 8.66 (d, J = 2.2 Hz, 1H), 8.56 (s, 1H), 8.00 (d, J = 5.0 Hz, 1H), 7.84 (s, 1H), 7.21 (d, J = 5.1 Hz, 1H), 4.25-4.10 (m, 1H), 4.03 (t, J = 16.4 Hz, 2H), 1.40 (d, J = 6.4 Hz, 6H), 1.34 (t, J = 1.2 Hz, 6H). |
| 117 | 1H NMR (400 MHz, Methanol-d4) δ 8.49 (s, 1H), 8.43-8.31 (m, 2H), 7.92 (s, 1H), 7.76 (d, J = 4.9 Hz, 1H), 7.01 (d, J = 4.9 Hz, 1H), 4.40 (ddd, J = 48.5, 8.8, 2.5 Hz, 1H), 4.08 (p, J = 7.6 Hz, 1H), 3.88 (ddd, J = 34.2, 14.5, 2.4 Hz, 1H), 3.45 (ddd, J = 17.2, 14.5, 8.8 Hz, 1H), 2.63-2.47 (m, 2H), 2.12-1.96 (m, 2H), 1.95-1.78 (m, 2H), 1.28 (t, J = 1.9 Hz, 6H). |
| 118 | 1H NMR (400 MHz, Methanol-d4) δ 8.53 (d, J = 1.6 Hz, 2H), 8.50 (d, J = 2.3 Hz, 1H), 8.44 (d, J = 2.2 Hz, 1H), 7.82-7.71 (m, 1H), 7.05 (d, J = 4.9 Hz, 1H), 4.41 (ddd, J = 48.9, 9.1, 2.3 Hz, 1H), 3.86 (ddd, J = 35.2, 14.5, 2.4 Hz, 1H), 3.46 (ddd, J = 16.6, 14.5, 9.1 Hz, 1H), 1.49 (s, 3H), 1.28 (d, J = 1.6 Hz, 6H), 0.86 (dt, J = 7.9, 1.9 Hz, 4H). |
| 119 | 1H NMR (400 MHz, Methanol-d4) δ 8.72 (d, J = 2.2 Hz, 1H), 8.66 (s, 1H), 8.62 (d, J = 2.2 Hz, 1H), 8.14 (s, 1H), 7.98 (s, 1H), 7.83 (d, J = 5.1 Hz, 1H), 7.72 (s, 1H), 7.18 (d, J = 5.0 Hz, 1H), 4.78-4.46 (m, 1H), 4.43-4.30 (m, 2H), 4.06-3.90 (m, 1H), 3.82 (t, J = 5.0 Hz, 2H), 3.52 (ddd, J = 16.1, 14.5, 9.3 Hz, 1H), 3.35 (s, 3H), 1.29 (d, J = 1.6 Hz, 6H). |
| 120 | 1H NMR (400 MHz, Methanol-d4) δ 8.74 (d, J = 2.2 Hz, 1H), 8.65 (d, J = 2.2 Hz, 1H), 8.56 (s, 1H), 7.98 (d, J = 5.0 Hz, 1H), 7.83 (s, 1H), 7.20 (d, J = 5.0 Hz, 1H), 4.14 (p, J = 6.3 Hz, 1H), 4.06 (q, J = 8.1 Hz, 1H), 2.49 (ddd, J = 9.3, 7.6, 2.9 Hz, 2H), 2.16 (td, J = 9.1, 2.8 Hz, 2H), 1.39 (d, J = 6.3 Hz, 9H). |
| 121 | 1H NMR (400 MHz, Methanol-d4) δ 8.74 (d, J = 2.2 Hz, 1H), 8.65 (d, J = 2.2 Hz, 1H), 8.56 (s, 1H), 7.99 (d, J = 5.1 Hz, 1H), 7.84 (s, 1H), 7.20 (d, J = 5.1 Hz, 1H), 4.26-4.00 (m, 1H), 3.42-3.33 (m, 2H), 3.23-2.97 (m, 4H), 2.19 (d, J = 13.9 Hz, 2H), 2.08-1.91 (m, 1H), 1.92-1.70 (m, 2H), 1.40 (d, J = 6.4 Hz, 6H). |
| 122 | 1H NMR (400 MHz, Methanol-d4) δ 8.74 (d, J = 2.2 Hz, 1H), 8.66 (d, J = 2.2 Hz, 1H), 8.60 (s, 1H), 7.99 (d, J = 5.1 Hz, 1H), 7.86 (s, 1H), 7.21 (d, J = 5.1 Hz, 1H), 4.15 (p, J = 6.4 Hz, 1H), 3.63 (s, 2H), 3.50-3.09 (m, 4H), 2.46-2.19 (m, 2H), 1.40 (d, J = 6.4 Hz, 6H) |
| 123 | 1H NMR (400 MHz, Methanol-d4) δ 8.74 (d, J = 2.2 Hz, 1H), 8.66 (d, J = 2.2 Hz, 1H), 8.60 (s, 1H), 7.99 (d, J = 5.1 Hz, 1H), 7.86 (s, 1H), 7.20 (d, J = 5.1 Hz, 1H), 4.82-4.66 (m, 1H), 4.16 (h, J = 6.4 Hz, 1H), 3.57 (dd, J = 13.6, 7.8 Hz, 1H), 3.45-3.33 (m, 1H), 3.26-3.05 (m, 2H), 2.64 (dq, J = 13.2, 6.3 Hz, 1H), 2.34 (dq, J = 13.5, 8.4 Hz, 1H), 1.40 (d, J = 6.4 Hz, 6H). |
| 124 | 1H NMR (400 MHz, Methanol-d4) δ 8.75 (d, J = 2.2 Hz, 1H), 8.67 (d, J = 2.2 Hz, 1H), 8.61 (s, 1H), 7.99 (d, J = 5.1 Hz, 1H), 7.85 (s, 1H), 7.21 (d, J = 5.1 Hz, 1H), 4.60-4.47 (m, 1H), 4.46-4.33 (m, 1H), 4.23-4.05 (m, 1H), 2.56-2.31 (m, 4H), 1.96 (s, 3H), 1.40 (d, J = 6.4 Hz, 6H). |
| 125 | 1H NMR (400 MHz, Methanol-d4) δ 8.75 (d, J = 2.2 Hz, 1H), 8.66 (d, J = 2.2 Hz, 1H), 8.53 (s, 1H), 7.98 (d, J = 5.1 Hz, 1H), 7.84 (s, 1H), 7.21 (d, J = 5.0 Hz, 1H), 4.20-4.09 (m, 1H), 3.95-3.81 (m, 1H), 3.76-3.60 (m, 1H), 2.03 (dd, J = 24.4, 12.3 Hz, 5H), 1.61-1.44 (m, 3H), 1.44-1.32 (m, 7H), 0.89-0.81 (m, 2H), 0.77-0.67 (m, 2H). |
| 126 | 1H NMR (400 MHz, Methanol-d4) δ 8.75 (d, J = 2.2 Hz, 1H), 8.66 (d, J = 2.2 Hz, 1H), 8.53 (s, 1H), 7.99 (d, J = 5.0 Hz, 1H), 7.84 (s, 1H), 7.21 (d, J = 5.1 Hz, 1H), 4.21-4.10 (m, 1H), 3.93-3.81 (m, 1H), 3.70-3.54 (m, 5H), 3.41-3.34 (m, 4H), 2.03 (dd, J = 23.5, 11.8 Hz, 4H), 1.57-1.36 (m, 10H). |
| 127 | 1H NMR (400 MHz, Methanol-d4) δ 8.74 (d, J = 2.2 Hz, 1H), 8.66 (d, J = 2.2 Hz, 1H), 8.53 (s, 1H), 7.98 (d, J = 5.1 Hz, 1H), 7.83 (s, 1H), 7.20 (d, J = 5.1 Hz, 1H), 4.22-4.05 (m, 1H), 3.93-3.84 (m, 1H), 3.83-3.70 (m, 1H), 2.17-1.91 (m, 4H), 1.65-1.45 (m, 4H), 1.40 (d, J = 6.4 Hz, 6H). |
| 128 | 1H NMR (400 MHz, Methanol-d4) δ 9.63 (s, 1H), 8.81 (s, 1H), 8.71 (d, J = 2.2 Hz, 1H), 8.63 (d, J = 2.2 Hz, 1H), 8.38 (s, 1H), 7.89 (d, J = 5.0 Hz, 1H), 7.19 (d, J = 5.0 Hz, 1H), 4.47 (ddd, J = 49.1, 9.2, 2.0 Hz, 1H), 4.30 (t, J = 7.3 Hz, 2H), 4.08-3.90 (m, 1H), 3.63-3.44 (m, 1H), 1.58 (t, J = 7.3 Hz, 3H), 1.30 (d, J = 1.6 Hz, 6H). |
| 129 | 1H NMR (400 MHz, Methanol-d4) δ 8.76-8.61 (m, 2H), 8.53 (d, J = 2.2 Hz, 1H), 7.94 (s, 1H), 7.81 (d, J = 5.1 Hz, 1H), 7.63 (s, 1H), 7.14 (d, J = 5.1 Hz, 1H), 4.45 (dd, J = 48.4, 7.7 Hz, 1H), 4.21 (t, J = 6.1 Hz, 2H), 3.97 (dd, J = 36.4, 14.4 Hz, 1H), 3.71-3.40 (m, 1H), 2.73 (t, J = 6.4 Hz, 2H), 2.11 (d, J = 6.0 Hz, 2H), 1.92 (q, J = 5.9 Hz, 2H), 1.29 (d, J = 1.7 Hz, 6H). |
| 130 | 1H NMR (400 MHz, Methanol-d4) δ 8.65 (d, J = 2.2 Hz, 1H), 8.60 (d, J = 1.1 Hz, 1H), 8.58 (d, J = 2.2 Hz, 1H), 8.08 (s, 1H), 7.91 (d, J = 5.0 Hz, 1H), 7.14 (d, J = 5.0 Hz, 1H), 4.42 (ddd, J = 49.0, 9.2, 2.1 Hz, 1H), 4.19 (dd, J = 7.4, 5.8 Hz, 1H), 4.09-3.80 (m, 3H), 3.49 (ddd, J = 16.1, 14.5, 9.3 Hz, 1H), 2.67 (dq, J = 13.4, 7.3 Hz, 1H), 2.08-1.94 (m, 1H), 1.41 (s, 3H), 1.28 (d, J = 1.7 Hz, 9H), 1.19 (s, 1H). |

TABLE 2-continued

| compound | 1H-NMR |
|---|---|
| 131 | 1H NMR (400 MHz, Methanol-d4) δ 8.75 (d, J = 2.2 Hz, 1H), 8.66 (d, J = 2.1 Hz, 1H), 8.47 (s, 1H), 7.98 (d, J = 5.0 Hz, 1H), 7.80 (s, 1H), 7.21 (d, J = 5.0 Hz, 1H), 4.19-4.07 (m, 1H), 2.20-2.00 (m, 12H), 1.87 (s, 3H), 1.40 (d, J = 6.4 Hz, 6H). |
| 132 | 1H NMR (400 MHz, Methanol-d4) δ 8.75 (d, J = 2.2 Hz, 1H), 8.66 (d, J = 2.2 Hz, 1H), 8.54 (s, 1H), 7.98 (d, J = 5.1 Hz, 1H), 7.85 (s, 1H), 7.21 (d, J = 5.1 Hz, 1H), 4.21-4.09 (m, 1H), 2.44 (s, 6H), 1.92 (s, 3H), 1.41 (d, J = 6.4 Hz, 6H). |
| 133 | 1H NMR (400 MHz, Methanol-d4) δ 8.73 (d, J = 2.2 Hz, 1H), 8.64 (d, J = 2.2 Hz, 1H), 8.51 (s, 1H), 7.97 (d, J = 5.1 Hz, 1H), 7.82 (s, 1H), 7.20 (d, J = 5.0 Hz, 1H), 4.42 (ddd, J = 49.0, 9.3, 2.2 Hz, 1H), 3.93 (ddd, J = 36.2, 14.5, 2.2 Hz, 1H), 3.64 (t, J = 6.6 Hz, 2H), 3.56 (t, J = 5.7 Hz, 2H), 3.53-3.41 (m, 1H), 3.37 (s, 3H), 2.01 (p, J = 6.3 Hz, 2H), 1.28 (d, J = 1.7 Hz, 6H). |
| 134 | 1H NMR (400 MHz, Methanol-d4) δ 8.75 (d, J = 2.2 Hz, 1H), 8.66 (d, J = 2.2 Hz, 1H), 8.55 (s, 1H), 7.99 (d, J = 5.1 Hz, 1H), 7.84 (s, 1H), 7.21 (d, J = 5.1 Hz, 1H), 4.91-4.85 (m, 2H), 4.39 (d, J = 6.1 Hz, 2H), 4.22-4.10 (m, 1H), 3.94-3.81 (m, 1H), 3.79-3.67 (m, 2H), 2.13-1.93 (m, 4H), 1.59 (s, 3H), 1.55-1.38 (m, 9H). |
| 135 | 1H NMR (400 MHz, Methanol-d4) δ 8.75 (d, J = 2.2 Hz, 1H), 8.66 (d, J = 2.2 Hz, 1H), 8.54 (s, 1H), 7.99 (d, J = 5.0 Hz, 1H), 7.84 (s, 1H), 7.21 (d, J = 5.1 Hz, 1H), 4.21-4.09 (m, 1H), 3.90 (s, 1H), 3.67 (s, 1H), 2.14-2.03 (m, 2H), 2.01-1.94 (m, 2H), 1.57-1.43 (m, 4H), 1.41 (d, J = 6.4 Hz, 6H), 1.36 (s, 6H). |
| 136 | 1H NMR (400 MHz, Methanol-d4) δ 8.74 (d, J = 2.2 Hz, 1H), 8.68 (d, J = 2.1 Hz, 1H), 8.60 (d, J = 3.5 Hz, 1H), 8.00 (d, J = 5.1 Hz, 1H), 7.70 (d, J = 1.7 Hz, 1H), 7.21 (dd, J = 5.1, 1.6 Hz, 1H), 4.63-4.30 (m, 2H), 3.93 (ddd, J = 36.4, 14.6, 2.3 Hz, 1H), 3.59-3.39 (m, 1H), 3.10-2.83 (m, 2H), 2.50-2.23 (m, 2H), 1.55 (d, J = 21.9 Hz, 3H), 1.29 (d, J = 1.7 Hz, 6H). |
| 137 | 1H NMR (400 MHz, Methanol-d4) δ 8.75 (d, J = 2.1 Hz, 1H), 8.66 (d, J = 2.2 Hz, 1H), 8.59 (s, 1H), 8.02 (d, J = 5.1 Hz, 1H), 7.85 (s, 1H), 7.21 (d, J = 5.1 Hz, 1H), 4.43 (ddd, J = 49.1, 9.4, 2.1 Hz, 1H), 3.94 (ddd, J = 36.6, 14.6, 2.1 Hz, 1H), 3.81-3.62 (m, 2H), 3.49 (dddd, J = 15.8, 14.6, 9.4, 1.1 Hz, 1H), 2.25-2.06 (m, 1H), 1.68 (tdd, J = 12.1, 8.0, 4.8 Hz, 1H), 1.43 (dtd, J = 13.4, 7.7, 3.7 Hz, 1H), 1.29 (d, J = 1.7 Hz, 6H). |
| 138 | 1H NMR (400 MHz, Methanol-d4) δ 9.02 (s, 1H), 8.73-8.63 (m, 2H), 8.60 (d, J = 2.2 Hz, 1H), 7.81 (d, J = 5.0 Hz, 1H), 7.70 (d, J = 2.4 Hz, 1H), 7.14 (d, J = 5.0 Hz, 1H), 6.31 (d, J = 2.4 Hz, 1H), 4.47 (ddd, J = 49.0, 9.3, 2.1 Hz, 1H), 4.14 (s, 2H), 3.97 (ddd, J = 36.3, 14.6, 2.2 Hz, 1H), 3.52 (ddd, J = 16.1, 14.6, 9.3 Hz, 1H), 1.30 (d, J = 1.6 Hz, 6H), 1.23 (s, 6H). |
| 139 | 1H NMR (400 MHz, Methanol-d4) δ 8.74 (d, J = 2.2 Hz, 1H), 8.66 (d, J = 2.1 Hz, 1H), 8.58 (s, 1H), 7.98 (d, J = 5.1 Hz, 1H), 7.85 (s, 1H), 7.20 (d, J = 5.1 Hz, 1H), 4.31-4.20 (m, 1H), 4.15 (p, J = 6.4 Hz, 1H), 3.43-3.30 (m, 2H), 3.13 (d, J = 13.6 Hz, 2H), 2.34 (t, J = 8.4 Hz, 2H), 2.22 (q, J = 11.3, 10.6 Hz, 2H), 1.39 (d, J = 6.4 Hz, 6H). |
| 140 | 1H NMR (400 MHz, Methanol-d4) δ 8.76 (d, J = 9.6 Hz, 2H), 8.51 (dd, J = 21.6, 2.2 Hz, 2H), 7.96-7.68 (m, 3H), 7.61-7.37 (m, 2H), 7.06 (d, J = 4.8 Hz, 1H), 4.45 (ddd, J = 49.0, 9.1, 2.2 Hz, 1H), 3.93 (ddd, J = 35.8, 14.5, 2.3 Hz, 1H), 3.65-3.41 (m, 1H), 1.29 (d, J = 1.7 Hz, 6H). |
| 141 | 1H NMR (400 MHz, DMSO-d6) δ 8.80 (s, 1H), 8.72-8.57 (m, 2H), 8.46 (d, J = 2.2 Hz, 1H), 7.91-7.74 (m, 2H), 7.74-7.39 (m, 4H), 7.05 (d, J = 4.9 Hz, 1H), 4.37 (ddd, J = 49.2, 9.3, 2.2 Hz, 1H), 3.92-3.59 (m, 1H), 3.42 (ddd, J = 16.1, 14.4, 9.2 Hz, 1H), 1.16 (dd, J = 4.2, 1.6 Hz, 6H). |
| 142 | |
| 143 | 1H NMR (400 MHz, Methanol-d4) δ 8.80 (s, 1H), 8.67 (d, J = 2.2 Hz, 1H), 8.49 (d, J = 2.2 Hz, 1H), 8.17 (s, 1H), 8.06-7.43 (m, 5H), 7.14 (d, J = 5.0 Hz, 1H), 4.48 (ddd, J = 49.1, 9.4, 2.1 Hz, 1H), 4.00 (ddd, J = 36.5, 14.5, 2.1 Hz, 1H), 3.53 (ddd, J = 15.9, 14.5, 9.4 Hz, 1H), 1.52-1.11 (m, 6H). |
| 144 | 1H NMR (400 MHz, DMSO-d6) δ 10.06 (s, 1H), 9.02 (s, 1H), 8.89 (d, J = 2.2 Hz, 1H), 8.72 (s, 1H), 8.41 (s, 1H), 7.99 (d, J = 4.9 Hz, 1H), 7.30 (d, J = 12.6 Hz, 1H), 7.14 (d, J = 4.9 Hz, 1H), 4.87 (d, J = 4.8 Hz, 1H), 4.84-4.50 (m, 2H), 4.08 (dd, J = 36.6, 14.1 Hz, 1H), 3.72 (s, 4H), 3.53 (s, 4H), 1.18 (s, 6H). |
| 145 | 1H NMR (400 MHz, DMSO-d6) δ 11.55 (s, 1H), 10.12 (s, 1H), 9.12 (s, 1H), 8.94 (s, 1H), 8.89-8.81 (m, 2H), 8.51 (d, J = 2.8 Hz, 1H), 8.48 (s, 1H), 8.23 (d, J = 2.4 Hz, 1H), 7.90 (d, J = 4.8 Hz, 1H), 7.12 (d, J = 4.8 Hz, 1H), 4.40 (m, 1H), 3.77 (m, 1H), 1.17 (d, J = 6.0 Hz, 6H). |
| 146 | 1H NMR (400 MHz, DMSO-d6) δ 12.06 (s, 1H), 9.42 (d, J = 22.2 Hz, 1H), 9.19 (s, 1H), 8.97 (s, 1H), 8.87 (d, J = 2.3 Hz, 1H), 8.80 (s, 1H), 7.89 (d, J = 4.8 Hz, 1H), 7.13 (d, J = 4.7 Hz, 1H), 2.69 (s, 3H), 1.17 (d, J = 6.3 Hz, 6H), 1.12 (d, J = 1.8 Hz, 3H). |
| 147 | 1H NMR (400 MHz, Methanol-d4) δ 8.76 (d, J = 2.2 Hz, 1H), 8.69 (dd, J = 2.2, 0.4 Hz, 1H), 8.58 (s, 1H), 8.24 (s, 1H), 7.95 (dd, J = 5.1, 0.5 Hz, 1H), 7.23 (d, J = 5.1 Hz, 1H), 4.42 (ddd, J = 49.0, 9.4, 2.2 Hz, 1H), 4.17 (d, J = 8.7 Hz, 2H), 3.99-3.78 (m, 3H), 3.48 (ddd, J = 16.2, 14.6, 9.3 Hz, 1H), 2.67 (t, J = 2.4 Hz, 1H), 2.13 (q, J = 2.1, 1.6 Hz, 2H), 1.28 (d, J = 1.7 Hz, 6H). |
| 148 | 1H NMR (400 MHz, Methanol-d4) δ 8.75 (d, J = 2.2 Hz, 1H), 8.68 (dd, J = 2.2, 0.4 Hz, 1H), 8.60 (s, 1H), 8.16 (s, 1H), 7.99 (dd, J = 5.1, 0.5 Hz, 1H), 7.21 (d, J = 5.1 Hz, 1H), 4.41 (ddd, J = 49.0, 9.4, 2.2 Hz, 1H), 4.15-3.77 (m, 5H), 3.47 (ddd, J = 16.1, 14.5, 9.4 Hz, 1H), 3.20 (t, J = 6.8 Hz, 1H), 2.33 (ddd, J = 6.8, 2.0, 1.1 Hz, 2H), 1.28 (d, J = 1.6 Hz, 6H). |

TABLE 2-continued

| compound | 1H-NMR |
|---|---|
| 149 | 1H NMR (400 MHz, DMSO-d6) δ 7.93 (d, J = 2.2 Hz, 1H), 7.84 (dd, J = 2.2, 0.4 Hz, 1H), 7.73 (s, 1H), 7.17 (dd, J = 5.1, 0.5 Hz, 1H), 7.01 (s, 1H), 6.39 (d, J = 5.0 Hz, 1H), 3.56 (p, J = 8.3 Hz, 1H), 3.43-3.21 (m, 2H), 1.75-1.60 (m, 2H), 1.60-1.40 (m, 2H), 1.38-1.24 (m, 2H), 1.16 (ddd, J = 14.5, 11.1, 7.7 Hz, 2H), 0.58 (d, J = 6.4 Hz, 6H). |
| 150 | 1H NMR (400 MHz, Methanol-d4) δ 8.75 (d, J = 2.2 Hz, 1H), 8.66 (dd, J = 2.2, 0.5 Hz, 1H), 8.61 (s, 1H), 8.02 (dd, J = 5.1, 0.5 Hz, 1H), 7.97 (s, 1H), 7.21 (dd, J = 5.1, 0.4 Hz, 1H), 4.70-4.52 (m, 1H), 4.52-4.29 (m, 2H), 4.14 (dt, J = 10.6, 5.0 Hz, 1H), 4.04-3.84 (m, 2H), 3.67-3.43 (m, 3H), 2.32-2.13 (m, 1H), 1.94-1.75 (m, 1H), 1.29 (d, J = 1.7 Hz, 6H). |
| 151 | 1H NMR (400 MHz, Methanol-d4) δ 8.75 (d, J = 2.1 Hz, 1H), 8.66 (d, J = 2.2 Hz, 1H), 8.61 (s, 1H), 8.06-8.00 (m, 1H), 7.97 (s, 1H), 7.21 (d, J = 5.0 Hz, 1H), 4.73-4.52 (m, 1H), 4.51-4.29 (m, 2H), 4.14 (dt, J = 10.7, 5.1 Hz, 1H), 4.07-3.86 (m, 2H), 3.74-3.41 (m, 3H), 2.30-2.14 (m, 1H), 1.93-1.78 (m, 1H), 1.29 (d, J = 1.7 Hz, 6H). |
| 152 | 1H NMR (400 MHz, Methanol-d4) δ 8.75 (d, J = 2.2 Hz, 1H), 8.66 (dd, J = 2.2, 0.4 Hz, 1H), 8.57 (s, 1H), 7.99 (dd, J = 5.0, 0.5 Hz, 1H), 7.84 (s, 1H), 7.21 (d, J = 5.2 Hz, 1H), 4.59-4.43 (m, 1H), 4.22-4.08 (m, 1H), 3.25-3.18 (m, 2H), 3.15-3.07 (m, 2H), 2.66 (ddd, J = 9.3, 7.7, 2.8 Hz, 2H), 2.47-2.36 (m, 2H), 1.40 (d, J = 6.4 Hz, 6H). |
| 153 | 1H NMR (400 MHz, Methanol-d4) δ 8.74 (d, J = 2.1 Hz, 1H), 8.69-8.59 (m, 1H), 8.54 (s, 1H), 8.04-7.91 (m, 1H), 7.82 (s, 1H), 7.20 (d, J = 5.1 Hz, 1H), 4.36 (p, J = 8.2 Hz, 1H), 4.13 (p, J = 6.4 Hz, 1H), 2.52 (ddd, J = 11.8, 7.4, 5.0 Hz, 2H), 2.47-2.37 (m, 1H), 2.31-1.97 (m, 6H), 1.39 (d, J = 6.4 Hz, 6H), 1.31 (s, 3H). |
| 154 | 1H NMR (400 MHz, Methanol-d4) δ 8.74 (d, J = 2.2 Hz, 1H), 8.65 (d, J = 2.2 Hz, 1H), 8.56 (s, 1H), 8.00 (d, J = 5.0 Hz, 1H), 7.86 (s, 1H), 7.20 (d, J = 5.1 Hz, 1H), 4.42 (ddd, J = 49.1, 9.3, 2.1 Hz, 1H), 4.02-3.74 (m, 2H), 3.48 (td, J = 15.3, 9.8 Hz, 1H), 2.04-1.89 (m, 2H), 1.91-1.71 (m, 4H), 1.66 (td, J = 13.3, 4.0 Hz, 2H), 1.31-1.23 (m, 9H). |
| 155 | 1H NMR (400 MHz, Methanol-d4) δ 8.76 (d, J = 2.2 Hz, 1H), 8.69 (d, J = 2.2 Hz, 1H), 8.62 (d, J = 0.8 Hz, 1H), 8.04 (d, J = 5.1 Hz, 1H), 7.90 (s, 1H), 7.22 (d, J = 5.1 Hz, 1H), 4.52-4.31 (m, 2H), 4.04-3.82 (m, 1H), 3.65-3.42 (m, 3H), 3.02 (s, 3H), 2.93 (dd, J = 17.1, 5.3 Hz, 1H), 2.54 (dd, J = 17.1, 8.4 Hz, 1H), 2.39-2.28 (m, 1H), 2.19-2.04 (m, 1H), 1.29 (d, J = 1.7 Hz, 6H). |
| 156 | 1H NMR (400 MHz, Methanol-d4) δ 8.77 (d, J = 2.2 Hz, 1H), 8.69 (d, J = 2.2 Hz, 1H), 8.61 (s, 1H), 8.06 (d, J = 5.1 Hz, 1H), 7.92 (d, J = 1.3 Hz, 2H), 7.61 (t, J = 1.7 Hz, 1H), 7.23 (d, J = 5.1 Hz, 1H), 6.67 (dd, J = 1.9, 0.9 Hz, 1H), 4.43 (ddd, J = 49.2, 9.3, 2.1 Hz, 1H), 4.31-4.15 (m, 2H), 4.03-3.84 (m, 1H), 3.58-3.39 (m, 2H), 2.21 (d, J = 12.8 Hz, 2H), 1.81-1.63 (m, 2H), 1.29 (d, J = 1.7 Hz, 6H). |
| 157 | 1H NMR (400 MHz, Methanol-d4) δ 8.74 (dd, J = 3.2, 2.2 Hz, 1H), 8.68-8.50 (m, 2H), 7.99 (dd, J = 7.8, 5.0 Hz, 1H), 7.85 (d, J = 9.0 Hz, 1H), 7.69-7.36 (m, 1H), 7.21 (dd, J = 5.1, 4.0 Hz, 1H), 6.60-6.36 (m, 2H), 4.52-4.27 (m, 2H), 4.27-4.07 (m, 1H), 1.40 (dd, J = 6.4, 1.7 Hz, 6H). |
| 158 | 1H NMR (400 MHz, Methanol-d4) δ 8.74 (dd, J = 7.7, 2.1 Hz, 2H), 8.55 (s, 1H), 8.32 (s, 1H), 7.94 (d, J = 5.1 Hz, 1H), 7.22 (d, J = 5.1 Hz, 1H), 4.40 (ddd, J = 49.1, 9.4, 2.1 Hz, 1H), 4.42-4.23 (m, 2H), 3.98-3.80 (m, 2H), 3.74 (d, J = 10.6 Hz, 1H), 3.47 (ddd, J = 16.0, 14.5, 9.4 Hz, 1H), 3.26 (s, 3H), 2.20-2.03 (m, 12H), 1.48 (s, 3H), 1.28 (d, J = 1.7 Hz, 6H). |
| 159 | 1H NMR (400 MHz, Methanol-d4) δ 8.78-8.70 (m, 2H), 8.54 (s, 1H), 8.31 (s, 1H), 7.94 (d, J = 5.1 Hz, 1H), 7.22 (d, J = 5.1 Hz, 1H), 4.51-4.26 (m, 3H), 3.99-3.79 (m, 3H), 3.47 (ddd, J = 16.0, 14.5, 9.4 Hz, 1H), 2.22-2.04 (m, 12H), 1.47 (s, 3H), 1.28 (d, J = 1.7 Hz, 6H). |
| 160 | 1H NMR (400 MHz, Methanol-d4) δ 8.99 (s, 1H), 8.69 (d, J = 2.2 Hz, 1H), 8.63 (d, J = 2.2 Hz, 1H), 8.26 (s, 1H), 8.01 (d, J = 5.0 Hz, 1H), 7.17 (d, J = 5.0 Hz, 1H), 5.29 (tt, J = 6.8, 3.5 Hz, 1H), 4.57-4.36 (m, 2H), 4.05 (ddd, J = 33.0, 14.5, 2.9 Hz, 1H), 3.58 (ddd, J = 16.7, 14.5, 8.7 Hz, 1H), 2.83-2.64 (m, 4H), 2.50 (tt, J = 7.0, 3.6 Hz, 1H), 1.30 (t, J = 2.1 Hz, 6H), 0.72 (td, J = 6.9, 4.8 Hz, 2H), 0.53-0.43 (m, 2H). |
| 161 | 1H NMR (400 MHz, Methanol-d4) δ 8.99 (s, 1H), 8.69 (d, J = 2.2 Hz, 1H), 8.63 (d, J = 2.2 Hz, 1H), 8.22 (s, 1H), 8.01 (d, J = 5.0 Hz, 1H), 7.17 (d, J = 5.0 Hz, 1H), 5.30 (tt, J = 6.7, 3.8 Hz, 1H), 4.59-4.35 (m, 2H), 4.05 (ddd, J = 33.1, 14.5, 2.9 Hz, 1H), 3.58 (ddd, J = 16.7, 14.5, 8.8 Hz, 1H), 2.93 (s, 6H), 2.83-2.67 (m, 4H), 1.35-1.26 (m, 6H). |
| 162 | 1H NMR (400 MHz, Methanol-d4) δ 8.98 (s, 1H), 8.69 (d, J = 2.2 Hz, 1H), 8.64 (d, J = 2.2 Hz, 1H), 8.23 (s, 1H), 8.02 (d, J = 5.0 Hz, 1H), 7.17 (d, J = 5.0 Hz, 1H), 5.29 (tt, J = 6.9, 3.7 Hz, 1H), 4.52 (dd, J = 8.8, 2.8 Hz, 1H), 4.41 (td, J = 8.9, 8.1, 2.4 Hz, 1H), 4.05 (ddd, J = 33.0, 14.5, 2.9 Hz, 1H), 3.58 (ddd, J = 16.7, 14.5, 8.7 Hz, 1H), 2.77 (ddt, J = 11.9, 8.0, 3.5 Hz, 1H), 2.72 (s, 3H), 2.65 (dt, J = 14.0, 6.4 Hz, 2H), 1.30 (dd, J = 2.9, 1.7 Hz, 6H). |
| 163 | 1H NMR (400 MHz, Methanol-d4) δ 9.00 (s, 1H), 8.75 (d, J = 2.2 Hz, 1H), 8.66 (d, J = 2.2 Hz, 1H), 8.44 (s, 1H), 8.14-8.09 (m, 1H), 7.21 (d, J = 5.1 Hz, 1H), 6.99-6.84 (m, 1H), 4.99 (dt, J = 10.4, 5.9 Hz, 1H), 4.43 (ddd, J = 48.6, 8.8, 2.8 Hz, 1H), 4.04 (ddd, J = 33.4, 14.5, 2.8 Hz, 1H), 3.72-3.62 (m, 0H), 3.61-3.49 (m, 1H), 2.48 (tt, J = 7.0, 3.6 Hz, 1H), 2.35 (d, J = 12.0 Hz, 2H), 2.10 (d, J = 12.6 Hz, 2H), 1.85 (q, J = 12.1 Hz, 2H), 1.55 (q, J = 11.1 Hz, 2H), 1.30 (dd, J = 3.5, 1.6 Hz, 6H), 0.70 (td, J = 6.9, 4.8 Hz, 2H), 0.51-0.42 (m, 2H). |

TABLE 2-continued

| compound | 1H-NMR |
|---|---|
| 164 | 1H NMR (400 MHz, Methanol-d4) δ 9.01 (s, 1H), 8.75 (d, J = 2.2 Hz, 1H), 8.65 (d, J = 2.2 Hz, 1H), 8.47 (s, 1H), 8.10 (d, J = 4.8 Hz, 1H), 7.21 (d, J = 5.1 Hz, 1H), 4.96 (dq, J = 10.6, 6.0, 5.1 Hz, 1H), 4.43 (ddd, J = 48.6, 8.8, 2.8 Hz, 1H), 4.04 (ddd, J = 33.2, 14.5, 2.8 Hz, 1H), 3.68 (tt, J = 11.3, 3.9 Hz, 1H), 3.62-3.49 (m, 1H), 2.91 (s, 6H), 2.45-2.31 (m, 2H), 2.09 (dd, J = 13.4, 3.7 Hz, 2H), 1.83 (q, J = 12.0 Hz, 2H), 1.69-1.51 (m, 2H), 1.29 (dd, J = 3.6, 1.6 Hz, 6H). |
| 165 | 1H NMR (400 MHz, Methanol-d4) δ 9.00 (s, 1H), 8.76 (d, J = 2.2 Hz, 1H), 8.67 (d, J = 2.2 Hz, 1H), 8.42 (s, 1H), 8.13 (d, J = 5.1 Hz, 1H), 7.22 (d, J = 5.0 Hz, 1H), 5.00 (dt, J = 10.3, 6.0 Hz, 1H), 4.43 (ddd, J = 48.6, 8.8, 2.8 Hz, 1H), 4.04 (ddd, J = 33.5, 14.5, 2.8 Hz, 1H), 3.70-3.50 (m, 1H), 2.70 (s, 3H), 2.34 (d, J = 12.6 Hz, 2H), 2.10 (d, J = 13.0 Hz, 2H), 1.85 (q, J = 11.7 Hz, 2H), 1.51 (q, J = 10.7 Hz, 2H), 1.30 (dd, J = 3.5, 1.6 Hz, 6H). |
| 166 | 1H NMR (400 MHz, Methanol-d4) δ 8.95 (s, 1H), 8.74 (d, J = 2.2 Hz, 1H), 8.68 (d, J = 2.2 Hz, 1H), 8.43 (s, 1H), 8.17-8.07 (m, 1H), 7.21 (d, J = 5.1 Hz, 1H), 5.21 (s, 1H), 4.46 (ddd, J = 49.1, 9.3, 2.3 Hz, 1H), 4.08 (ddd, J = 36.4, 14.6, 2.4 Hz, 1H), 3.79-3.65 (m, 1H), 3.61-3.49 (m, 1H), 2.47 (tt, J = 7.0, 3.6 Hz, 1H), 2.23 (d, J = 14.0 Hz, 2H), 2.05-1.82 (m, 4H), 1.67 (q, J = 11.4, 10.5 Hz, 2H), 1.29 (d, J = 1.6 Hz, 6H), 0.70 (td, J = 6.9, 4.8 Hz, 2H), 0.49-0.40 (m, 2H). |
| 167 | 1H NMR (400 MHz, Methanol-d4) δ 8.96 (s, 1H), 8.73 (d, J = 2.2 Hz, 1H), 8.67 (d, J = 2.2 Hz, 1H), 8.43 (s, 1H), 8.10 (d, J = 5.0 Hz, 1H), 7.20 (d, J = 5.0 Hz, 1H), 5.22 (s, 1H), 4.48 (ddd, J = 48.9, 9.2, 2.4 Hz, 1H), 4.10 (ddd, J = 36.1, 14.5, 2.4 Hz, 1H), 3.72 (t, J = 11.0 Hz, 1H), 3.63-3.50 (m, 1H), 2.90 (s, 6H), 2.36-2.24 (m, 2H), 1.95 (d, J = 13.7 Hz, 1H), 1.87 (d, J = 16.2 Hz, 3H), 1.77-1.60 (m, 2H), 1.29 (s, 6H). |
| 168 | 1H NMR (400 MHz, Methanol-d4) δ 8.94 (s, 1H), 8.74 (d, J = 2.2 Hz, 1H), 8.67 (d, J = 2.2 Hz, 1H), 8.43 (s, 1H), 8.10 (d, J = 5.0 Hz, 1H), 7.20 (d, J = 5.1 Hz, 1H), 5.20 (s, 1H), 4.46 (ddd, J = 49.0, 9.3, 2.4 Hz, 1H), 4.07 (ddd, J = 36.2, 14.5, 2.4 Hz, 1H), 3.67 (t, J = 10.1 Hz, 1H), 3.61-3.45 (m, 1H), 2.70 (s, 3H), 2.22 (d, J = 14.1 Hz, 2H), 1.96 (t, J = 13.3 Hz, 2H), 1.87 (d, J = 13.1, 4.3 Hz, 2H), 1.66 (d, J = 15.7 Hz, 2H), 1.30 (s, 6H). |
| 169 | 1H NMR (400 MHz, Methanol-d4) δ 8.96 (d, J = 0.8 Hz, 1H), 8.65 (d, J = 2.2 Hz, 1H), 8.54 (d, J = 2.2 Hz, 1H), 8.34 (s, 1H), 7.97 (d, J = 4.9 Hz, 1H), 7.14 (d, J = 4.9 Hz, 1H), 5.39-5.29 (m, 1H), 4.51 (dd, J = 8.8, 2.7 Hz, 1H), 4.39 (dd, J = 8.8, 2.7 Hz, 1H), 4.18-3.97 (m, 2H), 3.62-3.46 (m, 1H), 2.97-2.80 (m, 4H), 1.30 (t, J = 1.6 Hz, 6H). |
| 170 | 1H NMR (400 MHz, Methanol-d4) δ 8.87 (d, J = 2.1 Hz, 1H), 8.74 (d, J = 2.1 Hz, 1H), 8.68 (d, J = 4.4 Hz, 1H), 8.63 (s, 1H), 8.62 (d, J = 2.1 Hz, 1H), 8.34 (dt, J = 8.2, 1.8 Hz, 1H), 7.93 (d, J = 5.1 Hz, 1H), 7.91 (s, 1H), 7.84-7.78 (m, 1H), 7.18 (d, J = 5.1 Hz, 1H), 4.98 (s, 2H), 4.45 (ddd, J = 49.0, 9.4, 2.1 Hz, 1H), 3.96 (ddd, J = 36.5, 14.5, 2.1 Hz, 1H), 3.52 (ddd, J = 16.1, 14.5, 9.4 Hz, 1H), 1.29 (d, J = 1.7 Hz, 6H). |
| 171 | 1H NMR (400 MHz, Methanol-d4) δ 8.73 (d, J = 2.2 Hz, 1H), 8.63 (ddd, J = 5.0, 1.8, 0.9 Hz, 1H), 8.60 (d, J = 0.8 Hz, 2H), 8.60 (s, 1H), 7.96 (d, J = 5.1 Hz, 1H), 7.95-7.90 (m, 1H), 7.87 (s, 1H), 7.59 (dt, J = 7.9, 1.0 Hz, 1H), 7.42 (ddd, J = 7.6, 5.0, 1.1 Hz, 1H), 7.19 (d, J = 5.1 Hz, 1H), 4.45 (ddd, J = 49.0, 9.4, 2.2 Hz, 1H), 3.96 (ddd, J = 36.5, 14.5, 2.2 Hz, 1H), 3.51 (ddd, J = 16.0, 14.5, 9.4 Hz, 1H), 1.29 (d, J = 1.6 Hz, 7H). |
| 172 | 1H NMR (400 MHz, Methanol-d4) δ 8.75 (s, 1H), 8.70 (d, J = 2.2 Hz, 1H), 8.66 (d, J = 2.7 Hz, 1H), 8.58 (d, J = 2.2 Hz, 1H), 8.57 (d, J = 2.4 Hz, 1H), 8.17-8.07 (m, 3H), 7.85 (d, J = 5.1 Hz, 1H), 7.83 (s, 1H), 7.15 (d, J = 5.1 Hz, 1H), 6.60 (t, J = 2.2 Hz, 1H), 4.56-4.39 (m, 1H), 4.08-3.93 (m, 1H), 3.54 (td, J = 15.4, 9.4 Hz, 1H), 1.30 (d, J = 1.7 Hz, 6H). |
| 173 | 1H NMR (400 MHz, Methanol-d4) δ 8.75 (d, J = 2.1 Hz, 1H), 8.68 (d, J = 2.2 Hz, 1H), 8.56 (s, 1H), 8.03 (d, J = 5.0 Hz, 1H), 7.92 (s, 1H), 7.21 (d, J = 5.0 Hz, 1H), 4.41 (dd, J = 50.0, 8.7 Hz, 1H), 4.00-3.81 (m, 2H), 3.73-3.57 (m, 9H), 3.48 (td, J = 15.6, 9.4 Hz, 1H), 2.84-2.71 (m, 2H), 2.29-2.18 (m, 5H), 1.92 (d, J = 13.2 Hz, 2H), 1.77 (q, J = 12.7 Hz, 2H), 1.55 (q, J = 12.5, 12.1 Hz, 2H), 1.28 (d, J = 1.6 Hz, 6H). |
| 174 | 1H NMR (400 MHz, Methanol-d4) δ 8.75 (d, J = 2.2 Hz, 1H), 8.67 (d, J = 2.1 Hz, 1H), 8.56 (s, 1H), 8.03 (d, J = 5.1 Hz, 1H), 7.90 (s, 1H), 7.21 (d, J = 5.1 Hz, 1H), 4.66 (t, J = 11.5 Hz, 2H), 4.47 (d, J = 8.9 Hz, 1H), 4.33 (t, J = 12.4 Hz, 3H), 3.92 (dd, J = 34.8, 15.2 Hz, 2H), 3.48 (td, J = 15.5, 9.4 Hz, 1H), 2.44 (t, J = 11.9 Hz, 1H), 2.24 (d, J = 12.6 Hz, 2H), 1.96 (d, J = 13.6 Hz, 2H), 1.73 (q, J = 12.8, 12.4 Hz, 2H), 1.52 (d, J = 12.2 Hz, 1H), 1.28 (d, J = 1.6 Hz, 6H). |
| 175 | |
| 176 | 1H NMR (400 MHz, Methanol-d4) δ 8.94 (s, 1H), 8.76 (s, 1H), 8.64 (s, 1H), 8.54 (s, 1H), 8.50 (s, 1H), 8.33 (d, J = 9.0 Hz, 2H), 7.84 (d, J = 5.0 Hz, 1H), 7.72 (d, J = 8.7 Hz, 2H), 7.13 (d, J = 5.0 Hz, 1H), 4.47 (dd, J = 47.8, 8.5 Hz, 1H), 3.98 (dd, J = 36.4, 14.0 Hz, 1H), 3.66-3.44 (m, 2H), 1.35-1.26 (m, 6H). |
| 177 | 1H NMR (400 MHz, Methanol-d4) δ 8.71-8.69 (m, 2H), 8.59 (d, J = 2.2 Hz, 1H), 8.28 (s, 1H), 8.03-7.96 (m, 2H), 7.79 (d, J = 5.1 Hz, 1H), 7.73 (d, J = 2.3 Hz, 1H), 7.57-7.51 (m, 2H), 7.15 (d, J = 5.1 Hz, 1H), 6.77 (d, J = 2.3 Hz, 1H), 4.57-4.39 (m, 1H), 4.00 (dd, J = 36.6, 14.7 Hz, 1H), 3.53 (td, J = 15.4, 9.4 Hz, 1H), 1.30 (d, J = 1.6 Hz, 6H). |
| 178 | 1H NMR (400 MHz, Methanol-d4) δ 8.69 (d, J = 2.2 Hz, 2H), 8.56 (d, J = 2.2 Hz, 1H), 8.18 (s, 1H), 8.06 (s, 2H), 7.84-7.79 (m, 2H), 7.77 (d, J = 5.1 Hz, 1H), 7.50-7.44 (m, 2H), 7.15 (d, J = 5.1 Hz, 1H), 4.47 (ddd, J = 49.1, 9.3, 2.1 Hz, 1H), 4.07-3.92 (m, 1H), 3.53 (td, J = 15.4, 9.3 Hz, 1H), 1.30 (d, J = 1.6 Hz, 6H). |

TABLE 2-continued

| compound | 1H-NMR |
|---|---|
| 179 | 1H NMR (400 MHz, Methanol-d4) δ 8.71 (s, 1H), 8.70 (d, J = 2.2 Hz, 1H), 8.58 (d, J = 2.1 Hz, 1H), 8.50 (s, 1H), 8.34 (s, 1H), 8.25-8.18 (m, 2H), 7.81 (d, J = 5.1 Hz, 1H), 7.62-7.55 (m, 2H), 7.16 (d, J = 5.1 Hz, 1H), 4.47 (ddd, J = 49.0, 9.4, 2.1 Hz, 1H), 4.12-3.88 (m, 4H), 3.53 (ddd, J = 16.3, 14.8, 9.4 Hz, 1H), 1.30 (d, J = 1.6 Hz, 6H). |
| 180 | 1H NMR (400 MHz, Methanol-d4) δ 8.74 (s, 1H), 8.68 (d, J = 2.2 Hz, 1H), 8.63 (d, J = 1.2 Hz, 1H), 8.59 (d, J = 2.2 Hz, 1H), 8.36 (s, 1H), 8.12-8.05 (m, 2H), 7.95 (d, J = 1.2 Hz, 1H), 7.83 (d, J = 5.1 Hz, 1H), 7.75-7.67 (m, 2H), 7.15 (d, J = 5.1 Hz, 1H), 4.48 (ddd, J = 49.0, 9.3, 2.1 Hz, 1H), 4.00 (ddd, J = 36.3, 14.5, 2.1 Hz, 1H), 3.54 (ddd, J = 16.2, 14.6, 9.3 Hz, 1H), 1.30 (d, J = 1.6 Hz, 6H). |
| 181 | 1H NMR (400 MHz, Methanol-d4) δ 9.11 (s, 1H), 8.78 (d, J = 0.6 Hz, 1H), 8.62 (d, J = 2.2 Hz, 1H), 8.51 (d, J = 2.2 Hz, 1H), 8.33 (d, J = 0.8 Hz, 1H), 8.00 (d, J = 4.9 Hz, 1H), 7.89 (s, 1H), 7.13 (d, J = 4.8 Hz, 1H), 4.44 (ddd, J = 48.9, 9.4, 2.2 Hz, 1H), 4.15 (s, 2H), 3.87 (ddd, J = 36.5, 14.6, 2.2 Hz, 1H), 3.60-3.42 (m, 1H), 1.28 (d, J = 1.6 Hz, 6H). |
| 182 | 1H NMR (400 MHz, Methanol-d4) δ 8.75 (d, J = 2.2 Hz, 1H), 8.67 (d, J = 2.2 Hz, 1H), 8.56 (s, 1H), 8.03 (d, J = 5.1 Hz, 1H), 7.91 (s, 1H), 7.21 (d, J = 5.1 Hz, 1H), 4.41 (ddd, J = 49.0, 9.4, 2.1 Hz, 1H), 4.05-3.78 (m, 2H), 3.58-3.39 (m, 1H), 2.73 (s, 3H), 2.36-2.17 (m, 3H), 1.95 (d, J = 13.6 Hz, 2H), 1.82-1.68 (m, 2H), 1.58-1.41 (m, 2H), 1.28 (d, J = 1.6 Hz, 6H). |
| 183 | 1H NMR (400 MHz, DMSO-d6) δ 11.19 (m, 1H), 9.21-9.04 (m, 3H), 8.95 (s, 1H), 8.89 (d, J = 2.2 Hz, 1H), 8.84-8.73 (m, 2H), 7.90 (d, J = 4.8 Hz, 1H), 7.73 (s, 1H), 7.16 (d, J = 4.8 Hz, 1H), 4.31 (dd, J = 48.9, 9.2 Hz, 1H), 3.68-3.82 (m, 1H), 3.35 (t, J = 11.9 Hz, 1H), 1.18-1.10 (m, 6H). |
| 184 | 1H NMR (400 MHz, DMSO-d6) δ 10.73 (s, 1H), 9.13 (s, 1H), 8.88 (d, J = 2.2 Hz, 1H), 8.84 (s, 1H), 8.66 (d, J = 2.4 Hz, 1H), 8.42 (s, 1H), 8.11 (s, 1H), 7.88 (d, J = 4.8 Hz, 1H), 7.67 (d, J = 8.5 Hz, 1H), 7.14 (d, J = 4.9 Hz, 1H), 4.38 (dd, J = 49.5, 9.4 Hz, 1H), 3.87-3.67 (m, 1H), 3.52-3.35 (m, 1H), 3.15 (s, 1H), 2.60 (s, 3H), 1.22-1.12 (m, 6H). |
| 185 | 1H NMR (400 MHz, DMSO-d6) δ 11.58 (s, 1H), 10.12 (s, 1H), 9.17-9.09 (m, 1H), 8.93 (s, 1H), 8.87-8.79 (m, 2H), 8.51 (dd, J = 11.7, 2.0 Hz, 2H), 8.24 (d, J = 2.7 Hz, 1H), 7.91 (d, J = 4.8 Hz, 1H), 7.13 (d, J = 4.8 Hz, 1H), 4.41 (dd, J = 49.7, 9.2 Hz, 1H), 1.17 (dd, J = 6.2, 1.6 Hz, 7H). |
| 186 | 1H NMR (400 MHz, DMSO-d6) δ 10.87 (s, 1H), 9.21-9.04 (m, 1H), 8.91-8.83 (m, 2H), 8.74 (dd, J = 5.2, 2.4 Hz, 2H), 8.61 (s, 1H), 8.21-8.12 (m, 1H), 8.07 (d, J = 8.6 Hz, 1H), 7.88 (d, J = 4.9 Hz, 1H), 7.13 (d, J = 4.9 Hz, 1H), 4.38 (dd, J = 49.3, 9.3 Hz, 1H), 3.78 (dd, J = 37.8, 10.6 Hz, 1H), 3.53-3.34 (m, 1H), 1.16 (dd, J = 5.6, 1.6 Hz, 6H). |
| 187 | 1H NMR (400 MHz, DMSO-d6) δ 10.65 (s, 1H), 9.12 (s, 1H), 8.87 (d, J = 2.3 Hz, 1H), 8.81 (s, 1H), 8.59 (d, J = 2.2 Hz, 1H), 8.29 (s, 1H), 8.08 (s, 1H), 7.97 (d, J = 8.4 Hz, 1H), 7.90 (d, J = 4.9 Hz, 1H), 7.13 (d, J = 4.9 Hz, 1H), 4.38 (dd, J = 49.7, 9.0 Hz, 1H), 3.78 (dd, J = 36.5, 15.0 Hz, 1H), 3.50-3.32 (m, 1H), 2.32 (s, 3H), 1.17 (dd, J = 5.5, 1.6 Hz, 7H). |
| 188 | 1H NMR (400 MHz, DMSO-d6) δ 9.46 (s, 1H), 8.97 (d, J = 2.2 Hz, 1H), 8.82 (d, J = 2.2 Hz, 1H), 8.76 (d, J = 6.9 Hz, 1H), 8.61 (s, 1H), 7.98 (d, J = 5.0 Hz, 1H), 7.85 (s, 1H), 7.21 (d, J = 4.9 Hz, 1H), 4.40 (q, J = 7.3 Hz, 1H), 4.22 (s, 1H), 4.03 (d, J = 5.7 Hz, 1H), 2.13-1.99 (m, 1H), 1.89 (dt, J = 18.4, 7.4 Hz, 2H), 1.68 (dt, J = 13.2, 6.6 Hz, 2H), 1.56-1.40 (m, 2H), 1.29 (d, J = 6.3 Hz, 6H). |
| 189 | 1H NMR (400 MHz, DMSO-d6) δ 9.47 (s, 1H), 8.97 (d, J = 2.2 Hz, 1H), 8.82 (d, J = 2.2 Hz, 1H), 8.77 (d, J = 7.1 Hz, 1H), 8.61 (s, 1H), 7.98 (d, J = 5.0 Hz, 1H), 7.85 (s, 1H), 7.21 (d, J = 4.9 Hz, 1H), 4.40 (q, J = 7.4 Hz, 1H), 4.22 (dt, J = 5.9, 2.8 Hz, 1H), 4.04 (q, J = 6.7 Hz, 1H), 2.14-1.99 (m, 1H), 1.89 (dddt, J = 21.0, 12.1, 7.7, 4.4 Hz, 2H), 1.76-1.62 (m, 1H), 1.56-1.42 (m, 2H), 1.29 (d, J = 6.3 Hz, 6H). |
| 190 | 1H NMR (400 MHz, DMSO-d6) δ 9.52 (s, 1H), 8.98 (d, J = 2.2 Hz, 1H), 8.83 (d, J = 2.2 Hz, 1H), 8.66 (d, J = 7.7 Hz, 1H), 8.60 (s, 1H), 8.01 (d, J = 5.0 Hz, 1H), 7.83 (s, 1H), 7.22 (d, J = 5.0 Hz, 1H), 4.25-4.11 (m, 1H), 4.13-4.00 (m, 1H), 3.97 (s, 1H), 1.77 (d, J = 12.2 Hz, 2H), 1.72-1.60 (m, 1H), 1.53 (d, J = 12.8 Hz, 3H), 1.38 (t, J = 12.1 Hz, 1H), 1.29 (d, J = 6.3 Hz, 7H). |
| 191 | 1H NMR (400 MHz, DMSO-d6) δ 9.53 (d, J = 7.8 Hz, 1H), 8.98 (d, J = 2.2 Hz, 1H), 8.83 (d, J = 2.2 Hz, 1H), 8.67 (d, J = 7.7 Hz, 1H), 8.60 (s, 1H), 8.01 (d, J = 5.0 Hz, 1H), 7.83 (s, 1H), 7.22 (d, J = 5.0 Hz, 1H), 4.24-4.10 (m, 2H), 4.06 (h, J = 6.7 Hz, 1H), 3.97 (s, 1H), 1.77 (d, J = 12.7 Hz, 2H), 1.66 (t, J = 12.2 Hz, 1H), 1.58-1.44 (m, 3H), 1.38 (t, J = 11.6 Hz, 1H), 1.29 (d, J = 6.3 Hz, 6H). |
| 192 | 1H NMR (400 MHz, DMSO-d6) δ 9.55 (d, J = 7.8 Hz, 1H), 8.99 (d, J = 2.2 Hz, 1H), 8.83 (d, J = 2.2 Hz, 1H), 8.68 (d, J = 7.7 Hz, 1H), 8.61 (s, 1H), 8.01 (d, J = 5.0 Hz, 1H), 7.83 (s, 1H), 7.22 (d, J = 5.0 Hz, 1H), 4.24-4.12 (m, 1H), 4.06 (h, J = 6.6 Hz, 1H), 3.97 (s, 1H), 1.77 (d, J = 12.6 Hz, 2H), 1.66 (t, J = 12.1 Hz, 1H), 1.59-1.45 (m, 3H), 1.43-1.34 (m, 1H), 1.29 (d, J = 6.3 Hz, 7H). |
| 193 | 1H NMR (400 MHz, DMSO-d6) δ 9.63-9.47 (m, 1H), 8.98 (d, J = 2.2 Hz, 1H), 8.83 (d, J = 2.2 Hz, 1H), 8.80 (d, J = 7.6 Hz, 1H), 8.62 (s, 1H), 8.00 (d, J = 5.0 Hz, 1H), 7.85 (s, 1H), 7.22 (d, J = 5.0 Hz, 1H), 4.06 (h, J = 6.6 Hz, 1H), 3.76 (ddt, J = 22.8, 9.0, 3.9 Hz, 1H), 3.43 (dt, J = 11.0, 6.5 Hz, 1H), 2.03 (d, J = 12.1 Hz, 1H), 1.79 (s, 2H), 1.70 (d, J = 12.5 Hz, 1H), 1.29 (d, J = 6.3 Hz, 6H), 1.27-0.90 (m, 4H). |

TABLE 2-continued

| compound | 1H-NMR |
|---|---|
| 194 | |
| 195 | 1H NMR (400 MHz, DMSO-d6) δ 9.11 (s, 1H), 8.96 (s, 1H), 8.84 (d, J = 2.2 Hz, 1H), 8.68 (s, 1H), 7.99 (d, J = 4.9 Hz, 1H), 7.96 (s, 1H), 7.20 (d, J = 4.9 Hz, 1H), 4.52-4.42 (m, 1H), 4.34 (dd, J = 49.8, 9.3 Hz, 1H), 4.01-3.85 (m, 2H), 3.84-3.65 (m, 2H), 2.40 (d, J = 7.8 Hz, 1H), 1.91 (s, 1H), 1.20-1.07 (m, 8H). |
| 196 | 1H NMR (400 MHz, Methanol-d4) δ 8.69 (d, J = 1.4 Hz, 2H), 8.53 (s, 1H), 8.13 (d, J = 3.2 Hz, 1H), 7.77 (d, J = 5.1 Hz, 1H), 7.57-7.49 (m, 1H), 7.42 (d, J = 15.9 Hz, 2H), 7.14 (d, J = 5.0 Hz, 1H), 4.79 (d, J = 3.0 Hz, 4H), 4.55-4.30 (m, 1H), 4.10-3.88 (m, 1H), 3.79 (d, J = 2.8 Hz, 3H), 3.62-3.48 (m, 1H), 1.30 (d, J = 1.6 Hz, 6H). |
| 197 | 1H NMR (400 MHz, Methanol-d4) δ 8.71 (d, J = 2.2 Hz, 1H), 8.70 (d, J = 1.0 Hz, 1H), 8.55 (dd, J = 11.7, 2.2 Hz, 1H), 8.11 (d, J = 9.0 Hz, 1H), 7.81-7.74 (m, 1H), 7.60-7.51 (m, 1H), 7.49-7.39 (m, 2H), 7.15 (d, J = 5.1 Hz, 1H), 4.98 (s, 2H), 4.46 (dd, J = 48.4, 8.5 Hz, 1H), 3.99 (dd, J = 36.6, 15.2 Hz, 1H), 3.53 (dt, J = 15.0, 7.5 Hz, 1H), 2.21 (d, J = 5.0 Hz, 3H), 1.30 (d, J = 1.6 Hz, 6H). |
| 198 | 1H NMR (400 MHz, Methanol-d4) δ 8.74 (s, 1H), 8.70 (d, J = 2.2 Hz, 1H), 8.53 (d, J = 2.1 Hz, 1H), 8.25 (s, 1H), 7.80 (d, J = 5.1 Hz, 1H), 7.66 (d, J = 8.5 Hz, 2H), 7.53 (d, J = 8.4 Hz, 2H), 7.16 (d, J = 5.1 Hz, 1H), 4.47 (ddd, J = 49.1, 9.4, 2.1 Hz, 1H), 4.22 (s, 2H), 3.98 (ddd, J = 36.4, 14.6, 2.1 Hz, 1H), 3.69 (q, J = 9.3 Hz, 2H), 3.62-3.42 (m, 1H), 1.30 (d, J = 1.6 Hz, 6H). |
| 199 | 1H NMR (400 MHz, Methanol-d4) δ 8.74 (d, J = 2.2 Hz, 1H), 8.70 (s, 1H), 8.60 (d, J = 2.2 Hz, 1H), 8.15-8.02 (m, 2H), 7.89-7.80 (m, 2H), 7.18 (d, J = 5.1 Hz, 1H), 5.41 (tt, J = 7.2, 3.5 Hz, 1H), 5.03-4.89 (m, 2H), 4.79 (ddd, J = 8.2, 5.8, 5.0 Hz, 2H), 4.46 (ddd, J = 49.1, 9.3, 2.1 Hz, 1H), 4.13-3.77 (m, 2H), 3.68-3.42 (m, 2H), 2.73 (dt, J = 16.1, 7.9 Hz, 1H), 2.62-2.45 (m, 0H), 1.30 (d, J = 1.7 Hz, 6H). |
| 200 | 1H NMR (400 MHz, Methanol-d4) δ 8.71 (d, J = 1.8 Hz, 2H), 8.53 (d, J = 2.1 Hz, 1H), 8.17 (s, 1H), 7.79 (d, J = 5.1 Hz, 1H), 7.51-7.43 (m, 4H), 7.16 (d, J = 5.1 Hz, 1H), 4.55 (s, 2H), 4.47 (ddd, J = 49.0, 9.4, 2.1 Hz, 1H), 3.98 (ddd, J = 36.6, 14.6, 2.1 Hz, 1H), 3.63-3.49 (m, 1H), 3.48-3.38 (m, 2H), 2.49 (t, J = 8.1 Hz, 2H), 2.19-1.98 (m, 2H), 1.30 (d, J = 1.6 Hz, 6H). |
| 201 | 1H NMR (400 MHz, Methanol-d4) δ 8.73-8.68 (m, 2H), 8.54 (d, J = 2.2 Hz, 1H), 8.18 (s, 1H), 7.79 (d, J = 5.0 Hz, 1H), 7.64-7.40 (m, 4H), 7.16 (d, J = 5.1 Hz, 1H), 4.56-4.50 (m, 3H), 4.44-4.33 (m, 3H), 3.99 (ddd, J = 36.6, 14.6, 2.2 Hz, 1H), 3.66-3.56 (m, 2H), 3.58-3.45 (m, 1H), 1.30 (d, J = 1.6 Hz, 7H). |
| 202 | 1H NMR (400 MHz, Methanol-d4) δ 8.71 (d, J = 2.2 Hz, 1H), 8.68 (s, 1H), 8.53 (d, J = 2.2 Hz, 1H), 8.20 (s, 1H), 7.78 (d, J = 5.0 Hz, 1H), 7.52-7.5 (m, 2H), 7.47-7.36 (m, 2H), 7.16 (d, J = 5.1 Hz, 1H), 4.47 (ddd, J = 49.1, 9.4, 2.1 Hz, 1H), 4.46 (s, 2H), 3.99 (ddd, J = 36.6, 14.6, 2.1 Hz, 1H), 3.61-3.50 (m, 1H), 1.66 (ddd, J = 12.6, 8.0, 4.7 Hz, 1H), 1.30 (d, J = 1.6 Hz, 7H), 0.90 (dt, J = 4.6, 3.0 Hz, 2H), 0.81 (dt, J = 8.1, 3.2 Hz, 2H). |
| 203 | 1H NMR (400 MHz, Methanol-d4) δ 8.71 (d, J = 2.1 Hz, 1H), 8.68 (s, 1H), 8.54 (dd, J = 2.2, 0.4 Hz, 1H), 8.19 (s, 1H), 7.78 (dd, J = 5.1, 0.5 Hz, 1H), 7.50 (d, J = 8.7 Hz, 2H), 7.46-7.40 (m, 2H), 7.16 (d, J = 5.1 Hz, 1H), 4.47 (ddd, J = 49.0, 9.4, 2.1 Hz, 1H), 4.44 (s, 2H), 3.99 (ddd, J = 36.7, 14.5, 2.1 Hz, 1H), 3.65-3.43 (m, 1H), 2.54 (p, J = 6.9 Hz, 1H), 1.30 (d, J = 1.7 Hz, 6H), 1.17 (d, J = 6.9 Hz, 6H). |
| 204 | 1H NMR (400 MHz, Methanol-d4) δ 8.71 (d, J = 2.1 Hz, 1H), 8.69 (s, 1H), 8.54 (d, J = 2.2 Hz, 1H), 8.18 (s, 1H), 7.78 (d, J = 5.1 Hz, 1H), 7.50 (d, J = 8.4 Hz, 2H), 7.43 (d, J = 8.4 Hz, 2H), 7.16 (d, J = 5.1 Hz, 1H), 4.47 (ddd, J = 49.1, 9.4, 2.1 Hz, 1H), 4.45 (s, 2H), 3.99 (ddd, J = 36.6, 14.6, 2.1 Hz, 1H), 3.52 (ddd, J = 16.0, 14.5, 9.3 Hz, 1H), 2.31 (q, J = 7.6 Hz, 2H), 1.30 (d, J = 1.6 Hz, 6H), 1.19 (t, J = 7.6 Hz, 3H). |
| 205 | 1H NMR (400 MHz, Methanol-d4) δ 8.74 (s, 1H), 8.70 (d, J = 2.1 Hz, 1H), 8.56 (d, J = 2.1 Hz, 1H), 8.26 (s, 1H), 7.81 (d, J = 5.1 Hz, 1H), 7.67 (d, J = 8.2 Hz, 2H), 7.56 (d, J = 8.2 Hz, 2H), 7.16 (d, J = 5.1 Hz, 1H), 4.49 (t, J = 11.1 Hz, 5H), 4.40 (s, 2H), 4.08-3.85 (m, 1H), 3.54 (td, J = 15.3, 9.3 Hz, 1H), 1.29 (d, J = 1.7 Hz, 6H). |
| 206 | 1H NMR (400 MHz, Methanol-d4) δ 8.72 (d, J = 2.2 Hz, 1H), 8.70 (s, 1H), 8.59 (d, J = 2.2 Hz, 1H), 8.14-8.05 (m, 2H), 7.85 (d, J = 5.1 Hz, 1H), 7.83 (s, 1H), 7.18 (d, J = 5.1 Hz, 1H), 5.39 (s, 1H), 4.96 (td, J = 7.7, 3.2 Hz, 2H), 4.83-4.72 (m, 2H), 4.70 (d, J = 6.0 Hz, 1H), 4.45 (ddd, J = 49.1, 9.3, 2.1 Hz, 1H), 4.10-3.70 (m, 3H), 3.66-3.42 (m, 1H), 2.73 (dd, J = 14.7, 7.7 Hz, 1H), 2.61-2.45 (m, 1H), 1.29 (d, J = 1.6 Hz, 6H). |
| 207 | 1H NMR (400 MHz, Methanol-d4) δ 8.71 (s, 1H), 8.70 (d, J = 2.2 Hz, 1H), 8.57 (d, J = 2.1 Hz, 1H), 8.27 (s, 1H), 7.89 (d, J = 8.6 Hz, 2H), 7.80 (d, J = 5.1 Hz, 1H), 7.56 (d, J = 8.5 Hz, 2H), 7.47 (s, 1H), 7.16 (d, J = 5.1 Hz, 1H), 4.59-4.31 (m, 0H), 4.00 (dd, J = 36.9, 14.4 Hz, 1H), 3.63-3.50 (m, 1H), 2.56 (s, 3H), 1.30 (d, J = 1.6 Hz, 6H). |
| 208 | 1H NMR (400 MHz, Methanol-d4) δ 8.72 (d, J = 2.2 Hz, 1H), 8.70 (s, 1H), 8.58 (d, J = 2.1 Hz, 1H), 8.11 (s, 1H), 8.05 (s, 1H), 7.85 (d, J = 5.1 Hz, 1H), 7.80 (s, 1H), 7.17 (d, J = 5.0 Hz, 1H), 5.31 (s, J = 7.0 Hz, 2H), 4.45 (dd, J = 48.8, 8.0 Hz, 1H), 4.07-3.82 (m, 1H), 3.80-3.63 (m, 2H), 3.63-3.44 (m, 3H), 2.72-2.52 (m, 1H), 2.45 (s, 1H), 1.29 (d, J = 1.6 Hz, 6H). |
| 209 | 1H NMR (400 MHz, Methanol-d4) δ 8.75 (s, 1H), 8.67 (d, J = 2.2 Hz, 1H), 8.57 (d, J = 2.2 Hz, 1H), 8.49 (s, 1H), 8.20 (d, J = 8.7 Hz, 2H), 7.84 (d, J = 5.0 Hz, 1H), 7.67 (d, J = 8.7 Hz, 2H), 7.14 (d, J = 5.0 Hz, 1H), 4.61-4.35 (m, 1H), 4.11-3.86 (m, 1H), 3.64-3.50 (m, 1H), 2.65 (s, 3H), 1.30 (d, J = 1.6 Hz, 6H). |

TABLE 2-continued

| compound | 1H-NMR |
|---|---|
| 210 | 1H NMR (400 MHz, Methanol-d4) δ 9.02 (s, 1H), 8.77 (s, 1H), 8.70 (d, J = 2.1 Hz, 1H), 8.57 (d, J = 2.1 Hz, 1H), 8.44 (s, 1H), 7.85 (d, J = 5.1 Hz, 1H), 7.81 (s, 1H), 7.80-7.73 (m, 2H), 7.70 (d, J = 8.4 Hz, 2H), 7.17 (d, J = 5.0 Hz, 1H), 4.47 (dd, J = 48.9, 9.2 Hz, 1H), 3.97 (m, 4H), 3.55 (td, J = 15.4, 9.3 Hz, 1H), 1.30 (d, J = 1.6 Hz, 6H). |
| 211 | 1H NMR (400 MHz, Methanol-d4) δ 8.85 (s, 0H), 8.70 (d, J = 2.2 Hz, 1H), 8.66 (s, 1H), 8.56 (d, J = 2.1 Hz, 1H), 8.16 (s, 1H), 7.78 (d, J = 5.1 Hz, 1H), 7.45-7.33 (m, 4H), 7.15 (d, J = 5.1 Hz, 1H), 4.46 (ddd, J = 48.9, 9.2, 2.0 Hz, 1H), 4.10-3.84 (m, 1H), 3.68-3.42 (m, 1H), 2.02 (s, 3H), 1.32 (d, J = 3.1 Hz, 2H), 1.29 (d, J = 1.7 Hz, 6H), 1.27 (d, J = 1.7 Hz, 2H). |
| 212 | 1H NMR (400 MHz, Methanol-d4) δ 8.70 (d, J = 2.2 Hz, 1H), 8.66 (s, 1H), 8.57 (s, 1H), 8.25 (s, 1H), 7.80 (d, J = 5.1 Hz, 1H), 7.49-7.36 (m, 5H), 7.15 (d, J = 5.0 Hz, 1H), 4.57-4.31 (m, 1H), 3.99 (dd, J = 36.9, 15.1 Hz, 1H), 3.69 (s, 3H), 3.60-3.42 (m, 1H), 1.33-1.30 (m, 4H), 1.30 (d, J = 1.6 Hz, 6H). |
| 213 | 1H NMR (400 MHz, Methanol-d4) δ 8.71 (d, J = 2.2 Hz, 1H), 8.70 (s, 1H), 8.53 (d, J = 2.2 Hz, 1H), 8.29 (d, J = 2.6 Hz, 1H), 7.97 (s, 1H), 7.78 (d, J = 5.1 Hz, 1H), 7.75 (dd, J = 9.0, 2.8 Hz, 1H), 7.16 (d, J = 5.0 Hz, 1H), 7.12 (d, J = 9.0 Hz, 1H), 4.46 (ddd, J = 49.1, 9.3, 2.1 Hz, 1H), 4.10-3.94 (m, 1H), 3.91 (t, J = 5.3 Hz, 4H), 3.86-3.81 (m, 1H), 3.67-3.42 (m, 1H), 3.37 (t, J = 5.3 Hz, 4H), 1.30 (d, J = 1.6 Hz, 6H). |
| 214 | 1H NMR (400 MHz, Methanol-d4) δ 8.69 (d, J = 2.2 Hz, 1H), 8.67 (s, 1H), 8.61 (d, J = 2.2 Hz, 1H), 8.27 (s, 1H), 7.83 (d, J = 5.1 Hz, 1H), 7.67-7.52 (m, 2H), 7.38 (d, J = 8.6 Hz, 2H), 7.15 (d, J = 5.1 Hz, 1H), 4.47 (ddd, J = 49.1, 9.4, 2.1 Hz, 1H), 3.99 (ddd, J = 36.5, 14.6, 2.1 Hz, 1H), 3.61 (s, 3H), 3.52 (ddd, J = 16.2, 14.6, 9.4 Hz, 1H), 1.66 (s, 6H), 1.30 (d, J = 1.6 Hz, 6H). |
| 215 | 1H NMR (400 MHz, Methanol-d4) δ 8.69 (d, J = 2.2 Hz, 1H), 8.66 (s, 1H), 8.58 (d, J = 2.1 Hz, 1H), 8.34 (s, 1H), 8.22 (s, 1H), 7.81 (d, J = 5.0 Hz, 1H), 7.63-7.54 (m, 2H), 7.38 (d, J = 8.6 Hz, 2H), 7.15 (d, J = 5.1 Hz, 1H), 4.47 (ddd, J = 49.0, 9.3, 2.1 Hz, 1H), 3.99 (ddd, J = 36.6, 14.5, 2.1 Hz, 1H), 3.64-3.42 (m, 1H), 2.00 (s, 3H), 1.68 (s, 6H), 1.30 (d, J = 1.6 Hz, 6H). |
| 216 | 1H NMR (400 MHz, Methanol-d4) δ 8.72 (s, 1H), 8.69 (d, J = 2.2 Hz, 1H), 8.56 (d, J = 2.1 Hz, 1H), 8.33 (s, 1H), 8.31 (s, 1H), 7.94 (d, J = 8.5 Hz, 2H), 7.81 (d, J = 5.1 Hz, 1H), 7.62 (s, 1H), 7.58 (d, J = 8.5 Hz, 2H), 7.15 (d, J = 5.1 Hz, 1H), 4.57-4.33 (m, 1H), 3.99 (dd, J = 36.5, 13.7 Hz, 1H), 3.65-3.43 (m, 1H), 1.30 (d, J = 1.6 Hz, 6H). |
| 217 | 1H NMR (400 MHz, Methanol-d4) δ 8.77 (s, 1H), 8.72 (d, J = 2.2 Hz, 1H), 8.64 (d, J = 2.1 Hz, 1H), 8.55 (d, J = 2.2 Hz, 1H), 8.50 (d, J = 2.4 Hz, 1H), 8.24 (s, 1H), 7.87 (t, J = 2.4 Hz, 1H), 7.85 (d, J = 5.1 Hz, 1H), 7.17 (d, J = 5.0 Hz, 1H), 7.07 (t, J = 72.6 Hz, 1H), 4.47 (ddd, J = 48.9, 9.2, 2.0 Hz, 1H), 4.18-3.83 (m, 1H), 3.64-3.44 (m, 1H), 1.30 (d, J = 1.6 Hz, 6H). |
| 218 | 1H NMR (400 MHz, Methanol-d4) δ 8.72 (s, 1H), 8.70 (d, J = 2.2 Hz, 1H), 8.60 (d, J = 2.2 Hz, 1H), 8.37 (s, 1H), 8.17 (d, J = 8.6 Hz, 2H), 7.81 (d, J = 5.1 Hz, 1H), 7.60 (d, J = 8.6 Hz, 2H), 7.16 (d, J = 5.1 Hz, 1H), 4.47 (ddd, J = 49.1, 9.4, 2.1 Hz, 1H), 4.13-3.88 (m, 1H), 3.65-3.42 (m, 1H), 2.54 (s, 3H), 1.30 (d, J = 1.6 Hz, 6H). |
| 219 | 1H NMR (400 MHz, Methanol-d4) δ 8.86 (s, 1H), 8.75 (s, 1H), 8.66 (d, J = 2.2 Hz, 1H), 8.39 (s, 1H), 8.36-8.26 (m, 1H), 7.98-7.87 (m, 1H), 7.82 (d, J = 5.3 Hz, 2H), 7.75-7.64 (m, 2H), 7.59 (d, J = 7.5 Hz, 1H), 7.14 (d, J = 5.0 Hz, 1H), 4.60-4.31 (m, 1H), 4.00 (s, 1H), 3.68-3.51 (m, 1H), 1.30 (d, J = 1.6 Hz, 6H). |
| 220 | 1H NMR (400 MHz, Methanol-d4) δ 8.70 (d, J = 1.7 Hz, 2H), 8.54 (d, J = 2.2 Hz, 1H), 8.11 (s, 1H), 7.80 (d, J = 5.1 Hz, 1H), 7.55 (t, J = 7.8 Hz, 1H), 7.37 (ddd, J = 10.3, 8.2, 2.3 Hz, 3H), 7.15 (d, J = 5.1 Hz, 1H), 4.47 (ddd, J = 49.0, 9.4, 2.1 Hz, 1H), 4.44 (s, 2H), 3.98 (ddd, J = 36.5, 14.6, 2.1 Hz, 1H), 3.53 (ddd, J = 16.1, 14.5, 9.3 Hz, 1H), 1.98 (s, 3H), 1.30 (d, J = 1.6 Hz, 6H). |
| 221 | 1H NMR (400 MHz, Methanol-d4) δ 8.79 (s, 1H), 8.67 (d, J = 2.2 Hz, 1H), 8.39-8.31 (m, 2H), 7.99 (d, J = 1.9 Hz, 1H), 7.92 (dd, J = 7.5, 1.8 Hz, 1H), 7.89-7.80 (m, 3H), 7.67 (s, 2H), 7.14 (d, J = 5.0 Hz, 1H), 4.46 (dd, J = 49.2, 7.9 Hz, 1H), 3.97 (dd, J = 36.3, 14.7 Hz, 1H), 3.67-3.47 (m, 1H), 1.30 (d, J = 1.6 Hz, 6H). |
| 222 | 1H NMR (400 MHz, Methanol-d4) δ 8.77 (s, 1H), 8.70 (d, J = 2.1 Hz, 1H), 8.59 (s, 1H), 8.54 (d, J = 2.2 Hz, 1H), 8.47 (s, 1H), 8.24 (s, 1H), 7.85 (d, J = 5.1 Hz, 1H), 7.76 (s, 1H), 7.16 (d, J = 5.0 Hz, 1H), 4.64-4.30 (m, 1H), 3.97 (dd, J = 36.6, 14.8 Hz, 1H), 3.53 (ddd, J = 16.4, 14.7, 9.3 Hz, 1H), 2.14 (dt, J = 8.4, 3.7 Hz, 1H), 1.29 (d, J = 1.6 Hz, 6H), 1.25-1.09 (m, 2H), 0.96-0.78 (m, 2H). |
| 223 | 1H NMR (400 MHz, Methanol-d4) δ 8.72 (d, J = 2.2 Hz, 1H), 8.69 (s, 1H), 8.57 (d, J = 2.2 Hz, 1H), 8.11 (s, 1H), 8.05 (d, J = 0.8 Hz, 1H), 7.84 (d, J = 5.1 Hz, 1H), 7.80 (s, 1H), 7.17 (d, J = 5.1 Hz, 1H), 5.32 (t, J = 6.9 Hz, 1H), 4.45 (ddd, J = 48.9, 9.3, 2.1 Hz, 1H), 4.10-3.81 (m, 2H), 3.79-3.63 (m, 2H), 3.63-3.46 (m, 2H), 2.69-2.51 (m, 1H), 2.44 (s, 1H), 1.29 (d, J = 1.7 Hz, 6H). |
| 224 | 1H NMR (400 MHz, Methanol-d4) δ 8.73 (d, J = 2.2 Hz, 1H), 8.66 (s, 1H), 8.60 (d, J = 6.0 Hz, 1H), 8.07 (s, 1H), 8.01 (s, 1H), 7.83 (d, J = 5.1 Hz, 1H), 7.78-7.72 (m, 1H), 7.18 (d, J = 5.1 Hz, 1H), 5.07 (s, 1H), 4.39 (dd, J = 9.3, 2.1 Hz, 1H), 4.10-3.76 (m, 3H), 3.71 (s, 3H), 3.69-3.41 (m, 3H), 2.49 (d, J = 9.2 Hz, 2H), 1.29 (d, J = 1.6 Hz, 6H). |
| 225 | 1H NMR (400 MHz, Methanol-d4) δ 8.69 (d, J = 1.7 Hz, 2H), 8.52 (d, J = 2.2 Hz, 1H), 8.21 (s, 1H), 7.79 (d, J = 5.1 Hz, 1H), 7.51 (d, J = 8.4 Hz, 2H), 7.42 (d, J = 8.3 Hz, 2H), 7.15 (d, J = 5.1 Hz, 1H), 4.53 (dd, J = 9.4, 2.1 Hz, 1H), 4.36 (s, 2H), 3.98 (ddd, J = 36.6, 14.6, 2.1 Hz, 1H), 3.69 (s, 3H), 3.53 (ddd, J = 16.2, 14.5, 9.3 Hz, 1H), 1.30 (d, J = 1.7 Hz, 7H). |

TABLE 2-continued

| compound | 1H-NMR |
|---|---|
| 226 | 1H NMR (400 MHz, Methanol-d4) δ 8.91-8.84 (m, 1H), 8.78 (s, 2H), 8.71 (d, J = 2.2 Hz, 1H), 8.52 (d, J = 2.2 Hz, 1H), 8.26 (s, 1H), 8.22 (s, 1H), 7.86 (d, J = 5.0 Hz, 1H), 7.17 (d, J = 5.1 Hz, 1H), 7.06 (t, J = 55.2 Hz, 1H), 4.47 (ddd, J = 49.0, 9.3, 2.1 Hz, 1H), 4.00 (ddd, J = 36.5, 14.6, 2.1 Hz, 1H), 3.54 (ddd, J = 16.2, 14.6, 9.3 Hz, 1H), 1.30 (d, J = 1.6 Hz, 6H). |
| 227 | 1H NMR (400 MHz, Methanol-d4) δ 8.80 (d, J = 2.5 Hz, 1H), 8.78 (s, 1H), 8.71 (d, J = 2.2 Hz, 1H), 8.57 (d, J = 2.2 Hz, 1H), 8.25 (s, 1H), 8.13 (dd, J = 8.4, 2.5 Hz, 1H), 7.91 (d, J = 8.5 Hz, 1H), 7.86 (d, J = 5.1 Hz, 1H), 7.16 (d, J = 5.1 Hz, 1H), 6.82 (t, J = 55.2 Hz, 1H), 4.47 (ddd, J = 49.0, 9.2, 2.1 Hz, 1H), 3.99 (ddd, J = 36.4, 14.6, 2.1 Hz, 1H), 3.54 (td, J = 15.4, 9.3 Hz, 1H), 1.30 (d, J = 1.6 Hz, 6H). |
| 228 | 1H NMR (400 MHz, Methanol-d4) δ 8.74 (s, 1H), 8.69 (d, J = 2.2 Hz, 1H), 8.58 (d, J = 2.2 Hz, 1H), 8.36 (s, 1H), 8.20 (d, J = 8.6 Hz, 2H), 8.04 (d, J = 0.9 Hz, 1H), 7.83 (d, J = 5.1 Hz, 1H), 7.70-7.54 (m, 2H), 7.36 (d, J = 0.9 Hz, 1H), 7.15 (d, J = 5.1 Hz, 1H), 4.47 (ddd, J = 49.0, 9.3, 2.1 Hz, 1H), 3.99 (ddd, J = 36.4, 14.6, 2.1 Hz, 1H), 3.54 (ddd, J = 16.1, 14.6, 9.3 Hz, 1H), 1.30 (d, J = 1.6 Hz, 6H). |
| 229 | 1H NMR (400 MHz, Methanol-d4) δ 8.79 (s, 1H), 8.70 (d, J = 2.2 Hz, 1H), 8.54 (d, J = 2.2 Hz, 1H), 8.24 (dt, J = 5.0, 1.5 Hz, 1H), 8.18 (ddd, J = 9.7, 7.7, 1.8 Hz, 1H), 8.09 (d, J = 1.4 Hz, 1H), 7.88 (d, J = 5.1 Hz, 1H), 7.54 (dd, J = 7.7, 4.9, 1.1 Hz, 1H), 7.16 (d, J = 5.1 Hz, 1H), 4.47 (ddd, J = 49.0, 9.4, 2.1 Hz, 1H), 3.99 (ddd, J = 36.5, 14.6, 2.1 Hz, 1H), 3.54 (ddd, J = 16.1, 14.6, 9.4 Hz, 1H), 1.30 (d, J = 1.6 Hz, 6H). |
| 230 | 1H NMR (400 MHz, Methanol-d4) δ 8.80 (s, 1H), 8.68 (d, J = 2.2 Hz, 1H), 8.63 (s, 1H), 8.55 (d, J = 2.2 Hz, 1H), 8.07 (d, J = 8.7 Hz, 2H), 7.87 (d, J = 5.1 Hz, 1H), 7.82-7.72 (m, 2H), 7.68 (s, 2H), 7.16 (d, J = 5.0 Hz, 1H), 4.59-4.29 (m, 1H), 3.97 (dd, J = 36.2, 14.5 Hz, 1H), 3.65-3.42 (m, 1H), 1.30 (d, J = 1.6 Hz, 6H). |
| 231 | 1H NMR (400 MHz, Methanol-d4) δ 8.73 (d, J = 2.2 Hz, 1H), 8.68 (s, 1H), 8.60 (d, J = 2.2 Hz, 1H), 8.10-8.06 (m, 2H), 7.87-7.82 (m, 2H), 7.17 (d, J = 5.0 Hz, 1H), 5.30 (ddd, J = 8.0, 5.2, 2.7 Hz, 1H), 4.50 (dd, J = 9.7, 7.7 Hz, 2H), 4.40 (dd, J = 9.2, 6.0 Hz, 2H), 3.97 (ddd, J = 36.3, 14.5, 2.1 Hz, 1H), 3.72 (s, 3H), 3.60-3.39 (m, 1H), 1.29 (d, J = 1.7 Hz, 6H). |
| 232 | 1H NMR (400 MHz, Methanol-d4) δ 8.72 (d, J = 2.2 Hz, 1H), 8.70 (s, 1H), 8.57 (d, J = 2.2 Hz, 1H), 8.08 (s, 1H), 8.01 (s, 1H), 7.93 (s, 1H), 7.84 (d, J = 5.0 Hz, 1H), 7.17 (d, J = 5.0 Hz, 1H), 5.50 (p, J = 7.2 Hz, 1H), 4.61 (dd, J = 7.2, 4.0 Hz, 4H), 4.54-4.31 (m, 1H), 3.96 (dd, J = 36.3, 14.6 Hz, 1H), 3.53 (td, J = 15.6, 9.5 Hz, 1H), 1.29 (d, J = 1.6 Hz, 6H). |
| 233 | 1H NMR (400 MHz, Methanol-d4) δ 8.77 (s, 1H), 8.70 (d, J = 2.2 Hz, 1H), 8.62 (s, 1H), 8.55 (d, J = 2.2 Hz, 1H), 8.49 (s, 1H), 8.24 (s, 1H), 7.97 (s, 1H), 7.85 (d, J = 5.0 Hz, 1H), 7.16 (d, J = 5.0 Hz, 1H), 4.46 (ddd, J = 49.0, 9.2, 2.1 Hz, 1H), 3.98 (ddd, J = 36.4, 14.5, 2.1 Hz, 1H), 3.54 (td, J = 15.4, 9.4 Hz, 1H), 2.51 (s, 3H), 1.30 (d, J = 1.6 Hz, 6H). |
| 234 | 1H NMR (400 MHz, Methanol-d4) δ 9.01 (d, J = 1.4 Hz, 1H), 8.76 (s, 1H), 8.70 (d, J = 2.2 Hz, 1H), 8.55 (d, J = 2.2 Hz, 1H), 8.43 (s, 1H), 8.00 (d, J = 1.4 Hz, 1H), 7.94 (d, J = 8.5 Hz, 2H), 7.83 (d, J = 5.0 Hz, 1H), 7.66 (d, J = 8.6 Hz, 2H), 7.16 (d, J = 5.1 Hz, 1H), 4.47 (ddd, J = 48.9, 9.3, 2.1 Hz, 1H), 4.08-3.84 (m, 1H), 3.69-3.40 (m, 1H), 1.30 (d, J = 1.6 Hz, 6H). |
| 235 | 1H NMR (400 MHz, Methanol-d4) δ 8.72 (d, J = 2.2 Hz, 1H), 8.67 (s, 1H), 8.58 (d, J = 2.2 Hz, 1H), 8.07 (s, 1H), 8.01 (s, 1H), 7.82 (d, J = 5.0 Hz, 1H), 7.75 (d, J = 0.8 Hz, 1H), 7.17 (d, J = 5.0 Hz, 1H), 4.57-4.33 (m, 2H), 4.26 (d, J = 13.5 Hz, 2H), 4.07-3.86 (m, 1H), 3.71 (s, 3H), 3.52 (td, J = 15.3, 9.2 Hz, 1H), 3.06 (s, 3H), 2.17 (d, J = 12.8 Hz, 2H), 2.00 (td, J = 12.2, 4.4 Hz, 2H), 1.29 (d, J = 1.6 Hz, 6H). |
| 236 | 1H NMR (400 MHz, Methanol-d4) δ 8.71 (d, J = 2.2 Hz, 1H), 8.69 (s, 1H), 8.56 (d, J = 2.2 Hz, 1H), 8.11 (s, 1H), 8.01 (d, J = 0.8 Hz, 1H), 7.83 (d, J = 5.1 Hz, 1H), 7.80 (d, J = 0.8 Hz, 1H), 7.17 (d, J = 5.0 Hz, 1H), 4.63 (dt, J = 10.5, 5.6 Hz, 1H), 4.45 (ddd, J = 48.9, 9.3, 2.1 Hz, 1H), 4.08-3.84 (m, 1H), 3.70-3.56 (m, 2H), 3.56-3.43 (m, 1H), 3.28-3.19 (m, 2H), 2.48-2.21 (m, 4H), 1.29 (d, J = 1.6 Hz, 6H). |
| 237 | 1H NMR (400 MHz, Methanol-d4) δ 8.72 (d, J = 2.2 Hz, 1H), 8.66 (s, 1H), 8.63 (d, J = 2.2 Hz, 1H), 8.12 (s, 1H), 8.02 (d, J = 0.8 Hz, 1H), 7.83 (d, J = 5.1 Hz, 1H), 7.73 (d, J = 0.8 Hz, 1H), 7.18 (d, J = 5.1 Hz, 1H), 5.12 (td, J = 5.4, 2.8 Hz, 1H), 4.45 (ddd, J = 49.1, 9.4, 2.1 Hz, 1H), 4.22-4.10 (m, 2H), 4.05 (dd, J = 9.9, 5.8 Hz, 1H), 4.03-3.83 (m, 2H), 3.52 (ddd, J = 16.0, 14.5, 9.3 Hz, 1H), 2.68-2.46 (m, 1H), 2.46-2.32 (m, 1H), 1.29 (d, J = 1.7 Hz, 6H). |
| 238 | 1H NMR (400 MHz, Methanol-d4) δ 8.75 (d, J = 2.1 Hz, 1H), 8.71 (d, J = 2.2 Hz, 1H), 8.57 (s, 1H), 7.99 (d, J = 5.1 Hz, 1H), 7.97 (s, 1H), 7.21 (d, J = 5.1 Hz, 1H), 4.54-4.29 (m, 2H), 3.99-3.78 (m, 1H), 3.59 (dd, J = 10.9, 7.8 Hz, 1H), 3.49 (td, J = 15.0, 9.3 Hz, 1H), 3.34 (dd, J = 11.0, 3.3 Hz, 2H), 3.11-2.92 (m, 2H), 2.26-2.09 (m, 1H), 2.04 (dt, J = 13.5, 6.2 Hz, 2H), 1.28 (d, J = 1.7 Hz, 6H). |
| 239 | 1H NMR (400 MHz, Methanol-d4) δ 8.71 (d, J = 2.2 Hz, 1H), 8.67 (s, 1H), 8.63 (d, J = 2.2 Hz, 1H), 8.12 (s, 1H), 8.02 (d, J = 0.8 Hz, 1H), 7.83 (d, J = 5.1 Hz, 1H), 7.73 (d, J = 0.8 Hz, 1H), 7.17 (d, J = 5.1 Hz, 1H), 5.12 (td, J = 5.5, 2.9 Hz, 1H), 4.45 (ddd, J = 49.0, 9.3, 2.1 Hz, 1H), 4.23-4.09 (m, 2H), 4.09-3.98 (m, 2H), 3.98-3.86 (m, 1H), 3.52 (ddd, J = 16.2, 14.5, 9.3 Hz, 1H), 2.56 (dtd, J = 13.4, 8.4, 6.9 Hz, 1H), 2.47-2.30 (m, 1H), 1.29 (d, J = 1.7 Hz, 6H). |
| 240 | 1H NMR (400 MHz, Methanol-d4) δ 8.75 (d, J = 2.2 Hz, 1H), 8.74 (s, 1H), 8.66 (d, J = 2.1 Hz, 1H), 8.19 (d, J = 5.1 Hz, 1H), 8.07 (s, 1H), 7.20 (d, J = 5.1 Hz, 1H), 4.60-4.32 (m, 1H), 4.09-3.88 (m, 1H), 3.90-3.78 (m, 1H), 3.63 (d, J = 13.1 Hz, 1H), 2.60 (s, 2H), 1.29 (d, J = 1.6 Hz, 7H). |

TABLE 2-continued

| compound | 1H-NMR |
|---|---|
| 241 | 1H NMR (400 MHz, Methanol-d4) δ 8.70 (d, J = 2.2 Hz, 1H), 8.68 (s, 1H), 8.53 (d, J = 2.2 Hz, 1H), 8.16 (s, 1H), 7.77 (d, J = 5.1 Hz, 1H), 7.51 (d, J = 8.3 Hz, 2H), 7.43 (d, J = 8.4 Hz, 2H), 7.15 (d, J = 5.1 Hz, 1H), 4.46 (ddd, J = 49.0, 9.3, 2.0 Hz, 1H), 4.44 (s, 2H), 3.99 (ddd, J = 36.5, 14.4, 2.1 Hz, 1H), 3.65-3.43 (m, 1H), 2.04 (s, 3H), 1.30 (d, J = 1.6 Hz, 6H). |
| 242 | 1H NMR (400 MHz, Methanol-d4) δ 8.75 (d, J = 2.1 Hz, 1H), 8.67 (d, J = 2.2 Hz, 1H), 8.60 (s, 1H), 8.04 (d, J = 5.0 Hz, 1H), 7.89 (s, 1H), 7.21 (d, J = 5.0 Hz, 1H), 4.42 (ddd, J = 49.0, 9.4, 2.1 Hz, 1H), 4.10 (dd, J = 20.4, 12.3 Hz, 3H), 4.02-3.81 (m, 1H), 3.71 (s, 3H), 3.48 (td, J = 15.5, 9.4 Hz, 1H), 3.22 (s, 3H), 2.11 (d, J = 13.1 Hz, 2H), 1.80-1.54 (m, 2H), 1.28 (d, J = 1.6 Hz, 6H). |
| 243 | 1H NMR (400 MHz, Methanol-d4) δ 8.75 (d, J = 2.1 Hz, 1H), 8.67 (d, J = 2.2 Hz, 1H), 8.59 (s, 1H), 8.04 (d, J = 5.1 Hz, 1H), 7.89 (s, 1H), 7.21 (d, J = 5.0 Hz, 1H), 4.42 (ddd, J = 49.0, 9.4, 2.1 Hz, 1H), 4.09 (td, J = 9.8, 4.8 Hz, 1H), 3.93 (ddd, J = 36.6, 14.5, 2.1 Hz, 1H), 3.67 (d, J = 13.6 Hz, 2H), 3.48 (ddd, J = 16.0, 14.6, 9.4 Hz, 1H), 3.20-3.03 (m, 2H), 2.88 (s, 6H), 2.13 (d, J = 12.9 Hz, 2H), 1.89-1.61 (m, 2H), 1.28 (d, J = 1.6 Hz, 6H). |
| 244 | 1H NMR (400 MHz, Methanol-d4) δ 8.75 (d, J = 2.2 Hz, 1H), 8.68 (d, J = 2.2 Hz, 1H), 8.60 (s, 1H), 8.04 (d, J = 5.1 Hz, 1H), 7.87 (s, 1H), 7.21 (d, J = 5.1 Hz, 1H), 4.42 (ddd, J = 49.0, 9.4, 2.1 Hz, 1H), 4.07 (dt, J = 9.9, 5.5 Hz, 1H), 3.93 (ddd, J = 36.6, 14.5, 2.1 Hz, 1H), 3.69 (d, J = 13.0 Hz, 2H), 3.49 (ddd, J = 16.0, 14.5, 9.4 Hz, 1H), 3.26-3.13 (m, 2H), 2.84 (s, 6H), 2.17 (d, J = 13.1 Hz, 2H), 1.86-1.65 (m, 2H), 1.28 (d, J = 1.6 Hz, 6H). |
| 245 | 1H NMR (400 MHz, Methanol-d4) δ 8.76 (s, 1H), 8.67 (s, 1H), 8.62 (s, 1H), 8.01 (d, J = 5.1 Hz, 1H), 7.88 (s, 1H), 7.22 (d, J = 5.0 Hz, 1H), 4.41 (ddd, J = 49.3, 9.4, 2.0 Hz, 1H), 4.01-3.83 (m, 2H), 3.64-3.44 (m, 3H), 3.16-3.07 (m, 0H), 2.97 (d, J = 10.7 Hz, 6H), 2.25 (s, 2H), 2.02 (t, J = 18.2 Hz, 2H), 1.28 (d, J = 1.6 Hz, 6H). |
| 246 | 1H NMR (400 MHz, Methanol-d4) δ 8.76 (d, J = 2.2 Hz, 1H), 8.68 (d, J = 2.2 Hz, 1H), 8.57 (s, 1H), 8.02 (d, J = 5.1 Hz, 1H), 7.86 (s, 1H), 7.21 (d, J = 5.1 Hz, 1H), 4.41 (dd, J = 50.1, 8.6 Hz, 2H), 4.05-3.83 (m, 1H), 3.77 (dd, J = 11.2, 8.0 Hz, 1H), 3.64-3.40 (m, 4H), 3.07-2.79 (m, 2H), 2.62 (dt, J = 14.0, 7.8 Hz, 2H), 2.08 (s, 3H), 1.65 (ddd, J = 19.9, 13.4, 7.0 Hz, 2H), 1.28 (d, J = 1.6 Hz, 6H). |
| 247 | 1H NMR (400 MHz, Methanol-d4) δ 8.75 (d, J = 2.2 Hz, 1H), 8.68 (d, J = 2.2 Hz, 1H), 8.56 (s, 1H), 8.02 (d, J = 5.1 Hz, 1H), 7.87 (s, 1H), 7.21 (d, J = 5.0 Hz, 1H), 4.43 (dd, J = 48.8, 7.9 Hz, 1H), 4.24 (t, J = 7.6 Hz, 1H), 3.95 (dd, J = 36.4, 14.3 Hz, 1H), 3.57-3.39 (m, 1H), 2.91 (s, 4H), 2.60 (dt, J = 13.4, 6.9 Hz, 2H), 1.61 (dt, J = 13.8, 8.1 Hz, 2H), 1.28 (d, J = 1.6 Hz, 6H). |
| 248 | 1H NMR (400 MHz, Methanol-d4) δ 8.76 (d, J = 2.2 Hz, 1H), 8.67 (d, J = 2.2 Hz, 1H), 8.61 (s, 1H), 8.02 (d, J = 5.1 Hz, 1H), 7.90 (s, 1H), 7.21 (d, J = 5.1 Hz, 1H), 4.52-4.26 (m, 1H), 4.02-3.76 (m, 1H), 3.58-3.45 (m, 1H), 3.42 (dd, J = 12.1, 7.3 Hz, 2H), 3.16-2.95 (m, 2H), 2.68 (dd, J = 13.2, 6.8 Hz, 2H), 1.70-1.46 (m, 2H), 1.28 (d, J = 1.6 Hz, 6H). |
| 249 | 1H NMR (400 MHz, Methanol-d4) δ 8.75 (d, J = 2.2 Hz, 1H), 8.70 (d, J = 2.2 Hz, 1H), 8.58 (s, 1H), 7.99 (d, J = 5.1 Hz, 1H), 7.92 (s, 1H), 7.21 (d, J = 5.1 Hz, 1H), 4.53-4.29 (m, 2H), 3.92 (dd, J = 36.4, 14.6 Hz, 1H), 3.80 (dd, J = 11.2, 8.0 Hz, 1H), 3.68 (dd, J = 12.6, 8.4 Hz, 1H), 3.46 (ddd, J = 17.4, 11.8, 4.4 Hz, 3H), 3.02 (ddd, J = 32.2, 8.3, 4.3 Hz, 1H), 2.29-2.13 (m, 2H), 2.13-1.96 (m, 5H), 1.28 (d, J = 1.6 Hz, 6H). |
| 250 | 1H NMR (400 MHz, Methanol-d4) δ 8.80 (d, J = 2.2 Hz, 1H), 8.74 (d, J = 2.2 Hz, 1H), 8.57 (s, 1H), 8.19 (s, 1H), 7.97 (d, J = 5.1 Hz, 1H), 7.21 (d, J = 5.1 Hz, 1H), 4.57-4.29 (m, 2H), 3.92 (dd, J = 36.1, 14.8 Hz, 1H), 3.48 (td, J = 15.4, 9.3 Hz, 1H), 3.37-3.31 (m, 4H), 3.02 (d, J = 7.0 Hz, 2H), 2.92 (s, 3H), 2.18 (t, J = 9.3 Hz, 2H), 2.04 (dt, J = 13.9, 7.5 Hz, 2H), 1.28 (d, J = 1.6 Hz, 7H). |
| 251 | 1H NMR (400 MHz, Methanol-d4) δ 8.76 (d, J = 2.2 Hz, 1H), 8.66 (d, J = 2.2 Hz, 1H), 8.62 (s, 1H), 8.02 (d, J = 5.1 Hz, 1H), 7.90 (s, 1H), 7.21 (d, J = 5.0 Hz, 1H), 4.59-4.43 (m, 2H), 4.35 (dd, J = 9.4, 2.1 Hz, 1H), 3.91 (ddd, J = 36.3, 14.5, 2.1 Hz, 1H), 3.64-3.43 (m, 3H), 3.27-3.04 (m, 4H), 2.12 (dt, J = 13.5, 6.4 Hz, 5H), 1.28 (d, J = 1.7 Hz, 6H). |
| 252 | 1H NMR (400 MHz, Methanol-d4) δ 8.74 (d, J = 2.2 Hz, 1H), 8.65 (d, J = 2.2 Hz, 1H), 8.58 (s, 1H), 8.00 (d, J = 5.1 Hz, 1H), 7.86 (s, 1H), 7.20 (d, J = 5.1 Hz, 1H), 4.15 (p, J = 6.4 Hz, 1H), 3.59-3.43 (m, 2H), 2.01-1.93 (m, 2H), 1.42 (s, 6H), 1.40 (d, J = 6.4 Hz, 6H). |
| 253 | 1H NMR (400 MHz, Methanol-d4) δ 8.75 (d, J = 2.3 Hz, 1H), 8.68 (d, J = 2.2 Hz, 1H), 8.61 (d, J = 14.8 Hz, 1H), 8.04 (d, J = 5.2 Hz, 1H), 7.93 (s, 1H), 7.21 (d, J = 5.1 Hz, 1H), 4.42 (dd, J = 48.8, 9.2 Hz, 1H), 4.16-3.75 (m, 1H), 3.50 (ddd, J = 23.4, 19.2, 12.0 Hz, 3H), 2.18 (s, 3H), 2.00-1.83 (m, 2H), 1.76 (s, 1H), 1.28 (d, J = 1.7 Hz, 7H). |
| 254 | 1H NMR (400 MHz, Methanol-d4) δ 8.74 (d, J = 2.2 Hz, 1H), 8.67 (d, J = 2.2 Hz, 1H), 8.61 (s, 1H), 8.00 (d, J = 5.1 Hz, 1H), 7.95 (s, 1H), 7.20 (d, J = 5.1 Hz, 1H), 4.49 (dd, J = 9.4, 2.1 Hz, 1H), 4.40-4.30 (m, 1H), 4.16 (s, 1H), 4.02-3.83 (m, 1H), 3.80-3.73 (m, 1H), 3.73-3.61 (m, 2H), 3.43-3.33 (m, 1H), 3.28-3.15 (m, 1H), 3.09 (s, 1H), 2.91 (s, 3H), 2.08 (d, J = 12.1 Hz, 1H), 1.92 (dd, J = 14.0, 8.3 Hz, 1H), 1.88-1.78 (m, 2H), 1.28 (d, J = 1.6 Hz, 6H). |

TABLE 2-continued

| compound | 1H-NMR |
|---|---|
| 255 | 1H NMR (400 MHz, Methanol-d4) δ 8.75 (d, J = 2.2 Hz, 1H), 8.66 (s, 1H), 8.65 (d, J = 2.1 Hz, 1H), 8.10 (d, J = 5.1 Hz, 1H), 7.91 (s, 1H), 7.20 (d, J = 5.0 Hz, 1H), 4.49 (dd, J = 9.2, 2.1 Hz, 0H), 4.42-4.23 (m, 1H), 4.12-3.81 (m, 1H), 3.64 (d, J = 12.5 Hz, 1H), 3.51 (td, J = 15.2, 9.2 Hz, 1H), 3.40 (d, J = 12.8 Hz, 1H), 3.18-2.98 (m, 1H), 2.28 (d, J = 12.5 Hz, 1H), 2.12 (d, J = 15.1 Hz, 1H), 1.99 (d, J = 10.9 Hz, 0H), 1.88 (t, J = 11.6 Hz, 1H), 1.29 (d, J = 1.6 Hz, 6H). |
| 256 | 1H NMR (400 MHz, Methanol-d4) δ 8.78-8.71 (m, 1H), 8.67 (d, J = 2.2 Hz, 1H), 8.60 (s, 1H), 8.04 (d, J = 5.0 Hz, 1H), 7.94 (s, 1H), 7.88 (s, 0H), 7.21 (d, J = 5.1 Hz, 1H), 4.47 (dd, J = 9.3, 2.1 Hz, 1H), 4.35 (dd, J = 9.3, 2.1 Hz, 1H), 4.20 (s, 0H), 4.12 (d, J = 13.6 Hz, 1H), 3.97 (dd, J = 14.7, 2.5 Hz, 2H), 3.91-3.74 (m, 1H), 3.68 (dd, J = 13.8, 6.5 Hz, 1H), 3.63-3.40 (m, 2H), 2.18 (s, 3H), 1.92 (dd, J = 12.1, 6.2 Hz, 1H), 1.82-1.65 (m, 2H), 1.28 (d, J = 1.6 Hz, 6H). |
| 257 | 1H NMR (400 MHz, Methanol-d4) δ 8.74 (d, J = 2.2 Hz, 1H), 8.68 (d, J = 2.2 Hz, 1H), 8.61 (s, 1H), 8.00 (d, J = 5.1 Hz, 1H), 7.96 (s, 1H), 7.21 (d, J = 5.1 Hz, 1H), 4.42 (ddd, J = 49.1, 9.3, 2.1 Hz, 1H), 4.15 (s, 1H), 4.05-3.83 (m, 1H), 3.71 (d, J = 10.7 Hz, 1H), 3.58-3.35 (m, 2H), 3.26-3.13 (m, 1H), 2.91 (s, 3H), 2.08 (s, 1H), 1.93 (s, 2H), 1.84 (t, J = 8.4 Hz, 2H), 1.28 (d, J = 1.6 Hz, 6H). |
| 258 | 1H NMR (400 MHz, Methanol-d4) δ 8.76 (d, J = 2.2 Hz, 1H), 8.66 (s, 1H), 8.65 (d, J = 2.1 Hz, 1H), 8.09 (d, J = 5.0 Hz, 1H), 7.90 (s, 1H), 7.21 (d, J = 5.0 Hz, 1H), 4.42 (ddd, J = 49.2, 9.3, 2.1 Hz, 1H), 4.34-4.19 (m, 0H), 4.08-3.79 (m, 1H), 3.67-3.58 (m, 1H), 3.57-3.44 (m, 1H), 3.40 (d, J = 12.8 Hz, 1H), 3.21-3.00 (m, 2H), 2.28 (d, J = 12.5 Hz, 1H), 2.12 (d, J = 14.0 Hz, 1H), 2.05-1.93 (m, 0H), 1.88 (t, J = 11.8 Hz, 1H), 1.29 (d, J = 1.7 Hz, 7H)6 |
| 259 | 1H NMR (400 MHz, Methanol-d4) δ 8.76 (d, J = 2.1 Hz, 1H), 8.66 (d, J = 2.2 Hz, 2H), 8.25 (s, 1H), 7.93 (s, 1H), 7.20 (d, J = 5.1 Hz, 1H), 4.57-4.27 (m, 2H), 4.03-3.70 (m, 2H), 3.71-3.41 (m, 2H), 2.99 (s, 1H), 2.93 (s, 3H), 2.28 (s, 1H), 2.20-1.91 (m, 1H), 1.74 (s, 1H), 1.28 (d, J = 1.7 Hz, 6H). |
| 260 | 1H NMR (400 MHz, Methanol-d4) δ 8.76 (d, J = 2.2 Hz, 1H), 8.66 (d, J = 2.2 Hz, 2H), 8.27 (s, 1H), 7.93 (s, 1H), 7.19 (d, J = 5.1 Hz, 1H), 4.47 (dt, J = 14.5, 7.2 Hz, 2H), 4.36 (dd, J = 9.3, 2.1 Hz, 1H), 4.05-3.71 (m, 2H), 3.67-3.41 (m, 1H), 2.92 (s, 5H), 2.27 (s, 1H), 2.19-1.91 (m, 3H), 1.74 (s, 1H), 1.28 (d, J = 1.7 Hz, 6H). |
| 261 | 1H NMR (400 MHz, Methanol-d4) δ 8.73 (d, J = 2.2 Hz, 1H), 8.65 (d, J = 2.2 Hz, 1H), 8.55 (s, 1H), 8.00 (d, J = 5.0 Hz, 1H), 7.83 (s, 1H), 7.20 (d, J = 5.0 Hz, 1H), 4.48 (dd, J = 9.4, 2.1 Hz, 1H), 4.44-4.28 (m, 2H), 4.12 (td, J = 7.8, 4.9 Hz, 1H), 3.93 (ddd, J = 36.6, 14.6, 2.1 Hz, 1H), 3.47 (ddd, J = 16.0, 14.5, 9.4 Hz, 1H), 2.42-2.23 (m, 1H), 2.00 (dddd, J = 20.9, 18.9, 9.9, 5.3 Hz, 2H), 1.88-1.60 (m, 3H), 1.28 (d, J = 1.7 Hz, 7H). |
| 262 | 1H NMR (400 MHz, Methanol-d4) δ 8.73 (d, J = 2.1 Hz, 1H), 8.64 (d, J = 2.2 Hz, 1H), 8.56 (s, 1H), 8.01 (s, 1H), 7.95 (d, J = 5.0 Hz, 1H), 7.20 (d, J = 5.0 Hz, 1H), 4.55-4.30 (m, 1H), 4.15 (q, J = 5.5 Hz, 1H), 4.02 (d, J = 6.2 Hz, 1H), 3.93 (dd, J = 35.4, 15.3 Hz, 1H), 3.61-3.40 (m, 1H), 2.37 (dd, J = 13.6, 7.7 Hz, 1H), 2.13-2.01 (m, 1H), 1.86 (s, 0H), 1.80-1.58 (m, 1H), 1.28 (d, J = 1.7 Hz, 6H). |
| 263 | 1H NMR (400 MHz, Methanol-d4) δ 8.75 (d, J = 2.2 Hz, 1H), 8.71 (s, 1H), 8.67 (d, J = 2.2 Hz, 1H), 8.01 (d, J = 5.0 Hz, 1H), 7.90 (s, 1H), 7.22 (d, J = 5.0 Hz, 1H), 4.56-4.33 (m, 2H), 4.06-3.83 (m, 2H), 3.62-3.36 (m, 6H), 2.57-2.48 (m, 1H), 2.32-2.05 (m, 4H), 1.29 (d, J = 1.7 Hz, 6H). |
| 264 | 1H NMR (400 MHz, Methanol-d4) δ 8.49 (d, J = 2.2 Hz, 1H), 8.43 (s, 1H), 8.21 (d, J = 2.1 Hz, 1H), 7.33 (d, J = 4.7 Hz, 1H), 7.13-6.94 (m, 2H), 4.21-3.92 (m, 6H), 3.76-3.51 (m, 3H), 2.59-2.44 (m, 2H), 2.26-2.06 (m, 4H), 1.24-1.09 (m, 6H). |
| 265 | 1H NMR (400 MHz, Methanol-d4) δ 8.76 (d, J = 2.1 Hz, 1H), 8.67 (d, J = 2.2 Hz, 1H), 8.60 (s, 1H), 8.02 (d, J = 5.1 Hz, 1H), 7.89 (s, 1H), 7.22 (d, J = 5.1 Hz, 1H), 4.42 (ddd, J = 49.1, 9.4, 2.1 Hz, 1H), 4.02-3.85 (m, 1H), 3.61-3.41 (m, 1H), 2.42 (dd, J = 8.6, 7.5 Hz, 2H), 2.15-2.00 (m, 4H), 1.93-1.70 (m, 7H), 1.30 (d, J = 1.7 Hz, 6H). |
| 266 | 1H NMR (400 MHz, DMSO-d6) δ 9.69 (s, 1H), 9.00 (s, 1H), 8.94 (s, 1H), 8.82 (d, J = 2.2 Hz, 1H), 8.78 (s, 1H), 8.02 (s, 1H), 7.94 (d, J = 4.9 Hz, 1H), 7.19 (d, J = 4.9 Hz, 1H), 6.53 (s, 1H), 4.89 (s, 1H), 4.37 (ddd, J = 49.3, 9.5, 2.1 Hz, 1H), 4.20 (s, 1H), 3.86 (t, J = 11.2 Hz, 1H), 3.81-3.65 (m, 1H), 3.34-3.21 (m, 2H), 2.56-2.49 (m, 1H), 2.40-2.32 (m, 2H), 2.12-1.81 (m, 5H), 1.18 (dd, J = 5.6, 1.6 Hz, 6H). |
| 267 | 1H NMR (499 MHz, Methanol-d4) δ 8.77 (s, 2H), 8.56 (s, 1H), 8.43 (s, 1H), 7.94 (d, J = 5.0 Hz, 1H), 7.23 (d, J = 5.0 Hz, 1H), 4.35 (s, 2H), 3.60 (s, 3H), 2.30-2.20 (m, 6H), 2.18-2.07 (m, 6H). |
| 268 | 1H NMR (499 MHz, Methanol-d4) δ 8.76 (d, J = 2.1 Hz, 1H), 8.66 (d, J = 2.1 Hz, 1H), 8.58 (s, 1H), 8.02 (d, J = 5.0 Hz, 1H), 7.92 (s, 1H), 7.22 (d, J = 5.0 Hz, 1H), 4.37 (s, 2H), 3.90-3.79 (m, 1H), 3.64 (s, 3H), 3.54-3.47 (m, 1H), 2.22 (d, J = 12.5 Hz, 2H), 2.08 (d, J = 12.5 Hz, 2H), 1.56 (tt, J = 24.3, 12.1 Hz, 4H). |
| 269 | 1H NMR (400 MHz, Methanol-d4) δ 8.76 (d, J = 2.2 Hz, 1H), 8.65 (d, J = 2.2 Hz, 1H), 8.57 (s, 1H), 8.02 (d, J = 5.1 Hz, 1H), 7.87 (s, 1H), 7.22 (d, J = 5.1 Hz, 1H), 4.43 (ddd, J = 49.2, 9.5, 2.0 Hz, 1H), 4.04-3.81 (m, 2H), 3.59-3.41 (m, 2H), 2.37 (s, 3H), 2.31-2.15 (m, 4H), 1.72-1.53 (m, 4H), 1.30 (d, J = 1.6 Hz, 6H). |
| 270 | 1H NMR (400 MHz, Methanol-d4) δ 8.83-8.70 (m, 2H), 8.52 (s, 1H), 8.36 (s, 1H), 7.92 (d, J = 5.1 Hz, 1H), 7.23 (d, J = 5.1 Hz, 1H), 3.93-3.77 (m, 1H), 3.68-3.63 (m, 4H), 3.64-3.54 (m, 4H), 3.40-3.34 (m, 4H), 2.28-2.07 (m, 12H), 2.08-1.94 (m, 4H), 1.56-1.35 (m, 4H). |
| 271 | 1H NMR (400 MHz, Methanol-d4) δ 8.81-8.71 (m, 2H), 8.52 (s, 1H), 8.36 (s, 1H), 7.92 (d, J = 5.1 Hz, 1H), 7.22 (d, J = 5.1 Hz, 1H), 3.95-3.80 (m, 1H), 3.74-3.62 (m, 1H), 3.60 (s, 3H), 2.31-2.08 (m, 12H), 2.07-1.93 (m, 4H), 1.62-1.35 (m, 5H), 0.87-0.80 (m, 2H), 0.79-0.69 (m, 2H). |

TABLE 2-continued

| compound | 1H-NMR |
|---|---|
| 272 | 1H NMR (400 MHz, Methanol-d4) δ 8.79 (d, J = 2.2 Hz, 1H), 8.77 (d, J = 2.2 Hz, 1H), 8.53 (s, 1H), 8.46 (s, 1H), 7.92 (d, J = 5.1 Hz, 1H), 7.23 (d, J = 5.1 Hz, 1H), 4.41 (ddd, J = 49.0, 9.6, 2.1 Hz, 1H), 3.92 (ddd, J = 36.6, 14.5, 2.1 Hz, 1H), 3.56-3.41 (m, 1H), 2.88 (s, 6H), 2.32-2.07 (m, 12H), 1.29 (d, J = 1.6 Hz, 6H). |
| 273 | 1H NMR (400 MHz, Methanol-d4) δ 8.75 (d, J = 2.2 Hz, 1H), 8.67 (d, J = 2.2 Hz, 1H), 8.56 (s, 1H), 8.02 (d, J = 5.1 Hz, 1H), 7.87 (s, 1H), 7.21 (d, J = 5.1 Hz, 1H), 4.42 (ddd, J = 49.1, 9.4, 2.1 Hz, 1H), 3.93 (ddd, J = 36.5, 14.6, 2.2 Hz, 1H), 3.84-3.71 (m, 1H), 3.56-3.39 (m, 1H), 2.33-2.19 (m, 2H), 2.10-1.95 (m, 2H), 1.53-1.33 (m, 4H), 1.29 (d, J = 1.6 Hz, 6H), 1.27-1.14 (m, 7H). |
| 274 | 1H NMR (400 MHz, Methanol-d4) δ 8.75 (d, J = 2.2 Hz, 1H), 8.65 (d, J = 2.2 Hz, 1H), 8.50 (s, 1H), 8.00 (d, J = 5.1 Hz, 1H), 7.85 (s, 1H), 7.21 (d, J = 5.1 Hz, 1H), 3.91-3.78 (m, 1H), 3.64 (s, 3H), 3.56-3.44 (m, 1H), 2.93 (s, 3H), 2.28-2.14 (m, 2H), 2.12-2.01 (m, 2H), 1.66-1.42 (m, 4H). |
| 275 | 1H NMR (400 MHz, Methanol-d4) δ 8.75 (d, J = 2.2 Hz, 1H), 8.64 (d, J = 2.2 Hz, 1H), 8.52 (s, 1H), 8.01 (d, J = 5.1 Hz, 1H), 7.86 (s, 1H), 7.22 (d, J = 5.0 Hz, 1H), 3.92-3.76 (m, 2H), 2.93 (s, 3H), 2.33-2.17 (m, 2H), 2.14-1.96 (m, 2H), 1.75-1.50 (m, 4H). |
| 276 | 1H NMR (400 MHz, Methanol-d4) δ 8.75 (d, J = 2.2 Hz, 1H), 8.64 (d, J = 2.1 Hz, 1H), 8.50 (s, 1H), 8.00 (d, J = 5.0 Hz, 1H), 7.84 (s, 1H), 7.21 (d, J = 5.0 Hz, 1H), 3.94-3.64 (m, 2H), 2.93 (s, 3H), 2.28-2.15 (m, 2H), 2.11-1.99 (m, 2H), 1.95 (s, 3H), 1.55 (h, J = 12.0 Hz, 4H). |
| 277 | 1H NMR (400 MHz, Methanol-d4) δ 8.87-8.75 (m, 2H), 8.66 (d, J = 12.6 Hz, 2H), 7.98 (d, J = 5.1 Hz, 1H), 7.24 (d, J = 5.1 Hz, 1H), 4.14 (q, J = 9.3 Hz, 2H), 2.67 (s, 6H), 1.99 (s, 3H). |
| 278 | 1H NMR (400 MHz, Methanol-d4) δ 8.83-8.74 (m, 2H), 8.64 (d, J = 8.6 Hz, 2H), 7.98 (d, J = 5.1 Hz, 1H), 7.24 (d, J = 5.1 Hz, 1H), 6.05 (tt, J = 56.0, 4.0 Hz, 1H), 3.77 (td, J = 15.1, 4.0 Hz, 2H), 2.67 (s, 6H), 1.98 (s, 3H). |
| 279 | 1H NMR (400 MHz, Methanol-d4) δ 8.76 (t, J = 3.0 Hz, 2H), 8.54 (s, 1H), 8.37 (s, 1H), 7.93 (d, J = 5.1 Hz, 1H), 7.22 (d, J = 5.1 Hz, 1H), 5.38-5.28 (m, 1H), 4.93-4.84 (m, 2H), 4.63-4.55 (m, 2H), 4.52-4.31 (m, 1H), 4.02-3.80 (m, 1H), 3.55-3.39 (m, 1H), 2.33-2.18 (m, 6H), 2.17-2.06 (m, 6H), 1.29 (d, J = 1.6 Hz, 6H). |
| 280 | 1H NMR (400 MHz, Methanol-d4) δ 8.75 (d, J = 2.3 Hz, 1H), 8.65 (d, J = 2.2 Hz, 1H), 8.56 (s, 1H), 8.00 (d, J = 5.0 Hz, 1H), 7.88 (s, 1H), 7.21 (d, J = 5.1 Hz, 1H), 5.42-5.29 (m, 1H), 4.92-4.85 (m, 2H), 4.65-4.57 (m, 2H), 4.42 (ddd, J = 48.9, 9.3, 1.9 Hz, 1H), 4.03-3.77 (m, 2H), 3.56-3.40 (m, 2H), 2.28-2.18 (m, 2H), 2.14-1.98 (m, 2H), 1.65-1.45 (m, 4H), 1.29 (d, J = 1.6 Hz, 6H). |
| 281 | 1H NMR (400 MHz, Methanol-d4) δ 8.88-8.68 (m, 2H), 8.54 (s, 1H), 8.41 (s, 1H), 7.93 (d, J = 5.1 Hz, 1H), 7.23 (d, J = 5.1 Hz, 1H), 4.41 (ddd, J = 49.0, 9.6, 2.0 Hz, 1H), 3.92 (ddd, J = 37.0, 14.5, 2.0 Hz, 1H), 3.53-3.40 (m, 1H), 2.32-2.07 (m, 12H), 1.68-1.46 (m, 1H), 1.29 (d, J = 1.6 Hz, 6H), 0.86-0.75 (m, 2H), 0.75-0.63 (m, 2H). |
| 282 | 1H NMR (400 MHz, Methanol-d4) δ 8.76 (d, J = 2.2 Hz, 1H), 8.65 (d, J = 2.1 Hz, 1H), 8.57 (s, 1H), 8.01 (d, J = 5.1 Hz, 1H), 7.88 (s, 1H), 7.22 (d, J = 5.0 Hz, 1H), 4.87-4.86 (m, 2H), 4.52-4.33 (m, 3H), 4.03-3.73 (m, 3H), 3.55-3.40 (m, 1H), 2.30-2.17 (m, 2H), 2.12-1.99 (m, 2H), 1.69-1.48 (m, 7H), 1.30 (d, J = 1.6 Hz, 6H). |
| 283 | 1H NMR (400 MHz, Methanol-d4) δ 8.82-8.68 (m, 2H), 8.55 (s, 1H), 8.38 (s, 1H), 7.94 (d, J = 5.1 Hz, 1H), 7.23 (d, J = 5.1 Hz, 1H), 4.41 (ddd, J = 49.1, 9.4, 2.1 Hz, 1H), 3.91 (ddd, J = 36.6, 14.5, 2.1 Hz, 1H), 3.59-3.39 (m, 1H), 2.32-2.18 (m, 6H), 2.15-2.05 (m, 6H), 1.29 (d, J = 1.6 Hz, 6H). |
| 284 | 1H NMR (400 MHz, Methanol-d4) δ 8.76 (d, J = 2.2 Hz, 1H), 8.66 (d, J = 2.2 Hz, 1H), 8.57 (s, 1H), 8.01 (d, J = 5.1 Hz, 1H), 7.89 (s, 1H), 7.22 (d, J = 5.0 Hz, 1H), 4.42 (ddd, J = 48.6, 9.2, 1.9 Hz, 1H), 4.05-3.79 (m, 5H), 3.54-3.45 (m, 1H), 3.43 (s, 3H), 2.30-2.17 (m, 2H), 2.10-2.00 (m, 2H), 1.68-1.53 (m, 4H), 1.29 (d, J = 1.6 Hz, 6H). |
| 285 | 1H NMR (400 MHz, Methanol-d4) δ 8.76 (d, J = 2.1 Hz, 1H), 8.65 (d, J = 2.2 Hz, 1H), 8.56 (s, 1H), 8.01 (d, J = 5.1 Hz, 1H), 7.86 (s, 1H), 7.22 (d, J = 5.1 Hz, 1H), 4.53-4.27 (m, 1H), 4.03-3.71 (m, 2H), 3.56-3.41 (m, 2H), 2.77 (s, 6H), 2.28-2.07 (m, 4H), 1.67-1.49 (m, 4H), 1.29 (d, J = 1.6 Hz, 6H). |
| 286 | 1H NMR (400 MHz, Methanol-d4) δ 8.76 (d, J = 2.2 Hz, 1H), 8.65 (d, J = 2.2 Hz, 1H), 8.56 (s, 1H), 7.99 (d, J = 5.1 Hz, 1H), 7.90 (s, 1H), 7.22 (d, J = 5.1 Hz, 1H), 4.43 (ddd, J = 49.1, 9.2, 2.1 Hz, 1H), 4.04-3.86 (m, 1H), 3.86-3.75 (m, 1H), 3.69-3.57 (m, 1H), 3.55-3.41 (m, 1H), 2.91 (s, 6H), 2.33-2.16 (m, 2H), 2.12-2.00 (m, 2H), 1.64-1.47 (m, 4H), 1.29 (d, J = 1.6 Hz, 6H). |
| 287 | 1H NMR (400 MHz, Methanol-d4) δ 8.76 (d, J = 2.2 Hz, 1H), 8.66 (d, J = 2.1 Hz, 1H), 8.57 (s, 1H), 8.01 (d, J = 5.0 Hz, 1H), 7.88 (s, 1H), 7.22 (d, J = 5.1 Hz, 1H), 4.42 (ddd, J = 49.0, 9.3, 2.1 Hz, 1H), 4.02-3.78 (m, 4H), 3.58-3.39 (m, 2H), 2.27-2.15 (m, 2H), 2.12-2.02 (m, 2H), 1.67-1.44 (m, 4H), 1.29 (d, J = 1.6 Hz, 6H), 1.12 (s, 1H), 0.63-0.49 (m, 2H), 0.31-0.22 (m, 2H). |
| 288 | 1H NMR (400 MHz, Methanol-d4) δ 8.76 (d, J = 2.2 Hz, 1H), 8.66 (d, J = 2.2 Hz, 1H), 8.56 (s, 1H), 8.01 (d, J = 5.0 Hz, 1H), 7.87 (s, 1H), 7.22 (d, J = 5.0 Hz, 1H), 4.97-4.86 (m, 1H), 4.52-4.31 (m, 1H), 4.02-3.75 (m, 2H), 3.57-3.37 (m, 2H), 2.39-2.26 (m, 2H), 2.26-2.16 (m, 2H), 2.12-2.00 (m, 4H), 1.85-1.72 (m, 1H), 1.70-1.44 (m, 5H), 1.29 (d, J = 1.6 Hz, 6H). |

TABLE 2-continued

| compound | 1H-NMR |
|---|---|
| 289 | 1H NMR (400 MHz, Methanol-d4) δ 8.76 (d, J = 2.2 Hz, 1H), 8.65 (d, J = 2.2 Hz, 1H), 8.59 (s, 1H), 8.01 (d, J = 5.0 Hz, 1H), 7.88 (s, 1H), 7.22 (d, J = 5.1 Hz, 1H), 4.56-4.28 (m, 1H), 4.03-3.81 (m, 2H), 3.82-3.65 (m, 2H), 3.58-3.42 (m, 1H), 3.08-2.99 (m, 1H), 2.43-2.26 (m, 2H), 2.26-2.14 (m, 2H), 1.66-1.47 (m, 4H), 1.29 (d, J = 1.6 Hz, 6H). |
| 290 | 1H NMR (400 MHz, Methanol-d4) δ 8.75 (d, J = 2.2 Hz, 1H), 8.65 (d, J = 2.1 Hz, 1H), 8.57 (s, 1H), 8.01 (d, J = 5.0 Hz, 1H), 7.88 (s, 1H), 7.22 (d, J = 5.0 Hz, 1H), 4.42 (ddd, J = 49.1, 9.3, 2.1 Hz, 1H), 4.03-3.76 (m, 4H), 3.57-3.40 (m, 2H), 2.21 (d, J = 10.6 Hz, 2H), 2.07 (d, J = 10.9 Hz, 2H), 1.98-1.83 (m, 1H), 1.69-1.44 (m, 4H), 1.29 (d, J = 1.6 Hz, 6H), 0.95 (d, J = 6.7 Hz, 6H). |
| 291 | 1H NMR (400 MHz, Methanol-d4) δ 8.76 (d, J = 2.2 Hz, 1H), 8.66 (d, J = 2.2 Hz, 1H), 8.56 (s, 1H), 8.01 (d, J = 5.0 Hz, 1H), 7.88 (s, 1H), 7.22 (d, J = 5.1 Hz, 1H), 4.42 (ddd, J = 49.0, 9.4, 2.1 Hz, 1H), 3.94 (ddd, J = 36.6, 14.6, 2.1 Hz, 1H), 3.86-3.74 (m, 1H), 3.58-3.41 (m, 2H), 2.21 (d, J = 11.8 Hz, 2H), 2.07 (d, J = 11.8 Hz, 2H), 1.64-1.42 (m, 4H), 1.29 (d, J = 1.7 Hz, 6H), 1.23 (d, J = 6.3 Hz, 6H). |
| 292 | 1H NMR (400 MHz, Methanol-d4) δ 8.76 (d, J = 2.2 Hz, 1H), 8.66 (d, J = 2.2 Hz, 1H), 8.56 (s, 1H), 8.01 (d, J = 5.1 Hz, 1H), 7.87 (s, 1H), 7.22 (d, J = 5.0 Hz, 1H), 4.42 (ddd, J = 49.0, 9.3, 2.1 Hz, 1H), 4.14-4.02 (m, 2H), 4.02-3.74 (m, 2H), 3.58-3.39 (m, 2H), 2.26-2.16 (m, 2H), 2.14-2.02 (m, 2H), 1.65-1.44 (m, 4H), 1.29 (d, J = 1.6 Hz, 6H), 1.24 (t, J = 7.1 Hz, 3H). |
| 293 | 1H NMR (400 MHz, Methanol-d4) δ 8.76 (d, J = 2.2 Hz, 1H), 8.66 (d, J = 2.1 Hz, 1H), 8.58 (s, 1H), 8.01 (d, J = 5.1 Hz, 1H), 7.88 (s, 1H), 7.22 (d, J = 5.0 Hz, 1H), 4.83 (ddd, J = 49.0, 9.3, 1.9 Hz, 1H), 4.02-3.79 (m, 2H), 3.64 (s, 3H), 3.59-3.43 (m, 2H), 2.27-2.16 (m, 2H), 2.13-2.03 (m, 2H), 2.03 (s, 3H), 1.66-1.44 (m, 10H). |
| 294 | 1H NMR (400 MHz, Methanol-d4) δ 8.76 (d, J = 2.2 Hz, 1H), 8.65 (d, J = 2.2 Hz, 1H), 8.57 (s, 1H), 8.01 (d, J = 5.1 Hz, 1H), 7.87 (s, 1H), 7.22 (d, J = 5.0 Hz, 1H), 4.42 (ddd, J = 49.0, 9.4, 2.1 Hz, 1H), 4.03-3.66 (m, 4H), 3.55-3.38 (m, 4H), 2.44 (tt, J = 11.6, 3.9 Hz, 1H), 2.22 (d, J = 11.4 Hz, 2H), 2.04 (d, J = 10.9 Hz, 2H), 1.93-1.48 (m, 8H), 1.29 (d, J = 1.7 Hz, 6H). |
| 295 | 1H NMR (400 MHz, Methanol-d4) δ 8.76 (d, J = 2.2 Hz, 1H), 8.72 (d, J = 2.2 Hz, 1H), 8.55 (s, 1H), 8.33 (s, 1H), 7.94 (d, J = 5.1 Hz, 1H), 7.22 (d, J = 5.1 Hz, 1H), 4.40 (ddd, J = 49.1, 9.4, 2.1 Hz, 1H), 4.00-3.81 (m, 1H), 3.56-3.40 (m, 1H), 2.34-2.18 (m, 12H), 1.28 (d, J = 1.7 Hz, 6H). |
| 296 | 1H NMR (400 MHz, Methanol-d4) δ 8.76 (d, J = 2.2 Hz, 1H), 8.65 (d, J = 2.2 Hz, 1H), 8.57 (s, 1H), 7.99 (d, J = 5.0 Hz, 1H), 7.90 (s, 1H), 7.22 (d, J = 5.0 Hz, 1H), 4.43 (ddd, J = 49.1, 9.4, 2.1 Hz, 1H), 4.02-3.87 (m, 1H), 3.79 (d, J = 23.1 Hz, 2H), 3.57-3.42 (m, 1H), 2.29-2.18 (m, 2H), 2.03-1.94 (m, 2H), 1.67-1.50 (m, 4H), 1.29 (d, J = 1.6 Hz, 6H), 1.20 (s, 9H). |
| 297 | 1H NMR (400 MHz, Methanol-d4) δ 8.75 (d, J = 2.1 Hz, 1H), 8.64 (d, J = 2.2 Hz, 1H), 8.55 (s, 1H), 8.00 (d, J = 5.0 Hz, 1H), 7.86 (s, 1H), 7.21 (d, J = 5.0 Hz, 1H), 4.41 (ddd, J = 49.0, 9.4, 2.1 Hz, 1H), 4.02-3.68 (m, 3H), 3.54-3.40 (m, 1H), 2.26-2.17 (m, 2H), 2.11-2.03 (m, 2H), 1.64-1.49 (m, 5H), 1.28 (d, J = 1.7 Hz, 6H), 0.88-0.81 (m, 2H), 0.78-0.70 (m, 2H). |
| 298 | 1H NMR (400 MHz, Methanol-d4) δ 8.75 (d, J = 2.2 Hz, 1H), 8.65 (d, J = 2.1 Hz, 1H), 8.56 (s, 1H), 8.00 (d, J = 5.0 Hz, 1H), 7.87 (s, 1H), 7.21 (d, J = 5.1 Hz, 1H), 4.42 (ddd, J = 49.0, 9.2, 1.9 Hz, 1H), 4.04-3.64 (m, 3H), 3.57-3.40 (m, 1H), 2.51-2.35 (m, 1H), 2.29-2.16 (m, 2H), 2.08-1.99 (m, 2H), 1.67-1.45 (m, 4H), 1.29 (d, J = 1.7 Hz, 6H), 1.11 (d, J = 6.8 Hz, 6H). |
| 299 | 1H NMR (400 MHz, Methanol-d4) δ 8.76 (d, J = 2.1 Hz, 1H), 8.65 (d, J = 2.2 Hz, 1H), 8.56 (s, 1H), 8.01 (d, J = 5.1 Hz, 1H), 7.87 (s, 1H), 7.22 (d, J = 5.0 Hz, 1H), 4.43 (ddd, J = 48.8, 9.4, 1.9 Hz, 1H), 4.03-3.66 (m, 3H), 3.48 (td, J = 15.8, 9.3 Hz, 1H), 2.28-2.15 (m, 4H), 2.11-2.00 (m, 2H), 1.69-1.44 (m, 4H), 1.29 (d, J = 1.6 Hz, 6H), 1.14 (t, J = 7.6 Hz, 3H). |
| 300 | 1H NMR (400 MHz, Methanol-d4) δ 8.75 (d, J = 2.1 Hz, 1H), 8.65 (d, J = 2.2, 0.5 Hz, 1H), 8.53 (s, 1H), 7.99 (d, J = 5.1 Hz, 1H), 7.86 (s, 1H), 7.21 (d, J = 5.0 Hz, 1H), 3.97-3.75 (m, 2H), 3.67-3.61 (m, 6H), 3.59-3.35 (m, 2H), 2.28-2.16 (m, 2H), 2.12-1.94 (m, 6H), 1.69-1.29 (m, 8H). |
| 301 | 1H NMR (400 MHz, Methanol-d4) δ 8.79-8.72 (m, 1H), 8.64 (dd, J = 2.2, 0.4 Hz, 1H), 8.54 (s, 1H), 8.00 (d, J = 5.0 Hz, 1H), 7.85 (s, 1H), 7.21 (d, J = 5.1, 0.4 Hz, 1H), 3.94-3.78 (m, 2H), 3.79-3.60 (m, 2H), 2.25-2.19 (m, 2H), 2.09-2.03 (m, 3H), 1.99 (d, J = 14.0 Hz, 3H), 1.95 (s, 3H), 1.93 (s, 3H), 1.65-1.29 (m, 8H). |
| 302 | 1H NMR (400 MHz, Methanol-d4) δ 8.76 (d, J = 2.2 Hz, 1H), 8.68 (d, J = 2.1 Hz, 1H), 8.56 (s, 1H), 8.46 (s, 1H), 8.09 (d, J = 5.1 Hz, 1H), 7.21 (d, J = 5.0 Hz, 1H), 4.42 (ddd, J = 49.0, 9.3, 2.2 Hz, 1H), 4.03 (dd, J = 11.4, 4.9 Hz, 1H), 3.93 (ddd, J = 36.4, 14.6, 2.2 Hz, 1H), 3.55-3.38 (m, 1H), 3.24 (dd, J = 11.4, 9.2 Hz, 1H), 2.76-2.68 (m, 1H), 1.47-1.34 (m, 1H), 1.29 (d, J = 1.7 Hz, 6H), 1.14-0.99 (m, 2H). |
| 303 | 1H NMR (400 MHz, Methanol-d4) δ 8.76 (d, J = 2.2 Hz, 1H), 8.68 (d, J = 2.1 Hz, 1H), 8.56 (s, 1H), 8.46 (s, 1H), 8.09 (d, J = 5.0 Hz, 1H), 7.21 (d, J = 5.1 Hz, 1H), 4.43 (ddd, J = 49.1, 9.3, 2.2 Hz, 1H), 4.03 (dd, J = 11.4, 4.9 Hz, 1H), 3.93 (ddd, J = 36.4, 14.6, 2.1 Hz, 1H), 3.54-3.41 (m, 1H), 3.24 (dd, J = 11.4, 9.2 Hz, 1H), 2.73 (dt, J = 7.3, 3.7 Hz, 1H), 1.45-1.34 (m, 1H), 1.29 (d, J = 1.7 Hz, 6H), 1.14-0.99 (m, 2H). |
| 304 | 1H NMR (400 MHz, Methanol-d4) δ 8.80 (s, 1H), 8.77 (d, J = 2.1 Hz, 1H), 8.54 (s, 1H), 8.41 (s, 1H), 7.92 (d, J = 5.0 Hz, 1H), 7.23 (d, J = 5.1 Hz, 1H), 4.41 (ddd, J = 49.1, 9.4, 2.1 Hz, 1H), 3.92 (ddd, J = 36.6, 14.6, 2.2 Hz, 1H), 3.56-3.40 (m, 1H), 2.30-2.16 (m, 6H), 2.14-2.03 (m, 6H), 1.45 (s, 9H), 1.29 (d, J = 1.6 Hz, 6H). |
| 305 | 1H NMR (400 MHz, Methanol-d4) δ 8.76 (d, J = 2.2 Hz, 1H), 8.66 (d, J = 2.1 Hz, 1H), 8.57 (s, 1H), 8.01 (d, J = 5.1 Hz, 1H), 7.87 (s, 1H), 7.22 (d, J = 5.0 Hz, 1H), |

TABLE 2-continued

| compound | 1H-NMR |
|---|---|
| | 4.42 (ddd, J = 49.0, 9.3, 2.1 Hz, 1H), 4.03-3.77 (m, 2H), 3.58-3.38 (m, 2H), 2.28-2.14 (m, 2H), 2.13-1.98 (m, 2H), 1.65-1.39 (m, 13H), 1.29 (d, J = 1.6 Hz, 6H). |
| 306 | 1H NMR (400 MHz, Methanol-d4) δ 8.76 (d, J = 2.2 Hz, 1H), 8.67 (d, J = 2.2 Hz, 1H), 8.58 (s, 1H), 7.98 (d, J = 5.1 Hz, 1H), 7.86 (s, 1H), 7.22 (d, J = 5.1 Hz, 1H), 4.52-4.28 (m, 3H), 3.94 (ddd, J = 36.5, 14.5, 2.1 Hz, 1H), 3.55-3.41 (m, 1H), 2.51-2.40 (m, 1H), 2.29-2.18 (m, 1H), 2.17-2.10 (m, 2H), 1.96 (s, 3H), 1.86-1.61 (m, 2H), 1.29 (d, J = 1.7 Hz, 6H). |
| 307 | 1H NMR (400 MHz, Methanol-d4) δ 8.76 (d, J = 2.1 Hz, 1H), 8.69 (d, J = 2.2 Hz, 1H), 8.59 (s, 1H), 8.02 (d, J = 5.1 Hz, 1H), 7.87 (s, 1H), 7.22 (d, J = 5.0 Hz, 1H), 4.43 (ddd, J = 49.0, 9.3, 2.0 Hz, 1H), 4.34-4.20 (m, 2H), 3.93 (ddd, J = 36.7, 14.6, 2.2 Hz, 1H), 3.60-3.41 (m, 1H), 2.66 (dt, J = 14.0, 7.2 Hz, 1H), 2.40-2.25 (m, 1H), 2.17-2.05 (m, 1H), 1.96 (s, 3H), 1.93-1.83 (m, 1H), 1.85-1.71 (m, 1H), 1.67 (dt, J = 13.3, 6.6 Hz, 1H), 1.29 (d, J = 1.6 Hz, 6H). |
| 308 | 1H NMR (400 MHz, Methanol-d4) δ 8.77 (d, J = 2.2 Hz, 1H), 8.67 (d, J = 2.2 Hz, 1H), 8.63 (s, 1H), 8.02 (d, J = 5.1 Hz, 1H), 7.88 (s, 1H), 7.23 (d, J = 5.1 Hz, 1H), 4.57-4.33 (m, 2H), 4.00-3.82 (m, 2H), 3.58-3.43 (m, 1H), 2.57-2.47 (m, 1H), 2.44-2.32 (m, 1H), 2.34-2.22 (m, 2H), 1.95-1.77 (m, 2H), 1.29 (d, J = 1.6 Hz, 6H). |
| 309 | 1H NMR (400 MHz, Methanol-d4) δ 8.77 (d, J = 2.2 Hz, 1H), 8.68 (d, J = 2.2 Hz, 1H), 8.64 (s, 1H), 8.03 (d, J = 5.0 Hz, 1H), 7.88 (s, 1H), 7.23 (d, J = 5.1 Hz, 1H), 4.51-4.31 (m, 2H), 3.92 (ddd, J = 36.5, 14.6, 2.1 Hz, 1H), 3.77 (p, J = 7.7 Hz, 1H), 3.59-3.43 (m, 1H), 2.88 (dt, J = 14.3, 7.5 Hz, 1H), 2.44-2.20 (m, 2H), 2.01-1.85 (m, 2H), 1.71 (dt, J = 13.3, 8.1 Hz, 1H), 1.29 (d, J = 1.6 Hz, 6H). |
| 310 | 1H NMR (400 MHz, Methanol-d4) δ 8.77 (d, J = 2.2 Hz, 1H), 8.68 (d, J = 2.2 Hz, 1H), 8.64 (s, 1H), 8.03 (d, J = 5.1 Hz, 1H), 7.88 (s, 1H), 7.23 (d, J = 5.1 Hz, 1H), 4.52-4.32 (m, 2H), 3.92 (ddd, J = 36.5, 14.6, 2.1 Hz, 1H), 3.77 (p, J = 7.6 Hz, 1H), 3.60-3.44 (m, 1H), 2.88 (dt, J = 14.4, 7.6 Hz, 1H), 2.45-2.20 (m, 2H), 2.01-1.85 (m, 2H), 1.70 (dt, J = 13.3, 8.2 Hz, 1H), 1.29 (d, J = 1.6 Hz, 6H). |
| 311 | 1H NMR (400 MHz, Methanol-d4) δ 8.77 (s, 2H), 8.54 (s, 1H), 8.38 (s, 1H), 7.93 (d, J = 5.0 Hz, 1H), 7.23 (d, J = 5.0 Hz, 1H), 4.52-4.29 (m, 1H), 4.01-3.81 (m, 1H), 3.60 (s, 3H), 3.54-3.40 (m, 1H), 2.30-2.17 (m, 6H), 2.16-2.05 (m, 6H), 1.29 (d, J = 1.6 Hz, 6H). |
| 312 | 1H NMR (400 MHz, Methanol-d4) δ 8.76 (d, J = 2.2 Hz, 1H), 8.69 (d, J = 2.2 Hz, 1H), 8.59 (s, 1H), 8.02 (d, J = 5.1 Hz, 1H), 7.86 (s, 1H), 7.22 (d, J = 5.1 Hz, 1H), 4.54-4.19 (m, 3H), 4.04-3.82 (m, 1H), 3.58-3.42 (m, 1H), 2.66 (dt, J = 14.0, 7.2 Hz, 1H), 2.39-2.27 (m, 1H), 2.17-2.05 (m, 1H), 1.96 (s, 3H), 1.93-1.73 (m, 2H), 1.66 (dt, J = 13.4, 6.6 Hz, 1H), 1.29 (d, J = 1.6 Hz, 6H). |
| 313 | 1H NMR (400 MHz, Methanol-d4) δ 8.76 (d, J = 2.2 Hz, 1H), 8.66 (d, J = 2.2 Hz, 1H), 8.57 (s, 1H), 8.02 (d, J = 5.0 Hz, 1H), 7.88 (s, 1H), 7.22 (d, J = 5.0 Hz, 1H), 4.56-4.28 (m, 1H), 4.03-3.79 (m, 3H), 3.57-3.39 (m, 1H), 2.33-2.20 (m, 2H), 2.15-2.04 (m, 2H), 1.76-1.54 (m, 4H), 1.29 (d, J = 1.6 Hz, 6H). |
| 314 | 1H NMR (400 MHz, Methanol-d4) δ 8.76 (d, J = 2.2 Hz, 1H), 8.66 (d, J = 2.2 Hz, 1H), 8.56 (s, 1H), 8.01 (d, J = 5.1 Hz, 1H), 7.87 (s, 1H), 7.22 (d, J = 5.0 Hz, 1H), 4.53-4.24 (m, 1H), 4.02-3.78 (m, 2H), 3.64 (s, 3H), 3.55-3.40 (m, 2H), 2.30-2.14 (m, 2H), 2.13-2.00 (m, 2H), 1.67-1.42 (m, 4H), 1.29 (d, J = 1.6 Hz, 6H). |
| 315 | 1H NMR (400 MHz, Methanol-d4) δ 8.76 (d, J = 2.2 Hz, 1H), 8.66 (d, J = 2.2 Hz, 1H), 8.57 (s, 1H), 8.02 (d, J = 5.1 Hz, 1H), 7.87 (s, 1H), 7.22 (d, J = 5.1 Hz, 1H), 4.42 (dd, J = 49.0, 7.6 Hz, 1H), 4.02-3.79 (m, 2H), 3.58-3.41 (m, 2H), 2.99 (s, 3H), 2.30-2.09 (m, 4H), 1.68-1.48 (m, 4H), 1.29 (d, J = 1.6 Hz, 6H). |
| 316 | 1H NMR (400 MHz, Methanol-d4) δ 8.76 (d, J = 2.2 Hz, 1H), 8.64 (d, J = 2.2 Hz, 1H), 8.60 (s, 1H), 8.03 (d, J = 5.0 Hz, 1H), 7.87 (s, 1H), 7.22 (d, J = 5.1 Hz, 1H), 4.42 (ddd, J = 49.0, 9.3, 2.1 Hz, 1H), 4.02-3.81 (m, 2H), 3.50 (ddd, J = 16.1, 14.5, 9.4 Hz, 1H), 3.23 (tt, J = 11.4, 3.6 Hz, 1H), 2.34-2.25 (m, 2H), 2.24-2.14 (m, 2H), 1.79-1.54 (m, 4H), 1.29 (d, J = 1.7 Hz, 6H). |
| 317 | 1H NMR (400 MHz, Methanol-d4) δ 8.77 (d, J = 2.2 Hz, 1H), 8.74 (dd, J = 2.2, 0.5 Hz, 1H), 8.54 (s, 1H), 8.35 (s, 1H), 7.97-7.87 (m, 1H), 7.23 (d, J = 5.1 Hz, 1H), 4.41 (ddd, J = 49.0, 9.4, 2.1 Hz, 1H), 3.92 (ddd, J = 36.6, 14.5, 2.2 Hz, 1H), 3.47 (ddd, J = 16.0, 14.8, 9.4 Hz, 1H), 2.26-2.15 (m, 12H), 1.90 (s, 3H), 1.29 (d, J = 1.7 Hz, 6H). |
| 318 | 1H NMR (400 MHz, Methanol-d4) δ 8.77 (d, J = 2.1 Hz, 1H), 8.65 (d, J = 2.2 Hz, 1H), 8.60 (s, 1H), 8.26 (s, 1H), 7.96 (d, J = 5.0 Hz, 1H), 7.23 (d, J = 5.1 Hz, 1H), 4.41 (ddd, J = 49.0, 9.5, 2.1 Hz, 1H), 4.00-3.79 (m, 1H), 3.57-3.41 (m, 1H), 2.40-2.26 (m, 6H), 2.14-2.00 (m, 6H), 1.29 (d, J = 1.6 Hz, 6H). |
| 319 | 1H NMR (400 MHz, Methanol-d4) δ 8.76 (d, J = 2.2 Hz, 1H), 8.67 (d, J = 2.2 Hz, 1H), 8.63 (s, 1H), 8.01 (d, J = 5.0 Hz, 1H), 7.87 (s, 1H), 7.22 (d, J = 5.0 Hz, 1H), 4.54-4.32 (m, 1H), 4.23-4.14 (m, 1H), 4.03-3.83 (m, 2H), 3.60-3.43 (m, 1H), 2.12-1.86 (m, 6H), 1.82-1.62 (m, 2H), 1.30 (d, J = 1.7 Hz, 6H). |
| 320 | 1H NMR (400 MHz, Methanol-d4) δ 8.75 (d, J = 2.2 Hz, 1H), 8.67 (d, J = 2.1 Hz, 1H), 8.62 (s, 1H), 8.01 (d, J = 5.0 Hz, 1H), 7.87 (s, 1H), 7.21 (d, J = 5.0 Hz, 1H), 4.43 (ddd, J = 49.0, 9.4, 2.1 Hz, 1H), 4.17-4.08 (m, 1H), 4.02-3.81 (m, 2H), 3.60-3.45 (m, 1H), 1.96 (s, 9H), 1.71-1.54 (m, 2H), 1.30 (d, J = 1.6 Hz, 6H). |
| 321 | 1H NMR (400 MHz, Methanol-d4) δ 8.78-8.73 (m, 2H), 8.67 (d, J = 2.2 Hz, 1H), 8.55 (d, J = 0.7 Hz, 1H), 8.46 (s, 1H), 8.08 (d, J = 5.1 Hz, 1H), 7.20 (d, J = 5.1 Hz, 1H), 4.52-4.30 (m, 1H), 4.02 (dd, J = 11.4, 4.9 Hz, 1H), 3.92 (ddd, J = 36.4, 14.6 Hz, 1H), 3.53-3.40 (m, 1H), 3.23 (dd, J = 11.4, 9.2 Hz, 1H), 2.72 (dt, J = 7.3, 3.7 Hz, 1H), 1.43-1.33 (m, 1H), 1.28 (d, J = 1.6 Hz, 6H), 1.14-0.98 (m, 2H). |
| 322 | 1H NMR (400 MHz, Methanol-d4) δ 8.76 (d, J = 2.2 Hz, 1H), 8.67 (d, J = 2.2 Hz, 1H), 8.59 (s, 1H), 8.00 (d, J = 5.1 Hz, 1H), 7.87 (s, 1H), 7.22 (d, J = 5.1 Hz, 1H), 4.53 (dtd, J = 49.3, 9.3, 5.0 Hz, 1H), 4.30 (qd, J = 11.1, 4.8 Hz, 1H), 4.14 (dt, J = |

TABLE 2-continued

| compound | 1H-NMR |
|---|---|
| | 15.0, 5.5 Hz, 2H), 3.93 (d, J = 11.9 Hz, 1H), 3.53 (td, J = 11.6, 2.4 Hz, 1H), 3.41 (ddd, J = 11.1, 9.4, 4.1 Hz, 1H), 2.19-2.05 (m, 1H), 1.75 (qd, J = 11.5, 4.6 Hz, 1H), 1.41 (dd, J = 6.4, 1.7 Hz, 6H). |
| 323 | 1H NMR (400 MHz, Methanol-d4) δ 8.76 (d, J = 2.2 Hz, 1H), 8.67 (d, J = 2.2 Hz, 1H), 8.59 (s, 1H), 8.00 (d, J = 5.1 Hz, 1H), 7.86 (s, 1H), 7.22 (d, J = 5.1 Hz, 1H), 4.53 (dtd, J = 49.3, 9.3, 4.9 Hz, 1H), 4.30 (qd, J = 11.1, 4.9 Hz, 1H), 4.22-4.07 (m, 2H), 3.98-3.88 (m, 1H), 3.53 (td, J = 11.6, 2.4 Hz, 1H), 3.41 (ddd, J = 11.1, 9.4, 4.1 Hz, 1H), 2.18-2.05 (m, 1H), 1.75 (qd, J = 11.6, 4.6 Hz, 1H), 1.41 (dd, J = 6.4, 1.7 Hz, 6H). |
| 324 | 1H NMR (400 MHz, Methanol-d4) δ 8.76 (d, J = 2.1 Hz, 1H), 8.69 (d, J = 2.2 Hz, 1H), 8.61 (s, 1H), 8.05 (d, J = 5.1 Hz, 1H), 7.91 (s, 1H), 7.23 (d, J = 5.1 Hz, 1H), 4.67-4.28 (m, 2H), 4.26-4.03 (m, 2H), 4.02-3.82 (m, 1H), 3.62-3.37 (m, 1H), 3.26-3.04 (m, 1H), 2.30-2.05 (m, 2H), 1.82-1.39 (m, 3H), 1.40-1.32 (m, 4H), 1.29 (d, J = 1.6 Hz, 6H). |
| 325 | 1H NMR (400 MHz, Methanol-d4) δ 8.76 (d, J = 2.2 Hz, 1H), 8.69 (d, J = 2.2 Hz, 1H), 8.61 (s, 1H), 8.05 (d, J = 5.1 Hz, 1H), 7.91 (s, 1H), 7.23 (d, J = 5.1 Hz, 1H), 4.98 (d, J = 5.9 Hz, 2H), 4.52-4.33 (m, 4H), 4.23-4.11 (m, 1H), 3.93 (dd, J = 36.2, 14.4 Hz, 1H), 3.58-3.42 (m, 1H), 3.30-3.18 (m, 2H), 3.19-3.07 (m, 1H), 2.23-2.12 (m, 2H), 1.78-1.61 (m, 5H), 1.29 (d, J = 1.7 Hz, 6H). |
| 326 | 1H NMR (400 MHz, Methanol-d4) δ 8.99 (t, J = 5.4 Hz, 1H), 8.75 (d, J = 2.2 Hz, 1H), 8.64 (d, J = 2.1 Hz, 1H), 8.57 (s, 1H), 8.02 (d, J = 5.1 Hz, 1H), 7.86 (s, 1H), 7.22 (d, J = 5.1 Hz, 1H), 4.42 (ddd, J = 49.0, 9.3, 2.0 Hz, 1H), 4.04-3.80 (m, 2H), 3.79-3.67 (m, 1H), 3.57-3.41 (m, 1H), 2.22 (d, J = 11.2 Hz, 2H), 2.05 (d, J = 11.7 Hz, 2H), 1.95 (s, 3H), 1.65-1.45 (m, 4H), 1.29 (d, J = 1.6 Hz, 6H). |
| 327 | 1H NMR (400 MHz, Methanol-d4) δ 8.76 (d, J = 2.1 Hz, 1H), 8.68 (d, J = 2.2 Hz, 1H), 8.62 (d, J = 0.8 Hz, 1H), 8.04 (d, J = 5.1 Hz, 1H), 7.90 (s, 1H), 7.22 (d, J = 5.1 Hz, 1H), 4.55-4.32 (m, 2H), 3.94 (dd, J = 36.3, 14.5 Hz, 1H), 3.56-3.42 (m, 3H), 2.90 (dd, J = 17.4, 5.5 Hz, 1H), 2.51 (dd, J = 17.4, 8.1 Hz, 1H), 2.34-2.19 (m, 1H), 2.12-1.96 (m, 1H), 1.29 (d, J = 1.7 Hz, 6H). |
| 328 | 1H NMR (400 MHz, Methanol-d4) δ 8.76 (d, J = 2.2 Hz, 1H), 8.68 (d, J = 2.2 Hz, 1H), 8.60 (s, 1H), 8.05 (d, J = 5.0 Hz, 1H), 7.91 (s, 1H), 7.22 (d, J = 5.0 Hz, 1H), 4.52-4.33 (m, 2H), 4.24-4.12 (m, 3H), 4.01-3.85 (m, 2H), 3.57-3.35 (m, 5H), 3.21-3.08 (m, 1H), 2.25-2.12 (m, 2H), 1.79-1.53 (m, 2H), 1.29 (d, J = 1.7 Hz, 6H). |
| 329 | 1H NMR (400 MHz, Methanol-d4) δ 8.76 (d, J = 2.2 Hz, 1H), 8.67 (d, J = 2.2 Hz, 1H), 8.60 (s, 1H), 8.03 (d, J = 5.1 Hz, 1H), 7.87 (s, 1H), 7.22 (d, J = 5.1 Hz, 1H), 4.43 (ddd, J = 49.1, 9.4, 2.2 Hz, 1H), 4.04-3.83 (m, 2H), 3.50 (ddd, J = 16.0, 14.5, 9.4 Hz, 1H), 3.21 (q, J = 9.8 Hz, 2H), 3.10-2.99 (m, 2H), 2.83-2.68 (m, 2H), 2.15 (d, J = 13.0 Hz, 2H), 1.88-1.72 (m, 2H), 1.30 (d, J = 1.7 Hz, 6H). |
| 330 | 1H NMR (400 MHz, Methanol-d4) δ 8.75 (d, J = 2.2 Hz, 1H), 8.66 (dd, J = 2.2, 0.4 Hz, 1H), 8.54 (s, 1H), 8.03-7.97 (m, 1H), 7.83 (s, 1H), 7.21 (d, J = 5.1 Hz, 1H), 4.15 (p, J = 6.4 Hz, 1H), 3.76 (dd, J = 13.7, 2.8 Hz, 1H), 3.57 (dd, J = 9.4, 2.8 Hz, 1H), 1.40 (d, J = 6.4 Hz, 6H), 1.25 (d, J = 4.4 Hz, 6H). (1H obscured by solvent) |
| 331 | 1H NMR (400 MHz, Methanol-d4) δ 8.76 (d, J = 2.1 Hz, 1H), 8.70 (d, J = 2.2 Hz, 1H), 8.59 (s, 1H), 8.30 (s, 1H), 7.93 (d, J = 5.1 Hz, 1H), 7.22 (d, J = 5.1 Hz, 1H), 4.72 (t, J = 11.9 Hz, 2H), 4.41 (t, J = 12.1 Hz, 2H), 4.07 (s, 2H), 2.31-2.16 (m, 6H), 1.90 (dd, J = 10.3, 5.7 Hz, 6H). |
| 332 | 1H NMR (400 MHz, Methanol-d4) δ 8.75 (d, J = 2.1 Hz, 1H), 8.67 (d, J = 2.1 Hz, 1H), 8.59 (s, 1H), 8.01 (d, J = 5.0 Hz, 1H), 7.84 (s, 1H), 7.21 (d, J = 5.0 Hz, 1H), 4.58 (s, 2H), 4.16 (p, J = 6.4 Hz, 1H), 1.40 (d, J = 6.4 Hz, 6H), 1.38 (s, 6H). |
| 333 | 1H NMR (400 MHz, Methanol-d4) δ 8.76 (d, J = 2.1 Hz, 1H), 8.70 (d, J = 2.2 Hz, 1H), 8.59 (s, 1H), 8.29 (s, 1H), 7.93 (d, J = 5.1 Hz, 1H), 7.22 (d, J = 5.1 Hz, 1H), 4.24 (s, 2H), 3.11 (s, 3H), 3.00 (s, 3H), 2.31-2.15 (m, 6H), 1.96-1.76 (m, 6H). |
| 334 | 1H NMR (400 MHz, Methanol-d4) δ 8.33 (s, 1H), 6.85 (s, 1H), 3.91 (s, 2H), 2.74 (s, 3H), 2.15-1.95 (m, 8H), 1.89-1.65 (m, 8H).; 1H NMR (400 MHz, Methanol-d4) δ 8.77 (d, J = 2.2 Hz, 1H), 8.71 (d, J = 2.2 Hz, 1H), 8.60 (s, 1H), 8.31 (s, 1H), 7.93 (d, J = 5.0 Hz, 1H), 7.22 (d, J = 5.1 Hz, 1H), 4.00 (s, 2H), 2.78 (s, 3H), 2.30-2.17 (m, 6H), 1.90 (dd, J = 10.1, 5.9 Hz, 6H). |
| 335 | 1H NMR (400 MHz, Methanol-d4) δ 9.70 (s, 1H), 8.85 (s, 1H), 8.71 (s, 1H), 8.32 (s, 1H), 7.65 (d, J = 5.0 Hz, 1H), 7.41-7.22 (m, 5H), 7.19 (d, J = 5.0 Hz, 1H), 4.48 (dd, J = 48.6, 9.1 Hz, 1H), 4.28 (s, 2H), 3.99 (dd, J = 36.6, 15.4 Hz, 1H), 3.68-3.48 (m, 1H), 1.31 (d, J = 1.6 Hz, 6H). |
| 336 | 1H NMR (400 MHz, Methanol-d4) δ 8.94 (s, 1H), 8.69 (d, J = 2.2 Hz, 1H), 8.56 (d, J = 2.1 Hz, 1H), 7.90 (d, J = 5.1 Hz, 1H), 7.41-7.37 (m, 3H), 7.36-7.28 (m, 1H), 7.17 (d, J = 5.0 Hz, 1H), 4.58-4.34 (m, 1H), 4.27 (s, 2H), 3.98 (ddd, J = 36.1, 14.5, 2.2 Hz, 1H), 3.63-3.50 (m, 1H), 1.30 (d, J = 1.7 Hz, 6H). |
| 337 | 1H NMR (400 MHz, Methanol-d4) δ 9.68 (s, 1H), 8.81 (s, 1H), 8.63 (s, 1H), 8.11 (s, 1H), 7.62 (s, 1H), 7.32 (d, J = 3.4 Hz, 4H), 7.26 (d, J = 7.6 Hz, 1H), 7.13 (d, J = 5.0 Hz, 1H), 6.89 (s, 1H), 4.47 (ddd, J = 48.9, 9.2, 2.1 Hz, 1H), 4.11 (s, 2H), 3.98 (ddd, J = 36.1, 14.5, 2.3 Hz, 1H), 3.61-3.49 (m, 1H), 1.31 (d, J = 1.7 Hz, 6H). |
| 338 | 1H NMR (400 MHz, Methanol-d4) δ 9.78 (s, 1H), 8.84 (s, 1H), 8.67 (d, J = 2.2 Hz, 1H), 8.56 (d, J = 2.2 Hz, 1H), 7.94 (d, J = 5.0 Hz, 1H), 7.85 (s, 1H), 7.17 (d, J = 5.0 Hz, 1H), 4.57-4.32 (m, 1H), 3.97 (dd, J = 35.4, 13.6 Hz, 1H), 3.61-3.39 (m, 1H), 2.94 (s, 3H), 1.31 (d, J = 1.6 Hz, 6H). |
| 339 | 1H NMR (400 MHz, Methanol-d4) δ 8.76 (d, J = 2.2 Hz, 1H), 8.70 (d, J = 2.1 Hz, 1H), 8.61 (s, 1H), 8.30 (s, 1H), 7.93 (d, J = 5.1 Hz, 1H), 7.22 (d, J = 5.1 Hz, 1H), 4.59 (q, J = 7.4 Hz, 1H), 3.76 (s, 3H), 2.32-2.14 (m, 6H), 1.99-1.83 (m, 6H), 1.51 (d, J = 7.4 Hz, 3H). |

TABLE 2-continued

| compound | 1H-NMR |
|---|---|
| 340 | 1H NMR (400 MHz, Methanol-d4) δ 8.76 (d, J = 2.2 Hz, 1H), 8.70 (d, J = 2.1 Hz, 1H), 8.61 (s, 1H), 8.30 (s, 1H), 7.93 (d, J = 5.1 Hz, 1H), 7.22 (d, J = 5.0 Hz, 1H), 4.59 (q, J = 7.3 Hz, 1H), 3.76 (s, 3H), 2.30-2.17 (m, 6H), 1.97-1.82 (m, 6H), 1.51 (d, J = 7.4 Hz, 3H). |
| 341 | 1H NMR (400 MHz, Methanol-d4) δ 8.76 (d, J = 2.1 Hz, 1H), 8.70 (d, J = 2.2 Hz, 1H), 8.56 (s, 1H), 8.30 (s, 1H), 7.93 (d, J = 5.1 Hz, 1H), 7.22 (d, J = 5.0 Hz, 1H), 4.12 (s, 2H), 3.77 (s, 3H), 2.31-2.19 (m, 6H), 1.96-1.82 (m, 6H). |
| 342 | 1H NMR (400 MHz, Methanol-d4) δ 8.75 (d, J = 2.2 Hz, 1H), 8.69 (d, J = 2.2 Hz, 1H), 8.50 (s, 1H), 8.26 (s, 1H), 7.91 (d, J = 5.1 Hz, 1H), 7.21 (d, J = 5.1 Hz, 1H), 3.54-3.47 (m, 2H), 3.02 (s, 3H), 2.30-2.18 (m, 6H), 2.02-1.93 (m, 2H), 1.90 (t, J = 8.1 Hz, 6H), 1.40 (s, 6H). |
| 343 | 1H NMR (400 MHz, Methanol-d4) δ 8.75 (d, J = 2.2 Hz, 1H), 8.69 (d, J = 2.1 Hz, 1H), 8.47 (s, 1H), 8.25 (s, 1H), 7.91 (d, J = 5.1 Hz, 1H), 7.21 (d, J = 5.0 Hz, 1H), 3.56 (s, 3H), 3.42-3.35 (m, 2H), 2.25 (t, J = 7.8 Hz, 6H), 2.05-1.96 (m, 2H), 1.90 (dd, J = 10.3, 5.7 Hz, 6H), 1.31 (s, 6H). |
| 344 | 1H NMR (400 MHz, Methanol-d4) δ 8.75 (d, J = 2.2 Hz, 1H), 8.69 (d, J = 2.1 Hz, 1H), 8.47 (s, 1H), 8.25 (s, 1H), 7.92 (d, J = 5.1 Hz, 1H), 7.21 (d, J = 5.1 Hz, 1H), 3.39-3.33 (m, 3H), 2.31-2.16 (m, 6H), 2.16-2.04 (m, 2H), 1.91 (d, J = 7.5 Hz, 8H), 1.34 (s, 6H). |
| 345 | 1H NMR (400 MHz, Methanol-d4) δ 8.75 (d, J = 2.2 Hz, 1H), 8.69 (d, J = 2.1 Hz, 1H), 8.53 (s, 1H), 8.30 (s, 1H), 7.93 (d, J = 5.0 Hz, 1H), 7.21 (d, J = 5.1 Hz, 1H), 3.52-3.43 (m, 2H), 2.32-2.18 (m, 6H), 2.02-1.83 (m, 8H), 1.41 (s, 6H). |
| 346 | 1H NMR (400 MHz, Methanol-d4) δ 8.75 (d, J = 2.2 Hz, 1H), 8.69 (d, J = 2.2 Hz, 1H), 8.48 (s, 1H), 8.25 (s, 1H), 7.92 (d, J = 5.1 Hz, 1H), 7.21 (d, J = 5.1 Hz, 1H), 3.99-3.82 (m, 2H), 3.74 (td, J = 8.0, 6.3 Hz, 1H), 3.46 (t, J = 7.1 Hz, 2H), 2.24 (dd, J = 10.4, 5.6 Hz, 6H), 2.14-2.01 (m, 1H), 1.92 (ddt, J = 11.4, 7.5, 5.7 Hz, 8H), 1.87-1.75 (m, 2H), 1.55 (dq, J = 12.0, 8.0 Hz, 1H). |
| 347 | 1H NMR (400 MHz, Methanol-d4) δ 8.75 (d, J = 2.2 Hz, 1H), 8.69 (d, J = 2.2 Hz, 1H), 8.48 (s, 1H), 8.25 (s, 1H), 7.92 (d, J = 5.1 Hz, 1H), 7.21 (d, J = 5.1 Hz, 1H), 3.43-3.33 (m, 2H), 2.29-2.19 (m, 6H), 2.00 (dd, J = 9.6, 6.5 Hz, 2H), 1.95-1.85 (m, 6H), 1.42 (s, 9H), 1.29 (s, 6H). |
| 348 | 1H NMR (400 MHz, Methanol-d4) δ 8.76 (d, J = 2.1 Hz, 1H), 8.70 (d, J = 2.2 Hz, 1H), 8.55 (s, 1H), 8.33 (s, 1H), 7.93 (d, J = 5.1 Hz, 1H), 7.22 (d, J = 5.1 Hz, 1H), 4.34 (s, 2H), 2.34-2.19 (m, 6H), 2.02-1.81 (m, 6H). |
| 349 | 1H NMR (400 MHz, Methanol-d4) δ 8.73 (s, 1H), 8.71 (d, J = 2.2 Hz, 1H), 8.61 (d, J = 2.2 Hz, 1H), 8.35 (s, 1H), 7.85 (d, J = 8.5 Hz, 2H), 7.82 (d, J = 5.0 Hz, 1H), 7.58 (d, J = 8.5 Hz, 2H), 7.17 (d, J = 5.1 Hz, 1H), 4.57-4.36 (m, 3H), 4.25 (t, J = 7.9 Hz, 2H), 4.11-3.91 (m, 1H), 3.61-3.49 (m, 1H), 2.41 (p, J = 7.8 Hz, 2H), 1.30 (d, J = 1.6 Hz, 6H). |
| 350 | 1H NMR (400 MHz, Methanol-d4) δ 8.73 (s, 1H), 8.70 (d, J = 2.2 Hz, 1H), 8.60 (d, J = 2.2 Hz, 1H), 8.38 (s, 1H), 8.04-7.96 (m, 2H), 7.82 (d, J = 5.1 Hz, 1H), 7.62-7.53 (m, 2H), 7.16 (d, J = 5.1 Hz, 1H), 4.47 (ddd, J = 49.0, 9.3, 2.1 Hz, 1H), 3.99 (ddd, J = 36.5, 14.6, 2.1 Hz, 1H), 3.53 (ddd, J = 16.2, 14.5, 9.3 Hz, 1H), 2.97 (s, 3H), 1.30 (d, J = 1.6 Hz, 6H). |
| 351 | 1H NMR (400 MHz, Methanol-d4) δ 8.75 (d, J = 2.2 Hz, 1H), 8.70 (d, J = 2.2 Hz, 1H), 8.57 (s, 1H), 7.99 (d, J = 5.1 Hz, 1H), 7.77 (s, 1H), 7.21 (d, J = 5.1 Hz, 1H), 4.43 (ddd, J = 49.1, 9.4, 2.1 Hz, 1H), 4.07 (p, J = 7.8 Hz, 1H), 4.02-3.83 (m, 1H), 3.58-3.40 (m, 1H), 3.19-3.05 (m, 2H), 2.69 (s, 3H), 2.19 (q, J = 9.3 Hz, 2H), 1.29 (d, J = 1.6 Hz, 6H). (1H obscured by solvent) |
| 352 | 1H NMR (400 MHz, Methanol-d4) δ 8.76 (d, J = 2.1 Hz, 1H), 8.70 (d, J = 2.2 Hz, 1H), 8.53 (s, 1H), 8.30 (s, 1H), 7.93 (d, J = 5.0 Hz, 1H), 7.22 (d, J = 5.1 Hz, 1H), 3.63 (t, J = 6.4 Hz, 2H), 2.80 (t, J = 6.4 Hz, 2H), 2.25 (dd, J = 10.4, 5.6 Hz, 6H), 1.95-1.83 (m, 6H). |
| 353 | 1H NMR (400 MHz, Methanol-d4) δ 8.76 (d, J = 2.2 Hz, 1H), 8.70 (d, J = 2.2 Hz, 1H), 8.54 (s, 1H), 8.29 (s, 1H), 7.93 (d, J = 5.0 Hz, 1H), 7.22 (d, J = 5.1 Hz, 1H), 4.71-4.44 (m, 1H), 3.90 (ddd, J = 35.6, 14.5, 2.2 Hz, 1H), 3.49 (td, J = 15.5, 9.3 Hz, 1H), 2.35-2.14 (m, 6H), 1.99-1.79 (m, 6H), 1.47 (t, J = 1.4 Hz, 3H), 1.42 (t, J = 1.7 Hz, 3H). |
| 354 | 1H NMR (400 MHz, Methanol-d4) δ 8.76 (d, J = 2.2 Hz, 1H), 8.70 (d, J = 2.1 Hz, 1H), 8.53 (s, 1H), 8.28 (s, 1H), 7.93 (d, J = 5.0 Hz, 1H), 7.22 (d, J = 5.1 Hz, 1H), 4.47 (ddd, J = 48.9, 9.5, 2.1 Hz, 1H), 3.89 (ddd, J = 36.9, 14.6, 2.1 Hz, 1H), 3.56-3.38 (m, 1H), 2.29-2.17 (m, 6H), 1.97-1.82 (m, 6H), 1.27 (dd, J = 3.3, 1.7 Hz, 6H). (OMe obscured by solvent) |
| 355 | 1H NMR (400 MHz, Methanol-d4) δ 8.75 (d, J = 2.2 Hz, 1H), 8.69 (d, J = 2.2 Hz, 1H), 8.47 (s, 1H), 8.26 (s, 1H), 7.92 (d, J = 5.1 Hz, 1H), 7.21 (d, J = 5.0 Hz, 1H), 3.53-3.43 (m, 2H), 2.30-2.17 (m, 6H), 1.90 (dd, J = 10.3, 5.7 Hz, 6H), 1.84-1.73 (m, 2H), 1.26 (s, 6H). |
| 356 | 1H NMR (400 MHz, Methanol-d4) δ 8.74 (t, J = 1.6 Hz, 2H), 8.56 (s, 1H), 7.89 (t, J = 2.5 Hz, 2H), 7.21 (d, J = 5.1 Hz, 1H), 5.04-4.91 (m, 1H), 4.54-4.29 (m, 1H), 4.07-3.78 (m, 1H), 3.58-3.40 (m, 1H), 2.96 (dd, J = 11.8, 8.1 Hz, 2H), 2.67 (s, 3H), 2.45 (t, J = 9.9 Hz, 2H), 1.66 (s, 3H), 1.29 (d, J = 1.6 Hz, 6H). |
| 357 | 1H NMR (400 MHz, Methanol-d4) δ 8.75 (d, J = 2.2 Hz, 1H), 8.69 (d, J = 2.2 Hz, 1H), 8.45 (d, J = 1.0 Hz, 1H), 8.22 (s, 1H), 7.92 (d, J = 5.0 Hz, 1H), 7.21 (d, J = 5.1 Hz, 1H), 2.24 (dd, J = 9.5, 6.4 Hz, 6H), 1.96-1.81 (m, 6H), 1.45 (s, 9H). |
| 358 | 1H NMR (400 MHz, Methanol-d4) δ 8.75 (d, J = 2.2 Hz, 1H), 8.69 (d, J = 2.2 Hz, 1H), 8.47 (s, 1H), 8.26 (s, 1H), 7.91 (d, J = 5.1 Hz, 1H), 7.21 (d, J = 5.0 Hz, 1H), 2.30-2.17 (m, 6H), 1.90 (dd, J = 10.2, 5.8 Hz, 6H). |

TABLE 2-continued

| compound | 1H-NMR |
|---|---|
| 359 | 1H NMR (400 MHz, Methanol-d4) δ 9.93 (s, 1H), 8.75 (s, 1H), 8.57 (d, J = 2.2 Hz, 1H), 8.25 (s, 1H), 7.87 (d, J = 8.6 Hz, 2H), 7.81 (d, J = 5.0 Hz, 1H), 7.45-7.36 (m, 2H), 7.30 (s, 1H), 7.20-7.12 (m, 1H), 7.12-7.06 (m, 3H), 6.96 (d, J = 8.6 Hz, 2H), 4.49 (ddd, J = 49.0, 9.3, 2.1 Hz, 1H), 4.07-3.86 (m, 1H), 3.54 (td, J = 15.4, 9.4 Hz, 1H), 1.32 (d, J = 1.6 Hz, 6H). |
| 360 | 1H NMR (400 MHz, Methanol-d4) δ 8.87 (d, J = 3.8 Hz, 2H), 8.67 (d, J = 2.2 Hz, 1H), 8.58 (d, J = 2.2 Hz, 1H), 7.95 (d, J = 5.0 Hz, 1H), 7.16 (d, J = 5.0 Hz, 1H), 6.21 (s, 1H), 4.47 (ddd, J = 49.0, 9.3, 2.2 Hz, 1H), 3.97 (ddd, J = 35.9, 14.6, 2.1 Hz, 1H), 3.61-3.48 (m, 1H), 1.40 (s, 9H), 1.30 (d, J = 1.6 Hz, 6H). |
| 361 | 1H NMR (400 MHz, Methanol-d4) δ 8.75 (d, J = 2.2 Hz, 1H), 8.69 (d, J = 2.1 Hz, 1H), 8.47 (s, 1H), 8.25 (s, 1H), 7.91 (d, J = 5.1 Hz, 1H), 7.21 (d, J = 5.1 Hz, 1H), 2.90 (s, 3H), 2.31-2.18 (m, 7H), 1.99-1.79 (m, 5H). |
| 362 | 1H NMR (400 MHz, Methanol-d4) δ 8.74 (d, J = 2.2 Hz, 1H), 8.65 (d, J = 2.2 Hz, 1H), 8.60 (s, 1H), 7.98 (d, J = 5.1 Hz, 1H), 7.83 (s, 1H), 7.20 (d, J = 5.0 Hz, 1H), 4.43 (ddd, J = 49.1, 9.4, 2.1 Hz, 1H), 4.15 (s, 1H), 3.96 (ddd, J = 36.4, 14.6, 2.1 Hz, 1H), 3.49 (ddd, J = 15.8, 14.4, 9.4 Hz, 1H), 2.72 (s, 3H), 2.37 (t, J = 6.8 Hz, 1H), 2.08-1.97 (m, 3H), 1.94-1.76 (m, 6H), 1.29 (d, J = 1.6 Hz, 6H). |
| 363 | 1H NMR (400 MHz, Methanol-d4) δ 10.12 (s, 1H), 8.84 (s, 1H), 8.66 (s, 1H), 8.33 (s, 1H), 7.98 (d, J = 7.3 Hz, 2H), 7.89 (d, J = 5.0 Hz, 1H), 7.49 (s, 1H), 7.42 (q, J = 10.1, 8.4 Hz, 3H), 7.18 (d, J = 5.0 Hz, 1H), 4.61-4.37 (m, 1H), 4.00 (dd, J = 35.4, 14.6 Hz, 1H), 3.55 (td, J = 15.4, 9.2 Hz, 1H), 1.32 (d, J = 1.6 Hz, 6H). |
| 364 | 1H NMR (400 MHz, Methanol-d4) δ 8.71 (s, 1H), 8.65 (d, J = 2.2 Hz, 1H), 8.39 (d, J = 2.2 Hz, 1H), 8.17 (s, 1H), 7.85-7.77 (m, 3H), 7.68-7.62 (m, 2H), 7.50-7.43 (m, 2H), 7.43-7.35 (m, 1H), 7.31-7.25 (m, 2H), 7.12 (d, J = 5.1 Hz, 1H), 7.01 (s, 1H), 4.42 (ddd, J = 49.1, 9.3, 2.1 Hz, 1H), 3.91 (ddd, J = 36.5, 14.5, 2.1 Hz, 1H), 3.48 (ddd, J = 16.0, 14.5, 9.3 Hz, 1H), 2.39 (s, 3H), 1.28 (t, J = 1.3 Hz, 6H). |
| 365 | |
| 366 | 1H NMR (400 MHz, Methanol-d4) δ 8.74 (d, J = 2.2 Hz, 1H), 8.64 (d, J = 2.2 Hz, 1H), 8.57 (s, 1H), 8.01 (d, J = 5.1 Hz, 1H), 7.91 (s, 1H), 7.21 (d, J = 5.1 Hz, 1H), 4.22 (dt, J = 9.3, 5.2 Hz, 1H), 4.09 (s, 1H), 3.92 (t, J = 11.8 Hz, 1H), 3.25 (d, J = 12.0 Hz, 1H), 2.88 (s, 6H), 2.20 (t, J = 14.1 Hz, 5H), 2.04 (d, J = 15.2 Hz, 2H), 1.92 (d, J = 9.2 Hz, 1H), 1.71 (q, J = 15.2, 12.0 Hz, 5H), 1.54 (q, J = 12.4, 11.5 Hz, 3H). |
| 367 | 1H NMR (400 MHz, Methanol-d4) δ 8.74 (d, J = 2.2 Hz, 1H), 8.66 (d, J = 2.2 Hz, 1H), 8.58 (s, 1H), 8.00 (d, J = 5.1 Hz, 1H), 7.93-7.87 (m, 1H), 7.20 (d, J = 5.1 Hz, 1H), 4.53-4.32 (m, 1H), 4.08 (q, J = 5.8 Hz, 1H), 3.93 (ddd, J = 36.4, 14.6, 2.1 Hz, 1H), 3.71 (d, J = 5.3 Hz, 2H), 3.49 (td, J = 15.2, 9.4 Hz, 1H), 2.56-2.25 (m, 3H), 2.00 (dt, J = 13.2, 4.5 Hz, 1H), 1.28 (d, J = 1.6 Hz, 6H). |
| 368 | 1H NMR (400 MHz, Methanol-d4) δ 8.74 (d, J = 2.2 Hz, 1H), 8.66 (d, J = 2.2 Hz, 1H), 8.58 (s, 1H), 8.00 (d, J = 5.1 Hz, 1H), 7.93-7.87 (m, 1H), 7.20 (d, J = 5.1 Hz, 1H), 4.53-4.32 (m, 1H), 4.08 (q, J = 5.8 Hz, 1H), 3.93 (ddd, J = 36.4, 14.6, 2.1 Hz, 1H), 3.71 (d, J = 5.3 Hz, 2H), 3.49 (td, J = 15.2, 9.4 Hz, 1H), 2.56-2.25 (m, 3H), 2.00 (dt, J = 13.2, 4.5 Hz, 1H), 1.28 (d, J = 1.6 Hz, 6H). |
| 369 | 1H NMR (400 MHz, Methanol-d4) δ 8.74 (d, J = 2.1 Hz, 1H), 8.65 (dd, J = 2.2, 0.4 Hz, 1H), 8.53 (s, 1H), 7.98 (dd, J = 5.1, 0.5 Hz, 1H), 7.83 (d, J = 0.5 Hz, 1H), 7.20 (d, J = 5.1 Hz, 1H), 4.21 (td, J = 7.4, 6.6, 5.6 Hz, 1H), 4.17-4.09 (m, 1H), 1.40 (d, J = 6.4 Hz, 6H), 1.28 (d, J = 6.6 Hz, 6H). |
| 370 | 1H NMR (400 MHz, Methanol-d4) δ 9.12 (s, 1H), 8.74-8.65 (m, 2H), 8.22 (d, J = 2.1 Hz, 1H), 7.85 (d, J = 2.4 Hz, 1H), 7.55 (dd, J = 5.1, 0.5 Hz, 1H), 7.44-7.34 (m, 3H), 7.34-7.27 (m, 2H), 7.17 (d, J = 5.0 Hz, 1H), 6.33 (d, J = 2.4 Hz, 1H), 5.41 (s, 2H), 4.46 (ddd, J = 49.0, 9.3, 2.2 Hz, 1H), 3.99 (ddd, J = 36.4, 14.5, 2.1 Hz, 1H), 3.60-3.44 (m, 1H), 1.30 (d, J = 1.6 Hz, 6H). |
| 371 | 1H NMR (400 MHz, Methanol-d4) δ 9.15 (s, 1H), 8.73 (d, J = 2.2 Hz, 1H), 8.71 (s, 1H), 8.65 (d, J = 2.2 Hz, 1H), 7.87 (dd, J = 5.0, 0.5 Hz, 1H), 7.67 (d, J = 2.3 Hz, 1H), 4.09-3.84 (m, 1H), 7.20 (d, J = 5.0 Hz, 1H), 6.30 (d, J = 2.4 Hz, 1H), 4.47 (ddd, J = 49.0, 9.3, 2.1 Hz, 1H), 3.96 (s, 3H), 3.61-3.44 (m, 1H), 1.30 (d, J = 1.7 Hz, 6H). |
| 372 | 1H NMR (400 MHz, Methanol-d4) δ 8.69 (d, J = 2.2 Hz, 1H), 8.66 (s, 1H), 8.15 (s, 1H), 8.06 (d, J = 0.8 Hz, 1H), 8.04 (d, J = 2.2 Hz, 1H), 7.78 (d, J = 5.0 Hz, 1H), 7.73 (d, J = 0.8 Hz, 1H), 7.44-7.31 (m, 5H), 7.16 (d, J = 5.1 Hz, 1H), 5.44 (s, 2H), 4.45 (ddd, J = 49.0, 9.3, 2.1 Hz, 1H), 3.97 (ddd, J = 36.5, 14.5, 2.1 Hz, 1H), 3.51 (ddd, J = 16.1, 14.5, 9.3 Hz, 1H), 1.29 (d, J = 1.6 Hz, 7H). |
| 373 | 1H NMR (400 MHz, Methanol-d4) δ 8.84 (d, J = 2.1 Hz, 1H), 8.76 (d, J = 2.2 Hz, 1H), 8.61 (s, 1H), 8.50 (s, 1H), 7.93 (d, J = 5.1 Hz, 1H), 7.23 (d, J = 5.1 Hz, 1H), 4.42 (ddd, J = 49.0, 9.4, 2.0 Hz, 1H), 3.93 (ddd, J = 36.5, 14.6, 2.1 Hz, 1H), 3.47 (td, J = 15.8, 9.4 Hz, 1H), 2.61 (s, 6H), 1.28 (d, J = 1.6 Hz, 6H). |
| 374 | 1H NMR (400 MHz, Methanol-d4) δ 10.03 (s, 1H), 8.84 (s, 1H), 8.70 (d, J = 2.2 Hz, 1H), 8.52 (d, J = 2.1 Hz, 1H), 7.87 (d, J = 5.0 Hz, 2H), 7.18 (d, J = 5.0 Hz, 1H), 4.49 (dd, J = 49.2, 8.8 Hz, 1H), 4.00 (dd, J = 36.3, 14.9 Hz, 1H), 3.55 (td, J = 15.4, 9.3 Hz, 1H), 1.34-1.29 (m, 6H). |
| 375 | 1H NMR (400 MHz, Methanol-d4) δ 9.76 (s, 1H), 8.84 (s, 1H), 8.67 (d, J = 13.5 Hz, 2H), 7.91 (d, J = 4.9 Hz, 1H), 7.59 (d, J = 3.8 Hz, 1H), 7.27 (d, J = 3.7 Hz, 1H), 7.17 (d, J = 5.0 Hz, 1H), 4.48 (ddd, J = 49.0, 9.2, 2.2 Hz, 1H), 3.99 (ddd, J = 35.8, 14.5, 2.2 Hz, 1H), 3.65-3.48 (m, 1H), 1.31 (d, J = 1.7 Hz, 6H). |
| 376 | 1H NMR (400 MHz, Methanol-d4) δ 8.86 (s, 1H), 8.75-8.66 (m, 1H), 7.96 (d, J = 4.9 Hz, 1H), 7.46 (d, J = 2.4 Hz, 1H), 7.22 (d, J = 5.0 Hz, 1H), 7.12 (dd, J = 8.8, 2.6 Hz, 1H), 4.41 (s, 0H), 3.98 (s, 0H), 3.88 (s, 3H), 1.32 (d, J = 1.6 Hz, 6H). Poor solubility resulted in poor signal to noise. Not all peaks indentified. |

TABLE 2-continued

| compound | 1H-NMR |
|---|---|
| 377 | 1H NMR (400 MHz, Methanol-d4) δ 8.85 (s, 1H), 8.66 (d, J = 10.4 Hz, 2H), 7.93 (d, J = 5.0 Hz, 1H), 7.85 (d, J = 7.9 Hz, 1H), 7.50 (t, J = 7.7 Hz, 1H), 7.35 (t, J = 7.7 Hz, 1H), 7.17 (d, J = 5.0 Hz, 1H), 4.49 (ddd, J = 49.0, 9.3, 2.2 Hz, 1H), 3.99 (dd, J = 36.0, 14.6 Hz, 1H), 3.58 (dd, J = 15.3, 9.4 Hz, 1H), 1.32 (d, J = 1.6 Hz, 6H). |
| 378 | 1H NMR (400 MHz, Methanol-d4) δ 8.78 (d, J = 2.2 Hz, 1H), 8.74 (d, J = 2.2 Hz, 1H), 8.63 (s, 1H), 8.35 (s, 1H), 7.95 (d, J = 5.1 Hz, 1H), 7.21 (d, J = 5.0 Hz, 1H), 4.41 (ddd, J = 49.1, 9.3, 2.1 Hz, 1H), 3.92 (ddd, J = 36.5, 14.6, 2.1 Hz, 1H), 3.47 (ddd, J = 16.2, 14.5, 9.4 Hz, 1H), 2.85 (s, 6H), 1.28 (d, J = 1.6 Hz, 6H). |
| 379 | 1H NMR (400 MHz, Methanol-d4) δ 8.75 (d, J = 2.2 Hz, 1H), 8.66 (d, J = 2.2 Hz, 1H), 8.51 (s, 1H), 8.02 (d, J = 5.1 Hz, 1H), 7.76 (s, 1H), 7.21 (d, J = 5.1 Hz, 1H), 4.42 (ddd, J = 49.0, 9.3, 2.1 Hz, 1H), 3.93 (ddd, J = 36.4, 14.5, 2.2 Hz, 1H), 3.48 (ddd, J = 16.2, 14.5, 9.4 Hz, 1H), 3.19 (s, 3H), 1.28 (d, J = 1.7 Hz, 6H). |
| 380 | 1H NMR (400 MHz, Methanol-d4) δ 8.74 (d, J = 2.2 Hz, 1H), 8.65 (d, J = 2.2 Hz, 1H), 8.53 (s, 1H), 7.98 (d, J = 5.1 Hz, 1H), 7.85 (s, 1H), 7.20 (d, J = 5.1 Hz, 1H), 4.14 (p, J = 6.5 Hz, 1H), 2.65 (s, 6H), 1.39 (d, J = 6.4 Hz, 6H). |
| 381 | 1H NMR (400 MHz, Methanol-d4) δ 8.75 (s, 1H), 8.69 (d, J = 2.2 Hz, 1H), 8.60 (d, J = 2.2 Hz, 1H), 8.53 (s, 1H), 8.06 (d, J = 8.5 Hz, 2H), 7.84 (d, J = 4.9 Hz, 1H), 7.58 (d, J = 8.5 Hz, 2H), 7.15 (d, J = 5.0 Hz, 1H), 4.47 (dd, J = 49.1, 7.4 Hz, 1H), 3.98 (dd, J = 36.2, 15.1 Hz, 1H), 3.76-3.35 (m, 1H), 1.30 (d, J = 1.6 Hz, 6H). |
| 382 | 1H NMR (400 MHz, Methanol-d4) δ 8.67 (s, 1H), 8.62 (d, J = 2.2 Hz, 1H), 8.44 (d, J = 2.2 Hz, 1H), 8.34 (s, 1H), 7.83-7.59 (m, 4H), 7.45-7.36 (m, 1H), 7.11 (d, J = 5.0 Hz, 1H), 4.48 (ddd, J = 49.0, 9.3, 2.2 Hz, 1H), 4.13-3.85 (m, 1H), 3.61-3.39 (m, 1H), 1.30 (d, J = 1.8 Hz, 6H). |
| 383 | 1H NMR (400 MHz, Methanol-d4) δ 8.71 (s, 1H), 8.66 (d, J = 2.2 Hz, 1H), 8.50 (d, J = 2.2 Hz, 1H), 8.32 (s, 1H), 8.05 (t, J = 1.9 Hz, 1H), 7.88 (dt, J = 7.7, 1.4 Hz, 1H), 7.79 (d, J = 5.1 Hz, 1H), 7.66 (t, J = 7.8 Hz, 1H), 7.60 (ddd, J = 8.0, 2.3, 1.2 Hz, 1H), 7.13 (d, J = 5.1 Hz, 1H), 4.47 (ddd, J = 49.1, 9.3, 2.1 Hz, 1H), 3.99 (ddd, J = 36.4, 14.6, 2.1 Hz, 1H), 3.53 (ddd, J = 16.1, 14.6, 9.3 Hz, 1H), 1.30 (d, J = 1.6 Hz, 6H). |
| 384 | 1H NMR (400 MHz, DMSO-d6) δ 10.49 (s, 1H), 8.97 (t, J = 5.7 Hz, 1H), 8.91-8.73 (m, 2H), 8.68 (s, 1H), 8.54 (d, J = 2.2 Hz, 1H), 7.83 (d, J = 4.8 Hz, 1H), 7.51 (td, J = 8.2, 6.7 Hz, 1H), 7.35-7.17 (m, 2H), 7.09 (d, J = 4.8 Hz, 1H), 6.97 (td, J = 8.7, 2.0 Hz, 1H), 4.38 (ddd, J = 49.2, 9.3, 2.1 Hz, 1H), 3.90-3.61 (m, 1H), 3.54-3.35 (m, 1H), 1.30-1.02 (m, 6H). |
| 385 | 1H NMR (400 MHz, Methanol-d4) δ 8.72 (s, 1H), 8.68 (d, J = 2.2 Hz, 1H), 8.62 (d, J = 2.2 Hz, 1H), 8.35 (s, 1H), 7.87 (d, J = 5.0 Hz, 1H), 7.76-7.54 (m, 6H), 7.15 (d, J = 5.0 Hz, 1H), 6.70 (d, J = 9.1 Hz, 1H), 6.54 (td, J = 6.7, 1.3 Hz, 1H), 4.48 (ddd, J = 49.0, 9.3, 2.1 Hz, 1H), 4.20-3.87 (m, 1H), 3.67-3.40 (m, 1H), 1.31 (d, J = 1.6 Hz, 6H). |
| 386 | 1H NMR (400 MHz, Methanol-d4) δ 8.80 (s, 1H), 8.77 (d, J = 2.2 Hz, 1H), 8.75 (dd, J = 2.3, 0.9 Hz, 1H), 8.68 (d, J = 2.2 Hz, 1H), 8.38 (dd, J = 8.8, 0.9 Hz, 1H), 8.20 (dd, J = 8.8, 2.3 Hz, 1H), 8.06 (d, J = 5.1 Hz, 1H), 8.01 (s, 1H), 7.23 (d, J = 5.1 Hz, 1H), 4.27 (dt, J = 9.6, 5.3 Hz, 1H), 4.14 (s, 1H), 2.18-1.84 (m, 2H), 1.83-1.68 (m, 4H), 1.46-1.23 (m, 2H). |
| 387 | 1H NMR (400 MHz, Methanol-d4) δ 8.75 (d, J = 2.2 Hz, 1H), 8.65 (d, J = 2.2 Hz, 1H), 8.55 (s, 1H), 8.01 (d, J = 5.0 Hz, 1H), 7.90 (s, 1H), 7.21 (d, J = 5.1 Hz, 1H), 4.22 (dt, J = 9.1, 4.9 Hz, 1H), 4.10 (s, 1H), 3.84 (d, J = 11.6 Hz, 1H), 3.62 (s, 3H), 3.47-3.35 (m, 1H), 2.15-1.84 (m, 7H), 1.83-1.21 (m, 9H). |
| 388 | 1H NMR (400 MHz, Methanol-d4) δ 8.77-8.64 (m, 1H), 8.59 (dq, J = 9.6, 2.0, 1.6 Hz, 2H), 8.07-7.87 (m, 1H), 7.77 (t, J = 1.4 Hz, 1H), 7.16 (dt, J = 5.1, 1.4 Hz, 1H), 4.30 (t, J = 1.4 Hz, 2H), 3.89 (q, J = 7.6 Hz, 1H), 2.75 (ddd, J = 12.3, 7.4, 2.3 Hz, 2H), 2.24 (t, J = 9.5 Hz, 2H), 1.46 (s, 3H). |
| 389 | 1H NMR (400 MHz, Methanol-d4) δ 8.76 (d, J = 2.2 Hz, 1H), 8.70 (d, J = 2.2 Hz, 1H), 8.62 (s, 1H), 7.99 (d, J = 5.1 Hz, 1H), 7.80 (s, 1H), 7.22 (d, J = 5.1 Hz, 1H), 4.53-4.41 (m, 1H), 4.38 (s, 2H), 2.80-2.62 (m, 2H), 2.27-2.14 (m, 2H), 1.44 (s, 3H). |
| 390 | 1H NMR (400 MHz, Methanol-d4) δ 8.76 (d, J = 2.2 Hz, 1H), 8.68 (d, J = 2.2 Hz, 1H), 8.60 (s, 1H), 8.02 (d, J = 5.1 Hz, 1H), 7.89 (s, 1H), 7.22 (d, J = 5.0 Hz, 1H), 4.48-4.28 (m, 2H), 4.06 (s, 2H), 3.85 (tt, J = 11.4, 4.0 Hz, 1H), 3.74-3.59 (m, 3H), 2.26 (d, J = 12.5 Hz, 2H), 1.94 (d, J = 12.3 Hz, 2H), 1.82 (td, J = 12.6, 3.4 Hz, 2H), 1.63 (qd, J = 12.8, 3.6 Hz, 2H). |
| 391 | 1H NMR (400 MHz, Methanol-d4) δ 8.76 (d, J = 2.2 Hz, 1H), 8.69 (d, J = 2.2 Hz, 1H), 8.59 (s, 1H), 8.03 (d, J = 5.1 Hz, 1H), 7.93 (s, 1H), 7.22 (d, J = 5.1 Hz, 1H), 4.45-4.30 (m, 5H), 3.97-3.59 (m, 4H), 2.28 (d, J = 12.6 Hz, 2H), 1.96 (d, J = 11.9 Hz, 2H), 1.84 (qd, J = 12.8, 3.4 Hz, 2H), 1.74-1.56 (m, 2H). |
| 392 | 1H NMR (400 MHz, Methanol-d4) δ 8.76 (d, J = 2.2 Hz, 1H), 8.68 (d, J = 2.1 Hz, 1H), 8.57 (s, 1H), 8.03 (d, J = 5.0 Hz, 1H), 7.89 (s, 1H), 7.22 (d, J = 5.1 Hz, 1H), 4.54-4.28 (m, 3H), 4.01-3.59 (m, 5H), 3.55-3.39 (m, 1H), 2.27 (d, J = 12.6 Hz, 2H), 2.02-1.91 (m, 2H), 1.82 (td, J = 12.6, 3.3 Hz, 2H), 1.69-1.50 (m, 2H), 1.29 (d, J = 1.7 Hz, 6H). |
| 393 | 1H NMR (400 MHz, Methanol-d4) δ 8.82-8.68 (m, 2H), 8.54 (s, 1H), 8.30 (s, 1H), 7.94 (d, J = 5.1 Hz, 1H), 7.22 (d, J = 5.1 Hz, 1H), 6.12 (td, J = 56.3, 3.7 Hz, 1H), 4.61 (s, 1H), 4.40 (ddd, J = 49.1, 9.2, 1.9 Hz, 2H), 4.06 (s, 1H), 3.91 (ddd, J = 36.5, 14.9, 2.1 Hz, 2H), 3.57-3.39 (m, 1H), 3.10 (ddd, J = 15.5, 7.7, 4.7 Hz, 1H), 2.26-2.12 (m, 6H), 2.07 (dd, J = 9.9, 4.6 Hz, 6H), 1.28 (d, J = 1.6 Hz, 6H). |

TABLE 2-continued

| compound | 1H-NMR |
|---|---|
| 394 | 1H NMR (400 MHz, Methanol-d4) δ 8.88-8.63 (m, 2H), 8.54 (s, 1H), 8.32 (s, 1H), 7.93 (d, J = 5.1 Hz, 1H), 7.22 (d, J = 5.1 Hz, 1H), 4.71-4.19 (m, 3H), 4.25-3.9 (m, 2H), 3.91 (dd, J = 36.8, 14.2 Hz, 1H), 3.47 (td, J = 15.5, 9.3 Hz, 1H), 2.16 (d, J = 7.8 Hz, 6H), 2.08 (d, J = 7.6 Hz, 6H), 1.62 (d, J = 21.5 Hz, 3H), 1.28 (d, J = 1.7 Hz, 6H). |
| 395 | 1H NMR (400 MHz, Methanol-d4) δ 8.75 (d, J = 2.1 Hz, 1H), 8.67 (d, J = 2.2 Hz, 1H), 8.56 (s, 1H), 8.25 (s, 1H), 7.94 (d, J = 5.1 Hz, 1H), 7.22 (d, J = 5.1 Hz, 1H), 6.92 (d, J = 4.6 Hz, 1H), 4.83-4.74 (m, 3H), 4.40 (ddd, J = 49.0, 9.4, 2.1 Hz, 1H), 4.21 (t, J = 6.4 Hz, 1H), 4.03-3.76 (m, 4H), 3.48 (ddd, J = 16.0, 14.6, 9.4 Hz, 1H), 3.13-2.96 (m, 4H), 2.29-2.01 (m, 12H), 1.28 (d, J = 1.7 Hz, 6H). |
| 396 | 1H NMR (400 MHz, Methanol-d4) δ 8.82-8.67 (m, 2H), 8.54 (s, 1H), 8.32 (s, 1H), 7.93 (d, J = 5.1 Hz, 1H), 7.22 (d, J = 5.1 Hz, 1H), 4.68 (s, 1H), 4.40 (ddd, J = 49.0, 9.5, 2.1 Hz, 1H), 4.29 (s, 1H), 4.22 (td, J = 6.4, 3.4 Hz, 1H), 4.13 (s, 1H), 3.91 (ddd, J = 36.6, 14.5, 2.0 Hz, 1H), 3.79 (s, 1H), 3.47 (td, J = 15.3, 9.3 Hz, 1H), 2.15 (d, J = 7.9 Hz, 6H), 2.08 (d, J = 7.8 Hz, 6H), 1.28 (d, J = 1.7 Hz, 6H). |
| 397 | 1H NMR (400 MHz, Methanol-d4) δ 8.76 (s, 2H), 8.54 (s, 1H), 8.44 (s, 1H), 7.93 (d, J = 5.1 Hz, 1H), 7.22 (d, J = 5.0 Hz, 1H), 4.40 (ddd, J = 49.1, 9.4, 2.1 Hz, 1H), 3.91 (ddd, J = 36.7, 14.5, 2.1 Hz, 1H), 3.53-3.36 (m, 5H), 3.35 (s, 3H), 2.18 (dd, J = 10.3, 5.3 Hz, 6H), 2.03 (dd, J = 10.2, 5.4 Hz, 6H), 1.28 (d, J = 1.6 Hz, 6H). |
| 398 | 1H NMR (400 MHz, Methanol-d4) δ 8.77 (q, J = 2.2 Hz, 2H), 8.54 (s, 1H), 8.45 (s, 1H), 7.92 (d, J = 5.1 Hz, 1H), 7.22 (d, J = 5.1 Hz, 1H), 4.53-4.29 (m, 1H), 4.10-3.82 (m, 1H), 3.65-3.36 (m, 1H), 2.18 (dd, J = 10.2, 5.3 Hz, 6H), 2.05 (dd, J = 10.1, 5.4 Hz, 6H), 1.28 (d, J = 1.6 Hz, 6H). |
| 399 | 1H NMR (400 MHz, Chloroform-d) δ 8.38 (d, J = 0.9 Hz, 1H), 8.32-8.25 (m, 2H), 8.19 (dd, J = 2.3, 0.9 Hz, 1H), 7.73 (dd, J = 4.8, 1.0 Hz, 1H), 6.93 (dd, J = 4.8, 0.9 Hz, 1H), 4.46-4.24 (m, 1H), 4.19 (dd, J = 8.9, 6.8 Hz, 2H), 3.85 (ddd, J = 30.8, 14.6, 3.0 Hz, 1H), 3.61-3.56 (m, 2H), 3.48-3.40 (m, 1H), 2.11 (s, 12H), 1.28-1.19 (m, 6H). |
| 400 | 1H NMR (400 MHz, Methanol-d4) δ 8.80-8.67 (m, 2H), 8.54 (s, 1H), 8.32 (s, 1H), 7.94 (d, J = 5.1 Hz, 1H), 7.22 (d, J = 5.1 Hz, 1H), 5.33 (dtd, J = 60.4, 6.1, 3.1 Hz, 1H), 4.40 (ddd, J = 49.1, 9.3, 2.1 Hz, 1H), 3.91 (ddd, J = 36.5, 14.5, 2.1 Hz, 1H), 3.47 (td, J = 15.4, 9.4 Hz, 1H), 2.24-2.14 (m, 6H), 2.08 (d, J = 7.7 Hz, 6H), 1.28 (d, J = 1.6 Hz, 6H). |
| 401 | 1H NMR (400 MHz, Methanol-d4) δ 8.75 (d, J = 2.2 Hz, 1H), 8.69 (d, J = 2.2 Hz, 1H), 8.54 (s, 1H), 8.23 (s, 1H), 8.01-7.92 (m, 1H), 7.22 (d, J = 5.1 Hz, 1H), 4.53-4.28 (m, 1H), 4.03-3.78 (m, 1H), 3.70 (s, 4H), 3.68-3.61 (m, 4H), 3.59-3.39 (m, 1H), 2.17 (s, 12H), 1.28 (d, J = 1.6 Hz, 6H). |
| 402 | 1H NMR (400 MHz, Methanol-d4) δ 8.73 (d, J = 2.2 Hz, 1H), 8.67 (d, J = 2.2 Hz, 1H), 8.46 (s, 1H), 8.24 (s, 1H), 7.95 (d, J = 5.1 Hz, 1H), 7.20 (d, J = 5.1 Hz, 1H), 2.32-2.08 (m, 12H), 1.97-1.83 (m, 6H), 1.83-1.67 (m, 6H). |
| 403 | 1H NMR (400 MHz, Methanol-d4) δ 8.79 (s, 1H), 8.76 (d, J = 2.2 Hz, 1H), 8.57 (s, 1H), 8.41 (s, 1H), 7.91 (d, J = 5.1 Hz, 1H), 7.22 (d, J = 5.1 Hz, 1H), 4.41 (ddd, J = 49.0, 9.4, 2.1 Hz, 1H), 3.92 (ddd, J = 36.6, 14.6, 2.1 Hz, 1H), 3.60-3.38 (m, 1H), 2.20 (t, J = 7.7 Hz, 4H), 2.13 (s, 2H), 2.05-1.80 (m, 4H), 1.28 (d, J = 1.6 Hz, 6H). |
| 404 | 1H NMR (400 MHz, Methanol-d4) δ 8.75 (d, J = 2.2 Hz, 1H), 8.70 (d, J = 2.2 Hz, 1H), 8.54 (s, 1H), 8.28 (s, 1H), 7.95 (d, J = 5.1 Hz, 1H), 7.22 (d, J = 5.0 Hz, 1H), 4.40 (ddd, J = 49.0, 9.4, 2.1 Hz, 1H), 3.91 (ddd, J = 36.6, 14.6, 2.1 Hz, 1H), 3.59-3.40 (m, 1H), 2.18 (s, 12H), 1.28 (d, J = 1.7 Hz, 6H). |
| 405 | 1H NMR (400 MHz, Methanol-d4) δ 8.85-8.69 (m, 2H), 8.54 (s, 1H), 8.35 (s, 1H), 7.93 (d, J = 5.0 Hz, 1H), 7.22 (d, J = 5.1 Hz, 1H), 4.40 (ddd, J = 49.1, 9.4, 2.1 Hz, 1H), 3.91 (ddd, J = 36.5, 14.5, 2.1 Hz, 1H), 3.46 (ddd, J = 15.7, 14.6, 9.4 Hz, 1H), 2.79 (t, J = 4.0 Hz, 2H), 2.19 (dt, J = 24.1, 6.2 Hz, 12H), 1.28 (d, J = 1.7 Hz, 6H). |
| 406 | 1H NMR (400 MHz, Methanol-d4) δ 8.76 (s, 2H), 8.55 (s, 1H), 8.43 (s, 1H), 7.93 (d, J = 5.1 Hz, 1H), 7.22 (d, J = 5.1 Hz, 1H), 4.40 (ddd, J = 49.1, 9.4, 2.1 Hz, 1H), 4.06-3.79 (m, 1H), 3.62-3.37 (m, 1H), 2.62 (tt, J = 7.4, 3.9 Hz, 1H), 2.16 (dd, J = 10.3, 5.4 Hz, 6H), 2.00 (dd, J = 10.1, 5.4 Hz, 6H), 1.28 (d, J = 1.6 Hz, 6H), 0.79-0.66 (m, 2H), 0.58-0.42 (m, 2H). |
| 407 | 1H NMR (400 MHz, Methanol-d4) δ 8.76 (s, 2H), 8.54 (s, 1H), 8.44 (s, 1H), 7.92 (d, J = 5.1 Hz, 1H), 7.22 (d, J = 5.1 Hz, 1H), 4.40 (ddd, J = 49.2, 9.4, 2.1 Hz, 1H), 4.06-3.77 (m, 1H), 3.59-3.39 (m, 1H), 3.22 (q, J = 7.2 Hz, 2H), 2.17 (dd, J = 10.2, 5.5 Hz, 6H), 2.02 (dd, J = 10.0, 5.6 Hz, 6H), 1.28 (d, J = 1.6 Hz, 6H), 1.11 (t, J = 7.2 Hz, 3H). |
| 408 | 1H NMR (400 MHz, Methanol-d4) δ 8.81-8.65 (m, 2H), 8.54 (s, 1H), 8.33 (s, 1H), 7.93 (d, J = 5.1 Hz, 1H), 7.22 (d, J = 5.1 Hz, 1H), 4.52 (d, J = 8.0 Hz, 2H), 4.47-4.25 (m, 1H), 4.08-3.78 (m, 3H), 3.58-3.38 (m, 1H), 2.30 (p, J = 7.8 Hz, 2H), 2.22-2.12 (m, 6H), 2.08 (d, J = 7.6 Hz, 6H), 1.28 (d, J = 1.7 Hz, 6H). |
| 409 | 1H NMR (400 MHz, Methanol-d4) δ 8.80-8.68 (m, 2H), 8.54 (s, 1H), 8.32 (s, 1H), 7.94 (d, J = 5.1 Hz, 1H), 7.22 (d, J = 5.0 Hz, 1H), 4.40 (ddd, J = 49.1, 9.4, 2.0 Hz, 1H), 4.03-3.76 (m, 1H), 3.55-3.39 (m, 1H), 2.24-2.13 (m, 6H), 2.11-2.01 (m, 6H), 1.28 (d, J = 1.6 Hz, 6H). |
| 410 | 1H NMR (400 MHz, Methanol-d4) δ 8.76 (t, J = 1.9 Hz, 2H), 8.54 (s, 1H), 8.44 (s, 1H), 7.92 (d, J = 5.0 Hz, 1H), 7.22 (d, J = 5.1 Hz, 1H), 4.40 (ddd, J = 49.1, 9.4, 2.1 Hz, 1H), 4.01-3.81 (m, 1H), 3.46 (td, J = 15.4, 9.5 Hz, 1H), 2.42 (s, 1H), 2.16 (dd, J = 10.3, 5.4 Hz, 6H), 2.08 (s, 6H), 1.99 (dd, J = 10.0, 5.5 Hz, 6H), 1.28 (d, J = 1.6 Hz, 6H). |

TABLE 2-continued

| compound | 1H-NMR |
|---|---|
| 411 | 1H NMR (400 MHz, Methanol-d4) δ 8.82-8.70 (m, 2H), 8.54 (s, 1H), 8.38 (s, 1H), 7.93 (d, J = 5.1 Hz, 1H), 7.22 (d, J = 5.1 Hz, 1H), 4.40 (ddd, J = 49.0, 9.4, 2.1 Hz, 1H), 3.90 (ddd, J = 36.5, 14.6, 2.1 Hz, 1H), 3.63-3.35 (m, 1H), 2.87 (d, J = 7.0 Hz, 6H), 2.28 (s, 12H), 1.28 (d, J = 1.7 Hz, 6H). |
| 412 | 1H NMR (400 MHz, Methanol-d4) δ 8.75 (s, 2H), 8.55 (s, 1H), 8.36 (s, 1H), 7.94 (d, J = 5.1 Hz, 1H), 7.22 (d, J = 5.1 Hz, 1H), 4.40 (ddd, J = 49.1, 9.4, 2.1 Hz, 1H), 3.90 (ddd, J = 36.4, 14.6, 2.2 Hz, 1H), 3.47 (ddd, J = 16.0, 14.5, 9.4 Hz, 1H), 2.64 (s, 3H), 2.26 (s, 12H), 1.28 (d, J = 1.7 Hz, 6H). |
| 413 | 1H NMR (400 MHz, Chloroform-d) δ 10.04 (d, J = 0.6 Hz, 1H), 8.75 (d, J = 0.6 Hz, 1H), 8.64 (dd, J = 2.3, 0.8 Hz, 1H), 8.34 (d, J = 2.3 Hz, 1H), 8.21 (d, J = 2.2 Hz, 1H), 7.95-7.69 (m, 2H), 7.08-6.86 (m, 2H), 4.44 (ddd, J = 47.4, 7.3, 3.1 Hz, 1H), 4.04-3.87 (m, 1H), 3.55 (ddd, J = 21.0, 14.7, 7.3 Hz, 1H), 1.32 (dd, J = 11.9, 1.6 Hz, 6H). |
| 414 | 1H NMR (400 MHz, Chloroform-d) δ 8.43 (d, J = 1.5 Hz, 1H), 8.38-8.23 (m, 2H), 8.20 (d, J = 2.2 Hz, 1H), 7.90 (dd, J = 4.9, 2.2 Hz, 1H), 6.98 (d, J = 4.9 Hz, 1H), 4.74-4.41 (m, 1H), 4.13-3.91 (m, 1H), 3.73-3.39 (m, 1H), 2.30-2.11 (m, 6H), 1.88 (dq, J = 7.5, 4.5, 4.0 Hz, 6H), 1.33-1.22 (m, 6H). |
| 415 | 1H NMR (400 MHz, Methanol-d4) δ 8.75 (d, J = 2.2 Hz, 1H), 8.70 (d, J = 2.2 Hz, 1H), 8.54 (s, 1H), 8.28 (s, 1H), 7.95 (d, J = 5.1 Hz, 1H), 7.21 (d, J = 5.1 Hz, 1H), 4.52-4.28 (m, 1H), 3.91 (ddd, J = 36.5, 14.6, 2.1 Hz, 1H), 3.54-3.41 (m, 1H), 3.19-3.01 (m, 6H), 2.18 (s, 12H), 1.28 (d, J = 1.6 Hz, 6H). |
| 416 | 1H NMR (400 MHz, Methanol-d4) δ 8.76 (s, 2H), 8.54 (s, 1H), 8.45 (s, 1H), 7.93 (d, J = 5.1 Hz, 1H), 7.22 (d, J = 5.1 Hz, 1H), 4.40 (dd, J = 48.7, 9.0 Hz, 1H), 3.91 (dd, J = 36.5, 14.5 Hz, 1H), 3.72 (p, J = 6.6 Hz, 1H), 3.56-3.40 (m, 1H), 2.73 (d, J = 3.8 Hz, 3H), 2.18 (t, J = 7.8 Hz, 6H), 2.02 (t, J = 7.4 Hz, 6H), 1.28 (d, J = 1.7 Hz, 6H). |
| 417 | 1H NMR (400 MHz, Methanol-d4) δ 8.76 (d, J = 2.2 Hz, 1H), 8.72 (d, J = 2.2 Hz, 1H), 8.56 (s, 1H), 8.31 (s, 1H), 7.94 (d, J = 5.1 Hz, 1H), 7.22 (d, J = 5.1 Hz, 1H), 4.74 (dd, J = 9.4, 2.0 Hz, 1H), 3.88 (ddd, J = 36.8, 14.6, 2.0 Hz, 1H), 3.50 (ddd, J = 16.3, 14.6, 9.4 Hz, 1H), 2.28 (s, 12H), 2.01 (s, 3H), 1.56 (d, J = 1.7 Hz, 6H). |
| 418 | 1H NMR (400 MHz, Methanol-d4) δ 8.75 (d, J = 2.2 Hz, 1H), 8.72 (d, J = 2.2 Hz, 1H), 8.55 (s, 1H), 8.30 (s, 1H), 7.94 (d, J = 5.0 Hz, 1H), 7.22 (d, J = 5.1 Hz, 1H), 4.40 (ddd, J = 49.1, 9.4, 2.1 Hz, 1H), 3.90 (ddd, J = 36.5, 14.5, 2.1 Hz, 1H), 3.55-3.38 (m, 1H), 2.28 (s, 12H), 1.97 (s, 3H), 1.28 (d, J = 1.7 Hz, 6H). |
| 419 | 1H NMR (400 MHz, Methanol-d4) δ 8.74 (d, J = 2.2 Hz, 1H), 8.71-8.55 (m, 2H), 7.98 (d, J = 5.1 Hz, 1H), 7.90 (s, 1H), 7.20 (d, J = 5.0 Hz, 1H), 4.43 (ddd, J = 49.1, 9.4, 2.1 Hz, 1H), 4.09-3.84 (m, 2H), 3.50 (ddd, J = 15.9, 14.0, 9.4 Hz, 1H), 2.39 (s, 2H), 2.21 (s, 1H), 2.00-1.61 (m, 10H), 1.29 (d, J = 1.6 Hz, 6H). |
| 420 | 1H NMR (400 MHz, Methanol-d4) δ 10.24 (s, 1H), 9.08 (s, 2H), 8.90 (s, 1H), 8.72 (dd, J = 13.8, 2.2 Hz, 2H), 7.98 (d, J = 5.0 Hz, 1H), 7.19 (d, J = 5.0 Hz, 1H), 4.47 (ddd, J = 49.0, 9.4, 2.2 Hz, 1H), 4.11-3.89 (m, 1H), 3.67-3.43 (m, 1H), 1.39-1.20 (m, 6H). |
| 421 | 1H NMR (400 MHz, Methanol-d4) δ 8.75 (d, J = 2.2 Hz, 1H), 8.69 (d, J = 2.2 Hz, 1H), 8.51 (s, 1H), 8.35 (s, 1H), 7.91 (d, J = 5.1 Hz, 1H), 7.21 (d, J = 5.1 Hz, 1H), 4.40 (ddd, J = 49.1, 9.4, 2.1 Hz, 1H), 3.91 (ddd, J = 36.5, 14.5, 2.1 Hz, 1H), 3.58-3.38 (m, 1H), 2.09 (dd, J = 10.2, 5.6 Hz, 6H), 1.87 (dd, J = 9.3, 4.2 Hz, 6H), 1.76-1.64 (m, 1H), 1.28 (d, J = 1.6 Hz, 6H). |
| 422 | 1H NMR (400 MHz, Methanol-d4) δ 8.75 (d, J = 2.2 Hz, 1H), 8.66 (d, J = 2.2 Hz, 1H), 8.56 (s, 1H), 8.00 (d, J = 5.0 Hz, 1H), 7.88 (d, J = 13.1 Hz, 1H), 7.21 (d, J = 5.0 Hz, 1H), 4.54-4.28 (m, 1H), 4.04-3.77 (m, 3H), 3.57-3.36 (m, 1H), 2.24 (d, J = 11.8 Hz, 2H), 2.06 (d, J = 12.1 Hz, 2H), 1.76-1.51 (m, 4H), 1.35-1.24 (m, 10H). |
| 423 | 1H NMR (400 MHz, Methanol-d4) δ 8.75 (d, J = 2.2 Hz, 1H), 8.64 (d, J = 2.2 Hz, 1H), 8.56 (s, 1H), 7.99 (d, J = 5.0 Hz, 1H), 7.90 (s, 1H), 7.21 (d, J = 5.0 Hz, 1H), 4.42 (ddd, J = 49.1, 9.4, 2.1 Hz, 1H), 4.04-3.68 (m, 3H), 3.47 (ddd, J = 16.1, 14.5, 9.4 Hz, 1H), 2.22 (d, J = 10.4 Hz, 2H), 2.08-1.93 (m, 2H), 1.58 (q, J = 11.3 Hz, 4H), 1.33 (s, 3H), 1.28 (d, J = 1.7 Hz, 6H), 1.08 (q, J = 3.9 Hz, 2H), 0.60 (q, J = 3.9 Hz, 2H). |
| 424 | 1H NMR (400 MHz, Methanol-d4) δ 8.64-8.55 (m, 2H), 8.53 (d, J = 6.1 Hz, 2H), 7.82 (d, J = 4.9 Hz, 1H), 7.08 (d, J = 4.9 Hz, 1H), 6.38-6.26 (m, 1H), 6.23-6.16 (m, 1H), 5.91-5.77 (m, 1H), 4.49-4.30 (m, 1H), 3.95-3.77 (m, 1H), 3.49-3.40 (m, 1H), 2.18 (s, 13H), 1.28 (d, J = 1.6 Hz, 6H). |
| 425 | 1H NMR (400 MHz, Methanol-d4) δ 8.75 (d, J = 2.2 Hz, 1H), 8.64 (d, J = 2.1 Hz, 1H), 8.56 (s, 1H), 8.01 (d, J = 5.0 Hz, 1H), 7.86 (s, 1H), 7.21 (d, J = 5.1 Hz, 1H), 6.30-6.21 (m, 2H), 5.65 (dd, J = 7.5, 4.5 Hz, 1H), 4.52-4.26 (m, 1H), 4.11-3.68 (m, 3H), 3.58-3.39 (m, 1H), 2.23 (d, J = 10.5 Hz, 2H), 2.09 (d, J = 10.3 Hz, 2H), 1.58 (q, J = 11.4 Hz, 4H), 1.29 (d, J = 1.7 Hz, 6H). |
| 426 | 1H NMR (400 MHz, Methanol-d4) δ 8.74 (d, J = 2.2 Hz, 1H), 8.65 (d, J = 2.2 Hz, 1H), 8.56 (s, 1H), 8.01 (d, J = 5.1 Hz, 1H), 7.91 (s, 1H), 7.21 (d, J = 5.1 Hz, 1H), 4.67 (td, J = 5.6, 3.1 Hz, 1H), 4.23 (dq, J = 8.7, 4.4, 3.9 Hz, 1H), 4.11 (s, 1H), 2.94-2.87 (m, 1H), 2.17-1.51 (m, 2H), 1.84-1.49 (m, 5H), 1.36 (dd, J = 6.8, 3.3 Hz, 1H), 1.29-1.04 (m, 2H). |
| 427 | 1H NMR (400 MHz, Methanol-d4) δ 8.74 (d, J = 2.2 Hz, 1H), 8.65 (d, J = 2.2 Hz, 1H), 8.57 (s, 1H), 8.00 (d, J = 5.1 Hz, 1H), 7.90 (s, 1H), 7.20 (d, J = 5.1 Hz, 1H), 4.43 (td, J = 8.3, 5.0 Hz, 1H), 4.21 (dt, J = 9.2, 4.9 Hz, 1H), 4.09 (s, 1H), 2.68 (t, J = 12.2 Hz, 2H), 2.56 (dt, J = 12.4, 9.9 Hz, 5H), 2.27 (td, J = 9.2, 3.0 Hz, 2H), 2.13-1.83 (m, 3H), 1.83-1.48 (m, 4H). |
| 428 | 1H NMR (400 MHz, Methanol-d4) δ 8.74 (d, J = 2.2 Hz, 1H), 8.65 (d, J = 2.2 Hz, 1H), 8.61 (s, 1H), 8.03 (d, J = 5.1 Hz, 1H), 7.93 (s, 1H), 7.21 (d, J = 5.1 Hz, 1H), |

TABLE 2-continued

| compound | 1H-NMR |
|---|---|
| | 4.23 (tt, J = 8.7, 3.8 Hz, 1H), 4.10 (s, 1H), 3.53 (s, 2H), 2.04 (td, J = 14.8, 13.6, 7.4 Hz, 2H), 1.91 (dq, J = 9.9, 5.7 Hz, 1H), 1.78 (ddd, J = 13.0, 9.2, 3.0 Hz, 1H), 1.69 (t, J = 5.5 Hz, 3H), 1.59 (td, J = 11.6, 10.6, 8.4 Hz, 1H), 1.35-1.27 (m, 2H), 1.22-1.11 (m, 2H). |
| 429 | 1H NMR (400 MHz, Methanol-d4) δ 8.75 (d, J = 2.1 Hz, 1H), 8.69 (d, J = 2.2 Hz, 1H), 8.57 (s, 1H), 7.96-7.83 (m, 2H), 7.21 (d, J = 5.1 Hz, 1H), 4.57-4.24 (m, 2H), 4.06-3.82 (m, 1H), 3.48 (td, J = 15.4, 9.7 Hz, 1H), 2.93-2.72 (m, 2H), 2.44-2.19 (m, 2H), 1.72 (s, 3H), 1.29 (d, J = 1.7 Hz, 6H). |
| 430 | 1H NMR (400 MHz, Methanol-d4) δ 8.75 (d, J = 2.1 Hz, 1H), 8.66 (d, J = 2.2 Hz, 1H), 8.58 (s, 1H), 8.02 (d, J = 5.1 Hz, 1H), 7.94 (s, 1H), 7.21 (d, J = 5.1 Hz, 1H), 4.36-4.03 (m, 2H), 3.53-3.39 (m, 1H), 2.09-1.85 (m, 4H), 1.70 (s, 3H), 1.60 (d, J = 11.2 Hz, 3H). |
| 431 | 1H NMR (400 MHz, Methanol-d4) δ 8.74 (d, J = 2.2 Hz, 1H), 8.65 (d, J = 2.2 Hz, 1H), 8.58 (s, 1H), 8.01 (d, J = 5.1 Hz, 1H), 7.91 (s, 1H), 7.20 (d, J = 5.1 Hz, 1H), 4.22 (dt, J = 9.1, 4.9 Hz, 1H), 4.10 (s, 1H), 4.02 (d, J = 11.0 Hz, 1H), 2.23-1.82 (m, 8H), 1.82-1.51 (m, 8H). |
| 432 | 1H NMR (400 MHz, Methanol-d4) δ 8.75 (d, J = 2.2 Hz, 1H), 8.69 (d, J = 2.2 Hz, 1H), 8.57 (s, 1H), 8.27 (s, 1H), 7.91 (d, J = 5.0 Hz, 1H), 7.21 (d, J = 5.1 Hz, 1H), 4.41 (ddd, J = 49.1, 9.4, 2.1 Hz, 1H), 3.92 (ddd, J = 36.6, 14.5, 2.1 Hz, 2H), 3.59-3.40 (m, 1H), 2.05 (h, J = 11.6, 10.8 Hz, 4H), 1.80 (d, J = 10.1 Hz, 1H), 1.72-1.65 (m, 1H), 1.63 (s, 3H), 1.41-1.31 (m, 1H), 1.28 (d, J = 1.6 Hz, 6H). |
| 433 | 1H NMR (400 MHz, Methanol-d4) δ 8.75 (d, J = 2.2 Hz, 1H), 8.71 (d, J = 2.2 Hz, 1H), 8.57 (s, 1H), 7.96-7.81 (m, 2H), 7.21 (d, J = 5.1 Hz, 1H), 4.54-4.21 (m, 2H), 3.93 (ddd, J = 36.7, 14.5, 2.1 Hz, 1H), 3.48 (ddd, J = 16.0, 14.5, 9.4 Hz, 1H), 2.87 (ddd, J = 9.9, 7.2, 2.9 Hz, 2H), 2.41-2.15 (m, 2H), 1.61 (s, 3H), 1.28 (d, J = 1.7 Hz, 6H). |
| 434 | 1H NMR (400 MHz, Methanol-d4) δ 8.75 (s, 1H), 8.69 (d, J = 2.1 Hz, 1H), 8.55 (d, J = 2.1 Hz, 1H), 8.33 (s, 1H), 8.04-7.90 (m, 1H), 7.82 (d, J = 5.0 Hz, 1H), 7.68 (s, 1H), 7.64 (d, J = 8.1 Hz, 1H), 7.15 (d, J = 5.0 Hz, 1H), 4.56 (s, 2H), 4.56-4.33 (m, 1H), 4.16-3.79 (m, 1H), 3.65-3.42 (m, 1H), 1.30 (d, J = 1.6 Hz, 6H). |
| 435 | 1H NMR (400 MHz, Methanol-d4) δ 8.67 (d, J = 2.2 Hz, 1H), 8.57 (d, J = 2.2 Hz, 1H), 8.23 (s, 1H), 7.75 (d, J = 5.0 Hz, 2H), 7.43 (s, 1H), 7.27 (s, 1H), 7.20-7.06 (m, 2H), 4.54 (ddd, J = 62.2, 43.4, 11.9 Hz, 2H), 4.14-3.94 (m, 1H), 1.25 (s, 6H). |
| 436 | 1H NMR (400 MHz, Methanol-d4) δ 8.75 (d, J = 2.2 Hz, 1H), 8.66 (d, J = 2.2 Hz, 1H), 8.56 (s, 1H), 8.03 (d, J = 5.0 Hz, 1H), 7.86 (s, 1H), 7.21 (d, J = 5.0 Hz, 1H), 4.41 (ddd, J = 49.1, 9.4, 2.1 Hz, 1H), 4.03-3.60 (m, 3H), 3.59-3.38 (m, 1H), 2.18 (d, J = 7.1 Hz, 2H), 2.04 (dd, J = 9.7, 4.3 Hz, 2H), 1.65-1.41 (m, 4H), 1.28 (d, J = 1.7 Hz, 6H). |
| 437 | 1H NMR (400 MHz, Methanol-d4) δ 8.74 (d, J = 2.2 Hz, 1H), 8.65 (d, J = 2.2 Hz, 1H), 8.59 (s, 1H), 8.00 (d, J = 5.0 Hz, 1H), 7.86 (s, 1H), 7.20 (d, J = 5.0 Hz, 1H), 4.42 (ddd, J = 49.1, 9.4, 2.1 Hz, 1H), 4.05-3.80 (m, 3H), 3.56-3.39 (m, 1H), 2.00-1.58 (m, 8H), 1.29 (d, J = 1.7 Hz, 6H). |
| 438 | 1H NMR (400 MHz, DMSO-d6) δ 7.93 (d, J = 2.2 Hz, 1H), 7.87 (d, J = 2.2 Hz, 1H), 7.74 (s, 1H), 7.21 (d, J = 5.1 Hz, 1H), 7.04 (s, 1H), 6.39 (d, J = 5.1 Hz, 1H), 3.61 (ddd, J = 49.0, 9.3, 2.1 Hz, 1H), 3.12 (ddd, J = 36.5, 14.5, 2.1 Hz, 1H), 2.82 (t, J = 6.6 Hz, 2H), 2.67 (ddd, J = 16.0, 14.5, 9.3 Hz, 1H), 2.44 (t, J = 7.1 Hz, 2H), 2.17 (s, 3H), 1.30-1.04 (m, 4H), 0.47 (d, J = 1.7 Hz, 6H). |
| 439 | 1H NMR (400 MHz, Methanol-d4) δ 8.74 (d, J = 2.2 Hz, 1H), 8.67 (d, J = 2.2 Hz, 1H), 8.55 (s, 1H), 8.04 (d, J = 5.1 Hz, 1H), 7.90 (s, 1H), 7.20 (d, J = 5.1 Hz, 1H), 4.43 (ddd, J = 49.0, 9.3, 2.1 Hz, 1H), 3.93 (ddd, J = 36.4, 14.5, 2.1 Hz, 1H), 3.81-3.69 (m, 2H), 3.49 (ddd, J = 16.2, 14.5, 9.3 Hz, 1H), 3.26 (t, J = 7.1 Hz, 2H), 3.16 (q, J = 7.5 Hz, 2H), 2.35-2.18 (m, 2H), 1.37 (t, J = 7.5 Hz, 3H), 1.28 (d, J = 1.7 Hz, 6H). |
| 440 | 1H NMR (400 MHz, Methanol-d4) δ 8.74 (d, J = 2.2 Hz, 1H), 8.66 (d, J = 2.2 Hz, 1H), 8.58 (d, J = 0.9 Hz, 1H), 8.05 (d, J = 5.1 Hz, 1H), 7.89 (s, 1H), 7.20 (d, J = 5.1 Hz, 1H), 4.43 (ddt, J = 49.0, 9.3, 2.3 Hz, 1H), 4.30 (q, J = 6.5 Hz, 1H), 4.04-3.82 (m, 1H), 3.63-3.40 (m, 1H), 3.32 (d, J = 7.4 Hz, 2H), 3.07-3.00 (m, 3H), 2.29 (dd, J = 14.4, 7.1 Hz, 1H), 2.21-2.07 (m, 1H), 1.45 (d, J = 6.4 Hz, 3H), 1.29 (d, J = 1.6 Hz, 6H). |
| 441 | 1H NMR (400 MHz, Methanol-d4) δ 8.81-8.66 (m, 2H), 8.58 (d, J = 2.2 Hz, 1H), 7.97-7.78 (m, 3H), 7.63 (dd, J = 9.6, 2.9 Hz, 1H), 7.16 (d, J = 5.1 Hz, 1H), 6.72 (d, J = 9.6 Hz, 1H), 4.45 (ddd, J = 49.1, 9.3, 2.1 Hz, 1H), 3.97 (ddd, J = 36.5, 14.6, 2.1 Hz, 1H), 3.62 (s, 3H), 3.59-3.44 (m, 1H), 1.29 (d, J = 1.7 Hz, 6H). |
| 442 | 1H NMR (400 MHz, Methanol-d4) δ 8.80 (s, 1H), 8.76 (s, 1H), 8.69 (s, 2H), 7.91 (d, J = 5.0 Hz, 1H), 7.76 (d, J = 7.3 Hz, 1H), 7.17 (d, J = 5.0 Hz, 1H), 6.71 (d, J = 2.5 Hz, 1H), 6.45 (dd, J = 7.3, 2.5 Hz, 1H), 4.45 (ddd, J = 49.0, 9.2, 2.1 Hz, 1H), 3.97 (ddd, J = 36.4, 14.5, 2.2 Hz, 1H), 3.60 (s, 3H), 3.57-3.43 (m, 1H), 1.29 (d, J = 1.6 Hz, 6H). |
| 443 | 1H NMR (400 MHz, Methanol-d4) δ 8.75 (d, J = 2.2 Hz, 1H), 8.68 (d, J = 2.1 Hz, 1H), 8.60 (s, 1H), 8.01 (d, J = 5.1 Hz, 1H), 7.76 (s, 1H), 7.21 (d, J = 5.1 Hz, 1H), 4.68-4.27 (m, 2H), 4.15-3.73 (m, 2H), 3.50 (ddd, J = 16.1, 14.6, 9.3 Hz, 1H), 3.24-3.03 (m, 2H), 3.01 (s, 3H), 2.76-2.50 (m, 2H), 1.29 (d, J = 1.7 Hz, 6H). |
| 444 | 1H NMR (400 MHz, Methanol-d4) δ 8.76 (d, J = 2.2 Hz, 1H), 8.70 (d, J = 2.2 Hz, 1H), 8.53 (s, 1H), 8.28 (s, 1H), 7.93 (d, J = 5.1 Hz, 1H), 7.22 (d, J = 5.1 Hz, 1H), 4.40 (ddd, J = 49.1, 9.4, 2.1 Hz, 1H), 3.90 (ddd, J = 36.7, 14.6, 2.1 Hz, 1H), 3.46 (ddd, J = 15.9, 14.5, 9.4 Hz, 1H), 2.25 (dd, J = 10.2, 5.8 Hz, 6H), 1.95-1.84 (m, 6H), 1.28 (d, J = 1.6 Hz, 6H). |

TABLE 2-continued

| compound | 1H-NMR |
|---|---|
| 445 | 1H NMR (400 MHz, Methanol-d4) δ 8.68 (d, J = 2.2 Hz, 1H), 8.60 (d, J = 2.2 Hz, 1H), 8.56 (s, 1H), 7.95 (d, J = 5.0 Hz, 1H), 7.89 (s, 1H), 7.16 (d, J = 5.0 Hz, 1H), 4.43 (ddd, J = 49.1, 9.3, 2.2 Hz, 1H), 4.13-3.78 (m, 2H), 3.50 (ddd, J = 16.0, 14.5, 9.3 Hz, 1H), 2.15 (d, J = 10.6 Hz, 2H), 1.77-1.48 (m, 6H), 1.29 (d, J = 1.6 Hz, 9H). |
| 446 | 1H NMR (400 MHz, Methanol-d4) δ 8.75 (d, J = 2.2 Hz, 1H), 8.69 (d, J = 2.2 Hz, 1H), 8.58 (s, 1H), 7.96 (d, J = 5.1 Hz, 1H), 7.75 (s, 1H), 7.21 (d, J = 5.1 Hz, 1H), 4.55-4.30 (m, 2H), 3.94 (ddd, J = 36.6, 14.6, 2.1 Hz, 1H), 3.49 (ddd, J = 16.0, 14.5, 9.4 Hz, 1H), 2.81-2.58 (m, 2H), 2.31-2.11 (m, 2H), 1.44 (s, 3H), 1.29 (d, J = 1.6 Hz, 6H). |
| 447 | 1H NMR (400 MHz, Methanol-d4) δ 8.75 (dd, J = 2.2, 0.9 Hz, 1H), 8.70 (dd, J = 4.8, 2.2 Hz, 1H), 8.58 (s, 1H), 8.00 (dd, J = 6.5, 5.1 Hz, 1H), 7.73 (d, J = 5.6 Hz, 1H), 7.21 (d, J = 5.0 Hz, 1H), 4.58-4.25 (m, 3H), 4.21 (s, 1H), 4.14 (s, 1H), 4.05-3.83 (m, 2H), 3.59-3.39 (m, 1H), 2.99-2.81 (m, 2H), 2.40 (dd, J = 12.2, 8.8 Hz, 2H), 1.92-1.81 (m, 3H), 1.29 (d, J = 1.8 Hz, 6H). |
| 448 | 1H NMR (400 MHz, Methanol-d4) δ 8.75 (d, J = 2.2 Hz, 1H), 8.70 (d, J = 2.2 Hz, 1H), 8.56 (s, 1H), 8.00 (d, J = 5.1 Hz, 1H), 7.70 (s, 1H), 7.21 (d, J = 5.1 Hz, 1H), 4.55-4.17 (m, 2H), 4.09 (s, 2H), 4.03-3.79 (m, 3H), 3.61-3.38 (m, 1H), 2.87 (ddd, J = 10.3, 7.5, 3.0 Hz, 2H), 2.52-2.24 (m, 2H), 1.44 (s, 9H), 1.29 (d, J = 1.7 Hz, 6H). |
| 449 | 1H NMR (400 MHz, Methanol-d4) δ 8.76 (d, J = 2.2 Hz, 1H), 8.71 (d, J = 2.2 Hz, 1H), 8.64 (s, 1H), 8.02 (d, J = 5.1 Hz, 1H), 7.71 (s, 1H), 7.22 (d, J = 5.1 Hz, 1H), 4.82-4.67 (m, 2H), 4.58-4.26 (m, 3H), 4.08-3.83 (m, 2H), 3.60-3.41 (m, 1H), 1.93 (s, 3H), 1.29 (d, J = 1.7 Hz, 6H). |
| 450 | 1H NMR (400 MHz, Methanol-d4) δ 8.74 (d, J = 2.2 Hz, 1H), 8.67 (d, J = 2.1 Hz, 1H), 8.58 (s, 1H), 8.00 (d, J = 5.1 Hz, 1H), 7.70 (s, 1H), 7.20 (d, J = 5.0 Hz, 1H), 4.42 (ddd, J = 49.0, 9.4, 2.1 Hz, 1H), 4.06-3.81 (m, 2H), 3.62-3.42 (m, 1H), 2.76 (ddt, J = 9.6, 7.3, 2.5 Hz, 2H), 2.19 (ddd, J = 10.5, 8.0, 2.8 Hz, 2H), 1.46 (s, 3H), 1.29 (d, J = 1.7 Hz, 6H). |
| 451 | 1H NMR (400 MHz, Methanol-d4) δ 8.74 (s, 1H), 8.72 (d, J = 2.1 Hz, 1H), 8.60 (d, J = 2.1 Hz, 1H), 8.37 (s, 1H), 8.02 (d, J = 8.6 Hz, 2H), 7.82 (d, J = 5.0 Hz, 1H), 7.60 (d, J = 8.5 Hz, 2H), 7.17 (d, J = 5.1 Hz, 1H), 4.43 (s, 2H), 2.97 (s, 3H). |
| 452 | 1H NMR (400 MHz, Methanol-d4) δ 8.76 (d, J = 2.1 Hz, 1H), 8.68 (d, J = 2.2 Hz, 1H), 8.58 (s, 1H), 8.00 (d, J = 5.1 Hz, 1H), 7.72 (s, 1H), 7.21 (d, J = 5.1 Hz, 1H), 4.37 (s, 2H), 4.29 (p, J = 7.7 Hz, 1H), 2.87-2.62 (m, 2H), 2.41-2.25 (m, 2H), 2.24-2.09 (m, 4H), 1.33 (s, 3H). |
| 453 | 1H NMR (400 MHz, Methanol-d4) δ 8.75 (d, J = 2.1 Hz, 1H), 8.69 (d, J = 2.2 Hz, 1H), 8.57 (s, 1H), 8.04-7.95 (m, 1H), 7.72 (s, 1H), 7.21 (d, J = 5.1 Hz, 1H), 4.36 (s, 2H), 4.29 (p, J = 7.7 Hz, 1H), 4.22-4.10 (m, 1H), 2.80-2.50 (m, 3H), 2.37 (dt, J = 11.9, 6.2 Hz, 1H), 2.18 (dd, J = 11.5, 7.8 Hz, 2H), 2.13-1.93 (m, 2H). |
| 454 | 1H NMR (400 MHz, Methanol-d4) δ 8.64 (d, J = 2.2 Hz, 1H), 8.63 (d, J = 2.2 Hz, 1H), 8.55 (s, 1H), 7.86 (d, J = 4.7 Hz, 1H), 7.13 (d, J = 4.7 Hz, 1H), 4.86-4.79 (m, 2H), 4.68-4.54 (m, 2H), 4.38-4.19 (m, 3H), 2.24-2.12 (m, 6H), 2.08-1.94 (m, 6H). |
| 455 | 1H NMR (400 MHz, Methanol-d4) δ 8.75 (d, J = 2.2 Hz, 1H), 8.67 (d, J = 2.1 Hz, 1H), 8.59 (s, 1H), 7.96 (d, J = 5.1 Hz, 1H), 7.65 (s, 1H), 7.21 (d, J = 5.1 Hz, 1H), 4.58-4.34 (m, 2H), 4.34-4.22 (m, 1H), 4.09-3.85 (m, 1H), 3.65 (s, 3H), 3.58-3.43 (m, 1H), 2.74-2.57 (m, 2H), 2.57-2.45 (m, 2H), 1.29 (d, J = 1.6 Hz, 6H). |
| 456 | 1H NMR (400 MHz, Methanol-d4) δ 8.75 (d, J = 2.2 Hz, 1H), 8.67 (d, J = 2.1 Hz, 1H), 8.59 (s, 1H), 7.95 (d, J = 5.1 Hz, 1H), 7.64 (s, 1H), 7.21 (d, J = 5.1 Hz, 1H), 4.55-4.32 (m, 3H), 4.10-3.85 (m, 1H), 3.57-3.40 (m, 1H), 2.71-2.46 (m, 4H), 1.97 (s, 3H), 1.29 (d, J = 1.6 Hz, 6H). |
| 457 | 1H NMR (400 MHz, Methanol-d4) δ 8.75 (d, J = 2.2 Hz, 1H), 8.70 (d, J = 2.2 Hz, 1H), 8.57 (s, 1H), 7.99 (d, J = 5.1 Hz, 1H), 7.78 (s, 1H), 7.21 (d, J = 5.1 Hz, 1H), 4.42 (ddd, J = 49.2, 9.4, 2.1 Hz, 1H), 4.19-3.83 (m, 3H), 3.77-3.59 (m, 3H), 3.56-3.41 (m, 1H), 3.07-2.93 (m, 2H), 2.17-2.01 (m, 2H), 1.29 (d, J = 1.6 Hz, 6H). |
| 458 | 1H NMR (400 MHz, Methanol-d4) δ 8.75 (d, J = 2.2 Hz, 1H), 8.70 (d, J = 2.2 Hz, 1H), 8.58 (s, 1H), 8.00 (d, J = 5.1 Hz, 1H), 7.79 (s, 1H), 7.21 (d, J = 5.1 Hz, 1H), 4.42 (ddd, J = 49.0, 9.4, 2.1 Hz, 1H), 4.26-4.06 (m, 2H), 4.05-3.83 (m, 1H), 3.63-3.40 (m, 1H), 3.11-2.97 (m, 2H), 2.16-2.00 (m, 2H), 1.93 (s, 3H), 1.29 (d, J = 1.7 Hz, 6H). |
| 459 | 1H NMR (400 MHz, Methanol-d4) δ 8.75 (d, J = 2.2 Hz, 1H), 8.65 (d, J = 2.2 Hz, 1H), 8.58 (s, 1H), 8.02 (d, J = 5.1 Hz, 1H), 7.96 (s, 1H), 7.21 (d, J = 5.0 Hz, 1H), 4.36 (s, 2H), 4.30-4.18 (m, 1H), 4.16-4.05 (m, 1H), 2.21-1.98 (m, 2H), 1.98-1.84 (m, 1H), 1.84-1.75 (m, 1H), 1.75-1.53 (m, 4H). |
| 460 | 1H NMR (400 MHz, Methanol-d4) δ 8.75 (d, J = 2.2 Hz, 1H), 8.69 (d, J = 2.2 Hz, 1H), 8.64 (s, 1H), 7.99 (d, J = 5.1 Hz, 1H), 7.65 (s, 1H), 7.21 (d, J = 5.0 Hz, 1H), 5.22-5.06 (m, 3H), 4.76 (d, J = 3.4 Hz, 2H), 4.39 (s, 2H). |
| 461 | 1H NMR (400 MHz, Methanol-d4) δ 8.75 (d, J = 2.2 Hz, 1H), 8.68 (d, J = 2.2 Hz, 1H), 8.58 (s, 1H), 8.30 (s, 1H), 7.99 (d, J = 5.0 Hz, 1H), 7.22 (d, J = 5.1 Hz, 1H), 4.35 (s, 2H), 2.89 (dq, J = 7.0, 3.6 Hz, 1H), 1.16-1.06 (m, 2H), 0.89-0.75 (m, 2H). |
| 462 | 1H NMR (400 MHz, Methanol-d4) δ 8.75 (d, J = 2.2 Hz, 1H), 8.66 (d, J = 2.2 Hz, 1H), 8.58 (s, 1H), 8.00 (d, J = 5.1 Hz, 1H), 7.88 (s, 1H), 7.21 (d, J = 5.1 Hz, 1H), 4.36 (s, 2H), 4.26-4.08 (m, 1H), 1.41 (d, J = 6.4 Hz, 6H). |
| 463 | 1H NMR (400 MHz, Methanol-d4) δ 8.74 (d, J = 2.2 Hz, 1H), 8.66 (d, J = 2.2 Hz, 1H), 8.54 (s, 1H), 8.02 (d, J = 5.1 Hz, 1H), 7.81 (s, 1H), 7.21 (d, J = 5.0 Hz, 1H), 4.36 (s, 2H), 3.20 (s, 3H). |

TABLE 2-continued

| compound | 1H-NMR |
|---|---|
| 464 | 1H NMR (400 MHz, Methanol-d4) δ 8.74 (d, J = 2.2 Hz, 1H), 8.66 (d, J = 2.2 Hz, 1H), 8.54 (s, 1H), 8.04 (d, J = 5.1 Hz, 1H), 7.93 (s, 1H), 7.20 (d, J = 5.0 Hz, 1H), 4.37-4.24 (m, 1H), 2.94 (s, 3H), 2.73 (s, 3H), 2.65-2.53 (m, 1H), 2.19-2.07 (m, 1H), 1.97-1.59 (m, 7H). |
| 465 | 1H NMR (400 MHz, Methanol-d4) δ 8.74 (d, J = 2.1 Hz, 1H), 8.66 (d, J = 2.2 Hz, 1H), 8.46 (s, 1H), 7.98 (d, J = 5.0 Hz, 1H), 7.82 (s, 1H), 7.20 (d, J = 5.1 Hz, 1H), 4.39-4.26 (m, 1H), 2.93 (s, 3H), 2.91-2.83 (m, 1H), 2.73 (s, 3H), 2.53-2.36 (m, 1H), 2.29-2.17 (m, 1H), 2.12-2.02 (m, 1H), 2.02-1.80 (m, 3H). |
| 466 | 1H NMR (400 MHz, Methanol-d4) δ 8.74 (d, J = 2.1 Hz, 1H), 8.68 (d, J = 2.2 Hz, 1H), 8.51 (s, 1H), 8.01 (d, J = 5.1 Hz, 1H), 7.92 (s, 1H), 7.21 (d, J = 5.0 Hz, 1H), 4.52-4.32 (m, 1H), 3.02-2.93 (m, 1H), 2.92 (s, 3H), 2.75 (s, 3H), 2.52-2.31 (m, 2H), 2.22-2.05 (m, 1H), 1.97-1.83 (m, 2H), 1.84-1.67 (m, 1H). |
| 467 | 1H NMR (400 MHz, Methanol-d4) δ 8.74 (d, J = 2.2 Hz, 1H), 8.68 (d, J = 2.1 Hz, 1H), 8.51 (s, 1H), 8.01 (d, J = 5.1 Hz, 1H), 7.92 (s, 1H), 7.21 (d, J = 5.0 Hz, 1H), 4.48-4.34 (m, 1H), 3.02-2.93 (m, 1H), 2.92 (s, 3H), 2.75 (s, 3H), 2.52-2.31 (m, 2H), 2.23-2.06 (m, 1H), 1.99-1.83 (m, 2H), 1.83-1.67 (m, 1H). |
| 468 | 1H NMR (400 MHz, Methanol-d4) δ 8.75 (d, J = 2.2 Hz, 1H), 8.72 (d, J = 2.1 Hz, 1H), 8.52 (s, 1H), 8.29 (s, 1H), 7.92 (d, J = 5.0 Hz, 1H), 7.22 (d, J = 5.1 Hz, 1H), 2.92 (s, 3H), 2.77 (s, 3H), 2.31-2.08 (m, 8H), 2.00-1.90 (m, 2H). |
| 469 | 1H NMR (400 MHz, Methanol-d4) δ 8.74 (d, J = 2.1 Hz, 1H), 8.66 (d, J = 2.2 Hz, 1H), 8.46 (s, 1H), 7.98 (d, J = 5.0 Hz, 1H), 7.82 (s, 1H), 7.20 (d, J = 5.1 Hz, 1H), 4.41-4.26 (m, 1H), 2.93 (s, 3H), 2.92-2.85 (m, 1H), 2.73 (s, 3H), 2.45 (dt, J = 14.7, 7.7 Hz, 1H), 2.28-2.16 (m, 1H), 2.12-2.03 (m, 1H), 2.02-1.81 (m, 3H). |
| 470 | 1H NMR (400 MHz, Methanol-d4) δ 8.74 (d, J = 2.2 Hz, 1H), 8.65 (d, J = 2.2 Hz, 1H), 8.50 (s, 1H), 7.99 (d, J = 5.0 Hz, 1H), 7.85 (s, 1H), 7.20 (d, J = 5.0 Hz, 1H), 3.95-3.80 (m, 1H), 2.92 (s, 3H), 2.72 (s, 3H), 2.53-2.38 (m, 1H), 2.31-2.12 (m, 2H), 2.05-1.83 (m, 2H), 1.69-1.33 (m, 4H). |
| 471 | 1H NMR (400 MHz, Methanol-d4) δ 8.74 (d, J = 2.2 Hz, 1H), 8.70 (d, J = 2.2 Hz, 1H), 8.51 (s, 1H), 8.00 (d, J = 5.1 Hz, 1H), 7.73 (s, 1H), 7.21 (d, J = 5.0 Hz, 1H), 4.67-4.49 (m, 1H), 3.20-3.06 (m, 1H), 2.93 (s, 3H), 2.85-2.69 (m, 2H), 2.78 (s, 3H), 2.50-2.33 (m, 2H). |
| 472 | 1H NMR (400 MHz, Methanol-d4) δ 8.74 (d, J = 2.2 Hz, 1H), 8.67 (d, J = 2.2 Hz, 1H), 8.50 (s, 1H), 7.97 (d, J = 5.1 Hz, 1H), 7.74 (s, 1H), 7.20 (d, J = 5.0 Hz, 1H), 4.33 (p, J = 8.0 Hz, 1H), 3.02-2.94 (m, 1H), 2.93 (s, 3H), 2.88-2.76 (m, 2H), 2.73 (s, 3H), 2.42-2.24 (m, 2H). |
| 473 | 1H NMR (400 MHz, Methanol-d4) δ 8.82 (d, J = 2.2 Hz, 1H), 8.75 (d, J = 2.2 Hz, 1H), 8.50 (s, 1H), 8.45 (s, 1H), 7.91 (d, J = 5.1 Hz, 1H), 7.21 (d, J = 5.1 Hz, 1H), 2.91 (s, 3H), 2.43 (s, 2H), 2.33-2.06 (m, 6H), 1.96 (s, 3H), 1.94-1.87 (m, 2H). |
| 474 | 1H NMR (400 MHz, Methanol-d4) δ 8.81-8.71 (m, 2H), 8.56 (s, 1H), 8.37 (s, 1H), 7.94 (d, J = 5.1 Hz, 1H), 7.22 (d, J = 5.1 Hz, 1H), 4.34 (s, 2H), 2.26-2.14 (m, 6H), 2.14-2.01 (m, 6H). |
| 475 | 1H NMR (400 MHz, Methanol-d4) δ 8.81-8.73 (m, 2H), 8.56 (s, 1H), 8.51 (s, 1H), 7.93 (d, J = 5.1 Hz, 1H), 7.22 (d, J = 5.1 Hz, 1H), 4.34 (s, 2H), 2.73 (s, 3H), 2.26-2.13 (m, 6H), 2.09-1.95 (m, 6H). |
| 476 | 1H NMR (400 MHz, Methanol-d4) δ 8.76 (d, J = 2.2 Hz, 1H), 8.74 (d, J = 2.1 Hz, 1H), 8.56 (s, 1H), 8.40 (s, 1H), 7.93 (d, J = 5.1 Hz, 1H), 7.22 (d, J = 5.1 Hz, 1H), 4.34 (s, 2H), 2.28-2.20 (m, 6H), 2.20-2.12 (m, 6H), 1.89 (s, 3H). |
| 477 | 1H NMR (400 MHz, Methanol-d4) δ 8.79 (d, J = 2.2 Hz, 1H), 8.77 (d, J = 2.2 Hz, 1H), 8.60 (s, 1H), 8.56 (s, 1H), 7.96 (d, J = 5.1 Hz, 1H), 7.23 (d, J = 5.1 Hz, 1H), 3.97-3.81 (m, 1H), 3.75-3.54 (m, 8H), 2.65 (s, 6H), 2.65 (m, 1H), 2.09 (d, J = 12.2 Hz, 2H), 1.97 (s, 3H), 1.90-1.78 (m, 2H), 1.75-1.55 (m, 2H), 1.53-1.36 (m, 2H). |
| 478 | 1H NMR (400 MHz, Methanol-d4) δ 8.79 (d, J = 2.2 Hz, 1H), 8.77 (d, J = 2.2 Hz, 1H), 8.60 (s, 1H), 8.56 (s, 1H), 7.96 (d, J = 5.1 Hz, 1H), 7.23 (d, J = 5.1 Hz, 1H), 4.64 (t, J = 11.9 Hz, 2H), 4.31 (t, J = 12.2 Hz, 2H), 4.01-3.80 (m, 1H), 2.65 (s, 6H), 2.42-2.26 (m, 1H), 2.09 (d, J = 12.3 Hz, 2H), 1.97 (s, 3H), 1.91 (d, J = 14.8 Hz, 2H), 1.71-1.52 (m, 2H), 1.49-1.36 (m, 2H). |
| 479 | 1H NMR (400 MHz, Methanol-d4) δ 8.79 (d, J = 2.2 Hz, 1H), 8.77 (d, J = 2.2 Hz, 1H), 8.60 (s, 1H), 8.56 (s, 1H), 7.95 (d, J = 5.2 Hz, 1H), 7.23 (d, J = 5.1 Hz, 1H), 3.97-3.79 (m, 1H), 2.71 (s, 3H), 2.65 (s, 6H), 2.26-2.13 (m, 1H), 2.09 (d, J = 12.2 Hz, 2H), 1.97 (s, 3H), 1.92 (d, J = 13.0 Hz, 2H), 1.73-1.54 (m, 2H), 1.50-1.31 (m, 2H). |
| 480 | 1H NMR (400 MHz, Methanol-d4) δ 8.79-8.76 (m, 1H), 8.74 (d, J = 2.1 Hz, 1H), 8.55 (s, 1H), 8.53 (s, 1H), 7.93 (d, J = 5.0 Hz, 1H), 7.21 (d, J = 5.1 Hz, 1H), 2.92 (s, 3H), 2.64 (s, 6H), 1.62-1.50 (m, 1H), 0.94-0.85 (m, 2H), 0.85-0.75 (m, 2H). |
| 481 | 1H NMR (400 MHz, Methanol-d4) δ 8.79-8.72 (m, 2H), 8.48 (s, 1H), 8.40 (s, 1H), 7.91 (d, J = 5.1 Hz, 1H), 7.21 (d, J = 5.1 Hz, 1H), 2.90 (s, 3H), 2.69-2.55 (m, 1H), 2.22-2.09 (m, 6H), 2.09-1.94 (m, 6H), 0.79-0.67 (m, 2H), 0.55-0.45 (m, 2H). |
| 482 | 1H NMR (400 MHz, Methanol-d4) δ 8.75 (d, J = 2.2 Hz, 1H), 8.73 (d, J = 2.2 Hz, 1H), 8.47 (s, 1H), 8.33 (s, 1H), 7.92 (d, J = 5.1 Hz, 1H), 7.21 (d, J = 5.1 Hz, 1H), 2.90 (s, 3H), 2.30-2.08 (m, 12H), 1.89 (s, 3H). |
| 483 | 1H NMR (400 MHz, Methanol-d4) δ 8.75 (d, J = 2.1 Hz, 1H), 8.74 (d, J = 2.2 Hz, 1H), 8.48 (s, 1H), 8.29 (s, 1H), 7.92 (d, J = 5.1 Hz, 1H), 7.21 (d, J = 5.0 Hz, 1H), 2.91 (s, 3H), 2.23-2.12 (m, 6H), 2.12-2.01 (m, 6H). |
| 484 | 1H NMR (400 MHz, Methanol-d4) δ 8.75 (d, J = 2.2 Hz, 1H), 8.72 (d, J = 2.2 Hz, 1H), 8.47 (s, 1H), 8.30 (s, 1H), 7.92 (d, J = 5.1 Hz, 1H), 7.21 (d, J = 5.1 Hz, 1H), 4.59-4.47 (m, 2H), 4.10-3.92 (m, 2H), 2.90 (s, 3H), 2.30 (p, J = 7.8 Hz, 2H), 2.21-2.11 (m, 6H), 2.07 (d, J = 8.0 Hz, 6H). |

TABLE 2-continued

| compound | 1H-NMR |
|---|---|
| 485 | 1H NMR (400 MHz, Methanol-d4) δ 8.75 (s, 2H), 8.47 (s, 1H), 8.42 (s, 1H), 7.91 (d, J = 5.0 Hz, 1H), 7.21 (d, J = 5.1 Hz, 1H), 2.91 (s, 3H), 2.73 (d, J = 0.8 Hz, 3H), 2.23-2.11 (m, 6H), 2.07-1.95 (m, 6H). |
| 486 | 1H NMR (400 MHz, Methanol-d4) δ 8.80-8.71 (m, 2H), 8.47 (s, 1H), 8.34 (s, 1H), 7.91 (d, J = 5.1 Hz, 1H), 7.21 (d, J = 5.1 Hz, 1H), 3.59 (s, 3H), 2.90 (s, 3H), 2.27-2.16 (m, 6H), 2.14-2.05 (m, 6H). |
| 487 | 1H NMR (400 MHz, Methanol-d4) δ 8.81 (s, 1H), 8.77 (d, J = 2.2 Hz, 1H), 8.65 (s, 1H), 8.61 (s, 1H), 7.96 (d, J = 5.1 Hz, 1H), 7.23 (d, J = 5.1 Hz, 1H), 4.36 (s, 2H), 3.69 (s, 3H), 2.62 (s, 6H). |
| 488 | 1H NMR (400 MHz, Methanol-d4) δ 8.79 (s, 1H), 8.76 (d, J = 2.2 Hz, 1H), 8.57 (s, 1H), 8.54 (s, 1H), 7.94 (d, J = 5.1 Hz, 1H), 7.23 (d, J = 5.1 Hz, 1H), 3.68 (s, 3H), 2.92 (s, 3H), 2.61 (s, 6H). |
| 489 | 1H NMR (400 MHz, Methanol-d4) δ 8.75 (d, J = 2.2 Hz, 1H), 8.72 (d, J = 2.1 Hz, 1H), 8.52 (s, 1H), 8.46 (s, 1H), 7.91 (d, J = 5.1 Hz, 1H), 7.22 (d, J = 5.1 Hz, 1H), 2.92 (s, 3H), 2.70 (s, 1H), 2.40 (s, 6H). |
| 490 | 1H NMR (400 MHz, Methanol-d4) δ 8.80 (s, 1H), 8.75 (d, J = 2.2 Hz, 1H), 8.67 (d, J = 2.2 Hz, 1H), 8.45 (dd, J = 1.9, 0.8 Hz, 1H), 8.02 (d, J = 5.0 Hz, 1H), 7.95 (s, 1H), 7.85 (t, J = 2.2 Hz, 1H), 7.83 (dd, J = 2.4, 0.7 Hz, 1H), 7.22 (d, J = 5.0 Hz, 1H), 4.27-4.12 (m, 1H), 1.42 (d, J = 6.4 Hz, 6H). |
| 491 | 1H NMR (400 MHz, Methanol-d4) δ 8.77 (s, 1H), 8.76 (d, J = 2.2 Hz, 1H), 8.71 (t, J = 2.2 Hz, 1H), 8.70-8.65 (m, 2H), 8.51 (d, J = 2.2 Hz, 1H), 8.02 (d, J = 5.0 Hz, 1H), 7.92 (s, 1H), 7.22 (d, J = 5.1 Hz, 1H), 4.27-4.12 (m, 1H), 2.19 (s, 3H), 1.42 (d, J = 6.4 Hz, 6H). |
| 492 | 1H NMR (400 MHz, Methanol-d4) δ 8.79 (d, J = 2.2 Hz, 1H), 8.76 (d, J = 2.1 Hz, 1H), 8.67 (s, 1H), 8.60 (s, 1H), 7.96 (d, J = 5.1 Hz, 1H), 7.23 (d, J = 5.1 Hz, 1H), 4.36 (s, 2H), 2.67 (s, 6H), 1.98 (s, 3H). |
| 493 | 1H NMR (400 MHz, Methanol-d4) δ 8.81 (s, 1H), 8.74 (d, J = 2.1 Hz, 1H), 8.67 (d, J = 2.2 Hz, 1H), 8.01 (d, J = 5.1 Hz, 1H), 7.97 (s, 1H), 7.21 (d, J = 5.1 Hz, 1H), 7.20 (s, 1H), 4.28-4.08 (m, 1H), 2.14 (s, 3H), 1.44 (d, J = 6.4 Hz, 6H). |
| 494 | 1H NMR (400 MHz, Methanol-d4) δ 8.79 (d, J = 2.2 Hz, 1H), 8.77 (d, J = 2.2 Hz, 1H), 8.62 (s, 1H), 8.60 (s, 1H), 7.97 (d, J = 5.1 Hz, 1H), 7.23 (d, J = 5.1 Hz, 1H), 4.59 (dddd, J = 48.7, 16.5, 9.3, 2.2 Hz, 1H), 3.93 (ddd, J = 35.8, 14.6, 2.2 Hz, 1H), 3.59-3.40 (m, 1H), 2.66 (s, 6H), 1.97 (s, 3H), 1.45 (d, J = 21.7, 6H). |
| 495 | 1H NMR (400 MHz, Methanol-d4) δ 8.79 (d, J = 2.2 Hz, 1H), 8.77 (d, J = 2.2 Hz, 1H), 8.61 (s, 1H), 8.59 (s, 1H), 7.97 (d, J = 5.1 Hz, 1H), 7.23 (d, J = 5.1 Hz, 1H), 4.50 (dddd, J = 48.9, 9.4, 2.0 Hz, 1H), 3.92 (ddd, J = 37.1, 14.6, 2.0 Hz, 1H), 3.62-3.39 (m, 1H), 3.30 (s, 3H), 2.66 (s, 6H), 1.97 (s, 3H), 1.27 (dd, J = 3.4, 1.7 Hz, 6H). |
| 496 | 1H NMR (400 MHz, Methanol-d4) δ 8.79 (d, J = 2.2 Hz, 1H), 8.76 (d, J = 2.1 Hz, 1H), 8.67 (s, 1H), 8.60 (s, 1H), 7.96 (d, J = 5.1 Hz, 1H), 7.23 (d, J = 5.1 Hz, 1H), 4.36 (s, 2H), 2.67 (s, 6H), 1.98 (s, 3H). |
| 497 | 1H NMR (400 MHz, Methanol-d4) δ 8.78 (d, J = 2.2 Hz, 1H), 8.76 (d, J = 2.2 Hz, 1H), 8.59 (s, 1H), 8.53 (s, 1H), 7.95 (d, J = 5.1 Hz, 1H), 7.23 (d, J = 5.1 Hz, 1H), 2.65 (s, 6H), 1.97 (s, 3H). |
| 498 | 1H NMR (400 MHz, Methanol-d4) δ 8.78 (d, J = 2.2 Hz, 1H), 8.77 (d, J = 2.2 Hz, 1H), 8.59 (s, 1H), 8.53 (s, 1H), 7.95 (d, J = 5.1 Hz, 1H), 7.23 (d, J = 5.1 Hz, 1H), 2.92 (s, 3H), 2.65 (s, 6H), 1.97 (s, 3H). |
| 499 | 1H NMR (400 MHz, Methanol-d4) δ 8.83 (d, J = 2.1 Hz, 1H), 8.75 (d, J = 2.2 Hz, 1H), 8.56 (s, 1H), 8.47 (s, 1H), 7.92 (d, J = 5.1 Hz, 1H), 7.22 (d, J = 5.1 Hz, 1H), 4.53-4.31 (m, 1H), 4.04-3.77 (m, 1H), 3.56-3.40 (m, 1H), 3.34 (s, 3H), 2.43 (s, 2H), 2.34-2.07 (m, 6H), 1.95-1.88 (m, 2H), 1.28 (d, J = 1.6 Hz, 6H). |
| 500 | 1H NMR (400 MHz, Methanol-d4) δ 8.92 (s, 1H), 8.75 (d, J = 2.2 Hz, 1H), 8.57 (s, 1H), 8.53 (s, 1H), 7.92 (d, J = 5.1 Hz, 1H), 7.22 (d, J = 5.1 Hz, 1H), 4.41 (ddd, J = 49.1, 9.4, 2.0 Hz, 1H), 3.92 (ddd, J = 36.6, 14.6, 2.1 Hz, 1H), 3.65 (s, 3H), 3.57-3.40 (m, 1H), 2.40 (s, 2H), 2.32-2.04 (m, 6H), 1.89 (d, J = 11.0 Hz, 2H), 1.28 (d, J = 1.6 Hz, 6H). |
| 501 | 1H NMR (400 MHz, Methanol-d4) δ 8.75 (d, J = 2.2 Hz, 1H), 8.65 (d, J = 2.2 Hz, 1H), 8.59 (s, 1H), 7.94 (d, J = 5.1 Hz, 1H), 7.79 (s, 1H), 7.21 (d, J = 5.1 Hz, 1H), 5.20-5.05 (m, 1H), 4.42 (ddd, J = 49.1, 9.3, 2.1 Hz, 1H), 4.30-4.11 (m, 1H), 3.93 (ddd, J = 36.4, 14.6, 2.1 Hz, 1H), 3.58-3.41 (m, 1H), 2.27-2.15 (m, 1H), 2.12-2.06 (m, 1H), 2.08 (s, 3H), 1.95-1.70 (m, 5H), 1.70-1.55 (m, 1 H), 1.28 (d, J = 1.6 Hz, 6H). |
| 502 | 1H NMR (400 MHz, Methanol-d4) δ 8.79-8.75 (m, 1H), 8.74 (s, 1H), 8.70 (d, J = 2.2 Hz, 1H), 8.61 (dd, J = 4.9, 1.4 Hz, 1H), 8.56 (d, J = 2.2 Hz, 1H), 8.21 (s, 1H), 8.11-7.98 (m, 1H), 7.83 (d, J = 5.1 Hz, 1H), 7.76-7.65 (m, 1H), 7.16 (d, J = 5.1 Hz, 1H), 4.05-3.86 (m, 1H), 3.77-3.61 (m, 1H), 2.17-2.05 (m, 2H), 2.05-1.95 (m, 2H), 1.64-1.32 (m, 5H), 0.89-0.80 (m, 2H), 0.77-0.68 (m, 2H). |
| 503 | 1H NMR (400 MHz, Methanol-d4) δ 8.75 (d, J = 2.2 Hz, 1H), 8.73 (d, J = 2.2 Hz, 1H), 8.54 (s, 1H), 8.25 (s, 1H), 7.94 (d, J = 5.0 Hz, 1H), 7.21 (d, J = 5.1 Hz, 1H), 4.40 (ddd, J = 49.2, 9.5, 2.2 Hz, 1H), 4.03-3.78 (m, 1H), 3.61-3.36 (m, 1H), 2.40-2.22 (m, 6H), 2.19-1.92 (m, 6H), 1.28 (d, J = 1.7 Hz, 6H). |
| 504 | 1H NMR (400 MHz, Methanol-d4) δ 8.75 (d, J = 2.2 Hz, 1H), 8.69 (d, J = 2.2 Hz, 1H), 8.57 (s, 1H), 8.37 (s, 1H), 7.91 (d, J = 5.1 Hz, 1H), 7.21 (d, J = 5.1 Hz, 1H), 4.42 (ddd, J = 49.1, 9.4, 2.1 Hz, 1H), 4.05 (d, J = 6.6 Hz, 1H), 3.93 (ddd, J = 36.6, 14.6, 2.1 Hz, 1H), 3.56-3.39 (m, 1H), 2.45 (d, J = 9.4 Hz, 1H), 2.38-2.28 (m, 1H), 2.28-2.22 (m, 1H), 2.00-1.81 (m, 4H), 1.69 (d, J = 9.4 Hz, 1H), 1.47 (q, J = 8.9, 7.8 Hz, 1H), 1.28 (d, J = 1.6 Hz, 6H). |
| 505 | 1H NMR (400 MHz, Methanol-d4) δ 8.74 (d, J = 2.2 Hz, 1H), 8.65 (d, J = 2.2 Hz, 1H), 8.55 (s, 1H), 8.01 (d, J = 5.0 Hz, 1H), 7.90 (s, 1H), 7.21 (d, J = 5.0 Hz, 1H), 6.28-6.14 (m, 2H), 5.65 (t, J = 6.0 Hz, 1H), 4.31-4.15 (m, 1H), 4.15-4.03 (m, |

TABLE 2-continued

| compound | 1H-NMR |
|---|---|
| | 1H), 3.95-3.82 (m, 1H), 3.82-3.66 (m, 1H), 2.12-1.96 (m, 6H), 1.97-1.84 (m, 1H), 1.82-1.73 (m, 1H), 1.73-1.63 (m, 4H), 1.62-1.30 (m, 4H). |
| 506 | 1H NMR (400 MHz, Methanol-d4) δ 8.75 (d, J = 2.2 Hz, 1H), 8.69 (d, J = 2.2 Hz, 1H), 8.51 (d, J = 0.6 Hz, 1H), 8.27 (s, 1H), 7.92 (d, J = 5.1 Hz, 1H), 7.21 (d, J = 5.1 Hz, 1H), 3.97-3.77 (m, 1H), 3.75-3.58 (m, 1H), 2.35-2.14 (m, 6H), 2.10-1.95 (m, 4H), 1.95-1.80 (m, 6H), 1.66-1.26 (m, 5H), 0.88-0.80 (m, 2H), 0.76-0.67 (m, 2H). |
| 507 | 1H NMR (400 MHz, Methanol-d4) δ 8.81 (s, 1H), 8.77 (d, J = 2.1 Hz, 1H), 8.61 (s, 1H), 8.60 (s, 1H), 7.95 (d, J = 5.1 Hz, 1H), 7.23 (d, J = 5.1 Hz, 1H), 4.42 (ddd, J = 49.2, 9.3, 2.0 Hz, 1H), 4.10-3.82 (m, 1H), 3.68 (s, 3H), 3.53-3.39 (m, 1H), 2.61 (s, 6H), 1.28 (d, J = 1.6 Hz, 6H). |
| 508 | 1H NMR (400 MHz, Methanol-d4) δ 8.80 (d, J = 2.2 Hz, 1H), 8.77 (d, J = 2.2 Hz, 1H), 8.62 (s, 1H), 8.60 (s, 1H), 7.96 (d, J = 5.1 Hz, 1H), 7.23 (d, J = 5.1 Hz, 1H), 4.55-4.30 (m, 1H), 4.03-3.83 (m, 1H), 3.47 (td, J = 15.6, 9.4 Hz, 1H), 2.66 (s, 6H), 1.98 (s, 3H), 1.28 (d, J = 1.6 Hz, 6H). |
| 509 | 1H NMR (400 MHz, Methanol-d4) δ 8.75 (d, J = 2.2 Hz, 1H), 8.66 (d, J = 2.2 Hz, 1H), 8.56 (s, 1H), 8.02 (d, J = 5.1 Hz, 1H), 7.84 (s, 1H), 7.21 (d, J = 5.1 Hz, 1H), 4.81-4.70 (m, 1H), 4.42 (ddd, J = 49.0, 9.4, 2.1 Hz, 1H), 4.14-4.03 (m, 1H), 3.93 (ddd, J = 36.5, 14.5, 2.1 Hz, 1H), 3.53-3.41 (m, 1H), 2.45-2.28 (m, 1H), 2.09-1.78 (m, 4H), 1.78-1.47 (m, 3H), 1.28 (d, J = 1.6 Hz, 6H). |
| 510 | 1H NMR (400 MHz, Methanol-d4) δ 8.75 (d, J = 2.1 Hz, 1H), 8.68 (d, J = 2.1 Hz, 1H), 8.56 (s, 1H), 7.99 (d, J = 5.1 Hz, 1H), 7.67 (s, 1H), 7.21 (d, J = 5.1 Hz, 1H), 4.53-4.33 (m, 1H), 4.32-4.22 (m, 1H), 4.03-3.82 (m, 1H), 3.59-3.37 (m, 1H), 2.82-2.62 (m, 2H), 2.39-2.23 (m, 2H), 2.24-2.05 (m, 4H), 1.32 (s, 3H), 1.29 (d, J = 1.6 Hz, 6H). |
| 511 | 1H NMR (400 MHz, Methanol-d4) δ 8.75 (d, J = 2.2 Hz, 1H), 8.68 (d, J = 2.2 Hz, 1H), 8.55 (s, 1H), 7.99 (d, J = 5.0 Hz, 1H), 7.68 (s, 1H), 7.21 (d, J = 5.0 Hz, 1H), 4.42 (ddd, J = 49.0, 9.4, 2.1 Hz, 1H), 4.28 (p, J = 7.6 Hz, 1H), 4.16 (p, J = 7.4 Hz, 1H), 4.04-3.80 (m, 1H), 3.57-3.39 (m, 1H), 2.77-2.50 (m, 3H), 2.41-2.30 (m, 1H), 2.16 (dd, J = 11.4, 7.8 Hz, 2H), 2.10-1.92 (m, 2H), 1.28 (d, J = 1.7 Hz, 6H). |
| 512 | 1H NMR (400 MHz, Methanol-d4) δ 8.75 (d, J = 2.2 Hz, 1H), 8.65 (d, J = 2.2 Hz, 1H), 8.51 (s, 1H), 8.01 (d, J = 5.1 Hz, 1H), 7.89 (s, 1H), 7.20 (d, J = 5.0 Hz, 1H), 4.28-4.16 (m, 1H), 4.15-4.04 (m, 1H), 2.92 (s, 3H), 2.13-1.96 (m, 2H), 1.92-1.79 (m, 1H), 1.87-1.49 (m, 5H). |
| 513 | 1H NMR (400 MHz, Methanol-d4) δ 8.75 (d, J = 2.2 Hz, 1H), 8.66 (d, J = 2.2 Hz, 1H), 8.56 (s, 1H), 8.01 (d, J = 5.1 Hz, 1H), 7.97 (s, 1H), 7.21 (d, J = 5.1 Hz, 1H), 4.31-4.19 (m, 1H), 4.18-4.07 (m, 1H), 2.15-1.99 (m, 2H), 2.00-1.85 (m, 1H), 1.85-1.75 (m, 1H), 1.76-1.65 (m, 3H), 1.65-1.56 (m, 3H), 1.42-1.32 (m, 2H). |
| 514 | 1H NMR (400 MHz, Methanol-d4) δ 8.74 (d, J = 2.2 Hz, 1H), 8.65 (d, J = 2.2 Hz, 1H), 8.51 (s, 1H), 8.01 (d, J = 5.1 Hz, 1H), 7.90 (d, J = 5.1 Hz, 1H), 7.20 (d, J = 5.1 Hz, 1H), 4.27-4.17 (m, 1H), 4.15-4.04 (m, 1H), 2.91-2.80 (m, 1H), 2.12-1.96 (m, 2H), 1.97-1.84 (m, 1H), 1.83-1.46 (m, 5H), 0.90-0.80 (m, 2H), 0.70-0.60 (m, 2H). |
| 515 | 1H NMR (400 MHz, Methanol-d4) δ 8.75 (d, J = 2.2 Hz, 1H), 8.69 (d, J = 2.2 Hz, 1H), 8.59 (s, 1H), 7.99 (d, J = 5.1 Hz, 1H), 7.94 (s, 1H), 7.21 (d, J = 5.0 Hz, 1H), 4.57-4.30 (m, 1H), 4.06-3.83 (m, 2H), 3.62-3.41 (m, 1H), 3.37-3.31 (m, 1H), 2.96 (s, 3H), 2.70 (d, J = 12.4 Hz, 1H), 2.35-2.01 (m, 3H), 1.80-1.41 (m, 4H), 1.28 (d, J = 1.7 Hz, 6H). |
| 516 | |
| 517 | 1H NMR (400 MHz, Methanol-d4) δ 8.74 (d, J = 2.2 Hz, 1H), 8.67 (d, J = 2.2 Hz, 1H), 8.63 (s, 1H), 8.02 (d, J = 5.1 Hz, 1H), 7.93 (s, 1H), 7.21 (d, J = 5.1 Hz, 1H), 4.55-4.33 (m, 2H), 3.94 (ddd, J = 36.6, 14.5, 2.1 Hz, 1H), 3.62-3.43 (m, 1H), 3.41-3.31 (m, 1H), 2.98 (s, 3H), 2.36-2.21 (m, 2H), 2.21-2.10 (m, 1H), 2.09-1.98 (m, 1H), 1.98-1.84 (m, 3H), 1.83-1.69 (m, 1H), 1.29 (d, J = 1.6 Hz, 6H). |
| 518 | 1H NMR (400 MHz, Methanol-d4) δ 8.74 (d, J = 2.2 Hz, 1H), 8.66 (d, J = 2.2 Hz, 1H), 8.54 (s, 1H), 8.00 (d, J = 5.1 Hz, 1H), 7.86 (s, 1H), 7.20 (d, J = 5.1 Hz, 1H), 4.50 (ddd, J = 48.9, 9.4, 2.1 Hz, 1H), 4.04-3.76 (m, 3H), 3.58-3.37 (m, 1H), 3.31 (s, 3H), 2.31 (d, J = 12.3 Hz, 1H), 2.12-1.84 (m, 3H), 1.69-1.32 (m, 4H), 1.31-1.23 (m, 6H). |
| 519 | 1H NMR (400 MHz, Methanol-d4) δ 8.72 (d, J = 2.2 Hz, 1H), 8.66 (s, 1H), 8.56 (d, J = 2.2 Hz, 1H), 8.11 (s, 1H), 8.05 (s, 1H), 7.82 (d, J = 5.1 Hz, 1H), 7.78 (d, J = 0.8 Hz, 1H), 7.18 (d, J = 5.1 Hz, 1H), 6.29 (tt, J = 55.0, 3.7 Hz, 1H), 4.67 (td, J = 14.7, 3.6 Hz, 2H), 4.06-3.83 (m, 1H), 3.83-3.60 (m, 1H), 2.18-1.92 (m, 4H), 1.66-1.32 (m, 5H), 0.88-0.80 (m, 2H), 0.78-0.68 (m, 2H). |
| 520 | 1H NMR (400 MHz, Methanol-d4) δ 8.75 (d, J = 2.2 Hz, 1H), 8.67 (d, J = 2.1 Hz, 1H), 8.53 (s, 1H), 7.99 (d, J = 5.1 Hz, 1H), 7.84 (s, 1H), 7.21 (d, J = 5.1 Hz, 1H), 4.51-4.30 (m, 3H), 4.03-3.81 (m, 1H), 3.55-3.37 (m, 1H), 2.45-2.26 (m, 2H), 1.92 (d, J = 4.7 Hz, 3H), 1.80 (d, J = 14.2 Hz, 1H), 1.28 (d, J = 1.7 Hz, 6H). |
| 521 | 1H NMR (400 MHz, Methanol-d4) δ 8.75 (d, J = 2.2 Hz, 1H), 8.66 (d, J = 2.2 Hz, 1H), 8.55 (d, J = 0.8 Hz, 1H), 8.00 (d, J = 5.0 Hz, 1H), 7.81 (s, 1H), 7.21 (d, J = 5.0 Hz, 1H), 4.27-4.00 (m, 2H), 3.22 (p, J = 6.8 Hz, 1H), 2.96 (s, 3H), 2.22-2.08 (m, 2H), 2.09-1.98 (m, 4H), 1.88-1.73 (m, 2H), 1.39 (d, J = 6.4 Hz, 6H). |
| 522 | 1H NMR (400 MHz, Methanol-d4) δ 8.75 (d, J = 2.2 Hz, 1H), 8.68 (d, J = 2.2 Hz, 1H), 8.56 (s, 1H), 8.00 (d, J = 5.1 Hz, 1H), 7.90 (s, 1H), 7.21 (d, J = 5.0 Hz, 1H), 4.54-4.30 (m, 3H), 3.92 (ddd, J = 36.5, 14.5, 2.1 Hz, 1H), 3.57-3.41 (m, 1H), 2.55-2.41 (m, 1H), 2.34-2.24 (m, 1H), 2.20-2.08 (m, 1H), 1.97-1.82 (m, 1H), 1.82-1.63 (m, 1H), 1.28 (d, J = 1.7 Hz, 6H). |
| 523 | 1H NMR (400 MHz, Methanol-d4) δ 8.75 (d, J = 2.2 Hz, 1H), 8.66 (d, J = 2.2 Hz, 1H), 8.62 (s, 1H), 8.01 (d, J = 5.1 Hz, 1H), 7.85 (s, 1H), 7.21 (d, J = 5.1 Hz, 1H), |

TABLE 2-continued

| compound | 1H-NMR |
|---|---|
| | 4.43 (ddd, J = 49.1, 9.4, 2.1 Hz, 1H), 4.24 (s, 1H), 3.96 (ddd, J = 36.5, 14.5, 2.1 Hz, 1H), 3.58-3.39 (m, 1H), 3.28-3.18 (m, 1H), 2.96 (s, 3H), 2.31-2.10 (m, 4H), 2.00-1.79 (m, 4H), 1.28 (d, J = 1.6 Hz, 6H). |
| 524 | 1H NMR (400 MHz, Methanol-d4) δ 8.77 (d, J = 2.2 Hz, 1H), 8.67 (d, J = 2.2 Hz, 1H), 8.62 (s, 1H), 8.03 (d, J = 5.0 Hz, 1H), 7.88 (s, 1H), 7.22 (d, J = 5.1 Hz, 1H), 4.41 (ddd, J = 49.1, 9.4, 2.0 Hz, 1H), 4.23-3.98 (m, 4H), 3.99-3.83 (m, 1H), 3.82-3.70 (m, 4H), 3.58-3.42 (m, 3H), 2.64-2.54 (m, 1H), 2.29-2.17 (m, 2H), 2.17-2.05 (m, 1H), 1.79-1.38 (m, 4H), 1.28 (d, J = 1.6 Hz, 6H). |
| 525 | 1H NMR (400 MHz, Methanol-d4) δ 8.76 (d, J = 2.2 Hz, 1H), 8.72 (d, J = 2.2 Hz, 1H), 8.55 (s, 2H), 7.89 (d, J = 5.1 Hz, 1H), 7.22 (d, J = 5.1 Hz, 1H), 4.41 (dd, J = 49.7, 8.8 Hz, 1H), 3.92 (dd, J = 36.6, 14.5 Hz, 1H), 3.59-3.39 (m, 1H), 2.48-2.34 (m, 2H), 2.25-2.14 (m, 4H), 2.09 (d, J = 12.0 Hz, 2H), 1.89-1.78 (m, 3H), 1.78-1.65 (m, 2H), 1.28 (d, J = 1.6 Hz, 6H). |
| 526 | 1H NMR (400 MHz, Methanol-d4) δ 8.75 (d, J = 2.2 Hz, 1H), 8.69 (d, J = 2.2 Hz, 1H), 8.60 (s, 1H), 7.98 (d, J = 5.1 Hz, 1H), 7.60 (s, 1H), 7.21 (d, J = 5.0 Hz, 1H), 5.22-5.05 (m, 2H), 4.78-4.68 (m, 2H), 3.92 (s, 2H), 3.68 (s, 2H), 2.25-1.78 (m, 5H), 1.62-1.32 (m, 4H), 0.92-0.80 (m, 2H), 0.78-0.68 (m, 2H). |
| 527 | 1H NMR (400 MHz, Methanol-d4) δ 8.74 (d, J = 2.1 Hz, 1H), 8.66 (d, J = 2.1 Hz, 1H), 8.50 (s, 1H), 7.98 (d, J = 5.0 Hz, 1H), 7.84 (s, 1H), 7.20 (d, J = 5.0 Hz, 1H), 4.04-3.77 (m, 3H), 3.67 (s, 1H), 2.30 (d, J = 12.0 Hz, 1H), 2.15-1.83 (m, 8H), 1.65-1.33 (m, 8H), 0.91-0.79 (m, 2H), 0.74 (dt, J = 8.1, 3.2 Hz, 2H). |
| 528 | 1H NMR (400 MHz, Methanol-d4) δ 8.74 (d, J = 2.2 Hz, 1H), 8.64 (d, J = 2.2 Hz, 1H), 8.46 (s, 1H), 7.97 (d, J = 5.1 Hz, 1H), 7.80 (s, 1H), 7.20 (d, J = 5.0 Hz, 1H), 4.42 (ddd, J = 49.0, 9.3, 2.1 Hz, 1H), 4.28-4.13 (m, 1H), 4.04-3.81 (m, 1H), 3.52-3.36 (m, 1H), 2.04-1.85 (m, 2H), 1.85-1.65 (m, 3H), 1.62-1.48 (m, 1H), 1.29 (s, 3H), 1.28 (d, J = 1.7 Hz, 6H). |
| 529 | 1H NMR (400 MHz, Methanol-d4) δ 8.74 (d, J = 2.2 Hz, 1H), 8.65 (d, J = 2.2 Hz, 1H), 8.55 (s, 1H), 8.04 (d, J = 5.0 Hz, 1H), 7.89 (s, 1H), 7.21 (d, J = 5.1 Hz, 1H), 4.41 (ddd, J = 49.1, 9.4, 2.1 Hz, 1H), 4.18-4.04 (m, 1H), 4.01-3.79 (m, 1H), 3.58-3.40 (m, 1H), 2.22-2.02 (m, 2H), 2.00-1.82 (m, 1H), 1.78-1.65 (m, 2H), 1.53-1.32 (m, 3H), 1.30-1.25 (m, 9H). |
| 530 | 1H NMR (400 MHz, Methanol-d4) δ 8.75 (d, J = 2.1 Hz, 1H), 8.66 (d, J = 2.1 Hz, 1H), 8.54 (s, 1H), 8.00 (d, J = 5.0 Hz, 1H), 7.86 (s, 1H), 7.20 (d, J = 5.1 Hz, 1H), 4.75-4.43 (m, 1H), 4.03-3.74 (m, 3H), 3.61-3.41 (m, 1H), 2.31 (d, J = 12.7 Hz, 1H), 2.04 (d, J = 11.9 Hz, 1H), 1.94 (m, 2H), 1.67-1.24 (m, 10H). |
| 531 | 1H NMR (400 MHz, Methanol-d4) δ 8.75 (d, J = 2.2 Hz, 1H), 8.66 (d, J = 2.2 Hz, 1H), 8.56 (s, 1H), 8.00 (d, J = 5.0 Hz, 1H), 7.85 (s, 1H), 7.21 (d, J = 5.1 Hz, 1H), 4.59 (dddd, J = 48.6, 16.6, 9.3, 2.2 Hz, 1H), 4.16 (p, J = 6.4 Hz, 1H), 3.93 (ddd, J = 35.5, 14.6, 2.2 Hz, 1H), 3.61-3.42 (m, 1H), 1.46 (d, J = 21.8, 1.9 Hz, 6H), 1.40 (d, J = 6.4 Hz, 6H). |
| 532 | 1H NMR (400 MHz, Methanol-d4) δ 8.75 (d, J = 2.2 Hz, 1H), 8.70 (d, J = 2.2 Hz, 1H), 8.56 (s, 1H), 8.04 (d, J = 5.1 Hz, 1H), 7.94 (s, 1H), 7.21 (d, J = 5.1 Hz, 1H), 4.53-4.30 (m, 1H), 4.01-3.82 (m, 3H), 3.55-3.40 (m, 1H), 2.39 (d, J = 12.0 Hz, 1H), 2.13 (d, J = 13.1 Hz, 1H), 1.93 (s, 4H), 1.61 (d, J = 13.2 Hz, 1H), 1.42 (s, 1H), 1.28 (d, J = 1.6 Hz, 8H). |
| 533 | 1H NMR (400 MHz, Methanol-d4) δ 8.76 (d, J = 2.2 Hz, 1H), 8.67 (d, J = 2.2 Hz, 1H), 8.61 (s, 1H), 8.02 (d, J = 5.1 Hz, 1H), 7.88 (s, 1H), 7.22 (d, J = 5.1 Hz, 1H), 4.41 (ddd, J = 49.2, 9.4, 2.1 Hz, 1H), 4.10-3.80 (m, 2H), 3.59-3.45 (m, 1H), 3.42-3.32 (m, 1H), 2.45 (d, J = 11.9 Hz, 1H), 2.21 (d, J = 12.6 Hz, 1H), 2.16-1.94 (m, 2H), 1.73-1.57 (m, 1H), 1.58-1.47 (m, 1H), 1.48-1.36 (m, 2H), 1.28 (d, J = 1.7 Hz, 6H). |
| 534 | 1H NMR (400 MHz, Methanol-d4) δ 8.75 (d, J = 2.2 Hz, 1H), 8.73 (d, J = 2.2 Hz, 1H), 8.57 (s, 1H), 7.99 (d, J = 5.1 Hz, 1H), 7.78 (s, 1H), 7.21 (d, J = 5.1 Hz, 1H), 4.53-4.31 (m, 2H), 3.94 (ddd, J = 36.5, 14.6, 2.1 Hz, 1H), 3.56-3.40 (m, 3H), 2.57 (s, 1H), 2.45 (ddd, J = 12.2, 7.6, 3.6 Hz, 2H), 2.33-2.20 (m, 2H), 1.59 (ddd, J = 12.7, 8.0, 4.7 Hz, 1H), 1.29 (d, J = 1.7 Hz, 6H), 0.88 (dt, J = 4.5, 3.0 Hz, 2H), 0.78 (dt, J = 8.0, 3.2 Hz, 2H). |
| 535 | 1H NMR (400 MHz, Methanol-d4) δ 8.76 (d, J = 2.2 Hz, 1H), 8.67 (d, J = 2.1 Hz, 1H), 8.64 (s, 1H), 8.05-7.99 (m, 1H), 7.89 (s, 1H), 7.22 (d, J = 5.0 Hz, 1H), 4.42 (ddd, J = 49.1, 9.5, 2.2 Hz, 1H), 4.07 (s, 1H), 3.91 (ddd, J = 36.5, 14.6, 2.2 Hz, 1H), 3.61-3.43 (m, 1H), 2.23-1.71 (m, 8H), 1.45 (s, 3H), 1.29 (d, J = 1.7 Hz, 6H). |
| 536 | 1H NMR (400 MHz, Methanol-d4) δ 8.74 (d, J = 2.2 Hz, 1H), 8.70 (d, J = 2.1 Hz, 1H), 8.58 (s, 1H), 7.98 (d, J = 5.1 Hz, 1H), 7.70 (s, 1H), 7.21 (d, J = 5.1 Hz, 1H), 4.54-4.33 (m, 2H), 3.94 (ddd, J = 36.5, 14.5, 2.1 Hz, 1H), 3.71 (d, J = 6.2 Hz, 2H), 3.50 (ddd, J = 16.1, 14.5, 9.4 Hz, 1H), 2.65-2.41 (m, 3H), 2.34-2.20 (m, 2H), 1.29 (d, J = 1.7 Hz, 6H). |
| 537 | 1H NMR (400 MHz, Methanol-d4) δ 8.59 (d, J = 2.1 Hz, 1H), 8.55 (d, J = 1.8 Hz, 2H), 8.52 (s, 1H), 7.83 (d, J = 4.7 Hz, 1H), 7.10 (d, J = 4.8 Hz, 1H), 5.51 (d, J = 28.9 Hz, 1H), 4.61-4.32 (m, 2H), 3.95-3.75 (m, 1H), 2.21-2.07 (m, 6H), 1.89-1.73 (m, 6H), 1.28 (d, J = 1.7 Hz, 6H). |
| 538 | 1H NMR (400 MHz, Methanol-d4) δ 8.75 (m, 2H), 8.57 (s, 1H), 8.00 (d, J = 5.0 Hz, 1H), 7.77 (s, 1H), 7.21 (d, J = 5.1 Hz, 1H), 4.55-4.29 (m, 2H), 3.94 (ddd, J = 36.5, 14.6, 2.1 Hz, 1H), 3.57-3.44 (m, 1H), 3.43 (d, J = 7.6 Hz, 2H), 2.62-2.50 (m, 1H), 2.51-2.38 (m, 2H), 2.32-2.17 (m, 4H), 1.29 (d, J = 1.6 Hz, 6H), 1.16 (t, J = 7.6 Hz, 3H). |
| 539 | 1H NMR (400 MHz, Methanol-d4) δ 8.79 (s, 1H), 8.75 (d, J = 2.1 Hz, 1H), 8.57 (s, 1H), 7.99 (d, J = 5.1 Hz, 1H), 7.84 (s, 1H), 7.22 (d, J = 5.1 Hz, 1H), 4.95-4.87 (m, 1H), 4.55-4.30 (m, 2H), 4.05-3.83 (m, 1H), 3.57-3.40 (m, 1H), 3.34 (d, J = 7.4 |

TABLE 2-continued

| compound | 1H-NMR |
|---|---|
| | Hz, 2H), 2.59-2.39 (m, 3H), 2.26 (q, J = 10.2, 9.6 Hz, 2H), 1.29 (d, J = 1.6 Hz, 6H), 1.24 (d, J = 6.3 Hz, 6H). |
| 540 | 1H NMR (400 MHz, Methanol-d4) δ 8.78 (s, 1H), 8.75 (d, J = 2.2 Hz, 1H), 8.57 (s, 1H), 7.99 (d, J = 5.0 Hz, 1H), 7.83 (s, 1H), 7.22 (d, J = 5.0 Hz, 1H), 4.54-4.30 (m, 2H), 4.12 (q, J = 7.1 Hz, 2H), 3.94 (ddd, J = 36.6, 14.6, 2.0 Hz, 1H), 3.49 (td, J = 15.6, 9.4 Hz, 1H), 3.35 (d, J = 7.5 Hz, 2H), 2.54 (s, 1H), 2.47 (s, 2H), 2.26 (q, J = 9.4 Hz, 2H), 1.29 (d, J = 1.6 Hz, 6H), 1.25 (t, J = 7.1 Hz, 3H). |
| 541 | 1H NMR (400 MHz, Methanol-d4) δ 8.83-8.70 (m, 2H), 8.57 (s, 1H), 8.00 (d, J = 5.1 Hz, 1H), 7.81 (s, 1H), 7.21 (d, J = 5.1 Hz, 1H), 4.54-4.28 (m, 2H), 3.94 (dd, J = 36.5, 14.5 Hz, 1H), 3.48 (td, J = 15.4, 9.3 Hz, 1H), 3.41 (d, J = 7.7 Hz, 2H), 2.93 (d, J = 1.7 Hz, 6H), 2.56 (s, 1H), 2.46 (d, J = 8.7 Hz, 2H), 2.23 (q, J = 10.0, 9.6 Hz, 2H), 1.29 (d, J = 1.6 Hz, 6H). |
| 542 | 1H NMR (400 MHz, Methanol-d4) δ 8.75 (m, 2H), 8.58 (s, 1H), 7.98 (d, J = 5.0 Hz, 1H), 7.81 (s, 1H), 7.22 (d, J = 5.1 Hz, 1H), 4.56-4.31 (m, 2H), 3.94 (ddd, J = 36.6, 14.5, 2.1 Hz, 1H), 3.61-3.40 (m, 3H), 2.65 (dd, J = 8.2, 3.5 Hz, 1H), 2.48 (ddd, J = 11.8, 7.7, 3.8 Hz, 2H), 2.39-2.24 (m, 2H), 1.29 (d, J = 1.7 Hz, 6H). |
| 543 | 1H NMR (400 MHz, Methanol-d4) δ 8.76 (d, J = 2.1 Hz, 1H), 8.72 (d, J = 2.2 Hz, 1H), 8.55 (s, 1H), 8.22 (s, 1H), 7.91 (d, J = 5.1 Hz, 1H), 7.22 (d, J = 5.1 Hz, 1H), 4.40 (ddd, J = 49.1, 9.4, 2.1 Hz, 1H), 3.91 (ddd, J = 36.6, 14.5, 2.1 Hz, 1H), 3.67 (s, 3H), 3.47 (ddd, J = 15.9, 14.6, 9.4 Hz, 1H), 2.45 (t, J = 6.9 Hz, 2H), 2.26 (q, J = 6.3 Hz, 2H), 2.20-2.03 (m, 4H), 2.01-1.88 (m, 6H), 1.28 (d, J = 1.7 Hz, 6H). |
| 544 | 1H NMR (400 MHz, Methanol-d4) δ 8.76-8.69 (m, 2H), 8.57 (s, 1H), 7.99 (d, J = 5.0 Hz, 1H), 7.73 (s, 1H), 7.21 (d, J = 5.1 Hz, 1H), 4.57-4.25 (m, 2H), 3.93 (dd, J = 36.8, 14.4 Hz, 1H), 3.49 (td, J = 15.4, 9.4 Hz, 1H), 3.42 (d, J = 7.7 Hz, 2H), 2.57 (s, 1H), 2.50-2.35 (m, 1H), 2.27 (q, J = 9.5 Hz, 2H), 1.98 (s, 2H), 1.29 (d, J = 1.6 Hz, 6H). |
| 545 | 1H NMR (400 MHz, Methanol-d4) δ 8.76 (s, 1H), 8.75 (d, J = 2.1 Hz, 1H), 8.57 (s, 1H), 7.98 (d, J = 5.1 Hz, 1H), 7.81 (s, 1H), 7.21 (d, J = 5.1 Hz, 1H), 4.53-4.33 (m, 2H), 4.03-3.80 (m, 1H), 3.68 (s, 3H), 3.56-3.41 (m, 1H), 3.35 (d, J = 7.5 Hz, 2H), 2.55 (s, 1H), 2.46 (s, 2H), 2.26 (q, J = 9.4 Hz, 2H), 1.29 (d, J = 1.6 Hz, 6H). |
| 546 | 1H NMR (400 MHz, Methanol-d4) δ 8.76 (q, J = 2.2 Hz, 2H), 8.50 (s, 1H), 7.92 (d, J = 5.2 Hz, 1H), 7.23 (d, J = 5.1 Hz, 1H), 4.41 (ddd, J = 49.1, 9.4, 2.0 Hz, 1H), 4.02-3.79 (m, 1H), 3.56-3.38 (m, 3H), 2.28 (s, 6H), 2.00 (s, 3H), 1.28 (d, J = 1.7 Hz, 6H). |
| 547 | 1H NMR (400 MHz, Methanol-d4) δ 8.77 (d, J = 2.2 Hz, 1H), 8.73 (d, J = 2.2 Hz, 1H), 8.61 (s, 1H), 8.58 (s, 1H), 7.93 (d, J = 5.1 Hz, 1H), 7.23 (d, J = 5.1 Hz, 1H), 4.52-4.30 (m, 1H), 4.01-3.81 (m, 1H), 3.69 (s, 3H), 3.47 (td, J = 16.0, 9.4 Hz, 1H), 3.39 (s, 2H), 2.28 (s, 6H), 1.28 (d, J = 1.7 Hz, 6H). |
| 548 | 1H NMR (400 MHz, Methanol-d4) δ 8.72 (d, J = 2.2 Hz, 1H), 8.67 (d, J = 2.2 Hz, 1H), 8.58 (s, 1H), 7.98 (d, J = 5.1 Hz, 1H), 7.65 (s, 1H), 7.19 (d, J = 5.1 Hz, 1H), 4.29-4.17 (m, 1H), 3.92 (ddd, J = 36.4, 14.5, 2.1 Hz, 1H), 3.51 (ddd, J = 16.0, 14.5, 9.3 Hz, 1H), 2.66 (ddd, J = 13.5, 8.0, 5.8 Hz, 2H), 2.50 (tt, J = 10.8, 5.9 Hz, 1H), 2.17 (ddd, J = 12.8, 9.7, 5.6 Hz, 2H), 1.29 (d, J = 1.6 Hz, 6H), 1.20 (s, 6H). |
| 549 | 1H NMR (400 MHz, Methanol-d4) δ 8.75 (s, 2H), 8.56 (s, 1H), 7.98 (d, J = 5.1 Hz, 1H), 7.79 (s, 1H), 7.21 (d, J = 5.0 Hz, 1H), 4.53-4.31 (m, 2H), 4.02-3.84 (m, 1H), 3.49 (td, J = 15.3, 9.2 Hz, 1H), 3.31-3.25 (m, 3H), 2.63-2.34 (m, 3H), 2.34-2.12 (m, 2H), 1.46 (s, 9H), 1.29 (d, J = 1.6 Hz, 6H). |
| 550 | 1H NMR (400 MHz, Methanol-d4) δ 8.77 (s, 2H), 8.57 (d, J = 5.7 Hz, 2H), 7.92 (d, J = 5.1 Hz, 1H), 7.23 (d, J = 5.1 Hz, 1H), 4.41 (dd, J = 49.9, 8.4 Hz, 1H), 4.02-3.80 (m, 1H), 3.47 (td, J = 15.5, 15.0, 9.3 Hz, 1H), 2.26 (s, 6H), 1.46 (s, 9H), 1.28 (d, J = 1.6 Hz, 6H). |
| 551 | 1H NMR (400 MHz, Methanol-d4) δ 8.75 (d, J = 2.2 Hz, 1H), 8.66 (d, J = 2.2 Hz, 1H), 8.58 (s, 1H), 8.00 (d, J = 5.1 Hz, 1H), 7.84 (s, 1H), 7.21 (d, J = 5.1 Hz, 1H), 4.23-4.06 (m, 1H), 3.85 (t, J = 13.9 Hz, 2H), 3.78-3.62 (m, 2H), 2.02 (s, 3H), 1.40 (d, J = 6.4 Hz, 6H). |
| 552 | 1H NMR (400 MHz, Methanol-d4) δ 8.60-8.51 (m, 2H), 8.47 (d, J = 2.2 Hz, 1H), 8.15 (s, 1H), 7.79 (d, J = 4.9 Hz, 1H), 7.07 (d, J = 4.8 Hz, 1H), 3.94-3.78 (m, 3H), 2.97 (t, J = 14.0 Hz, 2H), 1.34 (d, J = 6.4 Hz, 6H). |
| 553 | 1H NMR (400 MHz, Methanol-d4) δ 8.74 (d, J = 2.2 Hz, 1H), 8.65 (d, J = 2.2 Hz, 1H), 8.50 (s, 1H), 7.98 (d, J = 5.1 Hz, 1H), 7.83 (s, 1H), 7.20 (d, J = 5.1 Hz, 1H), 6.16 (t, J = 57.3 Hz, 1H), 4.15 (p, J = 6.5 Hz, 1H), 3.85 (s, 0H), 3.60 (s, 3H), 3.57-3.33 (m, 2H), 2.54-2.29 (m, 1H), 1.96-1.73 (m, 1H), 1.40 (d, J = 6.4 Hz, 6H), 1.33 (s, 3H). |
| 554 | 1H NMR (400 MHz, Methanol-d4) δ 8.74 (d, J = 2.2 Hz, 1H), 8.66 (d, J = 2.2 Hz, 1H), 8.58 (s, 1H), 7.99 (d, J = 5.1 Hz, 1H), 7.86 (s, 1H), 7.20 (d, J = 5.1 Hz, 1H), 4.16 (p, J = 6.5 Hz, 1H), 3.85 (t, J = 14.0 Hz, 2H), 3.55 (t, J = 13.8 Hz, 2H), 1.46 (s, 9H), 1.40 (d, J = 6.4 Hz, 6H).; 1H NMR (400 MHz, Methanol-d4) δ 8.62 (d, J = 29.2 Hz, 1H), 8.55 (dd, J = 4.1, 2.2 Hz, 1H), 8.48 (d, J = 2.4 Hz, 1H), 8.15 (d, J = 2.8 Hz, 1H), 7.81 (t, J = 4.2 Hz, 1H), 7.10-7.02 (m, 2H), 3.83 (m, 2H), 3.54 (m, 1H), 2.95 (m, 1H), 1.34 (d, J = 6.4 Hz, 6H). |
| 555 | 1H NMR (400 MHz, Methanol-d4) δ 8.74 (d, J = 2.2 Hz, 1H), 8.65 (d, J = 2.1 Hz, 1H), 8.56 (d, J = 3.1 Hz, 1H), 7.99 (d, J = 5.0 Hz, 1H), 7.86 (d, J = 5.0 Hz, 1H), 6.16 (t, J = 53.8 Hz, 1H), 4.21-4.09 (m, 1H), 3.71-3.43 (m, 2H), 2.21-2.04 (m, 2H), 1.51 (s, 3H), 1.40 (d, J = 6.4 Hz, 6H). |
| 556 | 1H NMR (400 MHz, Methanol-d4) δ 8.74 (t, J = 2.3 Hz, 1H), 8.65 (d, J = 2.1 Hz, 1H), 8.55 (d, J = 1.5 Hz, 1H), 8.03-7.95 (m, 1H), 7.88 (d, J = 8.1 Hz, 1H), 7.23-7.17 (m, 1H), 4.41 (ddd, J = 49.2, 9.4, 2.1 Hz, 1H), 4.01-3.69 (m, 2H), 3.63 (s, |

TABLE 2-continued

| compound | 1H-NMR |
|---|---|
| | 3H), 3.47 (td, J = 15.4, 9.4 Hz, 1H), 3.04-3.00 (m, 2H), 2.30-2.10 (m, 2H), 1.98-1.83 (m, 2H), 1.44 (ddd, J = 20.7, 9.3, 4.1 Hz, 2H), 1.28 (d, J = 1.6 Hz, 7H), 1.28-1.17 (m, 2H). |
| 557 | 1H NMR (400 MHz, Methanol-d4) δ 8.74 (d, J = 2.1 Hz, 1H), 8.65 (d, J = 2.2 Hz, 1H), 8.55 (s, 1H), 8.00 (d, J = 5.0 Hz, 1H), 7.87 (s, 1H), 7.20 (d, J = 5.1 Hz, 1H), 4.51-4.28 (m, 1H), 4.01-3.72 (m, 2H), 3.48 (td, J = 15.3, 9.4 Hz, 1H), 3.10 (d, J = 6.8 Hz, 2H), 2.20 (d, J = 12.5 Hz, 2H), 1.95 (s, 3H), 1.92 (d, J = 13.7 Hz, 3H), 1.54-1.34 (m, 2H), 1.28 (d, J = 1.7 Hz, 7H), 1.29-1.18 (m, 2H). |
| 558 | 1H NMR (400 MHz, Methanol-d4) δ 8.75 (d, J = 2.2 Hz, 1H), 8.64 (d, J = 2.2 Hz, 1H), 8.58 (s, 1H), 8.00 (d, J = 5.0 Hz, 1H), 7.90 (s, 1H), 7.21 (d, J = 5.1 Hz, 1H), 4.55-4.25 (m, 1H), 3.86 (d, J = 13.8 Hz, 1H), 3.59-3.41 (m, 0H), 2.88 (d, J = 7.0 Hz, 2H), 2.26 (d, J = 12.9 Hz, 2H), 1.99 (d, J = 13.4 Hz, 2H), 1.51 (d, J = 13.4 Hz, 1H), 1.36 (s, 1H), 1.28 (d, J = 1.6 Hz, 7H). |
| 559 | 1H NMR (400 MHz, Methanol-d4) δ 8.76 (d, J = 2.1 Hz, 1H), 8.64 (d, J = 2.2 Hz, 1H), 8.61 (s, 1H), 7.99 (d, J = 5.1 Hz, 1H), 7.85 (s, 1H), 7.22 (d, J = 5.1 Hz, 1H), 6.24 (t, J = 53.8 Hz, 1H), 4.51-4.31 (m, 1H), 3.92 (dd, J = 35.7, 15.0 Hz, 1H), 3.76 (t, J = 7.9 Hz, 2H), 3.60-3.40 (m, 1H), 2.37-2.24 (m, 1H), 2.24-2.08 (m, 1H), 1.57 (s, 3H), 1.28 (d, J = 1.7 Hz, 7H). |
| 560 | 1H NMR (400 MHz, DMSO-d6) δ 8.81 (d, J = 2.3 Hz, 1H), 8.75-8.66 (m, 2H), 8.58 (d, J = 2.3 Hz, 1H), 8.10 (s, 1H), 7.83 (d, J = 4.8 Hz, 1H), 7.09 (d, J = 4.8 Hz, 1H), 4.90 (s, 1H), 4.82 (s, 1H), 4.43 (dd, J = 16.3, 8.4 Hz, 1H), 4.31 (dd, J = 16.6, 8.2 Hz, 1H), 3.75 (d, J = 14.9 Hz, 1H), 3.66 (d, J = 14.6 Hz, 1H), 3.51 (dd, J = 15.7, 9.4 Hz, 1H), 3.41-3.33 (m, 1H), 1.25-1.19 (m, 6H), 1.18-1.11 (m, 6H). |
| 561 | 1H NMR (400 MHz, Acetonitrile-d3) δ 8.45 (d, J = 5.1 Hz, 2H), 8.30 (s, 2H), 8.04 (s, 1H), 7.77 (t, J = 6.3 Hz, 1H), 7.74 (d, J = 4.8 Hz, 1H), 6.93 (d, J = 4.8 Hz, 1H), 3.79 (h, J = 6.5 Hz, 1H), 3.61 (dq, J = 13.1, 6.6 Hz, 1H), 3.53-3.36 (m, 1H), 2.25 (s, 2H), 1.85 (t, J = 7.3 Hz, 2H), 1.31 (s, 3H), 1.29 (d, J = 3.1 Hz, 6H). |
| 562 | 1H NMR (400 MHz, DMSO-d6) δ 8.81 (s, 1H), 8.72-8.47 (m, 3H), 8.08 (s, 1H), 7.83 (d, J = 4.8 Hz, 1H), 7.09 (d, J = 4.7 Hz, 1H), 4.82 (s, 1H), 4.34 (dd, J = 49.6, 8.8 Hz, 1H), 3.69 (dd, J = 36.9, 14.2 Hz, 1H), 2.10 (s, 2H), 1.81 (s, 2H), 1.24 (s, 3H), 1.19-1.11 (m, 6H). |
| 563 | 1H NMR (400 MHz, Methanol-d4) δ 8.98 (s, 1H), 8.90 (s, 1H), 8.71-8.53 (m, 3H), 7.95 (d, J = 4.9 Hz, 1H), 7.79 (s, 1H), 7.69 (d, J = 2.2 Hz, 1H), 7.44 (dd, J = 7.4, 2.2 Hz, 1H), 7.14 (d, J = 4.9 Hz, 1H), 4.43 (ddd, J = 48.9, 9.2, 2.1 Hz, 1H), 3.94 (ddd, J = 35.8, 14.4, 2.1 Hz, 1H), 3.64-3.43 (m, 1H), 2.53 (d, J = 1.1 Hz, 3H), 1.29 (d, J = 1.7 Hz, 6H). |
| 564 | 1H NMR (400 MHz, Methanol-d4) δ 8.72 (s, 1H), 8.67 (d, J = 2.2 Hz, 1H), 8.52 (d, J = 2.2 Hz, 1H), 8.43 (s, 1H), 7.94 (d, J = 8.3 Hz, 1H), 7.83 (d, J = 5.0 Hz, 1H), 7.24-7.03 (m, 3H), 4.46 (ddd, J = 49.0, 9.3, 2.1 Hz, 1H), 4.02 (dd, J = 14.5, 2.1 Hz, 1H), 3.90 (d, J = 3.5 Hz, 6H), 3.66-3.42 (m, 1H), 1.30 (d, J = 1.7 Hz, 6H). |
| 565 | 1H NMR (400 MHz, Methanol-d4) δ 8.77-8.64 (m, 2H), 8.54 (dd, J = 2.2, 0.4 Hz, 1H), 8.17 (s, 1H), 7.78 (dd, J = 5.1, 0.5 Hz, 1H), 7.46 (dd, J = 7.9, 0.5 Hz, 1H), 7.25-7.10 (m, 2H), 7.02 (dd, J = 2.0, 0.5 Hz, 1H), 4.47 (ddd, J = 49.0, 9.4, 2.1 Hz, 1H), 3.99 (ddd, J = 36.5, 14.6, 2.2 Hz, 1H), 3.63-3.42 (m, 1H), 1.42 (s, 6H), 1.30 (d, J = 1.6 Hz, 6H). |
| 566 | 1H NMR (400 MHz, Methanol-d4) δ 8.80 (s, 1H), 8.70 (dd, J = 17.2, 2.0 Hz, 2H), 8.49 (ddd, J = 27.4, 2.1, 0.7 Hz, 2H), 8.20-8.06 (m, 2H), 7.83 (dd, J = 5.1, 0.5 Hz, 1H), 7.20-7.05 (m, 1H), 6.91 (dd, J = 3.3, 0.9 Hz, 1H), 4.48 (ddd, J = 49.0, 9.3, 2.2 Hz, 1H), 3.99 (ddd, J = 36.3, 14.6, 2.2 Hz, 1H), 3.66-3.42 (m, 1H), 1.30 (d, J = 1.7 Hz, 6H). |
| 567 | 1H NMR (400 MHz, Methanol-d4) δ 8.76-8.63 (m, 2H), 8.54 (dd, J = 2.2, 0.4 Hz, 1H), 8.00 (s, 1H), 7.75 (dd, J = 5.1, 0.5 Hz, 1H), 7.44-7.34 (m, 2H), 7.19-7.07 (m, 1H), 7.07-6.89 (m, 2H), 5.37 (tt, J = 6.0, 4.9 Hz, 1H), 5.06 (ddd, J = 7.1, 6.0, 0.9 Hz, 2H), 4.73 (ddd, J = 7.2, 4.9, 0.9 Hz, 2H), 4.46 (ddd, J = 49.1, 9.4, 2.1 Hz, 1H), 4.11-3.82 (m, 1H), 3.65-3.40 (m, 1H), 1.30 (d, J = 1.7 Hz, 6H). |
| 568 | 1H NMR (400 MHz, Methanol-d4) δ 8.78-8.63 (m, 2H), 8.54 (d, J = 2.2 Hz, 1H), 8.11 (s, 1H), 7.78 (dd, J = 5.0, 0.5 Hz, 1H), 7.41 (d, J = 9.1 Hz, 1H), 7.29-7.19 (m, 2H), 7.14 (d, J = 5.0 Hz, 1H), 4.47 (ddd, J = 49.0, 9.4, 2.1 Hz, 1H), 3.99 (ddd, J = 36.6, 14.6, 2.1 Hz, 1H), 3.64-3.43 (m, 1H), 2.03 (s, 0H), 1.30 (d, J = 1.6 Hz, 6H). |
| 569 | 1H NMR (400 MHz, Methanol-d4) δ 9.58 (d, J = 0.5 Hz, 1H), 8.75 (d, J = 0.5 Hz, 1H), 8.59 (s, 2H), 7.98 (d, J = 4.9 Hz, 1H), 7.80 (dd, J = 9.2, 1.8 Hz, 1H), 7.29-7.01 (m, 2H), 4.59 (ddd, J = 48.9, 9.3, 2.0 Hz, 1H), 4.03 (ddd, J = 37.4, 14.5, 2.0 Hz, 1H), 3.51-3.35 (m, 1H), 1.31 (d, J = 1.6 Hz, 6H). |
| 570 | 1H NMR (400 MHz, Methanol-d4) δ 8.87 (d, J = 7.3 Hz, 2H), 8.78 (dd, J = 7.4, 0.7 Hz, 1H), 8.62 (d, J = 23.8, 2.2 Hz, 2H), 8.11 (dd, J = 2.3, 0.7 Hz, 1H), 8.02-7.90 (m, 2H), 7.90-7.81 (m, 1H), 7.50 (dd, J = 7.4, 2.2 Hz, 1H), 7.14 (d, J = 5.0 Hz, 1H), 4.45 (ddd, J = 49.0, 9.3, 2.1 Hz, 1H), 3.95 (ddd, J = 36.3, 14.5, 2.2 Hz, 1H), 3.65-3.44 (m, 1H), 1.30 (d, J = 1.6 Hz, 6H). |
| 571 | 1H NMR (400 MHz, Methanol-d4) δ 8.73-8.60 (m, 2H), 8.44 (d, J = 2.2 Hz, 1H), 8.15 (s, 1H), 8.09 (s, 1H), 7.83 (d, J = 8.4 Hz, 1H), 7.73 (d, J = 5.1 Hz, 1H), 7.63 (d, J = 1.8 Hz, 1H), 7.33 (dd, J = 8.5, 1.9 Hz, 1H), 7.11 (d, J = 5.0 Hz, 1H), 4.48 (ddd, J = 49.0, 9.3, 2.1 Hz, 1H), 3.99 (ddd, J = 36.4, 14.6, 2.1 Hz, 1H), 3.63-3.44 (m, 1H), 1.30 (d, J = 1.6 Hz, 6H). |
| 572 | 1H NMR (400 MHz, Methanol-d4) δ 9.35 (s, 1H), 8.74 (s, 1H), 8.68 (d, J = 2.2 Hz, 1H), 8.43 (d, J = 2.2 Hz, 1H), 8.32-8.15 (m, 3H), 7.78 (d, J = 5.1 Hz, 1H), 7.65 (dd, J = 8.7, 2.2 Hz, 1H), 7.13 (d, J = 5.1 Hz, 1H), 4.48 (ddd, J = 49.0, 9.4, 2.1 Hz, 1H), 4.00 (ddd, J = 36.5, 14.6, 2.1 Hz, 1H), 3.55 (ddd, J = 16.1, 14.5, 9.3 Hz, 1H), 1.30 (d, J = 1.6 Hz, 6H). |

TABLE 2-continued

| compound | 1H-NMR |
|---|---|
| 573 | 1H NMR (400 MHz, Methanol-d4) δ 8.69 (d, J = 2.8 Hz, 2H), 8.53 (d, J = 2.2 Hz, 1H), 8.21 (s, 1H), 7.77 (d, J = 5.1 Hz, 1H), 7.51-7.37 (m, 1H), 7.20-7.04 (m, 2H), 6.97 (d, J = 1.9 Hz, 1H), 4.46 (ddd, J = 49.0, 9.3, 2.1 Hz, 1H), 3.98 (ddd, J = 36.5, 14.6, 2.1 Hz, 1H), 3.71-3.44 (m, 3H), 1.30 (d, J = 1.6 Hz, 6H). |
| 574 | 1H NMR (400 MHz, Methanol-d4) δ 8.80-8.61 (m, 2H), 8.47 (d, J = 2.2 Hz, 1H), 8.23 (s, 1H), 8.15 (d, J = 1.1 Hz, 1H), 7.98 (dd, J = 8.6, 0.8 Hz, 1H), 7.75 (d, J = 5.1 Hz, 1H), 7.67 (dt, J = 1.9, 0.9 Hz, 1H), 7.23 (dd, J = 8.6, 1.8 Hz, 1H), 7.13 (d, J = 5.1 Hz, 1H), 6.92 (d, J = 4.6 Hz, 0H), 4.48 (ddd, J = 49.0, 9.3, 2.1 Hz, 1H), 4.00 (ddd, J = 36.5, 14.6, 2.1 Hz, 1H), 3.54 (ddd, J = 16.1, 14.5, 9.3 Hz, 1H), 1.30 (d, J = 1.6 Hz, 6H). |
| 575 | 1H NMR (400 MHz, Methanol-d4) δ 8.82-8.67 (m, 3H), 8.61 (d, J = 2.2 Hz, 1H), 8.30 (s, 1H), 8.10 (dd, J = 8.4, 2.6 Hz, 1H), 7.94-7.78 (m, 2H), 7.17 (d, J = 5.1 Hz, 1H), 4.47 (ddd, J = 49.1, 9.3, 2.1 Hz, 1H), 4.00 (ddd, J = 36.4, 14.6, 2.1 Hz, 1H), 3.64-3.46 (m, 1H), 3.15 (d, J = 21.1 Hz, 6H), 1.30 (d, J = 1.6 Hz, 6H). |
| 576 | 1H NMR (400 MHz, Methanol-d4) δ 8.72-8.59 (m, 2H), 8.33 (d, J = 2.2 Hz, 1H), 8.00 (s, 1H), 7.75-7.54 (m, 3H), 7.48-7.35 (m, 1H), 7.20-7.04 (m, 2H), 6.55 (dd, J = 3.1, 0.9 Hz, 1H), 4.48 (ddd, J = 48.9, 9.3, 2.1 Hz, 1H), 3.99 (ddd, J = 36.5, 14.6, 2.1 Hz, 1H), 3.65-3.43 (m, 1H), 1.30 (d, J = 1.6 Hz, 6H). |
| 577 | 1H NMR (400 MHz, Methanol-d4) δ 8.76-8.63 (m, 2H), 8.40 (d, J = 2.2 Hz, 1H), 8.17 (d, J = 1.1 Hz, 1H), 8.01 (s, 1H), 7.90 (dd, J = 2.0, 0.8 Hz, 1H), 7.82-7.67 (m, 2H), 7.46 (dd, J = 8.8, 2.0 Hz, 1H), 7.11 (d, J = 5.1 Hz, 1H), 4.48 (ddd, J = 49.0, 9.4, 2.1 Hz, 1H), 4.13-3.92 (m, 1H), 3.65-3.42 (m, 1H), 1.30 (d, J = 1.6 Hz, 6H). |
| 578 | 1H NMR (400 MHz, Methanol-d4) δ 8.66 (t, J = 1.1 Hz, 2H), 8.41 (d, J = 2.2 Hz, 1H), 8.09 (s, 1H), 7.81-7.61 (m, 2H), 7.48 (dd, J = 1.8, 0.9 Hz, 1H), 7.38 (d, J = 3.1 Hz, 1H), 7.17-7.02 (m, 2H), 6.56 (dd, J = 3.2, 1.0 Hz, 1H), 4.48 (ddd, J = 49.1, 9.3, 2.1 Hz, 1H), 4.00 (ddd, J = 36.5, 14.7, 2.1 Hz, 1H), 3.65 (s, 3H), 3.54 (ddd, J = 16.1, 14.7, 9.3 Hz, 1H), 1.30 (d, J = 1.6 Hz, 6H). |
| 579 | 1H NMR (400 MHz, Methanol-d4) δ 8.83-8.66 (m, 3H), 8.59 (d, J = 2.2 Hz, 1H), 8.36 (s, 1H), 8.25 (dd, J = 8.4, 0.8 Hz, 1H), 8.09 (dd, J = 8.5, 2.5 Hz, 1H), 7.85 (d, J = 5.0 Hz, 1H), 7.15 (d, J = 5.1 Hz, 1H), 4.47 (ddd, J = 49.0, 9.3, 2.1 Hz, 1H), 3.99 (ddd, J = 36.4, 14.5, 2.1 Hz, 1H), 3.66-3.44 (m, 1H), 3.00 (s, 3H), 1.30 (d, J = 1.6 Hz, 6H). |
| 580 | 1H NMR (400 MHz, Methanol-d4) δ 9.23 (s, 1H), 8.76 (s, 1H), 8.69 (d, J = 2.2 Hz, 1H), 8.49 (d, J = 2.2 Hz, 1H), 8.21 (s, 1H), 8.06-7.91 (m, 2H), 7.80 (d, J = 5.1 Hz, 1H), 7.66 (dd, J = 8.8, 2.0 Hz, 1H), 7.14 (d, J = 5.1 Hz, 1H), 4.48 (ddd, J = 49.1, 9.4, 2.1 Hz, 1H), 3.99 (ddd, J = 36.6, 14.6, 2.1 Hz, 1H), 3.69-3.43 (m, 1H), 1.30 (d, J = 1.6 Hz, 6H). |
| 581 | 1H NMR (400 MHz, Methanol-d4) δ 8.71 (d, J = 2.0 Hz, 2H), 8.59 (d, J = 2.2 Hz, 1H), 8.32 (s, 1H), 7.81 (d, J = 5.1 Hz, 1H), 7.63 (d, J = 7.9 Hz, 1H), 7.47-7.33 (m, 2H), 7.17 (d, J = 5.1 Hz, 1H), 4.46 (ddd, J = 49.1, 9.3, 2.0 Hz, 1H), 3.99 (ddd, J = 36.6, 14.5, 2.1 Hz, 1H), 3.60-3.43 (m, 1H), 2.53 (s, 3H), 1.30 (d, J = 1.6 Hz, 6H). |
| 582 | 1H NMR (400 MHz, Methanol-d4) δ 10.15 (s, 1H), 8.78 (s, 1H), 8.75-8.66 (m, 2H), 8.58 (s, 1H), 7.90 (d, J = 5.0 Hz, 1H), 7.19 (d, J = 5.0 Hz, 1H), 7.07 (s, 1H), 4.48 (ddd, J = 49.0, 9.3, 2.1 Hz, 1H), 4.14-3.86 (m, 1H), 3.66-3.43 (m, 1H), 2.53 (s, 3H), 1.31 (d, J = 1.6 Hz, 6H). |
| 583 | 1H NMR (400 MHz, Methanol-d4) δ 8.75 (s, 1H), 8.70 (d, J = 2.2 Hz, 1H), 8.58 (d, J = 2.1 Hz, 1H), 8.44 (s, 1H), 7.94-7.81 (m, 2H), 7.56-7.42 (m, 2H), 7.16 (d, J = 5.0 Hz, 1H), 4.45 (ddd, J = 49.0, 9.3, 2.1 Hz, 1H), 4.14-3.84 (m, 1H), 3.52 (td, J = 15.3, 9.2 Hz, 1H), 2.61 (s, 3H), 2.03 (s, 1H), 1.29 (d, J = 1.6 Hz, 6H). |
| 584 | 1H NMR (400 MHz, DMSO-d6) δ 11.88 (s, 1H), 10.33 (s, 1H), 9.16 (t, J = 5.6 Hz, 1H), 9.08-8.77 (m, 4H), 7.92 (d, J = 4.8 Hz, 1H), 7.12 (d, J = 4.9 Hz, 1H), 4.40 (ddd, J = 49.3, 9.4, 2.0 Hz, 1H), 4.04-3.31 (m, 25H), 1.17 (dd, J = 6.1, 1.6 Hz, 6H). |
| 585 | 1H NMR (400 MHz, Methanol-d4) δ 10.19 (s, 1H), 8.82 (d, J = 13.6 Hz, 2H), 8.73 (s, 2H), 7.95 (d, J = 4.9 Hz, 1H), 7.28-7.12 (m, 2H), 4.47 (dd, J = 48.5, 8.8 Hz, 1H), 3.99 (dd, J = 35.6, 15.0 Hz, 1H), 3.68-3.43 (m, 1H), 2.56 (s, 3H), 1.31 (d, J = 1.6 Hz, 6H). |
| 586 | 1H NMR (400 MHz, Methanol-d4) δ 9.90 (s, 1H), 8.73-8.52 (m, 3H), 8.49-8.34 (m, 1H), 7.87-7.72 (m, 2H), 7.19-7.01 (m, 2H), 4.47 (ddd, J = 49.0, 9.4, 2.1 Hz, 1H), 3.93 (ddd, J = 36.6, 14.6, 2.1 Hz, 1H), 3.54 (ddd, J = 16.0, 14.5, 9.4 Hz, 1H), 1.32 (d, J = 1.7 Hz, 6H). |
| 587 | 1H NMR (400 MHz, Methanol-d4) δ 10.25 (s, 1H), 8.81 (s, 1H), 8.72 (d, J = 4.9 Hz, 1H), 8.69-8.56 (m, 1H), 7.91 (d, J = 5.0 Hz, 1H), 7.15 (dt, J = 4.8, 2.4 Hz, 1H), 4.48 (ddd, J = 49.1, 9.3, 2.1 Hz, 1H), 3.99 (ddd, J = 36.2, 14.6, 2.1 Hz, 1H), 3.69-3.47 (m, 1H), 3.26-3.12 (m, 0H), 1.40-1.20 (m, 6H). |
| 588 | 1H NMR (400 MHz, Methanol-d4) δ 10.15 (s, 1H), 9.04 (s, 1H), 8.88 (s, 1H), 8.74 (s, 2H), 8.01 (d, J = 5.0 Hz, 1H), 7.81 (dd, J = 8.9, 4.7 Hz, 1H), 7.62 (d, J = 8.8 Hz, 1H), 7.22 (d, J = 5.1 Hz, 1H), 4.49 (dd, J = 49.2, 8.0 Hz, 1H), 4.01 (dd, J = 35.1, 13.7 Hz, 1H), 3.67-3.46 (m, 1H), 1.31 (d, J = 1.6 Hz, 6H). |
| 589 | 1H NMR (400 MHz, Methanol-d4) δ 8.77-8.64 (m, 2H), 8.49 (d, J = 2.2 Hz, 1H), 8.19 (s, 1H), 7.76 (d, J = 5.1 Hz, 1H), 7.59 (dd, J = 8.4, 7.3 Hz, 2H), 7.52-7.34 (m, 3H), 7.14 (d, J = 5.0 Hz, 1H), 4.47 (ddd, J = 49.1, 9.4, 2.1 Hz, 1H), 4.19-3.91 (m, 1H), 3.75-3.42 (m, 2H), 1.30 (d, J = 1.6 Hz, 6H). |
| 590 | 1H NMR (400 MHz, Methanol-d4) δ 8.77-8.66 (m, 3H), 8.57 (d, J = 2.1 Hz, 1H), 7.91 (s, 1H), 7.86 (d, J = 5.1 Hz, 1H), 7.15 (d, J = 5.1 Hz, 1H), 4.47 (ddd, J = 49.1, 9.3, 2.1 Hz, 1H), 4.10 (s, 3H), 4.07-3.90 (m, 1H), 3.63-3.44 (m, 1H), 1.30 (d, J = 1.7 Hz, 6H). |

TABLE 2-continued

| compound | 1H-NMR |
|---|---|
| 591 | 1H NMR (400 MHz, Methanol-d4) δ 8.83 (s, 1H), 8.76-8.65 (m, 2H), 8.58 (d, J = 2.2 Hz, 1H), 8.26 (d, J = 5.7 Hz, 1H), 7.91 (d, J = 5.0 Hz, 1H), 7.38 (dt, J = 5.8, 1.5 Hz, 1H), 7.26-7.14 (m, 2H), 6.93 (d, J = 4.6 Hz, 0H), 4.45 (ddd, J = 48.9, 9.3, 2.2 Hz, 1H), 3.97 (ddd, J = 36.2, 14.5, 2.1 Hz, 1H), 3.64-3.41 (m, 1H), 1.30 (d, J = 1.7 Hz, 6H). |
| 592 | 1H NMR (400 MHz, Methanol-d4) δ 9.03 (d, J = 1.9 Hz, 1H), 8.91-8.75 (m, 2H), 8.70 (d, J = 2.2 Hz, 1H), 8.60 (d, J = 2.1 Hz, 1H), 8.50 (t, J = 2.2 Hz, 1H), 8.33 (s, 1H), 7.85 (d, J = 5.1 Hz, 1H), 7.16 (d, J = 5.0 Hz, 1H), 4.61-4.36 (m, 1H), 4.10-3.90 (m, 1H), 3.65-3.44 (m, 1H), 1.30 (d, J = 1.6 Hz, 6H). |
| 593 | 1H NMR (400 MHz, Methanol-d4) δ 8.98 (d, J = 20.7 Hz, 2H), 8.60 (dd, J = 13.8, 2.2 Hz, 2H), 8.57-8.47 (m, 2H), 7.96 (d, J = 4.9 Hz, 1H), 7.76-7.62 (m, 2H), 7.13 (d, J = 4.9 Hz, 1H), 4.41 (ddd, J = 48.9, 9.3, 2.2 Hz, 1H), 3.91 (ddd, J = 36.0, 14.5, 2.2 Hz, 1H), 3.64-3.44 (m, 1H), 1.28 (d, J = 1.7 Hz, 6H). |
| 594 | 1H NMR (400 MHz, Methanol-d4) δ 9.11 (d, J = 1.8 Hz, 1H), 8.89 (d, J = 2.6 Hz, 1H), 8.78 (s, 1H), 8.70 (d, J = 2.2 Hz, 1H), 8.63-8.51 (m, 2H), 8.28 (s, 1H), 7.85 (d, J = 5.1 Hz, 1H), 7.16 (d, J = 5.1 Hz, 1H), 4.47 (ddd, J = 49.0, 9.3, 2.1 Hz, 1H), 4.02 (s, 3H), 3.54 (ddd, J = 16.1, 14.5, 9.3 Hz, 1H), 1.30 (d, J = 1.6 Hz, 6H). |
| 595 | 1H NMR (400 MHz, Methanol-d4) δ 8.86 (s, 2H), 8.77 (s, 1H), 8.61 (d, J = 2.2 Hz, 1H), 8.09 (s, 1H), 7.87 (d, J = 5.1 Hz, 1H), 7.16 (d, J = 5.1 Hz, 1H), 4.47 (ddd, J = 49.0, 9.3, 2.1 Hz, 1H), 3.99 (ddd, J = 36.4, 14.6, 2.1 Hz, 1H), 3.54 (ddd, J = 16.1, 14.5, 9.3 Hz, 1H), 2.79 (s, 3H), 1.30 (d, J = 1.7 Hz, 6H). |
| 596 | 1H NMR (400 MHz, Methanol-d4) δ 10.25 (s, 1H), 9.05 (s, 2H), 8.90 (s, 1H), 8.67 (dd, J = 19.8, 2.2 Hz, 2H), 7.95 (d, J = 5.0 Hz, 1H), 7.15 (d, J = 5.0 Hz, 1H), 4.62-4.39 (m, 1H), 3.98 (dd, J = 34.8, 13.9 Hz, 1H), 3.70-3.43 (m, 1H), 3.13 (d, J = 1.7 Hz, 1H), 1.31 (d, J = 1.6 Hz, 6H). |
| 597 | 1H NMR (400 MHz, Methanol-d4) δ 8.79-8.66 (m, 2H), 8.55 (d, J = 2.2 Hz, 1H), 8.35 (dd, J = 2.7, 0.7 Hz, 1H), 8.07-7.95 (m, 2H), 7.88-7.76 (m, 1H), 7.62 (s, 0H), 7.44 (s, 0H), 7.26-7.10 (m, 2H), 4.47 (ddd, J = 49.0, 9.3, 2.1 Hz, 1H), 3.99 (ddd, J = 36.4, 14.5, 2.1 Hz, 1H), 3.63-3.44 (m, 1H), 1.30 (d, J = 1.7 Hz, 6H). |
| 598 | 1H NMR (400 MHz, Methanol-d4) δ 8.77 (d, J = 16.0 Hz, 2H), 8.61 (d, J = 2.2 Hz, 1H), 8.48 (d, J = 2.2 Hz, 1H), 8.13 (d, J = 6.2 Hz, 1H), 7.86 (d, J = 5.0 Hz, 1H), 7.16-7.03 (m, 2H), 6.92 (d, J = 2.0 Hz, 1H), 4.44 (ddd, J = 49.0, 9.3, 2.2 Hz, 1H), 4.10-3.85 (m, 4H), 3.52 (ddd, J = 16.2, 14.6, 9.3 Hz, 1H), 1.29 (d, J = 1.7 Hz, 6H). |
| 599 | 1H NMR (400 MHz, Methanol-d4) δ 8.79-8.64 (m, 2H), 8.54 (d, J = 2.2 Hz, 1H), 8.38-8.31 (m, 1H), 8.16-8.01 (m, 2H), 7.83 (d, J = 5.1 Hz, 1H), 7.30 (dd, J = 8.7, 3.0 Hz, 1H), 7.14 (d, J = 5.1 Hz, 1H), 4.47 (ddd, J = 49.0, 9.3, 2.1 Hz, 1H), 4.09-3.92 (m, 1H), 3.65 (s, 1H), 3.57-3.47 (m, 1H), 1.30 (d, J = 1.7 Hz, 6H). |
| 600 | 1H NMR (400 MHz, Methanol-d4) δ 8.78 (s, 1H), 8.71 (d, J = 2.2 Hz, 1H), 8.66-8.50 (m, 3H), 8.25 (s, 1H), 7.95-7.80 (m, 2H), 7.17 (d, J = 5.1 Hz, 1H), 4.47 (ddd, J = 49.0, 9.3, 2.1 Hz, 1H), 3.99 (ddd, J = 36.4, 14.6, 2.1 Hz, 1H), 3.54 (ddd, J = 16.2, 14.5, 9.3 Hz, 1H), 1.30 (d, J = 1.7 Hz, 6H). |
| 601 | 1H NMR (400 MHz, Methanol-d4) δ 8.76 (d, J = 10.9 Hz, 2H), 8.69 (d, J = 2.1 Hz, 1H), 8.59 (d, J = 2.1 Hz, 1H), 8.39 (s, 1H), 8.28 (d, J = 8.3 Hz, 1H), 8.10 (dd, J = 8.3, 2.4 Hz, 1H), 7.86 (d, J = 5.0 Hz, 1H), 7.15 (d, J = 5.0 Hz, 1H), 4.47 (dd, J = 49.0, 9.2 Hz, 1H), 3.99 (dd, J = 36.4, 14.6 Hz, 1H), 3.53 (ddd, J = 21.8, 15.6, 7.9 Hz, 1H), 1.30 (d, J = 1.6 Hz, 6H). |
| 602 | 1H NMR (400 MHz, Methanol-d4) δ 8.79-8.63 (m, 2H), 8.54 (d, J = 2.1 Hz, 1H), 8.26 (dd, J = 2.8, 0.7 Hz, 1H), 7.91 (s, 1H), 7.87-7.75 (m, 2H), 7.15 (d, J = 5.1 Hz, 1H), 7.02 (dd, J = 8.8, 0.7 Hz, 1H), 5.49 (s, 0H), 4.47 (ddd, J = 49.1, 9.4, 2.1 Hz, 1H), 3.99 (s, 3H), 3.52 (ddd, J = 16.0, 14.6, 9.4 Hz, 1H), 1.35-1.23 (m, 6H). |
| 603 | 1H NMR (400 MHz, DMSO-d6) δ 10.70 (s, 1H), 9.05 (d, J = 6.1 Hz, 1H), 8.97-8.81 (m, 2H), 8.80-8.65 (m, 3H), 8.19-8.01 (m, 2H), 7.86 (d, J = 4.8 Hz, 1H), 7.11 (d, J = 4.8 Hz, 1H), 5.74 (s, 1H), 4.86 (s, 1H), 4.37 (ddd, J = 49.3, 9.4, 2.1 Hz, 1H), 4.01 (s, 0H), 3.88-3.70 (m, 1H), 3.43 (dd, J = 15.3, 10.4 Hz, 1H), 2.05 (s, 1H), 1.16 (dd, J = 5.3, 1.6 Hz, 6H). |
| 604 | 1H NMR (400 MHz, Methanol-d4) δ 8.80-8.66 (m, 2H), 8.58 (d, J = 2.1 Hz, 1H), 8.43 (s, 1H), 8.14 (d, J = 8.3 Hz, 1H), 7.84 (d, J = 5.0 Hz, 1H), 7.29-7.21 (m, 2H), 7.16 (d, J = 5.1 Hz, 1H), 4.47 (ddd, J = 49.0, 9.3, 2.1 Hz, 1H), 4.02 (s, 4H), 3.53 (ddd, J = 16.1, 14.5, 9.4 Hz, 1H), 1.30 (d, J = 1.7 Hz, 6H). |
| 605 | 1H NMR (400 MHz, Methanol-d4) δ 8.77 (s, 1H), 8.71 (d, J = 2.2 Hz, 1H), 8.56 (d, J = 2.2 Hz, 1H), 8.37 (dd, J = 14.5, 2.3 Hz, 2H), 8.25 (s, 1H), 7.86 (d, J = 5.1 Hz, 1H), 7.67 (t, J = 2.3 Hz, 1H), 7.17 (d, J = 5.1 Hz, 1H), 4.47 (ddd, J = 49.1, 9.4, 2.1 Hz, 1H), 4.10-3.84 (m, 4H), 3.53 (ddd, J = 16.1, 14.5, 9.4 Hz, 1H), 1.30 (d, J = 1.6 Hz, 6H). |
| 606 | 1H NMR (400 MHz, Methanol-d4) δ 8.75-8.67 (m, 2H), 8.50 (d, J = 2.2 Hz, 1H), 8.21 (s, 1H), 7.77 (d, J = 5.1 Hz, 1H), 7.58-7.44 (m, 1H), 7.16 (d, J = 5.1 Hz, 1H), 7.08-6.92 (m, 3H), 4.46 (ddd, J = 49.0, 9.4, 2.1 Hz, 1H), 4.12-3.92 (m, 1H), 3.87 (s, 3H), 3.61-3.38 (m, 1H), 1.30 (d, J = 1.6 Hz, 6H). |
| 607 | 1H NMR (400 MHz, Methanol-d4) δ 8.79-8.67 (m, 2H), 8.48 (d, J = 2.2 Hz, 1H), 8.21 (s, 1H), 7.80 (d, J = 5.1 Hz, 1H), 7.69 (t, J = 8.2 Hz, 1H), 7.60-7.30 (m, 3H), 7.16 (d, J = 5.1 Hz, 1H), 4.47 (ddd, J = 49.0, 9.3, 2.1 Hz, 1H), 3.98 (ddd, J = 36.4, 14.6, 2.1 Hz, 1H), 3.65 (s, 4H), 3.54 (ddd, J = 16.1, 14.6, 9.3 Hz, 1H), 1.30 (d, J = 1.6 Hz, 6H). |
| 608 | 1H NMR (400 MHz, Methanol-d4) δ 8.81-8.65 (m, 2H), 8.59-8.42 (m, 1H), 8.23 (s, 1H), 7.79 (d, J = 5.1 Hz, 1H), 7.61 (t, J = 8.2 Hz, 1H), 7.40-7.31 (m, 2H), 7.26-7.06 (m, 2H), 4.47 (ddd, J = 49.0, 9.3, 2.1 Hz, 1H), 4.10-3.89 (m, 1H), 3.53 (ddd, J = 16.2, 14.6, 9.4 Hz, 1H), 1.30 (d, J = 1.6 Hz, 6H). |

TABLE 2-continued

| compound | 1H-NMR |
|---|---|
| 609 | 1H NMR (400 MHz, Methanol-d4) δ 8.76-8.62 (m, 2H), 8.53 (d, J = 2.1 Hz, 1H), 7.98 (s, 1H), 7.73 (d, J = 5.1 Hz, 1H), 7.46-7.29 (m, 2H), 7.24-7.03 (m, 3H), 4.46 (ddd, J = 49.0, 9.4, 2.1 Hz, 1H), 4.15-3.93 (m, 1H), 3.88 (s, 3H), 3.64-3.42 (m, 1H), 1.30 (d, J = 1.6 Hz, 6H). |
| 610 | 1H NMR (400 MHz, Methanol-d4) δ 8.94 (d, J = 2.5 Hz, 1H), 8.88 (d, J = 1.8 Hz, 1H), 8.80 (s, 1H), 8.70 (d, J = 2.2 Hz, 1H), 8.58 (d, J = 2.2 Hz, 1H), 8.42 (dd, J = 2.5, 1.8 Hz, 1H), 8.28 (s, 1H), 7.88 (d, J = 5.0 Hz, 1H), 7.16 (d, J = 5.1 Hz, 1H), 4.47 (ddd, J = 49.1, 9.4, 2.1 Hz, 1H), 3.98 (ddd, J = 36.5, 14.5, 2.1 Hz, 1H), 3.66-3.43 (m, 1H), 1.30 (d, J = 1.6 Hz, 6H). |
| 611 | 1H NMR (400 MHz, Methanol-d4) δ 8.76 (s, 1H), 8.70 (d, J = 2.2 Hz, 1H), 8.58 (d, J = 2.2 Hz, 1H), 8.44 (d, J = 2.5 Hz, 1H), 7.84 (dd, J = 26.0, 7.0 Hz, 2H), 7.32-7.10 (m, 3H), 4.52 (dd, J = 9.0, 1.9 Hz, 1H), 4.46-4.35 (m, 1H), 3.99 (s, 4H), 3.53 (td, J = 15.5, 9.4 Hz, 1H), 1.41-1.17 (m, 6H). |
| 612 | 1H NMR (400 MHz, Methanol-d4) δ 8.75 (d, J = 2.2 Hz, 1H), 8.72 (d, J = 2.2 Hz, 1H), 8.64 (s, 1H), 7.91 (d, J = 5.1 Hz, 1H), 7.64 (s, 1H), 7.21 (d, J = 5.1 Hz, 1H), 4.95 (d, J = 6.6 Hz, 2H), 4.77 (d, J = 6.6 Hz, 2H), 4.38 (s, 2H), 1.88 (s, 3H). |
| 613 | 1H NMR (400 MHz, Methanol-d4) δ 8.78 (d, J = 2.2 Hz, 1H), 8.75 (d, J = 2.2 Hz, 1H), 8.59 (s, 1H), 7.99 (d, J = 5.1 Hz, 1H), 7.87 (s, 1H), 7.21 (d, J = 5.1 Hz, 1H), 4.46 (p, J = 7.5 Hz, 1H), 4.37 (s, 2H), 3.68 (s, 3H), 3.35 (d, J = 7.4 Hz, 2H), 2.62-2.41 (m, 3H), 2.35-2.20 (m, 2H). |
| 614 | 1H NMR (400 MHz, Methanol-d4) δ 8.75 (s, 2H), 8.57 (s, 1H), 7.99 (d, J = 5.1 Hz, 1H), 7.79 (s, 1H), 7.21 (d, J = 5.1 Hz, 1H), 5.13-5.01 (m, 1H), 4.79-4.71 (m, 1H), 4.71-4.60 (m, 1H), 4.53-4.31 (m, 2H), 4.06-3.84 (m, 1H), 3.64-3.40 (m, 3H), 3.09-2.99 (m, 1H), 2.74-2.55 (m, 2H), 2.55-2.39 (m, 2H), 2.38-2.20 (m, 2H), 1.29 (d, J = 1.6 Hz, 6H). |
| 615 | 1H NMR (400 MHz, Methanol-d4) δ 8.75 (d, J = 2.2 Hz, 1H), 8.69 (s, 1H), 8.55 (s, 1H), 8.01 (d, J = 5.1 Hz, 1H), 7.90 (s, 1H), 7.21 (d, J = 5.0 Hz, 1H), 4.42 (ddd, J = 49.0, 9.4, 2.1 Hz, 1H), 4.34-4.23 (m, 1H), 4.06-3.85 (m, 1H), 3.68 (d, J = 7.9 Hz, 2H), 3.62 (s, 3H), 3.55-3.40 (m, 1H), 2.71-2.57 (m, 1H), 2.43-2.10 (m, 4H), 1.28 (d, J = 1.7 Hz, 6H). |
| 616 | 1H NMR (400 MHz, Methanol-d4) δ 8.76 (d, J = 2.2 Hz, 1H), 8.70 (d, J = 2.2 Hz, 1H), 8.55 (s, 1H), 8.28 (s, 1H), 7.92 (d, J = 5.1 Hz, 1H), 7.22 (d, J = 5.0 Hz, 1H), 5.05-4.95 (m, 0H), 4.77-4.66 (m, 1H), 4.58 (dt, J = 9.2, 6.0 Hz, 1H), 3.70 (dd, J = 14.1, 6.7 Hz, 1H), 3.59 (dd, J = 14.1, 4.0 Hz, 1H), 2.81-2.67 (m, 1H), 2.57-2.41 (m, 1H), 2.25 (q, J = 8.6 Hz, 6H), 1.90 (dd, J = 10.0, 5.8 Hz, 5H). |
| 617 | |
| 618 | 1H NMR (400 MHz, Methanol-d4) δ 8.74 (d, J = 2.2 Hz, 1H), 8.66 (d, J = 2.2 Hz, 1H), 8.56 (s, 1H), 8.01 (d, J = 5.1 Hz, 1H), 7.85 (s, 1H), 7.20 (d, J = 5.1 Hz, 1H), 4.42 (ddd, J = 49.1, 9.3, 2.1 Hz, 1H), 4.02-3.80 (m, 2H), 3.60 (s, 3H), 3.55-3.41 (m, 1H), 2.30 (d, J = 12.9 Hz, 2H), 1.96 (d, J = 13.0 Hz, 2H), 1.71-1.49 (m, 4H), 1.34 (s, 3H), 1.28 (d, J = 1.6 Hz, 6H). |
| 619 | 1H NMR (400 MHz, Methanol-d4) δ 8.74 (d, J = 2.2 Hz, 1H), 8.66 (d, J = 2.2 Hz, 1H), 8.58 (s, 1H), 7.99 (d, J = 5.1 Hz, 1H), 7.87 (s, 1H), 7.20 (d, J = 5.1 Hz, 1H), 4.42 (ddd, J = 49.1, 9.4, 2.2 Hz, 1H), 4.03 (s, 1H), 3.94 (ddd, J = 36.4, 14.6, 2.1 Hz, 1H), 3.60 (s, 3H), 3.57-3.44 (m, 1H), 2.25-1.96 (m, 4H), 1.82-1.65 (m, 4H), 1.37 (s, 3H), 1.29 (d, J = 1.6 Hz, 6H). |
| 620 | 1H NMR (400 MHz, Methanol-d4) δ 8.74 (d, J = 2.2 Hz, 1H), 8.68 (d, J = 2.1 Hz, 1H), 8.56 (s, 1H), 7.98 (d, J = 5.1 Hz, 1H), 7.75 (s, 1H), 7.20 (d, J = 5.1 Hz, 1H), 4.43 (ddd, J = 49.0, 9.3, 2.1 Hz, 1H), 4.25 (p, J = 8.0 Hz, 1H), 3.94 (ddd, J = 36.3, 14.5, 2.1 Hz, 1H), 3.67 (s, 3H), 3.60-3.43 (m, 1H), 3.39 (d, J = 7.0 Hz, 2H), 2.93 (s, 3H), 2.80-2.68 (m, 2H), 2.58-2.41 (m, 1H), 2.05-1.79 (m, 2H), 1.29 (d, J = 1.6 Hz, 7H). |
| 621 | 1H NMR (400 MHz, Methanol-d4) δ 8.76 (d, J = 2.2 Hz, 1H), 8.70 (d, J = 2.2 Hz, 1H), 8.61 (s, 1H), 8.31 (s, 1H), 7.93 (d, J = 5.0 Hz, 1H), 7.91 (d, J = 0.9 Hz, 1H), 7.22 (d, J = 5.1 Hz, 1H), 7.17 (d, J = 0.9 Hz, 1H), 4.69 (s, 2H), 2.30-2.18 (m, 6H), 1.98-1.83 (m, 6H). |
| 622 | 1H NMR (400 MHz, Methanol-d4) δ 8.76 (d, J = 2.2 Hz, 1H), 8.70 (d, J = 2.2 Hz, 1H), 8.62 (s, 1H), 8.31 (s, 1H), 7.93 (d, J = 5.1 Hz, 1H), 7.69 (s, 1H), 7.22 (d, J = 5.1 Hz, 1H), 4.65 (s, 2H), 2.34-2.16 (m, 6H), 2.09-1.82 (m, 6H), 1.50 (s, 6H). |
| 623 | 1H NMR (400 MHz, Methanol-d4) δ 8.76 (d, J = 2.2 Hz, 1H), 8.70 (d, J = 2.1 Hz, 1H), 8.52 (s, 1H), 8.29 (s, 1H), 7.92 (d, J = 5.1 Hz, 1H), 7.22 (d, J = 5.1 Hz, 1H), 4.15 (d, J = 2.6 Hz, 2H), 2.69 (t, J = 2.6 Hz, 1H), 2.36-2.16 (m, 6H), 1.98-1.82 (m, 6H). |
| 624 | 1H NMR (400 MHz, Methanol-d4) δ 8.75 (d, J = 2.2 Hz, 1H), 8.69 (d, J = 2.2 Hz, 1H), 8.55 (s, 1H), 8.28 (s, 1H), 7.92 (d, J = 5.1 Hz, 1H), 7.66-7.57 (m, 1H), 7.40 (dd, J = 6.6, 2.1 Hz, 1H), 7.21 (d, J = 5.1 Hz, 1H), 6.40 (t, J = 6.7 Hz, 1H), 4.39 (s, 2H), 2.43-2.04 (m, 6H), 2.04-1.73 (m, 6H). |
| 625 | 1H NMR (400 MHz, Methanol-d4) δ 8.81-8.73 (m, 2H), 8.70 (d, J = 2.2 Hz, 1H), 8.60 (d, J = 2.2 Hz, 1H), 8.39 (s, 1H), 8.26 (s, 1H), 8.07 (dd, J = 8.6, 2.5 Hz, 1H), 8.05-7.99 (m, 1H), 7.85 (d, J = 5.0 Hz, 1H), 7.82 (s, 1H), 7.16 (d, J = 5.1 Hz, 1H), 4.58-4.35 (m, 1H), 4.18-3.87 (m, 1H), 3.66-3.48 (m, 1H), 1.30 (d, J = 1.6 Hz, 6H). |
| 626 | 1H NMR (400 MHz, Methanol-d4) δ 8.75 (d, J = 2.2 Hz, 1H), 8.69 (d, J = 2.1 Hz, 1H), 8.63 (s, 1H), 8.00 (d, J = 5.1 Hz, 1H), 7.61 (s, 1H), 7.21 (d, J = 5.1 Hz, 1H), 5.23-4.99 (m, 3H), 4.80-4.66 (m, 4H), 4.42 (t, J = 12.0 Hz, 2H), 4.13 (s, 2H). |
| 627 | 1H NMR (400 MHz, Methanol-d4) δ 9.06 (s, 1H), 8.75 (s, 1H), 8.68 (d, J = 2.2 Hz, 1H), 8.59 (d, J = 2.2 Hz, 1H), 8.45 (s, 1H), 8.26 (d, J = 8.5 Hz, 2H), 7.84 (d, J = 5.0 Hz, 1H), 7.70 (d, J = 8.5 Hz, 2H), 7.15 (d, J = 5.1 Hz, 1H), 4.61-4.35 (m, 1H), 4.08-3.85 (m, 1H), 3.61-3.47 (m, 1H), 1.30 (d, J = 1.6 Hz, 6H). |

TABLE 2-continued

| compound | 1H-NMR |
|---|---|
| 628 | 1H NMR (400 MHz, Methanol-d4) δ 8.70 (s, 1H), 8.68 (d, J = 2.2 Hz, 1H), 8.57 (d, J = 2.2 Hz, 1H), 8.42 (d, J = 1.0 Hz, 1H), 8.32 (d, J = 1.0 Hz, 1H), 8.31 (s, 1H), 7.98 (d, J = 8.5 Hz, 2H), 7.79 (d, J = 5.1 Hz, 1H), 7.54 (d, J = 8.5 Hz, 2H), 7.14 (d, J = 5.1 Hz, 1H), 4.58-4.31 (m, 1H), 4.08-3.85 (m, 1H), 3.62-3.44 (m, 1H), 1.30 (d, J = 1.6 Hz, 6H). |
| 629 | 1H NMR (400 MHz, Methanol-d4) δ 8.72 (s, 1H), 8.71 (d, J = 2.2 Hz, 1H), 8.57 (d, J = 2.1 Hz, 1H), 8.24 (s, 1H), 8.21 (s, 1H), 7.88 (d, J = 8.6 Hz, 2H), 7.80 (d, J = 5.0 Hz, 1H), 7.61 (d, J = 8.6 Hz, 2H), 7.16 (d, J = 5.1 Hz, 1H), 4.47 (ddd, J = 49.0, 9.3, 2.0 Hz, 1H), 4.08-3.90 (m, 1H), 3.62-3.43 (m, 1H), 2.48 (s, 3H), 1.30 (d, J = 1.6 Hz, 6H). |
| 630 | 1H NMR (400 MHz, Methanol-d4) δ 8.74 (d, J = 2.2 Hz, 1H), 8.66 (d, J = 2.2 Hz, 1H), 8.57 (s, 1H), 8.11 (s, 1H), 8.02 (d, J = 5.0 Hz, 1H), 7.88 (s, 1H), 7.21 (d, J = 5.0 Hz, 1H), 6.90 (d, J = 1.0 Hz, 1H), 4.42 (ddd, J = 49.1, 9.3, 2.1 Hz, 1H), 4.06-3.76 (m, 2H), 3.67-3.37 (m, 1H), 2.88 (t, J = 11.8 Hz, 1H), 2.46-2.11 (m, 4H), 1.89-1.51 (m, 4H), 1.29 (d, J = 1.6 Hz, 6H). |
| 631 | 1H NMR (400 MHz, Methanol-d4) δ 8.75 (d, J = 2.2 Hz, 1H), 8.66 (d, J = 2.2 Hz, 1H), 8.57 (s, 1H), 8.03 (d, J = 5.1 Hz, 1H), 8.00 (s, 1H), 7.88 (s, 1H), 7.21 (d, J = 5.1 Hz, 1H), 4.51-4.30 (m, 1H), 4.08-3.80 (m, 2H), 3.55-3.41 (m, 1H), 2.99-2.84 (m, 1H), 2.29 (d, J = 12.7 Hz, 2H), 2.16 (s, 3H), 2.05-1.81 (m, 4H), 1.72-1.55 (m, 2H), 1.29 (d, J = 1.7 Hz, 7H). |
| 632 | 1H NMR (400 MHz, Methanol-d4) δ 8.76 (d, J = 2.7 Hz, 1H), 8.75 (s, 1H), 8.69 (d, J = 2.2 Hz, 1H), 8.55 (d, J = 2.2 Hz, 1H), 8.26 (s, 1H), 8.22 (s, 1H), 8.02 (dd, J = 8.6, 2.6 Hz, 1H), 7.93 (d, J = 8.6 Hz, 1H), 7.84 (d, J = 5.0 Hz, 1H), 7.14 (d, J = 5.0 Hz, 1H), 4.58-4.35 (m, 1H), 4.10-3.86 (m, 1H), 3.67-3.43 (m, 1H), 2.63 (s, 3H), 1.30 (d, J = 1.6 Hz, 6H). |
| 633 | 1H NMR (400 MHz, Methanol-d4) δ 8.76 (d, J = 2.2 Hz, 1H), 8.75 (d, J = 2.2 Hz, 1H), 8.61 (s, 1H), 8.35 (s, 1H), 8.18 (s, 1H), 7.96 (d, J = 5.1 Hz, 1H), 7.22 (d, J = 5.1 Hz, 1H), 7.10 (s, 1H), 4.41 (ddd, J = 49.1, 9.4, 2.1 Hz, 1H), 4.30 (s, 2H), 3.92 (ddd, J = 36.6, 14.6, 2.1 Hz, 1H), 3.59-3.41 (m, 1H), 2.65-2.50 (m, 2H), 2.46-2.36 (m, 4H), 2.33-2.22 (m, 2H), 1.28 (d, J = 1.7 Hz, 6H). |
| 634 | 1H NMR (400 MHz, Methanol-d4) δ 8.76 (d, J = 2.2 Hz, 1H), 8.73 (d, J = 2.2 Hz, 1H), 8.60 (s, 1H), 8.32 (s, 1H), 8.03 (s, 1H), 7.96 (d, J = 5.1 Hz, 1H), 7.22 (d, J = 5.1 Hz, 1H), 4.41 (ddd, J = 49.1, 9.4, 2.1 Hz, 1H), 4.31 (s, 2H), 3.92 (ddd, J = 36.5, 14.5, 2.1 Hz, 1H), 3.61-3.38 (m, 1H), 2.50 (dd, J = 15.8, 9.0 Hz, 2H), 2.45-2.30 (m, 6H), 2.28 (s, 3H), 1.28 (d, J = 1.7 Hz, 6H). |
| 635 | 1H NMR (400 MHz, Methanol-d4) δ 8.76 (s, 1H), 8.69 (d, J = 2.1 Hz, 1H), 8.60 (d, J = 2.2 Hz, 1H), 8.44 (d, J = 2.0 Hz, 1H), 8.43 (s, 1H), 8.34 (s, 1H), 7.85 (d, J = 5.1 Hz, 1H), 7.84 (s, 1H), 7.68 (d, J = 2.0 Hz, 1H), 7.15 (d, J = 5.0 Hz, 1H), 4.57-4.39 (m, 1H), 4.33 (q, J = 7.0 Hz, 2H), 4.10-3.91 (m, 1H), 3.60-3.46 (m, 1H), 1.58 (t, J = 6.9 Hz, 3H), 1.30 (d, J = 1.6 Hz, 6H). |
| 636 | |
| 637 | 1H NMR (400 MHz, Methanol-d4) δ 8.89 (s, 1H), 8.74 (d, J = 2.1 Hz, 1H), 8.67 (d, J = 2.1 Hz, 1H), 8.58 (s, 1H), 8.03 (d, J = 5.1 Hz, 1H), 7.91 (s, 1H), 7.21 (d, J = 5.1 Hz, 1H), 4.42 (ddd, J = 49.0, 9.3, 2.1 Hz, 1H), 4.05-3.81 (m, 2H), 3.60-3.39 (m, 1H), 3.23-3.05 (m, 1H), 2.32 (d, J = 11.4 Hz, 4H), 1.91 (q, J = 11.4 Hz, 2H), 1.74-1.57 (m, 2H), 1.29 (d, J = 1.6 Hz, 6H). |
| 638 | 1H NMR (400 MHz, Methanol-d4) δ 8.75 (d, J = 2.2 Hz, 1H), 8.66 (d, J = 2.2 Hz, 1H), 8.57 (s, 1H), 8.11 (s, 1H), 7.98 (d, J = 5.1 Hz, 1H), 7.64 (s, 1H), 7.21 (d, J = 5.1 Hz, 1H), 6.92 (s, 1H), 4.57-4.30 (m, 2H), 4.08-3.83 (m, 1H), 3.58-3.42 (m, 1H), 3.08-2.95 (m, 2H), 2.88-2.73 (m, 1H), 2.59-2.43 (m, 2H), 2.42-2.30 (m, 2H), 1.29 (d, J = 1.7 Hz, 6H). |
| 639 | 1H NMR (400 MHz, Methanol-d4) δ 8.75 (d, J = 2.1 Hz, 1H), 8.67 (d, J = 2.2 Hz, 1H), 8.60 (s, 1H), 8.21 (s, 1H), 8.05 (d, J = 5.1 Hz, 1H), 7.95 (s, 1H), 7.21 (d, J = 5.1 Hz, 1H), 7.16 (d, J = 0.8 Hz, 1H), 4.72 (dd, J = 9.6, 3.6 Hz, 1H), 4.43 (ddd, J = 49.1, 9.3, 2.1 Hz, 1H), 4.31-4.21 (m, 1H), 4.20-4.08 (m, 1H), 3.93 (ddd, J = 36.3, 14.5, 2.1 Hz, 1H), 3.62-3.42 (m, 2H), 2.44-2.35 (m, 1H), 2.27-2.05 (m, 2H), 1.99-1.81 (m, 1H), 1.29 (d, J = 1.6 Hz, 6H). |
| 640 | 1H NMR (400 MHz, Methanol-d4) δ 8.74 (d, J = 2.2 Hz, 1H), 8.67 (d, J = 2.2 Hz, 1H), 8.55 (s, 1H), 8.09 (s, 1H), 7.97 (d, J = 5.1 Hz, 1H), 7.73 (s, 1H), 7.20 (d, J = 5.0 Hz, 1H), 6.88 (d, J = 1.1 Hz, 1H), 4.56-4.33 (m, 1H), 4.33-4.19 (m, 1H), 4.08-3.79 (m, 1H), 3.65-3.41 (m, 1H), 2.91 (d, J = 7.3 Hz, 2H), 2.89-2.77 (m, 2H), 2.68-2.48 (m, 1H), 1.95-1.76 (m, 2H), 1.29 (d, J = 1.6 Hz, 6H). |
| 641 | 1H NMR (400 MHz, Methanol-d4) δ 9.02 (s, 2H), 8.79 (s, 1H), 8.72 (d, J = 2.1 Hz, 1H), 8.63 (d, J = 2.1 Hz, 1H), 8.47 (s, 1H), 8.22 (s, 1H), 8.01 (s, 1H), 7.90 (d, J = 5.1 Hz, 1H), 7.16 (d, J = 5.1 Hz, 1H), 4.63-4.35 (m, 1H), 4.21-3.87 (m, 1H), 3.73-3.44 (m, 1H), 1.30 (d, J = 1.6 Hz, 6H). |
| 642 | 1H NMR (400 MHz, Methanol-d4) δ 9.38 (s, 1H), 8.75 (d, J = 2.2 Hz, 1H), 8.68 (d, J = 2.2 Hz, 1H), 8.58 (s, 1H), 8.04 (d, J = 5.1 Hz, 1H), 7.91 (s, 1H), 7.21 (d, J = 5.1 Hz, 1H), 4.43 (ddd, J = 49.1, 9.3, 2.1 Hz, 1H), 4.09-3.75 (m, 2H), 3.63-3.34 (m, 2H), 2.34 (t, J = 5.0 Hz, 5H), 2.05 (s, 1H), 1.95 (q, J = 11.6 Hz, 2H), 1.81-1.61 (m, 2H), 1.29 (d, J = 1.6 Hz, 6H). |
| 643 | 1H NMR (400 MHz, Methanol-d4) δ 8.74 (d, J = 2.2 Hz, 1H), 8.65 (d, J = 2.1 Hz, 1H), 8.54 (s, 1H), 7.99 (d, J = 5.1 Hz, 1H), 7.83 (s, 1H), 7.20 (d, J = 5.1 Hz, 1H), 4.34-4.08 (m, 2H), 4.04-3.83 (m, 1H), 3.82-3.62 (m, 1H), 1.40 (d, J = 6.4 Hz, 6H), 0.95-0.64 (m, 4H). |
| 644 | |
| 645 | 1H NMR (400 MHz, Methanol-d4) δ 8.75 (d, J = 2.2 Hz, 1H), 8.66 (d, J = 2.2 Hz, 1H), 8.60 (s, 1H), 8.00 (d, J = 5.1 Hz, 1H), 7.86 (s, 1H), 7.21 (d, J = 5.0 Hz, 1H), 6.76 (d, J = 1.2 Hz, 1H), 4.41 (ddd, J = 49.1, 9.4, 2.1 Hz, 1H), 4.24-4.15 (m, 1H), |

TABLE 2-continued

| compound | 1H-NMR |
|---|---|
|  | 4.05-3.82 (m, 1H), 3.59-3.42 (m, 1H), 3.02-2.90 (m, 1H), 2.42 (s, 3H), 2.17-1.90 (m, 6H), 1.90-1.74 (m, 2H), 1.28 (d, J = 1.7 Hz, 6H). |
| 646 | 1H NMR (400 MHz, Methanol-d4) δ 8.74 (d, J = 2.2 Hz, 1H), 8.66 (d, J = 2.2 Hz, 1H), 8.57 (s, 1H), 8.02 (d, J = 5.1 Hz, 1H), 7.88 (s, 1H), 7.21 (d, J = 5.1 Hz, 1H), 6.73 (d, J = 1.0 Hz, 1H), 4.56-4.29 (m, 1H), 4.04-3.82 (m, 2H), 3.60-3.42 (m, 1H), 2.90-2.73 (m, 1H), 2.41 (s, 3H), 2.32-2.13 (m, 4H), 1.83-1.52 (m, 4H), 1.29 (d, J = 1.7 Hz, 6H). |
| 647 | 1H NMR (400 MHz, Methanol-d4) δ 8.74 (s, 1H), 8.69 (d, J = 2.2 Hz, 1H), 8.49 (d, J = 2.2 Hz, 1H), 8.36 (s, 1H), 7.97 (dd, J = 8.7, 0.8 Hz, 1H), 7.80 (d, J = 5.1 Hz, 1H), 7.48 (dd, J = 1.7, 0.7 Hz, 1H), 7.28-7.03 (m, 2H), 4.47 (ddd, J = 49.0, 9.3, 2.1 Hz, 1H), 3.99 (ddd, J = 36.5, 14.6, 2.1 Hz, 1H), 3.66-3.44 (m, 1H), 1.30 (d, J = 1.7 Hz, 6H). |
| 648 | 1H NMR (400 MHz, Methanol-d4) δ 8.69 (t, J = 1.1 Hz, 2H), 8.53 (d, J = 2.2 Hz, 1H), 8.18 (s, 1H), 7.77 (d, J = 5.1 Hz, 1H), 7.64-7.52 (m, 2H), 7.51-7.40 (m, 2H), 7.15 (d, J = 5.1 Hz, 1H), 4.54 (s, 3H), 4.45-4.32 (m, 1H), 4.16-3.88 (m, 1H), 3.73-3.61 (m, 2H), 3.57-3.50 (m, 1H), 3.46 (s, 3H), 1.30 (d, J = 1.6 Hz, 6H). |
| 649 | 1H NMR (400 MHz, Methanol-d4) δ 8.71 (d, J = 1.9 Hz, 2H), 8.56 (d, J = 2.2 Hz, 1H), 8.11 (d, J = 2.8 Hz, 1H), 7.94-7.85 (m, 1H), 7.63 (dd, J = 9.6, 2.8 Hz, 1H), 7.47 (dt, J = 14.4, 1.7 Hz, 1H), 7.16 (d, J = 5.1 Hz, 1H), 6.74 (d, J = 9.7 Hz, 1H), 6.22 (dt, J = 14.3, 5.5 Hz, 1H), 4.46 (ddd, J = 49.0, 9.3, 2.1 Hz, 1H), 4.26 (dd, J = 5.5, 1.7 Hz, 2H), 3.97 (ddd, J = 36.5, 14.5, 2.1 Hz, 1H), 3.66-3.44 (m, 1H), 1.29 (d, J = 1.6 Hz, 6H). |
| 650 | 1H NMR (400 MHz, Methanol-d4) δ 8.78-8.62 (m, 2H), 8.52 (d, J = 2.2 Hz, 1H), 7.98 (s, 1H), 7.75 (d, J = 5.0 Hz, 1H), 7.39-7.25 (m, 2H), 7.14 (d, J = 5.1 Hz, 1H), 7.06 (d, J = 8.2 Hz, 1H), 4.46 (ddd, J = 49.0, 9.3, 2.0 Hz, 1H), 3.98 (ddd, J = 36.5, 14.6, 2.1 Hz, 1H), 3.64 (s, 2H), 3.60-3.41 (m, 1H), 1.30 (d, J = 1.6 Hz, 6H). |
| 651 | 1H NMR (400 MHz, Methanol-d4) δ 8.82-8.66 (m, 2H), 8.52 (d, J = 2.2 Hz, 1H), 8.02 (s, 1H), 7.82 (d, J = 5.1 Hz, 1H), 7.50-7.37 (m, 2H), 7.29 (dd, J = 8.6, 2.1 Hz, 1H), 7.15 (d, J = 5.1 Hz, 1H), 4.46 (ddd, J = 49.0, 9.3, 2.1 Hz, 1H), 3.98 (ddd, J = 36.6, 14.6, 2.1 Hz, 1H), 3.53 (ddd, J = 16.2, 14.6, 9.4 Hz, 1H), 1.29 (d, J = 1.6 Hz, 6H). |
| 652 | 1H NMR (400 MHz, Methanol-d4) δ 8.71 (d, J = 2.0 Hz, 2H), 8.51 (d, J = 2.2 Hz, 1H), 8.13 (s, 1H), 7.78 (d, J = 5.1 Hz, 1H), 7.51 (d, J = 7.8 Hz, 1H), 7.23 (d, J = 1.9 Hz, 1H), 7.22-7.09 (m, 2H), 4.47 (ddd, J = 49.0, 9.4, 2.1 Hz, 1H), 3.99 (ddd, J = 36.6, 14.5, 2.1 Hz, 1H), 3.67-3.42 (m, 1H), 3.24 (s, 3H), 1.41 (s, 6H), 1.30 (d, J = 1.6 Hz, 6H). |
| 653 | 1H NMR (400 MHz, Methanol-d4) δ 8.76-8.62 (m, 2H), 8.50 (d, J = 2.1 Hz, 1H), 7.99 (s, 1H), 7.73 (d, J = 5.0 Hz, 1H), 7.44-7.27 (m, 2H), 7.23-7.05 (m, 2H), 4.46 (ddd, J = 49.1, 9.2, 2.0 Hz, 1H),<br>3.99 (dd, J = 36.5, 14.6 Hz, 1H), 3.67-3.40 (m, 1H), 2.03 (s, 1H), 1.39 (s, 6H), 1.30 (d, J = 1.6 Hz, 6H). |
| 654 | 1H NMR (400 MHz, Methanol-d4) δ 8.75 (s, 2H), 8.58 (s, 1H), 7.98 (d, J = 5.1 Hz, 1H), 7.81 (s, 1H), 7.65-7.49 (m, 0H), 7.21 (d, J = 5.1 Hz, 1H), 4.70-4.29 (m, 4H), 3.93 (ddd, J = 36.6, 14.5, 2.1 Hz, 1H), 3.63-3.36 (m, 3H), 2.71-2.38 (m, 2H), 2.28 (td, J = 12.9, 11.1, 8.0 Hz, 2H), 1.29 (d, J = 1.7 Hz, 6H).; 1H NMR (400 MHz, Methanol-d4) δ 8.65-8.47 (m, 3H), 8.03 (s, 1H), 7.80 (d, J = 4.9 Hz, 1H), 7.05 (d, J = 4.9 Hz, 1H), 4.61 (t, J = 8.7 Hz, 2H), 4.49 (dd, J = 9.2, 2.3 Hz, 0H), 4.37 (dd, J = 9.1, 2.3 Hz, 1H), 4.19 (t, J = 7.4 Hz, 1H), 4.04-3.82 (m, 1H), 3.65 (s, 0H), 3.57-3.46 (m, 1H), 3.38 (d, J = 7.5 Hz, 2H), 2.52 (s, 0H), 2.41 (tt, J = 7.8, 3.1 Hz, 2H), 2.14 (q, J = 9.5 Hz, 2H), 1.29 (d, J = 1.7 Hz, 6H). |
| 655 | 1H NMR (400 MHz, Methanol-d4) δ 8.83-8.70 (m, 2H), 8.57 (s, 1H), 8.48 (d, J = 6.2 Hz, 1H), 7.98 (d, J = 5.1 Hz, 1H), 7.79 (s, 1H), 7.21 (d, J = 5.1 Hz, 1H), 4.58-4.32 (m, 2H), 3.93 (ddd, J = 36.5, 14.6, 2.1 Hz, 1H), 3.62-3.40 (m, 3H), 3.21 (q, J = 10.8 Hz, 2H), 2.70-2.42 (m, 3H), 2.29 (ddd, J = 12.5, 9.3, 7.0 Hz, 2H), 1.29 (d, J = 1.6 Hz, 6H). |
| 656 | 1H NMR (400 MHz, Methanol-d4) δ 8.83-8.69 (m, 2H), 8.57 (s, 1H), 8.36 (s, 1H), 7.98 (d, J = 5.1 Hz, 1H), 7.77 (s, 1H), 7.21 (d, J = 5.1 Hz, 1H), 6.22 (tt, J = 56.1, 4.8 Hz, 1H), 4.60-4.30 (m, 3H), 3.94 (ddd, J = 36.5, 14.5, 2.1 Hz, 1H), 3.65-3.41 (m, 3H), 2.86 (td, J = 16.5, 4.8 Hz, 2H), 2.69-2.23 (m, 5H), 1.29 (d, J = 1.7 Hz, 6H). |
| 657 | 1H NMR (400 MHz, Methanol-d4) δ 8.80-8.70 (m, 2H), 8.58 (d, J = 2.2 Hz, 1H), 8.08 (dd, J = 2.5, 0.7 Hz, 1H), 8.04-7.83 (m, 3H), 7.25-7.11 (m, 2H), 4.46 (ddd, J = 49.1, 9.3, 2.1 Hz, 1H), 3.97 (ddd, J = 36.5, 14.6, 2.1 Hz, 1H), 3.66-3.45 (m, 1H), 1.29 (d, J = 1.7 Hz, 6H). |
| 658 | 1H NMR (400 MHz, Methanol-d4) δ 8.76-8.65 (m, 2H), 8.56 (d, J = 2.2 Hz, 1H), 8.38 (s, 2H), 7.96-7.69 (m, 2H), 7.16 (d, J = 5.1 Hz, 1H), 4.46 (ddd, J = 49.0, 9.4, 2.1 Hz, 1H), 3.98 (ddd, J = 36.6, 14.6, 2.1 Hz, 1H), 3.68-3.44 (m, 1H), 1.29 (d, J = 1.7 Hz, 6H). |
| 659 | 1H NMR (400 MHz, Methanol-d4) δ 8.82-8.69 (m, 2H), 8.57 (s, 1H), 7.99 (d, J = 5.1 Hz, 1H), 7.76 (s, 1H), 7.21 (d, J = 5.0 Hz, 1H), 4.73-4.31 (m, 2H), 3.93 (ddd, J = 36.4, 14.5, 2.2 Hz, 1H), 3.65-3.38 (m, 3H), 2.69-2.39 (m, 3H), 2.29 (dt, J = 15.4, 9.7 Hz, 2H), 2.17-2.01 (m, 1H), 1.49-1.36 (m, 0H), 1.29 (d, J = 1.6 Hz, 6H), 1.26-1.19 (m, 1H). |
| 660 | 1H NMR (400 MHz, Methanol-d4) δ 8.78-8.63 (m, 2H), 8.49 (d, J = 2.2 Hz, 1H), 8.23 (s, 1H), 7.92 (dd, J = 8.5, 0.8 Hz, 1H), 7.74 (d, J = 5.1 Hz, 1H), 7.59 (dd, J = 1.8, 0.7 Hz, 1H), 7.26-7.09 (m, 2H), 4.47 (ddd, J = 49.0, 9.4, 2.1 Hz, 1H), 4.13-3.83 (m, 1H), 3.65-3.46 (m, 1H), 2.61 (s, 3H), 1.30 (d, J = 1.6 Hz, 6H). |
| 661 | 1H NMR (400 MHz, Methanol-d4) δ 8.82-8.67 (m, 2H), 8.58 (d, J = 2.1 Hz, 1H), 8.07 (dd, J = 2.4, 0.7 Hz, 1H), 8.01-7.81 (m, 3H), 7.28-7.03 (m, 2H), 4.46 (ddd, J = |

TABLE 2-continued

| compound | 1H-NMR |
|---|---|
| | 49.0, 9.3, 2.1 Hz, 1H), 3.97 (ddd, J = 36.4, 14.5, 2.1 Hz, 1H), 3.69-3.42 (m, 1H), 3.08 (s, 3H), 1.29 (d, J = 1.7 Hz, 6H). |
| 662 | 1H NMR (400 MHz, Methanol-d4) δ 8.79-8.66 (m, 2H), 8.54 (d, J = 2.2 Hz, 1H), 8.42 (dd, J = 2.7, 0.8 Hz, 1H), 8.28 (d, J = 8.9 Hz, 1H), 8.05 (s, 1H), 7.90 (dd, J = 8.9, 2.7 Hz, 1H), 7.81 (d, J = 5.1 Hz, 1H), 7.15 (d, J = 5.1 Hz, 1H), 4.47 (ddd, J = 49.0, 9.3, 2.1 Hz, 1H), 3.99 (ddd, J = 36.5, 14.5, 2.1 Hz, 1H), 3.67-3.46 (m, 1H), 2.22 (s, 3H), 1.30 (d, J = 1.7 Hz, 6H). |
| 663 | 1H NMR (400 MHz, Methanol-d4) δ 8.78-8.68 (m, 3H), 8.57 (d, J = 2.2 Hz, 1H), 7.94 (s, 1H), 7.87 (d, J = 5.1 Hz, 1H), 7.15 (d, J = 5.1 Hz, 1H), 4.68-4.58 (m, 2H), 4.59-4.35 (m, 1H), 3.99 (ddd, J = 36.4, 14.5, 2.1 Hz, 1H), 3.90-3.77 (m, 2H), 3.62-3.38 (m, 4H), 1.30 (d, J = 1.6 Hz, 6H), 1.26 (d, J = 1.8 Hz, 1H). |
| 664 | 1H NMR (400 MHz, Methanol-d4) δ 8.98 (s, 0H), 8.82-8.63 (m, 3H), 8.58 (dd, J = 6.0, 2.1 Hz, 1H), 8.20 (s, 1H), 8.17-8.00 (m, 1H), 7.83 (t, J = 6.7 Hz, 2H), 7.16 (d, J = 5.1 Hz, 1H), 5.48 (s, 0H), 4.47 (ddd, J = 49.0, 9.4, 2.1 Hz, 1H), 4.16-3.87 (m, 2H), 3.69-3.41 (m, 1H), 1.30 (d, J = 1.6 Hz, 6H). |
| 665 | 1H NMR (400 MHz, Methanol-d4) δ 8.75-8.60 (m, 2H), 8.45 (dd, J = 22.3, 2.2 Hz, 1H), 8.01 (d, J = 19.2 Hz, 1H), 7.79-7.64 (m, 2H), 7.42-7.29 (m, 1H), 7.20-7.01 (m, 2H), 4.47 (dd, J = 49.0, 8.3 Hz, 1H), 3.99 (dd, J = 36.6, 14.8 Hz, 1H), 3.65-3.39 (m, 1H), 2.28 (d, J = 7.6 Hz, 2H), 1.30 (d, J = 1.7 Hz, 6H). |
| 666 | 1H NMR (400 MHz, Methanol-d4) δ 8.75 (d, J = 5.5 Hz, 3H), 8.71 (d, J = 2.2 Hz, 1H), 8.57 (d, J = 2.2 Hz, 1H), 8.02 (s, 1H), 7.86 (d, J = 5.1 Hz, 1H), 7.16 (d, J = 5.1 Hz, 1H), 4.46 (ddd, J = 49.1, 9.3, 2.1 Hz, 1H), 3.98 (ddd, J = 36.5, 14.5, 2.1 Hz, 1H), 3.53 (ddd, J = 16.3, 14.6, 9.4 Hz, 1H), 2.34 (tt, J = 7.4, 5.4 Hz, 1H), 1.29 (d, J = 1.6 Hz, 6H), 1.25-1.12 (m, 4H). |
| 667 | 1H NMR (400 MHz, Methanol-d4) δ 9.68 (s, 1H), 8.70 (d, J = 2.5 Hz, 2H), 8.64 (d, J = 2.2 Hz, 1H), 8.22 (d, J = 3.0 Hz, 1H), 7.85 (d, J = 5.0 Hz, 1H), 7.50 (dd, J = 8.9, 3.0 Hz, 1H), 7.28-7.13 (m, 3H), 4.47 (ddd, J = 49.0, 9.4, 2.1 Hz, 1H), 3.93 (s, 5H), 3.60-3.45 (m, 1H), 1.31 (s, 6H). |
| 668 | 1H NMR (400 MHz, Methanol-d4) δ 8.70 (d, J = 2.0 Hz, 2H), 8.57 (d, J = 2.1 Hz, 1H), 8.20 (d, J = 2.3 Hz, 1H), 7.91 (s, 1H), 7.82 (d, J = 5.1 Hz, 1H), 7.70 (dd, J = 2.3, 1.2 Hz, 1H), 7.15 (d, J = 5.1 Hz, 1H), 4.46 (ddd, J = 49.0, 9.4, 2.1 Hz, 1H), 3.99 (ddd, J = 36.5, 14.5, 2.1 Hz, 1H), 3.71 (t, J = 1.0 Hz, 1H), 3.65-3.45 (m, 1H), 1.30 (d, J = 1.6 Hz, 6H). |
| 669 | 1H NMR (400 MHz, Methanol-d4) δ 8.75-8.64 (m, 2H), 8.54 (d, J = 2.1 Hz, 1H), 8.40 (s, 2H), 7.91-7.73 (m, 2H), 7.15 (d, J = 5.1 Hz, 1H), 4.46 (ddd, J = 49.0, 9.3, 2.1 Hz, 1H), 3.98 (ddd, J = 36.5, 14.5, 2.1 Hz, 1H), 3.52 (ddd, J = 16.1, 14.5, 9.3 Hz, 1H), 3.26 (s, 6H), 1.29 (d, J = 1.7 Hz, 6H). |
| 670 | 1H NMR (400 MHz, Methanol-d4) δ 8.86 (s, 1H), 8.62 (d, J = 2.2 Hz, 1H), 8.36 (d, J = 2.1 Hz, 1H), 7.42 (dd, J = 9.3, 2.2 Hz, 1H), 7.35-7.17 (m, 2H), 7.08 (d, J = 4.7 Hz, 1H), 6.81 (dd, J = 9.3, 0.8 Hz, 1H), 6.69 (s, 1H), 5.08 (s, 2H), 4.37 (ddd, J = 49.0, 9.2, 2.5 Hz, 1H), 3.98 (ddd, J = 35.5, 14.4, 2.5 Hz, 1H), 3.64-3.45 (m, 1H), 1.27 (d, J = 1.7 Hz, 6H). |
| 671 | 1H NMR (400 MHz, Methanol-d4) δ 8.77 (s, 1H), 8.70 (t, J = 1.8 Hz, 2H), 8.59 (d, J = 2.2 Hz, 1H), 8.21 (s, 1H), 8.13 (dd, J = 8.5, 2.5 Hz, 1H), 7.90-7.81 (m, 1H), 7.16 (d, J = 5.1 Hz, 1H), 4.47 (ddd, J = 49.0, 9.3, 2.1 Hz, 1H), 3.99 (ddd, J = 36.5, 14.5, 2.1 Hz, 1H), 3.54 (ddd, J = 16.1, 14.5, 9.3 Hz, 1H), 1.30 (d, J = 1.6 Hz, 6H). |
| 672 | 1H NMR (400 MHz, Methanol-d4) δ 8.77 (d, J = 2.0 Hz, 2H), 8.73-8.63 (m, 3H), 8.08 (d, J = 5.1 Hz, 1H), 8.02 (d, J = 8.8 Hz, 2H), 7.23 (d, J = 5.1 Hz, 1H), 5.06 (tt, J = 7.4, 5.0 Hz, 1H), 4.38 (ddd, J = 49.0, 9.4, 2.1 Hz, 1H), 4.06-3.78 (m, 3H), 3.60-3.34 (m, 3H), 1.25 (d, J = 1.6 Hz, 6H). |
| 673 | 1H NMR (400 MHz, Methanol-d4) δ 8.77-8.66 (m, 2H), 8.55 (d, J = 2.2 Hz, 1H), 8.22 (dd, J = 2.7, 0.7 Hz, 1H), 7.92 (s, 1H), 7.86-7.66 (m, 2H), 7.19-7.03 (m, 2H), 4.46 (ddd, J = 49.0, 9.4, 2.1 Hz, 1H), 3.98 (ddd, J = 36.5, 14.6, 2.1 Hz, 1H), 3.89-3.76 (m, 4H), 3.67-3.57 (m, 4H), 3.57-3.43 (m, 1H), 1.29 (d, J = 1.6 Hz, 6H). |
| 674 | 1H NMR (400 MHz, Methanol-d4) δ 8.79-8.67 (m, 3H), 8.66-8.54 (m, 1H), 8.37 (s, 0H), 8.04 (s, 1H), 7.88 (d, J = 5.2 Hz, 1H), 7.16 (d, J = 5.1 Hz, 1H), 4.47 (ddd, J = 49.0, 9.3, 2.1 Hz, 1H), 3.99 (ddd, J = 36.3, 14.6, 2.1 Hz, 1H), 3.65-3.40 (m, 1H), 2.29 (s, 3H), 1.30 (d, J = 1.6 Hz, 6H). |
| 675 | 1H NMR (400 MHz, Methanol-d4) δ 8.78-8.69 (m, 2H), 8.59 (d, J = 2.2 Hz, 1H), 8.09 (dd, J = 2.5, 0.8 Hz, 1H), 7.99-7.78 (m, 3H), 7.16 (d, J = 5.1 Hz, 1H), 6.87 (dd, J = 9.4, 0.8 Hz, 1H), 4.52 (dd, J = 9.3, 2.2 Hz, 1H), 4.41-4.20 (m, 5H), 3.97 (ddd, J = 36.3, 14.6, 2.1 Hz, 1H), 3.53 (ddd, J = 16.1, 14.6, 9.4 Hz, 1H), 2.58 (p, J = 7.6 Hz, 2H), 1.29 (d, J = 1.6 Hz, 6H). |
| 676 | 1H NMR (400 MHz, Methanol-d4) δ 8.83-8.73 (m, 2H), 8.72-8.59 (m, 3H), 8.06 (d, J = 5.1 Hz, 1H), 8.04-7.92 (m, 2H), 7.23 (d, J = 5.1 Hz, 1H), 5.04 (tt, J = 7.4, 5.0 Hz, 1H), 4.38 (ddd, J = 49.0, 9.3, 2.1 Hz, 1H), 4.01-3.73 (m, 3H), 3.58-3.35 (m, 3H), 1.25 (d, J = 1.7 Hz, 6H).; 1H NMR (400 MHz, Methanol-d4) δ 8.84-8.71 (m, 2H), 8.71-8.58 (m, 3H), 8.15-7.88 (m, 3H), 7.23 (d, J = 5.0 Hz, 1H), 5.03 (dd, J = 12.3, 7.4, 5.0 Hz, 1H), 4.38 (ddd, J = 49.0, 9.4, 2.1 Hz, 1H), 4.03-3.73 (m, 3H), 3.60-3.33 (m, 3H), 1.25 (d, J = 1.6 Hz, 6H). |
| 677 | 1H NMR (400 MHz, Methanol-d4) δ 8.84-8.71 (m, 2H), 8.71-8.58 (m, 3H), 8.15-7.88 (m, 3H), 7.23 (d, J = 5.0 Hz, 1H), 5.03 (ddd, J = 12.3, 7.4, 5.0 Hz, 1H), 4.38 (ddd, J = 49.0, 9.4, 2.1 Hz, 1H), 4.03-3.73 (m, 3H), 3.60-3.33 (m, 3H), 1.25 (d, J = 1.6 Hz, 6H). |
| 678 | 1H NMR (400 MHz, Methanol-d4) δ 8.80-8.66 (m, 2H), 8.58 (d, J = 2.2 Hz, 1H), 8.17 (s, 1H), 7.99 (dd, J = 8.4, 2.6 Hz, 1H), 7.84 (d, J = 5.1 Hz, 1H), 7.69 (dd, J = 8.4, 0.8 Hz, 1H), 7.16 (d, J = 5.1 Hz, 1H), 4.47 (ddd, J = 49.0, 9.3, |

TABLE 2-continued

| compound | 1H-NMR |
|---|---|
| | 2.1 Hz, 1H), 3.99 (ddd, J = 36.4, 14.5, 2.1 Hz, 1H), 3.54 (ddd, J = 16.1, 14.5, 9.3 Hz, 1H), 1.30 (d, J = 1.6 Hz, 6H). |
| 679 | 1H NMR (400 MHz, Methanol-d4) δ 8.70 (d, J = 2.1 Hz, 2H), 8.56 (d, J = 2.2 Hz, 1H), 8.12 (dd, J = 2.7, 0.7 Hz, 1H), 7.93 (s, 1H), 7.92-7.77 (m, 2H), 7.24-7.05 (m, 2H), 4.46 (ddd, J = 49.0, 9.3, 2.1 Hz, 1H), 3.97 (ddd, J = 36.3, 14.6, 2.1 Hz, 1H), 3.63-3.45 (m, 1H), 3.26 (s, 6H), 1.30 (d, J = 1.6 Hz, 6H). |
| 680 | 1H NMR (400 MHz, Methanol-d4) δ 8.88 (s, 2H), 8.78 (s, 1H), 8.70 (d, J = 2.1 Hz, 1H), 8.58 (d, J = 2.1 Hz, 1H), 8.10 (s, 1H), 7.87 (d, J = 5.1 Hz, 1H), 7.15 (d, J = 5.1 Hz, 1H), 4.47 (ddd, J = 49.0, 9.3, 2.1 Hz, 1H), 3.98 (ddd, J = 36.4, 14.6, 2.1 Hz, 1H), 3.55 (ddd, J = 16.1, 14.5, 9.3 Hz, 1H), 3.07 (q, J = 7.6 Hz, 2H), 1.42 (t, J = 7.6 Hz, 3H), 1.30 (d, J = 1.7 Hz, 6H). |
| 681 | 1H NMR (400 MHz, Methanol-d4) δ 8.79-8.65 (m, 2H), 8.57 (d, J = 2.2 Hz, 1H), 8.40 (s, 2H), 7.93-7.79 (m, 2H), 7.15 (d, J = 5.1 Hz, 1H), 4.46 (ddd, J = 49.0, 9.3, 2.1 Hz, 1H), 4.23 (t, J = 7.6 Hz, 4H), 3.98 (ddd, J = 36.5, 14.5, 2.1 Hz, 1H), 3.52 (ddd, J = 16.2, 14.5, 9.3 Hz, 1H), 2.65 (s, 1H), 2.45 (p, J = 7.6 Hz, 2H), 1.29 (d, J = 1.6 Hz, 6H). |
| 682 | 1H NMR (400 MHz, Methanol-d4) δ 8.78-8.62 (m, 2H), 8.57 (d, J = 2.1 Hz, 1H), 8.22 (dd, J = 2.6, 0.7 Hz, 1H), 7.90 (s, 1H), 7.86-7.63 (m, 2H), 7.15 (d, J = 5.1 Hz, 1H), 6.79 (dd, J = 8.9, 0.8 Hz, 1H), 4.62-4.34 (m, 5H), 3.98 (ddd, J = 36.5, 14.5, 2.1 Hz, 1H), 3.52 (ddd, J = 16.3, 14.6, 9.4 Hz, 1H), 1.29 (d, J = 1.7 Hz, 6H). |
| 683 | 1H NMR (400 MHz, Methanol-d4) δ 8.83-8.67 (m, 3H), 8.56 (d, J = 2.2 Hz, 1H), 8.16 (s, 1H), 8.00 (dd, J = 8.5, 2.6 Hz, 1H), 7.91-7.77 (m, 2H), 7.16 (d, J = 5.1 Hz, 1H), 4.47 (ddd, J = 49.0, 9.3, 2.1 Hz, 1H), 3.99 (ddd, J = 36.4, 14.5, 2.1 Hz, 1H), 3.70-3.44 (m, 1H), 1.83 (s, 6H), 1.30 (d, J = 1.6 Hz, 6H). |
| 684 | 1H NMR (400 MHz, Methanol-d4) δ 8.82-8.69 (m, 2H), 8.59 (d, J = 2.2 Hz, 1H), 8.24-8.07 (m, 1H), 7.96-7.90 (m, 2H), 7.85 (dd, J = 5.1, 1.9 Hz, 1H), 7.16 (d, J = 5.1 Hz, 1H), 6.90 (dt, J = 9.3, 1.1 Hz, 1H), 4.61-4.37 (m, 5H), 4.15 (q, J = 9.2 Hz, 1H), 4.12-3.78 (m, 1H), 3.53 (ddd, J = 16.0, 14.5, 9.4 Hz, 1H), 1.29 (d, J = 1.6 Hz, 6H). |
| 685 | 1H NMR (400 MHz, Methanol-d4) δ 8.76-8.63 (m, 2H), 8.53 (d, J = 2.2 Hz, 1H), 8.13 (s, 1H), 7.77 (d, J = 5.1 Hz, 1H), 7.27-7.16 (m, 2H), 7.06 (d, J = 7.7 Hz, 2H), 4.46 (ddd, J = 49.0, 9.3, 2.1 Hz, 1H), 4.03 (dd, J = 14.6, 2.1 Hz, 1H), 3.90 (d, J = 8.1 Hz, 8H), 3.53 (ddd, J = 16.1, 14.5, 9.3 Hz, 1H), 3.22-3.11 (m, 4H), 1.30 (d, J = 1.7 Hz, 6H). |
| 686 | 1H NMR (400 MHz, Methanol-d4) δ 8.77-8.62 (m, 2H), 8.53 (d, J = 2.2 Hz, 1H), 8.43 (s, 2H), 7.83 (d, J = 5.0 Hz, 2H), 7.14 (d, J = 5.1 Hz, 1H), 4.74-4.60 (m, 2H), 4.46 (ddd, J = 49.0, 9.3, 2.1 Hz, 1H), 3.97 (ddd, J = 36.4, 14.5, 2.1 Hz, 1H), 3.66 (dtd, J = 12.5, 6.2, 2.4 Hz, 2H), 3.53 (ddd, J = 16.1, 14.5, 9.3 Hz, 1H), 2.65 (dd, J = 13.3, 10.6 Hz, 2H), 1.29 (d, J = 1.7 Hz, 6H), 1.24 (d, J = 6.2 Hz, 6H). |
| 687 | 1H NMR (400 MHz, Methanol-d4) δ 9.90 (s, 1H), 8.82-8.66 (m, 3H), 8.47 (d, J = 3.1 Hz, 1H), 7.92 (d, J = 5.1 Hz, 1H), 7.72 (ddd, J = 9.0, 7.9, 3.0 Hz, 1H), 7.29 (dd, J = 9.0, 3.6 Hz, 1H), 7.20 (d, J = 5.0 Hz, 1H), 4.47 (ddd, J = 49.0, 9.3, 2.2 Hz, 1H), 3.99 (ddd, J = 36.2, 14.5, 2.2 Hz, 1H), 3.70-3.42 (m, 1H), 1.31 (d, J = 1.6 Hz, 6H). |
| 688 | 1H NMR (400 MHz, Methanol-d4) δ 8.70 (d, J = 2.2 Hz, 1H), 8.65 (s, 1H), 8.56 (d, J = 2.2 Hz, 1H), 8.03 (s, 1H), 7.74 (d, J = 5.1 Hz, 1H), 7.45-7.31 (m, 2H), 7.31-7.21 (m, 2H), 7.15 (d, J = 5.0 Hz, 1H), 4.46 (ddd, J = 48.9, 9.3, 2.1 Hz, 1H), 4.15-3.87 (m, 2H), 3.52 (td, J = 15.4, 9.3 Hz, 1H), 3.24-3.12 (m, 4H), 1.30 (d, J = 1.6 Hz, 6H). |
| 689 | 1H NMR (400 MHz, Methanol-d4) δ 8.78-8.64 (m, 2H), 8.56 (d, J = 2.1 Hz, 1H), 8.42 (s, 2H), 7.84 (d, J = 5.4 Hz, 2H), 7.15 (d, J = 5.1 Hz, 1H), 4.46 (ddd, J = 49.0, 9.3, 2.1 Hz, 1H), 3.97 (s, 5H), 3.69 (t, J = 5.3 Hz, 4H), 3.52 (ddd, J = 16.2, 14.5, 9.3 Hz, 1H), 1.87 (t, J = 5.3 Hz, 4H), 1.29 (d, J = 1.6 Hz, 6H). |
| 690 | 1H NMR (400 MHz, Methanol-d4) δ 8.75 (d, J = 2.2 Hz, 1H), 8.68 (d, J = 2.2 Hz, 1H), 8.60 (s, 1H), 8.03 (d, J = 5.1 Hz, 1H), 7.95 (s, 1H), 7.21 (d, J = 5.1 Hz, 1H), 4.42 (ddd, J = 49.0, 9.3, 2.1 Hz, 1H), 4.11 (d, J = 12.1 Hz, 2H), 4.04-3.81 (m, 4H), 3.61-3.41 (m, 3H), 3.25 (d, J = 12.8 Hz, 2H), 2.26 (d, J = 13.1 Hz, 2H), 2.20-1.97 (m, 4H), 1.75 (qd, J = 12.9, 3.9 Hz, 2H), 1.53 (s, 3H), 1.28 (d, J = 1.7 Hz, 6H). |
| 691 | 1H NMR (400 MHz, Methanol-d4) δ 8.75 (d, J = 2.1 Hz, 1H), 8.71-8.64 (m, 2H), 8.02 (t, J = 5.1 Hz, 1H), 7.89 (s, 1H), 7.21 (d, J = 5.1 Hz, 1H), 4.42 (dddd, J = 49.1, 9.4, 4.6, 2.1 Hz, 1H), 4.32-4.03 (m, 3H), 4.03-3.74 (m, 3H), 3.70-3.43 (m, 3H), 2.30-1.85 (m, 8H), 1.77 (t, J = 11.0 Hz, 0H), 1.53 (s, 3H), 1.29 (dd, J = 3.0, 1.6 Hz, 6H). |
| 692 | 1H NMR (400 MHz, Methanol-d4) δ 8.75 (d, J = 2.2 Hz, 1H), 8.68 (d, J = 2.1 Hz, 1H), 8.62 (s, 1H), 8.03 (d, J = 5.1 Hz, 1H), 7.67 (s, 1H), 7.20 (d, J = 5.1 Hz, 1H), 4.59-4.29 (m, 2H), 3.92 (ddd, J = 36.4, 14.7, 2.1 Hz, 1H), 3.51 (ddd, J = 16.0, 14.5, 9.4 Hz, 1H), 3.22 (d, J = 7.9 Hz, 2H), 2.74 (tt, J = 8.8, 4.5 Hz, 1H), 2.55 (ddd, J = 12.7, 7.4, 4.3 Hz, 2H), 2.41 (ddd, J = 13.2, 9.2, 6.4 Hz, 2H), 1.29 (d, J = 1.6 Hz, 6H). |
| 693 | 1H NMR (400 MHz, Methanol-d4) δ 9.11 (s, 1H), 8.87 (s, 1H), 8.58 (d, J = 2.2 Hz, 1H), 8.55 (d, J = 2.2 Hz, 1H), 8.50 (d, J = 2.3 Hz, 1H), 8.31 (d, J = 2.2 Hz, 1H), 7.96 (d, J = 4.9 Hz, 1H), 7.46 (d, J = 4.7 Hz, 1H), 7.11 (t, J = 4.9 Hz, 2H), 4.19 (dd, J = 48.6, 9.3 Hz, 1H), 3.88-3.57 (m, 2H), 1.21 (d, J = 1.6 Hz, 6H). |

TABLE 2-continued

| compound | 1H-NMR |
|---|---|
| 694 | 1H NMR (400 MHz, Methanol-d4) δ 8.75 (d, J = 2.2 Hz, 1H), 8.66 (d, J = 2.2 Hz, 1H), 8.57 (s, 1H), 7.99 (d, J = 5.0 Hz, 1H), 7.74 (s, 1H), 7.21 (d, J = 5.1 Hz, 1H), 4.58-4.31 (m, 2H), 3.93 (ddd, J = 36.5, 14.6, 2.1 Hz, 1H), 3.57-3.36 (m, 3H), 2.76-2.61 (m, 1H), 2.50 (ddd, J = 12.4, 7.4, 3.6 Hz, 2H), 2.38 (s, 3H), 2.37-2.23 (m, 2H), 1.29 (d, J = 1.6 Hz, 6H). |
| 695 | 1H NMR (400 MHz, Methanol-d4) δ 8.74 (br s, 2H), 8.57 (s, 1H), 8.46 (br t, 1H), 7.98 (d, J = 5.1 Hz, 1H), 7.83 (s, 1H), 7.21 (d, J = 5.1 Hz, 1H), 4.53-4.30 (m, 2H), 4.06-3.78 (m, 1H), 3.65-3.35 (m, 3H), 2.63-2.38 (m, 4H), 2.29 (ddd, J = 20.0, 13.4, 7.8 Hz, 2H), 2.05 (dt, J = 13.5, 7.1 Hz, 1H), 1.84-1.68 (m, 1H), 1.29 (d, J = 1.6 Hz, 6H). |
| 696 | 1H NMR (400 MHz, Methanol-d4) δ 8.75 (d, J = 2.2 Hz, 1H), 8.67 (d, J = 2.2 Hz, 1H), 8.57 (s, 1H), 7.99 (d, J = 5.1 Hz, 1H), 7.73 (s, 1H), 7.21 (d, J = 5.1 Hz, 1H), 4.56-4.31 (m, 2H), 3.94 (dd, J = 36.6, 14.5 Hz, 1H), 3.49 (d, J = 7.8 Hz, 3H), 2.68 (d, J = 10.6 Hz, 1H), 2.48 (d, J = 8.7 Hz, 2H), 2.32 (q, J = 10.3, 9.7 Hz, 2H), 2.12-1.98 (m, 1H), 1.29 (d, J = 1.6 Hz, 6H), 1.14-1.03 (m, 2H), 1.03-0.94 (m, 2H). |
| 697 | 1H NMR (400 MHz, Methanol-d4) δ 8.74 (d, J = 2.1 Hz, 1H), 8.67 (d, J = 2.2 Hz, 1H), 8.57 (s, 1H), 7.98 (d, J = 5.0 Hz, 1H), 7.75 (s, 1H), 7.21 (d, J = 5.0 Hz, 1H), 4.58-4.30 (m, 4H), 3.94 (dd, J = 36.8, 14.8 Hz, 1H), 3.54 (d, J = 7.6 Hz, 2H), 3.52-3.41 (m, 1H), 3.39 (s, 2H), 2.77-2.63 (m, 1H), 2.51 (t, J = 9.7 Hz, 2H), 2.33 (q, J = 10.5, 9.8 Hz, 2H), 1.29 (d, J = 1.6 Hz, 6H). |
| 698 | 1H NMR (400 MHz, Methanol-d4) δ 8.75 (d, J = 2.2 Hz, 1H), 8.68 (d, J = 2.2 Hz, 1H), 8.56 (s, 1H), 7.97 (d, J = 5.1 Hz, 1H), 7.74 (s, 1H), 7.21 (d, J = 5.1 Hz, 1H), 4.54-4.31 (m, 1H), 4.23 (t, J = 8.0 Hz, 1H), 4.04-3.82 (m, 1H), 3.62 (s, 3H), 3.56-3.36 (m, 1H), 3.19 (d, J = 6.4 Hz, 2H), 2.71 (t, J = 9.6 Hz, 2H), 2.41 (d, J = 9.0 Hz, 1H), 1.86 (t, J = 10.1 Hz, 2H), 1.29 (d, J = 1.6 Hz, 6H). |
| 699 | 1H NMR (400 MHz, Methanol-d4) δ 8.75 (s, 2H), 8.56 (s, 1H), 8.49-8.37 (m, 1H), 7.97 (d, J = 5.1 Hz, 1H), 7.83 (s, 1H), 7.21 (d, J = 5.1 Hz, 1H), 4.54-4.30 (m, 2H), 3.94 (dd, J = 36.5, 14.6 Hz, 1H), 3.65-3.34 (m, 3H), 2.66-2.36 (m, 4H), 2.38-2.17 (m, 2H), 2.15-1.90 (m, 1H), 1.87-1.70 (m, 1H), 1.29 (d, J = 1.6 Hz, 6H). |
| 700 | 1H NMR (400 MHz, Methanol-d4) δ 8.76 (d, J = 2.2 Hz, 1H), 8.67 (d, J = 2.2 Hz, 1H), 8.61 (d, J = 4.8 Hz, 1H), 8.02-7.95 (m, 1H), 7.77 (s, 1H), 7.64 (s, 1H), 7.22 (d, J = 5.1 Hz, 1H), 4.52-4.32 (m, 2H), 3.94 (qd, J = 9.1, 4.0 Hz, 3H), 3.59-3.41 (m, 1H), 3.40-3.33 (m, 1H), 3.25 (d, J = 7.0 Hz, 1H), 2.88 (d, J = 15.4 Hz, 1H), 2.67-2.51 (m, 2H), 2.51-2.35 (m, 1H), 1.99 (q, J = 10.0, 8.3 Hz, 1H), 1.29 (t, J = 1.5 Hz, 6H). |
| 701 | 1H NMR (400 MHz, Methanol-d4) δ 8.76 (d, J = 2.2 Hz, 1H), 8.68 (d, J = 2.3 Hz, 1H), 8.61 (d, J = 6.2 Hz, 1H), 7.98 (dd, J = 5.1, 2.3 Hz, 1H), 7.78 (s, 1H), 7.22 (d, J = 5.1 Hz, 1H), 4.54-4.26 (m, 2H), 4.18-3.99 (m, 2H), 4.01-3.83 (m, 1H), 3.84-3.67 (m, 2H), 3.59-3.38 (m, 3H), 3.33 (d, J = 7.1 Hz, 2H), 3.24-3.07 (m, 1H), 3.02-2.81 (m, 2H), 2.77-2.38 (m, 2H), 2.03 (m, 2H), 1.29 (t, J = 1.5 Hz, 6H). |
| 702 | 1H NMR (400 MHz, Methanol-d4) δ 8.78 (d, J = 2.1 Hz, 1H), 8.69 (s, 1H), 8.64 (s, 1H), 7.99 (d, J = 5.1 Hz, 1H), 7.70 (s, 1H), 7.24 (d, J = 5.0 Hz, 1H), 4.97 (t, J = 7.5 Hz, 1H), 4.72 (dd, J = 8.1, 5.2 Hz, 1H), 4.57-4.36 (m, 3H), 4.07-3.84 (m, 2H), 3.72-3.39 (m, 2H), 3.29 (d, J = 8.0 Hz, 2H), 2.83 (d, J = 5.3 Hz, 1H), 2.67-2.39 (m, 4H), 1.32 (d, J = 1.6 Hz, 6H). |
| 703 | 1H NMR (400 MHz, Methanol-d4) δ 8.74 (d, J = 2.2 Hz, 1H), 8.66 (d, J = 2.1 Hz, 1H), 8.55 (s, 1H), 8.01 (d, J = 5.1 Hz, 1H), 7.81 (s, 1H), 7.20 (d, J = 5.1 Hz, 1H), 4.58-4.23 (m, 1H), 3.92 (dd, J = 35.7, 14.7 Hz, 1H), 3.58 (d, J = 7.2 Hz, 2H), 3.49 (td, J = 15.3, 9.4 Hz, 1H), 2.78 (p, J = 7.6 Hz, 1H), 2.20 (dt, J = 12.1, 7.3 Hz, 2H), 2.06-1.94 (m, 3H), 1.98-1.84 (m, 2H), 1.28 (d, J = 1.7 Hz, 6H). |
| 704 | 1H NMR (400 MHz, Acetonitrile-d3) δ 8.68 (s, 1H), 8.60 (d, J = 1.9 Hz, 2H), 8.07 (d, J = 5.3 Hz, 1H), 7.54 (d, J = 6.4 Hz, 2H), 7.18 (d, J = 5.1 Hz, 1H), 4.52 (d, J = 7.6 Hz, 2H), 4.42-4.21 (m, 1H), 3.61-3.39 (m, 1H), 1.27 (m, 7H), 1.02-0.87 (m, 2H), 0.87-0.70 (m, 2H). |
| 705 | 1H NMR (400 MHz, Acetonitrile-d3) δ 8.69 (s, 1H), 8.62 (s, 1H), 8.48 (s, 1H), 8.05 (s, 1H), 7.41 (s, 1H), 7.20 (d, J = 5.0 Hz, 1H), 4.41 (dd, J = 8.8, 3.1 Hz, 1H), 4.09-3.91 (m, 2H), 3.64 (s, 3H), 3.34 (s, 3H), 2.47-2.39 (m, 5H), 1.84-1.74 (m, 1H), 1.35 (s, 7H). |
| 706 | 1H NMR (400 MHz, Methanol-d4) δ 8.78 (d, J = 2.1 Hz, 1H), 8.69 (s, 1H), 8.59 (s, 1H), 8.00 (d, J = 5.1 Hz, 1H), 7.67 (s, 1H), 7.24 (d, J = 5.2 Hz, 1H), 6.96 (d, J = 4.6 Hz, 1H), 4.57-4.35 (m, 2H), 4.07-3.87 (m, 1H), 3.59 (d, J = 6.5 Hz, 3H), 3.16 (s, 1H), 2.77-2.65 (m, 1H), 2.54 (d, J = 11.7 Hz, 2H), 2.33 (d, J = 13.6 Hz, 2H), 1.33-1.31 (m, 10H). |
| 707 | 1H NMR (400 MHz, Methanol-d4) δ 8.77 (d, J = 2.1 Hz, 1H), 8.68 (d, J = 2.1 Hz, 1H), 8.53 (s, 1H), 7.96 (d, J = 5.1 Hz, 1H), 7.71 (s, 1H), 7.36 (d, J = 8.3, 5.4 Hz, 2H), 7.23 (d, J = 5.1 Hz, 1H), 7.02 (t, J = 8.8 Hz, 2H), 4.60-4.22 (m, 1H), 4.03-3.87 (m, 1H), 3.86 (t, J = 7.1 Hz, 2H), 3.50 (td, J = 15.4, 9.5 Hz, 1H), 3.09 (t, J = 6.8 Hz, 2H), 1.32 (d, J = 1.7 Hz, 6H). |
| 708 | 1H NMR (400 MHz, DMSO-d6) δ 8.82 (d, J = 2.3 Hz, 1H), 8.79-8.69 (m, 3H), 8.61 (d, J = 2.3 Hz, 1H), 7.94 (s, 1H), 7.86 (d, J = 4.7 Hz, 1H), 7.30 (t, J = 7.8 Hz, 2H), 7.10 (d, J = 4.8 Hz, 1H), 6.96 (t, J = 7.4 Hz, 1H), 6.90 (d, J = 8.2 Hz, 2H), 4.98 (dq, J = 11.9, 5.9, 5.4 Hz, 1H), 4.54-4.29 (m, 1H), 4.23 (dt, J = 9.1, 4.3 Hz, 1H), 3.84-3.66 (m, 1H), 3.43 (dp, J = 14.8, 7.3 Hz, 1H), 2.68 (td, J = 10.4, 7.8, 4.3 Hz, 2H), 2.57 (q, J = 6.2 Hz, 2H), 1.23-1.16 (m, 6H). |
| 709 | 1H NMR (400 MHz, Methanol-d4) δ 8.79 (d, J = 2.2 Hz, 1H), 8.73 (d, J = 2.2 Hz, 1H), 8.60 (s, 1H), 8.32 (s, 1H), 7.96 (d, J = 5.0 Hz, 1H), 7.25 (d, J = 5.1 Hz, 1H), 3.79 (d, J = 21.7 Hz, 2H), 2.28 (t, J = 7.9 Hz, 6H), 1.93 (t, J = 8.0 Hz, 6H), 1.10 (d, J = 18.6 Hz, 2H), 0.86 (d, J = 7.9 Hz, 2H). |

TABLE 2-continued

| compound | 1H-NMR |
|---|---|
| 710 | 1H NMR (400 MHz, Methanol-d4) δ 8.79 (d, J = 2.2 Hz, 1H), 8.73 (d, J = 2.1 Hz, 1H), 8.57 (s, 1H), 8.31 (s, 1H), 7.96 (d, J = 5.0 Hz, 1H), 7.25 (d, J = 5.0 Hz, 1H), 6.24 (t, J = 55.8 Hz, 1H), 4.73 (d, J = 6.9 Hz, 2H), 4.61 (d, J = 6.9 Hz, 2H), 3.85 (s, 2H), 2.28 (t, J = 8.0 Hz, 6H), 1.94 (t, J = 7.5 Hz, 6H). |
| 711 | 1H NMR (400 MHz, Methanol-d4) δ 8.79 (s, 1H), 8.72 (d, J = 7.4 Hz, 1H), 8.58 (d, J = 18.1 Hz, 1H), 8.30 (s, 1H), 7.96 (d, J = 5.0 Hz, 1H), 7.25 (d, J = 4.9 Hz, 1H), 4.61-4.49 (m, 4H), 3.82 (s, 2H), 3.72 (s, 2H), 3.58 (s, 1H), 2.27 (d, J = 8.5 Hz, 6H), 1.94 (d, J = 8.4 Hz, 6H). |
| 712 | 1H NMR (400 MHz, Methanol-d4) δ 8.77 (d, J = 2.2 Hz, 1H), 8.68 (d, J = 2.2 Hz, 1H), 8.56 (s, 1H), 8.02 (d, J = 5.0 Hz, 1H), 7.86 (s, 1H), 7.23 (d, J = 5.0 Hz, 1H), 4.18 (p, J = 6.4 Hz, 1H), 4.07 (d, J = 8.9 Hz, 1H), 3.61 (t, J = 7.1 Hz, 2H), 2.12-1.98 (m, 1H), 1.88 (dq, J = 16.9, 6.5 Hz, 1H), 1.43 (d, J = 6.3 Hz, 6H). |
| 713 | 1H NMR (400 MHz, Methanol-d4) δ 8.77 (d, J = 2.2 Hz, 1H), 8.69 (d, J = 2.3 Hz, 1H), 8.55 (s, 1H), 8.03 (d, J = 4.8 Hz, 1H), 7.82 (d, J = 6.3 Hz, 1H), 7.23 (d, J = 5.0 Hz, 1H), 4.45 (dd, J = 49.1, 9.1 Hz, 1H), 3.96 (dd, J = 36.8, 14.7 Hz, 1H), 3.77-3.36 (m, 5H), 3.37 (s, 3H), 2.50 (dq, J = 38.8, 7.7 Hz, 2H), 2.08 (dt, J = 38.6, 9.3 Hz, 2H), 1.80 (ddt, J = 36.1, 18.7, 9.3 Hz, 2H), 1.31 (s, 6H). |
| 714 | 1H NMR (400 MHz, Methanol-d4) δ 8.73 (q, J = 2.2 Hz, 2H), 8.58 (s, 1H), 8.00 (d, J = 5.1 Hz, 1H), 7.80 (s, 1H), 7.20 (d, J = 5.1 Hz, 1H), 4.63-4.44 (m, 1H), 4.42-4.29 (m, 3H), 3.93 (ddd, J = 36.6, 14.6, 2.1 Hz, 1H), 3.70-3.57 (m, 2H), 3.56-3.38 (m, 3H), 2.73 (pt, J = 8.2, 3.9 Hz, 1H), 2.57-2.40 (m, 2H), 2.31 (dddd, J = 11.3, 9.2, 7.1, 2.4 Hz, 2H), 1.29 (d, J = 1.6 Hz, 6H). |
| 715 | 1H NMR (400 MHz, Methanol-d4) δ 8.74 (d, J = 2.2 Hz, 1H), 8.66 (d, J = 2.2 Hz, 1H), 8.56 (s, 1H), 8.02 (d, J = 5.0 Hz, 1H), 7.88 (s, 1H), 7.21 (d, J = 5.1 Hz, 1H), 4.56-4.25 (m, 3H), 4.08-3.72 (m, 2H), 3.71-3.59 (m, 2H), 3.48 (ddd, J = 16.0, 14.6, 9.4 Hz, 1H), 3.17 (d, J = 7.3 Hz, 2H), 2.22 (d, J = 12.5 Hz, 2H), 1.88 (m, 2H), 1.76 (tt, J = 7.7, 3.8 Hz, 1H), 1.58-1.39 (m, 2H), 1.28 (d, J = 1.6 Hz, 8H). |
| 716 | 1H NMR (400 MHz, Methanol-d4) δ 8.69 (d, J = 2.2 Hz, 1H), 8.63 (d, J = 2.2 Hz, 1H), 8.52 (s, 1H), 7.95 (d, J = 5.0 Hz, 1H), 7.88 (s, 1H), 7.17 (d, J = 5.0 Hz, 1H), 4.43 (ddd, J = 49.0, 9.3, 2.2 Hz, 1H), 3.92 (ddd, J = 36.3, 14.5, 2.2 Hz, 1H), 3.60 (s, 3H), 3.58-3.41 (m, 3H), 3.29-3.16 (m, 2H), 1.93 (p, J = 6.8 Hz, 2H), 1.28 (d, J = 1.6 Hz, 6H). |
| 717 | 1H NMR (400 MHz, Methanol-d4) δ 8.74 (d, J = 2.2 Hz, 1H), 8.67 (d, J = 2.2 Hz, 1H), 8.54 (s, 1H), 8.01 (d, J = 5.1 Hz, 1H), 7.86 (s, 1H), 7.20 (d, J = 5.1 Hz, 1H), 4.42 (ddd, J = 49.0, 9.3, 2.1 Hz, 1H), 3.92 (ddd, J = 36.4, 14.5, 2.1 Hz, 1H), 3.72-3.38 (m, 6H), 3.18 (t, J = 6.8 Hz, 2H), 1.93-1.74 (m, 2H), 1.66 (p, J = 6.9 Hz, 2H), 1.28 (d, J = 1.7 Hz, 6H). |
| 718 | 1H NMR (400 MHz, Methanol-d4) δ 8.74 (d, J = 2.2 Hz, 1H), 8.67 (d, J = 2.2 Hz, 1H), 8.55 (s, 1H), 8.00 (d, J = 5.0 Hz, 1H), 7.89 (s, 1H), 7.20 (d, J = 5.1 Hz, 1H), 4.45 (ddd, J = 49.1, 9.4, 2.1 Hz, 1H), 3.95 (ddd, J = 36.4, 14.6, 2.2 Hz, 1H), 3.58 (s, 4H), 3.39 (s, 2H), 3.10 (s, 2H), 1.35-1.24 (m, 6H), 1.05 (s, 6H). |
| 719 | 1H NMR (400 MHz, Methanol-d4) δ 8.80-8.59 (m, 2H), 8.42 (d, J = 2.2 Hz, 1H), 8.21 (s, 1H), 7.94-7.67 (m, 2H), 7.67-7.52 (m, 3H), 7.47-7.36 (m, 2H), 7.15 (d, J = 5.1 Hz, 1H), 6.72-6.56 (m, 1H), 6.46 (td, J = 6.7, 1.4 Hz, 1H), 5.28 (s, 2H), 4.46 (ddd, J = 49.0, 9.3, 2.1 Hz, 1H), 3.98 (ddd, J = 36.5, 14.6, 2.1 Hz, 1H), 3.66-3.40 (m, 1H), 1.29 (d, J = 1.6 Hz, 6H). |
| 720 | 1H NMR (400 MHz, Methanol-d4) δ 8.86-8.65 (m, 2H), 8.56 (s, 1H), 8.36 (s, 1H), 7.91 (d, J = 5.0 Hz, 1H), 7.22 (d, J = 5.1 Hz, 1H), 4.41 (ddd, J = 49.1, 9.4, 2.1 Hz, 1H), 3.92 (ddd, J = 36.6, 14.5, 2.1 Hz, 1H), 3.61-3.44 (m, 1H), 3.41 (s, 3H), 3.10 (t, J = 6.6 Hz, 2H), 1.99 (dd, J = 11.1, 5.7 Hz, 2H), 1.57 (s, 8H), 1.28 (d, J = 1.7 Hz, 6H). |
| 721 | 1H NMR (400 MHz, Methanol-d4) δ 8.75 (d, J = 2.2 Hz, 1H), 8.71 (d, J = 2.2 Hz, 1H), 8.57 (s, 1H), 8.31 (s, 1H), 7.93 (d, J = 5.1 Hz, 1H), 7.22 (d, J = 5.1 Hz, 1H), 4.43 (ddd, J = 49.1, 9.4, 2.1 Hz, 1H), 3.93 (ddd, J = 36.7, 14.5, 2.1 Hz, 1H), 3.56-3.40 (m, 4H), 3.23-3.16 (m, 2H), 2.24-2.09 (m, 2H), 1.60 (s, 6H), 1.28 (d, J = 1.6 Hz, 6H). |
| 722 | 1H NMR (400 MHz, Methanol-d4) δ 8.76 (d, J = 2.2 Hz, 1H), 8.71 (d, J = 2.2 Hz, 1H), 8.58 (s, 1H), 8.36 (s, 1H), 7.95 (d, J = 5.1 Hz, 1H), 7.23 (d, J = 5.1 Hz, 1H), 4.41 (ddd, J = 49.0, 9.3, 2.1 Hz, 1H), 4.00-3.80 (m, 3H), 3.72 (s, 3H), 3.68-3.57 (m, 2H), 3.54-3.37 (m, 1H), 2.61 (t, J = 2.3 Hz, 1H), 2.12 (s, 1H), 2.03 (s, 0H), 1.28 (d, J = 1.6 Hz, 6H). |
| 723 | 1H NMR (400 MHz, Methanol-d4) δ 8.75 (d, J = 2.2 Hz, 1H), 8.71-8.57 (m, 2H), 8.01 (d, J = 5.1 Hz, 1H), 7.87 (s, 1H), 7.21 (d, J = 5.1 Hz, 1H), 4.42 (ddd, J = 49.1, 9.4, 2.1 Hz, 1H), 4.25 (s, 1H), 4.01-3.77 (m, 3H), 3.69 (s, 2H), 3.64-3.42 (m, 1H), 2.64 (dt, J = 14.0, 6.8 Hz, 2H), 2.16 (d, J = 12.6 Hz, 4H), 1.94 (t, J = 13.1 Hz, 2H), 1.73 (d, J = 12.6 Hz, 2H), 1.29 (d, J = 1.6 Hz, 6H). |
| 724 | 1H NMR (400 MHz, Methanol-d4) δ 8.75 (d, J = 2.2 Hz, 1H), 8.66 (d, J = 2.2 Hz, 1H), 8.60 (s, 1H), 8.04 (d, J = 5.0 Hz, 1H), 7.90 (s, 1H), 7.21 (d, J = 5.1 Hz, 1H), 4.41 (ddd, J = 49.0, 9.4, 2.1 Hz, 1H), 4.17-3.68 (m, 5H), 3.49 (ddd, J = 16.0, 14.5, 9.4 Hz, 2H), 3.43-3.32 (m, 1H), 2.68 (tt, J = 14.1, 7.5 Hz, 2H), 2.33 (d, J = 10.2 Hz, 3H), 2.03 (s, 1H), 1.86-1.71 (m, 2H), 1.58 (q, J = 12.1 Hz, 2H), 1.28 (d, J = 1.7 Hz, 6H). |
| 725 | 1H NMR (400 MHz, Methanol-d4) δ 8.75 (d, J = 2.2 Hz, 1H), 8.71 (d, J = 2.2 Hz, 1H), 8.58 (s, 1H), 7.98 (d, J = 5.1 Hz, 1H), 7.75 (s, 1H), 7.21 (d, J = 5.1 Hz, 1H), 4.59-4.30 (m, 2H), 4.23 (d, J = 6.9 Hz, 2H), 3.94 (ddd, J = 36.6, 14.6, 2.1 Hz, 1H), 3.49 (ddd, J = 16.1, 14.6, 9.4 Hz, 1H), 2.73 (s, 3H), 2.70 (s, 1H), 2.52 (t, J = 9.8 Hz, 2H), 2.40-2.21 (m, 2H), 1.29 (d, J = 1.6 Hz, 6H). |

TABLE 2-continued

| compound | 1H-NMR |
|---|---|
| 726 | 1H NMR (400 MHz, Methanol-d4) δ 8.75 (d, J = 2.2 Hz, 1H), 8.69 (d, J = 2.2 Hz, 1H), 8.53 (s, 1H), 7.99 (d, J = 5.1 Hz, 1H), 7.83 (s, 1H), 7.21 (d, J = 5.1 Hz, 1H), 4.43 (ddd, J = 49.1, 9.3, 2.1 Hz, 1H), 3.94 (ddd, J = 36.5, 14.6, 2.2 Hz, 1H), 3.61-3.42 (m, 6H), 1.96-1.64 (m, 4H), 1.28 (d, J = 1.7 Hz, 6H), 1.27 (s, 6H). |
| 727 | 1H NMR (400 MHz, Methanol-d4) δ 8.74 (d, J = 2.2 Hz, 1H), 8.65 (d, J = 2.2 Hz, 1H), 8.52 (s, 1H), 8.20 (d, J = 5.0 Hz, 1H), 7.81 (s, 1H), 7.21 (d, J = 5.1 Hz, 1H), 4.42 (ddd, J = 49.1, 9.3, 2.1 Hz, 1H), 3.99-3.75 (m, 6H), 3.65-3.36 (m, 6H), 2.29-2.13 (m, 2H), 1.34 (s, 6H), 1.28 (d, J = 1.6 Hz, 6H). |
| 728 | 1H NMR (400 MHz, Methanol-d4) δ 9.00 (t, J = 5.7 Hz, 0H), 8.74 (s, 2H), 8.57 (s, 1H), 7.98 (d, J = 5.1 Hz, 1H), 7.80 (s, 1H), 7.21 (d, J = 5.1 Hz, 1H), 6.02 (tt, J = 55.0, 3.7 Hz, 1H), 4.53-4.22 (m, 4H), 3.93 (ddd, J = 36.4, 14.6, 2.1 Hz, 1H), 3.57-3.41 (m, 1H), 3.41-3.31 (m, 3H), 2.56 (d, J = 4.2 Hz, 1H), 2.52-2.41 (m, 2H), 2.27 (td, J = 12.3, 11.0, 8.0 Hz, 2H), 1.29 (d, J = 1.6 Hz, 6H). |
| 729 | 1H NMR (400 MHz, Methanol-d4) δ 8.74 (d, J = 2.2 Hz, 1H), 8.66-8.50 (m, 2H), 8.21-8.11 (m, 1H), 7.98 (d, J = 5.1 Hz, 1H), 7.80-7.65 (m, 2H), 7.20 (d, J = 5.1 Hz, 1H), 6.99 (ddd, J = 7.2, 5.1, 0.9 Hz, 1H), 6.88 (dt, J = 8.5, 0.9 Hz, 1H), 4.64-4.29 (m, 4H), 3.95 (ddd, J = 36.4, 14.5, 2.1 Hz, 1H), 3.50 (ddd, J = 16.1, 14.5, 9.4 Hz, 1H), 2.90 (s, 1H), 2.63 (ddd, J = 12.5, 7.5, 4.0 Hz, 2H), 2.39 (ddd, J = 13.0, 9.6, 6.8 Hz, 2H), 1.29 (d, J = 1.6 Hz, 6H). |
| 730 | 1H NMR (400 MHz, Methanol-d4) δ 8.74 (d, J = 2.2 Hz, 1H), 8.68 (d, J = 2.1 Hz, 1H), 8.56 (d, J = 6.6 Hz, 1H), 7.98 (d, J = 5.0 Hz, 1H), 7.76 (s, 1H), 7.20 (d, J = 5.1 Hz, 1H), 4.54-4.24 (m, 4H), 3.94 (ddd, J = 36.4, 14.6, 2.2 Hz, 1H), 3.66-3.41 (m, 1H), 2.90-2.75 (m, 2H), 2.72-2.62 (m, 1H), 2.05-1.89 (m, 2H), 1.29 (d, J = 1.6 Hz, 6H). |
| 731 | 1H NMR (400 MHz, Methanol-d4) δ 8.75 (d, J = 2.2 Hz, 1H), 8.69 (d, J = 2.2 Hz, 1H), 8.50 (s, 1H), 8.26 (s, 1H), 7.92 (d, J = 5.1 Hz, 1H), 7.21 (d, J = 5.1 Hz, 1H), 3.91 (p, J = 8.3 Hz, 1H), 3.60 (s, 3H), 3.43-3.34 (m, 2H), 2.42 (qd, J = 7.6, 2.8 Hz, 2H), 2.24 (t, J = 8.0 Hz, 7H), 1.96-1.83 (m, 6H), 1.72 (d, J = 10.3 Hz, 2H). |
| 732 | 1H NMR (400 MHz, Methanol-d4) δ 8.75 (d, J = 2.2 Hz, 1H), 8.69 (d, J = 2.2 Hz, 1H), 8.50 (s, 1H), 8.26 (s, 1H), 7.93 (d, J = 5.1 Hz, 1H), 7.21 (d, J = 5.1 Hz, 1H), 4.28-4.07 (m, 1H), 3.40 (d, J = 6.9 Hz, 2H), 2.45 (tdd, J = 10.3, 6.4, 2.7 Hz, 2H), 2.24 (dd, J = 10.2, 5.8 Hz, 7H), 1.99-1.86 (m, 6H), 1.73 (qd, J = 9.2, 2.8 Hz, 2H), 1.51 (tt, J = 8.0, 4.7 Hz, 1H), 0.90-0.76 (m, 2H), 0.73 (dt, J = 8.0, 3.0 Hz, 2H). |
| 733 | 1H NMR (400 MHz, Methanol-d4) δ 8.75 (d, J = 2.2 Hz, 1H), 8.69 (d, J = 2.2 Hz, 1H), 8.49 (s, 1H), 8.26 (s, 1H), 7.92 (d, J = 5.1 Hz, 1H), 7.21 (d, J = 5.1 Hz, 1H), 4.18 (p, J = 7.8 Hz, 1H), 3.72 (p, J = 6.6 Hz, 1H), 3.61 (s, 3H), 3.47 (d, J = 7.7 Hz, 2H), 3.22 (q, J = 7.4 Hz, 1H), 2.48 (ddd, J = 12.5, 8.2, 4.0 Hz, 1H), 2.32-2.20 (m, 6H), 2.21-2.04 (m, 3H), 2.00-1.84 (m, 6H). |
| 734 | 1H NMR (400 MHz, Methanol-d4) δ 8.74 (d, J = 2.2 Hz, 1H), 8.70 (d, J = 2.2 Hz, 1H), 8.58 (s, 1H), 7.99 (d, J = 5.1 Hz, 1H), 7.74 (s, 1H), 7.21 (d, J = 5.1 Hz, 1H), 4.54-4.32 (m, 2H), 4.26 (d, J = 7.2 Hz, 2H), 3.93 (ddd, J = 36.5, 14.5, 2.1 Hz, 1H), 3.50 (ddd, J = 16.1, 14.5, 9.3 Hz, 1H), 2.95 (s, 6H), 2.74 (d, J = 12.8 Hz, 1H), 2.64-2.47 (m, 2H), 2.40-2.24 (m, 2H), 1.29 (d, J = 1.6 Hz, 6H). |
| 735 | 1H NMR (400 MHz, Methanol-d4) δ 8.84-8.64 (m, 2H), 8.57 (s, 1H), 7.97 (d, J = 5.1 Hz, 1H), 7.76 (s, 1H), 7.21 (d, J = 5.1 Hz, 1H), 4.60-4.30 (m, 2H), 4.24 (d, J = 6.9 Hz, 2H), 4.08-3.84 (m, 1H), 3.49 (td, J = 15.3, 9.4 Hz, 1H), 2.70 (s, 1H), 2.55 (td, J = 7.3, 3.8 Hz, 3H), 2.31 (d, J = 9.9 Hz, 2H), 1.29 (d, J = 1.6 Hz, 6H), 0.68 (d, J = 6.8 Hz, 2H), 0.53-0.39 (m, 2H). |
| 736 | 1H NMR (400 MHz, Methanol-d4) δ 8.75 (d, J = 2.1 Hz, 1H), 8.69 (d, J = 2.2 Hz, 1H), 8.57 (s, 1H), 7.97 (d, J = 5.1 Hz, 1H), 7.73 (s, 1H), 7.21 (d, J = 5.1 Hz, 1H), 6.06-5.62 (m, 1H), 4.65-4.30 (m, 2H), 4.27 (d, J = 6.9 Hz, 2H), 4.11-3.70 (m, 1H), 3.49 (td, J = 15.2, 4.0 Hz, 2H), 2.73 (s, 1H), 2.53 (dd, J = 12.0, 6.8 Hz, 2H), 2.32 (q, J = 10.8, 9.9 Hz, 2H), 1.29 (d, J = 1.6 Hz, 6H). |
| 737 | 1H NMR (400 MHz, Methanol-d4) δ 8.75 (d, J = 2.2 Hz, 1H), 8.71 (s, 1H), 8.57 (s, 1H), 7.98 (d, J = 5.1 Hz, 1H), 7.72 (s, 1H), 7.21 (d, J = 5.1 Hz, 1H), 4.56-4.33 (m, 2H), 4.30 (d, J = 7.0 Hz, 2H), 4.11-3.84 (m, 1H), 3.85-3.39 (m, 5H), 2.76 (s, 1H), 2.54 (td, J = 8.7, 7.9, 4.2 Hz, 2H), 2.47-2.22 (m, 4H), 1.29 (d, J = 1.6 Hz, 6H). |
| 738 | 1H NMR (400 MHz, Methanol-d4) δ 8.72 (dd, J = 18.9, 2.2 Hz, 2H), 8.58 (s, 1H), 7.98 (d, J = 5.0 Hz, 1H), 7.72 (s, 1H), 7.21 (d, J = 5.1 Hz, 1H), 4.52-4.41 (m, 1H), 4.39-4.20 (m, 5H), 3.94 (ddd, J = 36.5, 14.6, 2.1 Hz, 1H), 3.63-3.39 (m, 1H), 2.75 (s, 1H), 2.53 (ddd, J = 12.5, 7.7, 3.9 Hz, 2H), 2.33 (ddd, J = 12.6, 9.2, 6.7 Hz, 2H), 1.29 (d, J = 1.6 Hz, 6H). |
| 739 | 1H NMR (400 MHz, Methanol-d4) δ 8.75 (d, J = 2.2 Hz, 1H), 8.69 (d, J = 2.2 Hz, 1H), 8.53 (s, 1H), 8.28 (s, 1H), 7.93 (d, J = 5.1 Hz, 1H), 7.21 (d, J = 5.1 Hz, 1H), 3.73 (d, J = 23.9 Hz, 2H), 2.45-2.10 (m, 9H), 1.95-1.73 (m, 6H), 1.63 (p, J = 9.2, 8.7 Hz, 1H), 1.19 (s, 1H). |
| 740 | 1H NMR (400 MHz, Methanol-d4) δ 8.75 (d, J = 2.2 Hz, 1H), 8.69 (d, J = 2.2 Hz, 1H), 8.55 (s, 1H), 8.28 (s, 1H), 7.93 (d, J = 5.0 Hz, 1H), 7.21 (d, J = 5.0 Hz, 1H), 3.57 (d, J = 20.6 Hz, 2H), 2.24 (dd, J = 9.5, 6.5 Hz, 6H), 1.93-1.83 (m, 6H), 1.39 (d, J = 21.1 Hz, 6H). |
| 741 | 1H NMR (400 MHz, Methanol-d4) δ 8.76 (d, J = 2.2 Hz, 1H), 8.51 (s, 1H), 8.27 (s, 1H), 7.93 (d, J = 5.1 Hz, 1H), 7.22 (d, J = 5.1 Hz, 1H), 3.68 (s, 3H), 3.52 (td, J = 14.1, 13.0, 7.8 Hz, 2H), 3.45-3.32 (m, 2H), 3.16 (dd, J = 10.9, 6.9 Hz, 2H), 2.54 (q, J = 7.6 Hz, 1H), 2.24 (dd, J = 10.3, 5.7 Hz, 6H), 2.07 (dt, J = 12.8, 6.3 Hz, 1H), 1.98-1.81 (m, 6H), 1.74 (dq, J = 14.1, 7.7 Hz, 1H). |
| 742 | 1H NMR (400 MHz, Methanol-d4) δ 8.75 (d, J = 2.2 Hz, 1H), 8.69 (d, J = 2.2 Hz, 1H), 8.52 (s, 1H), 8.28 (s, 1H), 7.93 (d, J = 5.1 Hz, 1H), 7.22 (d, J = 5.1 Hz, 1H), 3.68 (s, 3H), 3.62-3.46 (m, 2H), 3.37 (dd, J = 18.5, 8.1 Hz, 2H), 3.16 (dd, J = |

TABLE 2-continued

| compound | 1H-NMR |
|---|---|
| | 10.9, 6.9 Hz, 1H), 2.54 (q, J = 7.7 Hz, 1H), 2.32-2.18 (m, 6H), 2.07 (dt, J = 12.8, 6.5 Hz, 1H), 1.97-1.84 (m, 6H), 1.74 (dq, J = 15.0, 7.8 Hz, 1H). |
| 743 | 1H NMR (400 MHz, Methanol-d4) δ 8.74 (d, J = 2.2 Hz, 1H), 8.68 (d, J = 2.2 Hz, 1H), 8.54 (s, 1H), 8.31 (s, 1H), 7.92 (d, J = 5.0 Hz, 1H), 7.20 (d, J = 5.1 Hz, 1H), 4.78 (s, 1H), 4.44-4.10 (m, 2H), 3.78-3.55 (m, 2H), 2.71 (s, 3H), 2.24 (dd, J = 10.1, 6.0 Hz, 6H), 1.90 (dd, J = 10.3, 5.7 Hz, 6H). |
| 744 | 1H NMR (400 MHz, Methanol-d4) δ 8.75 (d, J = 2.2 Hz, 1H), 8.69 (d, J = 2.2 Hz, 1H), 8.51 (s, 1H), 8.28 (s, 1H), 7.93 (d, J = 5.1 Hz, 1H), 7.21 (d, J = 5.1 Hz, 1H), 4.09 (t, J = 8.5 Hz, 2H), 3.75 (dd, J = 8.8, 5.3 Hz, 2H), 3.64 (s, 3H), 3.59 (dd, J = 6.9, 4.4 Hz, 2H), 2.95-2.80 (m, 1H), 2.24 (dd, J = 10.4, 5.6 Hz, 6H), 1.90 (dd, J = 10.3, 5.7 Hz, 6H). |
| 745 | 1H NMR (400 MHz, Methanol-d4) δ 8.75 (d, J = 2.2 Hz, 1H), 8.69 (d, J = 2.2 Hz, 1H), 8.54 (s, 1H), 8.28 (s, 1H), 7.91 (d, J = 5.0 Hz, 1H), 7.21 (d, J = 5.1 Hz, 1H), 3.71 (t, J = 5.6 Hz, 2H), 3.57-3.42 (m, 2H), 2.24 (dd, J = 10.3, 5.8 Hz, 6H), 2.00-1.82 (m, 6H). |
| 746 | 1H NMR (400 MHz, Methanol-d4) δ 8.74 (d, J = 2.2 Hz, 1H), 8.68 (d, J = 2.1 Hz, 1H), 8.50 (s, 1H), 8.29 (s, 1H), 7.93 (d, J = 5.1 Hz, 1H), 7.21 (d, J = 5.1 Hz, 1H), 3.63 (s, 3H), 3.45 (dd, J = 6.6, 5.0 Hz, 2H), 3.33 (d, J = 6.0 Hz, 2H), 2.28-2.19 (m, 6H), 1.95-1.86 (m, 6H). |
| 747 | 1H NMR (400 MHz, Methanol-d4) δ 8.75 (d, J = 2.2 Hz, 1H), 8.69 (d, J = 2.2 Hz, 1H), 8.58 (s, 1H), 8.19 (s, 1H), 8.01 (d, J = 5.1 Hz, 1H), 7.22 (d, J = 5.1 Hz, 1H), 4.61-4.28 (m, 1H), 4.16 (qd, J = 11.6, 6.5 Hz, 2H), 3.91 (ddd, J = 36.4, 14.5, 2.2 Hz, 1H), 3.47 (ddd, J = 16.1, 14.5, 9.3 Hz, 1H), 2.86 (dt, J = 7.5, 3.8 Hz, 1H), 2.66 (s, 3H), 1.51 (d, J = 8.4 Hz, 1H), 1.28 (d, J = 1.7 Hz, 6H), 1.21-1.03 (m, 2H). |
| 748 | 1H NMR (400 MHz, Methanol-d4) δ 8.75 (d, J = 2.2 Hz, 1H), 8.63 (d, J = 2.2 Hz, 1H), 8.58 (s, 1H), 7.98-7.81 (m, 2H), 7.21 (d, J = 5.0 Hz, 1H), 5.03 (s, 1H), 4.42 (ddd, J = 49.1, 9.4, 2.1 Hz, 1H), 4.11 (d, J = 10.5 Hz, 1H), 3.93 (ddd, J = 36.5, 14.6, 2.1 Hz, 1H), 3.63-3.40 (m, 1H), 2.73 (s, 3H), 2.29 (d, J = 13.6 Hz, 1H), 2.09 (d, J = 12.4 Hz, 1H), 1.95-1.53 (m, 6H), 1.28 (d, J = 1.6 Hz, 6H). |
| 749 | 1H NMR (400 MHz, Methanol-d4) δ 8.75 (d, J = 2.2 Hz, 1H), 8.68 (d, J = 2.2 Hz, 1H), 8.57 (s, 1H), 8.00 (d, J = 5.1 Hz, 1H), 7.69 (s, 1H), 7.21 (d, J = 5.1 Hz, 1H), 4.56-4.25 (m, 2H), 3.93 (ddd, J = 36.5, 14.6, 2.2 Hz, 1H), 3.63-3.36 (m, 1H), 2.86-2.71 (m, 4H), 2.62 (t, J = 12.2 Hz, 2H), 2.43-2.25 (m, 2H), 1.29 (d, J = 1.6 Hz, 6H). |
| 750 | 1H NMR (400 MHz, Methanol-d4) δ 8.74 (d, J = 2.2 Hz, 1H), 8.65 (d, J = 2.2 Hz, 1H), 8.58 (s, 1H), 7.98 (d, J = 5.1 Hz, 1H), 7.90 (s, 1H), 7.21 (d, J = 5.1 Hz, 1H), 4.57-4.29 (m, 2H), 4.14 (p, J = 6.6 Hz, 1H), 3.92 (ddd, J = 36.4, 14.6, 2.2 Hz, 1H), 3.65 (s, 3H), 3.49 (ddd, J = 16.0, 14.5, 9.4 Hz, 1H), 2.54-2.32 (m, 1H), 2.21 (ddq, J = 16.2, 6.7, 3.4 Hz, 2H), 2.13-1.90 (m, 1H), 1.86-1.57 (m, 2H), 1.28 (d, J = 1.6 Hz, 6H). |
| 751 | 1H NMR (400 MHz, Methanol-d4) δ 8.75 (d, J = 2.2 Hz, 1H), 8.67 (s, 1H), 8.63 (s, 1H), 8.04 (d, J = 5.1 Hz, 1H), 7.90 (d, J = 6.6 Hz, 1H), 7.21 (d, J = 5.1 Hz, 1H), 4.60 (d, J = 9.5 Hz, 1H), 4.42 (ddd, J = 49.0, 9.4, 2.1 Hz, 1H), 3.88 (dt, J = 14.5, 3.2 Hz, 2H), 3.72 (d, J = 5.2 Hz, 3H), 3.60 (s, 2H), 3.56-3.42 (m, 2H), 2.46 (d, J = 16.4 Hz, 1H), 2.28-2.08 (m, 1H), 1.28 (d, J = 1.7 Hz, 6H). |
| 752 | 1H NMR (400 MHz, Methanol-d4) δ 8.75 (d, J = 2.2 Hz, 1H), 8.67 (s, 1H), 8.63 (s, 1H), 8.04 (d, J = 5.0 Hz, 1H), 7.90 (d, J = 6.9 Hz, 1H), 7.21 (d, J = 5.1 Hz, 1H), 4.59 (s, 1H), 4.42 (ddd, J = 49.1, 9.3, 2.1 Hz, 1H), 3.93-3.83 (m, 1H), 3.72 (d, J = 5.3 Hz, 3H), 3.60 (s, 2H), 3.56-3.41 (m, 2H), 2.56-2.31 (m, 1H), 2.29-2.08 (m, 1H), 1.28 (d, J = 1.6 Hz, 6H). |
| 753 | 1H NMR (400 MHz, Methanol-d4) δ 8.74 (d, J = 2.2 Hz, 1H), 8.68 (d, J = 2.2 Hz, 1H), 8.57 (s, 1H), 8.29 (s, 1H), 7.92 (d, J = 5.0 Hz, 1H), 7.20 (d, J = 5.1 Hz, 1H), 3.39 (s, 2H), 2.23 (dd, J = 10.4, 5.6 Hz, 6H), 1.90 (dd, J = 10.3, 5.8 Hz, 6H), 1.24 (s, 6H). |
| 754 | 1H NMR (400 MHz, Methanol-d4) δ 8.66 (d, J = 2.2 Hz, 1H), 8.60 (d, J = 2.2 Hz, 1H), 8.53 (s, 1H), 7.90 (d, J = 5.0 Hz, 1H), 7.75 (s, 1H), 7.14 (d, J = 5.0 Hz, 1H), 4.42 (ddd, J = 48.7, 9.3, 2.1 Hz, 1H), 4.15 (p, J = 7.6 Hz, 1H), 4.10-3.81 (m, 2H), 3.61 (s, 3H), 3.48 (ddd, J = 16.2, 14.5, 9.3 Hz, 1H), 2.77 (ddd, J = 11.6, 6.9, 4.3 Hz, 1H), 2.58 (tdd, J = 12.0, 7.4, 4.8 Hz, 2H), 2.34 (ddd, J = 12.2, 7.4, 5.1 Hz, 1H), 2.19-1.96 (m, 4H), 1.29 (d, J = 1.6 Hz, 6H). |
| 755 | 1H NMR (400 MHz, Methanol-d4) δ 8.77 (s, 1H), 8.52 (d, J = 4.8 Hz, 3H), 8.29 (s, 2H), 7.95-7.81 (m, 2H), 7.76-7.64 (m, 2H), 7.29 (t, J = 5.6 Hz, 1H), 7.03 (d, J = 5.0 Hz, 1H), 4.49 (ddd, J = 49.1, 9.3, 2.1 Hz, 1H), 4.14-3.82 (m, 1H), 3.52 (td, J = 15.3, 9.2 Hz, 1H), 1.33 (d, J = 1.6 Hz, 6H). |
| 756 | 1H NMR (400 MHz, Methanol-d4) δ 8.75 (d, J = 2.2 Hz, 1H), 8.68 (d, J = 2.2 Hz, 1H), 8.55 (s, 1H), 7.98 (d, J = 5.0 Hz, 1H), 7.69 (s, 1H), 7.21 (d, J = 5.1 Hz, 1H), 4.35 (dd, J = 9.3, 2.1 Hz, 1H), 4.26 (q, J = 7.7 Hz, 1H), 4.06-3.83 (m, 2H), 3.61 (s, 3H), 3.58-3.37 (m, 1H), 2.81-2.72 (m, J = 11.4 Hz, 1H), 2.60 (ddt, J = 17.5, 11.8, 6.7 Hz, 2H), 2.35 (dt, J = 12.2, 6.1 Hz, 1H), 2.24-1.96 (m, 4H), 1.28 (d, J = 1.6 Hz, 6H). |
| 757 | 1H NMR (400 MHz, Methanol-d4) δ 8.75 (d, J = 2.2 Hz, 1H), 8.68 (d, J = 2.2 Hz, 1H), 8.55 (s, 1H), 7.98 (d, J = 5.1 Hz, 1H), 7.69 (s, 1H), 7.21 (d, J = 5.1 Hz, 1H), 4.42 (ddd, J = 49.0, 9.3, 2.1 Hz, 1H), 4.27 (p, J = 7.6 Hz, 1H), 4.12-3.83 (m, 2H), 3.61 (s, 3H), 3.57-3.36 (m, 2H), 2.79 (t, J = 5.9 Hz, 1H), 2.60 (ddt, J = 17.2, 11.7, 6.5 Hz, 2H), 2.42-2.26 (m, 1H), 2.24-2.06 (m, 3H), 2.02 (s, 1H), 1.28 (d, J = 1.7 Hz, 6H). |
| 758 | 1H NMR (400 MHz, Methanol-d4) δ 8.89-8.70 (m, 1H), 8.73-8.54 (m, 2H), 8.10-7.91 (m, 2H), 7.21 (t, J = 5.2 Hz, 1H), 4.64-4.29 (m, 2H), 4.18-3.84 (m, 2H), 3.68 |

TABLE 2-continued

| compound | 1H-NMR |
|---|---|
| | (d, J = 44.8 Hz, 3H), 3.55-3.40 (m, 3H), 3.08-2.77 (m, 1H), 2.44 (dd, J = 13.8, 8.4 Hz, 2H), 1.40-1.21 (m, 6H). |
| 759 | 1H NMR (400 MHz, Methanol-d4) δ 8.75 (d, J = 2.2 Hz, 1H), 8.69 (d, J = 2.2 Hz, 1H), 8.57 (s, 1H), 7.96 (d, J = 5.1 Hz, 1H), 7.74 (s, 1H), 7.21 (d, J = 5.1 Hz, 1H), 4.58-4.32 (m, 2H), 4.05-3.83 (m, 1H), 3.62 (s, 3H), 3.54-3.39 (m, 1H), 3.27 (s, 2H), 2.61 (m, J = 13.4, 8.1 Hz, 2H), 2.29 (dd, J = 12.9, 6.8 Hz, 2H), 1.29 (d, J = 1.6 Hz, 6H). |
| 760 | 1H NMR (400 MHz, Methanol-d4) δ 8.82 (s, 1H), 8.75 (d, J = 2.1 Hz, 1H), 8.57 (s, 1H), 8.00 (d, J = 5.1 Hz, 1H), 7.95 (s, 1H), 7.22 (d, J = 5.1 Hz, 1H), 4.57-4.27 (m, 1H), 4.12-3.82 (m, 2H), 3.72 (s, 3H), 3.48 (td, J = 15.4, 9.3 Hz, 1H), 3.37 (s, 2H), 2.99-2.82 (m, 2H), 2.11 (t, J = 10.0 Hz, 2H), 1.29 (d, J = 1.7 Hz, 6H). |
| 761 | 1H NMR (400 MHz, Methanol-d4) δ 8.90 (s, 1H), 8.79-8.67 (m, 4H), 8.56 (d, J = 2.2 Hz, 1H), 8.31-8.10 (m, 4H), 7.90 (d, J = 5.0 Hz, 1H), 7.17 (d, J = 5.0 Hz, 1H), 4.47 (dd, J = 48.8, 9.1 Hz, 1H), 4.18-3.90 (m, 1H), 3.63-3.47 (m, 1H), 1.30 (d, J = 1.7 Hz, 6H). |
| 762 | 1H NMR (400 MHz, Methanol-d4) δ 9.18 (s, 1H), 8.73 (s, 1H), 8.67 (d, J = 2.2 Hz, 1H), 8.58 (d, J = 2.2 Hz, 1H), 8.37 (s, 1H), 8.23 (s, 1H), 8.03 (d, J = 8.8 Hz, 2H), 7.82 (d, J = 5.0 Hz, 1H), 7.67 (d, J = 8.8 Hz, 2H), 7.14 (d, J = 5.1 Hz, 1H), 4.57-4.25 (m, 1H), 3.99 (dd, J = 35.7, 14.4 Hz, 1H), 3.68-3.41 (m, 1H), 1.30 (d, J = 1.6 Hz, 6H). |
| 763 | 1H NMR (400 MHz, Methanol-d4) δ 8.74 (t, J = 1.6 Hz, 1H), 8.69 (t, J = 2.3 Hz, 1H), 8.59 (d, J = 2.0 Hz, 1H), 8.00 (t, J = 4.9 Hz, 1H), 7.75 (d, J = 11.7 Hz, 1H), 7.20 (d, J = 5.1 Hz, 1H), 4.62-4.29 (m, 2H), 4.02-3.81 (m, 1H), 3.73 (d, J = 45.0 Hz, 2H), 3.60-3.38 (m, 1H), 3.21-2.94 (m, 2H), 2.71-2.46 (m, 2H), 1.29 (t, J = 1.8 Hz, 6H). |
| 764 | 1H NMR (400 MHz, Methanol-d4) δ 8.79 (s, 1H), 8.62 (s, 1H), 8.54 (s, 1H), 8.03 (s, 1H), 7.90 (d, J = 5.0 Hz, 1H), 7.12 (d, J = 4.9 Hz, 1H), 4.55-4.31 (m, 1H), 4.09-3.81 (m, 2H), 3.75 (s, 3H), 3.53 (dt, J = 24.8, 7.7 Hz, 3H), 2.97 (d, J = 8.0 Hz, 2H), 2.51-2.16 (m, 2H), 1.29 (s, 6H). |
| 765 | 1H NMR (400 MHz, Methanol-d4) δ 8.69 (d, J = 2.2 Hz, 1H), 8.63 (d, J = 2.2 Hz, 1H), 8.58 (s, 1H), 7.95 (d, J = 5.0 Hz, 1H), 7.73 (s, 1H), 7.17 (d, J = 5.0 Hz, 1H), 4.56-4.33 (m, 2H), 3.94 (ddd, J = 36.2, 14.6, 2.2 Hz, 1H), 3.62 (s, 3H), 3.53-3.40 (m, 3H), 2.89 (ddd, J = 19.0, 14.3, 8.4 Hz, 2H), 2.42 (ddd, J = 19.8, 14.1, 5.7 Hz, 2H), 1.29 (d, J = 1.6 Hz, 6H). |
| 766 | 1H NMR (400 MHz, Methanol-d4) δ 9.40 (s, 1H), 8.82-8.51 (m, 4H), 8.34-8.07 (m, 4H), 7.85 (d, J = 5.1 Hz, 1H), 7.15 (d, J = 5.1 Hz, 1H), 4.48 (dd, J = 49.1, 9.3 Hz, 1H), 4.00 (dd, J = 36.1, 14.7 Hz, 1H), 3.66-3.45 (m, 1H), 1.30 (d, J = 1.6 Hz, 6H). |
| 767 | 1H NMR (400 MHz, Methanol-d4) δ 9.49 (t, J = 1.5 Hz, 1H), 8.78 (s, 1H), 8.71 (s, 1H), 8.61 (d, J = 2.2 Hz, 1H), 8.42 (s, 1H), 8.15 (t, J = 1.8 Hz, 1H), 8.02-7.90 (m, 2H), 7.86 (d, J = 5.1 Hz, 1H), 7.84-7.73 (m, 3H), 7.17 (d, J = 5.1 Hz, 1H), 4.47 (ddd, J = 49.0, 9.3, 2.1 Hz, 1H), 3.98 (ddd, J = 36.4, 14.5, 2.1 Hz, 1H), 3.76-3.41 (m, 1H), 1.30 (d, J = 1.6 Hz, 6H). |
| 768 | 1H NMR (400 MHz, Methanol-d4) δ 9.82 (d, J = 1.8 Hz, 1H), 8.82 (s, 1H), 8.77 (dd, J = 2.6, 0.7 Hz, 1H), 8.72 (d, J = 2.2 Hz, 1H), 8.61 (d, J = 2.2 Hz, 1H), 8.45 (t, J = 1.8 Hz, 1H), 8.36-8.27 (m, 2H), 8.15 (dd, J = 8.7, 0.7 Hz, 1H), 7.90 (d, J = 5.1 Hz, 1H), 7.82 (t, J = 1.8 Hz, 1H), 7.17 (d, J = 5.1 Hz, 1H), 4.48 (ddd, J = 49.0, 9.3, 2.1 Hz, 1H), 3.99 (ddd, J = 36.4, 14.6, 2.1 Hz, 1H), 3.56 (ddd, J = 16.1, 14.5, 9.3 Hz, 1H), 1.30 (d, J = 1.6 Hz, 6H). |
| 769 | 1H NMR (400 MHz, Methanol-d4) δ 8.78-8.67 (m, 2H), 8.60 (d, J = 2.2 Hz, 1H), 8.37-8.23 (m, 2H), 7.96 (d, J = 8.8 Hz, 2H), 7.86-7.75 (m, 2H), 7.66-7.53 (m, 2H), 7.15 (d, J = 5.1 Hz, 1H), 6.59 (dd, J = 2.5, 1.8 Hz, 1H), 4.47 (ddd, J = 49.0, 9.3, 2.1 Hz, 1H), 4.00 (ddd, J = 36.6, 14.8 Hz, 1H), 3.74-3.42 (m, 1H), 1.30 (d, J = 1.6 Hz, 6H). |
| 770 | 1H NMR (400 MHz, Methanol-d4) δ 8.74 (s, 1H), 8.69 (d, J = 2.2 Hz, 1H), 8.65 (dd, J = 2.6, 0.7 Hz, 1H), 8.60-8.51 (m, 2H), 8.21-8.01 (m, 3H), 7.89-7.73 (m, 2H), 7.14 (d, J = 5.1 Hz, 1H), 6.59 (dd, J = 2.6, 1.7 Hz, 1H), 4.48 (ddd, J = 49.0, 9.3, 2.1 Hz, 1H), 4.00 (ddd, J = 36.3, 14.6, 2.1 Hz, 1H), 3.72-3.42 (m, 1H), 1.30 (d, J = 1.6 Hz, 6H). |
| 771 | 1H NMR (400 MHz, Methanol-d4) δ 9.48 (s, 1H), 8.75 (s, 1H), 8.66 (d, J = 2.3 Hz, 1H), 8.59 (d, J = 2.1 Hz, 1H), 8.52 (s, 1H), 8.30-8.13 (m, 2H), 7.84 (d, J = 5.0 Hz, 1H), 7.66 (d, J = 8.6 Hz, 2H), 7.14 (d, J = 5.0 Hz, 1H), 4.61-4.36 (m, 1H), 4.18-3.84 (m, 1H), 3.64-3.40 (m, 1H), 1.30 (d, J = 1.6 Hz, 6H). |
| 772 | 1H NMR (400 MHz, Methanol-d4) δ 9.08 (s, 2H), 8.74 (s, 1H), 8.68 (d, J = 2.2 Hz, 1H), 8.62 (d, J = 2.2 Hz, 1H), 8.38 (s, 1H), 7.98-7.79 (m, 3H), 7.77-7.62 (m, 2H), 7.15 (d, J = 5.0 Hz, 1H), 4.47 (ddd, J = 49.1, 9.4, 2.2 Hz, 1H), 4.11-3.88 (m, 1H), 3.71-3.44 (m, 1H), 1.30 (d, J = 1.6 Hz, 6H). |
| 773 | 1H NMR (400 MHz, Methanol-d4) δ 8.77 (d, J = 1.7 Hz, 1H), 8.73 (s, 1H), 8.69 (d, J = 2.2 Hz, 1H), 8.58 (d, J = 2.1 Hz, 1H), 8.34 (s, 1H), 8.17-8.03 (m, 2H), 7.81 (d, J = 5.1 Hz, 1H), 7.67-7.57 (m, 2H), 7.15 (d, J = 5.0 Hz, 1H), 7.01 (d, J = 1.7 Hz, 1H), 4.47 (ddd, J = 48.9, 9.3, 2.1 Hz, 1H), 4.00 (ddd, J = 36.3, 14.6, 2.1 Hz, 1H), 3.70-3.46 (m, 1H), 1.30 (d, J = 1.6 Hz, 6H). |
| 774 | 1H NMR (400 MHz, Methanol-d4) δ 8.80-8.67 (m, 2H), 8.56 (d, J = 2.2 Hz, 1H), 8.34-8.19 (m, 3H), 7.98 (s, 2H), 7.80 (d, J = 5.1 Hz, 1H), 7.71-7.58 (m, 2H), 7.15 (d, J = 5.1 Hz, 1H), 4.48 (ddd, J = 49.0, 9.3, 2.1 Hz, 1H), 4.00 (ddd, J = 36.4, 14.6, 2.1 Hz, 1H), 3.65-3.51 (m, 1H), 1.30 (d, J = 1.6 Hz, 6H). |
| 775 | 1H NMR (400 MHz, Methanol-d4) δ 8.86-8.80 (m, 2H), 8.70 (d, J = 2.2 Hz, 1H), 8.60 (d, J = 2.2 Hz, 1H), 8.27 (d, J = 9.3 Hz, 2H), 8.10 (dd, J = 8.5, 2.6 Hz, 1H), |

TABLE 2-continued

| compound | 1H-NMR |
|---|---|
| | 7.86 (d, J = 5.1 Hz, 1H), 7.16 (d, J = 5.1 Hz, 1H), 7.12 (d, J = 1.7 Hz, 1H), 4.48 (ddd, J = 49.0, 9.3, 2.2 Hz, 1H), 4.00 (ddd, J = 36.3, 14.6, 2.1 Hz, 1H), 3.70-3.40 (m, 1H), 1.30 (d, J = 1.6 Hz, 6H). |
| 776 | 1H NMR (400 MHz, Methanol-d4) δ 8.75 (d, J = 2.2 Hz, 1H), 8.70 (d, J = 2.2 Hz, 1H), 8.56 (d, J = 6.9 Hz, 2H), 8.06-7.92 (m, 2H), 7.67 (s, 1H), 7.22 (d, J = 5.1 Hz, 1H), 4.48 (d, J = 7.6 Hz, 2H), 4.44-4.30 (m, 1H), 3.93 (ddd, J = 36.4, 14.6, 2.1 Hz, 1H), 3.72 (hept, J = 6.5 Hz, 1H), 3.56-3.46 (m, 1H), 3.22 (q, J = 7.4 Hz, 1H), 2.57 (ddd, J = 12.7, 7.6, 4.2 Hz, 2H), 2.34 (ddd, J = 13.1, 9.3, 6.5 Hz, 2H), 1.28 (d, J = 1.7 Hz, 6H). |
| 777 | 1H NMR (400 MHz, Methanol-d4) δ 8.74 (d, J = 2.2 Hz, 1H), 8.67 (d, J = 2.2 Hz, 1H), 8.61-8.51 (m, 2H), 8.02 (d, J = 5.1 Hz, 1H), 7.91 (s, 1H), 7.21 (d, J = 5.0 Hz, 1H), 6.47 (d, J = 1.7 Hz, 1H), 4.42 (ddd, J = 49.1, 9.3, 2.1 Hz, 1H), 4.07-3.81 (m, 2H), 3.61-3.40 (m, 1H), 3.00-2.82 (m, 1H), 2.38-2.24 (m, 2H), 2.19 (d, J = 13.5 Hz, 2H), 1.81 (q, J = 12.6 Hz, 2H), 1.64 (q, J = 11.7, 11.1 Hz, 2H), 1.29 (d, J = 1.7 Hz, 6H). |
| 778 | 1H NMR (400 MHz, Methanol-d4) δ 8.77 (s, 1H), 8.70 (dd, J = 7.7, 2.4 Hz, 2H), 8.64 (d, J = 2.1 Hz, 1H), 8.32 (d, J = 8.7 Hz, 1H), 8.25 (s, 1H), 8.16 (dd, J = 8.8, 2.6 Hz, 1H), 8.10 (s, 2H), 7.86 (d, J = 5.1 Hz, 1H), 7.15 (d, J = 5.1 Hz, 1H), 4.48 (ddd, J = 49.0, 9.4, 2.1 Hz, 1H), 3.99 (ddd, J = 36.5, 14.6, 2.1 Hz, 1H), 3.56 (ddd, J = 16.2, 14.5, 9.4 Hz, 1H), 1.30 (d, J = 1.6 Hz, 6H). |
| 779 | 1H NMR (400 MHz, Methanol-d4) δ 8.71 (d, J = 2.2 Hz, 1H), 8.66 (d, J = 2.2 Hz, 1H), 8.58 (s, 1H), 8.53 (s, 1H), 8.09-7.87 (m, 3H), 7.19 (d, J = 5.1 Hz, 1H), 4.51-4.30 (m, 2H), 3.92 (ddd, J = 36.2, 14.8, 2.3 Hz, 2H), 3.72 (hept, J = 6.6 Hz, 2H), 3.57-3.41 (m, 1H), 3.22 (q, J = 7.4 Hz, 2H), 2.16 (dt, J = 13.3, 10.7 Hz, 2H), 1.70 (q, J = 11.8 Hz, 2H), 1.29 (d, J = 1.7 Hz, 6H). |
| 780 | 1H NMR (400 MHz, Methanol-d4) δ 8.86-8.64 (m, 2H), 8.59 (s, 1H), 8.28 (s, 1H), 7.95 (d, J = 5.0 Hz, 1H), 7.22 (d, J = 5.0 Hz, 1H), 4.40 (ddd, J = 49.1, 9.4, 2.1 Hz, 1H), 4.12 (s, 2H), 3.90 (ddd, J = 36.4, 14.5, 2.0 Hz, 1H), 3.72 (p, J = 6.6 Hz, 2H), 3.49 (td, J = 15.2, 9.3 Hz, 2H), 3.22 (q, J = 7.4 Hz, 2H), 2.33 (t, J = 7.8 Hz, 6H), 2.24-2.11 (m, 6H), 1.28 (d, J = 1.6 Hz, 6H). |
| 781 | 1H NMR (400 MHz, Methanol-d4) δ 8.73 (d, J = 2.2 Hz, 1H), 8.64 (d, J = 2.2 Hz, 1H), 8.56 (s, 1H), 7.98 (d, J = 5.0 Hz, 1H), 7.88 (s, 1H), 7.19 (d, J = 5.1 Hz, 1H), 4.50 (s, 2H), 4.49-4.30 (m, 3H), 4.01-3.74 (m, 2H), 3.48 (ddd, J = 16.1, 14.5, 9.4 Hz, 1H), 2.16 (d, J = 13.5 Hz, 2H), 2.09-1.98 (m, 1H), 1.88-1.72 (m, 2H), 1.64-1.43 (m, 2H), 1.28 (d, J = 1.7 Hz, 6H). |
| 782 | 1H NMR (400 MHz, Methanol-d4) δ 8.72 (s, 1H), 8.57-8.38 (m, 4H), 8.27 (d, J = 2.2 Hz, 1H), 8.18 (d, J = 2.3 Hz, 1H), 7.77 (d, J = 4.9 Hz, 1H), 7.01 (d, J = 4.9 Hz, 1H), 4.48 (ddd, J = 49.0, 9.1, 2.2 Hz, 1H), 3.98 (s, 4H), 3.64-3.41 (m, 1H), 1.31 (d, J = 1.6 Hz, 6H). |
| 783 | 1H NMR (400 MHz, Methanol-d4) δ 8.99 (s, 1H), 8.75 (d, J = 2.2 Hz, 1H), 8.66 (d, J = 2.1 Hz, 1H), 8.60 (s, 1H), 7.98 (d, J = 5.1 Hz, 1H), 7.70 (d, J = 1.7 Hz, 1H), 7.64 (s, 1H), 7.60 (t, J = 1.7 Hz, 1H), 7.21 (d, J = 5.1 Hz, 1H), 4.66-4.31 (m, 3H), 3.92 (dd, J = 36.3, 14.6 Hz, 1H), 3.72 (dt, J = 13.2, 6.4 Hz, 1H), 3.50 (td, J = 15.4, 9.1 Hz, 1H), 3.09-2.94 (m, 1H), 2.54 (q, J = 7.1 Hz, 2H), 2.45-2.34 (m, 2H), 1.28 (d, J = 1.6 Hz, 5H). |
| 784 | 1H NMR (400 MHz, Methanol-d4) δ 8.75 (s, 1H), 8.72-8.61 (m, 2H), 8.56 (s, 2H), 8.29 (s, 1H), 8.02 (s, 1H), 7.84 (d, J = 5.1 Hz, 1H), 7.15 (d, J = 5.1 Hz, 1H), 4.62 (s, 2H), 4.47 (ddd, J = 49.0, 9.3, 2.1 Hz, 1H), 3.99 (ddd, J = 36.4, 14.6, 2.1 Hz, 1H), 3.55 (dd, J = 15.5, 9.3 Hz, 1H), 3.50 (s, 3H), 1.30 (d, J = 1.6 Hz, 6H). |
| 785 | 1H NMR (400 MHz, Methanol-d4) δ 8.76 (d, J = 2.2 Hz, 1H), 8.70 (d, J = 2.2 Hz, 1H), 8.58 (s, 1H), 8.29 (s, 1H), 7.93 (d, J = 5.1 Hz, 1H), 7.22 (d, J = 5.1 Hz, 1H), 5.48 (s, 2H), 4.26 (s, 2H), 3.71 (dt, J = 13.7, 4.7 Hz, 4H), 3.59 (dt, J = 16.1, 4.6 Hz, 4H), 2.30-2.19 (m, 6H), 1.90 (dd, J = 9.3, 6.0 Hz, 6H). |
| 786 | 1H NMR (400 MHz, Methanol-d4) δ 8.76 (d, J = 2.1 Hz, 1H), 8.70 (d, J = 2.2 Hz, 1H), 8.60 (s, 1H), 8.31 (s, 1H), 7.94 (d, J = 5.0 Hz, 1H), 7.22 (d, J = 5.1 Hz, 1H), 4.03 (s, 2H), 3.48 (ddd, J = 5.8, 5.1, 1.2 Hz, 2H), 3.42 (td, J = 5.3, 1.2 Hz, 2H), 3.36 (s, 3H), 2.29-2.19 (m, 6H), 1.91 (dt, J = 11.5, 4.8 Hz, 6H). |
| 787 | 1H NMR (400 MHz, Methanol-d4) δ 8.76 (d, J = 2.1 Hz, 1H), 8.71 (dd, J = 2.2, 0.4 Hz, 1H), 8.58 (s, 1H), 8.30 (s, 1H), 7.93 (dd, J = 5.0, 0.5 Hz, 1H), 7.22 (d, J = 5.1 Hz, 1H), 5.55-5.29 (m, 2H), 4.62 (dddd, J = 20.3, 10.6, 6.0, 1.7 Hz, 1H), 4.47-4.28 (m, 2H), 4.10 (dd, J = 24.5, 11.7 Hz, 1H), 4.02 (s, 2H), 2.24 (dd, J = 10.0, 5.7 Hz, 6H), 1.90 (dd, J = 10.2, 5.8 Hz, 6H). |
| 788 | 1H NMR (400 MHz, Methanol-d4) δ 8.78-8.71 (m, 2H), 8.56 (s, 1H), 7.99 (d, J = 5.1 Hz, 1H), 7.78 (s, 1H), 7.21 (d, J = 5.1 Hz, 1H), 4.52-4.31 (m, 2H), 3.94 (ddd, J = 36.3, 14.5, 2.2 Hz, 1H), 3.56-3.43 (m, 1H), 3.36 (d, J = 7.4 Hz, 2H), 2.74 (s, 3H), 2.59-2.40 (m, 3H), 2.25 (ddd, J = 13.0, 10.2, 7.9 Hz, 2H), 1.29 (d, J = 1.7 Hz, 6H). |
| 789 | 1H NMR (400 MHz, Methanol-d4) δ 8.76 (d, J = 2.1 Hz, 1H), 8.70 (d, J = 2.2 Hz, 1H), 8.60 (s, 1H), 8.30 (s, 1H), 7.94 (d, J = 5.0 Hz, 1H), 7.22 (d, J = 5.1 Hz, 1H), 4.32 (s, 2H), 3.37 (d, J = 21.1 Hz, 4H), 2.96 (s, 3H), 2.24 (dd, J = 10.0, 6.0 Hz, 6H), 1.95-1.85 (m, 6H). |
| 790 | 1H NMR (400 MHz, Methanol-d4) δ 8.76 (d, J = 2.2 Hz, 1H), 8.70 (dd, J = 2.2, 0.4 Hz, 1H), 8.59 (s, 1H), 8.29 (s, 1H), 7.93 (dd, J = 5.0, 0.5 Hz, 1H), 7.22 (d, J = 5.1 Hz, 1H), 4.16 (s, 2H), 3.56 (t, J = 6.8 Hz, 2H), 3.48 (t, J = 6.9 Hz, 2H), 2.29-2.20 (m, 6H), 2.12-1.99 (m, 2H), 1.97-1.85 (m, 8H). |
| 791 | 1H NMR (400 MHz, Methanol-d4) δ 8.76 (d, J = 2.1 Hz, 1H), 8.70 (d, J = 2.2 Hz, 1H), 8.57 (s, 1H), 8.29 (s, 1H), 7.94-7.89 (m, 1H), 7.22 (d, J = 5.1 Hz, 1H), 4.48 (ddd, J = 9.4, 6.4, 1.4 Hz, 1H), 4.32 (tt, J = 6.3, 3.9 Hz, 1H), 4.22 (dd, J = 10.6, 6.5 |

TABLE 2-continued

| compound | 1H-NMR |
|---|---|
| | Hz, 1H), 4.14 (dd, J = 9.5, 4.1 Hz, 1H), 4.00 (d, J = 1.2 Hz, 2H), 3.92-3.83 (m, 1H), 3.33 (s, 3H), 2.24 (dd, J = 10.2, 5.7 Hz, 6H), 1.90 (dd, J = 10.3, 5.8 Hz, 6H). |
| 792 | 1H NMR (400 MHz, Methanol-d4) δ 8.76 (d, J = 2.1 Hz, 1H), 8.70 (d, J = 2.2 Hz, 1H), 8.57 (s, 1H), 8.28 (s, 1H), 7.93 (d, J = 5.0 Hz, 1H), 7.22 (d, J = 5.1 Hz, 1H), 4.25 (s, 2H), 3.63-3.55 (m, 2H), 3.51 (t, J = 5.3 Hz, 2H), 2.24 (dd, J = 10.2, 5.8 Hz, 6H), 1.96-1.82 (m, 6H), 1.70 (dt, J = 17.5, 5.2 Hz, 4H), 1.63-1.54 (m, 2H). |
| 793 | 1H NMR (400 MHz, Methanol-d4) δ 8.78-8.70 (m, 2H), 8.59 (s, 1H), 7.99 (d, J = 5.1 Hz, 1H), 7.84 (s, 1H), 7.21 (d, J = 5.1 Hz, 1H), 4.53-4.33 (m, 2H), 4.23 (s, 2H), 3.92 (ddd, J = 36.4, 14.5, 2.1 Hz, 1H), 3.57-3.46 (m, 1H), 3.44 (d, J = 7.8 Hz, 2H), 3.27-3.02 (m, 6H), 2.92 (s, 3H), 2.57 (td, J = 8.3, 3.9 Hz, 1H), 2.47 (ddt, J = 11.3, 7.6, 3.5 Hz, 2H), 2.25 (dtd, J = 12.7, 7.1, 2.3 Hz, 2H), 1.29 (d, J = 1.6 Hz, 6H). |
| 794 | 1H NMR (400 MHz, Methanol-d4) δ 8.74 (q, J = 2.2 Hz, 2H), 8.59 (s, 1H), 7.99 (d, J = 5.1 Hz, 1H), 7.79 (s, 1H), 7.21 (d, J = 5.1 Hz, 1H), 4.52-4.41 (m, 2H), 4.36 (dd, J = 9.3, 2.1 Hz, 1H), 3.92 (ddd, J = 36.4, 14.6, 2.1 Hz, 1H), 3.64-3.41 (m, 5H), 3.02 (td, J = 12.9, 3.0 Hz, 2H), 2.86 (s, 3H), 2.65-2.38 (m, 4H), 2.28 (td, J = 12.6, 11.2, 8.0 Hz, 2H), 2.14-2.04 (m, 2H), 2.04-1.86 (m, 1H), 1.29 (d, J = 1.6 Hz, 6H). |
| 795 | 1H NMR (400 MHz, Methanol-d4) δ 8.74 (d, J = 2.2 Hz, 1H), 8.65 (d, J = 2.2 Hz, 1H), 8.60 (s, 1H), 7.98 (d, J = 5.1 Hz, 1H), 7.61 (s, 1H), 7.20 (d, J = 5.1 Hz, 1H), 4.55-4.44 (m, 2H), 4.37 (dd, J = 9.3, 2.1 Hz, 1H), 3.92 (ddd, J = 36.4, 14.6, 2.1 Hz, 1H), 3.52 (ddd, J = 16.1, 14.5, 9.3 Hz, 1H), 3.43 (d, J = 8.0 Hz, 2H), 3.01 (s, 7H), 2.71 (tt, J = 8.9, 4.7 Hz, 1H), 2.48 (ddd, J = 12.9, 7.6, 4.8 Hz, 2H), 2.36 (ddd, J = 13.0, 9.1, 6.1 Hz, 2H), 1.29 (d, J = 1.7 Hz, 6H). |
| 796 | 1H NMR (400 MHz, Methanol-d4) δ 8.76 (d, J = 2.1 Hz, 1H), 8.70 (d, J = 2.2 Hz, 1H), 8.58 (s, 1H), 8.29 (s, 1H), 7.93 (d, J = 5.1 Hz, 1H), 7.22 (d, J = 5.1 Hz, 1H), 4.75 (dd, J = 7.6, 5.6 Hz, 2H), 4.30 (s, 2H), 4.09 (p, J = 6.3 Hz, 1H), 3.82 (s, 4H), 2.96 (d, J = 24.7 Hz, 4H), 2.24 (t, J = 8.0 Hz, 6H), 1.90 (t, J = 7.9 Hz, 6H). |
| 797 | 1H NMR (400 MHz, Methanol-d4) δ 8.76 (d, J = 2.2 Hz, 1H), 8.70 (d, J = 2.2 Hz, 1H), 8.58 (s, 1H), 8.29 (s, 1H), 7.92 (d, J = 5.1 Hz, 1H), 7.22 (d, J = 5.1 Hz, 1H), 4.39 (ddd, J = 35.9, 18.9, 10.1 Hz, 2H), 4.22-4.03 (m, 2H), 4.01 (d, J = 1.8 Hz, 2H), 2.30-2.17 (m, 6H), 1.96-1.83 (m, 6H), 1.66 (d, J = 21.5 Hz, 3H). |
| 798 | 1H NMR (400 MHz, Methanol-d4) δ 8.76 (d, J = 2.2 Hz, 1H), 8.70 (d, J = 2.2 Hz, 1H), 8.59 (d, J = 0.8 Hz, 1H), 8.29 (s, 1H), 7.93 (d, J = 5.1 Hz, 1H), 7.22 (d, J = 5.1 Hz, 1H), 4.20 (s, 1H), 4.14 (s, 1H), 4.00 (t, J = 12.6 Hz, 1H), 3.90-3.67 (m, 3H), 2.54 (tt, J = 14.0, 7.4 Hz, 1H), 2.43 (tt, J = 14.1, 7.6 Hz, 1H), 2.29-2.18 (m, 6H), 1.94-1.85 (m, 6H). |
| 799 | 1H NMR (400 MHz, Methanol-d4) δ 8.79 (d, J = 2.1 Hz, 1H), 8.73 (d, J = 2.2 Hz, 1H), 8.62 (d, J = 1.7 Hz, 1H), 8.32 (s, 1H), 7.96 (d, J = 5.1 Hz, 1H), 7.25 (d, J = 5.1 Hz, 1H), 4.76-4.62 (m, 4H), 4.19 (d, J = 14.7 Hz, 2H), 3.87 (s, 1H), 3.75 (s, 1H), 3.63 (q, J = 7.2 Hz, 1H), 3.57-3.46 (m, 1H), 2.38 (t, J = 7.0 Hz, 1H), 2.32-2.19 (m, 7H), 1.93 (t, J = 8.1 Hz, 6H). |
| 800 | 1H NMR (400 MHz, Methanol-d4) δ 8.78 (d, J = 2.1 Hz, 1H), 8.72 (d, J = 2.1 Hz, 1H), 8.54 (s, 1H), 8.25 (s, 1H), 7.99 (d, J = 5.0 Hz, 1H), 7.25 (d, J = 5.0 Hz, 1H), 3.15 (s, 11H), 2.39-2.29 (m, 6H), 2.02-1.91 (m, 6H). |
| 801 | 1H NMR (400 MHz, Methanol-d4) δ 8.78 (d, J = 2.1 Hz, 1H), 8.72 (d, J = 2.1 Hz, 1H), 8.51 (s, 1H), 8.30 (s, 1H), 7.96 (d, J = 5.0 Hz, 1H), 7.24 (d, J = 5.1 Hz, 1H), 4.18 (q, J = 7.1 Hz, 2H), 3.65 (t, J = 6.7 Hz, 2H), 2.68 (t, J = 6.7 Hz, 2H), 2.27 (dd, J = 10.3, 5.7 Hz, 6H), 2.01-1.86 (m, 6H), 1.29 (t, J = 7.1 Hz, 3H). |
| 802 | 1H NMR (400 MHz, Methanol-d4) δ 8.79 (d, J = 2.1 Hz, 1H), 8.71 (d, J = 2.1 Hz, 1H), 8.59 (s, 1H), 8.28 (s, 1H), 7.97 (d, J = 5.1 Hz, 1H), 7.25 (d, J = 5.1 Hz, 1H), 4.55-4.32 (m, 1H), 3.93 (dd, J = 36.4, 14.6 Hz, 1H), 3.51 (td, J = 15.5, 9.4 Hz, 2H), 2.97 (s, 3H), 2.21 (d, J = 7.3 Hz, 15H), 1.31 (s, 6H). Some protons from the piperazine are under solvent. |
| 803 | 1H NMR (400 MHz, Methanol-d4) δ 8.79 (d, J = 2.1 Hz, 1H), 8.72 (d, J = 2.1 Hz, 1H), 8.50 (s, 1H), 8.29 (s, 1H), 7.95 (d, J = 5.1 Hz, 1H), 7.25 (d, J = 5.1 Hz, 1H), 3.64 (t, J = 6.6 Hz, 2H), 2.76 (s, 3H), 2.53 (t, J = 6.7 Hz, 2H), 2.27 (dd, J = 10.4, 5.7 Hz, 6H), 1.93 (dd, J = 10.3, 5.7 Hz, 6H). |
| 804 | 1H NMR (400 MHz, Methanol-d4) δ 8.78 (d, J = 2.1 Hz, 1H), 8.72 (d, J = 2.1 Hz, 1H), 8.51 (s, 1H), 8.29 (s, 1H), 7.95 (d, J = 5.1 Hz, 1H), 7.24 (d, J = 5.1 Hz, 1H), 3.65 (t, J = 6.6 Hz, 2H), 3.11 (s, 3H), 2.98 (s, 3H), 2.75 (t, J = 6.7 Hz, 2H), 2.27 (dd, J = 10.3, 5.6 Hz, 6H), 1.93 (dd, J = 10.3, 5.7 Hz, 6H). |
| 805 | 1H NMR (400 MHz, Methanol-d4) δ 8.78 (d, J = 2.1 Hz, 1H), 8.72 (d, J = 2.1 Hz, 1H), 8.51 (s, 1H), 8.30 (s, 1H), 7.95 (d, J = 5.0 Hz, 1H), 7.24 (d, J = 5.1 Hz, 1H), 4.63 (t, J = 12.0 Hz, 2H), 4.35 (t, J = 12.2 Hz, 2H), 3.65 (t, J = 6.6 Hz, 2H), 2.60 (t, J = 6.6 Hz, 2H), 2.27 (dd, J = 10.4, 5.6 Hz, 6H), 1.93 (dd, J = 10.1, 5.6 Hz, 6H). |
| 806 | 1H NMR (400 MHz, Methanol-d4) δ 8.78 (d, J = 2.1 Hz, 1H), 8.72 (d, J = 2.1 Hz, 1H), 8.54 (s, 1H), 8.30 (s, 1H), 7.96 (d, J = 5.1 Hz, 1H), 7.24 (d, J = 5.1 Hz, 1H), 3.67 (t, J = 6.6 Hz, 2H), 2.97 (s, 3H), 2.82 (t, J = 6.7 Hz, 2H), 2.32-2.22 (m, 6H), 1.93 (t, J = 8.0 Hz, 6H). Piperazine peaks obscured by solvent peaks |
| 807 | 1H NMR (400 MHz, Methanol-d4) δ 8.77 (d, J = 2.1 Hz, 1H), 8.69 (d, J = 2.1 Hz, 1H), 8.61 (s, 1H), 8.03 (d, J = 5.1 Hz, 1H), 7.87 (s, 1H), 7.23 (d, J = 5.0 Hz, 1H), 4.75 (t, J = 12.0 Hz, 2H), 4.44 (t, J = 12.2 Hz, 2H), 4.19 (p, J = 6.4 Hz, 1H), 4.12 (s, 2H), 1.42 (d, J = 6.3 Hz, 6H). |

TABLE 2-continued

| compound | 1H-NMR |
|---|---|
| 808 | 1H NMR (400 MHz, Methanol-d4) δ 8.80 (d, J = 2.1 Hz, 1H), 8.74 (d, J = 2.1 Hz, 1H), 8.58 (s, 1H), 8.33 (s, 1H), 7.97 (d, J = 5.1 Hz, 1H), 7.25 (d, J = 5.1 Hz, 1H), 4.04 (s, 2H), 2.28 (t, J = 8.0 Hz, 6H), 1.94 (t, J = 8.0 Hz, 6H), 1.53 (s, 9H). |
| 809 | |
| 810 | 1H NMR (400 MHz, Methanol-d4) δ 8.76 (d, J = 2.2 Hz, 1H), 8.70 (d, J = 2.1 Hz, 1H), 8.56 (s, 1H), 8.28 (s, 1H), 7.93 (d, J = 5.1 Hz, 1H), 7.22 (d, J = 5.0 Hz, 1H), 4.55 (s, 2H), 2.32-2.14 (m, 6H), 1.88 (dt, J = 12.7, 7.3 Hz, 6H), 1.37 (s, 6H). |
| 811 | 1H NMR (400 MHz, Methanol-d4) δ 8.80 (d, J = 2.1 Hz, 1H), 8.74 (d, J = 2.1 Hz, 1H), 8.67 (s, 1H), 8.34 (s, 1H), 8.14-8.06 (m, 2H), 7.98 (d, J = 5.1 Hz, 1H), 7.71 (t, J = 7.5 Hz, 1H), 7.60 (t, J = 7.7 Hz, 2H), 7.26 (d, J = 5.1 Hz, 1H), 4.94 (s, 2H), 2.28 (t, J = 7.8 Hz, 6H), 1.93 (t, J = 8.0 Hz, 6H). |
| 812 | 1H NMR (400 MHz, Methanol-d4) δ 8.78 (d, J = 2.1 Hz, 1H), 8.69 (d, J = 2.1 Hz, 1H), 8.60 (s, 1H), 8.03 (d, J = 5.1 Hz, 1H), 7.88 (s, 1H), 7.24 (d, J = 5.1 Hz, 1H), 4.19 (p, J = 6.5 Hz, 1H), 4.06 (s, 2H), 1.54 (s, 9H), 1.43 (d, J = 6.4 Hz, 6H). |
| 813 | 1H NMR (400 MHz, Methanol-d4) δ 8.79 (d, J = 2.1 Hz, 1H), 8.73 (d, J = 2.2 Hz, 1H), 8.60 (s, 1H), 8.32 (s, 1H), 7.95 (d, J = 5.0 Hz, 1H), 7.25 (d, J = 5.1 Hz, 1H), 3.98 (s, 2H), 2.34-2.22 (m, 6H), 1.93 (t, J = 8.0 Hz, 6H), 1.39 (s, 9H). |
| 814 | 1H NMR (400 MHz, Methanol-d4) δ 8.79 (d, J = 2.1 Hz, 1H), 8.73 (d, J = 2.2 Hz, 1H), 8.60 (s, 1H), 8.32 (s, 1H), 7.96 (d, J = 5.1 Hz, 1H), 7.25 (d, J = 5.0 Hz, 1H), 4.22 (s, 2H), 3.03 (s, 3H), 2.28 (t, J = 7.8 Hz, 6H), 1.93 (t, J = 7.9 Hz, 6H), 1.49 (s, 9H). |
| 815 | 1H NMR (400 MHz, Methanol-d4) δ 8.80 (d, J = 6.9 Hz, 2H), 8.62 (s, 1H), 8.03 (d, J = 5.1 Hz, 1H), 7.84 (s, 1H), 7.25 (d, J = 5.0 Hz, 1H), 4.62 (s, 2H), 4.55-4.40 (m, 1H), 3.71 (s, 4H), 3.38 (d, J = 7.5 Hz, 2H), 2.57 (s, 1H), 2.49 (t, J = 10.5 Hz, 2H), 2.29 (q, J = 10.5, 9.8 Hz, 2H), 1.41 (s, 6H). |
| 816 | 1H NMR (400 MHz, Methanol-d4) δ 8.82-8.75 (m, 2H), 8.55 (s, 1H), 8.01 (d, J = 5.1 Hz, 1H), 7.82 (s, 1H), 7.24 (d, J = 5.1 Hz, 1H), 4.53-4.39 (m, 1H), 3.71 (s, 3H), 3.44 (t, J = 8.0 Hz, 2H), 3.38 (d, J = 7.5 Hz, 2H), 2.57 (s, 1H), 2.49 (s, 2H), 2.28 (q, J = 10.0, 9.5 Hz, 2H), 2.04 (q, J = 7.3, 6.5 Hz, 2H), 1.46 (s, 9H), 1.34 (s, 6H). |
| 817 | 1H NMR (400 MHz, Methanol-d4) δ 8.58-8.49 (m, 2H), 8.23 (dd, J = 9.2, 1.8 Hz, 1H), 7.96 (d, J = 5.0 Hz, 1H), 7.74 (s, 1H), 7.10 (dd, J = 9.1, 4.5 Hz, 1H), 6.94 (d, J = 5.0 Hz, 1H), 4.51 (dd, J = 9.3, 2.1 Hz, 1H), 4.39 (d, J = 9.4 Hz, 0H), 4.18 (p, J = 6.4 Hz, 1H), 4.06-3.84 (m, 1H), 3.50 (td, J = 15.4, 9.3 Hz, 1H), 1.42 (d, J = 6.4 Hz, 6H), 1.32 (d, J = 1.7 Hz, 6H). |
| 818 | 1H NMR (400 MHz, Methanol-d4) δ 8.56 (d, J = 4.4 Hz, 1H), 8.51 (s, 1H), 8.20 (dd, J = 9.1, 1.8 Hz, 1H), 7.92 (d, J = 5.0 Hz, 1H), 7.57 (s, 1H), 7.08 (dd, J = 9.1, 4.5 Hz, 1H), 6.91 (d, J = 5.0 Hz, 1H), 4.52-4.31 (m, 2H), 3.93 (ddd, J = 36.5, 14.6, 2.1 Hz, 1H), 3.66 (s, 3H), 3.56-3.40 (m, 1H), 2.55 (s, 1H), 2.44 (d, J = 8.9 Hz, 2H), 2.24 (q, J = 9.6 Hz, 2H), 1.29 (d, J = 1.6 Hz, 6H). |
| 819 | 1H NMR (400 MHz, Methanol-d4) δ 8.75 (s, 1H), 8.73 (d, J = 2.2 Hz, 1H), 8.57 (s, 1H), 7.97 (d, J = 5.1 Hz, 1H), 7.85 (s, 1H), 7.20 (d, J = 5.0 Hz, 1H), 4.41 (q, J = 6.7, 6.0 Hz, 1H), 3.68 (s, 3H), 3.55-3.46 (m, 2H), 3.35 (d, J = 7.4 Hz, 2H), 2.54 (s, 1H), 2.47 (t, J = 10.1 Hz, 2H), 2.22 (q, J = 10.1, 9.6 Hz, 2H), 2.04-1.92 (m, 2H), 1.42 (s, 6H). |
| 820 | 1H NMR (400 MHz, Methanol-d4) δ 8.98 (dd, J = 4.6, 1.6 Hz, 1H), 8.77 (s, 1H), 8.68 (d, J = 2.2 Hz, 1H), 8.59 (d, J = 8.2 Hz, 1H), 8.45 (d, J = 2.2 Hz, 1H), 8.36 (s, 1H), 8.26 (d, J = 9.0 Hz, 1H), 8.15 (d, J = 2.4 Hz, 1H), 7.96 (dd, J = 9.0, 2.4 Hz, 1H), 7.81 (d, J = 5.1 Hz, 1H), 7.74 (dd, J = 8.3, 4.5 Hz, 1H), 7.14 (d, J = 5.0 Hz, 1H), 4.59-4.36 (m, 1H), 4.11-3.91 (m, 1H), 3.62-3.49 (m, 1H), 1.30 (d, J = 1.6 Hz, 6H). |
| 821 | 1H NMR (400 MHz, Methanol-d4) δ 10.50 (s, 1H), 9.32 (s, 1H), 8.95 (s, 1H), 8.68 (d, J = 6.6 Hz, 1H), 8.63 (d, J = 1.5 Hz, 2H), 8.49 (d, J = 9.1 Hz, 1H), 8.05 (d, J = 6.7 Hz, 1H), 7.98 (d, J = 4.9 Hz, 1H), 7.45 (d, J = 9.0 Hz, 1H), 7.15 (d, J = 4.8 Hz, 1H), 4.56-4.34 (m, 1H), 4.05-3.83 (m, 1H), 3.54 (dd, J = 14.9, 8.8 Hz, 1H), 1.30 (d, J = 1.6 Hz, 6H). |
| 822 | 1H NMR (400 MHz, Methanol-d4) δ 8.79 (d, J = 2.2 Hz, 1H), 8.70 (d, J = 2.2 Hz, 1H), 8.63 (s, 1H), 8.05 (d, J = 5.0 Hz, 1H), 7.94 (s, 1H), 7.25 (d, J = 5.0 Hz, 1H), 4.57-4.30 (m, 1H), 4.14 (s, 2H), 3.92 (dt, J = 37.2, 14.1 Hz, 4H), 3.52 (td, J = 15.2, 9.2 Hz, 2H), 3.40 (d, J = 12.3 Hz, 0H), 2.49-2.25 (m, 4H), 1.87 (h, J = 10.7 Hz, 2H), 1.64 (q, J = 12.3, 11.9 Hz, 2H), 1.31 (d, J = 1.8 Hz, 6H). (several protons obscured by solvent peak) |
| 823 | 1H NMR (400 MHz, Methanol-d4) δ 8.75 (q, J = 2.2 Hz, 2H), 8.57 (s, 1H), 7.99 (d, J = 5.1 Hz, 1H), 7.77 (s, 1H), 7.22 (d, J = 5.1 Hz, 1H), 4.53-4.34 (m, 2H), 4.02-3.85 (m, 3H), 3.57-3.46 (m, 3H), 3.44 (s, 3H), 2.69-2.56 (m, 1H), 2.54-2.40 (m, 2H), 2.35-2.19 (m, 2H), 1.30 (d, J = 1.7 Hz, 6H). |
| 824 | 1H NMR (400 MHz, Methanol-d4) δ 8.80 (d, J = 2.2 Hz, 1H), 8.75 (d, J = 2.2 Hz, 1H), 8.57 (s, 1H), 8.00 (d, J = 5.1 Hz, 1H), 7.81 (s, 1H), 7.22 (d, J = 5.1 Hz, 1H), 4.52-4.34 (m, 2H), 3.94 (ddd, J = 36.3, 14.6, 2.2 Hz, 1H), 3.56-3.41 (m, 3H), 2.66-2.53 (m, 1H), 2.51-2.40 (m, 2H), 2.32-2.17 (m, 2H), 1.30 (d, J = 1.7 Hz, 6H), 1.22 (s, 9H). |
| 825 | 1H NMR (400 MHz, Methanol-d4) δ 8.75 (s, 2H), 8.57 (s, 1H), 7.99 (d, J = 5.1 Hz, 1H), 7.78 (s, 1H), 7.22 (d, J = 5.1 Hz, 1H), 4.53-4.31 (m, 2H), 3.94 (ddd, J = 36.3, 14.5, 2.2 Hz, 1H), 3.56-3.41 (m, 3H), 2.67-2.52 (m, 1H), 2.51-2.40 (m, 2H), 2.34-2.23 (m, 2H), 2.25-2.18 (m, 2H), 1.68 (h, J = 7.4 Hz, 2H), 1.30 (d, J = 1.7 Hz, 6H), 0.96 (t, J = 7.4 Hz, 3H). |
| 826 | 1H NMR (400 MHz, Methanol-d4) δ 8.75 (s, 2H), 8.58 (s, 1H), 7.99 (d, J = 5.1 Hz, 1H), 7.79 (s, 1H), 7.22 (d, J = 5.1 Hz, 1H), 4.54-4.34 (m, 2H), 3.94 (ddd, J = 36.3, |

TABLE 2-continued

| compound | 1H-NMR |
|---|---|
| | 14.5, 2.2 Hz, 1H), 3.58-3.41 (m, 3H), 2.69-2.51 (m, 1H), 2.51-2.41 (m, 2H), 2.34-2.22 (m, 2H), 2.17-2.04 (m, 3H), 1.30 (d, J = 1.7 Hz, 6H), 1.02-0.88 (m, 6H). |
| 827 | 1H NMR (400 MHz, Methanol-d4) δ 8.79-8.70 (m, 2H), 8.57 (s, 1H), 8.00 (d, J = 5.1 Hz, 1H), 7.79 (s, 1H), 7.22 (d, J = 5.1 Hz, 1H), 4.56-4.29 (m, 2H), 3.94 (ddd, J = 36.3, 14.5, 2.2 Hz, 1H), 3.58-3.41 (m, 3H), 2.70-2.54 (m, 1H), 2.52-2.38 (m, 2H), 2.33-2.16 (m, 2H), 1.35 (s, 3H), 1.30 (d, J = 1.7 Hz, 6H), 1.13 (q, J = 3.8 Hz, 2H), 0.69-0.58 (m, 2H). |
| 828 | 1H NMR (400 MHz, Methanol-d4) δ 8.80-8.68 (m, 2H), 8.57 (s, 1H), 8.04-7.91 (m, 1H), 7.80 (s, 1H), 7.22 (d, J = 5.0 Hz, 1H), 4.54-4.30 (m, 2H), 3.95 (ddd, J = 36.3, 14.5, 2.2 Hz, 1H), 3.66-3.41 (m, 3H), 2.76-2.58 (m, 1H), 2.56-2.41 (m, 2H), 2.39-2.21 (m, 2H), 1.37-1.33 (m, 2H), 1.32-1.28 (m, 8H). |
| 829 | 1H NMR (400 MHz, Methanol-d4) δ 8.81-8.67 (m, 2H), 8.57 (s, 1H), 7.98 (d, J = 5.1 Hz, 1H), 7.81 (s, 1H), 7.22 (d, J = 5.1 Hz, 1H), 4.56-4.31 (m, 2H), 3.94 (ddd, J = 36.3, 14.5, 2.2 Hz, 1H), 3.65-3.41 (m, 3H), 2.73-2.54 (m, 1H), 2.52-2.41 (m, 2H), 2.34-2.18 (m, 2H), 1.36-1.32 (m, 2H), 1.31-1.27 (m, 8H). |
| 830 | 1H NMR (400 MHz, Methanol-d4) δ 8.85-8.71 (m, 2H), 8.56 (s, 1H), 7.98 (d, J = 5.0 Hz, 1H), 7.82 (s, 1H), 7.22 (d, J = 5.1 Hz, 1H), 4.52-4.31 (m, 1H), 4.05-3.81 (m, 1H), 3.82-3.58 (m, 4H), 3.36 (d, J = 7.4 Hz, 2H), 2.71-2.52 (m, 1H), 2.53-2.41 (m, 2H), 2.33-2.21 (m, 2H), 2.17-1.89 (m, 4H), 1.67-1.29 (m, 5H), 0.90-0.79 (m, 2H), 0.78-0.67 (m, 2H). |
| 831 | 1H NMR (400 MHz, Methanol-d4) δ 8.79-8.72 (m, 2H), 8.57 (s, 1H), 7.97 (d, J = 5.0 Hz, 1H), 7.85 (s, 1H), 7.21 (d, J = 5.1 Hz, 1H), 4.56-4.25 (m, 2H), 3.95 (ddd, J = 36.3, 14.6, 2.1 Hz, 1H), 3.62-3.41 (m, 1H), 3.32-3.26 (m, 2H), 3.01 (s, 3H), 2.71-2.50 (m, 3H), 2.41-2.22 (m, 2H), 1.30 (d, J = 1.6 Hz, 6H). |
| 832 | 1H NMR (400 MHz, Methanol-d4) δ 8.76 (d, J = 2.1 Hz, 1H), 8.65 (d, J = 2.1 Hz, 1H), 8.59 (s, 1H), 8.02 (d, J = 5.1 Hz, 1H), 7.91-7.83 (m, 1H), 7.22 (d, J = 5.1 Hz, 1H), 4.64-4.25 (m, 1H), 4.03-3.81 (m, 2H), 3.66-3.40 (m, 1H), 2.43 (dd, J = 8.7, 7.4 Hz, 2H), 2.27-2.01 (m, 4H), 1.96-1.59 (m, 6H), 1.30 (d, J = 1.6 Hz, 6H). |
| 833 | 1H NMR (400 MHz, Methanol-d4) δ 8.83-8.71 (m, 2H), 8.58 (s, 1H), 8.51 (s, 1H), 7.91 (d, J = 5.1 Hz, 1H), 7.23 (d, J = 5.1 Hz, 1H), 4.41 (ddd, J = 49.1, 9.3, 2.1 Hz, 1H), 3.92 (ddd, J = 36.5, 14.6, 2.1 Hz, 1H), 3.66-3.54 (m, 1H), 3.54-3.39 (m, 2H), 2.57 (ddd, J = 13.5, 10.8, 7.8 Hz, 1H), 2.28 (s, 6H), 2.11-1.97 (m, 1H), 1.88-1.68 (m, 1H), 1.31-1.22 (m, 6H). |
| 834 | 1H NMR (400 MHz, Methanol-d4) δ 8.72 (s, 2H), 8.55 (s, 1H), 8.31 (s, 1H), 7.83 (d, J = 5.1 Hz, 1H), 7.57 (t, J = 8.2 Hz, 1H), 7.30 (d, J = 8.0 Hz, 2H), 7.17 (d, J = 5.1 Hz, 1H), 4.60-4.33 (m, 3H), 3.99 (dd, J = 36.5, 14.5 Hz, 1H), 3.70 (s, 3H), 3.53 (td, J = 15.2, 9.2 Hz, 1H), 1.30 (d, J = 1.6 Hz, 6H). |
| 835 | 1H NMR (400 MHz, Methanol-d4) δ 8.77 (s, 1H), 8.72 (d, J = 2.2 Hz, 1H), 8.57 (d, J = 2.1 Hz, 1H), 8.37 (d, J = 2.1 Hz, 1H), 8.33 (d, J = 2.5 Hz, 1H), 8.26 (s, 1H), 7.85 (d, J = 5.1 Hz, 1H), 7.64 (t, J = 2.3 Hz, 1H), 7.18 (d, J = 5.1 Hz, 1H), 4.62-4.34 (m, 1H), 4.22 (q, J = 7.0 Hz, 2H), 4.08-3.87 (m, 1H), 3.64-3.42 (m, 1H), 1.48 (t, J = 7.0 Hz, 3H), 1.31 (d, J = 1.7 Hz, 6H). |
| 836 | 1H NMR (400 MHz, Methanol-d4) δ 8.70 (s, 1H), 8.66 (d, J = 2.2 Hz, 1H), 8.46 (d, J = 2.1 Hz, 1H), 8.39 (s, 1H), 7.78 (d, J = 5.0 Hz, 1H), 7.45 (t, J = 8.2 Hz, 1H), 7.14 (d, J = 5.0 Hz, 1H), 7.08-6.98 (m, 2H), 6.93 (d, J = 8.4 Hz, 1H), 4.47 (dd, J = 48.9, 9.0 Hz, 1H), 4.11 (q, J = 7.0 Hz, 2H), 3.98 (dd, J = 36.1, 14.5 Hz, 1H), 3.60-3.44 (m, 1H), 1.44 (t, J = 7.0 Hz, 3H), 1.31 (d, J = 1.7 Hz, 6H). |
| 837 | 1H NMR (400 MHz, Methanol-d4) δ 8.79-8.63 (m, 2H), 8.49 (d, J = 2.2 Hz, 1H), 8.31 (s, 1H), 7.77 (d, J = 5.0 Hz, 1H), 7.46 (t, J = 8.1 Hz, 1H), 7.15 (d, J = 5.1 Hz, 1H), 7.08-6.77 (m, 3H), 4.69 (p, J = 6.0 Hz, 1H), 4.58-4.29 (m, 1H), 3.99 (dd, J = 36.3, 14.5 Hz, 1H), 3.58-3.41 (m, 1H), 1.36 (d, J = 6.0 Hz, 6H), 1.31 (d, J = 1.7 Hz, 6H). |
| 838 | 1H NMR (400 MHz, Methanol-d4) δ 8.81-8.65 (m, 2H), 8.49 (d, J = 2.1 Hz, 1H), 8.09 (s, 1H), 7.73 (d, J = 5.1 Hz, 1H), 7.52 (t, J = 7.8 Hz, 1H), 7.32 (dd, J = 8.1, 1.9 Hz, 1H), 7.29-7.22 (m, 2H), 7.16 (d, J = 5.1 Hz, 1H), 4.59-4.35 (m, 1H), 4.12-3.87 (m, 1H), 3.53 (td, J = 15.3, 9.3 Hz, 1H), 2.59 (d, J = 7.2 Hz, 2H), 2.05-1.82 (m, 1H), 1.31 (d, J = 1.7 Hz, 6H), 0.94 (d, J = 6.6 Hz, 6H). |
| 839 | 1H NMR (400 MHz, Methanol-d4) δ 8.73 (s, 1H), 8.68 (d, J = 2.2 Hz, 1H), 8.50 (d, J = 2.2 Hz, 1H), 8.32 (s, 1H), 8.12 (d, J = 2.2 Hz, 1H), 8.03 (d, J = 7.3 Hz, 1H), 7.79 (d, J = 5.1 Hz, 1H), 7.75-7.61 (m, 2H), 7.15 (d, J = 5.1 Hz, 1H), 4.48 (dd, J = 49.5, 8.9 Hz, 1H), 4.00 (dd, J = 36.5, 14.6 Hz, 1H), 3.54 (td, J = 15.7, 9.5 Hz, 1H), 3.14 (q, J = 7.2 Hz, 2H), 1.31 (d, J = 1.6 Hz, 6H), 1.23 (t, J = 7.2 Hz, 3H). |
| 840 | 1H NMR (400 MHz, Methanol-d4) δ 9.44 (s, 1H), 8.76 (s, 1H), 8.72 (s, 1H), 8.67 (s, 1H), 8.23 (s, 1H), 8.21 (s, 1H), 7.89 (d, J = 5.1 Hz, 1H), 7.19 (d, J = 5.0 Hz, 1H), 4.64-4.29 (m, 1H), 4.03 (s, 4H), 3.55 (td, J = 15.5, 9.3 Hz, 1H), 1.32 (s, 6H). |
| 841 | 1H NMR (400 MHz, Methanol-d4) δ 9.43 (s, 1H), 8.74 (s, 1H), 8.71 (s, 1H), 8.65 (d, J = 2.1 Hz, 1H), 8.18 (s, 1H), 8.16 (s, 1H), 7.88 (d, J = 5.1 Hz, 1H), 7.17 (d, J = 5.1 Hz, 1H), 4.61-4.34 (m, 3H), 4.00 (dd, J = 36.2, 14.5 Hz, 1H), 3.55 (td, J = 15.4, 9.2 Hz, 1H), 1.44 (t, J = 7.1 Hz, 3H), 1.32 (s, 6H). |
| 842 | 1H NMR (400 MHz, Methanol-d4) δ 9.53 (s, 1H), 8.84 (s, 1H), 8.75 (d, J = 2.1 Hz, 1H), 8.65 (d, J = 2.1 Hz, 1H), 8.11 (s, 1H), 8.03 (s, 1H), 7.89 (d, J = 5.0 Hz, 1H), 7.21 (d, J = 5.0 Hz, 1H), 4.60-4.32 (m, 1H), 4.16-3.80 (m, 4H), 3.57 (td, J = 15.4, 9.3 Hz, 1H), 1.32 (s, 6H). |

TABLE 2-continued

| compound | 1H-NMR |
|---|---|
| 843 | 1H NMR (400 MHz, Methanol-d4) δ 9.86 (s, 1H), 8.98 (s, 1H), 8.66 (d, J = 2.2 Hz, 1H), 8.55 (d, J = 2.2 Hz, 1H), 8.47 (d, J = 6.8 Hz, 1H), 7.96 (d, J = 4.9 Hz, 1H), 7.25-7.05 (m, 2H), 4.65-4.24 (m, 1H), 3.94 (dd, J = 36.1, 14.5 Hz, 1H), 3.56 (td, J = 15.3, 9.2 Hz, 1H), 2.98 (t, J = 7.7 Hz, 2H), 2.12-1.66 (m, 2H), 1.30 (s, 6H), 1.00 (t, J = 7.4 Hz, 3H). |
| 844 | 1H NMR (400 MHz, Methanol-d4) δ 9.89 (s, 1H), 8.90 (s, 1H), 8.68 (d, J = 2.2 Hz, 1H), 8.60 (d, J = 2.3 Hz, 1H), 8.35 (d, J = 6.0 Hz, 1H), 7.94 (d, J = 5.0 Hz, 1H), 7.17 (d, J = 5.0 Hz, 1H), 6.83 (d, J = 6.1 Hz, 1H), 4.46 (dd, J = 49.0, 9.3 Hz, 1H), 4.11 (s, 3H), 3.97 (dd, J = 36.3, 14.7 Hz, 1H), 3.66-3.46 (m, 1H), 1.31 (s, 6H). |
| 845 | 1H NMR (400 MHz, Methanol-d4) δ 9.52 (s, 1H), 8.83 (s, 1H), 8.74 (d, J = 2.0 Hz, 1H), 8.64 (d, J = 1.7 Hz, 1H), 8.08 (s, 1H), 7.97 (d, J = 1.4 Hz, 1H), 7.87 (d, J = 5.0 Hz, 1H), 7.21 (d, J = 5.0 Hz, 1H), 4.63-4.35 (m, 3H), 4.00 (dd, J = 36.2, 15.0 Hz, 1H), 3.71-3.43 (m, 1H), 1.41 (t, J = 7.1 Hz, 3H), 1.32 (s, 6H). |
| 846 | 1H NMR (400 MHz, Methanol-d4) δ 10.05 (s, 1H), 8.81 (s, 1H), 8.73-8.61 (m, 3H), 7.93 (d, J = 5.0 Hz, 1H), 7.19 (d, J = 5.1 Hz, 1H), 6.57 (s, 1H), 4.62-4.29 (m, 1H), 4.14-3.82 (m, 4H), 3.70-3.44 (m, 1H), 1.31 (s, 6H). |
| 847 | 1H NMR (400 MHz, Methanol-d4) δ 8.87 (s, 1H), 8.84 (s, 1H), 8.67 (d, J = 2.2 Hz, 1H), 8.57 (d, J = 2.2 Hz, 1H), 8.16 (d, J = 6.5 Hz, 1H), 7.93 (d, J = 4.9 Hz, 1H), 7.16 (d, J = 4.4 Hz, 2H), 6.99 (d, J = 1.8 Hz, 1H), 4.53-4.31 (m, 3H), 3.95 (dd, J = 36.2, 14.6 Hz, 1H), 3.53 (td, J = 15.3, 9.4 Hz, 1H), 1.49 (t, J = 7.0 Hz, 3H), 1.29 (s, 6H). |
| 848 | 1H NMR (400 MHz, Methanol-d4) δ 9.88 (s, 1H), 8.89 (s, 1H), 8.67 (d, J = 2.2 Hz, 1H), 8.59 (d, J = 2.1 Hz, 1H), 8.32 (d, J = 6.2 Hz, 1H), 7.91 (d, J = 5.0 Hz, 1H), 7.17 (d, J = 4.9 Hz, 1H), 6.80 (d, J = 6.1 Hz, 1H), 4.61-4.30 (m, 3H), 3.96 (dd, J = 36.2, 14.5 Hz, 1H), 3.55 (td, J = 15.3, 9.3 Hz, 1H), 1.41 (t, J = 7.1 Hz, 3H), 1.31 (s, 5H). |
| 849 | 1H NMR (400 MHz, Methanol-d4) δ 8.77 (s, 1H), 8.72 (d, J = 2.2 Hz, 1H), 8.56 (d, J = 2.2 Hz, 1H), 8.36 (d, J = 2.0 Hz, 1H), 8.33 (d, J = 2.5 Hz, 1H), 8.27 (s, 1H), 7.85 (d, J = 5.1 Hz, 1H), 7.65 (d, J = 2.4 Hz, 1H), 7.18 (d, J = 5.0 Hz, 1H), 4.62-4.35 (m, 1H), 4.12 (t, J = 6.5 Hz, 2H), 4.00 (dd, J = 36.6, 14.3 Hz, 1H), 3.54 (td, J = 15.5, 9.6 Hz, 1H), 1.88 (h, J = 7.0 Hz, 2H), 1.31 (d, J = 1.7 Hz, 6H), 1.09 (t, J = 7.4 Hz, 3H). |
| 850 | 1H NMR (400 MHz, Methanol-d4) δ 8.77-8.66 (m, 2H), 8.58 (d, J = 2.1 Hz, 1H), 8.05 (s, 1H), 7.90 (d, J = 2.3 Hz, 1H), 7.83 (d, J = 5.1 Hz, 1H), 7.49 (d, J = 2.4 Hz, 1H), 7.17 (d, J = 5.1 Hz, 1H), 4.60-4.31 (m, 5H), 3.99 (dd, J = 36.4, 14.5 Hz, 1H), 3.53 (td, J = 15.2, 9.2 Hz, 1H), 1.30 (s, 6H). |
| 851 | 1H NMR (400 MHz, Methanol-d4) δ 8.76 (s, 1H), 8.72 (d, J = 2.2 Hz, 1H), 8.56 (d, J = 2.2 Hz, 1H), 8.34 (d, J = 2.1 Hz, 1H), 8.30 (d, J = 2.5 Hz, 1H), 8.25 (s, 1H), 7.85 (d, J = 5.0 Hz, 1H), 7.62 (d, J = 2.9 Hz, 1H), 7.18 (d, J = 5.0 Hz, 1H), 4.82-4.71 (m, 1H), 4.58-4.35 (m, 1H), 4.00 (dd, J = 36.4, 14.6 Hz, 1H), 3.54 (td, J = 16.5, 15.9, 10.0 Hz, 1H), 1.40 (d, J = 6.0 Hz, 6H), 1.31 (s, 6H). |
| 852 | 1H NMR (400 MHz, Methanol-d4) δ 8.78 (s, 1H), 8.72 (d, J = 2.2 Hz, 1H), 8.56 (d, J = 2.1 Hz, 1H), 8.42 (d, J = 2.0 Hz, 1H), 8.40 (d, J = 2.6 Hz, 1H), 8.27 (s, 1H), 7.86 (d, J = 5.1 Hz, 1H), 7.73 (d, J = 2.4 Hz, 1H), 7.18 (d, J = 5.0 Hz, 1H), 6.65-5.80 (m, 1H), 4.57-4.39 (m, 3H), 4.00 (dd, J = 36.5, 14.6 Hz, 1H), 3.55 (td, J = 15.5, 9.4 Hz, 1H), 1.31 (s, 6H). |
| 853 | 1H NMR (400 MHz, Methanol-d4) δ 8.74-8.66 (m, 2H), 8.51 (d, J = 2.2 Hz, 1H), 7.95 (s, 1H), 7.83 (d, J = 2.2 Hz, 1H), 7.81 (d, J = 5.1 Hz, 1H), 7.35 (d, J = 2.2 Hz, 1H), 7.16 (d, J = 5.1 Hz, 1H), 4.60-4.36 (m, 1H), 4.03 (s, 4H), 3.89 (s, 3H), 3.53 (td, J = 15.6, 9.5 Hz, 1H), 1.31 (d, J = 1.8 Hz, 6H). |
| 854 | 1H NMR (400 MHz, Methanol-d4) δ 8.71 (d, J = 2.2 Hz, 1H), 8.63 (s, 1H), 8.53 (d, J = 2.2 Hz, 1H), 8.06 (s, 1H), 7.73 (d, J = 5.0 Hz, 1H), 7.16 (d, J = 5.0 Hz, 1H), 6.96-6.76 (m, 3H), 4.46 (dd, J = 48.9, 9.3 Hz, 1H), 4.34 (t, J = 4.3 Hz, 2H), 3.98 (dd, J = 36.5, 14.6 Hz, 1H), 3.52 (td, J = 15.3, 9.2 Hz, 1H), 3.35 (t, J = 4.5 Hz, 2H), 2.96 (s, 3H), 1.30 (s, 6H). |
| 855 | 1H NMR (400 MHz, Methanol-d4) δ 8.78-8.66 (m, 2H), 8.56 (s, 1H), 7.99 (s, 1H), 7.84 (d, J = 5.0 Hz, 1H), 7.73 (d, J = 2.3 Hz, 1H), 7.33 (d, J = 2.2 Hz, 1H), 7.17 (d, J = 5.0 Hz, 1H), 4.46 (dd, J = 49.1, 9.2 Hz, 1H), 4.33 (t, J = 4.4 Hz, 2H), 3.98 (dd, J = 36.4, 14.6 Hz, 1H), 3.66 (t, J = 4.5 Hz, 2H), 3.58-3.44 (m, 1H), 1.30 (d, J = 1.8 Hz, 6H). |
| 856 | 1H NMR (400 MHz, Methanol-d4) δ 8.72 (d, J = 2.2 Hz, 1H), 8.69 (s, 1H), 8.55 (d, J = 2.2 Hz, 1H), 7.96 (s, 1H), 7.82 (d, J = 5.0 Hz, 1H), 7.78 (d, J = 2.3 Hz, 1H), 7.22 (d, J = 2.3 Hz, 1H), 7.17 (d, J = 5.0 Hz, 1H), 4.47 (dd, J = 49.2, 9.4 Hz, 1H), 4.37-4.25 (m, 2H), 3.98 (dd, J = 36.5, 14.7 Hz, 1H), 3.72-3.61 (m, 2H), 3.53 (td, J = 15.3, 9.3 Hz, 1H), 3.23 (s, 3H), 1.30 (s, 6H). |
| 857 | 1H NMR (400 MHz, Methanol-d4) δ 8.78 (s, 1H), 8.73 (d, J = 2.2 Hz, 1H), 8.56 (d, J = 2.2 Hz, 1H), 8.47 (d, J = 2.1 Hz, 1H), 8.43 (d, J = 2.6 Hz, 1H), 8.25 (s, 1H), 7.86 (d, J = 5.0 Hz, 1H), 7.75 (d, J = 2.5 Hz, 1H), 7.18 (d, J = 5.0 Hz, 1H), 4.79 (q, J = 8.4 Hz, 2H), 4.57-4.36 (m, 1H), 4.00 (dd, J = 36.5, 14.5 Hz, 1H), 3.55 (td, J = 15.4, 9.4 Hz, 1H), 1.31 (d, J = 1.8 Hz, 6H). |
| 858 | 1H NMR (400 MHz, Methanol-d4) δ 8.80-8.66 (m, 2H), 8.57 (d, J = 2.2 Hz, 1H), 8.05 (s, 1H), 7.89 (d, J = 2.4 Hz, 1H), 7.82 (d, J = 5.1 Hz, 1H), 7.48 (d, J = 2.4 Hz, 1H), 7.17 (d, J = 5.0 Hz, 1H), 4.62-4.52 (m, 2H), 4.39 (t, J = 3.9 Hz, 2H), 4.05-3.84 (m, 1H), 3.76-3.62 (m, 1H), 2.17-1.91 (m, 4H), 1.64-1.30 (m, 5H), 0.92-0.80 (m, 2H), 0.77-0.66 (m, 2H). |
| 859 | 1H NMR (400 MHz, Methanol-d4) δ 8.70 (d, J = 2.2 Hz, 1H), 8.60 (s, 1H), 8.52 (d, J = 2.1 Hz, 1H), 8.06 (s, 1H), 7.73 (d, J = 5.0 Hz, 1H), 7.15 (d, J = 5.0 Hz, 1H), 6.94-6.74 (m, 3H), 4.34 (t, J = 4.3 Hz, 2H), 4.00-3.83 (m, 1H), 3.69 (t, J = 11.7 |

TABLE 2-continued

| compound | 1H-NMR |
|---|---|
| | Hz, 1H), 3.42-3.31 (m, 2H), 2.96 (s, 3H), 2.05 (dd, J = 35.2, 12.4 Hz, 4H), 1.74 (p, J = 6.3 Hz, 1H), 1.68-1.32 (m, 4H), 0.87-0.81 (m, 2H), 0.76-0.71 (m, 2H). |
| 860 | 1H NMR (400 MHz, Methanol-d4) δ 8.70 (d, J = 2.2 Hz, 1H), 8.61 (s, 1H), 8.52 (d, J = 2.1 Hz, 1H), 8.06 (s, 1H), 7.73 (d, J = 5.0 Hz, 1H), 7.15 (d, J = 5.0 Hz, 1H), 6.93-6.72 (m, 3H), 4.34 (t, J = 4.3 Hz, 2H), 3.97-3.84 (m, 1H), 3.70-3.54 (m, 5H), 3.47-3.33 (m, 6H), 2.96 (s, 3H), 2.05 (dd, J = 34.3, 12.0 Hz, 4H), 1.48 (dp, J = 25.2, 12.7 Hz, 4H). |
| 861 | 1H NMR (400 MHz, Methanol-d4) δ 8.75-8.63 (m, 2H), 8.57 (d, J = 2.2 Hz, 1H), 8.05 (s, 1H), 7.89 (d, J = 2.4 Hz, 1H), 7.82 (d, J = 5.0 Hz, 1H), 7.48 (d, J = 2.4 Hz, 1H), 7.17 (d, J = 5.0 Hz, 1H), 4.55 (t, J = 4.0 Hz, 2H), 4.38 (t, J = 4.0 Hz, 2H), 3.93 (s, 1H), 3.72-3.52 (m, 5H), 3.37 (t, J = 4.8 Hz, 4H), 2.18-1.93 (m, 4H), 1.62-1.35 (m, 4H). |
| 862 | 1H NMR (400 MHz, Methanol-d4) δ 8.76 (s, 1H), 8.72 (d, J = 2.2 Hz, 1H), 8.64-8.52 (m, 2H), 8.13 (s, 1H), 7.85 (d, J = 5.0 Hz, 1H), 7.76 (d, J = 2.4 Hz, 1H), 7.17 (d, J = 5.0 Hz, 1H), 4.47 (dd, J = 49.2, 9.2 Hz, 1H), 4.15 (t, J = 5.8 Hz, 2H), 3.99 (dd, J = 36.5, 14.6 Hz, 1H), 3.54 (td, J = 15.6, 9.5 Hz, 1H), 3.09 (t, J = 5.9 Hz, 2H), 1.30 (d, J = 1.8 Hz, 6H). Two protons hiding under solvent peaks. |
| 863 | 1H NMR (400 MHz, Methanol-d4) δ 8.74 (s, 1H), 8.71 (d, J = 2.2 Hz, 1H), 8.52 (d, J = 2.2 Hz, 1H), 8.24 (s, 1H), 7.80 (d, J = 5.1 Hz, 1H), 7.64 (d, J = 8.4 Hz, 1H), 7.53 (d, J = 7.2 Hz, 2H), 7.16 (d, J = 5.0 Hz, 1H), 4.71 (s, 4H), 4.46 (ddd, J = 48.9, 9.4, 2.1 Hz, 1H), 4.11-3.85 (m, 1H), 3.63-3.45 (m, 1H), 1.30 (d, J = 1.6 Hz, 6H). |
| 864 | 1H NMR (400 MHz, Methanol-d4) δ 8.75 (s, 1H), 8.72 (d, J = 2.2 Hz, 1H), 8.55 (d, J = 2.2 Hz, 1H), 8.20 (s, 1H), 7.81 (d, J = 5.1 Hz, 1H), 7.64 (d, J = 8.2 Hz, 1H), 7.61-7.51 (m, 2H), 7.17 (d, J = 5.1 Hz, 1H), 5.02 (dd, J = 8.4, 6.7 Hz, 2H), 4.83-4.78 (m, 6H), 4.72 (d, J = 5.7 Hz, 1H), 4.46 (ddd, J = 49.1, 9.3, 2.1 Hz, 1H), 3.97 (ddd, J = 36.5, 14.6, 2.1 Hz, 1H), 3.54 (ddd, J = 16.1, 14.5, 9.4 Hz, 1H), 1.30 (d, J = 1.6 Hz, 6H). |
| 865 | 1H NMR (400 MHz, Methanol-d4) δ 8.71 (d, J = 2.5 Hz, 2H), 8.53 (d, J = 2.2 Hz, 1H), 8.21 (s, 1H), 8.14 (s, 1H), 7.89 (s, 1H), 7.83 (d, J = 5.0 Hz, 1H), 7.18 (d, J = 5.1 Hz, 1H), 5.55 (t, J = 8.5 Hz, 1H), 4.46 (dd, J = 49.0, 9.2 Hz, 1H), 4.33-4.06 (m, 2H), 4.05-3.84 (m, 3H), 3.53 (td, J = 15.6, 9.5 Hz, 1H), 1.29 (d, J = 1.6 Hz, 6H). |
| 866 | 1H NMR (400 MHz, Methanol-d4) δ 8.69 (d, J = 2.2 Hz, 1H), 8.65 (s, 1H), 8.57 (d, J = 2.1 Hz, 1H), 8.24 (s, 1H), 7.79 (d, J = 5.1 Hz, 1H), 7.49-7.34 (m, 4H), 7.15 (d, J = 5.1 Hz, 1H), 4.01-3.82 (m, 1H), 3.69 (s, 3H), 2.09 (d, J = 12.2 Hz, 2H), 2.00 (d, J = 12.5 Hz, 2H), 1.65-1.33 (m, 4H), 1.31 (s, 5H), 0.83 (q, J = 3.5 Hz, 2H), 0.74 (dt, J = 8.1, 3.2 Hz, 2H). |
| 867 | 1H NMR (400 MHz, Methanol-d4) δ 8.62 (d, J = 2.2 Hz, 1H), 8.55 (s, 1H), 8.53 (d, J = 2.2 Hz, 1H), 8.05 (s, 1H), 7.80 (d, J = 4.9 Hz, 1H), 7.05 (d, J = 4.9 Hz, 1H), 4.43 (ddd, J = 48.9, 9.1, 2.3 Hz, 1H), 4.19 (t, J = 7.3 Hz, 1H), 3.88 (ddd, J = 35.6, 14.5, 2.3 Hz, 1H), 3.48 (ddd, J = 16.3, 14.4, 9.0 Hz, 1H), 3.34 (d, J = 7.5 Hz, 2H), 2.50 (s, 1H), 2.40 (d, J = 9.1 Hz, 2H), 2.13 (q, J = 9.3 Hz, 2H), 1.29 (d, J = 1.6 Hz, 6H). |
| 868 | 1H NMR (400 MHz, Methanol-d4) δ 8.78-8.65 (m, 2H), 8.51 (d, J = 2.2 Hz, 1H), 8.20 (s, 1H), 8.18 (s, 1H), 7.88 (s, 1H), 7.82 (d, J = 5.0 Hz, 1H), 7.17 (d, J = 5.0 Hz, 1H), 5.54 (t, J = 8.1 Hz, 1H), 4.58-4.39 (m, 1H), 4.27 (d, J = 13.6 Hz, 1H), 4.11 (dd, J = 13.5, 7.1 Hz, 1H), 4.05-3.84 (m, 4H), 3.62-3.42 (m, 1H), 1.29 (d, J = 1.6 Hz, 7H). |
| 869 | 1H NMR (400 MHz, Methanol-d4) δ 8.71 (d, J = 2.2 Hz, 2H), 8.51 (d, J = 2.2 Hz, 1H), 8.20 (s, 1H), 8.17 (s, 1H), 7.89 (s, 1H), 7.83 (d, J = 5.0 Hz, 1H), 7.17 (d, J = 5.0 Hz, 1H), 5.54 (t, J = 8.5 Hz, 1H), 4.46 (ddd, J = 49.2, 9.2, 2.1 Hz, 1H), 4.34-4.23 (m, 1H), 4.12 (dd, J = 13.4, 7.0 Hz, 1H), 4.07-3.84 (m, 3H), 3.64-3.33 (m, 1H), 1.29 (d, J = 1.6 Hz, 6H). |
| 870 | 1H NMR (400 MHz, Methanol-d4) δ 8.70 (d, J = 2.2 Hz, 1H), 8.69 (s, 1H), 8.56 (d, J = 2.2 Hz, 1H), 8.21 (d, J = 2.6 Hz, 1H), 7.92 (s, 1H), 7.80 (d, J = 5.1 Hz, 1H), 7.75 (dd, J = 9.2, 2.7 Hz, 1H), 7.15 (d, J = 5.1 Hz, 1H), 7.11 (d, J = 9.2 Hz, 1H), 4.46 (ddd, J = 49.1, 9.4, 2.0 Hz, 1H), 3.97 (ddd, J = 36.6, 14.4, 2.1 Hz, 1H), 3.74 (s, 3H), 3.73-3.59 (m, 9H), 3.59-3.41 (m, 1H), 1.29 (d, J = 1.6 Hz, 6H). |
| 871 | 1H NMR (400 MHz, Methanol-d4) δ 8.71 (d, J = 2.7 Hz, 2H), 8.53 (d, J = 2.2 Hz, 1H), 8.29 (d, J = 2.7 Hz, 1H), 7.96 (s, 1H), 7.83-7.72 (m, 2H), 7.19-7.11 (m, 2H), 4.91 (d, J = 7.6 Hz, 4H), 4.56-4.37 (m, 2H), 4.06-3.88 (m, 5H), 3.60-3.45 (m, 1H), 3.35 (s, 4H), 1.29 (d, J = 1.7 Hz, 6H). |
| 872 | 1H NMR (400 MHz, Methanol-d4) δ 8.75 (s, 1H), 8.70 (d, J = 2.2 Hz, 1H), 8.53 (d, J = 2.2 Hz, 1H), 8.33 (s, 1H), 7.81 (d, J = 5.0 Hz, 1H), 7.72 (d, J = 8.0 Hz, 2H), 7.64-7.56 (m, 2H), 7.16 (d, J = 5.0 Hz, 1H), 6.55-6.14 (m, 1H), 4.59-4.27 (m, 3H), 4.07-3.76 (m, 1H), 3.68-3.44 (m, 3H), 1.30 (d, J = 1.6 Hz, 6H). |
| 873 | 1H NMR (400 MHz, Methanol-d4) δ 8.63 (d, J = 2.2 Hz, 1H), 8.56 (s, 1H), 8.54 (d, J = 2.2 Hz, 1H), 8.04 (s, 1H), 7.81 (d, J = 4.9 Hz, 1H), 7.06 (d, J = 4.9 Hz, 1H), 4.92 (d, J = 6.0 Hz, 2H), 4.56-4.30 (m, 3H), 4.23 (t, J = 7.3 Hz, 1H), 3.88 (ddd, J = 35.5, 14.5, 2.3 Hz, 1H), 3.60-3.40 (m, 3H), 2.56 (d, J = 7.3 Hz, 1H), 2.42 (ddd, J = 12.1, 7.5, 3.7 Hz, 2H), 2.16 (q, J = 9.5 Hz, 2H), 1.61 (s, 3H), 1.29 (d, J = 1.6 Hz, 6H). |
| 874 | 1H NMR (400 MHz, Methanol-d4) δ 8.69-8.67 (m, 2H), 8.55 (d, J = 2.2 Hz, 1H), 8.22 (s, 1H), 7.80 (d, J = 5.1 Hz, 1H), 7.69-7.61 (m, 2H), 7.47-7.38 (m, 2H), 7.14 (d, J = 5.1 Hz, 1H), 4.53 (dd, J = 9.3, 2.1 Hz, 1H), 4.47-4.32 (m, 3H), 4.11-3.96 (m, 1H), 3.92 (dd, J = 8.8, 7.1 Hz, 3H), 3.64-3.44 (m, 1H), 1.76 (s, 6H), 1.30 (d, J = 1.6 Hz, 6H). |

TABLE 2-continued

| compound | 1H-NMR |
|---|---|
| 875 | 1H NMR (400 MHz, Methanol-d4) δ 8.73-8.65 (m, 2H), 8.58 (d, J = 2.2 Hz, 1H), 8.23 (s, 1H), 7.82 (d, J = 5.1 Hz, 1H), 7.55 (d, J = 8.6 Hz, 2H), 7.38 (d, J = 8.6 Hz, 2H), 7.14 (d, J = 5.1 Hz, 1H), 4.47 (ddd, J = 49.0, 9.3, 2.1 Hz, 1H), 4.08-3.87 (m, 1H), 3.80 (t, J = 7.0 Hz, 2H), 3.53 (ddd, J = 16.1, 14.5, 9.4 Hz, 1H), 2.41 (t, J = 8.1 Hz, 2H), 2.20-2.06 (m, 2H), 1.74 (s, 6H), 1.30 (d, J = 1.6 Hz, 6H). |
| 876 | 1H NMR (400 MHz, Methanol-d4) δ 8.72-8.66 (m, 2H), 8.54 (d, J = 2.1 Hz, 1H), 8.15 (s, 1H), 7.78 (d, J = 5.1 Hz, 1H), 7.47 (q, J = 8.7 Hz, 4H), 7.15 (d, J = 5.1 Hz, 1H), 4.67-4.26 (m, 3H), 3.98 (ddd, J = 36.5, 14.5, 2.1 Hz, 1H), 3.84-3.66 (m, 2H), 3.52 (ddd, J = 16.1, 14.6, 9.4 Hz, 1H), 1.59-1.48 (m, 2H), 1.44-1.32 (m, 2H), 1.30 (d, J = 1.6 Hz, 6H). |
| 877 | 1H NMR (400 MHz, Methanol-d4) δ 8.79 (s, 1H), 8.75 (d, J = 2.1 Hz, 1H), 8.65 (d, J = 2.1 Hz, 1H), 8.15 (d, J = 2.4 Hz, 1H), 8.07 (dd, J = 9.7, 2.5 Hz, 1H), 7.96 (s, 1H), 7.93 (d, J = 5.1 Hz, 1H), 7.28 (d, J = 9.6 Hz, 1H), 7.19 (d, J = 5.0 Hz, 1H), 4.49 (ddd, J = 49.1, 9.4, 2.0 Hz, 1H), 4.00 (ddd, J = 36.5, 14.6, 2.1 Hz, 1H), 3.77-3.64 (m, 5H), 3.65-3.46 (m, 1H), 2.36-2.18 (m, 4H), 1.32 (d, J = 1.6 Hz, 6H). |
| 878 | 1H NMR (400 MHz, Methanol-d4) δ 8.77 (s, 1H), 8.72 (s, 2H), 8.23 (d, J = 2.4 Hz, 1H), 8.16 (s, 1H), 8.03 (d, J = 9.5 Hz, 1H), 7.87 (d, J = 5.0 Hz, 1H), 7.42 (d, J = 9.6 Hz, 1H), 7.19 (d, J = 5.0 Hz, 1H), 4.49 (dd, J = 49.0, 8.9 Hz, 1H), 4.25 (s, 1H), 4.09-3.88 (m, 1H), 3.76 (t, J = 8.3 Hz, 1H), 3.67-3.45 (m, 3H), 3.28-3.06 (m, 1H), 2.20 (d, J = 18.7 Hz, 3H), 2.08 (s, 4H), 1.33 (d, J = 1.6 Hz, 6H). |
| 879 | 1H NMR (400 MHz, Methanol-d4) δ 8.82-8.71 (m, 2H), 8.68 (d, J = 2.2 Hz, 1H), 8.18 (d, J = 2.5 Hz, 1H), 8.09 (s, 1H), 8.01 (d, J = 9.2 Hz, 1H), 7.88 (d, J = 5.0 Hz, 1H), 7.41 (d, J = 9.5 Hz, 1H), 7.19 (d, J = 5.0 Hz, 1H), 4.50 (dd, J = 49.3, 9.2 Hz, 1H), 4.28 (s, 1H), 4.08-3.89 (m, 1H), 3.71 (s, 4H), 3.64-3.38 (m, 3H), 3.17 (dd, J = 15.0, 7.5 Hz, 2H), 2.35-2.07 (m, 5H), 1.33 (d, J = 1.6 Hz, 6H). |
| 880 | 1H NMR (400 MHz, Methanol-d4) δ 8.75-8.67 (m, 2H), 8.59 (d, J = 2.1 Hz, 1H), 8.21 (d, J = 2.6 Hz, 1H), 7.97 (s, 1H), 7.84 (d, J = 5.1 Hz, 1H), 7.76 (dd, J = 9.3, 2.6 Hz, 1H), 7.18 (dd, J = 9.0, 7.1 Hz, 2H), 4.60-4.41 (m, 1H), 4.36 (d, J = 13.3 Hz, 2H), 4.11-3.87 (m, 2H), 3.68-3.46 (m, 1H), 3.19 (t, J = 13.0 Hz, 2H), 2.12-1.99 (m, 2H), 1.98 (s, 3H), 1.58 (q, J = 11.4, 10.7 Hz, 2H), 1.33 (d, J = 1.7 Hz, 6H). |
| 881 | 1H NMR (400 MHz, Methanol-d4) δ 8.75 (d, J = 2.1 Hz, 2H), 8.62 (d, J = 2.1 Hz, 1H), 8.20 (d, J = 2.6 Hz, 1H), 7.96 (s, 1H), 7.92-7.78 (m, 2H), 7.27 (d, J = 9.4 Hz, 1H), 7.19 (d, J = 5.1 Hz, 1H), 4.68-4.38 (m, 1H), 4.32 (d, J = 13.5 Hz, 2H), 4.11-3.91 (m, 1H), 3.84-3.70 (m, 0H), 3.68 (s, 3H), 3.63-3.44 (m, 1H), 3.27 (t, J = 12.8 Hz, 3H), 2.08 (d, J = 12.9 Hz, 2H), 1.61 (d, J = 11.8 Hz, 2H), 1.33 (d, J = 1.6 Hz, 6H). |
| 882 | 1H NMR (400 MHz, Methanol-d4) δ 8.83-8.68 (m, 2H), 8.62 (d, J = 2.1 Hz, 1H), 8.18 (s, 1H), 8.14 (s, 1H), 7.89 (d, J = 5.1 Hz, 1H), 7.86 (s, 1H), 7.20 (d, J = 5.0 Hz, 1H), 5.68-5.39 (m, 2H), 4.61-4.36 (m, 1H), 4.14-3.99 (m, 3H), 3.99-3.73 (m, 2H), 3.56 (td, J = 15.6, 9.4 Hz, 1H), 1.32 (d, J = 1.7 Hz, 6H). |
| 883 | 1H NMR (400 MHz, Methanol-d4) δ 8.83-8.69 (m, 2H), 8.56 (d, J = 2.1 Hz, 1H), 8.19 (s, 1H), 8.16 (s, 1H), 7.86 (d, J = 6.1 Hz, 2H), 7.20 (d, J = 5.1 Hz, 1H), 5.66 (dq, J = 52.4, 3.6 Hz, 1H), 5.55-5.37 (m, 1H), 4.49 (ddd, J = 49.0, 9.4, 2.1 Hz, 1H), 4.19 (dd, J = 12.4, 8.1 Hz, 1H), 4.09-3.91 (m, 2H), 3.91-3.72 (m, 2H), 3.56 (td, J = 15.4, 9.3 Hz, 1H), 1.41-1.24 (m, 6H). |
| 884 | 1H NMR (400 MHz, Methanol-d4) δ 8.77 (s, 1H), 8.75 (d, J = 2.2 Hz, 1H), 8.61 (d, J = 2.1 Hz, 1H), 8.15 (d, J = 2.5 Hz, 1H), 7.99 (d, J = 9.7 Hz, 2H), 7.89 (d, J = 5.1 Hz, 1H), 7.28 (d, J = 9.6 Hz, 1H), 7.19 (d, J = 5.1 Hz, 1H), 4.60-4.37 (m, 2H), 4.08-3.90 (m, 1H), 3.78 (t, J = 9.1 Hz, 1H), 3.69-3.46 (m, 4H), 3.42 (s, 3H), 2.21 (ddd, J = 38.8, 23.0, 8.4 Hz, 4H), 1.33 (d, J = 1.7 Hz, 6H). |
| 885 | 1H NMR (400 MHz, Methanol-d4) δ 8.77 (s, 1H), 8.74 (d, J = 2.2 Hz, 1H), 8.62 (d, J = 2.1 Hz, 1H), 8.13 (d, J = 2.5 Hz, 1H), 7.99 (d, J = 6.1 Hz, 2H), 7.89 (d, J = 5.1 Hz, 1H), 7.22-7.11 (m, 2H), 4.49 (ddd, J = 49.0, 9.4, 2.1 Hz, 1H), 4.00 (ddd, J = 36.5, 14.6, 2.1 Hz, 1H), 3.89-3.74 (m, 2H), 3.74-3.63 (m, 1H), 3.58 (tt, J = 8.8, 4.8 Hz, 2H), 3.49 (dt, J = 10.6, 7.2 Hz, 2H), 3.42 (s, 3H), 2.81 (p, J = 7.1 Hz, 1H), 2.42-2.20 (m, 1H), 2.12-1.93 (m, 1H), 1.33 (d, J = 1.7 Hz, 6H). |
| 886 | 1H NMR (400 MHz, Methanol-d4) δ 8.74 (d, J = 2.1 Hz, 1H), 8.71 (s, 1H), 8.59 (d, J = 2.1 Hz, 1H), 8.25 (s, 1H), 7.94 (s, 1H), 7.82 (d, J = 5.1 Hz, 1H), 7.75 (dd, J = 9.2, 2.7 Hz, 1H), 7.18 (d, J = 5.1 Hz, 1H), 7.10 (d, J = 9.2 Hz, 1H), 4.50 (dd, J = 49.0, 9.2 Hz, 1H), 4.24 (d, J = 12.7 Hz, 1H), 4.16-3.87 (m, 3H), 3.78-3.61 (m, 2H), 3.61-3.39 (m, 2H), 3.21-2.97 (m, 1H), 2.81 (dd, J = 12.8, 10.5 Hz, 1H), 2.01 (s, 3H), 1.33 (s, 6H). |
| 887 | 1H NMR (400 MHz, Methanol-d4) δ 8.74 (d, J = 2.2 Hz, 1H), 8.70 (s, 1H), 8.59 (d, J = 2.1 Hz, 1H), 8.25 (d, J = 2.6 Hz, 1H), 7.94 (s, 1H), 7.81 (d, J = 5.1 Hz, 1H), 7.72 (dd, J = 9.0, 2.7 Hz, 1H), 7.18 (d, J = 5.1 Hz, 1H), 7.06 (d, J = 9.1 Hz, 1H), 4.49 (dd, J = 49.0, 9.2 Hz, 1H), 4.25 (d, J = 12.7 Hz, 1H), 4.17-3.87 (m, 3H), 3.70 (d, J = 16.5 Hz, 5H), 3.55 (td, J = 14.8, 14.2, 8.7 Hz, 1H), 3.18-2.95 (m, 1H), 2.78 (t, J = 11.6 Hz, 1H), 1.33 (s, 6H). |
| 888 | 1H NMR (400 MHz, Methanol-d4) δ 8.74 (s, 1H), 8.58 (d, J = 2.1 Hz, 1H), 8.40 (s, 1H), 8.13 (d, J = 8.8 Hz, 1H), 8.07 (s, 1H), 7.91 (d, J = 9.0 Hz, 1H), 7.84 (d, J = 5.1 Hz, 1H), 7.19 (d, J = 5.1 Hz, 1H), 4.50 (dd, J = 48.9, 9.3 Hz, 1H), 4.12-3.89 (m, 1H), 3.83 (d, J = 10.7 Hz, 2H), 3.61-3.43 (m, 1H), 1.32 (d, J = 9.6 Hz, 6H). |

TABLE 2-continued

| compound | 1H-NMR |
|---|---|
| 889 | 1H NMR (400 MHz, Methanol-d4) δ 8.78 (d, J = 2.3 Hz, 1H), 8.70 (d, J = 2.2 Hz, 1H), 8.57 (s, 1H), 8.09 (d, J = 5.1 Hz, 1H), 7.91 (s, 1H), 7.24 (d, J = 5.0 Hz, 1H), 4.72 (s, 1H), 4.47 (dd, J = 49.2, 9.3 Hz, 1H), 4.18 (t, J = 7.9 Hz, 2H), 4.05 (dd, J = 14.5, 4.9 Hz, 2H), 4.00-3.72 (m, 1H), 3.54 (dd, J = 15.5, 9.7 Hz, 1H), 2.54 (dd, J = 11.7, 7.4 Hz, 1H), 2.27 (q, J = 10.6, 8.9 Hz, 1H), 1.86 (s, 3H), 1.32 (d, J = 1.7 Hz, 6H). |
| 890 | 1H NMR (400 MHz, Methanol-d4) δ 8.78 (d, J = 2.2 Hz, 1H), 8.70 (d, J = 2.2 Hz, 1H), 8.59 (s, 1H), 8.06 (s, 1H), 7.90 (s, 1H), 7.24 (d, J = 5.1 Hz, 1H), 4.68 (s, 1H), 4.56-4.31 (m, 1H), 4.16-3.73 (m, 5H), 3.64 (s, 3H), 3.59-3.44 (m, 1H), 2.49 (s, 1H), 2.24 (s, 1H), 1.32 (d, J = 1.7 Hz, 6H). |
| 891 | 1H NMR (400 MHz, Methanol-d4) δ 8.78 (d, J = 2.2 Hz, 1H), 8.69 (d, J = 2.2 Hz, 1H), 8.59 (s, 1H), 8.03 (d, J = 5.0 Hz, 1H), 7.87 (s, 1H), 7.24 (d, J = 5.0 Hz, 1H), 4.56-4.28 (m, 1H), 4.09-3.80 (m, 2H), 3.70-3.57 (m, 3H), 3.57-3.36 (m, 1H), 3.27-3.03 (m, 1H), 2.22 (q, J = 7.9 Hz, 2H), 1.32 (d, J = 1.8 Hz, 6H). |
| 892 | 1H NMR (400 MHz, Methanol-d4) δ 9.02 (s, 0H), 8.78 (d, J = 2.3 Hz, 1H), 8.70 (d, J = 2.1 Hz, 1H), 8.56 (s, 1H), 8.09 (d, J = 5.1 Hz, 1H), 7.90 (s, 1H), 7.24 (d, J = 4.9 Hz, 1H), 4.73 (d, J = 8.3 Hz, 1H), 4.49 (dd, J = 48.7, 9.6 Hz, 1H), 4.17 (t, J = 7.9 Hz, 2H), 4.05 (dd, J = 14.2, 4.7 Hz, 1H), 4.00-3.72 (m, 1H), 3.62-3.42 (m, 1H), 2.54 (t, J = 9.6 Hz, 1H), 2.27 (d, J = 9.2 Hz, 1H), 1.85 (s, 3H), 1.32 (d, J = 6H). |
| 893 | 1H NMR (400 MHz, Methanol-d4) δ 9.03 (s, 0H), 8.78 (d, J = 2.2 Hz, 1H), 8.69 (d, J = 2.2 Hz, 1H), 8.59 (s, 1H), 8.05 (d, J = 5.0 Hz, 1H), 7.89 (s, 1H), 7.24 (d, J = 5.0 Hz, 1H), 4.68 (s, 1H), 4.61-4.33 (m, 1H), 4.14-3.74 (m, 4H), 3.63 (s, 3H), 3.54 (dt, J = 15.6, 8.0 Hz, 1H), 2.49 (s, 1H), 2.24 (s, 1H), 1.32 (d, J = 6H). |
| 894 | 1H NMR (400 MHz, Methanol-d4) δ 8.77 (d, J = 2.2 Hz, 1H), 8.68 (d, J = 2.2 Hz, 1H), 8.59 (s, 1H), 8.03 (d, J = 5.0 Hz, 1H), 7.87 (s, 1H), 7.24 (d, J = 5.0 Hz, 1H), 4.47 (ddd, J = 49.1, 9.3, 2.2 Hz, 1H), 4.08-3.84 (m, 2H), 3.68 (d, J = 4.0 Hz, 2H), 3.63 (dt, J = 6.9, 3.4 Hz, 1H), 3.53 (td, J = 15.3, 9.3 Hz, 1H), 3.28-3.02 (m, 1H), 2.23 (q, J = 10.1, 6.5 Hz, 2H), 1.32 (d, J = 1.8 Hz, 6H). |
| 895 | 1H NMR (400 MHz, Methanol-d4) δ 8.78 (d, J = 2.2 Hz, 1H), 8.71 (d, J = 2.2 Hz, 1H), 8.63 (s, 1H), 8.01 (d, J = 5.0 Hz, 1H), 7.76 (s, 1H), 7.24 (d, J = 5.1 Hz, 1H), 4.61-4.45 (m, 0H), 4.45-4.20 (m, 3H), 4.14 (s, 2H), 4.02-3.79 (m, 1H), 3.53 (td, J = 15.2, 9.4 Hz, 1H), 3.07-2.93 (m, 2H), 2.61-2.41 (m, 2H), 1.32 (d, J = 1.8 Hz, 6H). |
| 896 | 1H NMR (400 MHz, Methanol-d4) δ 8.83-8.70 (m, 2H), 8.59 (d, J = 2.2 Hz, 1H), 8.21 (s, 1H), 8.08 (s, 1H), 7.88 (d, J = 5.0 Hz, 1H), 7.84 (s, 1H), 7.20 (d, J = 5.0 Hz, 1H), 5.44-5.28 (m, 1H), 3.99-3.83 (m, 1H), 3.75 (ddd, J = 17.2, 11.8, 7.6 Hz, 2H), 3.58 (td, J = 11.1, 10.5, 4.4 Hz, 1H), 2.64 (dq, J = 16.1, 8.6 Hz, 1H), 2.55-2.39 (m, 0H). |
| 897 | 1H NMR (400 MHz, Methanol-d4) δ 8.78 (d, J = 2.2 Hz, 1H), 8.73 (d, J = 2.2 Hz, 1H), 8.60 (s, 1H), 8.03 (d, J = 5.1 Hz, 1H), 7.73 (s, 1H), 7.24 (d, J = 5.0 Hz, 1H), 4.51 (dd, J = 9.0, 2.0 Hz, 1H), 4.46-4.28 (m, 1H), 4.18 (s, 2H), 4.12-3.86 (m, 3H), 3.68 (s, 3H), 3.52 (dt, J = 15.3, 7.6 Hz, 1H), 2.95-2.80 (m, 2H), 2.40 (dd, J = 11.8, 9.0 Hz, 2H), 1.32 (d, J = 1.7 Hz, 6H). |
| 898 | 1H NMR (400 MHz, Methanol-d4) δ 8.79 (d, J = 2.2 Hz, 1H), 8.73 (d, J = 2.2 Hz, 1H), 8.62 (s, 1H), 8.01 (d, J = 5.1 Hz, 1H), 7.74 (s, 1H), 7.25 (d, J = 5.0 Hz, 1H), 4.56-4.29 (m, 2H), 4.22 (s, 2H), 4.07 (s, 2H), 3.85 (q, J = 9.9, 9.2 Hz, 2H), 3.68-3.44 (m, 1H), 2.99 (dd, J = 11.8, 8.6 Hz, 2H), 2.47 (t, J = 10.4 Hz, 2H), 1.32 (d, J = 1.8 Hz, 6H). |
| 899 | 1H NMR (400 MHz, Methanol-d4) δ 8.79 (d, J = 2.2 Hz, 1H), 8.70 (d, J = 2.2 Hz, 1H), 8.64 (s, 1H), 8.07 (d, J = 5.0 Hz, 1H), 7.91 (s, 1H), 7.24 (d, J = 5.0 Hz, 1H), 4.46 (ddd, J = 49.0, 9.4, 2.1 Hz, 1H), 3.95 (ddd, J = 36.3, 14.5, 2.2 Hz, 1H), 3.73 (d, J = 7.3 Hz, 2H), 3.70-3.45 (m, 3H), 3.40 (d, J = 8.2 Hz, 0H), 3.15 (dd, J = 11.8, 8.5 Hz, 1H), 2.90 (p, J = 7.7 Hz, 1H), 2.36 (dt, J = 12.7, 6.8 Hz, 1H), 1.94 (dt, J = 13.2, 8.4 Hz, 1H), 1.32 (d, J = 1.7 Hz, 6H). |
| 900 | 1H NMR (400 MHz, Methanol-d4) δ 8.78 (d, J = 2.2 Hz, 1H), 8.70 (d, J = 2.2 Hz, 1H), 8.59 (s, 1H), 8.04 (d, J = 5.0 Hz, 1H), 7.89 (s, 1H), 7.24 (d, J = 5.1 Hz, 1H), 4.46 (dd, J = 49.0, 9.2 Hz, 1H), 3.97 (dd, J = 36.2, 14.5 Hz, 1H), 3.66 (t, J = 9.5 Hz, 6H), 3.58-3.40 (m, 1H), 3.27 (s, 1H), 2.73 (d, J = 9.8 Hz, 1H), 2.21 (s, 1H), 2.00-1.79 (m, 1H), 1.38-1.28 (m, 6H). |
| 901 | 1H NMR (400 MHz, Methanol-d4) δ 8.78 (d, J = 2.2 Hz, 1H), 8.69 (d, J = 2.2 Hz, 1H), 8.59 (s, 1H), 8.05 (d, J = 5.0 Hz, 1H), 7.86 (s, 1H), 7.24 (d, J = 5.0 Hz, 1H), 4.45 (dd, J = 49.1, 9.2 Hz, 1H), 4.11-3.80 (m, 1H), 3.64 (t, J = 6.4 Hz, 2H), 3.52 (td, J = 14.3, 12.5, 7.0 Hz, 3H), 3.16 (t, J = 8.9 Hz, 2H), 3.00 (q, J = 8.3 Hz, 1H), 2.94-2.85 (m, 1H), 2.80 (q, J = 7.4 Hz, 1H), 2.26 (q, J = 5.6 Hz, 1H), 1.80 (dq, J = 14.0, 7.3 Hz, 1H), 1.32 (d, J = 1.8 Hz, 6H). |
| 902 | 1H NMR (400 MHz, Methanol-d4) δ 8.78 (d, J = 2.2 Hz, 1H), 8.71 (d, J = 2.1 Hz, 1H), 8.64 (s, 1H), 8.05 (dd, J = 7.6, 5.1 Hz, 1H), 7.77 (s, 1H), 7.24 (d, J = 5.0 Hz, 1H), 4.46 (ddd, J = 34.2, 17.2, 9.1 Hz, 2H), 3.95 (dd, J = 36.3, 14.6 Hz, 1H), 3.65-3.51 (m, 1H), 3.42 (t, J = 7.2 Hz, 1H), 2.96-2.81 (m, 1H), 2.76 (ddd, J = 10.4, 7.6, 2.9 Hz, 1H), 2.34 (dq, J = 23.1, 7.8, 7.2 Hz, 3H), 2.19 (t, J = 7.5 Hz, 1H), 1.32 (s, 6H). |
| 903 | 1H NMR (400 MHz, Methanol-d4) δ 8.78 (d, J = 2.2 Hz, 1H), 8.71 (d, J = 2.2 Hz, 1H), 8.61 (s, 1H), 8.04 (d, J = 5.0 Hz, 1H), 7.81-7.68 (m, 1H), 7.24 (d, J = 5.0 Hz, 1H), 4.59-4.33 (m, 2H), 3.97 (dd, J = 36.4, 14.6 Hz, 1H), 3.81-3.66 (m, 3H), 3.65-3.46 (m, 3H), 3.42 (d, J = 6.5 Hz, 2H), 2.71 (dt, J = 20.0, 10.0 Hz, 2H), 2.38-2.07 (m, 3H), 2.03 (t, J = 7.4 Hz, 1H), 1.32 (d, J = 1.7 Hz, 6H). |
| 904 | 1H NMR (400 MHz, Methanol-d4) δ 8.79 (d, J = 2.2 Hz, 1H), 8.74-8.66 (m, 1H), 8.61 (s, 1H), 8.03 (t, J = 4.9 Hz, 1H), 7.75 (d, J = 10.1 Hz, 1H), 7.24 (d, J = 5.0 Hz, 1H), 4.57-4.27 (m, 1H), 3.96 (dd, J = 36.4, 14.6 Hz, 1H), 3.80-3.42 (m, 3H), 3.26 |

TABLE 2-continued

| compound | 1H-NMR |
|---|---|
| | (d, J = 11.5 Hz, 3H), 3.10 (t, J = 7.2 Hz, 1H), 2.79 (dt, J = 27.4, 9.7 Hz, 2H), 2.30 (dq, J = 18.1, 10.2 Hz, 3H), 2.13 (t, J = 7.3 Hz, 1H), 1.32 (d, J = 1.7 Hz, 6H). |
| 905 | 1H NMR (400 MHz, Methanol-d4) δ 8.79 (d, J = 2.2 Hz, 1H), 8.70 (s, 1H), 8.63 (s, 1H), 8.07 (d, J = 5.0 Hz, 1H), 7.88 (s, 1H), 7.24 (d, J = 5.0 Hz, 1H), 4.61-4.33 (m, 1H), 4.26 (t, J = 9.9 Hz, 2H), 4.15-3.99 (m, 2H), 3.90 (d, J = 7.3 Hz, 3H), 3.65-3.37 (m, 2H), 1.32 (s, 6H). |
| 906 | 1H NMR (400 MHz, Methanol-d4) δ 8.78 (d, J = 2.2 Hz, 1H), 8.69 (d, J = 2.2 Hz, 1H), 8.60 (s, 1H), 8.06 (d, J = 5.0 Hz, 1H), 7.89 (s, 1H), 7.24 (d, J = 5.0 Hz, 1H), 4.58-4.28 (m, 1H), 4.20 (t, J = 8.6 Hz, 2H), 4.05-3.92 (m, 1H), 3.85 (d, J = 7.1 Hz, 2H), 3.69 (s, 3H), 3.51 (td, J = 15.5, 9.3 Hz, 1H), 3.19-3.01 (m, 1H), 1.32 (s, 6H). |
| 907 | 1H NMR (400 MHz, Methanol-d4) δ 8.78 (d, J = 2.2 Hz, 1H), 8.69 (d, J = 2.2 Hz, 1H), 8.61 (s, 1H), 8.07 (d, J = 5.0 Hz, 1H), 7.87 (s, 1H), 7.24 (d, J = 5.0 Hz, 1H), 4.46 (ddd, J = 49.1, 9.3, 2.1 Hz, 1H), 4.10 (t, J = 8.7 Hz, 2H), 4.04-3.88 (m, 2H), 3.76 (q, J = 9.3 Hz, 2H), 3.54 (td, J = 15.4, 9.3 Hz, 1H), 3.29-3.11 (m, 1H), 1.31 (d, J = 1.7 Hz, 6H). |
| 908 | 1H NMR (400 MHz, Methanol-d4) δ 8.79 (d, J = 2.2 Hz, 1H), 8.73 (d, J = 2.1 Hz, 1H), 8.66 (s, 1H), 8.06 (d, J = 5.0 Hz, 1H), 7.78 (s, 1H), 7.25 (d, J = 5.0 Hz, 1H), 4.56-4.25 (m, 2H), 4.08-3.82 (m, 3H), 3.54 (td, J = 15.3, 9.3 Hz, 1H), 3.19 (ddd, J = 10.6, 7.4, 3.4 Hz, 2H), 2.85 (t, J = 8.3 Hz, 2H), 2.82-2.72 (m, 2H), 1.32 (d, J = 1.8 Hz, 6H). |
| 909 | 1H NMR (400 MHz, Methanol-d4) δ 8.78 (d, J = 2.2 Hz, 1H), 8.73 (d, J = 2.2 Hz, 1H), 8.60 (s, 1H), 8.03 (d, J = 5.1 Hz, 1H), 7.75 (s, 1H), 7.24 (d, J = 5.1 Hz, 1H), 4.47 (dd, J = 48.9, 9.3 Hz, 1H), 4.18 (t, J = 7.8 Hz, 1H), 3.98 (dd, J = 37.3, 15.2 Hz, 3H), 3.73 (d, J = 36.6 Hz, 2H), 3.52 (d, J = 13.8 Hz, 1H), 2.95 (s, 3H), 2.53 (t, J = 7.4 Hz, 2H), 1.32 (s, 6H). |
| 910 | 1H NMR (400 MHz, Methanol-d4) δ 8.79 (d, J = 2.2 Hz, 1H), 8.73 (d, J = 2.1 Hz, 1H), 8.59 (s, 1H), 8.04 (d, J = 5.0 Hz, 1H), 7.76 (s, 1H), 7.25 (d, J = 5.0 Hz, 1H), 4.45 (dd, J = 49.1, 9.2 Hz, 1H), 4.21-4.08 (m, 1H), 3.97 (dd, J = 36.4, 14.7 Hz, 1H), 3.51 (t, J = 7.2 Hz, 2H), 2.85 (t, J = 9.1 Hz, 2H), 2.48 (t, J = 7.1 Hz, 2H), 2.41 (t, J = 10.3 Hz, 2H), 1.32 (s, 6H). |
| 911 | 1H NMR (400 MHz, Methanol-d4) δ 8.79 (d, J = 2.2 Hz, 1H), 8.71 (d, J = 2.1 Hz, 1H), 8.66 (s, 1H), 8.04 (d, J = 5.0 Hz, 1H), 7.77 (s, 1H), 7.24 (d, J = 5.0 Hz, 1H), 4.64-4.33 (m, 2H), 4.09-3.85 (m, 3H), 3.54 (td, J = 15.3, 9.3 Hz, 1H), 2.81-2.59 (m, 4H), 1.32 (s, 6H). |
| 912 | 1H NMR (400 MHz, Methanol-d4) δ 8.78 (d, J = 2.2 Hz, 1H), 8.72 (s, 1H), 8.61 (s, 1H), 8.03 (s, 1H), 7.81 (s, 1H), 7.24 (d, J = 5.1 Hz, 1H), 4.67 (s, 1H), 4.58-4.32 (m, 1H), 4.09-3.80 (m, 4H), 3.75 (s, 3H), 3.52 (td, J = 15.3, 9.5 Hz, 1H), 2.55-2.30 (m, 4H), 1.32 (d, J = 1.7 Hz, 6H). |
| 913 | 1H NMR (400 MHz, Methanol-d4) δ 8.79 (d, J = 2.2 Hz, 1H), 8.71 (d, J = 2.2 Hz, 1H), 8.64 (s, 1H), 8.01 (d, J = 5.0 Hz, 1H), 7.68 (s, 1H), 7.25 (d, J = 5.0 Hz, 1H), 4.63-4.34 (m, 1H), 4.34-4.21 (m, 1H), 3.96 (dd, J = 36.3, 14.6 Hz, 1H), 3.68-3.42 (m, 4H), 3.17-3.01 (m, 2H), 2.49 (t, J = 7.3 Hz, 2H), 2.45-2.36 (m, 2H), 1.32 (d, J = 1.7 Hz, 6H). |
| 914 | 1H NMR (400 MHz, Methanol-d4) δ 8.57 (d, J = 2.2 Hz, 1H), 8.19 (s, 1H), 8.15 (s, 1H), 7.86 (d, J = 4.3 Hz, 2H), 7.21 (d, J = 5.0 Hz, 1H), 5.66 (dd, J = 52.5, 3.8 Hz, 1H), 5.54-5.34 (m, 1H), 4.64-4.35 (m, 1H), 4.19 (dd, J = 12.3, 8.2 Hz, 1H), 4.04 (dd, J = 12.2, 3.5 Hz, 1H), 4.01-3.92 (m, 1H), 3.88 (d, J = 3.3 Hz, 1H), 3.82 (d, J = 3.9 Hz, 1H), 3.56 (td, J = 15.4, 9.5 Hz, 1H), 1.33 (d, J = 1.7 Hz, 6H). |
| 915 | 1H NMR (400 MHz, Methanol-d4) δ 8.79-8.68 (m, 2H), 8.57 (d, J = 2.2 Hz, 1H), 8.14 (d, J = 2.5 Hz, 1H), 8.01 (s, 1H), 7.86 (d, J = 5.5 Hz, 2H), 7.18 (d, J = 5.0 Hz, 1H), 7.07 (d, J = 9.3 Hz, 1H), 4.73 (s, 1H), 4.61-4.38 (m, 1H), 4.31-4.20 (m, 1H), 4.20-4.12 (m, 1H), 4.00 (dd, J = 36.3, 14.6 Hz, 1H), 3.81 (d, J = 6.1 Hz, 2H), 3.68-3.53 (m, 1H), 3.50 (s, 3H), 2.60 (s, 1H), 2.38 (d, J = 9.8 Hz, 1H), 1.33 (d, J = 1.7 Hz, 6H). |
| 916 | 1H NMR (400 MHz, Methanol-d4) δ 8.79 (d, J = 2.2 Hz, 1H), 8.69 (d, J = 2.0 Hz, 1H), 8.67 (s, 1H), 8.12 (d, J = 5.0 Hz, 1H), 7.92 (s, 1H), 7.24 (d, J = 5.0 Hz, 1H), 4.47 (dd, J = 49.1, 9.0 Hz, 1H), 4.20 (dd, J = 12.3, 2.5 Hz, 1H), 4.13-3.63 (m, 7H), 3.63-3.39 (m, 2H), 1.32 (s, 5H). |
| 917 | 1H NMR (400 MHz, Methanol-d4) δ 8.79 (d, J = 2.2 Hz, 1H), 8.72-8.56 (m, 2H), 8.10 (d, J = 5.1 Hz, 1H), 7.93 (s, 1H), 7.24 (d, J = 5.0 Hz, 1H), 4.62-4.35 (m, 1H), 4.21 (d, J = 12.0 Hz, 1H), 4.08-3.69 (m, 7H), 3.69-3.37 (m, 2H), 1.32 (s, 6H). |
| 918 | 1H NMR (400 MHz, Methanol-d4) δ 8.79 (d, J = 2.2 Hz, 1H), 8.70 (d, J = 2.1 Hz, 1H), 8.58 (s, 1H), 8.08 (t, J = 56.8 Hz, 2H), 7.25 (d, J = 5.0 Hz, 1H), 4.63-4.27 (m, 2H), 4.10-3.62 (m, 7H), 3.52 (dd, J = 13.6, 5.7 Hz, 2H), 1.31 (s, 6H). |
| 919 | 1H NMR (400 MHz, Methanol-d4) δ 8.78 (d, J = 2.2 Hz, 1H), 8.70 (d, J = 2.2 Hz, 1H), 8.58 (s, 1H), 8.15 (d, J = 53.9 Hz, 2H), 7.25 (d, J = 5.0 Hz, 1H), 4.58-4.22 (m, 2H), 4.15-3.66 (m, 8H), 3.66-3.43 (m, 2H), 1.31 (s, 6H). |
| 920 | 1H NMR (400 MHz, Methanol-d4) δ 8.82-8.65 (m, 2H), 8.58 (d, J = 2.1 Hz, 1H), 8.47 (s, 2H), 7.87 (d, J = 3.9 Hz, 2H), 7.18 (d, J = 5.0 Hz, 1H), 6.01 (s, 1H), 4.71-4.38 (m, 1H), 4.32 (s, 2H), 4.28-4.02 (m, 1H), 4.02-3.81 (m, 1H), 3.55 (dd, J = 24.4, 14.4 Hz, 1H), 1.33 (s, 6H). |
| 921 | 1H NMR (400 MHz, Methanol-d4) δ 8.86-8.70 (m, 2H), 8.56 (d, J = 2.8 Hz, 3H), 7.97-7.83 (m, 2H), 7.18 (d, J = 5.0 Hz, 1H), 4.49 (ddd, J = 49.1, 9.4, 2.1 Hz, 1H), 4.20 (t, J = 5.2 Hz, 4H), 4.09-3.91 (m, 1H), 3.57 (td, J = 15.4, 9.4 Hz, 1H), 3.38 (t, J = 5.3 Hz, 4H), 1.37-1.26 (m, 6H). |
| 922 | 1H NMR (400 MHz, Methanol-d4) δ 8.74 (s, 2H), 8.61 (d, J = 2.2 Hz, 1H), 8.26 (d, J = 2.6 Hz, 1H), 7.94-7.78 (m, 2H), 7.18 (d, J = 5.0 Hz, 1H), 7.11 (d, J = 9.4 Hz, |

TABLE 2-continued

| compound | 1H-NMR |
|---|---|
| | 1H), 4.60-4.36 (m, 1H), 4.16-3.92 (m, 1H), 3.86 (q, J = 12.2 Hz, 4H), 3.57 (td, J = 15.4, 9.4 Hz, 1H), 3.37 (d, J = 7.5 Hz, 1H), 2.06 (d, J = 9.1 Hz, 1H), 1.33 (s, 6H). |
| 923 | 1H NMR (400 MHz, Methanol-d4) δ 8.75 (d, J = 2.1 Hz, 1H), 8.70 (d, J = 2.2 Hz, 1H), 8.57 (s, 1H), 8.29 (s, 1H), 7.92 (d, J = 5.0 Hz, 1H), 7.21 (d, J = 5.1 Hz, 1H), 4.33 (t, J = 7.7 Hz, 2H), 4.08 (t, J = 7.8 Hz, 2H), 3.97 (s, 2H), 2.39 (p, J = 7.8 Hz, 2H), 2.24 (t, J = 8.0 Hz, 6H), 1.96-1.85 (m, 6H). |
| 924 | 1H NMR (400 MHz, Methanol-d4) δ 8.76 (d, J = 2.2 Hz, 1H), 8.69 (d, J = 2.2 Hz, 1H), 8.51 (s, 1H), 8.25 (s, 1H), 7.93 (d, J = 5.1 Hz, 1H), 7.22 (d, J = 5.1 Hz, 1H), 3.45-3.31 (m, 2H), 2.24 (dd, J = 10.3, 5.7 Hz, 6H), 1.90 (dd, J = 10.3, 5.7 Hz, 6H), 1.15 (s, 3H), 1.09 (s, 3H), 0.98-0.88 (m, 1H), 0.53 (dd, J = 8.6, 4.4 Hz, 1H), 0.20 (t, J = 4.9 Hz, 1H). |
| 925 | 1H NMR (400 MHz, Methanol-d4) δ 8.88 (s, 1H), 8.75 (d, J = 2.2 Hz, 1H), 8.69 (d, J = 2.2 Hz, 1H), 8.60 (s, 1H), 8.33 (s, 1H), 7.93 (d, J = 5.1 Hz, 1H), 7.58 (d, J = 1.5 Hz, 1H), 7.21 (d, J = 5.1 Hz, 1H), 4.68 (s, 2H), 3.97 (s, 3H), 2.28-2.19 (m, 6H), 1.95-1.86 (m, 6H). |
| 926 | 1H NMR (400 MHz, Methanol-d4) δ 8.75 (d, J = 2.2 Hz, 1H), 8.69 (d, J = 2.2 Hz, 1H), 8.47 (s, 1H), 8.26 (s, 1H), 7.91 (d, J = 5.1 Hz, 1H), 7.61 (s, 1H), 7.48 (s, 1H), 7.21 (d, J = 5.1 Hz, 1H), 4.40 (s, 2H), 3.86 (s, 3H), 2.32-2.19 (m, 6H), 1.98-1.83 (m, 6H). |
| 927 | 1H NMR (400 MHz, Methanol-d4) δ 8.77 (dd, J = 15.4, 2.2 Hz, 2H), 8.56 (s, 1H), 7.99 (d, J = 5.1 Hz, 1H), 7.80 (s, 1H), 7.21 (d, J = 5.1 Hz, 1H), 5.48 (s, 1H), 4.53-4.32 (m, 2H), 3.94 (dd, J = 36.5, 14.5 Hz, 1H), 3.55-3.45 (m, 1H), 3.42 (d, J = 7.6 Hz, 2H), 3.13 (p, J = 8.7 Hz, 1H), 2.54 (s, 1H), 2.44 (dd, J = 11.6, 6.6 Hz, 2H), 2.33-2.21 (m, 3H), 2.15 (q, J = 8.9 Hz, 1H), 2.01 (dt, J = 18.6, 9.1 Hz, 1H), 1.88 (t, J = 10.0 Hz, 1H), 1.29 (d, J = 1.7 Hz, 6H). |
| 928 | 1H NMR (400 MHz, Methanol-d4) δ 8.70-8.64 (m, 2H), 8.65 (s, 1H), 8.61 (d, J = 1.8 Hz, 1H), 8.45 (s, 1H), 7.88 (d, J = 4.9 Hz, 1H), 7.46 (s, 1H), 7.39 (s, 1H), 7.15 (d, J = 5.0 Hz, 1H), 4.78 (s, 2H), 3.93 (s, 3H), 2.20 (t, J = 7.9 Hz, 6H), 1.88 (t, J = 8.0 Hz, 6H). |
| 929 | 1H NMR (400 MHz, Methanol-d4) δ 8.70 (dd, J = 24.6, 2.2 Hz, 2H), 8.59 (s, 1H), 8.57 (s, 1H), 8.35 (s, 1H), 7.91 (d, J = 5.0 Hz, 1H), 7.45 (s, 1H), 7.20 (d, J = 5.1 Hz, 1H), 4.56 (s, 2H), 3.88 (s, 3H), 2.24 (t, J = 7.9 Hz, 6H), 1.90 (t, J = 8.0 Hz, 6H). |
| 930 | 1H NMR (400 MHz, Methanol-d4) δ 8.76 (d, J = 2.2 Hz, 1H), 8.70 (d, J = 2.2 Hz, 1H), 8.69 (s, 1H), 8.65 (ddd, J = 5.4, 1.8, 0.9 Hz, 1H), 8.33 (s, 1H), 8.17 (td, J = 7.8, 1.7 Hz, 1H), 7.94 (d, J = 5.1 Hz, 1H), 7.75 (d, J = 8.0 Hz, 1H), 7.63 (dd, J = 7.6, 5.7 Hz, 1H), 7.22 (d, J = 5.1 Hz, 1H), 4.78 (s, 2H), 2.23 (dd, J = 10.0, 6.1 Hz, 6H), 1.95-1.84 (m, 6H). |
| 931 | 1H NMR (400 MHz, Methanol-d4) δ 8.82 (s, 1H), 8.76 (d, J = 2.2 Hz, 1H), 8.73-8.68 (m, 2H), 8.64 (d, J = 1.3 Hz, 1H), 8.42 (d, J = 8.2 Hz, 1H), 8.33 (s, 1H), 7.94 (d, J = 5.1 Hz, 1H), 7.92-7.84 (m, 1H), 7.22 (d, J = 5.1 Hz, 1H), 4.71 (s, 2H), 2.28-2.17 (m, 6H), 1.97-1.83 (m, 6H). |
| 932 | 1H NMR (400 MHz, Methanol-d4) δ 8.77 (d, J = 2.1 Hz, 1H), 8.74-8.68 (m, 4H), 8.34 (s, 1H), 7.95 (d, J = 5.1 Hz, 1H), 7.89 (d, J = 5.9 Hz, 2H), 7.23 (d, J = 5.0 Hz, 1H), 4.78 (s, 2H), 2.30-2.17 (m, 6H), 1.95-1.83 (m, 6H). |
| 933 | 1H NMR (400 MHz, Methanol-d4) δ 8.78 (d, J = 5.0 Hz, 2H), 8.76 (d, J = 2.2 Hz, 1H), 8.71 (d, J = 2.2 Hz, 1H), 8.68 (s, 1H), 8.30 (s, 1H), 7.94 (d, J = 5.0 Hz, 1H), 7.42 (t, J = 5.0 Hz, 1H), 7.22 (d, J = 5.0 Hz, 1H), 4.78 (s, 2H), 2.29-2.17 (m, 6H), 1.94-1.83 (m, 6H). |
| 934 | 1H NMR (400 MHz, Methanol-d4) δ 8.75 (d, J = 2.2 Hz, 1H), 8.70 (d, J = 2.2 Hz, 1H), 8.54 (s, 1H), 8.30 (s, 1H), 7.93 (d, J = 5.0 Hz, 1H), 7.40 (d, J = 2.0 Hz, 1H), 7.21 (d, J = 5.1 Hz, 1H), 6.31 (d, J = 1.9 Hz, 1H), 4.63 (s, 2H), 3.91 (s, 3H), 2.24 (dd, J = 10.4, 5.6 Hz, 6H), 1.97-1.84 (m, 6H). |
| 935 | 1H NMR (400 MHz, Methanol-d4) δ 8.75 (d, J = 2.2 Hz, 1H), 8.69 (d, J = 2.2 Hz, 1H), 8.55 (s, 1H), 8.29 (s, 1H), 7.92 (d, J = 5.0 Hz, 1H), 7.53 (d, J = 2.2 Hz, 1H), 7.21 (d, J = 5.1 Hz, 1H), 6.26 (d, J = 2.3 Hz, 1H), 4.52 (s, 2H), 3.86 (s, 3H), 2.25 (dd, J = 10.4, 5.6 Hz, 6H), 1.90 (dd, J = 10.1, 5.8 Hz, 6H). |
| 936 | 1H NMR (400 MHz, Methanol-d4) δ 9.16 (s, 1H), 8.74 (s, 1H), 8.61 (d, J = 2.2 Hz, 1H), 8.59 (s, 1H), 8.58 (d, J = 2.2 Hz, 1H), 8.30 (d, J = 1.5 Hz, 1H), 8.24 (s, 1H), 8.07 (s, 1H), 7.99 (d, J = 4.8 Hz, 1H), 7.12 (d, J = 4.9 Hz, 1H), 4.45 (dd, J = 48.9, 7.5 Hz, 1H), 3.93 (ddd, J = 36.9, 15.3, 1.9 Hz, 1H), 3.51-3.44 (m, 1H), 1.26 (d, J = 1.6 Hz, 6H). |
| 937 | 1H NMR (400 MHz, Methanol-d4) δ 8.78 (d, J = 2.2 Hz, 1H), 8.75 (d, J = 2.2 Hz, 1H), 8.56 (s, 1H), 7.99 (d, J = 5.1 Hz, 1H), 7.81 (s, 1H), 7.21 (d, J = 5.1 Hz, 1H), 4.54-4.31 (m, 2H), 3.94 (dd, J = 36.1, 14.2 Hz, 1H), 3.55-3.44 (m, 1H), 3.42 (d, J = 7.5 Hz, 2H), 2.56 (s, 1H), 2.44 (s, 2H), 2.25 (q, J = 9.5 Hz, 2H), 2.07 (s, 6H), 1.29 (d, J = 1.6 Hz, 7H). |
| 938 | 1H NMR (400 MHz, Methanol-d4) δ 8.78 (d, J = 2.2 Hz, 1H), 8.75 (d, J = 2.2 Hz, 1H), 8.57 (s, 1H), 7.99 (d, J = 5.1 Hz, 1H), 7.79 (s, 1H), 7.21 (d, J = 5.1 Hz, 1H), 4.53-4.33 (m, 2H), 4.05-3.83 (m, 1H), 3.55-3.45 (m, 1H), 3.43 (d, J = 7.6 Hz, 2H), 2.56 (s, 1H), 2.51-2.39 (m, 1H), 2.27 (q, J = 9.6 Hz, 2H), 1.29 (d, J = 1.6 Hz, 7H), 1.14 (d, J = 6.9 Hz, 7H). |
| 939 | 1H NMR (400 MHz, Methanol-d4) δ 9.16 (s, 1H), 8.78 (s, 1H), 8.62 (d, J = 2.3 Hz, 1H), 8.59 (s, 1H), 8.55 (d, J = 2.3 Hz, 1H), 8.28 (d, J = 9.8 Hz, 1H), 8.20 (s, 2H), 8.00 (d, J = 4.9 Hz, 1H), 7.15-7.06 (m, 2H), 4.44 (dd, J = 48.8, 8.7 Hz, 1H), 3.87 (dd, J = 36.6, 14.7 Hz, 1H), 3.59-3.44 (m, 1H), 1.26 (s, 6H). |
| 940 | 1H NMR (400 MHz, Methanol-d4) δ 8.76 (d, J = 1.7 Hz, 2H), 8.57 (s, 1H), 8.20 (s, 1H), 7.99 (d, J = 5.1 Hz, 1H), 7.77 (s, 1H), 7.21 (d, J = 5.0 Hz, 1H), 4.52-4.31 (m, |

TABLE 2-continued

| compound | 1H-NMR |
|---|---|
|  | 2H), 3.94 (dd, J = 36.4, 14.5 Hz, 1H), 3.55-3.42 (m, 3H), 3.00-2.87 (m, 1H), 2.87-2.66 (m, 2H), 2.55 (dd, J = 15.7, 7.9 Hz, 2H), 2.44 (q, J = 7.9, 5.9 Hz, 2H), 2.34-2.20 (m, 3H), 1.29 (d, J = 1.6 Hz, 6H). |
| 941 | 1H NMR (400 MHz, Methanol-d4) δ 8.99 (s, 0H), 8.78-8.71 (m, 2H), 8.56 (s, 1H), 7.96 (d, J = 5.1 Hz, 1H), 7.83 (s, 1H), 7.20 (d, J = 5.1 Hz, 1H), 4.68 (td, J = 6.3, 3.6 Hz, 1H), 4.52-4.33 (m, 2H), 3.94 (dd, J = 35.8, 14.2 Hz, 1H), 3.66-3.37 (m, 3H), 2.57 (s, 1H), 2.53-2.41 (m, 2H), 2.27 (dq, J = 19.3, 9.5, 8.9 Hz, 2H), 1.89-1.65 (m, 2H), 1.29 (d, J = 1.6 Hz, 6H), 1.10 (ddt, J = 12.7, 9.2, 6.5 Hz, 1H). |
| 942 | 1H NMR (400 MHz, Methanol-d4) δ 8.76 (d, J = 2.2 Hz, 1H), 8.70 (d, J = 2.2 Hz, 1H), 8.63 (s, 1H), 8.30 (s, 1H), 7.92 (d, J = 5.0 Hz, 1H), 7.22 (d, J = 5.1 Hz, 1H), 4.72 (q, J = 11.2, 10.7 Hz, 1H), 4.52 (q, J = 7.1 Hz, 1H), 4.50-4.27 (m, 2H), 2.24 (t, J = 8.0 Hz, 6H), 1.95-1.85 (m, 6H), 1.45 (d, J = 7.1 Hz, 3H). |
| 943 | 1H NMR (400 MHz, Methanol-d4) δ 8.76 (d, J = 2.2 Hz, 1H), 8.70 (d, J = 2.2 Hz, 1H), 8.63 (s, 1H), 8.29 (s, 1H), 7.92 (d, J = 5.1 Hz, 1H), 7.22 (d, J = 5.1 Hz, 1H), 4.98 (q, J = 7.0 Hz, 1H), 3.82-3.53 (m, 8H), 2.28-2.19 (m, 6H), 1.90 (t, J = 8.0 Hz, 6H), 1.43 (d, J = 7.1 Hz, 3H). |
| 944 | 1H NMR (400 MHz, Methanol-d4) δ 8.79 (d, J = 2.1 Hz, 1H), 8.73 (d, J = 2.1 Hz, 1H), 8.62 (s, 1H), 8.32 (s, 1H), 8.00 (s, 0H), 7.96 (d, J = 5.0 Hz, 1H), 7.25 (d, J = 5.1 Hz, 1H), 4.51 (d, J = 33.8 Hz, 1H), 4.32-4.13 (m, 1H), 4.18 (s, 1H), 3.72 (dd, J = 9.0, 4.8 Hz, 2H), 3.68-3.58 (m, 0H), 3.57-3.47 (m, 2H), 3.02 (s, 1H), 2.88 (s, 1H), 2.32-2.23 (m, 6H), 2.19-1.97 (m, 1H), 1.93 (t, J = 8.0 Hz, 6H). |
| 945 | 1H NMR (400 MHz, Methanol-d4) δ 8.79 (d, J = 2.1 Hz, 1H), 8.73 (d, J = 2.1 Hz, 1H), 8.54 (s, 1H), 8.31 (s, 1H), 7.95 (d, J = 5.1 Hz, 1H), 7.25 (d, J = 5.1 Hz, 1H), 5.19-5.01 (m, 1H), 4.04-3.90 (m, 1H), 3.77 (ddd, J = 21.8, 14.7, 7.1 Hz, 1H), 2.83 (d, J = 4.4 Hz, 3H), 2.28 (t, J = 8.0 Hz, 6H), 1.93 (t, J = 8.0 Hz, 6H). |
| 946 | 1H NMR (400 MHz, Methanol-d4) δ 8.79 (d, J = 2.2 Hz, 1H), 8.73 (d, J = 2.1 Hz, 1H), 8.55 (s, 1H), 8.32 (s, 1H), 7.95 (d, J = 5.1 Hz, 1H), 7.25 (d, J = 5.0 Hz, 1H), 5.69-5.51 (m, 1H), 3.94-3.73 (m, 2H), 3.20 (s, 3H), 3.00 (s, 3H), 2.28 (t, J = 7.9 Hz, 6H), 1.93 (t, J = 8.0 Hz, 6H). |
| 947 | 1H NMR (400 MHz, Methanol-d4) δ 8.79 (d, J = 2.1 Hz, 1H), 8.73 (s, 1H), 8.55 (s, 1H), 8.32 (s, 1H), 7.95 (d, J = 5.1 Hz, 1H), 7.25 (d, J = 5.0 Hz, 1H), 5.30 (d, J = 48.9 Hz, 1H), 4.84-4.74 (m, 1H), 4.43 (t, J = 12.3 Hz, 2H), 3.99-3.82 (m, 1H), 2.33-2.23 (m, 6H), 1.99-1.88 (m, 6H), 1.44-1.11 (m, 1H). |
| 948 | 1H NMR (400 MHz, Methanol-d4) δ 8.79 (s, 1H), 8.73 (d, J = 2.1 Hz, 1H), 8.56 (s, 1H), 8.34 (s, 1H), 7.96 (d, J = 5.0 Hz, 1H), 7.25 (d, J = 5.0 Hz, 1H), 5.74-5.54 (m, 2H), 3.88 (d, J = 25.6 Hz, 2H), 2.99 (s, 3H), 2.28 (t, J = 7.7 Hz, 6H), 1.93 (t, J = 8.0 Hz, 7H). |
| 949 | 1H NMR (400 MHz, Methanol-d4) δ 8.79 (d, J = 2.1 Hz, 1H), 8.73 (d, J = 2.1 Hz, 1H), 8.57 (s, 1H), 8.34 (s, 1H), 7.96 (d, J = 5.1 Hz, 1H), 7.25 (d, J = 5.1 Hz, 1H), 3.74 (s, 3H), 2.29 (dd, J = 9.4, 6.4 Hz, 6H), 1.94 (t, J = 8.0 Hz, 6H), 1.64 (q, J = 4.9 Hz, 2H), 1.30 (q, J = 4.9 Hz, 2H). |
| 950 | 1H NMR (400 MHz, Methanol-d4) δ 8.78 (d, J = 2.1 Hz, 1H), 8.72 (d, J = 2.1 Hz, 1H), 8.48 (s, 1H), 8.30 (s, 1H), 7.94 (d, J = 5.1 Hz, 1H), 7.24 (d, J = 5.1 Hz, 1H), 2.28 (dd, J = 10.5, 5.5 Hz, 6H), 1.94 (dd, J = 10.1, 5.8 Hz, 6H), 1.46 (s, 3H), 0.87 (d, J = 5.4 Hz, 2H), 0.75 (t, J = 3.4 Hz, 2H). |
| 951 | 1H NMR (400 MHz, Methanol-d4) δ 8.79 (d, J = 2.1 Hz, 1H), 8.73 (d, J = 2.2 Hz, 1H), 8.57 (s, 1H), 8.35 (s, 1H), 7.95 (d, J = 5.1 Hz, 1H), 7.25 (d, J = 5.1 Hz, 1H), 6.06 (t, J = 57.5 Hz, 1H), 2.34-2.23 (m, 6H), 1.94 (t, J = 8.0 Hz, 6H), 1.28-1.21 (m, 2H), 1.07 (s, 2H). |
| 952 | 1H NMR (400 MHz, Methanol-d4) δ 8.84-8.75 (m, 2H), 8.61 (s, 1H), 8.02 (d, J = 5.5 Hz, 1H), 7.85 (s, 1H), 7.24 (d, J = 5.0 Hz, 1H), 4.76 (t, J = 11.9 Hz, 2H), 4.45 (t, J = 11.6 Hz, 3H), 4.13 (s, 2H), 3.71 (s, 3H), 3.02 (s, 1H), 2.89 (s, 1H), 2.57 (s, 1H), 2.48 (s, 2H), 2.31 (t, J = 9.4 Hz, 2H), 1.40 (dd, J = 6.7, 3.3 Hz, 4H), 1.32 (s, 1H). |
| 953 | 1H NMR (400 MHz, Methanol-d4) δ 8.78 (s, 1H), 8.73 (d, J = 2.2 Hz, 1H), 8.62 (s, 1H), 8.33 (s, 1H), 7.95 (d, J = 5.1 Hz, 1H), 7.25 (d, J = 5.2 Hz, 1H), 4.51 (d, J = 34.0 Hz, 1H), 4.33-4.13 (m, 1H), 4.18 (s, 1H), 3.76-3.69 (m, 2H), 3.53 (d, J = 18.7 Hz, 2H), 3.16 (s, 1H), 2.27 (t, J = 8.0 Hz, 6H), 1.93 (t, J = 7.9 Hz, 6H). |
| 954 | 1H NMR (400 MHz, Methanol-d4) δ 8.79 (s, 1H), 8.73 (s, 1H), 8.61 (s, 1H), 8.32 (s, 1H), 7.95 (d, J = 5.1 Hz, 1H), 7.25 (d, J = 5.2 Hz, 1H), 4.25-4.15 (m, 2H), 4.03 (s, 1H), 3.95 (q, J = 10.4 Hz, 2H), 2.26 (d, J = 8.7 Hz, 6H), 1.94 (d, J = 8.4 Hz, 6H), 1.55 (s, 3H). |
| 955 | 1H NMR (400 MHz, Methanol-d4) δ 8.79 (d, J = 2.1 Hz, 1H), 8.73 (d, J = 2.1 Hz, 1H), 8.59 (s, 1H), 8.34 (s, 1H), 7.95 (d, J = 5.1 Hz, 1H), 7.25 (d, J = 5.1 Hz, 1H), 5.15 (dd, J = 5.2, 2.2 Hz, 2H), 3.69 (t, J = 5.6 Hz, 1H), 3.47 (dd, J = 6.1, 2.1 Hz, 1H), 2.28 (t, J = 7.9 Hz, 6H), 1.93 (t, J = 7.7 Hz, 6H). |
| 956 | 1H NMR (400 MHz, Methanol-d4) δ 10.01 (s, 1H), 8.80 (d, J = 9.2 Hz, 2H), 8.71 (d, J = 7.6 Hz, 2H), 8.11 (d, J = 16.6 Hz, 3H), 7.93 (d, J = 4.7 Hz, 1H), 7.26 (d, J = 8.2 Hz, 1H), 7.20 (d, J = 5.1 Hz, 1H), 1.68 (s, 4H), 1.34 (s, 6H). |
| 957 | 1H NMR (400 MHz, Methanol-d4) δ 8.79 (d, J = 2.2 Hz, 1H), 8.73 (d, J = 2.1 Hz, 1H), 8.57 (s, 1H), 8.32 (s, 1H), 7.95 (d, J = 5.1 Hz, 1H), 7.25 (d, J = 5.1 Hz, 1H), 4.53 (t, J = 8.6 Hz, 1H), 2.27 (q, J = 11.0, 9.4 Hz, 7H), 2.09-1.87 (m, 11H). |
| 958 | 1H NMR (400 MHz, Methanol-d4) δ 8.78 (s, 1H), 8.72 (s, 1H), 8.57 (s, 1H), 8.33 (s, 1H), 7.94 (d, J = 5.0 Hz, 2H), 7.24 (d, J = 5.0 Hz, 1H), 2.27 (d, J = 8.0 Hz, 10H), 2.08-1.84 (m, 14H). |

TABLE 2-continued

| compound | 1H-NMR |
|---|---|
| 959 | 1H NMR (400 MHz, Methanol-d4) δ 8.79 (d, J = 2.1 Hz, 1H), 8.73 (d, J = 2.2 Hz, 1H), 8.60 (s, 1H), 8.33 (s, 1H), 7.95 (d, J = 5.1 Hz, 1H), 7.25 (d, J = 5.1 Hz, 1H), 4.74 (dd, J = 10.6, 8.8 Hz, 1H), 3.50-3.41 (m, 2H), 2.59 (s, 1H), 2.28 (t, J = 8.0 Hz, 6H), 2.25-2.14 (m, 1H), 1.93 (t, J = 7.9 Hz, 6H). |
| 960 | 1H NMR (400 MHz, Methanol-d4) δ 8.79 (d, J = 2.1 Hz, 1H), 8.73 (d, J = 2.2 Hz, 1H), 8.60 (s, 1H), 8.33 (s, 1H), 7.95 (d, J = 5.1 Hz, 1H), 7.25 (d, J = 5.1 Hz, 1H), 4.74 (dd, J = 10.6, 8.9 Hz, 1H), 3.53-3.41 (m, 2H), 2.58 (d, J = 6.2 Hz, 1H), 2.28 (t, J = 7.9 Hz, 6H), 2.24-2.16 (m, 1H), 1.93 (t, J = 8.0 Hz, 6H). |
| 961 | 1H NMR (400 MHz, Methanol-d4) δ 8.76 (d, J = 2.2 Hz, 1H), 8.70 (d, J = 2.1 Hz, 1H), 8.54 (s, 1H), 8.31 (s, 1H), 7.93 (d, J = 5.1 Hz, 1H), 7.22 (d, J = 5.1 Hz, 1H), 4.45 (t, J = 12.0 Hz, 2H), 4.06 (t, J = 14.2 Hz, 2H), 2.31-2.18 (m, 7H), 1.96-1.86 (m, 7H). |
| 962 | 1H NMR (400 MHz, Methanol-d4) δ 8.69 (d, J = 2.3 Hz, 1H), 8.59 (d, J = 2.3 Hz, 1H), 8.52 (s, 1H), 8.40 (s, 1H), 7.96 (d, J = 5.2 Hz, 1H), 7.23 (d, J = 5.0 Hz, 1H), 3.96 (t, J = 13.7 Hz, 2H), 3.48 (q, J = 7.1 Hz, 4H), 3.16-3.10 (m, 1H), 2.99 (s, 1H), 2.85 (s, 1H), 2.26 (t, J = 7.9 Hz, 6H), 2.02 (s, 1H), 1.90 (t, J = 7.9 Hz, 6H), 1.36 (dd, J = 6.7, 3.2 Hz, 2H), 1.28 (s, 1H), 1.17 (t, J = 7.0 Hz, 5 H), 0.92-0.84 (m, 1H). |
| 963 | 1H NMR (400 MHz, Methanol-d4) δ 8.70 (s, 2H), 8.53 (s, 1H), 8.42 (s, 1H), 7.97 (d, J = 5.0 Hz, 1H), 7.29 (d, J = 5.1 Hz, 1H), 5.02 (t, J = 11.3 Hz, 2H), 4.92 (d, J = 11.4 Hz, 2H), 3.99 (t, J = 14.0 Hz, 2H), 3.48 (q, J = 7.1 Hz, 0H), 2.98 (d, J = 2.3 Hz, 2H), 2.33-2.18 (m, 6H), 2.02 (s, 0H), 1.96-1.87 (m, 6H), 1.28 (s, 0H), 1.17 (t, J = 7.0 Hz, 0H), 0.88 (d, J = 7.6 Hz, 0H). |
| 964 | 1H NMR (400 MHz, Methanol-d4) δ 8.75 (d, J = 2.2 Hz, 1H), 8.69 (d, J = 2.2 Hz, 1H), 8.51 (s, 1H), 8.29 (s, 1H), 7.91 (d, J = 5.1 Hz, 1H), 7.21 (d, J = 5.1 Hz, 1H), 4.47 (d, J = 48.9 Hz, 2H), 2.31-2.20 (m, 7H), 1.96-1.84 (m, 6H), 0.99 (d, J = 5.2 Hz, 4H). |
| 965 | 1H NMR (400 MHz, Methanol-d4) δ 8.75 (s, 1H), 8.71 (d, J = 2.2 Hz, 1H), 8.60 (d, J = 2.2 Hz, 1H), 8.54 (dd, J = 2.8, 0.7 Hz, 1H), 8.12 (s, 1H), 7.97 (dd, J = 8.5, 2.8 Hz, 1H), 7.85 (d, J = 5.1 Hz, 1H), 7.68 (dd, J = 8.5, 0.7 Hz, 1H), 7.16 (d, J = 5.1 Hz, 1H), 4.46 (ddd, J = 49.0, 9.3, 2.1 Hz, 1H), 3.99 (ddd, J = 36.4, 14.6, 2.1 Hz, 1H), 3.53 (ddd, J = 16.2, 14.6, 9.3 Hz, 1H), 1.30 (d, J = 1.7 Hz, 6H). |
| 966 | 1H NMR (400 MHz, Methanol-d4) δ 9.06 (s, 2H), 8.78 (s, 1H), 8.71 (d, J = 2.2 Hz, 1H), 8.64 (dd, J = 5.9, 2.2 Hz, 2H), 8.54 (d, J = 2.2 Hz, 1H), 8.29 (s, 1H), 7.94 (dd, J = 31.8, 5.0 Hz, 2H), 7.14 (dd, J = 14.6, 5.0 Hz, 2H), 5.48 (s, 0H), 4.49 (dd, J = 48.9, 9.2 Hz, 1H), 4.09 (q, J = 7.1 Hz, 0H), 4.05-3.94 (m, 1H), 3.55 (td, J = 15.5, 9.4 Hz, 1H), 2.00 (s, 0H), 1.30 (d, J = 1.6 Hz, 6H), 1.29-1.26 (m, 0H), 1.23 (t, J = 7.1 Hz, 0H). |
| 967 | n/a |
| 968 | 1H NMR (400 MHz, Methanol-d4) δ 8.73 (s, 1H), 8.66 (d, J = 2.2 Hz, 1H), 8.54 (d, J = 2.2 Hz, 1H), 8.45 (s, 1H), 8.20 (d, J = 8.6 Hz, 2H), 7.82 (d, J = 5.0 Hz, 1H), 7.62 (d, J = 8.6 Hz, 2H), 7.14 (d, J = 5.0 Hz, 1H), 5.48 (s, 1H), 4.47 (dd, J = 48.2, 8.4 Hz, 1H), 3.99 (dd, J = 36.3, 14.5 Hz, 1H), 3.62-3.44 (m, 1H), 2.69 (s, 3H), 1.30 (d, J = 1.6 Hz, 6H). |
| 969 | n/a |
| 970 | 1H NMR (400 MHz, Methanol-d4) δ 9.98 (s, 1H), 8.83 (s, 1H), 8.56 (d, J = 10.5 Hz, 2H), 8.47 (s, 1H), 8.24 (s, 1H), 7.86 (s, 1H), 7.07 (s, 1H), 4.62-4.30 (m, 1H), 4.07-3.82 (m, 1H), 3.61-3.48 (m, 1H), 2.21 (t, J = 7.6 Hz, 1H), 1.92 (s, 2H), 1.58 (s, 1H), 1.29 (d, J = 9.3 Hz, 33H), 0.88 (d, J = 7.1 Hz, 2H). |
| 971 | 1H NMR (400 MHz, Methanol-d4) δ 8.89 (s, 2H), 8.79 (s, 1H), 8.73 (d, J = 2.1 Hz, 1H), 8.62 (d, J = 2.2 Hz, 1H), 8.09 (s, 1H), 7.91 (d, J = 5.1 Hz, 1H), 7.17 (d, J = 5.1 Hz, 1H), 4.47 (ddd, J = 49.0, 9.2, 1.9 Hz, 1H), 3.99 (ddd, J = 36.3, 14.5, 1.7 Hz, 2H), 3.54 (ddd, J = 16.1, 14.7, 9.4 Hz, 2H), 1.29 (d, J = 1.7 Hz, 6H). |
| 972 | 1H NMR (400 MHz, Methanol-d4) δ 10.04 (s, 1H), 8.84 (d, J = 1.5 Hz, 1H), 8.80 (s, 1H), 8.75 (d, J = 2.2 Hz, 1H), 8.70 (d, J = 2.1 Hz, 1H), 8.47 (d, J = 1.4 Hz, 1H), 8.24 (s, 2H), 7.93 (d, J = 4.9 Hz, 1H), 7.19 (d, J = 5.0 Hz, 1H), 4.49 (ddd, J = 49.3, 9.1, 1.9 Hz, 1H), 4.00 (ddd, J = 36.1, 14.7, 1.8 Hz, 1H), 3.65-3.48 (m, 1H), 1.32 (s, 6H). |
| 973 | 1H NMR (400 MHz, Methanol-d4) δ 9.33 (d, J = 0.8 Hz, 1H), 8.83 (dd, J = 1.9, 1.0 Hz, 1H), 8.81 (s, 1H), 8.74 (d, J = 2.2 Hz, 1H), 8.60 (d, J = 2.2 Hz, 1H), 8.03 (dt, J = 9.7, 0.9 Hz, 1H), 8.00 (s, 1H), 7.91 (d, J = 5.1 Hz, 1H), 7.69 (d, J = 9.7, 1.9 Hz, 1H), 7.17 (d, J = 5.1 Hz, 1H), 4.50 (ddd, J = 49.1, 9.3, 2.1 Hz, 1H), 4.03 (ddd, J = 36.7, 14.6, 2.1 Hz, 1H), 3.64-3.51 (m, 1H), 1.33 (d, J = 1.7 Hz, 6H). |
| 974 | 1H NMR (400 MHz, Methanol-d4) δ 9.08 (t, J = 1.4 Hz, 1H), 8.85 (s, 1H), 8.72 (d, J = 2.2 Hz, 1H), 8.56 (d, J = 2.2 Hz, 1H), 8.33 (d, J = 2.1 Hz, 1H), 8.17 (d, J = 2.2 Hz, 1H), 8.15 (s, 1H), 8.13 (s, 1H), 8.13 (d, J = 2.9 Hz, 1H), 7.91 (d, J = 5.1 Hz, 1H), 7.16 (d, J = 5.1 Hz, 1H), 4.50 (ddd, J = 49.0, 9.3, 2.1 Hz, 1H), 4.01 (ddd, J = 36.5, 14.6, 2.1 Hz, 1H), 3.66-3.52 (m, 1H), 1.33 (d, J = 1.7 Hz, 6H). |
| 975 | 1H NMR (400 MHz, Methanol-d4) δ 8.78 (s, 1H), 8.76-8.72 (m, 2H), 8.57 (d, J = 2.2 Hz, 1H), 8.37 (s, 1H), 8.08 (d, J = 2.4 Hz, 1H), 7.88 (d, J = 5.1 Hz, 1H), 7.85-7.82 (m, 1H), 7.19 (d, J = 5.1 Hz, 1H), 7.03 (dd, J = 7.4, 2.4 Hz, 1H), 6.76 (dd, J = 2.4, 0.9 Hz, 1H), 4.50 (ddd, J = 49.0, 9.4, 2.1 Hz, 1H), 4.03 (ddd, J = 36.7, 14.7, 2.1 Hz, 1H), 3.56 (ddd, J = 16.1, 14.7, 9.4 Hz, 1H), 1.33 (d, J = 1.6 Hz, 6H). |

Biological Assays

Biological assays were conducted to measure activity against TNFα and IRAK4. As summarized in Table 3, the test compounds are inhibitors of IRAK4.

IRAK4 Monocyte TNFα Cell Based Assay Procedure:

Cryopreserved human monocytes (Stem Cell Technologies) were thawed, diluted in RPMI with GlutaMAX™ (Gibco® 200 mM L-alanyl-L-glutamine) (10 mM HEPES, 1× Pen-Strep, 55 µM ß-mercaptoethanol, 1 mM Sodium pyruvate) media containing 10% FBS to $0.125 \times 10^6$ cells/ml and recovered at 37° C. for 2 hours. The cell suspension was then plated at a density of 5,000 cells/well onto black 384 well Greiner clear bottom plates. Plates were pre-spotted with test compounds and serially diluted in DMSO where 200 nL/well were delivered using the Echo 550 acoustic liquid dispenser (Labcyte®) for a final DMSO concentration of 0.5%. Plated cells were treated with compound for 1 hour at 37° C. Cells were then stimulated with 50 pg/ml of LPS (Sigma) excluding outside columns of plate used for unstimulated cell control wells. Cells were incubated for an additional 4 hours at 37° C. Cells were then spun out of the media and 5 µl of sample were taken and analyzed for total TNFα content using the TR-FRET Human TNFα detection system (CisBio). This system utilizes two labeled antibodies (cryptate and XL665) that bind to two different epitopes of the TNFα molecule and produce FRET signal proportional to the concentration of TNFα in the sample. Detection antibodies are mixed 50:50 and 5 µL were dispensed into each well. Plates were covered with clear seals and incubated at room temp overnight. The following morning plates were read using an Envision 2103 Multilabeled reader (PerkinElmer) with excitation/emission/FRET emission at 340 nm/615 nm/665 nm, respectively. Fluorescence intensities at 615 nm and 665 nm emission wavelengths were expressed as a ratio (665 nm/615 nm). Percent of control was calculated as follows:

% Control=100×(Ratio$_{Sample}$−Ratio$_{0\% \; stimulation}$)/(Ratio$_{100\% \; Stimulation}$−Ratio$_{0\% \; Stimulation}$)

where unstimulated cells (0% stimulation) were the negative control and stimulated cells (100% stimulation) were used as the positive control.

IRAK4 Biochemical Assay Procedure:

IRAK4 enzyme (Carna Biosciences, Chuo-ku, Kobe, Japan) activity was measured by detecting phosphorylated peptide substrate formation using an antibody against the phosphorylated peptide substrate. This is a time-resolved fluorescence resonance energy transfer (TR-FRET) immunoassay, based on the STK1 KinEASE Assay (Cisbio, Bedford, Mass.). The assay was designed as a simple two-step, endpoint assay (a 5 µl enzyme reaction followed by 5 µl stop and detect Solution) performed in ProxiPlate-384 Plus plates (Perkin Elmer, Waltham, Mass.). Staurosporine, a non-selective kinase inhibitor was used as a positive control. Compounds diluted in DMSO were spotted into 384 well plates using a Labcyte® Echo 550 Liquid Handling System prior to addition of IRAK4 enzyme and peptide substrate. Reaction solutions were delivered using a Multi-Flo (Bio-Tek Instruments). The enzyme and peptide solution was incubated with compound for 15 minutes at room temp before the reaction was initiated by the addition of ATP. The standard 5 µl reaction mixture contained 500 µM ATP, 2 µM peptide (STK1 Peptide), 0.75 nM of IRAK4 in reaction buffer (50 mM HEPES, pH 7.0, 0.02% NaN$_3$, 0.01% BSA, 0.1 mM Orthovanadate, 5 mM MgCl$_2$, 0.025% NP-40, 1 mM DTT). After 120 min of incubation at room temperature, 5 µl of Stop and Detect Solution (1:100 Cryptate labeled anti-phosphorylated peptide antibody solution and 125 nM Tracer in a 50 mM HEPES pH 7.0 detection buffer containing sufficient EDTA) was added. The plate was then further incubated for 60 minutes at room temperature and read on Envision 2103 Multilabeled reader (PerkinElmer) with excitation/emission/FRET emission at 340 nm/615 nm/665 nm, respectively. Fluorescence intensities at 615 nm and 665 nm emission wavelengths were expressed as a ratio (665 nm/615 nm). Percentage of inhibition was calculated as below:

% Inhibition=100×(Ratio$_{Sample}$−Ratio$_{0\% \; Inhibition}$)/(Ratio$_{100\% \; Inhibition}$−Ratio$_{0\% \; Inhibition}$)

The 0% inhibition value comes from control wells lacking inhibitor. The 100% inhibition value comes from control wells containing a saturating amount of known inhibitor staurosporine.

TABLE 3

| compound | EC50 TNF(nM) | IC50 HTRF (nM) |
|---|---|---|
| 1 | 32 | <1 |
| 2 | 9 | <1 |
| 3 | 62 | <1 |
| 4 | 33 | <1 |
| 5 | 207 | <1 |
| 6 | 152 | 5 |
| 7 | 442 | 5 |
| 8 | 774 | <1 |
| 9 | 5097 | 16 |
| 10 | >10000 | 234 |
| 11 | 1040 | 7 |
| 12 | 97 | 2 |
| 13 | 79 | <1 |
| 14 | 626 | 3 |
| 15 | 302 | 4 |
| 16 | 204 | 2 |
| 17 | 5198 | 24 |
| 18 | 757 | 9 |
| 19 | 926 | 11 |
| 20 | 128 | 2 |
| 21 | 69 | <1 |
| 22 | 87 | <1 |
| 23 | 676 | 3 |
| 24 | 642 | 2 |
| 25 | 116 | 2 |
| 26 | 182 | 3 |
| 27 | 175 | 2 |
| 28 | 109 | <1 |
| 29 | 100 | <1 |
| 30 | 732 | 3 |
| 31 | 757 | 16 |
| 32 | >10000 | 3 |
| 33 | 29 | <1 |
| 34 | >10000 | 9377 |
| 35 | 218 | 3 |
| 36 | 221 | 15 |
| 37 | 283 | 12 |
| 38 | 91 | 2 |
| 39 | 507 | 4 |
| 40 | 73 | <1 |
| 41 | 78 | <1 |
| 42 | 35 | <1 |
| 43 | 30 | <1 |
| 44 | >10000 | 6627 |
| 45 | 255 | 10 |
| 46 | 37 | <1 |
| 47 | 37 | <1 |
| 48 | 28 | <1 |
| 49 | 8 | <1 |
| 50 | 351 | 3 |
| 51 | 159 | n/a |
| 52 | 86 | n/a |
| 53 | 65 | <1 |
| 54 | 26 | <1 |
| 55 | 28 | n/a |
| 56 | 13 | <1 |

TABLE 3-continued

| compound | EC50 TNF(nM) | IC50 HTRF (nM) |
|---|---|---|
| 57 | 46 | <1 |
| 58 | 91 | <1 |
| 59 | 57 | <1 |
| 60 | 512 | 1 |
| 61 | 89 | <1 |
| 62 | 83 | <1 |
| 63 | 57 | <1 |
| 64 | 70 | <1 |
| 65 | 149 | 2 |
| 66 | 458 | 46 |
| 67 | 43 | <1 |
| 68 | 327 | 3 |
| 69 | 515 | 7 |
| 70 | 47 | <1 |
| 71 | 298 | 9 |
| 72 | 159 | 4 |
| 73 | 119 | 3 |
| 74 | 1097 | 2 |
| 75 | 544 | 3 |
| 76 | 348 | 1 |
| 77 | 352 | 2 |
| 78 | 1625 | 27 |
| 79 | 1823 | 18 |
| 80 | 88 | <1 |
| 81 | 134 | 1 |
| 82 | 79 | <1 |
| 83 | 221 | 1 |
| 84 | 58 | <1 |
| 85 | 67 | 1 |
| 86 | 321 | 4 |
| 87 | 160 | 1 |
| 88 | 209 | 3 |
| 89 | 16 | <1 |
| 90 | 417 | 3 |
| 91 | 62 | <1 |
| 92 | 80 | 2 |
| 93 | 78 | 1 |
| 94 | 92 | 1 |
| 95 | 42 | 1 |
| 96 | 79 | 2 |
| 97 | 180 | 2 |
| 98 | 358 | 2 |
| 99 | 130 | 1 |
| 100 | 195 | 4 |
| 101 | 82 | <1 |
| 102 | 313 | 2 |
| 103 | 75 | <1 |
| 104 | 274 | 6 |
| 105 | 3165 | 9 |
| 106 | 1384 | 3 |
| 107 | 961 | 17 |
| 108 | >10000 | 88 |
| 109 | n/a | n/a |
| 110 | 191 | 4 |
| 111 | n/a | n/a |
| 112 | 399 | 4 |
| 113 | 3671 | 22 |
| 114 | 177 | 4 |
| 115 | 196 | 4 |
| 116 | 98 | <1 |
| 117 | 47 | <1 |
| 118 | 25 | <1 |
| 119 | 32 | <1 |
| 120 | 430 | 8 |
| 121 | 365 | 7 |
| 122 | 867 | 17 |
| 123 | 421 | 6 |
| 124 | 182 | 3 |
| 125 | 114 | 1 |
| 126 | 92 | 1 |
| 127 | 112 | <1 |
| 128 | 141 | 1 |
| 129 | 377 | 6 |
| 130 | 221 | 3 |
| 131 | 154 | 1 |
| 132 | 222 | 5 |
| 133 | 91 | 1 |
| 134 | 101 | 1 |
| 135 | 130 | 2 |
| 136 | 163 | 2 |
| 137 | 140 | 2 |
| 138 | 117 | 1 |
| 139 | 254 | 19 |
| 140 | 58 | <1 |
| 141 | 70 | <1 |
| 142 | 169 | 4 |
| 143 | 720 | 18 |
| 144 | >10000 | 656 |
| 145 | 70 | <1 |
| 146 | 117 | 1 |
| 147 | 47 | <1 |
| 148 | 206 | 2 |
| 149 | 148 | 1 |
| 150 | 51 | <1 |
| 151 | 96 | <1 |
| 152 | 191 | 2 |
| 153 | 91 | <1 |
| 154 | 34 | <1 |
| 155 | 150 | 1 |
| 156 | 179 | 4 |
| 157 | 501 | 23 |
| 158 | 99 | 2 |
| 159 | 184 | 1 |
| 160 | >10000 | 465 |
| 161 | >10000 | 1000 |
| 162 | >10000 | 376 |
| 163 | >10000 | 90 |
| 164 | 9941 | 132 |
| 165 | >10000 | 59 |
| 166 | >10000 | 741 |
| 167 | >10000 | 1000 |
| 168 | >10000 | 1000 |
| 169 | >10000 | 183 |
| 170 | 217 | 3 |
| 171 | 382 | 6 |
| 172 | 76 | <1 |
| 173 | 148 | 2 |
| 174 | 92 | 1 |
| 175 | 20 | <1 |
| 176 | >10000 | 1 |
| 177 | 29 | <1 |
| 178 | 10 | <1 |
| 179 | 59 | 1 |
| 180 | 34 | <1 |
| 181 | >10000 | 1000 |
| 182 | 70 | 1 |
| 183 | 657 | 6 |
| 184 | 48 | <1 |
| 185 | 46 | <1 |
| 186 | 145 | 1 |
| 187 | 152 | 1 |
| 188 | 275 | 8 |
| 189 | 136 | 6 |
| 190 | 209 | 8 |
| 191 | 128 | 4 |
| 192 | 157 | 5 |
| 193 | 141 | 3 |
| 194 | 48 | <1 |
| 195 | 37 | <1 |
| 196 | 53 | 2 |
| 197 | 42 | 1 |
| 198 | 16 | <1 |
| 199 | 82 | <1 |
| 200 | 15 | 1 |
| 201 | 11 | 1 |
| 202 | 22 | <1 |
| 203 | 44 | <1 |
| 204 | 27 | <1 |
| 205 | 115 | 1 |
| 206 | 133 | 1 |
| 207 | 96 | 1 |
| 208 | 92 | <1 |
| 209 | 84 | <1 |
| 210 | 39 | <1 |
| 211 | 50 | 1 |
| 212 | 13 | <1 |

TABLE 3-continued

| compound | EC50 TNF(nM) | IC50 HTRF (nM) |
|---|---|---|
| 213 | 51 | <1 |
| 214 | 36 | 3 |
| 215 | 53 | 2 |
| 216 | 32 | <1 |
| 217 | 63 | <1 |
| 218 | 41 | <1 |
| 219 | 209 | 1 |
| 220 | 123 | 1 |
| 221 | 98 | <1 |
| 222 | 151 | 1 |
| 223 | 13 | <1 |
| 224 | 75 | 1 |
| 225 | 6 | <1 |
| 226 | 75 | <1 |
| 227 | 31 | <1 |
| 228 | 114 | 2 |
| 229 | 135 | 1 |
| 230 | 58 | <1 |
| 231 | 61 | <1 |
| 232 | 425 | 1 |
| 233 | 170 | 1 |
| 234 | 33 | <1 |
| 235 | 166 | 2 |
| 236 | 379 | 1 |
| 237 | 23 | 1 |
| 238 | 225 | <1 |
| 239 | 24 | <1 |
| 240 | 27 | 1 |
| 241 | 16 | <1 |
| 242 | 191 | 2 |
| 243 | 218 | 2 |
| 244 | 102 | 1 |
| 245 | 92 | 2 |
| 246 | 637 | 17 |
| 247 | 262 | 6 |
| 248 | 545 | 3 |
| 249 | 100 | 2 |
| 250 | 37 | 1 |
| 251 | 117 | 1 |
| 252 | 78 | 2 |
| 253 | 510 | 3 |
| 254 | 2019 | 17 |
| 255 | 1274 | 14 |
| 256 | 389 | 2 |
| 257 | 129 | 1 |
| 258 | 83 | 1 |
| 259 | 152 | 6 |
| 260 | 165 | 8 |
| 261 | 41 | <1 |
| 262 | 21 | <1 |
| 263 | 193 | 3 |
| 264 | n/a | n/a |
| 265 | 690 | 2 |
| 266 | 7593 | 131 |
| 267 | 19 | <1 |
| 268 | 29 | <1 |
| 269 | 59 | 1 |
| 270 | 49 | 1 |
| 271 | 38 | 1 |
| 272 | 23 | 1 |
| 273 | 22 | 2 |
| 274 | 144 | 1 |
| 275 | 154 | 3 |
| 276 | 146 | 3 |
| 277 | 383 | 5 |
| 278 | 165 | 3 |
| 279 | 29 | 2 |
| 280 | 55 | 1 |
| 281 | 37 | 1 |
| 282 | 364 | 2 |
| 283 | 14 | 1 |
| 284 | 88 | 1 |
| 285 | 167 | 2 |
| 286 | 41 | 1 |
| 287 | 147 | 1 |
| 288 | 54 | 1 |
| 289 | 66 | 1 |
| 290 | 121 | 1 |
| 291 | 90 | 2 |
| 292 | 37 | 1 |
| 293 | 49 | 1 |
| 294 | 735 | 3 |
| 295 | 38 | 1 |
| 296 | 391 | 3 |
| 297 | 80 | 1 |
| 298 | 214 | 2 |
| 299 | 128 | 1 |
| 300 | 75 | 1 |
| 301 | 1410 | 2 |
| 302 | 61 | 1 |
| 303 | 26 | <1 |
| 304 | 677 | 4 |
| 305 | 337 | 1 |
| 306 | 453 | 3 |
| 307 | 320 | 2 |
| 308 | 46 | <1 |
| 309 | 623 | 2 |
| 310 | 362 | 2 |
| 311 | 15 | <1 |
| 312 | 198 | 2 |
| 313 | 37 | 1 |
| 314 | 20 | <1 |
| 315 | 59 | <1 |
| 316 | 136 | <1 |
| 317 | 11 | <1 |
| 318 | 23 | <1 |
| 319 | 2222 | 19 |
| 320 | 1906 | 3 |
| 321 | 38 | <1 |
| 322 | 169 | 5 |
| 323 | 187 | 5 |
| 324 | 157 | 2 |
| 325 | 228 | 3 |
| 326 | 56 | <1 |
| 327 | 738 | 1 |
| 328 | 300 | 6 |
| 329 | 62 | 1 |
| 330 | 171 | 6 |
| 331 | 25 | <1 |
| 332 | 43 | <1 |
| 333 | 87 | <1 |
| 334 | 292 | <1 |
| 335 | 100 | 3 |
| 336 | 522 | 5 |
| 337 | 73 | 5 |
| 338 | 304 | 3 |
| 339 | 264 | 1 |
| 340 | 139 | 1 |
| 341 | 16 | <1 |
| 342 | 83 | 1 |
| 343 | 38 | 1 |
| 344 | 48 | 2 |
| 345 | 116 | 1 |
| 346 | 18 | 1 |
| 347 | 45 | 2 |
| 348 | 19 | <1 |
| 349 | 77 | 1 |
| 350 | 12 | <1 |
| 351 | 120 | 2 |
| 352 | 76 | 1 |
| 353 | 16 | <1 |
| 354 | 19 | <1 |
| 355 | 23 | <1 |
| 356 | 800 | 6 |
| 357 | 413 | 9 |
| 358 | 122 | 3 |
| 359 | >10000 | 614 |
| 360 | >10000 | 2 |
| 361 | 50 | 1 |
| 362 | 1433 | 9 |
| 363 | 328 | 5 |
| 364 | >10000 | 1000 |
| 365 | 415 | 4 |
| 366 | 162 | 1 |
| 367 | 1565 | 3 |
| 368 | 2887 | 5 |

TABLE 3-continued

| compound | EC50 TNF(nM) | IC50 HTRF (nM) |
|---|---|---|
| 369 | 922 | 16 |
| 370 | 10 | 1 |
| 371 | 61 | <1 |
| 372 | 8 | <1 |
| 373 | 141 | <1 |
| 374 | 327 | 1 |
| 375 | 110 | 1 |
| 376 | 736 | 2 |
| 377 | 426 | 2 |
| 378 | 38 | <1 |
| 379 | 57 | 2 |
| 380 | 773 | 15 |
| 381 | 18 | <1 |
| 382 | 586 | 10 |
| 383 | 144 | <1 |
| 384 | 129 | 1 |
| 385 | 36 | <1 |
| 386 | 2382 | 8 |
| 387 | 112 | 2 |
| 388 | 96 | 1 |
| 389 | 137 | 3 |
| 390 | >10000 | 6 |
| 391 | 33 | <1 |
| 392 | 50 | <1 |
| 393 | 44 | <1 |
| 394 | 68 | 1 |
| 395 | 256 | 3 |
| 396 | 24 | 1 |
| 397 | 30 | 1 |
| 398 | 17 | <1 |
| 399 | 8 | <1 |
| 400 | 21 | 1 |
| 401 | 65 | 2 |
| 402 | 77 | 2 |
| 403 | 14 | <1 |
| 404 | 11 | 1 |
| 405 | 12 | 1 |
| 406 | 33 | 1 |
| 407 | 20 | 2 |
| 408 | 31 | 1 |
| 409 | 17 | 1 |
| 410 | 50 | 2 |
| 411 | 62 | 2 |
| 412 | 44 | 1 |
| 413 | 98 | <1 |
| 414 | 178 | 12 |
| 415 | 14 | 1 |
| 416 | 16 | 1 |
| 417 | 151 | 5 |
| 418 | 36 | 1 |
| 419 | 127 | 3 |
| 420 | 122 | 6 |
| 421 | 24 | 2 |
| 422 | 76 | 2 |
| 423 | 94 | 2 |
| 424 | 18 | 1 |
| 425 | 120 | 2 |
| 426 | 591 | 5 |
| 427 | 278 | 2 |
| 428 | 4271 | 63 |
| 429 | 36 | 1 |
| 430 | 488 | 14 |
| 431 | 441 | 11 |
| 432 | 37 | <1 |
| 433 | 47 | <1 |
| 434 | 107 | <1 |
| 435 | >10000 | 10000 |
| 436 | 34 | <1 |
| 437 | 76 | 1 |
| 438 | 135 | 1 |
| 439 | 40 | <1 |
| 440 | 715 | 2 |
| 441 | 1304 | 11 |
| 442 | 104 | 1 |
| 443 | 110 | 1 |
| 444 | 9 | <1 |
| 445 | 59 | 1 |
| 446 | 63 | 1 |
| 447 | 286 | 5 |
| 448 | 2041 | 32 |
| 449 | 361 | 3 |
| 450 | 44 | <1 |
| 451 | 30 | <1 |
| 452 | 112 | <1 |
| 453 | 68 | <1 |
| 454 | 207 | <1 |
| 455 | 118 | 1 |
| 456 | 394 | 1 |
| 457 | 370 | 3 |
| 458 | 2467 | 3 |
| 459 | 125 | 1 |
| 460 | 71 | <1 |
| 461 | 57 | <1 |
| 462 | 67 | <1 |
| 463 | 163 | 3 |
| 464 | 1107 | 23 |
| 465 | 411 | 8 |
| 466 | 259 | 8 |
| 467 | 167 | 4 |
| 468 | 112 | 1 |
| 469 | 1096 | 41 |
| 470 | 440 | 25 |
| 471 | 74 | 9 |
| 472 | 5410 | 43 |
| 473 | 33 | 1 |
| 474 | 23 | <1 |
| 475 | 16 | <1 |
| 476 | 27 | <1 |
| 477 | 98 | 1 |
| 478 | 73 | 1 |
| 479 | 71 | <1 |
| 480 | 92 | 2 |
| 481 | 63 | 2 |
| 482 | 48 | 1 |
| 483 | 64 | 1 |
| 484 | 63 | 1 |
| 485 | 39 | 1 |
| 486 | 64 | 1 |
| 487 | 51 | <1 |
| 488 | 71 | 1 |
| 489 | 121 | 2 |
| 490 | 220 | 7 |
| 491 | 219 | 19 |
| 492 | 101 | 1 |
| 493 | >10000 | 12 |
| 494 | 44 | <1 |
| 495 | 40 | <1 |
| 496 | 42 | <1 |
| 497 | 55 | 1 |
| 498 | 43 | 1 |
| 499 | 20 | 1 |
| 500 | 13 | 1 |
| 501 | 63 | 2 |
| 502 | 93 | 1 |
| 503 | 46 | 2 |
| 504 | 14 | <1 |
| 505 | 139 | 1 |
| 506 | 50 | <1 |
| 507 | 27 | <1 |
| 508 | 22 | <1 |
| 509 | 66 | <1 |
| 510 | 39 | <1 |
| 511 | 26 | <1 |
| 512 | 98 | 3 |
| 513 | 110 | 2 |
| 514 | 213 | 9 |
| 515 | 526 | 5 |
| 516 | 595 | 2 |
| 517 | 484 | <1 |
| 518 | 13 | <1 |
| 519 | 34 | <1 |
| 520 | 45 | <1 |
| 521 | 717 | 62 |
| 522 | 23 | <1 |
| 523 | 412 | 14 |
| 524 | 97 | 1 |

TABLE 3-continued

| compound | EC50 TNF(nM) | IC50 HTRF (nM) |
|---|---|---|
| 525 | 11 | <1 |
| 526 | 99 | 1 |
| 527 | 16 | <1 |
| 528 | 65 | 1 |
| 529 | 62 | 1 |
| 530 | 10 | <1 |
| 531 | 34 | <1 |
| 532 | 122 | 1 |
| 533 | 70 | <1 |
| 534 | 26 | <1 |
| 535 | 999 | 2 |
| 536 | 16 | <1 |
| 537 | 18 | 1 |
| 538 | 50 | <1 |
| 539 | 12 | <1 |
| 540 | 12 | <1 |
| 541 | 65 | <1 |
| 542 | 27 | <1 |
| 543 | 49 | 2 |
| 544 | 81 | 1 |
| 545 | 5 | <1 |
| 546 | 90 | 1 |
| 547 | 28 | <1 |
| 548 | 22 | 1 |
| 549 | 149 | 2 |
| 550 | 364 | 2 |
| 551 | 809 | 11 |
| 552 | 1157 | 7 |
| 553 | 183 | 2 |
| 554 | 439 | 35 |
| 555 | 95 | 1 |
| 556 | 18 | 1 |
| 557 | 27 | <1 |
| 558 | 190 | <1 |
| 559 | 78 | 1 |
| 560 | 83 | <1 |
| 561 | 121 | 1 |
| 562 | 75 | 1 |
| 563 | 114 | 2 |
| 564 | 315 | 23 |
| 565 | 23 | <1 |
| 566 | 27 | <1 |
| 567 | 50 | <1 |
| 568 | 214 | <1 |
| 569 | >10000 | 743 |
| 570 | 80 | <1 |
| 571 | 12 | <1 |
| 572 | 66 | <1 |
| 573 | 24 | <1 |
| 574 | 57 | <1 |
| 575 | 144 | 2 |
| 576 | 21 | <1 |
| 577 | 30 | <1 |
| 578 | 14 | 2 |
| 579 | 75 | <1 |
| 580 | 69 | <1 |
| 581 | 114 | <1 |
| 582 | 389 | 3 |
| 583 | 140 | 2 |
| 584 | 274 | 4 |
| 585 | 104 | 2 |
| 586 | 118 | 1 |
| 587 | 150 | 3 |
| 588 | 412 | 3 |
| 589 | 95 | <1 |
| 590 | 38 | <1 |
| 591 | 180 | 2 |
| 592 | 222 | 1 |
| 593 | 143 | 2 |
| 594 | 316 | 2 |
| 595 | 107 | <1 |
| 596 | >10000 | 3 |
| 597 | 106 | 1 |
| 598 | 106 | <1 |
| 599 | 68 | <1 |
| 600 | 72 | <1 |
| 601 | 64 | <1 |
| 602 | 70 | <1 |
| 603 | 81 | 1 |
| 604 | 283 | 7 |
| 605 | 24 | <1 |
| 606 | 33 | 1 |
| 607 | 1444 | 11 |
| 608 | 123 | 1 |
| 609 | 35 | <1 |
| 610 | 50 | <1 |
| 611 | >10000 | 15 |
| 612 | 51 | <1 |
| 613 | 15 | <1 |
| 614 | 156 | 2 |
| 615 | 46 | <1 |
| 616 | 144 | 2 |
| 617 | 144 | 2 |
| 618 | 335 | 4 |
| 619 | 168 | 3 |
| 620 | 54 | 1 |
| 621 | 98 | 1 |
| 622 | 407 | 2 |
| 623 | 63 | <1 |
| 624 | 1644 | 3 |
| 625 | 22 | <1 |
| 626 | 79 | <1 |
| 627 | 30 | <1 |
| 628 | 26 | <1 |
| 629 | 22 | <1 |
| 630 | 9 | <1 |
| 631 | 21 | 2 |
| 632 | 28 | <1 |
| 633 | 2 | <1 |
| 634 | 7 | <1 |
| 635 | >10000 | 8 |
| 636 | 33 | <1 |
| 637 | 21 | <1 |
| 638 | 26 | <1 |
| 639 | 43 | 1 |
| 640 | 117 | 1 |
| 641 | 21 | <1 |
| 642 | 13 | <1 |
| 643 | 8 | <1 |
| 644 | 36 | 1 |
| 645 | 301 | 10 |
| 646 | 15 | <1 |
| 647 | 48 | <1 |
| 648 | 51 | 1 |
| 649 | >10000 | 21 |
| 650 | 16 | <1 |
| 651 | 188 | 5 |
| 652 | 188 | 2 |
| 653 | 201 | 3 |
| 654 | 15 | <1 |
| 655 | 27 | <1 |
| 656 | 40 | <1 |
| 657 | 23 | <1 |
| 658 | 37 | <1 |
| 659 | 16 | <1 |
| 660 | 64 | 1 |
| 661 | 19 | <1 |
| 662 | 12 | <1 |
| 663 | 52 | <1 |
| 664 | 14 | <1 |
| 665 | 299 | 8 |
| 666 | 30 | <1 |
| 667 | 45 | <1 |
| 668 | 165 | 1 |
| 669 | 4 | <1 |
| 670 | >10000 | 93 |
| 671 | 22 | <1 |
| 672 | 66 | <1 |
| 673 | 19 | <1 |
| 674 | 67 | <1 |
| 675 | 23 | <1 |
| 676 | 81 | 1 |
| 677 | 54 | <1 |
| 678 | 9 | <1 |
| 679 | 17 | <1 |
| 680 | 15 | <1 |

TABLE 3-continued

| compound | EC50 TNF(nM) | IC50 HTRF (nM) |
|---|---|---|
| 681 | 6 | <1 |
| 682 | 22 | 1 |
| 683 | 45 | 1 |
| 684 | 89 | 1 |
| 685 | 398 | 10 |
| 686 | 20 | <1 |
| 687 | 42 | <1 |
| 688 | 24 | <1 |
| 689 | 180 | 1 |
| 690 | 71 | 1 |
| 691 | 345 | 5 |
| 692 | 315 | 1 |
| 693 | 821 | 35 |
| 694 | 102 | <1 |
| 695 | 15 | <1 |
| 696 | 103 | <1 |
| 697 | 171 | 1 |
| 698 | 201 | 3 |
| 699 | 36 | <1 |
| 700 | 151 | 2 |
| 701 | 191 | 4 |
| 702 | 119 | <1 |
| 703 | 45 | <1 |
| 704 | 69 | 1 |
| 705 | n/a | n/a |
| 706 | n/a | n/a |
| 707 | 42 | 1 |
| 708 | 57 | 1 |
| 709 | 151 | 3 |
| 710 | 183 | 4 |
| 711 | 231 | 2 |
| 712 | 47 | <1 |
| 713 | 264 | 2 |
| 714 | 35 | <1 |
| 715 | 57 | 1 |
| 716 | 55 | <1 |
| 717 | 66 | <1 |
| 718 | 280 | 2 |
| 719 | 11 | <1 |
| 720 | 243 | 2 |
| 721 | 87 | 1 |
| 722 | 35 | <1 |
| 723 | 793 | 7 |
| 724 | 59 | <1 |
| 725 | 23 | <1 |
| 726 | 169 | 4 |
| 727 | 203 | 3 |
| 728 | 4 | <1 |
| 729 | 58 | 1 |
| 730 | 40 | <1 |
| 731 | 59 | <1 |
| 732 | 89 | 1 |
| 733 | 248 | 2 |
| 734 | 29 | <1 |
| 735 | 100 | 1 |
| 736 | 48 | <1 |
| 737 | 26 | <1 |
| 738 | 29 | <1 |
| 739 | 277 | 4 |
| 740 | 265 | 4 |
| 741 | 124 | <1 |
| 742 | 126 | 1 |
| 743 | 54 | <1 |
| 744 | 157 | 2 |
| 745 | 87 | <1 |
| 746 | 105 | 1 |
| 747 | 169 | 2 |
| 748 | 38 | <1 |
| 749 | 52 | <1 |
| 750 | 198 | 1 |
| 751 | 333 | 4 |
| 752 | 80 | <1 |
| 753 | 225 | 7 |
| 754 | 20 | <1 |
| 755 | 16 | 1 |
| 756 | 59 | 1 |
| 757 | 12 | <1 |
| 758 | 11 | 1 |
| 759 | >10000 | 3 |
| 760 | 33 | <1 |
| 761 | 26 | <1 |
| 762 | 7 | <1 |
| 763 | 155 | <1 |
| 764 | 8 | <1 |
| 765 | 323 | 6 |
| 766 | 38 | <1 |
| 767 | 35 | <1 |
| 768 | 24 | <1 |
| 769 | 44 | <1 |
| 770 | 50 | <1 |
| 771 | 37 | <1 |
| 772 | 14 | <1 |
| 773 | 43 | 1 |
| 774 |  | 2 |
| 775 | 25 | <1 |
| 776 | 32 | 1 |
| 777 | 15 | <1 |
| 778 | 51 | <1 |
| 779 | 28 | <1 |
| 780 | 38 | 1 |
| 781 | 90 | <1 |
| 782 | 29 | <1 |
| 783 | 22 | <1 |
| 784 | 40 | <1 |
| 785 | 23 | <1 |
| 786 | 323 | 2 |
| 787 | 79 | <1 |
| 788 | 90 | <1 |
| 789 | 20 | <1 |
| 790 | 21 | <1 |
| 791 | 45 | 1 |
| 792 | 86 | 2 |
| 793 | 598 | 3 |
| 794 | 997 | 2 |
| 795 | >10000 | 7 |
| 796 | 75 | 2 |
| 797 | 38 | 1 |
| 798 | 42 | 1 |
| 799 | 62 | <1 |
| 800 | 133 | 3 |
| 801 | 57 | 1 |
| 802 | 157 | 2 |
| 803 | 327 | 1 |
| 804 | 48 | <1 |
| 805 | 129 | <1 |
| 806 | 349 | 3 |
| 807 | 75 | 2 |
| 808 | 15 | <1 |
| 809 | 166 | 1 |
| 810 | 9 | <1 |
| 811 | 32 | <1 |
| 812 | 38 | <1 |
| 813 | 92 | <1 |
| 814 | 40 | <1 |
| 815 | 15 | <1 |
| 816 | 41 | <1 |
| 817 | 165 | 6 |
| 818 | 224 | 4 |
| 819 | 27 | <1 |
| 820 | 59 | <1 |
| 821 | 51 | <1 |
| 822 | 73 | 1 |
| 823 | 47 | <1 |
| 824 | 39 | <1 |
| 825 | 48 | <1 |
| 826 | 32 | <1 |
| 827 | 15 | <1 |
| 828 | 12 | <1 |
| 829 | 23 | <1 |
| 830 | 23 | <1 |
| 831 | 49 | <1 |
| 832 | 132 | 1 |
| 833 | 192 | 1 |
| 834 | 23 | <1 |
| 835 | 8 | <1 |
| 836 | 43 | 2 |

TABLE 3-continued

| compound | EC50 TNF(nM) | IC50 HTRF (nM) |
|---|---|---|
| 837 | 117 | 3 |
| 838 | >10000 | 57 |
| 839 | 307 | 1 |
| 840 | 17 | <1 |
| 841 | 29 | <1 |
| 842 | 42 | <1 |
| 843 | 137 | 1 |
| 844 | 70 | 1 |
| 845 | >10000 | <1 |
| 846 | 97 | 2 |
| 847 | 69 | <1 |
| 848 | 112 | 2 |
| 849 | 11 | <1 |
| 850 | 10 | <1 |
| 851 | 12 | <1 |
| 852 | 3 | n/a |
| 853 | 127 | 14 |
| 854 | 10 | 1 |
| 855 | 9 | <1 |
| 856 | 24 | 1 |
| 857 | 9 | <1 |
| 858 | 20 | <1 |
| 859 | 89 | 3 |
| 860 | 31 | 2 |
| 861 | 16 | <1 |
| 862 | 46 | <1 |
| 863 | 74 | <1 |
| 864 | 69 | <1 |
| 865 | n/a | n/a |
| 866 | 37 | 1 |
| 867 | 6 | <1 |
| 868 | 53 | <1 |
| 869 | 14 | <1 |
| 870 | 81 | 1 |
| 871 | 51 | 1 |
| 872 | 14 | <1 |
| 873 | 102 | <1 |
| 874 | 13 | <1 |
| 875 | 64 | 2 |
| 876 | 24 | <1 |
| 877 | 46 | 2 |
| 878 | 141 | 2 |
| 879 | 225 | 1 |
| 880 | 58 | <1 |
| 881 | 84 | <1 |
| 882 | 22 | <1 |
| 883 | 90 | <1 |
| 884 | 29 | 2 |
| 885 | 70 | 1 |
| 886 | 29 | 2 |
| 887 | 88 | 1 |
| 888 | 21 | <1 |
| 889 | 436 | 9 |
| 890 | 357 | 14 |
| 891 | 249 | 4 |
| 892 | 808 | 3 |
| 893 | 217 | 2 |
| 894 | 245 | 7 |
| 895 | 1000 | 2 |
| 896 | 48 | <1 |
| 897 | 421 | 2 |
| 898 | 118 | <1 |
| 899 | >10000 | 5 |
| 900 | 134 | 2 |
| 901 | 126 | 3 |
| 902 | 1227 | 1 |
| 903 | 79 | 1 |
| 904 | 117 | 1 |
| 905 | >10000 | 15 |
| 906 | 186 | 10 |
| 907 | 91 | 10 |
| 908 | 611 | 6 |
| 909 | 372 | 15 |
| 910 | 1214 | 10 |
| 911 | 318 | 7 |
| 912 | 176 | 6 |
| 913 | 226 | 3 |
| 914 | 13 | <1 |
| 915 | 28 | 1 |
| 916 | 88 | 3 |
| 917 | 72 | 1 |
| 918 | 416 | 31 |
| 919 | 707 | 37 |
| 920 | 8 | <1 |
| 921 | 45 | <1 |
| 922 | 42 | <1 |
| 923 | 52 | <1 |
| 924 | 119 | 1 |
| 925 | 583 | 4 |
| 926 | 192 | 2 |
| 927 | 22 | <1 |
| 928 | 71 | 1 |
| 929 | 126 | 1 |
| 930 | 147 | 2 |
| 931 | 163 | 3 |
| 932 | 168 | 3 |
| 933 | 269 | 4 |
| 934 | 271 | 3 |
| 935 | 153 | 2 |
| 936 | >10000 | 147 |
| 937 | 133 | 2 |
| 938 | 68 | 1 |
| 939 | >10000 | 642 |
| 940 | 44 | <1 |
| 941 | 19 | <1 |
| 942 | 587 | 8 |
| 943 | 836 | 35 |
| 944 | 209 | <1 |
| 945 | 116 | 1 |
| 946 | 120 | 1 |
| 947 | 207 | <1 |
| 948 | 282 | 3 |
| 949 | 62 | 1 |
| 950 | 70 | 1 |
| 951 | 159 | 2 |
| 952 | 62 | <1 |
| 953 | 240 | <1 |
| 954 | 213 | <1 |
| 955 | 399 | <1 |
| 956 | 31 | <1 |
| 957 | 173 | <1 |
| 958 | 219 | 1 |
| 959 | 206 | <1 |
| 960 | 316 | 1 |
| 961 | 382 | 2 |
| 962 | >10000 | 650 |
| 963 | >10000 | 394 |
| 964 | 68 | 1 |
| 965 | 26 | <1 |
| 966 | >10000 | 2 |
| 967 | 156 | 3 |
| 968 | 81 | 1 |
| 969 | n/a | <1 |
| 970 | 57 | <1 |
| 971 | 74 | <1 |
| 972 | 12 | <1 |
| 973 | 1907 | 2 |
| 974 | 112 | 1 |
| 975 | 67 | <1 |

What is claimed:
1. A compound of Formula (I)

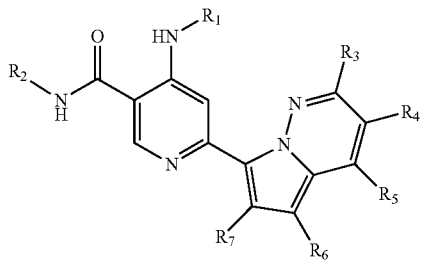

wherein:
$R^1$ and $R^2$ are each independently selected from:
a) $C_{1-10}$ alkyl optionally substituted with $Z^1$;
b) $C_{3-10}$ cycloalkyl optionally substituted with $Z^1$;
c) 5-10 membered heteroaryl optionally substituted with $Z^1$;
d) $C_{6-10}$ aryl optionally substituted with $Z^1$;
e) 4-7 membered monocyclic heterocyclyl optionally substituted with $Z^1$;
f) 6-12 membered bicyclic heterocyclyl optionally substituted with $Z^1$; or
g) $-N(R^{12})(R^{12})$, $-S(O)_2R^{12}$, $-S(O)_2N(R^{12})(R^{12})$, or $-H$;

$R^3$ and $R^4$ are each independently selected from:
a) H, halo, $-NO_2$, $-CN$, $-O-R^{12}$, $-C(O)-R^{12}$, $-C(O)-N(R^{12})(R^{12})$, $-N(R^{12})(R^{12})$, $-N(R^{12})C(O)-R^{12}$, $-N(R^{12})C(O)O-R^{12}$, $-N(R^{12})S(O)_2(R^{12})$, $-N(R^{12})C(O)-N(R^{12})(R^{12})$, $-S(O)_2R^{12}$ or $-S(O)_2N(R^{12})(R^{12})$;
b) $C_{1-9}$ alkyl optionally substituted with $Z^1$;
c) $C_{2-9}$ alkynyl optionally substituted with $Z^1$;
d) $C_{2-9}$ alkenyl optionally substituted with $Z^1$;
e) 5-10 membered heteroaryl optionally substituted with $Z^1$;
f) $C_{6-10}$ aryl optionally substituted with $Z^1$;
g) 4-12 membered heterocyclyl optionally substituted with $Z^1$; or
h) $C_{3-10}$ cycloalkyl optionally substituted with $Z^1$;

$R^5$, $R^6$ and $R^7$ are each independently selected from:
a) H, halo, $-NO_2$, $-CN$, $-O-R^{12}$, $-C(O)-R^{12}$, $-C(O)-N(R^{12})(R^{12})$, $-N(R^{12})(R^{12})$, $-N(R^{12})C(O)-R^{12}$, $-N(R^{12})C(O)O-R^{12}$, or $-N(R^{12})S(O)_2(R^{12})$;
b) $C_{1-5}$ alkyl optionally substituted with $Z^1$; or
c) Cyclopropyl, oxetanyl or azetidinyl optionally substituted with $Z^1$;

$Z^1$ is independently oxo, halo, $-NO_2$, $-N_3$, $-CN$, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, $-O-R^{12}$, $-C(O)-R^{12}$, $-C(O)O-R^{12}$, $-C(O)-N(R^{12})(R^{12})$, $-N(R^{12})(R^{12})$, $-N(R^{12})_2(R^{12})^+$, $-N(R^{12})C(O)-R^{12}$, $-N(R^{12})C(O)O-R^{12}$, $-N(R^{12})C(O)N(R^{12})(R^{12})$, $-N(R^{12})S(O)_2(R^{12})$, $-NR^{12}S(O)_2N(R^{12})(R^{12})$, $-NR^{12}S(O)_2O(R^{12})$, $-OC(O)R^{12}$, $-OC(O)OR^{12}$, $-OC(O)-N(R^{12})(R^{12})$, $-Si(R^{12})_3$, $-S-R^{12}$, $-S(O)R^{12}$, $-S(O)(NH)R^{12}$, $-S(O)_2R^{12}$ or $-S(O)_2N(R^{12})(R^{12})$;
wherein any alkyl, alkenyl, alkynyl, cycloalkyl, haloalkyl, aryl, heteroaryl or heterocyclyl is optionally substituted with $Z^{1a}$;

each $Z^{1a}$ is independently oxo, halo, $-NO_2$, $-CN$, $-N_3$, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, $-O-R^{12}$, $-C(O)R^{12}$, $-C(O)O-R^{12}$, $-C(O)N(R^{12})(R^{12})$, $-N(R^{12})(R^{12})$, $-N(R^{12})_2(R^{12})^+$, $-N(R^{12})-C(O)R^{12}$, $-N(R^{12})C(O)O(R^{12})$, $-N(R^{12})C(O)N(R^{12})(R^{12})$, $-N(R^{12})S(O)_2(R^{12})$, $-N(R^{12})S(O)_2-N(R^{12})(R^{12})$, $-N(R^{12})S(O)_2O(R^{12})$, $-OC(O)R^{12}$, $-OC(O)OR^{12}$, $-OC(O)-N(R^{12})(R^{12})$, $-Si(R^{12})_3$, $-S-R^{12}$, $-S(O)R^{12}$, $-S(O)(NH)R^{12}$, $-S(O)_2R^{12}$ or $-S(O)_2N(R^{12})(R^{12})$;
wherein any alkyl, alkenyl, alkynyl, cycloalkyl, haloalkyl, aryl, heteroaryl or heterocyclyl is optionally substituted with $Z^{1b}$;

each $R^{12}$ is independently H, $C_{1-9}$ alkyl, $C_{2-6}$ alkenyl, $C_{2-6}$ alkynyl, $C_{3-15}$ cycloalkyl, aryl, heteroaryl or heterocyclyl;
wherein any alkyl, alkenyl, alkynyl, cycloalkyl, aryl, heteroaryl or heterocyclyl is optionally substituted with $Z^{1a}$;

each $Z^{1b}$ is independently oxo, hydroxy, halo, $-NO_2$, $-N_3$, $-CN$, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, $-O(C_{1-9}$ alkyl), $-O(C_{2-6}$ alkenyl), $-O(C_{2-6}$ alkynyl), $-O(C_{3-15}$ cycloalkyl), $-O(C_{1-8}$ haloalkyl), $-O(aryl)$, $-O(heteroaryl)$, $-O(heterocyclyl)$, $-NH_2$, $-NH(C_{1-9}$ alkyl), $-NH(C_{2-6}$ alkenyl), $-NH(C_{2-6}$ alkynyl), $-NH(C_{3-15}$ cycloalkyl), $-NH(C_{1-8}$ haloalkyl), $-NH(aryl)$, $-NH(heteroaryl)$, $-NH(heterocyclyl)$, $-N(C_{1-9}$ alkyl)$_2$, $-N(C_{3-15}$ cycloalkyl)$_2$, $-N(C_{2-6}$ alkenyl)$_2$, $-N(C_{2-6}$ alkynyl)$_2$, $-N(C_{3-15}$ cycloalkyl)$_2$, $-N(C_{1-8}$ haloalkyl)$_2$, $-N(aryl)_2$, $-N(heteroaryl)_2$, $-N(heterocyclyl)_2$, $-N(C_{1-9}$ alkyl)$(C_{3-15}$ cycloalkyl), $-N(C_{1-9}$ alkyl)$(C_{2-6}$ alkenyl), $-N(C_{1-9}$ alkyl)$(C_{2-6}$ alkynyl), $-N(C_{1-9}$ alkyl)$(C_{3-15}$ cycloalkyl), $-N(C_{1-9}$ alkyl)$(C_{1-8}$ haloalkyl), $-N(C_{1-9}$ alkyl)(aryl), $-N(C_{1-9}$ alkyl)(heteroaryl), $-N(C_{1-9}$ alkyl)(heterocyclyl), $-C(O)(C_{1-9}$ alkyl), $-C(O)(C_{2-6}$ alkenyl), $-C(O)(C_{2-6}$ alkynyl), $-C(O)(C_{3-15}$ cycloalkyl), $-C(O)(C_{1-8}$ haloalkyl), $-C(O)(aryl)$, $-C(O)(heteroaryl)$, $-C(O)(heterocyclyl)$, $-C(O)O(C_{1-9}$ alkyl), $-C(O)O(C_{2-6}$ alkenyl), $-C(O)O(C_{2-6}$ alkynyl), $-C(O)O(C_{3-15}$ cycloalkyl), $-C(O)O(C_{1-8}$ haloalkyl), $-C(O)O(aryl)$, $-C(O)O(heteroaryl)$, $-C(O)O(heterocyclyl)$, $-C(O)NH_2$, $-C(O)NH(C_{1-9}$ alkyl), $-C(O)NH(C_{2-6}$ alkenyl), $-C(O)NH(C_{2-6}$ alkynyl), $-C(O)NH(C_{3-15}$ cycloalkyl), $-C(O)NH(C_{1-8}$ haloalkyl), $-C(O)NH(aryl)$, $-C(O)NH(heteroaryl)$, $-C(O)NH(heterocyclyl)$, $-C(O)N(C_{1-9}$ alkyl)$_2$, $-C(O)N(C_{3-15}$ cycloalkyl)$_2$, $-C(O)N(C_{2-6}$ alkenyl)$_2$, $-C(O)N(C_{2-6}$ alkynyl)$_2$, $-C(O)N(C_{3-15}$ cycloalkyl)$_2$, $-C(O)N(C_{1-8}$ haloalkyl)$_2$, $-C(O)N(aryl)_2$, $-C(O)N(heteroaryl)_2$, $-C(O)N(heterocyclyl)_2$, $-NHC(O)(C_{1-9}$ alkyl), $-NHC(O)(C_{2-6}$ alkenyl), $-NHC(O)(C_{2-6}$ alkynyl), $-NHC(O)(C_{3-15}$ cycloalkyl), $-NHC(O)(C_{1-8}$ haloalkyl), $-NHC(O)(aryl)$, $-NHC(O)(heteroaryl)$, $-NHC(O)(heterocyclyl)$, $-NHC(O)O(C_{1-9}$ alkyl), $-NHC(O)O(C_{2-6}$ alkenyl), $-NHC(O)O(C_{2-6}$ alkynyl), $-NHC(O)O(C_{3-15}$ cycloalkyl), $-NHC(O)O(C_{1-8}$ haloalkyl), $-NHC(O)O(aryl)$, $-NHC(O)O(heteroaryl)$, $-NHC(O)O(heterocyclyl)$, $-NHC(O)NH(C_{1-9}$ alkyl), $-NHC(O)NH(C_{2-6}$ alkenyl), $-NHC(O)NH(C_{2-6}$ alkynyl), $-NHC(O)NH(C_{3-15}$ cycloalkyl), $-NHC(O)NH(C_{1-8}$ haloalkyl), $-NHC(O)NH(aryl)$, $-NHC(O)NH(heteroaryl)$, $-NHC(O)NH(heterocyclyl)$, $-SH$, $-S(C_{1-9}$ alkyl), $-S(C_{2-6}$ alkenyl), —S($C_{2-6}$ alkynyl), —S($C_{3-15}$ cycloalkyl), —S($C_{1-8}$ haloalkyl), —S(aryl), —S(heteroaryl), —S(heterocyclyl), —NHS(O)($C_{1-9}$ alkyl), —N($C_{1-9}$ alkyl)(S(O)($C_{1-9}$ alkyl), —S(O)N($C_{1-9}$ alkyl)$_2$, —S(O)($C_{1-9}$ alkyl), —S(O)(NH)($C_{1-9}$ alkyl), —S(O)($C_{2-6}$ alkenyl), —S(O)($C_{2-6}$ alkynyl), —S(O)($C_{3-15}$ cycloalkyl), —S(O)($C_{1-8}$ haloalkyl), —S(O)(aryl), —S(O)(heteroaryl), —S(O)(heterocyclyl), —S(O)$_2$($C_{1-9}$ alkyl), —S(O)$_2$($C_{2-6}$ alkenyl), —S(O)$_2$($C_{2-6}$ alkynyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), or —S(O)$_2$N($C_{1-9}$ alkyl)$_2$;

wherein any alkyl, cycloalkyl, aryl, heteroaryl, or heterocyclyl is optionally substituted with one or more halo, $C_{1-9}$ alkyl, $C_{1-8}$ haloalkyl, —OH, —NH$_2$, —NH($C_{1-9}$ alkyl), —NH($C_{3-15}$ cycloalkyl), —NH($C_{1-8}$ haloalkyl), —NH(aryl), —NH(heteroaryl), —NH(heterocyclyl), —N($C_{1-9}$ alkyl)$_2$, —N($C_{3-15}$ cycloalkyl)$_2$, —NHC(O)($C_{3-15}$ cycloalkyl), —NHC(O)($C_{1-8}$ haloalkyl), —NHC(O)(aryl), —NHC(O)(heteroaryl), —NHC(O)(heterocyclyl), —NHC(O)O($C_{1-9}$ alkyl), —NHC(O)O($C_{2-6}$ alkynyl), —NHC(O)O($C_{3-15}$ cycloalkyl), —NHC(O)O($C_{1-8}$ haloalkyl), —NHC(O)O(aryl), —NHC(O)O(heteroaryl), —NHC(O)O(heterocyclyl), —NHC(O)NH($C_{1-9}$ alkyl), —S(O)(NH)($C_{1-9}$ alkyl), S(O)$_2$($C_{1-9}$ alkyl), —S(O)$_2$($C_{3-15}$ cycloalkyl), —S(O)$_2$($C_{1-8}$ haloalkyl), —S(O)$_2$(aryl), —S(O)$_2$(heteroaryl), —S(O)$_2$(heterocyclyl), —S(O)$_2$NH($C_{1-9}$ alkyl), —S(O)$_2$N($C_{1-9}$ alkyl)$_2$, —O($C_{3-15}$ cycloalkyl), —O($C_{1-8}$ haloalkyl), —O(aryl), —O(heteroaryl), —O(heterocyclyl), or —O($C_{1-9}$ alkyl); and with the proviso that when $R^1$ is $C_3$ alkyl, $R^2$ is $C_5$ alkyl substituted with F and hydroxyl, $R^3$, $R^5$, $R^6$, $R^7$ are H, and $R^4$ is CN, then $R^1$ is substituted with oxo, halo, —NO$_2$, —N$_3$, —CN, $C_{2-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^{12}$, —C(O)—$R^{12}$, —C(O)O—$R^{12}$, —C(O)—N($R^{12}$)($R^{12}$), —N($R^{12}$)($R^{12}$), —N($R^{12}$)$_2$($R^{12}$)$^+$, —N($R^{12}$)C(O)—$R^{12}$, —N($R^{12}$)C(O)O—$R^{12}$, —N($R^{12}$)C(O)N($R^{12}$)($R^{12}$), —N($R^{12}$)S(O)$_2$($R^{12}$), —NR$^{12}$S(O)$_2$N($R^{12}$)($R^{12}$), —NR$^{12}$S(O)$_2$O($R^{12}$), —OC(O)$R^{12}$, —OC(O)O$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2$$R^{12}$ or —S(O)$_2$N($R^{12}$)($R^{12}$);

wherein any alkyl, alkenyl, alkynyl, cycloalkyl, haloalkyl, aryl, heteroaryl or heterocyclyl is optionally substituted with $Z^{1a}$;

or a pharmaceutically acceptable salt, stereoisomer, mixture of stereoisomers, or deuterated analog thereof.

2. The compound of claim 1, or a pharmaceutically acceptable salt, stereoisomer, mixture of stereoisomers, or deuterated analog thereof, wherein:

$R^1$ is $C_{1-10}$ alkyl optionally substituted with $Z^1$, with the proviso that when $R^1$ is $C_3$ alkyl, $R^2$ is $C_5$ alkyl substituted with F and hydroxyl, $R^3$, $R^5$, $R^6$, $R^7$ are H, and $R^4$ is CN, then $R^1$ is substituted with oxo, halo, —NO$_2$, —N$_3$, —CN, $C_{2-9}$ alkyl, $C_{2-6}$ alkenyl, $C_{2-6}$ alkynyl, $C_{3-15}$ cycloalkyl, $C_{1-8}$ haloalkyl, aryl, heteroaryl, 4-20 membered heterocyclyl, —O—$R^{12}$, —C(O)$R^{12}$, C(O)O—$R^{12}$, —C(O)—N($R^{12}$)($R^{12}$), —N($R^{12}$)($R^{12}$), —N($R^{12}$)$_2$($R^{12}$)$^+$, —N($R^{12}$)C(O)—$R^{12}$, —N($R^{12}$)C(O)O—$R^{12}$, —N($R^{12}$)C(O)N($R^{12}$)($R^{12}$), —N($R^{12}$)S(O)$_2$($R^{12}$), —NR$^{12}$S(O)$_2$N($R^{12}$)($R^{12}$), —NR$^{12}$S(O)$_2$O($R^{12}$), —OC(O)$R^{12}$, —OC(O)O$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2$$R^{12}$ or —S(O)$_2$N($R^{12}$)($R^{12}$);

wherein any alkyl, alkenyl, alkynyl, cycloalkyl, haloalkyl, aryl, heteroaryl or 4-20 membered heterocyclyl is optionally substituted with $Z^{1a}$.

3. The compound of claim 1, or a pharmaceutically acceptable salt, stereoisomer, mixture of stereoisomers, or deuterated analog thereof, wherein $R^1$ is methyl.

4. The compound of claim 1, or a pharmaceutically acceptable salt, stereoisomer, mixture of stereoisomers, or deuterated analog thereof, wherein $R^1$ is $C_{6-10}$ alkyl optionally substituted with $Z^1$.

5. The compound of claim 1, or a pharmaceutically acceptable salt, stereoisomer, mixture of stereoisomers, or deuterated analog thereof, wherein:

$R^1$ is $C_{1-5}$ alkyl substituted with one or more substituents selected from —Cl, oxo, —CN, $C_{2-6}$ alkenyl, $C_{2-6}$ alkynyl, cyclopropyl, naphthyl, heteroaryl, nitrogen or sulfur containing monocyclic 4-20 membered heterocyclyl, bicyclic 4-20 membered heterocyclyl, $C_{7-15}$ cycloalkyl, —O—$R^9$, —C(O)—$R^{12}$, —C(O)O—$R^{12}$, —C(O)—N($R^{12}$)($R^{12}$), —N($R^{12}$)($R^{12}$), —N($R^{12}$)$_2$($R^{12}$)$^+$, —N($R^{12}$)C(O)—$R^{12}$, —N($R^{12}$)C(O)O—$R^{12}$, —N($R^{12}$)C(O)N($R^{12}$)($R^{12}$), —N($R^{12}$)S(O)$_2$($R^{12}$), —NR$^{12}$S(O)$_2$N($R^{12}$)($R^{12}$), —NR$^{12}$S(O)$_2$O($R^{12}$), —OC(O)$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2$$R^{12}$ or —S(O)$_2$N($R^{12}$)($R^{12}$);

$R^9$ at each occurrence is independently $C_{1-9}$ alkyl, $C_{2-6}$ alkenyl, $C_{2-6}$ alkynyl, $C_{1-6}$ haloalkyl, $C_{3-15}$ cycloalkyl, aryl, 4-20 membered heterocyclyl, or heteroaryl;

wherein each $C_{1-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl is optionally substituted with $Z^{1a}$;

wherein said $C_{1-5}$ alkyl is also optionally substituted with $Z^1$; and wherein each said $C_{2-6}$ alkenyl, $C_{2-6}$ alkynyl, cyclopropyl, naphthyl, heteroaryl, nitrogen or sulfur containing monocyclic 4-20 heterocyclyl, bicyclic 4-20 heterocyclyl, or $C_{7-15}$ cycloalkyl is optionally substituted with $Z^{1a}$.

6. The compound of claim 1, or a pharmaceutically acceptable salt, stereoisomer, mixture of stereoisomers, or deuterated analog thereof, wherein:

$R^1$ is $C_{1-5}$ alkyl optionally substituted with $Z^1$;

wherein said $C_{1-5}$ alkyl is substituted with one or more $C_{4-6}$ cycloalkyl, oxetanyl, tetrahydrofuranyl, tetrahydropyranyl, or phenyl;

wherein said $C_{4-6}$ cycloalkyl, oxetanyl, tetrahydrofuranyl, tetrahydropyranyl, or phenyl is optionally substituted with $Z^{1a}$;

wherein said $C_{4-6}$ cycloalkyl, oxetanyl, tetrahydrofuranyl, tetrahydropyranyl, or phenyl is substituted by one or more halo, oxo, —CN, $C_{2-6}$ alkyl, $C_{2-6}$ alkenyl, $C_{2-6}$ alkynyl, $C_{3-7}$ cycloalkyl, aryl, heteroaryl, 4-20 membered heterocyclyl, —O—$R^9$, —C(O)—$R^{12}$, —C(O)O—$R^{12}$, —C(O)—N($R^{12}$)($R^{12}$), —N($R^{12}$)($R^{12}$), —N($R^{12}$)$_2$($R^{12}$)$^+$, —N($R^{12}$)C(O)—$R^{12}$, —N($R^{12}$)C(O)O—$R^{12}$, —N($R^{12}$)C(O)N($R^{12}$)($R^{12}$), —N($R^{12}$)S(O)$_2$($R^{12}$), —NR$^{12}$S(O)$_2$N($R^{12}$)($R^{12}$), —NR$^{12}$S(O)$_2$O($R^{12}$), —OC(O)$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2$$R^{12}$ or —S(O)$_2$N($R^{12}$)($R^{12}$); and wherein said $C_{2-6}$ alkyl, $C_{2-6}$ alkenyl, $C_{2-6}$ alkynyl, $C_{3-7}$ cycloalkyl, aryl, heteroaryl, or heterocyclyl is optionally substituted with $Z^{1b}$.

7. The compound of claim 1, or a pharmaceutically acceptable salt, stereoisomer, mixture of stereoisomers, or deuterated analog thereof, wherein:

$R^1$ is $C_{1-5}$ alkyl optionally substituted with F or —OH and substituted with one or more substituents selected from $C_{4-6}$ cycloalkyl, oxetanyl, tetrahydrofuranyl, tetrahydropyranyl, or phenyl; wherein said $C_{4-6}$ cycloalkyl, oxetanyl, tetrahydrofuranyl, tetrahydropyranyl, or phenyl is substituted with two or more substituents selected from —OH and —CH$_3$ and optionally substituted with $Z^{1a}$.

8. The compound of claim 1, or a pharmaceutically acceptable salt, stereoisomer, mixture of stereoisomers, or deuterated analog thereof, wherein $R^1$ is $C_{3-10}$ cycloalkyl optionally substituted with $Z^1$.

9. The compound of claim 1, or a pharmaceutically acceptable salt, stereoisomer, mixture of stereoisomers, or deuterated analog thereof, wherein:
$R^1$ is $C_{7-10}$ cycloalkyl optionally substituted with $Z^1$, wherein when said $C_7$-$C_{10}$ cycloalkyl is bicyclo[2.2.1]heptanyl, then said $C_{7-10}$ cycloalkyl is substituted with at least one of oxo, —Cl, —NO$_2$, —CN, —N$_3$, $C_{5-9}$ alkyl, $C_{2-6}$ alkenyl, $C_{2-6}$ alkynyl, $C_{7-15}$ cycloalkyl, $C_{5-8}$ haloalkyl, aryl, pyrazolyl, —O—R$^9$, —C(O)O—R$^{12}$, —C(O)N(R$^{12}$)(R$^{12}$), —N(R$^{12}$)(R$^{12}$), —N(R$^{12}$)$_2$(R$^{12}$)$^+$, —N(R$^{12}$)—C(O)R$^{12}$, —N(R$^{12}$)C(O)O(R$^{12}$), —N(R$^{12}$)C(O)N(R$^{12}$)(R$^{12}$), —N(R$^{12}$)S(O)$_2$(R$^{12}$), —N(R$^{12}$)S(O)$_2$—N(R$^{12}$)(R$^{12}$), —N(R$^{12}$)S(O)$_2$O(R$^{12}$), —OC(O)R$^{12}$, —OC(O)OR$^{12}$, —OC(O)—N(R$^{12}$)(R$^{12}$), —Si(R$^{12}$)$_3$, —S—R$^{12}$, —S(O)R$^{12}$, —S(O)(NH)R$^{12}$, or —S(O)$_2$N(R$^{12}$)(R$^{12}$).

10. The compound of claim 1, or a pharmaceutically acceptable salt, stereoisomer, mixture of stereoisomers, or deuterated analog thereof, wherein:
$R^1$ is $C_{3-6}$ cycloalkyl substituted with one or more —O—R$^{16}$;
wherein said $C_{3-6}$ cycloalkyl is optionally substituted with $Z^1$;
$R^{16}$ at each occurrence is independently $C_{5-9}$ alkyl, $C_{2-6}$ alkenyl, $C_{2-6}$ alkynyl, $C_{1-6}$ haloalkyl, $C_{3-15}$ cycloalkyl, aryl, 4-20 membered heterocyclyl, or heteroaryl;
wherein each $C_{5-9}$ alkyl, $C_{2-6}$ alkenyl, $C_{2-6}$ alkynyl, $C_{1-6}$ haloalkyl, $C_{3-15}$ cycloalkyl, aryl, heterocyclyl, or heteroaryl is optionally substituted with $Z^{1a}$.

11. The compound of claim 1, or a pharmaceutically acceptable salt, stereoisomer, mixture of stereoisomers, or deuterated analog thereof, wherein:
$R^1$ is $C_{3-6}$ cycloalkyl substituted with one or more —C(O)—R$^{11}$;
wherein said $C_{3-6}$ cycloalkyl is optionally substituted with $Z^1$;
wherein $R^{11}$ at each occurrence is independently $C_{1-9}$ alkyl, $C_{2-6}$ alkenyl, $C_{2-6}$ alkynyl, $C_{3-15}$cycloalkyl, aryl, 4-20 membered heterocyclyl, or heteroaryl,
wherein each $C_{1-9}$ alkyl is optionally substituted with —NO$_2$, —N$_3$, —CN, $C_{2-6}$ alkenyl, $C_{2-6}$ alkynyl, $C_{3-15}$ cycloalkyl, $C_{4-8}$ haloalkyl, aryl, heteroaryl, 4-20 membered heterocyclyl, —O—R$^{12}$, —C(O)—R$^{12}$, —C(O)O—R$^{12}$, —C(O)—N(R$^{12}$)(R$^{12}$), —N(R$^{12}$)(R$^{12}$), —N(R$^{12}$)$_2$(R$^{12}$)$^+$, —N(R$^{12}$)C(O)—R$^{12}$, —N(R$^{12}$)C(O)O—R$^{12}$, —N(R$^{12}$)C(O)N(R$^{12}$)(R$^{12}$), —N(R$^{12}$)S(O)$_2$(R$^{12}$), —NR$^{12}$S(O)$_2$N(R$^{12}$)(R$^{12}$), —NR$^{12}$S(O)$_2$O(R$^{12}$), —OC(O)R$^{12}$, —OC(O)—N(R$^{12}$)(R$^{12}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{12}$)(R$^{12}$); and
wherein each said $C_{2-6}$ alkenyl, $C_{2-6}$ alkynyl, $C_{3-15}$ cycloalkyl, aryl, heterocyclyl, or heteroaryl is optionally substituted with $Z^{1a}$.

12. The compound of claim 1, or a pharmaceutically acceptable salt, stereoisomer, mixture of stereoisomers, or deuterated analog thereof, wherein:
$R^1$ is $C_{3-6}$ cycloalkyl substituted with one or more oxo, $C_{5-6}$ alkyl, $C_{2-6}$ alkenyl, $C_{2-6}$ alkynyl, $C_{3-15}$ cycloalkyl, aryl, heteroaryl, 4-20 membered heterocyclyl, —C(O)O—R$^{12}$, —C(O)—N(R$^9$)(R$^9$), —C(O)N(H)(C$_{4-9}$ alkyl), —C(O)N(H)(C$_{3-10}$ cycloalkyl), —C(O)N(H)(4-20 membered heterocyclyl), —C(O)N(H)(aryl), —C(O)N(H)(heteroaryl), —N(R$^{12}$)(R$^{12}$), —N(R$^{12}$)$_2$(R$^{12}$)$^+$, —N(R$^{12}$)C(O)—R$^{12}$, —N(R$^{12}$)C(O)O—R$^{12}$, —N(R$^{12}$)C(O)N(R$^{12}$)(R$^{12}$), —N(R$^{12}$)S(O)$_2$(R$^{12}$), —NR$^{12}$S(O)$_2$N(R$^{12}$)(R$^{12}$), —NR$^{12}$S(O)$_2$O(R$^{12}$), —OC(O)R$^{12}$, —OC(O)—N(R$^{12}$)(R$^{12}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{12}$)(R$^{12}$);
wherein said $C_{5-6}$ alkyl, $C_{2-6}$ alkenyl, $C_{2-6}$ alkynyl, $C_{3-15}$ cycloalkyl, aryl, heteroaryl, heterocyclyl, —C(O)N(H)(C$_{4-9}$ alkyl), —C(O)N(H)(C$_{3-10}$ cycloalkyl), —C(O)N(H)(4-20 membered heterocyclyl), —C(O)N(H)(aryl), or —C(O)N(H)(heteroaryl) is optionally substituted with $Z^{1a}$; and wherein said $C_{3-6}$ cycloalkyl is optionally substituted with $Z^1$;
wherein when $C_{3-6}$ cycloalkyl is bicyclo[1.1.1]pentanyl; then said bicyclo[1.1.1]pentanyl is substituted with one or more oxo, —NO$_2$, —N$_3$, $C_{5-9}$ alkyl, $C_{2-6}$ alkenyl, $C_{2-6}$ alkynyl, $C_{7-15}$ cycloalkyl, $C_{5-8}$ haloalkyl, aryl, pyrazolyl, —O—R$^{16}$, —C(O)R$^1$, —C(O)O—R$^{12}$, —C(O)N(R$^9$)(R$^9$), —C(O)N(H)(C$_4$ alkyl), —C(O)N(H)(R$^{16}$), —N(R$^{12}$)(R$^{12}$), —N(R$^{12}$)$_2$(R$^{12}$)$^+$, —N(R$^{12}$)—C(O)R$^{12}$, —N(R$^{12}$)C(O)O(R$^{12}$), —N(R$^{12}$)C(O)N(R$^{12}$)(R$^{12}$), —N(R$^{12}$)S(O)$_2$(R$^{12}$), —N(R$^{12}$)S(O)$_2$—N(R$^{12}$)(R$^{12}$), —N(R$^{12}$)S(O)$_2$O(R$^{12}$), —OC(O)R$^{12}$, —OC(O)OR$^{12}$, —OC(O)—N(R$^{12}$)(R$^{12}$), —Si(R$^{12}$)$_3$, —S—R$^{12}$, —S(O)R$^{12}$, —S(O)(NH)R$^{12}$, or —S(O)$_2$N(R$^{12}$)(R$^{12}$).

13. The compound of claim 1, or a pharmaceutically acceptable salt, stereoisomer, mixture of stereoisomers, or deuterated analog thereof, wherein
$R^1$ is $C_{3-6}$ cycloalkyl substituted with $C_4$ alkyl, wherein said $C_4$ alkyl is optionally substituted with halo, —NO$_2$, —CN, —N$_3$, $C_{2-6}$ alkenyl, $C_{2-6}$ alkynyl, $C_{3-15}$ cycloalkyl, aryl, heteroaryl, 4-20 membered heterocyclyl, —O—R$^9$, —C(O)—R$^{12}$, —C(O)O—R$^{12}$, —C(O)—N(R$^{12}$)(R$^{12}$), —N(R$^{12}$)(R$^{12}$), —N(R$^{12}$)$_2$(R$^{12}$)$^+$, —N(R$^{12}$)C(O)—R$^{12}$, —N(R$^{12}$)C(O)O—R$^{12}$, —N(R$^{12}$)C(O)N(R$^{12}$)(R$^{12}$), —N(R$^{12}$)S(O)$_2$(R$^{12}$), —NR$^{12}$S(O)$_2$N(R$^{12}$)(R$^{12}$), —NR$^{12}$S(O)$_2$O(R$^{12}$), —OC(O)R$^{12}$, —OC(O)—N(R$^{12}$)(R$^{12}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{12}$)(R$^{12}$);
wherein said $C_{2-6}$ alkenyl, $C_{2-6}$ alkynyl, $C_{3-15}$ cycloalkyl, aryl, heteroaryl, or heterocyclyl is optionally substituted with $Z^{1a}$; and
wherein said $C_{3-6}$ cycloalkyl is optionally substituted with $Z^1$;
wherein when said $C_{3-6}$ cycloalkyl is bicyclo[1.1.1]pentanyl substituted with $C_4$ alkyl then said $C_4$ alkyl is further substituted with oxo, —NO$_2$, —N$_3$, $C_{5-9}$ alkyl, $C_{2-6}$ alkenyl, $C_{2-6}$ alkynyl, $C_{7-15}$ cycloalkyl, $C_{5-8}$ haloalkyl, aryl, heteroaryl, —O—R$^9$, —C(O)R$^{12}$, —C(O)O—R$^{12}$, —C(O)N(R$^{12}$)(R$^{12}$), —N(R$^{12}$)(R$^{12}$), —N(R$^{12}$)$_2$(R$^{12}$)$^+$, —N(R$^{12}$)—C(O)R$^{12}$, —N(R$^{12}$)C(O)O(R$^{12}$), —N(R$^{12}$)C(O)N(R$^{12}$)(R$^{12}$), —N(R$^{12}$)S(O)$_2$(R$^{12}$), —N(R$^{12}$)S(O)$_2$—N(R$^{12}$)(R$^{12}$), —N(R$^{12}$)S(O)$_2$O(R$^{12}$), —OC(O)R$^{12}$, —OC(O)OR$^{12}$, —OC (O)—N($R^{12}$)($R^{12}$), —Si($R^{12}$)$_3$, —S—$R^{12}$, —S(O)$R^{12}$, —S(O)(NH)$R^{12}$, or —S(O)$_2$N($R^{12}$)($R^{12}$).

14. The compound of claim 1, or a pharmaceutically acceptable salt, stereoisomer, mixture of stereoisomers, or deuterated analog thereof, wherein $R^1$ is $C_{3-6}$ cycloalkyl optionally substituted with $Z^1$; and
wherein said $C_{3-6}$ cycloalkyl is substituted with four or more substituents selected from the group consisting of F, —OH, —Cl, —CN, $C_{1-3}$ alkyl, $C_{1-3}$ fluoroalkyl, $C_{1-4}$ hydroxyalkyl, $C_{1-4}$ alkoxy, —C(O)NH$_2$, —C(O)NH($C_{1-3}$ alkyl); and —C(O)($C_{1-3}$ fluoroalkyl).

15. The compound of claim 1, or a pharmaceutically acceptable salt, stereoisomer, mixture of stereoisomers, or deuterated analog thereof, wherein:
$R^1$ is $C_{3-6}$ cycloalkyl substituted with $C_{1-3}$ fluoroalkyl, or —C(O)($C_{1-3}$ fluoroalkyl)
wherein said $C_{3-6}$ cycloalkyl is also optionally substituted with $Z^1$;
wherein said $C_{1-3}$ fluoroalkyl or —C(O)($C_{1-3}$ fluoroalkyl) is further substituted with at least one oxo, —Cl, —NO$_2$, —CN, —N$_3$, $C_{3-9}$ alkyl, $C_{2-6}$ alkenyl, $C_{2-6}$ alkynyl, $C_{3-15}$ cycloalkyl, $C_{3-8}$ haloalkyl, aryl, heteroaryl, 4-20 membered heterocyclyl, —O—$R^{12}$, —C(O)$R^{12}$, —C(O)O—$R^{12}$, —C(O)N($R^{12}$)($R^{12}$), —N($R^{12}$)($R^{12}$), —N($R^{12}$)$_2$($R^{12}$)$^+$, —N($R^{12}$)—C(O)$R^{12}$, —N($R^{12}$)C(O)O($R^{12}$), —N($R^{12}$)C(O)N($R^{12}$)($R^{12}$), —N($R^{12}$)S(O)$_2$($R^{12}$), —N($R^{12}$)S(O)$_2$—N($R^{12}$)($R^{12}$), —N($R^{12}$)S(O)$_2$O($R^{12}$), —OC(O)$R^{12}$, —OC(O)O$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2$$R^{12}$ or —S(O)$_2$N($R^{12}$)($R^{12}$); and
wherein said $C_{3-9}$ alkyl, $C_{2-6}$ alkenyl, $C_{2-6}$ alkynyl, $C_{3-15}$ cycloalkyl, $C_{3-8}$ haloalkyl, aryl, heteroaryl, heterocyclyl is optionally substituted with $Z^{1b}$.

16. The compound of claim 1, or a pharmaceutically acceptable salt, stereoisomer, mixture of stereoisomers, or deuterated analog thereof, wherein:
$R^1$ is $C_{3-6}$ cycloalkyl substituted with at least one $C_{1-3}$ alkyl or $C_{1-4}$ hydroxyalkyl wherein said $C_{3-6}$ cycloalkyl is optionally substituted with $Z^1$;
wherein said $C_{1-3}$ alkyl or $C_{1-4}$ hydroxyalkyl is further substituted with oxo, chloro, —NO$_2$, —CN, —N$_3$, $C_{4-9}$ alkyl, $C_{2-6}$ alkenyl, $C_{2-6}$ alkynyl, $C_{3-15}$ cycloalkyl, $C_{1-8}$ haloalkyl, aryl, heteroaryl, 4-20 membered heterocyclyl, —O—$R^9$, —C(O)$R^{12}$, —C(O)O—$R^{12}$, —C(O)N($R^{12}$)($R^{12}$), —N($R^{12}$)($R^{12}$), —N($R^{12}$)$_2$($R^{12}$)$^+$, —N($R^{12}$)—C(O)$R^{12}$, —N($R^{12}$)C(O)O($R^{12}$), —N($R^{12}$)C(O)N($R^{12}$)($R^{12}$), —N($R^{12}$)S(O)$_2$($R^{12}$), —N($R^{12}$)S(O)$_2$—N($R^{12}$)($R^{12}$), —N($R^{12}$)S(O)$_2$O($R^{12}$), —OC(O)$R^{12}$, —OC(O)O$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2$$R^{12}$ or —S(O)$_2$N($R^{12}$)($R^{12}$); and
wherein said $C_{4-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl is optionally substituted with $Z^{1b}$.

17. The compound of claim 1, or a pharmaceutically acceptable salt, stereoisomer, mixture of stereoisomers, or deuterated analog thereof, wherein $R^1$ is $C_{3-6}$ cycloalkyl substituted with at least one $C_{1-4}$ alkoxy or C(O)NH($C_{1-3}$ alkyl);
wherein said $C_{3-6}$ cycloalkyl is optionally substituted with $Z^1$ and wherein said $C_{1-4}$ alkoxy or C(O)NH($C_{1-3}$ alkyl) is further substituted with oxo, halo, —NO$_2$, —CN, —N$_3$, $C_{4-9}$ alkyl, $C_{2-6}$ alkenyl, $C_{2-6}$ alkynyl, $C_{3-15}$ cycloalkyl, $C_{1-8}$ haloalkyl, aryl, heteroaryl, 4-20 membered heterocyclyl, —O—$R^9$, —C(O)$R^{12}$, —C(O)O—$R^{12}$, —C(O)N($R^{12}$)($R^{12}$), —N($R^{12}$)($R^{12}$), —N($R^{12}$)$_2$($R^{12}$)$^+$, —N($R^{12}$)—C(O)$R^{12}$, —N($R^{12}$)C(O)O($R^{12}$), —N($R^{12}$)C(O)N($R^{12}$)($R^{12}$), —N($R^{12}$)S(O)$_2$($R^{12}$), —N($R^{12}$)S(O)$_2$—N($R^{12}$)($R^{12}$), —N($R^{12}$)S(O)$_2$O($R^{12}$), —N($R^{12}$)S(O)$_2$O($R^{12}$), —OC(O)$R^{12}$, —OC(O)O$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2$$R^{12}$ or —S(O)$_2$N($R^{12}$)($R^{12}$);
wherein said $C_{4-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl is optionally substituted with $Z^{1b}$.

18. The compound of claim 1, or a pharmaceutically acceptable salt, stereoisomer, mixture of stereoisomers, or deuterated analog thereof, wherein $R^1$ is 5-10 membered heteroaryl optionally substituted with $Z^1$.

19. The compound of claim 1, or a pharmaceutically acceptable salt, stereoisomer, mixture of stereoisomers, or deuterated analog thereof, wherein $R^1$ is imidazolyl, triazolyl, oxazolyl, isoxazolyl, pyridinyl, thiadiazole, oxadiazole, pyrimidinyl, pyridizinyl, pyrazinyl, isothiazolyl, tetrazolyl, thiophenyl, furanyl, triazinyl, or 8-10 membered heteroaryl optionally substituted with $Z^1$.

20. The compound of claim 1, or a pharmaceutically acceptable salt, stereoisomer, mixture of stereoisomers, or deuterated analog thereof, wherein $R^1$ is a 6 membered heteroaryl optionally substituted with $Z^1$.

21. The compound of claim 1, or a pharmaceutically acceptable salt, stereoisomer, mixture of stereoisomers, or deuterated analog thereof, wherein $R^1$ is 4-7 membered monocyclic heterocyclyl optionally substituted with $Z^1$.

22. The compound of claim 1, or a pharmaceutically acceptable salt, stereoisomer, mixture of stereoisomers, or deuterated analog thereof, wherein $R^1$ is azetidinyl, morpholinyl, thiomorpholinyl, 4-7 membered sultam, 4-7 membered cyclic carbamate, 4-7 membered cyclic carbonate, or 4-7 membered cyclic sulfide optionally substituted with $Z^1$.

23. The compound of claim 1, or a pharmaceutically acceptable salt, stereoisomer, mixture of stereoisomers, or deuterated analog thereof, wherein:
$R^1$ is 6-12 membered bicyclic heterocyclyl optionally substituted with $Z^1$;
wherein when said 6-12 membered bicyclic heterocyclyl is 4,5,6,7-tetrahydropyrazolo[1,5-a]pyrazinyl then said 6-12 membered bicyclic heterocyclyl is substituted with at least one oxo, $C_{3-6}$ cycloalkyl, or C(O)($C_{1-5}$ alkyl).

24. The compound of claim 1, or a pharmaceutically acceptable salt, stereoisomer, mixture of stereoisomers, or deuterated analog thereof, wherein:
$R^1$ is oxetanyl, tetrahydrofuranyl, tetrahydropyranyl, pyrrolidinyl, piperidinyl, pyrazolyl, or thiazolyl;
wherein said oxetanyl, tetrahydrofuranyl, tetrahydropyranyl, pyrrolidinyl, piperidinyl, pyrazolyl or thiazolyl, is substituted with one or more substituents selected from —Cl, oxo, —CN, $C_{5-9}$ alkyl, $C_{2-6}$ alkenyl, $C_{2-6}$ alkynyl, $C_{7-10}$ cycloalkyl, aryl, pyridinyl, pyridizinyl, 5-10 membered bicyclic heteroaryl, 5-membered heteroaryl, nitrogen or sulfur containing monocyclic 4-20 membered heterocyclyl, bicyclic heterocyclyl, —O—$R^9$, —C(O)—$R^{11}$, —C(O)O—$R^{12}$, —C(O)—N($R^{12}$)($R^{12}$), —N($R^{12}$)($R^{12}$), —N($R^{12}$)$_2$($R^{12}$)$^+$, —N($R^{12}$)C(O)—$R^{12}$, —N($R^{12}$)C(O)O—$R^{12}$, —N($R^{12}$)C(O)N($R^{12}$)($R^{12}$), —N($R^{12}$)S(O)$_2$($R^{12}$), —N$R^{12}$S(O)$_2$N($R^{12}$)($R^{12}$), —N$R^{12}$S(O)$_2$O($R^{12}$), —OC(O)$R^{12}$, —OC(O)—N($R^{12}$)($R^{12}$), —Si($R^{12}$)$_3$, —S—$R^{12}$, —S(O)$R^{12}$, —S(O)(NH)$R^{12}$, or —S(O)$_2$N($R^{12}$)($R^{12}$);
wherein said $C_{5-9}$ alkyl, $C_{2-6}$ alkenyl, $C_{2-6}$ alkynyl, $C_{7-10}$ cycloalkyl, aryl, pyridinyl, pyridizinyl, 5-10 membered bicyclic heteroaryl, 5-membered heteroaryl, nitrogen or sulfur containing monocyclic heterocyclyl or bicyclic 4-10 membered heterocyclyl is optionally substituted with $Z^{1a}$;
wherein said oxetanyl, tetrahydrofuranyl, tetrahydropyranyl, pyrrolidinyl, piperidinyl, pyrazolyl, thiazolyl, is optionally substituted with $Z^1$.

25. The compound of claim 1, or a pharmaceutically acceptable salt, stereoisomer, mixture of stereoisomers, or deuterated analog thereof, wherein:
$R^1$ is oxetanyl, tetrahydrofuranyl, tetrahydropyranyl, pyrrolidinyl, piperidinyl, pyrazolyl, or thiazolyl;
wherein said oxetanyl, tetrahydrofuranyl, tetrahydropyranyl, pyrrolidinyl, piperidinyl, pyrazolyl, or thiazolyl, is optionally substituted with $Z^1$;
wherein said oxetanyl, tetrahydrofuranyl, tetrahydropyranyl, pyrrolidinyl, piperidinyl, pyrazolyl, thiazolyl, is substituted with 3 or more substituents selected from F, —OH, $C_{1-4}$ alkyl, $C_{1-3}$ hydroxyalkyl, $C_{1-4}$ fluoroalkyl, —$(CH_2)_{1-3}O(C_{1-3}$ alkyl), —$C(O)(C_{1-3}$fluoroalkyl), —$S(O)_2(C_{1-3}$ alkyl), $C_{3-6}$ cycloalkyl, $C_{3-6}$ fluorocycloalkyl, oxetanyl, tetrahydrofuranyl, tetrahydropyranyl, pyrimidinyl, fluoropyrimidinyl, or methoxyprimidinyl.

26. The compound of claim 1, or a pharmaceutically acceptable salt, stereoisomer, mixture of stereoisomers, or deuterated analog thereof, wherein
$R^1$ is pyrrolidinyl, piperidinyl, pyrazolyl or thiazolyl;
wherein said pyrrolidinyl, piperidinyl, pyrazolyl or thiazolyl is optionally substituted with $Z^1$;
wherein said pyrrolidinyl, piperidinyl, pyrazolyl or thiazolyl is substituted with one or more substituents independently selected from —$(CH_2)_{1-3}O(C_{1-3}$ alkyl), —$S(O)_2(C_{1-3}$ alkyl), oxetanyl, tetrahydrofuranyl, tetrahydropyranyl, or $CH_2(C_{3-6}$ cycloalkyl); and
wherein said —$(CH_2)_{1-3}O(C_{1-3}$ alkyl), —$S(O)_2(C_{1-3}$ alkyl), oxetanyl, tetrahydrofuranyl, tetrahydropyranyl or $CH_2(C_{3-6}$ cycloalkyl) are independently substituted with one or more oxo, halo, —$NO_2$, —CN, —$N_3$, $C_{3-9}$ alkyl, $C_{2-6}$ alkenyl, $C_{2-6}$ alkynyl, $C_{3-15}$ cycloalkyl, $C_{1-8}$ haloalkyl, aryl, heteroaryl, 4-20 membered heterocyclyl, —O—$R^{12}$, —$C(O)R^{12}$, —$C(O)O$—$R^{12}$, —$C(O)N(R^{12})(R^{12})$, —$N(R^{12})(R^{12})$, —$N(R^{12})_2(R^{12})^+$, —$N(R^{12})$—$C(O)R^{12}$, —$N(R^{12})C(O)O(R^{12})$, —$N(R^{12})C(O)N(R^{12})(R^{12})$, —$N(R^{12})S(O)_2(R^{12})$, —$N(R^{12})S(O)_2$—$N(R^{12})(R^{12})$, —$N(R^{12})S(O)_2O(R^{12})$, —$OC(O)R^{12}$, —$OC(O)OR^{12}$, —$OC(O)$—$N(R^{12})(R^{12})$, —$Si(R^{12})_3$, —S—$R^{12}$, —$S(O)R^{12}$, —$S(O)(NH)R^{12}$, —$S(O)_2R^{12}$ or —$S(O)_2N(R^{12})(R^{12})$;
wherein said $C_{3-9}$ alkyl, $C_{2-6}$ alkenyl, $C_{2-6}$ alkynyl, $C_{3-15}$ cycloalkyl, $C_{1-8}$ haloalkyl, aryl, heteroaryl, or heterocyclyl is optionally substituted with $Z^{1b}$.

27. The compound of claim 1, or a pharmaceutically acceptable salt, stereoisomer, mixture of stereoisomers, or deuterated analog thereof, wherein:
$R^1$ is oxetanyl, tetrahydrofuranyl, tetrahydropyranyl, pyrrolidinyl, piperidinyl, pyrazolyl, or thiazolyl; wherein said oxetanyl, tetrahydrofuranyl, tetrahydropyranyl, pyrrolidinyl, piperidinyl, pyrazolyl, or thiazolyl is optionally substituted with a —F or —OH and is substituted with one or more substituents independently selected from $C_{1-4}$ alkyl or $C_{1-3}$ hydroxyalkyl;
wherein said $C_{1-4}$ alkyl or $C_{1-3}$ hydroxyalkyl is substituted with one or more oxo, —Cl, —$NO_2$, —CN, —$N_3$, $C_{4-9}$ alkyl, $C_{2-6}$ alkenyl, $C_{2-6}$ alkynyl, $C_{7-15}$ cycloalkyl, $C_{1-8}$ haloalkyl, aryl, heteroaryl, 4-20 membered heterocyclyl, —O—$R^{16}$, —$C(O)R^{12}$, —$C(O)O$—$R^{12}$, —$C(O)N(R^{12})(R^{12})$, —$N(R^{12})(R^{12})$, —$N(R^{12})_2(R^{12})^+$, —$N(R^{12})$—$C(O)R^{12}$, —$N(R^{12})C(O)O(R^{12})$, —$N(R^{12})C(O)N(R^{12})(R^{12})$, —$N(R^{12})S(O)_2(R^{12})$, —$N(R^{12})S(O)_2$—$N(R^{12})(R^{12})$, —$N(R^{12})S(O)_2O(R^{12})$, —$OC(O)R^{12}$, —$OC(O)OR^{12}$, —$OC(O)$—$N(R^{12})(R^{12})$, —$Si(R^{12})_3$, —S—$R^{12}$, —$S(O)R^{12}$, —$S(O)(NH)R^{12}$, —$S(O)_2R^{12}$ or —$S(O)_2N(R^{12})(R^{12})$; and
wherein any alkyl, hydroxyalkyl, alkenyl, alkynyl, cycloalkyl, aryl, heteroaryl or heterocyclyl is optionally substituted with $Z^{1b}$.

28. The compound of claim 1, or a pharmaceutically acceptable salt, stereoisomer, mixture of stereoisomers, or deuterated analog thereof, wherein:
$R^1$ is oxetanyl, tetrahydrofuranyl, tetrahydropyranyl, pyrrolidinyl, piperidinyl, pyrazolyl, or thiazolyl;
wherein said oxetanyl, tetrahydrofuranyl, tetrahydropyranyl, pyrrolidinyl, piperidinyl, pyrazolyl, or thiazolyl is optionally substituted with a —F or —OH and is substituted with one or more substituents independently selected from $C_{1-4}$ fluoroalkyl, —$C(O)(C_{1-3}$ fluoroalkyl), $C_{3-6}$ cycloalkyl, $C_{3-6}$ fluorocycloalkyl, and fluoropyrimidinyl;
wherein said $C_{1-4}$ fluoroalkyl, —$C(O)(C_{1-3}$ fluoroalkyl), $C_{3-6}$ cycloalkyl, $C_{3-6}$ fluorocycloalkyl or fluoropyrimidyl is substituted with one or more oxo, —Cl, —$NO_2$, —CN, —$N_3$, $C_{4-9}$ alkyl, $C_{2-6}$ alkenyl, $C_{2-6}$ alkynyl, $C_{3-15}$ cycloalkyl, $C_{1-8}$ haloalkyl, aryl, heteroaryl, 4-20 membered heterocyclyl, —O—$R^{12}$, —$C(O)R^{12}$, —$C(O)O$—$R^{12}$, —$C(O)N(R^{12})(R^{12})$, —$N(R^{12})(R^{12})$, —$N(R^{12})_2(R^{12})^+$, —$N(R^{12})$—$C(O)R^{12}$, —$N(R^{12})C(O)O(R^{12})$, —$N(R^{12})C(O)N(R^{12})(R^{12})$, —$N(R^{12})S(O)_2(R^{12})$, —$N(R^{12})S(O)_2$—$N(R^{12})(R^{12})$, —$N(R^{12})S(O)_2O(R^{12})$, —$OC(O)R^{12}$, —$OC(O)OR^{12}$, —$OC(O)$—$N(R^{12})(R^{12})$, —$Si(R^{12})_3$, —S—$R^{12}$, —$S(O)R^{12}$, —$S(O)(NH)R^{12}$, —$S(O)_2R^{12}$ or —$S(O)_2N(R^{12})(R^{12})$;
wherein any alkyl, alkenyl, alkynyl, cycloalkyl, aryl, heteroaryl or heterocyclyl is optionally substituted with $Z^{1b}$.

29. The compound of claim 1, or a pharmaceutically acceptable salt, stereoisomer, mixture of stereoisomers, or deuterated analog thereof, wherein $R^1$ is $C_{6-10}$ aryl optionally substituted with $Z^1$.

30. The compound of claim 1, or a pharmaceutically acceptable salt, stereoisomer, mixture of stereoisomers, or deuterated analog thereof, wherein:
$R^1$ is $C_{6-10}$ aryl is substituted with one or more $C_{1-6}$ alkyl, $C_{2-6}$ alkenyl, $C_{2-6}$ alkynyl, $C_{3-15}$ cycloalkyl, aryl, heteroaryl, 4-20 membered heterocyclyl, —O—$R^9$, —$C(O)R^{11}$, —$C(O)O$—$R^{12}$, —$C(O)NH(C_{3-6}$ cycloalkyl), —$C(O)NH(C_{4-6}$ alkyl), —$C(O)$ 4-20 membered heterocyclyl, $N(R^{12})(R^{12})$, —$N(R^{12})_2(R^{12})^+$, —$N(R^{12})C(O)$—$R^{12}$, —$N(R^{12})C(O)O$—$R^{12}$, —$N(R^{12})C(O)N(R^{12})(R^{12})$, —$N(R^{12})S(O)_2(R^{12})$, —$NR^{12}S(O)_2N(R^{12})(R^{12})$, —$NR^{12}S(O)_2O(R^{12})$, —$OC(O)R^{12}$, —$OC(O)$—$N(R^{12})(R^{12})$, —$Si(R^{12})_3$, —S—$R^{12}$, —$S(O)R^{12}$, —$S(O)(NH)R^{12}$, —$S(O)_2R^{12}$ or —$S(O)_2N(R^{12})(R^{12})$;
wherein said $C_{1-6}$ alkyl, $C_{2-6}$ alkenyl, $C_{2-6}$ alkynyl, $C_{3-15}$ cycloalkyl, aryl, heteroaryl, heterocyclyl, —$C(O)NH(C_{3-6}$ cycloalkyl), —$C(O)NH(C_{4-6}$ alkyl), or —$C(O)$ 4-20 membered heterocyclyl is optionally substituted with $Z^{1a}$;
wherein said $C_{6-10}$ aryl is optionally substituted with $Z^1$.

31. The compound of claim 1, or a pharmaceutically acceptable salt, stereoisomer, mixture of stereoisomers, or deuterated analog thereof, wherein:
$R^1$ is $C_{6-10}$ aryl substituted with one or more —$C(O)NH(C_{1-3}$ alkyl) and optionally substituted with $Z^{1a}$;

wherein said —C(O)NH(C$_{1-3}$ alkyl) is substituted with one or more oxo, halo, —NO$_2$, —CN, —N$_3$, C$_{3-9}$ alkyl, C$_{2-6}$ alkenyl, C$_{2-6}$ alkynyl, C$_{3-15}$ cycloalkyl, C$_{1-8}$ haloalkyl, aryl, heteroaryl, 4-20 membered heterocyclyl, —O—R$^{12}$, —C(O)R$^{12}$, —C(O)O—R$^{12}$, —C(O)N(R$^{12}$)(R$^{12}$), —N(R$^{12}$)(R$^{12}$), —N(R$^{12}$)$_2$(R$^{12}$)$^+$, —N(R$^{12}$)—C(O)R$^{12}$, —N(R$^{12}$)C(O)O(R$^{12}$), —N(R$^{12}$)C(O)N(R$^{12}$)(R$^{12}$), —N(R$^{12}$)S(O)$_2$(R$^{12}$), —N(R$^{12}$)S(O)$_2$N(R$^{12}$)(R$^{12}$), —N(R$^{12}$)S(O)$_2$O(R$^{12}$), —OC(O)R$^{12}$, —OC(O)OR$^{12}$, —OC(O)—N(R$^{12}$)(R$^{12}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{12}$)(R$^{12}$);

wherein said C$_{3-9}$ alkyl, C$_{2-6}$ alkenyl, C$_{2-6}$ alkynyl, C$_{3-15}$ cycloalkyl, C$_{1-8}$ haloalkyl, aryl, heteroaryl, or heterocyclyl is optionally substituted with Z$^{1b}$.

32. The compound of claim 1, or a pharmaceutically acceptable salt, stereoisomer, mixture of stereoisomers, or deuterated analog thereof, wherein:

R$^1$ is C$_{6-10}$ aryl substituted with one or more —C(O)(C$_{1-3}$ fluoroalkyl);

wherein said —C(O)(C$_{1-3}$ fluoroalkyl) is substituted with one or more oxo, —Cl, —NO$_2$, —CN, —N$_3$, C$_{3-9}$ alkyl, C$_{2-6}$ alkenyl, C$_{2-6}$ alkynyl, C$_{3-15}$ cycloalkyl, C$_{3-8}$ haloalkyl, aryl, heteroaryl, 4-20 membered heterocyclyl, —O—R$^{12}$, —C(O)R$^{12}$, —C(O)O—R$^{12}$, —C(O)N(R$^{12}$)(R$^{12}$), —N(R$^{12}$)(R$^{12}$), —N(R$^{12}$)$_2$(R$^{12}$)$^+$, —N(R$^{12}$)—C(O)R$^{12}$, —N(R$^{12}$)C(O)O(R$^{12}$), —N(R$^{12}$)C(O)N(R$^{12}$)(R$^{12}$), —N(R$^{12}$)S(O)$_2$(R$^{12}$), —N(R$^{12}$)S(O)$_2$N(R$^{12}$)(R$^{12}$), —N(R$^{12}$)S(O)$_2$O(R$^{12}$), —OC(O)R$^{12}$, —OC(O)OR$^{12}$, —OC(O)—N(R$^{12}$)(R$^{12}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{12}$)(R$^{12}$);

wherein said C$_{3-9}$ alkyl, C$_{2-6}$ alkenyl, C$_{2-6}$ alkynyl, C$_{3-15}$ cycloalkyl, C$_{3-8}$ haloalkyl, aryl, heteroaryl, or heterocyclyl is optionally substituted with Z$^{1b}$; and wherein said C$_{6-10}$ aryl is optionally substituted with Z$^1$.

33. The compound of claim 1, or a pharmaceutically acceptable salt, stereoisomer, mixture of stereoisomers, or deuterated analog thereof, wherein R$^1$ is —N(R$^{12}$)(R$^{12}$), —S(O)$_2$R$^{12}$, —S(O)$_2$N(R$^{12}$)(R$^{12}$), or —H.

34. The compound of claim 1, or a pharmaceutically acceptable salt, stereoisomer, mixture of stereoisomers, or deuterated analog thereof, wherein R$^2$ is C$_{1-10}$ alkyl optionally substituted with Z$^1$.

35. The compound of claim 1, or a pharmaceutically acceptable salt, stereoisomer, mixture of stereoisomers, or deuterated analog thereof, wherein R$^2$ is C$_{1-10}$ alkyl.

36. The compound of claim 1, or a pharmaceutically acceptable salt, stereoisomer, mixture of stereoisomers, or deuterated analog thereof, wherein R$^2$ is C$_{7-10}$ alkyl, optionally substituted with Z$^1$.

37. The compound of claim 1, or a pharmaceutically acceptable salt, stereoisomer, mixture of stereoisomers, or deuterated analog thereof, wherein:

R$^2$ is C$_{1-6}$ alkyl substituted with one or more —O(C$_{1-2}$ alkyl), —NHC(O)(C$_{1-3}$ alkyl), or —S(O)$_2$(C$_{1-3}$ alkyl);

wherein said —O(C$_{1-2}$ alkyl) is substituted with one or more oxo, —Cl, —NO$_2$, —CN, —N$_3$, C$_{2-9}$ alkyl, C$_{2-6}$ alkenyl, C$_{2-6}$ alkynyl, C$_{3-15}$ cycloalkyl, C$_{2-8}$ haloalkyl, aryl, heteroaryl, 4-20 membered heterocyclyl, —O—R$^{12}$, —C(O)R$^{12}$, —C(O)O—R$^{12}$, —C(O)N(R$^{12}$)(R$^{12}$), —N(R$^{12}$)(R$^{12}$), —N(R$^{12}$)$_2$(R$^{12}$)$^+$, —N(R$^{12}$)—C(O)R$^{12}$, —N(R$^{12}$)C(O)O(R$^{12}$), —N(R$^{12}$)C(O)N(R$^{12}$)(R$^{12}$), —N(R$^{12}$)S(O)$_2$(R$^{12}$), —N(R$^{12}$)S(O)$_2$O(R$^{12}$), —OC(O)R$^{12}$, —OC(O)OR$^{12}$, —OC(O)—N(R$^{12}$)(R$^{12}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{12}$)(R$^{12}$); and said —O(C$_{1-2}$ alkyl) is optionally substituted with —F;

wherein said —NHC(O)(C$_{1-3}$ alkyl), or —S(O)$_2$(C$_{1-3}$ alkyl) is substituted with one or more oxo, halo, —NO$_2$, —CN, —N$_3$, C$_{3-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O—R$^{12}$, —C(O)R$^{12}$, —C(O)O—R$^{12}$, —C(O)N(R$^{12}$)(R$^{12}$), —N(R$^{12}$)(R$^{12}$), —N(R$^{12}$)$_2$(R$^{12}$)$^+$, —N(R$^{12}$)—C(O)R$^{12}$, —N(R$^{12}$)C(O)O(R$^{12}$), —N(R$^{12}$)C(O)N(R$^{12}$)(R$^{12}$), —N(R$^{12}$)S(O)$_2$(R$^{12}$), —N(R$^{12}$)S(O)$_2$—N(R$^{12}$)(R$^{12}$), —N(R$^{12}$)S(O)$_2$O(R$^{12}$), —OC(O)R$^{12}$, —OC(O)OR$^{12}$, —OC(O)—N(R$^{12}$)(R$^{12}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{12}$)(R$^{12}$);

wherein said C$_{1-6}$ alkyl is optionally substituted with Z$^{1a}$; and wherein each said C$_{2-9}$ alkyl, C$_{3-9}$ alkyl, C$_{2-6}$ alkenyl, C$_{2-6}$ alkynyl, C$_{3-15}$ cycloalkyl, C$_{1-8}$ haloalkyl, C$_{2-8}$ haloalkyl, aryl, heteroaryl, or heterocyclyl is optionally substituted with Z$^{1b}$.

38. The compound of claim 1, or a pharmaceutically acceptable salt, stereoisomer, mixture of stereoisomers, or deuterated analog thereof, wherein:

R$^2$ is C$_{4-6}$ alkyl substituted with one or more substituents selected from —Cl, C$_{2-6}$ alkenyl, C$_{2-6}$ alkynyl, C$_{3-15}$ cycloalkyl, aryl, heteroaryl, monocyclic 4-20 membered heterocyclyl, 4-10 membered bicyclic heterocyclyl, —O(C$_{3-9}$ alkyl), —O(C$_{3-10}$ cycloalkyl), —O(4-20 membered heterocyclyl), —O(aryl), —O(heteroaryl), —C(O)—R$^{12}$, —C(O)O—R$^{12}$, —C(O)—N(R$^{12}$)(R$^{12}$), —N(R$^{12}$)(R$^{12}$), —N(R$^{12}$)$_2$(R$^{12}$)$^+$, —N(R$^{12}$)C(O)(C$_{4-9}$ alkyl), —N(R$^{12}$)C(O)(C$_{3-10}$ cycloalkyl), —N(R$^{12}$)C(O)(4-20 membered heterocyclyl), —N(R$^{12}$)C(O)(aryl), —N(R$^{12}$)C(O)(heteroaryl), —N(R$^{12}$)C(O)O—R$^{12}$, —N(R$^{12}$)C(O)N(R$^{12}$)(R$^{12}$), —N(R$^{12}$)S(O)$_2$(R$^{12}$), —NR$^{12}$S(O)$_2$N(R$^{12}$)(R$^{12}$), —NR$^{12}$S(O)$_2$O(R$^{12}$), —OC(O)R$^{12}$, —OC(O)—N(R$^{12}$)(R$^{12}$), —Si(R$^{12}$)$_3$, —S—R$^{12}$, —S(O)R$^{12}$, —S(O)(NH)R$^{12}$, —S(O)$_2$(C$_{4-9}$ alkyl), —S(O)$_2$(aryl), —S(O)$_2$(C$_{3-10}$ cycloalkyl), —S(O)$_2$(4-20 membered heterocyclyl), —S(O)$_2$(heteroaryl), or —S(O)$_2$N(R$^{12}$)(R$^{12}$);

wherein said C$_{4-6}$ alkyl is also optionally substituted with Z$^1$; and wherein said C$_{2-6}$ alkenyl, C$_{2-6}$ alkynyl, C$_{3-15}$ cycloalkyl, aryl, heteroaryl, monocyclic 4-20 membered heterocyclyl, bicyclic 4-10 membered heterocyclyl, —O(C$_{3-9}$ alkyl), —O(C$_{3-10}$ cycloalkyl), —O(4-20 membered heterocyclyl), —O(aryl), —O(heteroaryl), —N(R$^{12}$)C(O)(C$_{4-9}$ alkyl), —N(R$^{12}$)C(O)(C$_{3-10}$ cycloalkyl), —N(R$^{12}$)C(O)(4-20 membered heterocyclyl), —N(R$^{12}$)C(O)(aryl), —N(R$^{12}$)C(O)(heteroaryl), —S(O)$_2$(C$_{4-9}$ alkyl), —S(O)$_2$(aryl), —S(O)$_2$(C$_{3-10}$ cycloalkyl), —S(O)$_2$(4-20 membered heterocyclyl), —S(O)$_2$(heteroaryl), —NHC(O)(C$_{1-3}$ alkyl), or —S(O)$_2$(C$_{1-3}$ alkyl) is optionally substituted with Z$^{1a}$.

39. The compound of claim 1, or a pharmaceutically acceptable salt, stereoisomer, mixture of stereoisomers, or deuterated analog thereof, wherein:

R$^2$ is C$_{4-6}$ alkyl substituted with one or more —O(CH$_2$)$_2$R$^{17}$ or —O(CH$_2$)R$^{17}$;

R$^{17}$ at each occurrence is independently C$_{3-15}$ cycloalkyl, aryl, 4-20 membered heterocyclyl, heteroaryl, —O—R$^{12}$, —C(O)—R$^{12}$, —C(O)O—R$^{12}$, —C(O)—N(R$^{12}$)(R$^{12}$), —N(R$^{12}$)(R$^{12}$), —N(R$^{12}$)$_2$(R$^{12}$)$^+$, —N(R$^{12}$)C(O)—R$^{12}$, —N(R$^{12}$)C(O)O—R$^{12}$, —N(R$^{12}$)C(O)N(R$^{12}$)(R$^{12}$), —N(R$^{12}$)S(O)$_2$(R$^{12}$), —NR$^{12}$S(O)$_2$N(R$^{12}$)(R$^{12}$), —NR$^{12}$S(O)$_2$O(R$^{12}$), —OC(O)R$^{12}$, —OC(O)—N(R$^{12}$)(R$^{12}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{12}$)(R$^{12}$);

wherein said C$_{3-15}$ cycloalkyl, aryl, heterocyclyl, and heteroaryl optionally is substituted with Z$^{1b}$; and wherein said C$_{4-6}$ alkyl is also optionally substituted with Z$^1$.

40. The compound of claim 1, or a pharmaceutically acceptable salt, stereoisomer, mixture of stereoisomers, or deuterated analog thereof, wherein:

R$^2$ is C$_{4-6}$ alkyl substituted with five or more substituents selected from F, hydroxyl, —CN, —OCH$_3$, —OCD$_3$, —NHC(O)(C$_{1-3}$ alkyl), —S(O)$_2$(C$_{1-3}$ alkyl), or C$_{1-2}$ fluoroalkoxy; and wherein said C$_{4-6}$ alkyl is optionally substituted with Z$^1$.

41. The compound of claim 1, or a pharmaceutically acceptable salt, stereoisomer, mixture of stereoisomers, or deuterated analog thereof, wherein:

R$^2$ is C$_{1-3}$ alkyl substituted with one or more substituents selected from —Cl, C$_{2-6}$ alkenyl, C$_{2-6}$ alkynyl, cyclopropyl, napthyl, bicyclic 4-10 membered heterocyclyl, C$_{7-15}$ cycloalkyl, —O(CH$_2$)$_2$R$^{17}$, —O(CH$_2$)R$^{17}$, —O(C$_{3-9}$ alkyl), —O(C$_{3-10}$ cycloalkyl), —O(4-20 membered heterocyclyl), —O(aryl), —O(heteroaryl), —C(O)(C$_{1-9}$ alkyl), —C(O)(cyclopropyl), —C(O)O—R$^{12}$, —C(O)—N(R$^{12}$)(R$^{12}$), —N(R$^{12}$)(R$^{12}$), —N(R$^{12}$)$_2$(R$^{12}$)$^+$, —N(R$^{12}$)C(O)(C$_{4-9}$ alkyl), —N(R$^{12}$)C(O)(C$_{3-10}$ cycloalkyl), —N(R$^{12}$)C(O)(4-20 membered heterocyclyl), —N(R$^{12}$)C(O)(aryl), —N(R$^{12}$)C(O)(heteroaryl), —N(R$^{12}$)C(O)O—R$^{12}$, —N(R$^{12}$)C(O)N(R$^{12}$)(R$^{12}$), —N(R$^{12}$)S(O)$_2$(R$^{12}$), —NR$^{12}$S(O)$_2$N(R$^{12}$)(R$^{12}$), —NR$^{12}$S(O)$_2$O(R$^{12}$), —OC(O)R$^{12}$, —OC(O)—N(R$^{12}$)(R$^{12}$), —Si(R$^{12}$)$_3$, —S—R$^{12}$, —S(O)R$^{12}$, —S(O)(NH)R$^{12}$, —S(O)$_2$(C$_{4-9}$ alkyl), —S(O)$_2$(aryl), —S(O)$_2$(C$_{3-10}$ cycloalkyl), —S(O)$_2$(4-20 membered heterocyclyl), —S(O)$_2$(heteroaryl), or —S(O)$_2$N(R$^9$)(R$^{12}$);

wherein said C$_{1-3}$ alkyl is also optionally substituted with Z$^1$; and wherein said C$_{2-6}$ alkenyl, C$_{2-6}$ alkynyl, cyclopropyl, napthyl, bicyclic heterocyclyl, C$_{7-15}$ cycloalkyl, —O(C$_{3-9}$ alkyl), —O(C$_{3-10}$ cycloalkyl), —O(heterocyclyl), —O(aryl), —O(heteroaryl), —N(R$^{12}$)C(O)(C$_{4-9}$ alkyl), —N(R$^{12}$)C(O)(C$_{3-10}$ cycloalkyl), —N(R$^{12}$)C(O)(heterocyclyl), —N(R$^{12}$)C(O)(aryl), —N(R$^{12}$)C(O)(heteroaryl), —S(O)$_2$(C$_{4-9}$ alkyl), —S(O)$_2$(aryl), —S(O)$_2$(C$_{3-10}$ cycloalkyl), —S(O)$_2$(heterocyclyl), or —S(O)$_2$(heteroaryl) is optionally substituted with Z$^{1a}$.

42. The compound of claim 1, or a pharmaceutically acceptable salt, stereoisomer, mixture of stereoisomers, or deuterated analog thereof, wherein:

R$^2$ is C$_{1-3}$ alkyl substituted with one or more substituents selected from azetidinyl, tetrahydrofuranyl, triazolyl, oxazolyl, isoxazolyl, thiadiazole, oxadiazole, pyrimidinyl, pyridizinyl, pyrazinyl, isothiazolyl, tetrazolyl, furanyl, thiomorpholinyl, 4-7 membered sultam, 4-7 membered cyclic carbamate, 4-7 membered cyclic carbonate, 4-7 membered cyclic sulfide, or 8-10 membered heteroaryl; any of which is optionally substituted with Z$^{1a}$; and wherein said C$_{1-3}$ alkyl is also optionally substituted with Z$^1$.

43. The compound of claim 1, or a pharmaceutically acceptable salt, stereoisomer, mixture of stereoisomers, or deuterated analog thereof, wherein:

R$^2$ is C$_{1-3}$ alkyl substituted with one substituent selected from phenyl, oxetanyl, tetrahydropyranyl, morpholinyl, piperidinyl, imidazolyl, pyridinyl, thiophenyl, or C$_{4-6}$ cycloalkyl;

wherein said phenyl, oxetanyl, tetrahydropyranyl, morpholinyl, piperidinyl, imidazolyl, pyridinyl, thiophenyl, or C$_{4-6}$ cycloalkyl is substituted with one or more oxo, —NO$_2$, —N$_3$, —CN, C$_{4-9}$ alkyl, C$_{2-6}$ alkenyl, C$_{2-6}$ alkynyl, C$_{3-15}$ cycloalkyl, C$_{1-8}$ haloalkyl, aryl, heteroaryl, 4-20 membered heterocyclyl, —O(C$_{3-6}$ alkyl), —O(C$_{3-6}$ cycloalkyl), —O(4-20 membered heterocyclyl), —C(O)—R$^{12}$, —C(O)O—R$^{12}$, —C(O)—N(R$^{12}$)(R$^{12}$), —N(R$^{12}$)(R$^{12}$), —N(R$^{12}$)$_2$(R$^{12}$)$^+$, —N(R$^{12}$)C(O)—R$^{12}$, —N(O)—O—R$^{12}$, —N(R$^{12}$)C(O)N(R$^{12}$)(R$^{12}$), —N(R$^{12}$)S(O)$_2$(R$^{12}$), —NR$^{12}$S(O)$_2$N(R$^{12}$)(R$^{12}$), —NR$^{12}$S(O)$_2$O(R$^{12}$), —OC(O)R$^{12}$, —OC(O)—N(R$^{12}$)(R$^{12}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^9$)(R$^{12}$); and wherein any alkyl, alkenyl, alkynyl, cycloalkyl, haloalkyl, aryl, heteroaryl or heterocyclyl is optionally substituted with Z$^{1a}$.

44. The compound of claim 1, or a pharmaceutically acceptable salt, stereoisomer, mixture of stereoisomers, or deuterated analog thereof, wherein:

R$^2$ is C$_{1-3}$ alkyl optionally substituted with Z$^1$ and is substituted with one substituent selected from phenyl, oxetanyl, tetrahydropyranyl, morpholinyl, piperidinyl, imidazolyl, pyridinyl, thiophenyl, or C$_{4-6}$ cycloalkyl;

wherein said phenyl, oxetanyl, tetrahydropyranyl, morpholinyl, piperidinyl, imidazolyl, pyridinyl, thiophenyl, or C$_{4-6}$ cycloalkyl is substituted with four or more substituents selected from —F, —Cl, —OH, C$_{1-3}$ alkyl, —O(C$_{1-2}$ alkyl) or —S(O)$_2$NH$_2$.

45. The compound of claim 1, or a pharmaceutically acceptable salt, stereoisomer, mixture of stereoisomers, or deuterated analog thereof, wherein:

R$^2$ is C$_{1-3}$ alkyl substituted with oxo and optionally substituted with one or more substituents selected from halo, azetidinyl, pyrrolidinyl, piperazinyl, tetrahydrofuranyl, thiomorpholinyl, —CN, C$_{1-9}$ alkyl, C$_{2-6}$ alkenyl, C$_{2-6}$ alkynyl, cyclopropyl, C$_{7-15}$ cycloalkyl, C$_{1-8}$ haloalkyl, —O—R$^{12}$, —C(O)—R$^{12}$, —C(O)O—R$^{12}$, —C(O)—N(R$^{12}$)(R$^{12}$), —N(R$^{12}$)(R$^{12}$), —N(R$^{12}$)$_2$(R$^{12}$)$^+$, —N(R$^{12}$)C(O)—R$^{12}$, —N(R$^{12}$)C(O)O—R$^{12}$, —N(R$^{12}$)C(O)N(R$^{12}$)(R$^{12}$), —N(R$^{12}$)S(O)$_2$(R$^{12}$), —NR$^{12}$S(O)$_2$N(R$^{12}$)(R$^{12}$), —NR$^{12}$S(O)$_2$O(R$^{12}$), —OC(O)R$^{12}$, —OC(O)—N(R$^{12}$)(R$^{12}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^9$)(R$^{12}$); and wherein said C$_{1-3}$ alkyl is optionally substituted with Z$^1$;

wherein said, C$_{1-9}$ alkyl, C$_{2-6}$ alkenyl, C$_{2-6}$ alkynyl, cyclopropyl, C$_{7-15}$ cycloalkyl, C$_{1-8}$ haloalkyl, azetidinyl, pyrrolidinyl, piperazinyl, tetrahydrofuranyl, or thiomorpholinyl is optionally substituted with Z$^{1a}$.

46. The compound of claim 1, or a pharmaceutically acceptable salt, stereoisomer, mixture of stereoisomers, or deuterated analog thereof, wherein R$^2$ is C$_3$ alkyl substituted with five or more substituents selected from —F, —OH, —OCH$_3$, —CN, —NHC(O)(C$_{1-3}$ alkyl), C$_{1-2}$ fluoroalkoxy, or —S(O)$_2$(C$_{1-3}$ alkyl).

47. The compound of claim 1, or a pharmaceutically acceptable salt, stereoisomer, mixture of stereoisomers, or deuterated analog thereof, wherein R$^2$ is C$_{3-10}$ cycloalkyl optionally substituted with Z$^1$.

48. The compound of claim 1, or a pharmaceutically acceptable salt, stereoisomer, mixture of stereoisomers, or deuterated analog thereof, wherein $R^2$ is cyclopropyl optionally substituted with $Z^1$.

49. The compound of claim 1, or a pharmaceutically acceptable salt, stereoisomer, mixture of stereoisomers, or deuterated analog thereof, wherein $R^2$ is $C_{7-10}$ cycloalkyl optionally substituted with $Z^1$.

50. The compound of claim 1, or a pharmaceutically acceptable salt, stereoisomer, mixture of stereoisomers, or deuterated analog thereof, wherein:

$R^2$ is $C_{4-6}$ cycloalkyl substituted with one or more substituents selected from -halo, oxo, —CN, $C_{1-4}$ alkyl, $C_{5-9}$ alkyl, $C_{2-6}$ alkenyl, $C_{2-6}$ alkynyl, $C_{3-15}$ cycloalkyl, $C_{1-8}$ haloalkyl, aryl, heteroaryl, 4-20 membered heterocyclyl, —O($C_{4-9}$ alkyl), —O($C_{3-10}$ cycloalkyl), —O(4-20 membered heterocyclyl), —O(aryl), —O(heteroaryl), —N($R^{12}$)C(O)($C_{5-9}$ alkyl), —N($R^{12}$)C(O)($C_{3-10}$ cycloalkyl), —N($R^{12}$)C(O)(4-20 membered heterocyclyl), —N($R^{12}$)C(O)(aryl), —N($R^{12}$)C(O)(4-20 membered heteroaryl), —NH($R^{12}$), —N($R^{12}$)($C_{4-9}$ alkyl), —N($R^{12}$)($C_{3-10}$ cycloalkyl), —N($R^{12}$)(4-20 membered heterocyclyl), —N($R^{12}$)(aryl), —N($R^{12}$)(heteroaryl), —N($R^{12}$)C(O)O($C_{4-9}$ alkyl), —N($R^{12}$)C(O)O($C_{3-10}$ cycloalkyl), —N($R^{12}$)C(O)O(4-20 membered heterocyclyl), —N($R^{12}$)C(O)O(aryl), —N($R^{12}$)C(O)O(heteroaryl), —C(O)N($R^{12}$)($C_{5-9}$ alkyl), —C(O)N($R^{12}$)($C_{7-10}$ cycloalkyl), —C(O)N($R^{12}$)(4-20 membered heterocyclyl), —C(O)N($R^{12}$)(aryl), —C(O)N($R^{12}$)(heteroaryl), —C(O)N($R^9$)($R^9$), —C(O)O—$R^{12}$, —N($R^{12}$)$_2$($R^{12}$)$^+$, —N($R^{12}$)C(O)N($R^{12}$)($R^{12}$), —N($R^{12}$)S(O)$_2$($R^{12}$), —N$R^{12}$S(O)$_2$N($R^{12}$)($R^{12}$), —N($R^{12}$)S(O)$_2$O($R^{12}$), —OC(O)$R^{12}$, —OC(O)—N($R^{12}$)($R^{12}$), —Si($R^{12}$)$_3$, —S—$R^{12}$, —S(O)$R^{12}$, —S(O)$_2R^{12}$, —S(O)(NH)$R^{12}$, or —S(O)$_2$N($R^{12}$)($R^{12}$);

wherein said $C_{4-6}$ cycloalkyl is also optionally substituted with $Z^1$;

wherein said $C_{1-4}$ alkyl is optionally substituted with oxo, halo, —NO$_2$, —CN, —N$_3$, $C_{4-9}$ alkyl, $C_{2-6}$ alkenyl, $C_{2-6}$ alkynyl, $C_{3-15}$ cycloalkyl, $C_{1-8}$ haloalkyl, aryl, heteroaryl, 4-20 membered heterocyclyl, —O—$R^{16}$, —O($C_{4-9}$ alkyl), —C(O)$R^{12}$, —C(O)O—$R^{12}$, —C(O)N($R^{12}$)($R^{12}$), —N($R^{12}$)($R^{12}$), —N($R^{12}$)$_2$($R^{12}$)$^+$, —N($R^{12}$)—C(O)$R^{12}$, —N($R^{12}$)C(O)O($R^{12}$), —N($R^{12}$)C(O)N($R^{12}$)($R^{12}$), —N($R^{12}$)S(O)$_2$($R^{12}$), —N($R^{12}$)S(O)$_2$—N($R^{12}$)($R^{12}$), —N($R^{12}$)S(O)$_2$O($R^{12}$), —OC(O)$R^{12}$, —OC(O)O$R^{12}$, —OC(O)—N($R^{12}$)($R^{12}$ $R^{12}$), —Si($R^{12}$)$_3$, —S—$R^{12}$, —S(O)$R^{12}$, —S(O)(NH)$R^{12}$, —S(O)$_2R^{12}$ or —S(O)$_2$N($R^{12}$)($R^{12}$); and wherein each said $C_{5-9}$ alkyl, $C_{2-6}$ alkenyl, $C_{2-6}$ alkynyl, $C_{3-15}$ cycloalkyl, $C_{1-8}$ haloalkyl, —O($C_{4-9}$ alkyl), —O($C_{3-10}$ cycloalkyl), —O(heterocyclyl), —O(aryl), —O(heteroaryl), —N($R^{12}$)C(O)($C_{5-9}$ alkyl), —N($R^{12}$)C(O)($C_{3-10}$ cycloalkyl), —N($R^{12}$)C(O)(heterocyclyl), —N($R^{12}$)C(O)(aryl), —N($R^{12}$)C(O)(heteroaryl), —N($R^{12}$)($C_{4-9}$ alkyl), —N($R^{12}$)($C_{3-10}$ cycloalkyl), —N($R^{12}$)(heterocyclyl), —N($R^{12}$)(aryl), —N($R^{12}$)(heteroaryl), —N($R^{12}$)C(O)O($C_{4-9}$ alkyl), —N($R^{12}$)C(O)O($C_{3-10}$ cycloalkyl), —N($R^{12}$)C(O)O(heterocyclyl), —N($R^{12}$)C(O)O(aryl), —N($R^{12}$)C(O)O(heteroaryl), —C(O)N($R^{12}$)($C_{5-9}$ alkyl), —C(O)N($R^{12}$)($C_{7-10}$ cycloalkyl), —C(O)N($R^{12}$)(heterocyclyl), —C(O)N($R^{12}$)(aryl), —C(O)N($R^{12}$)(heteroaryl), aryl, heteroaryl, or heterocyclyl is optionally substituted with $Z^{1a}$.

51. The compound of claim 1, or a pharmaceutically acceptable salt, stereoisomer, mixture of stereoisomers, or deuterated analog thereof, wherein:

$R^2$ is $C_{4-6}$ cycloalkyl substituted with one or more substituents selected from $C_{1-4}$ hydroxyalkyl, $C_{1-3}$ alkoxy, —(CH$_2$)$_{1-3}$O($C_{1-3}$ alkyl), —C(O)NH($C_{1-4}$ alkyl), —C(O)NH($C_{3-6}$ cycloalkyl), —N($C_{1-3}$ alkyl)$_2$, —NHC(O)O($C_{1-3}$ alkyl), —NHC(O)($C_{1-4}$ hydroxyalkyl);

wherein said $C_{4-6}$ cycloalkyl is optionally substituted with $Z^1$;

wherein said —C(O)NH($C_{3-6}$ cycloalkyl) is substituted with $Z^{1a}$;

wherein said $C_{1-4}$ hydroxyalkyl or —NHC(O)($C_{1-4}$ hydroxyalkyl) is substituted with oxo, halo, —NO$_2$, —CN, —N$_3$, $C_{4-9}$ alkyl, $C_{2-6}$ alkenyl, $C_{2-6}$ alkynyl, $C_{3-15}$ cycloalkyl, $C_{1-8}$ haloalkyl, aryl, heteroaryl, 4-20 membered heterocyclyl, —O—$R^9$, —C(O)$R^{12}$, —C(O)O—$R^{12}$, —C(O)N($R^{12}$)($R^{12}$), —N($R^{12}$)($R^{12}$), —N($R^{12}$)$_2$($R^{12}$)$^+$, —N($R^{12}$)—C(O)$R^{12}$, —N($R^{12}$)C(O)O($R^{12}$), —N($R^{12}$)C(O)N($R^{12}$)($R^{12}$), —N($R^{12}$)S(O)$_2$($R^{12}$), —N($R^{12}$) S(O)$_2$—N($R^{12}$)($R^{12}$), —N($R^{12}$)S(O)$_2$O($R^{12}$), —OC(O)$R^{12}$, —OC(O)O$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2R^{12}$ or —S(O)$_2$N($R^{12}$)($R^{12}$);

wherein said $C_{1-3}$ alkoxy, —(CH$_2$)$_{1-3}$O($C_{1-3}$ alkyl), —N($C_{1-3}$ alkyl)$_2$, —NHC(O)O($C_{1-3}$ alkyl) is substituted with oxo, halo, —NO$_2$, —CN, —N$_3$, $C_{3-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^{12}$, —C(O)$R^{12}$, —C(O)O—$R^{12}$, —C(O)N($R^{12}$)($R^{12}$), —N($R^{12}$)($R^{12}$), —N($R^{12}$)$_2$($R^{12}$)$^+$, —N($R^{12}$)—C(O)$R^{12}$, —N($R^{12}$)C(O)O($R^{12}$), —N($R^{12}$)C(O)N($R^{12}$)($R^{12}$), —N($R^{12}$)S(O)$_2$($R^{12}$), —N($R^{12}$)S(O)$_2$—N($R^{12}$)($R^{12}$), —N($R^{12}$)S(O)$_2$O($R^{12}$), —OC(O)$R^{12}$, —OC(O)O$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2R^{12}$ or —S(O)$_2$N($R^{12}$)($R^{12}$);

wherein said —C(O)NH($C_{1-4}$ alkyl) is substituted with oxo, halo, —NO$_2$, —CN, —N$_3$, $C_{4-9}$ alkyl, $C_{2-6}$ alkenyl, $C_{2-6}$ alkynyl, $C_{3-15}$ cycloalkyl, $C_{1-8}$ haloalkyl, aryl, heteroaryl, 4-20 membered heterocyclyl, —O—$R^{12}$, —C(O)$R^{12}$, —C(O)O—$R^{12}$, —C(O)N($R^{12}$)($R^{12}$), —N($R^{12}$)($R^{12}$), —N($R^{12}$)$_2$($R^{12}$)$^+$, —N($R^{12}$)—C(O)$R^{12}$, —N($R^{12}$)C(O)O($R^{12}$), —N($R^{12}$)C(O)N($R^{12}$)($R^{12}$), —N($R^{12}$)S(O)$_2$($R^{12}$), —N($R^{12}$)S(O)$_2$—N($R^{12}$)($R^{12}$), —N($R^{12}$)S(O)$_2$O($R^{12}$), —OC(O)$R^{12}$, —OC(O)O$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2R^{12}$ or —S(O)$_2$N($R^{12}$)($R^{12}$); and wherein each said $C_{3-9}$ alkyl, $C_{4-9}$ alkyl, $C_{2-6}$ alkenyl, $C_{2-6}$ alkynyl, $C_{3-15}$ cycloalkyl, $C_{1-8}$ haloalkyl, aryl, heteroaryl, or heterocyclyl is optionally substituted with $Z^{1b}$.

52. The compound of claim 1, or a pharmaceutically acceptable salt, stereoisomer, mixture of stereoisomers, or deuterated analog thereof, wherein:

$R^2$ is $C_{4-6}$ cycloalkyl substituted with one or more —NHC(O)($C_{1-3}$ alkyl);

wherein at least one —NHC(O)($C_{1-3}$ alkyl) is substituted with one or more oxo, halo, —NO$_2$, —CN, —N$_3$, $C_{3-9}$ alkyl, $C_{2-6}$ alkenyl, $C_{2-6}$ alkynyl, $C_{3-15}$ cycloalkyl, $C_{1-8}$ haloalkyl, aryl, heteroaryl, 4-20 membered heterocyclyl, —O—$R^9$, —C(O)$R^{12}$, —C(O)O—$R^{12}$, —C(O)N($R^{12}$)($R^{12}$), —N($R^{12}$)($R^{12}$), —N($R^{12}$)$_2$($R^{12}$)$^+$, —N($R^{12}$)—C(O)$R^{12}$, —N($R^{12}$)C(O)O($R^{12}$), —N($R^{12}$)C(O)N($R^{12}$)($R^{12}$), —N($R^{12}$)S(O)$_2$($R^{12}$), —N($R^{12}$)S(O)$_2$—N($R^{12}$)($R^{12}$), —N($R^{12}$)S(O)$_2$O($R^{12}$), —OC(O)

$R^{12}$, —OC(O)O$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2R^{12}$ or —S(O)$_2$N($R^{12}$)($R^{12}$);

wherein said C$_{4-6}$ cycloalkyl is optionally substituted with $Z^1$; and wherein said C$_{3-9}$ alkyl, C$_{2-6}$ alkenyl, C$_{2-6}$ alkynyl, C$_{3-15}$ cycloalkyl, C$_{1-8}$ haloalkyl, aryl, heteroaryl, or heterocyclyl is optionally substituted with $Z^{1a}$.

53. The compound of claim 1, or a pharmaceutically acceptable salt, stereoisomer, mixture of stereoisomers, or deuterated analog thereof, wherein:

$R^2$ is C$_{4-6}$ cycloalkyl substituted with three or more substituents selected from —OH, C$_{1-4}$ hydroxyalkyl, C$_{1-3}$ alkoxy, —(CH$_2$)$_{1-3}$O(C$_{1-3}$ alkyl), —C(O)NH(C$_{1-4}$ alkyl), —C(O)NH(C$_{3-6}$ cycloalkyl), —N(C$_{1-3}$ alkyl)$_2$, —NHC(O)(C$_{1-3}$ alkyl), —NHC(O)O(C$_{1-3}$ alkyl), or —NHC(O)(C$_{1-4}$ hydroxyalkyl);

wherein said C$_{4-6}$ cycloalkyl is optionally substituted with $Z^1$.

54. The compound of claim 1, or a pharmaceutically acceptable salt, stereoisomer, mixture of stereoisomers, or deuterated analog thereof, wherein $R^2$ is s 5-10 membered heteroaryl optionally substituted with $Z^1$.

55. The compound of claim 1, or a pharmaceutically acceptable salt, stereoisomer, mixture of stereoisomers, or deuterated analog thereof, wherein $R^2$ is oxazolyl, isoxazolyl, thiadiazole, thiazole, oxadiazole, isothiazolyl, tetrazolyl, thiophenyl, furanyl, or a 6-10 membered heteroaryl; any of which is optionally substituted with $Z^1$.

56. The compound of claim 1, or a pharmaceutically acceptable salt, stereoisomer, mixture of stereoisomers, or deuterated analog thereof, wherein $R^2$ is 4-7 membered monocyclic heterocyclyl optionally substituted with $Z^1$.

57. The compound of claim 1, or a pharmaceutically acceptable salt, stereoisomer, mixture of stereoisomers, or deuterated analog thereof, wherein $R^2$ is azetidinyl, oxetanyl, pyrrolidinyl, morpholinyl, thiomorpholinyl, 4-7 membereded sultam, 4-7 membered cyclic carbamate, 4-7 membered cyclic carbonate, or 4-7 membered cyclic sulfide; any of which is optionally substituted with $Z^1$.

58. The compound of claim 1, or a pharmaceutically acceptable salt, stereoisomer, mixture of stereoisomers, or deuterated analog thereof, wherein:

$R^2$ is tetrahydrofuranyl, tetrahydropyranyl, piperidinyl, piperazinyl pyrrolyl, pyrazolyl, imidazolyl, or triazolyl;

wherein said tetrahydrofuranyl, tetrahydropyranyl, piperidinyl, piperazinyl, pyrrolyl, pyrazolyl, imidazolyl, or triazolyl is substituted with one or more substituents selected from oxo, halo, —CN, C$_{2-4}$ alkyl, C$_{5-9}$ alkyl, C$_{2-6}$ alkenyl, C$_{2-6}$ alkynyl, C$_{3-15}$ cycloalkyl, C$_{1-8}$ haloalkyl, aryl, heteroaryl, 4-20 membered heterocyclyl, —O—$R^{12}$, —C(O)—$R^{12}$, —C(O)O—$R^{12}$, —C(O)—N($R^{12}$)($R^{12}$), —N($R^{12}$)($R^{12}$), —N($R^{12}$)$_2$($R^{12}$)$^+$, —N($R^{12}$)C(O)—$R^{12}$, —N($R^{12}$)C(O)O—$R^{12}$, —N($R^{12}$)C(O)N($R^{12}$)($R^{12}$), —N($R^{12}$)S(O)$_2$($R^{12}$), —NR$^{12}$S(O)$_2$N($R^{12}$)($R^{12}$), —NR$^{12}$S(O)$_2$O($R^{12}$), —OC(O)$R^{12}$, —OC(O)—N($R^{12}$)($R^{12}$), —Si($R^{12}$)$_3$, —S—$R^{12}$, —S(O)$R^{12}$, —S(O)$_2$(C$_{4-9}$ alkyl), —S(O)$_2$(C$_{3-10}$ cycloalkyl), —S(O)$_2$(4-20 membered heterocyclyl), —S(O)$_2$(aryl), —S(O)$_2$(heteroaryl), —S(O)(NH)R$^{12}$, or —S(O)$_2$N($R^{12}$)($R^{12}$);

wherein said tetrahydrofuranyl, tetrahydropyranyl, piperidinyl, piperazinyl, pyrrolyl, pyrazolyl, imidazolyl, or triazolyl is optionally substituted with $Z^{1a}$;

wherein said C$_{2-4}$ alkyl is optionally substituted with halo, —NO$_2$, —CN, —N$_3$, C$_{3-9}$ alkyl, C$_{2-6}$ alkenyl, C$_{2-6}$ alkynyl, C$_{3-15}$ cycloalkyl, C$_{1-8}$ haloalkyl, aryl, heteroaryl, 4-20 membered heterocyclyl, —O—$R^9$, —C(O)$R^{12}$, —C(O)O—$R^{12}$, —C(O)N($R^{12}$)($R^{12}$), —N($R^{12}$)($R^{12}$), —N($R^{12}$)$_2$($R^{12}$)$^+$, —N($R^{12}$)—C(O)$R^{12}$, —N($R^{12}$)C(O)O($R^{12}$), —N($R^{12}$)C(O)N($R^{12}$)($R^{12}$), —N($R^{12}$)S(O)$_2$($R^{12}$), —N($R^{12}$)S(O)$_2$—N($R^{12}$)($R^{12}$), —N($R^{12}$)S(O)$_2$O($R^{12}$), —OC(O)$R^{12}$, —OC(O)OR$^{12}$, —OC(O)—N($R^{12}$)($R^{12}$), —Si($R^{12}$)$_3$, —S—$R^{12}$, —S(O)$R^{12}$, —S(O)(NH)R$^{12}$, —S(O)$_2$R$^{12}$ or —S(O)$_2$N($R^{12}$)($R^{12}$); and wherein each said C$_{3-9}$ alkyl, C$_{5-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —S(O)$_2$(C$_{4-9}$ alkyl), —S(O)$_2$(C$_{3-10}$ cycloalkyl), —S(O)$_2$(heterocyclyl), —S(O)$_2$(aryl), or —S(O)$_2$(heteroaryl) is optionally substituted with $Z^{1a}$.

59. The compound of claim 1, or a pharmaceutically acceptable salt, stereoisomer, mixture of stereoisomers, or deuterated analog thereof, wherein:

$R^2$ is tetrahydrofuranyl, tetrahydropyranyl, piperidinyl, piperazinyl pyrrolyl, pyrazolyl, imidazolyl, or triazolyl;

wherein said tetrahydrofuranyl, tetrahydropyranyl, piperidinyl, piperazinyl, pyrrolyl, pyrazolyl, imidazolyl, or triazolyl is substituted with one or more C$_1$ alkyl;

wherein said tetrahydrofuranyl, tetrahydropyranyl, piperidinyl, piperazinyl, pyrrolyl, pyrazolyl, imidazolyl, or triazolyl is optionally substituted with $Z^1$;

wherein said C$_1$ alkyl is optionally substituted with oxo, halo, —NO$_2$, —CN, —N$_3$, C$_{2-6}$ alkenyl, C$_{2-6}$ alkynyl, C$_{3-15}$ cycloalkyl, C$_{1-8}$ haloalkyl, aryl, heteroaryl, 4-20 membered heterocyclyl, —O—$R^9$, —C(O)$R^{12}$, —C(O)O—$R^{12}$, —C(O)N($R^9$)($R^9$), —C(O)N($R^{12}$)(C$_{4-9}$ alkyl), —C(O)N($R^{12}$)(C$_{3-10}$ cycloalkyl), —C(O)N($R^{12}$)(4-20 membered heterocyclyl), —C(O)N($R^{12}$)(aryl), —C(O)N($R^{12}$)(heteroaryl), —N($R^{12}$)($R^{12}$), —N($R^{12}$)$_2$($R^{12}$)$^+$, —N($R^{12}$)—C(O)$R^{12}$, —N($R^{12}$)C(O)O($R^{12}$), —N($R^{12}$)C(O)N($R^{12}$)($R^{12}$), —N($R^{12}$)S(O)$_2$($R^{12}$), —N($R^{12}$)S(O)$_2$—N($R^{12}$)($R^{12}$), —N($R^{12}$)S(O)$_2$O($R^{12}$), —OC(O)$R^{12}$, —OC(O)OR$^{12}$, —OC(O)—N($R^{12}$)($R^{12}$), —Si($R^{12}$)$_3$, —S—$R^{12}$, —S(O)$R^{12}$, —S(O)(NH)R$^{12}$, —S(O)$_2$R$^{12}$ or —S(O)$_2$N($R^{12}$)($R^{12}$); and wherein said C$_{2-6}$ alkenyl, C$_{2-6}$ alkynyl, C$_{3-15}$ cycloalkyl, C$_{1-8}$ haloalkyl, aryl, heteroaryl, heterocyclyl, —C(O)N($R^{12}$)(C$_{3-10}$ cycloalkyl), —C(O)N($R^{12}$)(heterocyclyl), —C(O)N($R^{12}$)(aryl), —C(O)N($R^{12}$)(heteroaryl) is optionally substituted with $Z^{1a}$.

60. The compound of claim 1, or a pharmaceutically acceptable salt, stereoisomer, mixture of stereoisomers, or deuterated analog thereof, wherein:

$R^2$ is tetrahydrofuranyl, tetrahydropyranyl, piperidinyl, piperazinyl pyrrolyl, pyrazolyl, imidazolyl, or triazolyl; any of which is optionally substituted with $Z^1$;

wherein said tetrahydrofuranyl, tetrahydropyranyl, piperidinyl, piperazinyl, pyrrolyl, pyrazolyl, imidazolyl, or triazolyl is substituted with one or more S(O)$_2$(C$_{1-3}$ alkyl);

wherein said S(O)$_2$(C$_{1-3}$ alkyl) is substituted with oxo, halo, —NO$_2$, —CN, —N$_3$, C$_{3-9}$ alkyl, C$_{2-6}$ alkenyl, C$_{2-6}$ alkynyl, C$_{3-15}$ cycloalkyl, C$_{1-8}$ haloalkyl, aryl, heteroaryl, 4-20 membered heterocyclyl, —O—$R^{12}$, —C(O)$R^{12}$, —C(O)O—$R^{12}$, —C(O)N($R^{12}$)($R^{12}$), —N($R^{12}$)($R^{12}$), —N($R^{12}$)$_2$($R^{12}$)$^+$, —N($R^{12}$)—C(O)$R^{12}$, —N($R^{12}$)C(O)O($R^{12}$), —N($R^{12}$)C(O)N($R^{12}$)($R^{12}$), —N($R^{12}$)S(O)$_2$($R^{12}$), —N($R^{12}$)S(O)$_2$—N($R^{12}$)($R^{12}$), —N($R^{12}$)S(O)$_2$O($R^{12}$), —OC(O)$R^{12}$, —OC(O)OR$^{12}$, —OC(O)—N($R^{12}$)($R^{12}$), —Si($R^{12}$)$_3$, —S—$R^{12}$, —S(O)$R^{12}$, —S(O)(NH)R$^{12}$, —S(O)$_2$R$^{12}$ or —S(O)$_2$N($R^{12}$)($R^{12}$); and wherein said $C_{3-9}$ alkyl, $C_{2-6}$ alkenyl, $C_{2-6}$ alkynyl, $C_{3-15}$ cycloalkyl, $C_{1-8}$ haloalkyl, aryl, heteroaryl, or heterocyclyl is optionally substituted with $Z^{1b}$.

61. The compound of claim 1, or a pharmaceutically acceptable salt, stereoisomer, mixture of stereoisomers, or deuterated analog thereof, wherein:
$R^2$ is tetrahydrofuranyl, tetrahydropyranyl, piperidinyl, piperazinyl pyrrolyl, pyrazolyl, imidazolyl, or triazolyl; any of which is optionally substituted with $Z^1$;
wherein said tetrahydrofuranyl, tetrahydropyranyl, piperidinyl, piperazinyl pyrrolyl, pyrazolyl, imidazolyl, or triazolyl is substituted with one or more $C_{1-4}$ hydroxyalkyl;
wherein said $C_{1-4}$ hydroxyalkyl is substituted with oxo, halo, —$NO_2$, —CN, —$N_3$, $C_{4-9}$ alkyl, $C_{2-6}$ alkenyl, $C_{2-6}$ alkynyl, $C_{3-15}$ cycloalkyl, $C_{1-8}$ haloalkyl, aryl, heteroaryl, 4-20 membered heterocyclyl, —O—$R^9$, —C(O)$R^{12}$, —C(O)O—$R^{12}$, —C(O)N($R^{12}$)($R^{12}$), —N($R^{12}$)($R^{12}$), —N($R^{12}$)$_2$($R^{12}$)$^+$, —N($R^{12}$)—C(O)$R^{12}$, —N($R^{12}$)C(O)O($R^{12}$), —N($R^{12}$)C(O)N($R^{12}$)($R^{12}$), —N($R^{12}$)S(O)$_2$($R^{12}$), —N($R^{12}$)S(O)$_2$—N($R^{12}$)($R^{12}$), —N($R^{12}$)S(O)$_2$O($R^{12}$), —OC(O)$R^{12}$, —OC(O)O$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2R^{12}$ or —S(O)$_2$N($R^{12}$)($R^{12}$); and
wherein said $C_{4-9}$ alkyl, $C_{2-6}$ alkenyl, $C_{2-6}$ alkynyl, $C_{3-15}$ cycloalkyl, $C_{1-8}$ haloalkyl, aryl, heteroaryl, or heterocyclyl is optionally substituted with $Z^{1b}$.

62. The compound of claim 1, or a pharmaceutically acceptable salt, stereoisomer, mixture of stereoisomers, or deuterated analog thereof, wherein:
$R^2$ is tetrahydrofuranyl, tetrahydropyranyl, piperidinyl, piperazinyl pyrrolyl, pyrazolyl, imidazolyl, or triazolyl; any of which is optionally substituted with $Z^1$;
wherein said tetrahydrofuranyl, tetrahydropyranyl, piperidinyl, piperazinyl pyrrolyl, pyrazolyl, imidazolyl, or triazolyl is substituted with one or more —$CH_2C(O)NH(C_{1-6}$ alkyl);
wherein said —$CH_2C(O)NH(C_{1-6}$ alkyl) is substituted with oxo, —Cl, —$NO_2$, —CN, —$N_3$, $C_{6-9}$ alkyl, $C_{2-6}$ alkenyl, $C_{2-6}$ alkynyl, $C_{3-15}$ cycloalkyl, $C_{1-8}$ haloalkyl, aryl, heteroaryl, 4-20 membered heterocyclyl, —O—$R^9$, —C(O)$R^{12}$, —C(O)O—$R^{12}$, —C(O)N($R^{12}$)($R^{12}$), —N($R^{12}$)($R^{12}$), —N($R^{12}$)$_2$($R^{12}$)$^+$, —N($R^{12}$)—C(O)$R^{12}$, —N($R^{12}$)C(O)O($R^{12}$), —N($R^{12}$)C(O)N($R^{12}$)($R^{12}$), —N($R^{12}$)S(O)$_2$($R^{12}$), —N($R^{12}$)S(O)$_2$—N($R^{12}$)($R^{12}$), —N($R^{12}$)S(O)$_2$O($R^{12}$), —OC(O)$R^{12}$, —OC(O)O$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2R^{12}$ or —S(O)$_2$N($R^{12}$)($R^{12}$);
wherein said —$CH_2C(O)NH(C_{1-6}$ alkyl) is optionally substituted with $Z^{1a}$; and
wherein said $C_{6-9}$ alkyl, $C_{2-6}$ alkenyl, $C_{2-6}$ alkynyl, $C_{3-15}$ cycloalkyl, $C_{1-8}$ haloalkyl, aryl, heteroaryl, or heterocyclyl is optionally substituted with $Z^{1b}$.

63. The compound of claim 1, or a pharmaceutically acceptable salt, stereoisomer, mixture of stereoisomers, or deuterated analog thereof, wherein:
$R^2$ is tetrahydrofuranyl, tetrahydropyranyl, piperidinyl, piperazinyl, pyrrolyl, pyrazolyl, imidazolyl, or triazolyl;
wherein said tetrahydrofuranyl, tetrahydropyranyl, piperidinyl, piperazinyl, pyrrolyl, pyrazolyl, imidazolyl, or triazolyl is substituted with one or more —$CH_2C(O)NH(C_{4-6}$ alkyl); and wherein said tetrahydrofuranyl, tetrahydropyranyl, piperidinyl, piperazinyl pyrrolyl, pyrazolyl, imidazolyl, or triazolyl is optionally substituted with $Z^1$.

64. The compound of claim 1, or a pharmaceutically acceptable salt, stereoisomer, mixture of stereoisomers, or deuterated analog thereof, wherein $R^2$ is $C_{6-10}$ aryl optionally substituted with $Z^1$.

65. The compound of claim 1, or a pharmaceutically acceptable salt, stereoisomer, mixture of stereoisomers, or deuterated analog thereof, wherein:
$R^2$ is 6-12 membered bicyclic heterocyclyl optionally substituted with $Z^1$;
wherein when said 6-12 membered bicyclic heterocyclyl is 1-oxa-7-azaspiro[3.5]nonanyl, then said 1-oxa-7-azaspiro[3.5]nonanyl is substituted with one or more $Z^1$.

66. The compound of claim 1, or a pharmaceutically acceptable salt, stereoisomer, mixture of stereoisomers, or deuterated analog thereof, wherein $R^2$ is —N($R^{12}$)($R^{12}$) —S(O)$_2R^{12}$ —S(O)$_2$N($R^{12}$)($R^{12}$); or —H.

67. The compound of claim 1, or a pharmaceutically acceptable salt, stereoisomer, mixture of stereoisomers, or deuterated analog thereof, wherein:
$R^3$ is selected from H, halo, —$NO_2$, —CN, —O—$R^{12}$, —C(O)—$R^{12}$, —C(O)—N($R^{12}$)($R^{12}$), —N($R^{12}$)($R^{12}$), —N($R^{12}$)C(O)—$R^{12}$, —N($R^{12}$)C(O)O—$R^{12}$, —N($R^{12}$)S(O)$_2$($R^{12}$), —N($R^{12}$)C(O)—N($R^{12}$)($R^{12}$), —S(O)$_2R^{12}$, —S$R^{12}$ and —S(O)$_2$N($R^{12}$)($R^{12}$).

68. The compound of claim 1, or a pharmaceutically acceptable salt, stereoisomer, mixture of stereoisomers, or deuterated analog thereof, wherein:
$R^3$ is selected from —O—$R^{12}$, —C(O)—$R^{12}$, —C(O)—N($R^{12}$)($R^{12}$), —N($R^9$)($R^9$), —NH($R^9$), —N($R^{12}$)C(O)—$R^{12}$, —N($R^{12}$)C(O)O—$R^{12}$, —N($R^{12}$)S(O)$_2$($R^{12}$), —N($R^{12}$)C(O)—N($R^{12}$)($R^{12}$), —S(O)$_2$($R^{12}$), —S—$R^{12}$ or —S(O)$_2$N($R^{12}$)($R^{12}$);
wherein when said —N(H)($R^9$) is NH($C_{1-3}$ alkyl), —N(H)($R^9$) is NH($C_{1-4}$ hydroxyalkyl), or —O—$R^{12}$ is —O($C_{1-3}$ alkyl), then said NH($C_{1-3}$ alkyl), NH($C_{1-4}$ hydroxyalkyl), or —O($C_{1-3}$ alkyl) is further substituted with one or more oxo, halo, —$NO_2$, —CN, —$N_3$, $C_{4-9}$ alkyl, $C_{2-6}$ alkenyl, $C_{2-6}$ alkynyl, $C_{3-15}$ cycloalkyl, $C_{1-8}$ haloalkyl, aryl, heteroaryl, 4-20 membered heterocyclyl, —O—$R^9$, —C(O)$R^{12}$, —C(O)O—$R^{12}$, —C(O)N($R^{12}$)($R^{12}$), —N($R^{12}$)($R^{12}$), —N($R^{12}$)$_2$($R^{12}$)$^+$, —N($R^{12}$)—C(O)$R^{12}$, —N($R^{12}$)C(O)O($R^{12}$), —N($R^{12}$)C(O)N($R^{12}$)($R^{12}$), —N($R^{12}$)S(O)$_2$($R^{12}$), —N($R^{12}$)S(O)$_2$—N($R^{12}$)($R^{12}$), —N($R^{12}$)S(O)$_2$O($R^{12}$), —OC(O)$R^{12}$, —OC(O)O$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2R^{12}$ or —S(O)$_2$N($R^{12}$)($R^{12}$); and
wherein said $C_{4-9}$ alkyl, $C_{2-6}$ alkenyl, $C_{2-6}$ alkynyl, $C_{3-15}$ cycloalkyl, $C_{1-8}$ haloalkyl, aryl, heteroaryl, or heterocyclyl is optionally substituted with $Z^{1a}$.

69. The compound of claim 1, or a pharmaceutically acceptable salt, stereoisomer, mixture of stereoisomers, or deuterated analog thereof, wherein:
$R^3$ is selected from —O($C_4$ alkyl) or —N(H)($C_4$ alkyl);
wherein said —O($C_4$ alkyl) is optionally substituted with $Z^{1a}$; wherein said —N(H)($C_4$ alkyl) is optionally substituted with oxo, halo —$NO_2$, —CN, —$N_3$, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, 4-20 membered heterocyclyl, —O—$R^9$, —C(O)$R^{12}$, —C(O)O—$R^{12}$, —C(O)N($R^{12}$)($R^{12}$), —N($R^{12}$)($R^{12}$), —N($R^{12}$)$_2$($R^{12}$)$^+$, —N($R^{12}$)—C(O)$R^{12}$, —N($R^{12}$)C(O)O($R^{12}$), —N($R^{12}$)C(O)N($R^{12}$)($R^{12}$), —N($R^{12}$)S(O)$_2$($R^{12}$), —N($R^{12}$)

$S(O)_2-N(R^{12})(R^{12})$, $-N(R^{12})S(O)_2O(R^{12})$, $-OC(O)R^{12}$, $-OC(O)OR^{12}$, $-OC(O)-N(R^{12})(R^{12})$, $-Si(R^{12})_3$, $-S-R^{12}$, $-S(O)R^{12}$, $-S(O)(NH)R^{12}$, $-S(O)_2R^{12}$ or $-S(O)_2N(R^{12})(R^{12})$;

wherein said $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, or heterocyclyl is optionally substituted with $Z^{1a}$.

70. The compound of claims 1 claim 1, or a pharmaceutically acceptable salt, stereoisomer, mixture of stereoisomers, or deuterated analog thereof, wherein $R^3$ is $C_{1-9}$ alkyl optionally substituted with $Z^1$.

71. The compound of claim 1, or a pharmaceutically acceptable salt, stereoisomer, mixture of stereoisomers, or deuterated analog thereof, wherein:
$R^3$ is $C_{1-2}$ alkyl optionally substituted with F and further substituted with one or more oxo, $-Cl$, $-NO_2$, $-N_3$, $-CN$, $C_{3-9}$ alkyl, $C_{2-6}$ alkenyl, $C_{2-6}$ alkynyl, $C_{3-15}$ cycloalkyl, $C_{1-8}$ haloalkyl, aryl, heteroaryl, 4-20 membered heterocyclyl, $-O-R^{12}$, $-C(O)-R^{12}$, $-C(O)O-R^{12}$, $-C(O)-N(R^{12})(R^{12})$, $-N(R^{12})(R^{12})$, $-N(R^{12})_2(R^{12})^+$, $-N(R^{12})C(O)-R^{12}$, $-N(R^{12})C(O)O-R^{12}$, $-N(R^{12})C(O)N(R^{12})(R^{12})$, $-N(R^{12})S(O)_2(R^{12})$, $-NR^{12}S(O)_2N(R^{12})(R^{12})$, $-NR^{12}S(O)_2O(R^{12})$, $-OC(O)R^{12}$, $-OC(O)-N(R^{12})(R^{12})$, $-Si(R^{12})_3$, $-S-R^{12}$, $-S(O)R^{12}$, $-S(O)(NH)R^{12}$, $-S(O)_2R^{12}$ or $-S(O)_2N(R^{12})(R^{12})$; and
wherein said $C_{3-9}$ alkyl, $C_{2-6}$ alkenyl, $C_{2-6}$ alkynyl, $C_{3-15}$ cycloalkyl, $C_{1-8}$ haloalkyl, aryl, heteroaryl, or heterocyclyl is optionally substituted with $Z^{1a}$.

72. The compound of claim 1, or a pharmaceutically acceptable salt, stereoisomer, mixture of stereoisomers, or deuterated analog thereof, wherein $R^3$ is $C_3$ alkyl substituted with one or more $Z^1$.

73. The compound of claim 1, or a pharmaceutically acceptable salt, stereoisomer, mixture of stereoisomers, or deuterated analog thereof, wherein $R^3$ is $C_{4-9}$ alkyl optionally substituted with $Z^1$.

74. The compound of claim 1, or a pharmaceutically acceptable salt, stereoisomer, mixture of stereoisomers, or deuterated analog thereof, wherein $R^3$ is $C_{2-9}$ alkynyl optionally substituted with $Z^1$.

75. The compound of claim 1, or a pharmaceutically acceptable salt, stereoisomer, mixture of stereoisomers, or deuterated analog thereof, wherein $R^3$ is $C_{2-9}$ alkenyl optionally substituted with $Z^1$.

76. The compound of claim 1, or a pharmaceutically acceptable salt, stereoisomer, mixture of stereoisomers, or deuterated analog thereof, wherein $R^3$ is a 5-10 membered heteroaryl optionally substituted with $Z^1$.

77. The compound of claim 1, or a pharmaceutically acceptable salt, stereoisomer, mixture of stereoisomers, or deuterated analog thereof, wherein:
$R^3$ is a 5-10 membered heteroaryl optionally substituted with $Z^1$;
wherein if said 5-10 membered heteroaryl is pyridinyl, then said pyridinyl is further substituted with one or more $Z^1$.

78. The compound of claim 1, or a pharmaceutically acceptable salt, stereoisomer, mixture of stereoisomers, or deuterated analog thereof, wherein $R^3$ is $C_{6-10}$ aryl optionally substituted with $Z^1$.

79. The compound of claim 1, or a pharmaceutically acceptable salt, stereoisomer, mixture of stereoisomers, or deuterated analog thereof, wherein:
$R^3$ is $C_{6-10}$ aryl optionally substituted with $Z^1$;
wherein when said $C_{6-10}$ aryl is cyanophenyl then said cyanophenyl is further substituted with one or more oxo, halo $-NO_2$, $-N_3$, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, 4-20 membered heterocyclyl, $-O-R^{12}$, $-C(O)R^{12}$, $-C(O)O-R^{12}$, $-C(O)N(R^{12})(R^{12})$, $-N(R^{12})(R^{12})$, $-N(R^{12})_2(R^{12})^+$, $-N(R^{12})-C(O)R^{12}$, $-N(R^{12})C(O)O(R^{12})$, $-N(R^{12})C(O)N(R^{12})(R^{12})$, $-N(R^{12})S(O)_2(R^{12})$, $-N(R^{12})S(O)_2-N(R^{12})(R^{12})$, $-N(R^{12})S(O)_2O(R^{12})$, $-OC(O)R^{12}$, $-OC(O)OR^{12}$, $-OC(O)-N(R^{12})(R^{12})$, $-Si(R^{12})_3$, $-S-R^{12}$, $-S(O)R^{12}$, $-S(O)(NH)R^{12}$, $-S(O)_2R^{12}$ or $-S(O)_2N(R^{12})(R^{12})$; and
wherein said $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl is optionally substituted with $Z^{1a}$.

80. The compound of claim 1, or a pharmaceutically acceptable salt, stereoisomer, mixture of stereoisomers, or deuterated analog thereof, wherein $R^3$ is a 4-12 membered heterocyclyl optionally substituted with $Z^1$.

81. The compound of claim 1, or a pharmaceutically acceptable salt, stereoisomer, mixture of stereoisomers, or deuterated analog thereof, wherein:
$R^3$ is a 4-12 membered heterocyclyl optionally substituted with $Z^1$;
wherein when said 4-12 membered heterocyclyl is hydroxypyrrolidinyl then said hydroxypyrrolidinyl is further substituted with one or more oxo, halo, $-CN$, $-CN$, $-NO_2$, $-N_3$, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, 4-20 membered heterocyclyl, $-O-R^9$, $-C(O)R^{12}$, $-C(O)O-R^{12}$, $-C(O)N(R^{12})(R^{12})$, $-N(R^{12})(R^{12})$, $-N(R^{12})_2(R^{12})^+$, $-N(R^{12})-C(O)R^{12}$, $-N(R^{12})C(O)O(R^{12})$, $-N(R^{12})C(O)N(R^{12})(R^{12})$, $-N(R^{12})S(O)_2(R^{12})$, $-N(R^{12})S(O)_2-N(R^{12})(R^{12})$, $-N(R^{12})S(O)_2O(R^{12})$, $-OC(O)R^{12}$, $-OC(O)OR^{12}$, $-OC(O)-N(R^{12})(R^{12})$, $-Si(R^{12})_3$, $-S-R^{12}$, $-S(O)R^{12}$, $-S(O)(NH)R^{12}$, $-S(O)_2R^{12}$ or $-S(O)_2N(R^{12})(R^{12})$;
wherein said $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, or 4-20 membered heterocyclyl is optionally substituted with $Z^{1a}$.

82. The compound of claim 1, or a pharmaceutically acceptable salt, stereoisomer, mixture of stereoisomers, or deuterated analog thereof, wherein $R^3$ is $C_{3-10}$ cycloalkyl optionally substituted with $Z^1$.

83. The compound of claim 1, or a pharmaceutically acceptable salt, stereoisomer, mixture of stereoisomers, or deuterated analog thereof, wherein $R^3$ is $C_{3-6}$ cycloalkyl substituted with one or more $Z^1$.

84. The compound of claim 1, or a pharmaceutically acceptable salt, stereoisomer, mixture of stereoisomers, or deuterated analog thereof, wherein $R^3$ is $C_{7-10}$ cycloalkyl optionally substituted with $Z^1$.

85. The compound of claim 1, or a pharmaceutically acceptable salt, stereoisomer, mixture of stereoisomers, or deuterated analog thereof, wherein $R^4$ is H, halo, $-NO_2$, $-CN$, $-O-R^{12}$, $-C(O)-R^{12}$, $-C(O)-N(R^{12})(R^{12})$, $-N(R^{12})(R^{12})$, $-N(R^{12})C(O)-R^{12}$, $-N(R^{12})C(O)O-R^{12}$, $-N(R^{12})S(O)_2(R^{12})$, $-N(R^{12})C(O)-N(R^{12})(R^{12})$, $-S(O)_2R^{12}$, $-SR^{12}$ or $-S(O)_2N(R^{12})(R^{12})$.

86. The compound of claim 1, or a pharmaceutically acceptable salt, stereoisomer, mixture of stereoisomers, or deuterated analog thereof, wherein:
$R^4$ is $-O-R^{12}$, $-C(O)-R^{12}$, $-C(O)-N(R^{12})(R^{12})$, $-N(R^9)(R^9)$, $-NH(R^9)$, $-N(R^{12})C(O)-R^{12}$, $-N(R^{12})C(O)O-R^{12}$, $-N(R^{12})S(O)_2(R^{12})$, —N($R^{12}$)C(O)—N($R^{12}$)($R^{12}$), —S(O)$_2$($R^{12}$), —S—$R^{12}$ or —S(O)$_2$N($R^{12}$)($R^{12}$);

wherein when said —N(H)($R^9$) is NH($C_{1-3}$ alkyl), —N(H)($R^9$) is NH($C_{1-4}$ hydroxyalkyl), or —O—$R^{12}$ is —O($C_{1-3}$ alkyl), then said NH($C_{1-3}$ alkyl), NH($C_{1-4}$ hydroxyalkyl), or —O($C_{1-3}$ alkyl) is further substituted with one or more oxo, halo, —NO$_2$, —CN, —N$_3$, $C_{4-9}$ alkyl, $C_{2-6}$ alkenyl, $C_{2-6}$ alkynyl, $C_{3-15}$ cycloalkyl, $C_{1-8}$ haloalkyl, aryl, heteroaryl, 4-20 membered heterocyclyl, —O—$R^9$, —C(O)$R^{12}$, —C(O)O—$R^{12}$, —C(O)N($R^{12}$)($R^{12}$), —N($R^{12}$)($R^{12}$), —N($R^{12}$)$_2$($R^{12}$)$^+$, —N($R^{12}$)—C(O)$R^{12}$, —N($R^{12}$)C(O)O($R^{12}$), —N($R^{12}$)C(O)N($R^{12}$)($R^{12}$), —N($R^{12}$)S(O)$_2$($R^{12}$), —N($R^{12}$)S(O)$_2$—N($R^{12}$)($R^{12}$), —N($R^{12}$)S(O)$_{2O(R}$$^{12}$), —OC(O)$R^{12}$, —OC(O)O$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2R^{12}$ or —S(O)$_2$N($R^{12}$)($R^{12}$);

wherein said $C_{4-9}$ alkyl, $C_{2-6}$ alkenyl, $C_{2-6}$ alkynyl, $C_{3-15}$ cycloalkyl, $C_{1-8}$ haloalkyl, aryl, heteroaryl, or heterocyclyl is optionally substituted with $Z^{1a}$.

87. The compound of claim 1, or a pharmaceutically acceptable salt, stereoisomer, mixture of stereoisomers, or deuterated analog thereof, wherein:

$R^4$ is selected from —O($C_4$ alkyl) or —N(H)($C_4$ alkyl); wherein said —O($C_4$ alkyl) is optionally substituted with $Z^{1a}$;

wherein said —N(H)($C_4$ alkyl) is optionally substituted with oxo, halo, —NO$_2$, —CN, —N$_3$, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, 4-20 membered heterocyclyl, —O—$R^9$, —C(O)$R^{12}$, —C(O)O—$R^{12}$, —C(O)N($R^{12}$)($R^{12}$), —N($R^{12}$)(V), —N($R^{12}$)$_2$($R^{12}$)$^+$, —N($R^{12}$)—C(O)$R^{12}$, —N($R^{12}$)C(O)O($R^{12}$), —N($R^{12}$)C(O)N($R^{12}$)($R^{12}$), —N($R^{12}$)S(O)$_2$($R^{12}$), —N($R^{12}$)S(O)$_2$—N($R^{12}$)($R^{12}$), —N($R^{12}$)S(O)$_2$O($R^{12}$), —OC(O)$R^{12}$, —OC(O)O$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2R^{12}$ or —S(O)$_2$N($R^{12}$)($R^{12}$);

wherein said $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl is optionally substituted with $Z^{1a}$.

88. The compound of claim 1, or a pharmaceutically acceptable salt, stereoisomer, mixture of stereoisomers, or deuterated analog thereof, wherein $R^4$ is $C_{1-9}$ alkyl optionally substituted with $Z^1$.

89. The compound of claim 1, or a pharmaceutically acceptable salt, stereoisomer, mixture of stereoisomers, or deuterated analog thereof, wherein:

$R^4$ is $C_{1-2}$ alkyl optionally substituted with F and further substituted with one or more oxo, —Cl, —NO$_2$, —N$_3$, —CN, $C_{3-9}$ alkyl, $C_{2-6}$ alkenyl, $C_{2-6}$ alkynyl, $C_{3-15}$ cycloalkyl, $C_{1-8}$ haloalkyl, aryl, 4-20 membered heterocyclyl, —O—$R^{12}$, —C(O)—$R^{12}$, —C(O)O—$R^{12}$, —C(O)—N($R^{12}$)($R^{12}$), —N($R^{12}$)($R^{12}$), —N($R^{12}$)$_2$($R^{12}$)$^+$, —N($R^{12}$)C(O)—$R^{12}$, —N($R^{12}$)C(O)O—$R^{12}$, —N($R^{12}$)C(O)N($R^{12}$)($R^{12}$), —N($R^{12}$)S(O)$_2$($R^{12}$), —N$R^{12}$S(O)$_2$N($R^{12}$)($R^{12}$), —N$R^{12}$S(O)$_2$O($R^{12}$), —OC(O)$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2R^{12}$ or —S(O)$_2$N($R^{12}$)($R^{12}$); and wherein said $C_{3-9}$ alkyl, $C_{2-6}$ alkenyl, $C_{2-6}$ alkynyl, $C_{3-15}$ cycloalkyl, $C_{1-8}$ haloalkyl, aryl, heteroaryl, or heterocyclyl is optionally substituted with $Z^{1a}$.

90. The compound of claim 1, or a pharmaceutically acceptable salt, stereoisomer, mixture of stereoisomers, or deuterated analog thereof, wherein $R^4$ is $C_3$ alkyl substituted with one or more $Z^1$.

91. The compound of claim 1, or a pharmaceutically acceptable salt, stereoisomer, mixture of stereoisomers, or deuterated analog thereof, wherein $R^4$ is $C_{4-9}$ alkyl optionally substituted with $Z^1$.

92. The compound of claim 1, or a pharmaceutically acceptable salt, stereoisomer, mixture of stereoisomers, or deuterated analog thereof, wherein $R^4$ is $C_{2-9}$ alkynyl optionally substituted with $Z^1$.

93. The compound of claim 1, or a pharmaceutically acceptable salt, stereoisomer, mixture of stereoisomers, or deuterated analog thereof, wherein $R^4$ is $C_{2-9}$ alkenyl optionally substituted with $Z^1$.

94. The compound of claim 1, or a pharmaceutically acceptable salt, stereoisomer, mixture of stereoisomers, or deuterated analog thereof, wherein $R^4$ is a 5-10 membered heteroaryl optionally substituted with $Z^1$.

95. The compound of claim 1, or a pharmaceutically acceptable salt, stereoisomer, mixture of stereoisomers, or deuterated analog thereof, wherein:

$R^4$ is a 5-10 membered heteroaryl optionally substituted with $Z^1$;

wherein when said 5-10 membered heteroaryl is pyridinyl then said pyridinyl is further substituted with one or more $Z^1$.

96. The compound of claim 1, or a pharmaceutically acceptable salt, stereoisomer, mixture of stereoisomers, or deuterated analog thereof, wherein $R^4$ is $C_{6-10}$ aryl optionally substituted with $Z^1$.

97. The compound of claim 1, or a pharmaceutically acceptable salt, stereoisomer, mixture of stereoisomers, or deuterated analog thereof, wherein:

$R^4$ is $C_{6-10}$ aryl optionally substituted with $Z^1$;

wherein when said $C_{6-10}$ aryl is cyanophenyl then said cyanophenyl is further substituted with one or more oxo, halo, —NO$_2$, —N$_3$, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, 4-20 membered heterocyclyl, —O—$R^{12}$, —C(O)$R^{12}$, —C(O)O—$R^{12}$, —C(O)N($R^{12}$)($R^{12}$), —N($R^{12}$)($R^{12}$), —NR$^{12}$)$_2$($R^{12}$)$^+$, —N($R^{12}$)—C(O)$R^{12}$, —N($R^{12}$)C(O)O($R^{12}$), —N($R^{12}$)C(O)N($R^{12}$)($R^{12}$), —NR$^{12}$S(O)$_2$($R^{12}$), —N($R^{12}$)S(O)$_2$—N($R^{12}$)($R^{12}$), —NR$^{12}$S(O)$_2$O($R^{12}$), —OC(O)$R^{12}$, —OC(O)O$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2R^{12}$ or —S(O)$_2$N($R^{12}$)($R^{12}$); and wherein said $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl is optionally substituted with $Z^{1a}$.

98. The compound of claim 1, or a pharmaceutically acceptable salt, stereoisomer, mixture of stereoisomers, or deuterated analog thereof, wherein $R^4$ is a 4-12 membered heterocyclyl optionally substituted with $Z^1$.

99. The compound of claim 1, or a pharmaceutically acceptable salt, stereoisomer, mixture of stereoisomers, or deuterated analog thereof, wherein:

$R^4$ is a 4-12 membered heterocyclyl optionally substituted with $Z^1$; wherein when said 4-12 membered heterocyclyl is hydroxypyrrolidinyl then said hydroxypyrrolidinyl is further substituted with one or more oxo, halo, —CN, —NO$_2$, —N$_3$, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, 4-20 membered heterocyclyl, —O—$R^9$, —C(O)$R^{12}$, —C(O)O—$R^{12}$, —C(O)N($R^{12}$)($R^{12}$), —N($R^{12}$)($R^{12}$), —N($R^{12}$)$_2$($R^{12}$)$^+$, —N($R^{12}$)—C(O)$R^{12}$, —N($R^{12}$)C(O)O($R^{12}$), —N($R^{12}$)C(O)N($R^{12}$)($R^{12}$), —N($R^{12}$)S(O)$_2$($R^{12}$), —N($R^{12}$)S(O)$_2$—N($R^{12}$)($R^{12}$), —N($R^{12}$)S(O)$_2$O($R^{12}$), —OC(O)$R^{12}$, —OC(O)

OR$^{12}$, —OC(O)—N(R$^{12}$)(R$^{12}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{12}$)(R$^{12}$);

wherein said C$_{1-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl is optionally substituted with Z$^{1a}$.

100. The compound of claim 1, or a pharmaceutically acceptable salt, stereoisomer, mixture of stereoisomers, or deuterated analog thereof, wherein R$^4$ is C$_{3-10}$ cycloalkyl optionally substituted with Z$^1$.

101. The compound of claim 1, or a pharmaceutically acceptable salt, stereoisomer, mixture of stereoisomers, or deuterated analog thereof, wherein R$^4$ is C$_{3-6}$ cycloalkyl substituted with one or more Z$^1$.

102. The compound of claim 1, or a pharmaceutically acceptable salt, stereoisomer, mixture of stereoisomers, or deuterated analog thereof, wherein R$^4$ is C$_{7-10}$ cycloalkyl optionally substituted with Z$^1$.

103. The compound of claim 1, or a pharmaceutically acceptable salt, stereoisomer, mixture of stereoisomers, or deuterated analog thereof, wherein at least one of R$^5$, R$^6$ or R$^7$ is independently selected from H, halo, —NO$_2$, —CN, —O—R$^{12}$, —C(O)—R$^{12}$, —C(O)—N(R$^{12}$)(R$^{12}$), —N(R$^9$)(R$^9$), NH(R$^9$), —N(R$^{12}$)C(O)—R$^{12}$, —N(R$^{12}$)C(O)O—R$^{12}$, or —N(R$^{12}$)S(O)$_2$(R$^{12}$).

104. The compound of claim 1, or a pharmaceutically acceptable salt, stereoisomer, mixture of stereoisomers, or deuterated analog thereof, wherein at least one of R$^5$, R$^6$ or R$^7$ is independently selected from —NO$_2$, —O—R$^{12}$, —C(O)—R$^{12}$, —C(O)—N(R$^{12}$)(R$^{12}$), —N(R$^9$)(R$^9$), —N(R$^{12}$)C(O)—R$^{12}$, —N(R$^{12}$)C(O)O—R$^{12}$, or —N(R$^{12}$)S(O)$_2$(R$^{12}$).

105. The compound of claim 1, or a pharmaceutically acceptable salt, stereoisomer, mixture of stereoisomers, or deuterated analog thereof, wherein at least one of R$^5$, R$^6$ or R$^7$ is independently C$_{1-5}$ alkyl optionally substituted with Z$^1$.

106. The compound of claim 1, or a pharmaceutically acceptable salt, stereoisomer, mixture of stereoisomers, or deuterated analog thereof, wherein at least one of R$^5$, R$^6$ or R$^7$ is independently C$_{1-2}$ alkyl optionally substituted with F and substituted with one or more oxo, —Cl, —NO$_2$, —N$_3$, —CN, C$_{3-9}$ alkyl, C$_{2-6}$ alkenyl, C$_{2-6}$ alkynyl, C$_{3-15}$ cycloalkyl, C$_{1-8}$ haloalkyl, aryl, heteroaryl, 4-20 membered heterocyclyl, —O—R$^{12}$, —C(O)—R$^{12}$, —C(O)O—R$^{12}$, —C(O)—N(R$^{12}$)(R$^{12}$), —N(R$^{12}$)(R$^{12}$), —N(R$^{12}$)$_2$(R$^{12}$)$^+$, —N(R$^{12}$)C(O)—R$^{12}$, —N(R$^{12}$)C(O)O—R$^{12}$, —N(R$^{12}$)C(O)N(R$^{12}$)(R$^{12}$), —N(R$^{12}$)S(O)$_2$(R$^{12}$), —NR$^{12}$S(O)$_2$N(R$^{12}$)(R$^{12}$), —NR$^{12}$S(O)$_2$O(R$^{12}$), —OC(O)R$^{12}$, —OC(O)—N(R$^{12}$)(R$^{12}$), —Si(R$^{12}$)$_3$, —S—R$^{12}$, —S(O)R$^{12}$, —S(O)(NH)R$^2$, —S(O)$_2$R$^{12}$ or —S(O)$_2$N(R$^{12}$)(R$^{12}$); wherein any alkyl, alkenyl, alkynyl, cycloalkyl, haloalkyl, aryl, heteroaryl or heterocyclyl is optionally substituted with Z$^{1a}$.

107. The compound of claim 1, or a pharmaceutically acceptable salt, stereoisomer, mixture of stereoisomers, or deuterated analog thereof, wherein at least one of R$^5$, R$^6$ or R$^7$ is independently C$_3$ alkyl substituted with one or more Z$^1$.

108. The compound of claim 1, or a pharmaceutically acceptable salt, stereoisomer, mixture of stereoisomers, or deuterated analog thereof, wherein at least one of R$^5$, R$^6$ or R$^7$ is independently C$_{4-5}$ alkyl optionally substituted with Z$^1$.

109. The compound of claim 1, or a pharmaceutically acceptable salt, stereoisomer, mixture of stereoisomers, or deuterated analog thereof, wherein at least one of R$^5$, R$^6$ or R$^7$ is independently cyclopropyl, oxetanyl, or azetidinyl optionally substituted with Z$^1$.

110. The compound of claim 1, or a pharmaceutically acceptable salt, stereoisomer, mixture of stereoisomers, or deuterated analog thereof, wherein at least one of R$^5$, R$^6$ or R$^7$ is independently cyclopropyl, oxetanyl, or azetidinyl; wherein said cyclopropyl is substituted with one or more Z$^1$; wherein said oxetanyl or azetidinyl is optionally substituted with Z$^1$.

111. The compound of claim 1, or a pharmaceutically acceptable salt, stereoisomer, mixture of stereoisomers, or deuterated analog thereof, wherein no more than two of R$^3$, R$^4$, R$^5$, R$^6$ or R$^7$ are H.

112. The compound of any of claim 1, or a pharmaceutically acceptable salt, stereoisomer, mixture of stereoisomers, or deuterated analog thereof, wherein R$^3$ is H or F.

113. The compound of any of claim 1, or a pharmaceutically acceptable salt, stereoisomer, mixture of stereoisomers, or deuterated analog thereof, wherein R$^4$ is H, F, —CN or Cl.

114. The compound of any of claim 1, or a pharmaceutically acceptable salt, stereoisomer, mixture of stereoisomers, or deuterated analog thereof, wherein R$^5$ is H or F.

115. The compound of any of claim 1, or a pharmaceutically acceptable salt, stereoisomer, mixture of stereoisomers, or deuterated analog thereof, wherein R$^6$ is H or F.

116. The compound of any of claim 1, or a pharmaceutically acceptable salt, stereoisomer, mixture of stereoisomers, or deuterated analog thereof, wherein R$^7$ is H or F.

117. The compound of claim 1, or a pharmaceutically acceptable salt, stereoisomer, mixture of stereoisomers, or deuterated analog thereof, wherein:
Z$^1$ is selected H, halo, —CN, C$_{1-9}$ alkyl, C$_{3-15}$ cycloalkyl, aryl, heteroaryl, 4-20 membered heterocyclyl, —O—R$^{12}$, —C(O)—R$^{12}$, —C(O)—N(R$^{12}$)(R$^{12}$), —N(R$^{12}$)(R$^{12}$), —N(R$^{12}$)C(O)—R$^{12}$, —N(R$^{12}$)C(O)O—R$^{12}$, —N(R$^{12}$)S(O)$_2$(R$^{12}$), —OC(O)—N(R$^{12}$)(R$^{12}$), —S(O)$_2$R$^{12}$ or —S(O)$_2$N(R$^{12}$)(R$^{12}$); and
wherein any alkyl, cycloalkyl, aryl, heteroaryl or heterocyclyl is optionally substituted with Z$^{1a}$.

118. A pharmaceutical composition comprising an effective amount of a compound of claim 1, together with a pharmaceutically acceptable carrier, and optionally a diluent.

119. A method of treating an inflammation related disease or disorder in a patient in need thereof, comprising administering to said patient a compound of claim 1, or a pharmaceutical composition containing a compound of claim 1, and wherein the inflammation related disease or disorder is selected from the group consisting of: rheumatoid arthritis (RA), inflammatory bowel disease (IBD), gout, Lyme arthritis, systemic lupus erythematosus (SLE), Sjogren's syndrome, viral myocarditis. Aicardi-Goutieres syndrome, Familial chilblain lupus, and Retinal vasculopathy with cerebral leukodystrophy.

120. The compound of claim 1, or a pharmaceutically acceptable salt, stereoisomer, mixture of stereoisomers, or deuterated analog thereof, wherein R$^1$ is 5-10 membered heteroaryl optionally substituted with Z$^1$, wherein when said 5-10 membered heteroaryl is furanyl, pyranyl, pyrraolyl, imidazolyl, pyrazolyl, triazoyl, pyridinyl, pyrimidinyl, pyridazinyl, pyrazinyl, thiaphenyl, oxazoyl, thiazoyl, said 5-10 membered heteroaryl is optionally substituted with a 5-12 membered bicyclic ring or a 5-12 membered hetero bicyclic ring, wherein the bicyclic ring and the hetero bicyclic ring may be fused, spiro or bridged.

121. The compound of claim 1, or a pharmaceutically acceptable salt, stereoisomer, mixture of stereoisomers, or deuterated analog thereof, wherein $R^1$ is 5-12 membered bicyclic ring optionally substituted with $Z^1$.

122. The compound of claim 1, or a pharmaceutically acceptable salt, stereoisomer, mixture of stereoisomers, or deuterated analog thereof, $R^1$ is 5-12 membered bicyclic ring optionally substituted with $C_{1-3}$ alkyl, $C_{2-6}$ alkenyl, $C_{2-6}$ alkynl, 3-6 membered cyclo alkyl, 3-6 membered heterocyclyl, 5-6 membered aryl, or 5-6 membered heteroaryl, where the $C_{1-3}$ alkyl, $C_{2-6}$ alkenyl, $C_{2-6}$ alkynl, 3-6 membered cyclo alkyl, 3-6 membered heterocyclyl, 5-6 membered aryl, or 5-6 membered heteroaryl groups can further be substituted with one or more $Z^{1a}$ groups.

123. The compound of claim 1, or a pharmaceutically acceptable salt, stereoisomer, mixture of stereoisomers, or deuterated analog thereof, $R^1$ is 5-12 membered bicyclic heterocyclyl optionally substituted with $Z^1$.

124. The compound of claim 1, or a pharmaceutically acceptable salt, stereoisomer, mixture of stereoisomers, or deuterated analog thereof, $R^1$ is 5-12 membered bicyclic heterocyclyl optionally substituted with $C_{1-3}$ alkyl, $C_{2-6}$ alkenyl, $C_{2-6}$ alkynl, 3-6 membered cyclo alkyl, 3-6 membered heterocyclyl, 5-6 membered aryl, or 5-6 membered heteroaryl, where the $C_{1-3}$ alkyl, $C_{2-6}$ alkenyl, $C_{2-6}$ alkynl, 3-6 membered cyclo alkyl, 3-6 membered heterocyclyl, 5-6 membered aryl, or 5-6 membered heteroaryl groups can further be substituted with one or more $Z^{1a}$ groups.

125. A compound of Formula (I)

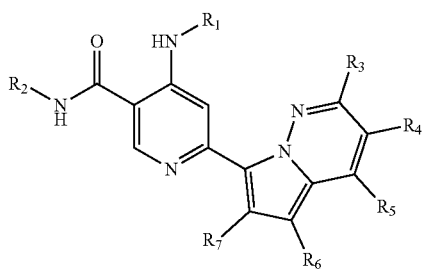

(I)

wherein:

$R^1$ and $R^2$ are each independently selected from:
h) $C_{1-10}$ alkyl optionally substituted with $Z^1$;
i) $C_{3-10}$ cycloalkyl optionally substituted with $Z^1$;
j) 5-10 membered heteroaryl optionally substituted with $Z^1$;
k) $C_{6-10}$ aryl optionally substituted with $Z^1$;
l) 4-7 membered monocyclic heterocyclyl optionally substituted with $Z^1$;
m) 6-12 membered bicyclic heterocyclyl optionally substituted with $Z^1$; or
n) —N($R^{12}$)($R^{12}$), —S(O)$_2R^{12}$, S(O)$_2$N($R^{12}$)($R^{12}$), or —H;

wherein when $R^1$ or $R^2$ is $C_{1-10}$ alkyl, $C_{3-10}$ cycloalkyl, 5-10 membered heteroaryl, $C_{6-10}$ aryl, 4-7 membered monocyclic heterocyclyl, 6-12 membered bicyclic heterocyclyl, two $Z^1$ groups either attached to the same atom on $R^1$ or $R^2$, or two $Z^1$ groups attached to adjacent atoms on $R^1$ or $R^2$, append together to form a 3-6 membered cycloalkyl or 3-6 membered heterocyclyl;

$R^3$ and $R^4$ are each independently selected from:
i) H, halo, —NO$_2$, —CN, —O—$R^{12}$, —C(O)—$R^{12}$, —C(O)—N($R^{12}$)($R^{12}$), —N($R^{12}$)($R^{12}$), —N($R^{12}$)C(O)—$R^{12}$, —N($R^{12}$)C(O)O—$R^{12}$, —N($R^{12}$)S(O)$_2$($R^{12}$), —N($R^{12}$)C(O)—N($R^{12}$)($R^{12}$), —S(O)$_2R^{12}$ or —S(O)$_2$N($R^{12}$)($R^{12}$);
j) $C_{1-9}$ alkyl optionally substituted with $Z^1$;
k) $C_{2-9}$ alkynyl optionally substituted with $Z^1$;
l) $C_{2-9}$ alkenyl optionally substituted with $Z^1$;
m) 5-10 membered heteroaryl optionally substituted with $Z^1$;
n) $C_{6-10}$ aryl optionally substituted with $Z^1$;
o) 4-12 membered heterocyclyl optionally substituted with $Z^1$; or
p) $C_{3-10}$ cycloalkyl optionally substituted with $Z^1$;

$R^5$, $R^6$ and $R^7$ are each independently selected from:
d) H, halo, —NO$_2$, —CN, —O—$R^{12}$, —C(O)—$R^{12}$, —C(O)—N($R^{12}$)($R^{12}$), —N($R^{12}$)($R^{12}$), —N($R^{12}$)—C(O)—$R^{12}$, —N($R^{12}$)C(O)O—$R^{12}$, or —N($R^{12}$)S(O)$_2$($R^{12}$);
e) $C_{1-5}$ alkyl optionally substituted with $Z^1$; or
f) Cyclopropyl, oxetanyl or azetidinyl optionally substituted with $Z^1$;

$Z^1$ is independently oxo, halo, —NO$_2$, —N$_3$, —CN, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, 4-20 membered heterocyclyl, —O—$R^{12}$, —C(O)—$R^{12}$, —C(O)O—$R^{12}$, —C(O)—N($R^{12}$)($R^{12}$), —N($R^{12}$)($R^{12}$), —N($R^{12}$)$_2$($R^{12}$)$^+$, —N($R^{12}$)C(O)—$R^{12}$, —N($R^{12}$)C(O)O—$R^{12}$, —N($R^{12}$)C(O)N($R^{12}$)($R^{12}$), —N($R^{12}$)S(O)$_2$($R^{12}$), —NR$^{12}$S(O)$_2$N($R^{12}$)($R^{12}$), —NR$^{12}$S(O)$_2$O($R^{12}$), —OC(O)$R^{12}$, —OC(O)O$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2R^{12}$ or —S(O)$_2$N($R^{12}$)($R^{12}$);

wherein any alkyl, alkenyl, alkynyl, cycloalkyl, haloalkyl, aryl, heteroaryl or heterocyclyl is optionally substituted with $Z^{1a}$;

each $Z^{1a}$ is independently oxo, halo, —NO$_2$, —CN, —N$_3$, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, heterocyclyl, —O—$R^{12}$, —C(O)$R^{12}$, —C(O)O—$R^{12}$, —C(O)N($R^{12}$)($R^{12}$), —N($R^{12}$)($R^{12}$), —N($R^{12}$)$_2$($R^{12}$)$^+$, —N($R^{12}$)—C(O)$R^{12}$, —N($R^{12}$)C(O)O($R^{12}$), —N($R^{12}$)C(O)N($R^{12}$)($R^{12}$), —N($R^{12}$)S(O)$_2$($R^{12}$), —N($R^{12}$)S(O)$_2$—N($R^{12}$)($R^{12}$), —N($R^{12}$)S(O)$_2$O($R^{12}$), —OC(O)$R^{12}$, —OC(O)O$R^{12}$, —OC(O)—N($R^{12}$)($R^{12}$), —Si($R^{12}$)$_3$, —S—$R^{12}$, —S(O)$R^{12}$, —S(O)(NH)$R^{12}$, —S(O)$_2R^{12}$ or —S(O)$_2$N($R^{12}$)($R^{12}$);

wherein any alkyl, alkenyl, alkynyl, cycloalkyl, haloalkyl, aryl, heteroaryl or heterocyclyl is optionally substituted with $Z^{ib}$;

each $R^{12}$ is independently H, $C_{1-9}$ alkyl, $C_{2-6}$ alkenyl, $C_{2-6}$ alkynyl, $C_{3-15}$ cycloalkyl, aryl, heteroaryl or 4-20 membered heterocyclyl, wherein the $C_{1-9}$ alkyl, $C_{2-6}$ alkenyl, $C_{2-6}$ alkynyl, $C_{3-15}$ cycloalkyl, aryl, heteroaryl or heterocyclyl can further optionally be substituted with one or more $Z^{1a}$ group;

each $Z^{1b}$ is independently oxo, hydroxy, halo, —NO$_2$, —N$_3$, —CN, $C_{1-9}$ alkyl, $C_{2-6}$ alkenyl, $C_{2-6}$ alkynyl, $C_{3-15}$ cycloalkyl, $C_{1-8}$ haloalkyl, aryl, heteroaryl, 4-20 membered heterocyclyl, —O($C_{1-9}$ alkyl), —O($C_{2-6}$ alkenyl), —O($C_{2-6}$ alkynyl), —O($C_{3-15}$ cycloalkyl), —O($C_{1-8}$ haloalkyl), —O(aryl), —O(heteroaryl), —O(4-20 membered heterocyclyl), —NH$_2$, —NH($C_{1-9}$ alkyl), —NH($C_{2-6}$ alkenyl), —NH($C_{2-6}$ alkynyl), —NH($C_{3-15}$ cycloalkyl), —NH($C_{1-8}$ haloalkyl), —NH(aryl), —NH(heteroaryl), —NH(4-20 membered heterocyclyl), —N($C_{1-9}$ alkyl)$_2$, —N($C_{3-15}$ cycloalkyl)$_2$, —N($C_{2-6}$ alkenyl)$_2$, —N($C_{2-6}$ alkynyl)$_2$, —N($C_{3-15}$ cycloalkyl)$_2$, —N($C_{1-8}$ haloalkyl)$_2$, —N(aryl)$_2$, —N(heteroaryl)$_2$, —N(4-20 membered heterocyclyl)$_2$, —N(C$_{1-9}$ alkyl)(C$_{3-15}$ cycloalkyl), —N(C$_{1-9}$ alkyl)(C$_{2-6}$ alkenyl), —N(C$_{1-9}$ alkyl)(C$_{2-6}$ alkynyl), —N(C$_{1-9}$ alkyl)(C$_{3-15}$ cycloalkyl), —N(C$_{1-9}$ alkyl)(C$_{1-8}$ haloalkyl), —N(C$_{1-9}$ alkyl)(aryl), —N(C$_{1-9}$ alkyl)(heteroaryl), —N(C$_{1-9}$ alkyl)(4-20 membered heterocyclyl), —C(O)(C$_{1-9}$ alkyl), —C(O)(C$_{2-6}$ alkenyl), —C(O)(C$_{2-6}$ alkynyl), —C(O)(C$_{3-15}$ cycloalkyl), —C(O)(C$_{1-8}$ haloalkyl), —C(O)(aryl), —C(O)(heteroaryl), —C(O)(4-20 membered heterocyclyl), —C(O)O(C$_{1-9}$ alkyl), —C(O)O(C$_{2-6}$ alkenyl), —C(O)O(C$_{2-6}$ alkynyl), —C(O)O(C$_{3-15}$ cycloalkyl), —C(O)O(C$_{1-8}$ haloalkyl), —C(O)O(aryl), —C(O)O(heteroaryl), —C(O)O(4-20 membered heterocyclyl), —C(O)NH$_2$, —C(O)NH(C$_{1-9}$ alkyl), —C(O)NH(C$_{2-6}$ alkenyl), —C(O)NH(C$_{2-6}$ alkynyl), —C(O)NH(C$_{3-15}$ cycloalkyl), —C(O)NH(C$_{1-8}$ haloalkyl), —C(O)NH(aryl), —C(O)NH(heteroaryl), —C(O)NH(4-20 membered heterocyclyl), —C(O)N(C$_{1-9}$ alkyl)$_2$, —C(O)N(C$_{3-15}$ cycloalkyl)$_2$, —C(O)N(C$_{2-6}$ alkenyl)$_2$, —C(O)N(C$_{2-6}$ alkynyl)$_2$, —C(O)N(C$_{3-15}$ cycloalkyl)$_2$, —C(O)N(C$_{1-8}$ haloalkyl)$_2$, —C(O)N(aryl)$_2$, —C(O)N(heteroaryl)$_2$, —C(O)N(4-20 membered heterocyclyl)$_2$, —NHC(O)(C$_{1-9}$ alkyl), —NHC(O)(C$_{2-6}$ alkenyl), —NHC(O)(C$_{2-6}$ alkynyl), —NHC(O)(C$_{3-15}$ cycloalkyl), —NHC(O)(C$_{1-8}$ haloalkyl), —NHC(O)(aryl), —NHC(O)(heteroaryl), —NHC(O)(4-20 membered heterocyclyl), —NHC(O)O(C$_{1-9}$ alkyl), —NHC(O)O(C$_{2-6}$ alkenyl), —NHC(O)O(C$_{2-6}$ alkynyl), —NHC(O)O(C$_{3-15}$ cycloalkyl), —NHC(O)O(C$_{1-8}$ haloalkyl), —NHC(O)O(aryl), —NHC(O)O(heteroaryl), —NHC(O)O(4-20 membered heterocyclyl), —NHC(O)NH(C$_{1-9}$ alkyl), —NHC(O)NH(C$_{2-6}$ alkenyl), —NHC(O)NH(C$_{2-6}$ alkynyl), —NHC(O)NH(C$_{3-15}$ cycloalkyl), —NHC(O)NH(C$_{1-8}$ haloalkyl), —NHC(O)NH(aryl), —NHC(O)NH(heteroaryl), —NHC(O)NH(4-20 membered heterocyclyl), —SH, —S(C$_{1-9}$ alkyl), —S(C$_{2-6}$ alkenyl), —S(C$_{2-6}$ alkynyl), —S(C$_{3-15}$ cycloalkyl), —S(C$_{1-8}$ haloalkyl), —S(aryl), —S(heteroaryl), —S(4-20 membered heterocyclyl), —NHS(O)(C$_{1-9}$ alkyl), —N(C$_{1-9}$ alkyl)(S(O)(C$_{1-9}$ alkyl), —S(O)N(C$_{1-9}$ alkyl)$_2$, —S(O)(C$_{1-9}$ alkyl), —S(O)(NH)(C$_{1-9}$ alkyl), —S(O)(C$_{2-6}$ alkenyl), —S(O)(C$_{2-6}$ alkynyl), —S(O)(C$_{3-15}$ cycloalkyl), —S(O)(C$_{1-8}$ haloalkyl), —S(O)(aryl), —S(O)(heteroaryl), —S(O)(4-20 membered heterocyclyl), —S(O)$_2$(C$_{1-9}$ alkyl), —S(O)$_2$(C$_{2-6}$ alkenyl), —S(O)$_2$(C$_{2-6}$ alkynyl), —S(O)$_2$(C$_{3-15}$ cycloalkyl), —S(O)$_2$(C$_{1-8}$ haloalkyl), —S(O)$_2$(aryl), —S(O)$_2$(heteroaryl), —S(O)$_2$(heterocyclyl), —S(O)$_2$NH(C$_{1-9}$ alkyl), or —S(O)$_2$N(C$_{1-9}$ alkyl)$_2$;

wherein any alkyl, cycloalkyl, aryl, heteroaryl, or heterocyclyl is optionally substituted with one or more halo, C$_{1-9}$ alkyl, C$_{1-8}$ haloalkyl, —OH, —NH$_2$, —NH(C$_{1-9}$ alkyl), —NH(C$_{3-15}$ cycloalkyl), —NH(C$_{1-8}$ haloalkyl), —NH(aryl), —NH(heteroaryl), —NH(heterocyclyl), —N(C$_{1-9}$ alkyl)$_2$, —N(C$_{3-15}$ cycloalkyl)$_2$, —NHC(O)(C$_{3-15}$ cycloalkyl), —NHC(O)(C$_{1-8}$ haloalkyl), —NHC(O)(aryl), —NHC(O)(heteroaryl), —NHC(O)(heterocyclyl), —NHC(O)O(C$_{1-9}$ alkyl), —NHC(O)O(C$_{2-6}$ alkynyl), —NHC(O)O(C$_{3-15}$ cycloalkyl), —NHC(O)O(C$_{1-8}$ haloalkyl), —NHC(O)O(aryl), —NHC(O)O(heteroaryl), —NHC(O)O(heterocyclyl), —NHC(O)NH(C$_{1-9}$ alkyl), —S(O)(NH)(C$_{1-9}$ alkyl), S(O)$_2$(C$_{1-9}$ alkyl), —S(O)$_2$(C$_{3-15}$ cycloalkyl), —S(O)$_2$(C$_{1-8}$ haloalkyl), —S(O)$_2$(aryl), —S(O)$_2$(heteroaryl), —S(O)$_2$(heterocyclyl), —S(O)$_2$NH(C$_{1-9}$ alkyl), —S(O)$_2$N(C$_{1-9}$ alkyl)$_2$, —O(C$_{3-15}$ cycloalkyl), —O(C$_{1-8}$ haloalkyl), —O(aryl), —O(heteroaryl), —O(heterocyclyl), or —O(C$_{1-9}$ alkyl); and with the proviso that when R$^1$ is C$_3$ alkyl, R$^2$ is C$_5$ alkyl substituted with F and hydroxyl, R$^3$, R$^5$, R$^{6, R7}$ are H, and R$^4$ is CN, then R$^1$ is substituted with oxo, halo, —NO$_2$, —N$_3$, —CN, C$_{2-9}$ alkyl, C$_{2-6}$ alkenyl, C$_{2-6}$ alkynyl, C$_{3-15}$ cycloalkyl, C$_{1-8}$ haloalkyl, aryl, heteroaryl, heterocyclyl, —O—R$^{12}$, —C(O)O—R$^{12}$, —C(O)—N(R$^{12}$)(R$^{12}$), —N(R12)(R$^{12}$), —N(R$^{12}$)$_2$(R$^{12}$)$^+$, —N(R$^{12}$)C(O)O—R$^{12}$, —N(R12)C(O)N(R$^{12}$)(R$^{12}$), —N(R$^{12}$)S(O)$_2$(R$^{12}$), —NR$^{12}$S(O)$_2$N(R$^{12}$)(R$^{12}$), —NR$^{12}$S(O)$_2$O(R$^{12}$), —OC(O)R$^{12}$, —OC(O)OR$^{12}$, —OC(O)—N(R$^{12}$)(R$^{12}$), —Si(R$^{12}$)$_3$, —S—R$^{12}$, —S(O)R$^{12}$, —S(O)(NH)R$^{12}$, —S(O)$_2$R$^{12}$ or —S(O)$_2$N(R$^{12}$)(R$^{12}$);

wherein any alkyl, alkenyl, alkynyl, cycloalkyl, haloalkyl, aryl, heteroaryl or heterocyclyl is optionally substituted with Z$^{1a}$;

or a pharmaceutically acceptable salt, stereoisomer, mixture of stereoisomers, or deuterated analog thereof.

\* \* \* \* \*